United States Patent
McGeehan et al.

(10) Patent No.: US 11,919,901 B2
(45) Date of Patent: Mar. 5, 2024

(54) INHIBITORS OF THE MENIN-MLL INTERACTION

(71) Applicants: Syndax Pharmaceuticals, Inc., Waltham, MA (US); Vitae Pharmaceuticals, LLC, North Chicago, IL (US)

(72) Inventors: Gerard M. McGeehan, Newtown Square, PA (US); William H. Miller, Collegeville, PA (US); Nicholas Paul Camp, Devon (GB); Salvacion Cacatian, Norristown, PA (US); Santosh S. Kulkarni, Bangalore (IN); Swapan Kumar Samanta, Bangalore (IN); Virsinha Venkat Reddy, Bangalore (IN)

(73) Assignees: Syndax Pharmaceuticals, Inc., Waltham, MA (US); Vitae Pharmaceuticals, LLC, North Chicago, IL (US)

( * ) Notice: Subject to any disclaimer, the term of this patent is extended or adjusted under 35 U.S.C. 154(b) by 0 days.

(21) Appl. No.: 17/744,249

(22) Filed: May 13, 2022

(65) Prior Publication Data
US 2023/0021684 A1    Jan. 26, 2023

Related U.S. Application Data

(60) Provisional application No. 63/188,704, filed on May 14, 2021.

(51) Int. Cl.
| | | |
|---|---|---|
| *C07D 405/14* | (2006.01) | |
| *A61K 31/506* | (2006.01) | |
| *C07D 471/10* | (2006.01) | |
| *A61P 35/02* | (2006.01) | |
| *C07D 519/00* | (2006.01) | |

(52) U.S. Cl.
CPC ............ *C07D 471/10* (2013.01); *A61P 35/02* (2018.01); *C07D 519/00* (2013.01)

(58) Field of Classification Search
CPC .... C07D 405/14; A61K 31/506; A61K 35/02; A61P 35/00; A61P 35/02
USPC .......................................... 544/298; 514/269
See application file for complete search history.

(56) References Cited

U.S. PATENT DOCUMENTS

| | | | |
|---|---|---|---|
| 5,820,915 A | 10/1998 | Harris | |
| 5,990,154 A | 11/1999 | Harris | |
| 5,993,887 A | 11/1999 | Harris | |
| 6,054,477 A | 4/2000 | Harris | |
| 6,063,809 A | 5/2000 | Harris | |
| 6,124,477 A | 9/2000 | Harris | |
| 6,162,479 A | 12/2000 | Harris | |
| 6,248,776 B1 | 6/2001 | Harris | |
| 6,255,337 B1 | 7/2001 | Harris | |
| 6,309,687 B1 | 10/2001 | Harris | |
| 6,476,066 B1 | 11/2002 | Harris | |
| 6,660,766 B2 | 12/2003 | Harris | |
| 9,969,727 B2 | 5/2018 | Le et al. | |
| 10,683,302 B2 * | 6/2020 | Cacatian | ................. A61P 35/02 |
| 10,752,639 B2 | 8/2020 | Wu et al. | |
| 11,479,557 B2 | 10/2022 | Cacatian et al. | |
| 2004/0058982 A1 | 3/2004 | Harris | |
| 2005/0209301 A1 | 9/2005 | Eissenstat et al. | |

(Continued)

FOREIGN PATENT DOCUMENTS

| | | |
|---|---|---|
| CN | 105732636 A | 7/2016 |
| JP | 2014517016 A | 7/2014 |

(Continued)

OTHER PUBLICATIONS

Fiskus et al., "Effective Menin inhibitor-based combinations against AML with MLL rearrangement or NPM1 mutation (NPM1c)," Blood Cancer J. (Jan. 2022); 12(1):5, 11 pages.

(Continued)

*Primary Examiner* — Charanjit Aulakh
(74) *Attorney, Agent, or Firm* — COOLEY LLP; Heidi A. Erlacher; Eric A. Owens

(57) ABSTRACT

The present disclosure is directed to inhibitors of Formula (0), or a stereoisomer thereof, or pharmaceutically acceptable salt thereof, of the interaction of menin with MLL and MLL fusion proteins, pharmaceutical compositions containing the same, and their use in the treatment of cancer and other diseases mediated by the menin-MLL interaction, Formula (0)

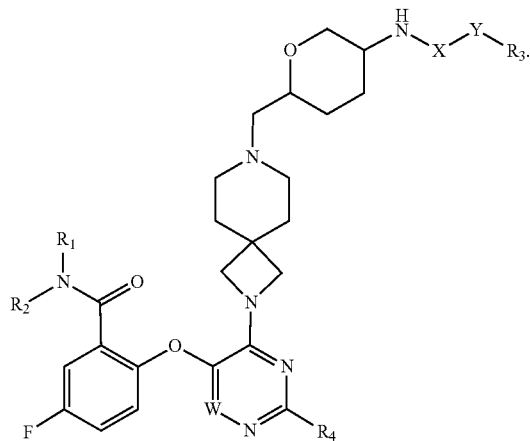

28 Claims, No Drawings

(56) References Cited

U.S. PATENT DOCUMENTS

| | | |
|---|---|---|
| 2005/0267074 A1 | 12/2005 | Eissenstat et al. |
| 2013/0102525 A1 | 4/2013 | Bernstein et al. |
| 2016/0339035 A1 | 11/2016 | Berger et al. |
| 2019/0076540 A1 | 3/2019 | Phillips et al. |
| 2019/0144459 A1 | 5/2019 | Cacatian et al. |
| 2019/0307750 A1 | 10/2019 | Armstrong |
| 2020/0030355 A1 | 1/2020 | Klaus et al. |
| 2020/0223853 A1 | 7/2020 | Butler et al. |
| 2021/0053974 A1 | 2/2021 | Cacatian et al. |
| 2021/0115018 A1 | 4/2021 | Wang et al. |
| 2021/0317214 A1 | 10/2021 | Chartash et al. |
| 2023/0165858 A1 | 6/2023 | McGEEHAN et al. |
| 2023/0174541 A1 | 6/2023 | Cacatian et al. |

FOREIGN PATENT DOCUMENTS

| | | |
|---|---|---|
| JP | 2018538330 A | 12/2018 |
| WO | WO-0054768 A1 | 9/2000 |
| WO | WO-2004037827 A1 | 5/2004 |
| WO | WO-2009137733 A1 | 11/2009 |
| WO | WO-2012170976 A2 | 12/2012 |
| WO | WO-2014164543 A1 | 10/2014 |
| WO | WO-2015191701 A1 | 12/2015 |
| WO | WO-2017112768 A1 | 6/2017 |
| WO | WO-2017214367 A1 | 12/2017 |
| WO | WO-2018053267 A1 | 3/2018 |
| WO | WO-2019120209 A1 | 6/2019 |
| WO | WO-2019143977 A1 | 7/2019 |
| WO | WO-2020069027 A1 | 4/2020 |
| WO | WO-2021207335 A1 | 10/2021 |
| WO | WO-2022241265 A1 | 11/2022 |
| WO | WO-2023018825 A1 | 2/2023 |

OTHER PUBLICATIONS

McGeehan et al., "A first-in-class Menin-MLL1 antagonist for the treatment of MLL-r and NPM1 mutant leukemias," Syndax Pharmaceuticals, Inc., AACR Virtual Annual Meeting, Apr. 27, 2020, retrieved online: https://www.oncozine.com/study-shows-inhibition-of-the-menin-mll 1-interaction-to-induce-a-response-in-mll-r-acute-leukemias/, 19. pages.

Medchemexpress, SNDX-5613, Aug. 3, 2022, [Retrieved online Sep. 18, 2023] URL: https://web.archive.org/web/20220308174847/https://www.medchemexpress.com/sndx-5613.html; 3 pages.

Borkin et al. "Pharmacologic Inhibition of the Menin-MLL Interaction Blocks Progression of MLL Leukemia In Vivo", Cancer Cell, vol. 27, p. 589-602 (2015).

Chamberlain et al. "Menin determines K-RAS proliferative outputs in endocrine cells", The Journal of Clinical Investigation, vol. 124, No. 9, p. 4093-4101 (2014).

Cierpicki T. et al. "Challenges and opportunities in targeting the menin-MLL interaction", Future Med. Chem. Vol. 6, No. 4, p. 447-462 (2014).

Database STN, CAS Registry No. 1048962-49-7 "3-Oxabicyclo[3.1.0]hexan-6-amine, hydrochloride (1:1), (1α,5α,6α)-(CA Index Name)", Chemical Abstracts Service, American Chemical Society entered Sep. 12, 2008; retrieved Apr. 18, 2023; 1 page.

Database STN, CAS Registry No. 58564-87-7 "7-Oxabicyclo[2.2.1]heptan-2-amine, (1R,2R,4S)-rel-(CA Index Name)", Chemical Abstracts Service, American Chemical Society entered Nov. 16, 1984; retrieved Apr. 18, 2023; 1 page.

Freedman et al., "Non-Hodgkin's Lymphomas" Chapter 134, Cancer Medicine, American Cancer Society, B.C. Decker Inc., Hamilton, Ontario, (2003), 30 pages.

Grembecka J. et al. "Menin-MLL inhibitors reverse oncogenic activity of MLL fusion proteins in leukemia", Nature Chemical Biology, vol. 8, p. 277-284 (2012).

International Preliminary Report on Patentability for International Application No. PCT/US2021/026141 dated Oct. 20, 2022, 7 pages.

International Preliminary Report on Patentability of International Application No. PCT/US2017/036506, dated Dec. 11, 2018, 6 pages.

International Search Report and Written Opinion for International Application No. PCT/US2022/029271, dated Aug. 2, 2022, 10 pages.

International Search Report and Written Opinion of International Application No. PCT/US2017/036506, dated Sep. 11, 2017, 9 pages.

International Search Report and Written Opinion of International Application No. PCT/US2021/026141, dated Jun. 30, 2021, 8 pages.

Jagtap et al. "Synthesis of (R)-3, 4-dihydro-2H-pyran-2-carboxaldehyde: application to the synthesis of potent adenosine A2A and A3 receptor agonist", Tetrahedron Letters, (2009); 50(22):2693-2696.

Kang et al. "Enzymatic synthesis of optically active (S)-(+)-2-hydroxymethyl-3, 4-dihydro-2H-pyran and (S)-(+)-2-acetoxymethyl-3, 4-dihydro-2H-pyran", Tetrahedron: Asymmetry, (1995); 6(1):97-100.

Karageorgis et al. "Activity-Directed Synthesis with Intermolecular Reactions: Development of a Fragment into a Range of Androgen Receptor Agonists", Angewandte Chemie, International Edition, (2015); 54(46): 13538-13544.

Kress et al. "Chemistry of Pyrimidine. 2. Synthesis of Pyrimidine JV-Oxides and 4-Pyrimidinones by Reaction of 5-Substituted Pyrimidines with Peracids. Evidence for Covalent Hydrates as Reaction Intermediates", J. Org. Chem., vol. 50, p. 3073-3076 (1985).

Maiti D. et al. "Cu-Catalyzed Arylation of Phenols: Synthesis of Sterically Hindered and Heteroaryl Diaryl Ethers", J. Org. Chem. vol. 75, p. 1791-1794 (2010).

Malik R. et al. "Targeting the MLL complex in castration-resistant prostate cancer", Nature Medicine, vol. 21, No. 4, p. 344-354 (2015).

Salvi L. et al. "A New Biarylphosphine Ligand for the Pd-Catalyzed Synthesis of Diaryl Ethers under Mild Conditions", Organic Letters, vol. 14, No. 1, p. 170-173 (2012).

Yang Y. et al. "Reversal of preexisting hyperglycemia in diabetic mice by acute deletion of the Men1 gene", PNAS, vol. 107, No. 47, p. 20358-20363 (2010).

Yokoyama A. et al. "The Menin Tumor Suppressor Protein Is an Essential Oncogenic Cofactor for MLL-Associated Leukemogenesis", Cell, vol. 123, p. 207-218, (2005).

Zhang et al. "Design, synthesis, and preliminary SAR study of 3-and 6-side-chain-extended tetrahydro-pyran analogues of cis-and trans-(6-benzhydryl-tetrahydropyran-3-yl)-benzylamine", Bioorganic & Medicinal Chemistry, (2006); 14(11):3953-3966.

\* cited by examiner

INHIBITORS OF THE MENIN-MLL INTERACTION

CROSS REFERENCE TO RELATED APPLICATIONS

This application claims the benefit on U.S. Provisional Application No. 63/188,704, filed May 14, 2021, which is incorporated by reference herein in its entirety.

BACKGROUND

The mixed-lineage leukemia (MLL) protein is a histone methyltransferase that is mutated in clinically and biologically distinctive subsets of acute leukemia. Rearranged mixed lineage leukemia (MLL-r) involves recurrent translocations of the 11q23 chromosome locus which lead to an aggressive form of acute leukemia with limited therapeutic options. These translocations target the MLL gene creating an oncogenic fusion protein comprising the amino-terminus of MLL fused in frame with more than 60 different fusion protein partners. Menin, a ubiquitously expressed, nuclear protein encoded by the multiple endocrine neoplasia type 1 (MEN1) tumor suppressor gene, has a high affinity binding interaction with MLL fusion proteins and is an essential co-factor of oncogenic MLL-r fusion proteins. Disruption of this interaction leads to selective growth inhibition and apoptosis of MLL-r leukemia cells both in vitro and in vivo.

The menin-MLL complex plays a role in castration-resistant/advanced prostate cancer, and a menin-MLL inhibitor has been shown to reduce tumor growth in vivo. Additionally, a menin-MLL inhibitor has been shown to enhance human P cell proliferation, supporting a role for inhibitors of the menin-MLL interaction in the treatment of diabetes. The interaction between menin and MLL or MLL fusion proteins is an attractive target for therapeutic intervention, and there is a need for novel agents that inhibit the menin-MLL interaction for the treatment of various diseases and conditions, including leukemia, other cancers and diabetes.

Additionally, hERG potassium channels are essential for normal electrical activity in the heart. Inherited mutations in the hERG gene cause long QT syndrome, a disorder that predisposes individuals to life-threatening arrhythmias. Arrhythmia can also be induced by a blockage of hERG channels by a surprisingly diverse group of drugs. This side effect is a common reason for drug failure in preclinical safety trials and compounds displaying low off-target hERG binding are of paramount importance in drug design with significant clinical need. Therefore, in drug development it is extremely important to determine the potential of a candidate compound to block hERG channels, but this property is not easily determined from the structure of the compound and closely related compounds may have vastly different potential to block hERG channels. Therefore, there is an urgent need to develop efficacious compounds that cause minimum blockage of hERG channels.

SUMMARY

In one aspect, the present disclosure is directed to a compound of Formula 0,

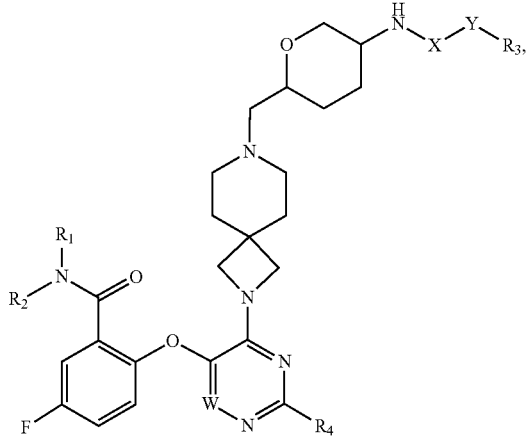

Formula (0)

a stereoisomer thereof, or a pharmaceutically acceptable salt thereof, wherein W, X, Y, $R_1$, $R_2$, $R_3$, $R_4$, and $R_5$ are defined herein.

In some aspects, the present application relates to a pharmaceutical composition comprising a compound of the application, or a pharmaceutically acceptable salt, and a pharmaceutically acceptable carrier.

In some aspects, the present application relates to a pharmaceutical composition comprising a therapeutically effective amount of a compound of the application, or a pharmaceutically acceptable salt, and a pharmaceutically acceptable carrier.

In some aspects, the present application relates to a pharmaceutical composition comprising a compound of the application, and a pharmaceutically acceptable carrier.

In some aspects, the present application relates to a pharmaceutical composition comprising a therapeutically effective amount of a compound of the application, and a pharmaceutically acceptable carrier.

The present disclosure further provides a method of inhibiting the interaction between menin and MLL comprising contacting the menin and MLL with a compound of Formulae I, Ia, II, IIa, III, or IIIa, or a stereoisomer, or pharmaceutically acceptable salt thereof.

The present disclosure further provides a method of treating cancer in a patient comprising administering to the patient a therapeutically effective amount of a compound of Formulae 0, 0a, I, Ia, II, IIa, III, or IIIa, or a stereoisomer, or a pharmaceutically acceptable salt thereof.

The present disclosure further provides a method of inhibiting the interaction between menin and MLL comprising contacting the menin and MLL with a compound of Formulae 0, 0a, I, Ia, II, IIa, III, or IIIa.

The present disclosure further provides a method of treating cancer in a patient comprising administering to the patient a therapeutically effective amount of a compound of Formulae 0, 0a, I, Ia, II, IIa, III, or IIIa.

The details of the disclosure are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

The contents of all references (including literature references, issued patents, published patent applications, and co-pending patent applications) cited throughout this application are hereby expressly incorporated herein in their entireties by reference. The references cited herein are not admitted to be prior art to the application.

DETAILED DESCRIPTION

In one aspect, the present disclosure is directed to a compound of Formula 0,

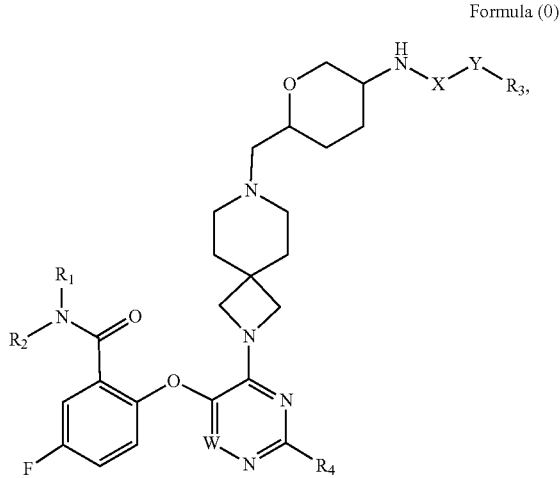

Formula (0)

a stereoisomer thereof, or a pharmaceutically acceptable salt thereof, wherein

W is N or CH;
X is C=O, S(=O)(=NR$_5$), or S(=O)$_2$;
Y is NH, O, or a bond;
R$_1$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted by one or more halo, OH, OBn, oxo, CN, N(R$_N$)$_2$, $C_1$-$C_6$ alkyl, $C_1$-$C_6$ haloalkyl, $C_3$-$C_6$ cycloalkyl, or $C_1$-$C_6$ alkoxy;
R$_2$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted with one or more halo, OH, OBn, oxo, CN, N(R$_N$)$_2$, $C_1$-$C_6$ alkyl, $C_1$-$C_6$ haloalkyl, $C_3$-$C_6$ cycloalkyl, or $C_1$-$C_6$ alkoxy;
R$_1$ and R$_2$ optionally form a 3- to 12-membered heterocyclyl, wherein the heterocyclyl is optionally substituted with one or more $C_1$-$C_6$ alkyl, halo, OH, CN, or $C_1$-$C_6$ alkoxy;
R$_3$ is H, $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, NH$_2$, NH—$C_1$-$C_6$ alkyl, N—($C_1$-$C_6$ alkyl)$_2$, $C_6$-$C_{10}$ aryl, 5- to 10-membered heteroaryl, 3- to 12-membered heterocyclyl, wherein the alkyl, alkenyl, alkynyl, alkoxy, cycloalkyl, aryl, heteroaryl, or heterocyclyl is optionally substituted with one or more halo, OH, OBn, oxo, CN, N(RN)$_2$, $C_1$-$C_6$ alkyl, $C_1$-$C_6$ haloalkyl, $C_3$-$C_6$ cycloalkyl, $C_1$-$C_6$ alkoxy, or aryl;
R$_4$ is H, halo, $C_1$-$C_6$ alkyl, $C_1$-$C_6$ alkoxy, $C_1$-$C_6$ haloalkyl, or N(R$_N$)$_2$;
each R$_N$ is independently H, $C_1$-$C_6$ alkyl, or $C_1$-$C_6$ haloalkyl; and
each R$_5$ is independently H, $C_1$-$C_6$ alkyl, or $C_1$-$C_6$ haloalkyl.

In one aspect, the present disclosure is directed to a compound of Formula 0a,

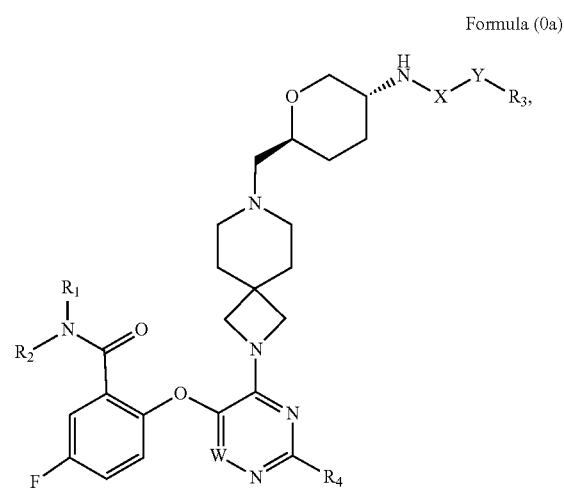

Formula (0a)

a stereoisomer thereof, or a pharmaceutically acceptable salt thereof, wherein

W is N or CH;
X is C=O, S(=O)(=NR$_5$), or S(=O)$_2$;
Y is NH, O, or a bond;
R$_1$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted by one or more halo, OH, OBn, oxo, CN, N(R$_N$)$_2$, $C_1$-$C_6$ alkyl, $C_1$-$C_6$ haloalkyl, $C_3$-$C_6$ cycloalkyl, or $C_1$-$C_6$ alkoxy;
R$_2$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted with one or more halo, OH, OBn, oxo, CN, N(R$_N$)$_2$, $C_1$-$C_6$ alkyl, $C_1$-$C_6$ haloalkyl, $C_3$-$C_6$ cycloalkyl, or $C_1$-$C_6$ alkoxy;
R$_1$ and R$_2$ optionally form a 3- to 12-membered heterocyclyl, wherein the heterocyclyl is optionally substituted with one or more $C_1$-$C_6$ alkyl, halo, OH, CN, or $C_1$-$C_6$ alkoxy;
R$_3$ is H, $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, NH$_2$, NH—$C_1$-$C_6$ alkyl, N—($C_1$-$C_6$ alkyl)$_2$, $C_6$-$C_{10}$ aryl, 5- to 10-membered heteroaryl, 3- to 12-membered heterocyclyl, wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, $C_1$-$C_6$ alkoxy, or aryl;

$R_4$ is H, halo, $C_1$-$C_6$ alkyl, $C_1$-$C_6$ alkoxy, $C_1$-$C_6$ haloalkyl, or $N(R_N)_2$;

each $R_N$ is independently H, $C_1$-$C_6$ alkyl, or $C_1$-$C_6$ haloalkyl; and each $R_5$ is independently H, $C_1$-$C_6$ alkyl, or $C_1$-$C_6$ haloalkyl.

In one aspect, the present disclosure is directed to a compound of Formula I,

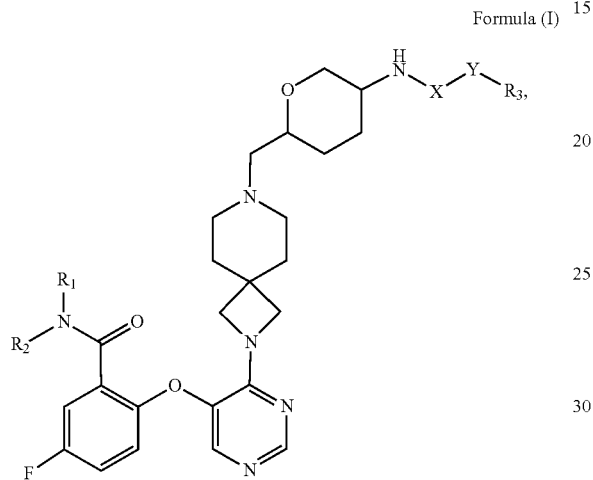

Formula (I)

a stereoisomer thereof, or a pharmaceutically acceptable salt thereof, wherein

X is C=O, S(=O)(=NR$_5$), or S(=O)$_2$;

Y is NH, O, or a bond;

$R_1$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted by one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_2$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_1$ and $R_2$ optionally form a 3- to 12-membered heterocyclyl, wherein the heterocyclyl is optionally substituted with one or more $C_1$-$C_6$ alkyl, halo, OH, CN, or $C_1$-$C_6$ alkoxy;

$R_3$ is H, $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, NH$_2$, NH—$C_1$-$C_6$ alkyl, N—($C_1$-$C_6$ alkyl)$_2$, $C_6$-$C_{10}$ aryl, 5- to 10-membered heteroaryl, 3- to 12-membered heterocyclyl, wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, $C_1$-$C_6$ alkoxy, or aryl;

$R_4$ is H, halo, $C_1$-$C_6$ alkyl, or $C_1$-$C_6$ haloalkyl;

each $R_N$ is independently H, $C_1$-$C_6$ alkyl, or $C_1$-$C_6$ haloalkyl; and each $R_5$ is independently H, $C_1$-$C_6$ alkyl, or $C_1$-$C_6$ haloalkyl.

In one aspect, the present disclosure is directed to a compound of Formula Ia,

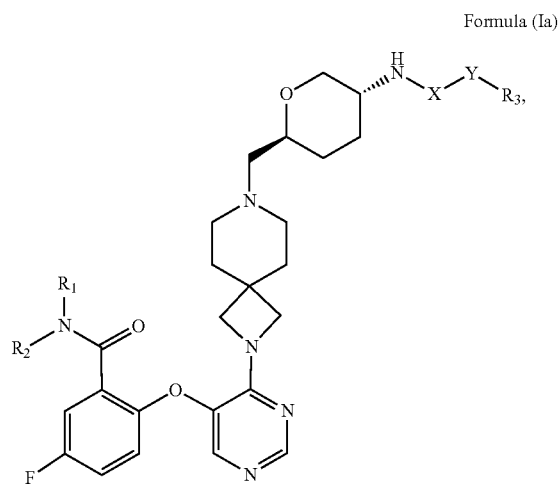

Formula (Ia)

a stereoisomer thereof, or a pharmaceutically acceptable salt thereof, wherein

X is C=O, S(=O)(=NR$_5$), or S(=O)$_2$;

Y is NH, O, or a bond;

$R_1$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted by one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_2$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_1$ and $R_2$ optionally form a 3- to 12-membered heterocyclyl, wherein the heterocyclyl is optionally substituted with one or more $C_1$-$C_6$ alkyl, halo, OH, CN, or $C_1$-$C_6$ alkoxy;

$R_3$ is H, $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, NH$_2$, NH—$C_1$-$C_6$ alkyl, N—($C_1$-$C_6$ alkyl)$_2$, $C_6$-$C_{10}$ aryl, 5- to 10-membered heteroaryl, 3- to 12-membered heterocyclyl, wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, $C_1$-$C_6$ alkoxy, or aryl;

$R_4$ is H, halo, $C_1$-$C_6$ alkyl, or $C_1$-$C_6$ haloalkyl;

each $R_N$ is independently H, $C_1$-$C_6$ alkyl, or $C_1$-$C_6$ haloalkyl; and each $R_5$ is independently H, $C_1$-$C_6$ alkyl, or $C_1$-$C_6$ haloalkyl.

In one aspect, the present disclosure is directed to a compound of Formula II,

Formula (II)

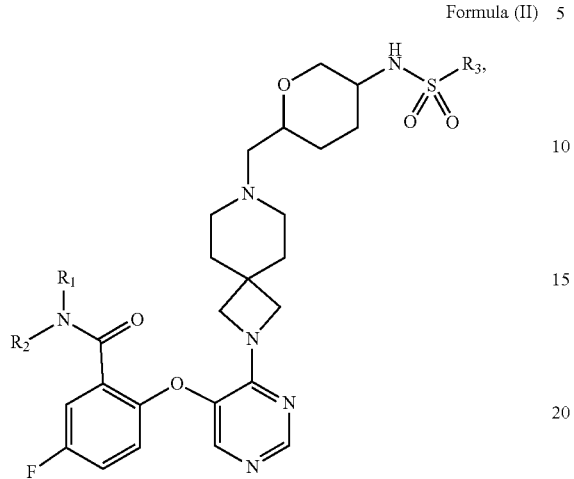

a stereoisomer thereof, or a pharmaceutically acceptable salt thereof, wherein $R_1$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted by one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_2$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_1$ and $R_2$ optionally form a 3- to 12-membered heterocyclyl, wherein the heterocyclyl is optionally substituted with one or more $C_1$-$C_6$ alkyl, halo, OH, CN, or $C_1$-$C_6$ alkoxy;

$R_3$ is H, $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $NH_2$, NH—$C_1$-$C_6$ alkyl, N—($C_1$-$C_6$ alkyl)$_2$, $C_6$-$C_{10}$ aryl, 5- to 10-membered heteroaryl, 3- to 12-membered heterocyclyl, wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, $C_1$-$C_6$ alkoxy, or aryl; and each $R_N$ is independently H, $C_1$-$C_6$ alkyl, or $C_1$-$C_6$ haloalkyl; and In one aspect, the present disclosure is directed to a compound of Formula IIa, Formula (IIa)

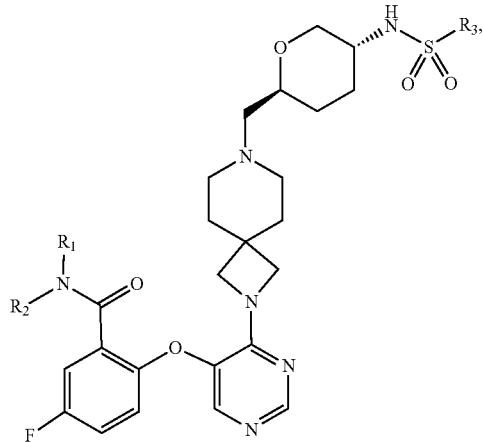

a stereoisomer thereof, or a pharmaceutically acceptable salt thereof, wherein $R_1$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted by one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_2$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_1$ and $R_2$ optionally form a 3- to 12-membered heterocyclyl, wherein the heterocyclyl is optionally substituted with one or more $C_1$-$C_6$ alkyl, halo, OH, CN, or $C_1$-$C_6$ alkoxy;

$R_3$ is H, $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $NH_2$, NH—$C_1$-$C_6$ alkyl, N—($C_1$-$C_6$ alkyl)$_2$, $C_6$-$C_{10}$ aryl, 5- to 10-membered heteroaryl, 3- to 12-membered heterocyclyl, wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, $C_1$-$C_6$ alkoxy, or aryl; and each $R_N$ is independently H, $C_1$-$C_6$ alkyl, or $C_1$-$C_6$ haloalkyl; and In one aspect, the present disclosure is directed to a compound of Formula III, Formula (III)

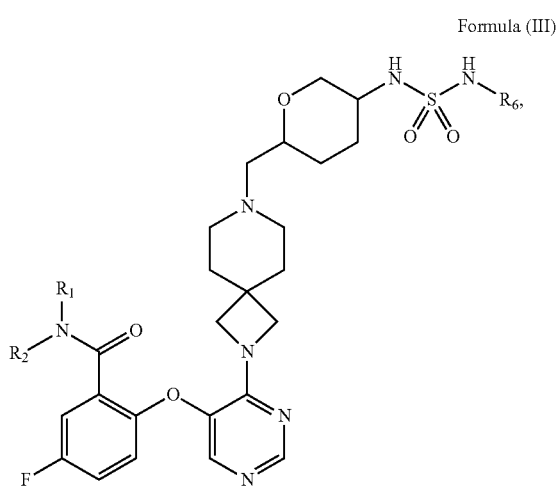

Formula (IIIa)

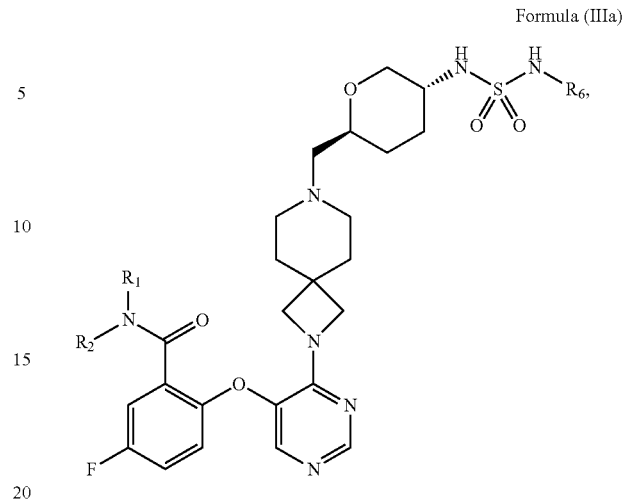

a stereoisomer thereof, or a pharmaceutically acceptable salt thereof, wherein $R_1$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted by one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_2$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted with one or more halo, OH, OBn, oxo, CN, $C_1$-$C_6$ alkyl, $C_1$-$C_6$ haloalkyl, $C_3$-$C_6$ cycloalkyl, or $C_1$-$C_6$ alkoxy;

$R_1$ and $R_2$ optionally form a 3- to 12-membered heterocyclyl, wherein the heterocyclyl is optionally substituted with one or more $C_1$-$C_6$ alkyl, halo, OH, CN, or $C_1$-$C_6$ alkoxy; $R_6$ is H, $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, 3- to 12-membered heterocyclyl, wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, $C_1$-$C_6$ alkoxy, or aryl; and each $R_N$ is independently H, $C_1$-$C_6$ alkyl, or $C_1$-$C_6$ haloalkyl; and In one aspect, the present disclosure is directed to a compound of Formula IIIa, a stereoisomer thereof, or a pharmaceutically acceptable salt thereof, wherein $R_1$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted by one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_2$ is $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, or $C_1$-$C_6$ alkoxy;

$R_1$ and $R_2$ optionally form a 3- to 12-membered heterocyclyl, wherein the heterocyclyl is optionally substituted with one or more $C_1$-$C_6$ alkyl, halo, OH, CN, or $C_1$-$C_6$ alkoxy;

$R_6$ is H, $C_1$-$C_6$ alkyl, $C_2$-$C_6$ alkenyl, $C_2$-$C_6$ alkynyl, $C_1$-$C_6$ alkoxy, $C_3$-$C_{12}$ cycloalkyl, $C_6$-$C_{10}$ aryl, 5- to 10-membered heteroaryl, 3- to 12-membered heterocyclyl, wherein the alkyl, alkenyl, alkynyl, alkoxy, cycloalkyl, aryl, heteroaryl, or heterocyclyl is optionally substituted with one or more halo, OH, OBn, oxo, CN, $N(R_N)_2$, $C_1$-$C_6$ alkyl, $C_1$-$C_6$ haloalkyl, $C_3$-$C_6$ cycloalkyl, $C_1$-$C_6$ alkoxy, or aryl; and each $R_N$ is independently H, $C_1$-$C_6$ alkyl, or $C_1$-$C_6$ haloalkyl; and

EMBODIMENTS

For any of Formulae 0, 0a, I, Ia, II, IIa, III, or IIIa where applicable, the following embodiments are considered both alone and in conjunction with another where a stable compound is formed.

In some embodiments, X is C=O, S(=O)(=NR$_5$), or S(=O)$_2$. In some embodiments, X is C=O. In some embodiments, X is S(=O)(=NR$_5$). In some embodiments, X is S(=NR$_5$)$_2$. In some embodiments, when X is each R$_5$ is independently selected and can be the same or different. In some embodiments, X is S(=O)$_2$. In some embodiments, X is C=O, or S(=O)$_2$. In some embodiments, X is C=O, S(=O)(=NR$_5$), or S(=O)$_2$. In some embodiments, X is S(=O)(=NR$_5$), or S(=O)$_2$.

In some embodiments, Y is NH. In some embodiments, Y is O. In some embodiments, Y is a bond. In some embodiments, Y is absent. In some embodiments, Y being a bond or absent means that R$_3$ is directly connected to X. In some embodiments, Y being a bond or absent means that R$_6$ is directly connected to X. In some embodiments, R$_1$ is C$_1$-C$_6$ alkyl. In some embodiments, R$_1$ is C$_1$-C$_5$ alkyl. In some embodiments, R$_1$ is C$_1$-C$_4$ alkyl. In some embodiments, R$_1$ is C$_1$-C$_3$ alkyl. In some embodiments, R$_1$ is C$_1$-C$_2$ alkyl. In some embodiments, R$_1$ is methyl. In some embodiments, R$_1$ is ethyl. In some embodiments, R$_1$ is propyl. In some embodiments, R$_1$ is isopropyl. In some embodiments, R$_1$ is butyl. In some embodiments, R$_1$ is tert-butyl.

In some embodiments, R$_1$ is methyl substituted with cyclopropane. In some embodiments, R$_1$ is methyl substituted with cyclobutene. In some embodiments, R$_1$ is methyl substituted with methoxy. In some embodiments, R$_1$ is ethyl substituted with methoxy. In some embodiments, R$_1$ is methyl, substituted with one or more halo. In some embodiments, R$_1$ is methyl substituted with 1 halo, with 2 halo, or with 3 halo. In some embodiments, R$_1$ is ethyl, substituted with one or more halo. In some embodiments, R$_1$ is ethyl substituted with 1 halo, with 2 halo, or with 3 halo.

In some embodiments, R$_1$ is —CH$_2$—CHF$_2$.

In some embodiments, R$_1$ is ethyl, substituted with 2 halo atoms. In some embodiments, R$_1$ is ethyl, substituted with 3 halo atoms. In some embodiments, R$_1$ is ethyl substituted by 1 fluorine atoms. In some embodiments, R$_1$ is ethyl substituted by 2 fluorine atoms. In some embodiments, R$_1$ is ethyl substituted by 3 fluorine atoms. In some embodiments, R$_1$ is —CH$_2$—CF$_3$. In some embodiments, R$_1$ is —CF$_2$—CF$_3$. In some embodiments, R$_1$ is difluoroethyl.

In some embodiments, R$_1$ is cyclopropyl. In some embodiments, R$_1$ is cyclobutyl. In some embodiments, R$_1$ is oxetanyl. In some embodiments, R$_1$ is 2-oxetanyl. In some embodiments, R$_1$ is 3-oxetanyl.

In some embodiments, R$_1$ is C$_2$-C$_6$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_3$-C$_6$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_1$-C$_5$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_2$-C$_5$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_3$-C$_5$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_1$-C$_4$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_2$-C$_4$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_3$-C$_4$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_1$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_2$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_3$ alkyl, wherein alkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_3$-C$_6$ cycloalkyl, wherein cycloalkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_3$-cycloalkyl, wherein cycloalkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_4$-cycloalkyl, wherein cycloalkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_5$-cycloalkyl, wherein cycloalkyl is optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is 4-, 5- or 6-membered heterocyclyl with 1 or 2 heteroatoms each selected from N or O, wherein the heterocyclyl optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is 4- or 5-membered heterocyclyl with 1 or 2 heteroatoms each selected from N or O, wherein the heterocyclyl optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is 5- or 6-membered heterocyclyl with 1 or 2 heteroatoms each selected from N or O, wherein the heterocyclyl optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is 4-membered heterocyclyl with 1 or 2 heteroatoms each selected from N or O, wherein the heterocyclyl optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is 5-membered heterocyclyl with 1 or 2 heteroatoms each selected from N or O, wherein the heterocyclyl optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is 6-membered heterocyclyl with 1 or 2 heteroatoms each selected from N or O, wherein the heterocyclyl optionally substituted by one or more halo, OH, OBn, oxo, CN, C$_1$-C$_6$ alkyl, C$_1$-C$_6$ haloalkyl, C$_3$-C$_6$ cycloalkyl, or C$_1$-C$_6$ alkoxy.

In some embodiments, R$_1$ is C$_1$-C$_6$ alkyl or C$_3$-C$_6$ cycloalkyl, wherein the alkyl or cycloalkyl is optionally substituted by one or more halo, OH, oxo, CN, C$_1$-C$_6$ alkyl, C$_1$-C$_6$ haloalkyl, C$_3$-C$_6$ cycloalkyl, or C$_1$-C$_6$ alkoxy. In some embodiments, R$_1$ is C$_1$-C$_6$ alkyl or 4-, 5- or 6-membered heterocyclyl with 1 or 2 heteroatoms each selected from N or O, wherein the alkyl or heterocyclyl is optionally substituted by one or more halo, OH, oxo, CN, $C_1$-$C_6$ alkyl, $C_1$-$C_6$ haloalkyl, $C_3$-$C_6$ cycloalkyl, or $C_1$-$C_6$ alkoxy.

In some embodiments, $R_1$ is $C_3$-$C_6$ cycloalkyl or 4-, 5- or 6-membered heterocyclyl with 1 or 2 heteroatoms each selected from N or O, optionally substituted by one or more halo, $C_1$-$C_6$ alkoxy or CN.

In some embodiments, $R_1$ is $C_2$-$C_6$ alkenyl. In some embodiments, $R_1$ is $C_2$-$C_6$ alkynyl. In some embodiments, $R_1$ is $C_1$-$C_6$ alkoxy. In some embodiments, $R_1$ is $C_1$-$C_6$ alkoxy substituted with one, with two, or with three halo. In some embodiments, $R_1$ is $C_3$-$C_{12}$ cycloalkyl. In some embodiments, $R_1$ is $C_3$-$C_6$ cycloalkyl. In some embodiments, $R_1$ is $C_3$-$C_5$ cycloalkyl. In some embodiments, $R_1$ is $C_3$-$C_4$ cycloalkyl.

In some embodiments, $R_1$ is $C_3$-$C_{12}$ cycloalkyl substituted with one, with two or with three halo. In some embodiments, $R_1$ is $C_3$-$C_6$ cycloalkyl substituted with one, with two or with three halo. In some embodiments, $R_1$ is $C_3$-$C_5$ cycloalkyl substituted with one, with two or with three halo. In some embodiments, $R_1$ is $C_3$-$C_4$ cycloalkyl substituted with one, with two or with three halo. In some embodiments, $R_1$ is $C_3$-$C_5$ cycloalkyl substituted with $C_1$-$C_6$ haloalkyl. In some embodiments, $R_1$ is $C_3$-$C_4$ cycloalkyl substituted with $C_1$-$C_6$ haloalkyl. In some embodiments, $R_1$ is cyclopropyl substituted with $C_1$-$C_6$ haloalkyl. In some embodiments, $R_1$ is cyclobutyl substituted with $C_1$-$C_6$ haloalkyl. In some embodiments, $R_1$ is cyclobutyl substituted with $CHF_2$. In some embodiments, $R_1$ is cis-cyclobutyl substituted with $CHF_2$. In some embodiments, $R_1$ is trans-cyclobutyl substituted with $CHF_2$. In some embodiments, $R_1$ is cyclobutyl substituted with $CF_3$. In some embodiments, $R_1$ is cis-cyclobutyl substituted with $CF_3$. In some embodiments, $R_1$ is trans-cyclobutyl substituted with $CF_3$. In some embodiments, $R_1$ is cyclobutyl substituted with halo. In some embodiments, $R_1$ is cis-cyclobutyl substituted with halo. In some embodiments, $R_1$ is trans-cyclobutyl substituted with halo. In some embodiments, $R_1$ is cyclobutyl substituted with fluorine. In some embodiments, $R_1$ is cis-cyclobutyl substituted with fluorine. In some embodiments, $R_1$ is trans-cyclobutyl substituted with fluorine. In some embodiments, $R_1$ is trans-cyclobutyl substituted with OH. In some embodiments, $R_1$ is cyclobutyl substituted with OH. In some embodiments, $R_1$ is cis-cyclobutyl substituted with OH. In some embodiments, $R_1$ is trans-cyclobutyl substituted with 3-OH. In some embodiments, $R_1$ is cyclobutyl substituted with 3-OH. In some embodiments, $R_1$ is cis-cyclobutyl substituted with 3-OH.

In some embodiments, $R_1$ is oxabicyclo[3.1.0]hexan-6-yl.
In some embodiments, $R_1$ is 2-oxaspiro[3.3]heptan-6-yl.
In some embodiments, $R_1$ is oxabicyclo[2.2.1]heptan-2-yl.
In some embodiments, $R_1$ is oxetanyl.
In some embodiments, $R_1$ is tetrahydro-2H-pyran-4-yl.
In some embodiments, $R_1$ is 3-hydroxycyclobutyl.
In some embodiments, $R_1$ is 3,3-difluorocyclobutyl.
In some embodiments, $R_1$ is (E1)-2-hydroxycyclobutyl.
In some embodiments, $R_1$ is (E2)-2-hydroxycyclobutyl.
In some embodiments, $R_1$ is (1R,2S)-2-hydroxycyclobutyl.
In some embodiments, $R_1$ is (1r,3r)-3-hydroxycyclobutyl.
In some embodiments, $R_1$ is (3R,5R)-3,5-dimethylmorpholinyl.
In some embodiments, $R_1$ is (R)-tetrahydrofuran-3-yl.
In some embodiments, $R_1$ is (S)-tetrahydrofuran-3-yl.
In some embodiments, $R_1$ is cyanomethyl.
In some embodiments, $R_1$ is 2-cyanoethyl.
In some embodiments, $R_1$ is (1r,3r)-3-fluorocyclobutyl.
In some embodiments, $R_1$ is (1s,3s)-3-fluorocyclobutyl.
In some embodiments, $R_1$ is (1r,3r)-3-(difluoromethyl)cyclobutyl.
In some embodiments, $R_1$ is (1s,3s)-3-(difluoromethyl)cyclobutyl.

In some embodiments, $R_1$ is $C_6$-$C_{10}$ aryl. In some embodiments, $R_1$ is $C_6$ aryl. In some embodiments, $R_1$ is $C_6$-$C_{10}$ aryl substituted with one, with two or with three halo. In some embodiments, $R_1$ is $C_6$ aryl substituted with one, with two or with three halo. In some embodiments, $R_1$ is 5- to 10-membered heteroaryl. In some embodiments, $R_1$ is 5- to 7-membered heteroaryl. In some embodiments, $R_1$ is 5- to 6-membered heteroaryl. In some embodiments, $R_1$ is 5-membered heteroaryl with 2 heteroatoms selected from N, O, and S. In some embodiments, $R_1$ is 6-membered heteroaryl with 2 heteroatoms selected from N, O, and S. In some embodiments, $R_1$ is 5-membered heteroaryl with 2 nitrogen heteroatoms. In some embodiments, $R_1$ is 6-membered heteroaryl with 2 nitrogen heteroatoms. In some embodiments, $R_1$ is 5-membered heteroaryl with 1 heteroatom selected from N, O, and S. In some embodiments, $R_1$ is 6-membered heteroaryl with 1 heteroatom selected from N, O, and S. In some embodiments, $R_1$ is 3- to 10-membered heterocyclyl.

In some embodiments, $R_1$ is 3- to 9-membered heterocyclyl. In some embodiments, $R_1$ is 3- to 8-membered heterocyclyl. In some embodiments, $R_1$ is 3- to 7-membered heterocyclyl. In some embodiments, $R_1$ is 3- to 6-membered heterocyclyl. In some embodiments, $R_1$ is 3- to 5-membered heterocyclyl. In some embodiments, $R_1$ is 3-membered heterocyclyl. In some embodiments, $R_1$ is 4-membered heterocyclyl. In some embodiments, $R_1$ is 3-membered heterocyclyl, optionally substituted with one, with two or with three halo. In some embodiments, $R_1$ is 4-membered heterocyclyl, optionally substituted with one, with two or with three halo. In some embodiments, $R_1$ is 5-membered heterocyclyl, optionally substituted with one, with two or with three halo. In some embodiments, $R_1$ is 6-membered heterocyclyl, optionally substituted with one, with two or with three halo. In some embodiments, $R_1$ is 3-membered heterocyclyl, substituted with one, with two or with three halo. In some embodiments, $R_1$ is 4-membered heterocyclyl, substituted with one, with two or with three halo. In some embodiments, $R_1$ is 5-membered heterocyclyl, substituted with one, with two or with three halo. In some embodiments, $R_1$ is 6-membered heterocyclyl, substituted with one, with two or with three halo.

In some embodiments, $R_1$ is oxetanyl. In some embodiments, $R_1$ is 2-oxetanyl. In some embodiments, $R_1$ is 3-oxetanyl. In some embodiments, $R_1$ is oxetanyl, optionally substituted with haloalkyl. In some embodiments, $R_1$ is oxetanyl, optionally substituted with —$CHF_2$. In some embodiments, $R_1$ is oxetanyl, optionally substituted with —$CF_3$. In some embodiments, $R_1$ is 2-oxetanyl, optionally substituted with haloalkyl. In some embodiments, $R_1$ is 2-oxetanyl, optionally substituted with —$CHF_2$. In some embodiments, $R_1$ is 2-oxetanyl, optionally substituted with —$CF_3$. In some embodiments, $R_1$ is 3-oxetanyl, optionally substituted with haloalkyl. In some embodiments, $R_1$ is 3-oxetanyl, optionally substituted with —$CHF_2$. In some embodiments, $R_1$ is 3-oxetanyl, optionally substituted with —$CF_3$. In some embodiments, $R_1$ is tetrahydrofuranyl. In some embodiments, $R_1$ is 2-tetrahydrofuranyl. In some embodiments, $R_1$ is 3-tetrahydrofuranyl. In some embodiments, $R_1$ is tetrahydrofuranyl, optionally substituted with haloalkyl. In some embodiments, $R_1$ is tetrahydrofuranyl, optionally substituted with —CHF$_2$. In some embodiments, R$_1$ is tetrahydrofuranyl, optionally substituted with —CF$_3$. In some embodiments, R$_1$ is 2-tetrahydrofuranyl, optionally substituted with haloalkyl. In some embodiments, R$_1$ is 2-tetrahydrofuranyl, optionally substituted with —CHF$_2$. In some embodiments, R$_1$ is 2-tetrahydrofuranyl, optionally substituted with —CF$_3$. In some embodiments, R$_1$ is 3-tetrahydrofuranyl, optionally substituted with haloalkyl. In some embodiments, R$_1$ is 3-tetrahydrofuranyl, optionally substituted with —CHF$_2$. In some embodiments, R$_1$ is 3-tetrahydrofuranyl, optionally substituted with —CF$_3$. In some embodiments, R$_1$ is a 7-10 membered spirocyclic heterocycyl. In some embodiments, R$_1$ is a 7 membered spirocyclic heterocycyl. In some embodiments, R$_1$ is a 7 membered bicyclic heterocycyl. In some embodiments, R$_1$ is a 2-oxaspiro[3.3]heptanyl.

In some embodiments, R$_1$ and R$_2$ form a 4-, 5- or 6-membered heterocyclyl with 1 or 2 heteroatoms each selected from N, O, or S, wherein the heterocyclyl is optionally substituted by one or more alkyl groups. In some embodiments, R$_1$ and R$_2$ form a 5-membered heterocyclyl with 1 or 2 heteroatoms each selected from N, O, or S, wherein the heterocyclyl is optionally substituted by one or more alkyl groups. In some embodiments, R$_1$ and R$_2$ form a 5-membered heterocyclyl with 1 heteroatom selected from N, O, or S, wherein the heterocyclyl is optionally substituted by one or more alkyl groups. In some embodiments, R$_1$ and R$_2$ form a 5-membered heterocyclyl with 2 heteroatoms each selected from N, O, or S, wherein the heterocyclyl is optionally substituted by one or more alkyl groups. In some embodiments, R$_1$ and R$_2$ form a 6-membered heterocyclyl with 1 or 2 heteroatoms each selected from N, O, or S, wherein the heterocyclyl is optionally substituted by one or more alkyl groups. In some embodiments, R$_1$ and R$_2$ form a 6-membered heterocyclyl with 1 heteroatom selected from N, O, or S, wherein the heterocyclyl is optionally substituted by one or more alkyl groups. In some embodiments, R$_1$ and R$_2$ form a 6-membered heterocyclyl with 2 heteroatoms each selected from N or O, wherein the heterocyclyl is optionally substituted by one or more alkyl groups. In some embodiments, R$_1$ and R$_2$ form a 4-, 5- or 6-membered heterocyclyl with 1 or 2 heteroatoms each selected from N or O, wherein the heterocyclyl is substituted by two alkyl groups. In some embodiments, R$_1$ and R$_2$ form a 5-membered heterocyclyl with 1 or 2 heteroatoms each selected from N or O, wherein the heterocyclyl is substituted by two alkyl groups. In some embodiments, R$_1$ and R$_2$ form a 5-membered heterocyclyl with 1 heteroatom selected from N or O, wherein the heterocyclyl is substituted by two alkyl groups. In some embodiments, R$_1$ and R$_2$ form a 5-membered heterocyclyl with 2 heteroatoms each selected from N or O, wherein the heterocyclyl is substituted by two alkyl groups. In some embodiments, R$_1$ and R$_2$ form a 6-membered heterocyclyl with 1 or 2 heteroatoms each selected from N or O, wherein the heterocyclyl is substituted by two alkyl groups. In some embodiments, R$_1$ and R$_2$ form a 6-membered heterocyclyl with 1 heteroatom selected from N or O, wherein the heterocyclyl is substituted by two alkyl groups. In some embodiments, R$_1$ and R$_2$ form a 6-membered heterocyclyl with 2 heteroatoms each selected from N or O, wherein the heterocyclyl is substituted by two alkyl groups.

In some embodiments, R$_3$ is C$_1$-C$_6$ alkyl, C$_3$-C$_6$ cycloalkyl, NH—C$_1$-C$_6$ alkyl, N—(C$_1$-C$_6$ alkyl)$_2$, phenyl, 3-6 membered heterocyclyl with 1 or 2 heteroatoms each selected from N, O, or S, wherein the alkyl, cycloalkyl, or heterocyclyl is optionally substituted by C$_1$-C$_6$ alkyl, or C$_1$-C$_6$ alkoxy. In some embodiments, R$_3$ is C$_1$-C$_6$ alkyl, wherein alkyl is optionally substituted by C$_3$-C$_6$ cycloalkyl or C$_1$-C$_6$ alkoxy. In some embodiments, R$_3$ is C$_1$-C$_6$ alkyl, wherein alkyl is optionally substituted by C$_3$-C$_6$ cycloalkyl. In some embodiments, R$_3$ is C$_1$-alkyl, wherein alkyl is optionally substituted by C$_3$-cycloalkyl. In some embodiments, R$_3$ is C$_2$-alkyl, wherein alkyl is optionally substituted by C$_3$-cycloalkyl. In some embodiments, R$_3$ is C$_3$-alkyl, wherein alkyl is optionally substituted by C$_3$-cycloalkyl. In some embodiments, R$_3$ is C$_4$-alkyl, wherein alkyl is optionally substituted by C$_3$-cycloalkyl. In some embodiments, R$_3$ is C$_5$-alkyl, wherein alkyl is optionally substituted by C$_3$-cycloalkyl. In some embodiments, R$_3$ is C$_6$-alkyl, wherein alkyl is optionally substituted by C$_3$-cycloalkyl. In some embodiments, R$_3$ is C$_1$-C$_2$ alkyl, wherein alkyl is optionally substituted by C$_3$-cycloalkyl. In some embodiments, R$_3$ is C$_1$-C$_3$ alkyl, wherein alkyl is optionally substituted by C$_3$-cycloalkyl. In some embodiments, R$_3$ is C$_1$-C$_4$ alkyl, wherein alkyl is optionally substituted by C$_3$-cycloalkyl. In some embodiments, R$_3$ is C$_1$-C$_5$ alkyl, wherein alkyl is optionally substituted by C$_3$-cycloalkyl. In some embodiments, R$_3$ is C$_1$-C$_6$ alkyl, wherein alkyl is optionally substituted by C$_3$-cycloalkyl. In some embodiments, R$_3$ is C$_1$-C$_6$ alkyl, wherein alkyl is optionally substituted by C$_1$-alkoxy. In some embodiments, R$_3$ is C$_1$-C$_6$ alkyl, wherein alkyl is optionally substituted by C$_1$-C$_6$ alkoxy. In some embodiments, R$_3$ is C$_1$-C$_6$ alkyl, wherein alkyl is optionally substituted by C$_1$-C$_6$ alkoxy. In some embodiments, R$_3$ is C$_3$-C$_6$ cycloalkyl, wherein cycloalkyl is optionally substituted by C$_3$-C$_6$ cycloalkyl or C$_1$-C$_6$ alkoxy. In some embodiments, R$_3$ is C$_3$-C$_6$-heterocyclyl with 1 or 2 heteroatoms each selected from N or O, wherein the heterocyclyl is optionally substituted by C$_3$-C$_6$ cycloalkyl or C$_1$-C$_6$ alkoxy. In some embodiments, R$_1$ and R$_2$ together form a morpholino ring, optionally substituted with one or more C$_1$-C$_6$ alkyl. In some embodiments, R$_1$ and R$_2$ together form a 3,5-dimethylmorpholino ring. In some embodiments, R$_1$ is ethyl, optionally substituted by one or more halo or C$_1$-C$_6$ alkoxy, and R$_2$ is iso-propyl, optionally substituted by one or more halo or C$_1$-C$_6$ alkoxy.

In some embodiments, R$_1$ is isopropyl, optionally substituted by one or more halo or C$_1$-C$_6$ alkoxy, and R$_2$ is isopropyl, optionally substituted by one or more halo or C$_1$-C$_6$ alkoxy. In some embodiments, R$_1$ is tetrahydrofuranyl and R$_2$ is isopropyl. In some embodiments, R$_1$ is tetrahydrofuranyl and R$_2$ is ethyl. In some embodiments, R$_1$ is cyclopropyl and R$_2$ is isopropyl. In some embodiments, R$_1$ is cyclopropyl and R$_2$ is ethyl. In some embodiments, R$_1$ and R$_2$ together form a methylmorpholino ring. In some embodiments, R$_1$ and R$_2$ together form a (3R,5R)-3,5-dimethylmorpholine ring. In some embodiments, R$_1$ and R$_2$ together form a (3S,5R)-3,5-dimethylmorpholine ring. In some embodiments, R$_1$ and R$_2$ together form a (3R,5S)-3,5-dimethylmorpholine ring. In some embodiments, R$_1$ and R$_2$ together form a (3S,5S)-3,5-dimethylmorpholine ring.

In some embodiments, R$_2$ is methyl. In some embodiments, R$_2$ is ethyl. In some embodiments, R$_2$ is propyl. In some embodiments, R$_2$ is isopropyl. In some embodiments, R$_2$ is butyl. In some embodiments, R$_2$ is tert-butyl. In some embodiments, R$_2$ is methyl substituted with cyclopropane. In some embodiments, R$_2$ is methyl substituted with cyclobutene. In some embodiments, R$_2$ is CH$_2$—O—OH$_3$. In some embodiments, R$_2$ is ethyl substituted with methoxy. In some embodiments, R$_2$ is ethyl, substituted with one or more halo. In some embodiments, R$_2$ is ethyl substituted with 1 halo, with 2 halo, or with 3 halo. In some embodiments, R$_2$ is —CH$_2$—CHF$_2$. In some embodiments, R$_2$ is ethyl, substituted with 2 halo. In some embodiments, R$_2$ is ethyl, substituted with 3 halo. In some embodiments, $R_2$ is ethyl substituted by 1 fluorine. In some embodiments, $R_2$ is ethyl substituted by 2 fluorine. In some embodiments, $R_2$ is ethyl substituted by 3 fluorine. In some embodiments, $R_2$ is —$CH_2$—$CF_3$. In some embodiments, $R_2$ is propyl, substituted with 2 halo. In some embodiments, $R_2$ is propyl, substituted with 3 halo. In some embodiments, $R_2$ is propyl substituted by 1 fluorine. In some embodiments, $R_2$ is propyl substituted by 2 fluorine. In some embodiments, $R_2$ is propyl substituted by 3 fluorine. In some embodiments, $R_2$ is isopropyl, substituted with 2 halo. In some embodiments, $R_2$ is isopropyl, substituted with 3 halo. In some embodiments, $R_2$ is isopropyl substituted by 1 fluorine. In some embodiments, $R_2$ is isopropyl substituted by 2 fluorine. In some embodiments, $R_2$ is isopropyl substituted by 3 fluorine. In some embodiments, $R_2$ is cyclopropyl. In some embodiments, $R_2$ is cyclobutyl. In some embodiments, $R_2$ is oxetanyl. In some embodiments, $R_2$ is 2-oxetanyl or 3-oxetanyl. In some embodiments, $R_2$ is tetrahydrofunanyl.

In some embodiments, $R_1$ and $R_2$ are the same. In some embodiments, $R_1$ and $R_2$ are different.

In some embodiments, $R_3$ is methyl. In some embodiments, $R_3$ is ethyl. In some embodiments, $R_3$ is propyl. In some embodiments, $R_3$ is isopropyl. In some embodiments, $R_3$ is butyl. In some embodiments, $R_3$ is tert-butyl. In some embodiments, $R_3$ is methyl substituted with cyclopropane. In some embodiments, $R_3$ is methyl substituted with cyclobutene. In some embodiments, $R_3$ is $CH_2$—O—$OH_3$. In some embodiments, $R_3$ is ethyl substituted with methoxy. In some embodiments, $R_3$ is ethyl, substituted with one or more halo. In some embodiments, $R_3$ is ethyl substituted with 1 halo, with 2 halo, or with 3 halo. In some embodiments, $R_3$ is —$CH_2$—$CHF_2$. In some embodiments, $R_3$ is ethyl, substituted with 2 halo. In some embodiments, $R_3$ is ethyl, substituted with 3 halo. In some embodiments, $R_3$ is ethyl substituted by 1 fluorine. In some embodiments, $R_3$ is ethyl substituted by 2 fluorine. In some embodiments, $R_3$ is ethyl substituted by 3 fluorine. In some embodiments, $R_3$ is —$CH_2$—$CF_3$. In some embodiments, $R_3$ is cyclopropyl.

In some embodiments, $R_3$ is dialkyl amino. In some embodiments, $R_3$ is dimethylamino. In some embodiments, $R_3$ is a NH—$C_1$-$C_6$ alkyl. In some embodiments, $R_3$ is a NH—$C_1$-$C_3$ alkyl. In some embodiments, $R_3$ is a NH—$C_1$-$C_2$ alkyl. In some embodiments, $R_3$ is a NH-methyl. In some embodiments, $R_3$ is a NH-ethyl. In some embodiments, $R_3$ is a NH-propyl. In some embodiments, $R_3$ is a NH-i-propyl. In some embodiments, $R_3$ is a NH-butyl. In some embodiments, $R_3$ is a NH-i-butyl. In some embodiments, $R_3$ is a NH-sec-butyl. In some embodiments, $R_3$ is a NH-t-butyl.

In some embodiments, $R_3$ is a 4-membered heterocyclyl. In some embodiments, $R_3$ is a 4-membered N-heterocycle. In some embodiments, $R_3$ is an azetane. In some embodiments, $R_3$ is a N-azetane. In some embodiments, $R_3$ is a 5-membered heterocyclyl, optionally substituted with $C_1$-$C_6$ alkyl. In some embodiments, $R_3$ is a 6-membered heterocyclyl, optionally substituted with $C_1$-$C_6$ alkyl. In some embodiments, $R_3$ is a morpholinyl. In some embodiments, $R_3$ is an N-morpholinyl. In some embodiments, $R_3$ is a 2-oxaspiro[3.3]heptanyl.

In some embodiments, $R_3$ is a 5-membered heteroaryl, optionally substituted with $C_1$-$C_6$ alkyl. In some embodiments, $R_3$ is a 6-membered heteroaryl, optionally substituted with $C_1$-$C_6$ alkyl. In some embodiments, $R_3$ is a 5-membered heterocycle, optionally substituted with methyl. In some embodiments, $R_3$ is a 6-membered heterocycle, optionally substituted with methyl.

In some embodiments, $R_3$ is a 5-membered heteroaryl, optionally substituted with methyl. In some embodiments, $R_3$ is a 6-membered heteroaryl, optionally substituted with methyl. In some embodiments, $R_3$ is a diazolyl, optionally substituted with $C_1$-$C_6$ alkyl. In some embodiments, $R_3$ is a pyrazolyl ring, optionally substituted with $C_1$-$C_6$ alkyl. In some embodiments, $R_3$ is a diazolyl, optionally substituted with one or more methyl. In some embodiments, $R_3$ is a diazolyl, optionally substituted with one or more $C_1$-$C_6$ alkyl. In some embodiments, $R_3$ is a diazolyl, optionally substituted with a methyl and an ethyl. In some embodiments, $R_3$ is a diazolyl, optionally substituted with a heterocyclic N—$C_1$-$C_6$ alkyl. In some embodiments, $R_3$ is a diazolyl, optionally substituted with a heterocyclic N—$C_1$-$C_2$ alkyl.

In some embodiments, $R_3$ is 5- to 10-membered heteroaryl. In some embodiments, $R_3$ is 5-to 7-membered heteroaryl. In some embodiments, $R_3$ is 5- to 6-membered heteroaryl. In some embodiments, $R_3$ is 5-membered heteroaryl with 2 heteroatoms selected from N, O, and S. In some embodiments, $R_3$ is 6-membered heteroaryl with 2 heteroatoms selected from N, O, and S. In some embodiments, $R_3$ is 5-membered heteroaryl with 2 nitrogen heteroatoms. In some embodiments, $R_3$ is 6-membered heteroaryl with 2 nitrogen heteroatoms. In some embodiments, $R_3$ is 5-membered heteroaryl with 1 heteroatom selected from N, O, and S. In some embodiments, $R_3$ is 6-membered heteroaryl with 1 heteroatom selected from N, O, and S. In some embodiments, $R_3$ is 3- to 10-membered heterocyclyl.

In some embodiments, $R_3$ is a diazoyl ring, optionally substituted with methyl. In some embodiments, $R_3$ is a pyrazolyl ring, optionally substituted with methyl. In some embodiments, $R_3$ is a diazoyl ring, substituted with —$CHF_2$. In some embodiments, $R_3$ is a pyrazolyl ring, substituted with —$CHF_2$. In some embodiments, $R_3$ is a pyrazolyl ring, substituted with N-methyl. In some embodiments, $R_3$ is a diazoyl ring, substituted with N-methyl. In some embodiments, $R_3$ is a pyrazolyl ring, substituted with N—$CHF_2$. In some embodiments, $R_3$ is a diazoyl ring, substituted with N—$CHF_2$. In some embodiments, $R_3$ is a 1-methyl-1H-pyrazolyl. In some embodiments, $R_3$ is a 1-methyl-1H-pyrazolyl, connected at the 3-position. In some embodiments, $R_3$ is a 1-methyl-1H-pyrazolyl, connected at the 4 position. In some embodiments, $R_3$ is a 1-methyl-1H-pyrazolyl connected at the 5-position. In some embodiments, $R_3$ is an oxa-6-azaspiro[3.3]heptane. In some embodiments, $R_3$ is an azaspiro[3.3]heptane. In some embodiments, $R_3$ is an azaspiro[3.3]heptane with an oxygen heteroatom in the ring.

In some embodiments, $R_3$ is cyclobutyl. In some embodiments, $R_3$ is oxetanyl. In some embodiments, $R_3$ is 2-oxetanyl or 3-oxetanyl. In some embodiments, $R_3$ is tetrahydrofunanyl.

In some embodiments, $R_3$ is aryl, wherein the aryl is optionally substituted.

In some embodiments, $R_3$ is phenyl.
In some embodiments, $R_3$ is pyrazolyl.
In some embodiments, $R_3$ is 1-methyl-1H-pyrazolyl.
In some embodiments, $R_3$ is thiazolyl.
In some embodiments, $R_3$ is 2-methylthiazolyl.
In some embodiments, $R_3$ is morpholinyl.
In some embodiments, $R_3$ is tetrahydro-2H-pyranyl.
In some embodiments, $R_3$ is azetidinyl.
In some embodiments, $R_3$ is 3,3-difluoroazetidiyl.
In some embodiments, $R_3$ is oxazolyl.
In some embodiments, $R_3$ is 2-methyloxazolyl.
In some embodiments, $R_3$ is 3-methyloxazolyl.
In some embodiments, $R_3$ is 4-methyloxazolyl.

In some embodiments, $R_3$ is 1-methyl-6-oxo-1,6-dihydropyridinyl.

In some embodiments, $R_3$ is 4-methyl-6-oxo-1,6-dihydropyridinyl.

In some embodiments, $R_3$ is 5-chloro-1-methyl-1H-pyrazolyl.

In some embodiments, $R_3$ is 1-cyclopropyl-1H-pyrazolyl.

In some embodiments, $R_3$ is 1-(difluoromethyl)-1H-pyrazolyl.

In some embodiments, $R_3$ is N-isopropyl-N-methyl.

In some embodiments, $R_3$ is 1,5-dimethyl-1H-pyrazolyl.

In some embodiments, $R_3$ is 1-ethyl-1H-pyrazolyl.

In some embodiments, $R_3$ is tetrahydro-2H-pyran-3-yl.

In some embodiments, $R_3$ is (R)-2-methylpyrrolidinyl.

In some embodiments, $R_3$ is (S)-2-methoxypyrrolidinyl.

In some embodiments, $R_3$ is (R)-2-methoxypyrrolidinyl.

In some embodiments, $R_3$ is (S)-2-methylpyrrolidinyl.

In some embodiments, $R_3$ is (R)-3-methylpyrrolidinyl.

In some embodiments, $R_3$ is (S)-3-methylpyrrolidinyl.

In some embodiments, $R_3$ is (R)-3-methoxypyrrolidinyl.

In some embodiments, $R_3$ is (S)-3-methoxypyrrolidinyl.

In some embodiments, $R_3$ is (R)-2-(methoxymethyl)pyrrolidinyl.

In some embodiments, $R_3$ is (S)-2-(methoxymethyl)pyrrolidinyl.

In some embodiments, $R_3$ is N-(3-hydroxypropyl)-N-methyl.

In some embodiments, $R_3$ is 2-methyl-6-oxo-1,6-dihydropyridinyl.

In some embodiments, $R_3$ is 5-methyl-6-oxo-1,6-dihydropyridinyl.

In some embodiments, $R_3$ is 2,7-diazaspiro[3.5]nonan-2-yl.

In some embodiments, $R_3$ is 2-oxa-6-azaspiro[3.3]heptanyl.

In some embodiments, $R_3$ is 6-oxa-2-azaspiro[3.4]octanyl.

In some embodiments, $R_3$ is hexahydro-1H-furo[3,4-c]pyrrolyl.

In some embodiments, $R_3$ is 3-(benzyloxy)azetidinyl.

In some embodiments, $R_3$ is 3-hydroxyazetidinyl.

In some embodiments, $R_3$ is N-(2-hydroxyethyl)-N-methyl.

In some embodiments, $R_3$ is 4-fluoro-1-methyl-1H-pyrazolyl.

In some embodiments, $R_3$ is a diazoyl ring, optionally substituted with cyclopropyl. In some embodiments, $R_3$ is a pyrazolyl ring, optionally substituted with cyclopropyl.

In some embodiments, $R_3$ is a thiazolyl. In some embodiments, $R_3$ is a thiazolyl optionally substituted. In some embodiments, $R_3$ is a thiazolyl optionally substituted with a methyl group. In some embodiments, $R_3$ is a thiazolyl optionally substituted with a 2-methyl group. In some embodiments, $R_3$ is a phenyl. In some embodiments, $R_3$ is tolyl. In some embodiments, $R_3$ is ortho-tolyl. In some embodiments, $R_3$ is meta-tolyl. In some embodiments, $R_3$ is para-tolyl. In some embodiments, $R_3$ is a phenyl optionally substituted by a methyl. In some embodiments, $R_3$ is a phenyl optionally substituted by a halo. In some embodiments, $R_3$ is a phenyl optionally substituted by a chloro. In some embodiments, $R_3$ is a phenyl optionally substituted by a 2-chloro. In some embodiments, $R_3$ is a phenyl optionally substituted by a 3-chloro. In some embodiments, $R_3$ is a phenyl optionally substituted by a 4-chloro. In some embodiments, $R_3$ is a pyridyl. In some embodiments, $R_3$ is an ortho-pyridyl. In some embodiments, $R_3$ is a meta-pyridyl. In some embodiments, $R_3$ is a para-pyridyl. In some embodiments, $R_3$ is an anisolyl In some embodiments, $R_3$ is an ortho-anisolyl. In some embodiments, $R_3$ is a meta-anisolyl. In some embodiments, $R_3$ is a para-anisolyl.

In some embodiments, $R_3$ is —CDH-$CD_3$. In some embodiments, $R_3$ is —$CD_2$-$CHD_2$. In some embodiments, $R_3$ is —$CH_2$-$CD_3$. In some embodiments, $R_3$ is —$CD_2$-$CH_3$. In some embodiments, $R_3$ is —$CD_2$-$CD_3$. In some embodiments, $R_3$ is —$CD_2$-$CD_3$.

In some embodiments, $R_4$ is H, halo, or $C_1$-$C_6$ alkyl. In some embodiments, $R_4$ is H. In some embodiments, $R_4$ is halo. In some embodiments, $R_4$ is fluorine. In some embodiments, $R_4$ is $CH_3$. In some embodiments, $R_4$ is ethyl. In some embodiments, $R_4$ is propyl.

In some embodiments, $R_5$ is H or $C_1$-$C_6$ alkyl. In some embodiments, $R_5$ is H. In some embodiments, $R_5$ is $CH_3$. In some embodiments, $R_5$ is ethyl. In some embodiments, $R_5$ is propyl.

In some embodiments, X is absent.

In some embodiments, Y is absent.

In some embodiments, X and Y are both absent.

In some embodiments, X and Y are both absent and $R_3$ is H.

In some embodiments, $R_1$ is $C_1$-$C_6$ alkyl and $R_2$ is $C_1$-$C_6$ alkyl, wherein the alkyl is optionally substituted with 1, 2 or 3 halogens.

In some embodiments, $R_1$ is methyl, ethyl, or propyl, and $R_2$ is methyl, ethyl, or propyl, wherein the methyl, ethyl, or propyl is optionally substituted with 1, 2 or 3 halogens.

In some embodiments, $R_1$ is $C_{1-3}$ alkyl, and $R_2$ is $C_{1-3}$ alkyl, wherein the alkyl is optionally substituted with 2 or 3 fluorine.

In some embodiments, $R_1$ is $C_3$ alkyl, and $R_2$ is ethyl optionally substituted 2 or 3 fluorine.

In some embodiments, $R_1$ is isopropyl, and $R_2$ is ethyl optionally substituted with 2 or 3 fluorine.

In some embodiments, $R_1$ is isopropyl, and $R_2$ is ethyl substituted with 2 or 3 fluorine.

In some embodiments, $R_1$ is isopropyl, and $R_2$ is ethyl substituted with 2 fluorine.

In some embodiments, $R_1$ is isopropyl, and $R_2$ is ethyl substituted with 3 fluorine.

In some embodiments, $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is H, $C_1$-$C_6$ alkyl, 5- to 6-membered heteroaryl, 3- to 6-membered heterocyclyl, wherein the alkyl, heteroaryl or heterocyclyl is optionally substituted with one or more halo, OH, oxo, CN, $C_1$-$C_6$ alkyl, $R_4$ is H; and each $R_5$ is H.

In some embodiments, $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is $C_1$-$C_6$ alkyl, 5-membered heteroaryl, wherein the alkyl, heteroaryl is optionally substituted with one or more halo, or $C_1$-$C_6$ alkyl, $R_4$ is H; and each $R_5$ is H.

In some embodiments, $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two methyl groups, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, $R_1$ is $C_1$-$C_4$ alkyl, or $C_3$-$C_4$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two methyl groups, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, Y is NH, or a bond; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is H, $C_1$-$C_6$ alkyl, 5- to 6-membered heteroaryl, 3- to 6-membered heterocyclyl, wherein the alkyl, heteroaryl or heterocyclyl is optionally substituted with one or more halo, OH, oxo, CN, $C_1$-$C_6$ alkyl, $R_4$ is H; and each $R_5$ is H.

In some embodiments, Y is NH; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, Y is NH; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy;
$R_2$ is ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is $C_1$-$C_6$ alkyl, 5-membered heteroaryl, wherein the alkyl, heteroaryl is optionally substituted with one or more halo, or $C_1$-$C_6$ alkyl, $R_4$ is H; and each $R_5$ is H.

In some embodiments, Y is NH; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two methyl groups, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H In some embodiments, X is C=O, or S(=O)$_2$; Y is NH, or a bond; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is H, $C_1$-$C_6$ alkyl, 5- to 6-membered heteroaryl, 3- to 6-membered heterocyclyl, wherein the alkyl, heteroaryl or heterocyclyl is optionally substituted with one or more halo, OH, oxo, CN, $C_1$-$C_6$ alkyl, $R_4$ is H; and each $R_5$ is H.

In some embodiments, X is S(=O)$_2$; Y is NH; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, X is S(=O)$_2$; Y is NH; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is $C_1$-$C_6$ alkyl, 5-membered heteroaryl, wherein the alkyl, heteroaryl is optionally substituted with one or more halo, or $C_1$-$C_6$ alkyl, $R_4$ is H; and each $R_5$ is H.

In some embodiments, X is S(=O)$_2$; Y is NH; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two methyl groups, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, X is S(=O)$_2$; Y is NH; $R_1$ is $C_1$-$C_4$ alkyl, or $C_3$-$C_4$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two methyl groups, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, W is CH; X is C=O, or S(=O)$_2$; Y is NH, or a bond; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is H, $C_1$-$C_6$ alkyl, 5- to 6-membered heteroaryl, 3- to 6-membered heterocyclyl, wherein the alkyl, heteroaryl or heterocyclyl is optionally substituted with one or more halo, OH, oxo, CN, $C_1$-$C_6$ alkyl, $R_4$ is H; and each $R_5$ is H.

In some embodiments, W is CH; X is $S(=O)_2$; Y is NH; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, W is CH; X is $S(=O)_2$; Y is NH; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two $C_1$-$C_6$ alkyl, or halo; $R_3$ is $C_1$-$C_6$ alkyl, 5-membered heteroaryl, wherein the alkyl, heteroaryl is optionally substituted with one or more halo, or $C_1$-$C_6$ alkyl, $R_4$ is H; and each $R_5$ is H.

In some embodiments, W is CH; X is $S(=O)_2$; Y is NH; $R_1$ is $C_1$-$C_6$ alkyl, or $C_3$-$C_{12}$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two methyl groups, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, W is CH; X is $S(=O)_2$; Y is NH; $R_1$ is $C_1$-$C_4$ alkyl, or $C_3$-$C_4$ cycloalkyl; wherein the alkyl, or cycloalkyl, is optionally substituted by one or more halo, OH, $C_1$-$C_6$ haloalkyl, or $C_1$-$C_6$ alkoxy; $R_2$ is ethyl, propyl, or isopropyl; $R_1$ and $R_2$ optionally form 6-membered heterocyclyl, wherein the heterocyclyl is optionally substituted with two methyl groups, or halo; $R_3$ is $C_1$-$C_6$ alkyl, 5-membered heteroaryl, 5-membered heterocyclyl, wherein the alkyl, heteroaryl or heterocyclyl is optionally substituted with one or more halo, or $C_1$-$C_6$ alkyl, $R_4$ is H; and each $R_5$ is H.

In some embodiments, the compound of the present disclosure is of Formula III or IIIa, wherein $R_1$ is $C_1$-$C_6$ alkyl, wherein the alkyl is optionally substituted with one halo, with two halo, or with three halo; $R_2$ is isopropyl; $R_6$ is $C_1$-$C_3$ alkyl, optionally substituted with one or more deuterium, or a $C_5$-$C_6$ heteroaryl, optionally substituted with one or more methyl, wherein the methyl is optionally substituted with one or more fluorine.

In some embodiments, each $R_N$ is independently H or $C_1$-$C_6$ alkyl.

In some embodiments, each $R_N$ is independently H or $C_1$-$C_6$ alkyl.

In some embodiments, each $R_N$ is independently H or $C_1$-$C_3$ alkyl.

In some embodiments, each $R_N$ is independently H or $C_1$-$C_2$ alkyl.

In some embodiments, each $R_N$ is independently H or $C_1$ alkyl.

In some embodiments, each $R_N$ is independently H or $C_2$ alkyl.

In some embodiments, each $R_N$ is independently H or $C_3$ alkyl.

In some embodiments, each $R_N$ is H.

In some embodiments, each $R_N$ is $C_1$-$C_6$ alkyl.

In some embodiments, each $R_N$ is $C_1$-$C_3$ alkyl.

In some embodiments, each $R_N$ is $C_1$-$C_2$ alkyl.

In some embodiments, each $R_N$ is $C_1$ alkyl.

In some embodiments, each $R_N$ is $C_2$ alkyl.

In some embodiments, each $R_N$ is $C_3$ alkyl.

In some embodiments, $R_1$ is $C_1$-$C_6$ alkyl, substituted with one halo, with two halo, or with three halo; $R_2$ is isopropyl; $R_6$ is $CD_2$-$CD_3$.

In some embodiments, $R_1$ is $C_1$-$C_3$ alkyl, substituted with one halo, with two halo, or with three halo; $R_2$ is isopropyl; $R_6$ is $CD_2$-$CD_3$.

In some embodiments, $R_1$ is $C_1$-$C_2$ alkyl, substituted with one halo, with two halo, or with three halo; $R_2$ is isopropyl; $R_6$ is $CD_2$-$CD_3$.

In some embodiments, $R_1$ is $C_1$ alkyl, substituted with one halo, with two halo, or with three halo; $R_2$ is isopropyl; $R_6$ is $CD_2$-$CD_3$.

In some embodiments, $R_1$ is $C_2$ alkyl, substituted with one halo, with two halo, or with three halo; $R_2$ is isopropyl; $R_6$ is $CD_2$-$CD_3$.

In some embodiments, $R_1$ is $C_1$-$C_6$ alkyl, substituted with two halo, or with three halo; $R_2$ is isopropyl; $R_6$ is $CD_2$-$CD_3$.

In some embodiments, $R_1$ is $C_1$-$C_3$ alkyl, substituted with two halo, or with three halo; $R_2$ is isopropyl; $R_6$ is $CD_2$-$CD_3$.

In some embodiments, $R_1$ is $C_1$-$C_2$ alkyl, substituted with two halo, or with three halo; $R_2$ is isopropyl; $R_6$ is $CD_2$-$CD_3$.

In some embodiments, $R_1$ is $C_1$ alkyl, substituted with two halo, or with three halo; $R_2$ is isopropyl; $R_6$ is $CD_2$-$CD_3$.

In some embodiments, $R_1$ is $C_2$ alkyl, substituted with two halo, or with three halo; $R_2$ is isopropyl; $R_6$ is $CD_2$-$CD_3$.

In some embodiments, $R_1$ is $C_1$-$C_6$ alkyl, substituted with three halo; $R_2$ is isopropyl; $R_6$ is $CD_2$-$CD_3$.

In some embodiments, $R_1$ is $C_1$-$C_3$ alkyl, substituted with three halo; $R_2$ is isopropyl; $R_6$ is $CD_2$-$CD_3$.

In some embodiments, $R_1$ is $C_1$-$C_2$ alkyl, substituted with three halo; $R_2$ is isopropyl; $R_6$ is $CD_2$-$CD_3$.

In some embodiments, $R_1$ is $C_1$ alkyl, substituted with three halo; $R_2$ is isopropyl; $R_6$ is $CD_2$-$CD_3$.

In some embodiments, $R_1$ is $C_2$ alkyl, substituted three halo; $R_2$ is isopropyl; $R_6$ is $CD_2$-$CD_3$.

In some embodiments, $R_1$ is $C_1$-$C_6$ alkyl, substituted with two halo; $R_2$ is isopropyl; $R_6$ is $CD_2$-$CD_3$.

In some embodiments, $R_1$ is $C_1$-$C_3$ alkyl, substituted with two halo; $R_2$ is isopropyl; $R_6$ is $CD_2$-$CD_3$.

In some embodiments, $R_1$ is $C_1$-$C_2$ alkyl, substituted with two halo; $R_2$ is isopropyl; $R_6$ is $CD_2$-$CD_3$.

In some embodiments, $R_1$ is $C_1$ alkyl, substituted with two halo; $R_2$ is isopropyl; $R_6$ is $CD_2$-$CD_3$.

In some embodiments, $R_1$ is $C_2$ alkyl, substituted with two halo; $R_2$ is isopropyl; $R_6$ is $CD_2$-$CD_3$.

In some embodiments, $R_1$ is $C_1$-$C_6$ alkyl, substituted with one halo, with two halo, or with three halo; $R_2$ is isopropyl; $R_6$ is ethyl.

In some embodiments, $R_1$ is $C_1$-$C_3$ alkyl, substituted with one halo, with two halo, or with three halo; $R_2$ is isopropyl; $R_6$ is ethyl.

In some embodiments, $R_1$ is $C_1$-$C_2$ alkyl, substituted with one halo, with two halo, or with three halo; $R_2$ is isopropyl; $R_6$ is ethyl.

In some embodiments, $R_1$ is $C_1$ alkyl, substituted with one halo, with two halo, or with three halo; $R_2$ is isopropyl; $R_6$ is ethyl.

In some embodiments, $R_1$ is $C_2$ alkyl, substituted with one halo, with two halo, or with three halo; $R_2$ is isopropyl; $R_6$ is ethyl.

In some embodiments, $R_1$ is $C_1$-$C_6$ alkyl, substituted with two halo, or with three halo; $R_2$ is isopropyl; $R_6$ is ethyl.

In some embodiments, $R_1$ is $C_1$-$C_3$ alkyl, substituted with two halo, or with three halo; $R_2$ is isopropyl; $R_6$ is ethyl.

In some embodiments, $R_1$ is $C_1$-$C_2$ alkyl, substituted with two halo, or with three halo; $R_2$ is isopropyl; $R_6$ is ethyl.

In some embodiments, $R_1$ is $C_1$ alkyl, substituted with two halo, or with three halo; $R_2$ is isopropyl; $R_6$ is ethyl.

In some embodiments, $R_1$ is $C_2$ alkyl, substituted with two halo, or with three halo; $R_2$ is isopropyl; $R_6$ is ethyl.

In some embodiments, $R_1$ is $C_1$-$C_6$ alkyl, substituted with three halo; $R_2$ is isopropyl; $R_6$ is ethyl.

In some embodiments, $R_1$ is $C_1$-$C_3$ alkyl, substituted with three halo; $R_2$ is isopropyl; $R_6$ is ethyl.

In some embodiments, $R_1$ is $C_1$-$C_2$ alkyl, substituted with three halo; $R_2$ is isopropyl; $R_6$ is ethyl.

In some embodiments, $R_1$ is $C_1$ alkyl, substituted with three halo; $R_2$ is isopropyl; $R_6$ is ethyl.

In some embodiments, $R_1$ is $C_2$ alkyl, substituted three halo; $R_2$ is isopropyl; $R_6$ is ethyl.

In some embodiments, $R_1$ is $C_1$-$C_6$ alkyl, substituted with two halo; $R_2$ is isopropyl; $R_6$ is ethyl.

In some embodiments, $R_1$ is $C_1$-$C_3$ alkyl, substituted with two halo; $R_2$ is isopropyl; $R_6$ is ethyl.

In some embodiments, $R_1$ is $C_1$-$C_2$ alkyl, substituted with two halo; $R_2$ is isopropyl; $R_6$ is ethyl.

In some embodiments, $R_1$ is $C_1$ alkyl, substituted with two halo; $R_2$ is isopropyl; $R_6$ is ethyl.

In some embodiments, $R_1$ is $C_2$ alkyl, substituted with two halo; $R_2$ is isopropyl; $R_6$ is ethyl.

In some embodiments, $R_1$ is $C_1$-$C_6$ alkyl, substituted with $N(R_N)_2$.

In some embodiments, $R_1$ is $C_1$-$C_3$ alkyl, $N(R_N)_2$.

In some embodiments, $R_1$ is $C_1$-$C_2$ alkyl, $N(R_N)_2$.

In some embodiments, $R_1$ is $C_1$ alkyl, $N(R_N)_2$.

In some embodiments, $R_1$ is $C_2$ alkyl, $N(R_N)_2$.

In some embodiments, $R_1$ is $C_1$-$C_6$ alkyl, $N(R_N)_2$; $R_2$ is isopropyl.

In some embodiments, $R_1$ is $C_1$-$C_3$ alkyl, $N(R_N)_2$; $R_2$ is isopropyl.

In some embodiments, $R_1$ is $C_1$-$C_2$ alkyl, $N(R_N)_2$; $R_2$ is isopropyl.

In some embodiments, $R_1$ is $C_1$ alkyl, $N(R_N)_2$; $R_2$ is isopropyl.

In some embodiments, $R_1$ is $C_2$ alkyl, $N(R_N)_2$; $R_2$ is isopropyl.

In some embodiments, $R_1$ is $C_1$-$C_6$ alkyl, $N(R_N)_2$; $R_6$ is ethyl.

In some embodiments, $R_1$ is $C_1$-$C_3$ alkyl, $N(R_N)_2$; $R_6$ is ethyl.

In some embodiments, $R_1$ is $C_1$-$C_2$ alkyl, substituted $N(R_N)_2$; $R_6$ is ethyl.

In some embodiments, $R_1$ is $C_1$ alkyl, substituted $N(R_N)_2$; $R_6$ is ethyl.

In some embodiments, $R_1$ is $C_2$ alkyl, substituted $N(R_N)_2$; $R_6$ is ethyl.

In some embodiments, $R_1$ is $C_1$-$C_6$ alkyl, $N(R_N)_2$; $R_2$ is $CD_2$-$CD_3$.

In some embodiments, $R_1$ is $C_1$-$C_3$ alkyl, $N(R_N)_2$; $R_2$ is $CD_2$-$CD_3$.

In some embodiments, $R_1$ is $C_1$-$C_2$ alkyl, $N(R_N)_2$; $R_2$ is $CD_2$-$CD_3$.

In some embodiments, $R_1$ is $C_1$ alkyl, $N(R_N)_2$; $R_2$ is $CD_2$-$CD_3$.

In some embodiments, $R_1$ is $C_2$ alkyl, $N(R_N)_2$; $R_2$ is $CD_2$-$CD_3$.

In some embodiments, $R_3$ is $C_1$-$C_6$ alkyl, substituted with $N(R_N)_2$.

In some embodiments, $R_3$ is $C_1$-$C_3$ alkyl, $N(R_N)_2$.

In some embodiments, $R_3$ is $C_1$-$C_2$ alkyl, $N(R_N)_2$.

In some embodiments, $R_3$ is $C_1$ alkyl, $N(R_N)_2$.

In some embodiments, $R_3$ is $C_2$ alkyl, $N(R_N)_2$.

In some embodiments, $R_3$ is $C_1$-$C_6$ alkyl, $N(R_N)_2$; $R_2$ is isopropyl.

In some embodiments, $R_3$ is $C_1$-$C_3$ alkyl, $N(R_N)_2$; $R_2$ is isopropyl.

In some embodiments, $R_3$ is $C_1$-$C_2$ alkyl, $N(R_N)_2$; $R_2$ is isopropyl.

In some embodiments, $R_3$ is $C_1$ alkyl, $N(R_N)_2$; $R_2$ is isopropyl.

In some embodiments, $R_3$ is $C_2$ alkyl, $N(R_N)_2$; $R_2$ is isopropyl.

In some embodiments, $R_3$ is $C_1$-$C_6$ alkyl, $N(R_N)_2$; $R_6$ is ethyl.

In some embodiments, $R_3$ is $C_1$-$C_3$ alkyl, $N(R_N)_2$; $R_6$ is ethyl.

In some embodiments, $R_3$ is $C_1$-$C_2$ alkyl, substituted $N(R_N)_2$; $R_6$ is ethyl.

In some embodiments, $R_3$ is $C_1$ alkyl, substituted $N(R_N)_2$; $R_6$ is ethyl.

In some embodiments, $R_3$ is $C_2$ alkyl, substituted $N(R_N)_2$; $R_6$ is ethyl.

In some embodiments, $R_3$ is $C_1$-$C_6$ alkyl, $N(R_N)_2$; $R_2$ is $CD_2$-$CD_3$.

In some embodiments, $R_3$ is $C_1$-$C_3$ alkyl, $N(R_N)_2$; $R_2$ is $CD_2$-$CD_3$.

In some embodiments, $R_3$ is $C_1$-$C_2$ alkyl, $N(R_N)_2$; $R_2$ is $CD_2$-$CD_3$.

In some embodiments, $R_3$ is $C_1$ alkyl, $N(R_N)_2$; $R_2$ is $CD_2$-$CD_3$.

In some embodiments, $R_3$ is $C_2$ alkyl, $N(R_N)_2$; $R_2$ is $CD_2$-$CD_3$.

In some embodiments, $R_1$ is $C_1$-$C_6$ alkyl, substituted with $N(R_N)_2$; $R_2$ is isopropyl; $R_6$ is $CD_2$-$CD_3$.

In some embodiments, $R_1$ is $C_1$-$C_3$ alkyl, $N(R_N)_2$; $R_2$ is isopropyl; $R_6$ is $CD_2$-$CD_3$.

In some embodiments, $R_1$ is $C_1$-$C_2$ alkyl, $N(R_N)_2$; $R_2$ is isopropyl; $R_6$ is $CD_2$-$CD_3$.

In some embodiments, $R_1$ is $C_1$ alkyl, $N(R_N)_2$; $R_2$ is isopropyl; $R_6$ is $CD_2$-$CD_3$.

In some embodiments, $R_1$ is $C_2$ alkyl, $N(R_N)_2$; $R_2$ is isopropyl; $R_6$ is $CD_2$-$CD_3$.

In some embodiments, $R_1$ is $C_1$-$C_6$ alkyl, $N(R_N)_2$; $R_2$ is isopropyl; $R_6$ is ethyl.

In some embodiments, $R_1$ is $C_1$-$C_3$ alkyl, $N(R_N)_2$; $R_2$ is isopropyl; $R_6$ is ethyl.

In some embodiments, $R_1$ is $C_1$-$C_2$ alkyl, $N(R_N)_2$; $R_2$ is isopropyl; $R_6$ is ethyl.

In some embodiments, $R_1$ is $C_1$ alkyl, $N(R_N)_2$; $R_2$ is isopropyl; $R_6$ is ethyl.

In some embodiments, $R_1$ is $C_2$ alkyl, $N(R_N)_2$; $R_2$ is isopropyl; $R_6$ is ethyl.

In some embodiments, $R_1$ is $C_1$-$C_6$ alkyl, $N(R_N)_2$; $R_2$ is isopropyl; $R_6$ is ethyl.

In some embodiments, $R_1$ is $C_1$-$C_3$ alkyl, $N(R_N)_2$; $R_2$ is isopropyl; $R_6$ is ethyl.

In some embodiments, $R_1$ is $C_1$-$C_2$ alkyl, substituted $N(R_N)_2$; $R_2$ is isopropyl; $R_6$ is ethyl.

In some embodiments, $R_1$ is $C_1$ alkyl, substituted $N(R_N)_2$; $R_2$ is isopropyl; $R_6$ is ethyl.

In some embodiments, $R_1$ is $C_2$ alkyl, substituted $N(R_N)_2$; $R_2$ is isopropyl; $R_6$ is ethyl.

In some embodiments, the compound of Formulae 0, 0a, I, Ia, II, IIa, III, or IIIa is not 5-fluoro-N,N-diisopropyl-2-((4-(7-(((2R,5S)-5-(methylsulfonamido)tetrahydro-2H-pyran-2-yl)methyl)-2,7-diazaspiro[3.5]nonan-2-yl)pyrimidin-5-yl)oxy)benzamide.

In some embodiments, the compound is of Formulae 0, 0a, I, Ia, II, IIa, III, or IIIa combined with any of the embodiments described herein.

Any of the groups described above for any variable can be combined with any of the other groups described above, where applicable, for any of the Formulae described herein.

Representative compounds of the present disclosure are shown in the table below.

TABLE 1

Representative Compounds of the Present Disclosure

| Compound | Structure | IUPAC Name |
|---|---|---|
| 1 | 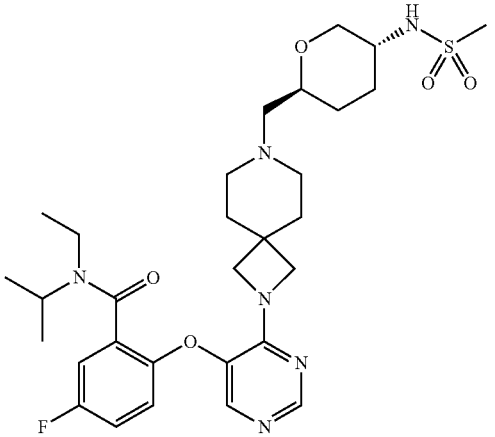 [SMILES: CCN(C(=O)c1cc(F)ccc1Oc1cncnc1N1CC2(CCN(C[C@@H]3CC[C@@H](NS(C)(=O)=O)CO3)CC2)C1)C(C)C] | N-ethyl-5-fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide |
| 2 | 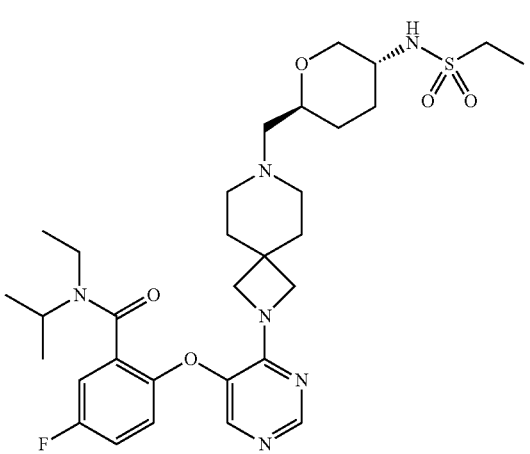 [SMILES: CCN(C(=O)c1cc(F)ccc1Oc1cncnc1N1CC2(CCN(C[C@@H]3CC[C@@H](NS(=O)(=O)CC)CO3)CC2)C1)C(C)C] | N-ethyl-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |

TABLE 1-continued

Representative Compounds of the Present Disclosure

| Compound | Structure | IUPAC Name |
|---|---|---|
| 3 | 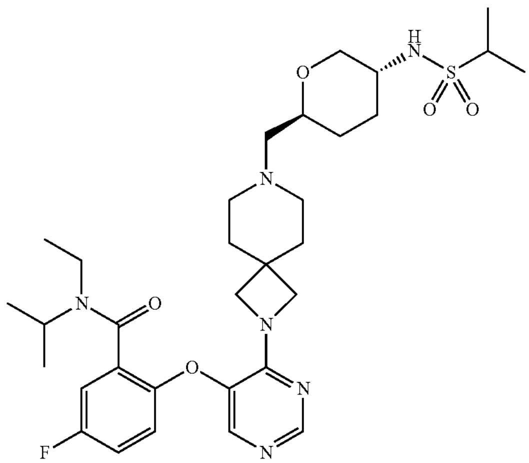 | N-ethyl-5-fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide |
| 4 | 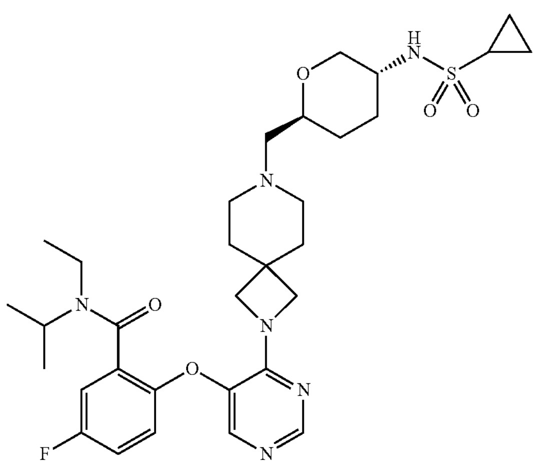 [SMILES: CCN(C(=O)c1cc(F)ccc1Oc1cncnc1N1CC2(CCN(C[C@@H]3CC[C@@H](NS(=O)(=O)C4CC4)CO3)CC2)C1)C(C)C] | 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 5 | 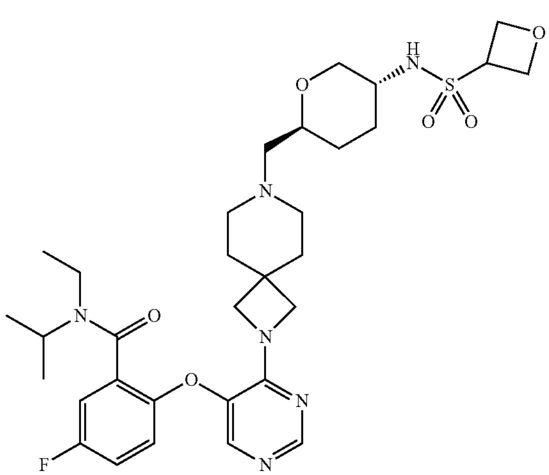 [SMILES: CCN(C(=O)c1cc(F)ccc1Oc1cncnc1N1CC2(CCN(C[C@@H]3CC[C@@H](NS(=O)(=O)C4COC4)CO3)CC2)C1)C(C)C] | N-ethyl-5-fluoro-N-isopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 6 | 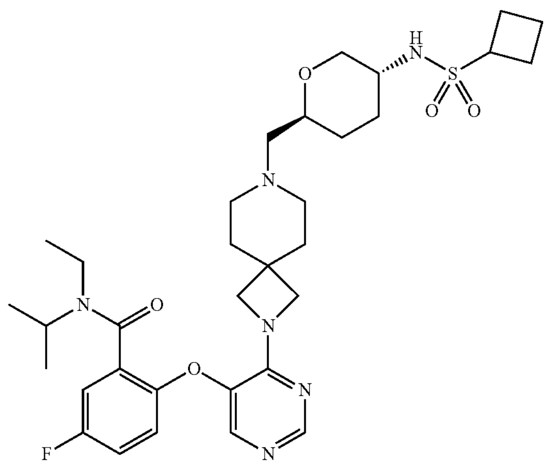 [SMILES: CCN(C(=O)c1cc(F)ccc1Oc1cncnc1N1CC2(CCN(C[C@@H]3CC[C@@H](NS(=O)(=O)C4CCC4)CO3)CC2)C1)C(C)C] | 2-((4-(7-(((2S,5R)-5-(cyclobutanesulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 7 | 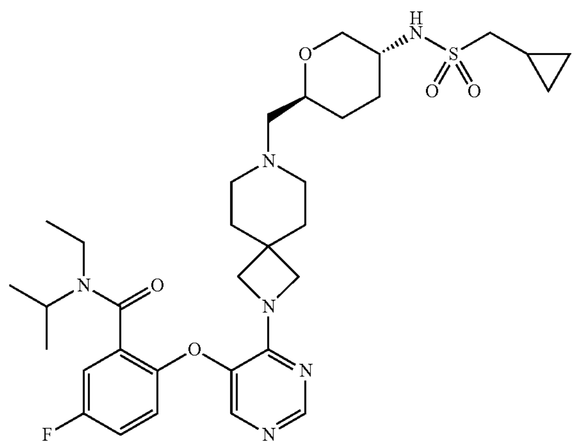 [SMILES: CCN(C(=O)c1cc(F)ccc1Oc1cncnc1N1CC2(CCN(C[C@@H]3CC[C@@H](NS(=O)(=O)CC4CC4)CO3)CC2)C1)C(C)C] | 2-((4-(7-(((2S,5R)-5-((cyclopropylmethyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 8 | 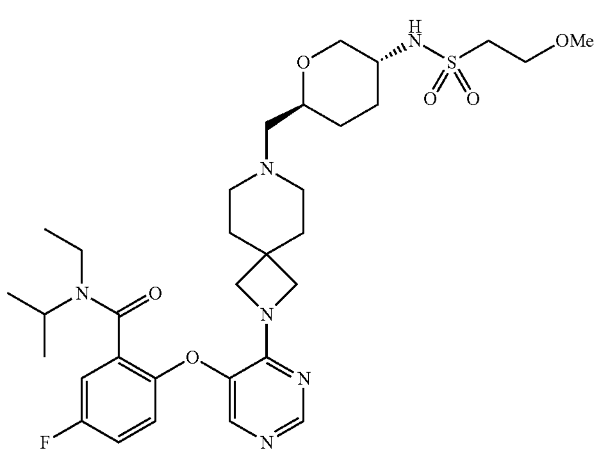 [SMILES: CCN(C(=O)c1cc(F)ccc1Oc1cncnc1N1CC2(CCN(C[C@@H]3CC[C@@H](NS(=O)(=O)CCOC)CO3)CC2)C1)C(C)C] | N-ethyl-5-fluoro-N-isopropyl-2-((4-(7-(((2S,5R)-5-((2-methoxyethyl)sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 9 | 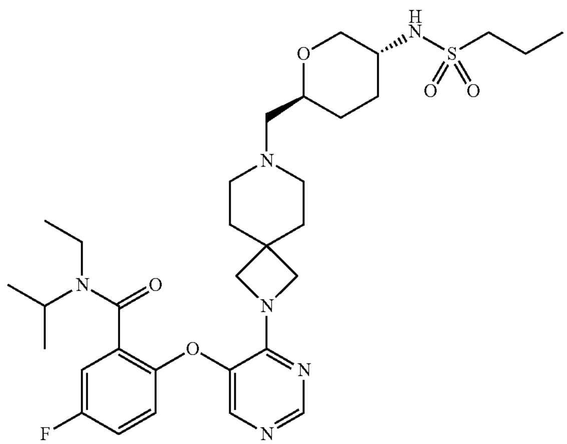 [SMILES: CCCS(=O)(=O)N[C@@H]1CC[C@@H](CN2CCC3(CC2)CN(c2ncncc2Oc2ccc(F)cc2C(=O)N(CC)C(C)C)C3)OC1] | N-ethyl-5-fluoro-N-isopropyl-2-((4-(7-(((2S,5R)-5-(propylsulfonamido)tetrahydro-2H-pyran-2-yl)methyl)-2,7-diazaspiro[3.5]nonan-2-yl)pyrimidin-5-yl)oxy)benzamide |
| 10 | 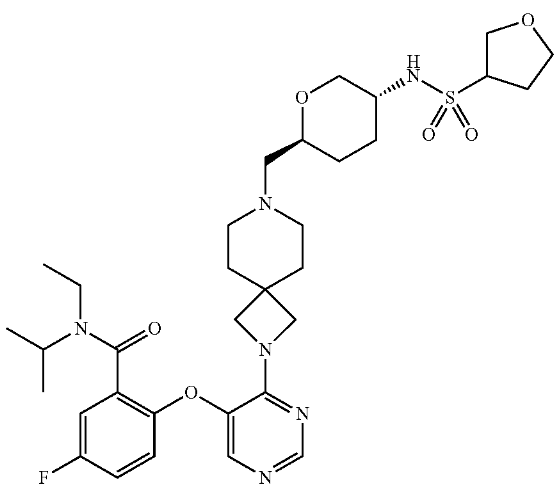 [SMILES: CCN(C(=O)c1cc(F)ccc1Oc1cncnc1N1CC2(CCN(C[C@@H]3CC[C@@H](NS(=O)(=O)C4CCOC4)CO3)CC2)C1)C(C)C] | N-ethyl-5-fluoro-N-isopropyl-2-((4-(7-(((2S,5R)-5-((tetrahydrofuran)-3-sulfonamido)tetrahydro-2H-pyran-2-yl)methyl)-2,7-diazaspiro[3.5]nonan-2-yl)pyrimidin-5-yl)oxy)benzamide |
| 11 | 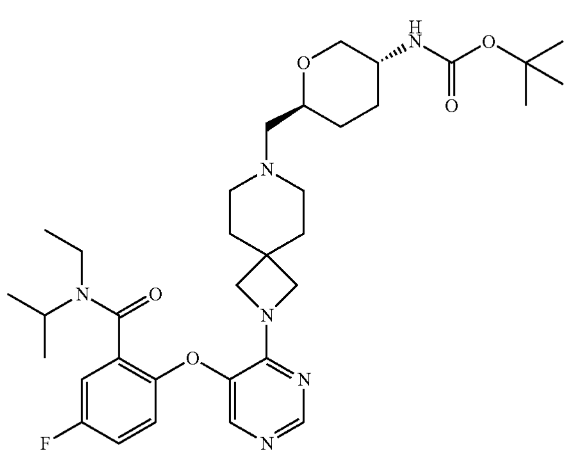 [SMILES: CCN(C(=O)c1cc(F)ccc1Oc1cncnc1N1CC2(CCN(C[C@@H]3CC[C@@H](NC(=O)OC(C)(C)C)CO3)CC2)C1)C(C)C] | tert-butyl ((3R,6S)-6-((2-(5-(2-(ethyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate |

TABLE 1-continued

Representative Compounds of the Present Disclosure

| Compound | Structure | IUPAC Name |
|---|---|---|
| 12 | 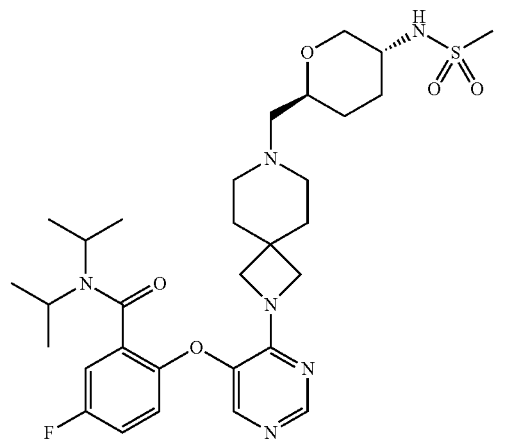 [SMILES: CC(C)N(C(=O)c1cc(F)ccc1Oc1cncnc1N1CC2(CCN(C[C@@H]3CC[C@@H](NS(C)(=O)=O)CO3)CC2)C1)C(C)C] | 5-fluoro-N,N-diisopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide |
| 13 | 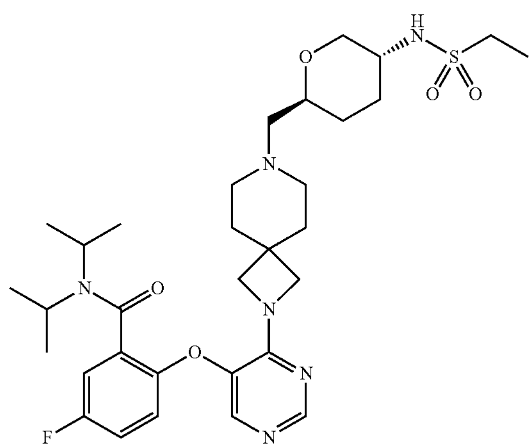 [SMILES: CCS(=O)(=O)N[C@@H]1CC[C@@H](CN2CCC3(CC2)CN(c2ncncc2Oc2ccc(F)cc2C(=O)N(C(C)C)C(C)C)C3)OC1] | 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 14 | 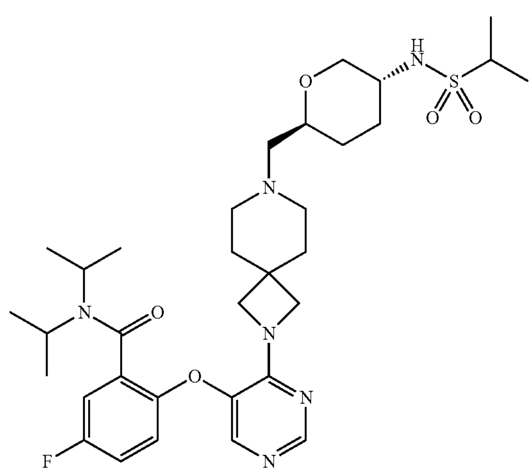 [SMILES: CC(C)N(C(=O)c1cc(F)ccc1Oc1cncnc1N1CC2(CCN(C[C@@H]3CC[C@@H](NS(=O)(=O)C(C)C)CO3)CC2)C1)C(C)C] | 5-fluoro-N,N-diisopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 15 | 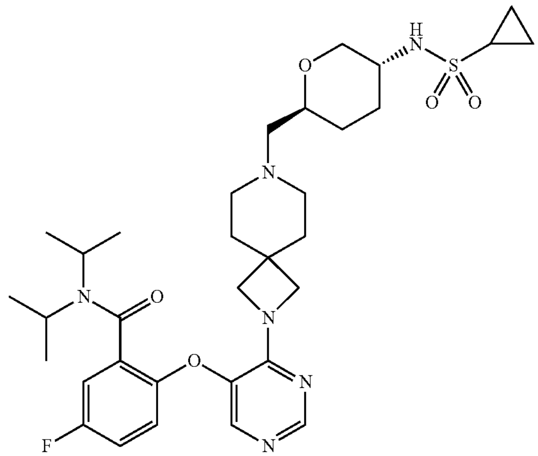 [SMILES: CC(C)N(C(=O)c1cc(F)ccc1Oc1cncnc1N1CC2(CCN(C[C@@H]3CC[C@@H](NS(=O)(=O)C4CC4)CO3)CC2)C1)C(C)C] | 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 16 | 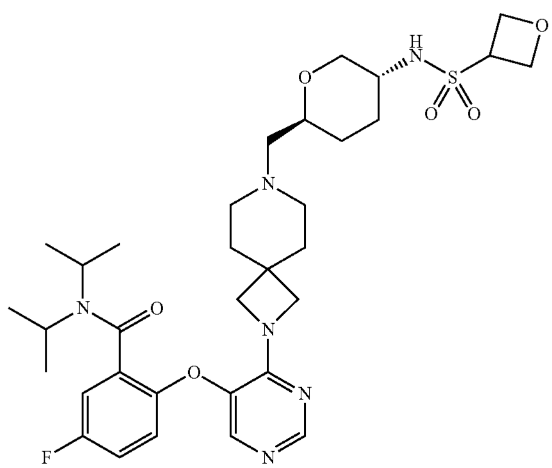 [SMILES: CC(C)N(C(=O)c1cc(F)ccc1Oc1cncnc1N1CC2(CCN(C[C@@H]3CC[C@@H](NS(=O)(=O)C4COC4)CO3)CC2)C1)C(C)C] | 5-fluoro-N,N-diisopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide |
| 17 | 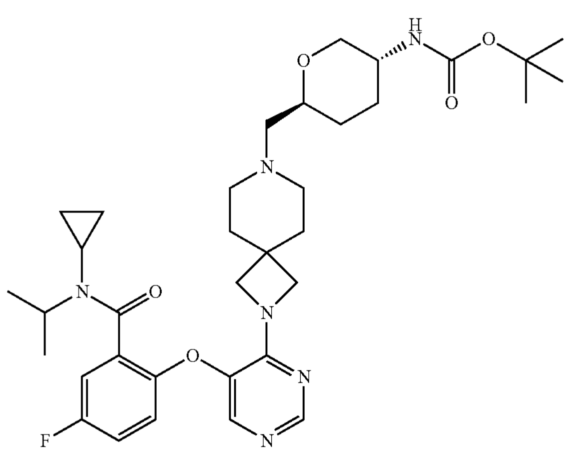 [SMILES: CC(C)N(C(=O)c1cc(F)ccc1Oc1cncnc1N1CC2(CCN(C[C@@H]3CC[C@@H](NC(=O)OC(C)(C)C)CO3)CC2)C1)C1CC1] | tert-butyl ((3R,6S)-6-((2-(5-(2-(cyclopropyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate |

TABLE 1-continued

Representative Compounds of the Present Disclosure

| Compound | Structure | IUPAC Name |
|---|---|---|
| 18 | 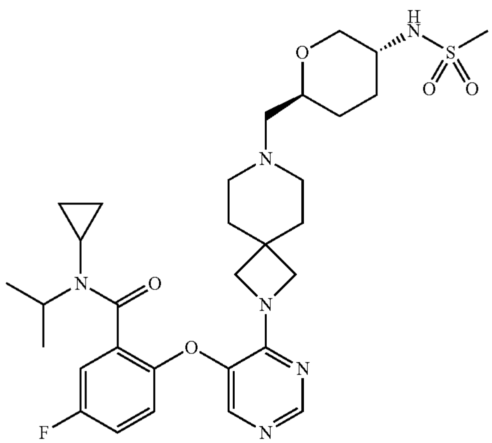 [SMILES: CC(C)N(C(=O)c1cc(F)ccc1Oc1cncnc1N1CC2(CCN(C[C@@H]3CC[C@@H](NS(C)(=O)=O)CO3)CC2)C1)C1CC1] | N-cyclopropyl-5-fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide |
| 19 | 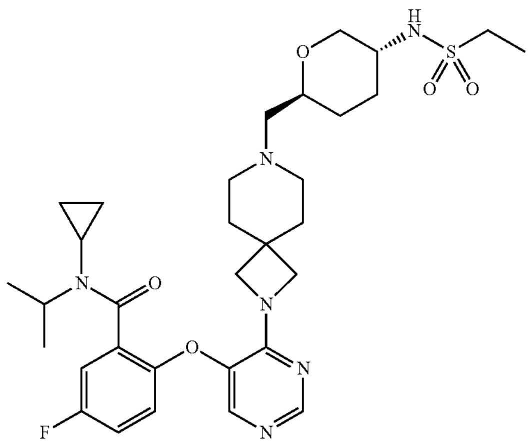 [SMILES: CCS(=O)(=O)N[C@@H]1CC[C@@H](CN2CCC3(CC2)CN(c2ncncc2Oc2ccc(F)cc2C(=O)N(C(C)C)C2CC2)C3)OC1] | N-cyclopropyl-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 20 | 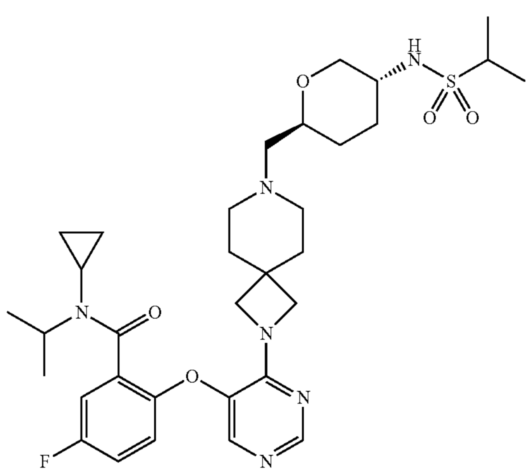 [SMILES: CC(C)N(C(=O)c1cc(F)ccc1Oc1cncnc1N1CC2(CCN(C[C@@H]3CC[C@@H](NS(=O)(=O)C(C)C)CO3)CC2)C1)C1CC1] | N-cyclopropyl-5-fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 21 | 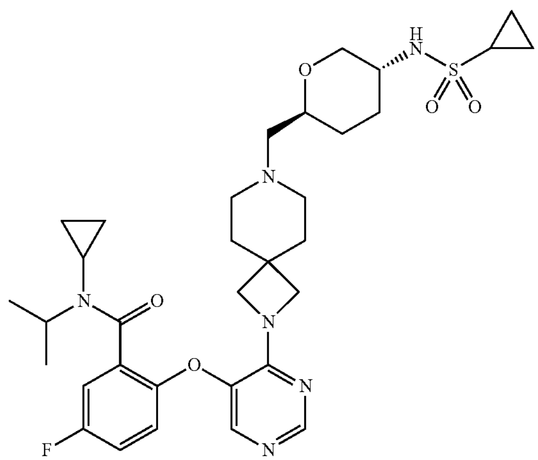 [SMILES: CC(C)N(C(=O)c1cc(F)ccc1Oc1cncnc1N1CC2(CCN(C[C@@H]3CC[C@@H](NS(=O)(=O)C4CC4)CO3)CC2)C1)C1CC1] | 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide |
| 22 | 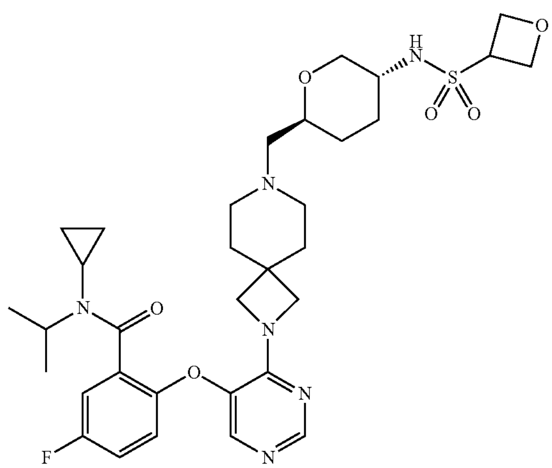 [SMILES: CC(C)N(C(=O)c1cc(F)ccc1Oc1cncnc1N1CC2(CCN(C[C@@H]3CC[C@@H](NS(=O)(=O)C4COC4)CO3)CC2)C1)C1CC1] | N-cyclopropyl-5-fluoro-N-isopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide |
| 23 | 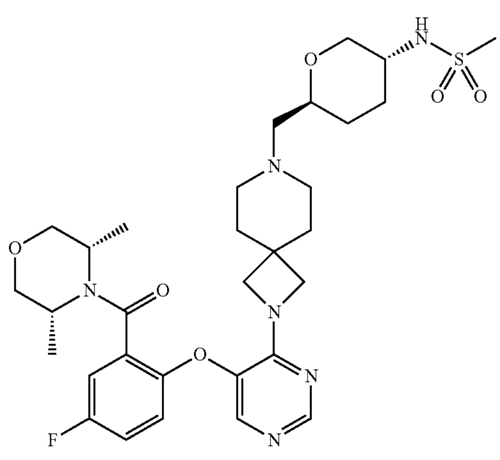 [SMILES: C[C@@H]1COC[C@H](C)N1C(=O)c1cc(F)ccc1Oc1cncnc1N1CC2(CCN(C[C@@H]3CC[C@@H](NS(C)(=O)=O)CO3)CC2)C1] | N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)methanesulfonamide |

TABLE 1-continued

Representative Compounds of the Present Disclosure

| Compound | Structure | IUPAC Name |
|---|---|---|
| 24 | 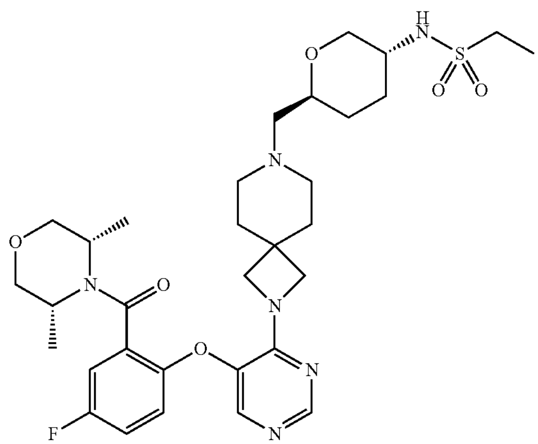 [SMILES: CCS(=O)(=O)N[C@@H]1CC[C@@H](CN2CCC3(CC2)CN(c2ncncc2Oc2ccc(F)cc2C(=O)N2[C@H](C)COC[C@@H]2C)C3)OC1] | N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)ethanesulfonamide |
| 25 | 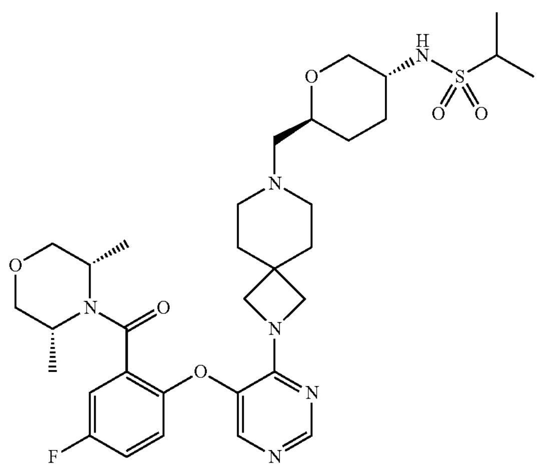 [SMILES: CC(C)S(=O)(=O)N[C@@H]1CC[C@@H](CN2CCC3(CC2)CN(c2ncncc2Oc2ccc(F)cc2C(=O)N2[C@H](C)COC[C@@H]2C)C3)OC1] | N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)propane-2-sulfonamide |
| 26 | 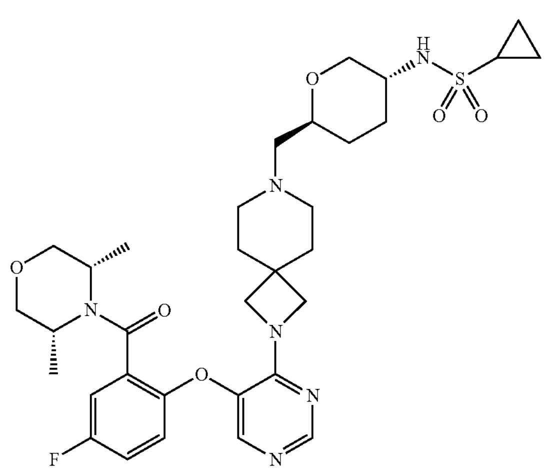 [SMILES: C[C@@H]1COC[C@H](C)N1C(=O)c1cc(F)ccc1Oc1cncnc1N1CC2(CCN(C[C@@H]3CC[C@@H](NS(=O)(=O)C4CC4)CO3)CC2)C1] | N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)cyclopropanesulfonamide |

TABLE 1-continued

Representative Compounds of the Present Disclosure

| Compound | Structure | IUPAC Name |
|---|---|---|
| 27 | 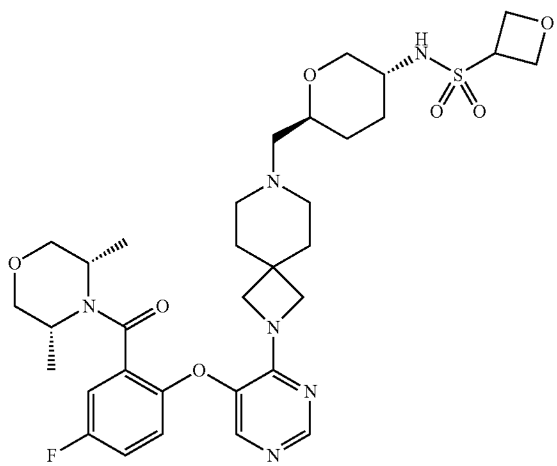 [SMILES: C[C@@H]1COC[C@H](C)N1C(=O)c1cc(F)ccc1Oc1cncnc1N1CC2(CCN(C[C@@H]3CC[C@@H](NS(=O)(=O)C4COC4)CO3)CC2)C1] | N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)oxetane-3-sulfonamide |
| 28 | 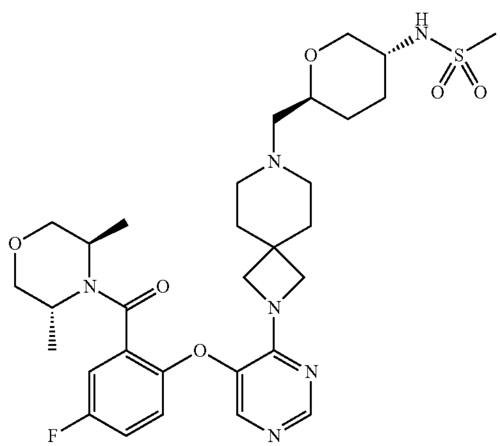 [SMILES: C[C@@H]1COC[C@@H](C)N1C(=O)c1cc(F)ccc1Oc1cncnc1N1CC2(CCN(C[C@@H]3CC[C@@H](NS(C)(=O)=O)CO3)CC2)C1] | N-((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)methanesulfonamide |
| 29 | 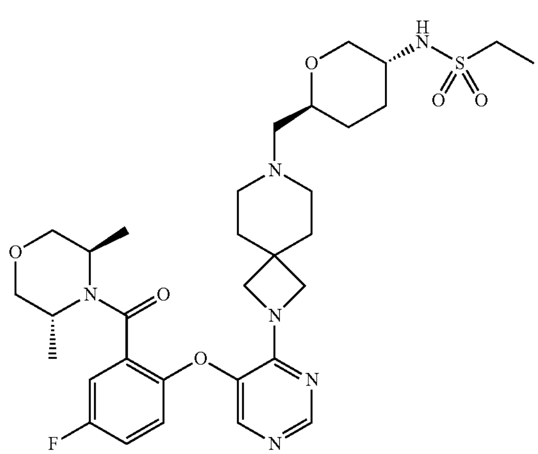 [SMILES: CCS(=O)(=O)N[C@@H]1CC[C@@H](CN2CCC3(CC2)CN(c2ncncc2Oc2ccc(F)cc2C(=O)N2[C@H](C)COC[C@H]2C)C3)OC1] | N-(3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)ethanesulfonamide |

TABLE 1-continued

Representative Compounds of the Present Disclosure

| Compound | Structure | IUPAC Name |
|---|---|---|
| 30 | 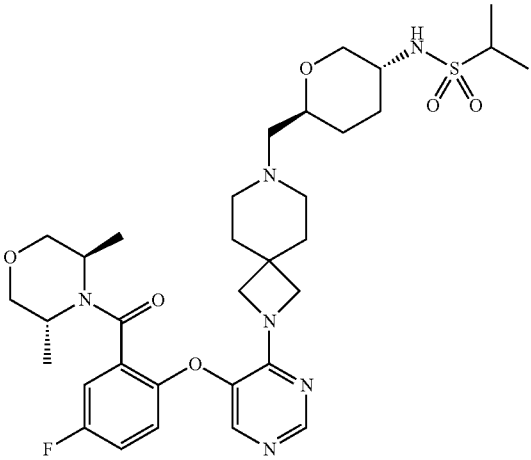 [SMILES: CC(C)S(=O)(=O)N[C@@H]1CC[C@@H](CN2CCC3(CC2)CN(c2ncncc2Oc2ccc(F)cc2C(=O)N2[C@H](C)COC[C@H]2C)C3)OC1] | N-(3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)propane-2-sulfonamide |
| 31 | 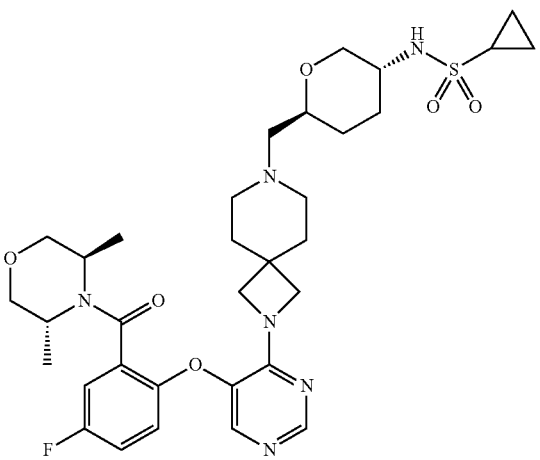 [SMILES: C[C@@H]1COC[C@@H](C)N1C(=O)c1cc(F)ccc1Oc1cncnc1N1CC2(CCN(C[C@@H]3CC[C@@H](NS(=O)(=O)C4CC4)CO3)CC2)C1] | N-((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)cyclopropanesulfonamide |
| 32 | 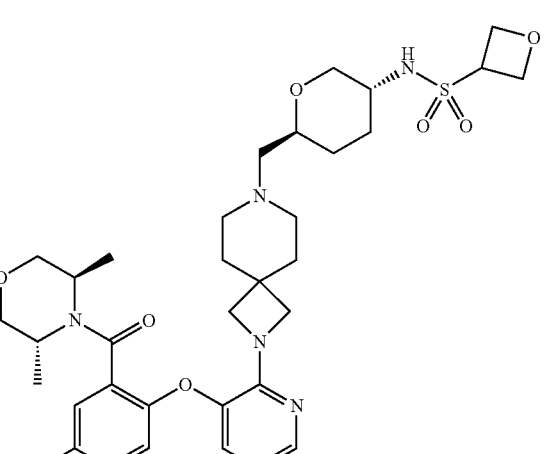 | N-(3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)oxetane-3-sulfonamide |

TABLE 1-continued

Representative Compounds of the Present Disclosure

| Compound | Structure | IUPAC Name |
|---|---|---|
| 33 | 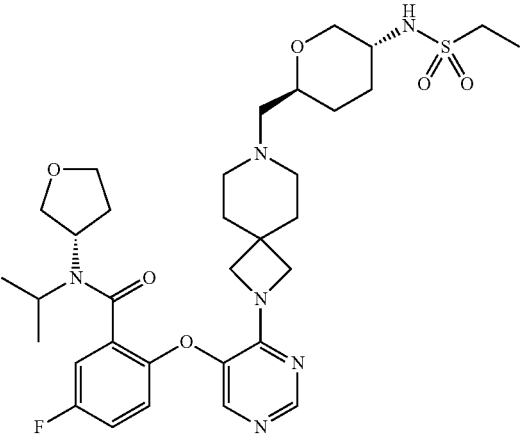 [SMILES: CCS(=O)(=O)N[C@@H]1CC[C@@H](CN2CCC3(CC2)CN(c2ncncc2Oc2ccc(F)cc2C(=O)N(C(C)C)[C@H]2CCOC2)C3)OC1] | 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-((S)-tetrahydrofuran-3-yl)benzamide |
| 34 | 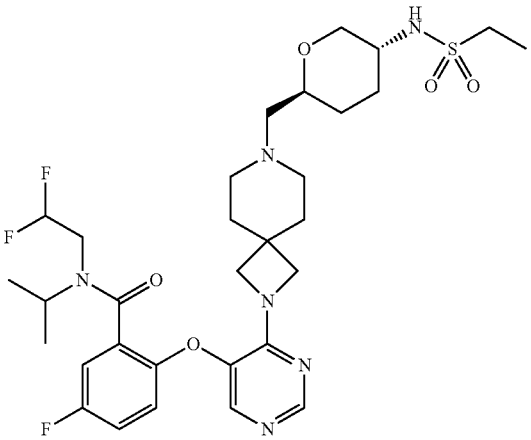 [SMILES: CCS(=O)(=O)N[C@@H]1CC[C@@H](CN2CCC3(CC2)CN(c2ncncc2Oc2ccc(F)cc2C(=O)N(CC(F)F)C(C)C)C3)OC1] | N-(2,2-difluoroethyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 35 | 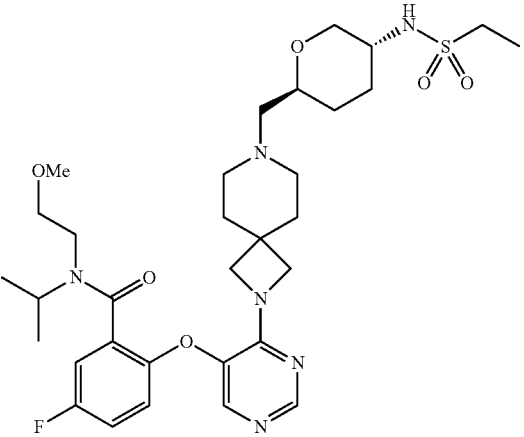 [SMILES: CCS(=O)(=O)N[C@@H]1CC[C@@H](CN2CCC3(CC2)CN(c2ncncc2Oc2ccc(F)cc2C(=O)N(CCOC)C(C)C)C3)OC1] | 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide |

TABLE 1-continued

Representative Compounds of the Present Disclosure

| Compound | Structure | IUPAC Name |
|---|---|---|
| 36 | 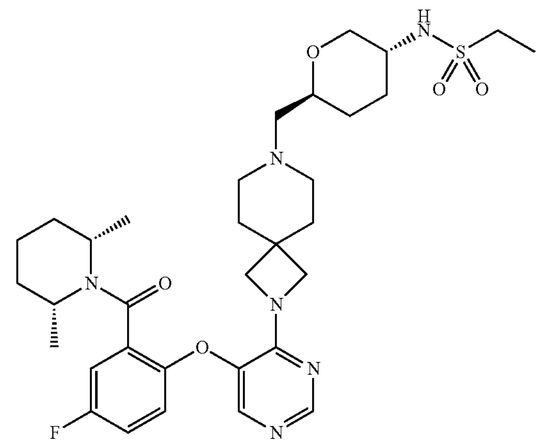 [SMILES: CCS(=O)(=O)N[C@@H]1CC[C@@H](CN2CCC3(CC2)CN(c2ncncc2Oc2ccc(F)cc2C(=O)N2[C@H](C)CCC[C@@H]2C)C3)OC1] | N-((3R,6S)-6-((2-(5-(2-(((2S,6R)-2,6-dimethylpiperidine-1-carbonyl)-4-fluorophenoxy)pyrimidin-4-yl)-2,7-diazaspiro[3.5]nonan-7-yl)methyl)tetrahydro-2H-pyran-3-yl)ethanesulfonamide |
| 37 | 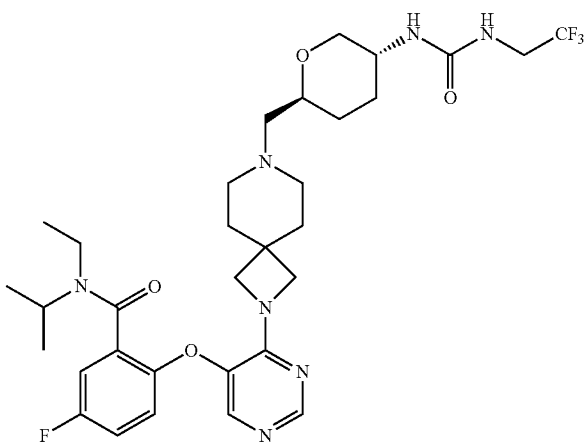 [SMILES: CCN(C(=O)c1cc(F)ccc1Oc1cncnc1N1CC2(CCN(C[C@@H]3CC[C@@H](NC(=O)NCC(F)(F)F)CO3)CC2)C1)C(C)C] | N-ethyl-5-fluoro-N-isopropyl-2-((4-(7-(((2S,5R)-5-(3-(2,2,2-trifluoroethyl)ureido)tetrahydro-2H-pyran-2-yl)methyl)-2,7-diazaspiro[3.5]nonan-2-yl)pyrimidin-5-yl)oxy)benzamide |
| 38 | 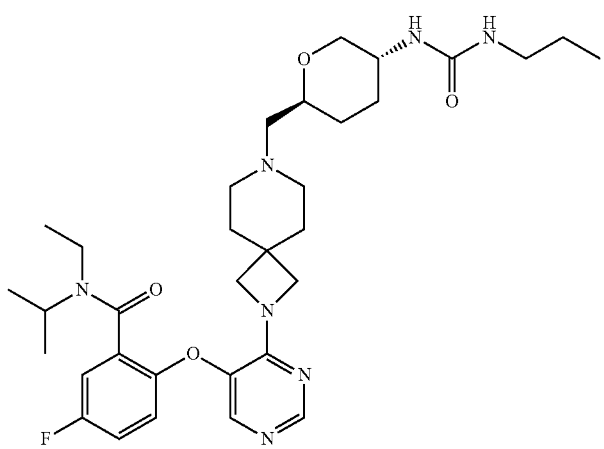 [SMILES: CCCNC(=O)N[C@@H]1CC[C@@H](CN2CCC3(CC2)CN(c2ncncc2Oc2ccc(F)cc2C(=O)N(CC)C(C)C)C3)OC1] | N-ethyl-5-fluoro-N-isopropyl-2-((4-(7-(((2S,5R)-5-(3-propylureido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 39 | 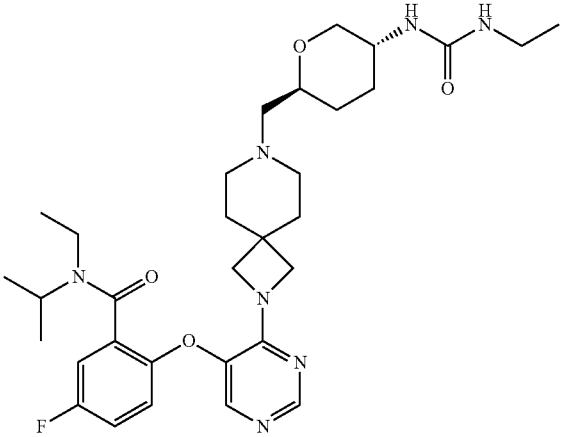 [SMILES: CCNC(=O)N[C@@H]1CC[C@@H](CN2CCC3(CC2)CN(c2ncncc2Oc2ccc(F)cc2C(=O)N(CC)C(C)C)C3)OC1] | N-ethyl-2-((4-(7-((((2S,5R)-5-(3-ethylureido)tetrahydro-2H-pyran-2-yl)methyl)-2,7-diazaspiro[3.5]nonan-2-yl)pyrimidin-5-yl)oxy)-5-fluoro-N-isopropylbenzamide |
| 40 | 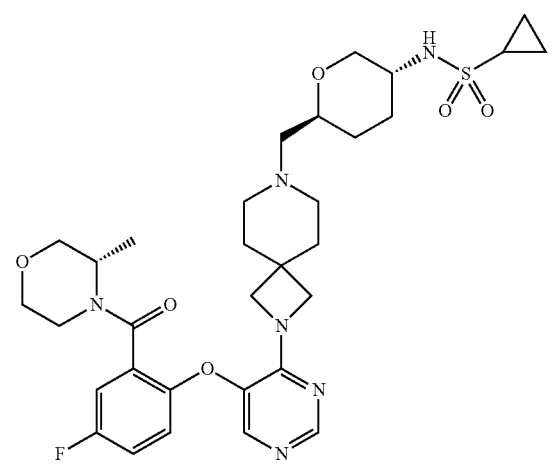 [SMILES: C[C@H]1COCCN1C(=O)c1cc(F)ccc1Oc1cncnc1N1CC2(CCN(C[C@@H]3CC[C@@H](NS(=O)(=O)C4CC4)CO3)CC2)C1] | N-((3R,6S)-6-((2-(5-(4-fluoro-2-((S)-3-methylmorpholine-4-carbonyl)phenoxy)pyrimidin-4-yl)-2,7-diazaspiro[3.5]nonan-7-yl)methyl)tetrahydro-2H-pyran-3-yl)cyclopropanesulfonamide |
| 41 | 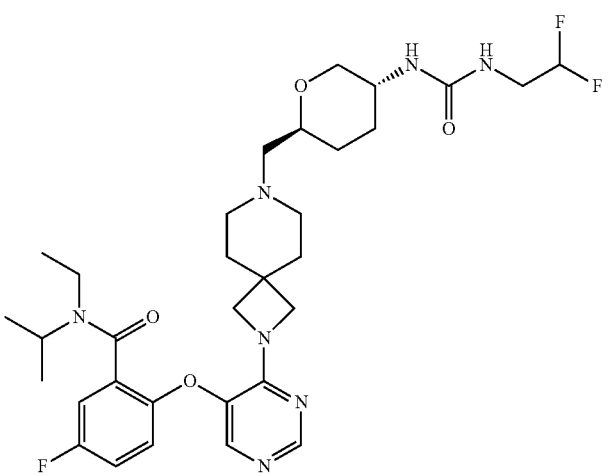 [SMILES: CCN(C(=O)c1cc(F)ccc1Oc1cncnc1N1CC2(CCN(C[C@@H]3CC[C@@H](NC(=O)NCC(F)F)CO3)CC2)C1)C(C)C] | 2-((4-(7-((((2S,5R)-5-(3-(2,2-difluoroethyl)ureido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |

TABLE 1-continued

Representative Compounds of the Present Disclosure

| Compound | Structure | IUPAC Name |
|---|---|---|
| 42 | 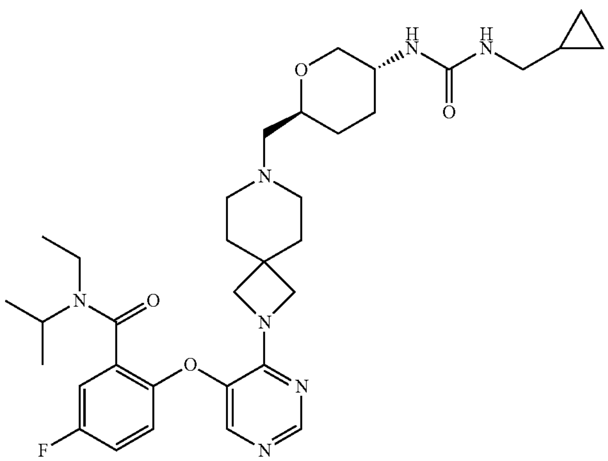 [SMILES: CCN(C(=O)c1cc(F)ccc1Oc1cncnc1N1CC2(CCN(C[C@@H]3CC[C@@H](NC(=O)NCC4CC4)CO3)CC2)C1)C(C)C] | 2-((4-(7-(((2S,5R)-5-(3-(cyclopropylmethyl)ureido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 43 | 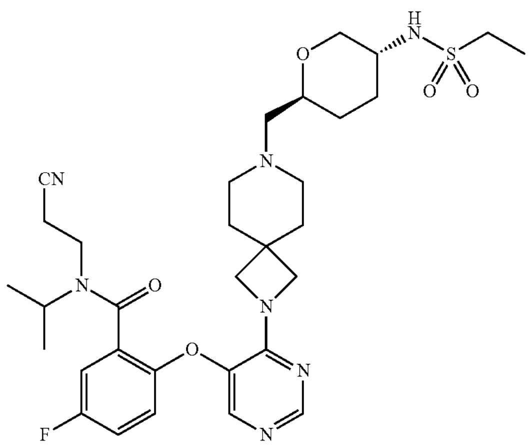 [SMILES: CCS(=O)(=O)N[C@@H]1CC[C@@H](CN2CCC3(CC2)CN(c2ncncc2Oc2ccc(F)cc2C(=O)N(CCC#N)C(C)C)C3)OC1] | N-(2-cyanoethyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 44 | 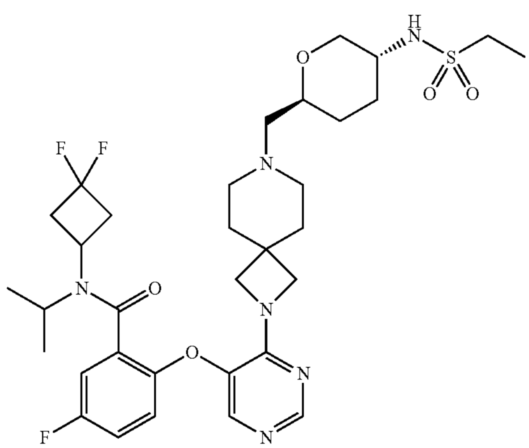 [SMILES: CCS(=O)(=O)N[C@@H]1CC[C@@H](CN2CCC3(CC2)CN(c2ncncc2Oc2ccc(F)cc2C(=O)N(C(C)C)C2CC(F)(F)C2)C3)OC1] | N-(3,3-difluorocyclobutyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |

TABLE 1-continued

Representative Compounds of the Present Disclosure

| Compound | Structure | IUPAC Name |
|---|---|---|
| 45 | 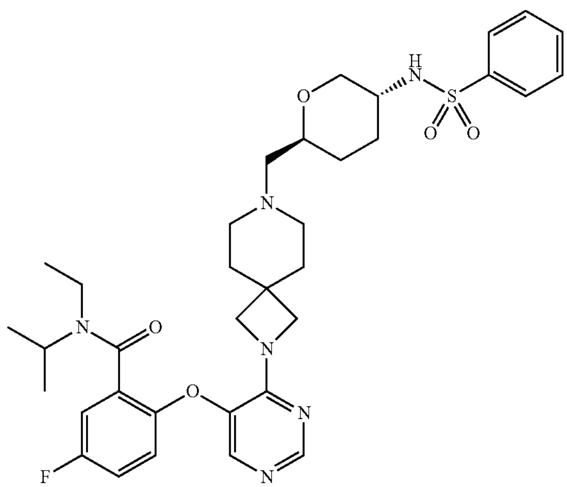 [SMILES: CCN(C(=O)c1cc(F)ccc1Oc1cncnc1N1CC2(CCN(C[C@@H]3CC[C@@H](NS(=O)(=O)c4ccccc4)CO3)CC2)C1)C(C)C] | N-ethyl-5-fluoro-N-isopropyl-2-((4-(7-(((2S,5R)-5-(phenylsulfonamido)tetrahydro-2H-pyran-2-yl)methyl)-2,7-diazaspiro[3.5]nonan-2-yl)pyrimidin-5-yl)oxy)benzamide |
| 46 | 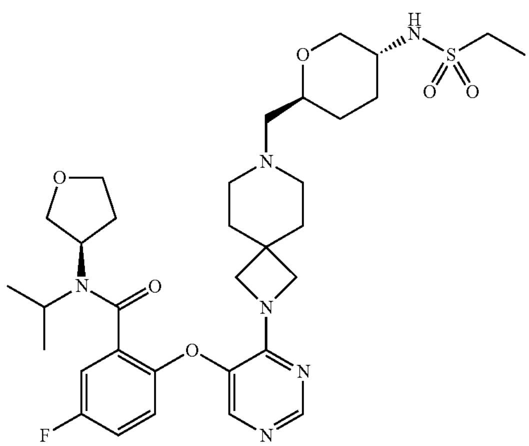 [SMILES: CCS(=O)(=O)N[C@@H]1CC[C@@H](CN2CCC3(CC2)CN(c2ncncc2Oc2ccc(F)cc2C(=O)N(C(C)C)[C@@H]2CCOC2)C3)OC1] | 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-((R)-tetrahydrofuran-3-yl)benzamide |
| 47 | 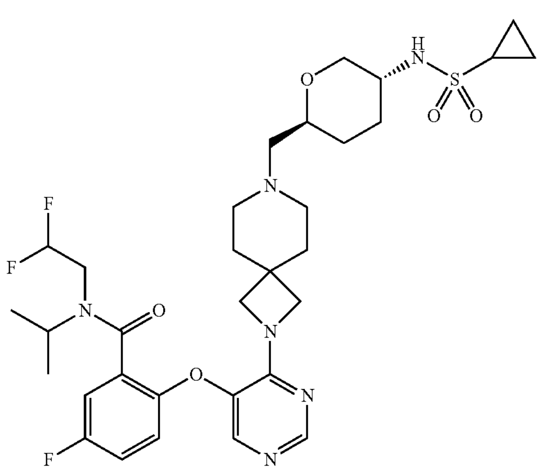 [SMILES: CC(C)N(CC(F)F)C(=O)c1cc(F)ccc1Oc1cncnc1N1CC2(CCN(C[C@@H]3CC[C@@H](NS(=O)(=O)C4CC4)CO3)CC2)C1] | 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide |

TABLE 1-continued

Representative Compounds of the Present Disclosure

| Compound | Structure | IUPAC Name |
|---|---|---|
| 48 | 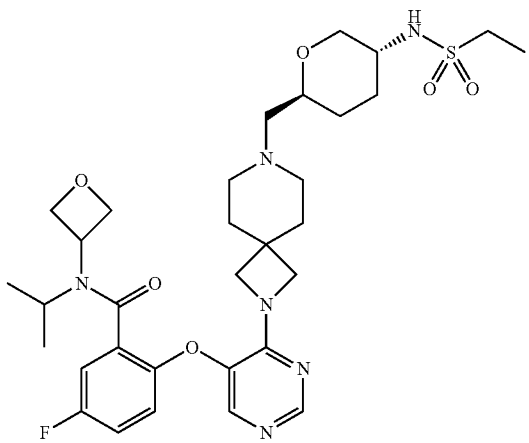 [SMILES: CCS(=O)(=O)N[C@@H]1CC[C@@H](CN2CCC3(CC2)CN(c2ncncc2Oc2ccc(F)cc2C(=O)N(C(C)C)C2COC2)C3)OC1] | 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide |
| 49 | 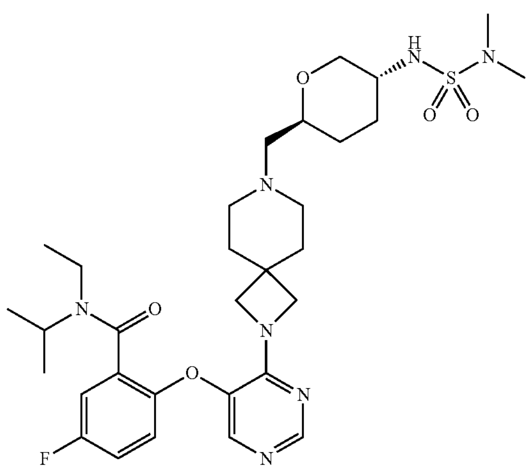 [SMILES: CCN(C(=O)c1cc(F)ccc1Oc1cncnc1N1CC2(CCN(C[C@@H]3CC[C@@H](NS(=O)(=O)N(C)C)CO3)CC2)C1)C(C)C] | 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 50 | 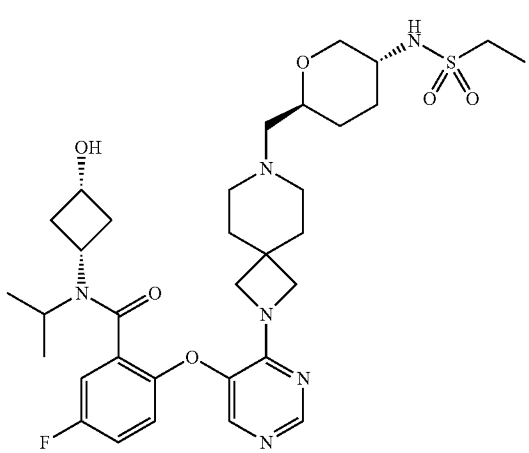 [SMILES: CCS(=O)(=O)N[C@@H]1CC[C@@H](CN2CCC3(CC2)CN(c2ncncc2Oc2ccc(F)cc2C(=O)N(C(C)C)[C@H]2C[C@@H](O)C2)C3)OC1] | 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((1s,3s)-3-hydroxycyclobutyl)-N-isopropylbenzamide |

TABLE 1-continued

Representative Compounds of the Present Disclosure

| Compound | Structure | IUPAC Name |
|---|---|---|
| 51 | 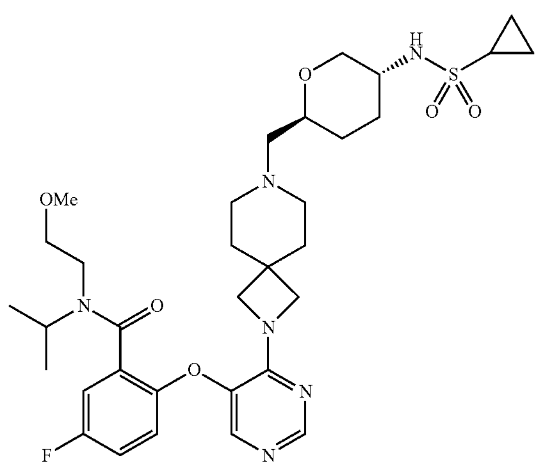 [SMILES: COCCN(C(=O)c1cc(F)ccc1Oc1cncnc1N1CC2(CCN(C[C@@H]3CC[C@@H](NS(=O)(=O)C4CC4)CO3)CC2)C1)C(C)C] | 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide |
| 52 | 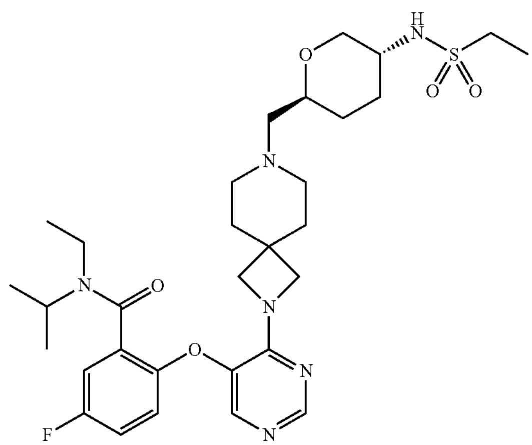 | N-ethyl-2-((4-(7-(((2R,5S)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 53 | 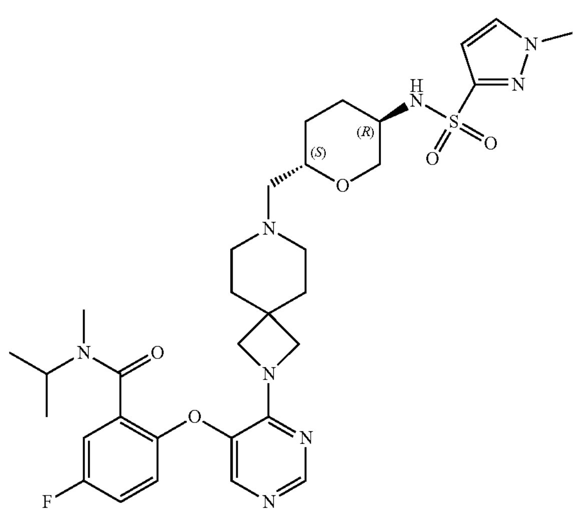 | Fluoro-N-isopropyl-N-methyl-2-((4-(7-(((2S,5R)-5-((1-methyl-1H-pyrazole)-3-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 54 | 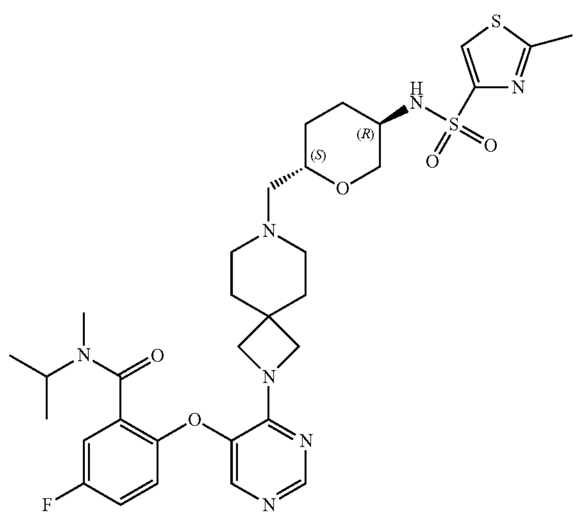 | 5-Fluoro-N-isopropyl-N-methyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)benzamide |
| 55 | 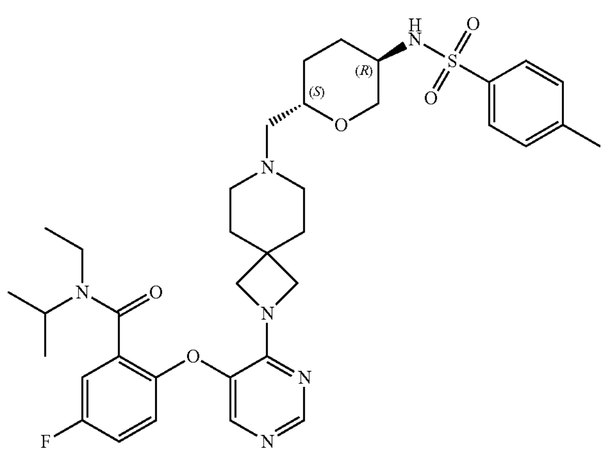 | N-Ethyl-5-fluoro-N-isopropyl-2-((4-(7-(((2S,5R)-5-((4-methylphenyl)sulfonamido)tetrahydro-2H-pyran-2-yl)methyl)-2,7-diazaspiro[3.5]nonan-2-yl)pyrimidin-5-yl)oxy)benzamide |
| 56 | 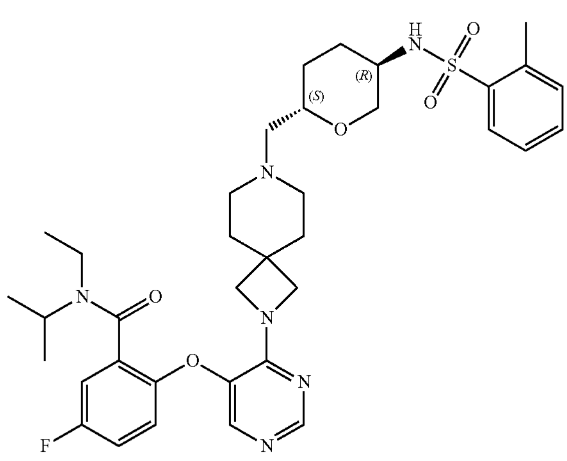 | N-Ethyl-5-fluoro-N-isopropyl-2-((4-(7-(((2S,5R)-5-((2-methylphenyl)sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 57 | 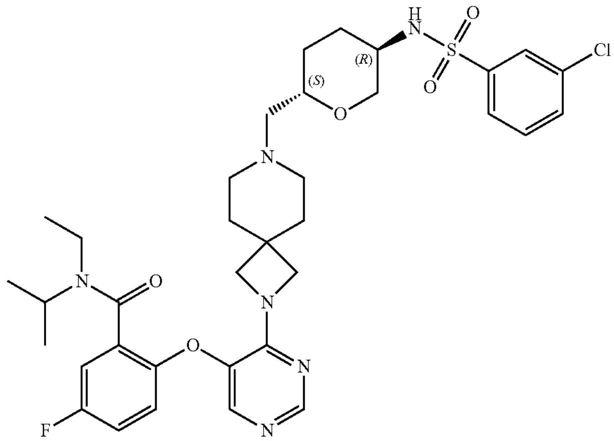 | 2-((4-(7-(((2S,5R)-5-((3-Chlorophenyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 58 | 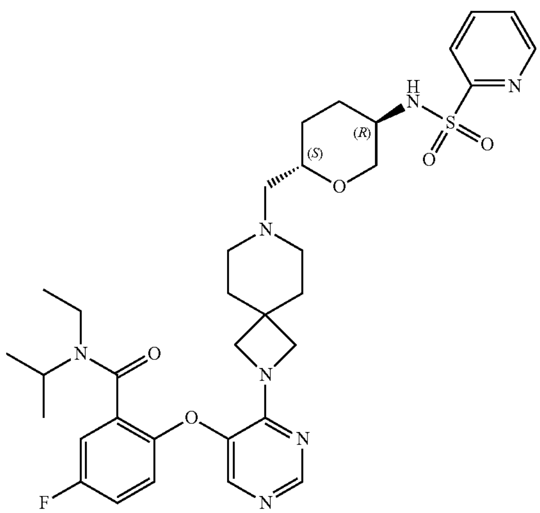 | N-ethyl-5-fluoro-N-isopropyl-2-((4-(7-(((2S,5R)-5-(pyridine-2-sulfonamido)tetrahydro-2H-pyran-2-yl)methyl)-2,7-diazaspiro[3.5]nonan-2-yl)pyrimidin-5-yl)oxy)benzamide |
| 59 | 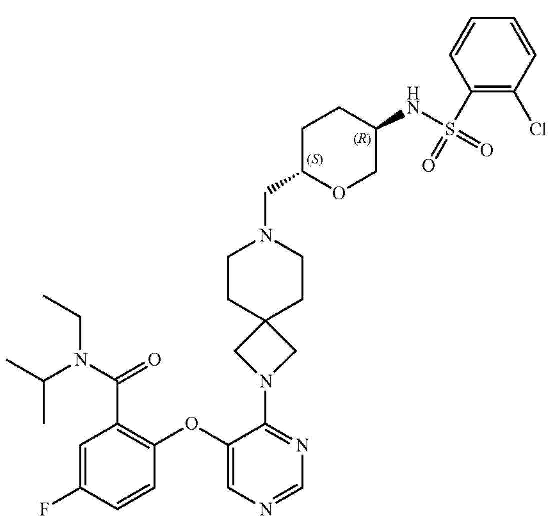 | 2-((4-(7-(((2S,5R)-5-((2-Chlorophenyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |

TABLE 1-continued

Representative Compounds of the Present Disclosure

| Compound | Structure | IUPAC Name |
|---|---|---|
| 60 | 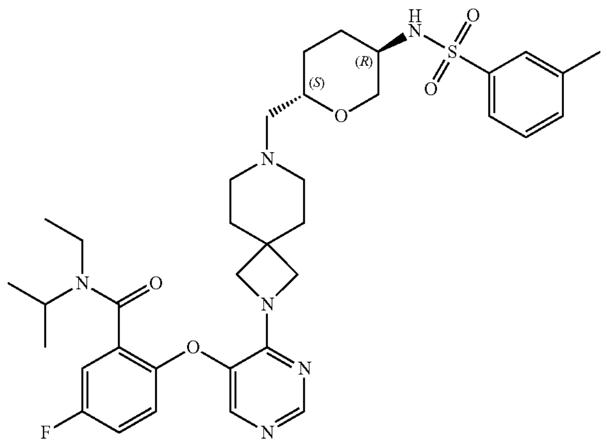 | N-ethyl-5-fluoro-N-isopropyl-2-((4-(7-(((2S,5R)-5-((3-methylphenyl)sulfonamido)tetrahydro-2H-pyran-2-yl)methyl)-2,7-diazaspiro[3.5]nonan-2-yl)pyrimidin-5-yl)oxy)benzamide |
| 61 | 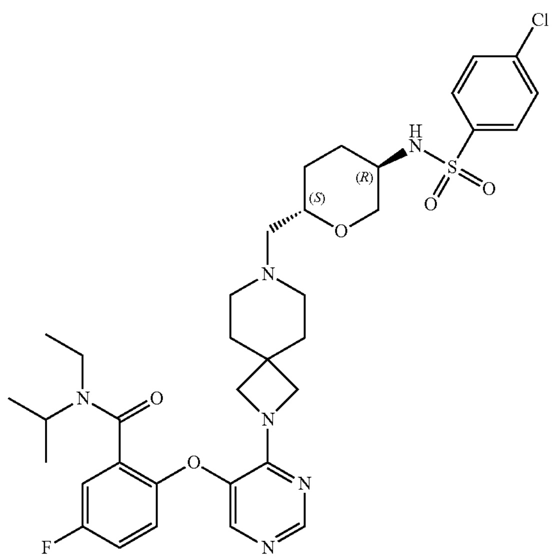 | 2-((4-(7-(((2S,5R)-5-((4-Chlorophenyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 62 | 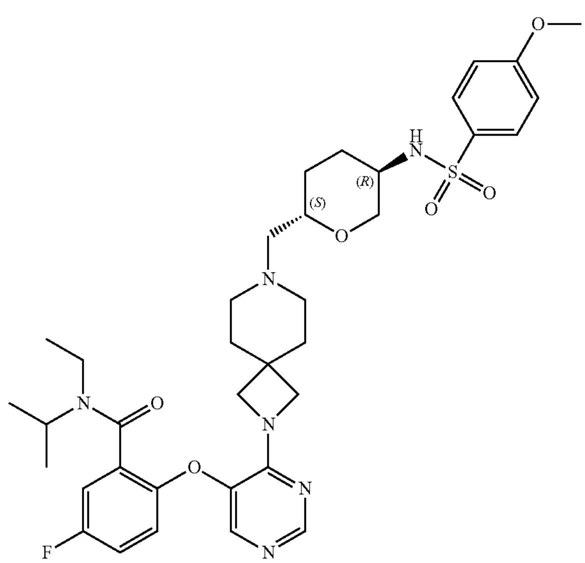 | N-Ethyl-5-fluoro-N-isopropyl-2-((4-(7-(((2S,5R)-5-((4-methoxyphenyl)sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 63 | 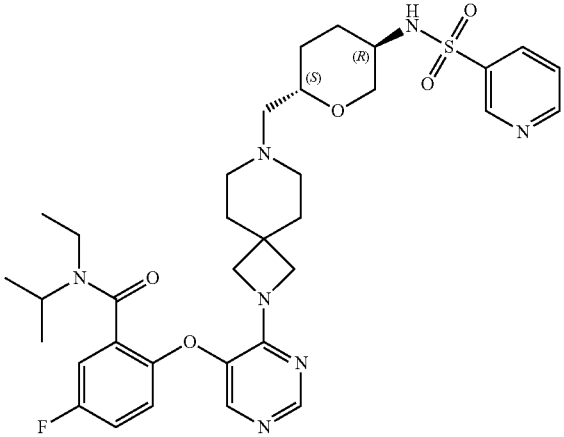 | N-Ethyl-5-fluoro-N-isopropyl-2-((4-(7-(((2S,5R)-5-(pyridine-3-sulfonamido)tetrahydro-2H-pyran-2-yl)methyl)-2,7-diazaspiro[3.5]nonan-2-yl)pyrimidin-5-yl)oxy)benzamide |
| 64 | 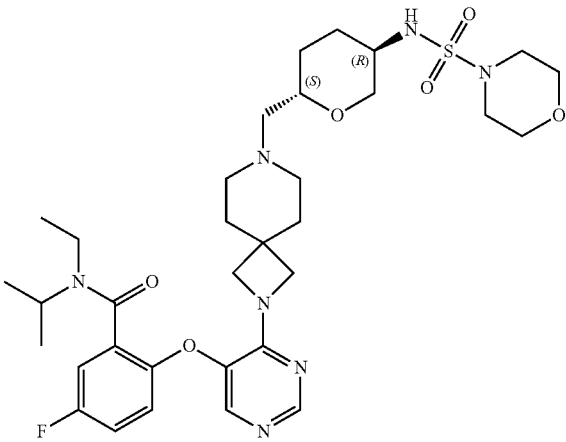 | N-Ethyl-5-fluoro-N-isopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)benzamide |
| 65 | 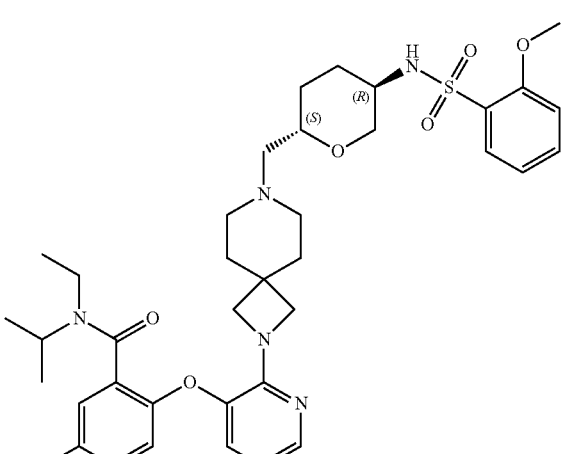 | N-Ethyl-5-fluoro-N-isopropyl-2-((4-(7-(((2S,5R)-5-((2-methoxyphenyl)sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 66 | 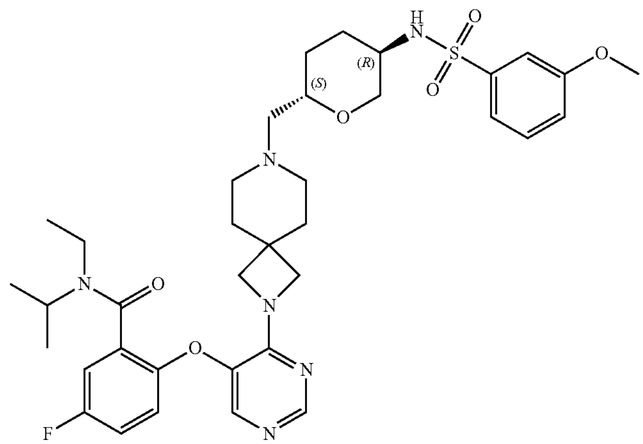 | N-Ethyl-5-fluoro-N-isopropyl-2-((4-(7-(((2S,5R)-5-((3-methoxyphenyl)sulfonamido)tetrahydro-2H-pyran-2-yl)methyl)-2,7-diazaspiro[3.5]nonan-2-yl)pyrimidin-5-yl)oxy)benzamide |
| 67 | 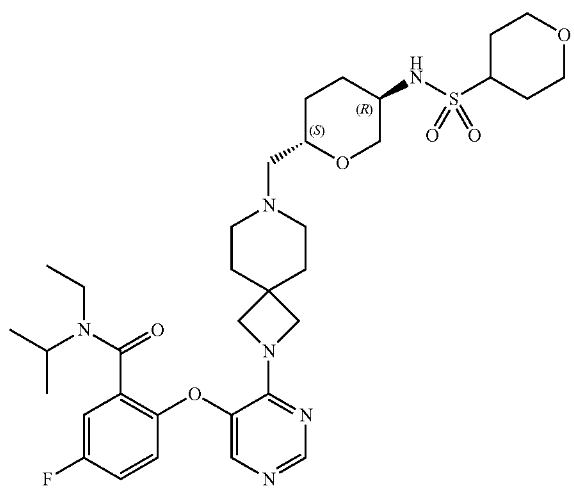 | N-Ethyl-5-fluoro-N-isopropyl-2-((4-(7-(((2S,5R)-5-((tetrahydro-2H-pyran)-4-sulfonamido)tetrahydro-2H-pyran-2-yl)methyl)-2,7-diazaspiro[3.5]nonan-2-yl)pyrimidin-5-yl)oxy)benzamide |
| 68 | 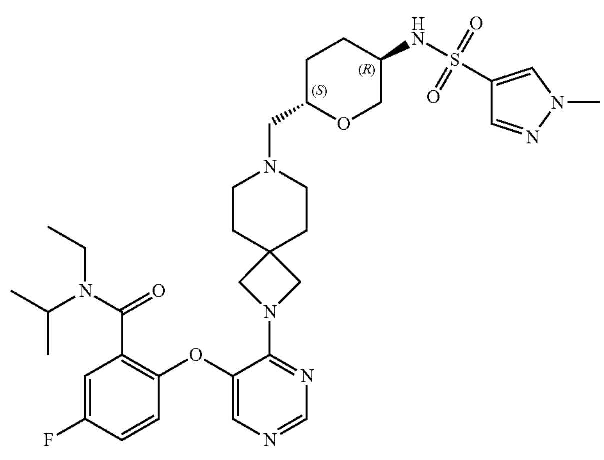 | N-Ethyl-5-fluoro-N-isopropyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 69 | 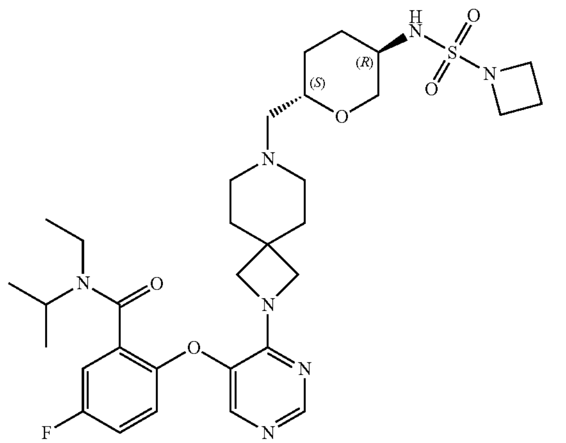 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 70 | 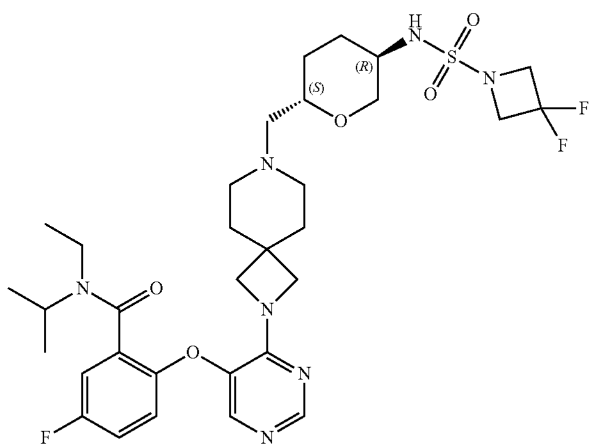 | 2-((4-(7-(((2S,5R)-5-((3,3-Difluoroazetidine)-1-sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 71 | 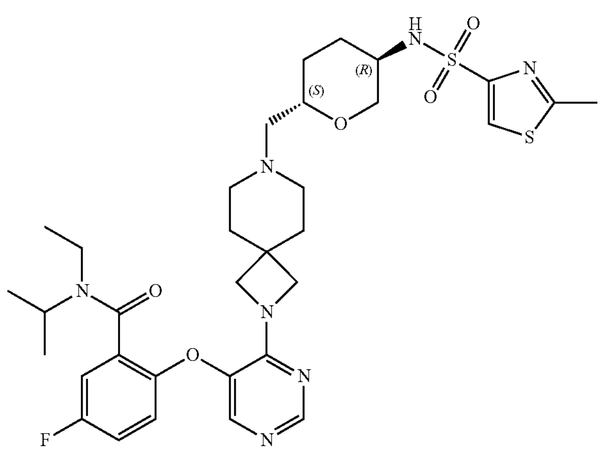 | N-Ethyl-5-fluoro-N-isopropyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 72 | 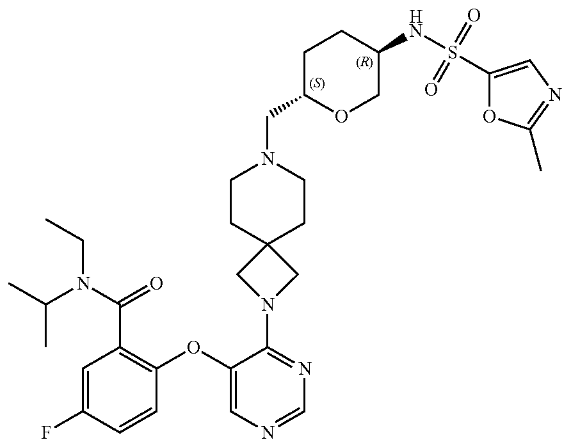 | N-Ethyl-5-fluoro-N-isopropyl-2-((4-(7-(((2S,5R)-5-((2-methyloxazole)-5-sulfonamido)tetrahydro-2H-pyran-2-yl)methyl)-2,7-diazaspiro[3.5]nonan-2-yl)pyrimidin-5-yl)oxy)benzamide |
| 73 | 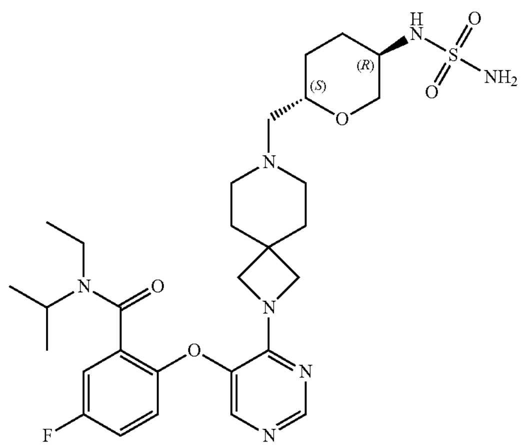 | N-Ethyl-5-fluoro-N-isopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide |
| 74 | 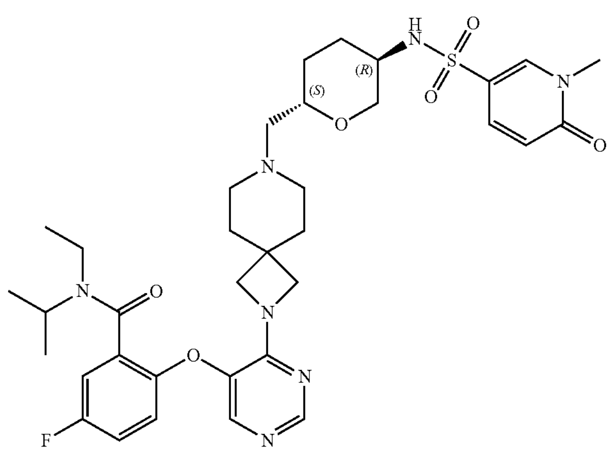 | N-Ethyl-5-fluoro-N-isopropyl-2-((4-(7-(((2S,5R)-5-((1-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 75 | 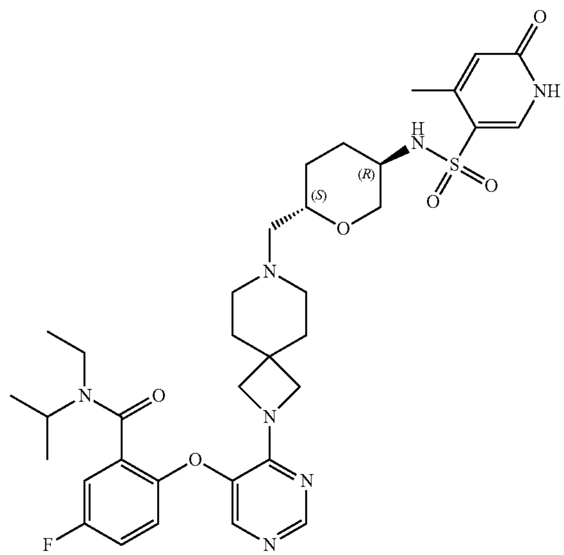 | N-Ethyl-5-fluoro-N-isopropyl-2-((4-(7-(((2S,5R)-5-((4-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy)benzamide |
| 76 | 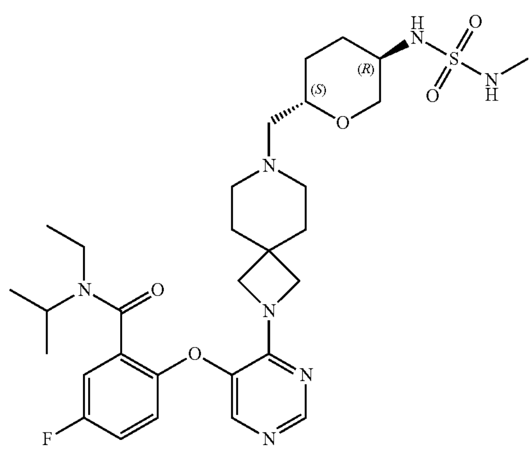 | N-Ethyl-5-fluoro-N-isopropyl-2-((4-(7-(((2S,5R)-5-((N-methylsulfamoyl)amino)tetrahydro-2H-pyran-2-yl)methyl)-2,7-diazaspiro[3.5]nonan-2-yl)pyrimidin-5-yl)oxy)benzamide |
| 77 | 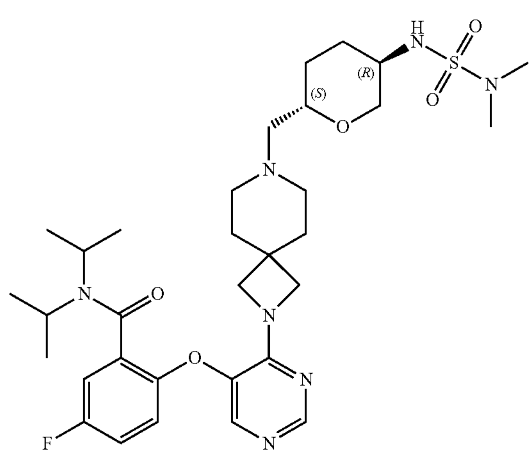 | 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N,N-diisopropylbenzamide |

TABLE 1-continued

Representative Compounds of the Present Disclosure

| Compound | Structure | IUPAC Name |
|---|---|---|
| 78 | 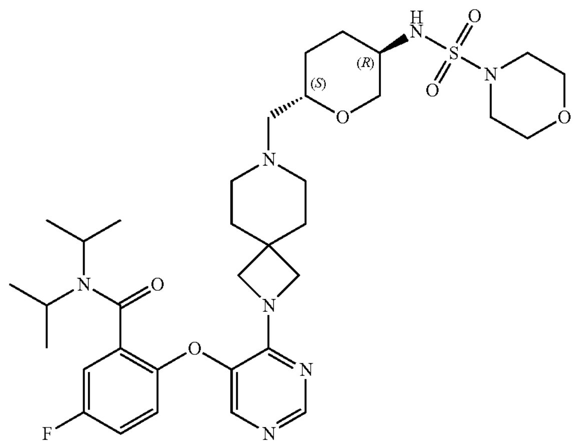 | 5-Fluoro-N,N-diisopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)benzamide |
| 79 | 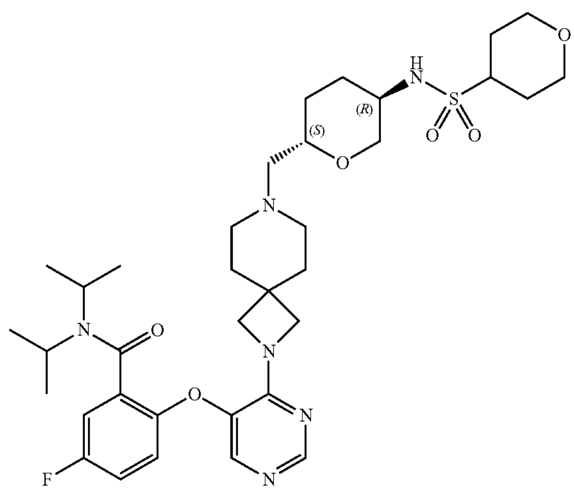 | 5-Fluoro-N,N-diisopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)benzamide |
| 80 | 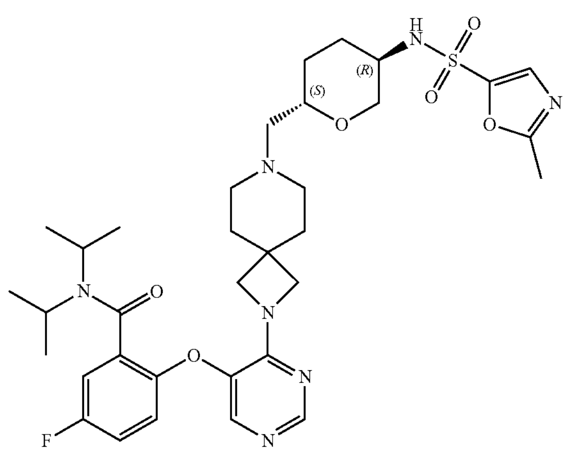 | 5-Fluoro-N,N-diisopropyl-2-((4-(7-(((2S,5R)-5-((2-methyloxazole)-5-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 81 | 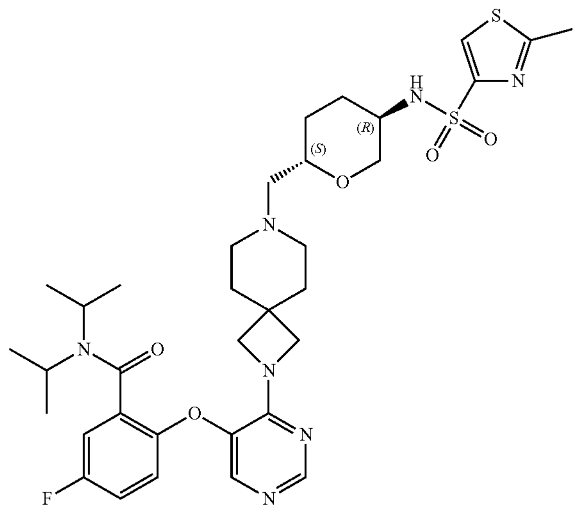 | 5-Fluoro-N,N-diisopropyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)benzamide |
| 82 | 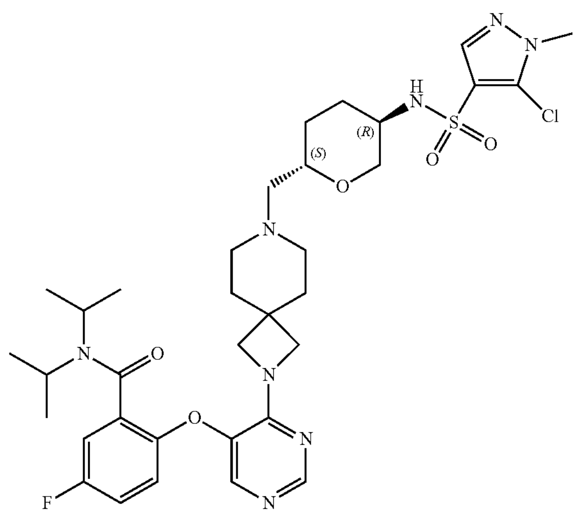 | 2-((4-(7-(((2S,5R)-5-((5-Chloro-1-methyl-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 83 | 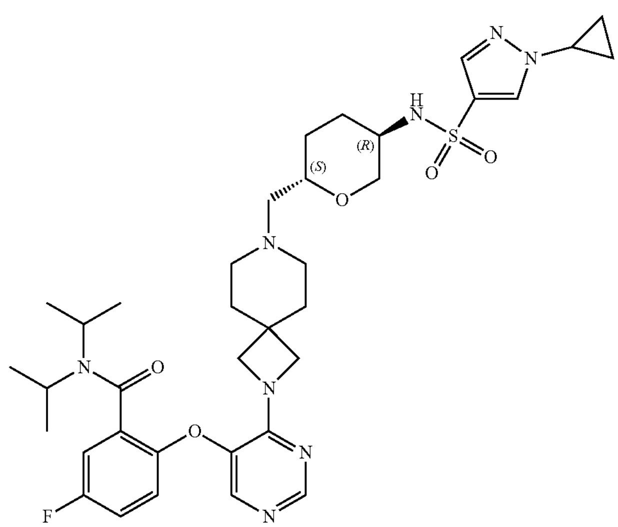 | 2-((4-(7-(((2S,5R)-5-((1-Cyclopropyl-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |

TABLE 1-continued

Representative Compounds of the Present Disclosure

| Compound | Structure | IUPAC Name |
|---|---|---|
| 84 | 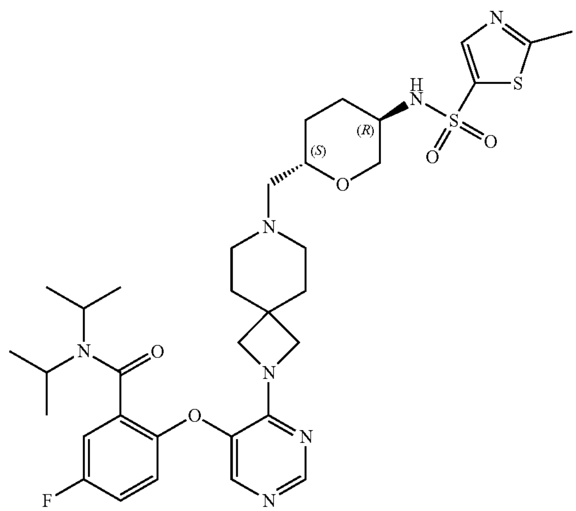 | 5-Fluoro-N,N-diisopropyl-2-((4-(7-(((2S,5R)-5-((2-methylthiazole)-5-sulfonamido)tetrahydro-2H-pyran-2-yl)methyl)-2,7-diazaspiro[3.5]nonan-2-yl)pyrimidin-5-yl)oxy)benzamide |
| 85 | 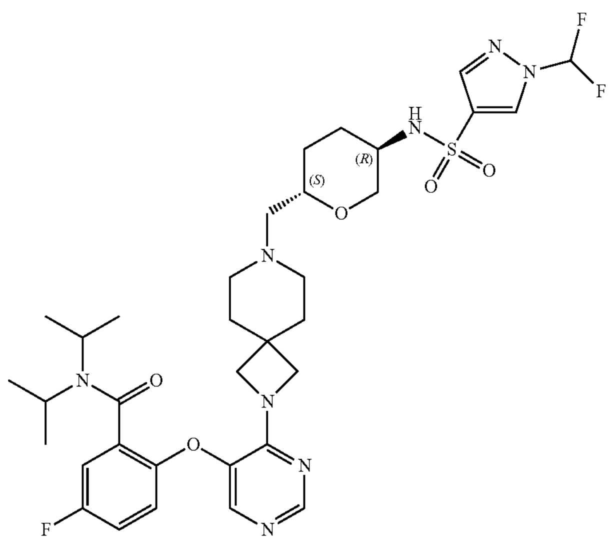 | 2-((4-(7-(((2S,5R)-5-((1-(Difluoromethyl)-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 86 | 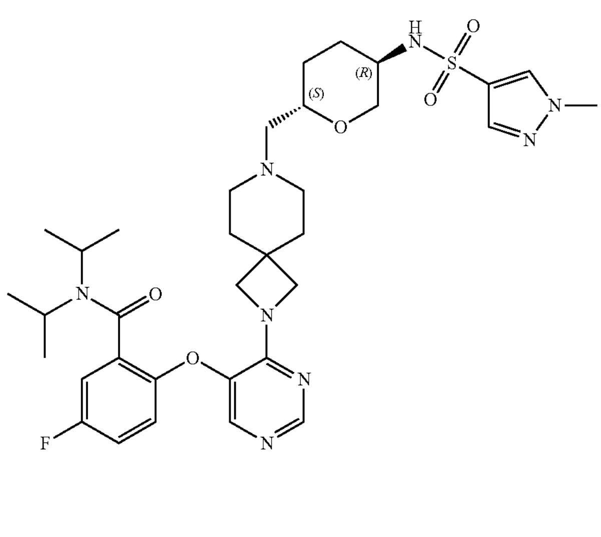 | 5-Fluoro-N,N-diisopropyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 87 | 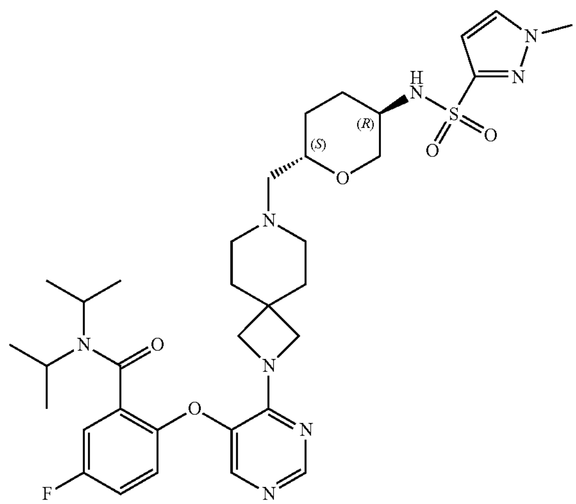 | 5-Fluoro-N,N-diisopropyl-2-((4-(7-(((2S,5R)-5-((1-methyl-1H-pyrazole)-3-sulfonamido)tetrahydro-2H-pyran-2-yl)methyl)-2,7-diazaspiro[3.5]nonan-2-yl)pyrimidin-5-yl)oxy)benzamide |
| 88 | 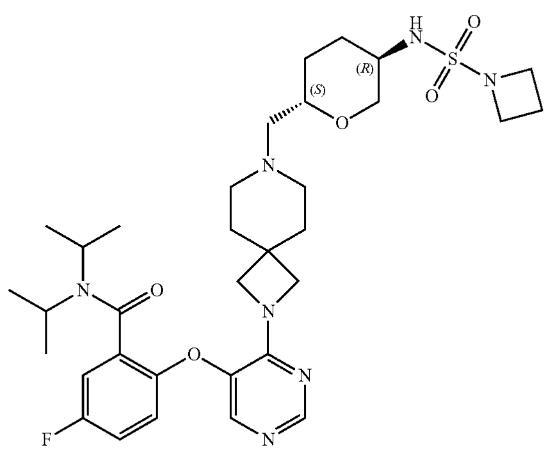 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 89 | 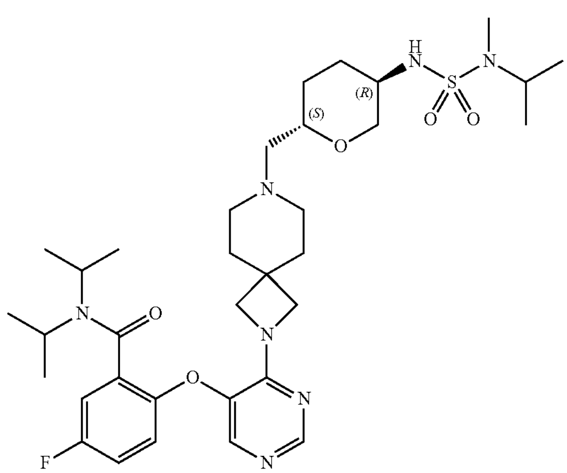 | 5-Fluoro-N,N-diisopropyl-2-((4-(7-(((2S,5R)-5-((N-isopropyl-N-methylsulfamoyl)amino)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 90 | 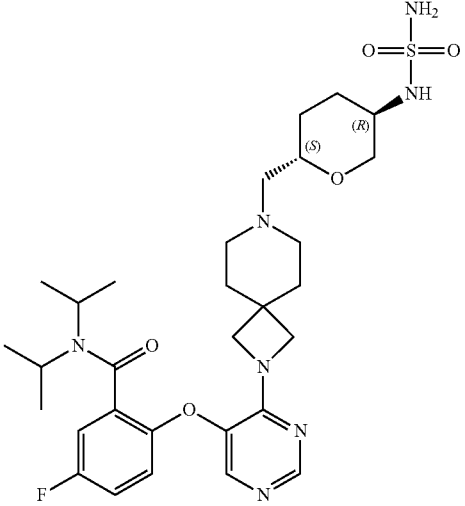 | 5-Fluoro-N,N-diisopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide |
| 91 | 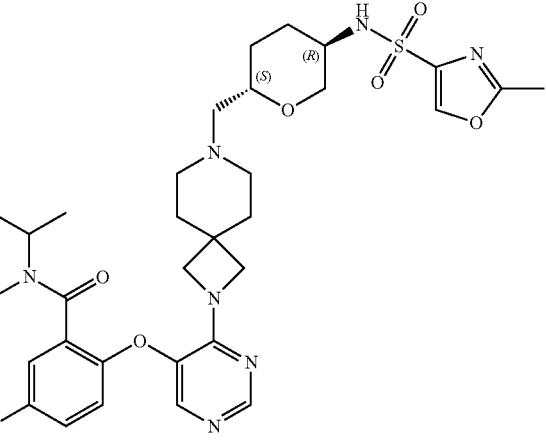 | 5-Fluoro-N,N-diisopropyl-2-((4-(7-(((2S,5R)-5-((2-methyloxazole)-4-sulfonamido)tetrahydro-2H-pyran-2-yl)methyl)-2,7-diazaspiro[3.5]nonan-2-yl)pyrimidin-5-yl)oxy)benzamide |
| 92 | 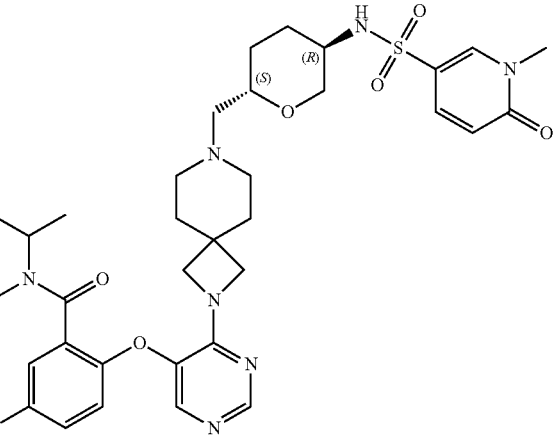 | 5-Fluoro-N,N-diisopropyl-2-((4-(7-(((2S,5R)-5-((1-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy)benzamide |

/ TABLE 1-continued

Representative Compounds of the Present Disclosure

| Compound | Structure | IUPAC Name |
|---|---|---|
| 93 | 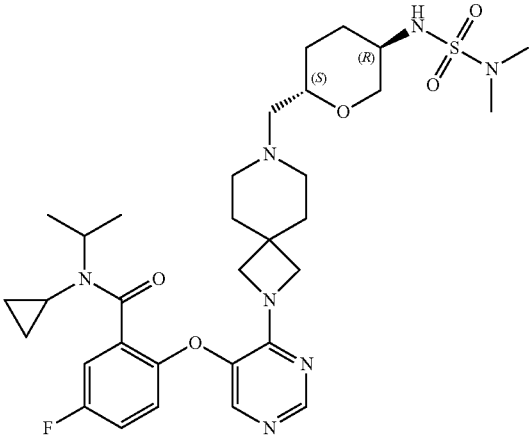 | N-Cyclopropyl-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |
| 94 | 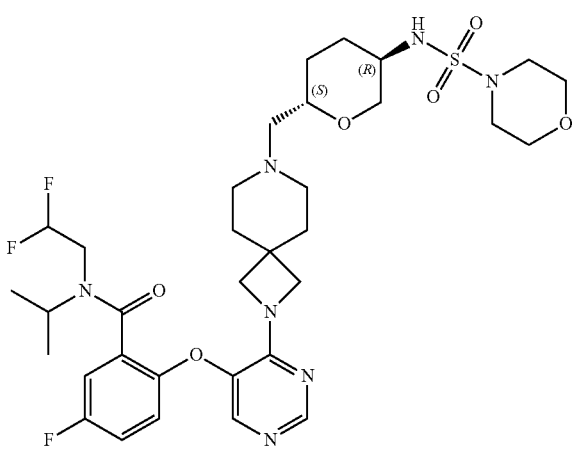 | N-(2,2-Difluoroethyl)-5-fluoro-N-isopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)benzamide |
| 95 | 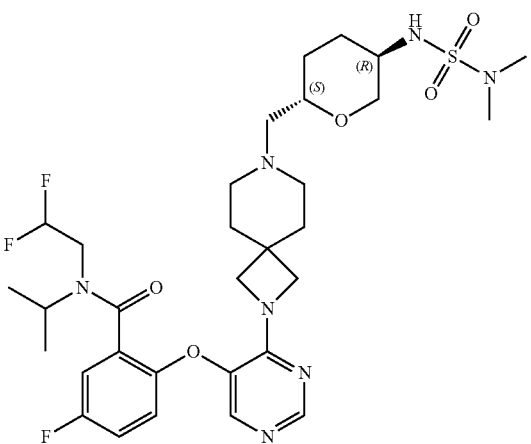 | N-(2,2-Difluoroethyl)-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |

TABLE 1-continued

Representative Compounds of the Present Disclosure

| Compound | Structure | IUPAC Name |
|---|---|---|
| 96 | 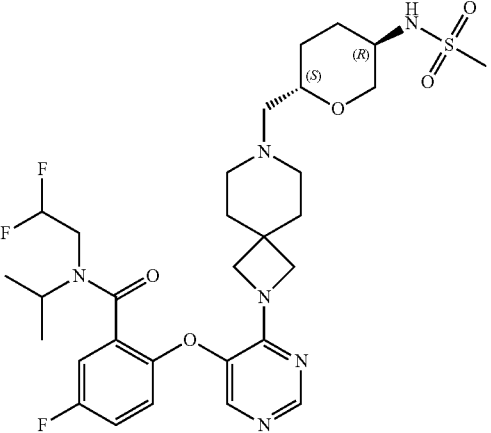 | N-(2,2-Difluoroethyl)-5-fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide |
| 97 | 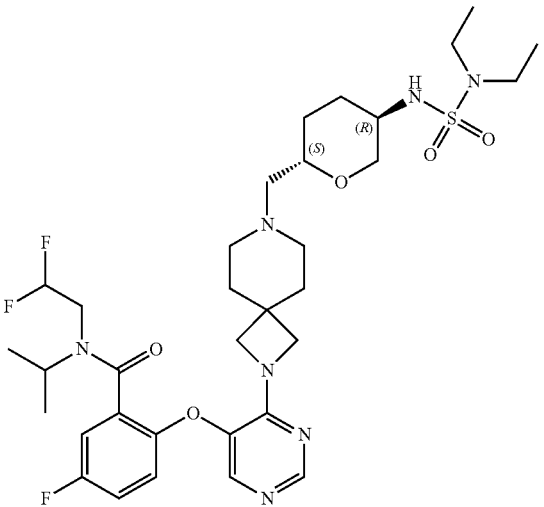 | 2-((4-(7-(((2S,5R)-5-((N,N-Diethylsulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide |
| 98 | 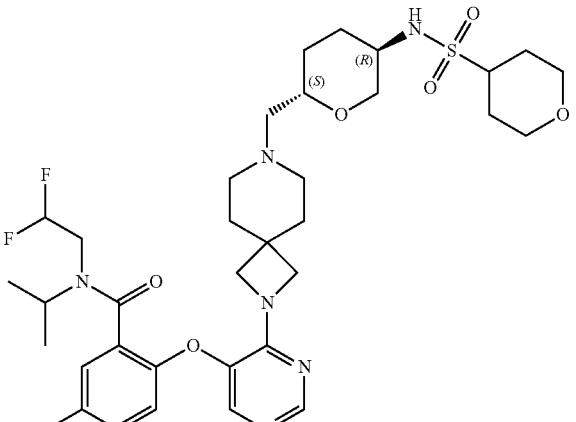 | N-(2,2-Difluoroethyl)-5-fluoro-N-isopropyl-2-((4-(7-(((2S,5R)-5-((tetrahydro-2H-pyran)-4-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 99 | 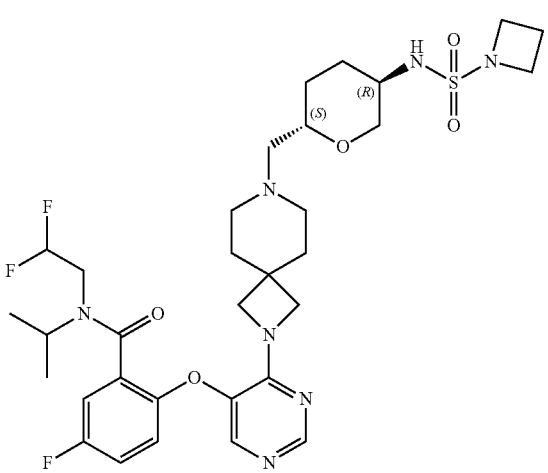 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide |
| 100 | 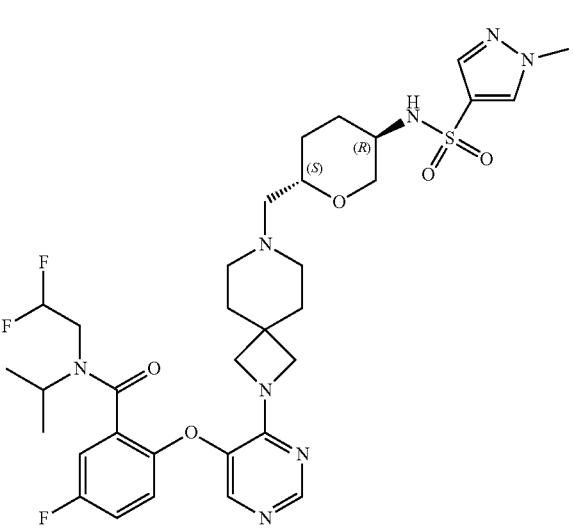 | N-(2,2-Difluoroethyl)-5-fluoro-N-isopropyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide |
| 101 | 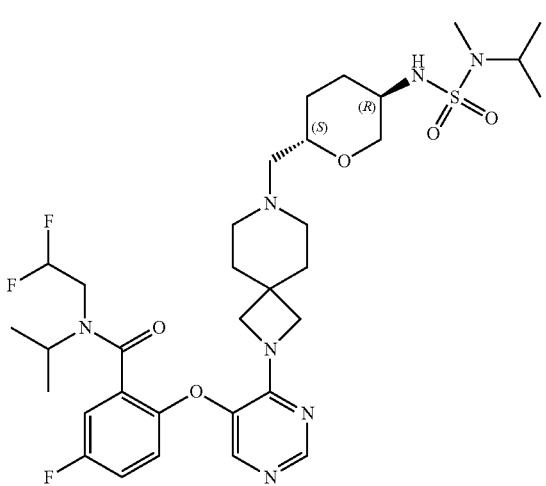 | N-(2,2-Difluoroethyl)-5-fluoro-N-isopropyl-2-((4-(7-(((2S,5R)-5-((N-isopropyl-N-methylsulfamoyl)amino)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 102 | 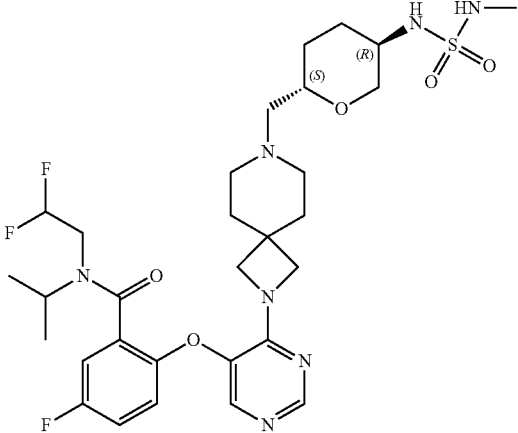 | N-(2,2-Difluoroethyl)-5-fluoro-N-isopropyl-2-((4-(7-(((2S,5R)-5-((N-methylsulfamoyl)amino)tetrahydro-2H-pyran-2-yl)methyl)-2,7-diazaspiro[3.5]nonan-2-yl)pyrimidin-5-yl)oxy)benzamide |
| 103 | 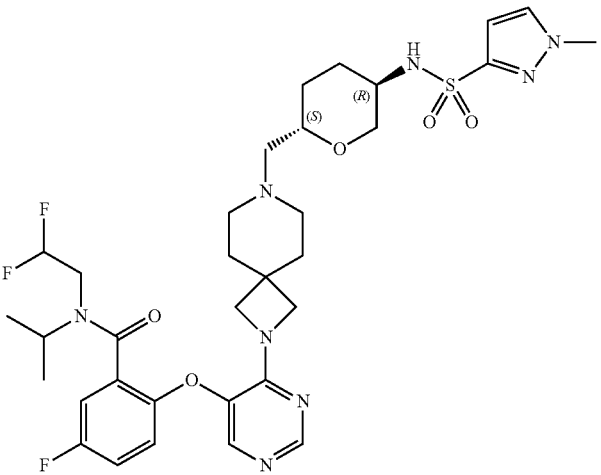 | N-(2,2-Difluoroethyl)-5-fluoro-N-isopropyl-2-((4-(7-(((2S,5R)-5-((1-methyl-1H-pyrazole)-3-sulfonamido)tetrahydro-2H-pyran-2-yl)methyl)-2,7-diazaspiro[3.5]nonan-2-yl)pyrimidin-5-yl)oxy)benzamide |
| 104 | 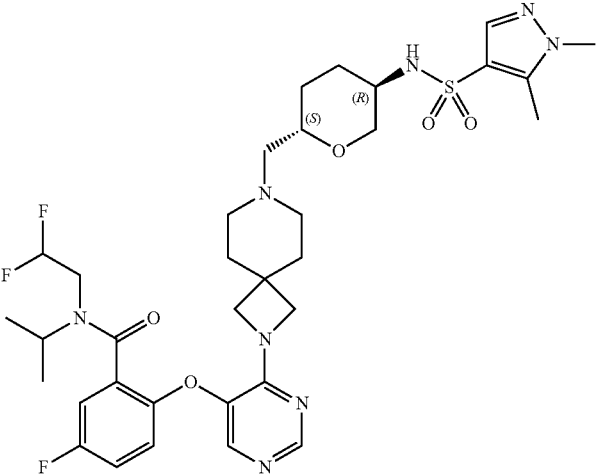 | N-(2,2-Difluoroethyl)-2-((4-(7-(((2S,5R)-5-((1,5-dimethyl-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |

TABLE 1-continued

Representative Compounds of the Present Disclosure

| Compound | Structure | IUPAC Name |
|---|---|---|
| 105 | 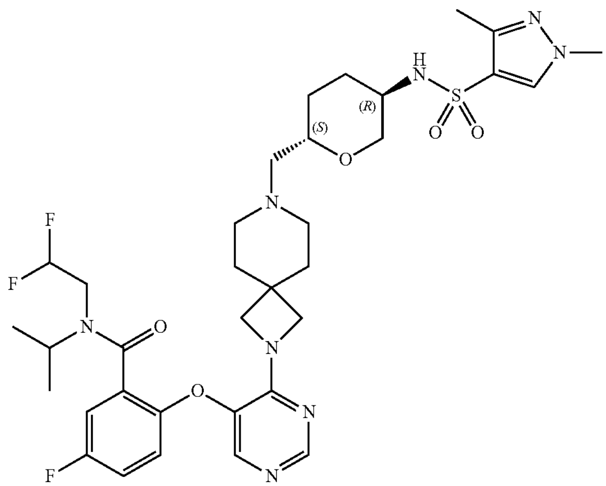 | N-(2,2-Difluoroethyl)-2-((4-(7-(((2S,5R)-5-((1,3-dimethyl-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 106 | 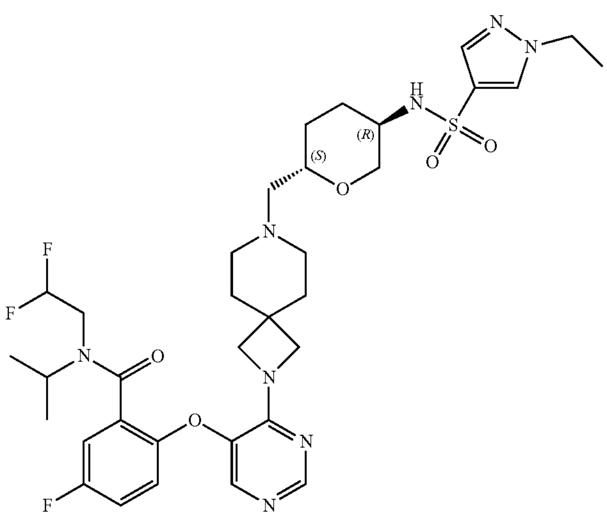 | N-(2,2-Difluoroethyl)-2-((4-(7-(((2S,5R)-5-((1-ethyl-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 107 | 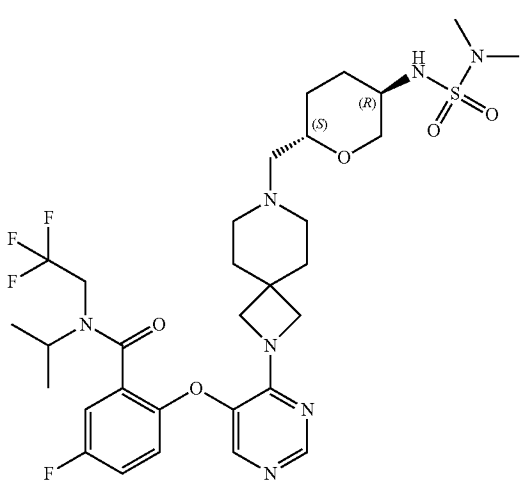 | 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-(2,2,2-trifluoroethyl)benzamide |

TABLE 1-continued

Representative Compounds of the Present Disclosure

| Compound | Structure | IUPAC Name |
|---|---|---|
| 108 | 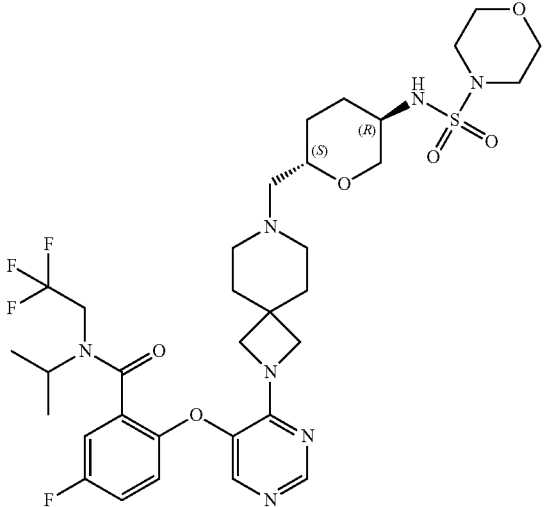 | 5-Fluoro-N-isopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)-N-(2,2,2-trifluoroethyl)benzamide |
| 109 | 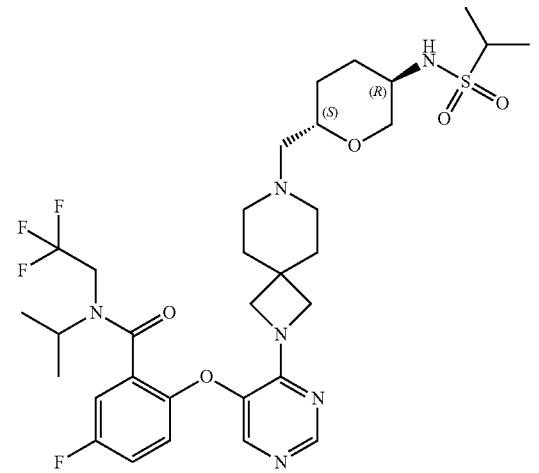 | 5-Fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)-N-(2,2,2-trifluoroethyl)benzamide |
| 110 | 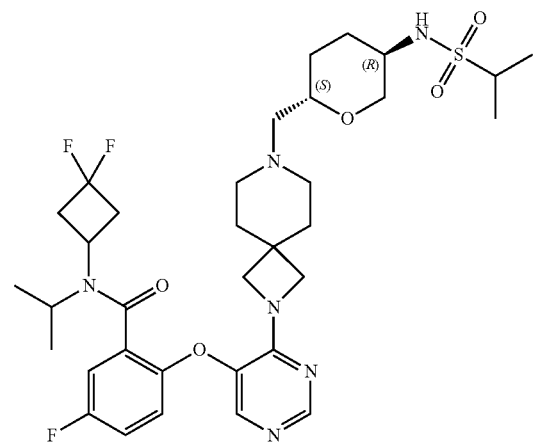 | N-(3,3-Difluorocyclobutyl)-5-fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 111 | 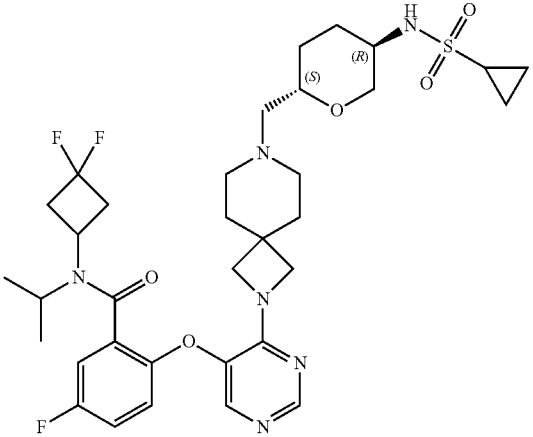 | 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-N-(3,3-difluorocyclobutyl)-5-fluoro-N-isopropylbenzamide |
| 112 | 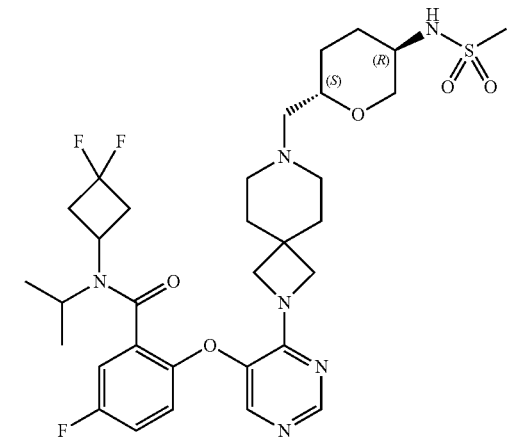 | N-(3,3-Difluorocyclobutyl)-5-fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide |
| 113 | 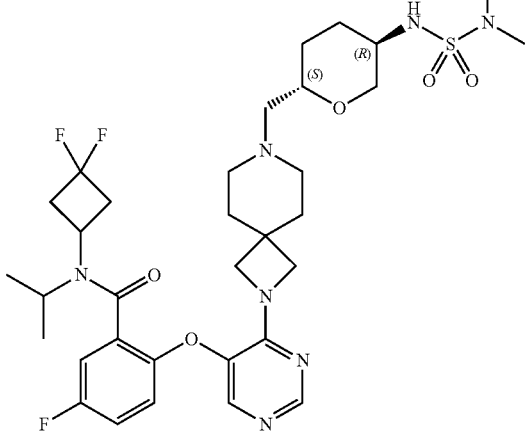 | N-(3,3-Difluorocyclobutyl)-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |

TABLE 1-continued

Representative Compounds of the Present Disclosure

| Compound | Structure | IUPAC Name |
|---|---|---|
| 114 | 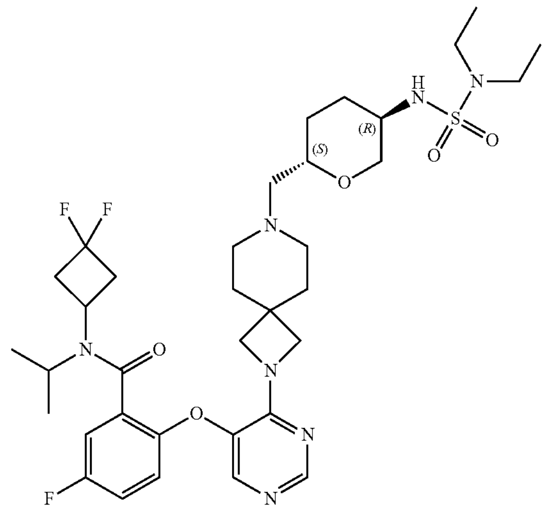 | 2-((4-(7-(((2S,5R)-5-((N,N-Diethylsulfamoyl)amino)tetrahydro-2H-pyran-2-yl)methyl)-2,7-diazaspiro[3.5]nonan-2-yl)pyrimidin-5-yl)oxy)-N-(3,3-difluorocyclobutyl)-5-fluoro-N-isopropylbenzamide |
| 115 | 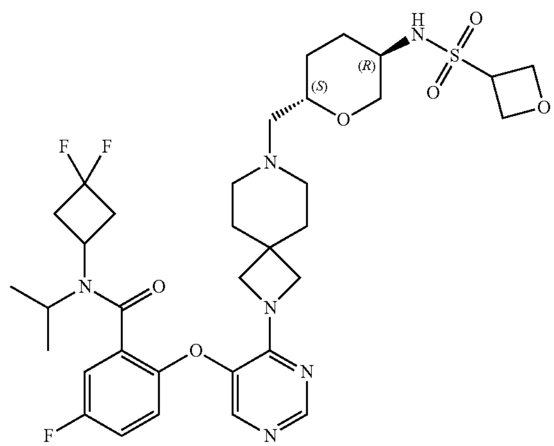 | N-(3,3-Difluorocyclobutyl)-5-fluoro-N-isopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide |
| 116 | 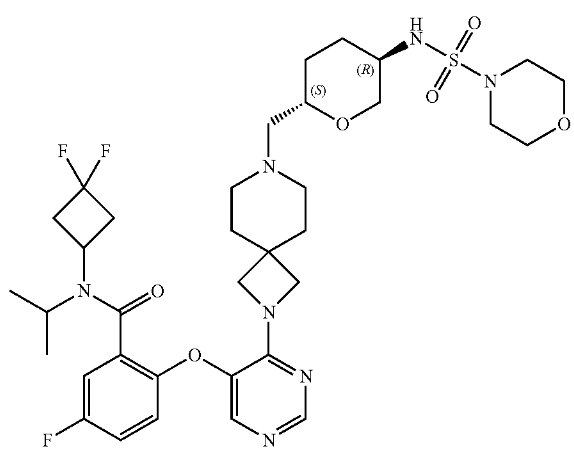 | N-(3,3-Difluorocyclobutyl)-5-fluoro-N-isopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 117 | 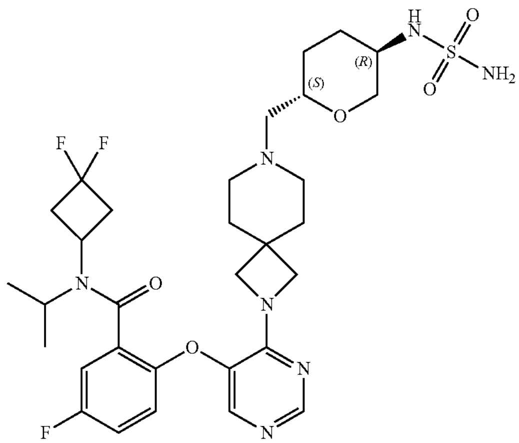 | N-(3,3-Difluorocyclobutyl)-5-fluoro-N-isopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide |
| 118 | 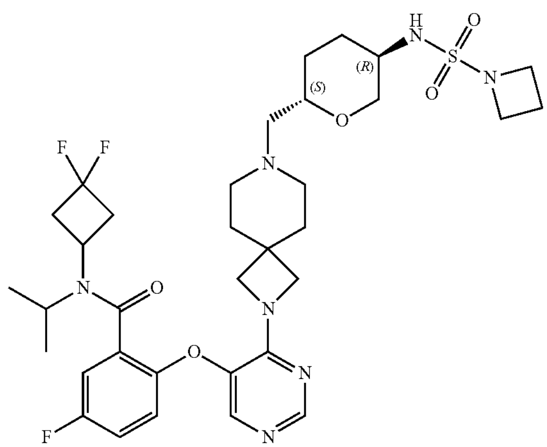 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-(3,3-difluorocyclobutyl)-5-fluoro-N-isopropylbenzamide |
| 119 | 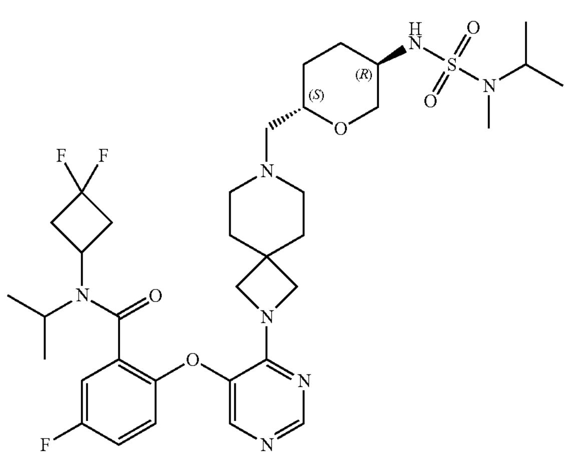 | N-(3,3-Difluorocyclobutyl)-5-fluoro-N-isopropyl-2-((4-(7-(((2S,5R)-5-((N-isopropyl-N-methylsulfamoyl)amino)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 120 | 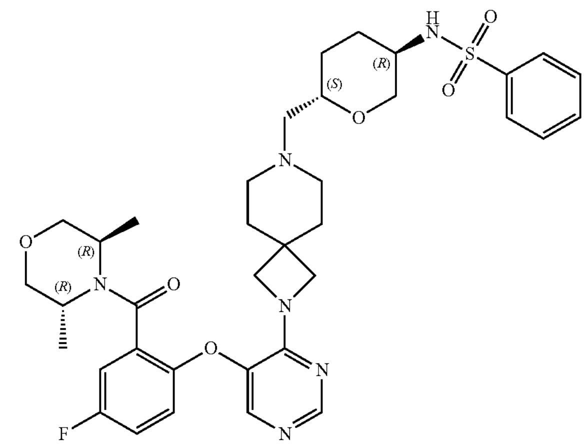 | N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)benzenesulfonamide |
| 121 | 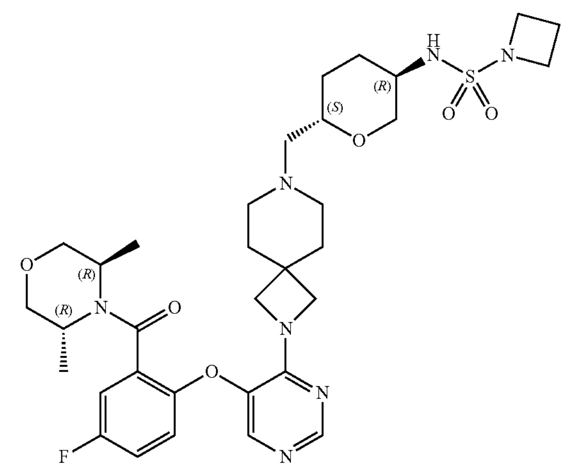 | N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)azetidine-1-sulfonamide |
| 122 | 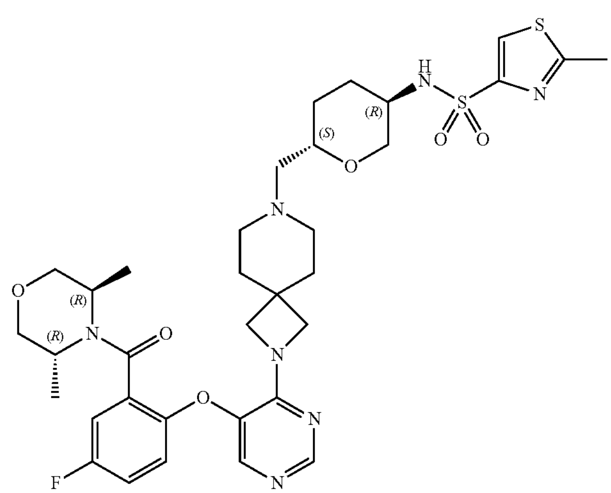 | N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-2-methylthiazole-4-sulfonamide |

TABLE 1-continued

Representative Compounds of the Present Disclosure

| Compound | Structure | IUPAC Name |
|---|---|---|
| 123 | 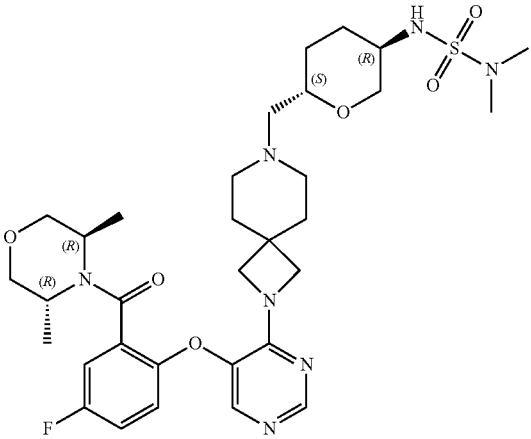 | {[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}dimethylamine |
| 124 | 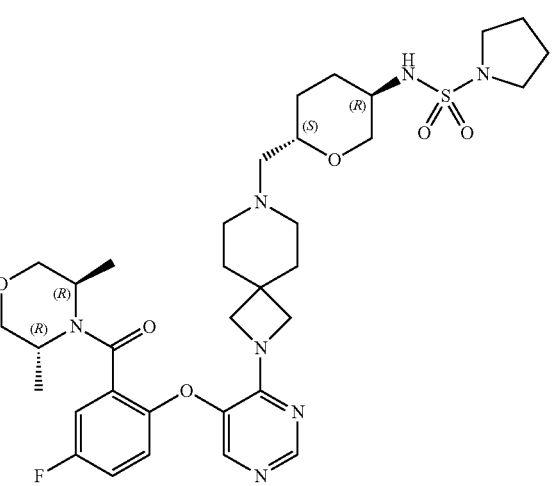 | N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)pyrrolidine-1-sulfonamide |
| 125 | 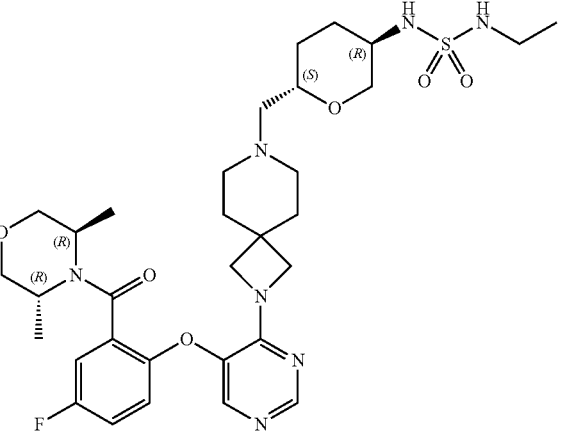 | {[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}(ethyl)amine |

TABLE 1-continued

Representative Compounds of the Present Disclosure

| Compound | Structure | IUPAC Name |
|---|---|---|
| 126 | 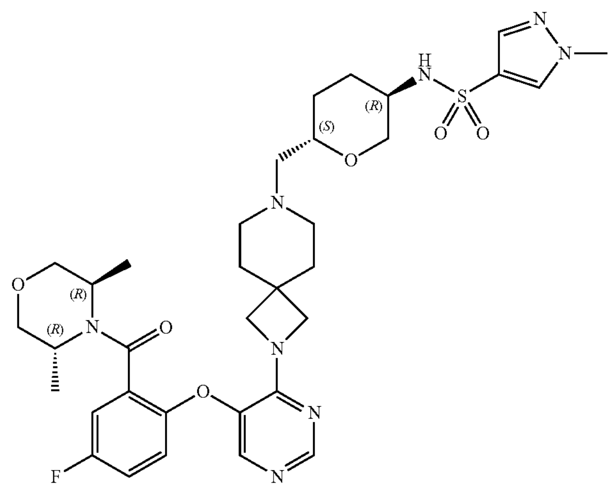 | N-(3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-1-methyl-1H-pyrazole-4-sulfonamide |
| 127 | 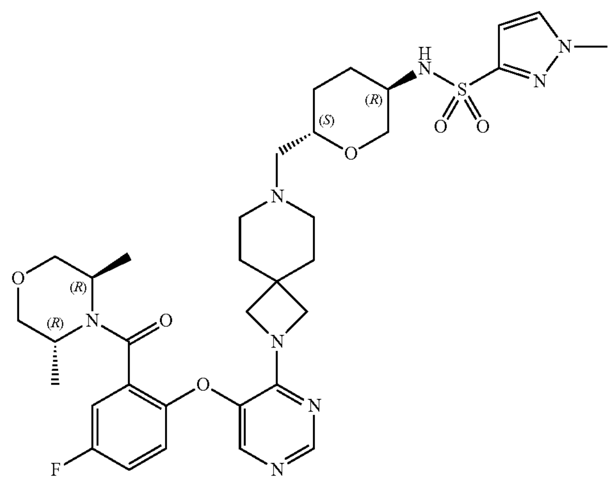 | N-(3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-1-methyl-1H-pyrazole-3-sulfonamide |
| 128 | 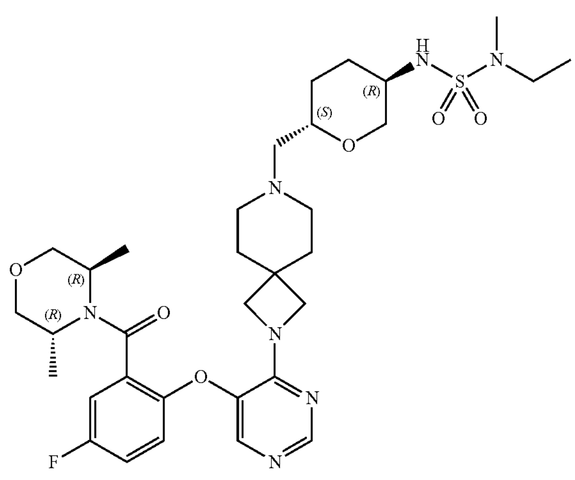 | {[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}(ethyl)methylamine |

TABLE 1-continued

Representative Compounds of the Present Disclosure

| Compound | Structure | IUPAC Name |
|---|---|---|
| 129 | 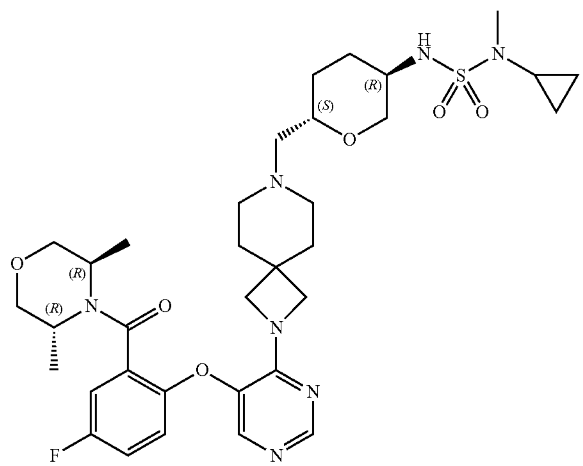 | N-{[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}-N-methylcyclopropanamine |
| 130 | 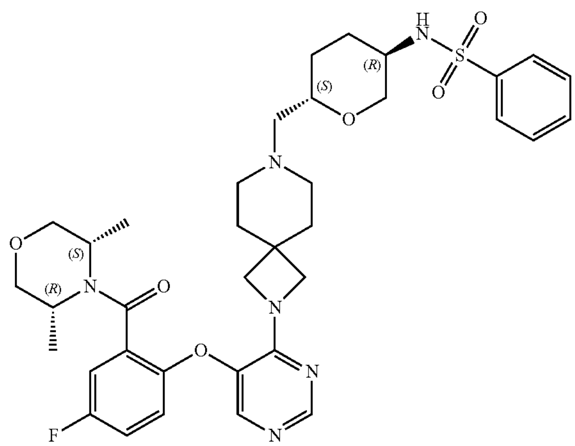 | N-((3R,6S)-6-((2-(5-(2-((3S,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)benzenesulfonamide |
| 131 | 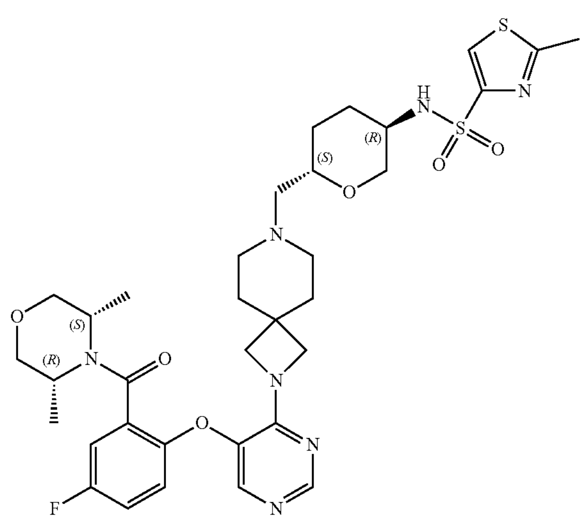 | N-((3R,6S)-6-((2-(5-(2-((3S,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-2-methylthiazole-4-sulfonamide |

TABLE 1-continued

Representative Compounds of the Present Disclosure

| Compound | Structure | IUPAC Name |
|---|---|---|
| 132 | 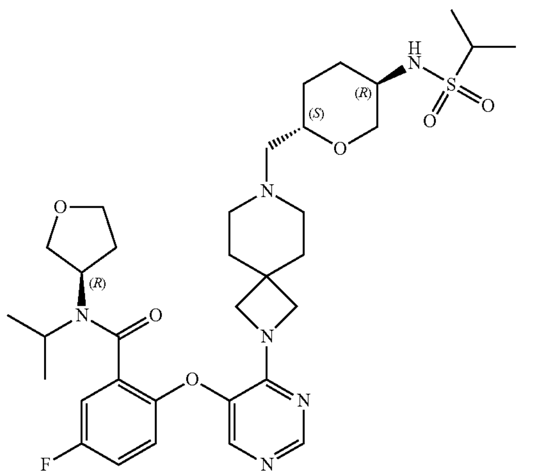 | 5-Fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)-N-((R)-tetrahydrofuran-3-yl)benzamide |
| 133 | 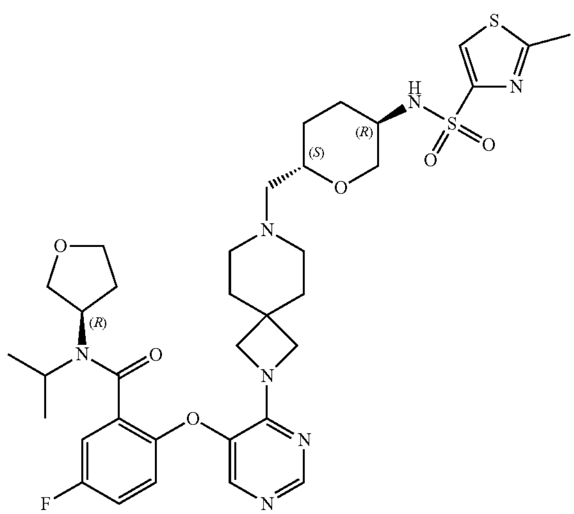 | 5-Fluoro-N-isopropyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)-N-((R)-tetrahydrofuran-3-yl)benzamide |
| 134 | 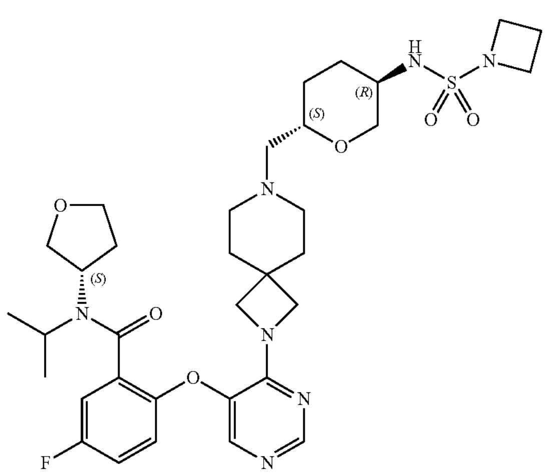 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N-isopropyl-N-((S)-tetrahydrofuran-3-yl)benzamide |

TABLE 1-continued

Representative Compounds of the Present Disclosure

| Compound | Structure | IUPAC Name |
|---|---|---|
| 135 | 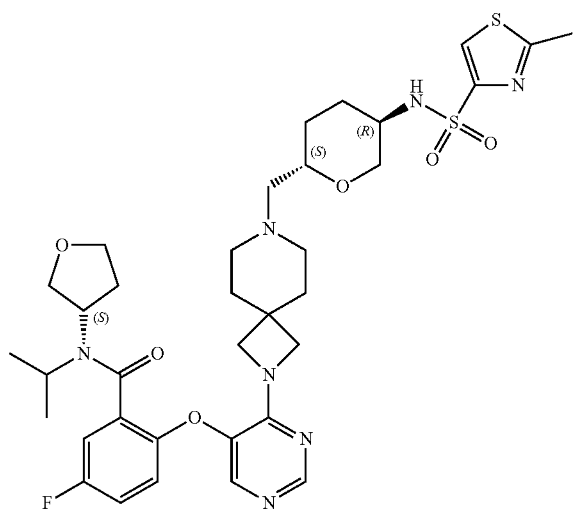 | 5-Fluoro-N-isopropyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)-N-((S)-tetrahydrofuran-3-yl)benzamide |
| 136 | 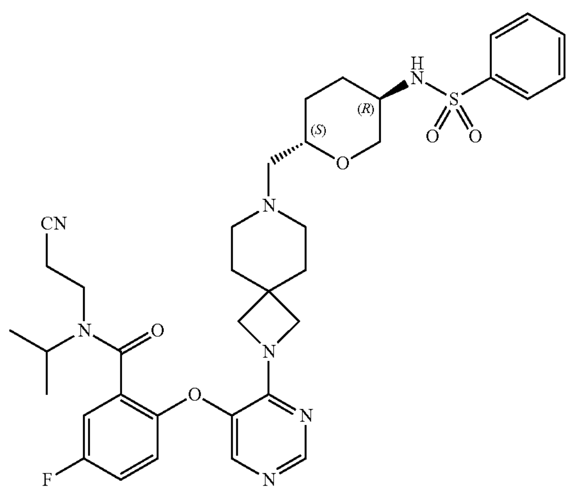 | N-(2-Cyanoethyl)-5-fluoro-N-isopropyl-2-((4-(7-(((2S,5R)-5-(phenylsulfonamido)tetrahydro-2H-pyran-2-yl)methyl)-2,7-diazaspiro[3.5]nonan-2-yl)pyrimidin-5-yl)oxy)benzamide |
| 137 | 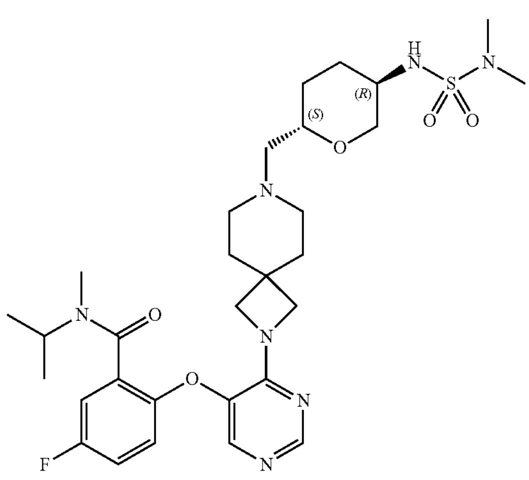 | 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-methylbenzamide |

TABLE 1-continued

Representative Compounds of the Present Disclosure

| Compound | Structure | IUPAC Name |
|---|---|---|
| 138 | 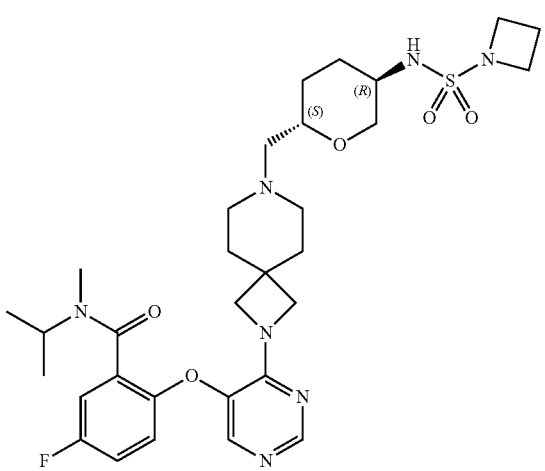 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N-isopropyl-N-methylbenzamide |
| 139 | 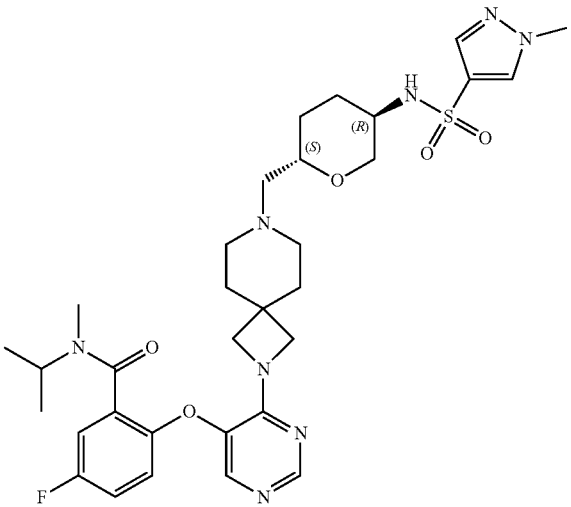 | 5-Fluoro-N-isopropyl-N-methyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide |
| 140 | 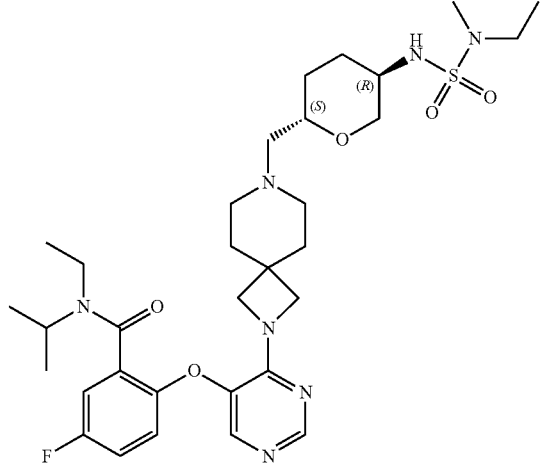 | N-Ethyl-2-((4-(7-(((2S,5R)-5-((N-ethyl-N-methylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |

TABLE 1-continued

Representative Compounds of the Present Disclosure

| Compound | Structure | IUPAC Name |
|---|---|---|
| 141 | 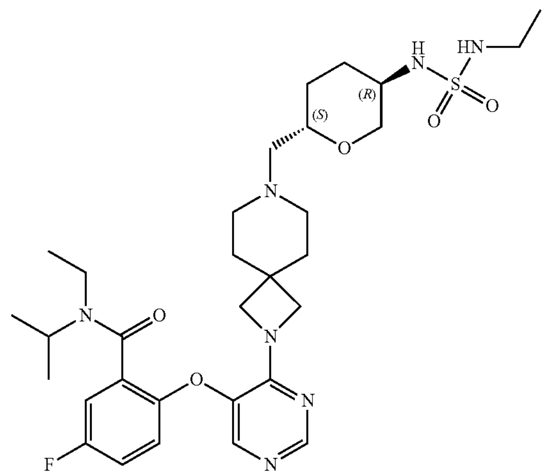 | N-Ethyl-2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |
| 142 | 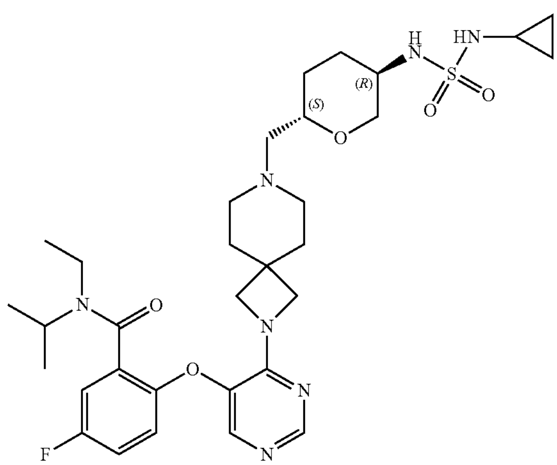 | 2-((4-(7-(((2S,5R)-5-((N-Cyclopropylsulfamoyl)amino)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |
| 143 | 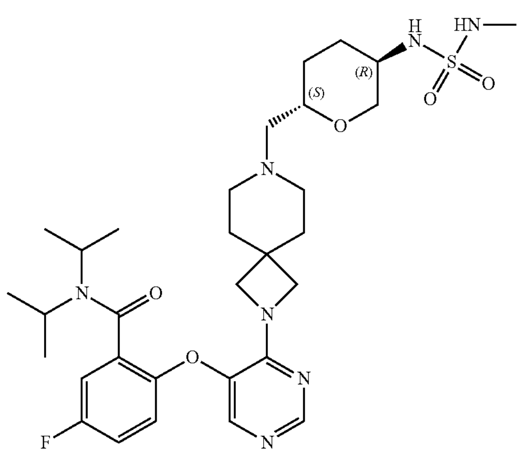 | 5-Fluoro-N,N-diisopropyl-2-((4-(7-(((2S,5R)-5-((N-methylsulfamoyl)amino)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 144 | 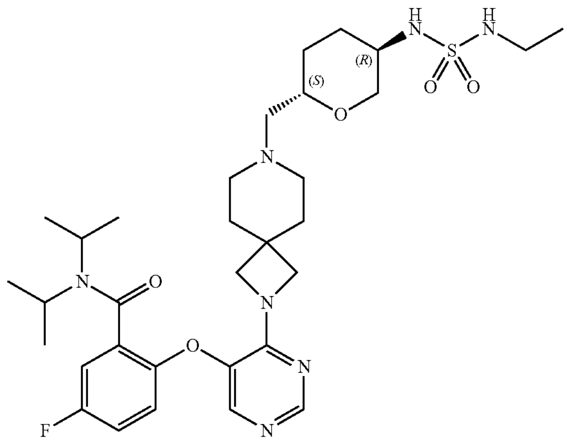 | 2-((4-(7-(((2S,5R)-5-((N-Ethylsulfamoyl)amino)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 145 | 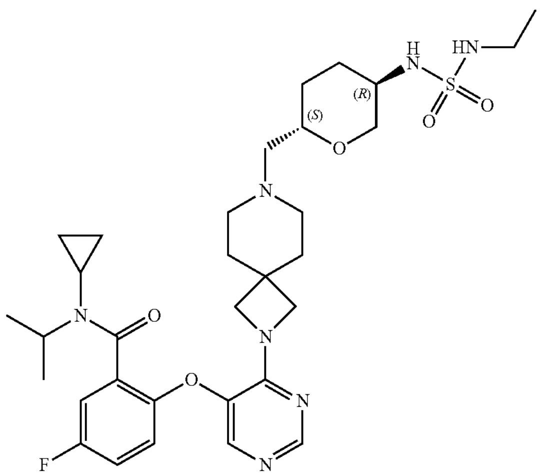 | N-Cyclopropyl-2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |
| 146 | 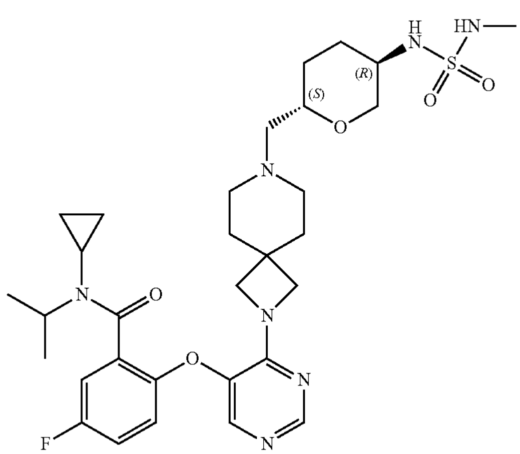 | N-Cyclopropyl-5-fluoro-N-isopropyl-2-((4-(7-(((2R,5S)-5-((N-methylsulfamoyl)amino)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 147 | 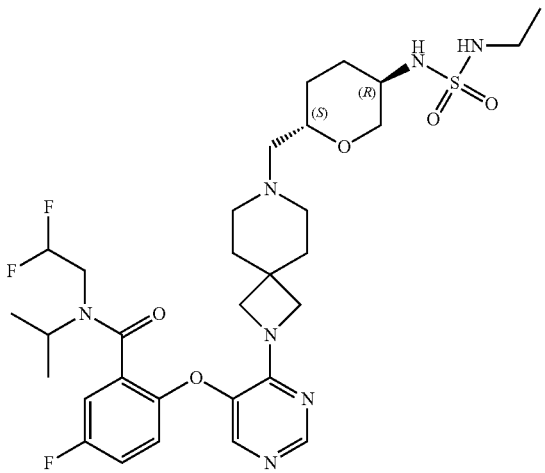 | N-(2,2-Difluoroethyl)-2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |
| 148 | 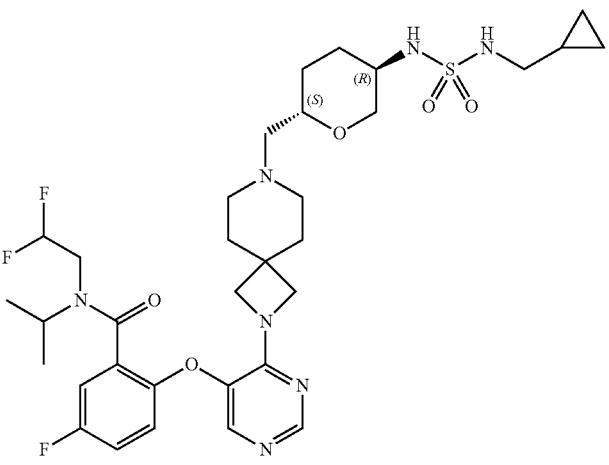 | 2-((4-(7-(((2S,5R)-5-((N-(Cyclopropylmethyl)sulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide |
| 149 | 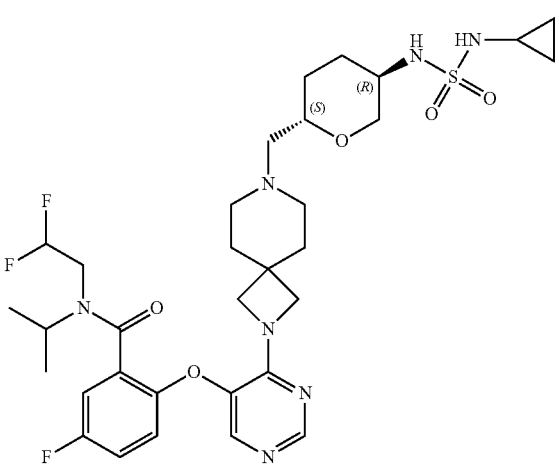 | 2-((4-(7-(((2S,5R)-5-((N-Cyclopropylsulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide |

TABLE 1-continued

Representative Compounds of the Present Disclosure

| Compound | Structure | IUPAC Name |
|---|---|---|
| 150 | 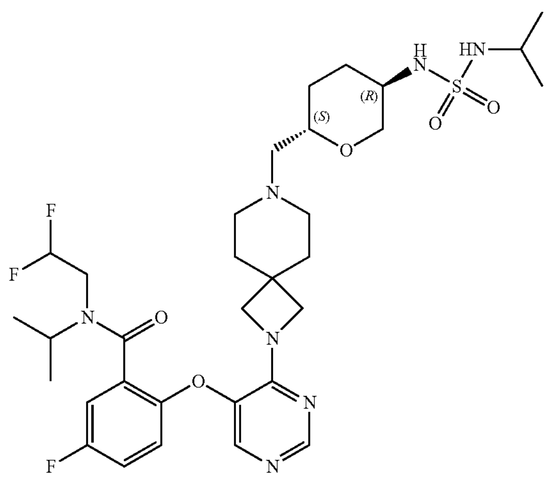 | N-(2,2-Difluoroethyl)-5-fluoro-N-isopropyl-2-((4-(7-(((2S,5R)-5-((N-isopropylsulfamoyl)amino)tetrahydro-2H-pyran-2-yl)methyl)-2,7-diazaspiro[3.5]nonan-2-yl)pyrimidin-5-yl)oxy)benzamide |
| 151 | 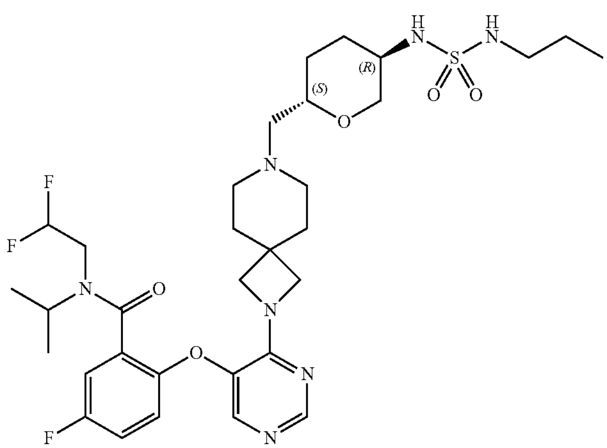 | N-(2,2-Difluoroethyl)-5-fluoro-N-isopropyl-2-((4-(7-(((2S,5R)-5-((N-propylsulfamoyl)amino)tetrahydro-2H-pyran-2-yl)methyl)-2,7-diazaspiro[3.5]nonan-2-yl)pyrimidin-5-yl)oxy)benzamide |
| 152 | 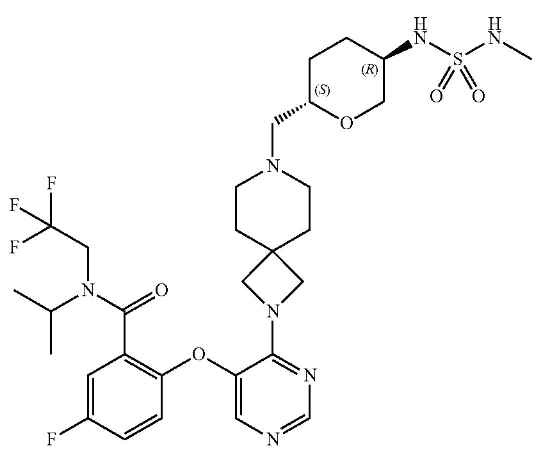 | 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2,2,2-trifluoroethyl)benzamide |

TABLE 1-continued

Representative Compounds of the Present Disclosure

| Compound | Structure | IUPAC Name |
|---|---|---|
| 153 | 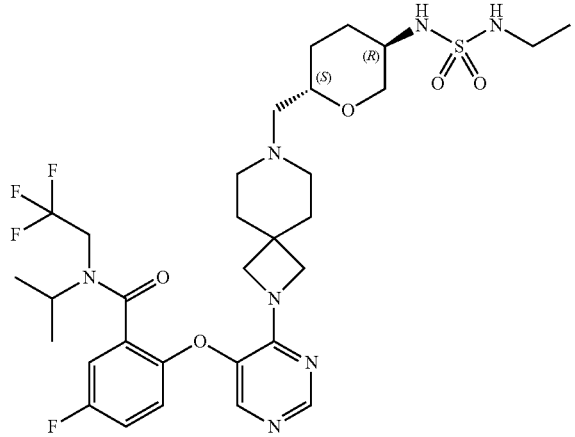 | 2-((4-(7-(((2S,5R)-5-((N-Ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-(2,2,2-trifluoroethyl)benzamide |
| 154 | 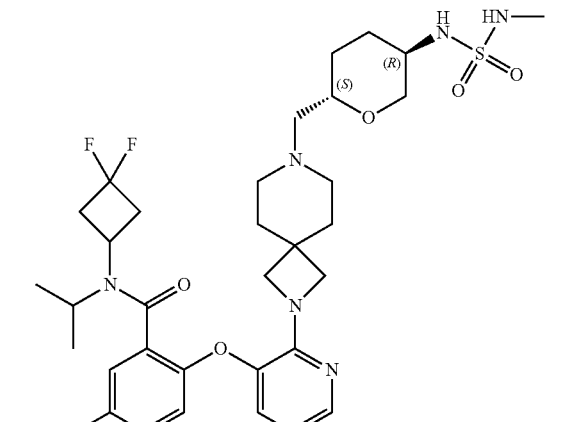 | N-(3,3-Difluorocyclobutyl)-5-fluoro-N-isopropyl-2-(4-(7-(((2S,5R)-5-((N-methylsulfamoyl)amino)tetrahydro-2H-pyran-2-yl)methyl)-2,7-diazaspiro[3.5]nonan-2-yl)pyrimidin-5-yl)oxy)benzamide |
| 155 | 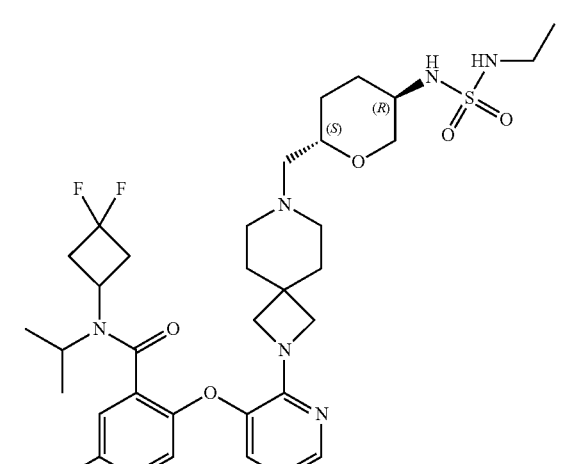 | N-(3,3-Difluorocyclobutyl)-2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |

TABLE 1-continued

Representative Compounds of the Present Disclosure

| Compound | Structure | IUPAC Name |
|---|---|---|
| 156 | 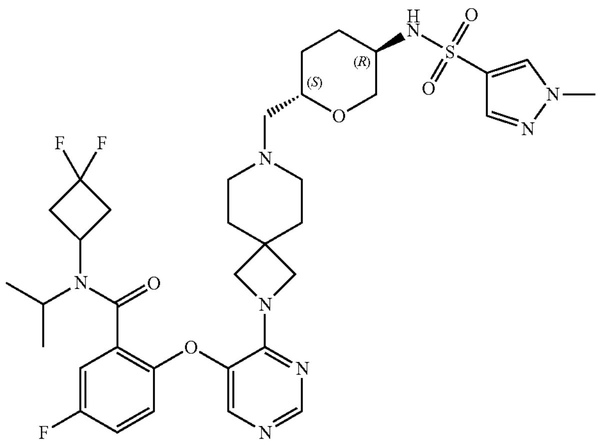 | N-(3,3-Difluorocyclobutyl)-5-fluoro-N-isopropyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide |
| 157 | 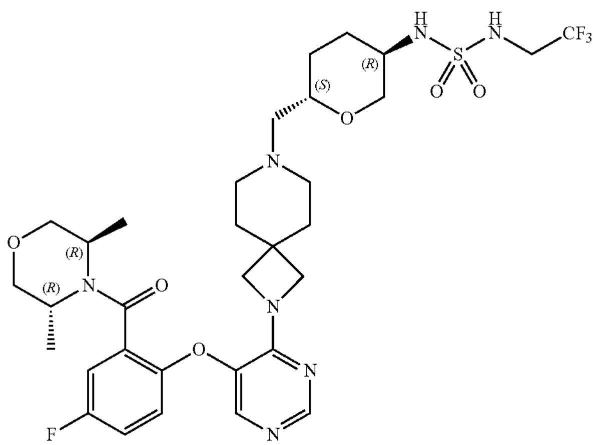 | {[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}(2,2,2-trifluoroethyl)amine |
| 158 | 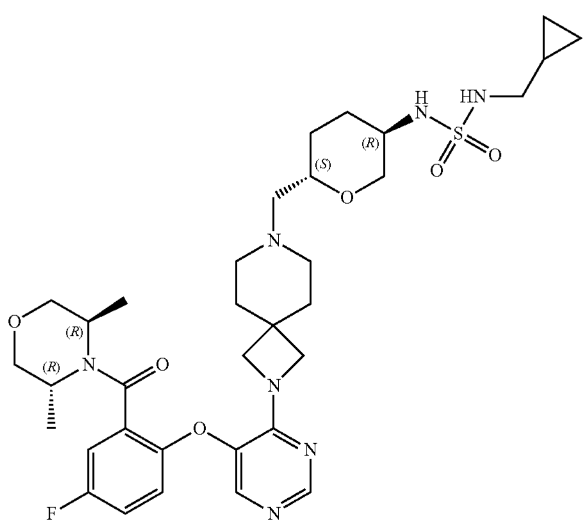 | (Cyclopropylmethyl)({[(3R,6S)-6-{[2-(5-{2-[(3R,5R)-3,5-dimethylmorpholine-4-carbonyl]-4-fluorophenoxy}pyrimidin-4-yl)-2,7-diazaspiro[3.5]nonan-7-yl]methyl}oxan-3-yl]sulfamoyl})amine |

TABLE 1-continued

Representative Compounds of the Present Disclosure

| Compound | Structure | IUPAC Name |
|---|---|---|
| 159 | 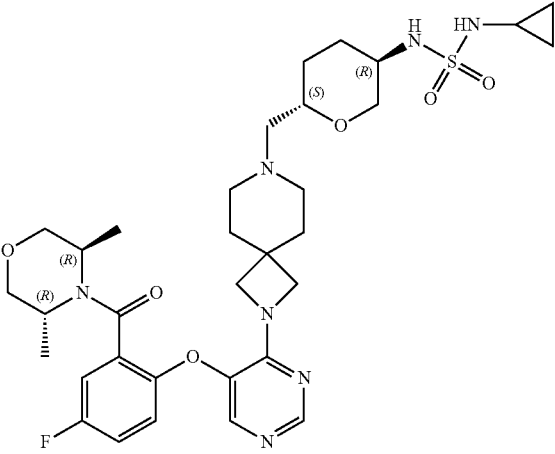 | N-[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl](cyclopropylamino)sulfonamide |
| 160 | 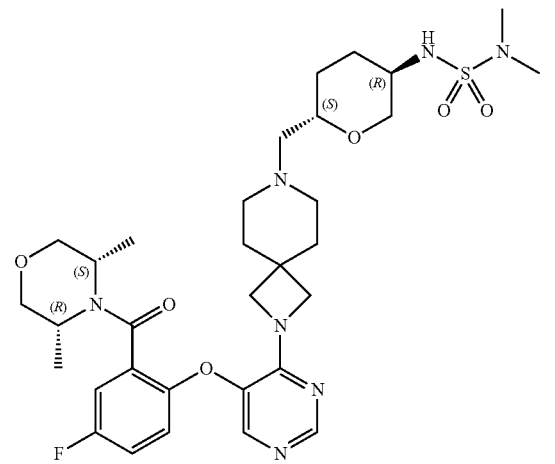 | {[(3R,6S)-6-{[2-(5-{2-[(3R,5S)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}dimethylamine |
| 161 | 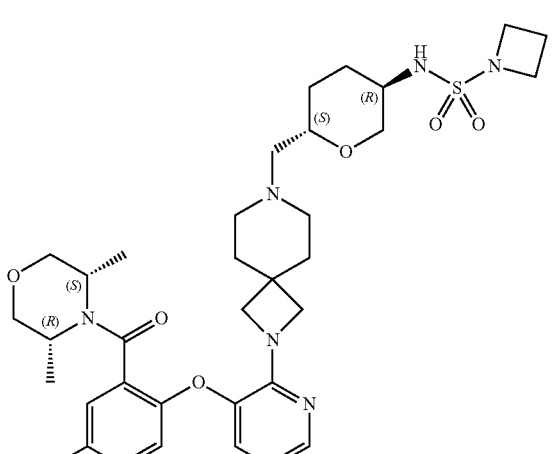 | N-((3R,6S)-6-((2-(5-(2-((3R,5S)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)azetidine-1-sulfonamide |

TABLE 1-continued

Representative Compounds of the Present Disclosure

| Compound | Structure | IUPAC Name |
|---|---|---|
| 162 | 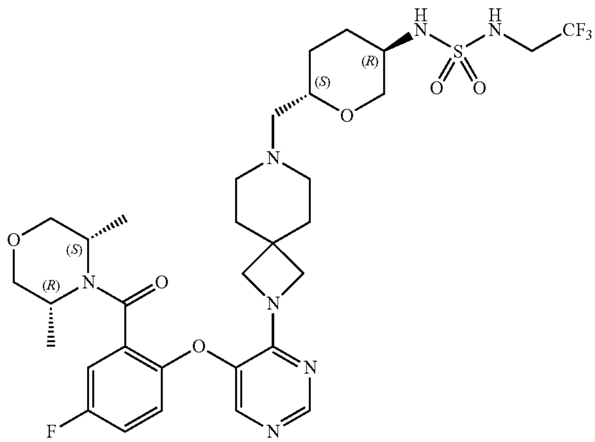 | {[(3R,6S)-6-{[2-(5-{2-[(3R,5S)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}(2,2,2-trifluoroethyl)amine |
| 163 | 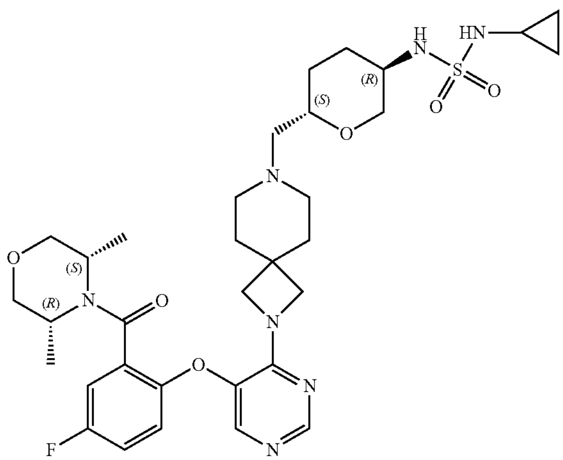 | N-[(3R,6S)-6-{[2-(5-{2-[(3R,5S)-3,5-Dimethylmorpholine-4-carbonyl]-4-fluorophenoxy}pyrimidin-4-yl)-2,7-diazaspiro[3.5]nonan-7-yl]methyl}oxan-3-yl](cyclopropylamino)sulfonamide |
| 164 | 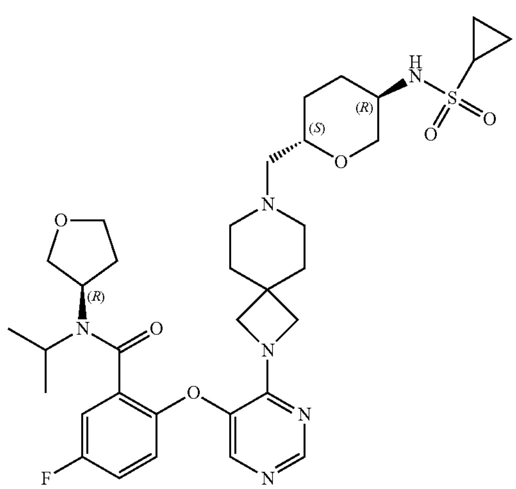 | 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-5-fluoro-N-isopropyl-N-((R)-tetrahydrofuran-3-yl)benzamide |

TABLE 1-continued

Representative Compounds of the Present Disclosure

| Compound | Structure | IUPAC Name |
|---|---|---|
| 165 | 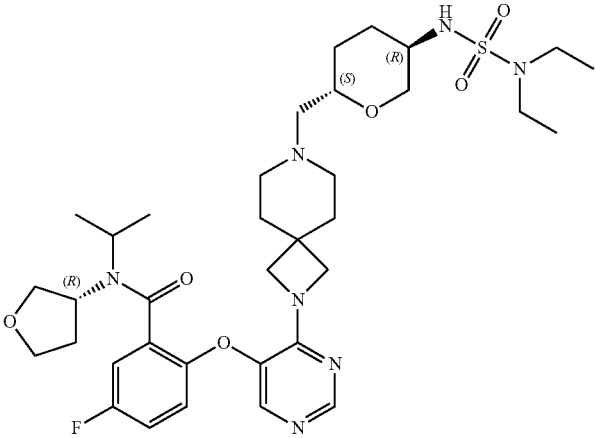 | 2-((4-(7-(((2S,5R)-5-((N,N-Diethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-((R)-tetrahydrofuran-3-yl)benzamide |
| 166 | 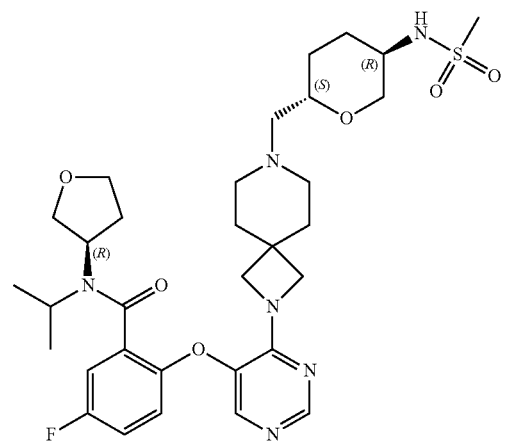 | 5-Fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)-N-((R)-tetrahydrofuran-3-yl)benzamide |
| 167 | 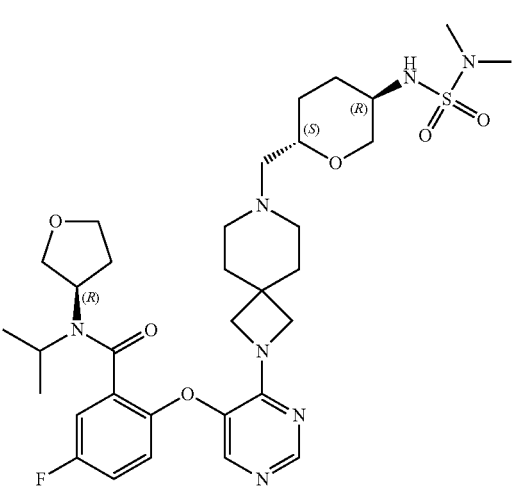 | 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-((R)-tetrahydrofuran-3-yl)benzamide |

TABLE 1-continued

Representative Compounds of the Present Disclosure

| Compound | Structure | IUPAC Name |
| --- | --- | --- |
| 168 | 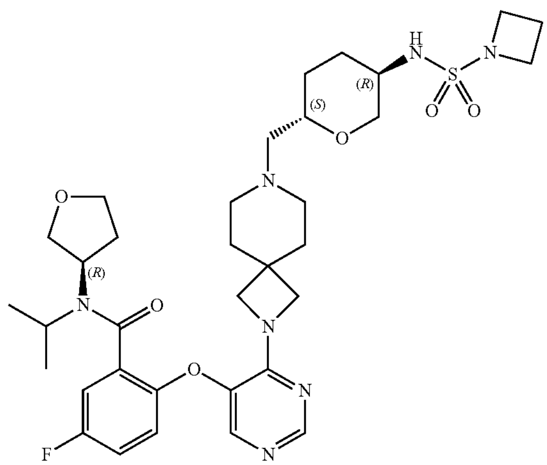 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N-isopropyl-N-((R)-tetrahydrofuran-3-yl)benzamide |
| 169 | 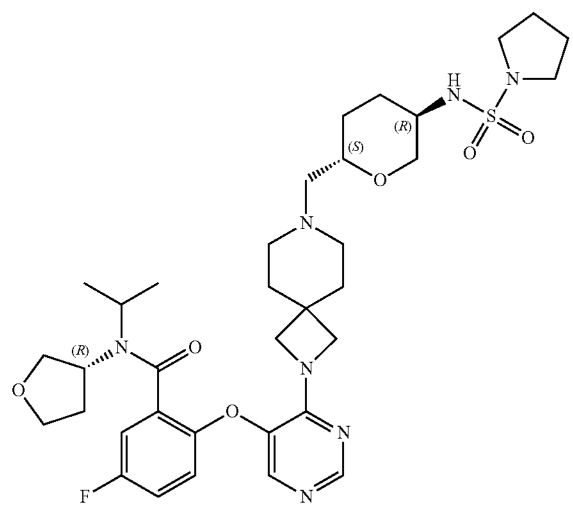 | 5-Fluoro-N-isopropyl-2-((4-(7-(((2S,5R)-5-(pyrrolidine-1-sulfonamido)tetrahydro-2H-pyran-2-yl)methyl)-2,7-diazaspiro[3.5]nonan-2-yl)pyrimidin-5-yl)oxy)-N-((R)-tetrahydrofuran-3-yl)benzamide |
| 170 | 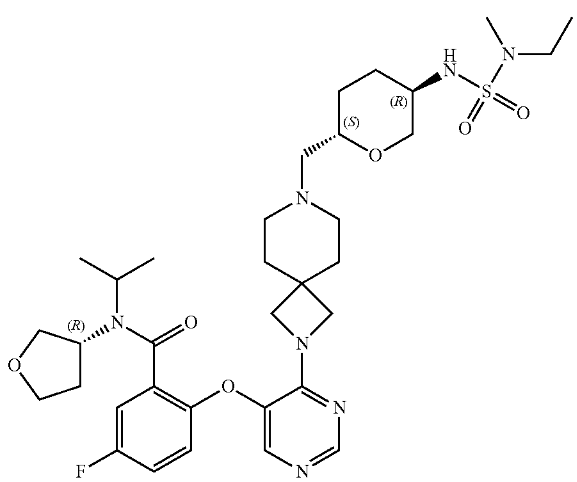 | 2-((4-(7-(((2S,5R)-5-((N-Ethyl-N-methylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-((R)-tetrahydrofuran-3-yl)benzamide |

TABLE 1-continued

Representative Compounds of the Present Disclosure

| Compound | Structure | IUPAC Name |
|---|---|---|
| 171 | 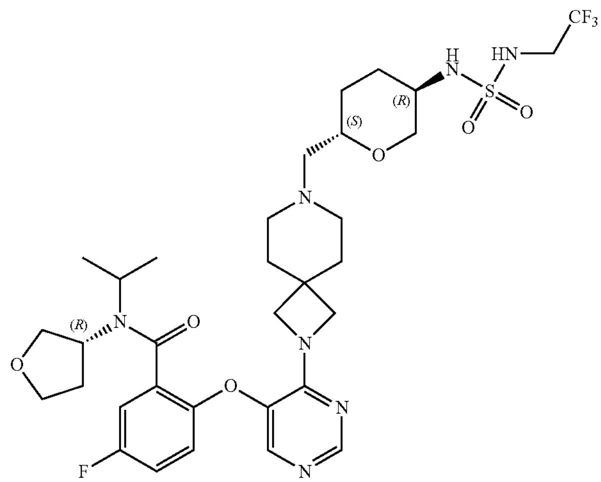 | 5-Fluoro-N-isopropyl-N-((R)-tetrahydrofuran-3-yl)-2-((4-(7-(((2S,5R)-5-((N-(2,2,2-trifluoroethyl)sulfamoyl)amino)tetrahydro-2H-pyran-2-yl)methyl)-2,7-diazaspiro[3.5]nonan-2-yl)pyrimidin-5-yl)oxy)benzamide |
| 172 | 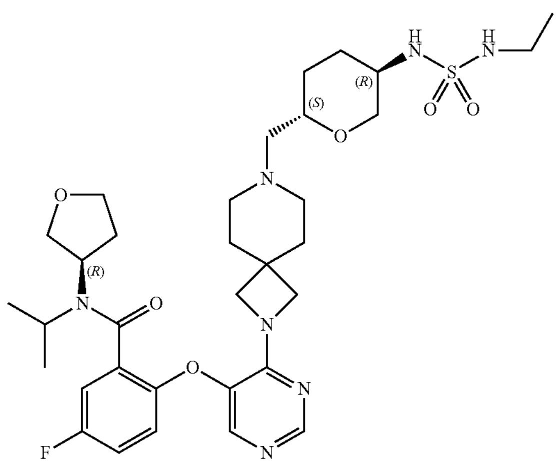 | 2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-((R)-tetrahydrofuran-3-yl)benzamide |
| 173 | 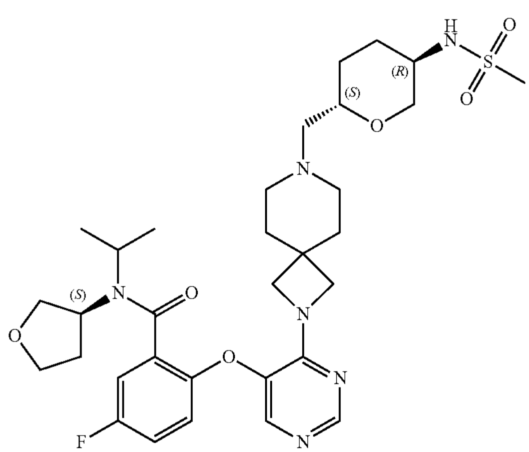 | 5-Fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)-N-((S)-tetrahydrofuran-3-yl)benzamide |

TABLE 1-continued

Representative Compounds of the Present Disclosure

| Compound | Structure | IUPAC Name |
|---|---|---|
| 174 | 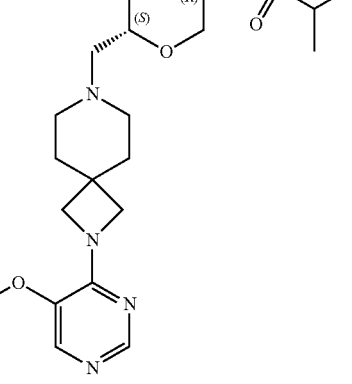 | 5-Fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)-N-((S)-tetrahydrofuran-3-yl)benzamide |
| 175 | 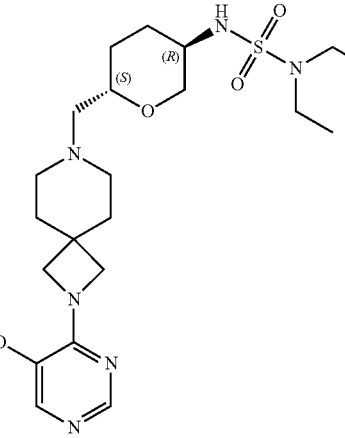 | 2-((4-(7-(((2S,5R)-5-((N,N-Diethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-((S)-tetrahydrofuran-3-yl)benzamide |
| 176 | 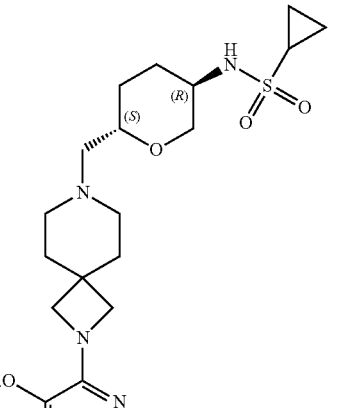 | 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-5-fluoro-N-isopropyl-N-((S)-tetrahydrofuran-3-yl)benzamide |

US 11,919,901 B2

145 146

TABLE 1-continued

Representative Compounds of the Present Disclosure

| Compound | Structure | IUPAC Name |
|---|---|---|
| 177 | 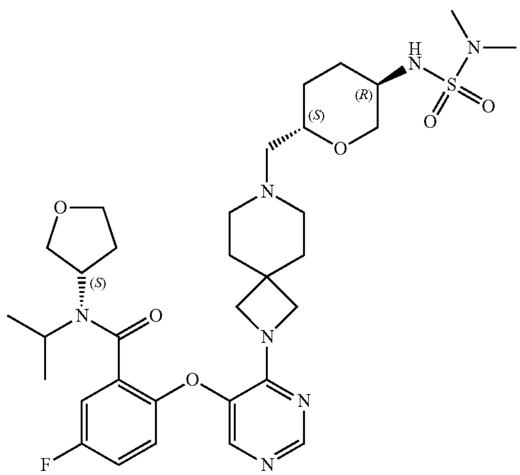 | 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-((S)-tetrahydrofuran-3-yl)benzamide |
| 178 | 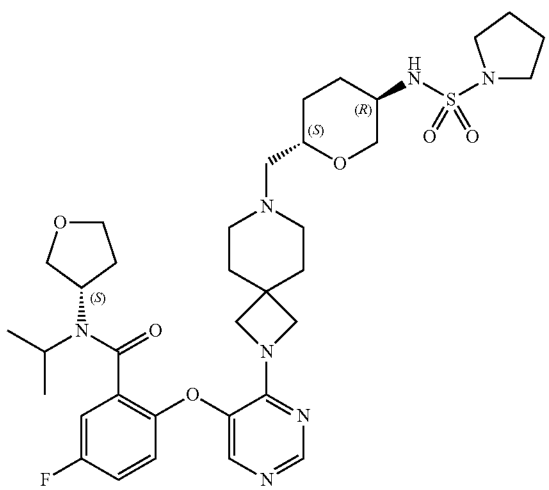 | 5-Fluoro-N-isopropyl-2-((4-(7-(((2S,5R)-5-(pyrrolidine-1-sulfonamido)tetrahydro-2H-pyran-2-yl)methyl)-2,7-diazaspiro[3.5]nonan-2-yl)pyrimidin-5-yl)oxy)-N-((S)-tetrahydrofuran-3-yl)benzamide |
| 179 | 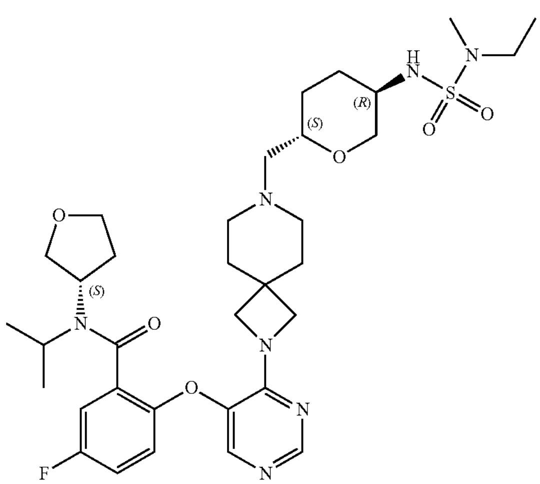 | 2-((4-(7-(((2S,5R)-5-((N-Ethyl-N-methylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-((S)-tetrahydrofuran-3-yl)benzamide |

TABLE 1-continued

Representative Compounds of the Present Disclosure

| Compound | Structure | IUPAC Name |
|---|---|---|
| 180 | 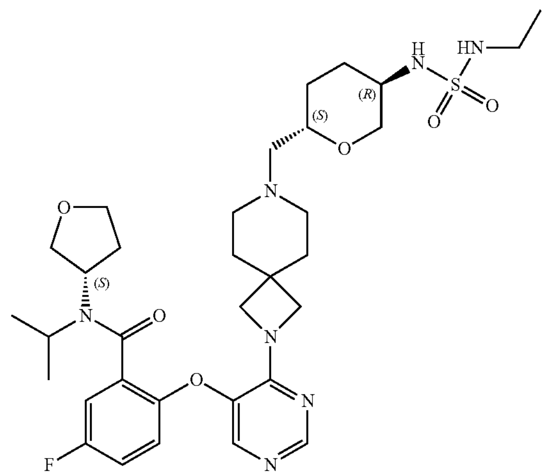 | 2-((4-(7-(((2S,5R)-5-((N-Ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-((S)-tetrahydrofuran-3-yl)benzamide |
| 181 | 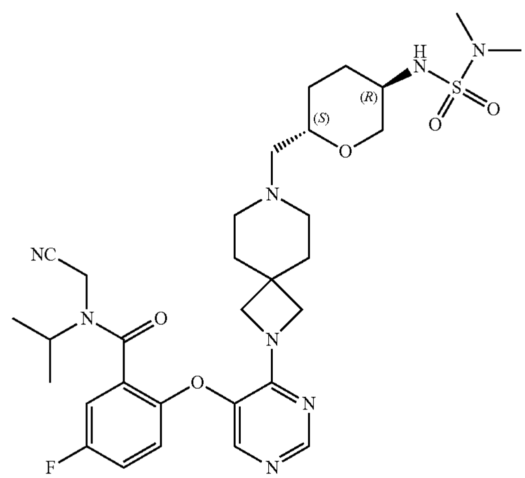 | N-(Cyanomethyl)-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |
| 182 | 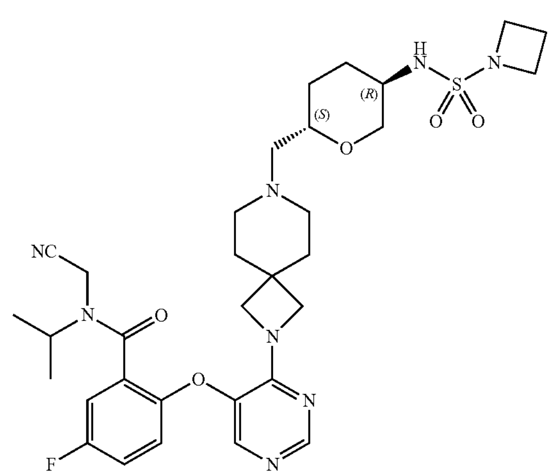 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-(cyanomethyl)-5-fluoro-N-isopropylbenzamide |

TABLE 1-continued

Representative Compounds of the Present Disclosure

| Compound | Structure | IUPAC Name |
|---|---|---|
| 183 | 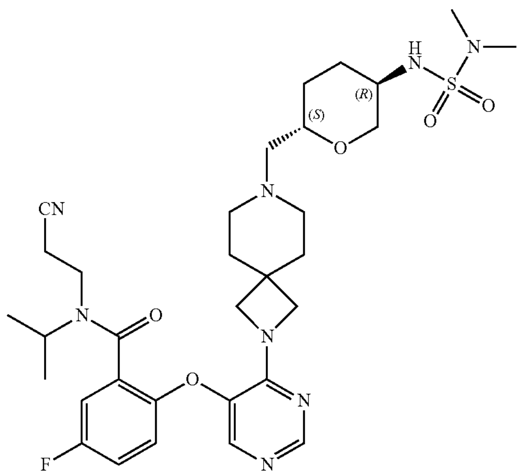 | N-(2-Cyanoethyl)-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |
| 184 | 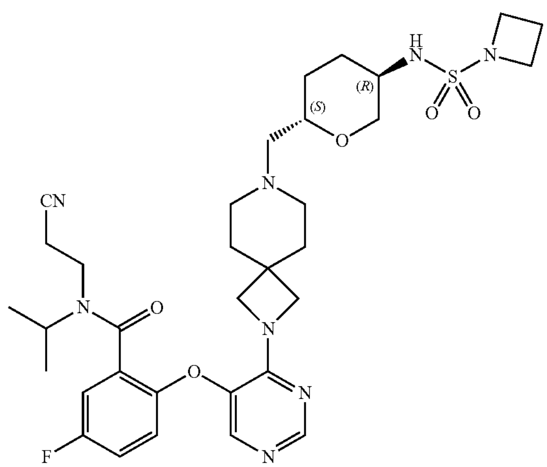 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-(2-cyanoethyl)-5-fluoro-N-isopropylbenzamide |
| 185 | 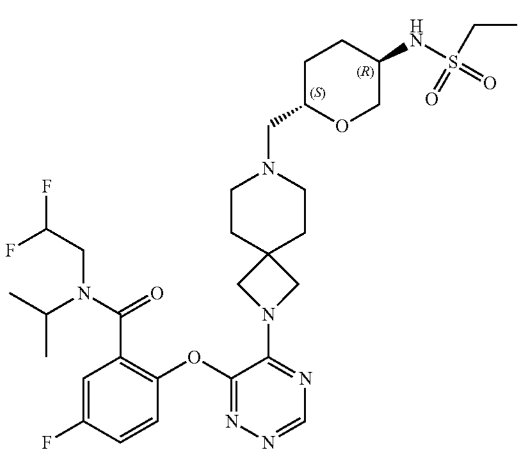 | N-(2,2-Difluoroethyl)-2-((5-(7-(((2S,5R)-5-(ethylsulfonamido)tetrahydro-2H-pyran-2-yl)methyl)-2,7-diazaspiro[3.5]nonan-2-yl)-1,2,4-triazin-6-yl)oxy)-5-fluoro-N-isopropylbenzamide |

TABLE 1-continued

Representative Compounds of the Present Disclosure

| Compound | Structure | IUPAC Name |
|---|---|---|
| 186 | 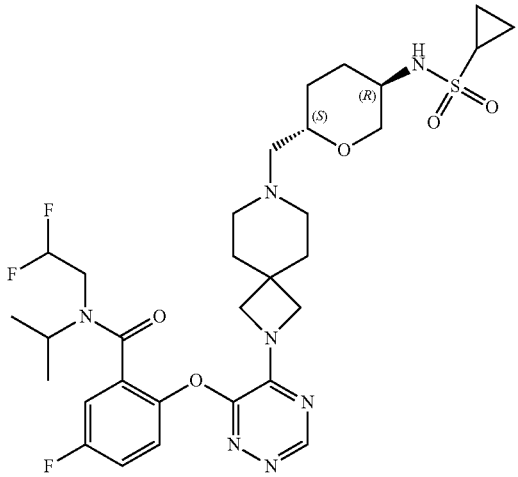 | 2-((5-(7-(((2S,5R)-5-(Cyclopropanesulfonamido)tetrahydro-2H-pyran-2-yl)methyl)-2,7-diazaspiro[3.5]nonan-2-yl)-1,2,4-triazin-6-yl)oxy)-N-(2,2-difluoroethyl)-5-fluoro-N-isopropylbenzamide |
| 187 | 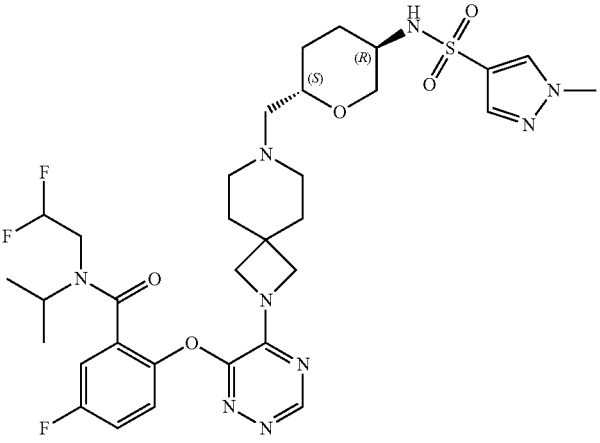 | N-(2,2-Difluoroethyl)-5-fluoro-N-isopropyl-2-((5-(7-(((2S,5R)-5-((1-methyl-1H-pyrazole)-4-sulfonamido)tetrahydro-2H-pyran-2-yl)methyl)-2,7-diazaspiro[3.5]nonan-2-yl)-1,2,4-triazin-6-yl)oxy)benzamide |
| 188 | 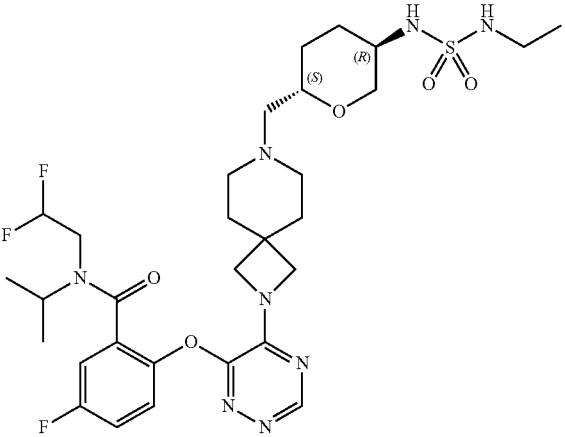 | N-(2,2-Difluoroethyl)-2-((5-(7-(((2S,5R)-5-((N-ethylsulfamoyl)amino)tetrahydro-2H-pyran-2-yl)methyl)-2,7-diazaspiro[3.5]nonan-2-yl)-1,2,4-triazin-6-yl)oxy)-5-fluoro-N-isopropylbenzamide |

TABLE 1-continued

Representative Compounds of the Present Disclosure

| Compound | Structure | IUPAC Name |
|---|---|---|
| 189 | 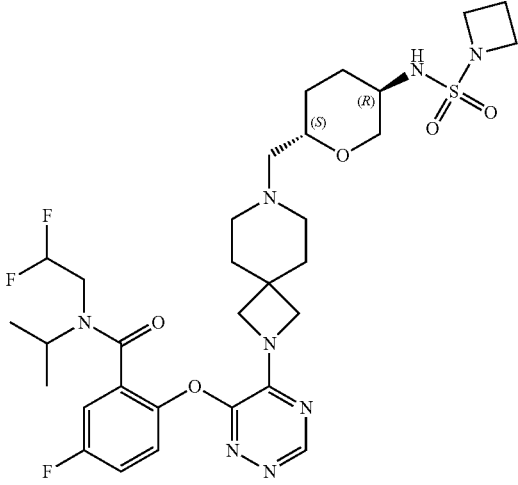 | 2-((5-(7-(((2S,5R)-5-(Azetidine-1-sulfonamido)tetrahydro-2H-pyran-2-yl)methyl)-2,7-diazaspiro[3.5]nonan-2-yl)-1,2,4-triazin-6-yl)oxy)-N-(2,2-difluoroethyl)-5-fluoro-N-isopropylbenzamide |
| 190 | 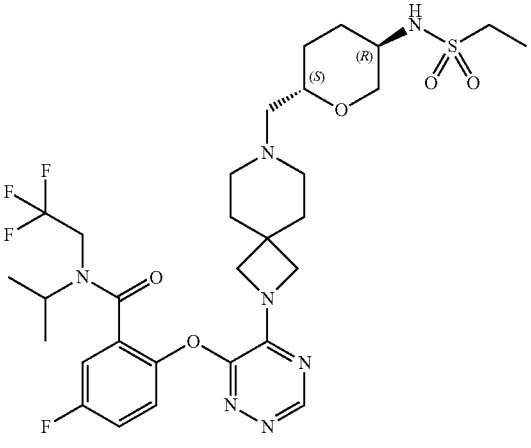 | 2-((5-(7-(((2S,5R)-5-(Ethylsulfonamido)tetrahydro-2H-pyran-2-yl)methyl)-2,7-diazaspiro[3.5]nonan-2-yl)-1,2,4-triazin-6-yl)oxy)-5-fluoro-N-isopropyl-N-(2,2,2-trifluoroethyl)benzamide |
| 191 | 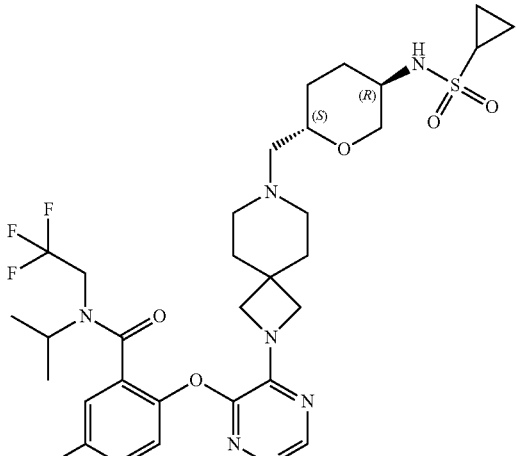 | 2-((5-(7-(((2S,5R)-5-(Cyclopropanesulfonamido)tetrahydro-2H-pyran-2-yl)methyl)-2,7-diazaspiro[3.5]nonan-2-yl)-1,2,4-triazin-6-yl)oxy)-5-fluoro-N-isopropyl-N-(2,2,2-trifluoroethyl)benzamide |

TABLE 1-continued

Representative Compounds of the Present Disclosure

| Compound | Structure | IUPAC Name |
|---|---|---|
| 192 | 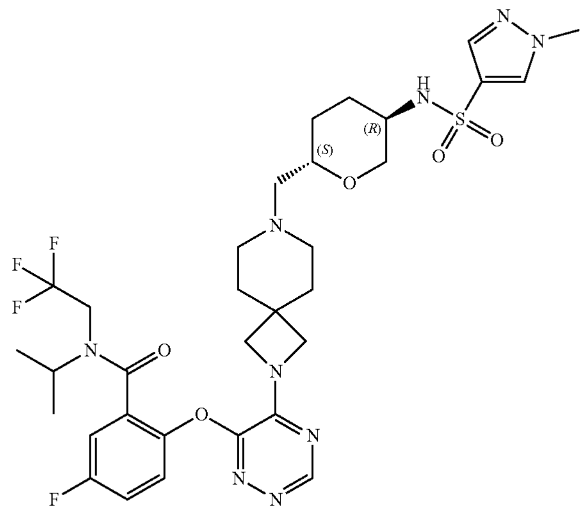 | 5-Fluoro-N-isopropyl-2-((5-(7-(((2R,5S)-5-((1-methyl-1H-pyrazole)-4-sulfonamido)tetrahydro-2H-pyran-2-yl)methyl)-2,7-diazaspiro[3.5]nonan-2-yl)-1,2,4-triazin-6-yl)oxy)-N-(2,2,2-trifluoroethyl)benzamide |
| 193 | 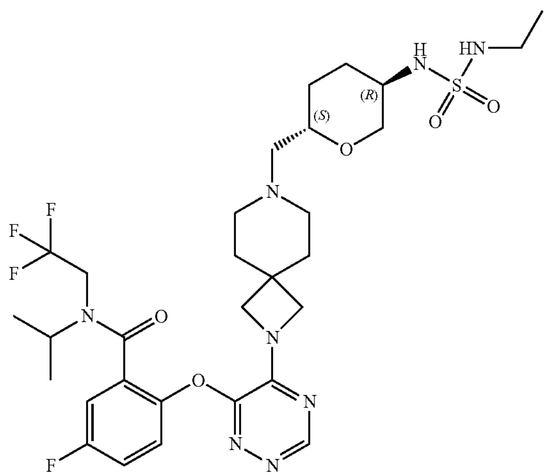 | 2-((5-(7-(((2R,5S)-5-(N-Ethylsulfamoyl)amino)tetrahydro-2H-pyran-2-yl)methyl)-2,7-diazaspiro[3.5]nonan-2-yl)-1,2,4-triazin-6-yl)oxy)-5-fluoro-N-isopropyl-N-(2,2,2-trifluoroethyl)benzamide |
| 194 | 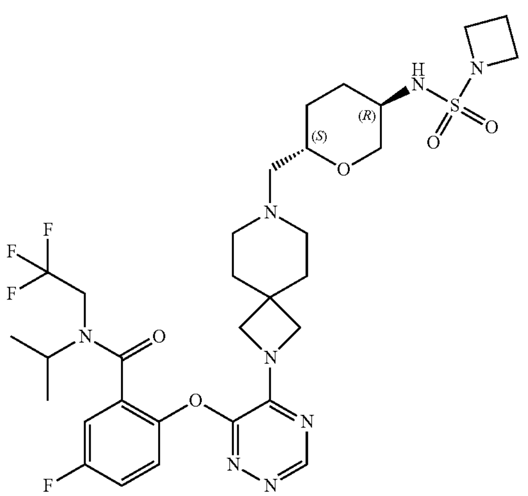 | 2-((5-(7-(((2R,5S)-5-(Azetidine-1-sulfonamido)tetrahydro-2H-pyran-2-yl)methyl)-2,7-diazaspiro[3.5]nonan-2-yl)-1,2,4-triazin-6-yl)oxy)-5-fluoro-N-isopropyl-N-(2,2,2-trifluoroethyl)benzamide |

TABLE 1-continued

Representative Compounds of the Present Disclosure

| Compound | Structure | IUPAC Name |
|---|---|---|
| 195 | 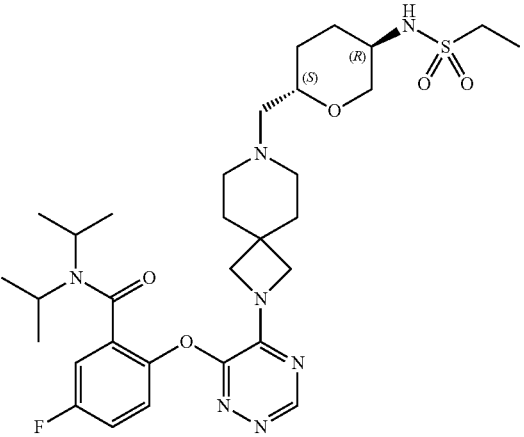 | 2-((5-(7-(((2S,5R)-5-(Ethylsulfonamido)tetrahydro-2H-pyran-2-yl)methyl)-2,7-diazaspiro[3.5]nonan-2-yl)-1,2,4-triazin-6-yl)oxy)-5-fluoro-N,N-diisopropylbenzamide |
| 196 | 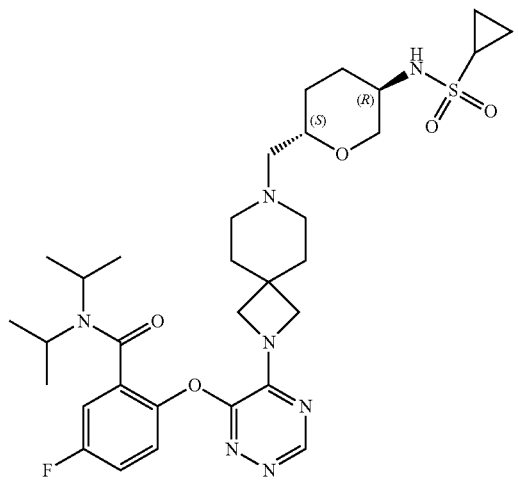 | 2-((5-(7-(((2S,5R)-5-(Cyclopropanesulfonamido)tetrahydro-2H-pyran-2-yl)methyl)-2,7-diazaspiro[3.5]nonan-2-yl)-1,2,4-triazin-6-yl)oxy)-5-fluoro-N,N-diisopropylbenzamide |
| 197 | 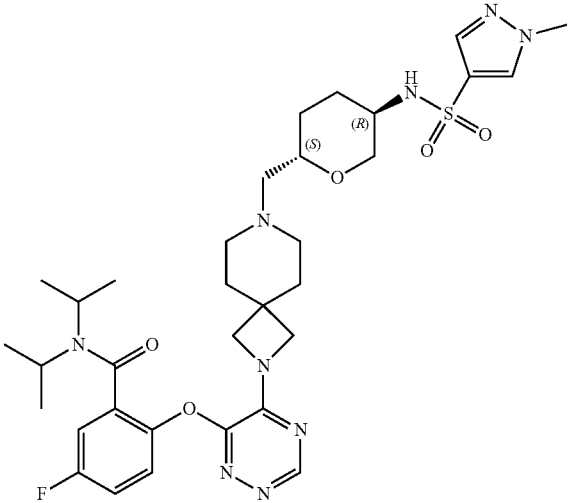 | 5-Fluoro-N,N-diisopropyl-2-((5-(7-(((2S,5R)-5-((1-methyl-1H-pyrazole)-4-sulfonamido)tetrahydro-2H-pyran-2-yl)methyl)-2,7-diazaspiro[3.5]nonan-2-yl)-1,2,4-triazin-6-yl)oxy)benzamide |

TABLE 1-continued

Representative Compounds of the Present Disclosure

| Compound | Structure | IUPAC Name |
|---|---|---|
| 198 | 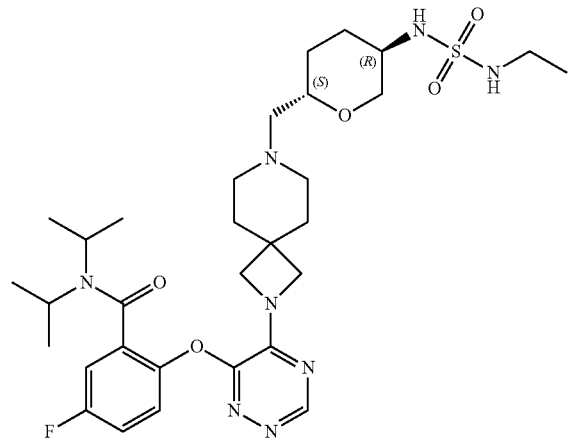 | 2-(5-(7-((2S,5R)-5-(N-Ethylsulfamoyl)amino)tetrahydro-2H-pyran-2-yl)methyl)-2,7-diazaspiro[3.5]nonan-2-yl)-1,2,4-triazin-6-yl)oxy)-5-fluoro-N,N-diisopropylbenzamide |
| 199 | 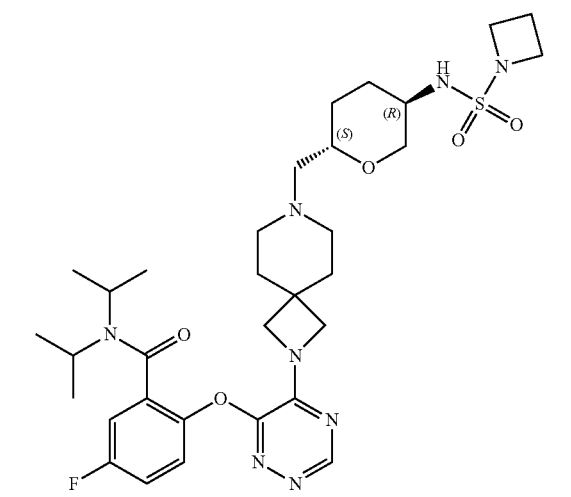 | 2-((5-(7-(((2S,5R)-5-(Azetidine-1-sulfonamido)tetrahydro-2H-pyran-2-yl)methyl)-2,7-diazaspiro[3.5]nonan-2-yl)-1,2,4-triazin-6-yl)oxy)-5-fluoro-N,N-diisopropylbenzamide |
| 200 | 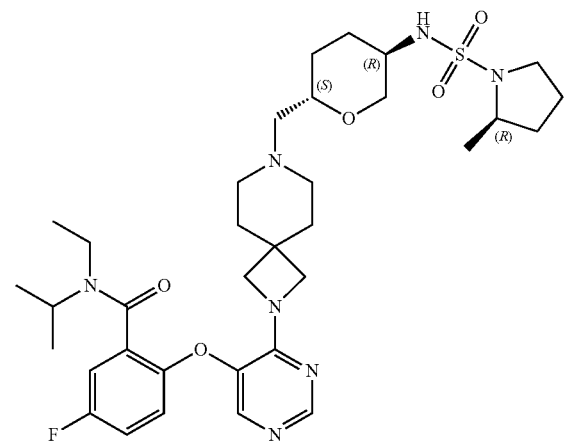 | N-Ethyl-5-fluoro-N-isopropyl-2-((4-(7-(((2S,5R)-5-(((R)-2-methylpyrrolidine)-1-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 201 | 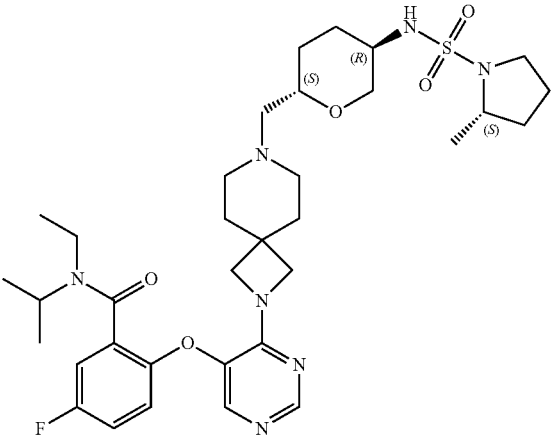 | N-Ethyl-5-fluoro-N-isopropyl-2-((4-(7-(((2S,5R)-5-(((S)-2-methylpyrrolidine)-1-sulfonamido)tetrahydro-2H-pyran-2-yl)methyl)-2,7-diazaspiro[3.5]nonan-2-yl)pyrimidin-5-yl)oxy)benzamide |
| 202 | 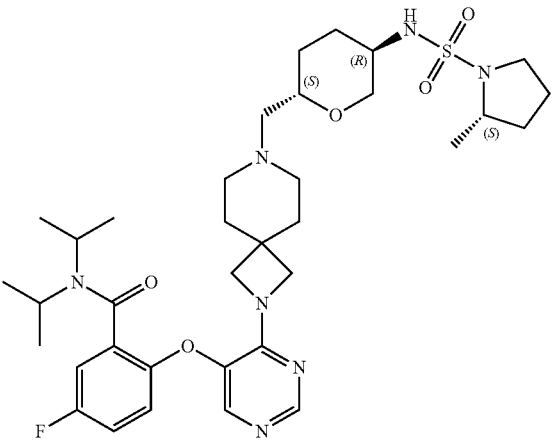 | 5-Fluoro-N,N-diisopropyl-2-((4-(7-(((2S,5R)-5-(((S)-2-methylpyrrolidine)-1-sulfonamido)tetrahydro-2H-pyran-2-yl)methyl)-2,7-diazaspiro[3.5]nonan-2-yl)pyrimidin-5-yl)oxy)benzamide |
| 203 | 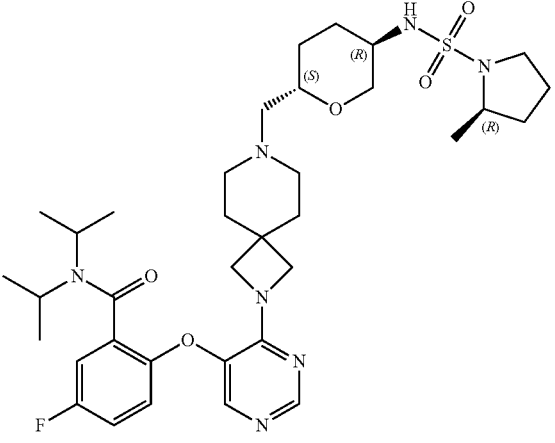 | 5-Fluoro-N,N-diisopropyl-2-((4-(7-(((2S,5R)-5-(((R)-2-methylpyrrolidine)-1-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 204 | 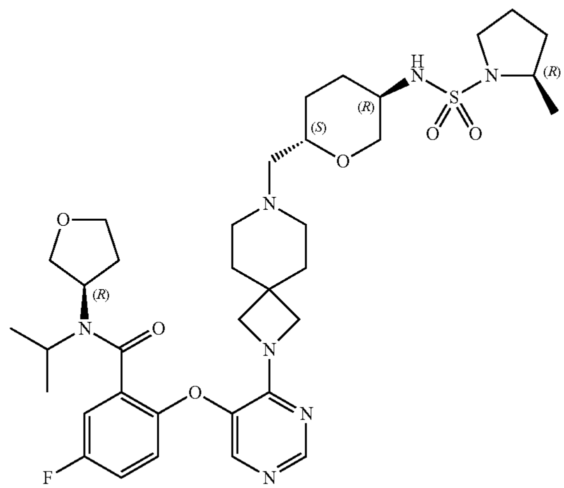 | 5-Fluoro-N-isopropyl-2-((4-(7-(((2S,5R)-5-(((R)-2-methylpyrrolidine)-1-sulfonamido)tetrahydro-2H-pyran-2-yl)methyl)-2,7-diazaspiro[3.5]nonan-2-yl)pyrimidin-5-yl)oxy)-N-((R)-tetrahydrofuran-3-yl)benzamide |
| 205 | 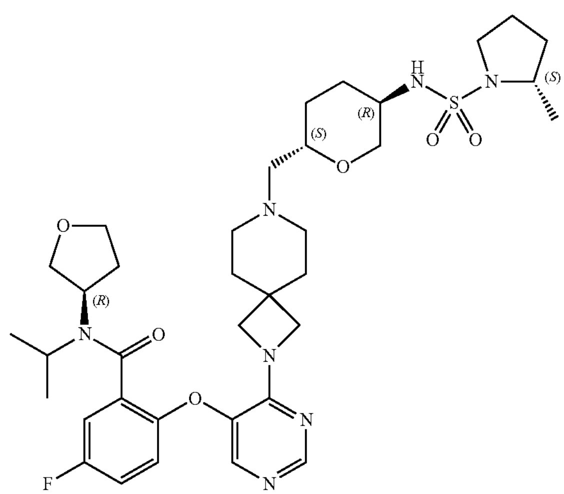 | 5-Fluoro-N-isopropyl-2-((4-(7-(((2S,5R)-5-(((S)-2-methylpyrrolidine)-1-sulfonamido)tetrahydro-2H-pyran-2-yl)methyl)-2,7-diazaspiro[3.5]nonan-2-yl)pyrimidin-5-yl)oxy)-N-((R)-tetrahydrofuran-3-yl)benzamide |
| 206 | 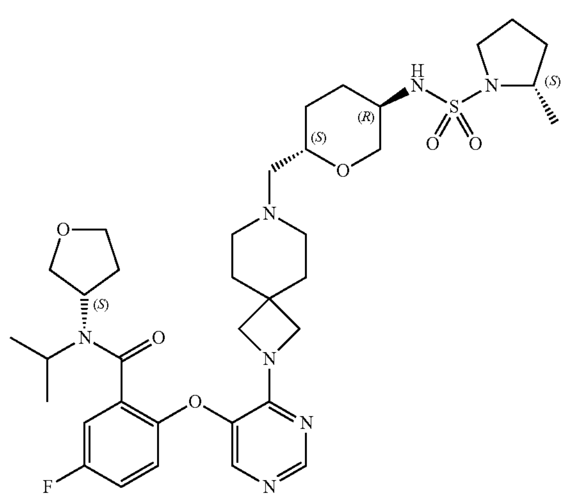 | 5-Fluoro-N-isopropyl-2-((4-(7-(((2S,5R)-5-(((S)-2-methylpyrrolidine)-1-sulfonamido)tetrahydro-2H-pyran-2-yl)methyl)-2,7-diazaspiro[3.5]nonan-2-yl)pyrimidin-5-yl)oxy)-N-((S)-tetrahydrofuran-3-yl)benzamide |

TABLE 1-continued

Representative Compounds of the Present Disclosure

| Compound | Structure | IUPAC Name |
|---|---|---|
| 207 | 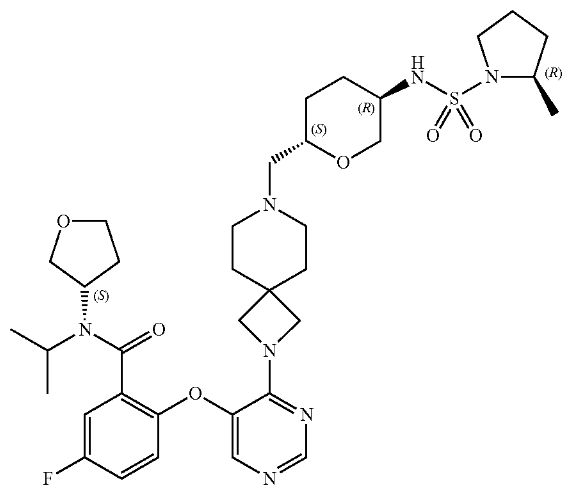 | 5-Fluoro-N-isopropyl-2-((4-(7-(((2S,5R)-5-(((R)-2-methylpyrrolidine)-1-sulfonamido)tetrahydro-2H-pyran-2-yl)methyl)-2,7-diazaspiro[3.5]nonan-2-yl)pyrimidin-5-yl)oxy)-N-((S)-tetrahydrofuran-3-yl)benzamide |
| 208 | 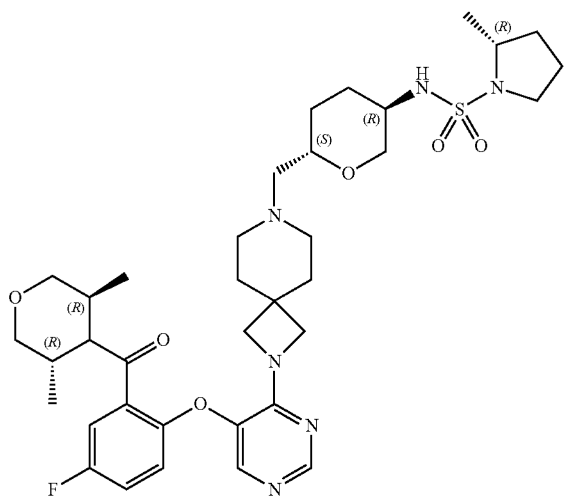 | (R)-N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-2-methylpyrrolidine-1-sulfonamide |
| 209 | 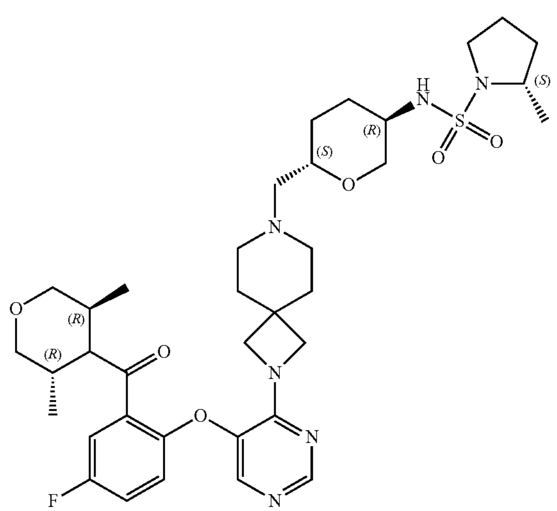 | (S)-N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-2-methylpyrrolidine-1-sulfonamide |

TABLE 1-continued

Representative Compounds of the Present Disclosure

| Compound | Structure | IUPAC Name |
|---|---|---|
| 210 | 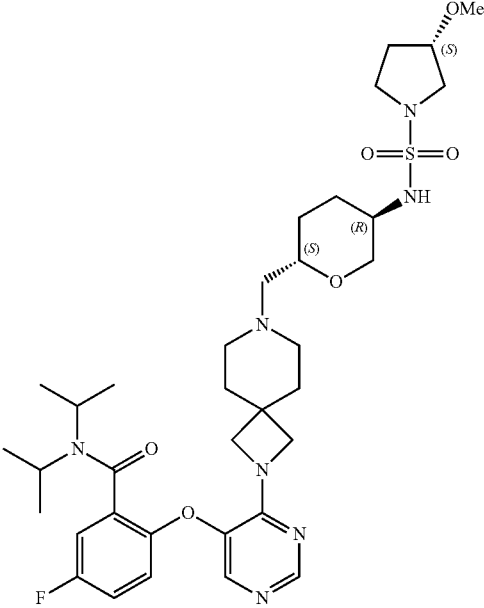 | 5-Fluoro-N,N-diisopropyl-2-((4-(7-(((2S,5R)-5-(((S)-3-methoxypyrrolidine)-1-sulfonamido)tetrahydro-2H-pyran-2-yl)methyl)-2,7-diazaspiro[3.5]nonan-2-yl)pyrimidin-5-yl)oxy)benzamide |
| 211 | 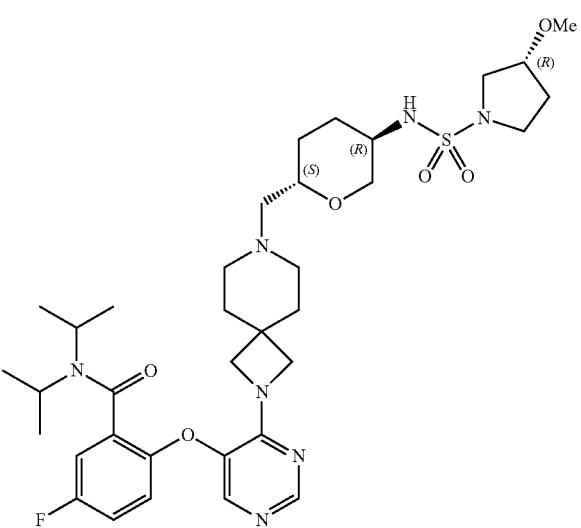 | 5-Fluoro-N,N-diisopropyl-2-((4-(7-(((2S,5R)-5-(((R)-3-methoxypyrrolidine)-1-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 212 | 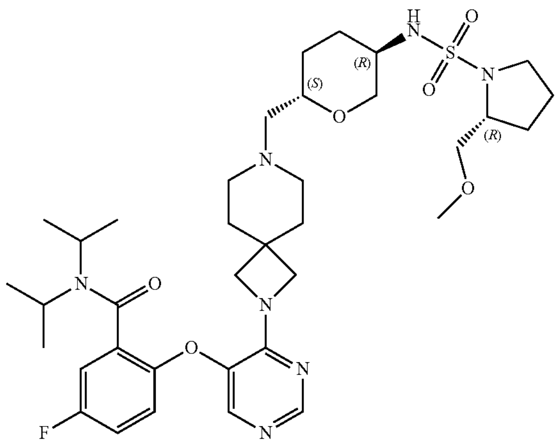 | 5-Fluoro-N,N-diisopropyl-2-((4-(7-(((2S,5R)-5-(((R)-2-(methoxymethyl)pyrrolidine)-1-sulfonamido)tetrahydro-2H-pyran-2-yl)methyl)-2,7-diazaspiro[3.5]nonan-2-yl)pyrimidin-5-yl)oxy)benzamide |
| 213 | 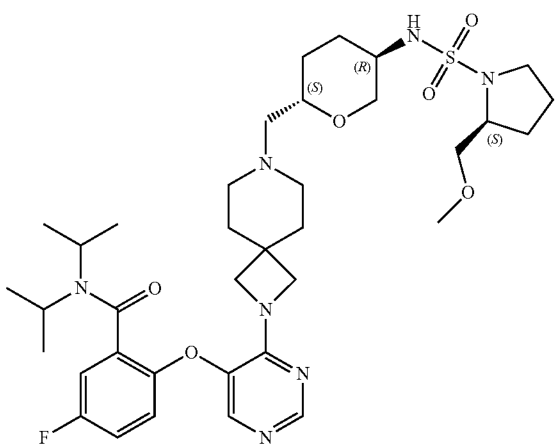 | 5-Fluoro-N,N-diisopropyl-2-((4-(7-(((2S,5R)-5-(((S)-2-(methoxymethyl)pyrrolidine)-1-sulfonamido)tetrahydro-2H-pyran-2-yl)methyl)-2,7-diazaspiro[3.5]nonan-2-yl)pyrimidin-5-yl)oxy)benzamide |
| 214 | 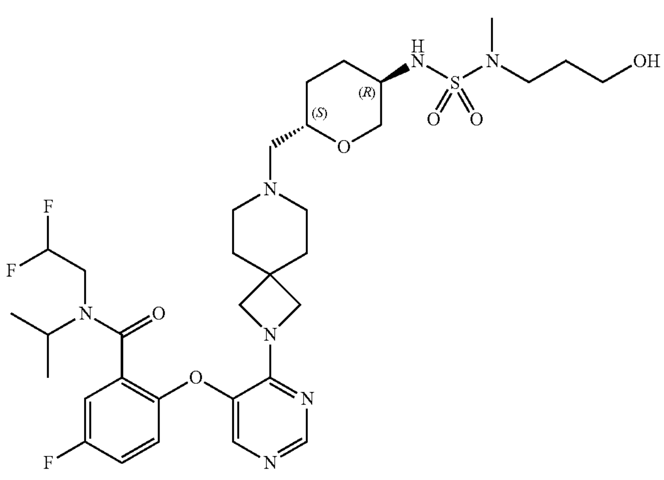 | N-(2,2-difluoroethyl)-5-fluoro-2-((4-(7-(((2S,5R)-5-((N-(3-hydroxypropyl)-N-methylsulfamoyl)amino)tetrahydro-2H-pyran-2-yl)methyl)-2,7-diazaspiro[3.5]nonan-2-yl)pyrimidin-5-yl)oxy)-N-isopropylbenzamide |

TABLE 1-continued

Representative Compounds of the Present Disclosure

| Compound | Structure | IUPAC Name |
|---|---|---|
| 215 | 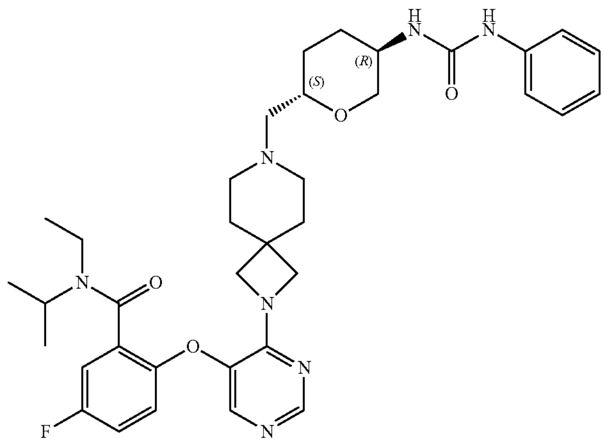 | N-Ethyl-5-fluoro-N-isopropyl-2-((4-(7-(((2S,5R)-5-(3-phenylureido)tetrahydro-2H-pyran-2-yl)methyl)-2,7-diazaspiro[3.5]nonan-2-yl)pyrimidin-5-yl)oxy)benzamide |
| 216 | 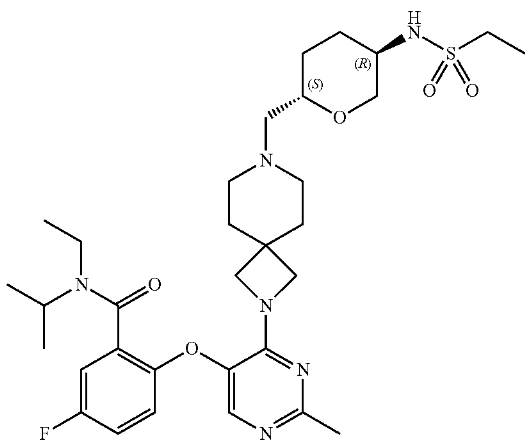 | N-Ethyl-2-((4-(7-(((2S,5R)-5-(ethylsulfonamido)tetrahydro-2H-pyran-2-yl)methyl)-2,7-diazaspiro[3.5]nonan-2-yl)-2-methylpyrimidin-5-yl)oxy)-5-fluoro-N-isopropylbenzamide |
| 217 | 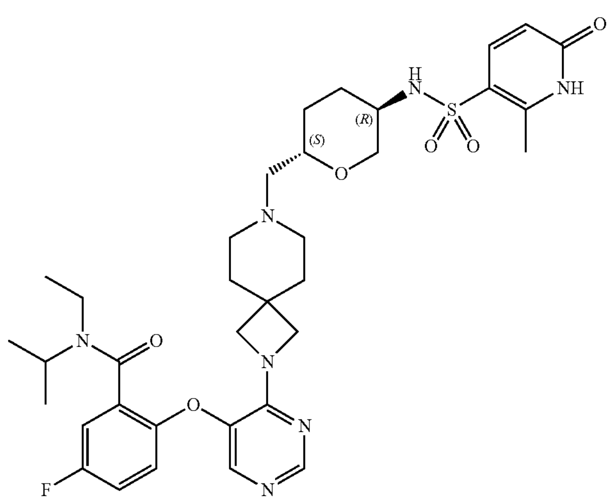 | N-Ethyl-5-fluoro-N-isopropyl-2-((4-(7-(((2S,5R)-5-((2-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 218 | 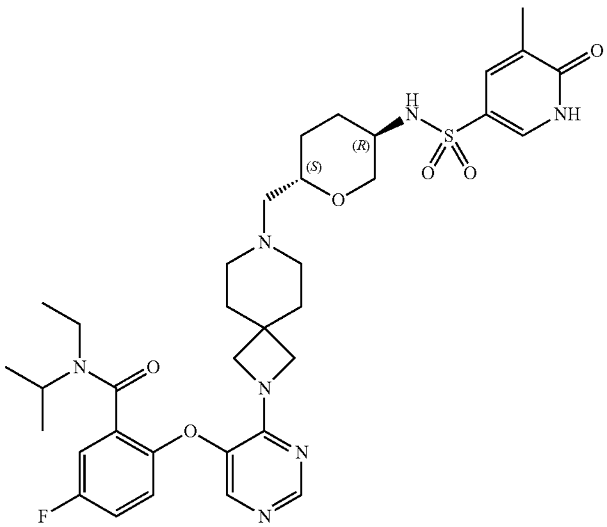 | N-Ethyl-5-fluoro-N-isopropyl-2-((4-(7-(((2S,5R)-5-((5-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy)benzamide |
| 219 | 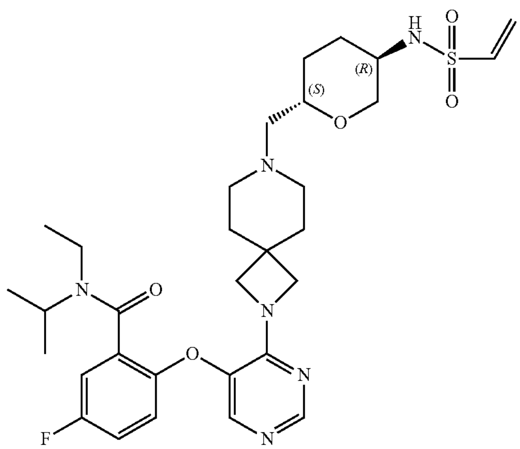 | N-Ethyl-5-fluoro-N-isopropyl-2-((4-(7-(((2S,5R)-5-(vinylsulfonamido)tetrahydro-2H-pyran-2-yl)methyl)-2,7-diazaspiro[3.5]nonan-2-yl)pyrimidin-5-yl)oxy)benzamide |
| 220 | 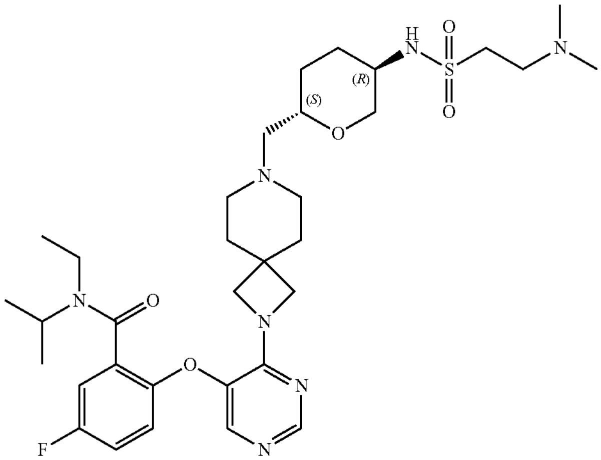 | 2-((4-(7-(((2S,5R)-5-((2-(Dimethylamino)ethyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide |

TABLE 1-continued

Representative Compounds of the Present Disclosure

| Compound | Structure | IUPAC Name |
|---|---|---|
| 221 | | 2-((4-(7-(((2S,5R)-5-(1-Oxa-6-azaspiro[3.3]heptane-6-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 222 | | 2-((4-(7-(((2S,5R)-5-(2-Oxa-6-azaspiro[3.3]heptane-6-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 223 | | 2-((4-(7-(((2S,5R)-5-(6-Oxa-2-azaspiro[3.4]octane-2-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |

TABLE 1-continued

Representative Compounds of the Present Disclosure

| Compound | Structure | IUPAC Name |
|---|---|---|
| 224 | 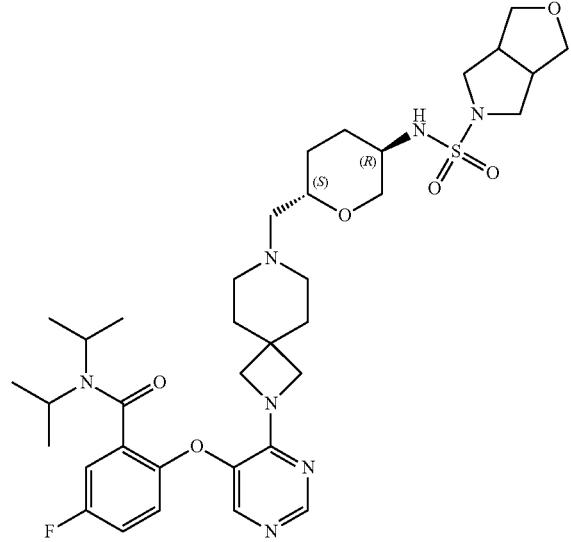 | 5-Fluoro-2-((4-(7-(((2S,5R)-5-((hexahydro-1H-furo[3,4-c]pyrrole)-5-sulfonamido)tetrahydro-2H-pyran-2-yl)methyl)-2,7-diazaspiro[3.5]nonan-2-yl)pyrimidin-5-yl)oxy)-N,N-diisopropylbenzamide |
| 225 | 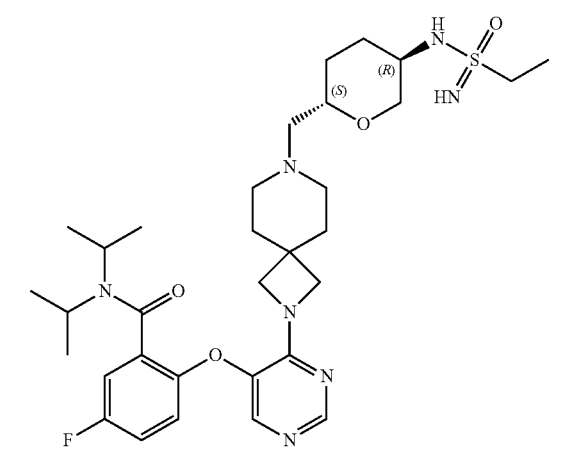 | 2-((4-(7-(((2S,5R)-5-(Ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 226 | 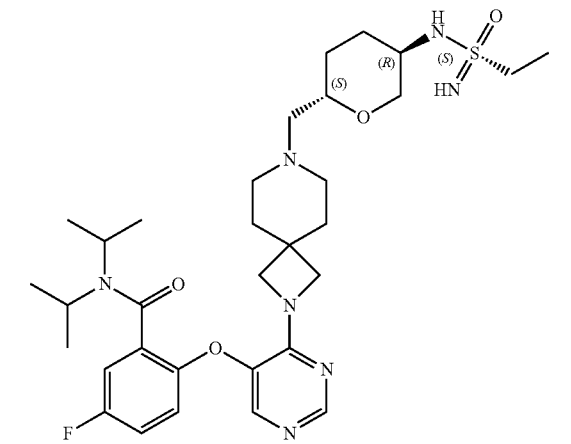 | 2-((4-(7-(((2S,5R)-5-((S)-Ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide and |

TABLE 1-continued

Representative Compounds of the Present Disclosure

| Compound | Structure | IUPAC Name |
|---|---|---|
| 227 | 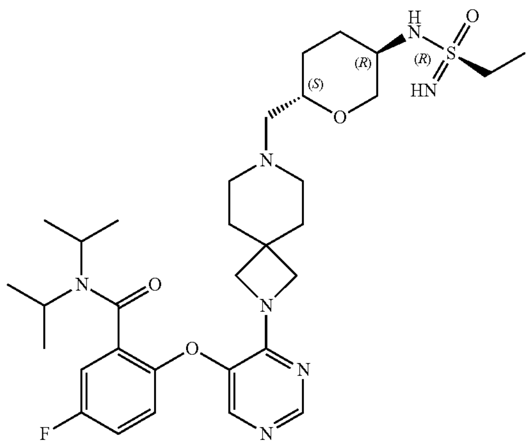 | 2-((4-(7-(((2S,5R)-5-((R)-Ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 228 | 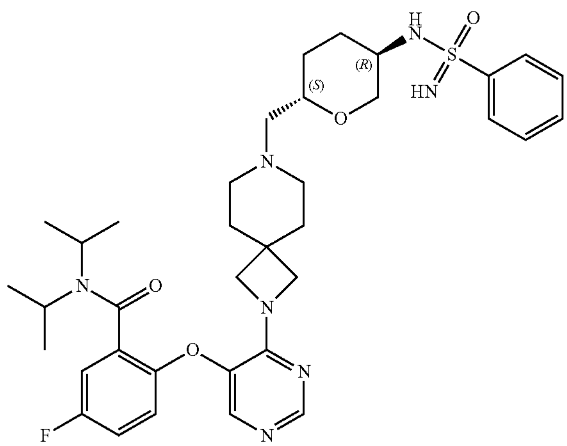 | 5-Fluoro-N,N-diisopropyl-2-((4-(7-(((2S,5R)-5-(phenylsulfonoamidimidamido)tetrahydro-2H-pyran-2-yl)methyl)-2,7-diazaspiro[3.5]nonan-2-yl)pyrimidin-5-yl)oxy)benzamide |
| 229 | 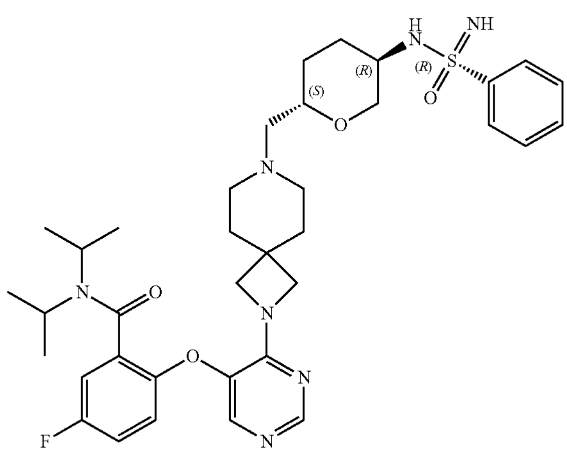 | 5-Fluoro-N,N-diisopropyl-2-((4-(7-(((2S,5R)-5-((R)-phenylsulfonoamidimidamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 230 | 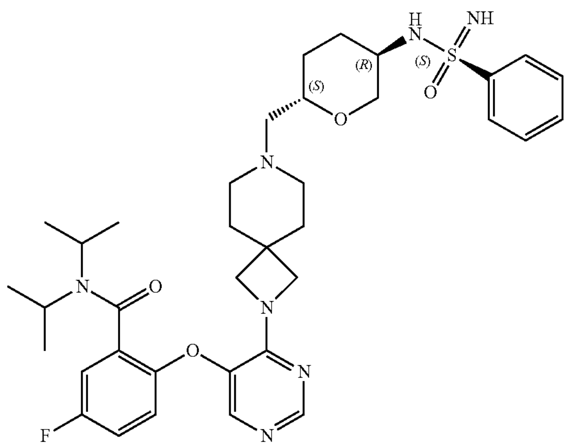 | 5-Fluoro-N,N-diisopropyl-2-((4-(7-(((2S,5R)-5-((S)-phenylsulfonoamidimidamido)tetrahydro-2H-pyran-2-yl)methyl)-2,7-diazaspiro[3.5]nonan-2-yl)pyrimidin-5-yl)oxy)benzamide |
| 231 | 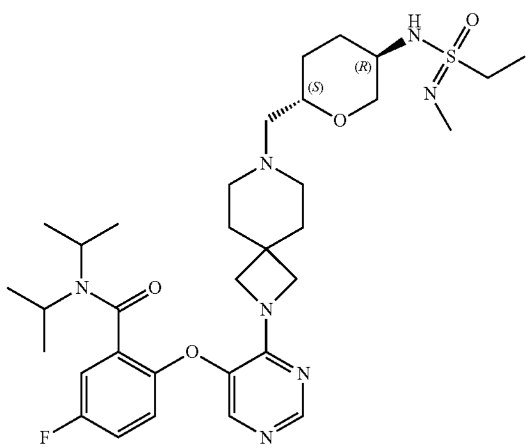 | 5-Fluoro-N,N-diisopropyl-2-((4-(7-(((2S,5R)-5-(N'-methylethylsulfonoamidimidamido)tetrahydro-2H-pyran-2-yl)methyl)-2,7-diazaspiro[3.5]nonan-2-yl)pyrimidin-5-yl)oxy)benzamide |
| 232 | 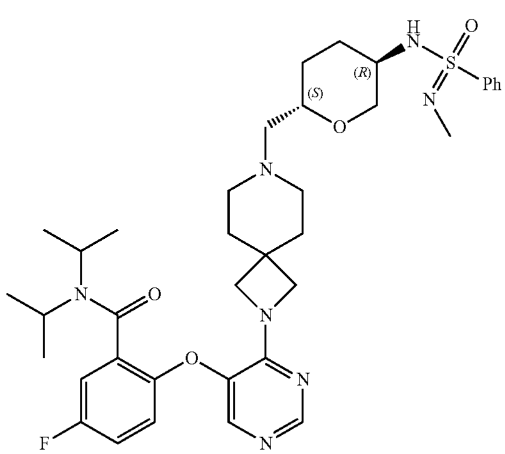 | 5-Fluoro-N,N-diisopropyl-2-((4-(7-(((2S,5R)-5-(N'-methylphenylsulfonoamidimidamido)tetrahydro-2H-pyran-2-yl)methyl)-2,7-diazaspiro[3.5]nonan-2-yl)pyrimidin-5-yl)oxy)benzamide |

TABLE 1-continued

Representative Compounds of the Present Disclosure

| Compound | Structure | IUPAC Name |
|---|---|---|
| 233 | 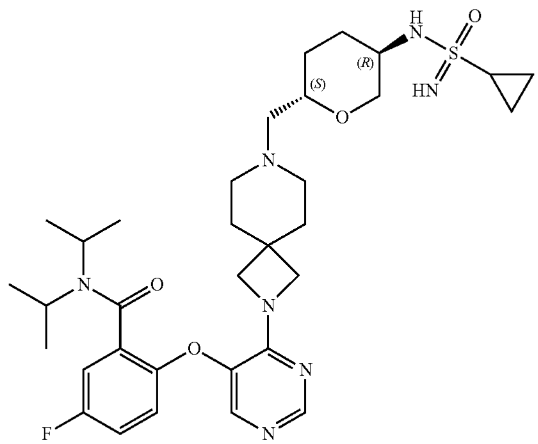 | 2-((4-(7-(((2S,5R)-5-(Cyclopropanesulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide |
| 234 | 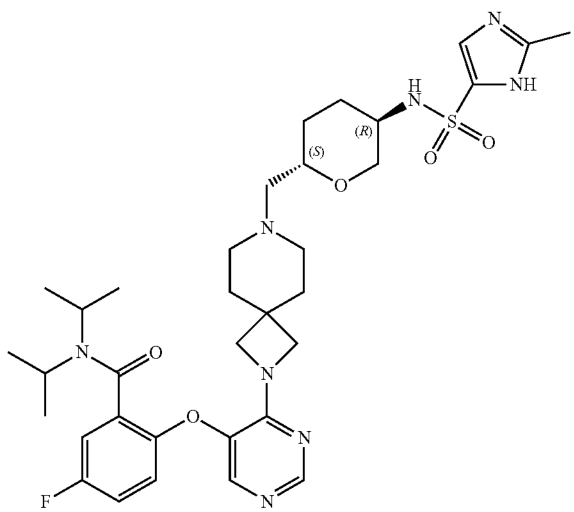 | 5-Fluoro-N,N-diisopropyl-2-((4-(7-(((2S,5R)-5-((2-methyl-1H-imidazole)-5-sulfonamido)tetrahydro-2H-pyran-2-yl)methyl)-2,7-diazaspiro[3.5]nonan-2-yl)pyrimidin-5-yl)oxy)benzamide |
| 235 | 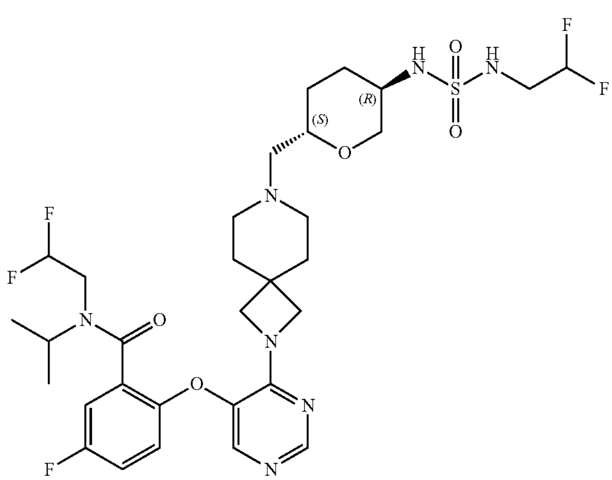 | N-(2,2-Difluoroethyl)-2-((4-(7-(((2S,5R)-5-((N-(2,2-difluoroethyl)sulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |

TABLE 1-continued

Representative Compounds of the Present Disclosure

| Compound | Structure | IUPAC Name |
|---|---|---|
| 236 | 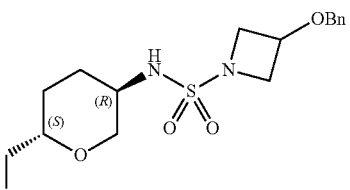 | 2-((4-(7-(((2S,5R)-5-((3-(Benzyloxy)azetidine)-1-sulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide |
| 237 | 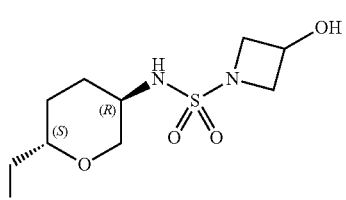 | N-(2,2-Difluoroethyl)-5-fluoro-2-((4-(7-(((2S,5R)-5-((3-hydroxyazetidine)-1-sulfonamido)tetrahydro-2H-pyran-2-yl)methyl)-2,7-diazaspiro[3.5]nonan-2-yl)pyrimidin-5-yl)oxy)-N-isopropylbenzamide |
| 238 | 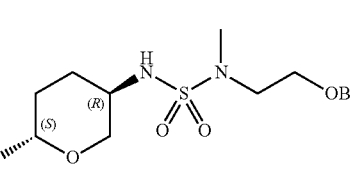 | 2-((4-(7-(((2S,5R)-5-((N-(2-Benzyloxy)ethyl)-N-methylsulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide |

TABLE 1-continued

Representative Compounds of the Present Disclosure

| Compound | Structure | IUPAC Name |
|---|---|---|
| 239 | 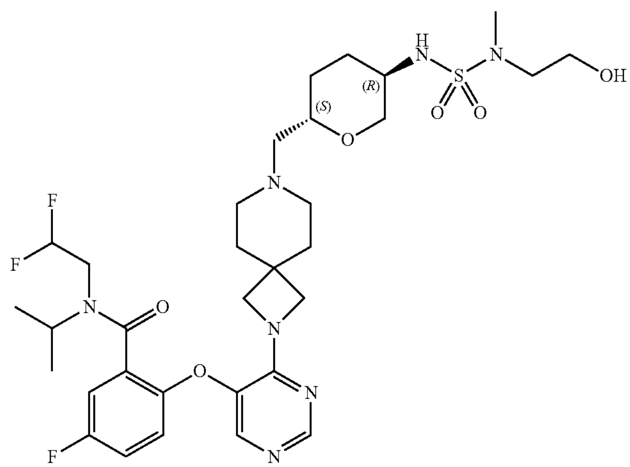 | N-(2,2-difluoroethyl)-5-fluoro-2-((4-(7-(((2S,5R)-5-((N-(2-hydroxyethyl)-N-methylsulfamoyl)amino)tetrahydro-2H-pyran-2-yl)methyl)-2,7-diazaspiro[3.5]nonan-2-yl)pyrimidin-5-yl)oxy)-N-isopropylbenzamide |
| 240 | 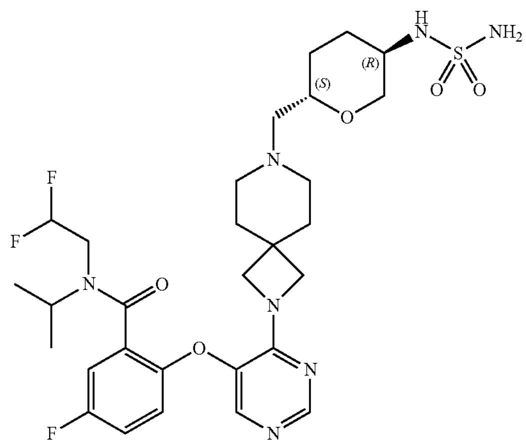 | N-(2,2-Difluoroethyl)-5-fluoro-N-isopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide |
| 241 | 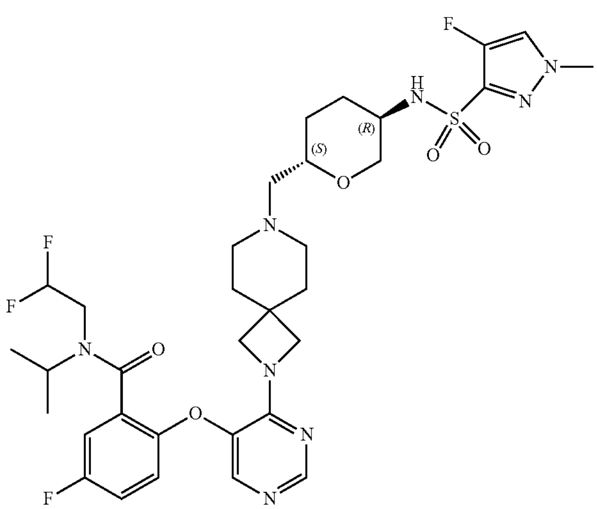 | N-(2,2-Difluoroethyl)-5-fluoro-2-((4-(7-(((2S,5R)-5-((4-fluoro-1-methyl-1H-pyrazole)-3-sulfonamido)tetrahydro-2H-pyran-2-yl)methyl)-2,7-diazaspiro[3.5]nonan-2-yl)pyrimidin-5-yl)oxy)-N-isopropylbenzamide |

TABLE 1-continued

Representative Compounds of the Present Disclosure

| Compound | Structure | IUPAC Name |
|---|---|---|
| 242 | 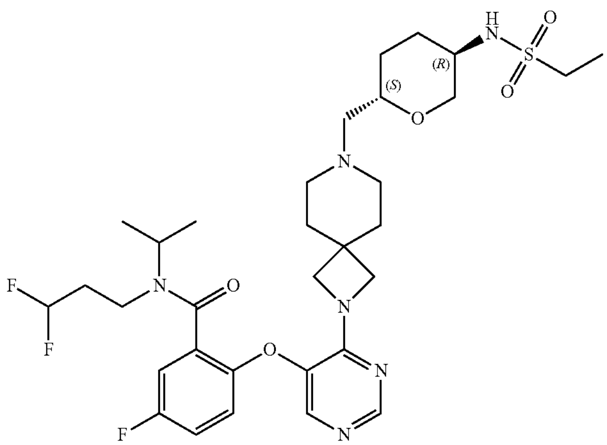 | N-(3,3-Difluoropropyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 243 | 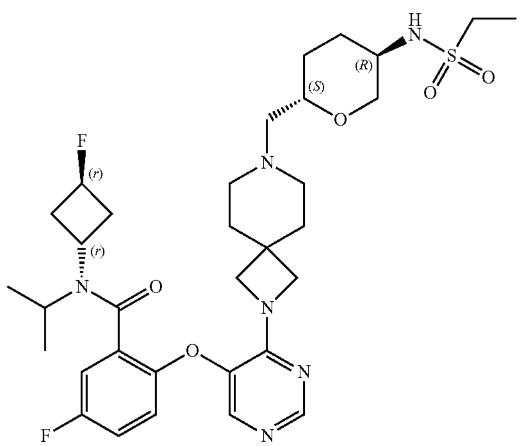 | 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((1r,3r)-3-fluorocyclobutyl)-N-isopropylbenzamide |
| 244 | 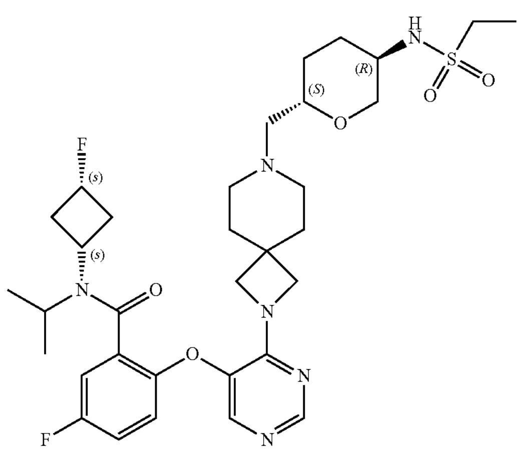 | 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((1s,3s)-3-fluorocyclobutyl)-N-isopropylbenzamide |

TABLE 1-continued

Representative Compounds of the Present Disclosure

| Compound | Structure | IUPAC Name |
|---|---|---|
| 245 | 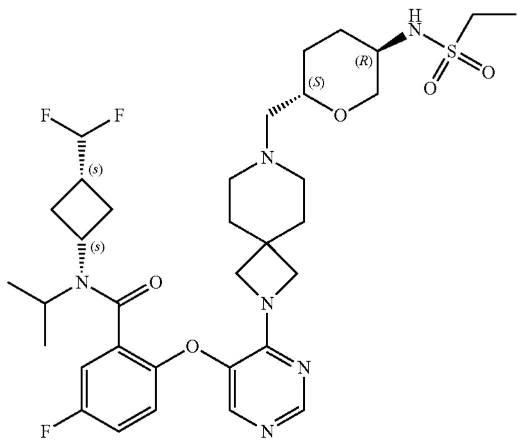 | N-((1s,3s)-3-(difluoromethyl)cyclobutyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 246 | 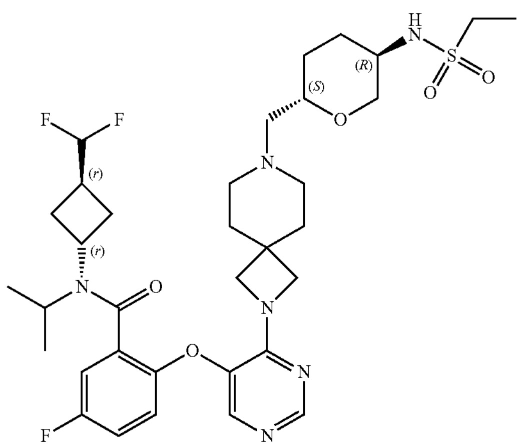 | N-((1r,3r)-3-(Difluoromethyl)cyclobutyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 247 | 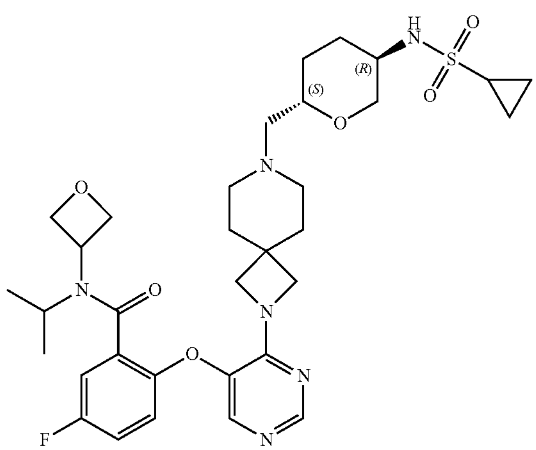 | 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide |

TABLE 1-continued

Representative Compounds of the Present Disclosure

| Compound | Structure | IUPAC Name |
|---|---|---|
| 248 | 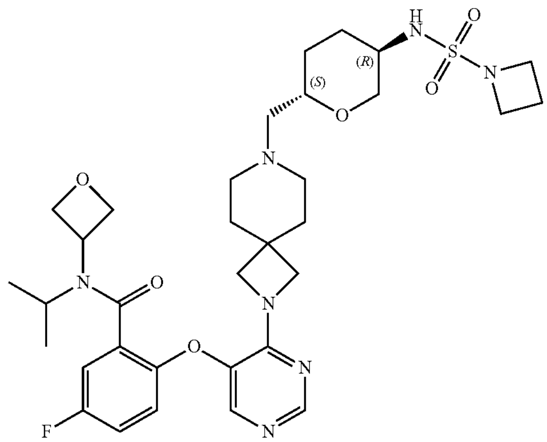 | 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide |
| 249 | 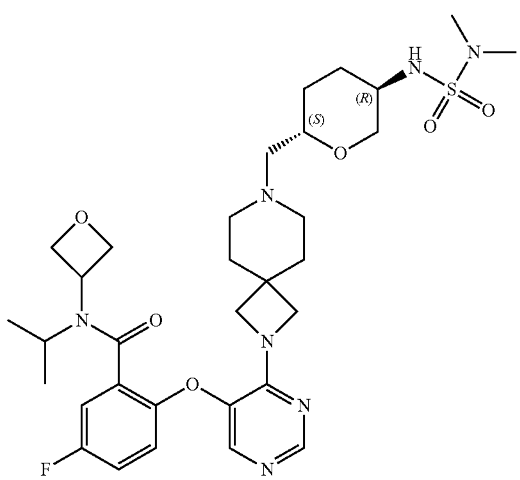 | 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide |
| 250 | 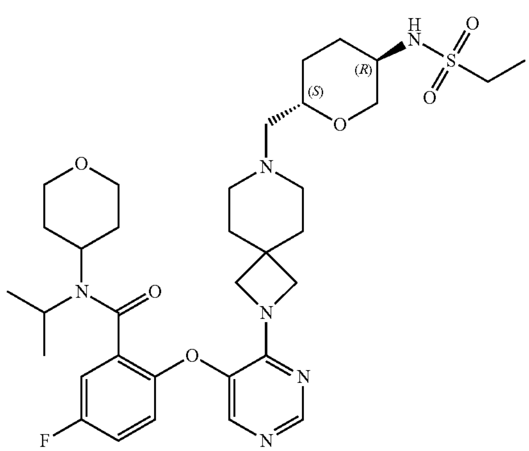 | 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(tetrahydro-2H-pyran-4-yl)benzamide |

TABLE 1-continued

Representative Compounds of the Present Disclosure

| Compound | Structure | IUPAC Name |
|---|---|---|
| 251 | 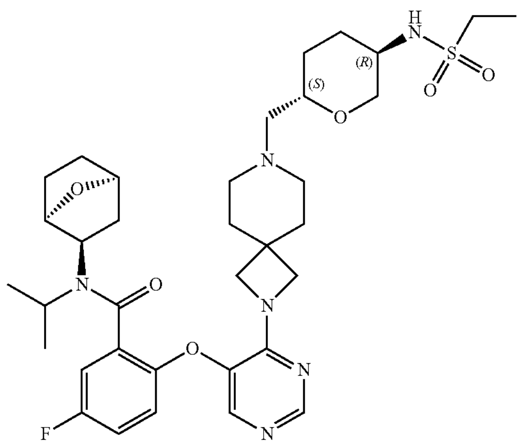 | N-((1R,2R,4S)-7-Oxabicyclo[2.2.1]heptan-2-yl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 252 | 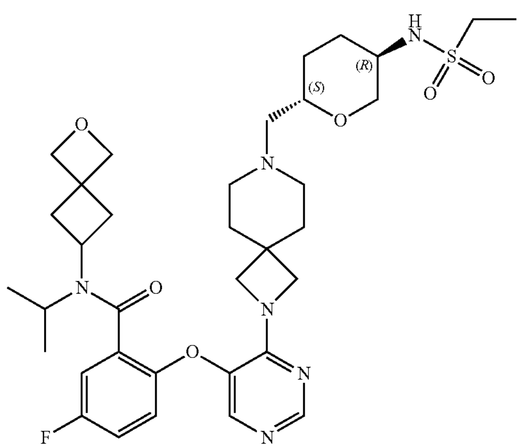 | 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-oxaspiro[3.3]heptan-6-yl)benzamide |
| 253 | 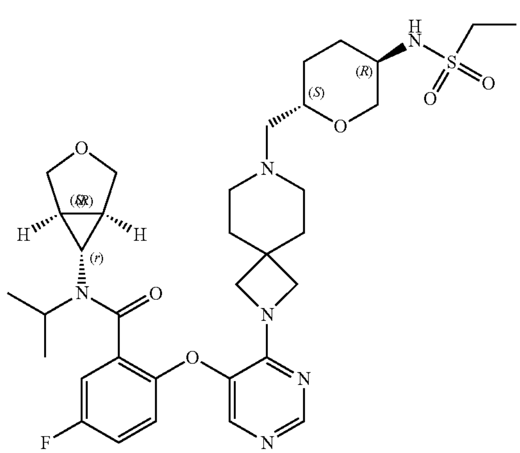 | N-((1R,5S,6r)-3-c)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |

TABLE 1-continued

Representative Compounds of the Present Disclosure

| Compound | Structure | IUPAC Name |
|---|---|---|
| 254 | 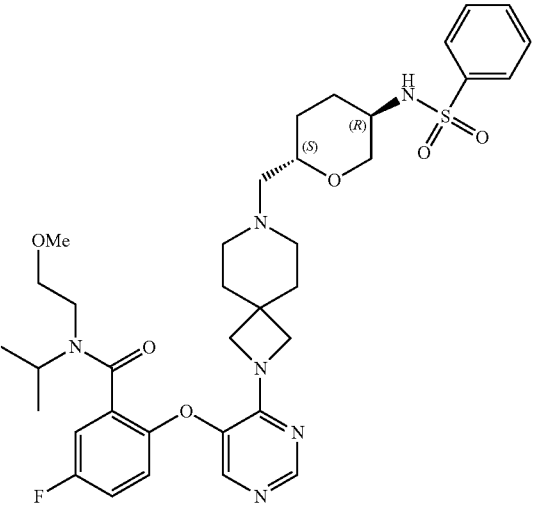 | 5-Fluoro-N-isopropyl-N-(2-methoxyethyl)-2-((4-(7-(((2S,5R)-5-(phenylsulfonamido)tetrahydro-2H-pyran-2-yl)methyl)-2,7-diazaspiro[3.5]nonan-2-yl)pyrimidin-5-yl)oxy)benzamide |
| 255 | 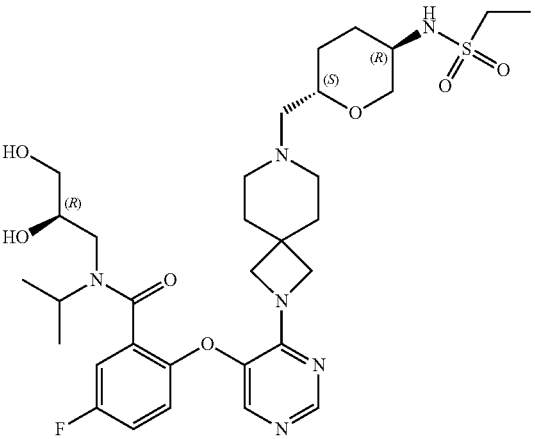 | N-((R)-2,3-Dihydroxypropyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide |
| 256 | 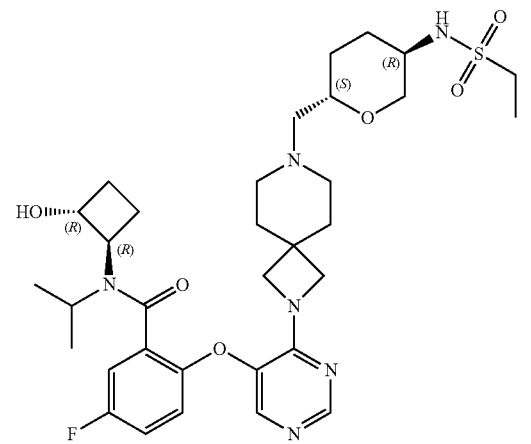 | 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((E1)-2-hydroxycyclobutyl)-N-isopropylbenzamide |

TABLE 1-continued

Representative Compounds of the Present Disclosure

| Compound | Structure | IUPAC Name |
|---|---|---|
| 257 | 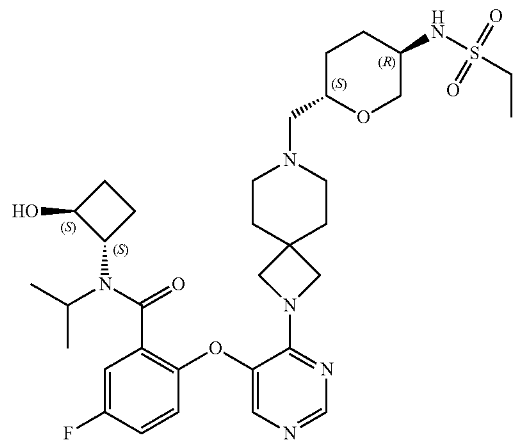 | 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((E2)-2-hydroxycyclobutyl)-N-isopropylbenzamide |
| 258 | 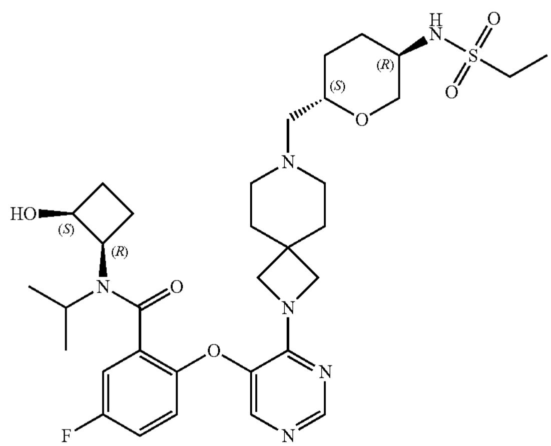 | 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((1R,2S)-2-hydroxycyclobutyl)-N-isopropylbenzamide |
| 259 | 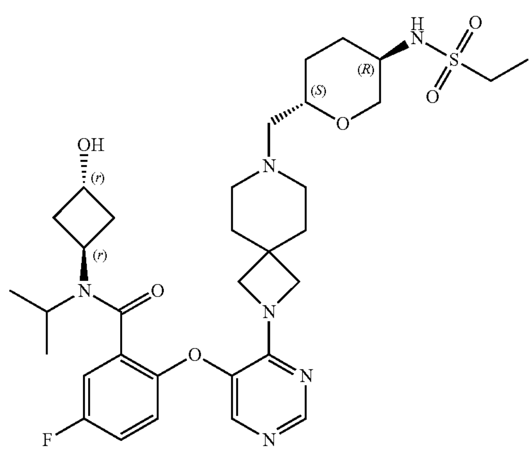 | 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((1r,3r)-3-hydroxycyclobutyl)-N-isopropylbenzamide |

TABLE 1-continued

Representative Compounds of the Present Disclosure

| Compound | Structure | IUPAC Name |
|---|---|---|
| 260 | 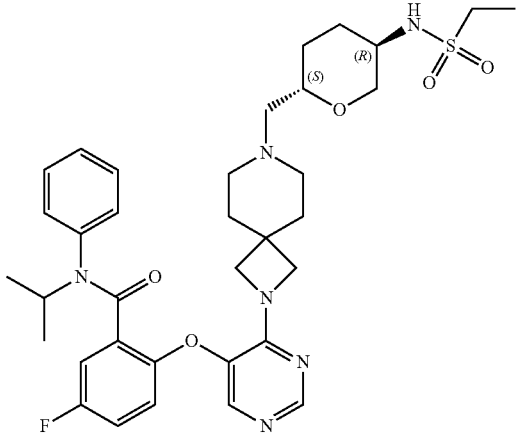 | 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-phenylbenzamide |
| 261 | 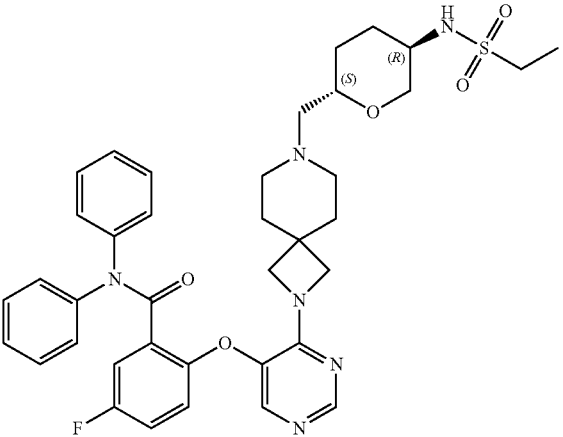 | N-ethyl-5-fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide |
| 262 | 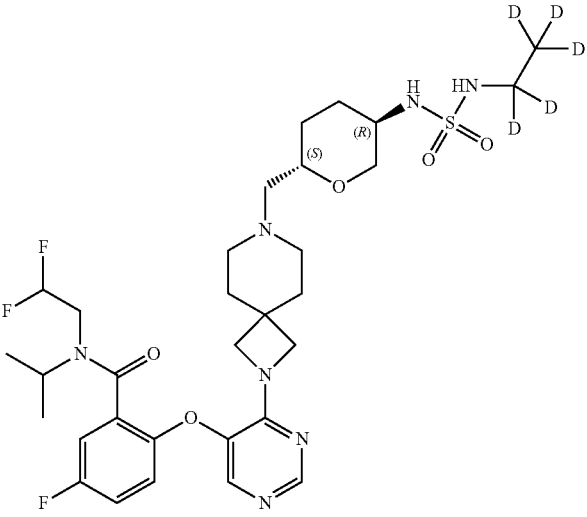 | N-(2,2-Difluoroethyl)-2-((4-(7-(((2S,5R)-5-((N-(ethyl-$d_5$)sulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide |

In some embodiments, a compound according to any embodiments herein (e.g., Formulae 0, 0a, I, Ia, II, IIa, III, IIIa, and Table 1) exhibits an inhibition activity against the binding of menin and MLL. In some embodiments, a compound according to any embodiments herein (e.g., Formulae 0, 0a, I, Ia, II, IIa, III, IIIa, and Table 1) exhibits an inhibition activity against the binding of menin and MLL. In some embodiments, a compound according to any embodiments herein e.g., Formulae 0, 0a, I, Ia, II, IIa, III, IIIa, and Table 1) exhibits an inhibition activity against the binding of menin and MLL which is useful in the treatment and/or prevention of one or more diseases in which menin and MLL play a role. In some embodiments, a compound according to any embodiments herein (e.g., Formulae 0, 0a, I, Ia, II, IIa, III, IIIa, and Table 1) exhibits low hERG binding. In some embodiments, a compound according to any embodiments herein (e.g., Formulae 0, 0a, I, Ia, II, IIa, III, IIIa, and Table 1) is useful for the treatment of one or more diseases in which menin and MLL play a role and minimizes hERG binding. Without being bound to any theory, one of the primary causes of QT prolongation is thought to be blockage of the hERG potassium channel in cardiac myocytes. In some embodiments, the compounds of the present disclosure (e.g., Formulae 0, 0a, I, Ia, II, IIa, III, IIIa, and Table 1) do not significantly block the hERG potassium channel.

In some embodiments, the compounds of the present disclosure (e.g., Formulae 0, 0a, I, Ia, II, IIa, III, IIIa, and Table 1) do not significantly block the hERG potassium channel (e.g., an $IC_{50}$ greater than 1 μM, 5 μM, 10 μM, 15 μM, 20 μM, 25 μM, 30 μM, 35 μM, 40 μM, or 50 μM) as measured by a standard patch clamp hERG assay.

In some embodiments, the compounds of the present disclosure (e.g., Formulae 0, 0a, I, Ia, II, IIa, III, IIIa, and Table 1) do not significantly block the hERG potassium channel (e.g., an $IC_{50}$ greater than 1 μM, 5 μM, 10 μM, 15 μM, 20 μM, 25 μM, 30 μM, 35 μM, 40 μM, or 50 μM).

In some embodiments and without wishing to be bound to any theory, the present disclosure is directed to inhibitors of the menin-MLL interaction comprising a pyran substitution (e.g., Formulae 0, 0a, I, Ia, II, IIa, III, IIIa, and Table 1) where the pyran substitution has been found to reduce hERG inhibition.

In some embodiments and without wishing to be bound to any theory, the present disclosure is directed to inhibitors of the menin-MLL interaction (e.g., Formulae 0, 0a, I, Ia, II, IIa, III, IIIa, and Table 1) which are resistant to metabolism. In some embodiments and without wishing to be bound to any theory, the present disclosure is directed to inhibitors of the menin-MLL interaction (e.g., Formulae 0, 0a, I, Ia, II, IIa, III, IIIa, and Table 1) which are resistant to metabolism, where the metabolites are inhibitors of the hERG potassium channel. In some embodiments and without wishing to be bound to any theory, the present disclosure is directed to inhibitors of the menin-MLL interaction (e.g., Formulae 0, 0a, I, Ia, II, IIa, III, IIIa, and Table 1) which are resistant to metabolism, where the metabolism decreases the bioavailability of the inhibitor. In some embodiments and without wishing to be bound to any theory, the present disclosure is directed to inhibitors of the menin-MLL interaction (e.g., Formulae 0, 0a, I, Ia, II, IIa, III, IIIa, and Table 1) which are resistant to metabolism, where the metabolism decreases the bioavailability of the inhibitor and the corresponding metabolites are more effective (e.g., by IC50, etc.) at binding the hERG potassium channel.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications. In some embodiments, the compound is an isotopic derivative of any one of the compounds described in Table I, or a pharmaceutically acceptable salt thereof.

It is understood that the deuterium labeled compound comprises a deuterium atom having an abundance of deuterium that is substantially greater than the natural abundance of deuterium, which is 0.015%.

In some embodiments, the deuterium labeled compound has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). As used herein, the term "deuterium enrichment factor" means the ratio between the deuterium abundance and the natural abundance of a deuterium.

It is understood that the deuterium labeled compound can be prepared using any of a variety of art-recognized techniques. For example, the deuterium labeled compound can generally be prepared by carrying out the procedures disclosed in the Schemes and/or in the Examples described herein, by substituting a deuterium labeled reagent for a non-deuterium labeled reagent.

A compound of the present disclosure or a pharmaceutically acceptable salt or solvate thereof that contains the aforementioned deuterium atom(s) is within the scope of the disclosure. Further, substitution with deuterium (i.e., 2H) may afford certain therapeutic advantages resulting from greater metabolic stability, e.g., increased in vivo half-life or reduced dosage requirements.

For the avoidance of doubt, it is to be understood that, where in this specification a group is qualified by "described herein", the said group encompasses the first occurring and broadest definition as well as each and all of the particular definitions for that group.

Potency can also be determined by $IC_{50}$ value. A compound with a lower $IC_{50}$ value, as determined under substantially similar conditions, is more potent relative to a compound with a higher $IC_{50}$ value.

The compounds of the application are defined herein by their chemical structures and/or chemical names. Where a compound is referred to by both a chemical structure and a chemical name, and the chemical structure and chemical name conflict, the chemical structure is determinative of the compound's identity.

In another aspect, the application provides a method of synthesizing a compound disclosed herein. The synthesis of the compounds of the application can be found herein and in the Examples below. Other embodiments are a method of making a compound of any of the formulae herein using any one, or combination of, reactions delineated herein. The method can include the use of one or more intermediates or chemical reagents delineated herein.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various cycloalkyl, and heterocyclyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

For compounds of the disclosure in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the term "amino," employed alone or in combination with other terms, refers to a group of formula —$NH_2$. In some embodiments, an amine can be substituted by one or more groups, e.g., —N—($C_1$-$C_6$ alkyl)$_2$. In some embodiments, when two groups are attached to an amine they can be the same or different. Each group is selected independently of each other and can be each independently optionally substituted.

As used herein, "$C_{i-j}$ haloalkoxy," employed alone or in combination with other terms, refers to a group of formula —O-haloalkyl having i to j carbon atoms. An example haloalkoxy group is $OCF_3$. An additional example haloalkoxy group is $OCHF_2$. In some embodiments, the haloalkoxy group is fluorinated only. In some embodiments, the alkyl group has 1 to 6 or 1 to 4 carbon atoms. In some embodiments, the haloalkoxy group is $C_{1-4}$haloalkoxy.

As used herein, the term "halogen" or "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

The term "haloalkyl" or "haloalkoxyl" refers to an alkyl or alkoxyl substituted with one or more halogen atoms. In some embodiments, the haloalkyl group is fluorinated. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the haloalkyl group is 2,2,2-trifluoroethyl. In some embodiments, the haloalkyl group is 2,2-difluoroethyl. In some embodiments, the haloalkyl group has 1 to 6 or 1 to 4 carbon atoms.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and c As used herein, the term "cycloalkyl" refers to a saturated or partially unsaturated hydrocarbon monocyclic or polycyclic (e.g., fused, bridged, or spiro rings) system having 3 to 30 carbon atoms (e.g., C3-C12, C3-C10, or C3-C8). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic. In some embodiments, cycloalkyl may optionally contain one or more alkenylene groups as part of the ring structure. Cycloalkyl groups can include mono- or polycyclic ring systems. Polycyclic ring systems can include fused ring systems and spirocycles. Also included in the definition of cycloalkyl are moieties that have one or more aromatic rings fused (i.e., having a bond in common with) to the cycloalkyl ring, for example, benzo or pyrido derivatives of cyclopentane, cyclopentene, cyclohexane, and the like. A heterocyclyl group that includes a fused aromatic (e.g., aryl or heteroaryl) moiety can be attached to the molecule through an atom from either the aromatic or non-aromatic portion. One or more ring-forming carbon atoms of a cycloalkyl group can be oxidized to form carbonyl linkages. In some embodiments, cycloalkyl is $C_{3-10}$ cycloalkyl, $C_{3-7}$ cycloalkyl, or $C_{5-6}$ cycloalkyl. Exemplary cycloalkyl groups include cyclopropyl, cyclobutyl, cyclopentyl, cyclohexyl, cycloheptyl, cyclopentenyl, cyclohex-enyl, cyclohexadienyl, cycloheptatrienyl, norbornyl, norpinyl, norcarnyl, and the like. Further exemplary cycloalkyl groups include cyclopropyl, cyclobutyl, cyclopentyl, and cyclohexyl. Additional example cycloalkyl groups, where the cycloalkyl group has a fused aryl or heteroaryl moiety, include tetrahydronaphthalen-2-yl, 2,3-dihydro-1H-inden-2-yl; 2,3,4,9-tetrahydro-1H-carbazol-7-yl; 2,6,7,8-tetrahydrobenzo[cd]indazol-4-yl; and 5,6,7,8,9,10-hexahydrocyclohepta[b]indol-3-yl.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, aryl is $C_{6-14}$ aryl. In some embodiments, the aryl group is a naphthalene ring or phenyl ring. In some embodiments, the aryl group is phenyl.

As used herein, the term "heteroaryl," employed alone or in combination with other terms, refers to a monocyclic or polycyclic (e.g., having 2, 3 or 4 fused rings) aromatic heterocylic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered or 5- to 6-membered. In some embodiments, the heteroaryl group is 5-membered. In some embodiments, the heteroaryl group is 6-membered. In some embodiments, the heteroaryl group is 9- or 10-membered bicyclic. In some embodiments, the heteroaryl is 9-member bicyclic. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridinyl, pyrimidinyl, pyrazinyl, pyridazinyl, pyrrolyl, pyrazolyl, azolyl, oxazolyl, isoxazolyl, thiazolyl, isothiazolyl, imidazolyl, furanyl, thiophenyl, triazolyl, tetrazolyl, thiadiazolyl, quinolinyl, isoquinolinyl, indolyl, benzothiopheneyl, benzofuranyl, benzisoxazolyl, benzoimidazolyl, imidazo[1, 2-b]thiazolyl, purinyl, triazinyl, and the like. In some embodiments, the heteroaryl group is 9H-carbazol-2-yl; 1H-benzo[d]imidazol-6-yl; 1H-indol-6-yl; 1H-indazol-6-yl; 2H-indazol-4-yl; 1H-benzo[d][1,2,3]triazol-6-yl; benzo[d]oxazol-2-yl; quinolin-6-yl; or benzo[d]thiazol-2-yl.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthyridine, indole, benzofuran, purine, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the phrase "optionally substituted" means unsubstituted or substituted. As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "heterocyclyl," employed alone or in combination with other terms, refers to a non-aromatic heterocyclic ring system, which may optionally contain one or more unsaturations as part of the ring structure, and which has at least one heteroatom ring member independently selected from nitrogen, sulfur and oxygen. In some embodiments, the heterocyclyl group has 1, 2, 3, or 4 heteroatom ring members. In some embodiments, the heterocyclyl group has 1, 2, or 3 heteroatom ring members. In some embodiments, the heterocyclyl group has 1 or 2 heteroatom ring members. In some embodiments, the heterocyclyl group has 1 heteroatom ring member. When the heterocyclyl group contains more than one heteroatom in the ring, the heteroatoms may be the same or different. Example ring-forming members include CH, $CH_2$, C(O), N, NH, O, S, S(O), and $S(=O)_2$. Heterocyclyl groups can include mono- or polycyclic (e.g., having 2, 3 or 4 fused rings) ring systems. Polycyclic rings can include both fused systems and spirocycles. Also included in the definition of heterocyclyl are moieties that have one or more aromatic rings fused (i.e., having a bond in common with) to the non-aromatic ring, for example, 1, 2, 3, 4-tetrahydro-quinoline, dihydrobenzofuran and the like. A heterocyclyl group that includes a fused aromatic moiety can be attached to the molecule through an atom from either the aromatic or non-aromatic portion. The carbon atoms or heteroatoms in the ring(s) of the heterocyclyl group can be oxidized to form a carbonyl, sulfinyl, or sulfonyl group (or other oxidized linkage) or a nitrogen atom can be quaternized. In some embodiments, heterocyclyl is 5- to 10-membered, 4- to 10-membered, 4- to 7-membered, 5-membered, or 6-membered. Examples of heterocyclyl groups include 1, 2, 3, 4-tetrahydro-quinolinyl, dihydrobenzofuranyl, azetidinyl, azepanyl, pyrrolidinyl, piperidinyl, piperazinyl, morpholinyl, thiomorpholinyl, and pyranyl. Examples of heterocyclyl groups that include one or more fused aromatic groups (e.g., aryl or heteroaryl) include N-(2'-oxospiro[cyclohexane-1,3'-indolin]-6'-yl; 1,2,3,4-tetrahydroisoquinolin-6-yl; 2,3-dihydro-1H-benzo[d]imidazol-5-yl; 1,3-dihydrospiro[indene-2,3'-indolin]-6'-yl; 2,3-dihydrobenzo[d]oxazol-5-yl; 1,2-dihydroquinolin-7-yl; indolin-6-yl; spiro[cyclopentane-1,3'-indolin]-6'-yl; spiro[cyclohexane-1,3'-indolin]-6'-yl; chroman-6-yl; 3,4-dihydro-2H-benzo[b][1,4]oxazin-6-yl; and benzo[d][1,3]dioxol-5-yl.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R and S sequencing rules of Cahn and Prelog, or by the manner in which the molecule rotates the plane of polarised light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture". The compounds described herein can be asymmetric (e.g., having one or more stereocenters). All stereoisomers, such as enantiomers and diastereoisomers, are intended unless otherwise indicated. Where a compound name or structure is silent with respect to the stereochemistry of a stereocenter, all possible configurations at the stereocenter are intended. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

When the compounds of the disclosure contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1, 2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

When a disclosed compound is named or depicted without indicating the stereochemistry of one or more stereocenters, each of the stereoisomers resulting from the possible stereochemistries at the undefined stereocenter(s) are intended to be encompassed. For example, if a stereocenter is not designated as R or S, then either or both are intended.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H- 1,2, 4-triazole, 1H- and 2H-isoindole, and 1H- and 2H-pyrazole. Tautomeric forms can be in equilibrium or sterically locked into one form by appropriate substitution.

Compounds of the disclosure can also include all isotopes of atoms occurring in the intermediates or final compounds. Isotopes include those atoms having the same atomic number but different mass numbers. Isotopes of constituent atoms of the compounds of the disclosure can be present in natural or non-natural abundance. Examples of isotopes of hydrogen include deuterium and tritium. In some embodiments, the compounds of the disclosure are deuterated, meaning at least one deuterium atom is present in the place of a hydrogen atom. In some embodiments, 1, 2, 3, 4, 5, 6, 7, or 8 hydrogens in a compound of the disclosure are replaced by deuterium. Methods for replacing hydrogen with deuterium in a molecule are known in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

It will be understood that the compounds of the present disclosure and any pharmaceutically acceptable salts thereof, comprise stereoisomers, mixtures of stereoisomers, polymorphs of all isomeric forms of said compounds.

In some embodiments, the compounds of the disclosure, or salts thereof, or crystalline forms of any of the aforementioned, are purified or substantially isolated. By "substantially isolated" is meant that the compound is at least partially or substantially separated from the environment in which it was formed or detected. Partial separation can include, for example, a composition enriched in a compound of the disclosure. Substantial separation can include compositions containing at least about 50%, at least about 60%, at least about 70%, at least about 80%, at least about 90%, at least about 95%, at least about 97%, or at least about 99% by weight of the compounds of the disclosure, or salt thereof. In some embodiments, the compounds of the disclosure, or salts thereof, or crystalline forms of any of the aforementioned, can be prepared with a purity of about 75% or more, 80% or more, 85% or more, 90% or more, 95% or more, 98% or more, or 99% or more.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred.

The compounds disclosed herein include the compounds themselves, as well as their salts, their solvates, and their prodrugs, if applicable. A salt, for example, can be formed between an anion and a positively charged group (e.g., protonated amino) on a compound of this disclosure. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of this disclosure. Suitable cations include sodium ion, potassium ion, magnesium ion, calcium ion, and an ammonium cation such as tetramethylammonium ion. The compounds of this disclosure also include those salts containing quaternary nitrogen atoms. Examples of prodrugs include esters and other pharmaceutically acceptable derivatives, which, upon administration to a subject, are capable of providing active compounds of this disclosure.

Additionally, physiologically acceptable, i.e., pharmaceutically compatible, salts can be salts of the compounds disclosed herein with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, trifluoroacetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Other pharmaceutically compatible salts which may be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine or methylpiperidine.

As used herein, "pharmaceutically acceptable salts" can refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts can include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, or an alkaline earth metal ion, e.g., an aluminum ion; or coordinates with an organic base such as ethanolamine, diethanolamine, triethanolamine, tromethamine, N-methylglucamine, diethylamine, diethylaminoethanol, ethylenediamine, imidazole, lysine, arginine, morpholine, 2-hydroxyethylmorpholine, dibenzylethylenediamine, trimethylamine, piperidine, pyrrolidine, benzylamine, tetramethylammonium hydroxide and the like.

It should be understood that all references to pharmaceutically acceptable salts include solvent addition forms (solvates) or crystal forms (polymorphs) as defined herein, of the same salt.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. It is to be further understood, unless otherwise stated, any description of a method of treatment includes use of the compounds to prepare a medicament to treat such condition. The treatment includes treatment of human or non-human animals including rodents and other disease models.

As used herein, the term "subject" includes human and non-human animals, as well as cell lines, cell cultures, tissues, and organs. In some embodiments, the subject is a mammal. The mammal can be e.g., a human or appropriate non-human mammal, such as primate, mouse, rat, dog, cat, cow, horse, goat, camel, sheep or a pig. The subject can also be a bird or fowl. In some embodiments, the subject is a human.

As used herein, the term "subject in need thereof" refers to a subject having a disease or having an increased risk of developing the disease. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

The compounds of the present disclosure may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the sulfonylurea group in a compound of the any one of the Formulae disclosed herein.

Accordingly, the present disclosure includes those compounds of the present disclosure as defined hereinbefore when made available by organic synthesis and when made available within the human or animal body by way of cleavage of a prodrug thereof. Accordingly, the present disclosure includes those compounds of the present disclosure that are produced by organic synthetic means and also such compounds that are produced in the human or animal body by way of metabolism of a precursor compound, that is a compound of the present disclosure may be a synthetically-produced compound or a metabolically-produced compound.

A suitable pharmaceutically acceptable prodrug of a compound of the present disclosure is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of the present disclosure that possesses a hydroxy group is, for example, an in vivo cleavable ester or ether thereof. An in vivo cleavable ester or ether of a compound of the present disclosure containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include C1-C10 alkanoyl groups such as acetyl, benzoyl, phenylacetyl and substituted benzoyl and phenylacetyl groups, C1-C10 alkoxycarbonyl groups such as ethoxycarbonyl, N,N—(C1-C6 alkyl)2carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-C4 alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of the present disclosure that possesses a carboxy group is, for example, an in vivo cleavable amide thereof, for example an amide formed with an amine such as ammonia, a $C_1$-$C_4$ alkylamine such as methylamine, a ($C_1$-$C_4$ alkyl)$_2$amine such as dimethylamine, N-ethyl N-methylamine or diethylamine, a C1-C4 alkoxy C2-C4 alkylamine such as 2 methoxyethylamine, a phenyl $C_1$-$C_4$ alkylamine such as benzylamine and amino acids such as glycine or an ester thereof.

A suitable pharmaceutically acceptable prodrug of a compound of the present disclosure that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl, and 4-(C1-C4 alkyl)piperazin-1-ylmethyl.

The in vivo effects of a compound of the present disclosure may be exerted in part by one or more metabolites that are formed within the human or animal body after administration of a compound of the present disclosure. As stated hereinbefore, the in vivo effects of a compound of the present disclosure may also be exerted by way of metabolism of a precursor compound (a prodrug).

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Synthesis

In some aspects, the present disclosure provides a method of preparing a compound disclosed herein.

In some aspects, the present disclosure provides a method of preparing a compound, comprising one or more steps as described herein.

In some aspects, the present disclosure provides a compound obtainable by, or obtained by, or directly obtained by a method for preparing a compound described herein.

In some aspects, the present disclosure provides an intermediate being suitable for use in a method for preparing a compound described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl (Bn). The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively, an acyl group such as a tert butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively, an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of the present disclosure has been synthesized by any one of the processes defined herein, the processes may then further comprise the additional steps of: (i) removing any protecting groups present; (ii) converting the compound of the present disclosure into another compound of the present disclosure; (iii) forming a pharmaceutically acceptable salt, hydrate or solvate thereof; and/or (iv) forming a prodrug thereof.

The resultant compounds of the present disclosure can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilizing the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognize which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesized by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons). The compounds of the disclosure can be synthesized by the methods described in Schemes 1-8 below. The synthesis of various hydroxyl-substituted heterocycles is well documented in the literature and can be synthesized by known literature methods. The depicted intermediates may also be available as commercial reagents from numerous vendors.

The compounds of the present disclosure can be prepared according to the general methods illustrated in the following Schemes.

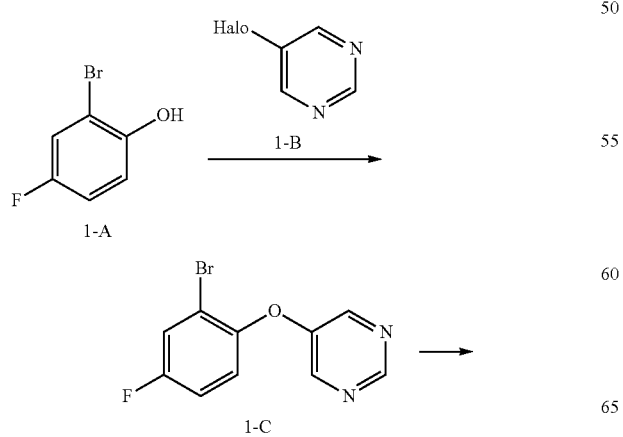

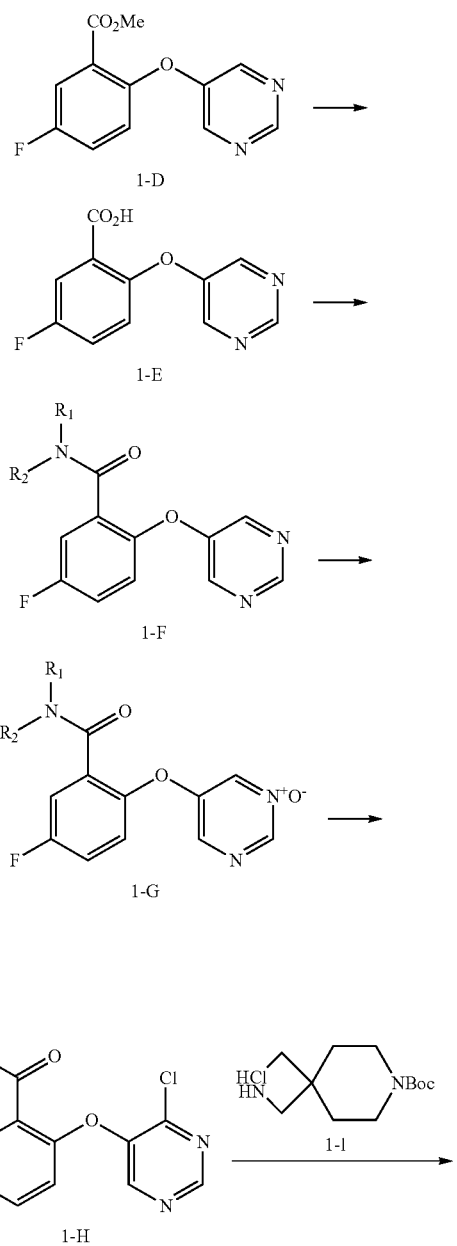

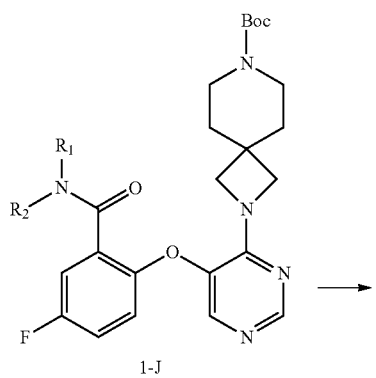

-continued

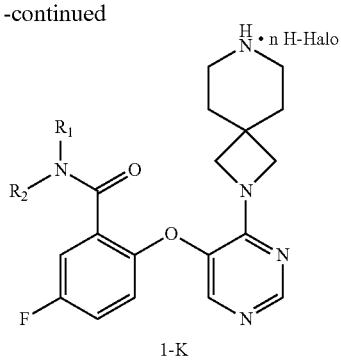

1-K

Scheme 1 illustrates the general methods for the preparation of key intermediates like compound 1-K. A suitably substituted 2-halophenol, for instance 4-fluoro-2-bromophenol (1-A), is reacted with a 5-halopyrimidine (1-B), for example 5-bromopyrimidine or 5-iodopyrimidine, to afford the corresponding diaryl ether (1-C). This reaction is typically conducted in the presence of an acid scavenger like $Na_2CO_3$, $K_2CO_3$, $Cs_2CO_3$, $K_3PO_4$, $Et_3N$ (triethylamine) or $(iPr)_2NEt$ (diisopropylethylamine, also known as Huning's base), in a suitable, neutral solvent, such as DMA (dimethyl acetamide) or NMP (N-methylpyrrolidinone). In some instances, this transformation can be facilitated by addition of an appropriate catalyst, typically $Cu_2O$ or CuI, in the presence of a suitable ligand, for example rel-(1R,2R)—$N^1$,$N^2$-bis(2-pyridinylmethylene)-1,2-cyclohexanediamine or 3,4,7,8-tetramethyl-1,10-phenanthroline. Conversion of compound 1-C to compound 1-D can be readily achieved by carbonylation under Pd catalysis, in the presence of an acid scavenger and suitable alcohol (typically used as the solvent in the reaction). Oftentimes, $Pd(dppf)Cl_2$ (dppf=1,1-bis(diphenylphosphino)ferrocene) is used as the palladium catalyst, but other catalyst systems, such as $Pd(Ph_3P)_2Cl_2$ ($Ph_3P$=triphenylphosphine) or $Pd(OAc)_2$ with $Ph_3P$, can also be used. Commonly, $Et_3N$ or $(i-Pr)_2NEt$ are used as the acid scavengers, and methanol is used as the solvent. These reactions are most typically run under an atmosphere of CO, but other CO sources, for example oxalic acid, can be used in some instances. The ester group of compound 1-D is subsequently saponified to the corresponding carboxylic acid 1-E. Typically, this transformation is accomplished using LiOH, NaOH or KOH, in an aqueous solvent system, such as methanol/water or THF/water. The carboxylic acid is then converted to an amide (1-F). Many different conditions have been developed to achieve this type of transformation, and will be generally familiar to those of skill in the art. For instance, the carboxylic acid can be reacted with thionyl chloride or oxalyl chloride, which forms the corresponding acid chloride. This reaction can be conducted in a suitable, neutral solvent like $CH_2Cl_2$, or if thionyl chloride is used, can be run with thionyl chloride as the reactant and solvent. The acid chloride is subsequently reacted with a suitable amine, $R_1R_2NH$, in the presence of an appropriate acid scavenger, for example $Et_3N$, $(i-Pr)_2NEt$, or pyridine, in a neutral solvent like $CH_2Cl_2$ or THF. In some instances, pyridine can be used as the acid scavenger and the solvent for the reaction. Alternatively, the carboxylic acid and amine R1R2NH can be combined together and coupled using a reagent such as DCC (dicyclohexyl carbodiimide), EDC (1-ethyl-3-(4-dimethylaminopropyl)carbodiimide), or HATU (1-[bis(dimethylamino)methylene]-1H-1,2,3-triazolo[4,5-b]pyridinium 3-oxide hexafluorophosphate), in a neutral solvent, oftentimes DMF, $CH_2Cl_2$ or THF. In some instances, when DCC or EDC is used as the coupling reagent, HOBt (hydroxybenzotriazole) might be added to the reaction to facilitate the desired coupling reaction. Reaction of 1-F with a suitable oxidizing agent, such as urea hydroperoxide in the presence of trifluoroacetic anhydride, or meta-chloroperoxybenzoic acid (mCPBA), in a suitable solvent, typically $CH_2Cl_2$ or THF, affords the pyrimidine N-oxide 1-G. This then can be chlorinated to afford compound 1-H using an appropriate chlorinating agent, typically $POCl_3$ or oxalyl chloride, in the presence of an acid scavenger, usually $Et_3N$, $(i-Pr)_2NEt$, in a neutral solvent like $CH_2Cl_2$ or isopropyl acetate. The chloride of compound 1-H can be readily displaced with an amine, or a suitably protected diamine, for instance tert-butyl 2,7-diazaspiro[3.5]nonane-7-carboxylate (1-I), to afford compounds like 1-J. This reaction is conducted in the presence of an acid scavenger, usually $Et_3N$ or $(i-Pr)_2NEt$, in a neutral solvent like $CH_2Cl_2$, THF, DMF, or isopropyl acetate. When a protected diamine is used, the protecting group can be removed subsequently according to the nature of the protecting group.

The use of protecting groups in organic synthesis is well-known to those of skill in the art, and conditions for adding and removing protecting groups are described in established reference volumes, for instance Greene's Protective Groups in Organic Synthesis, $4^{th}$ Edition (ISBN: 9780470053485). For example, the Boc (tert-butyloxycarbonyl) protecting group in compound 1-J can be removed under acidic conditions, using acids like HCl, TFA (trifluoroacetic acid), or p-TsOH (para-toluenesulfonic acid), in a suitable solvent, oftentimes $CH_2Cl_2$ or THF. The Boc group can also be removed using TMSCI in 2,2,2-trifluoroethanol. The desired, deprotected amine can be isolated as the salt, for instance the salt 1-K, wherein HX denotes the salt form, or as the free base, following work-up under standard basic conditions. After removal of the protecting group, the amine can be alkylated with a wide range of alkylating agents, as illustrated in Scheme 3.

General Scheme 2

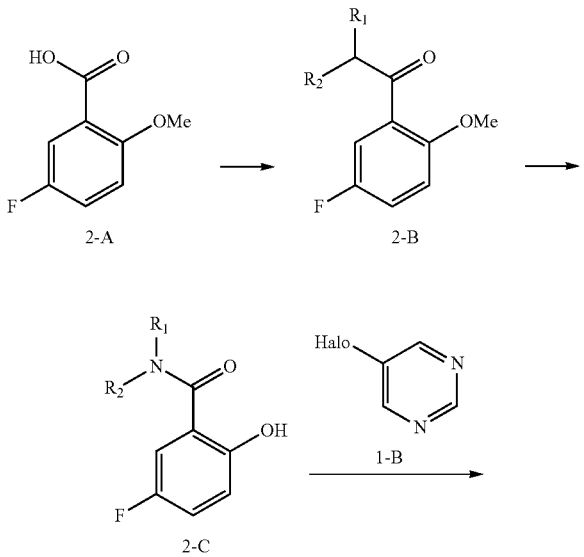

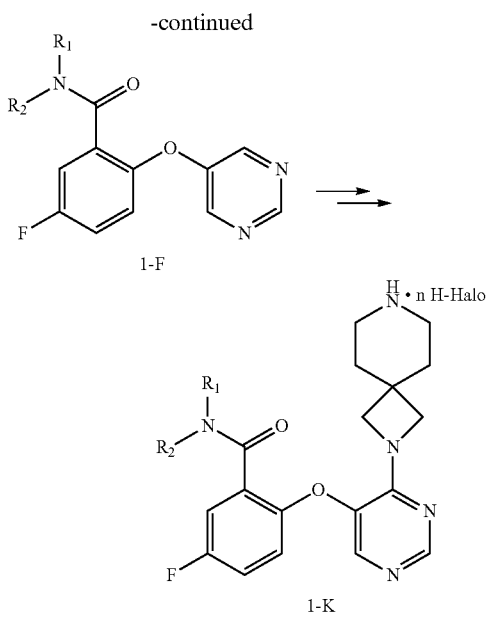

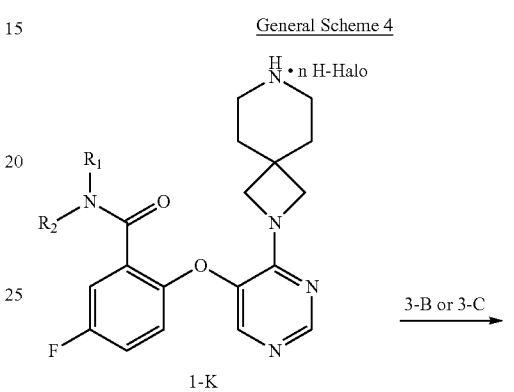

Scheme 2 illustrates an alternative method to prepare the key intermediate 1-K. The benzoic acid derivative 2-A is converted to the corresponding amide 2-B, according to the general conditions for preparing amides from carboxylic acids described in Scheme 1 (see 1-E to 1-F). The methyl ether protecting group in 2-B can then be removed in a variety of ways as described in Greene's Protective Groups in Organic Synthesis, 4$^{th}$ Edition (ISBN:9780470053485). For example, reaction of 2-B with boron tribromide (BBr$_3$), in a neutral solvent, typically CH$_2$Cl$_2$, provides phenol 2-C. This phenol can be reacted with a 5-halopyrimidine (1-B), as described in Scheme 1 (see 1-A to 1-C), to afford the diaryl ether 1-F. This compound can then be transformed into the key intermediate 1-K as described in Scheme 1.

General Scheme 3

Scheme 3 illustrates methods for preparing selected, pyran-based alkylating agents, that can be used to alkylate key intermediates like 1-K. Commercially available 1,5-anhydro-2,3,4-trideoxy-2-[[(1,1-dimethylethoxy)carbonyl]amino]-D-erythro-hexitol (3-A) is reacted with a suitable sulfonyl chloride, preferably p-toluenesulfonyl chloride (TsCl) or methanesulfonyl chloride (MsCl), to afford the sulfonate derivative 3-B (R$_3$=p-MePh or Me) Alternatively, 3-A might be converted to the corresponding bromide or iodide under standard conditions know to those of skill in the art. For example, reaction of 3-A with CBr$_4$ in the presence of PPh$_3$, in a neutral solvent, typically CH$_2$Cl$_2$, can provide the halide 3-C(X=Br). Compound 2-C(X=Br or I) might also be obtained by reaction of 3-B with a source of anionic halide, like LiBr or LiI, in a neutral solvent like THF or diethyl ether. Compounds 3-B and 3-C can be used to alkylate key intermediates like 1-K as illustrated in Scheme 4.

General Scheme 4

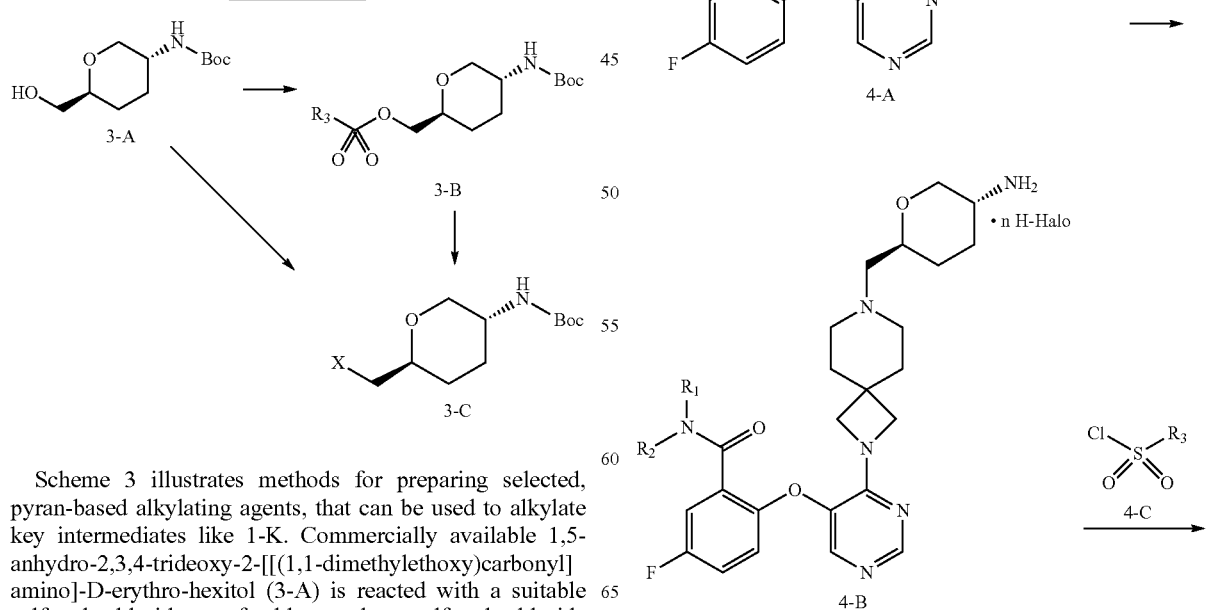

227
-continued

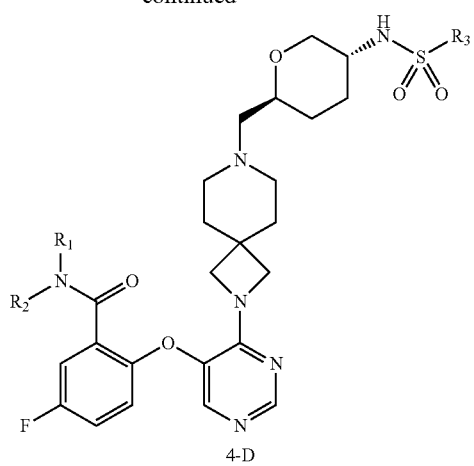

4-D

Scheme 4 illustrates methods for converting the key intermediate 1-K into the compounds of the present disclosure (4-D). Reaction of 1-K, which can be prepared according to the general procedures described in Schemes 1 and 2, with an appropriate alkylating agent, for instance compounds 3-B or 3-C, in the presence of an acid scavenger like $Et_3N$, or $(iPr)_2NEt$, in a neutral solvent like $CH_2Cl_2$, THF, DMF or NMP, affords compound 4-A. Sometimes, KI or tetrabutylammonium iodide (TBAI) can be added to facilitate the reaction. The Boc protecting group in 4-A can be removed according to the general methods for removing Boc groups described in Scheme 1 (see 1-J to 1-K), to afford 4-B, which can be prepared as the free base or a suitable salt, as described in Scheme 1. Reaction of 4-B with a suitable acylating or sulfonylating agent, in the presence of an acid scavenger like $Et_3N$, or $(iPr)_2NEt$, in a neutral solvent like $CH_2Cl_2$, THF, DMF or NMP, affords the compounds of the present disclosure (4-D). For illustrative purposes, reaction of 4-B with an alkylsulfonyl chloride (4-C, R3=an alkyl group) affords the sulfonyl derivative 4-D. Other compounds of the present disclosure can be formed similarly, via reaction with appropriate acylating agents like acid chlorides (to afford amides), alkyl chloroformates (to afford carbamates), or alkyl carbamoyl chlorides or alkyl isocyanates (to afford ureas).

228
-continued

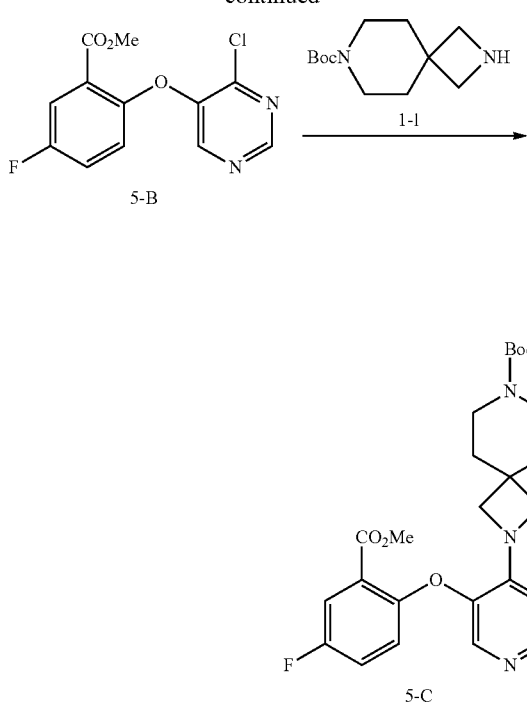

Scheme 5 illustrates the general methods for preparing the key intermediate 5-C. Compound 1-D, which can be prepared according to the general procedures described in Scheme 1, can be oxidized to the pyrimidine-N-oxide 5-A, according to the general methods described in Scheme 1 (see 1-F to 1-G). The N-oxide 5-A can then be chlorinated to the 4-chloropyrimidine derivative 5-B, according to the general methods described in Scheme 1 (see 1-G to 1-H). Subsequently, the chloro group of 5-B can be displaced by a suitable amine, for instance tert-butyl 2,7-diazaspiro[3.5]nonane-7-carboxylate (1-I), to afford compound 5-C, according to the general methods described in Scheme 1 (see 1-H to 1-J). It will be appreciated by those of skill in the art that compound 5-C is a flexible intermediate that can be converted into the compounds of the present disclosure (4-D) in a variety of ways. Several of these ways are described below (see Schemes 6-8).

General Scheme 5

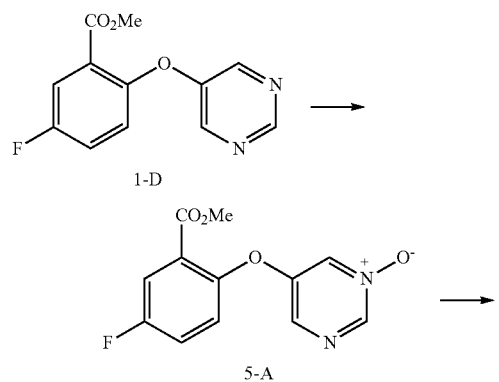

General Scheme 6

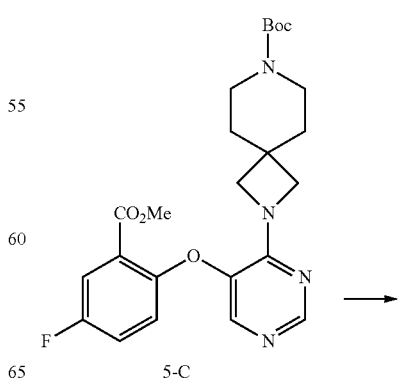

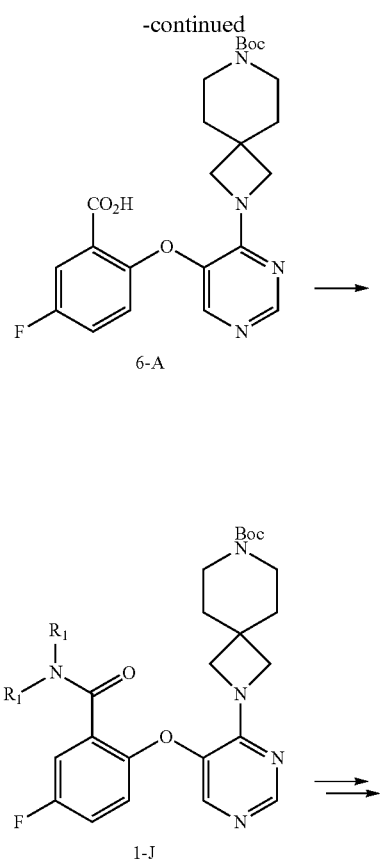

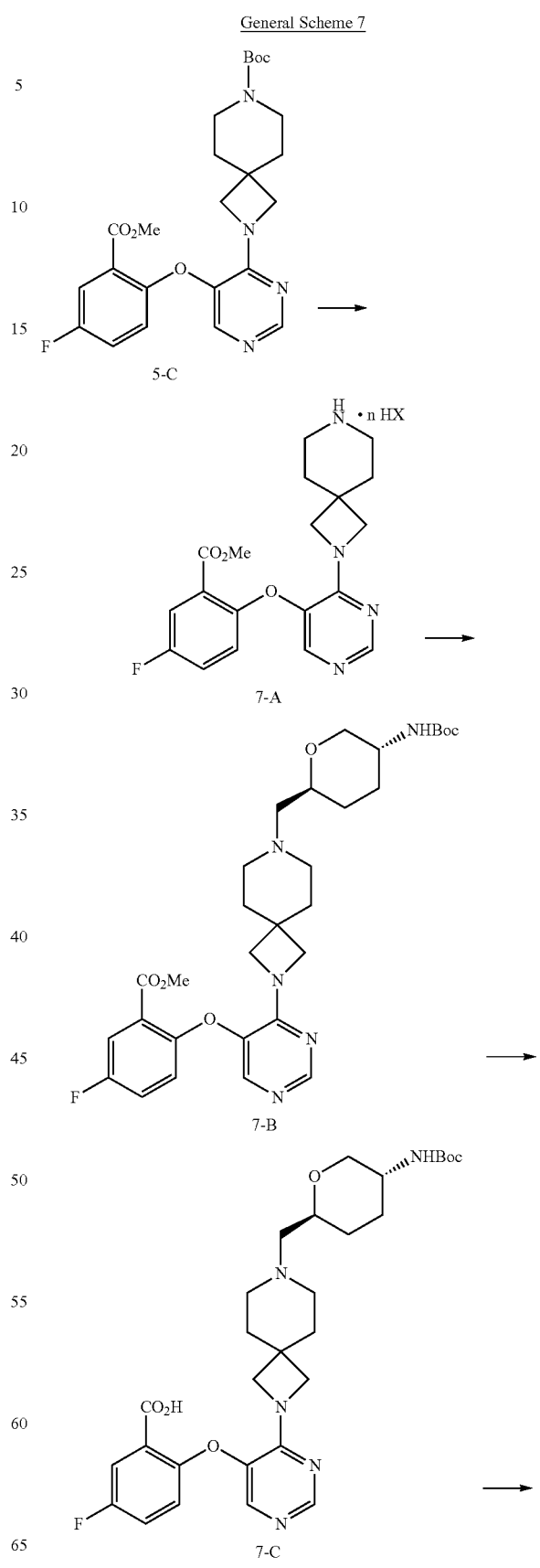

General Scheme 7

Scheme 6 illustrates one general method for converting compound 5-C into the compounds of the present disclosure. The ester of compound 5-C (prepared according to the general procedures described in Scheme 5) can be saponified according to the general procedures described in Scheme 1 (see 1-D to 1-E). The resulting carboxylic acid 6-A can be converted to the corresponding amide 1-J according to the general methods for preparing amides from carboxylic acids described in Scheme 1 (see 1-E to 1-F). Compound 1-J can then be converted to the compounds of the present disclosure (4-D) as described above (see Schemes 1 and 4).

231
-continued

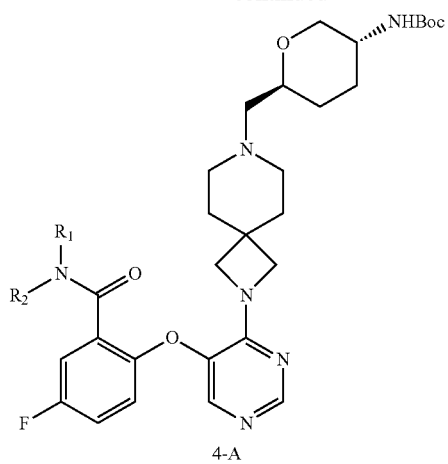

4-A

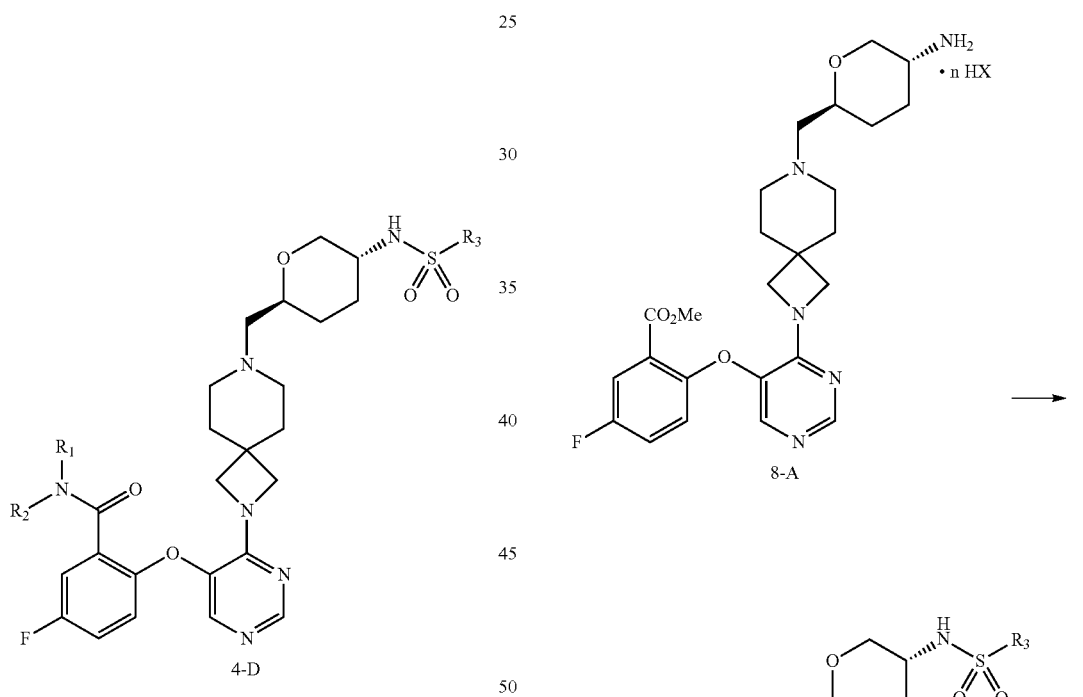

4-D

Scheme 7 illustrates another general method for converting compound 5-C into the compounds of the present disclosure. Removal of the Boc group of 5-C can be accomplished using the general procedures for removing Boc groups described in Scheme 1 (see 1-J to 1-K). The resulting amine 7-A can be isolated as the free base or a suitable salt form, as is discussed in Scheme 1. The amine of compound 7-A can be alkylated as described in Scheme 4 (see 1-K to 4-A), to afford compound 7-B. Saponification of the ester of 7-B, as described in Scheme 1 (see 1-D to 1-E), provides the carboxylic acid derivative 7-C. This can be converted to the corresponding amide 4-A according to the general methods for amide formation described in Scheme 1 (see 1-E to 1-F). Compound 4-A can then be converted to the compounds of the present disclosure (4-D) as described in Scheme 4.

232

General Scheme 8

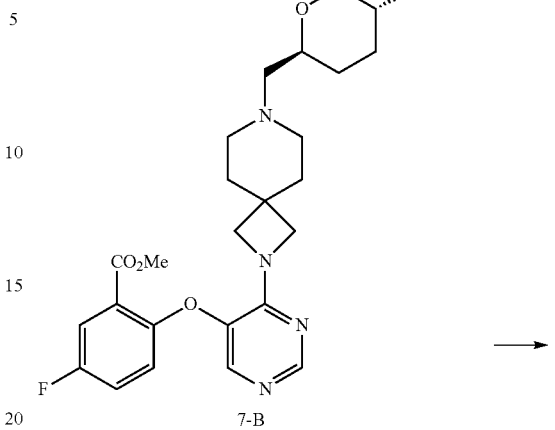

7-B

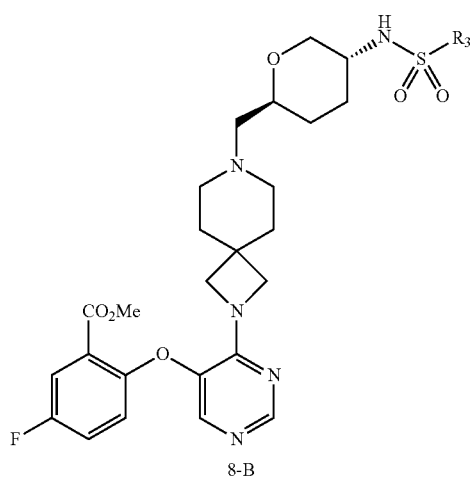

8-A

8-B

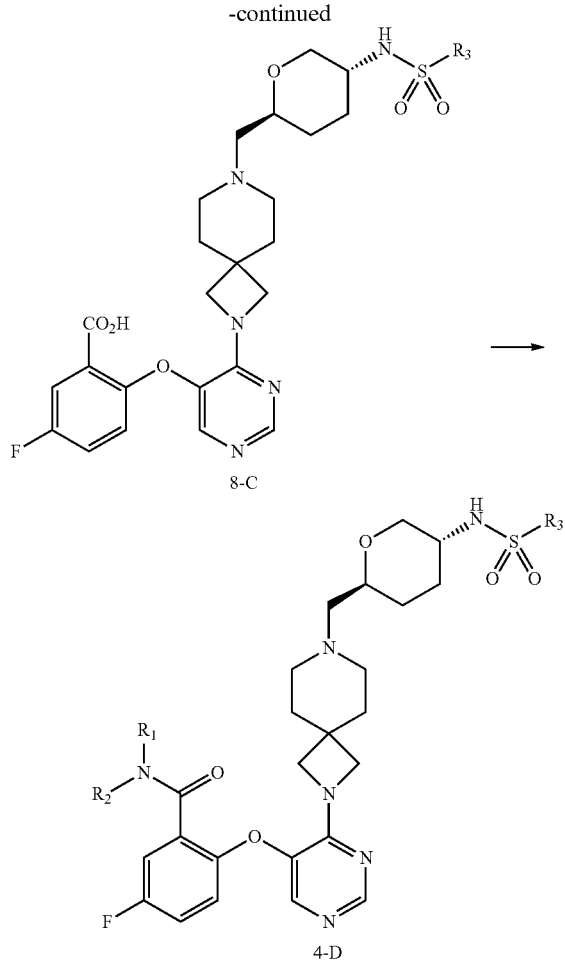

Scheme 8 illustrates another general method for converting compound 7-B into the compounds of the present disclosure. The Boc group in compound 7-B (prepared according to the general procedures described in Scheme 7) can be removed using the general procedures for removing Boc groups described in Scheme 1 (see 1-J to 1-K). The resulting amine 8-A can be isolated as the free base or a suitable salt form, as is discussed in Scheme 1. The amine of compound 8-A can be acylated according to the general methods discussed in Scheme 4 (see 4-B to 4-D), to afford compound 8-B. Saponification of the ester of compound 8-B can be achieved via the general procedures for ester saponification described in Scheme 1 (see 1-D to 1-E). The resulting carboxylic acid 8-C can then the converted to the corresponding amide using the general methods for amide formation described in Scheme 1 (see 1-E to 1-F), to afford the compounds of the present disclosure (4-D).

General Biological Methods
Homogeneous Time-Resolved Fluorescence (HTRF)

HTRF, is a premier TR-FRET (Time-Resolved Fluorescence Resonance Energy Transfer) technology on the market. TR-FRET technologies such as HTRF bring together the sensitivity of fluorescence with the homogeneous nature of FRET (Fluorescence Resonance Energy Transfer) and the low background of time resolution. HTRF uses two fluorophores, a donor and an acceptor dye, that transfer energy when in close proximity to each other. This creates a homogeneous assay format in which bound and unbound partners do not need to be separated as fluorescence emission from the acceptor is generated only upon binding. HTRF can be used in competitive and non-competitive formats and performed as cellular or biochemical assays in 96-, 384- and 1536-well plate formats. It has been applied to a variety of applications including GPCRs, kinases, epigenetics, biotherapeutics and quantification of a range of biomarkers and can be used according to the knowledge of a person of ordinary skill in the art to assess the compounds of the present disclosure.

hERG Patch Clamp Assay

The hERG inhibition assay uses a high throughput single cell planar patch clamp approach. Chinese hamster ovary cells transfected with the hERG gene (CHO-hERG) are dispensed into the PatchPlate. Amphotericin is used as a perforating agent to gain electrical access to the cells. The hERG tail current is measured prior to the addition of the test compound by perforated patch clamping. Following addition of the test compound at a defined concentration or range of concentrations a second recording of the hERG current is performed. The degree of inhibition (%) is obtained by measuring the tail current amplitude, which is induced by a one second test pulse to −40 mV after a two second pulse to +20 mV, before and after drug incubation (the difference current is normalized to control and multiplied by 100 to obtain the percent of inhibition). The patch clamp assay can be used according to the knowledge of a person of ordinary skill in the art to accordingly assess the compounds of the present disclosure.

In any one of the embodiments described herein, the compound has an $IC_{50}$ of more than 10, 15, 20, 25, or 30 µM in a standard human ether-a-go-go related gene (hERG) patch clamp assay.

A number of drugs have been withdrawn from late-stage clinical trials due to cardiotoxic effects, therefore it is important to identify and avoid compounds with potential for cardiotoxic effects early in drug discovery. The cardiovascular toxicity of a compound can be measured using a standard human ether-a-go-go related gene (hERG) assay. The human ether-a-go-go related gene (hERG) encodes the inward rectifying voltage gated potassium channel in the heart (IKr), which is involved in cardiac repolarization. Inhibition of the hERG current causes QT interval prolongation resulting in potentially fatal ventricular tachyarrhythmia called Torsade de Pointes. A compound having an IC50 of more than about 10 µM or more than about 15 µM, in the hERG assay may be considered as free from any cardiovascular toxicity. In some embodiments, the compounds of Formulae 0, 0a, I, Ia, II, IIa, III, IIIa, and/or Table 1 have reduced hERG binding compared to structural analogs. In some embodiments, the compounds of Formulae 0, 0a, I, Ia, II, IIa, III, IIIa, and/or Table 1 IC50 of more than 10 µM, 15 µM, 20 µM, 25 µM, or 30 µM in the standard patch clamp hERG assay.

In some embodiments, the compounds of the present disclosure (e.g., Formulae 0, 0a, I, Ia, II, IIa, III, IIIa, and Table 1) do not significantly block the hERG potassium channel (e.g., an $IC_{50}$ greater than 1 µM, µM, 10 µM, 15 µM, 20 µM, 25 µM, 30 µM, 35 µM, 40 µM, or 50 µM) in the standard patch clamp hERG assay.

Methods of Use

The compounds of the invention are inhibitors of the interaction of menin with MLL and MLL fusion proteins. In some embodiments, the present disclosure is directed to a method of inhibiting the interaction between menin and MLL or an MLL fusion protein by contacting menin and MLL or the MLL fusion protein with a compound of the disclosure. The contacting can be carried out in vitro or in vivo. In some embodiments, the compounds of the disclosure can bind to menin, thereby interfering with the binding of MLL to menin. In some embodiments, the present disclosure provides a method of inhibiting the activity of menin by contacting menin with a compound of the disclosure in the presence of MLL or an MLL fusion protein. In further embodiments, the present disclosure provides a method of inhibiting the binding of MLL or an MLL fusion protein to menin, comprising contacting menin with a compound of the disclosure in the presence of the MLL or MLL fusion protein.

In some embodiments, compounds of the present disclosure minimize hERG interactions. In some embodiments, the present disclosure is directed to a method of inhibiting the interaction between menin and MLL or an MLL fusion protein by contacting menin and MLL or the MLL fusion protein with a compound of the disclosure while the compounds of the disclosure minimize hERG activity. In some embodiments, the present disclosure is directed to a method of inhibiting the interaction between menin and MLL or an MLL fusion protein by contacting menin and MLL or the MLL fusion protein with a compound of the disclosure while the compound of the disclosure avoids drug-induced blockade of hERG.

Evaluating the hERG activity can be accomplished by many methods known in the art. Including, such methods for the assessment of hERG liability is the patch-clamp electrophysiological assay on hERG transfected cells. Various other strategies including radiolabeled binding assays, functional assays, and rubidium efflux assays also quantify hERG potency.

The compounds of the disclosure are also useful in treating diseases associated with the menin-MLL interaction or menin-MLL fusion protein interaction. For example, diseases and conditions treatable according to the methods of the disclosure include cancer, such as leukemia, and other diseases or disorders mediated by the menin-MLL interaction or menin-MLL fusion protein interaction such as diabetes.

Accordingly, the compounds of the disclosure are believed to be effective against a broad range of cancers, including, but not limited to, hematological cancer (e.g., leukemia and lymphoma), bladder cancer, brain cancer (e.g., glioma, diffuse intrinsic pontine glioma (DIPG)), breast cancer (e.g., triple-negative breast cancer, estrogen-receptor-positive breast cancer (i.e., ER+ breast cancer)), colorectal cancer, cervical cancer, gastrointestinal cancer (e.g., colorectal carcinoma, gastric cancer), genitourinary cancer, head and neck cancer, liver cancer, lung cancer, melanoma, ovarian cancer, pancreatic cancer, prostate cancer (e.g., castration resistant prostate cancer), renal cancer (e.g., renal cell carcinoma), skin cancer, thyroid cancer (e.g., papillary thyroid carcinoma), testicular cancer, sarcoma (e.g., Ewing's sarcoma), and AIDS-related cancers. In some embodiments, the cancer is associated with a rearranged MLL gene. In some embodiments, the pathophysiology of the cancer is dependent on the MLL gene. In some embodiments, the cancer is associated with mutant p53 gain-of-function.

In some embodiments, the specific cancers that may be treated by the compounds, compositions and methods described herein include cardiac cancers, such as for example, sarcoma (e.g., angiosarcoma, fibrosarcoma, rhabdomyosarcoma, and liposarcoma), myxoma, rhabdomyoma, fibroma, lipoma and teratoma; lung cancers, including, for example, bronchogenic carcinoma (e.g., squamous cell, undifferentiated small cell, undifferentiated large cell, and adenocarcinoma), alveolar and bronchiolar carcinoma, bronchial adenoma, sarcoma, lymphoma, chondromatous hamartoma, mesothelioma, non-small cell lung cancer, small cell lung cancer, bronchial adenomas/carcinoids, and pleuropulmonary blastoma; gastrointestinal cancer, including, for example, cancers of the esophagus (e.g., squamous cell carcinoma, adenocarcinoma, leiomyosarcoma, and lymphoma), cancers of the stomach (e.g., carcinoma, lymphoma, and leiomyosarcoma), cancers of the pancreas (e.g., ductal adenocarcinoma, insulinoma, glucagonoma, gastrinoma, carcinoid tumors, and vipoma), cancers of the small bowel (e.g., adenocarcinoma, lymphoma, carcinoid tumors, Kaposi's sarcoma, leiomyoma, hemangioma, lipoma, neurofibroma, and fibroma), cancers of the large bowel or colon, (e.g., adenocarcinoma, tubular adenoma, villous adenoma, hamartoma, and leiomyoma), and other cancers of the digestive tract (e.g., anal cancer, anorectal cancer, appendix cancer, cancer of the anal canal, cancer of the tongue, gallbladder cancer, gastrointestinal stromal tumor (GIST), colon cancer, colorectal cancer, extrahepatic bile duct cancer, intrahepatic bile duct cancer, rectal cancer, and small intestine cancer); genitourinary tract cancers, including, for example, cancers of the kidney (e.g., adenocarcinoma, Wilm's tumor (nephroblastoma), lymphoma, and leukemia), cancers of the bladder and urethra (e.g., squamous cell carcinoma, transitional cell carcinoma, and adenocarcinoma), cancers of the prostate (e.g., adenocarcinoma and sarcoma), cancers of the testis, (e.g., seminoma, teratoma, embryonal carcinoma, teratocarcinoma, choriocarcinoma, sarcoma, interstitial cell carcinoma, fibroma, fibroadenoma, adenomatoid tumors, and lipoma), as well as transitional cell cancer, transitional cell cancer of the renal pelvis and ureter and other urinary organs, urethral cancer, and urinary bladder cancer; liver cancers, including, for example, hepatoma (e.g., hepatocellular carcinoma), cholangiocarcinoma, hepatoblastoma, angiosarcoma, hepatocellular adenoma, and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull (e.g., osteoma, hemangioma, granuloma, xanthoma, and osteitis deformans); cancers of the meninges (e.g., meningioma, meningiosarcoma, and gliomatosis); cancers of the brain (e.g., astrocytoma, medulloblastoma, glioma, ependymoma, germinoma (pinealoma), glioblastoma multiforme, oligodendroglioma, schwannoma, retinoblastoma, and congenital tumors); cancers of the spinal cord (e.g., neurofibroma, meningioma, glioma, and sarcoma), and other nervous system cancers (e.g., brain stem glioma, diffuse intrinsic pontine glioma (DIPG), brain tumor, central nervous system cancer, cerebellar astrocytoma, cerebral astrocytoma/malignant glioma, childhood cerebellar astrocytoma, childhood cerebral astrocytoma, primary central nervous system lymphoma, visual pathway and hypothalamic glioma, nervous system lymphoma, supratentorial primitive neuroectodeimal tumors, pineoblastoma and supratentorial primitive neuroectodermal tumors); gynecological cancers, including, for example, cancers of the uterus (e.g., endometrial carcinoma), cancers of the cervix (e.g., cervical carcinoma, and pre tumor cervical dysplasia), cancers of the ovaries (e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma), cancers of the vulva (e.g., squamous cell carcinoma, intraepithelial carcinoma, adenocarcinoma, fibrosarcoma, and melanoma), cancers of the vagina (e.g., clear cell carcinoma, squamous cell carcinoma, botryoid sarcoma, and embryonal rhabdomyosarcoma), and cancers of the fallopian tubes (e.g., carcinoma); other reproductive tract cancers, including, for example, endometrial cancer, endometrial uterine cancer, germ cell tumor, gestational trophoblastic tumor, gestational trophoblastic tumor glioma, ovarian epithelial cancer, ovarian germ cell tumor, ovarian low malignant potential tumor, penile cancer, vaginal cancer, vulvar cancer, extracranial germ cell tumor, extragonadal germ cell tumor, uterine cancer, uterine corpus cancer, uterine sarcoma; lymphatic and hematologic cancers, including, for example, cancers of the blood (e.g., acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia), and other lymphatic or hematologic cancers including, for example, childhood leukemia, myeloproliferative disorders (e.g., primary myelofibrosis), plasma cell neoplasm/multiple myeloma, myelodysplasia, myelodysplastic syndrome, cutaneous T-cell lymphoma, lymphoid neoplasm, AIDS-related lymphoma, thymoma, thymoma and thymic carcinoma, mycosis fungoides, and Sézary Syndrome; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis, merkel cell carcinoma, merkel cell skin carcinoma, melanoma, and carcinoid tumor; adrenal gland cancers, including, for example, neuroblastoma; other cancers associated with the endocrine system including, for example, adrenocortical carcinoma, multiple endocrine neoplasia (e.g., multiple endocrine neoplasia type I), multiple endocrine neoplasia syndrome, parathyroid cancer, pituitary tumor, pheochromocytoma, islet cell pancreatic cancer, and islet cell tumors); connective tissue cancer (e.g., bone cancer, bone and joint cancer, osteosarcoma and malignant fibrous histiocytoma); cancer associated with the head, neck, and mouth (e.g., head and neck cancer, paranasal sinus and nasal cavity cancer, metastatic squamous neck cancer, mouth cancer, throat cancer, esophageal cancer, laryngeal cancer, pharyngeal cancer, hypopharyngeal cancer, lip and oral cavity cancer, nasopharyngeal cancer, oral cancer, oropharyngeal cancer, and salivary gland cancer); and cancer associated with the eye (e.g., ocular cancer, intraocular melanoma). In some embodiments, the cancer is Ewing's sarcoma.

In some embodiments, the cancer is a hematological cancer such as leukemia or lymphoma. Example leukemia and lymphomas treatable by the compounds of the disclosure include mixed lineage leukemia (MLL), MLL-related leukemia, MLL-associated leukemia, MLL-positive leukemia, MLL-induced leukemia, rearranged mixed lineage leukemia (MLL-r), leukemia associated with a MLL rearrangement or a rearrangement of the MLL gene, acute leukemia, chronic leukemia, indolent leukemia, lymphoblastic leukemia, lymphocytic leukemia, myeloid leukemia, myelogenous leukemia, childhood leukemia, acute lymphocytic leukemia (ALL) (also referred to as acute lymphoblastic leukemia or acute lymphoid leukemia), acute myeloid leukemia (AML) (also referred to as acute myelogenous leukemia or acute myeloblastic leukemia), acute granulocytic leukemia, acute nonlymphocytic leukemia, chronic lymphocytic leukemia (CLL) (also referred to as chronic lymphoblastic leukemia), chronic myelogenous leukemia (CML) (also referred to as chronic myeloid leukemia), therapy related leukemia, myelodysplastic syndrome (MDS), myeloproliferative disease (MPD) (such as primary myelofibrosis (PMF)), myeloproliferative neoplasia (MPN), plasma cell neoplasm, multiple myeloma, myelodysplasia, cutaneous T-cell lymphoma, lymphoid neoplasm, AIDS-related lymphoma, thymoma, thymic carcinoma, mycosis fungoides, Alibert-Bazin syndrome, granuloma fungoides, Sézary Syndrome, hairy cell leukemia, T-cell prolymphocytic leukemia (T-PLL), large granular lymphocytic leukemia, meningeal leukemia, leukemic leptomeningitis, leukemic meningitis, multiple myeloma, Hodgkin's lymphoma, non-Hodgkin's lymphoma (malignant lymphoma), and Waldenstrom's macroglobulinemia. In some embodiments, the acute myeloid leukemia (AML) is abstract nucleophosmin (NPM1)-mutated acute myeloid leukemia (i.e., $NPM1^{mut}$ acute myloid leukemia).

In particular embodiments, compounds of the disclosure are used to treat leukemia associated with a MLL rearrangement, acute lymphocytic leukemia associated with a MLL rearrangement, acute lymphoblastic leukemia associated with a MLL rearrangement, acute lymphoid leukemia associated with a MLL rearrangement, acute myeloid leukemia associated with a MLL rearrangement, acute myelogenous leukemia associated with a MLL rearrangement, or acute myeloblastic leukemia associated with a MLL rearrangement. As used herein, "MLL rearrangement" means a rearrangement of the MLL gene.

In some embodiments, diseases and conditions treatable with compounds of the disclosure include insulin resistance, pre-diabetes, diabetes (e.g., Type 2 diabetes or Type 1 diabetes), and risk of diabetes. In some embodiments, diseases and conditions treatable with compounds of the disclosure include hyperglycemia. In some embodiments, the hyperglycemia is associated with diabetes, such as Type 2 diabetes. In some embodiments, compounds of the disclosure are used to treat loss of response to other anti-diabetic agents and/or reduced beta cell function in a patient or subject. In some embodiments, compounds of the disclosure are used to restore response to other anti-diabetic agents and/or to restore beta cell function and/or to reduce the need for insulin in a patient or subject. In some embodiments, compounds of the disclosure are used to reduce insulin resistance, reduce the risk of diabetes, or reduce increases in blood glucose caused by a statin in a subject taking a statin. In some embodiments, compounds of the disclosure are used to treat diabetes in a subject taking a statin or to prevent diabetes in a subject taking a statin. Methods of the disclosure include decreasing, reducing, inhibiting, suppressing, limiting or controlling in the patient elevated blood glucose levels. In further aspects, methods of the disclosure include increasing, stimulating, enhancing, promoting, inducing or activating in the subject insulin sensitivity. Statins include, but are not limited to atorvastatin, cerivastatin, fluvastatin, lovastatin, mevastatin, pitavastatin, pravastatin, rousuvastatin and simvastatin.

In some embodiments, a patient is treated with (e.g., administered) a compound of the present disclosure in an amount sufficient to treat or ameliorate one or more of the diseases and conditions recited above (e.g., a therapeutically effective amount). The compounds of the disclosure may also be useful in the prevention of one or more of the diseases recited therein.

Combination Therapy

The disclosure further relates to a combination therapy for treating a disease or a disorder described herein. In some embodiments, the combination therapy comprises administering at least one compound of the present disclosure in combination with one or more other pharmaceutically active agents for treating cancer or other disorders mediated by menin/MLL. In some embodiments, the combination therapy comprises administering at least one compound of the present disclosure in combination with one or more other pharmaceutically active agents, such as for the treatment of cancer. The pharmaceutically active agents can be combined with a compound of the disclosure in a single dosage form, or the therapeutics can be administered simultaneously or sequentially as separate dosage forms.

In some embodiments, the invention provides a combination therapy comprising a menin inhibitor of the present disclosure (e.g., a compound of Formula 0, Formula 0a, Formula I, Formula Ia, Formula II, Formula IIa, etc.) and a CYP3A4 inhibitor. In certain embodiments, the invention provides for a pharmaceutical composition comprising: (a) a menin inhibitor of the present disclosure (e.g., a compound of Formula 0, Formula 0a, Formula I, Formula Ia, Formula II, Formula IIa, etc.), and (b) a CYP3A4 inhibitor. In some embodiments, the invention is directed to a method for treating a patient comprising (a) administering a menin inhibitor of the present disclosure (e.g., a compound of Formula 0, Formula 0a, Formula I, Formula Ia, Formula II, Formula IIa, etc.), and (b) administering a CYP3A4 inhibitor.

Some embodiments of this invention are directed to combination therapies designed to treat or manage cancer in a subject, wherein the combination therapies comprise administering a menin inhibitor of the present disclosure (e.g., a compound of Formula 0, Formula 0a, Formula I, Formula Ia, Formula II, Formula IIa, etc.) in combination with a CYP3A4 inhibitor. In particular, some embodiments of this invention are directed to methods of treating or managing cancer in a subject, comprising administering a menin inhibitor in combination with a therapeutically effective amount of a CYP3A4 inhibitor administered simultaneously, separately or sequentially.

In some embodiments, the CYP3A inhibitor is: an anti-arrhythmic; an antihistamine; an azole antifungal; a benzodiazepine; a calcium channel blocker; a HIV antiviral; a HMG CoA Reductase inhibitor; a macrolide antibiotic; a prokinetic; a protease inhibitor; or any combinations thereof. In some embodiments, the CYP3A inhibitor is: posaconazole, alprazolam; amiodarone; amlodipine; aprepitant; aripiprazole; astemizole; atorvastatin; boceprevir; buspirone; chloramphenicol; chlorpheniramine; cimetidine; ciprofloxacin; cisapride; clarithromycin; cobicistat (GS-9350); analogs or derivatives of cobicistat (GS-9350); cyclosporine; delaviridine; diazepam→3-OH; diethyl-dithiocarbamate; diltiazem; erythromycin; felodipine; fluconazole; fluvoxamine; gestodene; gleevec; grapefruit juice; haloperidol; imatinib; indinavir; itraconazole; ketoconazole; lovastatin; methadone; mibefradil; midazolam; mifepristone; nefazodone; nelfinavir; nifedipine; nisoldipine; nitrendipine; norfloxacin; norfluoxetine; pimozide; quinine; quinidine→3-OH; ritonavir; saquinavir; sildenafil; simvastatin; starfruit; tacrolimus (FK506); tamoxifen; telaprevir; telithromycin; trazodone; triazolam; verapamil; telaprevir; vincristine; voriconazole; or any combinations thereof.

In some embodiments, the CYP3A4 inhibitor is posaconazole, cobicistat (GS-9350) or analogs or derivatives of cobicistat (GS-9350). In some embodiments, the CYP3A4 inhibitor is ketoconazole. In some embodiments, the CYP3A4 inhibitor is ritonavir. In some embodiments, the menin inhibitor and the CYP3A4 inhibitor are in separate dosage forms. In some embodiments, the pharmaceutical composition is in a combined dosage form. In some embodiments, the CYP3A4 inhibitor is posaconazole.

In some embodiments, the pharmaceutical composition comprises an amount of the CYP3A4 inhibitor that is effective to increase the oral bioavailability of the menin inhibitor. The compounds according to the disclosure may also be used in combination with immunotherapies, including but not limited to cell-based therapies, antibody therapies and cytokine therapies, for the treatment of a disease or disorder disclosed herein.

In certain embodiments, compounds according to the disclosure are used in combination with one or more passive immunotherapies, including but not limited to naked monoclonal antibody drugs and conjugated monoclonal antibody drugs. Examples of naked monoclonal antibody drugs that can be used include, but are not limited to, rituximab (Rituxan®), an antibody against the CD20 antigen; trastuzumab (Herceptin®), an antibody against the HER2 protein; alemtuzumab (Lemtrada®, Campath®), an antibody against the CD52 antigen; cetuximab (Erbitux®), an antibody against the EGFR protein; and bevacizumab (Avastin®) which is an anti-angiogenesis inhibitor of VEGF protein.

Examples of conjugated monoclonal antibodies that can be used include, but are not limited to, radiolabeled antibody ibritumomab tiuxetan (Zevalin®); radiolabeled antibody tositumomab (Bexxar®); and immunotoxin gemtuzumab ozogamicin (Mylotarg®) which contains calicheamicin; BL22, an anti-CD22 monoclonal antibody-immunotoxin conjugate; radiolabeled antibodies such as OncoScint® and ProstaScint®; brentuximab vedotin (Adcetris®); ado-trastuzumab emtansine (Kadcyla®, also called TDM-1).

Further examples of therapeutic antibodies that can be used include, but are not limited to, REOPRO® (abciximab), an antibody against the glycoprotein IIb/IIIa receptor on platelets; ZENAPAX® (daclizumab) an immunosuppressive, humanized anti-CD25 monoclonal antibody; PANOREX™, a murine anti-17-IA cell surface antigen IgG2a antibody; BEC2, a murine anti-idiotype (GD3 epitope) IgG antibody; IMC-C225, a chimeric anti-EGFR IgG antibody; VITAXIN™ a humanized anti-αVβ3 integrin antibody; Campath 1H/LDP-03, a humanized anti CD52 IgG1 antibody; Smart M195, a humanized anti-CD33 IgG antibody; LYMPHOCIDE™, a humanized anti-CD22 IgG antibody; LYMPHOCIDE™ Y-90; Lymphoscan; Nuvion® (against CD3; CM3, a humanized anti-ICAM3 antibody; IDEC-114 a primatized anti-CD80 antibody; IDEC-131 a humanized anti-CD40L antibody; IDEC-151 a primatized anti-CD4 antibody; IDEC-152 a primatized anti-CD23 antibody; SMART anti-CD3, a humanized antiCD3 IgG; 5G1.1, a humanized anti-complement factor 5 (C5) antibody; D2E7, a humanized anti-TNF-α antibody; CDP870, a humanized anti-TNF-α Fab fragment; IDEC-151, a primatized anti-CD4 IgG1 antibody; MDX-CD4, a human anti-CD4 IgG antibody; CD20-streptdavidin (+biotin-yttrium 90); CDP571, a humanized anti-TNF-α IgG4 antibody; LDP-02, a humanized anti-α4β7 antibody; OrthoClone OKT4A, a humanized anti-CD4 IgG antibody; ANTOVA™, a humanized anti-CD40L IgG antibody; ANTEGREN™, a humanized anti-VLA-4 IgG antibody; and CAT-152, a human anti-TGF-β$_2$ antibody.

In certain embodiments, compounds according to the disclosure are used in combination with one or more targeted immunotherapies containing toxins but not an antibody, including but not limited to denileukin diftitox (Ontak®), IL-2 linked to diphtheria toxin.

The compounds according to the disclosure may also be used in combination with adjuvant immunotherapies for the treatment of a disease or disorder disclosed herein. Such adjuvant immunotherapies include, but are not limited to, cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of interleukins, for example IL-2, with other cytokines, such as IFN-alpha.

In certain embodiments, compounds according to the disclosure are used in combination with vaccine therapy, including but not limited to autologous and allogeneic tumor cell vaccines, antigen vaccines (including polyvalent antigen vaccines), dendritic cell vaccines, and viral vaccines.

In another embodiment, the present disclosure comprises administering to a subject with cancer an effective amount of a compound of the disclosure and one or more additional anti-cancer therapies selected from: surgery, anti-cancer agents/drugs, biological therapy, radiation therapy, anti-angiogenesis therapy, immunotherapy, adoptive transfer of effector cells, gene therapy or hormonal therapy. Examples of anti-cancer agents/drugs are described below.

In some embodiments, the anti-cancer agents/drug is, for example, adriamycin, aactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; palbociclib; Yervoy® (ipilimumab); Mekinist™ (trametinib); peginterferon alfa-2b, recombinant interferon alfa-2b; Sylatron™ (peginterferon alfa-2b); Tafinlar® (dabrafenib); Zelboraf® (vemurafenib); or nivolumab.

The compounds according to the present disclosure can be administered in combination with existing methods of treating cancers, for example by chemotherapy, irradiation, or surgery. Thus, there is further provided a method of treating cancer comprising administering an effective amount of a compound of the disclosure, or a pharmaceutically acceptable salt form thereof, to a subject in need of such treatment, wherein an effective amount of at least one additional cancer chemotherapeutic agent is administered to the subject. Examples of suitable cancer chemotherapeutic agents include any of: abarelix, ado-trastuzumab emtansine, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, emtansine, epirubicin, eribulin, erlotinib, estramustine, etoposide phosphate, etoposide, everolimus, exemestane, fentanyl citrate, filgrastim, floxuridine, fludarabine, fluorouracil, fruquintinib, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, ixabepilone, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, paclitaxel albumin-stabilized nanoparticle formulation, pamidronate, panitumumab, pegaspargase, pegfilgrastim, pemetrexed disodium, pentostatin, pertuzuma, pipobroman, plicamycin, procarbazine, quinacrine, rasburicase, rituximab, sorafenib, streptozocin, sulfatinib, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, volitinib, vorinostat, and zoledronate.

In particular embodiments, compounds according to the disclosure are used in combination with one or more anti-cancer agent selected from methotrexate, paclitaxel albumin-stabilized nanoparticle formulation, ado-trastuzumab emtansine, eribulin, doxorubicin, fluorouracil, everolimus, anastrozole, pamidronate disodium, exemestane, capecitabine, cyclophosphamide, docetaxel, epirubicin, toremifene, fulvestrant, letrozole, gemcitabine, gemcitabine hydrochloride, goserelin acetate, trastuzumab, ixabepilone, lapatinib ditosylate, megestrol acetate, tamoxifen citrate, pamidronate disodium, palbociclib, and pertuzumab for the treatment of breast cancer.

Other anti-cancer agents/drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; andrographolide; angiogenesis inhibitors; antagonist D; antagonist G; antarelix; anti-dorsalizing morphogenetic protein-1; antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclin-dependent kinase inhibitors; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors; microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine;

triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; zanoterone; zilascorb; zinostatin stimalamer; 5-fluorouracil; and leucovorin.

In some embodiments, the anti-cancer agent/drug is an agent that stabilizes microtubules. As used herein, a "microtubulin stabilizer" means an anti-cancer agent/drug which acts by arresting cells in the G2-M phases due to stabilization of microtubules. Examples of microtubulin stabilizers include ACLITAXEL® and Taxol® analogues. Additional examples of microtubulin stabilizers include without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser·HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

In another embodiment, the anti-cancer agent/drug is an agent that inhibits microtubules. As used herein, a "microtubulin inhibitor" means an anti-cancer agent which acts by inhibiting tubulin polymerization or microtubule assembly. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbott, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; eribulin (Halaven®); and analogs and derivatives thereof.

In further embodiments, compounds according to the disclosure are used in combination with one or more alkylating agents, antimetabolites, natural products, or hormones.

Examples of alkylating agents useful in the methods of the disclosure include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.).

Examples of antimetabolites useful in the methods of the disclosure include but are not limited to folic acid analog (e.g., methotrexate), or pyrimidine analogs (e.g., fluorouracil, floxouridine, cytarabine), and purine analogs (e.g., mercaptopurine, thioguanine, pentostatin).

Examples of natural products useful in the methods of the disclosure include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin) or enzymes (e.g., L-asparaginase).

Examples of hormones and antagonists useful for the treatment of cancer include but are not limited to adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), and gonadotropin releasing hormone analog (e.g., leuprolide).

Other agents that can be used in combination with the compounds of the disclosure for the treatment of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), and adrenocortical suppressant (e.g., mitotane, aminoglutethimide). Other anti-cancer agents/drugs that can be used in combination with the compounds of the disclosure include, but are not limited to, liver X receptor (LXR) modulators, including LXR agonists and LXR beta-selective agonists; aryl hydrocarbon receptor (AhR) inhibitors; inhibitors of the enzyme poly ADP ribose polymerase (PARP), including olaparib, iniparib, rucaparib, veliparib; inhibitors of vascular endothelial growth factor (VEGF) receptor tyrosine kinases, including cediranib; programmed cell death protein 1 (PD-1) inhibitors, including nivolumab (Bristol-Myers Squibb Co.) and pembrolizumab (Merck & Co., Inc.; MK-3475); MEK inhibitors, including cobimetinib; B-Raf enzyme inhibitors, including vemurafenib; cytotoxic T lymphocyte antigen (CTLA-4) inhibitors, including tremelimumab; programmed death-ligand 1 (PD-L1) inhibitors, including MEDI4736 (AstraZeneca); inhibitors of the Wnt pathway; inhibitors of epidermal growth factor receptor (EGFR) including AZD9291 (AstraZeneca), erlotinib, gefitinib, panitumumab, and cetuximab; adenosine A2A receptor inhibitors; adenosine A2B receptor inhibitors; colony-stimulating factor-1 receptor (CSF1R) inhibitors, including PLX3397 (Plexxikon), and inhibitors of CD73.

The compounds of the disclosure can be used in combination with one or more therapeutic strategies including immune checkpoint inhibitors, including inhibitors of PD-1, PD-L1, and CTLA-4.

The compounds of the disclosure can be used in combination with one or more anti-cancer agents selected from MCL-1 inhibitors, e.g., homoharringtonin (HHT) and omacetaxine; BCL-2 inhibitors, e.g., venetoclax (ABT-199), navitoclax (ABT-263), ABT-737, gossypol (AT-101), apogossypolone (ApoG2) and obatoclax; selective inhibitors of nuclear export (SINEs), e.g., selinexor (KPT-330).

In particular embodiments, the compounds of the disclosure are used in combination with one or more anti-cancer agents selected from methotrexate (Abitrexate®; Folex®; Folex PFS®; Mexate®; Mexate-AQ®); nelarabine (Arranon®); blinatumomab (Blincyto®); rubidomycin hydrochloride or daunorubicin hydrochloride (Cerubidine®); cyclophosphamide (Clafen®; Cytoxan®; Neosar®); clofarabine (Clofarex®; Clolar®); cytarabine (Cytosar-U®; Tarabine PFS®); dasatinib (Sprycel®); doxorubicin hydrochloride; asparaginase Erwinia chrysanthemi (Erwinaze); imatinib mesylate (Gleevec®); ponatinib hydrochloride (Iclusig®); mercaptopurine (Purinethol; Purixan); pegaspargase (Oncaspar®); prednisone; vincristine sulfate (Oncovin®, Vincasar PFS®, Vincrex®); vincristine sulfate liposome (Margibo®); hyper-CVAD (fractionated cyclophosphamide, vincristine, adriamycin, and dexamethasone); arsenic trioxide (Trisenox®); idarubicin hydrochloride (Idamycin®); mitoxantrone hydrochloride; thioguanine (Tabloid®); ADE (cytarabine, daunorubicin, and etoposide); alemtuzumab (Lemtrada®, Campath®); chlorambucil (Ambochlorin®, Amboclorin®, Leukeran®, Linfolizin®); ofatumumab (Arzerra®); bendamustine hydrochloride (Treanda®); fludarabine phosphate (Fludara®); obinutuzumab (Gazyva®); ibrutinib (Imbruvica®); idelalisib (Zydelig®); mechlorethamine hydrochloride (Mustargen®); rituximab (Rituxan®); chlorambucil-prednisone; CVP (cyclophosphamide, vincristine, and prednisone); bosutinib (Bosulif®); busulfan (Busulfex®; Myleran®); omacetaxine mepesuccinate (Synribo®); nilotinib (Tasigna®); Intron® A (recombinant interferon Alfa-2b); DOT1L inhibitors, including EPZ-5676 (Epizyme, Inc.); and inhibitors of bromodomain and extra-terminal motif (BET) proteins (BET inhibitors), including MS417, JQ1, I-BET 762, and I-BET 151 for the treatment of leukemia.

Compounds of the disclosure can be used in combination with one or more other agents or therapies for the treatment of insulin resistance, pre-diabetes, diabetes (e.g., Type 2 diabetes or Type 1 diabetes), and risk of diabetes, including but not limited to insulins and insulin analogues, such as Humulin® (Eli Lilly), Lantus® (Sanofi Aventis), Novolin® (Novo Nordisk), and Exubera® (Pfizer); Avandamet® (metformin HCI and rosiglitazone maleate, GSK); Avandaryl® (glimepiride and rosiglitazone maleate, GSK); Metaglip® (glipizide and metformin HCI, Bristol Myers Squibb); Glucovance® (glyburide and metformin HCI, Bristol Myers Squibb); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCI, Bristol Myers Squibb) and Glumetza® (metformin HCI, Depomed); thiazolidinediones; amylin analogs; GLP-1 analogs; DPP-IV inhibitors such as Januvia® (sitagliptin, Merck) and Galvus® (vildagliptin, Novartis); PTB-1 B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors; and alpha-glucosidase inhibitors, such as Glycet® (miglitol, Pfizer); statins, fibrates, and Zetia® (ezetimibe); alpha-blockers; beta-blockers; calcium channel blockers; diuretics; angiotensin converting enzyme (ACE) inhibitors; dual ACE and neutral endopeptidase (NEP) inhibitors; angiotensin-receptor blockers (ARBs); aldosterone synthase inhibitors; aldosterone-receptor antagonists; endothelin receptor antagonists; orlistat; phentermine; sibutramine; Acomplia® (rimonabant); thiazolidinediones (e.g., rosiglitazone, pioglitazone); SGLT 2 inhibitors (e.g., dapagliflozin, remogliflozin etabonate, sergliflozin, canagliflozin, and 1-chloro-4-(β-D-glucopyranos-1-yl)-2-[4-(('S)-tetrahydrofuran-3-yloxy)-benzyl]-benzene); PPAR-gamma-agonists (e.g., GI 262570) and antagonists; PPAR-gamma/alpha modulators (e.g., KRP 297); alpha-glucosidase inhibitors (e.g., acarbose, voglibose); DPPIV inhibitors (e.g., Januvia® (sitagliptin), Galvus®/Zomelis® (vildagliptin), Onglyza® (saxagliptin), Nesina®/Vipidia® (alogliptin), and Tradjenta®/Trajenta® (linagliptin)); alpha2-antagonists; glucagon-like protein-1 (GLP-1) receptor agonists and analogues (e.g., exendin-4); amylin; inhibitors of protein tyrosinephosphatase 1; substances that affect deregulated glucose production in the liver, e.g., inhibitors of glucose-6-phosphatase, or fructose-1,6-bisphosphatase, glycogen phosphorylase; glucagon receptor antagonists; inhibitors of phosphoenol pyruvate carboxykinase; glycogen synthase kinase and glucokinase activators; lipid lowering agents such as HMG-CoA-reductase inhibitors (e.g., simvastatin, atorvastatin); fibrates (e.g., bezafibrate, fenofibrate), nicotinic acid and the derivatives thereof, PPAR-alpha agonists, PPAR-delta agonists; ACAT inhibitors (e.g., avasimibe); cholesterol absorption inhibitors such as ezetimibe; bile acid-binding substances such as cholestyramine; inhibitors of ileac bile acid transport; HDL-raising compounds such as CETP inhibitors and ABC1 regulators; active substances for treating obesity such as sibutramine and tetrahydrolipostatin; SDRIs; axokine; leptin; leptin mimetics; antagonists of the cannabinoid 1 receptor; and MCH-1 receptor antagonists; MC4 receptor agonists; NPY5 and NPY2 antagonists; beta3 adrenergic agonists such as SB-418790 and AD-9677; agonists of the 5HT2c receptor; GABA-receptor antagonists; Na-channel blockers; topiramate; protein-kinase C inhibitors; advanced glycation end product inhibitors; and aldose reductase inhibitors.

Pharmaceutical Formulations, Administration, and Dosage Forms

When employed as pharmaceuticals, the compounds of the disclosure can be administered in the form of a pharmaceutical composition which refers to a combination of a compound of the disclosure, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, one or more of the compounds of the disclosure above in combination with one or more pharmaceutically acceptable carriers. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Compounds or compositions described herein may be administered to a patient using any amount and any route of administration effective for treating or lessening the severity of one or more of the diseases and conditions described herein. The exact amount required will vary from subject to subject, depending on the species, age, and general condition of the subject, the severity of the infection, disease or disorder, the particular agent, its mode of administration, and the like. Provided compounds are preferably formulated in a particular unit dosage form for ease of administration and uniformity of dosage. The expression "unit dosage form" as used herein refers to a physically discrete unit of agent appropriate for the patient to be treated.

The therapeutic dosage of the compounds of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. The dosage is likely to depend on such variables as the type and extent of progression of the disease or disorder, the overall health status of the particular patient, the relative biological efficacy of the compound selected, formulation of the excipient, and its route of administration.

EXAMPLES

As depicted in the Examples below, compounds of the disclosure were prepared and isolated according to the following general procedures. It will be appreciated that, although the general methods may depict the synthesis of certain compounds of the present disclosure, the following general methods, and other methods known to one of ordinary skill in the art, can be applied to all compounds and subclasses and species of each of these compounds, as described herein.

| Abbreviation | Meaning |
|---|---|
| ACN | acetonitrile |
| BEH | ethylene bridged hybrid |
| BOP | (benzotriazol-1-yloxy)tris(dimethylamino)phosphonium hexafluorophosphate |
| BTC | bis(trichloromethyl) carbonate |
| CDI | carbonyldiimadazole |
| DBU | 1,8-diazabicyclo[5.4.0]undec-7-ene |
| DCE | 1,2-dichloroethane |
| DCM | methylene chloride |
| DIEA | diisopropylethyl amine |
| DMA | dimethyl acetamide |
| DMF | dimethyl formamide |
| dppf | 1,1-bis(diphenylphosphino)ferrocene |
| DSC | differential scanning calorimetry |
| DVS | dynamic vapor sorption/desorption |
| EDX | energy-dispersive X-ray spectroscopy |
| EtN or Et$_3$N | triethylamine |
| EtOAc | ethyl acetate |
| EtOH | ethanol |
| h | hour(s) |
| HATU | 1-[bis(dimethylamino)methylene]-1H-1,2,3-triazolo[4,5-b]pyridinium 3-oxid hexafluorophosphate. |
| HBTU | 2-(1H-benzotriazole-1-yl)-1,1,3,3 -tetramethyluronium hexafluorophosphate |
| HCl | hydrochloric acid |
| HPLC | high performance liquid chromatography |
| Im | imidazaole |
| IPA | isopropyl alcohol |
| KI | potassium iodide |
| K3PO4 | Potassium phosphate |
| LCMS | liquid chromatography-mass spectrometry |
| MeOTf | methyl trifluoromethanesulfonate |
| min | minute(s) |
| Me | methyl |
| mL | milliliters |
| mmol | millimoles |
| mg | milligram |
| NaBH$_3$CN | sodium cyanoborohydride |
| NMP | N-methyl-2-pyrrolidone |
| PLM | polarized light microscopy |
| psig | PSI Gauge. Gauge pressure is measured relative to ambient atmospheric pressure. |
| RP | reverse phase |
| RT | room temperature |

-continued

| Abbreviation | Meaning |
|---|---|
| Rt | Retention time |
| SFC | supercritical fluid chromatography |
| SPhos Gen 2 | Chloro(2-dicyclohexylphosphino-2',6'-dimethoxy-1,1'-biphenyl)[2-(2'-amino-1,1'-biphenyl)]palladium(II), |
| $t_R$; $t_r$; $R_t$ | retention time |
| TBAF | tetra butyl ammonium fluoride |
| TBDMS | tert butyl dimethyl silyl |
| TEA | triethylamine |
| TFA | trifluoroacetic acid |
| TFAA | trifluoroacetic anhydride |
| THF | tetrahydrofuran |
| TGA | thermogravimetric analysis |
| TLC | thin layer chromatography |
| UPLC | Ultra performance liquid chromatography |
| XPhos | dicyclohexyphosphino-2',4',6'triiso-propyl-1,1'-biphenyl |
| $^1$H qNMR | quantitative 1H nuclear magnetic resonance |

LCMS
Instrument names: Shimadzu LC2020 Nexera Series; Shimadzu MS2020 N-Series; Agilent 1290
  Method A: Mobile Phase A: 10 mM Ammonium Bicarbonate in water; Mobile Phase B: ACN; Flow Rate: 0.8 mL/min; Column: X Bridge C8 (50×4.6 mm), 3.5 um
  Method B: Mobile Phase: 0.1% HCOOH in water/ACN (95:5); Flow Rate: 0.8 mL/min; Column: ZORBAX ECLIPSE PLUS C18 (50×2.1 mm), 1.8 um
  Method C: Mobile Phase: 10 mM NH4OAc in water/ACN (95:5); Flow Rate: 0.6 mL/min; Column: Acquity UPLC BEH C18 (2.1×50 mm), 1.7 um
  Method D: Mobile phase: A: 0.1% TFA in water, B: ACN; Column: Acquity UPLC BEH C18 (2.1×50)mm, 1.7 µm.
  Method E: Mobile Phase: A: 10 mM $NH_4HCO_3$ in water, B: ACN; Column: Phenomenex Kinetex EVO C18 (3.0×50 mm), 2.6 µm.
  Method F: Mobile Phase: A: 0.1% TFA in water, B: ACN; Column: ZORBAX ECLIPSE PLUS C18 (50×2.1 mm), 1.8 µm.
HPLC
  Instrument names: Shimadzu LC; Prominence-I series instruments as followed using % with UV detection (Maxplot)
  Method A: Mobile Phase: A-10 mM $NH_4HCO_3$ in water, B: ACN; flow rate: 2.0 mL/min; Column: X-Bridge C8 (150×4.6 mm, 5 µm).
  Method B: Mobile Phase: A; 0.1% TFA in water, B: ACN; flow rate: 2.0 mL/min; Column: X-Bridge C8 (50×4.6 mm, 3.5 µm).
  Method C: Mobile Phase: A-0.1% TFA in water, B: ACN; flow rate: 1.0 mL/min; Column: Atlantis column C18 (4.6×250 mm, 5 µm).
  Method D: Mobile Phase: A-10 mm NH40Ac in water, B: ACN; flow rate: 1.5 mL/min; Column: Gemini NX C18 (4.6×150 mm, 3 µm).
  Method E: Mobile Phase A: 0.1% HCOOH in water, B: ACN; Flow Rate: 2.0 mL/min; Column: X-Select C18 (4.6×150 mm, 5 µm).
  Method F: Mobile Phase A: 0.1% HCOOH in water, B: ACN; Flow Rate: 2.0 mL/min; Column: X-Select C18 (4.6×150 mm, 5 µm).
  Method G: Mobile Phase A: 0.1% TFA in water, B: ACN; Flow Rate: 2.0 mL/min; Column: X-Select C18 (4.6×150 mm, 5 µm).
Prep-HPLC
  Instrument names: Agilent Technologies 1260 Infinity II Series LC/6125 Quadrupole MSD
  Shimadzu Nexera Prep HPLC with LCMS 2020
  Method A: Mobile phase A: 10 mM $NH_4HCO_3$ in water; mobile Phase B: ACN; Flow Rate: 15 mL/min; Column: XBridge C18 (150×19 mm), 5 um
Prep-HPLC
  Instrument names: Agilent Technologies 1260 Infinity II Series LC/6125 MSD; Shimadzu Prep HPLC-MS2020
  Method A: Mobile phase A: 10 mm $NH_4HCO_3$ in water; mobile Phase B: ACN; Flow Rate: 15.0 mL/min; Column: ZORBAX C18 (50×21.2 mm), 5 µm.
  Method B: Mobile phase A: 10 mm $NH_4HCO_3$ in water; mobile Phase B: ACN; Flow Rate: 15.0 mL/min; Column: X-Bridge C18 (150×19.0 mm), 5 µm.
  Method C: Mobile phase A: 10 mm $NH_4HCO_3$ in water; mobile Phase B: ACN; Flow Rate: 15.0 mL/min; Column: SHIMPACK GIST C18 (150×20.0 mm) 5 µm.
  Method D: Mobile phase A: 10 mm $NH_4HCO_3$ in water; mobile Phase B: ACN; Flow Rate: 15.0 mL/min; Column: SHIMPACK GIST C18 (250×20.0 mm) 5 µm.
  Method E: Mobile phase A: 10 mm $NH_4HCO_3$ in water; mobile Phase B: ACN; Flow Rate: 15.0 mL/min; Column: SHIMPACK SCEPTER C8 (150×20.0 mm) 5 µm.
  Method F: Mobile phase A: 10 mm $NH_4HCO_3$ in water; mobile Phase B: ACN; Flow Rate: 15.0 mL/min; Column: SHIMPACK SCEPTER C8 (250×20.0 mm) 5 µm.
  Method G: Mobile phase A: 10 mm NH4HCO3 in water; mobile Phase B: ACN; Flow Rate: 15.0 mL/min; Column: Gemini-NX-C18 ((250×21.2 mm), 5 µm.
  Method H: Mobile phase A: 0.1% Formic acid in water, mobile phase B: ACN; Flow Rate: 15.0 mL/min; Column: X-Select-C18 (250×19.0 mm), 5 µm.
  Method I: Mobile phase A: 10 mm $NH_4HCO_3$ in water; mobile Phase B: ACN; Flow Rate: 15.0 mL/min; Column: X-Bridge C18 (250×19.0 mm), 5 µm.
  Method J: Mobile phase A: 10 mm $NH_4HCO_3$ in water; mobile Phase B: ACN; Flow Rate: 15.0 mL/min; Column: ZORBAX C18 (50×21.2 mm), 5 µm.
  Method K: Mobile phase A: 0.1% Formic acid in water, mobile phase B: ACN; Flow Rate: 15.0 mL/min; Column: ZORBAX C18 (250×21.2 mm), 5 µm.
  Method L: Mobile phase A: 10 mm $NH_4HCO_3$ in water; mobile Phase B: ACN; Flow Rate: 15.0 mL/min; Column: YMC C18 (250×20.0 mm), 5 µm.
Chiral SFC
  Instrument names: SFC Analytical—PIC 10-20 and Shimadzu Analytical with MS and ELSD detectors.
  Method A: Mobile Phase A: CO2; Co-solvent–0.5% isopropylamine in IPA:MeOH (50:50); Flow Rate: 4.0 mL/min; % Co-Solvent: 35%, Column: Lux-A1 (250×4.6), 5 µm.
  Method B: Mobile Phase A: CO2; Co-solvent–0.5% isopropylamine in IPA; Flow Rate: 5.0 mL/min; % Co-Solvent: 40%, Column: Lux-A1 (250×4.6), 5 µm.
  Method C: Mobile Phase A: $CO_2$; Co-solvent–0.5% isopropylamine in MeOH; Flow Rate: 5.0 mL/min; % Co-Solvent: 40%, Column: Lux-A1(250×4.6), 5 µm.
  Method D: Mobile Phase A: $CO_2$; Co-solvent–0.5% isopropylamine in MeOH; Flow Rate: 5.0 mL/min; % Co-Solvent: 40%, Run time: 12 min; Column: LUX-C4, (250×4.6), 5 µm.
  Method E: Mobile Phase A: $CO_2$; Co-solvent–0.5% isopropylamine in MeOH; Flow Rate: 4.0 mL/min; % Co-Solvent: 40%, Run time: 12 min; Column: LUX-C4, (250×4.6), 5 µm.
  Method F: Mobile Phase A: $CO_2$; Co-solvent–0.5% isopropylamine in MeOH; Flow Rate: 5.0 mL/min; % Co-Solvent: 50%, Run time: 12 min; Column: LUX-C4, (250×4.6), 5 µm.

Method G: Mobile Phase A: $CO_2$; Co-solvent–0.5% isopropylamine in IPA; Flow Rate: 4.0 mL/min; % Co-Solvent: 40%; Column: I-Cellulose B (250×4.6), 5 μm.

Method H: Mobile Phase A: $CO_2$; Co-solvent–0.5% isopropylamine in IPA; Flow Rate: 5.0 mL/min; % Co-Solvent: 50%; Column: I-Cellulose B (250×4.6), 5 μm.

Method I: Mobile Phase A: $CO_2$; Co-solvent–0.5% isopropylamine in MeOH; Flow Rate: 4.0 mL/min; % Co-Solvent: 40%; Column: I-Cellulose B (250×4.6), 5 μm.

Method J: Mobile Phase A: $CO_2$; Co-solvent–0.5% isopropylamine in MeOH; Flow Rate: 4.0 mL/min; % Co-Solvent: 40%, Column: Whelk-01_(R,R) (250×4.6), 5 μm.

Method K: Mobile Phase A: $CO_2$; Co-solvent–0.1% $NH_3$ in IPA:MeOH (50:50); Flow Rate: 4.0 mL/min; % Co-Solvent: 20%, Column: Reflect I-Amylose A (250×4.6), 5 μm.

Method L: Mobile Phase A: $CO_2$; Co-solvent–0.5% isopropylamine in IPA; Flow Rate: 4.0 mL/min; % Co-Solvent: 40%, Column: YMC Amylose-SA (250×4.6), 5 μm.

Method M: Mobile Phase A: $CO_2$; Co-solvent–0.5% isopropylamine in MeOH; Flow Rate: 5.0 mL/min; % Co-Solvent: 50%, Column: Chiralpak AS-H, (250×4.6), 5 μm.

Method K: Mobile Phase A: CO2; Co-solvent–0.5% isopropylamine in IPA; Flow Rate: 5.0 mL/min; % Co-Solvent: 35%, Column: Lux-A3, (250×4.6), 5 μm.

Method L: Mobile Phase A: $CO_2$; Co-solvent–0.5% isopropylamine in MeOH; Flow Rate: 5.0 mL/min; % Co-Solvent: 30%; Column: I-Cellulose B (250×4.6), 5 μm.

Prep-SFC

Instrument names SFC Preparative—PIC-175

Method A: Mobile Phase: CO2: 0.5% Isopropylamine in IPA: ACN (70:30); Flow Rate: 100 mL/min; Column: Lux Amylose-1 (250*30) mm, 5 μm.

Method B: Mobile Phase: CO2: 0.5% Isopropylamine in IPA (65:35); Flow Rate: 100 mL/min; Column: YMC Amylose-SA (250*30) mm, 5 μm.

Method C: Mobile Phase: CO2: 0.5% isopropylamine in IPA:ACN(1:1) [65:35]; Flow Rate: 100 mL/min; Column: Lux Amylose-3(250*30)mm, 5 μm.

Synthesis of Intermediates

Intermediate 1. 2-((4-(2,7-Diazaspiro[3.5]nonan-2-yl)pyrimidin-5-yl)oxy)-N-ethyl-5-fluoro-N-isopropylbenzamide, hydrochloride

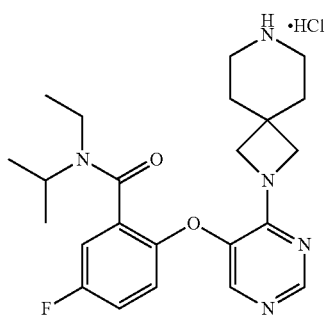 [SMILES: Cl ; CCN(C(=O)c1cc(F)ccc1Oc1cncnc1N1CC2(CCNCC2)C1)C(C)C]

Step 1. 5-(2-Bromo-4-fluorophenoxy)pyrimidine

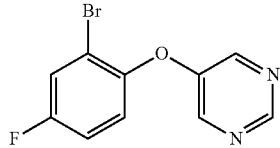

In a dried, 1000 mL three-necked round bottom flask under nitrogen atmosphere, 2-bromo-4-fluorophenol (50 g, 262 mmol) was dissolved in DMA (300 mL). To this reaction mixture cesium carbonate (111 g, 340 mmol) and 5-bromopyrimidine (42.9 g, 270 mmol) were added at 25° C. under nitrogen atmosphere. The reaction mixture was stirred at 120° C. for 64 h under nitrogen atmosphere. Reaction progress was monitored by LCMS (Method B; 58% product, 20.7% bromopyridine, 14.5% phenolic compound). After this time, the reaction was cooled to 25° C. and reverse-quenched in water (1000 mL). The aqueous layer was then extracted with MTBE (3×300 mL). The combined organic layer was washed with 2 N sodium hydroxide solution (250 mL), followed by 0.5 M citric acid solution (250 mL), and finally with 5 wt % sodium bicarbonate solution (250 mL). The organic layer was dried over anhydrous sodium sulfate and concentrated on a rotary evaporator under reduced pressure (bath temperature 45° C.) to obtain crude compound as yellow oil (51.4 g). The crude compound was purified on Isolera column chromatography using 100-200 silica and eluting with ethyl acetate in hexane (the desired product eluted with 20% ethyl acetate in hexane) to obtain 5-(2-bromo-4-fluorophenoxy)pyrimidine (38 g, 117 mmol, 44.8% yield) as pale yellow oil: Rf=0.52 (20% EtOAc in petroleum ether; $^1$H NMR (400 MHz, DMSO-$d_6$): δ 8.99 (s, 1H), 8.57 (s, 2H), 7.82-7.79 (m, 1H), 7.45-7.37 (m, 2H); LCMS (Method B): Rt=1.97 min, 271.9 (M+2)$^+$.

Step 2. Methyl 5-fluoro-2-(pyrimidin-5-yloxy)benzoate

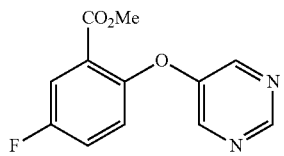

In a 250 mL tiny clave charged with 5-(2-bromo-4-fluorophenoxy)pyrimidine (9 g, 33.4 mmol) and methanol (125 mL) purged with nitrogen, was added triethylamine (23.34 mL, 167 mmol) followed by 1,1'-bis(diphenylphosphino)ferrocenedichloro palladium(II) dichloromethane complex (2.447 g, 3.34 mmol). The reaction was stirred under 100 psi carbon monoxide gas (Caution: toxic gas) at 80° C. for 48 hr. The reaction was monitored by TLC (30% EtOAc in hexane; at 36 hr, LCMS Method B showed 34% product, 30% SM). After completion of the reaction, the reaction mixture was cooled to 25° C., and filtered over a Celite® pad to remove the palladium catalyst. The Celite® pad was washed with methanol (2×50 mL). The organic layers were dried over sodium sulfate and concentrated on a rotary evaporator under reduced pressure (bath temperature 45° C.) to afford crude product (12 g, brown-colored liquid).

The crude product was purified by column chromatography (Isolera), using ethyl acetate and hexane as an eluting solvent system (the product eluted at 20% ethyl acetate in hexane) to afford pure methyl 5-fluoro-2-(pyrimidin-5-yloxy)benzoate (3.6 g, 41.5% yield) as a colorless liquid: $^1$H NMR (400 MHz, CDCl$_3$): δ ppm 8.96 (s, 1H), 8.39 (s, 2H), 7.75 (dd, J=2.8, 8.6 Hz, 1H), 7.36-7.33 (m, 1H), 7.15 (dd, J=4.4, 9.0 Hz, 1H), 3.83 (s, 3H); LCMS (Method B): Rt=1.77 min, 249.2 (M+H)$^+$.

Step 3. 5-Fluoro-2-(pyrimidin-5-yloxy)benzoic acid

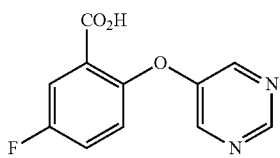

In 500 mL three necked round bottom flask methyl 5-fluoro-2-(pyrimidin-5-yloxy)benzoate (16 g, 64.5 mmol) was dissolved in MeOH (112 mL) and water (48 mL). To this reaction mixture was added NaOH (10.31 g, 258 mmol) and the reaction mixture was stirred at 25° C. for 20 h. Reaction progress was monitored by TLC (100% EtOAc). After complete consumption of the ester, the reaction mixture was concentrated on a rotary evaporator under reduced pressure (bath temperature 45° C.) and diluted with water (200 mL). The reaction mixture was extracted with ethyl acetate (3×100 mL). These organic extracts were discarded. The remaining aqueous layer was acidified by dropwise addition of 6N HCl (100 mL) and extracted with ethyl acetate (3×100 mL). Combined organic layers were dried over sodium sulfate and concentrated on a rotary evaporator under reduced pressure (bath temperature 45° C.) to obtain 5-fluoro-2-(pyrimidin-5-yloxy)benzoic acid (14.1 g, 91%) as an off-white solid: $^1$-NMR (400 MHz, DMSO-d$_6$): δ 8.92 (s, 1H), 8.47 (s, 2H), 7.70 (dd, J=3.20, 8.80 Hz, 1H), 7.58-7.53 (m, 1H), 7.40 (dd, J=4.80, 9.00 Hz, 1H); LCMS (Method B): Rt=1.49 min, 235.2 (M+H)$^+$.

Step 4. N-Ethyl-5-fluoro-N-isopropyl-2-(pyrimidin-5-yloxy)benzamide

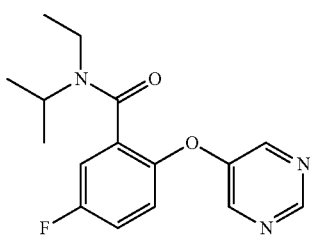 [SMILES: CCN(C(=O)c1cc(F)ccc1Oc1cncnc1)C(C)C]

In a dried, 500 mL two-necked round bottom flask under nitrogen atmosphere 5-fluoro-2-(pyrimidin-5-yloxy) benzoic acid (14 g, 59.8 mmol) was dissolved in DMF (140 mL). To this solution, N-ethylpropan-2-amine (7.96 mL, 65.8 mmol), HATU (27.3 g, 71.7 mmol) and TEA (16.67 mL, 120 mmol) were added at 25° C. under nitrogen atmosphere and the reaction mixture was stirred at 25° C. for 11 h. The reaction progress was monitored by TLC (100% EtOAc). After completion of the reaction, the reaction mixture was quenched with water (500 mL) and the aqueous layer was extracted with ethyl acetate (3×150 mL). The organic layer was dried over anhydrous sodium sulfate and filtered, and the filtrate was concentrated on a rotary evaporator (bath temperature 40° C.) to afford the crude compound. The crude compound was purified by column chromatography (Isolera) using 100-200 silica gel eluting with ethyl acetate in hexane (desired product eluted in 55-60% EtOAc in hexane). The fractions containing the required product were concentrated under reduced pressure to obtain N-ethyl-5-fluoro-N-isopropyl-2-(pyrimidin-5-yloxy)benzamide (16.1 g, 86.0% yield) as an oily mass: $^1$H NMR (400 MHz, DMSO-d$_6$): δ 8.95 (s, 1H), 8.52 (d, J=8.80 Hz, 2H), 7.37-7.34 (m, 3H), 4.27-3.74 (m, 1H), 3.38-3.36 (m, 1H), 3.19-3.12 (m, 1H), 1.14-0.96 (m, 9H). LCMS (Method B): Rt=1.85 min, 304.0 (M+H)$^+$.

Step 5. 5-(2-(Ethyl(isopropyl)carbamoyl)-4-fluoro-phenoxy)pyrimidine 1-oxide

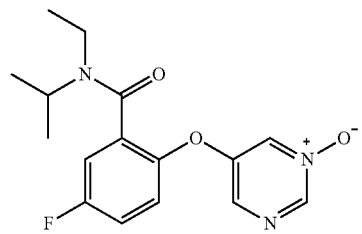 [SMILES: CCN(C(=O)c1cc(F)ccc1Oc1cnc[n+]([O-])c1)C(C)C]

In a dried, 250 mL three-necked round bottom flask was added N-ethyl-5-fluoro-N-isopropyl-2-(pyrimidin-5-yloxy) benzamide (16 g, 52.7 mmol) in tetrahydrofuran (160 mL). The resulting mixture was cooled to 0° C. and urea-hydrogen peroxide (1/1; 9.92 g, 105 mmol) was added, followed by dropwise addition of TFAA (15.17 mL, 108 mmol), maintaining the reaction temperature below 10° C. The reaction mixture was then stirred at 0 to 10° C. for 1 h, and the reaction progress was monitored by TLC (100% ethyl acetate). After 1 h, the reaction was quenched by adding 5% NaHCO$_3$ (60 mL), maintaining the temperature below 10° C. The product was extracted with DCM (2×150 mL) and the organic layer was washed with 5% NaHCO$_3$ (2×60 mL). To the organic layer 1M Na$_2$S$_2$O$_3$ solution (70 mL) was added and the mixture was stirred for 15 min. The organic layer was separated, dried over anhydrous sodium sulfate, and filtered, and the filtrate was concentrated on a rotary evaporator under reduced pressure (bath temperature 30° C.) to approximately one volume remaining in the flask. Ethyl acetate (2×60 mL) was added to the one volume solution remaining in the flask and concentrated on a rotary evaporator again to one volume remaining in the flask (Note: do not dry the mass completely). Hexane (250 mL) was added to the flask containing the concentrate. The precipitate obtained was stirred for 30 min at 25° C. The solid was collected by filtration and suction-dried to obtain 5-(2-(ethyl (isopropyl)carbamoyl)-4-fluorophenoxy)pyrimidine 1-oxide (16.0 g, 77.0% yield) as an off-white solid: LCMS (Method B): Rt=1.58 min, 320.0 (M+H)$^+$.

Step 6. 2-((4-Chloropyrimidin-5-yl)oxy)-N-ethyl-5-fluoro-N-isopropylbenzamide

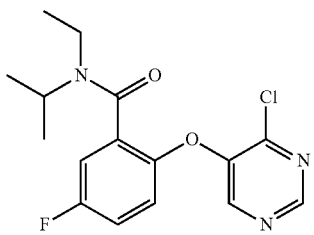 [SMILES: CCN(C(=O)c1cc(F)ccc1Oc1cncnc1Cl)C(C)C]

To a dried, 500 mL three-necked round bottom flask under nitrogen atmosphere, 5-(2-(ethyl-(isopropyl)carbamoyl)-4-fluorophenoxy)pyrimidine 1-oxide (16 g, 50.1 mmol) was added to ethyl acetate (200 mL). DIPEA (43.6 mL, 251 mmol) was added at 0° C. The reaction mixture was stirred for 10 min at 0° C. and then phosphoryl trichloride (5.62 mL, 60.1 mmol) was added dropwise at 0° C. After complete addition, the reaction mixture was stirred for 30 min at 0° C., slowly allowed to warm to 25° C., and stirred for 2 h. The reaction progress was monitored by TLC (100% EtOAc). After completion of the reaction, the reaction mixture was quenched with cold water (25 mL) and extracted with ethyl acetate (3×100 mL). The combined organic layer was dried over sodium sulfate, filtered, and the filtrate was concentrated on a rotary evaporator under reduced pressure (bath temperature 45° C.) to afford the crude compound. The crude compound was purified by column chromatography (Isolera) by using 100-200 mesh silica gel and eluting with ethyl acetate in hexane (the desired product eluted in 25% ethyl acetate in hexane). The fractions containing the required product were concentrated under reduced pressure to obtain 2-((4-chloropyrimidin-5-yl)oxy)-N-ethyl-5-fluoro-N-isopropylbenzamide (5.82 g, 30.0% yield) as a brown gummy liquid: LCMS (Method B): Rt=1.96 min, 338.0 (M+H)+.

Step 7. tert-Butyl 2-(5-(2-(ethyl(isopropyl)carbamoyl)-4-fluorophenoxy)pyrimidin-4-yl)-2,7-diazaspiro[3.5]nonane-7-carboxylate

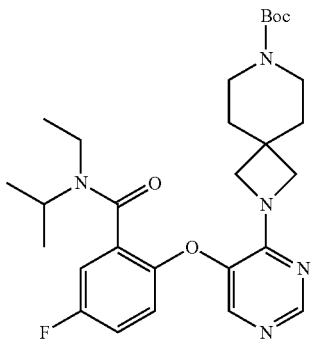 [SMILES: CCN(C(=O)c1cc(F)ccc1Oc1cncnc1N1CC2(CCN(C(=O)OC(C)(C)C)CC2)C1)C(C)C]

In a dried, 250 mL three-necked round bottom flask, 2-((4-chloropyrimidin-5-yl)oxy)-N-ethyl-5-fluoro-N-isopropylbenzamide (5.82 g, 17.23 mmol) was dissolved in 2-propanol (50 mL). To this solution, TEA (7.20 mL, 51.7 mmol) and tert-butyl 2,7-diazaspiro[3.5]nonane-7-carboxylate hydrochloride (5.43 g, 20.68 mmol) were added at 25° C. under nitrogen atmosphere, and the resulting reaction was heated at 80° C. for 18 h. The reaction progress was monitored by TLC (100% EtOAc). After complete consumption of the amine, the solvent was distilled off and the residue was quenched with ice water (20 mL) and extracted with ethyl acetate (3×50 mL). The combined organic layer was washed with brine, dried over Na$_2$SO$_4$, and filtered. The filtrate was concentrated on a rotary evaporator under reduced pressure (bath temperature 45° C.) to afford the crude product. The crude product was purified by column chromatography (Isolera) by using 100-200 mesh silica gel and eluting with ethyl acetate in hexane (the desired product eluted in 30-70% ethyl acetate in hexane). The fractions containing the desired product were concentrated under reduced pressure to obtain tert-butyl 2-(5-(2-(ethyl(isopropyl)carbamoyl)-4-fluorophenoxy)pyrimidin-4-yl)-2,7-diazaspiro[3.5]nonane-7-carboxylate (6.1 g, 61.5% yield) as a semi-solid: $^1$H NMR (400 MHz, CDCl$_3$): δ 8.40 (s, 1H), 7.81 (s, 1H), 7.05-7.01 (m, 2H), 6.77-6.74 (m, 1H), 4.00-3.85 (m, 5H), 3.50-3.20 (m, 6H), 1.72 (t, J=6.80 Hz, 3H), 1.47 (s, 9H), 1.29-1.15 (m, 9H).); LCMS (Method C): Rt=2.12 min, 528.2 (M+H)+.

Step 8. 2-((4-(2,7-Diazaspiro[3.5]nonan-2-yl)pyrimidin-S-yl)oxy)-N-ethyl-5-fluoro-N-isopropylbenzamide, hydrochloride

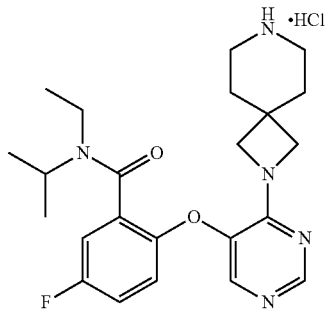 [SMILES: Cl ; CCN(C(=O)c1cc(F)ccc1Oc1cncnc1N1CC2(CCNCC2)C1)C(C)C]

In a dried, 250 mL three-necked round bottom flask under nitrogen atmosphere was charged tert-butyl 2-(5-(2-(ethyl(isopropyl)carbamoyl)-4-fluorophenoxy)pyrimidin-4-yl)-2,7-diazaspiro [3.5] nonane-7-carboxylate (6.8 g, 12.89 mmol) in 2,2,2-triflouroethanol (40 mL). To this solution, TMS-Cl (6.59 mL, 51.6 mmol) was added dropwise at 0° C., and then the reaction mixture was stirred for 2 h at 25° C. The reaction progress was monitored by TLC (10% MeOH in DCM). After 2 h, the solvent was removed under reduced pressure on a rotary evaporator and the residue was co-distilled with ethyl acetate (2×20 mL). The residue was triturated with hexane to obtain 2-((4-(2,7-diazaspiro[3.5]nonan-2-yl)pyrimidin-5-yl)oxy)-N-ethyl-5-fluoro-N-isopropylbenzamide, hydrochloride (5.9 g, 86.0% yield) as an off-white solid: LCMS (Method A): Rt=1.54 min, 428.3 (M+H)+.

Intermediate 1 (Large-Scale Preparation). 2-((4-(2,7-diazaspiro[3.5]nonan-2-yl)pyrimidin-5-yl)oxy)-N-ethyl-5-fluoro-N-isopropylbenzamide, bis-tosylate salt

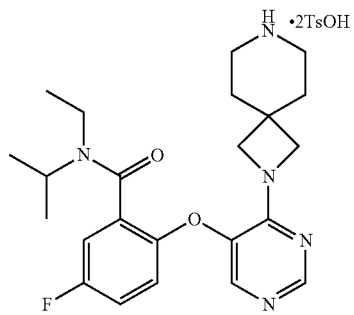

Step 1. 5-(2-Bromo-4-fluorophenoxy)pyrimidine

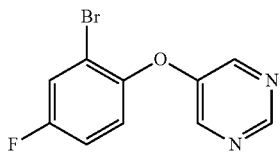

Step 1 was performed in three batches, an 8.00 kg batch (4.00 kg and 4.00 kg from in one reactor and divided into two reactors for workup) and a 3.00 kg batch.

In a 100-L, cylindrical reactor, 2-bromo-4-fluorophenol (8.00 kg, 41.9 mol, 1.00 equiv), 5-bromopyrimidine (6.86 kg, 43.1 mol, 1.03 equiv), cesium carbonate (17.7 kg, 54.5 mol, 1.3 equiv), and DMAc (48 L, 6 vol) were charged. The batch was heated to 119° C. over 9 h and held at temperature for 82 h. The batches were then cooled to 34° C. and an IPC sample was taken, which indicated 82.2% conversion by NMR from the phenol. The internal temperature of the batch was adjusted to 25° C. and the batch was split into two 100-L reactors. To each batch, MTBE (10.6 L, 2.66 vol) and deionized water (48 L, 12 vol), were added and agitated 15 min. The extraction of the resulting aqueous phase was repeated on each batch 5 times with MTBE (5×10.6 L, 5×2.66 vol for each). The MTBE extracts were combined and washed sequentially with 2 N sodium hydroxide (8 L, 2 vol, 50% NaOH), 0.5 M citric acid (4 L, 1 vol, solid), and finally by 5 wt % sodium bicarbonate (4 L, 1 vol). The MTBE solutions were combined and concentrated via rotary evaporation (bath temperature 55° C.). The residue from the combined batch was then stored in a carboy prior to wiped film evaporation purification. Similarly, a 3.00 kg batch was completed and the crude oil was stored in a carboy at ambient temperature until purification (3.50 kg).

A 4" Pope wiped-film evaporator (WFE) was used to purify 8.17 kg crude 5-(2-bromo-4-fluorophenoxy)pyrimidine through multiple passes. The conditions for WFE distillation first pass were as follows: vacuum 10-12 Torr (empty), wiper speed 328-333 rpm, jacket temperature 160° C., condenser temperature 85° C., addition rate ≈4 mL/min. The conditions for WFE distillation second pass were as follows: vacuum 0.8 Torr (empty), wiper speed 320-330 rpm, jacket temperature 150° C., condenser temperature 50° C., addition rate ≈10 mL/min. A third pass was completed to re-pass pot fractions that contained large amounts of products. The conditions for WFE distillation third pass were as follows: vacuum 0.8 Torr (empty), wiper speed 320-330 rpm, jacket temperature 130° C., condenser temperature 50° C., addition rate ≈15 mL/min. After the third pass, the product spontaneously crystallized upon cooling. All the material was collected and combined in several jars with the purified material (6.58 kg, 43% yield combined, 95.9% AUC, 91.2 wt % 1H qNMR).

Steps 2 and 3.
5-Fluoro-2-(pyrimidin-5-yloxy)benzoic acid

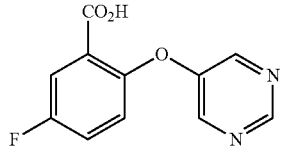

A 22-gal, jacketed, stainless steel pressure vessel was charged with [1,1'-bis(diphenylphosphino) ferrocene]dichloro-palladium(II) dichloromethane adduct (Pd(dppf)Cl$_2$ DCM complex, 0.989 kg, 1.21 moles, 0.05 equiv), 5-(2-bromo-4-fluorophenoxy)pyrimidine (6.52 kg, 24.2 moles, 1.00 equiv), triethylamine (4.93 kg, 48.4 moles, 2.00 equiv), and methanol (32.6 L, 5 vol). The reactor was purged with nitrogen (3 times up to 60 psig of nitrogen pressure) and then with carbon monoxide gas [3 times up to 50 psig of carbon monoxide]. The reactor internal temperature was adjusted to 70±5° C. over 1 h and the internal pressure was adjusted to 40±5 psig with carbon monoxide gas. The batch was stirred at 70±5° C. for 13 h, cooled to 25° C., and purged with nitrogen three times with 50 psig pressure. The batch was filtered over a Celite® pad to remove the palladium catalyst, which was rinsed with MeOH (6.5 L, 1 vol). The solution containing methyl 5-fluoro-2-(pyrimidin-5-yloxy)benzoate was transferred to a 100-L, jacketed, glass reactor and diluted with water (13 L, 2 vol). 50 wt % sodium hydroxide aqueous solution (7.8 kg, 96.9 moles, 4 equiv) was added keeping the batch internal temperature <45° C. (max temperature 42.4° C.). The batch was stirred for 14 h then concentrated under reduced pressure (28.5 in Hg, 42° C.) to 4 vol (24 L). The batch was diluted with water (34 L, 7 vol), cooled to 25° C., and filtered through a Celite® pad to remove the remaining catalyst. The pad was washed with water (6.5 L, 1 vol). The batch was extracted with MTBE (13 L, 2 vol) two times for 30 min each time. The batch was acidified to pH ≈2 using 6 M hydrochloric acid (about 13 L, 2.3 vol; conc. HCl), maintaining an internal batch temperature of 20° C. Once the acid addition was complete, the batch was stirred for 20 h, then filtered over a polypropylene cloth using a filter/dryer. The filter cake was washed three times with water (3×13 L, 3×2 vol) and dried under stream of nitrogen at 40-45° C. over five days until the water level was 0.3 wt % by KF analysis. The product was isolated in 98% yield (, 5.58 kg, 98.8% AUC).

Step 4. N-Ethyl-5-fluoro-N-isopropyl-2-(pyrimidin-5-yloxy)benzamide

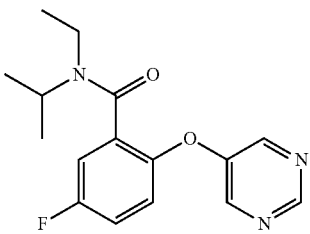 [SMILES: CCN(C(=O)c1cc(F)ccc1Oc1cncnc1)C(C)C]

Step 4 was performed following the same procedure in two batches, a 2.80 kg batch and a 5.00 kg batch.

A 100-L, cylindrical, glass jacketed reactor was inerted by flow-through with $N_2$ and connected to a 2 N NaOH scrubber. 5-Fluoro-2-(pyrimidin-5-yloxy)benzoic acid (5.00 kg, 21.3 mol, 1.00 equiv) and DCM (50 L, 10 vol) were charged to the reactor. Agitation began to form a light beige suspension and the batch was cooled to <10° C. DMF (100 mL, 1.28 mol, 0.06 equiv,) was charged, followed by oxalyl chloride (470 mL, 5.55 mol, 0.26 equiv) over 20 min. Triethylamine (2.71 L, 19.4 mol) and oxalyl chloride (1.88 L, 22.2 mol, 1.04 equiv) were charged simultaneously over 90 min with the oxalyl chloride rate of addition slightly faster than that of triethylamine. The temperature was adjusted to 15° C. and held for 80 min. The batch was sampled for IPC, which indicated 94.6% conversion to the acid chloride (an aliquot of the reaction mixture was quenched with benzylamine prior to analysis). After holding for 1 h at 15° C., the batch was cooled to <5° C. and a solution of N-ethyl-2-propanamine (5.16 L, 42.7 mol, 2.00 equiv) and triethylamine (3.27 L, 23.5 mol, 1.10 equiv.) was charged in small portions over 3 h, maintaining batch temperature <10° C. After warming to 15° C. over 1 h, the reaction was held at 15-20° C. for 12 h at which point HPLC indicated 97.2% conversion (an aliquot of the reaction mixture was quenched with benzylamine). The batch was washed sequentially with 1 N HCl (20.0 L, 4 vol, concentrated HCl) and 2 N NaOH (20.0 L, 4 vol, 50% NaOH), stirring each for 20 min, and allowing layers to separate for 10 min. The batch was then concentrated to near-dryness via rotary evaporation to 1.6 vol (8 L) and MTBE (6 L, 1.2 vol) was added in portions. The batch was then distilled again to near-dryness (6.25 L) via rotovap, at which time the batch started to crash out, indicating low levels of DCM. The batch was transferred back into the reactor using 3 L of MTBE as a rinse and cooled to 0° C. Once at 0° C., heptanes (9.3 L, 1.9 vol, with 0.005% Statsafe 6000) was charged slowly over 1 h to obtain an approximate 1:1 ratio of MTBE/heptanes. The batch initially oiled and became a thick slurry with a thin shell along the reactor walls after 1 h at 20° C. While cooling to 0-5° C., the remaining heptanes (60 L) were slowly added over 70 min and the shell was physically scraped off the reactor wall. The batch was aged at 0° C. for 13 h and then filtered through a Nutsche filter equipped with a polypropylene cloth. The reactor was rinsed once with heptanes (5 L, 1 vol) and the rinse was applied to the filer cake. The isolated solids were dried in a vacuum oven at 30-40° C. over five days to yield N-ethyl-5-fluoro-N-isopropyl-2-(pyrimidin-5-yloxy)benzamide as a tan solid (5.60 kg, 87% yield, 96.4% AUC, 89.0% by weight).

Step 5. 5-(2-(Ethyl(isopropyl)carbamoyl)-4-fluorophenoxy)pyrimidine 1-oxide

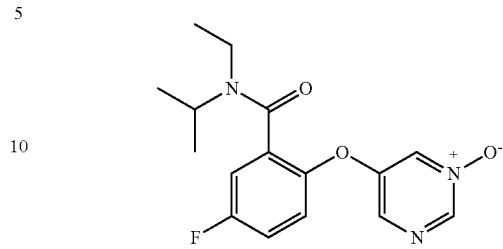

Step 5 was performed following the same procedure in two batches, a 3.40 kg batch and a 4.65 kg batch. N-Ethyl-5-fluoro-N-isopropyl-2-(pyrimidin-5-yloxy)benzamide (4.65 kg, 15.3 mol, 1.00 equiv.) and DCM (23 L, 4.9 vol) were charged to a 100-L, cylindrical, jacketed reactor and cooled to 5° C. over 15 min. Urea hydrogen peroxide (UHP, 2.16 kg, 23.0 mol, 1.50 equiv.) was charged followed by DCM (5 L, 1.1 vol) as a rinse. Trifluoroacetic anhydride (TFAA, 1.6 L, 11.5 mol, 0.75 equiv.) was added over 2 h, maintaining batch temperature <10° C. Then, the reactor was purged with $N_2$ for 30 min, to ensure the atmosphere was free from $O_2$ that may have been produced. This was followed by addition of a second portion of TFAA (1.6 L, 11.5 mol, 0.75 equiv) over 2 h. The reactor was again inerted with $N_2$ for 30 min. After stirring for 17 h, conversion was 92.0% by HPLC. To drive conversion further, UHP (288 g, 3.06 mol, 0.2 equiv) was charged and TFAA (426 mL, 3.06 mol, 0.2 equiv,) was added over 15 min. After stirring for 1 h, conversion reached 96.7% by HPLC. The reaction was quenched with a solution of 1 M sodium sulfite (12.4 L, 2.6 vol, 0.8 equiv), which was stirred for 30 min prior to charging 5% $NaHCO_3$ (23.2 L, 5.0 vol, solid $NaHCO_3$), while maintaining <20° C. over 30 min. The mixture was stirred for 2 h due to residual bubbling that indicated ongoing neutralization. The layers were separated, and the organic phase tested negative for peroxides using KI-starch test paper. The batch was washed a second time with 5% $NaHCO_3$ (32.9 L, 5 vol) for 15 min. The organic phase was distributed into two glass carboys and 4A molecular sieves (3.0 kg, 10% w/v) were charged to the carboys and held at ambient temperature. The batch was periodically stirred and checked by KF. After 135 h, the water content was 416 ppm. The batch was filtered into a 100-L, cylindrical, jacketed reactor. The sieves were washed with DCM (9.3 L, 2 vol) and the wash charged to the reactor. The batch (88.5% AUC, 7.6 wt % by qNMR corresponding to 3.58 kg, 73% yield,) was held at 0° C. for 18 h prior to performing Step 6.

Step 6. 2-((4-Chloropyrimidin-5-yl)oxy)-N-ethyl-5-fluoro-N-isopropylbenzamide

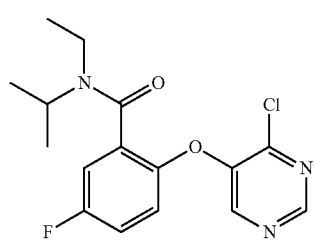 [SMILES: CCN(C(=O)c1cc(F)ccc1Oc1cncnc1Cl)C(C)C]

Step 6 was performed following the same procedure in two batches, a 2.86 kg batch and a 3.58 kg batch.

To a 100-L, cylindrical, jacketed reactor was charged a solution of 5-(2-(ethyl(isopropyl)carbamoyl)-4-fluorophenoxy)pyrimidine 1-oxide in DCM (total volume ≈36 L). The amount of 5-(2-(ethyl(isopropyl)carbamoyl)-4-fluorophenoxy)pyrimidine 1-oxide in the DCM solution was 3.58 kg (11.2 mol, 1 equiv) by 1H qNMR weight assay. The batch temperature was adjusted from 4° C. to 11° C. and triethylamine (2.34 L, 16.8 mol, 1.5 equiv) was added while maintaining a batch temperature <15° C. Oxalyl chloride (1.23 L, 14.6 mol, 1.3 equiv) was charged in small increments over 3 h to control the vigorous gas evolution. The batch was adjusted to 30° C. over 1 h and held at 30-35° C. for 1 h, after which 2.6% of 5-(2-(ethyl(isopropyl)carbamoyl)-4-fluorophenoxy)pyrimidine 1-oxide remained, so additional charges of triethylamine (90 mL, 0.65 mol, 0.06 equiv) and oxalyl chloride (71 g, 0.56 mol, 0.05) were added, and the batch was stirred an additional 15 h. 1 N HCl (17.9 L, 5 vol, concentrated HCl) was charged over 30 min maintaining batch temperature <20° C. and then stirred for 2 h while sparging with 10 psi $N_2$ gas through the bottom outlet valve (BOV). The opaque dark brown phases were separated, and the organic phase was held overnight before washing with 5% $NaHCO_3$ solution (17.9 L, 5 vol). The batch was sparged again with $N_2$ gas through the BOV for 30 min. Both phases were again dark brown and opaque. The phases separated and the organic phase was stripped to dryness via rotary evaporation (bath temp 35° C.) to produce 4.92 kg of crude 2-((4-chloropyrimidin-5-yl)oxy)-N-ethyl-5-fluoro-N-isopropylbenzamide as a thick dark brown oil (2.96 kg adjusted for purity, 78% adjusted yield, 81.8% AUC, 60.1% potency by 1H qNMR) which was held in IPAc (19.6 L, 6.6 vol relative to 2-((4-chloropyrimidin-5-yl)oxy)-N-ethyl-5-fluoro-N-isopropylbenzamide) at 0° C. prior to use.

Step 7. tert-butyl 2-(5-(2-(ethyl(isopropyl)carbamoyl)-4-fluorophenoxy)pyrimidin-4-yl)-2,7-diazaspiro[3.5]nonane-7-carboxylate

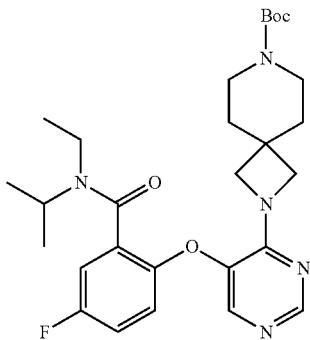

Step 7 was performed following the same procedure in two batches, a 2.06 kg batch and a 2.96 kg batch.

Crude 2-((4-chloropyrimidin-5-yl)oxy)-N-ethyl-5-fluoro-N-isopropylbenzamide (2.96 kg adjusted input based on weight potency, 8.8 mol), tert-butyl 2,7-diazaspiro[3.5]nonane-7-carboxylate HCl (2.5 g, 9.6 mol, 0.3 equiv.) and IPAc (29.6 L, 6.0 vol) were charged to a 100-L, cylindrical, jacketed reactor. DIPEA (6.1 L, 35.1 mol) was charged and the batch was heated to 75-80° C. over 3 h and stirred at temperature for 8 h. HPLC analysis of the reaction indicated 95.0% conversion, so another 0.1 equiv of tert-butyl 2,7-diazaspiro[3.5]nonane-7-carboxylate HCl (230 g, 0.88 mol, 0.1 equiv) was charged. Conversion reached 96.5% after 3 h of heating, so the batch was cooled to 50° C. A 0.5 M citric acid solution (14.8 L, 5 vol) was charged over 10 min maintaining temperature >40° C. and agitated at 40° C. for 20 min. The dark opaque brown phases were separated and 0.5 M citric acid solution (14.8 L, 5 vol) was charged, stirred for 20 min, and the phases separated. The batch was cooled and held at 20° C. overnight, then 5 wt % $NaHCO_3$ (29.6 L, 5 vol) was charged over 45 min maintaining batch temperature 35-40° C. After agitating for 20 min, the phases were separated. The organic phase was rotovapped over 1 h to 4 vol (≈20 L). The batch spontaneously solidified in the rotovap bulb, and was transferred into the reactor, then the brown suspension was cooled to 20° C., and n-heptane (35.5 L, 12 vol) was charged over 1 h. The light brown suspension was stirred at ≈20° C. for 13 h, cooled to 5° C. over 1 h, and held at 5° C. for 2 h prior to filtering. The filtrate was analyzed by HPLC to confirm that no further precipitation occurred after an additional hour and then the batch was filtered over 2 h through a Nutsche funnel equipped with a polypropylene cloth. n-Heptane (5.9 L, 2 vol) was then used to wash the reactor and the wash was pulled through the wet cake over 20 min. The wet cake was conditioned for 42 h prior to drying under high vacuum at 40-45° C. to produce crude tert-butyl 2-(5-(2-(ethyl(isopropyl)carbamoyl)-4-fluorophenoxy)pyrimidin-4-yl)-2,7-diazaspiro[3.5]nonane-7-carboxylate as an off-white to light tan solid (3.99 kg, 92.2% AUC, 88.2 wt % by 1H qNMR, 76% yield adjusted for potency of product).

tert-Butyl 2-(5-(2-(ethyl(isopropyl)carbamoyl)-4-fluorophenoxy)pyrimidin-4-yl)-2,7-diazaspiro[3.5]nonane-7-carboxylate was purified in one batch. Crude tert-butyl 2-(5-(2-(ethyl(isopropyl)carbamoyl)-4-fluorophenoxy)pyrimidin-4-yl)-2,7-diazaspiro[3.5]nonane-7-carboxylate (7.04 kg) was charged to a 100-L, cylindrical, jacketed reactor. IPAc (31.7 L, 4.5 vol,) and MTBE (31.7 L, 4.5 vol) were charged, and the batch was heated to 70±5° C. and held for 1 h. After cooling to 5° C. (target 0° C.) over 4.5 h, the batch was held for 16 h and filtered using a Nutche filter with polypropylene cloth. Two portions of MTBE (2×14 L, 2×2 vol) were used to rinse the reactor, cooled to 5° C., and washed through the wet cake. The pale brown solid was dried under high vacuum at 40° C. to produce purified tert-butyl 2-(5-(2-(ethyl(isopropyl)carbamoyl)-4-fluorophenoxy)pyrimidin-4-yl)-2,7-diazaspiro[3.5]nonane-7-carboxylate (4.54 kg, 76% yield, 98.9% AUC UV-HPLC, 97.4 wt % 1H qNMR, 99.4% AUC CAD-HPLC).

Step 8. 2-((4-(2,7-diazaspiro[3.5]nonan-2-yl)pyrimidin-5-yl)oxy)-N-ethyl-5-fluoro-N-isopropylbenzamide, bis-tosylate Salt

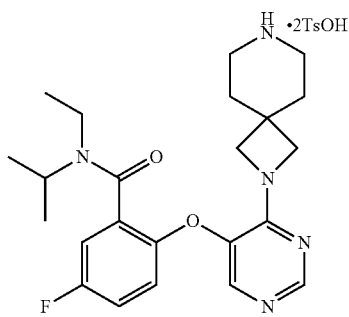

In a 100-L, cylindrical, jacketed reactor, tert-butyl 2-(5-(2-(ethyl(isopropyl)carbamoyl)-4-fluorophenoxy)pyrimidin-4-yl)-2,7-diazaspiro[3.5]nonane-7-carboxylate (3.50 kg, 6.63 mol, 1.0 equiv.) was dissolved in THF (36 L, 10 vol). The solution was transferred to a glass carboy, then p-toluene sulfonic acid monohydrate (pTSA, 3.90 kg, 19.9 mol, 3.0 equiv) was dissolved in THF (18 L, 5 vol) and purified water (540 mL, 0.15 vol), and the solution was heated to 55±5° C. The tert-butyl 2-(5-(2-(ethyl(isopropyl)carbamoyl)-4-fluorophenoxy)pyrimidin-4-yl)-2,7-diazaspiro[3.5]nonane-7-carboxylate solution was transferred to the reactor over 4 h while maintaining the batch at 55±5° C. After 16 h, the batch was cooled to 20±5° C. over 1.5 h and held for 2 h prior to filtration. The wet cake was washed three times with THF (3×18 L, 3×5 vol,). The filtration and washes were completed in 1.75 h, then the wet cake was conditioned under vacuum for 17.5 h prior to drying under reduced pressure at 45±5° C. 2-((4-(2,7-Diazaspiro[3.5]nonan-2-yl)pyrimidin-5-yl)oxy)-N-ethyl-5-fluoro-N-isopropylbenzamide, bis-tosylate salt was isolated in 94% yield (4.80 kg).

Intermediate 2. ((2S,5R)-5-((tert-Butoxycarbonyl)amino)tetrahydro-2H-pyran-2-yl)methyl 4-methylbenzenesulfonate

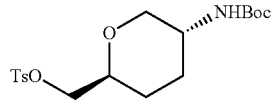 [SMILES: Cc1ccc(S(=O)(=O)OC[C@@H]2CC[C@@H](NC(=O)OC(C)(C)C)CO2)cc1]

In a dried, 100 mL three-necked round bottom flask, tert-butyl ((3R,6S)-6-(hydroxymethyl)tetrahydro-2H-pyran-3-yl)carbamate (500 mg, 2.16 mmol) was dissolved in $CH_2Cl_2$ (20 mL) and the solution was cooled to 0° C. over 5 min. To this solution was added DIPEA (1.15 mL, 6.49 mmol) followed by DMAP (31.7 mg, 0.25 mmol) and 4-methylbenzenesulfonyl chloride (495 mg, 2.59 mmol) at 0° C. The reaction mixture was then brought to 25° C. over a period of 30 min and stirred at 25° C. for 16 h. The reaction progress was monitored by TLC (100% EtOAc). After 16 h, the reaction was quenched with water (50 mL) and extracted with DCM (2×50 mL). The organic layer was washed with brine (2×25 mL) followed by aqueous $NaHCO_3$ (2×50 mL). The organic layer was dried over anhydrous sodium sulfate and filtered, and the filtrate was concentrated on a rotary evaporator (bath temperature 40° C.) to afford the crude product (810 mg). The crude product was purified by column chromatography (SepaBean) using 100-200 silica gel and eluting with ethyl acetate in hexane (required product eluted in 40% ethyl acetate in hexane). The fractions containing the required product were concentrated under reduced pressure to obtain ((2S,5R)-5-((tert-butoxycarbonyl)amino)tetrahydro-2H-pyran-2-yl)methyl 4-methylbenzenesulfonate (680 mg, 81% yield) as a white solid: $^1H$ NMR (400 MHz, DMSO-$d_6$): δ 7.78 (d, J=8.00 Hz, 2H), 7.49 (d, J=8 Hz, 2H), 6.76-6.74 (m, 1H), 4.00-3.98 (m, 1H), 3.92-3.88 (m, 1H), 3.73-3.71 (m, 1H), 3.39-3.37 (m, 1H), 3.32-3.24 (m, 1H), 2.90-2.85 (m, 1H), 2.43 (s, 3H), 1.82-1.80 (m, 1H), 1.56-1.52 (m, 1H), 1.37 (s, 9H), 1.37-1.21 (m, 2H). LCMS (Method B): Rt=2.92 min, 330.2 (M-56).

Intermediate 3: 2-((4-(2,7-Diazaspiro[3.5]nonan-2-yl)pyrimidin-5-yl)oxy)-5-fluoro-N,N-diisopropyl benzamide, hydrochloride

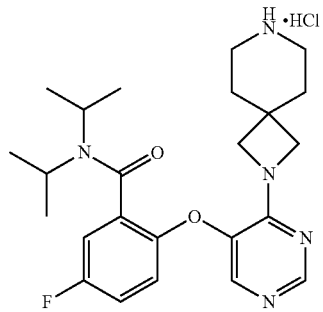

Step 1. 5-Fluoro-N,N-diisopropyl-2-(pyrimidin-5-yloxy)benzamide

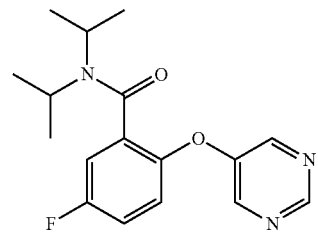 [SMILES: CC(C)N(C(=O)c1cc(F)ccc1Oc1cncnc1)C(C)C]

In a 500 mL two-necked dried round bottom flask under nitrogen atmosphere, 5-fluoro-2-(pyrimidin-5-yloxy) benzoic acid (10 g, 42.7 mmol) was dissolved in DMF (100 mL). To this solution, diisopropylamine (9.00 mL, 64.1 mmol), HATU (19.48 g, 51.2 mmol) and DIPEA (38.1 mL, 214 mmol) were added at 25° C. under nitrogen atmosphere, and the reaction was stirred at 25° C. for 20 h. The reaction progress was monitored by TLC (50% EtOAc in hexane). After completion of the reaction, the reaction mixture was quenched with water (500 mL) and extracted with ethyl acetate (3×300 mL). The combined organic layer was dried over anhydrous sodium sulfate, filtered, and the filtrate was concentrated on a rotary evaporator (bath temperature 40° C.) to obtain the crude product. The crude product was purified by column chromatography (Isolera) using 100-200 mesh silica gel and eluting with ethyl acetate in hexane (desired product eluted in 25% EtOAc in hexane). The fractions containing the desired product were concentrated under reduced pressure to obtain 5-fluoro-N, N-diisopropyl-2-(pyrimidin-5-yloxy) benzamide (7.2 g, 48.9% yield) as an off-white solid: $^1H$ NMR (400 MHz, DMSO-$d_6$): δ 8.94 (s, 1H), 8.51 (s, 2H), 3.73-3.63 (m, 1H), 3.56-3.46 (m, 1H), 1.39 (d, J=6.80 Hz, 3H), 1.17 (d, J=6.80 Hz, 3H), 1.09 (d, J=6.40 Hz, 3H); LCMS (Method B): Rt=1.99 min, 318.2 $(M+H)^+$.

Step 2. 5-(2-(Diisopropylcarbamoyl)-4-fluorophenoxy)pyrimidine 1-oxide

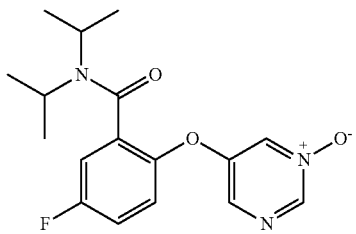

In a dried, 250 mL three-necked round bottom flask under nitrogen atmosphere, 5-fluoro-N,N-diisopropyl-2-(pyrimidin-5-yloxy)benzamide (6.0 g, 18.91 mmol) was dissolved in tetrahydrofuran (60 mL). The resulting solution was cooled to 0° C. and urea hydrogen peroxide (3.56 g, 37.8 mmol) was added, followed by the dropwise addition of TFAA (5.42 mL, 38.4 mmol) while maintaining the temperature below 10° C. The reaction was stirred at 0° C. to 10° C. for 1 h, and the reaction progress was monitored by TLC (100% EtOAc). After complete consumption of the starting material, the reaction was quenched by adding 5% NaHCO$_3$ (50 mL), maintaining the temperature below 10° C. The reaction was extracted with DCM (2×100 mL) and the combined organic layer was sequentially washed with 5% NaHCO$_3$(2×50 mL) and 1M Na$_2$S$_2$O$_3$ solution (60 mL). The organic layer was dried over anhydrous sodium sulfate and filtered, and the filtrate was minimized on a rotary evaporator (bath temperature 30° C.) up to one volume remaining in RBF. This was co-distilled with ethyl acetate (2×60 mL) and the organic layer was again minimized to one volume remaining in RBF (Note: Do not evaporate to dryness). Hexane (250 mL) was added slowly to the remaining reaction volume in the evaporation flask. The precipitate obtained was stirred for 30 min at 25° C., filtered and suction-dried to obtain 5-(2-(diisopropylcarbamoyl)-4-fluorophenoxy)pyrimidine 1-oxide (6 g, 77.64% yield) as an off-white solid: $^1$H NMR (400 MHz, DMSO-d$_6$): δ 8.87 (d, J=1.60 Hz, 1H), 8.39 (t, J=1.60 Hz, 1H), 8.05 (d, J=2.40 Hz, 1H), 7.45-7.42 (m, 1H), 7.37-7.36 (m, 1H), 7.35-7.30 (m, 1H), 3.67-3.64 (m, 1H), 3.55-3.51 (m, 1H), 1.40 (d, J=6.40 Hz, 3H), 1.40 (d, J=6.40 Hz, 3H), 1.09 (d, J=6.40 Hz, 3H), 1.06 (d, J=6.80 Hz, 3H); LCMS (Method B): Rt=1.64 min, 334.0 (M+H)$^+$.

Step 3. 2-((4-Chloropyrimidin-5-yl)oxy)-5-fluoro-N,N-diisopropylbenzamide

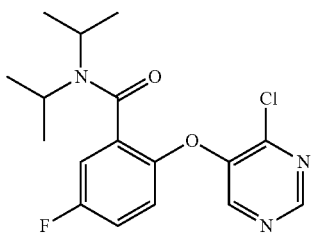 [SMILES: CC(C)N(C(=O)c1cc(F)ccc1Oc1cncnc1Cl)C(C)C]

In a 250 mL three-necked round bottom flask under nitrogen atmosphere, 5-(2-(diisopropylcarbamoyl)-4-fluorophenoxy)pyrimidine-1-oxide (5.0 g, 15.00 mmol) was dissolved in ethyl acetate (50 mL). To this solution, DIPEA (43.6 mL, 251 mmol) was added at −5° C. and then stirred for 10 min. After that, POCl$_3$ (1.678 mL, 18.00 mmol) was added dropwise at −5° C. The reaction mixture was stirred for 30 min at 0° C. and then allowed to warm slowly to 25° C. and stirred for 1 h, monitoring the reaction progress by TLC (30% EtOAc in Hexane). After completion of the reaction, the reaction mixture was quenched with cold water (20 mL) and extracted with ethyl acetate (3×40 mL). The combined organic layer was dried over sodium sulfate and filtered, and the filtrate was concentrated on a rotary evaporator under reduced pressure (bath temperature 45° C.) to obtain the crude product. The crude product was purified by column chromatography (Isolera) using 100-200 mesh silica gel and eluting with ethyl acetate in hexane (the desired product eluted in 22% ethyl acetate in hexane). The fractions containing the required product were concentrated under reduced pressure to obtain 2-((4-chloropyrimidin-5-yl)oxy)-5-fluoro-N,N-diisopropylbenzamide (2.4 g, 39.0% yield) as a yellow solid: $^1$H NMR (400 MHz, DMSO-d$_6$): δ 8.79 (s, 1H), 8.26 (s, 1H), 7.40-7.33 (m, 3H), 3.68-3.64 (m, 1H), 3.55-3.51 (m, 1H), 1.39 (d, J=6.80 Hz, 3H), 1.21 (d, J=6.80 Hz, 3H), 1.10 (d, J=6.80 Hz, 6H); LCMS (Method B): Rt=2.54 min, 352.3 (M+H)$^+$.

Step 4. tert-Butyl 2-(5-(2-(diisopropylcarbamoyl)-4-fluorophenoxy)pyrimidin-4-yl)-2,7-diazaspiro[3.5]nonane-7-carboxylate

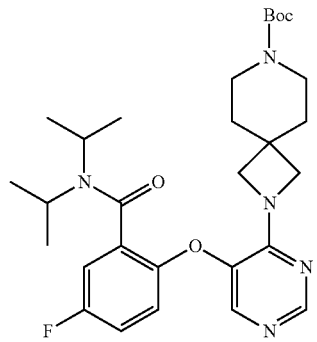 [SMILES: CC(C)N(C(=O)c1cc(F)ccc1Oc1cncnc1N1CC2(CCN(C(=O)OC(C)(C)C)CC2)C1)C(C)C]

In a 100 mL three-necked dried round bottom flask under nitrogen atmosphere, 2-((4-chloropyrimidin-5-yl)oxy)-5-fluoro-N,N-diisopropylbenzamide (2.4 g, 6.82 mmol) was dissolved in 2-propanol (25 mL). To this solution, TEA (2.85 mL, 20.47 mmol) and tert-butyl 2,7-diazaspiro[3.5]nonane-7-carboxylate hydrochloride (2.151 g, 8.19 mmol) were added at 25° C. under nitrogen atmosphere. The resulting reaction was heated at 80° C. for 13 h, monitoring the reaction progress by TLC (100% EtOAc). After 13 h, the solvent was distilled off and the residue was dissolved in ethyl acetate (50 mL) and washed with water (50 mL). The organic layer was dried over Na$_2$SO$_4$ and filtered, and the filtrate was concentrated on a rotary evaporator under reduced pressure (bath temperature 45° C.) to obtain the crude product. The crude product was purified by column chromatography (Isolera) using 100-200 silica gel and eluting with ethyl acetate in hexane (the required product eluted in 67-70% ethyl acetate in hexane). The fractions containing the required product were concentrated under reduced pressure to obtain tert-butyl 2-(5-(2-(diisopropylcarbamoyl)-4-fluorophenoxy)pyrimidin-4-yl)-2,7-diazaspiro[3.5]nonane-7-carboxylate (2.7 g, 70.0% yield) as a foam: $^1$H NMR (400 MHz, DMSO-d$_6$): δ 8.27 (s, 1H), 7.74 (s, 1H), 7.32-7.14 (m, 2H), 7.13-7.02 (m, 1H), 4.05-3.84 (m, 4H), 3.70-3.67 (m, 1H), 3.55-3.49 (m, 1H), 3.26 (s, 4H), 1.63 (t, J=4.80 Hz, 4H), 1.44 (d, J=6.80 Hz, 3H), 1.40 (s, 9H), 1.34 (d, J=6.80 Hz, 3H), 1.09 (d, J=6.40 Hz, 3H), 1.00 (d, J=6.40 Hz, 3H); LCMS (Method B): Rt=2.25 min, 542.4 (M+H)$^+$.

Step 5. 2-((4-(2,7-diazaspiro[3.5]nonan-2-yl)pyrimidin-5-yl)oxy)-5-fluoro-N,N-diisopropylbenzamide, hydrochloride

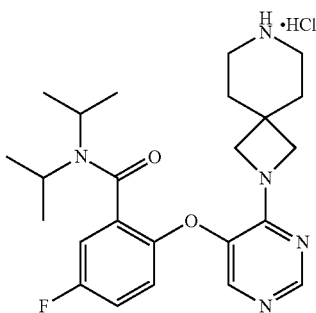 [SMILES: Cl ; CC(C)N(C(=O)c1cc(F)ccc1Oc1cncnc1N1CC2(CCNCC2)C1)C(C)C]

In a 100 mL three-necked dried round bottom flask under nitrogen atmosphere, tert-butyl 2-(5-(2-(diisopropylcarbamoyl)-4-fluorophenoxy)pyrimidin-4-yl)-2,7-diazaspiro[3.5]nonane-7-carboxylate (2.7 g, 4.98 mmol) was dissolved in 2,2,2-triflouroethanol (27 mL). To this solution, TMS-Cl (2.230 mL, 17.45 mmol) was added dropwise at 10° C. and the reaction mixture was stirred for 1 h at 25° C. The reaction progress was monitored by TLC (10% MeOH in DCM). After 1 h, the solvent was distilled off under reduced pressure on a rotary evaporator and the residue was co-distilled with ethyl acetate (2×20 mL). The residue obtained was triturated with hexane and dried under vacuum to obtain 2-((4-(2,7-diazaspiro[3.5]nonan-2-yl)pyrimidin-5-yl)oxy)-5-fluoro-N,N-diisopropylbenzamide hydrochloride (2.5 g, 99.0% yield) as a light brown solid: $^1$H NMR (400 MHz, DMSO-d$_6$): δ 9.05 (br s, 2H), 8.62 (s, 11H), 7.90 (s, 11H), 7.36-7.32 (m, 3H), 4.04-3.84 (m, 4H), 3.71-3.68 (m, 1H), 3.56-3.53 (m, 1H), 3.03 (s, 4H), 1.98 (t, J=9.20 Hz, 4H), 1.43 (d, J=6.40 Hz, 3H), 1.33 (d, J=6.80 Hz, 3H), 1.11 (d, J=6.40 Hz, 3H), 0.95 (d, J=6.40 Hz, 3H); LCMS (Method B): Rt=0.94 min, 442.2 (M+H)$^+$.

Intermediate 4. 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride

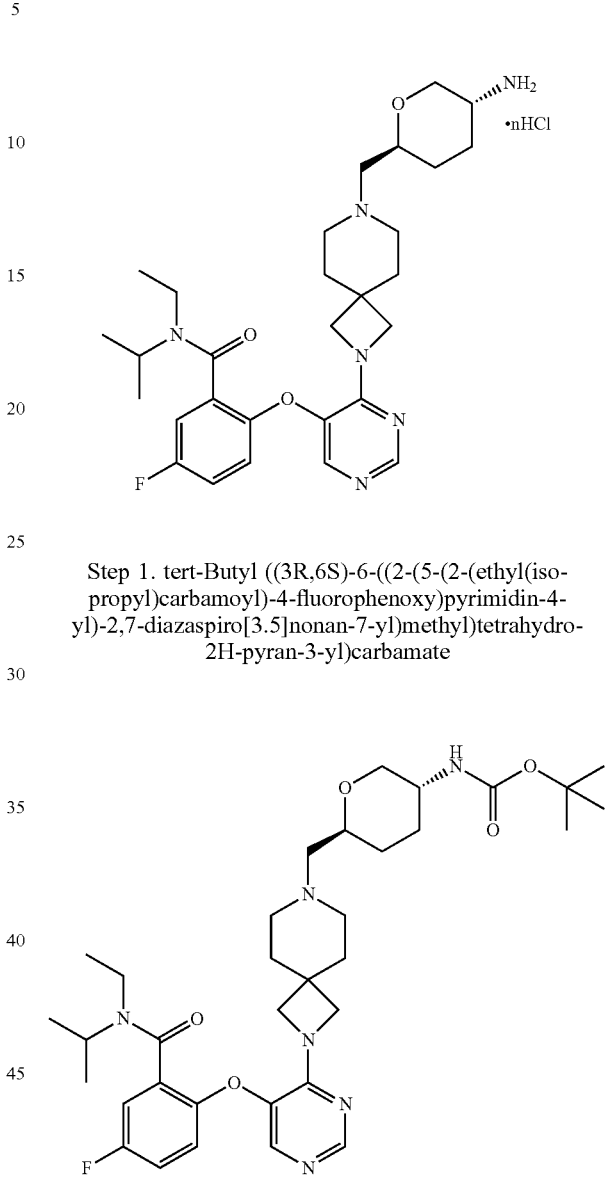

Step 1. tert-Butyl ((3R,6S)-6-((2-(5-(2-(ethyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate In a dried, 250 mL two-necked round bottom flask under nitrogen atmosphere, 2-((4-(2,7-diazaspiro[3.5]nonan-2-yl)pyrimidin-5-yl)oxy)-N-ethyl-5-fluoro-N-isopropylbenzamide, bis-tosylate salt (1.3 g, 1.68 mmol) was dissolved in N-methyl-2-pyrrolidinone (5 mL). To this solution, K$_2$CO$_3$ (0.93 g, 6.74 mmol), KI (0.308 g, 1.853 mmol) and ((2S,5R)-5-((tert-butoxycarbonyl)amino)tetrahydro-2H-pyran-2-yl)methyl 4-methylbenzenesulfonate (0.649 g, 1.68 mmol) were added at 25° C. under nitrogen atmosphere. The resulting reaction was heated at 70° C. for 17 h and the reaction progress was monitored by TLC (5% MeOH in DCM). After completion of the reaction, the reaction mixture was cooled to 25° C. and quenched with water (100 mL). The aqueous layer was extracted with ethyl acetate (2×150 mL). The combined organic layer was dried over anhydrous sodium sulfate and filtered, and the filtrate was concentrated on a rotary evaporator (bath temperature 40°

C.) to afford the crude product (1.2 g). The crude product was purified by column chromatography (Isolera) using 100-200 mesh silica gel and eluting with methanol in DCM (desired product eluted in 4-5% methanol in DCM). The fractions containing the desired product were concentrated under reduced pressure to obtain tert-butyl ((3R,6S)-6-((2-(5-(2-(ethyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (650 mg, 59.7% yield) as a light brown syrup: $^1$H NMR (400 MHz, DMSO-d$_6$): δ 8.27-8.26 (m, 1H), 7.72-7.67 (m, 1H), 7.30-7.23 (m, 2H), 7.05-7.02 (m, 1H), 6.74 (d, J=8.00 Hz, 1H), 3.85-3.73 (m, 6H), 3.43-3.21 (m, 4H), 2.95-2.88 (m, 1H), 2.28-2.18 (m, 6H), 1.84-1.81 (m, 1H), 1.65 (t, J=8.00 Hz, 4H), 1.37 (s, 9H), 1.26-1.16 (m, 4H), 1.01-0.98 (m, 7H); LCMS (Method B): Rt. 1.49 min, 641.4 (M+H)$^+$.

Step 2. 2-((4-(7-(((2S,5R)-5-Aminotetrahydro-2H-pyran-2-yl)methyl)-2,7-diazaspiro[3.5]nonan-2-yl) pyrimidin-5-yl)oxy)-N-ethyl-5-fluoro-N-isopropylbenzamide, hydrochloride

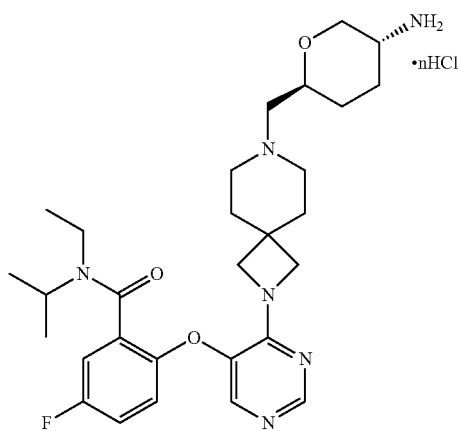 [SMILES: CCN(C(=O)c1cc(F)ccc1Oc1cncnc1N1CC2(CCN(C[C@@H]3CC[C@@H](N)CO3)CC2)C1)C(C)C]

In a dried, 100 mL three-necked round bottom flask under nitrogen atmosphere was added tert-butyl ((3R,6S)-6-((2-(5-(2-(ethyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (300 mg, 0.468 mmol) in trifluoroethanol (2 mL). The resulting mixture was cooled to 10° C. and chlorotrimethylsilane (153 mg, 1.40 mmol) was added. The reaction mixture was then stirred at 26° C. for 2.5 h and the reaction progress was monitored by TLC (10% Methanol in DCM). After complete consumption of the starting material, the reaction was concentrated on a rotary evaporator (bath temperature 40° C.) to afford the crude product. The crude product was stirred with ethyl acetate (10 mL), filtered through a Buchner funnel, and washed with ethyl acetate (5 mL). The solid obtained was dried under vacuum to afford 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (230 mg, 90.0% yield) as an off-white solid: LCMS (Method B): Rt=0.321 min, 541.40 (M+H)$^+$.

Intermediate 5. 2-((4-(7-(((2S,5R)-5-Aminotetrahydro-2H-pyran-2-yl)methyl)-2,7-diazaspiro[3.5] nonan-2-yl)pyrimidin-5-yl)oxy)-5-fluoro-N,N-diisopropylbenzamide, hydrochloride

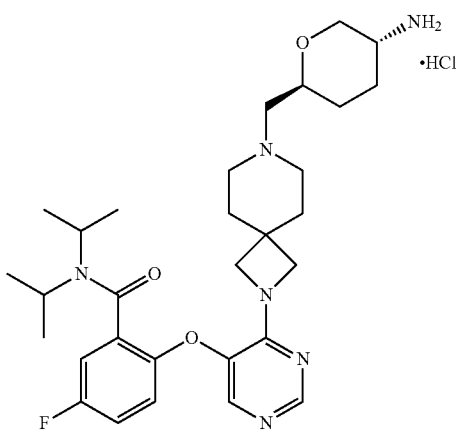 [SMILES: CC(C)N(C(=O)c1cc(F)ccc1Oc1cncnc1N1CC2(CCN(C[C@@H]3CC[C@@H](N)CO3)CC2)C1)C(C)C ; Cl]

Step 1. tert-Butyl ((3R,6S)-6-((2-(5-(2-(diisopropylcarbamoyl)-4-fluorophenoxy)pyrimidin-4-yl)-2,7-diazaspiro[3.5]nonan-7-yl)methyl)tetrahydro-2H-pyran-3-yl)carbamate

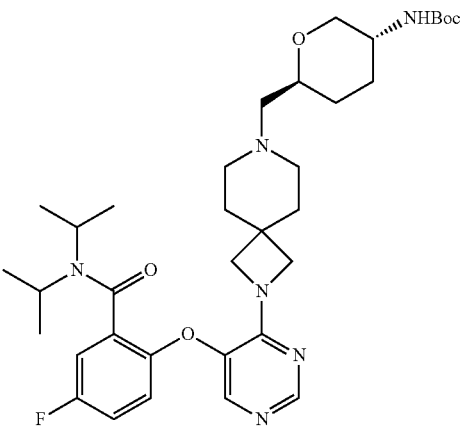 [SMILES: CC(C)N(C(=O)c1cc(F)ccc1Oc1cncnc1N1CC2(CCN(C[C@@H]3CC[C@@H](NC(=O)OC(C)(C)C)CO3)CC2)C1)C(C)C]

In a dried, 100 mL two-necked round bottom flask under nitrogen atmosphere, 2-((4-(2,7-diazaspiro[3.5]nonan-2-yl) pyrimidin-5-yl)oxy)-5-fluoro-N,N-diisopropylbenzamide, hydrochloride (2.5 g, 5.23 mmol) was dissolved in N-methyl-2-pyrrolidinone (5 mL). To this solution, K$_2$CO$_3$ (2.89 g, 20.92 mmol), KI (0.868 g, 5.23 mmol) and ((2S,5R)-5-((tert-butoxycarbonyl)amino)tetrahydro-2H-pyran-2-yl)methyl 4-methylbenzenesulfonate (2.419 g, 6.28 mmol) were added at 25° C. under nitrogen atmosphere. The resulting reaction was heated at 70° C. for 12 h, monitoring the reaction progress by TLC (10% MeOH in DCM). After completion of reaction, the reaction mixture was cooled to room temperature and quenched with water (500 mL). The aqueous layer was extracted with ethyl acetate (2×150 mL). The combined organic layer was dried over anhydrous sodium sulfate and filtered, and the filtrate was concentrated on a rotary evaporator (bath temperature 40° C.) to obtain the crude product. The crude compound was purified by column chromatography (Isolera) using 100-200 silica and eluting with methanol in DCM (the desired product was eluted at 8-9% methanol in DCM). The fractions containing the required product were concentrated under reduced pressure to obtain tert-Butyl ((3R,6S)-6-((2-(5-(2-(diisopropylcarbamoyl)-4-fluorophenoxy)pyrimidin-4-yl)-2,7-diazaspiro[3.5]nonan-7-yl)methyl)tetrahydro-2H-pyran-3-yl)carbamate (3.5 g, 73.6% yield) as a light brown syrup: LCMS (Method A): Rt=2.08 min, 655.8 (M+H)+.

Step 2. 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide, hydrochloride

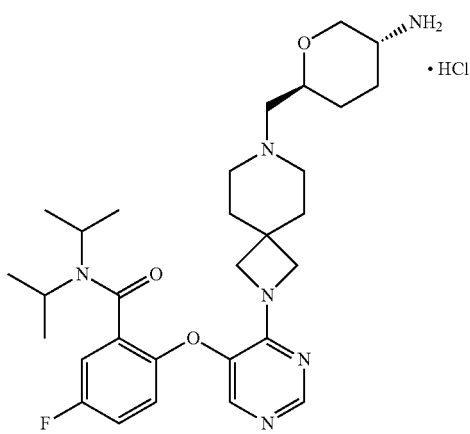 [SMILES: CC(C)N(C(=O)c1cc(F)ccc1Oc1cncnc1N1CC2(CCN(C[C@@H]3CC[C@@H](N)CO3)CC2)C1)C(C)C ; "· HCl"]

In a dried, 100 mL three-necked round bottom flask under nitrogen atmosphere, tert-butyl ((3R,6S)-6-((2-(5-(2-(diisopropylcarbamoyl)-4-fluorophenoxy)pyrimidin-4-yl)-2,7-diazaspiro[3.5]nonan-7-yl)methyl)tetrahydro-2H-pyran-3-yl)carbamate (3.5 g, 5.34 mmol) was dissolved in 2,2,2 trifluoroethanol (35 mL). The resulting solution was cooled to 10° C. and TMS-Cl (2.391 mL, 18.71 mmol) was added to it. The reaction was stirred at 25° C. for 1 h, monitoring the reaction progress by TLC (10% methanol in DCM). After 1 h, the reaction mixture was concentrated on a rotary evaporator (bath temperature 40° C.) to obtain the crude compound. The crude compound was stirred with ethyl acetate (50 mL). The solid obtained was filtered, washed with ethyl acetate (5 mL), and dried under vacuum to obtain 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide, hydrochloride (2.9 g, 75.0% yield) as a light pink solid: LCMS (Method A): Rt=1.76 min, 555.2 (M+H)+.

Intermediate 6. tert-Butyl 2-(5-(4-fluoro-2-(methoxycarbonyl)phenoxy)pyrimidin-4-yl)-2,7-diazaspiro[3.5]nonane-7-carboxylate

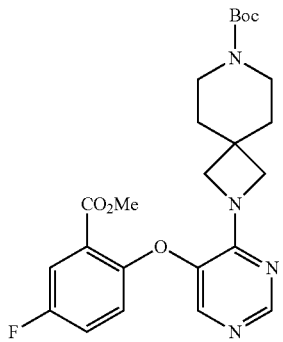 [SMILES: COC(=O)c1cc(F)ccc1Oc1cncnc1N1CC2(CCN(C(=O)OC(C)(C)C)CC2)C1]

Step 1. 5-(2-Bromo-4-fluorophenoxy)pyrimidine

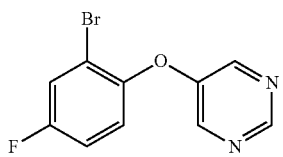

To a mixture of 2-bromo-4-fluorophenol (350 g, 1.83 mol, 1.00 eq) in DMA (2.10 L) was added Cs$_2$CO$_3$ (776 g, 2.38 mol, 1.30 eq) and 5-bromopyrimidine (335 g, 2.11 mol, 1.15 eq) at 25° C. under nitrogen atmosphere. The mixture was stirred at 140° C. for 64 hours under nitrogen. LCMS_IPC showed that most starting material was consumed. The reaction mixture was cooled to 20~25° C. Multiple reactions (1×300 g and 8×350 g) were combined and worked up together. The combined mixture was poured into water (61.4 L) and extracted with MTBE (18.6 L×3). The combined organic layer was washed with sodium hydroxide solution (15.4 L, 2 N), citric acid solution (15.4 L, 0.50 M) and sodium bicarbonate solution (15.4 L, 5%) dried with anhydrous Na$_2$SO$_4$ and concentrated in vacuo. The residue was purified by silica gel chromatography (100-200 mesh silica gel, petroleum ether/ethyl acetate=50/1, 10/1, TLC (petroleum ether/ethyl acetate=8/1, Rf (product=0.3)) to give 5-(2-bromo-4-fluorophenoxy)pyrimidine (2.00 kg, 4.79 mol, 29.5% yield, 64.5% purity) as a yellow oil, and crude 5-(2-bromo-4-fluorophenoxy)pyrimidine (1.10 kg): $^1$H NMR (400 MHz, DMSO-d$_6$) δ 8.98 (d, 1H, J=2.4 Hz), 8.55 (s, 2H), 7.80-7.77 (m, 1H), 7.44-7.36 (m, 2H).

Step 2. Methyl 5-fluoro-2-(pyrimidin-5-yloxy)benzoate

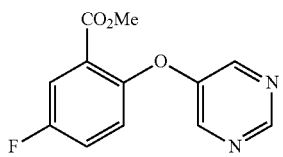

To a solution of 5-(2-bromo-4-fluorophenoxy)pyrimidine (100, 372 mmol, 1.00 eq) in MeOH (700 mL) was added TEA (188 g, 1.86 mol, 259 mL, 5.00 eq) and Pd(dppf)Cl₂·CH₂Cl₂ (9.11 g, 11.2 mmol, 0.03 eq) under N₂. The suspension was degassed under vacuum and purged with CO three times. The mixture was stirred under CO (40 psi) at 80° C. for 48 hours. LCMS_IPC showed that the starting material was consumed completely. The reaction mixture was cooled to 20~25° C. Fifteen reactions (15×100 g) were combined and filtered over a Celite® pad to remove the palladium catalyst. The Celite® pad was washed with methanol (200 mL, 200 mL). The filtrate was concentrated under reduced pressure. The residue was purified by silica gel chromatography (100-200 mesh silica gel, petroleum ether/ethyl acetate=20/1 to 8/1, TLC (petroleum ether/ethyl acetate=3/1, Rf (product)=0.3)) to give methyl 5-fluoro-2-(pyrimidin-5-yloxy)benzoate (427 g, 1.54 mol, 43.0% yield, 89.7% purity) as a light yellow solid, and crude methyl 5-fluoro-2-(pyrimidin-5-yloxy)benzoate (500 g, 37.3% yield, 66.5% purity): ¹H NMR (400 MHz CDCl₃) δ 8.96 (s, 1H), 8.39 (s, 2H), 7.73 (dd, J=3.6, 8.8 Hz, 1H), 7.33-7.30 (m, 1H), 7.13 (dd, J=4.4, 8.8 Hz, 1H), 3.82 (s, 3H).

Step 3.
5-(4-Fluoro-2-(methoxycarbonyl)phenoxy)pyrimidine 1-oxide

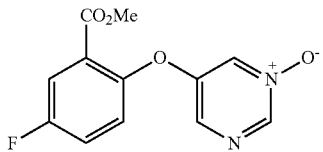

To a solution of methyl 5-fluoro-2-(pyrimidin-5-yloxy)benzoate (190 g, 765 mmol, 1.00 eq) in THF (1.90 L) was added UHP (144 g, 1.53 mol, 2.00 eq) and TFAA (322 g, 1.53 mol, 213 mL, 2.00 eq) under N₂ at 0–10° C. The mixture was stirred at 0~10° C. for 1 hour. LCMS_IPC showed that the starting material was consumed completely. The reaction was quenched by adding 5% NaHCO₃ (950 mL), maintaining temperature below 10° C. Two reactions (2×190 g) were combined. The product was extracted with DCM (2×1.90 L). Organic layer was washed with 5% NaHCO₃ (2×1.90 L). The organic layer was treated with 5% NaHCO₃ (2.30 L) and 1M Na₂S₂O₃ solution (1.90 L) and stirred for 15 min at 20° C. The organic layer was separated, dried with anhydrous Na₂SO₄, filtered, and concentrated in vacuo at 45° C. to give the residue. Three reactions (1×200 g and 2×190 g) were combined. The crude product was triturated with n-heptane (8.0 L)) and stirred at 25° C. for 30 min. The mixture was filtered, the filter cake was washed with n-heptane (800 mL) and dried under vacuum to give 5-(4-fluoro-2-(methoxycarbonyl)phenoxy)pyrimidine 1-oxide (552 g, 1.89 mol, 80.7% yield, 90.3% purity) as a white solid: ¹H NMR (400 MHz DMSO-d₆) δ 8.86 (s, 1H), 8.44 (t, J=1.60 Hz, 1H), 8.01 (d, J=2.40 Hz, 1H), 7.74 (dd, J=3.6, 9.2 Hz, 1H), 7.62-7.61 (m, 1H), 7.52-7.50 (m, 1H), 3.76 (s, 3H).

Step 4. Methyl 2-((4-chloropyrimidin-5-yl)oxy)-5-fluorobenzoate

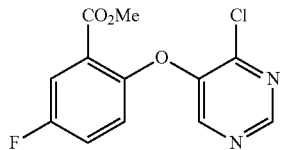 [SMILES: COC(=O)c1cc(F)ccc1Oc1cncnc1Cl]

To a solution of 5-(4-fluoro-2-(methoxycarbonyl)phenoxy)pyrimidine 1-oxide (268 g, 1.01 mol, 1.00 eq) in EtOAc (2.70 L) was added DIPEA (655 g, 5.07 mol, 883 mL, 5.00 eq) under N₂ at −5° C. POCl₃ (187 g, 1.22 mol, 113 mL, 1.2 eq) was added the reaction mixture under N₂ at 0° C. Reaction mixture was stirred at 20~25° C. for 1.5 hours under N₂. LCMS_IPC showed that the starting material was consumed completely. The reaction mixture was concentrated in vacuo at 45° C. give the crude product (834 g). Multiple reactions (54.0 g crude product from 2×9.5 g; 300 g crude product from 1×100 g; 12.0 g crude product from 1×4.00 g; 1.30 kg crude product from 2×224 g; 834 g crude product from 1×268 g) were combined and purified together. The crude product (2.5 kg) was purified through a silica pad and the silica pad was eluted by a pre-mixed solution (petroleum ether/ethyl acetate=2/1) to give the product as yellow solid (575 g). The crude product (575 g) was triturated with n-heptane/ethyl acetate (2/1, 3 V) and stirred at 25° C. for 12 hours to give a yellow suspension. The mixture was filtered, the filter cake was washed with n-heptane/ethyl acetate (2/1, 0.2 V) and dried under vacuum to give methyl 2-((4-chloropyrimidin-5-yl)oxy)-5-fluorobenzoate (415 g, 1.45 mol, 45.7% yield, 98.8% purity) as a white solid: ¹H NMR (400 MHz CDCl₃) δ 8.72 (s, 1H), 8.01 (s, 1H), 7.76 (dd, J=3.20, 8.40 Hz, 1H), 7.34-7.31 (m, 1H), 7.15-7.11 (m, 1H), 3.82 (s, 3H).

Step 5. tert-Butyl 2-(5-(4-fluoro-2-(methoxycarbonyl)phenoxy)pyrimidin-4-yl)-2,7-diazaspiro[3.5]nonane-7-carboxylate

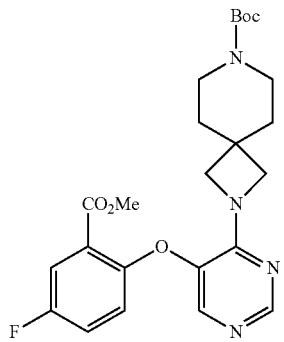 [SMILES: COC(=O)c1cc(F)ccc1Oc1cncnc1N1CC2(CCN(C(=O)OC(C)(C)C)CC2)C1]

To a mixture of methyl 2-((4-chloropyrimidin-5-yl)oxy)-5-fluorobenzoate (80.0 g, 283 mmol, 1.00 eq) in IPA (800 mL) was added TEA (85.9 g, 849 mmol, 118 mL, 3.00 eq) and tert-butyl 2,7-diazaspiro[3.5]nonane-7-carboxylate (89.2 g, 340 mmol, 1.20 eq, HCl) at 25° C. under nitrogen atmosphere. The mixture was stirred at 80° C. for 3 hours under nitrogen. HPLC_IPC and LCMS_IPC showed that the starting material was consumed completely. The reaction mixture was cooled to 25° C. and concentrated in vacuo at 50° C. Multiple reactions (10.0 g crude product from 1×5.00 g; 80.0 g crude product from 2×20.0 g; crude product from 2×80.0 g) were combined. The crude product (410 g) was triturated with n-heptane (600 mL) and stirred at 25° C. for 12 hour. The mixture was filtered, the filter cake was washed with n-heptane (60.0 mL) and dried under vacuum give crude product (330 g). The crude product (330 g) was triturated with water (3.30 L) and stirred at 25° C. for 12 hour to remove the residual TEA.HCl. The mixture was filtered, the filter cake was washed with water (300 mL) and dried under vacuum give crude product (300 g). The crude product (300 g) was dissolved in dichloromethane (300 mL), dried over anhydrous $Na_2SO_4$, filtered and concentrated in vacuo to give tert-butyl 2-(5-(4-fluoro-2-(methoxycarbonyl) phenoxy)pyrimidin-4-yl)-2,7-diazaspiro[3.5]nonane-7-carboxylate (265 g, 558 mmol, 76.9% yield, 99.5% purity) as a white solid: $^1$H NMR (400 MHz DMSO-$d_6$) δ 8.27 (s, 1H), 7.67-7.64 (m, 2H), 7.49-7.46 (m, 1H), 7.14-7.11 (m, 1H), 3.91 (s, 4H), 3.79 (s, 3H), 3.26 (s, 4H), 1.66 (t, J=5.20 Hz, 4H), 1.38 (s, 9H).

Intermediate 7. (2-((4-(7-(((2S,5R)-5-Aminotetra-hydro-2H-pyran-2-yl)methyl)-2,7-diazaspiro[3.5]nonan-2-yl)pyrimidin-5-yl)oxy)-5-fluorophenyl)((3S,5R)-3,5-dimethylmorpholino)methanone, hydrochloride In a 250 mL three-necked reaction flask was added tert-butyl 2-(5-(4-fluoro-2-(methoxycarbonyl)phenoxy)pyrimidin-4-yl)-2,7-diazaspiro[3.5]nonane-7-carboxylate (20 g, 42.3 mmol) in MeOH (50 mL) and THF (50 mL). To this reaction mixture was added a solution of LiOH (1.216 g, 50.8 mmol) in water (25 mL) at 25° C. and the reaction mixture was stirred at 25° C. for 18 h. The reaction progress was monitored by TLC (20% MeOH in DCM). After complete consumption of the ester, the reaction was concentrated to dryness on a rotary evaporator. The residue was azeotroped with toluene (3×25 mL) to remove traces of water, and dried under vacuum to obtain the desired lithium 2-((4-(7-(tert-butoxycarbonyl)-2,7-diazaspiro[3.5]nonan-2-yl)pyrimidin-5-yl)oxy)-5-fluorobenzoate (19.5 g, 99% yield) as a white solid: $^1$H NMR (400 MHz, DMSO-$d_6$): δ 8.12 (s, 1H), 7.36 (s, 1H), 7.17 (dd, J=3.20, 9.20 Hz, 1H), 7.00-6.97 (m, 1H), 6.93-6.89 (m, 1H), 4.01-4.00 (m, 4H), 3.29 (br s, 4H), 1.67 (t, J=5.60 Hz, 4H), 1.40 (s, 9H); LCMS (Method B): Rt=1.4 min, 459.2 (M+H)$^+$.

Step 2. tert-Butyl 2-(5-(2-((3S,5R)-3,5-dimethyl-morpholine-4-carbonyl)-4-fluorophenoxy)pyrimidin-4-yl)-2, 7-diazaspiro[3.5]nonane-7-carboxylate

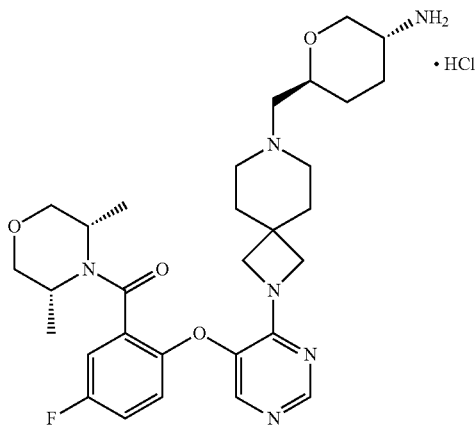 [SMILES: C[C@@H]1COC[C@H](C)N1C(=O)c1cc(F)ccc1Oc1cncnc1N1CC2(CCN(C[C@@H]3CC[C@@H](N)CO3)CC2)C1 ; "· HCl"]

Step 1. Lithium 2-((4-(7-(tert-butoxycarbonyl)-2,7-diazaspiro[3.5]nonan-2-yl)pyrimidin-5-yl)oxy)-5-fluorobenzoate

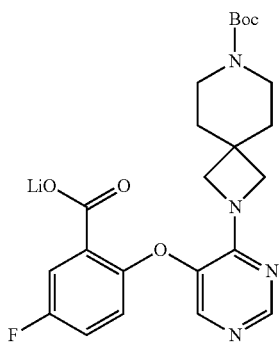

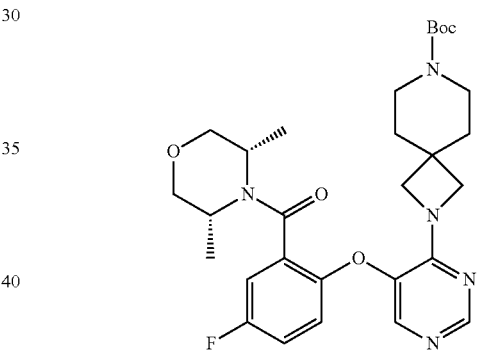

In a 50 mL three-necked reaction flask under nitrogen atmosphere was added lithium 2-((4-(7-(tert-butoxycarbonyl)-2,7-diazaspiro[3.5]nonan-2-yl)pyrimidin-5-yl)oxy)-5-fluorobenzoate (2.5 g, 5.38 mmol) in DMF (10 mL). To the resulting solution, HATU (3.07 g, 8.07 mmol) and DIPEA (3.13 g, 24.22 mmol) were added. After that (3S,5R)-3,5-dimethylmorpholine hydrochloride (1.224 g, 8.07 mmol) was added at 25° C. under nitrogen atmosphere and the reaction mixture stirred at 25° C. for 18 h. The reaction progress was monitored by TLC (5% MeOH in DCM). After 18 h, the reaction was quenched with water (200 mL) and extracted with EtOAc (3×150 mL). The combined organic layer was washed with water (3×100 mL), brine (100 mL), dried over anhydrous sodium sulfate, and filtered. The filtrate was concentrated on a rotary evaporator under reduced pressure to obtain tert-butyl 2-(5-(2-((3S,5R)-3,5-dimethylmorpholine-4-carbonyl)-4-fluorophenoxy)pyrimidin-4-yl)-2,7-diazaspiro[3.5]nonane-7-carboxylate (2.9 g, 70.8% yield) as a yellow gummy solid: LCMS (Method B): Rt=1.48 min, 556.2 (M+H)$^+$.

Step 3. (2-((4-(2,7-Diazaspiro[3.5]nonan-2-yl)pyrimidin-5-yl)oxy)-5-fluorophenyl)((3S,5R)-3,5-dimethylmorpholino)methanone, hydrochloride

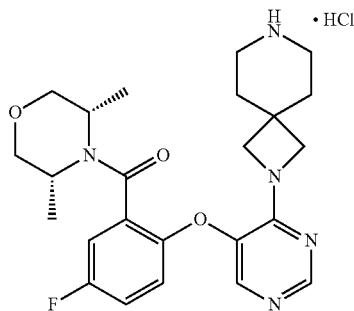 [SMILES: "· HCl" ; C[C@@H]1COC[C@H](C)N1C(=O)c1cc(F)ccc1Oc1cncnc1N1CC2(CCNCC2)C1]

In a 50 mL three-necked round bottom flask under nitrogen atmosphere, tert-butyl 2-(5-(2-((3S,5R)-3,5-dimethylmorpholine-4-carbonyl)-4-fluorophenoxy)pyrimidin-4-yl)-2,7-diazaspiro[3.5]nonane-7-carboxylate (2.9 g, 5.22 mmol) was added to dioxane (10 mL). To the resulting solution, 4M HCl in dioxane (7.83 mL, 31.3 mmol) was added at 25° C. The reaction mixture was then stirred at 25° C. for 2 h, monitoring the reaction progress by TLC (10% MeOH in DCM). After 2 h, the reaction was concentrated to dryness on a rotary evaporator to obtain the crude residue. The crude residue was triturated with ethyl acetate. The supernatant layer was decanted and the remaining solid was dried under vacuum to obtain (2-((4-(2,7-diazaspiro[3.5]nonan-2-yl)pyrimidin-5-yl)oxy)-5-fluorophenyl)((3S,5R)-3,5-dimethylmorpholino)methanone, hydrochloride (2.5 g, 64% yield) as a yellow solid: LCMS (Method A): Rt=1.23 min, 456.2 (M+H)⁺.

Step 4. tert-Butyl ((3S,6R)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)carbamate

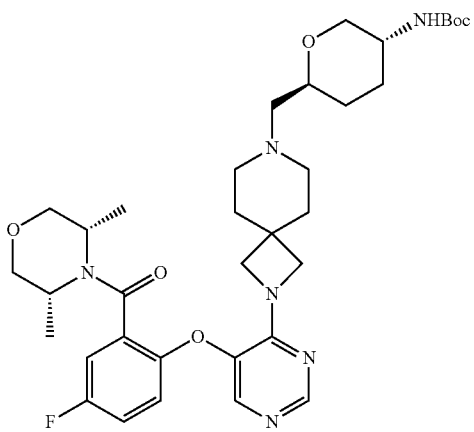 [SMILES: C[C@@H]1COC[C@H](C)N1C(=O)c1cc(F)ccc1Oc1cncnc1N1CC2(CCN(C[C@@H]3CC[C@@H](NC(=O)OC(C)(C)C)CO3)CC2)C1]

In a dried, 50 mL three-necked round bottom flask under nitrogen atmosphere, (2-((4-(2,7-diazaspiro[3.5]nonan-2-yl)pyrimidin-5-yl)oxy)-5-fluorophenyl)((3S,5R)-3,5-dimethylmorpholino)methanone, hydrochloride (2.5 g, 5.08 mmol), K₂CO₃ (2.81 g, 20.33 mmol) and KI (0.844 g, 5.08 mmol) were suspended in NMP (10 mL). To this suspension was added ((2S,5R)-5-((tert-butoxycarbonyl)amino)tetrahydro-2H-pyran-2-yl)methyl 4-methylbenzenesulfonate (1.959 g, 5.08 mmol) at 25° C. The reaction mixture was then stirred at 75° C. for 18 h, monitoring the reaction progress by TLC (10% MeOH in DCM). After 18 h, the reaction was quenched with water (200 mL) and extracted with EtOAc (3×150 mL). The combined organic layer was washed with water (3×100 mL) and brine (100 mL). The organic layer was dried over anhydrous sodium sulfate and filtered, and the filtrate was concentrated on a rotary evaporator under reduced pressure to obtain the crude product. The crude product was purified by flash column chromatography (Isolera) eluting with methanol in DCM (the desired product eluted in 0 to 6%). The fractions containing the desired product were concentrated under reduced pressure to obtain tert-butyl ((3S,6R)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)carbamate (2.0 g, 58.82% yield) as a yellow gummy solid: LCMS (Method B): Rt=1.14 min, 669.4 (M+H)⁺.

Step 5. (2-((4-(7-(((2S,5R)-5-Aminotetrahydro-2H-pyran-2-yl)methyl)-2,7-diazaspiro[3.5]nonan-2-yl)pyrimidin-5-yl)oxy)-5-fluorophenyl)((3S,5R)-3,5-dimethylmorpholino)methanone, hydrochloride

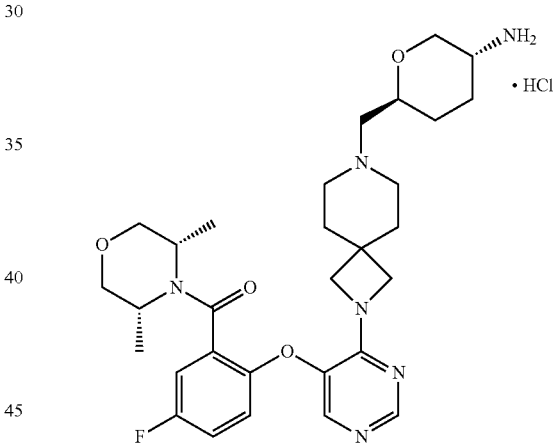

In a 50 mL three necked round bottom flask under nitrogen atmosphere, tert-butyl ((3S,6R)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)carbamate (2.5 g, 3.74 mmol) was dissolved in 2,2,2-trifluoroethanol (25 mL). To this solution was added TMS-Cl (1.911 mL, 14.95 mmol) at 10° C. The reaction was stirred at 25° C. for 2 h, monitoring the reaction progress by TLC (10% MeOH in DCM). After 2 h, the reaction was concentrated to dryness under reduced pressure on a rotary evaporator to obtain the crude product. The crude residue was triturated with ethyl acetate. The supernatant layer was decanted and remaining solid was dried under vacuum to obtain (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3S,5R)-3,5-dimethylmorpholino)methanone, hydrochloride (2.5 g, 92% yield) as a yellow solid: LCMS (Method A): Rt=1.28 min, 569.2 (M+H)⁺.

Intermediate 8. (2-((4-(7-(((2S,5R)-5-Aminotetrahydro-2H-pyran-2-yl)methyl)-2,7-diazaspiro[3.5]nonan-2-yl)pyrimidin-5-yl)oxy)-5-fluorophenyl)((3R,5R)-3,5-dimethylmorpholino)methanone, hydrochloride

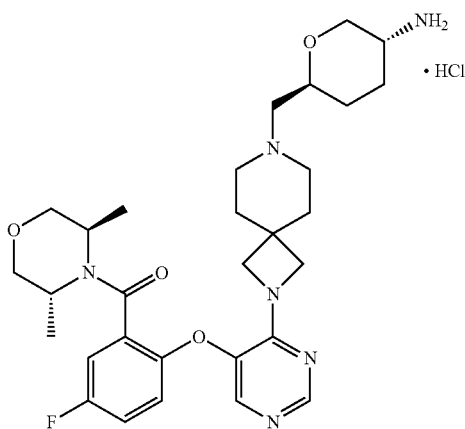 [SMILES: C[C@@H]1COC[C@@H](C)N1C(=O)c1cc(F)ccc1Oc1cncnc1N1CC2(CCN(C[C@@H]3CC[C@@H](N)CO3)CC2)C1 ; "· HCl"]

Step 1. tert-Butyl 2-(5-(2-((3R,5R)-3,5-dimethylmorpholine-4-carbonyl)-4-fluorophenoxy)pyrimidin-4-yl)-2,7-diazaspiro[3.5]nonane-7-carboxylate

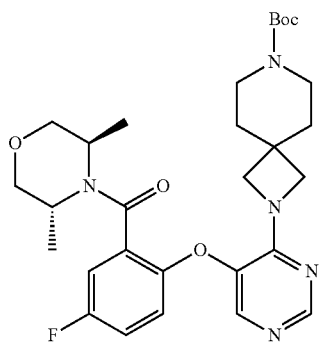 [SMILES: C[C@@H]1COC[C@@H](C)N1C(=O)c1cc(F)ccc1Oc1cncnc1N1CC2(CCN(C(=O)OC(C)(C)C)CC2)C1]

In a dried, 100 mL three-necked round bottom flask under nitrogen atmosphere, lithium 2-((4-(7-(tert-butoxycarbonyl)-2,7-diazaspiro[3.5]nonan-2-yl)pyrimidin-5-yl)oxy)-5-fluorobenzoate (4 g, 8.61 mmol), HATU (4.91 g, 12.92 mmol) and DIPEA (5.01 g, 38.8 mmol) were added to DMF (40 mL). To this solution, (3R,5R)-3,5-dimethylmorpholine hydrochloride (1.959 g, 12.92 mmol) was added at 25° C. and the reaction mixture stirred at 25° C. for 18 h. The reaction progress was monitored by TLC (10% MeOH in DCM). After 18 h, the reaction was quenched with water (200 mL) and extracted with EtOAc (3×150 mL). The combined organic layer was washed with water (3×100 mL) and brine (100 mL). The organic layer was dried over anhydrous sodium sulfate and filtered, and the filtrate was concentrated on a rotary evaporator under reduced pressure to obtain tert-butyl 2-(5-(2-((3R,5R)-3,5-dimethylmorpholine-4-carbonyl)-4-fluorophenoxy)pyrimidin-4-yl)-2,7-diazaspiro[3.5]nonane-7-carboxylate (4.4 g, 74.5% yield) as a yellow gummy solid: $^1$H NMR (400 MHz, CDCl$_3$) δ 8.29 (s, 1H), 7.78-7.70 (m, 1H), 7.38-7.27 (m, 2H), 7.07-7.04 (m, 1H), 4.04-3.89 (m, 8H), 3.30 (br s, 4H), 2.90-2.74 (m, 2H), 1.65 (t, J=5.20 Hz, 4H), 1.39 (s, 9H), 1.28-1.16 (m, 6H); LCMS (Method B): Rt=1.59 min, 556.3 (M+H)$^+$.

Step 2. (2-((4-(2,7-Diazaspiro[3.5]nonan-2-yl)pyrimidin-5-yl)oxy)-5-fluorophenyl)((3R,5R)-3,5-dimethylmorpholino)methanone,_hydrochloride

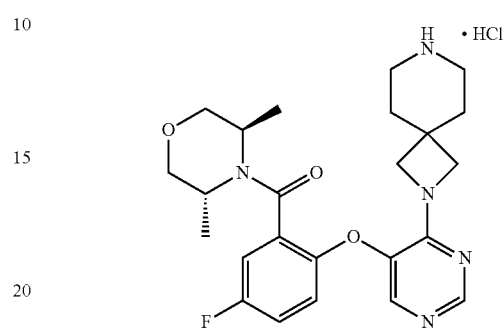

In a dried, 100 mL three-necked round bottom flask under nitrogen atmosphere, tert-butyl 2-(5-(2-((3R,5R)-3,5-dimethylmorpholine-4-carbonyl)-4-fluorophenoxy)pyrimidin-4-yl)-2,7-diazaspiro[3.5]nonane-7-carboxylate (4.4 g, 7.92 mmol) was dissolved in dioxane (20 mL). To this solution, hydrochloric acid (4M in dioxane, 19.80 mL, 79 mmol) was added slowly at 25° C. The reaction mixture was then stirred at 25° C. for 1 h, monitoring the reaction progress by TLC (10% MeOH in DCM). After 1 h, the reaction was concentrated to dryness on a rotary evaporator. The resulting gummy solid was triturated with ethyl acetate twice. The supernatant layer was decanted and the solid obtained was dried under reduced pressure to afford (2-((4-(2,7-diazaspiro[3.5]nonan-2-yl)pyrimidin-5-yl)oxy)-5-fluorophenyl)((3R,5R)-3,5-dimethylmorpholino)methanone, hydrochloride (3.8 g, 73.6% yield) as yellow solid: LCMS (Method A): Rt=1.17 min, 456.2 (M+H)$^+$ Step 3. tert-Butyl ((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)carbamate

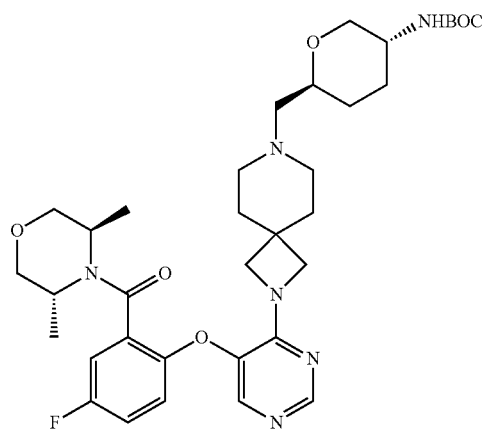

In a 50 mL three-necked round bottom flask under nitrogen atmosphere, (2-((4-(2,7-diazaspiro[3.5]nonan-2-yl)pyrimidin-5-yl)oxy)-5-fluorophenyl)((3R,5R)-3,5-dimethylmorpholino)methanone, hydrochloride (3.8 g, 7.72 mmol), $K_2CO_3$ (4.27 g, 30.9 mmol) and KI (1.282 g, 7.72 mmol) were suspended in NMP (25 mL). To this suspension was added ((2S,5R)-5-((tert-butoxycarbonyl)amino)tetrahydro-2H-pyran-2-yl)methyl 4-methylbenzenesulfonate (2.98 g, 7.72 mmol) at 25° C. The reaction mixture was then stirred at 75° C. for 18 h, monitoring the reaction progress by TLC (10% MeOH in DCM). After 18 h, the reaction was quenched with water (250 mL) and extracted with EtOAc (3×150 mL). The combined organic layer was washed with water (3×150 mL), dried over anhydrous sodium sulfate, and filtered, and the filtrate was concentrated under reduced pressure on a rotary evaporator to obtain the crude product. The crude product was purified by flash column chromatography (Isolera) using methanol in DCM (the desired product eluted in 0 to 6% MeOH in DCM). The fractions containing the required product were concentrated under reduced pressure to obtain tert-butyl ((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)carbamate (4.1 g, 66% yield) as a yellow gummy solid: LCMS (Method B): Rt=1.15 min, 669.4 (M+1)⁺.

Step 4. (2-((4-(7-(((2S,5R)-5-Aminotetrahydro-2H-pyran-2-yl)methyl)-2,7-diazaspiro[3.5]nonan-2-yl)pyrimidin-5-yl)oxy)-5-fluorophenyl)((3R,5R)-3,5-dimethylmorpholino)methanone, hydrochloride

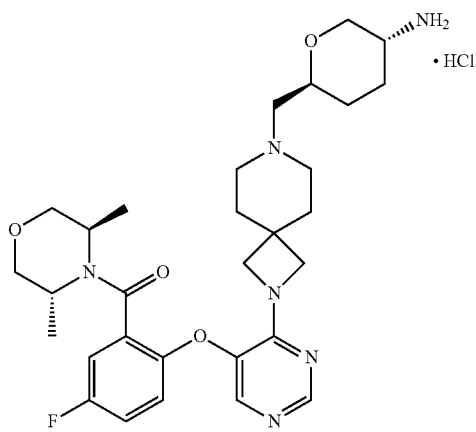 [SMILES: C[C@@H]1COC[C@@H](C)N1C(=O)c1cc(F)ccc1Oc1cncnc1N1CC2(CCN(C[C@@H]3CC[C@@H](N)CO3)CC2)C1 ; "· HCl"]

In a 25 mL three-necked round bottom flask, tert-butyl ((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)carbamate (4 g, 5.98 mmol) was dissolved in 2,2,2-trifluoroethanol (30 mL). To this solution, TMS-Cl (7.64 mL, 59.8 mmol) was added slowly at 25° C. and the reaction mixture was stirred at 25° C. for 1 h. The reaction progress was monitored by TLC (10% MeOH in DCM). After 1 h, the reaction was concentrated to dryness on a rotary evaporator under reduced pressure to obtain the crude residue. The crude residue was triturated with ethyl acetate. The supernatant layer was decanted and the remaining solid dried under vacuum to afford (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3R,5R)-3,5-dimethylmorpholino)methanone, hydrochloride (3.1 g, 75% yield) as a yellow solid: LCMS (Method A): Rt=1.28 min, 569.3 (M+H)⁺.

Intermediate 9. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluorobenzoic acid

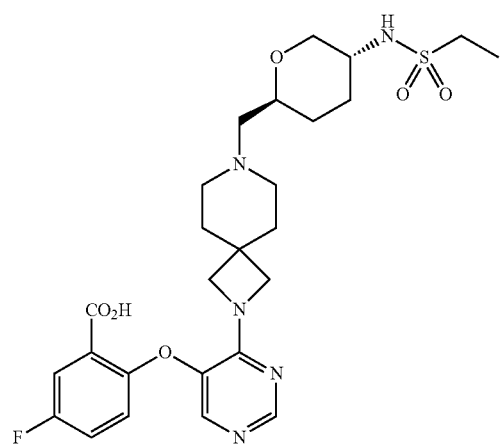 [SMILES: CCS(=O)(=O)N[C@@H]1CC[C@@H](CN2CCC3(CC2)CN(c2ncncc2Oc2ccc(F)cc2C(=O)O)C3)OC1]

Step 1. Methyl 2-((4-(2,7-diazaspiro[3.5]nonan-2-yl)pyrimidin-5-yl)oxy)-5-fluorobenzoate, hydrochloride

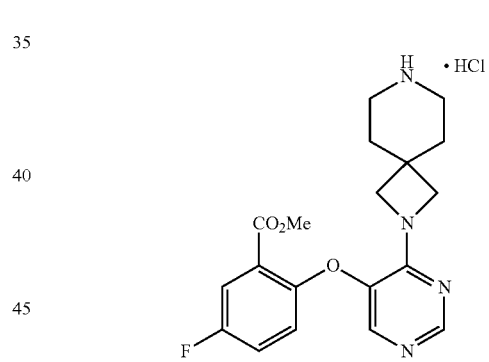

In a dried, 500 mL three-necked round bottom flask under nitrogen atmosphere was charged tert-butyl 2-(5-(4-fluoro-2-(methoxycarbonyl)phenoxy)pyrimidin-4-yl)-2,7-diazaspiro[3.5]nonane-7-carboxylate (25 g, 52.9 mmol) in 2,2,2-triflouroethanol (200 mL). To this solution, TMS-Cl (20.29 mL, 159 mmol) was added dropwise at 10° C. The reaction mixture was then stirred for 1 h at 25° C., monitoring the progress by TLC (10% MeOH in DCM). After 1 h, the solvent was distilled off under reduced pressure on a rotary evaporator and the residue was co-distilled with ethyl acetate (2×100 mL). The residue obtained was triturated with hexane to afford methyl 2-((4-(2,7-diazaspiro[3.5] nonan-2-yl)pyrimidin-5-yl)oxy)-5-fluorobenzoate, hydrochloride (20.1 g, 93% yield) as an off-white solid: ¹H NMR (400 MHz, DMSO-$d_6$): δ 9.17 (br s, 2H), 8.62 (s, 1H), 7.78-7.75 (m, 1H), 7.70 (s, 1H), 7.66-7.62 (m, 1H), 7.50-7.47 (m, 1H), 4.29-3.84 (m, 4H), 3.81 (s, 3H), 3.04 (s, 4H), 2.02 (t, J=5.20 Hz, 4H); LCMS (Method A): Rt=1.33 min, 373.1 (M+H)⁺.

Step 2. Methyl 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate

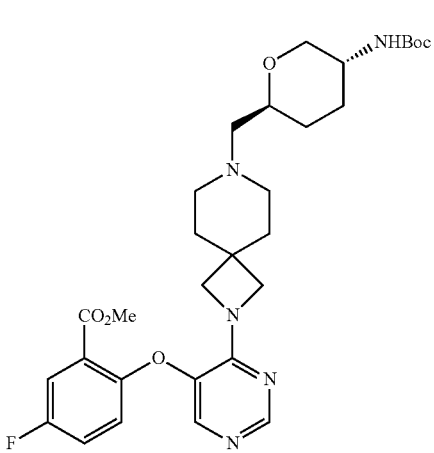 [SMILES: COC(=O)c1cc(F)ccc1Oc1cncnc1N1CC2(CCN(C[C@@H]3CC[C@@H](NC(=O)OC(C)(C)C)CO3)CC2)C1]

In a dried, 250 mL two-necked round bottom flask under nitrogen atmosphere, methyl 2-((4-(2,7-diazaspiro[3.5]nonan-2-yl)pyrimidin-5-yl)oxy)-5-fluorobenzoate, hydrochloride (5 g, 12.23 mmol) was dissolved in N-methyl-2-pyrrolidinone (50 mL). To this solution, K₂CO₃ (6.76 g, 48.9 mmol), KI (2.233 g, 13.45 mmol) and ((2S,5R)-5-((tert-butoxycarbonyl)amino)tetrahydro-2H-pyran-2-yl)methyl 4-methylbenzenesulfonate (5.66 g, 14.68 mmol) were added at 25° C. under nitrogen atmosphere. The resulting reaction was heated at 70° C. for 12 h, monitoring the reaction progress by TLC (10% MeOH in DCM). After 12 h, the reaction mixture was cooled to room temperature, quenched with water (200 mL), and extracted with ethyl acetate (2×150 mL). The combined organic layer was dried over anhydrous sodium sulfate and filtered, and the filtrate was concentrated on a rotary evaporator (bath temperature 40° C.) to obtain the crude product. The crude product was purified by column chromatography (Isolera) using 100-200 silica gel eluting with methanol in DCM (desired product was eluted at 4% methanol in DCM). The fractions containing the desired product were concentrated under reduced pressure to obtain methyl 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (5 g, 59.1% yield) as a light brown solid: ¹H NMR (400 MHz, DMSO-d₆): δ 8.28 (s, 1H), 7.67-7.64 (m, 2H), 7.50-7.45 (m, 1H), 7.12-7.09 (m, 1H), 6.74 (d, J=7.60 Hz, 1H), 3.86-3.73 (m, 8H), 3.31-3.28 (m, 2H), 2.93-2.88 (m, 1H), 2.33-2.27 (m, 3H), 2.20-2.16 (m, 3H), 1.87-1.81 (m, 1H), 1.68-1.64 (m, 5H), 1.37 (s, 9H), 1.33-1.22 (m, 2H); LCMS (Method B): Rt=1.10 min, 586.4 (M+H)⁺.

Step 3. Methyl 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorobenzoate, hydrochloride

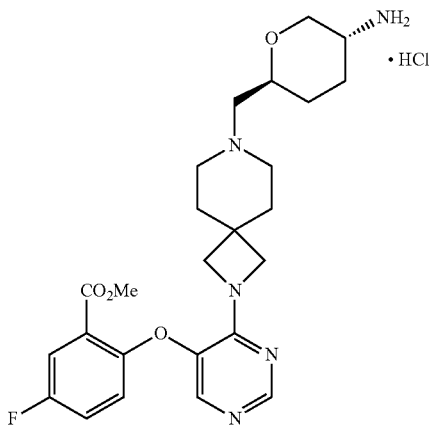 [SMILES: COC(=O)c1cc(F)ccc1Oc1cncnc1N1CC2(CCN(C[C@@H]3CC[C@@H](N)CO3)CC2)C1 ; "· HCl"]

In a dried, 500 mL three-necked round bottom flask under nitrogen atmosphere was charged methyl 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (5 g, 8.54 mmol) in 2,2,2-triflouro ethanol (50 mL). To this solution, TMS-CI (3.27 mL, 25.6 mmol) was added dropwise at 10° C. The reaction was then stirred for 1 h at 25° C., monitoring the progress by TLC (10% MeOH in DCM). After 1 h, the solvent was distilled off under reduced pressure on a rotary evaporator and the residue was co-distilled with ethyl acetate (2×50 mL). The residue obtained was triturated with hexane and dried to afford methyl 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorobenzoate, hydrochloride (4.2 g, 76% yield) as an off-white solid: LCMS (Method A): Rt=1.290 min, 486.2 (M+H)⁺.

Step 4. Methyl 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoate

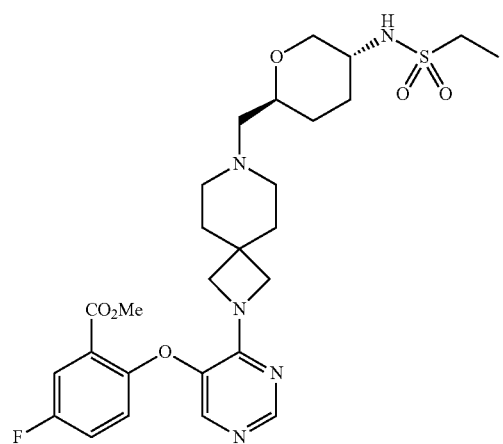 [SMILES: CCS(=O)(=O)N[C@@H]1CC[C@@H](CN2CCC3(CC2)CN(c2ncncc2Oc2ccc(F)cc2C(=O)OC)C3)OC1]

In a dried, 25 mL three-necked round bottom flask under nitrogen atmosphere, methyl 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorobenzoate, hydrochloride (4.2 g, 8.65 mmol) was dissolved in $CH_2Cl_2$ (50 mL) and cooled to 0° C. To this solution, TEA (12.16 mL, 86 mmol) was added and the reaction was stirred at 0° C. for 30 min. After that ethanesulfonyl chloride (4.12 mL, 43.2 mmol) was added slowly and the reaction was stirred at 25° C. for 16 h, monitoring the reaction progress by TLC (10% Methanol in DCM). After 16 h, the reaction was quenched with water (10 mL) and extracted with DCM (2×15 mL). The organic layer was washed with aq. $NaHCO_3$ (2×10 mL) and brine (2×10 mL). The combined organic layer was dried over anhydrous sodium sulfate and filtered, and the filtrate was concentrated on a rotary evaporator (bath temperature 40° C.) to obtain the crude product. The crude product was purified by column chromatography (Isolera) using 100-200 silica and eluting with methanol in DCM (desired product was eluted at 5% methanol in DCM). The fractions containing the pure product were concentrated under reduced pressure to obtain methyl 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoate (3.8 g, 64.6% yield) as a yellow solid: $^1$H NMR (400 MHz, DMSO-$d_6$): δ 8.28 (s, 1H), 7.67-7.64 (m, 2H), 7.49-7.47 (m, 1H), 7.11-7.09 (m, 2H), 3.86-3.80 (m, 7H), 3.09-2.98 (m, 6H), 2.29-2.21 (m, 5H), 1.95-1.93 (m, 1H), 1.74-1.69 (m, 5H), 1.43-1.24 (m, 3H), 1.18 (t, J=7.20 Hz, 3H); LCMS (Method B): Rt=0.889 min, 578.3 (M+H)$^+$.

Step 5. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluorobenzoic acid

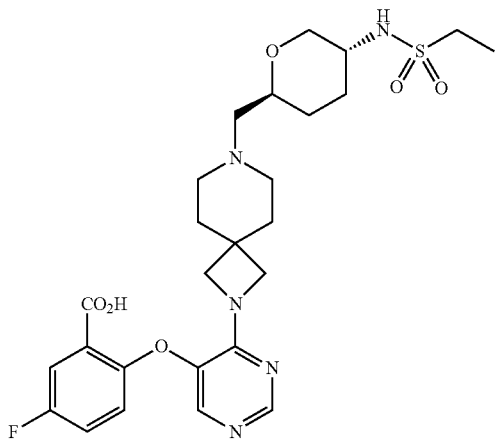 [SMILES: CCS(=O)(=O)N[C@@H]1CC[C@@H](CN2CCC3(CC2)CN(c2ncncc2Oc2ccc(F)cc2C(=O)O)C3)OC1]

In a dried, 250 mL three-necked round bottom flask under nitrogen atmosphere, methyl 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoate (3.8 g, 6.58 mmol) was dissolved in THF (20 mL), MeOH (16.00 mL) and $H_2O$ (4 mL). To the resulting solution, LiOH (0.315 g, 13.16 mmol) was added at 25° C. and the reaction mixture was stirred at 25° C. for 16 h. The reaction progress was monitored by TLC (10% MeOH in DCM). After 16 h, the solvent was distilled off under reduced pressure on a rotary evaporator to obtain the crude product. The crude residue was co distilled with ethyl acetate (2×25 mL) to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (3.5 g, 92% yield) as a light brown solid: $^1$H NMR (400 MHz, DMSO-$d_6$): δ 8.12 (s, 1H), 7.35 (s, 1H), 7.21 (dd, J=3.20, 8.80 Hz, 1H), 7.04-6.99 (m, 1H), 6.93-6.90 (m, 1H), 3.99-3.88 (m, 4H), 3.66 (d, J=5.20 Hz, 1H), 3.26-3.17 (m, 3H), 2.85 (d, J=6.40 Hz, 2H), 2.57-2.51 (m, 2H), 2.36-2.26 (m, 5H), 1.82-1.79 (m, 1H), 1.71-1.58 (m, 5H), 1.24-0.14 (m, 3H), 1.06 (t, J=2.40 Hz, 3H); LCMS (Method A): Rt=1.05 min, 564.2 (M+H)$^+$.

Intermediate 10. Lithium 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate

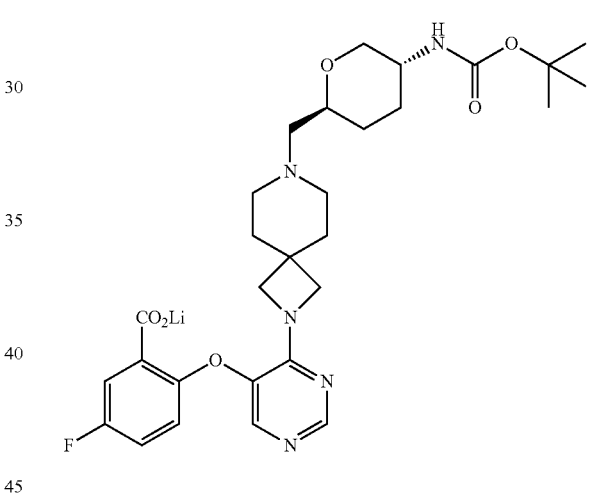

In 100 mL three necked round bottom flask methyl 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (4.0 g, 6.83 mmol) was dissolved in THF (28 mL), MeOH (8 mL), and water (4 mL). To the resulting mixture LiOH (0.196 g, 8.20 mmol) was added at 25° C., and the reaction mixture was stirred at 25° C. for 16 h. Reaction progress was monitored by TLC (10% MeOH in DCM). The solvent was evaporated on a rotary evaporator completely to obtain a crude mass, which was co-distilled with ethyl acetate (2×25 mL) to obtain lithium 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (3.8 g, 87%) as a yellow solid): LCMS: (Method C) Rt. 1.354 min, 572.4 (M+H)$^+$. The crude product was used without any further purification Intermediate 11. Lithium 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluorobenzoate

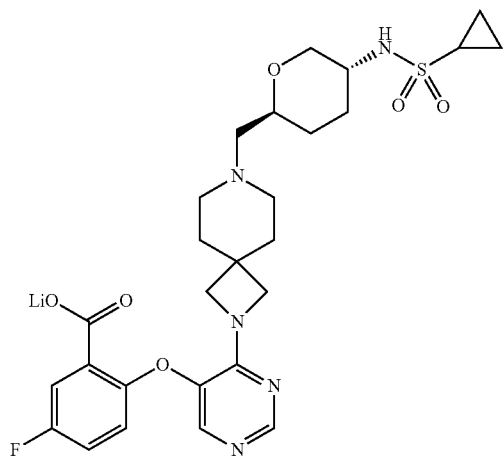

Step 1. Methyl 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorobenzoate, hydrochloride

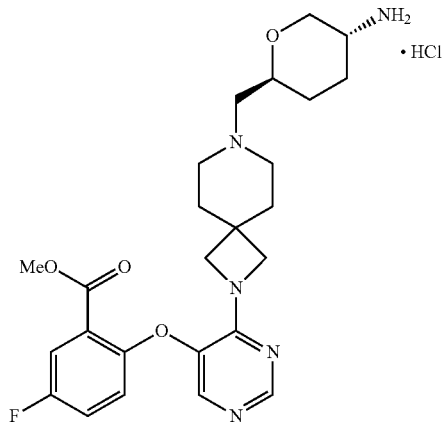 [SMILES: COC(=O)c1cc(F)ccc1Oc1cncnc1N1CC2(CCN(C[C@@H]3CC[C@@H](N)CO3)CC2)C1 ; "· HCl"]

In a dried, 100 mL single-necked round bottom flask under nitrogen atmosphere, methyl 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (1.49 g, 2.188 mmol) was added to trifluoroethanol (8 mL). The resulting reaction mixture was cooled to 0° C. and TMS-Cl (1.11 mL, 8.75 mmol) was added to it. The reaction was then stirred at 25° C. for 1.5 h, monitoring the reaction progress by TLC (10% methanol in dichloromethane). After 1.5 h, the reaction mixture was concentrated on a rotary evaporator under reduced pressure to obtain the crude product. The crude product was co-distilled with ethyl acetate to obtain methyl 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorobenzoate, hydrochloride (1.5 g, 1.695 mmol, 77% yield) as a light brown semi-solid: LCMS (Method C): Rt=1.462 min, m/z: 486.2 (M+H)$^+$. This was taken as such to the next step without further purification.

Step 2. Methyl 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluorobenzoate

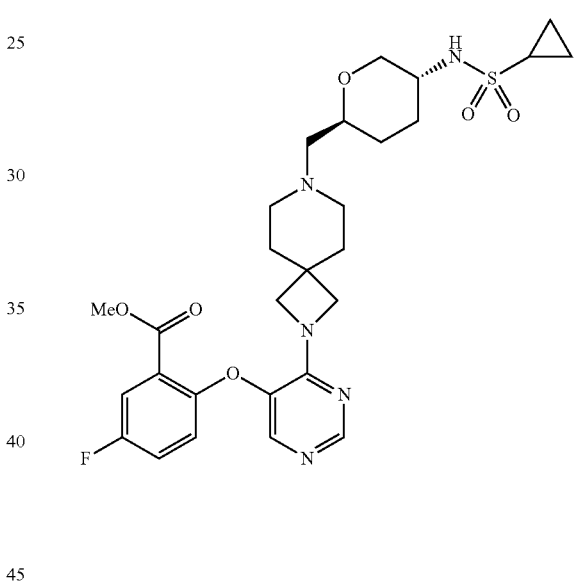

In a dried, 100 mL three-necked round bottom flask under nitrogen atmosphere, methyl 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorobenzoate, hydrochloride (1.5 g, 2.87 mmol)) was dissolved in DCM (30 mL) and the resulting solution was cooled to 0° C. Triethylamine (4.01 mL, 28.7 mmol) was added to the reaction mixture and stirred at 0° C. for 5 min. After this, cyclopropanesulfonyl chloride (0.585 mL, 5.75 mmol) was added and then the reaction was stirred at 26° C. for 16 h, monitoring the reaction progress by TLC (10% methanol in dichloromethane). After 16 h, the reaction was concentrated on a rotary evaporator (bath temperature 40° C.) under reduced pressure to obtain the crude compound. The crude compound was purified by prep HPLC (Method A). The fractions containing the desired product were lyophilized to obtain methyl 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluorobenzoate (0.06 g, 0.097 mmol, 3.36% yield) as an off white solid: LCMS (Method C): Rt=1.685 min, m/z: 590.4 (M+H)⁺.

Step 3. Lithium 2-((4-(7-((((2S,5R)-5-(cyclopropane-sulfonamido)tetrahydro-2H-pyran-2-yl)methyl)-2,7-diazaspiro[3.5]nonan-2-yl)pyrimidin-5-yl)oxy)-5-fluorobenzoate

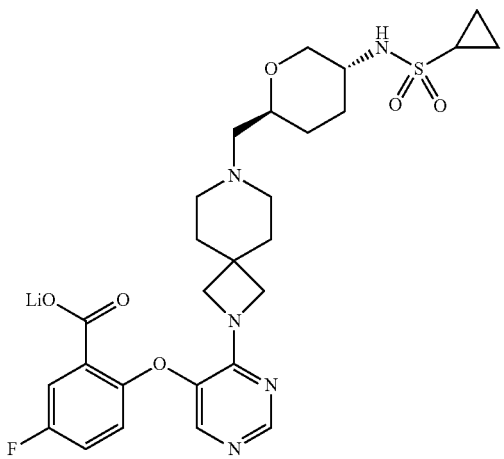

In a dried, 25 mL two-necked round bottom flask under nitrogen atmosphere, methyl 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluorobenzoate (0.06 g, 0.102 mmol) was dissolved in THF (2.67 mL), methanol (2 mL) and water (0.667 mL). To this reaction mixture, lithium hydroxide (9.75 mg, 0.407 mmol) was added at 25° C. under nitrogen atmosphere and the reaction mixture stirred at 25° C. for 16 h, monitoring the reaction progress by TLC. After 16 h, the reaction mixture was concentrated on a rotary evaporator (bath temperature 45° C.) under reduced pressure to obtain the crude lithium 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluorobenzoate (0.066 g, 0.107 mmol, 105% yield) as a light yellow solid: LCMS (Method C): Rt=1.33 min, m/z: 576.5 (M+H)⁺. This was taken as such to next step without purification.

Intermediate 12. 2-((4-(7-(((2S,5R)-5-Aminotetra-hydro-2H-pyran-2-yl)methyl)-2,7-diazaspiro[3.5] nonan-2-yl)pyrimidin-5-yl)oxy)-5-fluoro-N-isopropyl-N-(2-methoxyethyl)benzamide, hydrochloride Step 1. tert-Butyl ((3R,6S)-6-((2-(5-(4-fluoro-2-(isopropyl(2-methoxyethyl)carbamoyl)phenoxy) pyrimidin-4-yl)-2,7-diazaspiro[3.5]nonan-7-yl) methyl)tetrahydro-2H-pyran-3-yl)carbamate

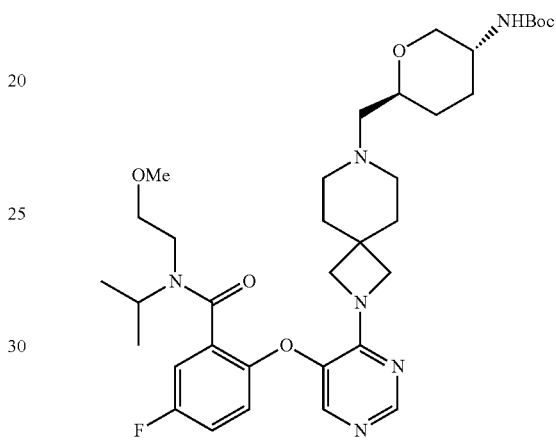

In a dried, 50 mL two-necked round bottom flask under nitrogen atmosphere, lithium 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (1.0 g, 1.749 mmol) was dissolved in DMF (10 mL). To this solution, TEA (0.975 mL, 7.00 mmol), HATU (0.998 g, 2.62 mmol) and N-(2-methoxyethyl)propan-2-amine (0.246 g, 2.099 mmol) were added at 25° C. under nitrogen atmosphere. The reaction was stirred at 25° C. for 19 h, monitoring the reaction progress by TLC (10% methanol in dichloromethane). After 19 h, the reaction mixture was quenched with water (50 mL) and the aqueous layer was extracted with ethyl acetate (3×50 mL). The organic layer was dried over anhydrous sodium sulfate and filtered, and the filtrate was concentrated on a rotary evaporator (bath temperature 40° C.) under reduced pressure to obtain crude tert-butyl ((3R,6S)-6-((2-(5-(4-fluoro-2-(isopropyl(2-methoxyethyl)carbamoyl)phenoxy)pyrimidin-4-yl)-2,7-diazaspiro[3.5]nonan-7-yl)methyl)tetrahydro-2H-pyran-3-yl) carbamate (1.1 g, 1.185 mmol, 67.8% yield) as an oily mass: LCMS (Method C): Rt=2.085 min, m/z: 671.2 (M+H)⁺. This was taken as such to next step without further purification.

Step 2. 2-((4-(7-(((2S,5R)-5-Aminotetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide, hydrochloride

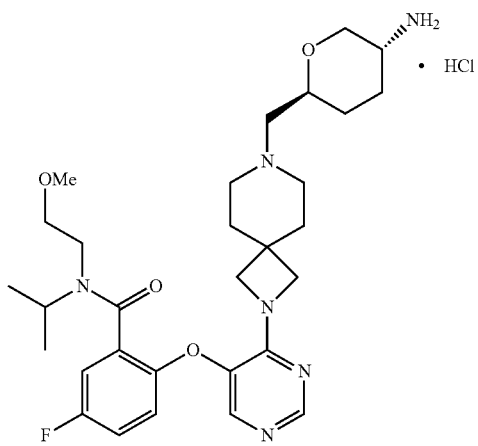 [SMILES: COCCN(C(=O)c1cc(F)ccc1Oc1cncnc1N1CC2(CCN(C[C@@H]3CC[C@@H](N)CO3)CC2)C1)C(C)C ; Cl]

In a dried, 50 mL two-necked round bottom flask under nitrogen atmosphere, tert-butyl ((3R,6S)-6-((2-(5-(4-fluoro-2-(isopropyl(2-methoxyethyl)carbamoyl)phenoxy)pyrimidin-4-yl)-2,7-diazaspiro[3.5]nonan-7-yl)methyl)tetrahydro-2H-pyran-3-yl)carbamate (1.1 g, 1.640 mmol) was dissolved in 2,2,2 trifluoroethanol (10 mL). The resulting solution was cooled to 0° C. and TMS-Cl (0.734 mL, 5.74 mmol) was added to it. The reaction was then stirred at 25° C. for 1 h, monitoring the reaction progress by TLC (10% methanol in dichloromethane). After 1 h, the reaction was concentrated on a rotary evaporator (bath temperature 40° C.) under reduced pressure to obtain the crude product. The crude product was co-distilled with ethyl acetate (2×15 mL) to obtain 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide, hydrochloride (0.98 g, 1.437 mmol, 88% yield) as a light brown solid: LCMS (Method B): Rt=0.291 min, m/z: 571.4 (M+H)$^+$. This was taken as such to next step without further purification.

Intermediate 13. 2-((4-(7-(((2S,5R)-5-Aminotetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide, hydrochloride

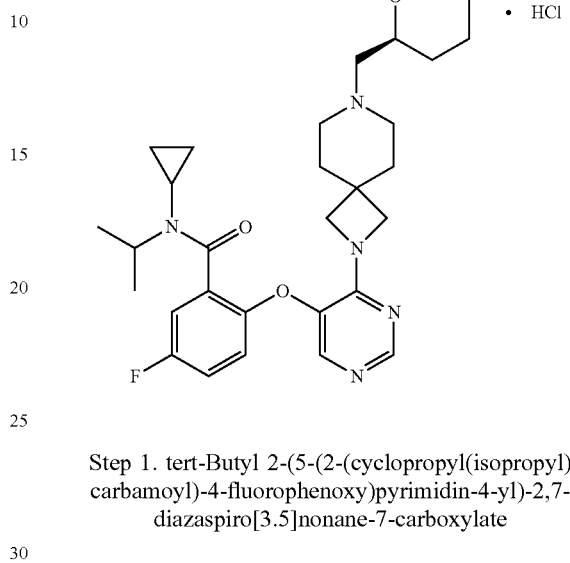

Step 1. tert-Butyl 2-(5-(2-(cyclopropyl(isopropyl)carbamoyl)-4-fluorophenoxy)pyrimidin-4-yl)-2,7-diazaspiro[3.5]nonane-7-carboxylate

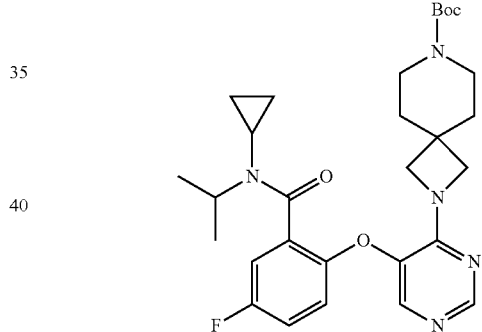

In a dried, 100 mL two necked round bottom flask under nitrogen atmosphere lithium 2-((4-(7-(tert-butoxycarbonyl)-2,7-diazaspiro[3.5]nonan-2-yl)pyrimidin-5-yl)oxy)-5-fluorobenzoic acid (2.5 g, 5.45 mmol) was dissolved in N,N-dimethylformamide (25 mL). To this reaction mixture N-isopropylcyclopropanamine (0.649 g, 6.54 mmol), HATU (3.11 g, 8.18 mmol) and TEA (3.04 mL, 21.81 mmol) were added at 25° C. under nitrogen atmosphere, and the reaction was stirred at 25° C. for 19 h. Reaction progress was monitored by TLC (10% MeOH in DCM). After completion of the reaction, the reaction mixture was quenched with water (250 mL) and the aqueous layer was extracted with ethyl acetate (3×100 mL). The organic layer was dried over anhydrous sodium sulfate and concentrated on a rotary evaporator (bath temperature 40° C.). Crude tert-butyl 2-(5-(2-(cyclopropyl(isopropyl)carbamoyl)-4-fluorophenoxy)pyrimidin-4-yl)-2,7-diazaspiro[3.5]nonane-7-carboxylate (2.65 g, 86%) was obtained as a yellow oil: LCMS: (Method C) 540.6 (M+1), Rt. 2.016 min, 95.32% (Max). This crude material was not purified further and was taken as such for next reaction.

Step 2. 2-((4-(2,7-Diazaspiro[3.5]nonan-2-yl)pyrimidin-5-yl)oxy)-N-cyclopropyl-5-fluoro-N-isopropylbenzamide, hydrochloride

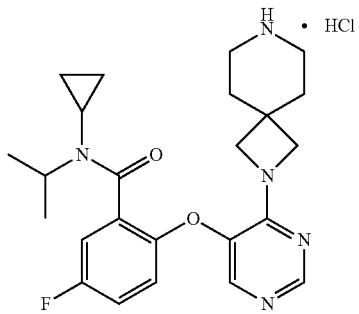 [SMILES: Cl ; CC(C)N(C(=O)c1cc(F)ccc1Oc1cncnc1N1CC2(CCNCC2)C1)C1CC1]

A dried, 100 mL two necked round bottom flask under nitrogen atmosphere was charged with tert-butyl 2-(5-(2-(cyclopropyl(isopropyl)carbamoyl)-4-fluorophenoxy)pyrimidin-4-yl)-2,7-diazaspiro[3.5]nonane-7-carboxylate (2.6 g, 4.82 mmol) in 2,2,2-triflouroethanol (26 mL). The resulting mixture cooled to 0° C. and TMS-Cl (2.155 mL, 16.86 mmol) was added. The reaction was stirred at 25° C. for 1 h, monitoring reaction progress by TLC (mobile phase: 10% MeOH in DCM). The solvent was distilled under reduced pressure on a rotary evaporator, and the residue was co-distilled with ethyl acetate (2×20 mL), followed by a hexane wash, to afford 2-((4-(2,7-diazaspiro[3.5]nonan-2-yl)pyrimidin-5-yl)oxy)-N-cyclopropyl-5-fluoro-N-isopropylbenzamide, hydrochloride as a light brown solid (2.2 g, 83.0%): LCMS: (Method C) 440.3 (M+1), Rt. 1.345 min, 86.42% (Max).

Step 3. tert-Butyl ((3R,6S)-6-((2-(5-(2-(cyclopropyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate

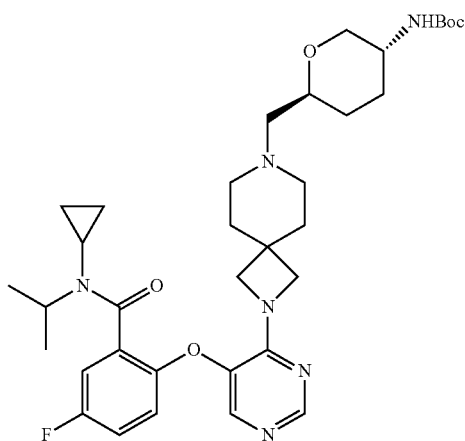 [SMILES: CC(C)N(C(=O)c1cc(F)ccc1Oc1cncnc1N1CC2(CCN(C[C@@H]3CC[C@@H](NC(=O)OC(C)(C)C)CO3)CC2)C1)C1CC1]

In a dried, 100 mL two necked round bottom flask under nitrogen atmosphere, 2-((4-(2,7-diazaspiro[3.5]nonan-2-yl)pyrimidin-5-yl)oxy)-N-cyclopropyl-5-fluoro-N-isopropylbenzamide, hydrochloride (2.1 g, 4.41 mmol) was dissolved in N-methyl-2-pyrrolidinone (20 mL). To this reaction mixture $K_2CO_3$ (2.439 g, 17.65 mmol), KI (0.806 g, 4.85 mmol) and ((2S,5R)-5-((tert-butoxycarbonyl)amino)tetrahydro-2H-pyran-2-yl)methyl 4-methylbenzenesulfonate (2.041 g, 5.29 mmol) were added at 25° C. under nitrogen atmosphere. The resulting mass was heated at 70° C. for 10 h, monitoring reaction progress by TLC (10% MeOH in DCM). After completion of the reaction, the reaction mixture was cooled at room temperature and quenched with water (500 mL). The aqueous layer was extracted with ethyl acetate (2×150 mL). The organic layer was dried over anhydrous sodium sulfate and concentrated on a rotary evaporator (bath temperature 40° C.) to obtain the crude compound. The crude compound was purified on (Isolera) column chromatography using 100-200 silica gel and eluting with methanol in DCM (desired product was eluted at 5% methanol in DCM). tert-Butyl ((3R,6S)-6-((2-(5-(2-(cyclopropyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (2.1 g, 58.5%) was obtained as a yellow syrup: LCMS: (Method C) 653.7 (M+1), Rt. 1.717 min, 80.26% (Max).

Step 4. 2-((4-(7-(((2S,5R)-5-Aminotetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide, hydrochloride

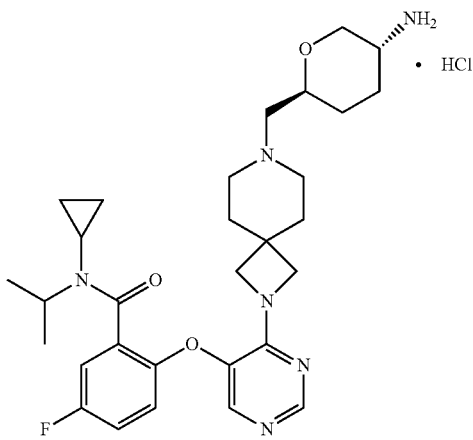 [SMILES: CC(C)N(C(=O)c1cc(F)ccc1Oc1cncnc1N1CC2(CCN(C[C@@H]3CC[C@@H](N)CO3)CC2)C1)C1CC1 ; Cl]

A dried, 25 mL two necked round bottom flask under nitrogen atmosphere was charged with tert-butyl ((3R,6S)-6-((2-(5-(2-(cyclopropyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (2.0 g, 3.06 mmol) in 2,2,2-triflouroethanol (20 mL). TMS-Cl (1.371 ml, 10.72 mmol) was added dropwise at 0° C., and the reaction mixture was stirred for 25° C. for 1 h. The reaction progress was monitored by TLC (mobile phase: 10% MeOH in DCM). The solvent was distilled under reduced pressure on a rotary evaporator, and the residue was co-distilled with ethyl acetate (2×20 mL), followed by a hexane wash, to afford ((4-(7-(((2S,5R)-5-aminotetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide, hydrochloride (1.9 g, 90% yield) as a light brown solid: LCMS: (Method C) 553.3 (M+1), Rt. 1.450 min, 85.59% (Max).

Intermediate 14. 3-(Isopropylamino)propanenitrile

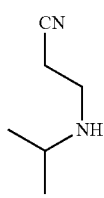

In a dried, 50 mL three-necked round bottom flask under nitrogen atmosphere, propan-2-amine (2.65 g, 44.8 mmol) and $K_2CO_3$ (6.19 g, 44.8 mmol) were combined in DMF (10 mL). 3-Bromopropanenitrile (2.0 g, 14.93 mmol) was slowly added to the suspension at 25° C., and the reaction mixture was stirred at 25° C. for 18 h, monitoring the reaction progress by TLC (1:1 ethyl acetate/pet ether). After 18 h, the reaction was quenched with water (100 mL) and extracted with ethyl acetate (3×150 mL). The combined organic layer was washed with water (2×100 mL) and brine (100 ml), dried over anhydrous sodium sulfate, and filtered. The filtrate was concentrated on a rotary evaporator under reduced pressure to afford 3-(isopropylamino)propanenitrile (820 mg, 49% yield) as a pale yellow oil: $^1$H NMR (400 MHz, $CDCl_3$): δ 3.00-2.83 (m, 3H), 2.53 (t, J=6.7 Hz, 2H), 1.09 (d, J=6.3 Hz, 6H). This was taken as such to the next step without further purification.

Intermediate 15. 3,3-Difluoro-N-isopropylcyclobutan-1-amine

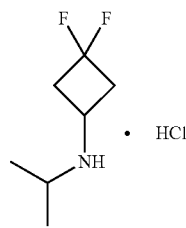

In a dried, 50 mL two-necked round bottom flask under nitrogen atmosphere, 3,3-difluorocyclobutan-1-amine hydrochloride (500 mg, 2.69 mmol) was dissolved in methanol (10 mL). To this solution, acetone (680 mg, 11.70 mmol) and acetic acid (0.172 mL, 2.93 mmol) were added at 25° C. under nitrogen atmosphere, and the reaction mixture was stirred at 25° C. for 10 minutes. After that, sodium cyanoborohydride (460 mg, 7.31 mmol) and molecular sieves 4 Å (420 mg, 2.93 mmol) were added, and the reaction mixture was stirred at 80° C. for 2 h. After 2 h, the reaction mixture was filtered over Celite® and washed with dichloromethane. The combined filtrate was diluted with water and extracted with dichloromethane. The organic layer was dried over sodium sulfate and filtered, and the filtrate was concentrated on a rotary evaporator under reduced pressure (bath temperature 45° C.) to obtain crude 3,3-difluoro-N-isopropyl-cyclobutan-1-amine (500 mg, 92% yield) as a light yellow oil: $^1$H NMR (400 MHz, DMSO-$d_6$): δ 3.66-3.44 (m, 1H), 3.16-2.96 (m, 1H), 2.96-2.78 (m, 2H), 2.66-2.54 (m, 2H), 1.10 (br d, J=6.1 Hz, 6H). This was taken as such to the next step without further purification.

Intermediate 16. (1s,3s)-3-(Isopropylamino)cyclobutan-1-ol

In a dried, 50 mL two-necked round bottom flask under nitrogen atmosphere, (1s,3s)-3-amino cyclobutan-1-ol hydrochloride (0.25 g, 2.023 mmol) was dissolved in methanol (10 mL). To this solution, acetone (0.599 mL, 8.09 mmol) and acetic acid (0.121 g, 2.023 mmol) were added at 25° C. under nitrogen atmosphere and the reaction mixture was then stirred at 25° C. for 10 minutes. After 10 minutes, sodium cyanoborohydride (0.318 g, 5.06 mmol) and molecular sieves 4 Å (0.25 g) were added and the reaction mixture was stirred at 80° C. for 3 h and then at 25° C. for 16 h. After 16 h, the reaction mixture was concentrated on a rotary evaporator under reduced pressure to obtain the crude residue. Ethyl acetate was added to the residue, stirred for 5 min, and filtered through Celite®, and the filter pad was washed with ethyl acetate. The combined filtrate was concentrated on a rotary evaporator under reduced pressure (bath temperature 40° C.) to obtain the crude product. The crude product was purified by prep-HLPC (ELSD) to obtain (1s,3s)-3-(isopropylamino)cyclobutan-1-ol (0.198 g, 1.532 mmol, 76% yield) as a colorless gummy solid: $^1$H NMR (400 MHz, DMSO-$d_6$): δ 5.37-4.86 (m, 1H), 3.80 (q, J=7.3 Hz, 2H), 3.01-2.79 (m, 2H), 2.49-2.44 (m, 2H), 1.66 (dq, J=2.8, 8.4 Hz, 2H), 1.02 (d, J=6.4 Hz, 6H); LCMS (Method C): Rt=0.4 min, m/z: 130.2 (M+H)$^+$.

Intermediate 17. (S)—N-Isopropyltetrahydrofuran-3-amine

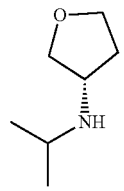

In a dried, 50 mL two-necked round bottom flask under nitrogen atmosphere, (S)-tetrahydrofuran-3-amine (0.25 g, 2.87 mmol) was dissolved in MeOH (5 mL). To this solution acetone (0.421 mL, 5.74 mmol) and AcOH (0.172 g, 2.87 mmol) were added at 25° C. under nitrogen atmosphere. The reaction mixture was stirred at 25° C. for 10 minutes and then $NaCNBH_4$ (0.451 g, 7.17 mmol) and molecular sieves 4A (0.1 g, 5.61 mmol) were added. The reaction mixture was then stirred at 80° C. for 2 h, monitoring the reaction progress by TLC (10% MeOH in DCM). After 2 h, the reaction mixture was filtered over a Celite® bed and washed with ethyl acetate. The filtrate was washed with water. The organic layer was dried over sodium sulfate and filtered, and the filtrate was concentrated on a rotary evaporator under reduced pressure (bath temperature 45° C.) to afford (S)—N-isopropyltetrahydrofuran-3-amine (0.21 g, 56.6% yield) as an off-white semisolid: ¹H NMR (400 MHz, DMSO-d₆): δ 3.76-3.71 (m, 2H), 3.65-3.60 (m, 1H), 3.38-3.25 (m, 2H), 2.76-2.71 (m, 1H), 1.99-1.94 (m, 1H), 1.60-1.57 (m, 1H), 0.99-0.95 (m, 6H).

Intermediate 18.
(R)—N-Isopropyltetrahydrofuran-3-amine

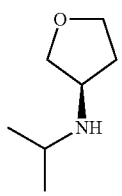

In a dried, 50 mL two-necked round bottom flask under nitrogen atmosphere, (R)-tetrahydrofuran-3-amine (0.5 g, 5.74 mmol) was dissolved in methanol (10 mL). To this reaction mixture acetone (1.587 ml, 22.96 mmol) and AcOH (0.034 mL, 5.74 mmol) were added at 25° C. under nitrogen atmosphere. The reaction mixture was stirred at 25° C. for 10 minutes and then NaCNBH₄ (1.058 g, 16.84 mmol) and molecular sieves 4 Å (2.5 g, 5.61 mmol) were added. The reaction mixture was stirred at 80° C. for 2 h, monitoring the reaction progress by TLC (10% MeOH in DCM). After completion of the reaction, the reaction mixture was filtered over a Celite® bed and washed with DCM. The filtrate was diluted water and extracted with DCM (2×50 mL). The combined organic layers were dried over sodium sulfate and concentrated on a rotary evaporator under reduced pressure (bath temperature 45° C.) to obtain the crude product, (R)—N-isopropyltetrahydrofuran-3-amine (2.65 g, 80%), as a light yellow oil: ¹H NMR: (400 MHz, DMSO-d₆): δ 3.69-3.79 (m, 2H) 3.58-3.68 (m, 1H) 3.32-3.45 (m, 3H) 2.71-2.83 (m, 1H) 1.92-2.04 (m, 1H) 1.54-1.65 (m, 1H) 0.91-1.04 (m, 6H).

Intermediate 19. 2-((4-(2,7-Diazaspiro[3.5]nonan-2-yl)pyrimidin-5-yl)oxy)-5-fluoro-N-isopropyl-N-methylbenzamide hydrochloride and Intermediate 20: 2-((4-(7-(((2S,5R)-5-Aminotetrahydro-2H-pyran-2-yl)methyl)-2,7-diazaspiro[3.5]nonan-2-yl)pyrimidin-5-yl)oxy)-5-fluoro-N-isopropyl-N-methylbenzamide hydrochloride

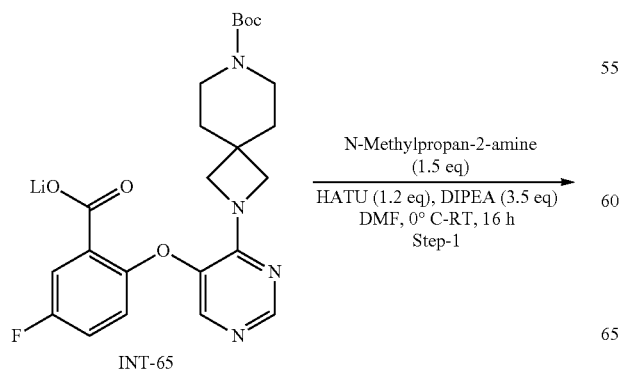

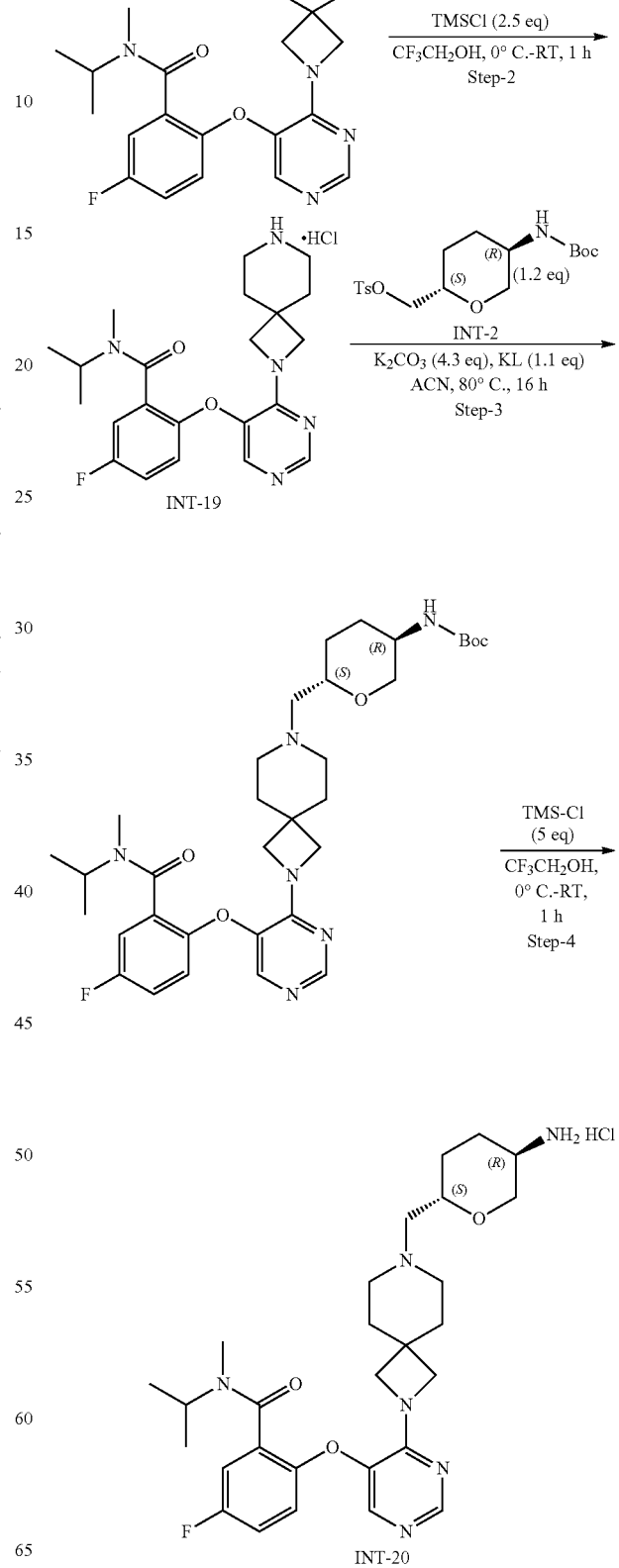

Step 1. tert-Butyl-2-(5-(4-fluoro-2-(isopropyl (methyl)carbamoyl)phenoxy)pyrimidin-4-yl)-2,7-diazaspiro[3.5]nonane-7-carboxylate

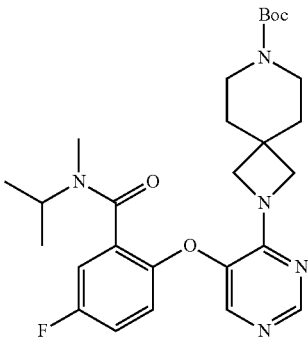 [SMILES: CC(C)N(C)C(=O)c1cc(F)ccc1Oc1cncnc1N1CC2(CCN(C(=O)OC(C)(C)C)CC2)C1]

To a dried 250 mL two necked round bottom flask under nitrogen atmosphere, lithium 2-((4-(7-(tert-butoxycarbonyl)-2,7-diazaspiro[3.5]nonan-2-yl)pyrimidin-5-yl)oxy)-5-fluorobenzoate (5 g, 10.77 mmol) in DMF (50 mL) was added, followed by DIPEA (6.72 mL, 37.7 mmol), HATU (4.91 g, 12.92 mmol) and N-methylpropan-2-amine (1.181 g, 16.15 mmol) at 0° C. The resulting reaction mixture was stirred at RT for 16 h, monitoring the reaction progress by TLC (10% MeOH in DCM). The reaction was quenched with water (100 mL) and extracted with EtOAc (2×150 mL). The combined organic layer was dried over anhydrous sodium sulfate, filtered, and concentrated under reduced pressure to afford the crude product.

The crude product was purified by silica gel column chromatography using 0-10% MeOH in DCM as an eluent to obtain tert-butyl 2-(5-(4-fluoro-2-(isopropyl(methyl)carbamoyl)phenoxy)pyrimidin-4-yl)-2,7-diazaspiro[3.5]nonane-7-carboxylate (3.21 g, 55.4% yield) as a solid. $^1$H NMR (400 MHz, DMSO-$d_6$) δ 8.32-8.23 (m, 1H), 7.80-7.66 (m, 1H), 7.33-7.21 (m, 2H), 7.11-6.98 (m, 1H), 3.94-3.78 (m, 5H), 3.31-3.20 (m, 3H), 3.27-3.26 (m, 4H), 1.73-1.54 (m, 4H), 1.39 (d, J=1.00 Hz, 9H), 1.14-1.00 (m, 6H); LCMS (Method B): Rt 1.811 min, m/z: 514.3 [M+H]$^+$, 95.46%.

Step 2. 2-((4-(2,7-Diazaspiro[3.5]nonan-2-yl)pyrimidin-5-yl)oxy)-5-fluoro-N-isopropyl-N-methlbenzamide hydrochloride (Intermediate 19)

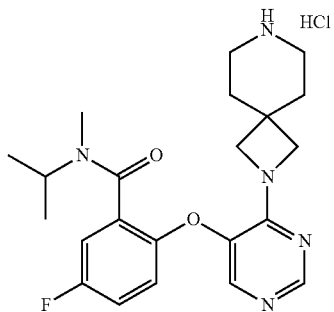 [SMILES: Cl ; CC(C)N(C)C(=O)c1cc(F)ccc1Oc1cncnc1N1CC2(CCNCC2)C1]

To a dried 100 mL two necked round bottom flask under nitrogen atmosphere, tert-butyl 2-(5-(4-fluoro-2-(isopropyl(methyl)carbamoyl)phenoxy)pyrimidin-4-yl)-2,7-diazaspiro[3.5]nonane-7-carboxylate (3.28 g, 6.39 mmol) was added in 2,2,2-trifluoroethanol (30 mL). To this reaction mixture, TMSCI (2.041 mL, 15.97 mmol) was added at 0° C. and the resulting reaction was stirred at RT for 1 h. The reaction progress was monitored by TLC (10% MeOH in DCM). After completion of reaction, the reaction mixture was concentrated on a rotary evaporator to obtain crude 2-((4-(2,7-diazaspiro[3.5]nonan-2-yl)pyrimidin-5-yl)oxy)-5-fluoro-N-isopropyl-N-methylbenzamide hydrochloride (2.61 g, 90% yield) as a solid. LCMS (Method B): Rt 0.945 min, m/z: 414.4 [M+H]$^+$, 99.16%.

Step 3. tert-Butyl((3R,6S)-6-((2-(5-(4-fluoro-2-(isopropyl(methyl)carbamoyl)phenoxy)pyrimidin-4-yl)-2,7-diazaspiro[3.5]nonan-7-yl)methyl)tetrahydro-2H-pyran-3-yl)carbamate

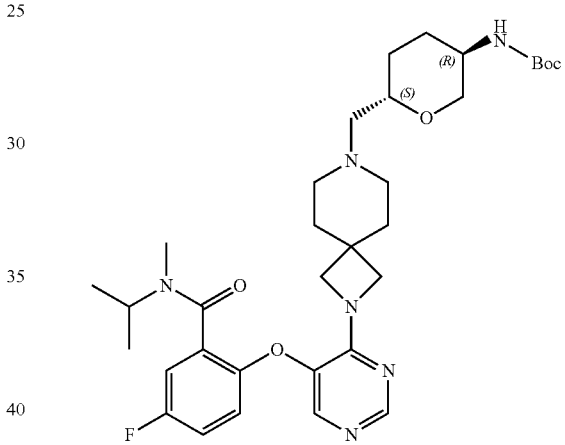

In a dried 250 mL two necked round bottom flask under nitrogen atmosphere, 2-((4-(2,7-diazaspiro[3.5]nonan-2-yl)pyrimidin-5-yl)oxy)-5-fluoro-N-isopropyl-N-methylbenzamide hydrochloride (1 g, 2.222 mmol) was added to ACN (20 mL). To this reaction mixture $K_2CO_3$ (1.321 g, 9.56 mmol), KI (0.406 g, 2.445 mmol) and ((2S,5R)-5-((tert-butoxycarbonyl)amino)tetrahydro-2H-pyran-2-yl)methyl4-methylbenzenesulfonate (1.028 g, 2.67 mmol) were added at RT under nitrogen atmosphere. The resulting reaction was heated at 80° C. for 16 h. The reaction progress was monitored by TLC (10% MeOH in DCM). After 16 h, the reaction mixture was quenched with water (20 mL) and extracted with EtOAc (2×50 mL). The combined organic layer was dried over anhydrous sodium sulfate, filtered, and concentrated on a rotary evaporator. The residue was purified by silica gel column chromatography using 0-15% MeOH in DCM as an eluent to obtain tert-butyl ((3R,6S)-6-((2-(5-(4-fluoro-2-(isopropyl(methyl)carbamoyl)phenoxy)pyrimidin-4-yl)-2,7-diazaspiro[3.5]nonan-7-yl)methyl)tetrahydro-2H-pyran-3-yl)carbamate (900 mg, 63.3% yield) as a gummy liquid. LCMS (Method B): Rt 1.608 min, m/z: 627.6 [M+H]+, 97.96%.

Step 4. 2-((4-(7-(((2S,5R)-5-Aminotetrahydro-2H-pyran-2-yl)methyl)-2,7-diazaspiro[3.5]nonan-2-yl)pyrimidin-5-yl)oxy)-5-fluoro-N-isopropyl-N-methyl-benzamide hydrochloride (Intermediate 20)

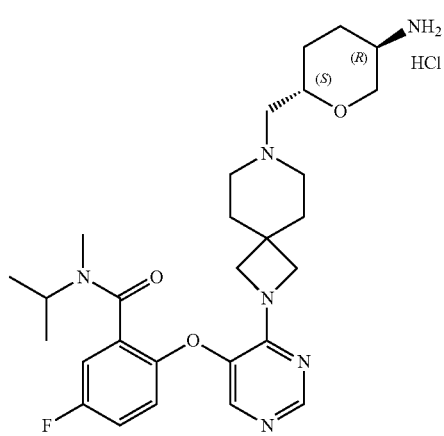

In a dried 100 mL two necked round bottom flask under nitrogen atmosphere, tert-butyl ((3R,6S)-6-((2-(5-(4-fluoro-2-(isopropyl(methyl)carbamoyl)phenoxy)pyrimidin-4-yl)-2,7-diazaspiro[3.5]nonan-7-yl)methyl)tetrahydro-2H-pyran-3-yl)carbamate (900 mg, 1.436 mmol) was added to 2,2,2-trifluoroethanol (5 mL). To this reaction mixture, TMSCl (0.918 mL, 7.18 mmol)) was added at 0° C., and the resulting reaction was stirred at RT for 1 h. The reaction progress was monitored by TLC (10% MeOH in DCM). After completion of reaction, the reaction mixture was concentrated on a rotary evaporator to obtain 2-((4-(7-(((2S,5R)-5-aminotetrahydro-2H-pyran-2-yl)methyl)-2,7-diazaspiro[3.5]nonan-2-yl) pyrimidin-5-yl)oxy)-5-fluoro-N-isopropyl-N-methylbenzamide hydrochloride (795 mg, 97% yield) as a solid. LCMS (Method B): Rt 1.327 min, m/z: 527.4 [M+H]+, 98.60%.

Intermediate 21. 2-((4-(2,7-Diazaspiro[3.5]nonan-2-yl)pyrimidin-5-yl)oxy)-N-(2,2-difluoroethyl)-5-fluoro-N-isopropylbenzamide hydrochloride and Intermediate 22: 2-((4-(2,7-Diazaspiro[3.5]nonan-2-yl)pyrimidin-5-yl)oxy)-N-(2,2-difluoroethyl)-5-fluoro-N-isopropylbenzamide

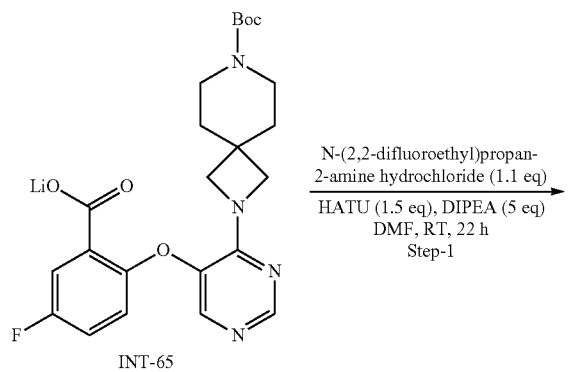

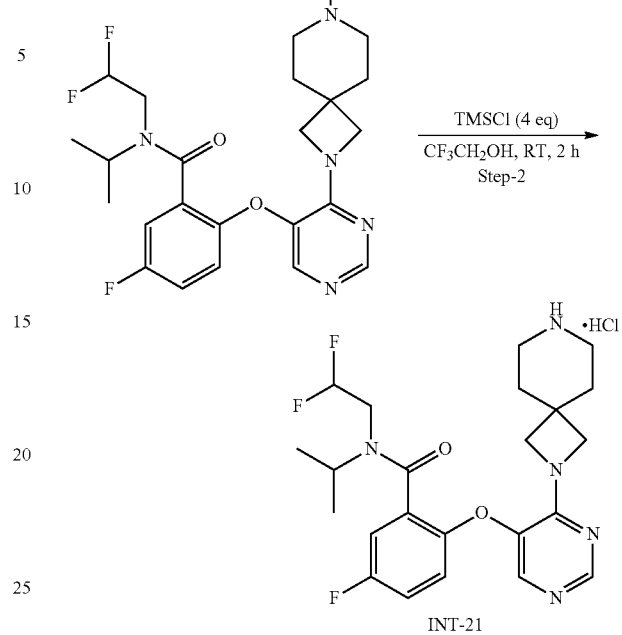

Step 1. tert-Butyl 2-(5-(2-((2,2-difluoroethyl)(isopropyl)carbamoyl)-4-fluorophenoxy)pyrimidin-4-yl)-2,7-diazaspiro[3.5]nonane-7-carboxylate

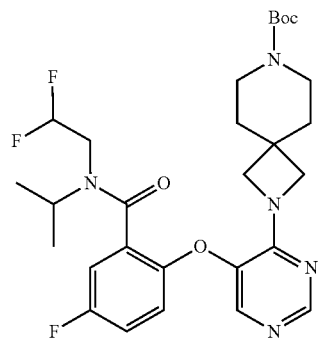 [SMILES: CC(C)N(CC(F)F)C(=O)c1cc(F)ccc1Oc1cncnc1N1CC2(CCN(C(=O)OC(C)(C)C)CC2)C1]

To a dried 50 mL two-necked round bottom flask under nitrogen atmosphere, lithium 2-((4-(7-(tert-butoxycarbonyl)-2,7-diazaspiro[3.5]nonan-2-yl)pyrimidin-5-yl)oxy)-5-fluoro benzoate (6.0 g, 12.92 mmol) was added in DMF (60 mL). To this reaction mixture, DIPEA (11.93 mL, 64.6 mmol), HATU (7.37 g, 19.38 mmol) and N-(2,2-difluoroethyl)propan-2-amine hydrochloride (2.268 g, 14.21 mmol) were added at 0° C. under nitrogen atmosphere, and the reaction mixture was stirred at RT for 22 h. The reaction progress was monitored by TLC (70% EtOAc in Hexane). After 22 h, the reaction was quenched with water (100 mL) and diluted with EtOAc (200 mL). The organic layer was separated, and the aqueous layer was extracted with EtOAc (2×200 mL). The combined organic layer was washed with brine solution (2×100 mL), dried over Na₂SO₄, and filtered, and the filtrate was concentrated under vacuum to afford crude product. The crude product was purified by Biotage-isolera one, eluting with 70-80% EtOAc in hexane. The fractions containing the desired product were concentrated under vacuum to afford tert-butyl 2-(5-(2-((2,2-difluoroethyl)(isopropyl)carbamoyl)-4-fluoro phenoxy)pyrimidin-4-yl)-2,7-diazaspiro[3.5]nonane-7-carboxylate (5.0 g, 64.2% yield) as a liquid. $^1$H NMR (400 MHz, DMSO-$d_6$) δ 8.34-8.23 (m, 1H), 7.81-7.69 (m, 1H), 7.35 (dd, J=8.25, 3.13 Hz, 1H), 7.32-7.26 (m, 1H), 7.03 (dd, J=9.07, 4.32 Hz, 1H), 6.37-6.01 (m, 1H), 3.94-3.65 (m, 7H), 3.29-3.20 (m, 4H), 1.71-1.56 (m, 4H), 1.39 (s, 9H), 0.93-1.16 (m, 6H); LCMS (Method E): Rt 2.155 min, m/z: 564.6 [M+H]$^+$, 93.48%.

Step 2. 2-((4-(2,7-Diazaspiro[3.5]nonan-2-yl)pyrimidin-5-yl)oxy)-N-(2,2-difluoroethyl)-5-fluoro-N-isopropylbenzamide hydrochloride (Intermediate 21)

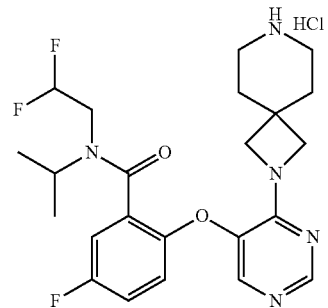 [SMILES: Cl ; CC(C)N(CC(F)F)C(=O)c1cc(F)ccc1Oc1cncnc1N1CC2(CCNCC2)C1]

To a dried 100 mL three necked reaction flask under nitrogen atmosphere, tert-butyl 2-(5-(2-((2,2-difluoroethyl)(isopropyl)carbamoyl)-4-fluorophenoxy)pyrimidin-4-yl)-2,7-diazaspiro[3.5]nonane-7-carboxylate (5.0 g, 8.87 mmol) was added in 2,2,2 trifluoroethanol (50 mL). To this reaction mixture, TMSCl (4.54 mL, 35.5 mmol) was added at 0° C., and the resulting reaction was stirred at RT for 1 h. The reaction progress was monitored by TLC (10% MeOH in DCM). After 1 h, the reaction mixture was concentrated under reduced pressure to afford crude product, which was triturated with EtOAc (30 mL) to afford 2-((4-(2,7-diazaspiro[3.5]nonan-2-yl)pyrimidin-5-yl)oxy)-N-(2,2-difluoroethyl)-5-fluoro-N-isopropylbenzamide hydrochloride (4.5 g, 100% yield) as a solid. LCMS (Method E): Rt 1.546 min, m/z: 464.1 [M+H]$^+$, 98.50%.

Intermediate 23. 2-((4-(7-(((2S,5R)-5-Aminotetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide hydrochloride

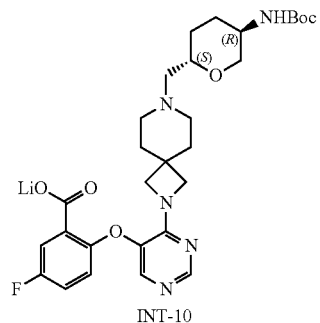

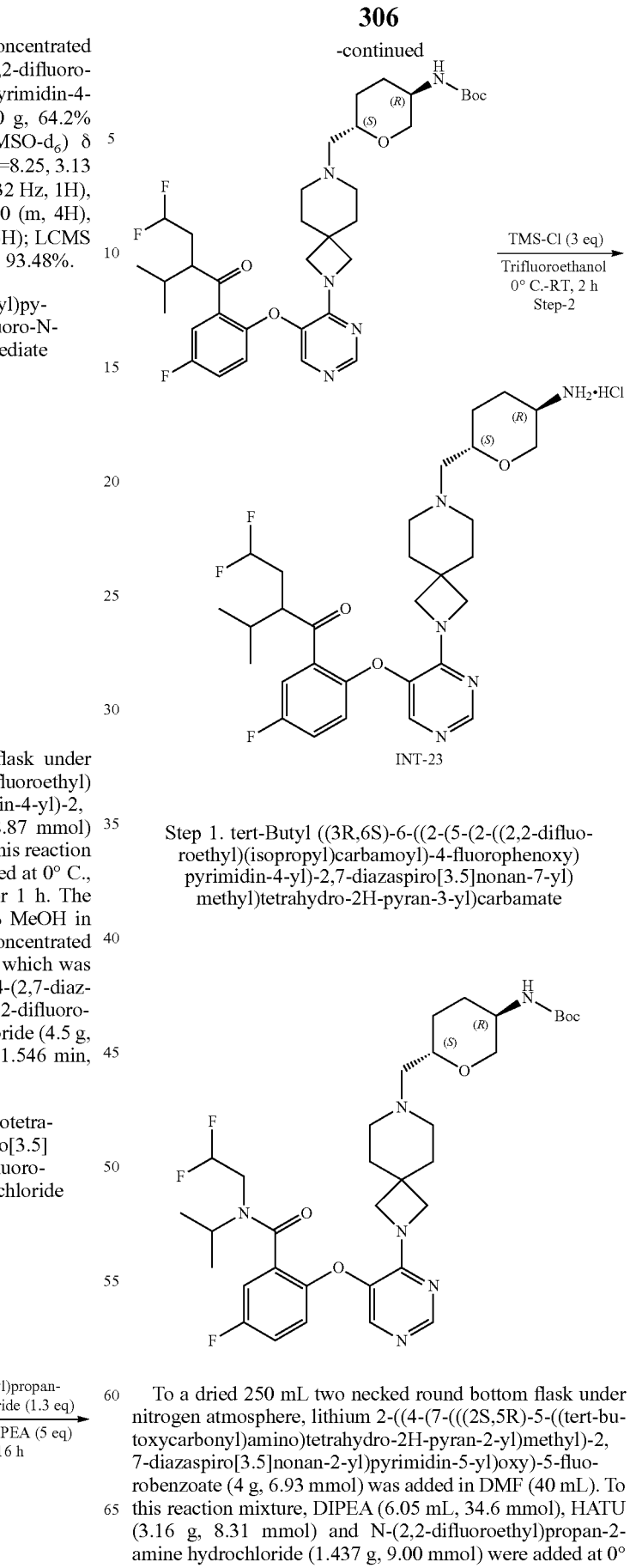

Step 1. tert-Butyl ((3R,6S)-6-((2-(5-(2-((2,2-difluoroethyl)(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate To a dried 250 mL two necked round bottom flask under nitrogen atmosphere, lithium 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (4 g, 6.93 mmol) was added in DMF (40 mL). To this reaction mixture, DIPEA (6.05 mL, 34.6 mmol), HATU (3.16 g, 8.31 mmol) and N-(2,2-difluoroethyl)propan-2-amine hydrochloride (1.437 g, 9.00 mmol) were added at 0°

C. under nitrogen atmosphere, and the resulting reaction was stirred at RT for 16 h. The reaction progress was monitored by TLC (10% MeOH in DCM). After completion of the reaction, the reaction mixture was quenched with water (10 mL) and extracted with EtOAc (2×150 mL). The combined organic layer was dried over anhydrous sodium sulfate and filtered, and the filtrate was concentrated on a rotary evaporator to obtain crude product (5.1 g, LCMS-77%) as a liquid. The crude product was purified by silica gel chromatography using 0-10% MeOH in DCM as an eluent. The fractions containing the desired product were concentrated under reduced pressure to obtain tert-butyl ((3R,6S)-6-((2-(5-(2-((2,2-difluoroethyl)(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (2.0863 g, 39.1% yield) as a solid. $^{1}$H NMR (400 MHz, DMSO-$d_6$) δ 8.25-8.33 (m, 1H), 7.72-7.79 (m, 1H), 7.35 (dd, J=8.13, 3.13 Hz, 1H), 7.24-7.32 (m, 1H), 7.03 (dd, J=9.07, 4.32 Hz, 1H), 6.76 (br d, J=7.63 Hz, 1H), 5.99-6.39 (m, 1H), 3.65-3.94 (m, 8H), 3.17 (d, J=3.00 Hz, 2H), 2.96-2.91 (m, 1H), 2.29-2.47 (m, 4H), 1.60-1.90 (m, 7H), 1.34-1.41 (m, 9H), 1.19-1.34 (m, 3H), 0.96-1.17 (m, 6H); LCMS (Method C): Rt 1.879 min, m/z: 677.2 [M+H]$^+$, 88.16%.

Step 2. 2-((4-(7-(((2S,5R)-5-Aminotetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide hydrochloride (Intermediate 23)

To a stirred solution of tert-butyl ((3R,6S)-6-((2-(5-(2-((2,2-difluoroethyl)(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (2 g, 2.96 mmol) in 2,2,2-trifluoroethanol (15 mL), TMSCl (1.133 ml, 8.87 mmol) was added at 0° C. The reaction mixture was stirred at RT for 2 h. TLC indicated complete consumption of the SM. The solvent was concentrated under reduced pressure and co-distilled with EtOAc to obtain 2-((4-(7-(((2S,5R)-5-aminotetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide hydrochloride (2.081 g, 102% yield) as a solid. LCMS (Method C): Rt 1.519 min, m/z: 577.2 [M+H]$^+$, 88.73%.

Intermediate 24. 2-((4-(2,7-Diazaspiro[3.5]nonan-2-yl)pyrimidin-5-yl)oxy)-5-fluoro-N-isopropyl-N-(2,2,2-trifluoroethyl)benzamide hydrochloride

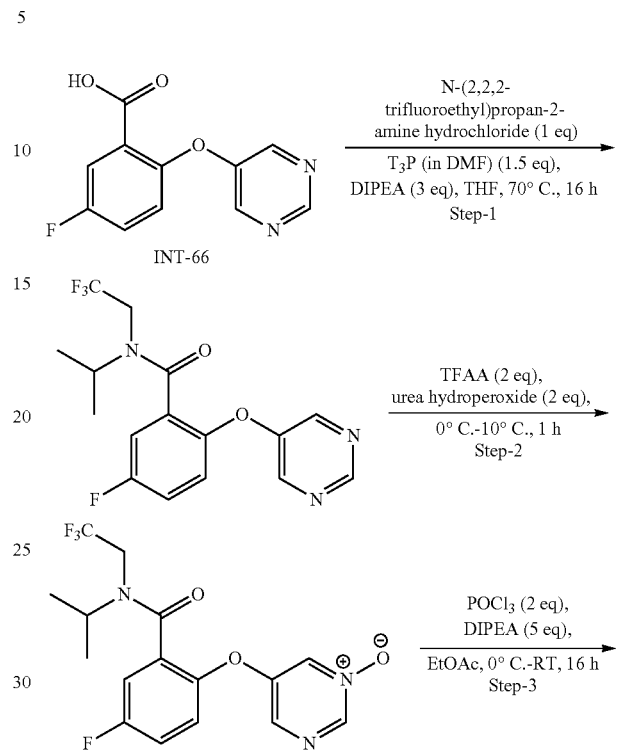

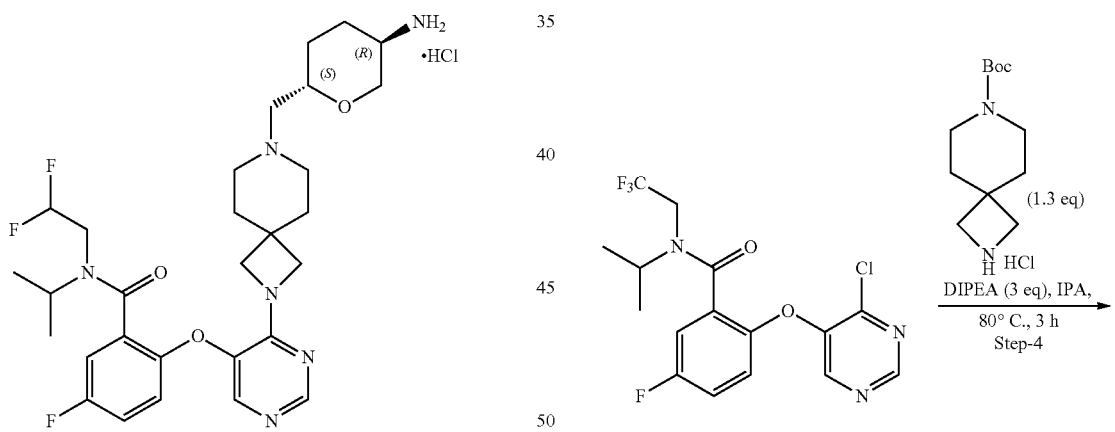

-continued

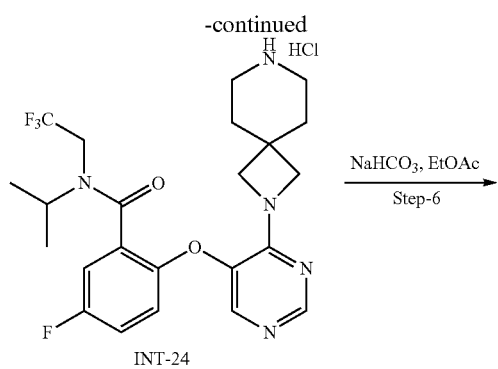

INT-24

Step 1. 5-Fluoro-N-isopropyl-2-(pyrimidin-5-yloxy)-N-(2,2,2-trifluoroethyl)benzamide

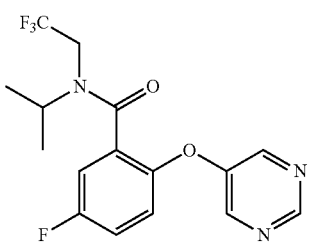 [SMILES: CC(C)N(CC(F)(F)F)C(=O)c1cc(F)ccc1Oc1cncnc1]

To a dried 100 mL two necked round bottom flask under nitrogen atmosphere, 5-fluoro-2-(pyrimidin-5-yloxy)benzoic acid (2.2 g, 9.39 mmol) was added in THF (20 mL). To this solution, N-(2,2,2-trifluoroethyl)propan-2-amine hydrochloride (1.668 g, 9.39 mmol), propanephosphonic acid anhydride (8.97 g, 14.09 mmol, 50% in DMF) and DIPEA (5.06 mL, 28.2 mmol) were sequentially added. The resulting reaction mixture was stirred at 70° C. for 16 h. The progress of the reaction was monitored by TLC (10% MeOH in DCM). After 16 h, the reaction mixture was quenched with cold water (100 mL) and extracted with EtOAc (2×30 mL). The combined organic layer was dried over anhydrous sodium sulfate and filtered, and the filtrate was concentrated under reduced pressure to obtain 4 g crude product as brown gum. The crude product was purified by Biotage-isolera one, using 230-400 mesh silica-gel. The desired product was eluted in 3% MeOH in DCM. The fractions containing the desired product were collected and concentrated under reduced pressure to obtain 5-fluoro-N-isopropyl-2-(pyrimidin-5-yloxy)-N-(2,2,2-trifluoroethyl)benzamide (2.2 g, 5.86 mmol, 62.4% yield) as brown gum. LCMS (Method B): Rt 1.80 min, m/z: 358.0 [M+H]+, 52.87%.

Step 2. 5-(4-Fluoro-2-(isopropyl(2,2,2-trifluoroethyl) carbamoyl)phenoxy) pyrimidine 1-oxide

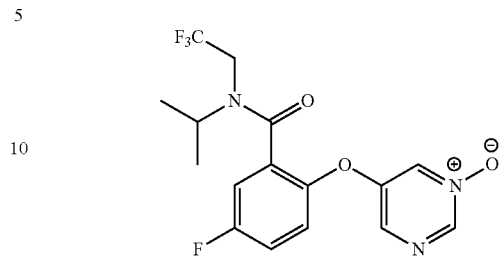

To a dried 100 mL two necked round bottom flask, 5-fluoro-N-isopropyl-2-(pyrimidin-5-yloxy)N-(2,2,2-trifluoroethyl)benzamide (2 g, 5.60 mmol) was added in THF (3 mL), and the solution was cooled to 0° C. To this solution, urea hydrogen peroxide (1.053 g, 11.19 mmol) and TFAA (2.398 g, 11.42 mmol) were added. The reaction mixture was then stirred at 0° C. to 10° C. for 1 h, monitoring the reaction progress by TLC (100% in EtOAc). After completion of the reaction, the reaction mixture was quenched with sat. ammonium bicarbonate (50 mL) and extracted with EtOAc (2×30 mL). The organic layer was dried over anhydrous sodium sulfate and filtered, and the filtrate was concentrated under reduced pressure to obtain 5-(4-fluoro-2-(isopropyl(2,2,2-trifluoroethyl)carbamoyl)phenoxy) pyrimidine 1-oxide (2.5 g, 4.32 mmol, 77% yield) as a liquid. LCMS (Method B): Rt 1.65 min, m/z: 372.2 [M–H]−, 66.62%.

Step 3. 2-((4-Chloropyrimidin-5-yl)oxy)-5-fluoro-N-isopropyl-N-(2,2,2-trifluoroethyl)benzamide

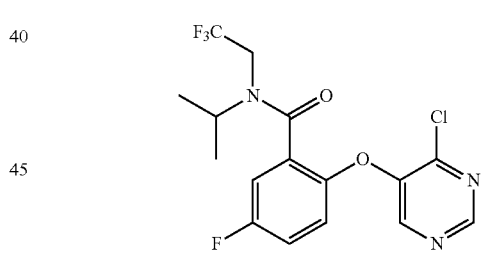

To a dried 100 mL two necked round bottom flask under nitrogen atmosphere, 5-(4-fluoro-2-(isopropyl(2,2,2-trifluoroethyl)carbamoyl)phenoxy)pyrimidine 1-oxide (2.5 g, 6.70 mmol) was added in EtOAc (20 mL), and the solution was cooled to −15° C. To this solution, DIPEA (6.18 mL, 33.5 mmol) and POCl3 (2.054 g, 13.39 mmol) were added, and the reaction was stirred at 0° C. for 30 min. The reaction mixture was allowed to attain RT and stirred for 16 h. The progress of the reaction was monitored by TLC (50% EtOAc in hexane). After 16 h, the reaction mixture was concentrated under reduced pressure to obtain 4 g of crude compound as brown gum. The crude compound was purified by Biotage-isolera one, using 230-400 mesh silica-gel. The desired product was eluted in 50% EtOAc in hexane. The fractions containing the desired product were collected and concentrated under reduced pressure to obtain 2-((4-chloropyrimidin-5-yl)oxy)-5-fluoro-N-isopropyl-N-(2,2,2-trifluoroethyl)benzamide (1.3 g, 2.65 mmol, 39.6% yield) as a liquid. LCMS (Method B): Rt 2.02 min, m/z: 392.0 [M+H]⁺, 79.94%.

Step 4. tert-Butyl 2-(5-(4-fluoro-2-(isopropyl(2,2,2-trifluoroethyl)carbamoyl)phenoxy)pyrimidin-4-yl)-2,7-diazaspiro[3.5]nonane-7-carboxylate

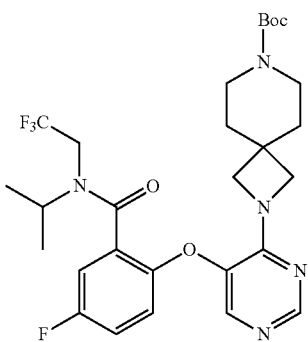

To a dried 100 mL single necked round bottom flask under nitrogen atmosphere, 2-((4-chloropyrimidin-5-yl)oxy)-5-fluoro-N-isopropyl-N-(2,2,2-trifluoroethyl)benzamide (1.3 g, 3.32 mmol) and tert-butyl 2,7-diazaspiro[3.5]nonane-7-carboxylate hydrochloride (1.134 g, 4.31 mmol) were added in 2-propanol (20 mL). To this solution, DIPEA (1.739 mL, 9.96 mmol) was added and the reaction mixture stirred at 80° C. for 3 h. The reaction progress was monitored by TLC (100% EtOAc). After 3 h, the reaction mixture was concentrated on a rotary evaporator to obtain 2.6 g of crude product as brown gum. The crude product was purified by Biotage-isolera one, using 230-400 mesh silica gel. The desired product eluted in 60% EtOAc in hexane. The fractions containing the desired product were collected and concentrated under reduced pressure to obtain tert-butyl 2-(5-(4-fluoro-2-(isopropyl(2,2,2-trifluoroethyl)carbamoyl)phenoxy)pyrimidin-4-yl)-2,7-diazaspiro[3.5] nonane-7-carboxylate (1.3 g, 62.0% yield) as a gummy solid. LCMS (Method B): Rt 1.851 min, m/z: 582.2 [M+H]⁺, 92.04%.

Step 5. 2-((4-(2,7-Diazaspiro[3.5]nonan-2-yl)pyrimidin-5-yl)oxy)-5-fluoro-N-isopropyl-N-(2,2,2-trifluoroethyl)benzamide hydrochloride (Intermediate 24)

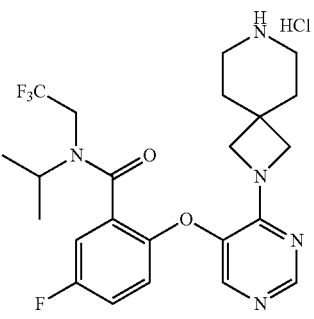 [SMILES: Cl ; CC(C)N(CC(F)(F)F)C(=O)c1cc(F)ccc1Oc1cncnc1N1CC2(CCNCC2)C1]

To a dried 100 mL round bottom flask under nitrogen atmosphere, tert-butyl 2-(5-(4-fluoro-2-(isopropyl(2,2,2-trifluoroethyl)carbamoyl)phenoxy)pyrimidin-4-yl)-2,7-diaz-aspiro[3.5]nonane-7-carboxylate (1.3 g, 2.235 mmol) was added in 2,2,2-trifluoroethanol (5 mL). The solution was cooled to 0° C., then TMSCI (1.143 ml, 8.94 mmol) was added. The reaction mixture was stirred at RT for 1 h, monitoring the reaction progress by TLC (10% MeOH in DCM). After 1 h, the reaction mixture was concentrated on a rotary evaporator to afford 2-((4-(2,7-diazaspiro[3.5]nonan-2-yl)pyrimidin-5-yl)oxy)-5-fluoro-N-isopropyl-N-(2,2,2-trifluoroethyl)benzamide hydrochloride (1.1 g, 1.950 mmol, 87% yield) as a solid. LCMS (Method B): Rt 0.860 min, 482.2 [M+H]⁺, 91.8%.

Step 6. 2-((4-(2,7-Diazaspiro[3.5]nonan-2-yl)pyrimidin-5-yl)oxy)-5-fluoro-N-isopropyl-N-(2,2,2-trifluoroethyl)benzamide (Intermediate 22)

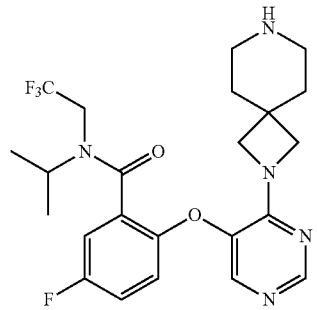 [SMILES: CC(C)N(CC(F)(F)F)C(=O)c1cc(F)ccc1Oc1cncnc1N1CC2(CCNCC2)C1]

Crude intermediate 24 (4 g) was basified with sat. ammonium bicarbonate (200 mL), and extracted with EtOAc (2×50 mL). The organic layer was dried over anhydrous sodium sulfate, filtered, and concentrated under reduced pressure to obtain crude 2-((4-(2,7-diazaspiro[3.5]nonan-2-yl)pyrimidin-5-yl)oxy)-5-fluoro-N-isopropyl-N-(2,2,2-trifluoroethyl)benzamide (3.1 g, 5.71 mmol, 72.1% yield) as a liquid. LCMS (Method B): Rt 0.99 min, 482.2 [M+H]⁺, 88.62%.

Intermediate 25. 2-((4-(7-(((2S,5R)-5-Aminotetrahydro-2H-pyran-2-yl)methyl)-2,7diazaspiro[3.5]nonan-2-yl)pyrimidin-5-yl)oxy)-5-fluoro-N-isopropyl-N-(2,2,2-trifluoroethyl)benzamide hydrochloride

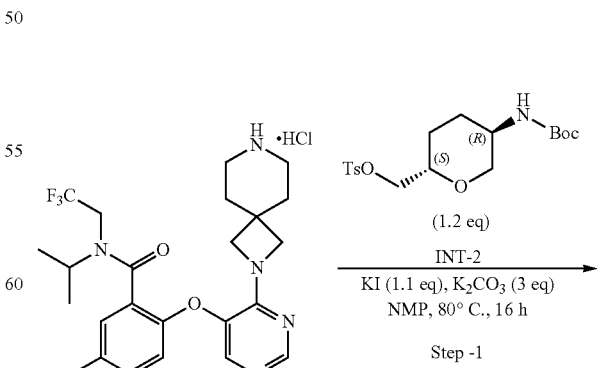

-continued

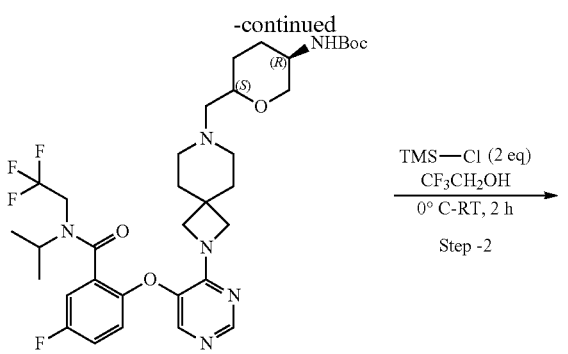

Step 1. tert-Butyl ((3R,6S)-6-((2-(5-(4-fluoro-2-(isopropyl(2,2,2-trifluoroethyl)carbamoyl)phenoxy)pyrimidin-4-yl)-2,7-diazaspiro[3.5]nonan-7-yl)methyl)tetrahydro-2H-pyran-3-yl)carbamate

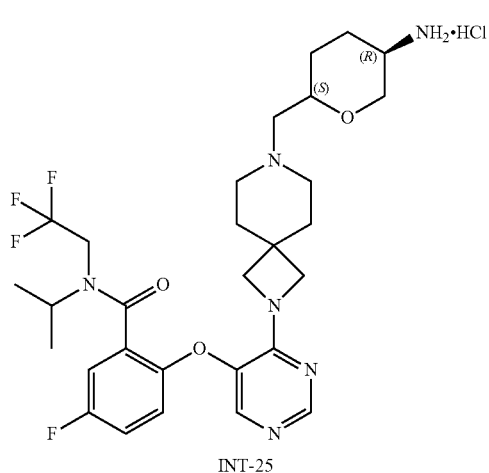

INT-25

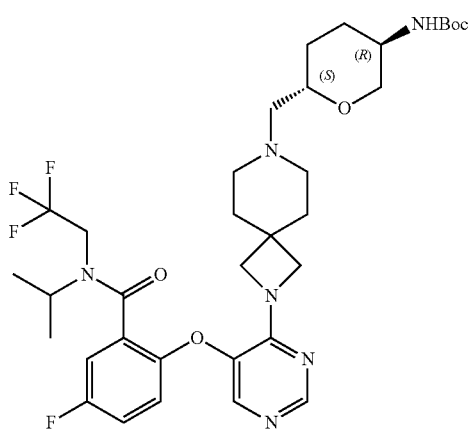

To a dried 100 mL two necked round bottom flask under nitrogen atmosphere, 2-((4-(2,7-diazaspiro[3.5]nonan-2-yl)pyrimidin-5-yl)oxy)-5-fluoro-N-isopropyl-N-(2,2,2-trifluoroethyl)benzamide hydrochloride (900 mg, 1.738 mmol) and ((2S,5R)-5-((tert-butoxycarbonyl)amino)tetrahydro-2H-pyran-2-yl)methyl-4-methylbenzenesulfonate (737 mg, 1.911 mmol) were added in NMP (10 mL) at RT. To this solution, K₂CO₃ (720 mg, 5.21 mmol) and KI (346 mg, 2.085 mmol) were added, and the reaction mixture was stirred at 80° C. for 16 h. The progress of the reaction was monitored with TLC (5% MeOH in DCM). After 16 h, the reaction mixture was quenched with cold water (50 mL) and extracted with EtOAc (2×30 mL). The combined organic layer was dried over anhydrous sodium sulfate and filtered, and the filtrate was concentrated under reduced pressure to obtained 2.5 g of crude compound as brown gum. The crude compound was purified by Biotage-isolera one, using 230-400 mesh silica gel. The desired product was eluted in 3% MeOH in DCM. The fractions containing the desired product were collected and concentrated under reduced pressure to obtain tert-butyl ((3R,6S)-6-((2-(5-(4-fluoro-2-(isopropyl (2,2,2-trifluoroethyl)carbamoyl)phenoxy)pyrimidin-4-yl)-2,7-diazaspiro[3.5]nonan-7-yl)methyl)tetrahydro-2H-pyran-3-yl)carbamate (1.2 g, 0.858 mmol, 49.4% yield) as a viscous liquid. LCMS (Method B): Rt 1.47 min, m/z: 695.2 [M+H]⁺, 49.66%.

Step 2. 2-((4-(7-(((2S,5R)-5-Aminotetrahydro-2H-pyran-2-yl)methyl)-2,7diazaspiro[3.5]nonan-2-yl)pyrimidin-5-yl)oxy)-5-fluoro-N-isopropyl-N-(2,2,2 trifluoroethyl)benzamide hydrochloride (Intermediate 25)

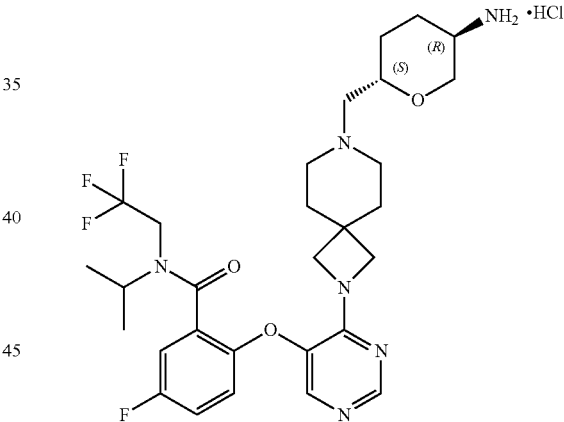

To a dried 100 mL round bottom flask under nitrogen atmosphere, tert-butyl ((3R,6S)-6-((2-(5-(4-fluoro-2-(isopropyl(2,2,2-trifluoroethyl)carbamoyl)phenoxy)pyrimidin-4-yl)-2,7-diazaspiro[3.5]nonan-7-yl)methyl)tetrahydro-2H-pyran-3-yl)carbamate (1.2 g, 1.727 mmol) was added in 2,2,2-trifluoroethanol (10 mL). To this solution TMSCl (0.883 ml, 6.91 mmol) was added at 0° C., and the reaction mixture was stirred at RT for 2 h. The progress of the reaction was monitored with TLC (10% MeOH/DCM). After 2 h, the reaction mixture was concentrated under reduced pressure to obtain 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N-isopropyl-N-(2,2,2-trifluoroethyl)benzamide hydrochloride (1 g, 1.244 mmol, 72.0% yield) as a solid. LCMS (Method B): Rt 1.03 min, m/z: 595.2 [M+H]⁺, 78.53%.

Intermediate 26. 2-((4-(2,7-Diazaspiro[3.5]nonan-2-yl)pyrimidin-5-yl)oxy)-N-(3,3-difluorocyclobutyl)-5-fluoro-N-isopropylbenzamide hydrochloride

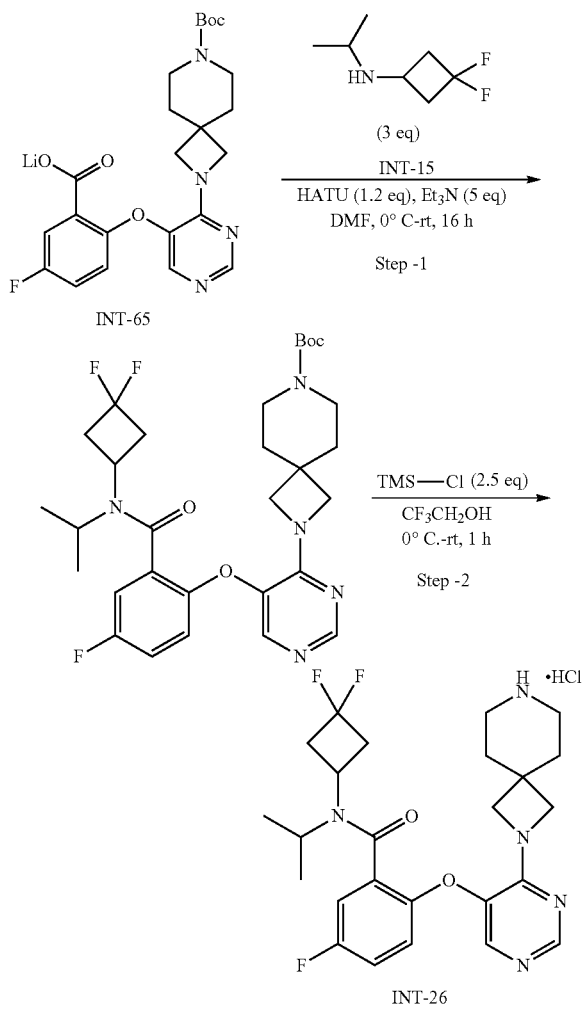

Step 1. tert-Butyl 2-(5-(2-((3,3-difluorocyclobutyl)(isopropyl)carbamoyl)-4-fluorophenoxy)pyrimidin-4-yl)-2,7-diazaspiro[3.5]nonane-7-carboxylate

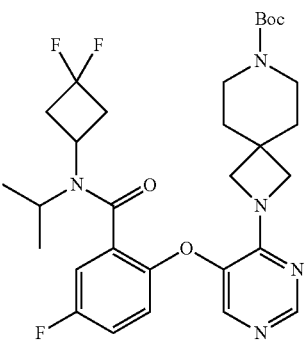 [SMILES: CC(C)N(C(=O)c1cc(F)ccc1Oc1cncnc1N1CC2(CCN(C(=O)OC(C)(C)C)CC2)C1)C1CC(F)(F)C1]

To a dried 250 mL round bottom flask under nitrogen atmosphere, lithium 2-((4-(7-(tert-butoxycarbonyl)-2,7-diazaspiro[3.5]nonan-2-yl)pyrimidin-5-yl)oxy)-5-fluorobenzoate (2 g, 4.31 mmol) was added in DMF (15 mL). To this solution, HATU (1.965 g, 5.17 mmol), 3,3-difluoro-N-isopropylcyclobutan-1-amine (1.927 g, 12.92 mmol) and Et₃N (3.00 ml, 21.53 mmol) were added sequentially, and the reaction mixture was stirred at RT for 16 h. Progress of the reaction was monitored by TLC (100% EtOAc). The reaction mixture was quenched with water (40 mL) and extracted with EtOAc (3×50 mL). The combined organic layers were dried over sodium sulfate, filtered, and concentrated under reduced pressure to obtain crude compound. The crude compound was purified by Biotage-isolera one, using 230-400 mesh silica-gel. The desired product eluted in 5% MeOH in DCM. The fractions containing the desired product were concentrated under reduced pressure to obtain pure tert-butyl 2-(5-(2-((3,3-difluorocyclobutyl)(isopropyl)carbamoyl)-4-fluorophenoxy)pyrimidin-4-yl)-2,7-diazaspiro[3.5]nonane-7-carboxylate (1.82 g, 2.137 mmol, 49.6% yield) as a solid. LCMS (Method C): Rt 2.11 min, m/z: 590.8 [M+H]⁺, 66.63%.

Step 2. 2-((4-(2,7-Diazaspiro[3.5]nonan-2-yl)pyrimidin-5-yl)oxy)-N-(3,3-difluorocyclobutyl)-5-fluoro-N-isopropylbenzamide hydrochloride (Intermediate 26)

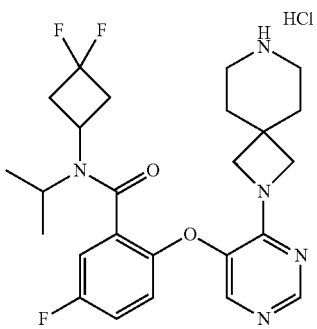 [SMILES: Cl ; CC(C)N(C(=O)c1cc(F)ccc1Oc1cncnc1N1CC2(CCNCC2)C1)C1CC(F)(F)C1]

To a dried 50 mL three necked round bottom flask under nitrogen atmosphere, tert-butyl 2-(5-(2-((3,3-difluorocyclobutyl)(isopropyl)carbamoyl)-4-fluorophenoxy)pyrimidin-4-yl)-2,7-diazaspiro[3.5]nonane-7-carboxylate (1.93 g, 3.27 mmol) was added and dissolved in 2,2,2-trifluoroethanol (15 mL). The solution was cooled to 0° C. and TMSCl (1.039 mL, 8.18 mmol) was added, and the reaction was stirred at RT for 1 h. Progress of the reaction was monitored by TLC (10% MeOH in DCM). The reaction mixture was concentrated under reduced pressure to obtain the crude product which was co-distilled with EtOAc (2×20 mL) to obtain 2-((4-(2,7-diazaspiro[3.5]nonan-2-yl)pyrimidin-5-yl)oxy)-N-(3,3-difluorocyclobutyl)-5-fluoro-N-isopropylbenzamide hydrochloride (1.66 g, 2.56 mmol, 78% yield) as a solid. LCMS (Method C): Rt 1.57 min, m/z: 490.3 [M+H]⁺, 48.13%.

317

Intermediate 27. 2-((4-(7-(((2S,5R)-5-Aminotetrahydro-2H-pyran-2-yl)methyl)-2,7-diazaspiro[3.5]nonan-2-yl)pyrimidin-5-yl)oxy)-N-(3,3-difluorocyclobutyl)-5-fluoro-N-isopropylbenzamide hydrochloride

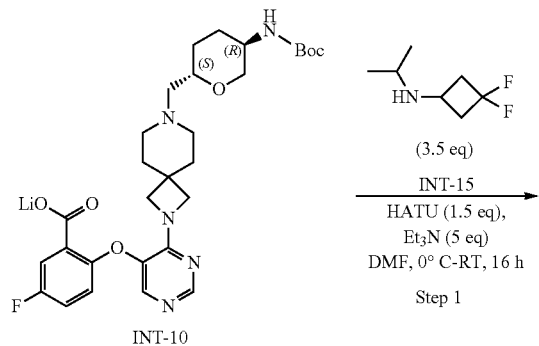

318

Step 1. tert-Butyl ((3R,6S)-6-((2-(S-(2-((3,3-difluorocyclobutyl)(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate

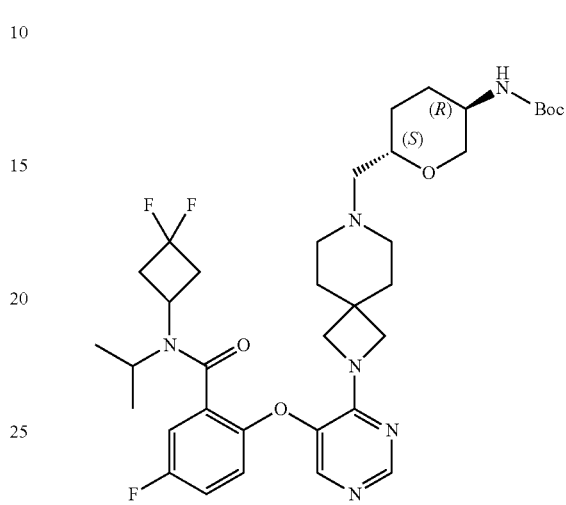

To a dried 250 mL single necked round bottom flask under nitrogen atmosphere, lithium 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (5 g, 8.66 mmol) was added and dissolved in DMF (60 mL). To this solution, Et$_3$N (6.03 mL, 43.3 mmol) and HATU (4.94 g, 12.99 mmol) were added at RT. The solution was stirred for 10 min, then 3,3-difluoro-N-isopropylcyclobutan-1-amine (4.52 g, 30.3 mmol) was added, and the mixture was stirred for 16 h. Progress of the reaction was monitored by TLC (10% MeOH in DCM). The reaction mixture was quenched with water (100 mL) and extracted with EtOAc (2×100 mL). The combined organic layer was washed with brine solution (100 mL), dried over sodium sulfate, and filtered, and the filtrate was concentrated under reduced pressure. The crude compound was purified by Biotage-isolera one, using 230-400 mesh silica-gel. The desired product was eluted in 5% MeOH in DCM. The fractions containing the desired product were collected and concentrated under reduced pressure to obtain tert-butyl ((3R,6S)-6-((2-(5-(2-((3,3-difluorocyclobutyl)(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (5.1 g, 5.95 mmol, 68.8% yield) as a viscous liquid. LCMS (Method A): Rt 2.25 min, m/z: 703.5 [M+H]$^+$, 82.07%.

319

Step 2. 2-((4-(7-(((2S,5R)-5-Aminotetrahydro-2H-pyran-2-yl)methyl)-2,7-diazaspiro[3.5]nonan-2-yl)pyrimidin-5-yl)oxy)-N-(3,3-difluorocyclobutyl)-5-fluoro-N-isopropylbenzamide hydrochloride (Intermediate 27)

320

Intermediate 28. (R)-2-((4-(2,7-Diazaspiro[3.5]nonan-2-yl)pyrimidin-5-yl)oxy)-5-fluoro-N-isopropyl-N-(tetrahydrofuran-3-yl)benzamide hydrochloride and Intermediate 29: 2-((4-(7-(((2R,5S)-5-aminotetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide hydrochloride

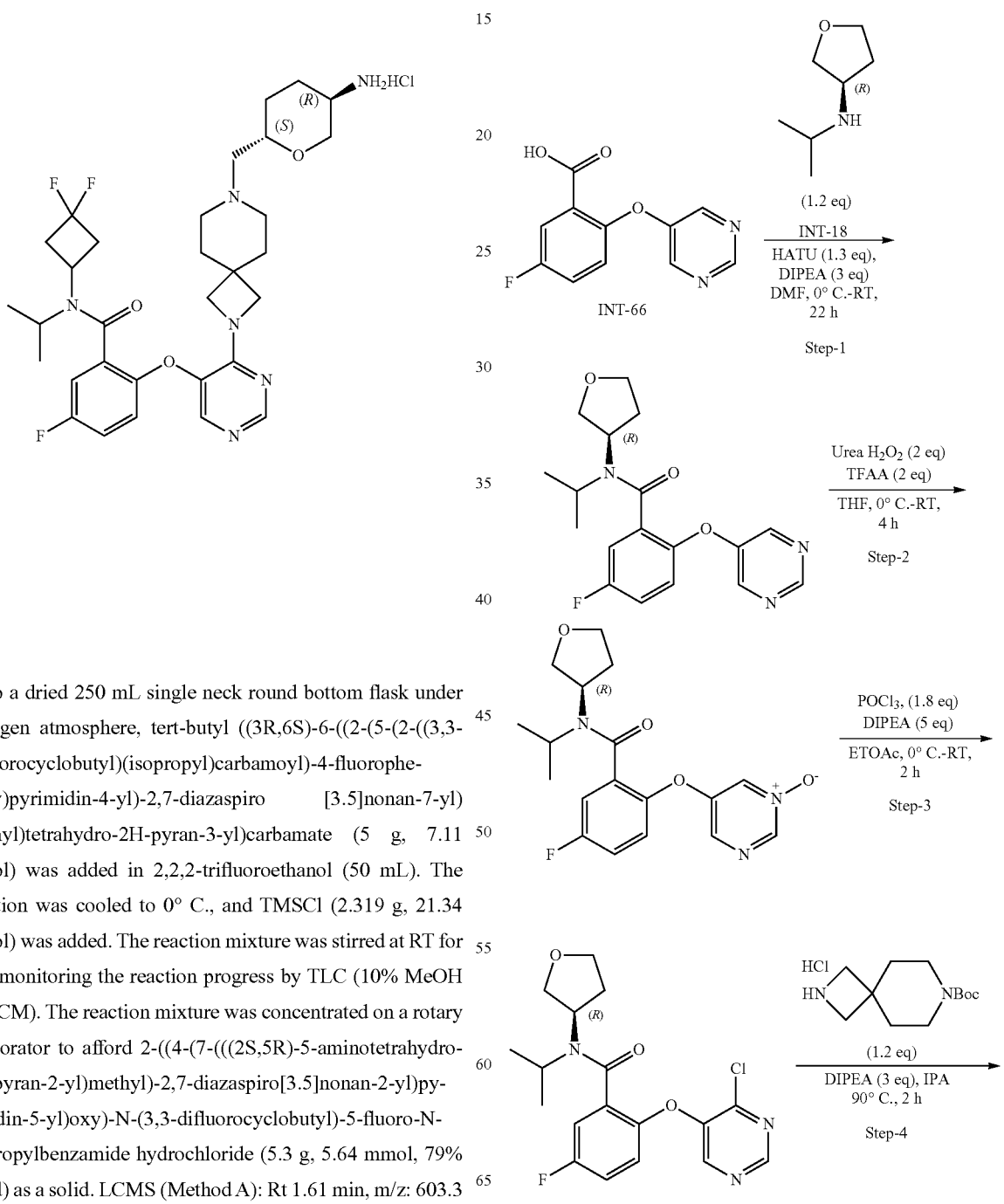

To a dried 250 mL single neck round bottom flask under nitrogen atmosphere, tert-butyl ((3R,6S)-6-((2-(5-(2-(((3,3-difluorocyclobutyl)(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (5 g, 7.11 mmol) was added in 2,2,2-trifluoroethanol (50 mL). The solution was cooled to 0° C., and TMSCl (2.319 g, 21.34 mmol) was added. The reaction mixture was stirred at RT for 1 h, monitoring the reaction progress by TLC (10% MeOH in DCM). The reaction mixture was concentrated on a rotary evaporator to afford 2-((4-(7-(((2S,5R)-5-aminotetrahydro-2H-pyran-2-yl)methyl)-2,7-diazaspiro[3.5]nonan-2-yl)pyrimidin-5-yl)oxy)-N-(3,3-difluorocyclobutyl)-5-fluoro-N-isopropylbenzamide hydrochloride (5.3 g, 5.64 mmol, 79% yield) as a solid. LCMS (Method A): Rt 1.61 min, m/z: 603.3 [M+H]$^+$, 67.99%.

-continued

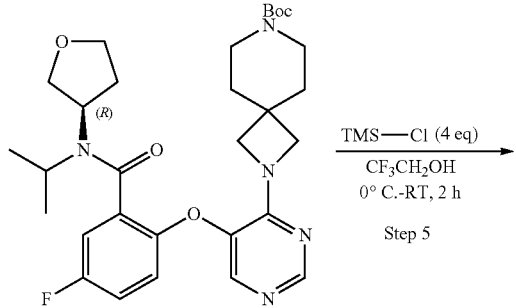

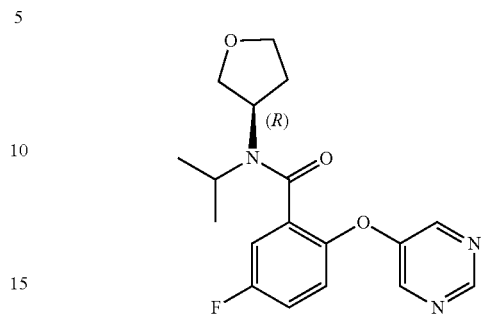

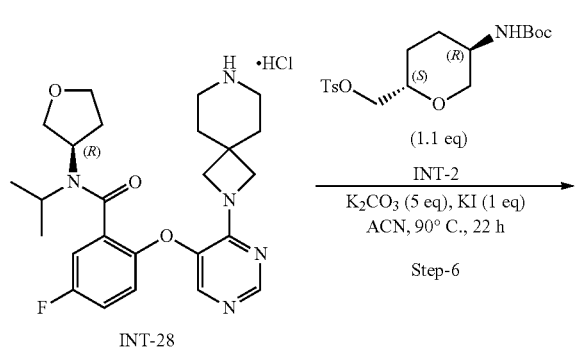

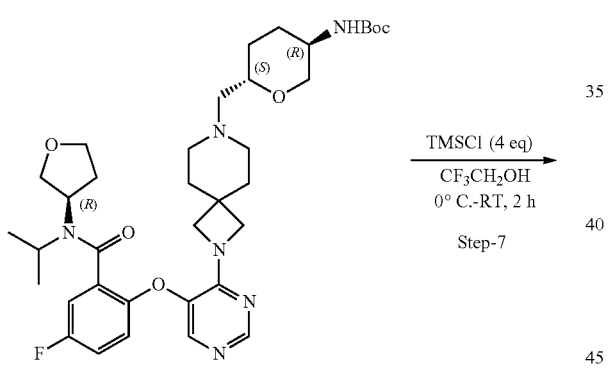

Step 1. (R)-5-Fluoro-N-isopropyl-2-(pyrimidin-5-yloxy)-N-(tetrahydrofuran-3-yl)benzamide

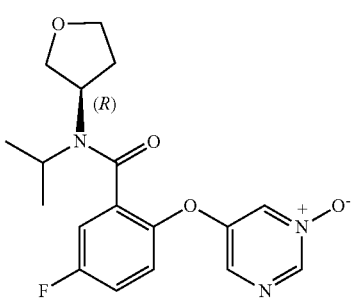

To a dried 1000 mL two necked round bottom flask under nitrogen atmosphere, 5-fluoro-2-(pyrimidin-5-yloxy)benzoic acid (25.0 g, 107 mmol) was added in DMF (250 mL). To this solution, DIPEA (59.1 mL, 320 mmol), HATU (60.9 g, 160 mmol) and (R)—N-isopropyltetrahydrofuran-3-amine (16.55 g, 128 mmol) were added at 0° C. The reaction was stirred at 0° C. for 10 min, then was allowed to warm to RT and stirred 22 h. Progress of the reaction was monitored by TLC (100% EtOAc in hexane). The reaction mixture was diluted with water (300 mL) and extracted with EtOAc (2×500 mL). The combined organic layers were washed with brine solution (2×300 mL), dried over $Na_2SO_4$, and filtered, and the filtrate was concentrated on a rotary evaporator to afford crude (R)-5-fluoro-N-isopropyl-2-(pyrimidin-5-yloxy)-N-(tetrahydrofuran-3-yl)benzamide (22.5 g, 34.9 mmol, 32.7% yield) as a liquid. LCMS (Method B): Rt 1.63 min, m/z: 346.2 [M+H]$^+$, 53.64%.

Step 2. ((R)-5-(4-Fluoro-2-(isopropyl(tetrahydrofuran-3-yl)carbamoyl)phenoxy)pyrimidine 1-oxide

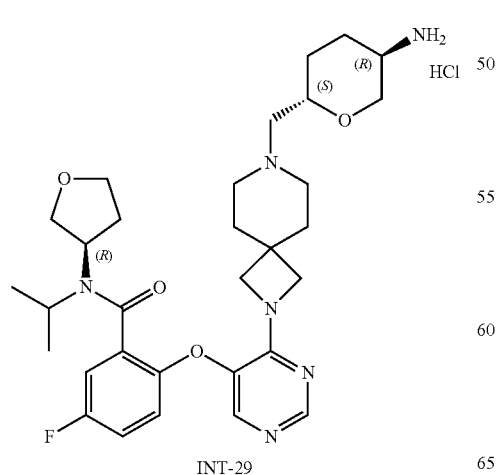

To a dried 1000 mL three neck RB under nitrogen atmosphere, (R)-5-fluoro-N-isopropyl-2-(pyrimidin-5-yloxy)-N-(tetrahydrofuran-3-yl)benzamide (17.0 g, 49.2 mmol) was added in THF (170 mL). To this solution, urea hydrogen peroxide (9.26 g, 98 mmol) was added followed by dropwise addition of TFAA (13.68 mL, 98 mmol) at 0° C. The resulting mixture was stirred at RT for 2 h. Another portion of urea hydrogen peroxide (9.26 g, 98 mmol) mmol) and TFAA (136.8 ml, 98 mmol) were added at 0° C., and the reaction mixture was further stirred at RT for 2 h. Progress of the reaction was monitored by TLC (100% EtOAc). After completion, the reaction mixture was quenched with saturated bicarbonate solution (200 mL), and the reaction mixture was extracted with EtOAc (3×500 mL). The combined organic layers were washed with saturated sodium thiosulfate solution (2×250 mL), dried over sodium sulfate, and filtered, and the filtrate was concentrated on a rotary evaporator to obtain the crude product. The crude product was washed with 20% EtOAc in hexane (60 mL) and dried under reduced pressure to afford ((R)-5-(4-fluoro-2-(isopropyl(tetrahydrofuran-3-yl)carbamoyl)phenoxy)pyrimidine 1-oxide (15.0 g, 23.66 mmol, 48.1% yield) as a solid. LCMS (Method B): Rt 1.335 min, m/z: 362.2 [M+H]$^+$, 56.67%.

Step 3. (R)-2-((4-Chloropyrimidin-5-yl)oxy)-5-fluoro-N-isopropyl-N-(tetrahydrofuran-3-yl)benzamide

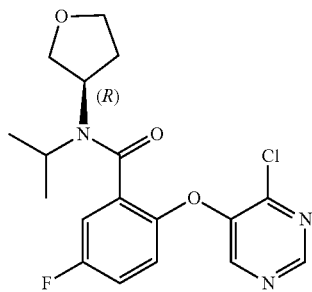

To a dried 250 mL three necked round bottom flask under nitrogen atmosphere, (R)-5-(4-fluoro-2-(isopropyl(tetrahydrofuran-3-yl)carbamoyl)phenoxy)pyrimidine 1-oxide (18.0 g, 49.8 mmol) was suspended in EtOAc (180 mL). To this solution, DIPEA (43.4 mL, 249 mmol) was added followed by dropwise addition of POCl$_3$ (8.38 mL, 90 mmol) at 0° C. The resulting reaction was stirred at RT for 2 h. The progress of the reaction was monitored by TLC (30% EtOAc in hexane). The reaction mixture was concentrated under reduced pressure to afford crude compound. The crude compound was purified by Biotage-isolera one, using 230-400 mesh silica-gel. The desired product was eluted in 30-45% EtOAc in hexane. The fractions containing the desired product were concentrated under reduced pressure to obtain ((R)-2-((4-chloropyrimidin-5-yl)oxy)-5-fluoro-N-isopropyl-N-(tetrahydrofuran-3-yl)benzamide (2.4 g, 5.06 mmol, 10.15% yield) as a viscous liquid. LCMS (Method E): Rt 1.72 min, m/z: 380.1 [M+H]$^+$, 80.23%.

Step 4. tert-Butyl (R)-2-(5-(4-fluoro-2-(isopropyl(tetrahydrofuran-3-yl)carbamoyl)phenoxy)pyrimidin-4-yl)-2,7-diazaspiro[3.5]nonane-7-carboxylate

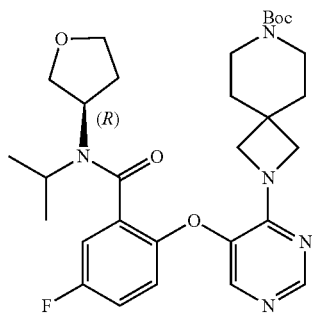

To a dried 250 mL three necked round bottom flask under nitrogen atmosphere, (R)-2-((4-chloropyrimidin-5-yl)oxy)-5-fluoro-N-isopropyl-N-(tetrahydrofuran-3-yl)benzamide (2.4 g, 6.32 mmol) was added in 2-propanol (10 mL). To this solution, DIPEA (3.50 mL, 18.96 mmol) and added followed by the dropwise addition of tert-butyl 2,7-diazaspiro[3.5]nonane-7-carboxylate hydrochloride (1.993 g, 7.58 mmol)) at 0° C. The resulting reaction mixture was stirred at 90° C. for 2 h. The reaction progress was monitored by TLC (50% EtOAc in hexane). After 2 h, the reaction mixture was concentrated under reduced pressure, diluted with water (100 mL), and extracted with EtOAc (3×75 mL). The combined organic layer was washed with brine solution (20 mL), dried over sodium sulfate, and filtered, and the filtrate was concentrated on a rotary evaporator to obtain the crude product. The crude product was purified by Biotage-isolera one, using 230-400 mesh silica-gel. The desired product was eluted in 100% EtOAc. The fractions containing the desired product were concentrated under reduced pressure to afford tert-butyl (R)-2-(5-(4-fluoro-2-(isopropyl(tetrahydrofuran-3-yl)carbamoyl)phenoxy)pyrimidin-4-yl)-2,7-diazaspiro[3.5]nonane-7-carboxylate (2.0 g, 3.31 mmol, 52.4% yield) as a solid. LCMS (Method A): Rt 1.718 min, m/z: 570.4 [M+H]), 94.64%.

Step 5. (R)-2-((4-(2,7-Diazaspiro[3.5]nonan-2-yl)pyrimidin-5-yl)oxy)-5-fluoro-N-isopropyl-N-(tetrahydrofuran-3-yl)benzamide hydrochloride (Intermediate 28)

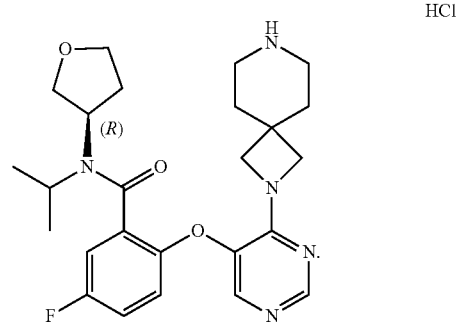

To a dried 100 mL three necked round bottom flask under nitrogen atmosphere, tert-butyl (R)-2-(5-(4-fluoro-2-(isopropyl(tetrahydrofuran-3-yl)carbamoyl)phenoxy)pyrimidin-4-yl)-2,7-diazaspiro[3.5]nonane-7-carboxylate (2.0 g, 3.51 mmol) was added in 2,2,2-trifluoroethanol (11.0 mL). To this reaction mixture TMSCI (1.782 mL, 14.04 mmol) was added at 0° C., and the resulting reaction was stirred at RT for 2 h. The progress of the reaction was monitored by TLC (10% MeOH in DCM). After 2 h, the reaction mixture was concentrated under reduced pressure to afford crude product. The crude product was triturated with EtOAc to afford (R)-2-((4-(2,7-diazaspiro[3.5]nonan-2-yl)pyrimidin-5-yl)oxy)-5-fluoro-N-isopropyl-N-(tetrahydrofuran-3-yl)benzamide hydrochloride ((1.7 g, 3.23 mmol, 92% yield) as a solid. LCMS (Method B): Rt 1.09 min, m/z: 470.2 [M+H]$^+$, 96.42%.

Step 7. tert-Butyl ((3S,6R)-6-((2-(5-(4-fluoro-2-(isopropyl((R)-tetrahydrofuran-3-yl)carbamoyl)phenoxy)pyrimidin-4-yl)-2,7-diazaspiro[3.5]nonan-7-yl)methyl)tetrahydro-2H-pyran-3-yl)carbamate

Step 8. 2-((4-(7-(((2R,5S)-5-aminotetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide hydrochloride (Intermediate 29)

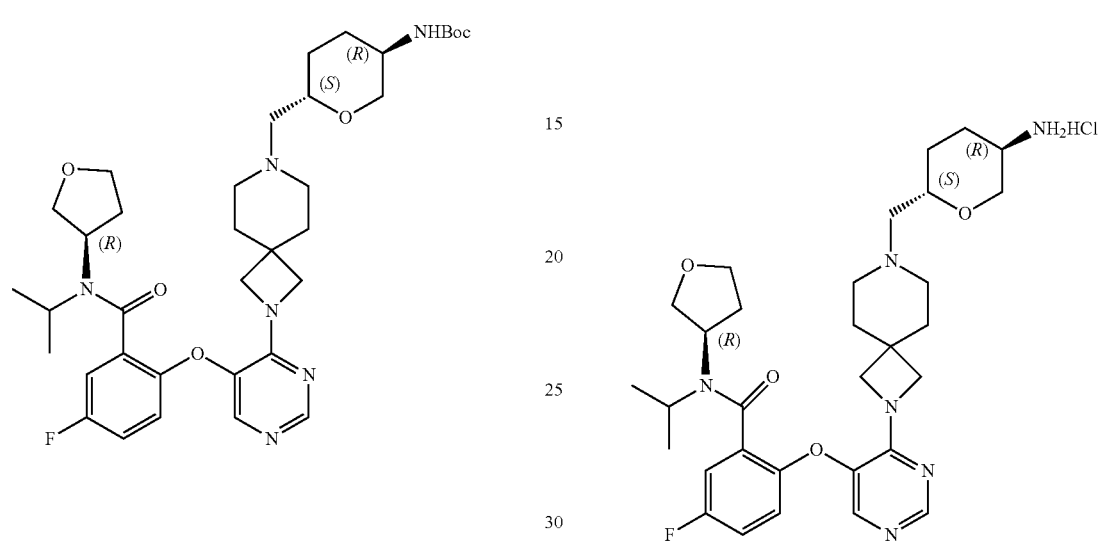

To a dried 100 mL two necked round bottom flask under nitrogen atmosphere, (R)-2-((4-(2,7-diazaspiro[3.5]nonan-2-yl)pyrimidin-5-yl)oxy)-5-fluoro-N-isopropyl-N-(tetrahydrofuran-3-yl)benzamide hydrochloride (0.6 g, 1.186 mmol) was added in ACN (10 mL). To this reaction mixture K$_2$CO$_3$ (0.819 g, 5.93 mmol), KI (0.197 g, 1.186 mmol)) and ((2R,5S)-5-((tert-butoxycarbonyl)amino)tetrahydro-2H-pyran-2-yl)methyl 4-methylbenzenesulfonate (0.503 g, 1.304 mmol) were added at RT, and the resulting reaction mixture was stirred at 90° C. for 22 h. TLC showed presence of both the starting materials. NMP (5 mL) was added to the reaction mixture and the reaction was continued at 90° C. for 22 h. The reaction progress was monitored by TLC (10% MeOH in DCM). The reaction mixture was diluted with ice cold water (30 mL) and diluted with EtOAc (100 mL). The organic layer was separated, and the aqueous layer was further extracted with EtOAc (2×30 mL). The combined organic layers were washed with saturated ammonium chloride solution (50 mL), dried over Na$_2$SO$_4$, and filtered, and the filtrate was concentrated under reduced pressure afford the crude compound. The crude compound was purified by Biotage-isolera one, using 230-400 mesh silica-gel. The desired product was eluted in 8% MeOH in DCM. The fractions containing the desired product were concentrated under reduced pressure to afford tert-butyl ((3S,6R)-6-((2-(5-(4-fluoro-2-(isopropyl((R)-tetrahydrofuran-3-yl)carbamoyl)phenoxy)pyrimidin-4-yl)-2,7-diazaspiro[3.5]nonan-7-yl)methyl)tetrahydro-2H-pyran-3-yl)carbamate (0.72 g, 0.852 mmol, 71.9% yield) as a viscous liquid. LCMS (Method E): Rt 1.80 min, 683.6 [M+H]$^+$, 80.82%.

To a dried 100 mL three necked round bottom flask under nitrogen atmosphere, tert-butyl ((3S,6R)-6-((2-(5-(4-fluoro-2-(isopropyl((R)-tetrahydrofuran-3-yl)carbamoyl)phenoxy)pyrimidin-4-yl)-2,7-diazaspiro[3.5]nonan-7-yl)methyl)tetrahydro-2H-pyran-3-yl)carbamate (0.72 g, 1.054 mmol) was added in 2,2,2-trifluoroethanol (10 mL). To this reaction mixture TMSCI (0.539 ml, 4.22 mmol) was added at 0° C., and the resulting reaction was stirred at RT for 2 h. The reaction progress was monitored by TLC (10% methanol in DCM). After 2 h, the reaction mixture was concentrated under reduced pressure and triturated with EtOAc (3 mL) to afford crude compound. The crude material was basified with 10% NaHCO$_3$ and extracted with 10% MeOH in DCM (3×20 mL). The combined organic layers were dried over Na$_2$SO$_4$ and concentrated under vacuum to afford 2-((4-(7-(((2R,5S)-5-aminotetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide hydrochloride (0.3 g, 0.319 mmol, 30.2% yield) as a viscous liquid. LCMS (Method E): Rt 1.34 min, m/z: 583.5 [M+H]$^+$, 61.98%.

327
Intermediate 30. (S)-2-((4-(2,7-Diazaspiro[3.5]nonan-2-yl)pyrimidin-5-yl)oxy)-5-fluoro-N-isopropyl-N-(tetrahydrofuran-3-yl)benzamide hydrochloride and
Intermediate 31: 2-((4-(7-(((2R,5S)-5-Aminotetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide hydrochloride
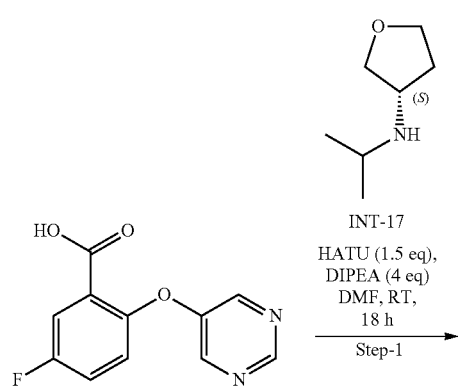
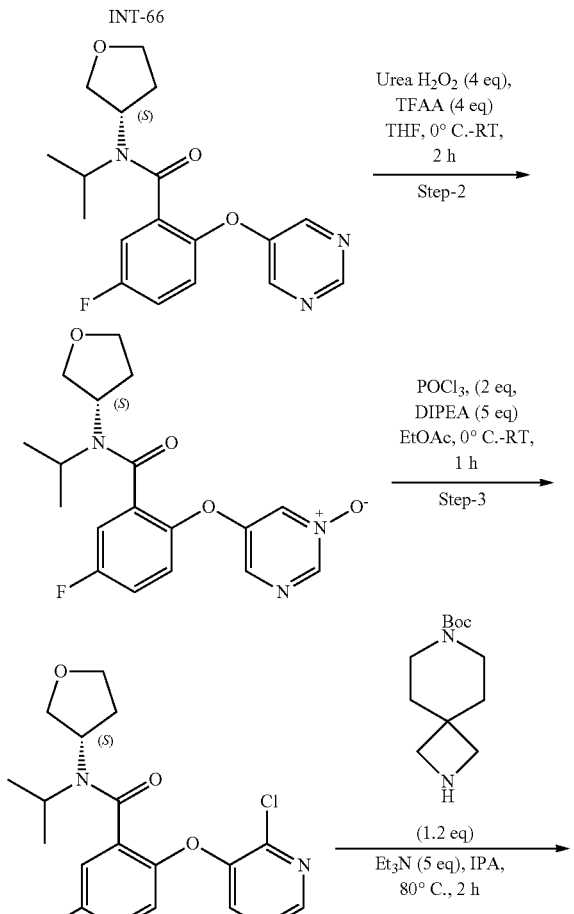
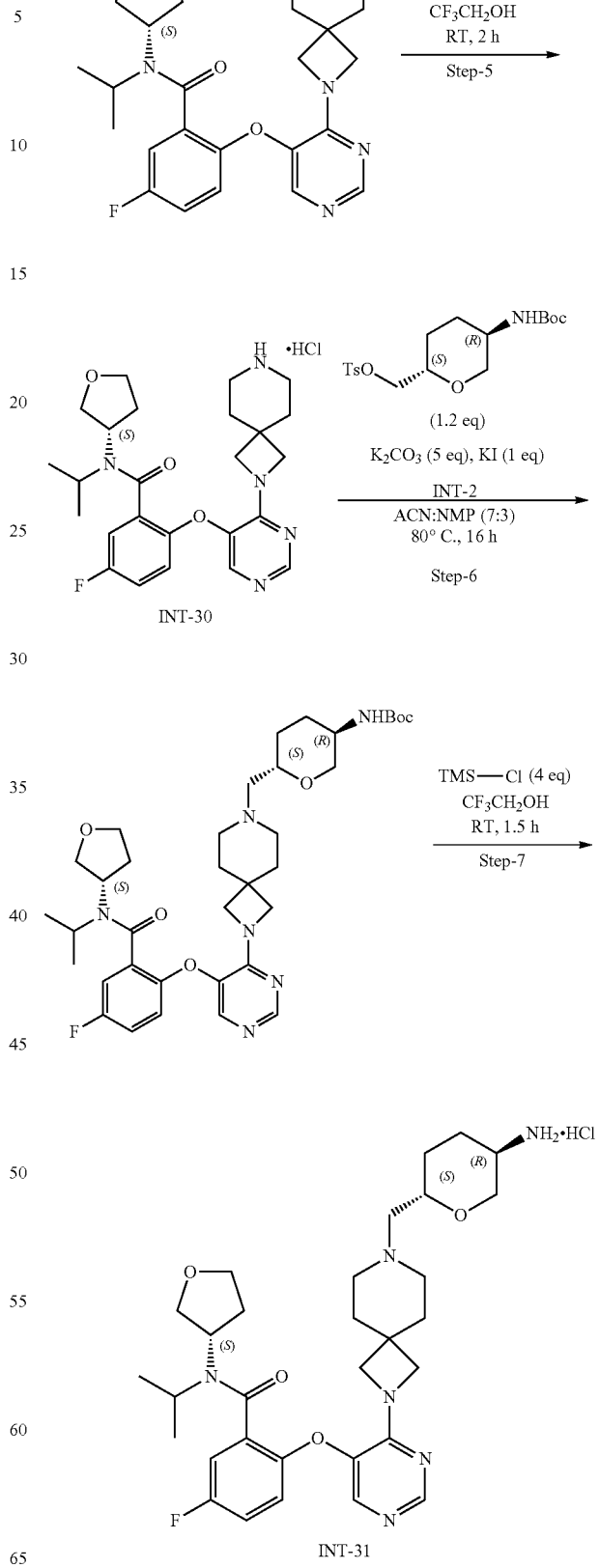

Step 1. (S)-5-Fluoro-N-isopropyl-2-(pyrimidin-5-yloxy)-N-(tetrahydrofuran-3-yl)benzamide

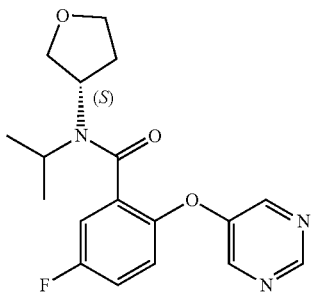

To a dried 250 mL two necked round bottom flask under nitrogen atmosphere, 5-fluoro-2-(pyrimidin-5-yloxy)benzoic acid (4 g, 17.08 mmol) was added in DMF (20 mL). To this solution, Et₃N (9.52 mL, 68.3 mmol), HATU (9.74 g, 25.6 mmol) and (S)—N-isopropyltetrahydrofuran-3-amine (3.31 g, 25.6 mmol) were added at RT, and the reaction mixture was stirred at RT for 16 h. The reaction progress was monitored by TLC and LCMS. After 16 h, the reaction mixture was cooled to 0° C., quenched with saturated ammonium chloride (100 mL) and extracted with EtOAc (2×250 mL). The combined organic extract was washed with brine (150 mL), dried over anhydrous sodium sulfate, and filtered, and the filtrate was concentrated under reduced pressure to afford the crude material. The crude material was purified by silica gel column chromatography, eluting with 50% EtOAc in hexane. The fractions containing the desired product were concentrated under reduced pressure to obtain (S)-5-fluoro-N-isopropyl-2-(pyrimidin-5-yloxy)-N-(tetrahydrofuran-3-yl)benzamide (0.7 g, 1.581 mmol, 9.26% yield) as a light brown gum. ¹H NMR (400 MHz, DMSO-d₆) δ 9.00-8.90 (m, 1H), 8.60-8.48 (m, 2H), 7.49-7.27 (m, 3H), 4.00-3.83 (m, 2H), 3.80-3.65 (m, 2H), 3.55-3.38 (m, 2H), 3.23-3.06 (m, 1H), 1.19-0.97 (m, 7H); LCMS (Method B): Rt 1.50 min, 346.2 [M+H]⁺, 77.69%.

Step 3. (S)-5-(4-Fluoro-2-(isopropyl(tetrahydrofuran-3-yl)carbamoyl)phenoxy)pyrimidine 1-oxide

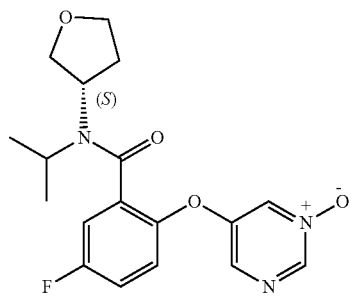

To a dried 100 mL three necked round bottom flask under nitrogen, was added (S)-5-fluoro-N-isopropyl-2-(pyrimidin-5-yloxy)-N-(tetrahydrofuran-3-yl)benzamide (0.7 g, 2.027 mmol) in THF (12 mL). The resulting solution was cooled to 0° C., and urea hydrogen peroxide (0.381 g, 4.05 mmol)) was added, followed by dropwise addition of TFAA (0.573 mL, 4.05 mmol), maintaining the temperature below RT. The reaction was stirred at RT for 2 h. Another portion of urea hydrogen peroxide (0.381 g, 4.05 mmol) and TFAA (0.573 mL, 4.05 mmol) were added to the reaction mixture at 0° C., and the reaction was stirred at RT for 2 h, monitoring the reaction progress by TLC. After completion of the reaction, the reaction mixture was quenched with bicarbonate solution (20 mL) and extracted with ethyl acetate (3×100 mL). The combined organic layers were dried over sodium sulfate and filtered, and the filtrate was concentrated on a rotary evaporator under reduced pressure to obtain the crude product. The crude product was washed with hexane (3×100 mL) and dried to afford crude (S)-5-(4-fluoro-2-(isopropyl(tetrahydrofuran-3-yl)carbamoyl)phenoxy) pyrimidine 1-oxide (0.94 g, 1.509 mmol, 74.4% yield) as a semi solid. LCMS (Method A): Rt 1.33 min, m/z: 362.1 [M+H]⁺, 58.03%.

Step 4. (S)-2-((4-Chloropyrimidin-5-yl)oxy)-5-fluoro-N-isopropyl-N-(tetrahydrofuran-3-yl)benzamide

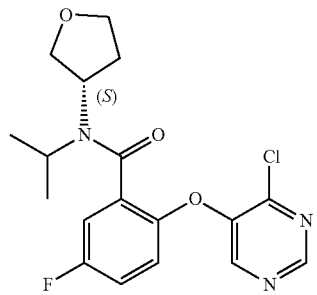

To a stirred solution of (S)-5-(4-fluoro-2-(isopropyl(tetrahydrofuran-3-yl)carbamoyl)phenoxy)pyrimidine 1-oxide (9.3 g, 25.7 mmol) in dry EtOAc (120 mL) was added DIPEA (23.76 mL, 129 mmol) and POCl₃ (4.81 ml, 51.5 mmol) dropwise at 0° C. under nitrogen atmosphere. The reaction was stirred at RT for 1 h. The reaction progress was monitored by TLC. After completion of the reaction, the reaction mixture was concentrated under reduced pressure to afford crude product. The crude product was purified by silica gel column chromatography using 50-80% EtOAc in hexane as an eluent. The fractions containing the desired product were concentrated under reduced pressure to obtain (S)-2-((4-chloropyrimidin-5-yl)oxy)-5-fluoro-N-isopropyl-N-(tetrahydrofuran-3-yl)benzamide (2.1 g, 4.15 mmol, 16.11% yield) as a light brown gum. LCMS (Method A): Rt 1.88 min, m/z: 380.1 [M+H]⁺, 74.82%.

Step 5. tert-Butyl(S)-2-(5-(4-fluoro-2-(isopropyl (tetrahydrofuran-3-yl)carbamoyl)phenoxy)pyrimidin-4-yl)-2,7-diazaspiro[3.5]nonane-7-carboxylate

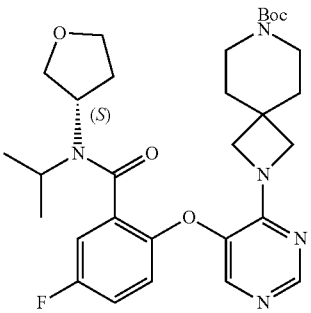

To a stirred solution of tert-butyl 2,7-diazaspiro[3.5] nonane-7-carboxylate hydrochloride (1.5 g, 5.71 mmol) in dry IPA (25 mL) was added Et₃N (3.98 mL, 28.5 mmol) and (S)-2-((4-chloropyrimidin-5-yl)oxy)-5-fluoro-N-isopropyl-N-(tetrahydrofuran-3-yl)benzamide (2.168 g, 5.71 mmol) at RT under nitrogen atmosphere. The reaction was heated at 80° C. for 2 h. The reaction progress was monitored by TLC. After completion, the reaction mixture was concentrated under reduced pressure to afford the crude product. The crude product was purified by silica gel column chromatography using 2% MeOH in DCM as an eluent. The fractions containing the desired product were concentrated under reduced pressure to obtain tert-butyl (S)-2-(5-(4-fluoro-2-(isopropyl(tetrahydrofuran-3-yl)carbamoyl) phenoxy)pyrimidin-4-yl)-2,7-diazaspiro[3.5]nonane-7-carboxylate (2.5 g, 3.48 mmol, 60.9% yield) as a solid. LCMS (Method A): Rt 1.95 min, m/z: 570.8 [M+H]⁺, 79.19%.

Step 6. (S)-2-((4-(2,7-Diazaspiro[3.5]nonan-2-yl) pyrimidin-5-yl)oxy)-5-fluoro-N-isopropyl-N-(tetrahydrofuran-3-yl)benzamide hydrochloride (Intermediate 30)

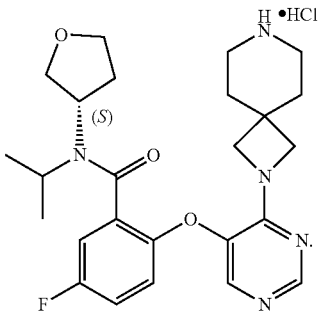

To a stirred solution of tert-butyl (S)-2-(5-(4-fluoro-2-(isopropyl(tetrahydrofuran-3-yl)carbamoyl)phenoxy)pyrimidin-4-yl)-2,7-diazaspiro[3.5]nonane-7-carboxylate (2.5 g, 4.39 mmol) in dry trifluoroethanol (10 mL) was slowly added dropwise TMSCI (2.228 mL, 17.55 mmol) at 0° C. under nitrogen atmosphere. The reaction was stirred at room temperature for 2 h. The reaction progress was monitored by TLC and LCMS. After completion, the reaction mixture was concentrated under reduced pressure to afford crude (S)-2-((4-(2,7-diazaspiro[3.5]nonan-2-yl)pyrimidin-5-yl)oxy)-5-fluoro-N-isopropyl-N-(tetrahydrofuran-3-yl) benzamide hydrochloride (2.6 g, 4.01 mmol, 91% yield) as a solid. LCMS (Method A): Rt 1.28 min, m/z: 470.2 [M+H]⁺, 76.72%.

Step 7. tert-Butyl((3S,6R)-6-((2-(5-(4-fluoro-2-(isopropyl((S)-tetrahydrofuran-3-yl)carbamoyl)phenoxy) pyrimidin-4-yl)-2,7-diazaspiro[3.5]nonan-7-yl) methyl)tetrahydro-2H-pyran-3-yl)carbamate

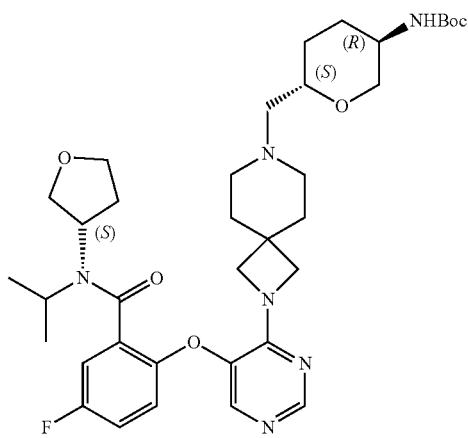

To a stirred solution of (S)-2-((4-(2,7-diazaspiro[3.5] nonan-2-yl)pyrimidin-5-yl)oxy)-5-fluoro-N-isopropyl-N-(tetrahydrofuran-3-yl)benzamide hydrochloride (0.3 g, 0.593 mmol) in CH₃CN:NMP (7:3, 13 mL) was added K₂CO₃ (0.410 g, 2.96 mmol) and KI (0.098 g, 0.593 mmol), followed by ((2S,5R)-5-((tert-butoxycarbonyl)amino)tetrahydro-2H-pyran-2-yl)methyl 4-methyl benzene sulfonate (0.274 g, 0.711 mmol) at RT under nitrogen atmosphere. The resulting reaction mixture was heated at 90° C. for 48 h, and reaction progress was monitored by TLC and LCMS. The reaction mixture was cooled to room temperature, quenched with saturated sodium chloride (10 mL), and extracted with ethyl acetate (2×50 mL). The combined organic extract was washed with brine (50 mL), dried over anhydrous sodium sulfate and filtered, and the filtrate was concentrated under reduced pressure to afford crude tert-butyl ((3R,6S)-6-((2-(5-(4-fluoro-2-(isopropyl((S)-tetrahydrofuran-3-yl)carbamoyl)phenoxy)pyrimidin-4-yl)-2,7-diazaspiro[3.5]nonan-7-yl)methyl)tetrahydro-2H-pyran-3-yl)carbamate ((0.29 g, 0.293 mmol, 49.4% yield) as a light brown gum. LCMS (Method A): Rt 1.89 min, m/z: 683.4 [M+H]⁺, 69.02%.

Step 8. 2-((4-(7-(((2R,5S)—5-Aminotetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide hydrochloride (Intermediate 31)

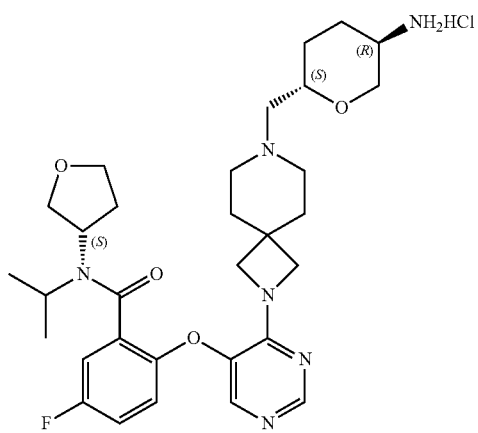

To a stirred solution of tert-butyl ((3R,6S)-6-((2-(5-(4-fluoro-2-(isopropyl((S)-tetrahydrofuran-3-yl)carbamoyl)phenoxy)pyrimidin-4-yl)-2,7-diazaspiro[3.5]nonan-7-yl)methyl)tetrahydro-2H-pyran-3-yl)carbamate (0.29 g, 0.425 mmol) in dry trifluoroethanol (7.5 mL) was slowly added dropwise TMSCl (0.217 mL, 1.699 mmol) at 0° C. under nitrogen atmosphere. The reaction mixture was stirred at room temperature for 1.5 h, monitoring the reaction progress by TLC and LCMS. After completion, the reaction mixture was concentrated under reduced pressure to afford crude 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide hydrochloride (0.26 g, 0.370 mmol, 87% yield) as a solid. LCMS (Method A): Rt 1.434 min, m/z: 583.3 [M+H]+, 61.26%.

Intermediate 32. 2-((4-(2,7-Diazaspiro[3.5]nonan-2-yl)pyrimidin-5-yl)oxy)-N-(cyanomethyl)-5-fluoro-N-isopropylbenzamide hydrochloride

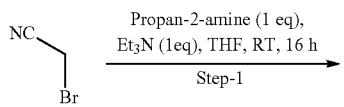

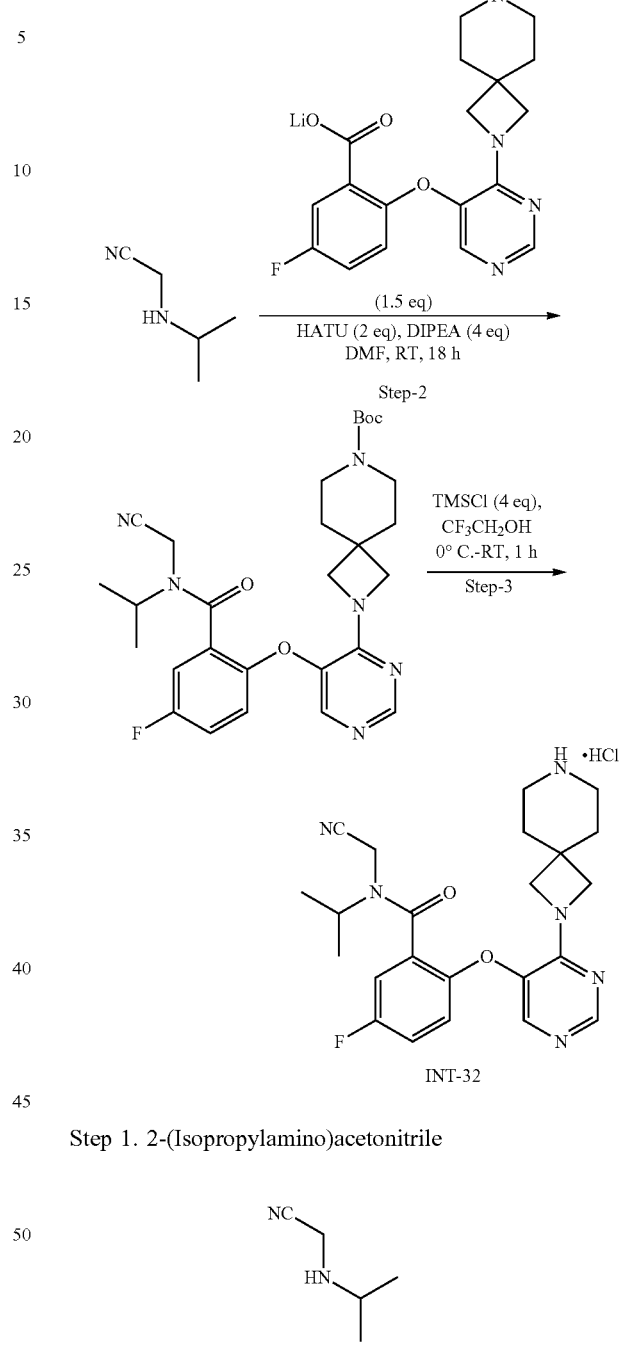

Step 1. 2-(Isopropylamino)acetonitrile

To a stirred solution of 2-bromoacetonitrile (500 mg, 4.17 mmol) in THF (10 mL) was added Et₃N (422 mg, 4.17 mmol), followed by propan-2-amine (246 mg, 4.17 mmol) under nitrogen atmosphere at 0° C. The reaction mixture was stirred at RT for 16 h. The reaction progress was monitored by TLC (10% methanol in DCM). After completion of the reaction, the reaction mixture was quenched with water (10 mL) and extracted with ethyl acetate (3×100 mL). The combined organic layer was dried over anhydrous sodium sulfate and filtered, and the filtrate was concentrated on a rotary evaporator under reduced pressure to obtain crude 2-(isopropylamino)acetonitrile (300 mg, 3.06 mmol, 73.3% yield) as a semisolid. ¹H NMR (400 MHz, DMSO-d₆) δ 3.51-3.42 (m, 1H), 3.15-3.03 (m, 2H), 1.03-0.93 (m, 6H).

Step 2. tert-Butyl 2-(5-(2-((cyanomethyl)(isopropyl)carbamoyl)-4-fluorophenoxy)pyrimidin-4-yl)-2,7-diazaspiro[3.5]nonane-7-carboxylate

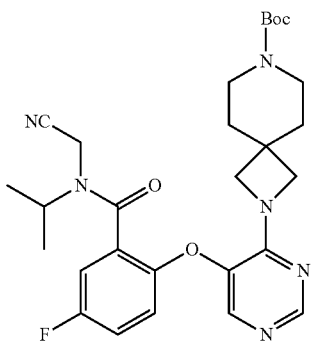 [SMILES: CC(C)N(CC#N)C(=O)c1cc(F)ccc1Oc1cncnc1N1CC2(CCN(C(=O)OC(C)(C)C)CC2)C1]

To a stirred solution of lithium 2-((4-(7-(tert-butoxycarbonyl)-2,7-diazaspiro[3.5]nonan-2-yl)pyrimidin-5-yl)oxy)-5-fluorobenzoate (300 mg, 0.654 mmol) in DMF (10 mL) was added Et₃N (0.365 mL, 2.62 mmol) and HATU (498 mg, 1.309 mmol), followed by 2-(isopropylamino)acetonitrile (96 mg, 0.981 mmol) at 0° C. The reaction mixture was stirred at RT for 16 h. The reaction progress was monitored by TLC (10% methanol in DCM). After completion of reaction, the reaction mixture was quenched with water (25 mL) and extracted with ethyl acetate (2×50 mL). The organic layer was washed with ice cold water (3×20 mL), dried over anhydrous sodium sulfate, and filtered, and the filtrate was concentrated on a rotary evaporator under reduced pressure to obtain the crude compound. The crude compound was purified by prep-HPLC (Method A) to obtain the pure compound tert-butyl 2-(5-(2-((cyanomethyl)(isopropyl)carbamoyl)-4-fluorophenoxy)pyrimidin-4-yl)-2,7-diazaspiro[3.5]nonane-7-carboxylate (300 mg, 0.557 mmol, 85% yield) as pale yellow gum. The product formation was confirmed by LCMS and used in next step. LCMS (Method B): Rt 1.91 min, m/z: 500.4 [M+H]⁺, 99.74%.

Step 3. 2-((4-(2,7-Diazaspiro[3.5]nonan-2-yl)pyrimidin-5-yl)oxy)-N-(cyanomethyl)-5-fluoro-N-isopropylbenzamide hydrochloride (Intermediate 32)

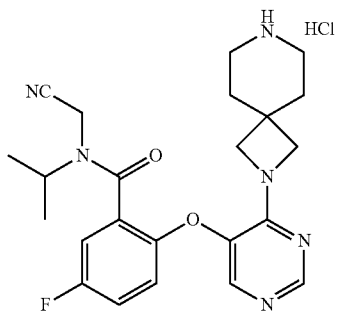 [SMILES: Cl ; CC(C)N(CC#N)C(=O)c1cc(F)ccc1Oc1cncnc1N1CC2(CCNCC2)C1]

To a stirred solution of tert-butyl 2-(5-(2-((cyanomethyl)(isopropyl)carbamoyl)-4-fluorophenoxy)pyrimidin-4-yl)-2,7-diazaspiro[3.5]nonane-7-carboxylate (300 mg, 0.557 mmol) in 2,2,2-trifluoroethanol (10 mL), was added TMSCl (0.285 mL, 2.228 mmol) under nitrogen atmosphere at 0° C. The reaction mixture was stirred at RT for 1 h. The reaction progress was monitored by TLC (10% methanol in DCM). After completion of the reaction, the reaction mixture was concentrated under reduced pressure to obtain crude 2-((4-(2,7-diazaspiro[3.5]nonan-2-yl)pyrimidin-5-yl)oxy)-N-(cyanomethyl)-5-fluoro-N-isopropylbenzamide hydrochloride (255 mg, 0.537 mmol, 96% yield) as a solid. ¹H NMR (400 MHz, DMSO-d₆) δ 8.37 (s, 1H), 7.95-7.80 (m, 1H), 7.45-7.02 (m, 2H), 6.19-5.99 (m, 1H), 4.54-4.37 (m, 2H), 4.11-3.77 (m, 6H), 3.11-2.88 (m, 4H), 1.97-1.81 (m, 4H), 1.25-1.00 (m, 6H).

Intermediate 33. 2-((4-(2,7-Diazaspiro[3.5]nonan-2-yl)pyrimidin-5-yl)oxy)-N-(2-cyanoethyl)-5-fluoro-N-isopropylbenzamide hydrochloride

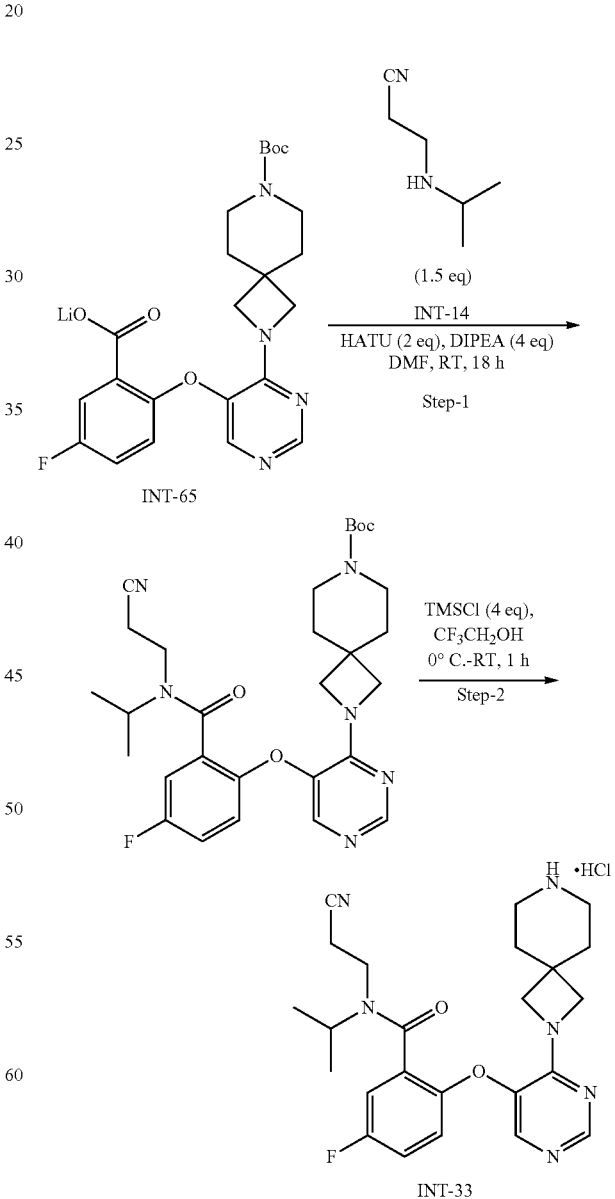

Step 1. tert-Butyl 2-(5-(2-((2-cyanoethyl)(isopropyl) carbamoyl)-4-fluorophenoxy)pyrimidin-4-yl)-2,7-diazaspiro[3.5]nonane-7-carboxylate

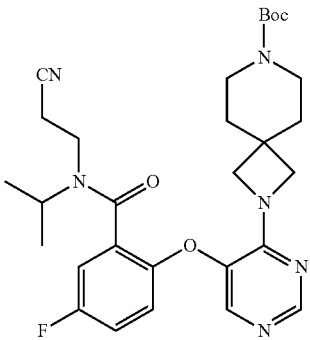 [SMILES: CC(C)N(CCC#N)C(=O)c1cc(F)ccc1Oc1cncnc1N1CC2(CCN(C(=O)OC(C)(C)C)CC2)C1]

To a stirred solution of lithium 2-((4-(7-(tert-butoxycarbonyl)-2,7-diazaspiro[3.5]nonan-2-yl)pyrimidin-5-yl)oxy)-5-fluorobenzoate (500 mg, 1.091 mmol) dissolved in DMF (10 mL) under nitrogen atmosphere, Et$_3$N (0.631 mL, 4.36 mmol), HATU (829 mg, 2.181 mmol) and 3-(isopropylamino)propanenitrile (183 mg, 1.636 mmol) were added at 0° C. The resulting reaction was stirred at RT for 16 h, monitoring the reaction progress by TLC (5% MeOH in DCM). After completion of the reaction, the reaction mixture was diluted with water (50 mL) and extracted with EtOAc (2×50 mL). The organic layer was washed with ice cold water (2×30 mL), dried over anhydrous sodium sulfate, and filtered, and the filtrate was concentrated on a rotary evaporator to obtain the crude product. The crude product was purified by Biotage-isolera one column chromatography using 230-400 mesh silica-gel and eluting with (5-8%) methanol in DCM. The fractions containing the desired product were concentrated under reduced pressure to obtain tert-butyl 2-(5-(2-((2-cyanoethyl)(isopropyl)carbamoyl)-4-fluoro phenoxy)pyrimidin-4-yl)-2,7-diazaspiro[3.5]nonane-7-carboxylate (400 mg, 0.507 mmol, 46.5% yield) as a semisolid. $^1$H NMR (400 MHz, DMSO-d$_6$) δ 8.35-8.27 (m, 1H), 7.87-7.78 (m, 1H), 7.44-7.23 (m, 2H), 7.12-6.98 (m, 1H), 4.51-4.35 (m, 2H), 4.08-3.66 (m, 5H), 3.38-3.34 (m, 2H), 3.29-3.19 (m, 4H), 1.75-1.55 (m, 4H), 1.49-1.31 (m, 9H), 1.22-1.03 (m, 6H); LCMS (Method B): Rt 1.677 min, m/z: 553.5 [M+H]$^+$, 76.57%.

Step 2. 2-((4-(2,7-diazaspiro[3.5]nonan-2-yl)pyrimidin-5-yl)oxy)-N-(2-cyanoethyl)-5-fluoro-N-isopropylbenzamide hydrochloride (Intermediate 33)

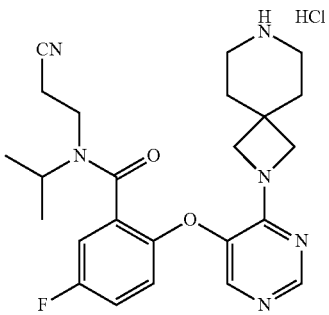 [SMILES: Cl ; CC(C)N(CCC#N)C(=O)c1cc(F)ccc1Oc1cncnc1N1CC2(CCNCC2)C1]

To a stirred solution of tert-butyl 2-(5-(2-((2-cyanoethyl)(isopropyl)carbamoyl)-4-fluorophenoxy)pyrimidin-4-yl)-2,7-diazaspiro[3.5]nonane-7-carboxylate (400 mg, 0.724 mmol) in 2,2,2-trifluoroethanol (10 mL), was added TMSCl (0.370 mL, 2.90 mmol) at 0° C. The reaction mixture was stirred at RT for 1 h, monitoring the reaction progress by TLC (10% MeOH in DCM). After completion of the reaction, the reaction mixture was concentrated on a rotary evaporator under reduced pressure to obtain crude 2-((4-(2,7-diazaspiro[3.5]nonan-2-yl)pyrimidin-5-yl)oxy)-N-(2-cyanoethyl)-5-fluoro-N-isopropylbenzamide hydrochloride (300 mg, 0.472 mmol, 65.3% yield) as a solid. LCMS (Method B): Rt 0.862 min, m/z: 453.4 [M+H]$^+$, 77.64%.

Intermediate 34. 2-((4-(7-(((2S,5R)-5-Aminotetrahydro-2H-pyran-2-yl)methyl)-2,7-diazaspiro[3.5]nonan-2-yl)pyrimidin-5-yl)oxy)-N-(2-cyanoethyl)-5-fluoro-N-isopropylbenzamide hydrochloride

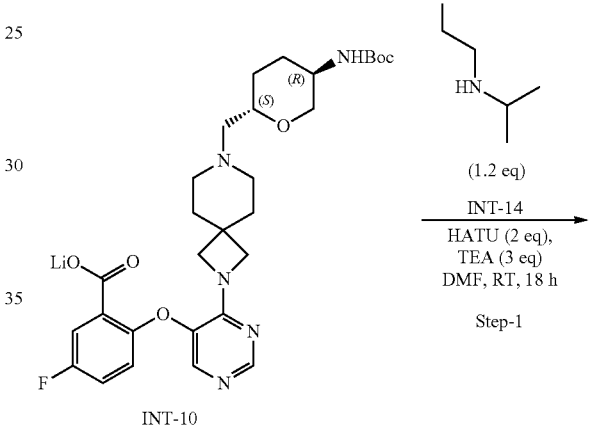

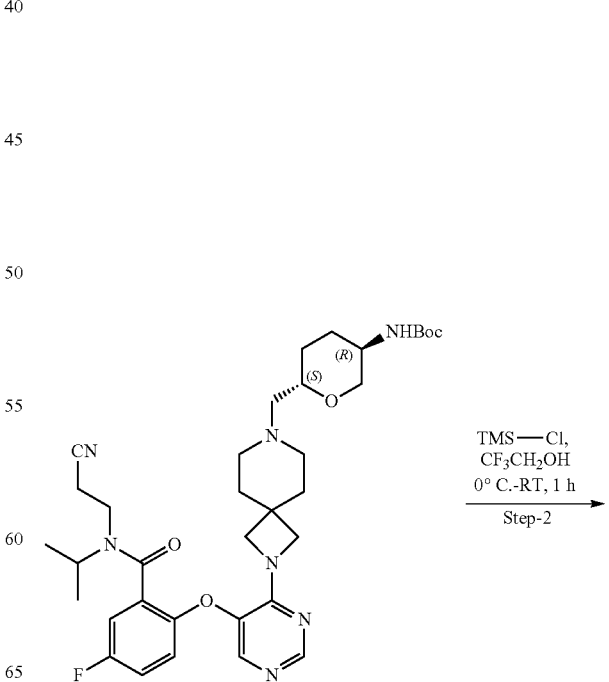

339

-continued

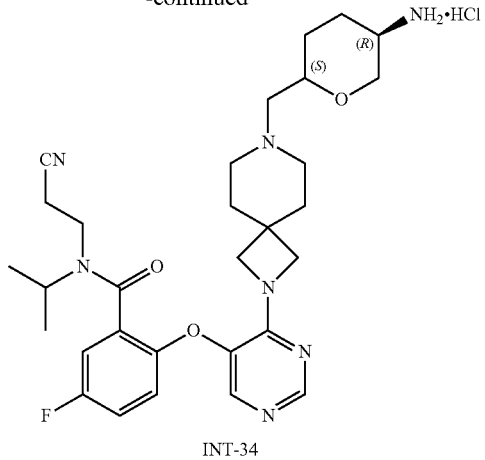

INT-34

Step 1. tert-Butyl ((3R,6S)-6-((2-(5-(2-((2-cyano-ethyl)(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate

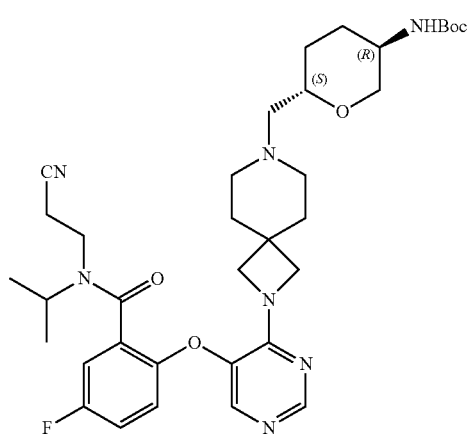

To a solution of lithium 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (400 mg, 0.700 mmol) in DMF (10 mL) were added HATU (532 mg, 1.399 mmol) and triethylamine (0.293 mL, 2.099 mmol), followed by 3-(isopropylamino)propanenitrile (94 mg, 0.840 mmol) at room temperature under nitrogen atmosphere. The resulting reaction mixture was stirred at room temperature for 18 h. The reaction progress was monitored by TLC. The reaction mixture was quenched with ice-cold water (30 mL). The solid obtained was collected by filtration and dissolved in DCM. The solution was dried over sodium sulfate, filtered, and concentrated to afford tert-butyl ((3R,6S)-6-((2-(5-(2-((2-cyanoethyl)(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (430 mg, 0.288 mmol, 41.2% yield) as a semisolid. LCMS (Method B): Rt 1.391 min, m/z: 666.4 [M+H]+, 44.67%.

340

Step 2. 2-((4-(7-(((2S,5R)-5-Aminotetrahydro-2H-pyran-2-yl)methyl)-2,7-diazaspiro[3.5]nonan-2-yl)pyrimidin-5-yl)oxy)-N-(2-cyanoethyl)-5-fluoro-N-isopropylbenzamide hydrochloride (Intermediate 34)

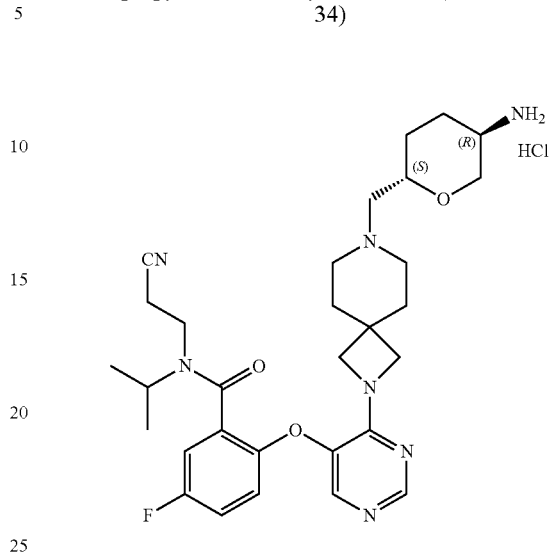

To a solution of tert-butyl ((3R,6S)-6-((2-(5-(2-((2-cyanoethyl)(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (430 mg, 0.646 mmol) in 2,2,2-trifluoroethanol (5 mL) was added TMSCl (0.165 mL, 1.292 mmol) at RT. The reaction was monitored by TLC. Upon completion, the reaction was concentrated to dryness on a rotary evaporator. The crude mass obtained was triturated with EtOAc (1 mL) to afford 2-((4-(7-(((2S,5R)-5-aminotetrahydro-2H-pyran-2-yl)methyl)-2,7-diazaspiro[3.5]nonan-2-yl)pyrimidin-5-yl)oxy)-N-(2-cyanoethyl)-5-fluoro-N-isopropylbenzamide hydrochloride (355 mg, 0.412 mmol, 63.7% yield) as a solid. LCMS (Method A): Rt 1.863 min, 566.3 [M+H]+, 65.6%.

Intermediate 35. ((2S,5R)-5-Aminotetrahydro-2H-pyran-2-yl)methyl 4-methylbenzenesulfonate hydrochloride

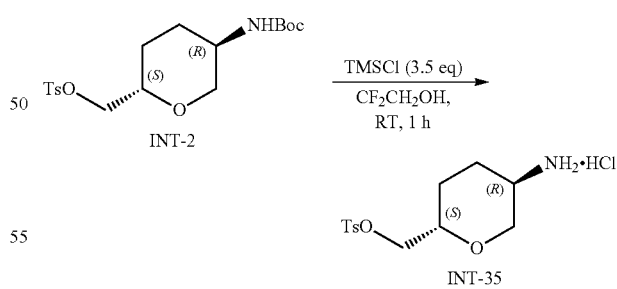

To a solution of ((2S,5R)-5-((tert-butoxycarbonyl)amino)tetrahydro-2H-pyran-2-yl)methyl 4-methylbenzenesulfonate (10 g, 25.9 mmol) in trifluoroethanol (100 mL) was added TMSCl (9.86 g, 91 mmol) over a period of 15 minutes at 0° C. The reaction mixture was stirred at RT for 1 h. The reaction progress was monitored by TLC (10% methanol in DCM). The reaction mixture was concentrated under vacuum, co-distilled with EtOAc (2×100 mL), and dried under vacuum to obtain ((2S,5R)-5-aminotetrahydro- 2H-pyran-2-yl)methyl 4-methylbenzenesulfonate hydrochloride (8 g, 24.86 mmol, 96% yield) as a solid. LCMS (Method E): Rt 1.44 min, m/z: 286.1 [M+H]⁺; HPLC (Method A): Rt 4.36 min, 97.52%.

Intermediate 37. ((2S,5R)-5-(Methylsulfonamido)tetrahydro-2H-pyran-2-yl)methyl 4-methylbenzenesulfonate

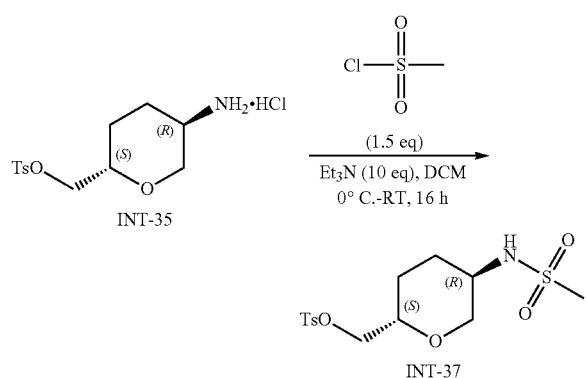

A solution of ((2S,5R)-5-aminotetrahydro-2H-pyran-2-yl)methyl 4-methylbenzenesulfonate hydrochloride (95 g, 295 mmol) in DCM (950 mL) was cooled to 0° C.

To this solution, triethylamine (411 mL, 2952 mmol) was slowly added. The reaction was stirred for 30 minutes, then methanesulfonyl chloride (34.3 mL, 443 mmol) was added at 0° C. over a period of 10 minutes. The reaction mixture was stirred at RT for 16 h. Reaction progress was monitored by TLC. The reaction mixture was diluted with DCM (1000 mL), washed with saturated NaHCO₃ solution (2 L), then H₂O (2×2 L), then brine solution (2 L), dried over Na₂SO₄ and filtered. The filtrate was concentrated to obtain crude compound (110 g). The crude compound was purified by silica gel column chromatography with (50-75%) EtOAc in hexane as an eluent to obtain ((2S,5R)-5-(methylsulfonamido)tetrahydro-2H-pyran-2-yl)methyl 4-methylbenzenesulfonate (75 g, 196 mmol, 66.5% yield) as a solid. ¹H NMR (400 MHz, DMSO-d₆) δ 7.78 (d, J=8.38 Hz, 2H), 7.49 (d, J=8.00 Hz, 2H), 7.09 (d, J=7.38 Hz, 1H), 4.02-3.97 (m, 1H), 3.93-3.87 (m, 1H), 3.86-3.79 (m, 1H), 3.37-3.47 (m, 1H), 3.07-3.19 (m, 1H), 2.98 (d, J=10.76 Hz, 1H), 2.92 (s, 3H), 2.43 (s, 3H), 2.02-1.92 (m, 1H), 1.63-1.51 (m, 1H), 1.42-1.23 (m, 2H); LCMS (Method A): Rt 1.69 min, m/z: 361.9 [M−H]⁻; HPLC (Method A): Rt 5.22 min, 93.54%.

Intermediate 36. ((2S,5R)-5-((1-Methylethyl)sulfonamido)tetrahydro-2H-pyran-2-yl)methyl4-methylbenzenesulfonate

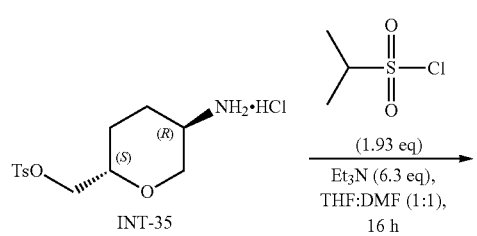

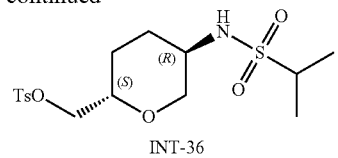

This compound was synthesized following the general procedure described for the synthesis of Intermediate 37, except 6.3 equivalents of Et₃N and 1.93 equivalents of propane-2-sulfonyl chloride were used, and THF:DMF (1:1) was used as solvent.

Yield: 46.8%;

¹H NMR (400 MHz, DMSO-d₆) δ 7.80-7.75 (m, 2H), 7.51-7.46 (m, 2H), 7.05 (d, J=7.88 Hz, 1H), 4.03-3.96 (m, 1H), 3.93-3.86 (m, 1H), 3.83-3.76 (m, 1H), 3.44-3.36 (m, 1H), 3.21-3.12 (m, 1H), 3.12-3.03 (m, 1H), 3.03-2.94 (m, 1H), 2.45-2.41 (m, 3H), 1.98-1.88 (m, 1H), 1.61-1.52 (m, 1H), 1.45-1.25 (m, 3H), 1.23-1.17 (m, 6H); LCMS (Method B): Rt 1.90 min, m/z: 390.2 [M−H]⁻; HPLC (Method A): Rt 5.70 min, 92.71%.

Intermediate 38. ((2S,5R)-5-(Ethylsulfonamido)tetrahydro-2H-pyran-2-yl)methyl 4-methylbenzenesulfonate This compound was synthesized following the general procedure described for the synthesis of Intermediate 37, except 1.5 equivalents of ethanesulfonyl chloride was used.

Yield: 100%; ¹H NMR (400 MHz, DMSO-d₆) δ 7.80-7.75 (m, 2H), 7.49 (d, J=7.88 Hz, 2H), 7.11 (d, J=7.63 Hz, 1H), 4.03-3.97 (m, 1H), 3.94-3.85 (m, 1H), 3.84-3.76 (m, 1H), 3.45-3.38 (m, 1H), 3.12-3.05 (m, 1H), 3.04-2.95 (m, 3H), 2.43 (s, 3H), 1.99-1.89 (m, 1H), 1.62-1.51 (m, 1H), 1.44-1.23 (m, 2H), 1.17 (t, J=7.32 Hz, 3H); LCMS (Method B): Rt 1.79 min, m/z: 376.2 [M−H]⁻; HPLC (Method A): Rt 5.46 min, 97.21%.

Intermediate 39. ((2S,5R)-5-(cyclopropanesulfona-mido)tetrahydro-2H-pyran-2-yl)methyl 4-methyl-benzenesulfonate

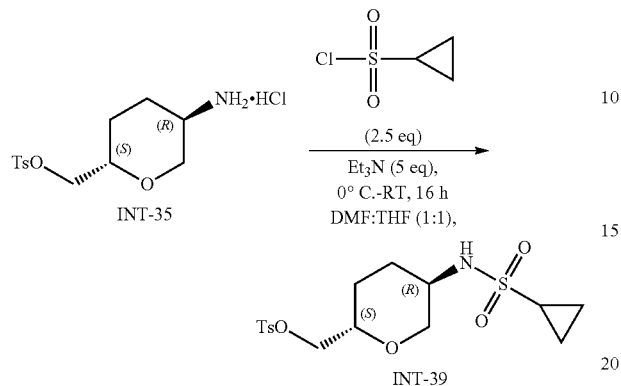

This compound was synthesized following the general procedure described for the synthesis of Intermediate 37, except that 2.5 equivalents of cyclopropanesulfonyl chloride and 5 equivalents of Et$_3$N were used, and DMF:THF (1:1) was used as solvent. Yield: 79%; $^1$H NMR (400 MHz, DMSO-d$_6$) δ 7.78 (d, J=8.38 Hz, 2H), 7.49 (d, J=8.00 Hz, 2H), 7.13 (d, J=7.88 Hz, 1H), 4.03-3.97 (m, 1H), 3.94-3.88 (m, 1H), 3.88-3.81 (m, 1H), 3.46-3.38 (m, 1H), 3.20-3.07 (m, 1H), 3.04-2.95 (m, 1H), 2.63-2.54 (m, 1H), 2.45-2.40 (s, 3H), 2.03-1.94 (m, 1H), 1.62-1.54 (m, 1H), 1.45-1.22 (m, 2H), 1.00-0.81 (m, 4H); LCMS (Method B): Rt 1.82 min, m/z: 388.0 [M−H]$^−$; HPLC (Method A): Rt 5.56 min, 99.82%.

Intermediate 40. ((2S,5R)-5-((N-Methylsulfamoyl)amino)tetrahydro-2H-pyran-2-yl)methyl 4-methyl-benzenesulfonate

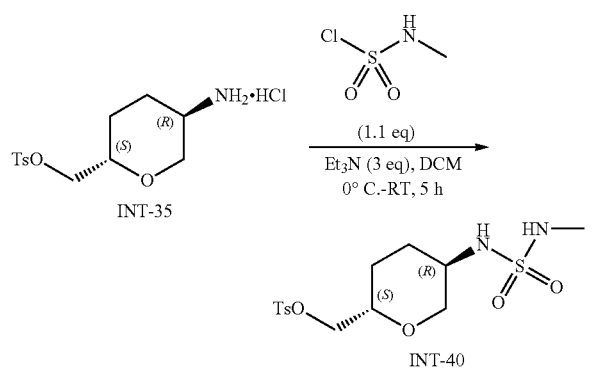

This compound was synthesized following the general procedure described for the synthesis of Intermediate 37, except that 3 equivalents of Et$_3$N and 1.1 equivalents of methyl sulfamoyl chloride were used. Yield: 45%; $^1$H NMR (400 MHz, DMSO-d$_6$) δ 7.78 (d, J=8.25 Hz, 2H), 7.49 (d, J=8.00 Hz, 2H), 6.91 (d, J=7.13 Hz, 1H), 6.70 (q, J=5.13 Hz, 1H), 4.01-3.97 (m, 1H), 3.93-3.88 (m, 1H), 3.84 (dd, J=6.13, 1.88 Hz, 1H), 3.44-3.36 (m, 1H), 3.01-2.92 (m, 2H), 2.44- 2.41 (m, 5H), 1.99-1.91 (m, 1H), 1.63-1.53 (m, 1H), 1.43-1.17 (m, 2H); LCMS (Method B): Rt 1.686 min, m/z: 379.2 [M+H]$^+$, 99.91%.

Intermediate 41. ((2S,5R)-5-((N-Ethylsulfamoyl)amino)tetrahydro-2H-pyran-2-yl)methyl 4-methyl-benzenesulfonate

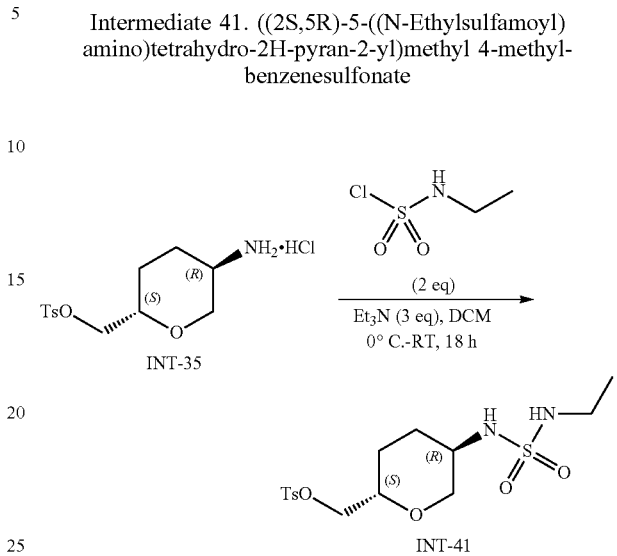

This compound was synthesized following the general procedure described for the synthesis of Intermediate 37, except that 3 equivalents of Et$_3$N and 2 equivalents of ethylsulfamoyl chloride were used. Yield: 69%; $^1$H NMR (400 MHz, DMSO-d$_6$) δ 7.78 (d, J=8.25 Hz, 2H), 7.49 (d, J=8.00 Hz, 2H), 6.87 (d, J=7.00 Hz, 1H), 6.79 (t, J=5.82 Hz, 1H), 4.01-3.97 (m, 1H), 3.93-3.88 (m, 1H), 3.88-3.80 (m, 1H), 3.40 (ddd, J=11.19, 6.19, 2.50 Hz, 1H), 3.03-2.89 (m, 2H), 2.86-2.77 (m, 2H), 2.43 (s, 3H), 1.97-1.90 (m, 1H), 1.60-1.52 (m, 1H), 1.37-1.20 (m, 2H), 1.05 (t, J=7.25 Hz, 3H); LCMS (Method B): Rt 1.79 min, m/z: 393.2 [M+H]$^+$, 91.82%.

Intermediate 42. ((2S,5R)-5-((N-Cyclopropylsulfamoyl)amino)tetrahydro-2H-pyran-2-yl)methyl 4-methyl benzenesulfonate

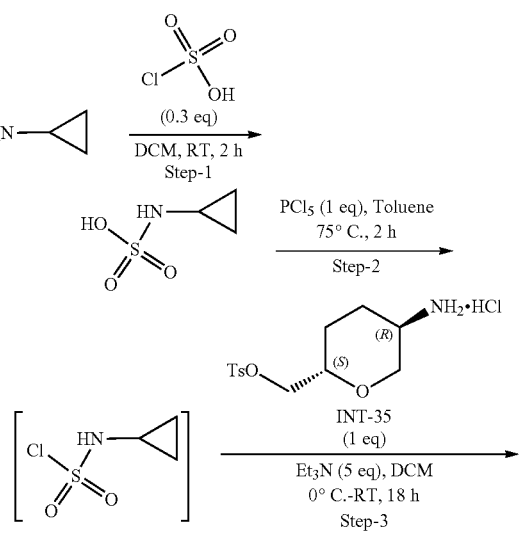

-continued

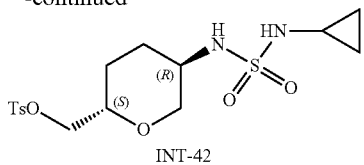

INT-42

Step 1. Cyclopropylsulfamic acid

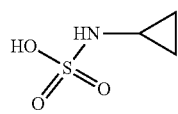

To a dried 100 mL single necked round bottom flask, cyclopropanamine (2.0 g, 35.0 mmol) was added in DCM (20 mL). To this, a solution of chlorosulfuric acid (0.700 mL, 10.51 mmol) in DCM (5 mL) was added at 0° C. dropwise, and the reaction was allowed to stir at RT for 2 h. The reaction was monitored by TLC (20% methanol in DCM). After completion, the reaction mixture was concentrated on a rotary evaporator, triturated with DCM (50 mL), filtered, and dried to afford cyclopropylsulfamic acid (2.1 g, 43.7% yield) as a gummy liquid. $^1$H NMR (400 MHz, DMSO-$d_6$) δ 8.40-8.23 (m, 2H), 2.58-2.51 (m, 1H), 0.83-0.58 (m, 4H).

Step 2 and Step 3. ((2S,5R)-5-((N-Cyclopropylsulfamoyl)amino)tetrahydro-2H-pyran-2-yl)methyl 4-methyl benzenesulfonate (Intermediate 42)

To a 100 mL single neck round bottom flask under nitrogen atmosphere, cyclopropylsulfamic acid (1 g, 7.29 mmol) in toluene (10 mL) was added. To this, PCl$_5$ (1.518 g, 7.29 mmol) was added at 0° C., and the reaction was heated at 75° C. for 2 h. The reaction mixture was cooled to RT and concentrated under vacuum to obtain crude the sulfonyl chloride.

Intermediate 42 was synthesized following the general procedure described for the synthesis of Intermediate 37, except that 5 equivalents of Et$_3$N and 1.0 equivalents of Intermediate 35 were used. Yield: 45%; LCMS (Method E): Rt 1.749 min, m/z: 405.1 [M+H]$^+$, 98.49%.

Intermediate 43. ((2S,5R)-5-((N-Isopropylsulfamoyl)amino)tetrahydro-2H-pyran-2-yl)methyl 4-methylbenzenesulfonate

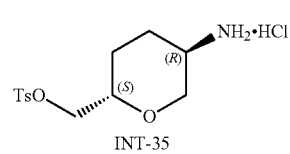 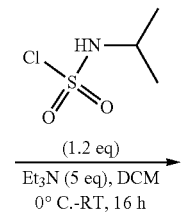

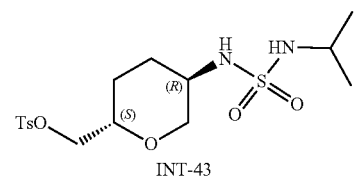

INT-43

This compound was synthesized following the general procedure described for the synthesis of Intermediate 37, except that 5 equivalents of Et$_3$N and 1.2 equivalents of isopropylsulfamoyl chloride were used. Yield: 94%; LCMS (Method E): Rt 1.987 min, m/z: 405.2 [M−H]$^−$, 99.32%.

Intermediate 44. ((2S,5R)-5-((N-propylsulfamoyl)amino)tetrahydro-2H-pyran-2-yl)methyl 4-methylbenzenesulfonate

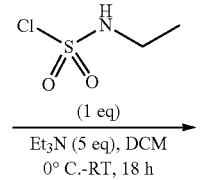

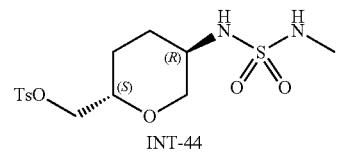

INT-44

This compound was synthesized following the general procedure described for the synthesis of Intermediate 37, except that 1 equivalent of propane-1-sulfonyl chloride and 5 equivalents of Et$_3$N were used. Yield: 62.5%; $^1$H NMR (400 MHz, DMSO-$d_6$) δ 7.80-7.74 (m, 2H), 7.52-7.46 (m, 2H), 6.86 (d, J=7.00 Hz, 1H), 6.81 (t, J=5.94 Hz, 1H), 4.02-3.96 (m, 1H), 3.93-3.82 (m, 2H), 3.43-3.37 (m, 1H), 3.00-2.96 (m, 1H), 2.77-2.70 (m, 2H), 2.43 (s, 3H), 2.03-1.86 (m, 1H), 1.52-1.63 (m, 1H), 1.50-1.39 (m, 2H), 1.38-1.21 (m, 2H), 0.86 (t, J=7.38 Hz, 3H); LCMS (Method A): Rt 2.01 min, m/z: 405.2 [M−H]$^−$, 98.65%.

Intermediate 45. ((2S,5R)-5-((N-(2,2,2-Trifluoro-ethyl)sulfamoyl)amino)tetrahydro-2H-pyran-2-yl) methyl 4-methylbenzenesulfonate

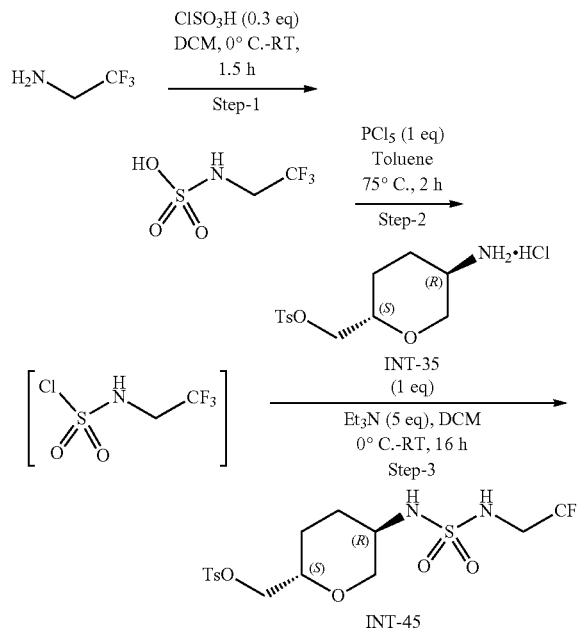

Step 1. (2,2,2-Trifluoroethyl)sulfamic acid

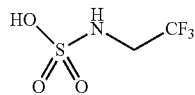

This compound was synthesized following the general procedure described for the synthesis of Intermediate 42 in Step 1.

The solid obtained was co-distilled with toluene (10 mL) and dried under vacuum to obtain the crude compound, which was used in the subsequent step without further purification.

$^1$H NMR (400 MHz, DMSO-$d_6$) δ 8.89 (br s, 2H), 3.89 (q, J=9.71 Hz, 2H).

Step 2 and Step 3. ((2S,5R)-5-((N-(2,2,2-Trifluoro-ethyl)sulfamoyl)amino)tetrahydro-2H-pyran-2-yl) methyl 4-methylbenzenesulfonate (Intermediate 45)

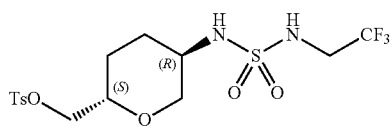

This compound was synthesized following the general procedure described for the synthesis of Intermediate 37, and the sulfonyl chloride was prepared as described for the synthesis of Intermediate 42 in Step 2. Yield: 31.2%; $^1$H NMR (400 MHz, DMSO-$d_6$) δ 7.84-7.80 (m, 1H), 7.78 (d, J=8.25 Hz, 2H), 7.49 (d, J=8.00 Hz, 2H), 7.19 (d, J=7.13 Hz, 1H), 4.00-3.83 (m, 3H), 3.66-3.52 (m, 2H), 3.46-3.37 (m, 1H), 3.07-2.93 (m, 2H), 2.43 (s, 3H), 1.92-1.97 (m, 1H), 1.62-1.53 (m, 1H), 1.39-1.22 (m, 2H); LCMS (Method E): Rt 1.914 min, m/z: (455.0) (M−H)$^-$, 99.94%.

Intermediate 46. ((2S,5R)-5-((N-(Cyclopropylm-ethyl)sulfamoyl)amino)tetrahydro-2H-pyran-2-yl) methyl 4-methylbenzenesulfonate

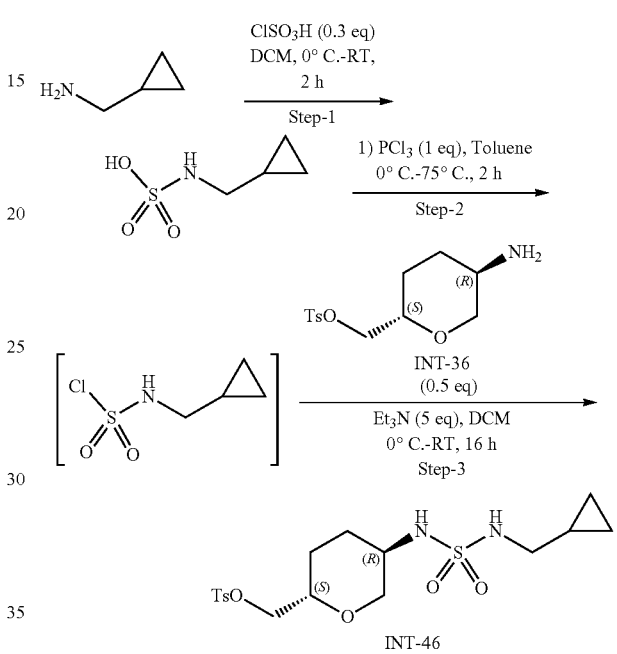

Step 1. (Cyclopropylmethyl)Sulfamic Acid

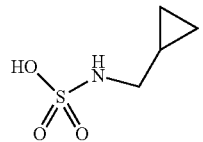

This compound was synthesized following the general procedure described for the synthesis of Intermediate 42 in Step 1. $^1$H NMR (400 MHz, DMSO-$d_6$) δ 7.38 (s, 1H), 4.05 (s, 1H), 2.64 (d, J=7.25 Hz, 2H), 0.94-1.06 (m, 1H), 0.47-0.56 (m, 2H), 0.26-0.31 (m, 2H).

Step 2. ((2S,5R)-5-((N-(Cyclopropylmethyl)sulfa-moyl)amino)tetrahydro-2H-pyran-2-yl)methyl 4-methylbenzenesulfonate (Intermediate 46)

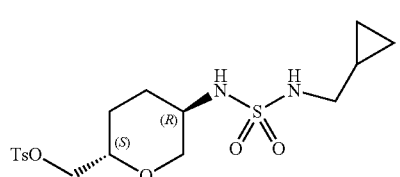

This compound was synthesized following the general procedure described for the synthesis of Intermediate 37, and the sulfonyl chloride was prepared as described for the synthesis of Intermediate 42 in Step 2. Yield: 2.5%; $^1$H NMR (400 MHz, DMSO-$d_6$) δ 7.74-7.81 (m, 2H), 7.44-7.52 (m, 2H), 6.94 (t, J=6.07 Hz, 1H), 6.84 (d, J=7.25 Hz, 1H), 3.96-4.02 (m, 1H), 3.83-3.93 (m, 2H), 3.36-3.43 (m, 1H), 2.89-3.07 (m, 2H), 2.66 (t, J=6.38 Hz, 2H), 2.43 (s, 3H), 1.89-1.99 (m, 1H), 1.56 (dd, J=12.51, 2.13 Hz, 1H), 1.17-1.40 (m, 2H), 0.84-1.02 (m, 1H), 0.37-0.47 (m, 2H), 0.11-0.19 (m, 2H).

Intermediate 47. ((2S,5R)-5-((N,N-Dimethylsulfamoyl)amino)tetrahydro-2H-pyran-2-yl)methyl 4-methylbenzenesulfonate

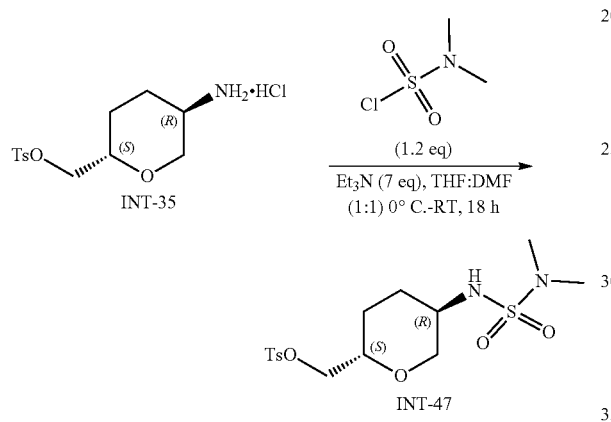

This compound was synthesized following the general procedure described for the synthesis of Intermediate 37, except that 1.2 equivalents of dimethyl sulfamoyl chloride and 7 equivalents of Et$_3$N were used, and THF:DMF (1:1) was used as the solvent. Yield: 50.6%; $^1$H NMR (400 MHz, CDCl$_3$) δ 7.81 (d, J=8.25 Hz, 2H), 7.37 (d, J=8.00 Hz, 2H), 4.11 (ddd, J=10.98, 4.72, 2.19 Hz, 1H), 3.99 (d, J=5.13 Hz, 2H), 3.84-3.83 (m, 1H), 3.56 3.44-(m, 1H), 3.37-3.22 (m, 1H), 3.05 (t, J=10.82 Hz, 1H), 2.81 (s, 6H), 2.48 (s, 3H), 2.27-2.19 (m, 1H), 1.79-1.73 (m, 1H), 1.51-1.30 (m, 2H); LCMS (Method A): Rt 1.749 min, m/z: 393.5 [M+H]$^+$, 95.64%.

Intermediate 48. ((2S,5R)-5-((N-Ethyl-N-methylsulfamoyl)amino)tetrahydro-2H-pyran-2-yl)methyl 4-methylbenzenesulfonate

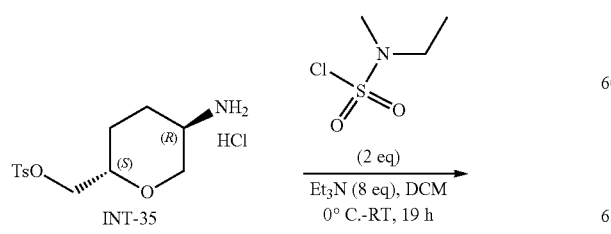

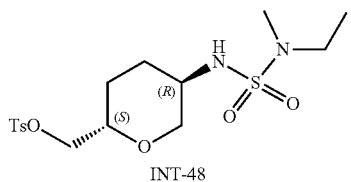

This compound was synthesized following the general procedure described for the synthesis of Intermediate 37, except that 8 equivalents of Et$_3$N and 2 equivalents of ethyl(methyl)sulfamoyl chloride were used. Yield: 62.1%; $^1$H NMR (400 MHz, DMSO-$d_6$) δ 7.80-7.75 (m, 2H), 7.51-7.46 (m, 2H), 7.16 (d, J=7.38 Hz, 1H), 4.01-3.97 (m, 1H), 3.92-3.86 (m, 1H), 3.84-3.78 (m, 1H), 3.45-3.37 (m, 1H), 3.13-3.02 (m, 2H), 3.01-2.91 (m, 2H), 2.64 (s, 3H), 2.43 (s, 3H), 1.95-1.88 (m, 1H), 1.60-1.51 (m, 1H), 1.43-1.22 (m, 2H), 1.08 (t, J=7.13 Hz, 3H); LCMS (Method B): Rt 2.017 min, m/z: (407.2) [M+H]$^+$, 98.01%.

Intermediate 49. ((2S,5R)-5-(pyrrolidine-1-sulfonamido)tetrahydro-2H-pyran-2-yl)methyl 4-methylbenzenesulfonate

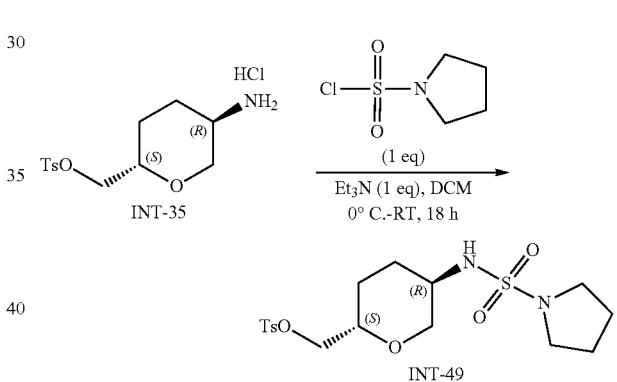

This compound was synthesized following the general procedure described for the synthesis of Intermediate 37, except that 1 equivalent of pyrrolidine-1-sulfonyl chloride and 1 equivalent of Et$_3$N were used. Yield: 48.7%; LCMS (Method A): 1.92 min, m/z: 419.2 [M+H]$^+$, 99.95%.

Intermediate 50. ((2S,5R)-5-((N,N-diethylsulfamoyl)amino)tetrahydro-2H-pyran-2-yl)methyl 4-methylbenzenesulfonate

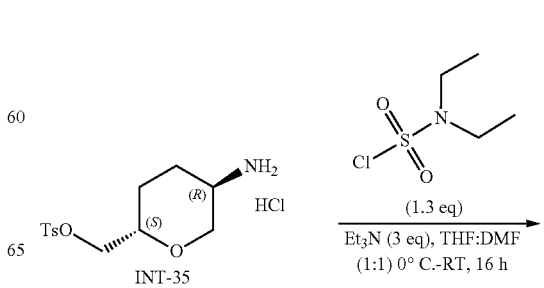

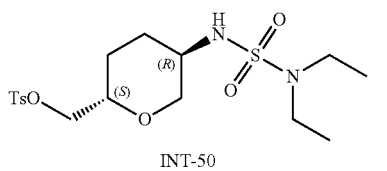

INT-50

This compound was synthesized following the general procedure described for the synthesis of Intermediate 37, except that 1.3 equivalents of diethylsulfamoyl chloride and 3 equivalents of Et$_3$N were used, and THF:DMF (1:1) was used as the solvent. $^1$H NMR (400 MHz, DMSO-d$_6$) δ 7.78 (d, J=8.25 Hz, 2H), 7.49 (dd, J=8.50, 0.63 Hz, 2H), 7.14 (d, J=7.63 Hz, 1H), 3.99 (dd, J=10.51, 2.88 Hz, 1H), 3.89 (dd, J=10.57, 6.57 Hz, 11H), 3.80-3.85 (m, 1H), 3.37-3.46 (m, 1H), 3.08-3.14 (m, 4H), 2.93-3.06 (m, 2H), 2.53-250 (m, 2H), 2.43 (s, 3H), 1.91-1.97 (m, 1H), 1.73-1.88 (m, 4H), 1.52-1.61 (m, 1H), 1.24-1.43 (m, 2H)

Intermediate 51. ((2S,5R)-5-(Azetidine-1-sulfonamido)tetrahydro-2H-pyran-2-yl)methyl 4-methylbenzenesulfonate

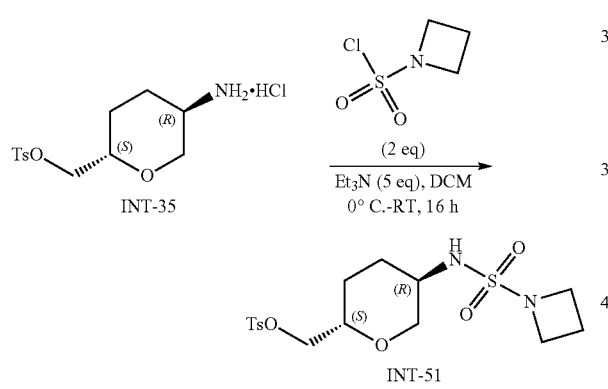

This compound was synthesized following the general procedure described for the synthesis of Intermediate 37, except that 5 equivalents of Et$_3$N and 2 equivalents of azetidine-1-sulfonyl chloride were used. Yield: 78%; LCMS (Method A): Rt 1.941 min, m/z: 404.9 [M+H]$^+$, 98.24%.

Intermediate 52. ((2S,5R)-5-((1-Methyl-1H-pyrazole)-4-sulfonamido)tetrahydro-2H-pyran-2-yl) methyl 4-methylbenzenesulfonate

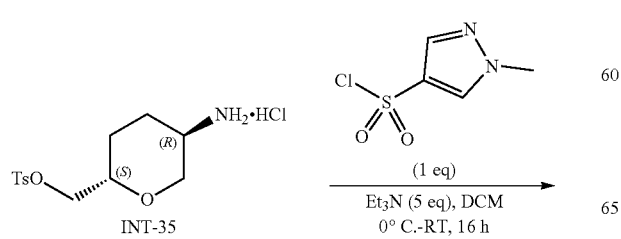

INT-52

This compound was synthesized following the general procedure described for the synthesis of Intermediate 37, except that 5 equivalents of Et$_3$N and 1 equivalent of 1-methyl-1H-pyrazole-4-sulfonyl chloride were used. Yield: 77%; $^1$H NMR (400 MHz, DMSO-d$_6$) δ 8.23 (s, 1H), 7.76 (d, J=8.38 Hz, 2H), 7.72 (d, J=0.50 Hz, 1H), 7.53 (br d, J=6.25 Hz, 1H), 7.48 (d, J=8.00 Hz, 2H), 3.99-3.93 (m, 1H), 3.88 (s, 3H), 3.87-3.83 (m, 1H), 3.72-3.66 (m, 1H), 3.43-3.38 (m, 1H), 3.01-2.89 (m, 2H), 2.42 (s, 3H), 1.80-1.67 (m, 1H), 1.55-1.46 (m, 1H), 1.38-1.20 (m, 2H); LCMS (Method B): Rt 1.822 min, m/z: 430.2 [M+H]$^+$, 81.75%.

Intermediate 53. ((2S,5R)-5-(N'-(tert-Butyldimethylsilyl)ethylsulfonoamidimidamido) tetrahydro-2H-pyran-2-yl)methyl 4-methylbenzenesulfonate

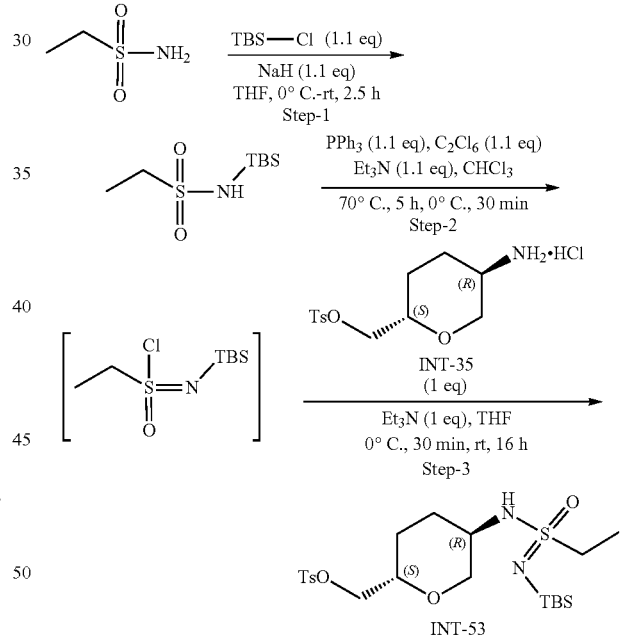

Step 1:
N-(tert-Butyldimethylsilyl)ethanesulfonamide

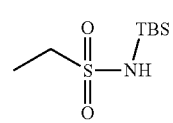

To a 250 mL two necked round bottom flask under nitrogen atmosphere, ethane sulfonamide (5.0 g, 45.8 mmol)

was added in THF (50 mL). To this reaction mixture, NaH (2.016 g, 50.4 mmol) was added portionwise at 0° C., and stirring was continued for 30 min. Then, TBDMSCl (7.60 g, 50.4 mmol) was added at 0° C., and the reaction was stirred at RT for 2 h. The reaction progress was monitored by TLC (50% EtOAc in hexane). After 2 h, the reaction was quenched with ice cold water (20 mL) and extracted with EtOAc (50 mL). The organic layer was separated, and the aqueous layer was re-extracted with EtOAc (2×50 mL). The combined organic layers were washed with brine, dried over anhydrous Na$_2$SO$_4$, and filtered, and the filtrate was concentrated under vacuum to afford N-(tert-butyldimethylsilyl)ethanesulfonamide (7.0 g, 68.4% yield) as an off-white solid. $^1$H NMR (400 MHz, DMSO-d$_6$) δ 6.89 (s, 1H), 2.96-2.94 (m, 2H), 1.22 (t, J=14.8 Hz, 3H), 0.90 (s, 9H), 0.02 (s, 6H).

Step 2 and Step 3: ((2S,5R)-5-(N'-(tert-butyldimethylsilyl)ethylsulfonoamidimidamido)tetrahydro-2H-pyran-2-yl)methyl 4-methylbenzenesulfonate (Intermediate 53)

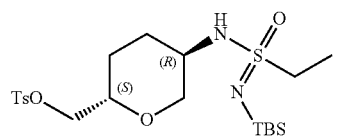

To a dried 25 mL two necked round bottom flask under argon atmosphere, triphenylphosphine (646 mg, 2.462 mmol) and perchloroethane (583 mg, 2.462 mmol) were added in CHCl$_3$ (3.5 mL). The resulting solution was heated at 70° C. for 5 h. Formation of a white suspension was observed. The reaction mixture was cooled to RT. Et$_3$N (0.469 mL, 3.36 mmol) was added, and the reaction was stirred for an additional 10 min. Formation of a yellow suspension was observed. To this reaction mixture, a solution of N-(tert-butyldimethylsilyl)ethanesulfonamide (500 mg, 2.238 mmol) in chloroform (0.80 mL) was added dropwise at 0° C., and the reaction was stirred for 30 min. To this reaction mixture, ((2S,5R)-5-aminotetrahydro-2H-pyran-2-yl)methyl 4-methylbenzenesulfonate hydrochloride (720 mg, 2.238 mmol) and Et$_3$N (0.312 mL, 2.238 mmol) in THF (0.60 mL) were added, and the reaction was stirred for an additional 30 min at 0° C. The reaction mixture was allowed to warm to RT and stirred for 16 h. The reaction progress was monitored by TLC (60% EtOAc in hexane). After completion of the reaction, the reaction mixture was concentrated, quenched with water (20 mL), and extracted with EtOAc (3×50 mL). The combined organic layer was dried over anhydrous sodium sulfate and filtered, and the filtrate was concentrated under reduced pressure to obtain the crude product. The crude compound was purified by silica gel column chromatography and eluting with 0-40% EtOAc in hexane as an eluent. The fractions containing the desired product were concentrated under reduced pressure to obtain ((2S,5R)-5-(N'-(tert-butyldimethylsilyl)ethylsulfonoamidimidamido)tetrahydro-2H-pyran-2-yl)methyl 4-methylbenzenesulfonate (250 mg, 22.10% yield) as gummy liquid. LCMS (Method E): Rt 2.322 min, m/z: 491.2 [M+H]$^+$, 97.09%.

Intermediate 54. ((2S,5R)-5-(N'-(tert-Butyldimethylsilyl)phenylsulfonoamidimidamido)tetrahydro-2H-pyran-2-yl)methyl 4-methylbenzenesulfonate

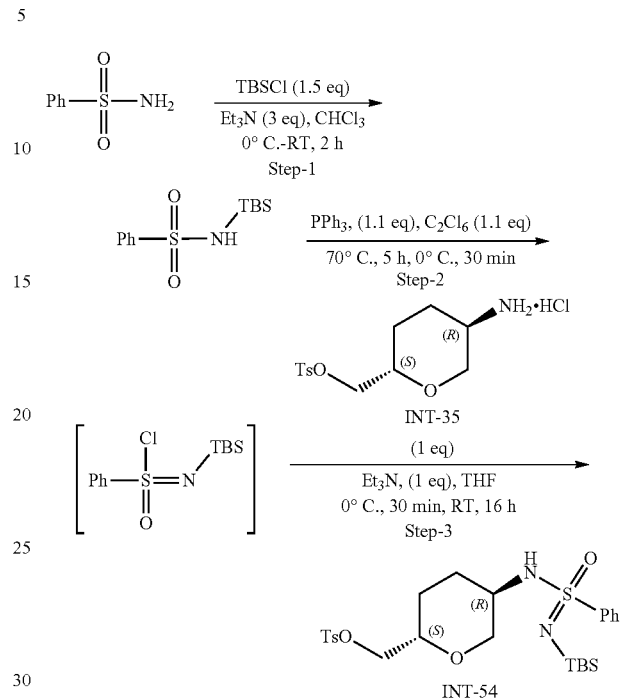

Step 1.
N-(tert-Butyldimethylsilyl)benzenesulfonamide

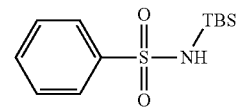

This compound was synthesized following the general procedure described for the synthesis of Intermediate 53, except that 3 equivalents of Et$_3$N and 1.5 equivalents of TBDMSCl were used, and CHCl$_3$ was used as the solvent. The reaction mixture was extracted with DCM (2×100 mL). The crude product was purified by column chromatography (230-400 mesh silica-gel) (Biotage-isolera one), eluting with 0-20% EtOAc in hexane. Yield: 95%; $^1$H NMR (400 MHz, CDCl$_3$) δ 7.92-7.87 (m, 2H), 7.59-7.45 (m, 3H), 4.68 (s, 1H), 0.91 (s, 9H), 0.23 (s, 6H); LCMS (Method A): Rt 2.17 min, m/z: 272.1 [M+H]$^+$; HPLC: (Method F) Rt. 6.83 min, 99.97%.

Step 2 and Step 3: ((2S,5R)-5-(N'-(tert-Butyldimethylsilyl)phenylsulfonoamidimidamido)tetrahydro-2H-pyran-2-yl)methyl 4-methylbenzenesulfonate

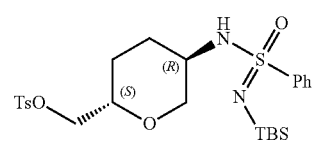

This compound was synthesized following the general procedure described for the synthesis of Intermediate 53. Yield: 55.4%; ¹H NMR (400 MHz, DMSO-d₆) δ 7.84-7.79 (m, 2H), 7.74 (dd, J=8.25, 1.00 Hz, 1H), 7.71-7.77 (m, 1H), 7.56-7.50 (m, 3H), 7.48-7.44 (m, 2H), 6.93 (dd, J=11.01, 7.13 Hz, 11H), 3.95-3.88 (m, 1H), 3.87-3.76 (m, 1H), 3.55-3.39 (m, 1H), 3.32-3.26 (m, 1H), 2.96-2.84 (m, 2H), 2.42 (s, 3H), 1.59-1.39 (m, 2H), 1.33-1.22 (m, 1H), 1.13-1.00 (m, 1H), 0.87 (d, J=4.75 Hz, 9H), 0.01 (d, J=3.13 Hz, 3H), −0.01 (d, J=2.50 Hz, 3H); LCMS (Method E): Rt 2.599 min, m/z: 540.1 [M+H]⁺, 98.30%.

Intermediate 55.
1-Methyl-6-oxo-1,6-dihydropyridine-3-sulfonyl chloride

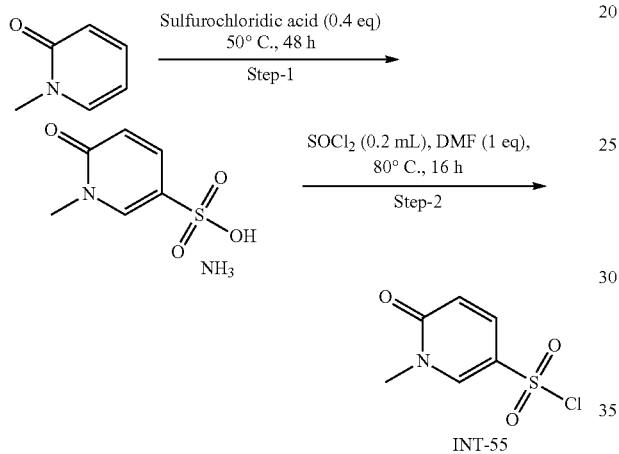

Step 1. 1-Methyl-6-oxo-1,6-dihydropyridine-3-sulfonic acid

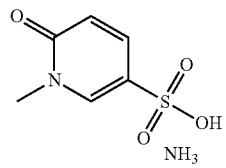

Sulfurochloridic acid (1.220 mL, 18.33 mmol) was slowly added to 1-methylpyridin-2(1H)-one (5.0 g, 45.8 mmol) under vigorous stirring at RT under nitrogen atmosphere, and then the reaction was heated at 50° C. for 48 h. The reaction mixture was quenched with ice water (25 mL), basified with aq. ammonia solution (25 mL), and washed with dichloromethane (6×100 mL). The aqueous phase was then concentrated to obtain a brown slurry which was triturated with methanol and filtered. The filtrate was concentrated to afford 1-methyl-6-oxo-1,6-dihydropyridine-3-sulfonic acid, ammonia salt (2.3 g, 11.14 mmol, 24.32% yield) as a solid. ¹H NMR (400 MHz, DMSO-d₆) δ 7.94-7.83 (m, 1H), 7.58-7.47 (m, 1H), 6.39-6.27 (m, 1H), 3.44-3.38 (m, 3H); LCMS (Method B): Rt 0.385 min, m/z: 188.0 [M−H]⁻, 99.94%.

Step 2:
1-Methyl-6-oxo-1,6-dihydropyridine-3-sulfonyl chloride (Intermediate 55)

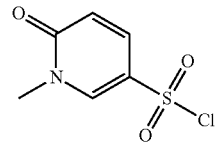

SOCl₂ (0.2 mL) was slowly added to 1-methyl-6-oxo-1,6-dihydropyridine-3-sulfonic acid ammonia salt (0.2 g, 0.970 mmol) under vigorous stirring at RT, and then DMF (0.075 mL, 0.970 mmol) was added. The resulting reaction mixture was heated at 80° C. for 16 h under nitrogen atmosphere. After completion of the reaction, the reaction mixture was cooled to room temperature, and the solvent was removed under reduced pressure to afford crude 1-methyl-6-oxo-1,6-dihydropyridine-3-sulfonyl chloride (0.2 g, 0.963 mmol, 99% yield) as a semisolid. This crude material was used in the next step without further purification.

Intermediate 64. 3-((1H-Imidazol-1-yl)sulfonyl)-1-methyl-1H-imidazol-3-ium trifluoromethanesulfonate and Intermediate 56: (S)-1-((2-Methylpyrrolidin-1-yl)sulfonyl)-1H-imidazole

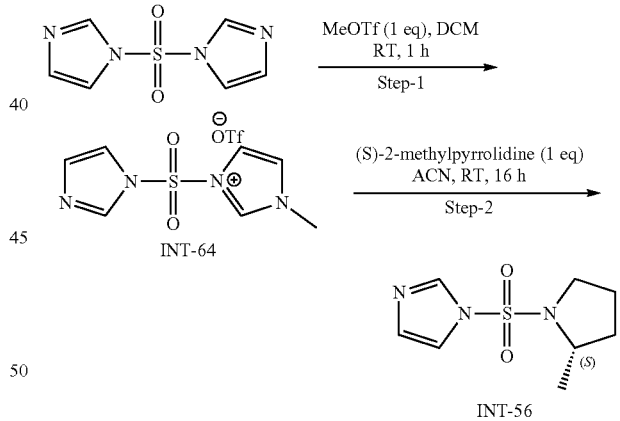

Step 1. 3-((1H-Imidazol-1-yl)sulfonyl)-1-methyl-1H-imidazol-3-ium trifluoromethanesulfonate (Intermediate 64)

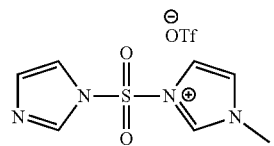

To a dried 50 mL round bottom flask under nitrogen atmosphere, 1,1'-sulfonylbis(1H-imidazole) (500 mg, 2.52 mmol) was added in DCM (10 mL), then methyl trifluoromethanesulfonate (0.285 mL, 2.52 mmol) was added at 0° C. The reaction mixture was stirred at RT under 1 h. The resulting solid was filtered and dried to give 3-((1H-imidazol-1-yl)sulfonyl)-1-methyl-1H-imidazol-3-ium trifluoromethanesulfonate (900 mg, 2.484 mmol, 98% yield) as a solid. This crude product was used in the next reaction without further purification.

Step 2. (S)-1-((2-Methylpyrrolidin-1-yl)sulfonyl)-1H-imidazole (Intermediate 56)

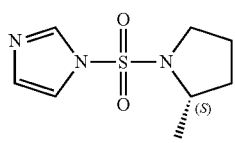

To a stirred solution of 3-((1H-imidazol-1-yl)sulfonyl)-1-methyl-1H-imidazol-3-ium trifluoromethanesulfonate (800 mg, 2.208 mmol) in ACN (15 mL) was added (S)-2-methylpyrrolidine (209 mg, 2.457 mmol) at 0° C. under nitrogen. The reaction mixture was stirred at RT for 16 h. The progress of the reaction was monitored by LCMS. After completion, the reaction mixture was concentrated under reduced pressure to obtain the crude. The crude product was purified by Prep-HPLC to obtain pure compound (S)-1-((2-methylpyrrolidin-1-yl)sulfonyl)-1H-imidazole (150 mg, 0.648 mmol, 29.4% yield) as a solid. LCMS (Method A): Rt 1.484 min, m/z: 216.2 [M+H]$^+$, 93.04%.

Intermediate 57. (R)-1-((2-Methylpyrrolidin-1-yl)sulfonyl)-1H-imidazole

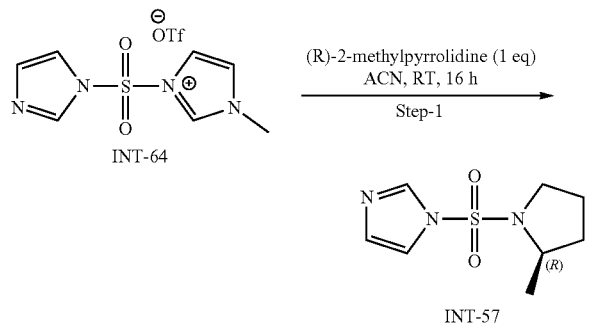

This compound was synthesized following the general procedure described for the synthesis of Intermediate 56, using 1 equivalent of (R)-2-methylpyrrolidine. Yield: 23.60%; LCMS (Method B): Rt 1.473 min, m/z: 216.2 [M+H]$^+$, 99.65%.

Intermediate 58. Methyloxazole-4-sulfonyl chloride

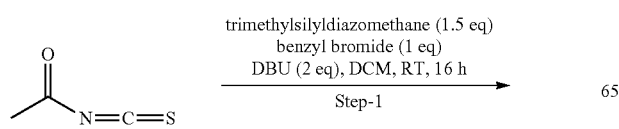

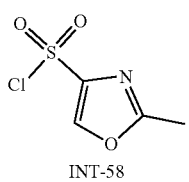

Step 1. 4-(Benzylthio)-2-methyloxazole

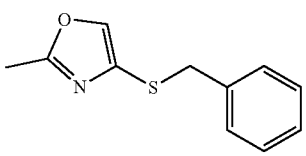

To a solution of acetyl isothiocyanate (0.5 g, 4.94 mmol) in DCM (15 mL) was slowly added trimethylsilyldiazomethane (3.71 mL, 7.42 mmol) at 0° C. over a period of 15 minutes. The mixture became orange upon addition. The resulting reaction mixture was allowed to stir at 0° C. for 1 hour. A yellow suspension formed. Then DBU (1.491 mL, 9.89 mmol) was slowly added to the mixture, followed by the addition of benzyl bromide (0.588 mL, 4.94 mmol) at the same temperature. The reaction mixture was then allowed to stir at RT for 16 h. After completion of the reaction, the reaction mixture was quenched with water and extracted with DCM (3×100 mL). The combined organic layer was dried over sodium sulfate and concentrated on a rotary evaporator under reduced pressure. The crude was diluted with DCM (15 mL). The mixture was cooled to 0° C. (ice-water bath), then 2 M HCl in diethyl ether was added. The reaction was stirred for 3 h at RT. After completion of the reaction, the reaction mixture was quenched with water (10 mL) and extracted with DCM (3×50 mL). The combined organic layer was dried over sodium sulfate and concentrated on a rotary evaporator under reduced pressure to obtain the crude product. The crude product was purified by column chromatography (Mesh 200-400) by using 10% EtOAc in hexane as an eluent, to afford crude 4-(benzylthio)-2-methyloxazole (0.07 g, 0.341 mmol, 6.90% yield) as a pale-yellow oil. $^1$H NMR (400 MHz, DMSO-d$_6$) δ 7.30-7.24 (m, 5H), 7.49 (s, 1H), 4.06 (s, 2H), 2.40 (s, 3H).

Step 2. Methyloxazole-4-sulfonyl chloride (Intermediate 58)

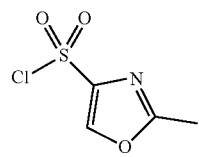

To a stirred solution of 4-(benzylthio)-2-methyloxazole (0.07 g, 0.341 mmol) in AcOH (1 mL):water (0.250 mL), NCS (0.114 g, 0.853 mmol) was added at 0° C. under nitrogen atmosphere. The reaction mixture was stirred at room temperature for 3 h. After completion of the reaction, the reaction mixture was quenched with water (2 mL) and extracted with EtOAc (15 mL). The combined organic layers were dried over sodium sulfate and concentrated on a rotary evaporator under reduced pressure to obtain 2-methyloxazole-4-sulfonyl chloride (0.12 g 0.341 mmol) as a semisolid. $^{1}$H NMR (400 MHz, DMSO-d$_6$) δ 2.62 (S, 3H), 7.49 (s, 1H).

Intermediate 59. 5-Fluoro-2-methoxybenzoic acid

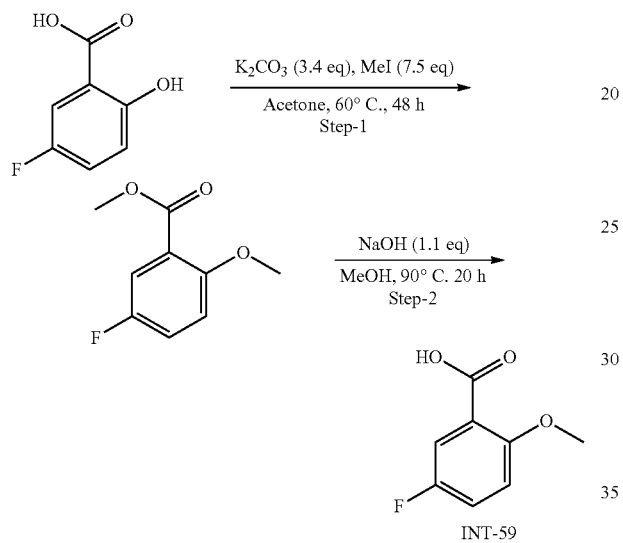

Step 1. Methyl 5-fluoro-2-methoxybenzoate

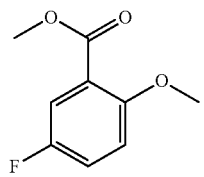

To a dried 25 L four neck round bottom flask under nitrogen atmosphere, 5-fluoro-2-hydroxybenzoic acid (800 g, 5.125 mmol) was added in acetone (7 L). To this solution K$_2$CO$_3$ (2387 g, 39.77 mol) was added, followed by dropwise addition of MeI (2394 mL, 38.43 mol) at RT. The resulting reaction mixture was heated at 60° C. for 48 h. Progress of the reaction was monitored by TLC (50% EtOAc in hexane). The reaction mixture was filtered and concentrated under reduced pressure. The residue was diluted with water (4000 mL) and extracted with EtOAc (3×2000 mL). The combined organic layer was dried over anhydrous sodium sulfate, filtered, and concentrated under reduced pressure to obtain methyl 5-fluoro-2-methoxybenzoate (930 g, 4952 mmol, 97% yield) as gummy liquid. LCMS (Method B): Rt 1.69 min, 185.2 [M+H]$^+$; HPLC (Method A): Rt 5.05 min, 98.07%.

Step 2. 5-fluoro-2-methoxybenzoic acid (Intermediate 59)

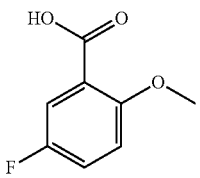

To a 25 L four neck round bottom flask, methyl 5-fluoro-2-methoxybenzoate (1.45 kg, 7.87 mol) was added in MeOH (5000 mL). To this solution NaOH (4330 mL, 8.66 mol, 2 M in H$_2$O) was added at RT, and the reaction was stirred at 90° C. for 20 h. Progress of the reaction was monitored by TLC (50% EtOAc in Hexane). The reaction mixture was concentrated, diluted with water (5000 mL), and acetified to pH-2 with 1.5 N HCl. The resulting solid compound was filtered and dried under reduced pressure to obtain 5-fluoro-2-methoxybenzoic acid (1200 g, 7.03 mol, 89% yield) as a solid. LCMS (Method B): Rt 1.31 min, 169.2 [M–H]$^-$, 99.65%.

Intermediate 60. tert-Butyl 2-(3,6-dichloro-1,2,4-triazin-5-yl)-2,7-diazaspiro[3.5]nonane-7-carboxylate

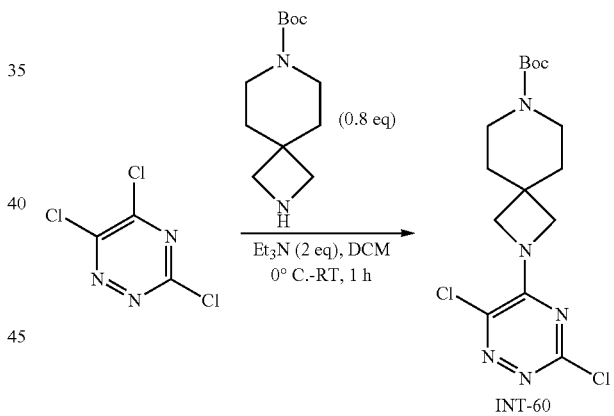

To a dried 500 mL three necked round bottom flask under nitrogen atmosphere, 3,5,6-trichloro-1,2,4-triazine (6 g, 32.5 mmol) was added to DCM (80 mL). To this reaction mixture, Et$_3$N (9.07 mL, 65.1 mmol) and tert-butyl 2,7-diazaspiro[3.5]nonane-7-carboxylate hydrochloride (6.84 g, 26.0 mmol) were added at 0° C. under nitrogen atmosphere. The reaction mixture was stirred at RT for 1 h, monitoring the reaction progress by TLC (30% EtOAc in hexane). After completion of the reaction, the reaction mixture was quenched with water (300 mL) and extracted with DCM (3×200 mL). The combined organic layers were dried over sodium sulfate and filtered, and the filtrate was concentrated on a rotary evaporator under reduced pressure to obtain the crude product. The crude product was purified by column chromatography (Biotage-isolera one), with 25% EtOAc in hexane as an eluent. The fractions containing the desired product were concentrated under reduced pressure to obtain tert-butyl 2-(3,6-dichloro-1,2,4-triazin-5-yl)-2,7-diazaspiro

[3.5]nonane-7-carboxylate (9 g, 73.1% yield) as a solid. $^1$H NMR (400 MHz, DMSO-d$_6$) δ 4.44 (s, 2H), 3.89 (s, 2H), 3.40-3.33 (m, 2H), 3.30-3.21 (m, 2H), 1.70 (t, J=5.57 Hz, 4H), 1.40 (s, 9H); LCMS (Method E): Rt 2.01 min, m/z: 374.0 [M+H]$^+$, 98.94%.
Intermediate 61: 2-((5-(2,7-Diazaspiro[3.5]nonan-2-yl)-1,2,4-triazin-6-yl)oxy)-N-(2,2-difluoroethyl)-5-fluoro-N-isopropylbenzamide hydrochloride
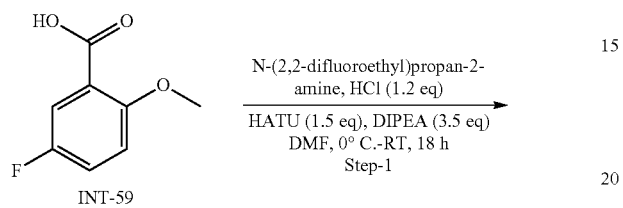
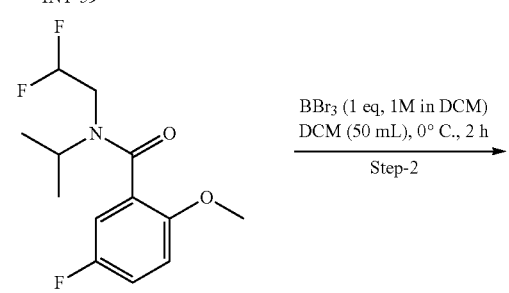
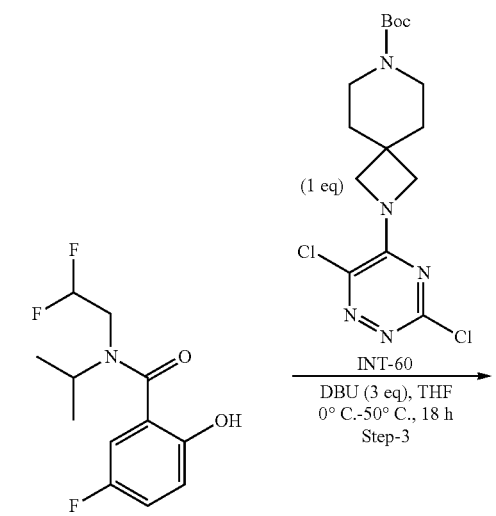
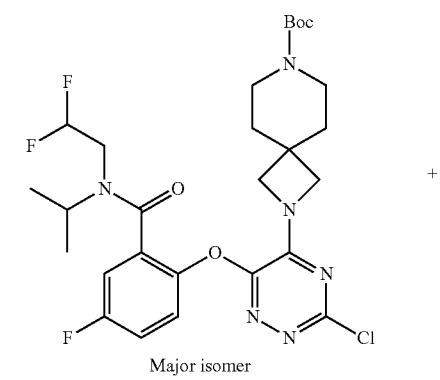
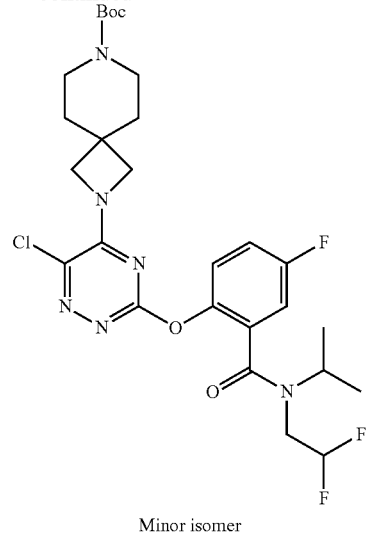
Minor isomer
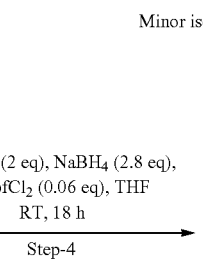
Major isomer
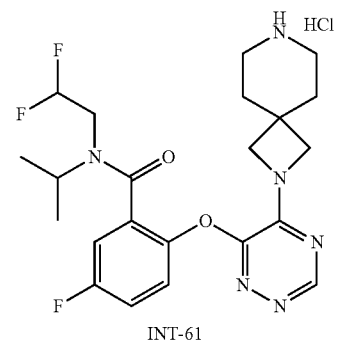
INT-61

Step 1. N-(2,2-Difluoroethyl)-5-fluoro-N-isopropyl-2-methoxybenzamide

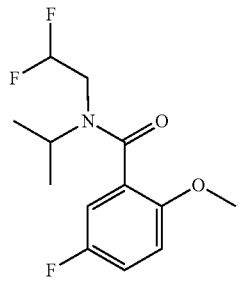 [SMILES: COc1ccc(F)cc1C(=O)N(CC(F)F)C(C)C]

To a 100 mL two necked round bottom flask under nitrogen atmosphere, 5-fluoro-2-methoxybenzoic acid 3.3 g, 19.40 mmol) and N-(2,2-difluoroethyl)propan-2-amine hydrochloride (3.41 g, 21.34 mmol) were added to DMF (30 mL). To this reaction mixture, HATU (11.06 g, 29.1 mmol) and DIPEA (11.86 mL, 67.9 mmol) were added at 0° C. The reaction was stirred at RT for 18 h, monitoring the reaction progress by TLC (60% EtOAc in hexane). The reaction mixture was diluted with ice cold water (200 mL) and extracted with EtOAc (3×100 mL). The combined organic extracts were washed with cold water (5×100 mL) then brine (100 mL), dried over anhydrous sodium sulfate, and filtered, and the filtrate was concentrated under reduced pressure to afford 5.3 g of crude product as a yellow solid. The crude product was purified by flash column chromatography using EtOAc in hexane. The product was eluted in 25-30% EtOAc in hexane. The fractions containing the desired product were concentrated under reduced pressure to obtain N-(2,2-difluoroethyl)-5-fluoro-N-isopropyl-2-methoxybenzamide (3.62 g, 66.6% yield) as a solid. $^1$H NMR (400 MHz, DMSO-$d_6$) δ 7.28-7.20 (m, 1H), 7.14-7.10 (m, 2H), 6.40-6.07 (m, 1H), 3.78 (s, 3H), 3.75-3.60 (m, 3H), 1.11 (d, J=6.63 Hz, 3H), 1.02 (d, J=6.63 Hz, 3H); LCMS (Method E): Rt 1.88 min, m/z: 276.0 [M+H]$^+$, 98.2%.

Step 2. N-(2,2-Difluoroethyl)-5-fluoro-2-hydroxy-N-isopropylbenzamide

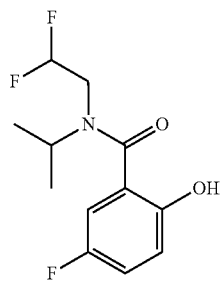 [SMILES: CC(C)N(CC(F)F)C(=O)c1cc(F)ccc1O]

To a dried 250 mL two necked round bottom flask under nitrogen atmosphere, N-(2,2-difluoroethyl)-5-fluoro-N-isopropyl-2-methoxybenzamide (3.6 g, 13.08 mmol) was added to DCM (50 mL). To this reaction mixture, BBr$_3$ (1 M in DCM, 13.08 mL, 13.08 mmol) was added at 0° C. The reaction mixture was stirred at 0° C. for 2 h, monitoring the reaction progress by TLC (30% EtOAc in hexane). After completion, the reaction mixture was diluted with water (100 mL) and extracted with DCM (3×100 mL). The combined organic extract was washed with brine (100 mL), dried over anhydrous sodium sulfate, and filtered, and the filtrate was concentrated under reduced pressure to afford crude N-(2,2-difluoroethyl)-5-fluoro-2-hydroxy-N-isopropylbenzamide (3.2 g, 92% yield) as a solid. $^1$H NMR (400 MHz, DMSO-$d_6$) δ 9.80 (s, 1H), 7.07 (td, J=8.69, 3.25 Hz, 1H), 7.00-6.97 (m, 1H), 6.87 (dd, J=8.88, 4.50 Hz, 1H), 6.43-6.06 (m, 1H), 3.77-3.61 (m, 3H), 1.19-1.01 (m, 6H); LCMS (Method E): Rt 1.62 min, m/z: 262.1 [M+H]$^+$, 98.2%.

Step 3. tert-Butyl 2-(3-chloro-6-(2-((2,2-difluoroethyl)(isopropyl)carbamoyl)-4-fluorophenoxy)-1,2,4-triazin-5-yl)-2,7-diazaspiro[3.5]nonane-7-carboxylate and tert-butyl 2-(6-chloro-3-(2-((2,2-difluoroethyl)(isopropyl)carbamoyl)-4-fluorophenoxy)-1,2,4-triazin-5-yl)-2,7-diazaspiro[3.5]nonane-7-carboxylate

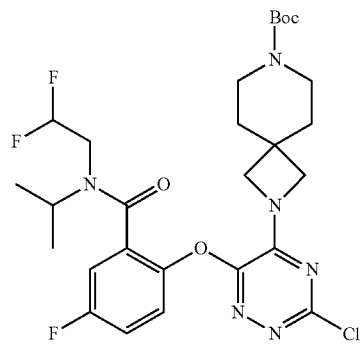 [SMILES: CC(C)N(CC(F)F)C(=O)c1cc(F)ccc1Oc1nnc(Cl)nc1N1CC2(CCN(C(=O)OC(C)(C)C)CC2)C1]

To a 50 mL two necked round bottom flask under nitrogen atmosphere, tert-butyl 2-(3,6-dichloro-1,2,4-triazin-5-yl)-2,7-diazaspiro[3.5]nonane-7-carboxylate (2.15 g, 5.74 mmol) and N-(2,2-difluoroethyl)-5-fluoro-2-hydroxy-N-isopropylbenzamide (3.15 g, 12.06 mmol) were added to THF (25 mL). To this reaction mixture, DBU (2.60 mL, 17.23 mmol) was added at 0° C., and the mixture was stirred at 50° C. for 18 h, monitoring the reaction progress by TLC (30% EtOAc in hexane). After completion, the reaction mixture was diluted with water (50 mL) and extracted with EtOAc (3×100 mL). The combined organic extract was washed with brine (2×50 mL), dried over anhydrous sodium sulfate, and filtered, and the filtrate was concentrated under reduced pressure to afford crude product as brown gum. The crude product was purified by flash column chromatography (230-400 mesh silica-gel,), eluting with (0-30)% EtOAc in hexane. The fractions containing the desired product were concentrated under reduced pressure to obtain tert-butyl 2-(3-chloro-6-(2-((2,2-difluoroethyl) (isopropyl)carbamoyl)-4-fluorophenoxy)-1,2,4-triazin-5-yl)-2,7-diazaspiro[3.5]nonane-7-carboxylate (1.6 g, , 44.6% yield). The structure was confirmed by NOE. $^1$H NMR (400 MHz, DMSO-$d_6$) δ 7.51-7.46 (m, 1H), 7.44-7.38 (m, 2H), 6.37-5.95 (m, 1H), 4.26 (br s, 2H), 3.92 (s, 2H), 3.79-3.51 (m, 3H), 3.39-3.33 (m, 1H), 3.29-3.21 (m, 2H), 1.78-1.58 (m, 5H), 1.40 (s, 9H), 1.14-0.76 (m, 6H); LCMS (Method E): Rt 2.25 min, m/z: 599.1 [M+H]$^+$, 95.87%.

tert-Butyl 2-(6-chloro-3-(2-((2,2-difluoroethyl)(iso-propyl)carbamoyl)-4-fluorophenoxy)-1,2,4-triazin-5-yl)-2,7-diazaspiro[3.5]nonane-7-carboxylate

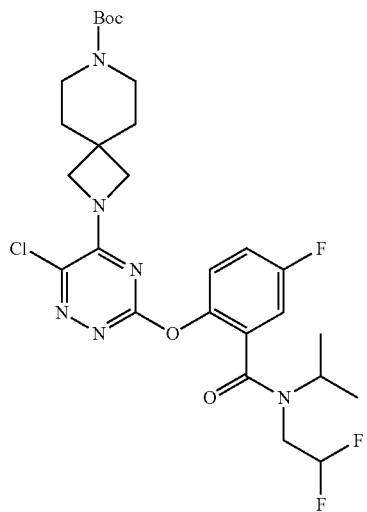 [SMILES: CC(C)N(CC(F)F)C(=O)c1cc(F)ccc1Oc1nnc(Cl)c(N2CC3(CCN(C(=O)OC(C)(C)C)CC3)C2)n1]

Minor isomer: tert-Butyl 2-(6-chloro-3-(2-((2,2-difluoroethyl)(isopropyl)carbamoyl)-4-fluorophenoxy)-1,2,4-triazin-5-yl)-2,7-diazaspiro[3.5]nonane-7-carboxylate (900 mg, 26.2% yield) as a solid. LCMS (Method E): Rt 2.28 min, m/z: 599.1 [M+H]⁺, 93.55%.

Step 4. tert-Butyl 2-(6-(2-((2,2-difluoroethyl)(iso-propyl)carbamoyl)-4-fluorophenoxy)-1,2,4-triazin-5-yl)-2,7-diazaspiro[3.5]nonane-7-carboxylate

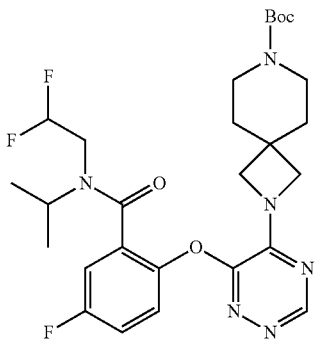

To a dried 100 mL two necked round bottom flask, tert-butyl 2-(3-chloro-6-(2-((2,2-difluoroethyl)(isopropyl)carbamoyl)-4-fluorophenoxy)-1,2,4-triazin-5-yl)-2,7-diazaspiro[3.5]nonane-7-carboxylate (1.6 g, 2.67 mmol) was added in THF (30 mL), and the reaction mixture was purged with nitrogen for 5 min. To this reaction mixture, NaBH₄ (0.283 g, 7.48 mmol), TMEDA (0.806 mL, 5.34 mmol) and PdCl₂(dppf)·CH₂Cl₂ complex (0.131 g, 0.160 mmol) were added at RT under nitrogen atmosphere. The reaction was stirred for 18 h, monitoring progress by TLC (70% EtOAc in hexane). After completion, the reaction was diluted with EtOAc (50 mL). The mixture was filtered, and the residue was washed with EtOAc (50 mL). The combined filtrate was washed with brine (50 mL), dried over anhydrous sodium sulfate, and filtered, and the filtrate was concentrated under reduced pressure to afford crude product as brown sticky liquid (2.1 g). The crude product was purified by silica gel column chromatography using 80% EtOAc in hexane as an eluent to obtain tert-butyl 2-(6-(2-((2,2-difluoroethyl) (iso-propyl)carbamoyl)-4-fluorophenoxy)-1,2,4-triazin-5-yl)-2,7-diazaspiro[3.5]nonane-7-carboxylate (920 mg, 59.7% yield)) as a solid. ¹H NMR (400 MHz, DMSO-d₆) δ 8.46 (s, 1H), 7.51-7.44 (m, 1H), 7.44-7.38 (m, 2H), 6.41-5.87 (m, 1H), 4.22 (br s, 2H), 3.87 (br s, 2H), 3.83-3.48 (m, 5H), 1.70 (br s, 5H), 1.40 (s, 9H), 1.15 (d, J=6.7 Hz, 1H), 1.13-0.67 (m, 6H); LCMS (Method E): Rt 2.07 min, m/z: 565.1 [M+H]⁺, 97.83%.

Step 5. 2-((5-(2,7-Diazaspiro[3.5]nonan-2-yl)-1,2,4-triazin-6-yl)oxy)-N-(2,2-difluoroethyl)-5-fluoro-N-isopropylbenzamide hydrochloride (Intermediate 61)

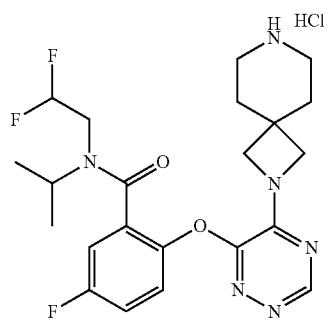 [SMILES: Cl ; CC(C)N(CC(F)F)C(=O)c1cc(F)ccc1Oc1nncnc1N1CC2(CCNCC2)C1]

To a dried 50 mL single necked round bottom flask under nitrogen atmosphere, tert-butyl 2-(6-(2-((2,2-difluoroethyl)(isopropyl)carbamoyl)-4-fluorophenoxy)-1,2,4-triazin-5-yl)-2,7-diazaspiro[3.5]nonane-7-carboxylate (920 mg, 1.629 mmol) was added in 2,2,2-trifluoroethanol (10 mL). To this reaction mixture, TMSCl (0.625 mL, 4.89 mmol) was added at 0° C., and the reaction was stirred at RT for 1 h, monitoring the reaction progress by TLC (100% EtOAc). After completion, the reaction mixture was concentrated on rotary evaporator and the residue obtained was co-distilled with EtOAc (10 mL) to obtain crude 2-((5-(2,7-diazaspiro [3.5]nonan-2-yl)-1,2,4-triazin-6-yl) oxy)-N-(2,2-difluoroethyl)-5-fluoro-N-isopropylbenzamide hydrochloride (820 mg, 97%) as a solid. LCMS (Method E): Rt 1.36 min, m/z: 465.1 [M+H]⁺, 96.12%.

Intermediate 62. 2-((5-(2,7-Diazaspiro[3.5]nonan-2-yl)-1,2,4-triazin-6-yl)oxy)-5-fluoro-N-isopropyl-N-(2,2,2-trifluoroethyl)benzamide hydrochloride

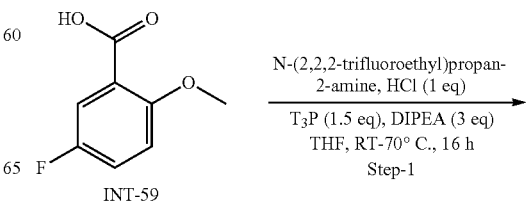

367
-continued

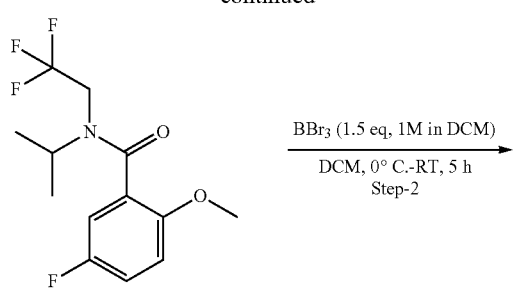

BBr₃ (1.5 eq, 1M in DCM)
DCM, 0° C.-RT, 5 h
Step-2

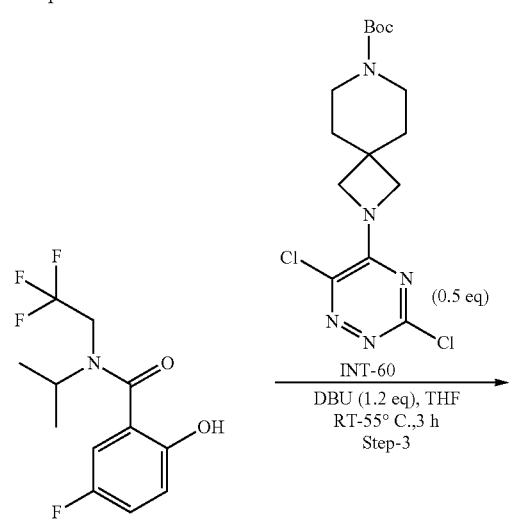

INT-60
DBU (1.2 eq), THF
RT-55° C., 3 h
Step-3

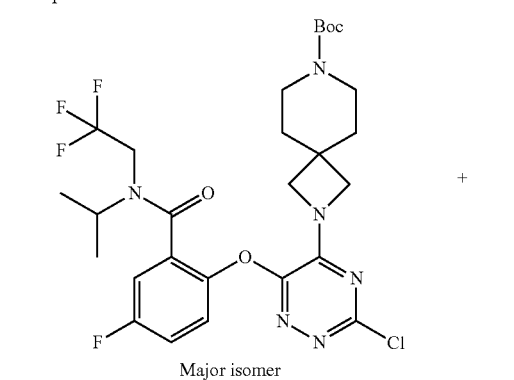

Major isomer

+

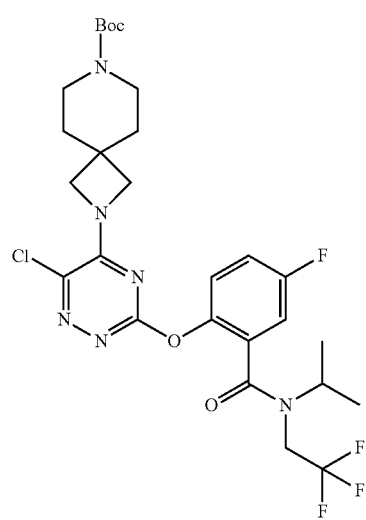

Minor isomer

368
-continued

TEMDA (2 eq), NaBH₄ (2.8 eq),
PddppfCl₂ (0.06 eq)
THF, RT, 24 h
Step-4

Major isomer →

TMS—Cl (4 eq)
CF₃CH₂OH
0° C.-RT, 2 h
Step-5

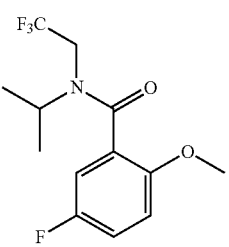 [SMILES: COc1ccc(F)cc1C(=O)N(CC(F)(F)F)C(C)C]

INT-62

Step 1. 5-Fluoro-N-isopropyl-2-methoxy-N-(2,2,2-trifluoroethyl)benzamide

To a 500 mL round bottom flask, 5-fluoro-2-methoxybenzoic acid (20 g, 118 mmol) was added in THF (200 mL), and N-(2,2,2-trifluoroethyl)propan-2-amine hydrochloride (20.88 g, 118 mmol) and DIPEA (63.3 mL, 353 mmol) were added. To this reaction mixture, propanephosphonic acid anhydride (104 mL, 176 mmol) was added at RT. The reaction was stirred at 75° C. for 16 h. Progress of the reaction was monitored by TLC (30% EtOAc in hexane). The reaction mixture was diluted with water (300 mL) and extracted with EtOAc (2×100 mL). The organic layer was dried over Na₂SO₄, filtered, and concentrated under reduced pressure to obtain crude compound which was further purified by silica gel column chromatography (30% EtOAc in hexane as an eluent) to obtain 5-fluoro-N-isopropyl-2-methoxy-N-(2,2,2-trifluoroethyl)benzamide (27 g, 85 mmol, 72.2% yield) as a solid. LCMS (Method B): Rt 1.99 min, m/z: 294.2 [M+H]⁺, 92.22%.

Step 2. 5-Fluoro-2-hydroxy-N-isopropyl-N-(2,2,2-trifluoroethyl)benzamide

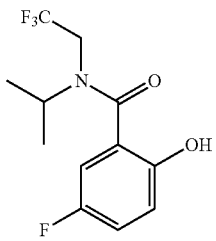 [SMILES: CC(C)N(CC(F)(F)F)C(=O)c1cc(F)ccc1O]

To a dried 2000 mL three necked round bottom flask under nitrogen atmosphere, 5-fluoro-N-isopropyl-2-methoxy-N-(2,2,2-trifluoroethyl)benzamide (27 g, 92 mmol) was added in DCM (300 mL). To this reaction mixture, BBr₃ (138 mL, 138 mmol) was added at 0° C. The reaction mixture was stirred at RT for 5 h, monitoring reaction progress by TLC. After completion, the reaction mixture was quenched with ice cold water (500 mL), and extracted with DCM (3×100 mL). The combined organic layer was dried over Na₂SO₄, filtered, and concentrated under reduced pressure to obtain 5-fluoro-2-hydroxy-N-isopropyl-N-(2,2,2-trifluoroethyl)benzamide (25 g, 87 mmol, 95%) as a solid. $^1$H NMR (400 MHz, DMSO-d₆) δ 9.77-9.93 (s, 1H), 7.09 (td, J=8.69, 3.25 Hz, 1H), 6.95 (dd, J=8.32, 2.81 Hz, 1H), 6.87 (dd, J=9.01, 4.50 Hz, 1H), 4.21 (q, J=9.01 Hz, 2H), 3.74-3.89 (m, 1H), 1.10 (d, J=5.88 Hz, 6H); LCMS (Method B): Rt 1.85 min, m/z: 280.2 [M+H]⁺, 97.45%.

Step 3. tert-Butyl 2-(3-chloro-6-(4-fluoro-2-(isopropyl(2,2,2-trifluoroethyl)carbamoyl)phenoxy)-1,2,4-triazin-S-yl)-2,7-diazaspiro[3.5]nonane-7-carboxylate

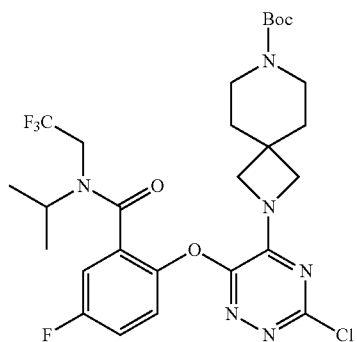 [SMILES: CC(C)N(CC(F)(F)F)C(=O)c1cc(F)ccc1Oc1nnc(Cl)nc1N1CC2(CCN(C(=O)OC(C)(C)C)CC2)C1]

To a 250 mL round bottom flask under nitrogen atmosphere, tert-butyl 2-(3,6-dichloro-1,2,4-triazin-5-yl)-2,7-diazaspiro[3.5]nonane-7-carboxylate (1.6 g, 4.28 mmol) and 5-fluoro-2-hydroxy-N-isopropyl-N-(2,2,2-trifluoroethyl) benzamide (2.51 g, 8.98 mmol) were added in THF (30 mL) at RT, then DBU (1.595 mL, 10.69 mmol) was added. The reaction mixture was stirred at 55° C. for 3 h. After completion of the reaction, the reaction mixture was diluted with water (50 mL) and extracted with EtOAc (2×30 mL). The combined organic layer was dried over Na₂SO₄, filtered, and concentrated under reduced pressure. The residue was purified by column chromatography using 230-400 mesh silicagel with 5% MeOH in DCM as an eluent to obtain tert-butyl 2-(3-chloro-6-(4-fluoro-2-(isopropyl(2,2,2-trifluoroethyl) carbamoyl)phenoxy)-1,2,4-triazin-5-yl)-2,7-diazaspiro [3.5] nonane-7-carboxylate (750 mg, 1.215 mmol, 28.4% yield) as a solid. The structure was confirmed by NOE. $^1$H NMR (400 MHz, DMSO-d₆) δ 7.54-7.37 (m, 3H), 4.39-4.17 (m, 3H), 4.17-4.07 (br s, 1H), 3.92 (br s, 2H), 3.77 (m, 1H), 3.30-3.19 (m, 4H), 1.69 (br s, 4H), 1.40 (s, 9H), 1.13-0.74 (m, 6H); LCMS (Method B): Rt 2.36 min, 617.2 [M+H]⁺, 97.62%.

tert-Butyl 2-(6-chloro-3-(4-fluoro-2-(isopropyl(2,2,2-trifluoroethyl)carbamoyl)phenoxy)-1,2,4-triazin-5-yl)-2,7-diazaspiro[3.5]nonane-7-carboxylate

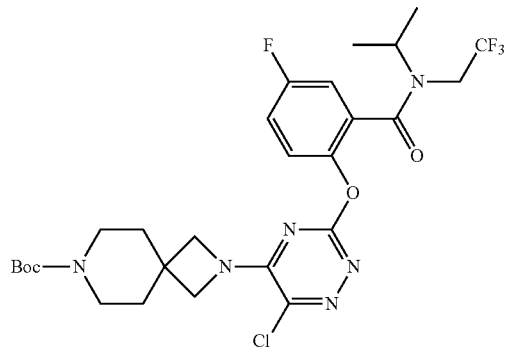 [SMILES: CC(C)N(CC(F)(F)F)C(=O)c1cc(F)ccc1Oc1nnc(Cl)c(N2CC3(CCN(C(=O)OC(C)(C)C)CC3)C2)n1]

Minor isomer: tert-Butyl 2-(6-chloro-3-(4-fluoro-2-(isopropyl(2,2,2-trifluoroethyl)carbamoyl)phenoxy)-1,2,4-triazin-5-yl)-2,7-diazaspiro[3.5]nonane-7-carboxylate (600 mg, 0.972 mmol, 22.75% yield). LCMS (Method B): 2.42 min, m/z: 617.2 [M+H]⁺, 93.39%.

Step 4. tert-Butyl 2-(6-(4-fluoro-2-(isopropyl(2,2,2-trifluoroethyl)carbamoyl)phenoxy)-1,2,4-triazin-5-yl)-2,7-diazaspiro[3.5]nonane-7-carboxylate

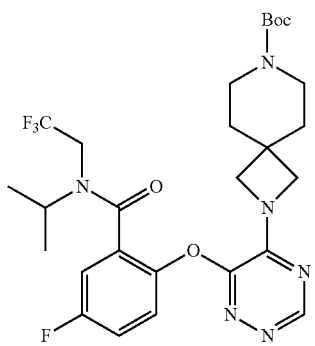 [SMILES: CC(C)N(CC(F)(F)F)C(=O)c1cc(F)ccc1Oc1nncnc1N1CC2(CCN(C(=O)OC(C)(C)C)CC2)C1]

To a dried 100 mL two necked round bottom flask, tert-butyl 2-(3-chloro-6-(4-fluoro-2-(isopropyl(2,2,2-trifluoroethyl)carbamoyl)phenoxy)-1,2,4-triazin-5-yl)-2,7-diazaspiro[3.5]nonane-7-carboxylate (550 mg, 0.891 mmol) was added in THF (10 mL). The reaction mixture was purged with nitrogen for 5 min. To this reaction mixture NaBH₄ (94 mg, 2.496 mmol) and TMEDA (207 mg, 1.783 mmol) were added at 0° C. under nitrogen atmosphere, followed by addition of PdCl$_2$(dppf)-CH$_2$Cl$_2$ adduct (43.7 mg, 0.053 mmol). The rection mixture was stirred at RT for 24 h, monitoring reaction progress by TLC. After completion, the reaction mixture was diluted with water (50 mL) and extracted with EtOAc (2×30 mL). The combined organic layer was dried over Na$_2$SO$_4$, filtered, and concentrated under reduced pressure. The residue was purified by column chromatography using 230-400 mesh silica-gel with 60% EtOAc in petroleum ether as an eluent to obtain tert-butyl 2-(6-(4-fluoro-2-(isopropyl(2,2,2-trifluoroethyl) carbamoyl)phenoxy)-1,2,4-triazin-5-yl)-2,7-diazaspiro[3.5] nonane-7-carboxylate (280 mg, 0.469 mmol, 52.6%) as a solid. $^1$H NMR (400 MHz, DMSO-d$_6$) δ 8.45 (s, 1H), 7.51-7.38 (m, 3H), 4.37-4.14 (m, 3H), 3.95-3.75 (m, 4H), 3.31-3.23 (m, 4H), 1.69 (br s, 4H), 1.49-1.32 (m, 9H), 1.14-0.67 (m, 6H); LCMS (Method B): Rt 2.06 min, m/z: 583.2 [M+H]$^+$, 97.51%.

Step 5. 2-((5-(2,7-Diazaspiro[3.5]nonan-2-yl)-1,2,4-triazin-6-yl)oxy)-5-fluoro-N-isopropyl-N-(2,2,2-trifluoroethyl)benzamide hydrochloride (Intermediate 62)

Intermediate 63. 2-((5-(2,7-diazaspiro[3.5]nonan-2-yl)-1,2,4-triazin-6-yl)oxy)-5-fluoro-N-isopropyl-N-(2,2,2-trifluoroethyl)benzamide hydrochloride

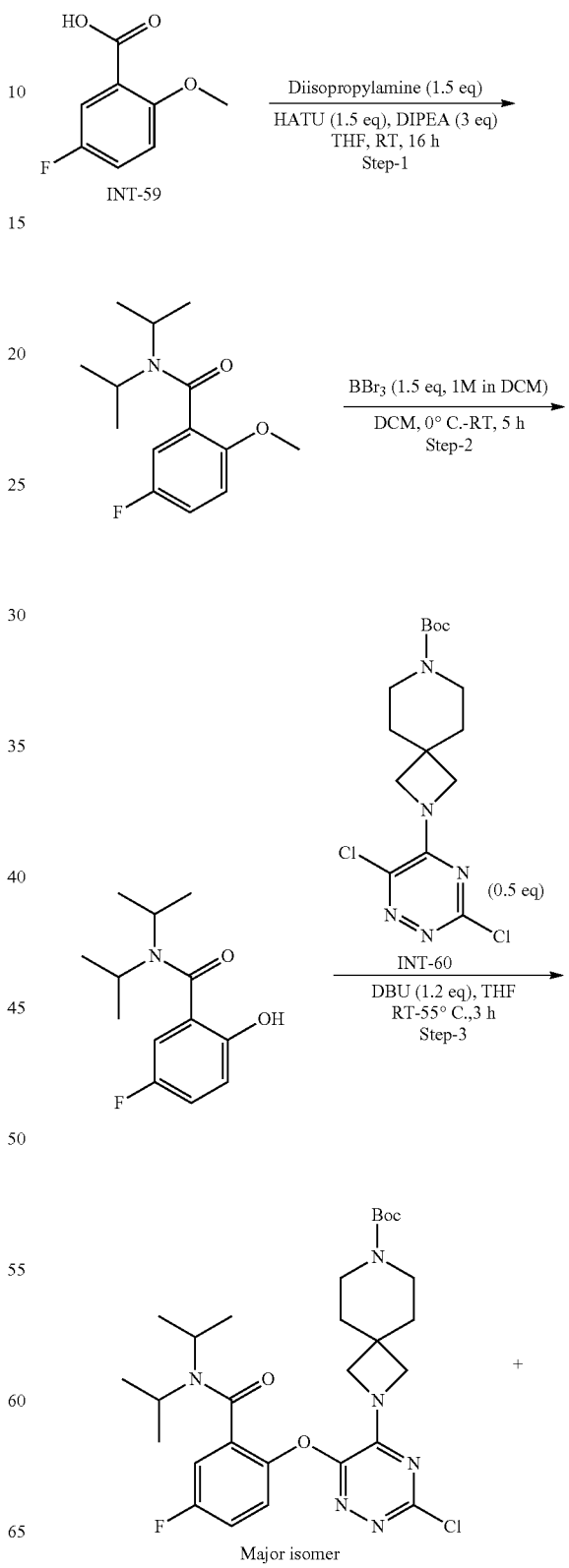

To a dried 50 mL single necked round bottom flask, tert-butyl 2-(6-(2-((2,2-difluoroethyl)(isopropyl)carbamoyl)-4-fluorophenoxy)-1,2,4-triazin-5-yl)-2,7-diazaspiro [3.5]nonane-7-carboxylate (920 mg, 1.629 mmol) was added in 2,2,2-trifluoroethanol (10 mL). TMSCl (0.625 ml, 4.89 mmol) was added at 0° C. under nitrogen atmosphere, and the reaction was stirred at RT for 1 h. Reaction progress was monitored by TLC. The reaction mixture was concentrated under reduced pressure to obtain crude 2-((5-(2,7-diazaspiro[3.5]nonan-2-yl)-1,2,4-triazin-6-yl)oxy)-N-(2,2-difluoroethyl)-5-fluoro-N-isopropylbenzamide hydrochloride (820 mg, 1.573 mmol, 97%) as a solid. $^1$H NMR (400 MHz, DMSO-d$_6$) δ 9.26-9.09 (m, 2H), 8.94 (s, 1H), 7.59-7.47 (m, 3H), 4.46 (s, 2H), 4.40 (s, 2H), 3.91-3.84 (m, 4H), 3.80-3.78 (m, 1H), 3.06 (br s, 4H), 2.00-1.99 (m, 4H), 1.28-0.80 (m, 6H); LCMS (Method B): Rt 1.09 min, m/z: 483.2 [M+H]$^+$, 89.47%;

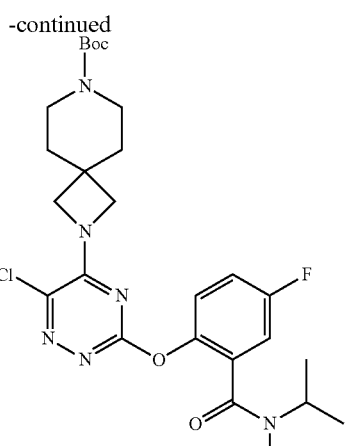

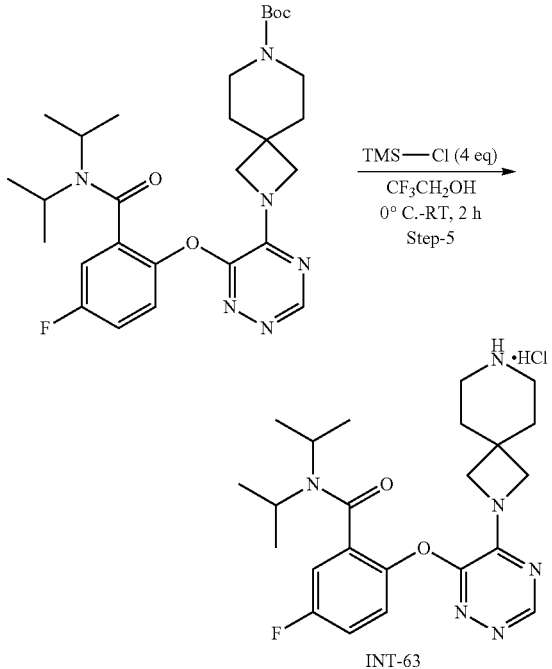

INT-63

Step 1.
5-Fluoro-N,N-diisopropyl-2-methoxybenzamide

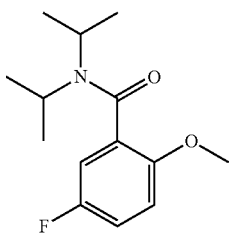 [SMILES: COc1ccc(F)cc1C(=O)N(C(C)C)C(C)C]

To a solution of 5-fluoro-2-methoxybenzoic acid (5 g, 29.4 mmol) was added DIPEA (15.40 mL, 88 mmol) and HATU (16.76 g, 44.1 mmol) at 0° C. To the reaction mixture was added diisopropylamine (4.46 g, 44.1 mmol) at 0° C. The reaction was continued at RT for 16 h. The reaction mixture was diluted with water (200 mL) and extracted with ethyl acetate (2×200 mL). The combined organic extract was washed with brine (200 mL), dried over anhydrous sodium sulfate, filtered, and concentrated under reduced pressure. The residue was purified by Biotage-isolera one with 230-400 mesh silica-gel cartridge (80 g) using EtOAc in hexane (0 to 100%) as an eluent to obtain 5-fluoro-N,N-diisopropyl-2-methoxybenzamide (4 g, 67.2%) as a solid. LCMS (Method E): Rt 1.93 min, m/z: 254.1 [M+H]⁺, 96.4%.

Step 2.
5-Fluoro-2-hydroxy-N,N-diisopropylbenzamide

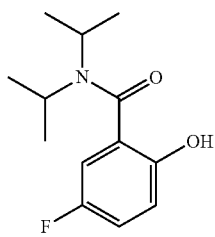 [SMILES: CC(C)N(C(=O)c1cc(F)ccc1O)C(C)C]

To a solution of 5-fluoro-N,N-diisopropyl-2-methoxybenzamide (2 g, 7.90 mmol) in DCM (15 mL) was added BBr₃ (7.90 mL, 7.90 mmol) dropwise at −10° C. The reaction mixture was allowed to stir at −10° C. for 2 h, then was stirred at RT for 16 h. The reaction mixture was diluted with water (500 mL) and extracted with DCM (2×500 mL). The combined organic extract was washed with brine (500 mL), dried over anhydrous sodium sulfate, filtered, and concentrated under reduced pressure to afford crude 5-fluoro-2-hydroxy-N,N-diisopropylbenzamide (1.8 g, 99%) as a solid. LCMS (Method E): Rt 1.71 min, m/z: 240.1 [M+H]⁺, 98.6%.

Step 3. tert-Butyl 2-(3-chloro-6-(2-(diisopropylcarbamoyl)-4-fluorophenoxy)-1,2,4-triazin-5-yl)-2,7-diazaspiro[3.5]nonane-7-carboxylate

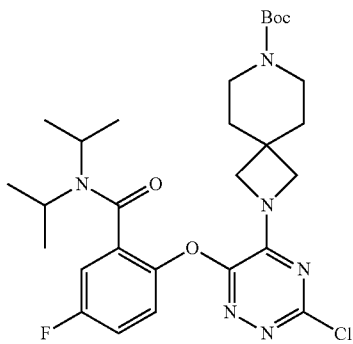 [SMILES: CC(C)N(C(=O)c1cc(F)ccc1Oc1nnc(Cl)nc1N1CC2(CCN(C(=O)OC(C)(C)C)CC2)C1)C(C)C]

To a solution of 5-fluoro-2-hydroxy-N,N-diisopropylbenzamide (2.110 g, 8.82 mmol) in THF (20 mL) was added tert-butyl 2-(3,6-dichloro-1,2,4-triazin-5-yl)-2,7-diazaspiro[3.5]nonane-7-carboxylate (1.5 g, 4.01 mmol) and tert-butyl 2-(3,6-dichloro-1,2,4-triazin-5-yl)-2,7-diazaspiro[3.5]nonane-7-carboxylate (1.5 g, 4.01 mmol) at 0° C. The reaction was allowed to stir at RT for 16 h, monitoring reaction progress by TLC. The reaction mixture was diluted with water (100 mL) and extracted with EtOAc (2×100 mL). The combined organic extract was washed with brine (100 mL), dried over anhydrous sodium sulfate, filtered, and concentrated under reduced pressure to afford crude material. The crude product was purified by Combiflash with a 230-400 mesh silica-gel cartridge, using EtOAc in hexane (0 to 100%) as an eluent, to obtain tert-butyl 2-(3-chloro-6-(2-(diisopropylcarbamoyl)-4-fluorophenoxy)-1,2,4-triazin-5-yl)-2,7-diazaspiro[3.5]nonane-7-carboxylate (0.9 g, 1.263 mmol, 31.5%) as a solid. The structure was confirmed by NOE. LCMS (Method B): Rt 2.38 min, m/z: 577.2 [M+H]$^+$, 81.97%.

Minor isomer: tert-Butyl 2-(6-chloro-3-(4-fluoro-2-(isopropyl(1,1,1-trifluoropropan-2-yl)carbamoyl)phenoxy)-1,2,4-triazin-5-yl)-2,7-diazaspiro[3.5]nonane-7-carboxylate

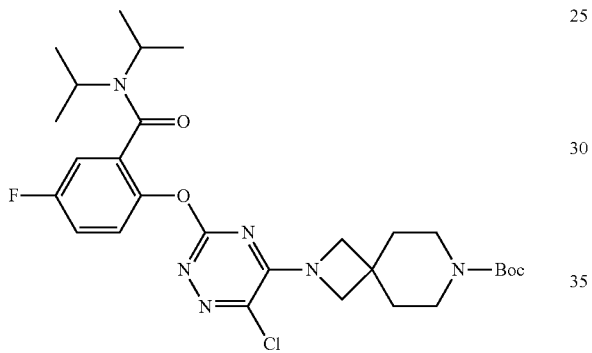

Minor isomer: tert-Butyl 2-(6-chloro-3-(4-fluoro-2-(isopropyl(1,1,1-trifluoropropan-2-yl)carbamoyl)phenoxy)-1,2,4-triazin-5-yl)-2,7-diazaspiro[3.5]nonane-7-carboxylate. LCMS (Method E): Rt 2.29 min, m/z: 577.1 [M+H]$^+$, 85.11%.

Step 4. tert-Butyl 2-(6-(2-(diisopropylcarbamoyl)-4-fluorophenoxy)-1,2,4-triazin-5-yl)-2,7-diazaspiro[3.5]nonane-7-carboxylate

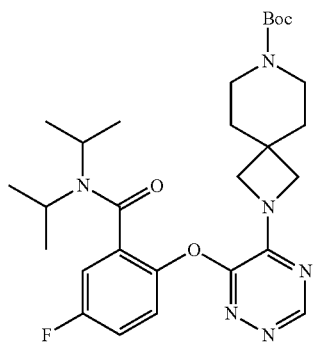

A solution of tert-butyl 2-(3-chloro-6-(2-(diisopropylcarbamoyl)-4-fluorophenoxy)-1,2,4-triazin-5-yl)-2,7-diazaspiro[3.5]nonane-7-carboxylate (0.9 g, 1.560 mmol) in MeOH (30 mL) was purged with nitrogen gas for 10 min. To this reaction mixture, Pd/C (0.166 g, 1.560 mmol) was added under nitrogen atmosphere. The reaction mixture was stirred under hydrogen gas (35 bar/kg) atmosphere at RT for 16 h, monitoring reaction progress by TLC. The reaction mixture was purged with nitrogen for 10 min, then was filtered through Celite®. The filter pad was washed with methanol (30 mL), and the filtrate was concentrated under reduced pressure to afford crude tert-butyl 2-(6-(2-(diisopropylcarbamoyl)-4-fluorophenoxy)-1,2,4-triazin-5-yl)-2,7-diazaspiro[3.5]nonane-7-carboxylate (0.75 g, 84%) as a solid. LCMS (Method E): Rt 2.09 min, m/z: 548.4 [M+H]$^+$, 95.94%.

Step 5. 2-((5-(2,7-Diazaspiro[3.5]nonan-2-yl)-1,2,4-triazin-6-yl)oxy)-5-fluoro-N,N-diisopropylbenzamide hydrochloride (Intermediate 63)

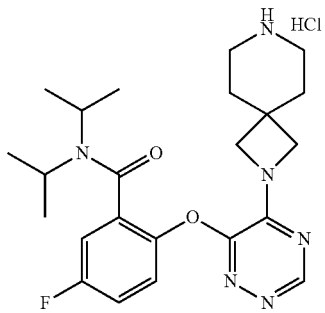 [SMILES: Cl ; CC(C)N(C(=O)c1cc(F)ccc1Oc1nncnc1N1CC2(CCNCC2)C1)C(C)C]

To a stirred solution of tert-butyl 2-(6-(2-(diisopropylcarbamoyl)-4-fluorophenoxy)-1,2,4-triazin-5-yl)-2,7-diazaspiro[3.5]nonane-7-carboxylate (450 mg, 0.829 mmol) in 2,2,2-triflouro ethanol (10 mL) at 0° C. was added TMSCI (0.530 mL, 4.15 mmol). The resulting reaction mixture was stirred at RT for 2 h, monitoring progress of the reaction by LCMS and TLC. The reaction mixture was concentrated under reduced pressure to obtain crude 2-((5-(2,7-diazaspiro[3.5]nonan-2-yl)-1,2,4-triazin-6-yl)oxy)-5-fluoro-N,N-diisopropylbenzamide (380 mg, 0.816 mmol, 98%) as a solid. LCMS (Method E): Rt 1.44 min, m/z: 443.1 [M+H]$^+$, 95.06%.

Synthesis of Compounds

Example 1. N-Ethyl-5-fluoro-N-isopropyl-2-((4-(7-(((2S,5R)-5-(methylsulfonamido) tetrahydro-2H-pyran-2-yl)methyl)-2,7-diazaspiro[3.5]nonan-2-yl) pyrimidin-5-yl)oxy)benzamide (1)

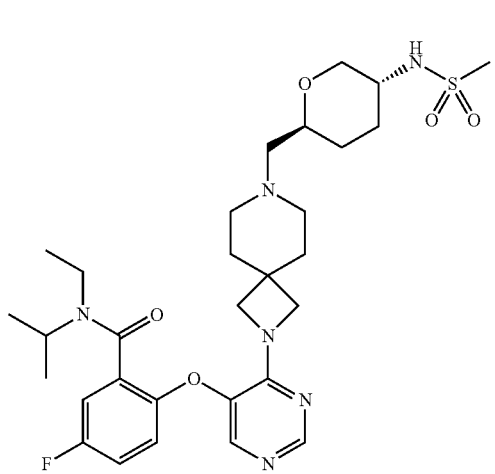 [SMILES: CCN(C(=O)c1cc(F)ccc1Oc1cncnc1N1CC2(CCN(C[C@@H]3CC[C@@H](NS(C)(=O)=O)CO3)CC2)C1)C(C)C]

In a dried, 25 mL two-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (0.35 g, 0.606 mmol) was added to DCM (5 mL) and the mixture was cooled to 0° C. TEA (0.338 mL, 2.426 mmol) was added to the reaction mixture and stirred at 0° C. for 0.5 h. After that, MsCl (0.057 mL, 0.728 mmol) was added and the reaction mixture was stirred at 25° C. for 18 h, monitoring the reaction progress by TLC (10% MeOH in DCM). After 18 h, the reaction mixture was quenched with water (10 mL) and extracted with DCM (2×30 mL). The combined organic layer was dried over anhydrous sodium sulfate and filtered, and the filtrate was concentrated under reduced pressure (bath temperature 40° C.) to afford the crude product. The crude product was purified by Prep HPLC (Method A). The fractions containing the pure product were lyophilized to obtain N-ethyl-5-fluoro-N-isopropyl-2-((4-(7-(((2S,5R)-5-(methylsulfonamido)tetrahydro-2H-pyran-2-yl)methyl)-2,7-diazaspiro[3.5]nonan-2-yl) pyrimidin-5-yl)oxy)benzamide (79 mg, 20.80% yield) as an off-white solid: $^1$H NMR (400 MHz, DMSO-$d_6$): δ 8.29-8.24 (m, 1H), 7.74-7.66 (m, 1H), 7.33-7.22 (m, 2H), 7.11-7.01 (m, 2H), 3.92-3.81 (m, 3H), 3.81-3.70 (m, 3H), 3.46-3.39 (m, 1H), 3.26-3.19 (m, 1H), 3.18-3.08 (m, 2H), 3.05-2.96 (m, 1H), 2.92 (s, 3H), 2.32-2.17 (m, 5H), 1.97 (br d, J=11.9 Hz, 1H), 1.66 (br s, 5H), 1.38 (dq, J=3.4, 12.3 Hz, 1H), 1.31-1.15 (m, 3H), 1.14-1.07 (m, 5H), 1.06-0.96 (m, 3H); LCMS (Method A): Rt=1.72 min, 619.5 (M+H)$^+$; HPLC (Method A): Rt=4.7 min, 98.82%.

Example 2. N-Ethyl-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (2)

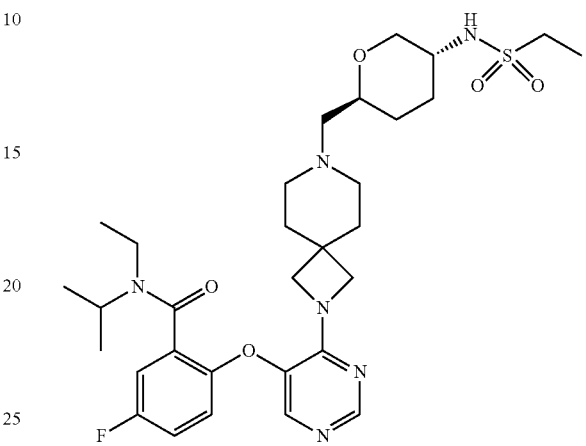

In a 100 mL dried three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (250 mg, 0.46 mmol) was added to $CH_2Cl_2$ (5 mL) and the mixture was cooled to 0° C. Triethylamine (0.226 mL, 1.618 mmol) was added to the reaction mixture and stirred at 0° C. for 30 min. Ethanesulfonyl chloride (0.049 mL, 0.518 mmol) was added slowly and the mixture was then stirred at 25° C. for 12 h, monitoring the reaction progress by TLC (10% Methanol in DCM). After 12 h, the reaction was quenched with water (150 mL) and extracted with DCM (2×50 mL). The organic layer was washed with aqueous $NaHCO_3$ (2×50 mL) and brine (2×25 mL). The organic layer was dried over anhydrous sodium sulfate and filtered, and the filtrate was concentrated on a rotary evaporator (bath temperature 40° C.) to afford the crude compound. The crude compound was purified by Prep HPLC (Method A). The fractions containing the pure product were lyophilized to obtain N-ethyl-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (150 mg, 51.0% yield) as an off-white solid: $^1$H NMR (400 MHz, DMSO-$d_6$): δ 8.30-8.24 (m, 1H), 7.75-7.66 (m, 1H), 7.34-7.21 (m, 2H), 7.14-7.07 (m, 1H), 7.07-7.00 (m, 1H), 3.91-3.80 (m, 3H), 3.80-3.71 (m, 3H), 3.45-3.39 (m, 1H), 3.26-3.17 (m, 1H), 3.16-3.05 (m, 2H), 3.05-2.96 (m, 3H), 2.32-2.17 (m, 5H), 1.94 (br d, J=12.6 Hz, 1H), 1.66 (br s, 5H), 1.47-1.34 (m, 1H), 1.31-1.24 (m, 1H), 1.22-1.15 (m, 5H), 1.14-1.07 (m, 5H), 1.07-0.98 (m, 3H); LCMS (Method A): Rt=2.22 min, 633.0 (M+H)$^+$; HPLC (Method A): Rt=4.96 min, 99.52%.

Example 3. N-Ethyl-5-fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide (3)

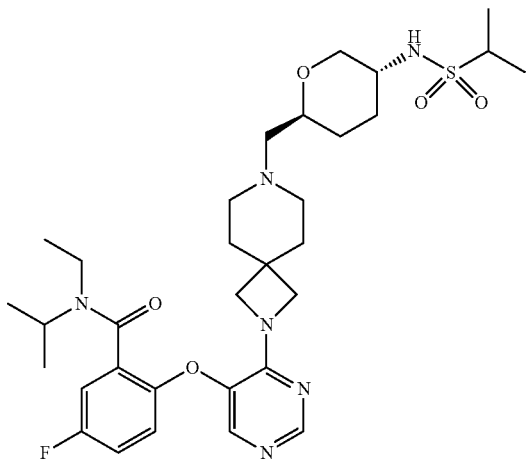 [SMILES: CCN(C(=O)c1cc(F)ccc1Oc1cncnc1N1CC2(CCN(C[C@@H]3CC[C@@H](NS(=O)(=O)C(C)C)CO3)CC2)C1)C(C)C]

In a dried, 25 mL two-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (0.35 g, 0.606 mmol) was dissolved in DCM (5 mL) and the reaction was cooled to 0° C. To this solution, DBU (0.366 ml, 2.426 mmol) was added and the reaction was stirred at 0° C. for 0.5 h. After that propane-2-sulfonyl chloride (0.104 g, 0.728 mmol) was added and the reaction was then stirred at 25° C. for 11 h, monitoring the reaction progress by TLC (10% MeOH in DCM). After 11 h, the reaction mixture was quenched with water (20 mL) and extracted with DCM (2×30 mL). The combined organic layer was dried over anhydrous sodium sulfate and filtered, and the filtrate was concentrated on a rotary evaporator (bath temperature 40° C.) to afford the crude product. The crude product was purified by Prep HPLC (Method A). The fractions containing the pure product were lyophilized to obtain N-ethyl-5-fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide (35 mg, 8.80% yield) as an off-white solid: $^1$H NMR (400 MHz, DMSO-$d_6$): δ 8.30-8.25 (m, 1H), 7.76-7.66 (m, 1H), 7.33-7.22 (m, 2H), 7.13-7.02 (m, 2H), 3.92-3.71 (m, 6H), 3.46-3.38 (m, 1H), 3.24-3.18 (m, 1H), 3.17-2.98 (m, 4H), 2.32-2.15 (m, 4H), 2.01-1.92 (m, 1H), 1.76-1.61 (m, 5H), 1.50-1.36 (m, 1H), 1.29 (br d, J=6.9 Hz, 1H), 1.21 (d, J=6.8 Hz, 9H), 1.14-1.07 (m, 5H), 1.05-0.97 (m, 3H); LCMS (Method A): Rt=1.88 min, 647.2 (M+H)$^+$; HPLC (Method A): Rt=5.13 min, 98.61%.

Example 4. 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (4)

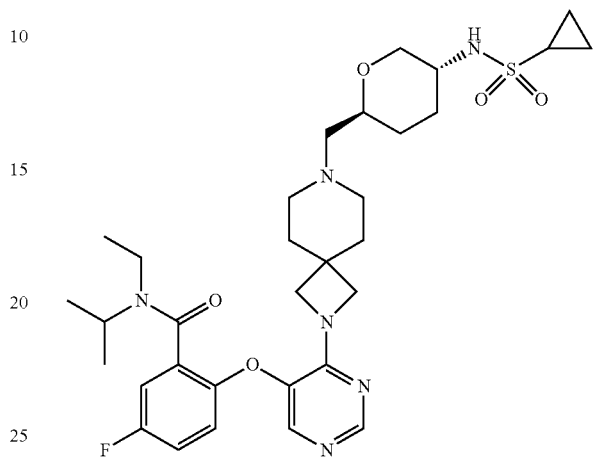

In a dried, 100 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (380 mg, 0.703 mmol) was added to CH$_2$Cl$_2$ (5 mL). The solution was cooled to 0° C. and triethylamine (0.343 mL, 2.460 mmol) was added to it. The reaction mixture was stirred at 0° C. for 30 min and then cyclopropanesulfonyl chloride (111 mg, 0.787 mmol) was added. The reaction mixture was stirred then at 25° C. for 12 h, monitoring the progress by TLC (10% methanol in DCM). After 12 h, the reaction was quenched with water (150 mL) and extracted with DCM (2×50 mL). The organic layer was washed with aqueous NaHCO$_3$ (2×50 mL) and brine (2×25 mL). The organic layer was dried over anhydrous sodium sulfate and filtered, and the filtrate was concentrated on a rotary evaporator (bath temperature 40° C.) to obtain the crude compound. The crude compound was purified by Prep HPLC (Method A). The fractions containing the pure product were lyophilized to obtain 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (20 mg, 4.38% yield) as a white solid: $^1$H NMR (400 MHz, DMSO-$d_6$): δ 8.30-8.25 (m, 1H), 7.75-7.66 (m, 1H), 7.33-7.22 (m, 2H), 7.13 (d, J=7.8 Hz, 1H), 7.09-7.01 (m, 1H), 3.86 (br d, J=7.6 Hz, 3H), 3.82-3.71 (m, 3H), 3.18-3.10 (m, 2H), 3.07-2.98 (m, 1H), 2.63-2.56 (m, 2H), 2.32-2.16 (m, 5H), 1.99 (br d, J=11.4 Hz, 11H), 1.66 (br s, 6H), 1.48-1.36 (m, 1H), 1.31-1.15 (m, 3H), 1.14-1.07 (m, 5H), 1.06-0.97 (m, 3H), 0.96-0.85 (m, 4H); LCMS (Method C): Rt=2.24 min, 645.6 (M+H)$^+$; HPLC (Method C): Rt=5.35 min, 99.14% (Max).

Example 5. N-Ethyl-5-fluoro-N-isopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide (5)

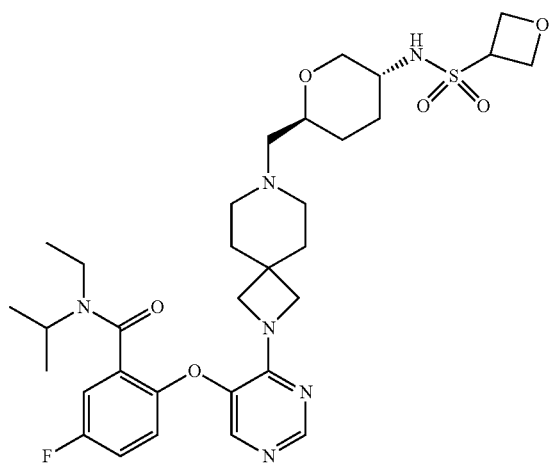 [SMILES: CCN(C(=O)c1cc(F)ccc1Oc1cncnc1N1CC2(CCN(C[C@@H]3CC[C@@H](NS(=O)(=O)C4COC4)CO3)CC2)C1)C(C)C]

In a dried, 25 mL two-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (0.3 g, 0.520 mmol) was added to DCM (5 mL) and the reaction mixture was cooled to 0° C. To this reaction mass, DBU (0.313 ml, 2.079 mmol) was added and stirred at 0° C. for 0.5 h. After that, oxetane-3-sulfonyl chloride (0.090 g, 0.572 mmol) was added to the reaction mixture and stirred at 25° C. for 20 h, monitoring the reaction progress by TLC (10% MeOH in DCM). After 20 h, the reaction mixture was quenched with water (20 mL) and extracted with DCM (2×30 mL). The combined organic layer was dried over anhydrous sodium sulfate and filtered, and the filtrate was concentrated under reduced pressure (bath temperature 40° C.) to obtain the crude product. The crude was purified by Prep HPLC (Method A). The fractions containing the pure product were lyophilized to obtain N-ethyl-5-fluoro-N-isopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide (80 mg, 23.21% yield) as an off-white solid: $^1$H NMR (400 MHz, DMSO-$d_6$): δ 8.29-8.25 (m, 1H), 7.74-7.66 (m, 1H), 7.47 (br s, 1H), 7.33-7.22 (m, 2H), 7.10-7.00 (m, 1H), 4.83-4.72 (m, 2H), 4.69-4.59 (m, 3H), 3.85 (br s, 2H), 3.81-3.70 (m, 4H), 3.13 (br d, J=6.3 Hz, 2H), 3.03-2.94 (m, 1H), 2.32-2.16 (m, 6H), 1.88 (br d, J=11.5 Hz, 1H), 1.67 (br d, J=4.3 Hz, 6H), 1.38 (dq, J=3.3, 12.2 Hz, 1H), 1.30-1.15 (m, 3H), 1.14-1.07 (m, 5H), 1.06-0.97 (m, 3H); LCMS (Method A): Rt=1.46 min, 661.1 (M+H)$^+$; HPLC (Method A): Rt=4.80 min, 99.66%.

Example 6. 2-((4-(7-(((2S,5R)-5-(Cyclobutanesulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (6)

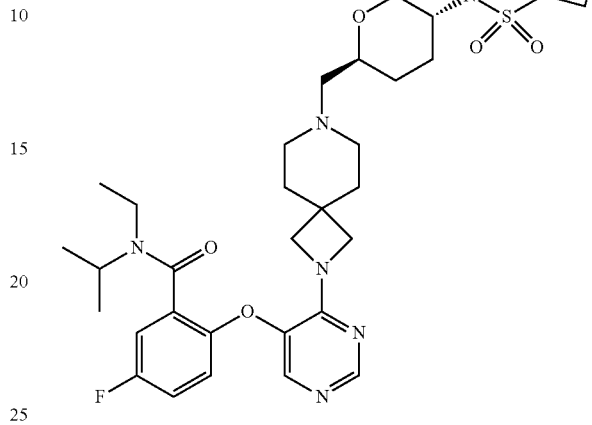

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (0.3 g, 0.520 mmol) was dissolved in $CH_2Cl_2$ (3 mL). The solution was cooled to 0° C. and added DBU (0.313 ml, 2.079 mmol). The reaction was stirred at 0° C. for 30 min and then cyclobutanesulfonyl chloride (0.096 g, 0.624 mmol) was added. The reaction was stirred at 25° C. for 20 h monitoring the reaction progress by TLC (10% Methanol in DCM). After 20 h, the reaction was quenched with water (20 mL) and extracted with DCM (2×30 mL). The combined organic layer was washed with aq. $NaHCO_3$ (2×20 mL) and brine (2×20 mL). The organic layer was dried over anhydrous sodium sulfate and filtered, and the filtrate was concentrated on a rotary evaporator (bath temperature 40° C.) to obtain the crude product. The crude product was purified by Prep HPLC (Method A). The fractions containing the pure product were concentrated under reduced pressure followed by lyophilization to obtain 2-((4-(7-(((2S,5R)-5-(cyclobutanesulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (55 mg, 15.85% yield) as an off-white solid: $^1$H NMR (400 MHz, DMSO-$d_6$): δ 8.29-8.24 (m, 1H), 7.75-7.65 (m, 1H), 7.33-7.21 (m, 2H), 7.09-7.00 (m, 2H), 3.92-3.81 (m, 3H), 3.81-3.71 (m, 4H), 3.16-3.02 (m, 2H), 3.01-2.94 (m, 1H), 2.32-2.23 (m, 5H), 2.22-2.16 (m, 4H), 1.96-1.81 (m, 4H), 1.67 (br d, J=4.0 Hz, 6H), 1.45-1.32 (m, 1H), 1.29-1.15 (m, 3H), 1.14-1.07 (m, 5H), 1.07-0.98 (m, 3H); LCMS (Method A): Rt=2.52 min, 659.4 (M+H)$^+$; HPLC (Method A): Rt=5.28 min, 98.70%.

Example 7. 2-((4-(7-(((2S,5R)-5-((Cyclopropylmethyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (7)

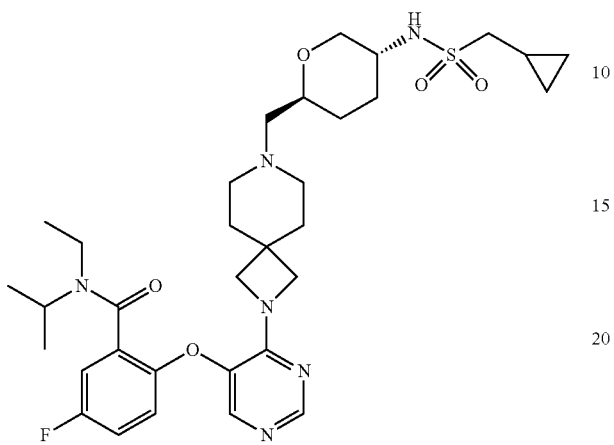

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (0.35 g, 0.606 mmol) was dissolved in CH$_2$Cl$_2$ (5 mL). The solution was cooled to 0° C. and DBU (0.457 mL, 3.03 mmol) was added. The reaction was stirred at 0° C. for 30 min and then added cyclopropylmethanesulfonyl chloride (0.188 g, 1.213 mmol). After that the reaction was stirred at 25° C. for 19 h, monitoring the progress by TLC (10% Methanol in DCM). After 19 h, the reaction was quenched with water (20 mL) and extracted with DCM (2×30 mL). The separated organic layer was washed with aq. NaHCO$_3$ (2×20 mL), brine (2×20 mL), dried over anhydrous sodium sulfate and filtered, and the filtrate was concentrated on a rotary evaporator (Bath temperature 40° C.) to obtain the crude product. The crude product was purified by Prep HPLC (Method A). The fractions containing the pure product were lyophilized to obtain 2-((4-(7-(((2S,5R)-5-((cyclopropylmethyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (91 mg, 22.75% yield) as an off-white solid: $^1$H NMR (400 MHz, DMSO-d$_6$): δ 8.29-8.25 (m, 1H), 7.74-7.66 (m, 1H), 7.33-7.21 (m, 2H), 7.10 (d, J=7.4 Hz, 1H), 7.08-7.01 (m, 1H), 3.90-3.81 (m, 3H), 3.80-3.71 (m, 3H), 3.18-3.09 (m, 2H), 3.04-2.90 (m, 3H), 2.32-2.16 (m, 6H), 1.95 (br d, J=11.6 Hz, 1H), 1.67 (br d, J=4.5 Hz, 6H), 1.40 (dq, J=3.8, 12.3 Hz, 1H), 1.30-1.15 (m, 3H), 1.14-1.07 (m, 5H), 1.06-0.96 (m, 4H), 0.59-0.52 (m, 2H), 0.37-0.29 (m, 2H); LCMS (Method A): Rt=1.51 min, 659.1 (M+H)$^+$; HPLC (Method A): Rt=5.56 min, 99.88% (Max).

Example 8. N-Ethyl-5-fluoro-N-isopropyl-2-((4-(7-(((2S,5R)-5-((2-methoxyethyl)sulfonamido)tetrahydro-2H-pyran-2-yl)methyl)-2,7-diazaspiro[3.5]nonan-2-yl)pyrimidin-5-yl)oxy)benzamide (8)

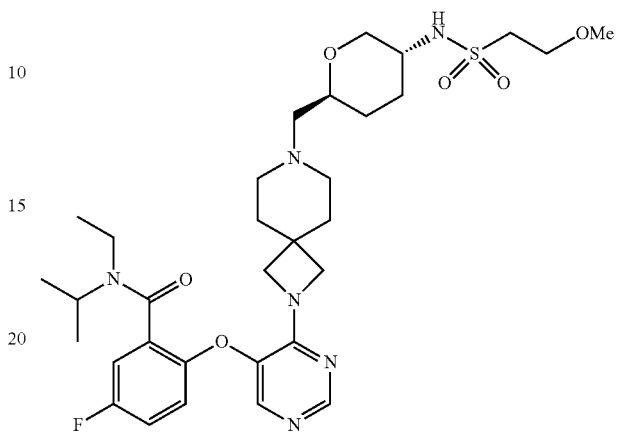

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (0.35 g, 0.606 mmol) was dissolved in CH$_2$Cl$_2$ (5 mL). This solution was cooled to 0° C. and DBU (0.457 ml, 3.03 mmol) was added to it. The reaction was then stirred at 0° C. for 30 min and 2-methoxyethane-1-sulfonyl chloride (0.106 mL, 0.910 mmol) was added. The reaction was further stirred at 25° C. for 17 h, monitoring the reaction progress by TLC (10% Methanol in DCM). After 17 h, the reaction was quenched with water (20 mL) and extracted with DCM (2×30 mL). The combined organic layer was washed with aq. NaHCO$_3$ (2×20 mL) and brine (2×20 mL). The organic layer was dried over anhydrous sodium sulfate and filtered, and the filtrate was concentrated on a rotary evaporator (bath temperature 40° C.) to obtain the crude product. The crude product was purified by Prep HPLC (Method A). The fractions containing the pure product were lyophilized to obtain N-ethyl-5-fluoro-N-isopropyl-2-((4-(7-(((2S,5R)-5-((2-methoxyethyl)sulfonamido)tetrahydro-2H-pyran-2-yl)methyl)-2,7-diazaspiro[3.5]nonan-2-yl)pyrimidin-5-yl)oxy)benzamide (90 mg, 22.33% yield) as an off-white solid: $^1$H NMR (400 MHz, DMSO-d$_6$): δ 8.29-8.24 (m, 1H), 7.74-7.66 (m, 1H), 7.33-7.22 (m, 2H), 7.15 (d, J=7.3 Hz, 1H), 7.09-7.01 (m, 1H), 3.91-3.71 (m, 6H), 3.63 (t, J=6.4 Hz, 2H), 3.45-3.37 (m, 1H), 3.30-3.28 (m, 2H), 3.26 (s, 3H), 3.23-3.09 (m, 2H), 3.03-2.95 (m, 1H), 2.32-2.16 (m, 5H), 1.95 (br d, J=11.5 Hz, 1H), 1.67 (br d, J=4.9 Hz, 6H), 1.38 (dq, J=3.5, 12.3 Hz, 1H), 1.31-1.17 (m, 3H), 1.14-1.07 (m, 5H), 1.06-0.97 (m, 3H); LCMS (Method A): Rt=1.429 min, 663.0 M+H)$^+$; HPLC (Method A): Rt=5.23 min, 99.72%.

Example 9. N-Ethyl-5-fluoro-N-isopropyl-2-((4-(7-(((2S,5R)-5-(propylsulfonamido)tetrahydro-2H-pyran-2-yl)methyl)-2,7-diazaspiro[3.5]nonan-2-yl)pyrimidin-5-yl)oxy)benzamide (9)

Example 10. N-Ethyl-5-fluoro-N-isopropyl-2-((4-(7-(((2S,5R)-5-((tetrahydrofuran)-3-sulfonamido)tetrahydro-2H-pyran-2-yl)methyl)-2,7-diazaspiro[3.5]nonan-2-yl)pyrimidin-5-yl)oxy)benzamide (10)

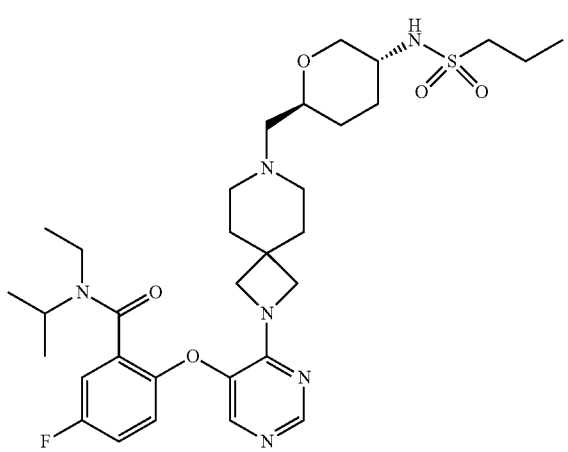 [SMILES: CCCS(=O)(=O)N[C@@H]1CC[C@@H](CN2CCC3(CC2)CN(c2ncncc2Oc2ccc(F)cc2C(=O)N(CC)C(C)C)C3)OC1]

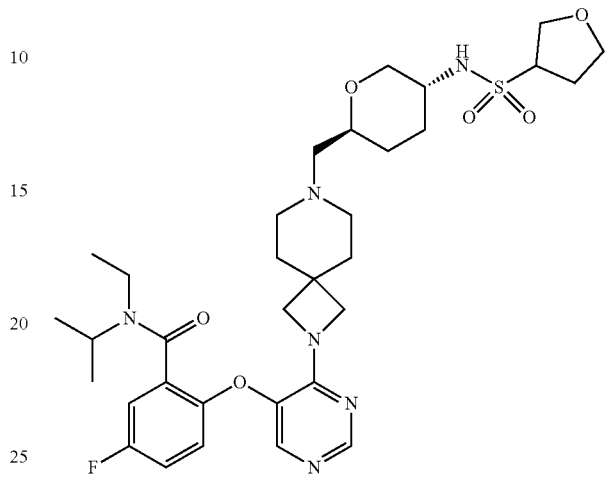

In a dried, 25 mL two-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (350 mg, 0.647 mmol) was dissolved in DCM (5 mL) and the solution was cooled to 0° C. TEA (0.902 mL, 6.47 mmol) was added and the reaction was stirred at 0° C. for 0.5 h. After that, propane-1-sulfonyl chloride (0.364 mL, 3.24 mmol) was added and the reaction stirred at 25° C. for 11 h, monitoring the reaction progress by TLC (10% MeOH in DCM). After 11 h, the reaction mixture was quenched with ice water (25 mL) and extracted with DCM (3×25 mL). The combined organic layer was dried over anhydrous sodium sulfate and filtered, and the filtrate was concentrated on a rotary evaporator (bath temperature 40° C.) to obtain the crude product. The crude product was purified by Prep HPLC (Method A). The fractions containing the pure product were lyophilized to obtain N-ethyl-5-fluoro-N-isopropyl-2-((4-(7-(((2S,5R)-5-(propylsulfonamido)tetrahydro-2H-pyran-2-yl)methyl)-2,7-diazaspiro[3.5]nonan-2-yl)pyrimidin-5-yl)oxy)benzamide (156 mg, 36.8% yield) as an off-white solid: $^1$H NMR (400 MHz, DMSO-$d_6$): δ 8.29-8.25 (m, 1H), 7.73-7.66 (m, 1H), 7.33-7.22 (m, 2H), 7.13-7.07 (m, 1H), 7.03 (dd, J=4.4, 8.9 Hz, 1H), 3.89-3.73 (m, 6H), 3.16-3.05 (m, 2H), 3.01-2.96 (m, 3H), 2.32-2.17 (m, 5H), 1.97-1.90 (m, 1H), 1.70-1.63 (m, 7H), 1.46-1.35 (m, 1H), 1.31-1.22 (m, 2H), 1.22-1.15 (m, 2H), 1.13-1.09 (m, 5H), 1.07-1.01 (m, 3H), 0.97 (t, J=7.5 Hz, 4H); LCMS (Method A): Rt=1.50 min, 647.1 (M+H)$^+$; HPLC (Method A): Rt=5.51 min, 99.34% (Max).

In a dried, 10 mL two-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (350 mg, 0.606 mmol) was added to DCM (8 mL) and the reaction was cooled to 0° C. DBU (554 mg, 3.64 mmol) was added and the reaction was stirred at 0° C. for 0.5 h. After that tetrahydrofuran-3-sulfonyl chloride (155 mg, 0.910 mmol) was added and the reaction was stirred at 0° C. for 10 min and then at 25° C. for 11 h. The reaction progress was monitored by TLC (10% MeOH in DCM). After 11 h, the reaction mixture was quenched with water (15 mL) and extracted with DCM (3×15 mL). The combined organic layer was dried over anhydrous sodium sulfate and filtered, and the filtrate was concentrated on a rotary evaporator (bath temperature 40° C.) to obtain the crude product. The crude product was purified by Prep HPLC (Method A). The fractions containing the pure product were lyophilized to obtain N-ethyl-5-fluoro-N-isopropyl-2-((4-(7-(((2S,5R)-5-((tetrahydrofuran)-3-sulfonamido)tetrahydro-2H-pyran-2-yl)methyl)-2,7-diazaspiro[3.5]nonan-2-yl)pyrimidin-5-yl)oxy)benzamide (77 mg, 18.34% yield) as an off-white solid: $^1$H NMR (400 MHz, DMSO-$d_6$): δ 8.28-8.24 (m, 1H), 7.73-7.66 (m, 1H), 7.33 (dd, J=3.8, 8.0 Hz, 1H), 7.30-7.22 (m, 2H), 7.08-7.01 (m, 1H), 3.98-3.91 (m, 1H), 3.90-3.83 (m, 4H), 3.81-3.73 (m, 4H), 3.71-3.65 (m, 1H), 3.19-3.10 (m, 2H), 3.06-2.96 (m, 1H), 2.28 (br dd, J=6.3, 12.9 Hz, 4H), 2.23-2.14 (m, 2H), 2.13-2.04 (m, 2H), 1.99-1.90 (m, 1H), 1.66 (br s, 6H), 1.44-1.34 (m, 1H), 1.30-1.15 (m, 3H), 1.14-1.07 (m, 5H), 1.07-0.97 (m, 4H); LCMS (Method A): Rt=1.58 min, 675.1 (M+H)$^+$; HPLC (Method A): Rt=5.17 min, 99.29% (Max).

Example 11. tert-Butyl ((3R,6S)-6-((2-(5-(2-(ethyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (11)

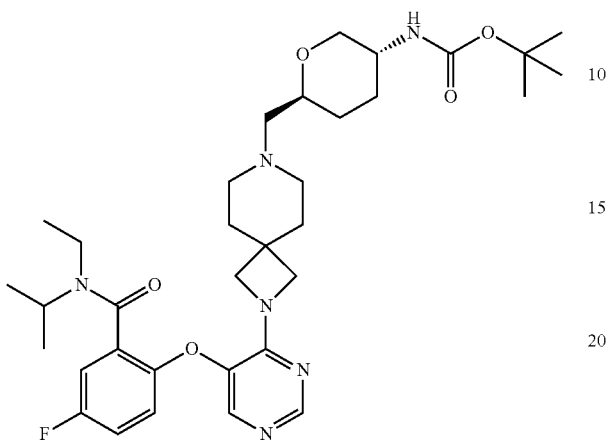

In a dried, 250 mL two-necked round bottom flask under nitrogen atmosphere, 2-((4-(2,7-diaza spiro[3.5]nonan-2-yl)pyrimidin-5-yl)oxy)-N-ethyl-5-fluoro-N-isopropylbenzamide, bis-tosylate salt (1.3 g, 1.68 mmol) was dissolved in N-methyl-2-pyrrolidinone (5 mL). To this solution, $K_2CO_3$ (0.93 g, 6.74 mmol), KI (0.308 g, 1.853 mmol) and ((2S,5R)-5-((tert-butoxycarbonyl)amino)tetrahydro-2H-pyran-2-yl)methyl 4-methylbenzenesulfonate (0.649 g, 1.68 mmol) were added at 25° C. under nitrogen atmosphere, and the resulting reaction was heated at 70° C. for 17 h. The reaction progress was monitored by TLC (5% MeOH in DCM). After 17 h, the reaction mixture was cooled to 25° C. and quenched with water (100 mL). The aqueous layer was extracted with ethyl acetate (2×150 mL). The combined organic layer was dried over anhydrous sodium sulfate and filtered, and the filtrate was concentrated on a rotary evaporator (bath temperature 40° C.) to afford the crude product. The crude product was purified by column chromatography (Isolera) using 100-200 silica gel and eluting with methanol in DCM (desired product was eluted in 4-5% methanol in DCM). The fractions containing the pure product were concentrated under reduced pressure to obtain tert-butyl ((3R,6S)-6-((2-(5-(2-(ethyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (650 mg, 59.7% yield) as a light brown syrup: $^1$H NMR (400 MHz, DMSO-$d_6$): δ 8.29-8.25 (m, 1H), 7.74-7.65 (m, 1H), 7.33-7.22 (m, 2H), 7.09-7.01 (m, 1H), 6.78-6.71 (m, 1H), 3.93-3.82 (m, 2H), 3.81-3.69 (m, 4H), 3.44-3.37 (m, 1H), 3.27-3.19 (m, 2H), 2.91 (t, J=10.6 Hz, 1H), 2.32-2.23 (m, 4H), 2.22-2.16 (m, 1H), 1.87-1.79 (m, 1H), 1.72-1.63 (m, 5H), 1.39 (br s, 2H), 1.37 (s, 9H), 1.24 (s, 1H), 1.22-1.17 (m, 2H), 1.13-1.07 (m, 5H), 1.06-0.97 (m, 3H); LCMS (Method B): Rt=1.49 min, 441.4 (M+H)$^+$.

Example 12. 5-Fluoro-N,N-diisopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide (12)

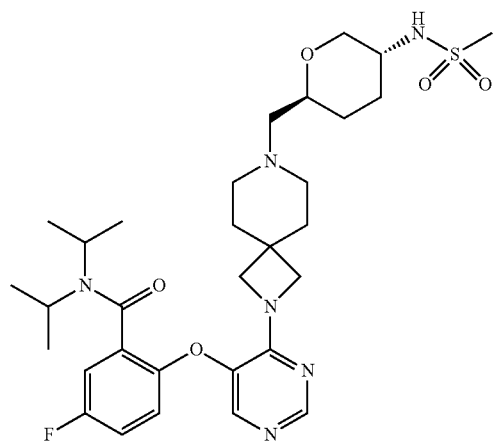 [SMILES: CC(C)N(C(=O)c1cc(F)ccc1Oc1cncnc1N1CC2(CCN(C[C@@H]3CC[C@@H](NS(C)(=O)=O)CO3)CC2)C1)C(C)C]

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide, hydrochloride (0.27 g, 0.487 mmol) was dissolved in dichloromethane (3 mL) and the resulting solution was cooled to 0° C. TEA (0.271 mL, 1.947 mmol) was added and the reaction was stirred at 0° C. for 30 min. After that, methanesulfonyl chloride (0.046 mL, 0.584 mmol) was added and the reaction was stirred at 25° C. for 1 h, monitoring the reaction progress by TLC (10% methanol in DCM). After 1 h, the reaction was quenched with water (10 mL) and extracted with DCM (2×15 mL). The combined organic layer was washed with aq. $NaHCO_3$ (2×10 mL) and brine (2×10 mL). The organic layer was dried over anhydrous sodium sulfate and filtered, and the filtrate was concentrated on a rotary evaporator (bath temperature 40° C.) to obtain the crude product. The crude compound was purified by Prep HPLC (Method A). The fractions containing the pure product were lyophilized to obtain 5-fluoro-N,N-diisopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide (37 mg, 22.62%) as an off-white solid: $^1$H NMR (400 MHz, DMSO-$d_6$): δ 8.26 (s, 1H), 7.71 (s, 1H), 7.26-7.19 (m, 2H), 7.10-7.01 (m, 2H), 3.94-3.77 (m, 5H), 3.74-3.64 (m, 1H), 3.53 (td, J=6.7, 13.5 Hz, 11H), 3.20-3.08 (m, 1H), 3.05-2.96 (m, 1H), 2.92 (s, 3H), 2.56 (br dd, J=2.0, 3.8 Hz, 1H), 2.33-2.18 (m, 5H), 1.97 (br d, J=12.4 Hz, 11H), 1.67 (br s, 6H), 1.44 (d, J=6.8 Hz, 3H), 1.41-1.33 (m, 4H), 1.31-1.23 (m, 1H), 1.09 (d, J=6.5 Hz, 3H), 1.00 (d, J=6.6 Hz, 3H); LCMS (Method B): Rt=0.85 min, 633.0 (M+H)$^+$; HPLC: (Method D): Rt=5.23 min, 99.51% (Max).

Example 13. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (13)

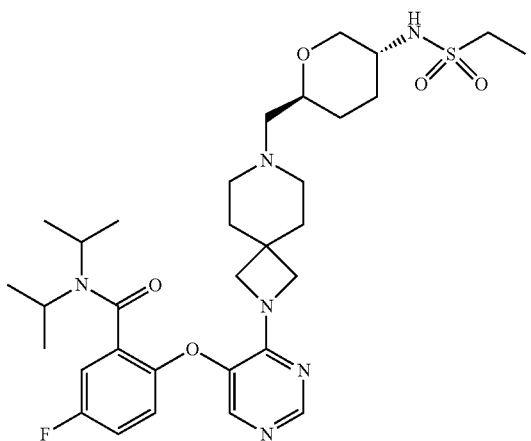 [SMILES: CCS(=O)(=O)N[C@@H]1CC[C@@H](CN2CCC3(CC2)CN(c2ncncc2Oc2ccc(F)cc2C(=O)N(C(C)C)C(C)C)C3)OC1]

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide, hydrochloride (0.35 g, 0.592 mmol) was dissolved in $CH_2Cl_2$ (5 mL) and the solution was cooled to 0° C. To this solution, TEA (0.330 mL, 2.368 mmol) was added and the reaction was stirred at 0° C. for 30 min. After that, ethanesulfonyl chloride (0.091 g, 0.710 mmol) was added slowly and the reaction was stirred at 25° C. for 17 h, monitoring the reaction progress by TLC (10% Methanol in DCM). After 17 h, the reaction was quenched with water (10 mL) and extracted with DCM (2×15 mL). The combined organic layer was washed with aq. $NaHCO_3$ (2×10 mL) and brine (2×10 mL). The organic layer was dried over anhydrous sodium sulfate and filtered, and the filtrate was concentrated on a rotary evaporator (bath temperature 40° C.) to obtain the crude product. The crude compound was purified by Prep HPLC (Method A). The fractions containing the pure product were lyophilized to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (70 mg, 18.15% yield) as an off-white solid: $^1$H NMR (400 MHz, DMSO-$d_6$): δ 8.26 (s, 1H), 7.71 (s, 1H), 7.27-7.19 (m, 2H), 7.10 (d, J=7.5 Hz, 1H), 7.07-7.01 (m, 1H), 3.94-3.76 (m, 5H), 3.74-3.64 (m, 1H), 3.57-3.48 (m, 1H), 3.16-3.04 (m, 1H), 3.04-2.96 (m, 3H), 2.32-2.18 (m, 5H), 1.98-1.90 (m, 1H), 1.71-1.61 (m, 6H), 1.47-1.38 (m, 4H), 1.35 (d, J=6.8 Hz, 3H), 1.31-1.21 (m, 2H), 1.18 (t, J=7.3 Hz, 3H), 1.09 (d, J=6.5 Hz, 3H), 1.00 (d, J=6.5 Hz, 3H); LCMS (Method A): Rt=1.80 min, 647.2 (M+H)$^+$; HPLC (Method B): Rt=3.81 min, 99.27%.

Example 14. 5-Fluoro-N,N-diisopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide (14)

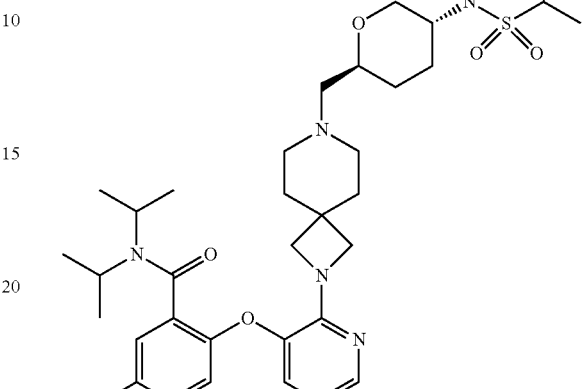

In a dried, 10 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide, hydrochloride (0.35 g, 0.592 mmol) was dissolved in $CH_2Cl_2$ (5 mL) and the solution was cooled to 0° C. DBU (0.357 mL, 2.368 mmol) was added to the reaction mixture and then stirred at 0° C. for 30 min. After that propane-2-sulfonyl chloride (0.104 g, 0.728 mmol) was added and the reaction was stirred at 25° C. for 20 h, monitoring the reaction progress by TLC (10% methanol in DCM). After 20 h, the reaction was quenched with water (10 mL) and extracted with DCM (2×15 mL). The combined organic layer was washed with aq. $NaHCO_3$ (2×10 mL) and brine (2×10 mL). The organic layer was dried over anhydrous sodium sulfate and filtered, and the filtrate was concentrated on a rotary evaporator (bath temperature 40° C.) to obtain the crude product. The crude product was purified by Prep HPLC (Method A). The fractions containing the pure product were lyophilized to obtain 5-fluoro-N,N-diisopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide (40 mg, 10.06% yield) as an off-white solid: $^1$H NMR (400 MHz, DMSO-$d_6$): δ 8.33-8.21 (m, 1H), 7.71 (s, 1H), 7.27-7.19 (m, 2H), 7.09-7.01 (m, 2H), 3.88 (br s, 2H), 3.80 (br d, J=8.4 Hz, 3H), 3.69 (td, J=6.6, 13.2 Hz, 1H), 3.58-3.48 (m, 1H), 3.21-3.05 (m, 2H), 3.05-2.98 (m, 1H), 2.32-2.16 (m, 5H), 1.98-1.90 (m, 1H), 1.67 (br d, J=5.3 Hz, 6H), 1.44 (d, J=6.6 Hz, 3H), 1.41-1.37 (m, 1H), 1.35 (d, J=6.6 Hz, 3H), 1.29-1.24 (m, 1H), 1.21 (d, J=6.8 Hz, 7H), 1.09 (d, J=6.5 Hz, 3H), 1.00 (d, J=6.6 Hz, 3H); LCMS (Method A): Rt=2.01 min, 661.6 (M+H)$^+$; HPLC (Method A): Rt=5.45 min, 98.38% (Max).

Example 15. 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (15)

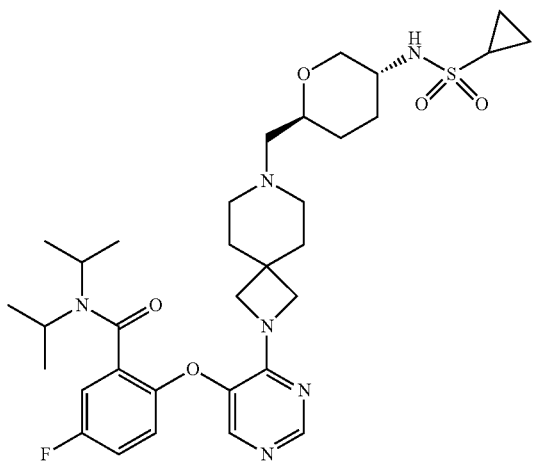 [SMILES: CC(C)N(C(=O)c1cc(F)ccc1Oc1cncnc1N1CC2(CCN(C[C@@H]3CC[C@@H](NS(=O)(=O)C4CC4)CO3)CC2)C1)C(C)C]

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide, hydrochloride (0.35 g, 0.592 mmol) was dissolved in DCM (5 mL) and the solution was cooled to 0° C. To this solution, TEA (0.330 mL, 2.368 mmol) was added and the reaction was stirred at 0° C. for 30 min. After that, cyclopropanesulfonyl chloride (0.100 g, 0.710 mmol) was added and the reaction mixture was stirred at 25° C. for 17 h, monitoring the progress by TLC (10% methanol in DCM). After 17 h, the reaction was quenched with water (10 mL) and extracted with DCM (2×15 mL). The combined organic layer was washed with aq. NaHCO$_3$ (2×10 mL) and brine (2×10 mL). The organic layer was dried over anhydrous sodium sulfate and filtered, and the filtrate was concentrated on a rotary evaporator (bath temperature 40° C.) to obtain the crude product. The crude product was purified by Prep HPLC (Method A). The fractions containing the pure product were lyophilized to obtain 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (37 mg, 9.26% yield) as an off-white solid: $^1$H NMR (400 MHz, DMSO-d$_6$): δ 8.26 (s, 1H), 7.72 (s, 1H), 7.27-7.19 (m, 2H), 7.12 (d, J=7.9 Hz, 1H), 7.04 (dd, J=4.2, 9.8 Hz, 1H), 3.95-3.84 (m, 3H), 3.83-3.77 (m, 2H), 3.69 (td, J=6.5, 13.1 Hz, 1H), 3.58-3.49 (m, 1H), 3.19-3.11 (m, 1H), 3.06-2.98 (m, 1H), 2.32-2.20 (m, 5H), 1.99 (br d, J=11.6 Hz, 1H), 1.67 (br s, 6H), 1.47-1.39 (m, 5H), 1.35 (br d, J=6.6 Hz, 3H), 1.29-1.17 (m, 2H), 1.09 (br d, J=6.5 Hz, 3H), 1.00 (br d, J=6.5 Hz, 3H), 0.95-0.86 (m, 4H); LCMS (Method A): Rt=1.88 min, 659.5 (M+H)$^+$; HPLC (Method B): Rt=3.93 min, 97.63%.

Example 16. 5-Fluoro-N,N-diisopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide (16)

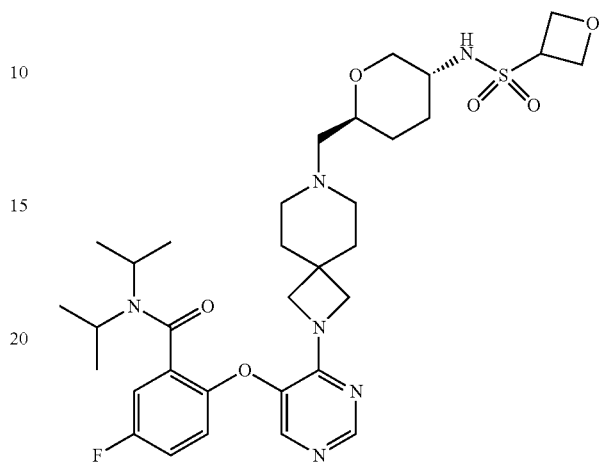

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide, hydrochloride (0.35 g, 0.592 mmol) was dissolved in CH$_2$Cl$_2$ (5 mL) and the resulting solution was cooled to 0° C. TEA (0.330 mL, 2.368 mmol) was added and the reaction was stirred at 0° C. for 30 min. After that, oxetane-3-sulfonyl chloride (0.102 g, 0.651 mmol) was added and the reaction was stirred at 25° C. for 18 h, monitoring the reaction progress by TLC (10% methanol in DCM). After 18 h, the reaction was quenched with water (10 mL) and extracted with DCM (2×15 mL). The combined organic layer was washed with aq. NaHCO$_3$(2×10 mL) and brine (2×10 mL). The organic layer was dried over anhydrous sodium sulfate and filtered, and the filtrate was concentrated on a rotary evaporator (bath temperature 40° C.) to obtain the crude product. The crude product was purified by Prep HPLC (Method A). The fractions containing the pure product were lyophilized to obtain 5-fluoro-N,N-diisopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide (46 mg, 11.03% yield) as an off-white solid: $^1$H NMR (400 MHz, DMSO-d$_6$): δ 8.30-8.22 (m, 1H), 7.72 (s, 1H), 7.51-7.44 (m, 1H), 7.26-7.19 (m, 2H), 7.07-7.01 (m, 1H), 4.83-4.73 (m, 2H), 4.69-4.58 (m, 3H), 3.94-3.83 (m, 2H), 3.83-3.74 (m, 3H), 3.69 (quin, J=6.6 Hz, 1H), 3.53 (td, J=6.8, 13.5 Hz, 1H), 3.17-3.07 (m, 1H), 3.02-2.94 (m, 1H), 2.32-2.17 (m, 5H), 1.92-1.82 (m, 1H), 1.66 (br t, J=4.9 Hz, 6H), 1.44 (d, J=6.8 Hz, 3H), 1.41-1.31 (m, 5H), 1.30-1.19 (m, 1H), 1.09 (d, J=6.5 Hz, 3H), 0.99 (d, J=6.6 Hz, 3H); LCMS (Method A): Rt=1.76 min, 675.2 (M+H)$^+$; HPLC (Method B): Rt. 3.71 min, 95.77%.

Example 17. tert-Butyl ((3R,6S)-6-((2-(5-(2-(cyclopropyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (17)

Example 18: N-Cyclopropyl-5-fluoro-N-isopropyl-2-((4-(7-(((2S,5R)-5-(methylsulfonamido)tetrahydro-2H1-pyran-2-yl)methyl)-2,7-diazaspiro[3.5]nonan-2-yl)pyrimidin-5-yl)oxy)benzamide (18)

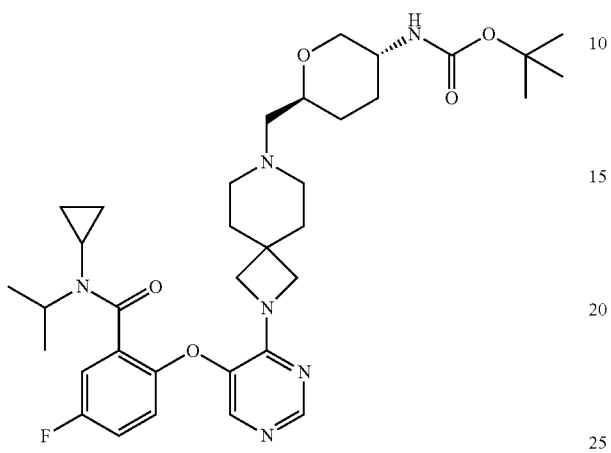

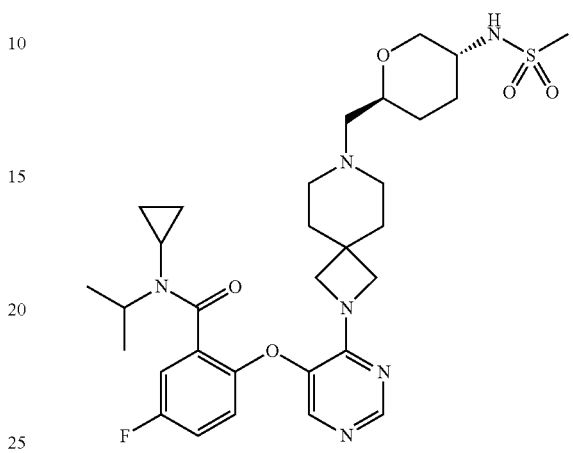

In a dried, 25 mL two-necked round bottom flask under nitrogen atmosphere, lithium 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (0.5 g, 0.875 mmol) was dissolved in DCM (5 mL). To the resulting solution, N-isopropylcyclopropanamine hydrochloride (0.130 g, 0.962 mmol), HATU (0.399 g, 1.050 mmol) and TEA (0.354 g, 3.50 mmol) were added at 25° C. under nitrogen atmosphere and the reaction was stirred at 25° C. for 14 h. The reaction progress was monitored by TLC (10% MeOH in DCM). After 14 h, the reaction mixture was quenched with water (25 mL) and extracted with ethyl acetate (3×25 mL). The combined organic layer was dried over anhydrous sodium sulfate and filtered, and the filtrate was concentrated on a rotary evaporator (bath temperature 40° C.) to obtain the crude product. The crude product was purified by Prep HPLC (Method A). The fractions containing the pure product were lyophilized to obtain tert-butyl ((3R,6S)-6-((2-(5-(2-(cyclopropyl(isopropyl)carbamoyl)-4-fluorophenoxy)pyrimidin-4-yl)-2,7-diazaspiro[3.5]nonan-7-yl)methyl)tetrahydro-2H-pyran-3-yl)carbamate (40 mg, 6.88% yield) as an off-white solid: $^1$H NMR (400 MHz, DMSO-d$_6$): δ 8.32-8.24 (m, 1H), 7.71 (s, 1H), 7.37-7.28 (m, 1H), 7.23 (dt, J=3.1, 8.6 Hz, 1H), 7.01 (dd, J=4.4, 9.1 Hz, 1H), 6.79-6.70 (m, 1H), 4.37-4.24 (m, 1H), 3.91-3.69 (m, 5H), 3.30-3.23 (m, 2H), 2.91 (br t, J=10.7 Hz, 1H), 2.65-2.55 (m, 1H), 2.32-2.16 (m, 5H), 1.82 (br d, J=11.1 Hz, 1H), 1.73-1.60 (m, 5H), 1.40-1.31 (m, 11H), 1.31-1.15 (m, 7H), 0.59-0.44 (m, 4H); LCMS (Method A): Rt=1.80 min, 653.4 (M+H)$^+$; HPLC: (Method D) Rt=6.37 min, 98.26%.

In a dried, 25 mL three necked round bottom flask was added 2-((4-(7-(((2S,5R)-5-aminotetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide, hydrochloride (0.3 g, 0.509 mmol), dissolved in CH$_2$Cl$_2$ (5 mL). The reaction mixture was cooled to 0° C. and TEA (0.284 ml, 2.037 mmol) was added. The reaction was stirred at 0° C. for 30 min and methanesulfonyl chloride (0.087 g, 0.764 mmol) was added. The reaction was stirred at 25° C. for 21 h, and reaction progress was monitored by TLC (10% methanol in DCM). The reaction was quenched with water (20 mL) and extracted with DCM (2×30 mL)> After partition, the organic layer was washed with aq. NaHCO$_3$ (2×20 mL) and brine (2×20 mL). The organic layer was dried over anhydrous sodium sulfate and concentrated on a rotary evaporator (bath temperature 40° C.) to obtain the crude compound. The crude compound was purified on preparative prep HPLC (Method A) by using ammonium bicarbonate and acetonitrile. After lyophilization, N-cyclopropyl-5-fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide (103 mg, 31.8% yield) was obtained as an off-white solid: $^1$H NMR (400 MHz, DMSO-d$_6$) δ 8.26-8.29 (m, 1H), 7.68-7.74 (m, 1H), 7.36 (s, 1H), 7.19-7.28 (m, 1H), 7.05-7.11 (m, 1H), 6.97-7.05 (m, 1H), 4.25-4.38 (m, 1H), 3.77-3.88 (m, 5H), 3.10-3.20 (m, 1H), 2.96-3.04 (m, 1H), 2.92 (s, 3H), 2.58-2.65 (m, 1H), 2.18-2.36 (m, 7H), 1.94-2.01 (m, 1H), 1.63-1.71 (m, 6H), 1.23-1.32 (m, 7H), 0.49-0.58 (m, 4H); LCMS: (Method C) Rt. 2.432 min, 631.4 (M+H)$^+$; HPLC: (Method A) Rt. 5.088 min, 99.29%.

Example 19. N-Cyclopropyl-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (19)

Example 20: N-Cyclopropyl-5-fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide (20)

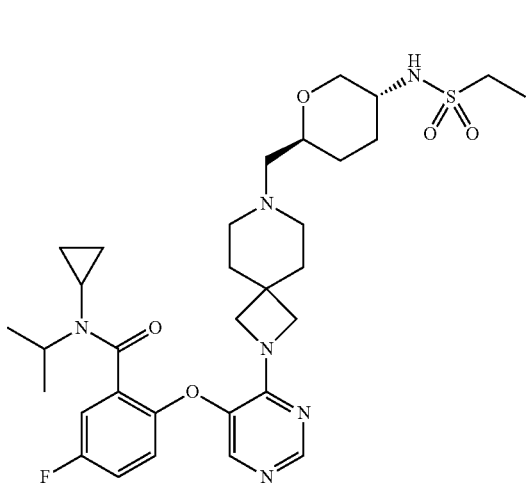 [SMILES: CCS(=O)(=O)N[C@@H]1CC[C@@H](CN2CCC3(CC2)CN(c2ncncc2Oc2ccc(F)cc2C(=O)N(C(C)C)C2CC2)C3)OC1]

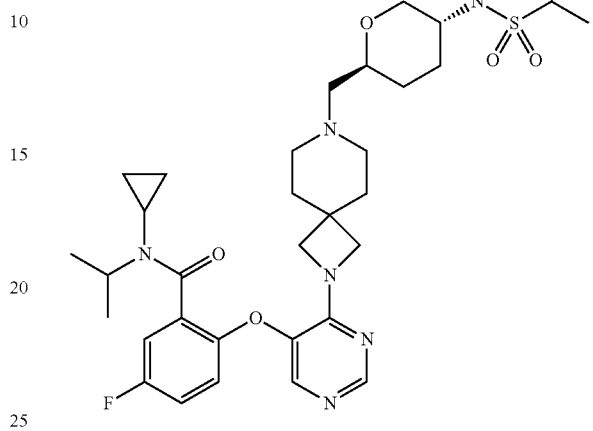

In a dried, 25 mL two-necked round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.35 g, 0.621 mmol) was dissolved in DMF (10 mL). To this solution, N-isopropylcyclopropanamine (0.062 g, 0.621 mmol), HATU (0.472 g, 1.242 mmol), and Et$_3$N (0.314 g, 3.10 mmol) were added at 25° C. under nitrogen atmosphere and the reaction mixture was stirred at 25° C. for 16 h. The reaction progress was monitored by TLC (10% Methanol in DCM). After 16 h, the reaction mixture was diluted with EtOAc (30 mL) and washed with water (2×30 mL). The organic layer was collected, dried over anhydrous sodium sulfate, and filtered, and the filtrate was concentrated on a rotary evaporator (bath temperature 40° C.) to obtain the crude product. The crude product was purified by Prep HPLC (Method-A). The fractions containing the pure product were lyophilized to obtain N-cyclopropyl-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (0.07 g, 17.29% yield) an off-white solid: $^1$H NMR (400 MHz, DMSO-d$_6$): δ 8.27 (s, 1H), 7.71 (br s, 1H), 7.32 (br d, J=5.6 Hz, 1H), 7.22 (br d, J=7.4 Hz, 1H), 7.14-7.06 (m, 1H), 7.05-6.97 (m, 1H), 4.38-4.24 (m, 1H), 3.94-3.69 (m, 6H), 3.09 (br s, 1H), 3.01 (br d, J=7.0 Hz, 3H), 2.31-2.16 (m, 5H), 1.94 (br d, J=9.9 Hz, 1H), 1.66 (br s, 6H), 1.49-1.32 (m, 2H), 1.28 (br d, J=4.0 Hz, 6H), 1.18 (br t, J=6.9 Hz, 4H), 0.52 (br s, 4H); LCMS (Method A): Rt=1.49 min, 645.1(M+H)$^+$, 98.90%; HPLC (Method A): Rt=5.19 min, 98.34%.

In a dried, 25 mL three necked round bottom flask was added 2-((4-(7-(((2S,5R)-5-aminotetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide, hydrochloride (0.4 g, 0.679 mmol), dissolved in CH$_2$Cl$_2$ (5 mL). The reaction was cooled to 0° C. and DBU (0.614 ml, 4.07 mmol) was added. The reaction was stirred at 0° C. for 30 min and propane-2-sulfonyl chloride (0.290 g, 2.037 mmol) was added. The reaction was stirred at 25° C. for 17 h, and reaction progress was monitored by TLC (10% methanol in DCM). The reaction was quenched with water (20 mL) and extracted with DCM (2×30 mL). After partition, the organic layer was washed with aq. NaHCO$_3$(2×20 mL) and brine (2×20 mL). The organic layer was dried over anhydrous sodium sulfate and concentrated on a rotary evaporator (bath temperature 40° C.) to obtain the crude compound. The crude compound was purified on preparative prep HPLC (Method A) by using ammonium bicarbonate and acetonitrile. After lyophilization, N-cyclopropyl-5-fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide (170 mg, 38%) was obtained as an off-white solid: $^1$H NMR (400 MHz, DMSO-d$_6$) δ 8.27 (s, 1H), 7.71 (s, 1H), 7.33 (dd, J=8.25, 2.75 Hz, 1H), 7.20-7.26 (m, 1H), 6.96-7.08 (m, 2H), 4.26-4.38 (m, 1H), 3.79-3.85 (m, 4H), 3.05-3.21 (m, 3H), 2.97-3.05 (m, 1H), 2.58-2.66 (m, 1H), 2.16-2.35 (m, 7H), 1.90-1.98 (m, 1H), 1.62-1.71 (m, 6H), 1.28 (br d, J=6.00 Hz, 6H), 1.19-1.23 (m, 8H), 0.52 (br s, 3H); LCMS: (Method A) Rt. 2.593 min, 659.4 (M+H)$^+$; HPLC: (Method C) Rt. 3.531 min, 99.95%.

Example 21: 2-((4-(7-(((2S,5R)-5-(Cyclopropane-sulfonamido)tetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide (21)

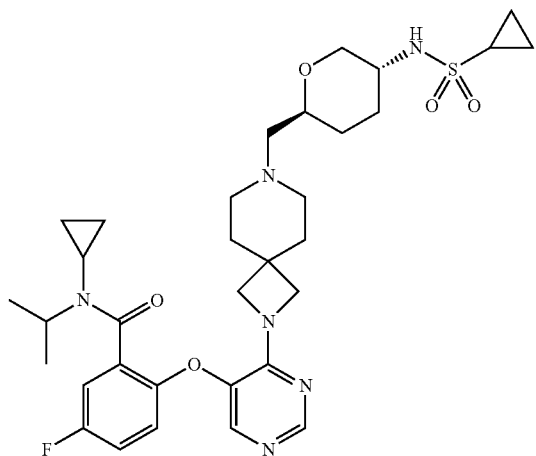 [SMILES: CC(C)N(C(=O)c1cc(F)ccc1Oc1cncnc1N1CC2(CCN(C[C@@H]3CC[C@@H](NS(=O)(=O)C4CC4)CO3)CC2)C1)C1CC1]

In a dried, 25 mL three necked round bottom flask was added 2-((4-(7-(((2S,5R)-5-aminotetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide, hydrochloride (0.4 g, 0.679 mmol), dissolved in $CH_2Cl_2$ (5 mL). The reaction mixture was cooled to 0° C. and DBU (0.614 ml, 4.07 mmol) was added. The reaction was stirred at 0° C. for 30 min and cyclopropanesulfonyl chloride (0.286 g, 2.037 mmol) was added. The reaction was stirred at 25° C. for 17 h, and reaction progress was monitored by TLC (10% methanol in DCM). The reaction was quenched with water (20 mL) and extracted with DCM (2×30 mL). After partition, the organic layer was washed with aq. $NaHCO_3$ (2×20 mL) and brine (2×20 mL). The organic layer was dried over anhydrous sodium sulfate and concentrated on a rotary evaporator (bath temperature 40° C.) to obtain the crude compound. The crude compound was purified on preparative prep HPLC (Method A) by using ammonium bicarbonate and acetonitrile. After lyophilization, 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide (42 mg, 8.96%) was obtained as an off-white solid: $^1$H NMR (400 MHz, DMSO-$d_6$) δ 8.27 (s, 1H), 7.68-7.73 (m, 1H), 7.28-7.36 (m, 1H), 7.19-7.27 (m, 1H), 7.07-7.17 (m, 1H), 6.97-7.04 (m, 1H), 4.26-4.39 (m, 1H), 3.76-3.86 (m, 4H), 3.08-3.20 (m, 2H), 2.96-3.07 (m, 1H), 2.59 (dt, J=5.00, 2.50 Hz, 1H), 2.20-2.31 (m, 5H), 2.19 (br d, J=4.50 Hz, 1H), 1.94-2.05 (m, 1H), 1.67 (br s, 6H), 1.56 (s, 3H), 1.27 (br s, 6H), 0.86-1.00 (m, 5H), 0.52 (br s, 3H); LCMS: (Method A) Rt. 2.552 min, 657.4 (M+H)$^+$; HPLC: (Method C) Rt. 3.489 min, 95.17%.

Example 22: N-Cyclopropyl-5-fluoro-N-isopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide (22)

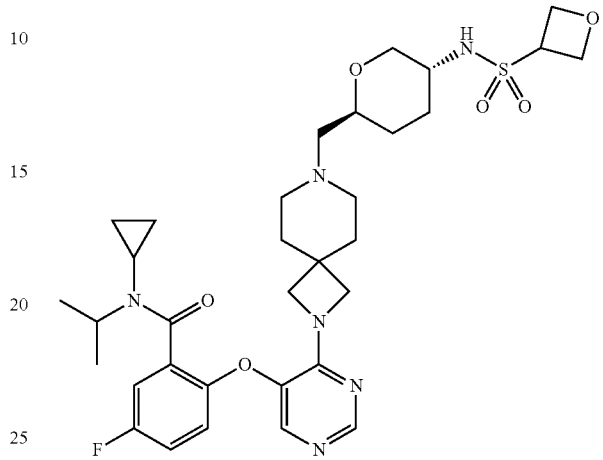

In a dried, 25 mL three necked round bottom flask was added 2-((4-(7-(((2S,5R)-5-aminotetrahydro-2H-pyran-2-yl)methyl)-2,7-diazaspiro[3.5]nonan-2-yl)pyrimidin-5-yl)oxy)-N-cyclopropyl-5-fluoro-N-isopropylbenzamide, hydrochloride (0.35 g, 0.594 mmol), dissolved in $CH_2Cl_2$ (5 mL). The reaction mixture was cooled to 0° C. and DBU (0.448 ml, 2.97 mmol) was added. The reaction was stirred at 0° C. for 30 min and oxetane-3-sulfonyl chloride (0.186 g, 1.188 mmol) was added. The reaction was stirred at 25° C. for 21 h, and reaction progress was monitored by TLC (10% methanol in DCM). The reaction was quenched with water (20 mL) and extracted with DCM (2×30 mL). After partition, the organic layer was washed with aq. $NaHCO_3$ (2×20 mL) and brine (2×20 mL). The organic layer was dried over anhydrous sodium sulfate and concentrated on a rotary evaporator (bath temperature 40° C.) to obtain the crude compound. The crude compound was purified on preparative prep HPLC (Method A) by using ammonium bicarbonate and acetonitrile. After lyophilization, N-cyclopropyl-5-fluoro-N-isopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide (82 mg, 19.69%) was obtained as an off-white solid: $^1$H NMR (400 MHz, DMSO-$d_6$) δ 8.26-8.29 (m, 1H), 7.69-7.73 (m, 1H), 7.43-7.51 (m, 1H), 7.29-7.36 (m, 1H), 7.19-7.28 (m, 1H), 6.96-7.05 (m, 1H), 4.72-4.81 (m, 3H), 4.58-4.69 (m, 4H), 4.27-4.38 (m, 1H), 3.74-3.85 (m, 5H), 3.08-3.19 (m, 1H), 2.94-3.02 (m, 1H), 2.57-2.65 (m, 1H), 2.21-2.37 (m, 6H), 1.84-1.92 (m, 1H), 1.62-1.71 (m, 6H), 1.28 (br d, J=6.50 Hz, 6H), 0.48-0.58 (m, 4H); LCMS: (Method C) Rt. 2.428 min 673.4 (M+H)$^+$; HPLC: (Method A) Rt. 5.120 min, 95.97%.

Example 23. N-((3R,6S)-6-((2-(5-(2-((3S,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)methanesulfonamide (23)

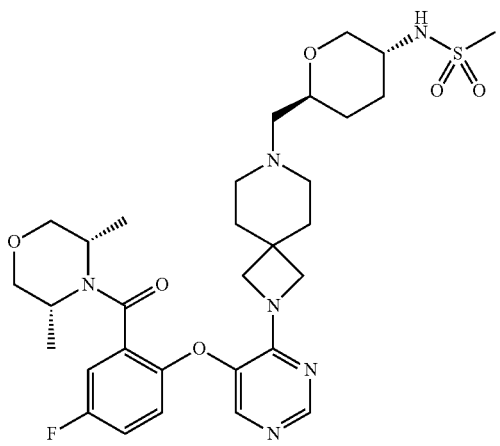 [SMILES: C[C@@H]1COC[C@H](C)N1C(=O)c1cc(F)ccc1Oc1cncnc1N1CC2(CCN(C[C@@H]3CC[C@@H](NS(C)(=O)=O)CO3)CC2)C1]

In a 25 mL three-necked reaction flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3S,5R)-3,5-dimethylmorpholino)methanone hydrochloride (250 mg, 0.413 mmol) was dissolved in DCM (5 mL). To this solution, triethylamine (0.173 mL, 1.239 mmol) was added followed by the addition of mesyl-Cl (0.039 mL, 0.496 mmol) at 25° C. The reaction mixture was stirred at 25° C. for 2 h, monitoring the progress by TLC (10% MeOH in DCM). After 2 h, the reaction was quenched with water (50 mL) and 1 mL of triethylamine was added to it. The resulting suspension was extracted with 5% methanol in DCM (3×50 mL). The combined organic layer was washed with brine (20 mL), dried over anhydrous sodium sulfate, and filtered, and the filtrate was concentrated under reduced pressure on a rotary evaporator to obtain the crude product. The crude product was purified by Prep HPLC (Method A). The fractions containing the pure product were lyophilized to obtain N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)methanesulfonamide (65 mg, 24.1% yield) as an off-white solid: $^1$H NMR (400 MHz, DMSO-$d_6$): δ 8.32-8.24 (m, 1H), 7.80-7.64 (m, 1H), 7.44-7.33 (m, 1H), 7.28 (dt, J=3.1, 8.6 Hz, 11H), 7.14-7.00 (m, 2H), 4.43-4.28 (m, 1H), 3.93-3.70 (m, 6H), 3.70-3.54 (m, 3H), 3.21-3.07 (m, 2H), 3.03-2.95 (m, 1H), 2.92 (s, 3H), 2.32-2.17 (m, 5H), 1.97 (br d, J=12.4 Hz, 1H), 1.67 (br s, 6H), 1.45-1.17 (m, 9H); LCMS (Method A): Rt=1.35 min, 647.1 (M+H)$^+$; HPLC (Method A): Rt=4.48 min, 99.26%.

Example 24. N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)ethanesulfonamide (24)

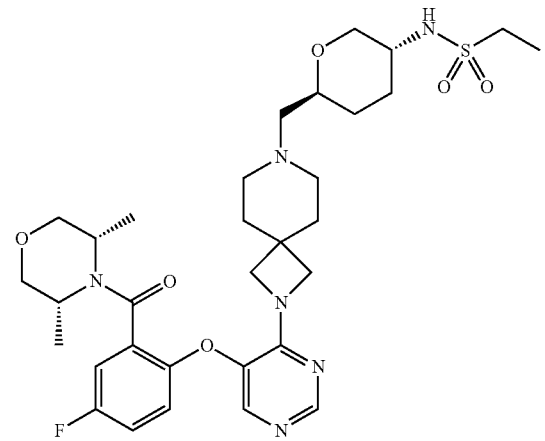 [SMILES: CCS(=O)(=O)N[C@@H]1CC[C@@H](CN2CCC3(CC2)CN(c2ncncc2Oc2ccc(F)cc2C(=O)N2[C@H](C)COC[C@@H]2C)C3)OC1]

In a 25 mL three-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3S,5R)-3,5-dimethylmorpholino)methanone, hydrochloride (300 mg, 0.496 mmol) was dissolved in DCM (5 mL). To this solution, triethylamine (150 mg, 1.487 mmol) was added followed by the addition of ethanesulfonyl chloride (76 mg, 0.595 mmol) at 25° C. The reaction mixture was stirred at 25° C. for 18 h, monitoring the reaction progress by TLC (10% MeOH in DCM). After 18 h, the reaction mixture was quenched with water (50 mL) and 1 mL of triethylamine was added to it. The resulting suspension was extracted with 5% methanol in DCM (3×50 mL). The combined organic layer was washed with brine (20 mL), dried over anhydrous sodium sulfate, and filtered, and the filtrate was concentrated on a rotary evaporator under reduced pressure to obtain the crude product. The crude product was purified by Prep HPLC (Method A). The fractions containing the pure product were lyophilized to obtain N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)ethanesulfonamide (51 mg, 15.40% yield)) as an off-white solid: $^1$H NMR (400 MHz, DMSO-$d_6$): δ 8.32-8.24 (m, 1H), 7.79-7.65 (m, 1H), 7.44-7.33 (m, 1H), 7.31-7.23 (m, 1H), 7.10 (d, J=7.6 Hz, 1H), 7.03 (br dd, J=4.4, 8.8 Hz, 1H), 4.43-4.29 (m, 1H), 3.92-3.55 (m, 9H), 3.16-3.07 (m, 1H), 3.05-2.96 (m, 3H), 2.58-2.54 (m, 1H), 2.28 (br dd, J=6.3, 12.9 Hz, 4H), 2.22-2.16 (m, 1H), 1.98-1.90 (m, 1H), 1.67 (br s, 5H), 1.47-1.20 (m, 9H), 1.18 (t, J=7.3 Hz, 3H); LCMS (Method A): Rt=1.36 min, 661.1 (M+H)$^+$; HPLC (Method A): Rt=4.64 min, 98.89% (Max).

Example 25. N-((3R,6S)-6-((2-(5-(2-((3S,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)propane-2-sulfonamide (25)

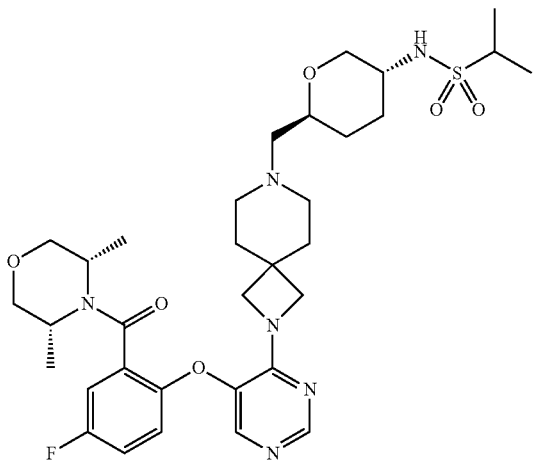 [SMILES: CC(C)S(=O)(=O)N[C@@H]1CC[C@@H](CN2CCC3(CC2)CN(c2ncncc2Oc2ccc(F)cc2C(=O)N2[C@H](C)COC[C@@H]2C)C3)OC1]

In a 25 mL three-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3S,5R)-3,5-dimethylmorpholino)methanone, hydrochloride (300 mg, 0.496 mmol) was dissolved in DCM (5 mL). To this solution, DBU (0.299 mL, 1.983 mmol) was added followed by the addition of propane-2-sulfonyl chloride (85 mg, 0.595 mmol) at 25° C. The reaction mixture was stirred at 25° C. for 18 h, monitoring the reaction progress by TLC (10% MeOH in DCM). After 18 h, the reaction was quenched with water (50 mL) and 1 mL of triethyl amine was added to it. The resulting suspension was extracted with 5% methanol in DCM (3×50 mL). The combined organic layer was washed with brine (20 mL), dried over anhydrous sodium sulfate, and filtered, and the filtrate was concentrated under reduced pressure to obtain the crude product. The crude product was purified by Prep HPLC (Method A). The fractions containing the pure product were lyophilized to obtain N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)propane-2-sulfonamide (27 mg, 8.06% yield) as an off-white solid: $^1$H NMR (400 MHz, DMSO-$d_6$): δ 8.31-8.24 (m, 1H), 7.79-7.65 (m, 1H), 7.44-7.32 (m, 1H), 7.32-7.23 (m, 1H), 7.14-6.99 (m, 2H), 4.42-4.30 (m, 1H), 3.93-3.53 (m, 9H), 3.19-3.04 (m, 3H), 3.04-2.97 (m, 1H), 2.56 (br dd, J=1.8, 3.6 Hz, 1H), 2.32-2.16 (m, 5H), 1.94 (br d, J=12.6 Hz, 11H), 1.67 (br d, J=3.0 Hz, 6H), 1.48-1.37 (m, 1H), 1.35-1.24 (m, 5H), 1.21 (d, J=6.8 Hz, 8H); LCMS (Method A): Rt=1.45 min, 675.2 (M+H)$^+$; HPLC (Method D): Rt=4.86 min, 99.85%.

Example 26. N-((3R,6S)-6-((2-(5-(2-((3S,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)cyclopropanesulfonamide (26)

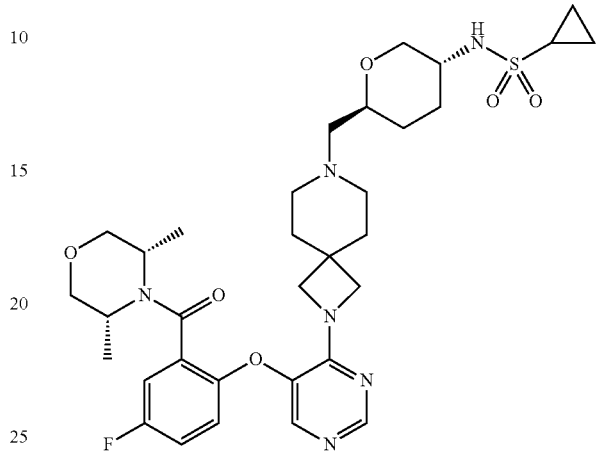

In a 25 mL three-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3S,5R)-3,5-dimethylmorpholino)methanone, hydrochloride (300 mg, 0.496 mmol) was dissolved in DCM (5 mL). To this solution, DBU (302 mg, 1.983 mmol) and cyclopropanesulfonyl chloride (84 mg, 0.595 mmol) were added sequentially at 25° C. The reaction mixture was stirred at 25° C. for 18 h, monitoring the reaction progress by TLC (10% MeOH in DCM). After 18 h, the reaction mixture was quenched with water (50 mL) and 1 mL of triethyl amine was added to it. The resulting suspension was extracted with 5% methanol in DCM (3×50 mL). The combined organic layer was dried over anhydrous sodium sulfate and filtered, and the filtrate was concentrated under reduced pressure to obtain the crude product. The crude product was purified twice by Prep HPLC (Method A). The fractions containing the pure product were lyophilized to obtain N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)cyclopropanesulfonamide (34 mg, 5% yield) as an off-white solid: $^1$H NMR (400 MHz, DMSO-$d_6$): δ 8.33-8.24 (m, 1H), 7.80-7.64 (m, 1H), 7.46-7.32 (m, 1H), 7.28 (dt, J=3.0, 8.6 Hz, 1H), 7.12 (d, J=7.8 Hz, 1H), 7.03 (br dd, J=4.2, 8.9 Hz, 1H), 4.36 (br s, 1H), 3.96-3.54 (m, 9H), 3.21-3.08 (m, 2H), 3.06-2.98 (m, 1H), 2.62-2.57 (m, 1H), 2.32-2.17 (m, 6H), 1.99 (br d, J=12.3 Hz, 1H), 1.67 (br s, 5H), 1.48-1.35 (m, 2H), 1.34-1.19 (m, 7H), 0.99-0.87 (m, 4H); LCMS (Method A): Rt=1.46 min, 673.2 (M+H)$^+$; HPLC (Method A): Rt=5.08 min, 98.77%.

Example 27. N-((3R,6S)-6-((2-(5-(2-((3S,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)oxetane-3-sulfonamide (27)

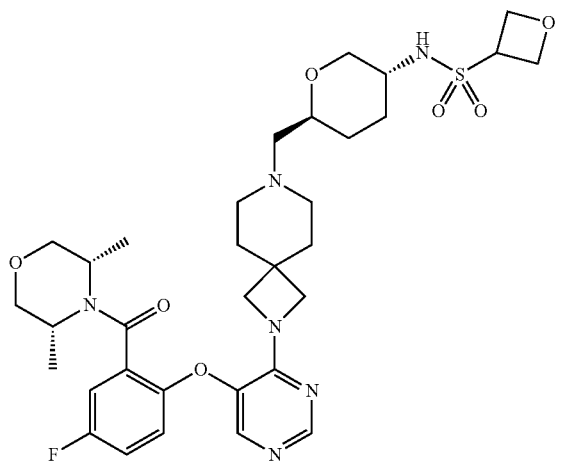 [SMILES: C[C@@H]1COC[C@H](C)N1C(=O)c1cc(F)ccc1Oc1cncnc1N1CC2(CCN(C[C@@H]3CC[C@@H](NS(=O)(=O)C4COC4)CO3)CC2)C1]

In a 25 mL three-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3S,5R)-3,5-dimethylmorpholino)methanone, hydrochloride (300 mg, 0.496 mmol) was dissolved in DCM(5 mL). To this solution, DBU (0.299 mL, 1.983 mmol) was added followed by the addition of oxetane-3-sulfonyl chloride (93 mg, 0.595 mmol) at 25° C. The reaction mixture was then stirred at 25° C. for 18 h and the reaction progress was monitored by TLC (10% MeOH in DCM). After 18 h, the reaction was quenched with water (50 mL) and 1 mL of triethyl amine was added to it. The resulting suspension was extracted with 5% methanol in DCM (3×50 mL). The combined organic layer was washed with brine (20 mL), dried over anhydrous sodium sulfate, and filtered, and the filtrate was concentrated on a rotary evaporator under reduced pressure to obtain the crude compound. The crude compound was purified by Prep HPLC (Method A). The fractions containing the pure product were lyophilized to obtain N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)oxetane-3-sulfonamide (68 mg, 19.29% yield) as a white solid: $^1$H NMR (400 MHz, DMSO-$d_6$): δ 8.29 (s, 1H), 7.81-7.65 (m, 1H), 7.47 (br d, J=7.9 Hz, 1H), 7.43-7.32 (m, 1H), 7.28 (dt, J=3.1, 8.6 Hz, 1H), 7.15-7.00 (m, 1H), 4.81-4.73 (m, 2H), 4.69-4.58 (m, 3H), 4.36 (br s, 1H), 3.96-3.54 (m, 9H), 3.21-3.07 (m, 2H), 3.03-2.95 (m, 1H), 2.31-2.16 (m, 5H), 1.88 (br d, J=11.6 Hz, 1H), 1.67 (br s, 6H), 1.44-1.17 (m, 9H); LCMS (Method A): Rt=1.37 min, 689.0 (M+H)$^+$; HPLC (Method A): Rt=4.50 min, 96.85%.

Example 28. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)methanesulfonamide (28)

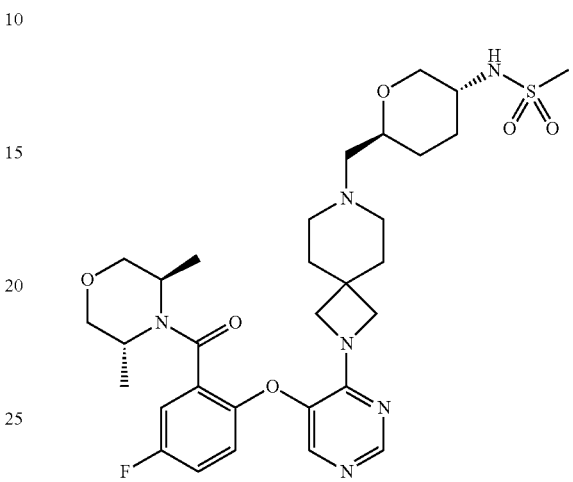

In a 25 mL three-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3R,5R)-3,5-dimethylmorpholino)methanone, hydrochloride (300 mg, 0.496 mmol) was dissolved in DCM (5 mL). To this solution, triethylamine (0.276 mL, 1.983 mmol) was added followed by the dropwise addition of methanesulfonyl chloride (85 mg, 0.744 mmol) at 25° C. The reaction mixture was stirred at 25° C. for 18 h, monitoring the reaction progress by TLC (10% MeOH in DCM). After 18 h, the reaction was quenched with water (50 mL) and 1 mL of triethyl amine was added to it. The resulting suspension was extracted with 5% methanol in DCM (3×50 mL). The combined organic layer was dried over anhydrous sodium sulfate and filtered, and the filtrate was concentrated on a rotary evaporator under reduced pressure to obtain the crude residue. The crude residue was purified by Prep HPLC (Method A). The fractions containing the pure product were lyophilized to obtain N-((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)methanesulfonamide (98 mg, 30.5% yield) as an off-white solid: $^1$H NMR (400 MHz, DMSO-$d_6$): δ 8.34-8.24 (m, 1H), 7.69 (s, 1H), 7.43-7.34 (m, 1H), 7.29 (dt, J=3.1, 8.6 Hz, 1H), 7.12-6.99 (m, 2H), 3.96-3.58 (m, 10H), 3.57-3.44 (m, 1H), 3.21-3.08 (m, 1H), 3.05-2.96 (m, 1H), 2.92 (s, 3H), 2.32-2.15 (m, 5H), 2.02-1.93 (m, 1H), 1.76-1.60 (m, 6H), 1.45-1.10 (m, 9H); LCMS (Method A): Rt=1.34 min, 647.1 (M+H)$^+$; HPLC (Method A) Rt. 4.75 min, 99.65%.

Example 29. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)ethanesulfonamide (29)

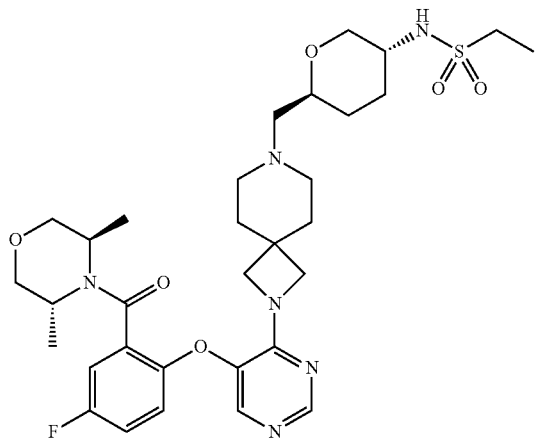 [SMILES: CCS(=O)(=O)N[C@@H]1CC[C@@H](CN2CCC3(CC2)CN(c2ncncc2Oc2ccc(F)cc2C(=O)N2[C@H](C)COC[C@H]2C)C3)OC1]

In a 25 mL three-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3R,5R)-3,5-dimethylmorpholino)methanone, hydrochloride (300 mg, 0.496 mmol) was dissolved in DCM (5 mL). To this solution, triethylamine (201 mg, 1.983 mmol) was added followed by the dropwise addition of ethanesulfonyl chloride (96 mg, 0.744 mmol) at 25° C. The reaction mixture was stirred at 25° C. for 18 h, monitoring the reaction progress by TLC (10% MeOH in DCM). After 18 h, the reaction was quenched with water (50 mL) and 1 mL of triethyl amine was added to it. The resulting suspension was extracted with 5% methanol in DCM (3×50 mL). The combined organic layer was dried over anhydrous sodium sulfate and filtered, and the filtrate was concentrated under reduced pressure to obtain the crude residue. The crude residue was purified by Prep HPLC (Method A). The fractions containing the pure product were lyophilized to obtain N-((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)ethanesulfonamide (90 mg, 27.4% yield)) as an off-white solid: $^1$H NMR (400 MHz, DMSO-$d_6$): δ 8.32-8.25 (m, 1H), 7.73-7.66 (m, 1H), 7.43-7.34 (m, 1H), 7.29 (dt, J=3.1, 8.6 Hz, 1H), 7.15-7.07 (m, 1H), 7.07-7.00 (m, 1H), 3.98-3.57 (m, 10H), 3.56-3.42 (m, 1H), 3.16-3.05 (m, 1H), 3.05-2.97 (m, 3H), 2.32-2.15 (m, 5H), 1.94 (br d, J=12.1 Hz, 1H), 1.75-1.62 (m, 6H), 1.48-1.32 (m, 1H), 1.31-1.11 (m, 11H); LCMS (Method A): Rt=1.37 min, 661.1 (M+H)$^+$; HPLC (Method A): Rt=4.94 min, 99.75%.

Example 30. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)propane-2-sulfonamide (30)

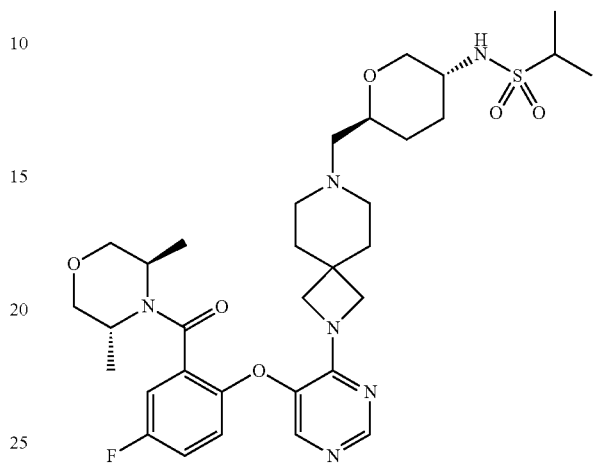

In a 25 mL three-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3R,5R)-3,5-dimethylmorpholino)methanone, hydrochloride (300 mg, 0.496 mmol) was dissolved in DCM (5 mL). To this solution, DBU (0.299 mL, 1.983 mmol) was added followed by the dropwise addition of propane-2-sulfonyl chloride (106 mg, 0.744 mmol) at 25° C. The reaction mixture was stirred at 25° C. for 18 h, monitoring the reaction progress TLC (10% MeOH in DCM). After 18 h, the reaction was quenched with water (50 mL) and 1 mL of triethyl amine was added to it. The resulting suspension was extracted with 5% methanol in DCM (3×50 mL). The combined organic layer was dried over anhydrous sodium sulfate and filtered, and the filtrate was concentrated on a rotary evaporator under reduced pressure to obtain the crude residue. The crude residue was purified by Prep HPLC (Method A). The fractions containing the pure product were lyophilized to obtain N-((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)propane-2-sulfonamide (38 mg, 10.79% yield) as an off-white solid: $^1$H NMR (400 MHz, DMSO-$d_6$): δ 8.31-8.26 (m, 1H), 7.69 (s, 1H), 7.37 (br dd, J=2.3, 8.0 Hz, 1H), 7.29 (dt, J=3.1, 8.6 Hz, 1H), 7.09-7.01 (m, 2H), 3.96-3.60 (m, 10H), 3.57-3.44 (m, 1H), 3.21-2.96 (m, 4H), 2.32-2.16 (m, 5H), 1.99-1.88 (m, 1H), 1.75-1.60 (m, 6H), 1.48-1.34 (m, 1H), 1.30-1.24 (m, 1H), 1.21 (d, J=6.8 Hz, 12H); LCMS (Method A): Rt=1.42 min, 675.1 (M+H)$^+$; HPLC (Method D), Rt=5.17 min, 95.00%.

Example 31. N-((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)cyclopropanesulfonamide (31)

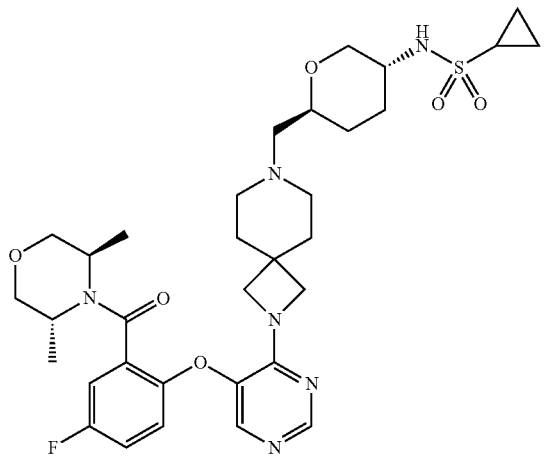 [SMILES: C[C@@H]1COC[C@@H](C)N1C(=O)c1cc(F)ccc1Oc1cncnc1N1CC2(CCN(C[C@@H]3CC[C@@H](NS(=O)(=O)C4CC4)CO3)CC2)C1]

Into a 25 mL three-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3R,5R)-3,5-dimethylmorpholino)methanone, hydrochloride (500 mg, 0.826 mmol) and DBU (503 mg, 3.30 mmol) were dissolved in DCM (5 mL). To this solution cyclopropanesulfonyl chloride (116 mg, 0.826 mmol) was added dropwise at 0° C. and the reaction was stirred at 25° C. for 18 h. The reaction progress was monitored by LCMS and TLC (10% MeOH in DCM). After 18 h, the reaction was quenched with water (50 mL) and 1 mL of triethyl amine was added to it. The resulting suspension was extracted with 5% methanol in DCM (3×50 mL). The combined organic layer was dried over anhydrous sodium sulfate and filtered, and the filtrate was concentrated on a rotary evaporator under reduced pressure to obtain the crude product. The crude product was purified by prep HPLC (method A). The fractions containing the desired product were lyophilized to obtain N-((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)cyclopropanesulfonamide (73 mg, 12.69% yield) as an off-white solid: $^1$H NMR (400 MHz, DMSO-$d_6$): δ 8.35-8.22 (m, 1H), 7.69 (s, 1H), 7.38 (br dd, J=2.6, 7.9 Hz, 1H), 7.29 (dt, J=3.2, 8.6 Hz, 1H), 7.13 (d, J=7.9 Hz, 1H), 7.04 (dd, J=4.4, 9.0 Hz, 1H), 3.95-3.61 (m, 9H), 3.55-3.44 (m, 1H), 3.21-3.09 (m, 1H), 3.05-2.98 (m, 1H), 2.63-2.53 (m, 1H), 2.32-2.16 (m, 5H), 2.04-1.94 (m, 1H), 1.68 (br d, J=4.8 Hz, 6H), 1.48-1.34 (m, 1H), 1.31-1.08 (m, 8H), 0.97-0.83 (m, 5H); LCMS (Method A): Rt=1.67 min, 671.3 (M−H); HPLC (Method A): Rt=4.83 min, 96.66%.

Example 32. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)oxetane-3-sulfonamide (32)

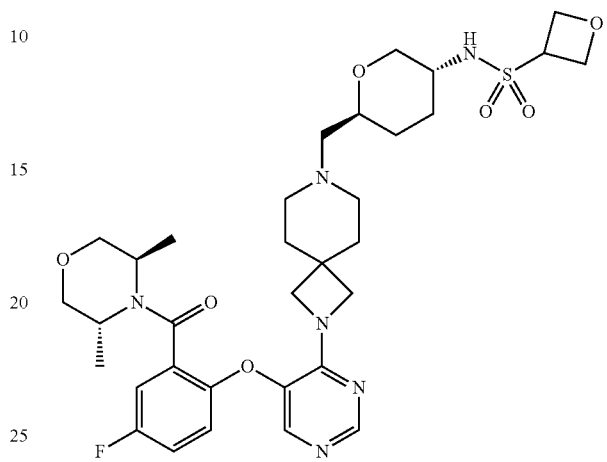

In a 25 mL three-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3R,5R)-3,5-dimethylmorpholino)methanone, hydrochloride (300 mg, 0.496 mmol) was dissolved in DCM (5 mL). To this solution, DBU (302 mg, 1.983 mmol) was added followed by the dropwise addition of oxetane-3-sulfonyl chloride (116 mg, 0.744 mmol) at 25° C. The reaction mixture was then stirred at 25° C. for 18 h, monitoring the progress by TLC (10% MeOH in DCM). After 18 h, the reaction was quenched with water (50 mL) and 1 mL of triethyl amine was added to it. The resulting suspension was extracted with 5% methanol in DCM (3×50 mL). The combined organic layer was dried over anhydrous sodium sulfate and filtered, and the filtrate was concentrated on a rotary evaporator under reduced pressure to obtain the crude residue. The crude residue was purified by Prep HPLC (Method A). The fractions containing the pure product were lyophilized to obtain N-((3R,6S)-6-((2-(5-(2-((3R,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)oxetane-3-sulfonamide (58 mg, 16.99% yield) as an off-white solid: $^1$H NMR (400 MHz, DMSO-$d_6$): δ 8.33-8.24 (m, 1H), 7.69 (s, 1H), 7.47 (br d, J=7.8 Hz, 1H), 7.41-7.33 (m, 1H), 7.29 (dt, J=3.1, 8.6 Hz, 1H), 7.10-7.00 (m, 1H), 4.83-4.70 (m, 2H), 4.69-4.58 (m, 3H), 3.97-3.57 (m, 10H), 3.56-3.44 (m, 1H), 3.20-3.07 (m, 1H), 3.04-2.94 (m, 1H), 2.32-2.18 (m, 5H), 1.92-1.85 (m, 1H), 1.67 (br s, 6H), 1.45-1.09 (m, 9H); LCMS (Method A): Rt=1.35 min, 689.0 (M+H)$^+$; HPLC (Method A): Rt=4.69 min, 99.14% (Max).

Example 33. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide (33)

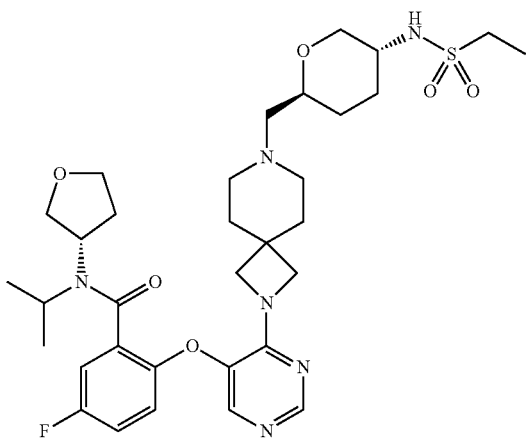 [SMILES: CCS(=O)(=O)N[C@@H]1CC[C@@H](CN2CCC3(CC2)CN(c2ncncc2Oc2ccc(F)cc2C(=O)N(C(C)C)[C@H]2CCOC2)C3)OC1]

In a dried, 50 mL two-necked round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.25 g, 0.444 mmol) was dissolved in DMF (8 mL). To this solution, TEA (0.309 mL, 2.218 mmol), HATU (0.337 g, 0.887 mmol) and (S)—N-isopropyltetrahydrofuran-3-amine (0.115 g, 0.887 mmol) were added at 25° C. under nitrogen atmosphere. The reaction mixture was stirred at 25° C. for 16 h under nitrogen atmosphere, monitoring the reaction progress by TLC (10% MeOH in DCM). After 16 h, the reaction mixture was quenched with water and extracted with ethyl acetate. The combined organic layer was dried over sodium sulfate and filtered, and the filtrate was concentrated on a rotary evaporator under reduced pressure (bath temperature 45° C.) to obtain the crude product. The crude product was purified by Prep HPLC (Method A). The fractions containing the pure product were lyophilized to obtain 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide (0.025 g, 8.27% yield) as an off-white solid: $^1$H NMR (400 MHz, DMSO-$d_6$): δ 8.34-8.21 (m, 1H), 7.86-7.69 (m, 1H), 7.37-7.19 (m, 2H), 7.15-7.08 (m, 1H), 7.07-6.99 (m, 1H), 4.07-3.63 (m, 11H), 3.61-3.44 (m, 1H), 3.16-3.05 (m, 1H), 3.04-2.94 (m, 3H), 2.31-2.15 (m, 6H), 2.05-1.88 (m, 2H), 1.76-1.60 (m, 6H), 1.50-1.31 (m, 3H), 1.30-1.21 (m, 1H), 1.18 (t, J=7.3 Hz, 3H), 1.13 (br d, J=6.5 Hz, 1H), 1.06 (br dd, J=6.6, 12.5 Hz, 2H), 0.98 (br d, J=6.6 Hz, 1H); LCMS (Method A): Rt=2.35 min, 675.3 (M+H)$^+$; HPLC (Method A): Rt=5.01 min, 99.47%.

Example 34. N-(2,2-Difluoroethyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (34)

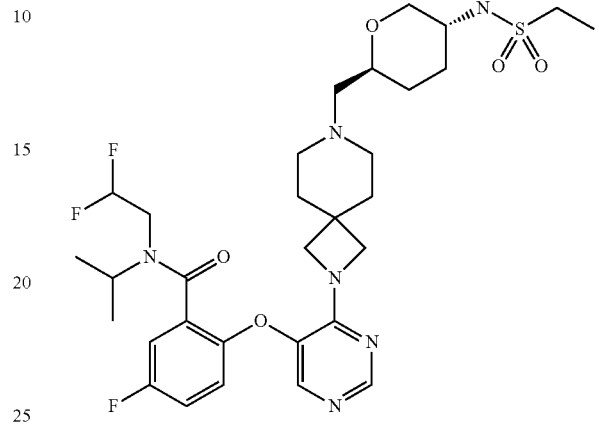

In a 50 mL single-necked dried round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.20 g, 0.355 mmol) was dissolved in DMF (7.5 mL). To this solution, TEA (0.247 mL, 1.774 mmol), HATU (0.270 g, 0.710 mmol) and N-(2,2-difluoroethyl) propan-2-amine hydrochloride (0.057 g, 0.355 mmol) were added at 25° C. under nitrogen atmosphere. The resulting reaction mixture was stirred at 25° C. for 16 h, monitoring the reaction progress by TLC (10% MeOH in DCM). After 16 h, the reaction mixture was quenched with water and extracted with ethyl acetate (2×25 mL). The combined organic layer was dried over sodium sulfate and filtered, and the filtrate was concentrated on a rotary evaporator under reduced pressure (bath temperature 45° C.) to obtain the crude product. The crude product was purified by Prep HPLC (Method-A). The fractions containing the pure product were lyophilized to obtain N-(2,2-difluoroethyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (55 mg, 22.95% yield) as an off-white solid: $^1$H NMR (400 MHz, DMSO-$d_6$): δ 8.35-8.24 (m, 1H), 7.84-7.69 (m, 1H), 7.41-7.21 (m, 2H), 7.15-7.07 (m, 1H), 7.02 (dd, J=4.4, 9.1 Hz, 1H), 6.39-6.02 (m, 1H), 3.90-3.79 (m, 4H), 3.78-3.65 (m, 4H), 3.16-3.05 (m, 1H), 3.04-2.94 (m, 3H), 2.32-2.17 (m, 5H), 1.94 (br d, J=12.5 Hz, 1H), 1.66 (br s, 6H), 1.48-1.32 (m, 1H), 1.30-1.22 (m, 2H), 1.18 (t, J=7.3 Hz, 3H), 1.08 (br dd, J=6.5, 16.0 Hz, 6H); LCMS (Method A): Rt=1.69 min, 669.1 (M+H)$^+$; HPLC (Method A): Rt=5.50 min, 99.51% (Max).

Example 35. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide (35)

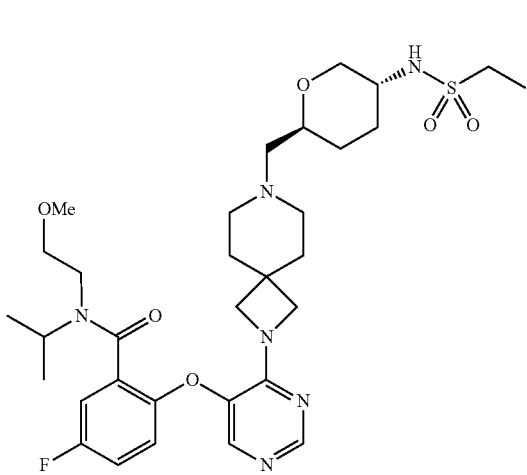 [SMILES: CCS(=O)(=O)N[C@@H]1CC[C@@H](CN2CCC3(CC2)CN(c2ncncc2Oc2ccc(F)cc2C(=O)N(CCOC)C(C)C)C3)OC1]

In a 50 mL two-necked dried round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.25 g, 0.444 mmol) was dissolved in DMF (8 mL). To this solution, TEA (0.309 mL, 2.218 mmol), HATU (0.337 g, 0.887 mmol) and N-(2-methoxyethyl)propan-2-amine (0.104 g, 0.887 mmol) were added at 25° C. under nitrogen atmosphere. The reaction was stirred at 25° C. for 19 h and the reaction progress was monitored by TLC (10% MeOH in DCM). After 19 h, the reaction mixture was quenched with water and extracted with ethyl acetate (2×25 mL). The combined organic layer was dried over anhydrous sodium sulfate and filtered, and the filtrate was concentrated on a rotary evaporator (bath temperature 40° C.) to obtain the crude product. The crude product was purified by Prep HPLC (Method-A). The fractions containing the pure product were lyophilized to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide (0.1 g, 33.9% yield) as an off-white solid: $^1$H NMR (400 MHz, DMSO-d$_6$): δ 8.33-8.22 (m, 1H), 7.77-7.63 (m, 1H), 7.35-7.21 (m, 2H), 7.10 (d, J=7.6 Hz, 1H), 7.07-6.99 (m, 1H), 3.95-3.70 (m, 7H), 3.55-3.43 (m, 2H), 3.25 (s, 3H), 3.16-3.05 (m, 2H), 3.04-2.97 (m, 3H), 2.32-2.17 (m, 5H), 1.94 (br d, J=12.1 Hz, 1H), 1.67 (br s, 6H), 1.47-1.33 (m, 1H), 1.31-1.14 (m, 6H), 1.13-1.00 (m, 5H); LCMS (Method A): Rt=1.40 min, 663.0 (M+H)$^+$; HPLC (Method A): Rt=5.50 min, 99.74%.

Example 36. N-((3R,6S)-6-((2-(5-(2-((2S,6R)-2,6-Dimethylpiperidine-1-carbonyl)-4-fluorophenoxy)pyrimidin-4-yl)-2,7-diazaspiro[3.5]nonan-7-yl)methyl)tetrahydro-2H-pyran-3-yl)ethanesulfonamide (36)

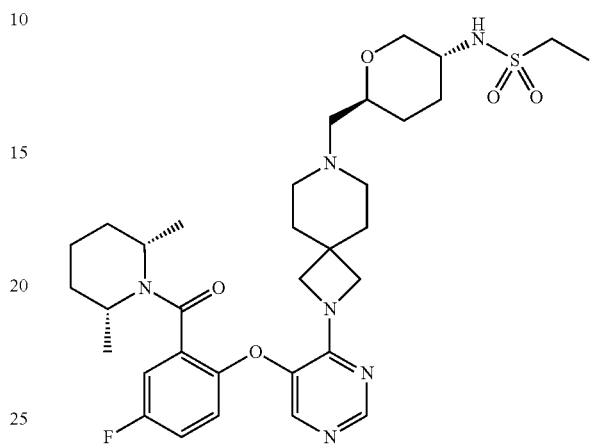

In a 50 mL two-necked dried round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.25 g, 0.444 mmol) was dissolved in DMF (8 mL). To this solution, TEA (0.309 mL, 2.218 mmol), HATU (0.337 g, 0.887 mmol) and (2S,6R)-2,6-dimethylpiperidine (0.100 g, 0.887 mmol) were added at 25° C. under nitrogen atmosphere. The reaction was stirred at 25° C. for 19 h and the reaction progress was monitored by TLC (10% MeOH in DCM). After 19 h, the reaction mixture was quenched with water and extracted with ethyl acetate (2×25 mL). The organic layer was dried over anhydrous sodium sulfate and filtered, and the filtrate was concentrated on a rotary evaporator (bath temperature 40° C.) to obtain the crude product. The crude product was purified by Prep HPLC (Method-A). The fractions containing the pure product were lyophilized to obtain N-((3R,6S)-6-((2-(5-(2-((2S,6R)-2,6-dimethylpiperidine-1-carbonyl)-4-fluorophenoxy)pyrimidin-4-yl)-2,7-diazaspiro[3.5]nonan-7-yl)methyl)tetrahydro-2H-pyran-3-yl)ethanesulfonamide (0.08 g, 27.3% yield) as an off-white solid: $^1$H NMR (400 MHz, DMSO-d$_6$): δ 8.30-8.24 (m, 1H), 7.72-7.65 (m, 1H), 7.36 (dd, J=3.0, 8.3 Hz, 1H), 7.31-7.21 (m, 1H), 7.15-7.05 (m, 2H), 4.78-4.60 (m, 1H), 3.94-3.74 (m, 6H), 3.72-3.62 (m, 1H), 3.17-3.04 (m, 1H), 3.04-2.94 (m, 3H), 2.32-2.16 (m, 6H), 1.94 (br d, J=11.8 Hz, 1H), 1.86-1.73 (m, 1H), 1.67 (br d, J=5.4 Hz, 6H), 1.52-1.34 (m, 4H), 1.30-1.20 (m, 5H), 1.18 (br t, J=7.3 Hz, 6H); LCMS (Method A): Rt=1.49 min, 659.1 (M+H)$^+$; HPLC (Method A): Rt=5.55 min, 99.54%.

Example 37. N-Ethyl-5-fluoro-N-isopropyl-2-((4-(7-(((2S,5R)-5-(3-(2,2,2-trifluoroethyl)ureido)tetrahydro-2H-pyran-2-yl)methyl)-2,7-diazaspiro[3.5]nonan-2-yl)pyrimidin-5-yl)oxy)benzamide (37)

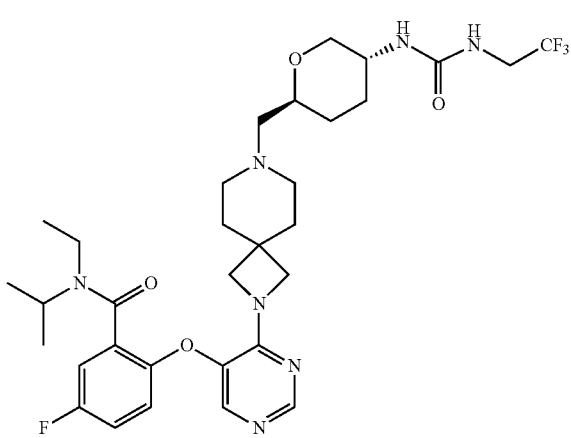 [SMILES: CCN(C(=O)c1cc(F)ccc1Oc1cncnc1N1CC2(CCN(C[C@@H]3CC[C@@H](NC(=O)NCC(F)(F)F)CO3)CC2)C1)C(C)C]

In a dried, 25 mL two-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (300 mg, 0.520 mmol) was dissolved in DCM (5 mL). To this solution, CDI (110 mg, 0.676 mmol) and DIPEA (0.324 mL, 1.819 mmol) were added at 25° C. under nitrogen atmosphere, and the resulting reaction was stirred at 25° C. for 1 h. After that, 2,2,2-trifluoroethan-1-amine (77 mg, 0.780 mmol) was added and the reaction was stirred at 25° C. for 24 h, monitoring the reaction progress by LCMS and TLC (10% methanol in DCM). After 24 h, the reaction mixture was diluted with DCM (25 mL) and washed with water. The organic extract was concentrated on a rotary evaporator to obtain the crude product. The crude product was purified by Prep HPLC (Method A). The fractions containing the pure product were lyophilized to obtain N-ethyl-5-fluoro-N-isopropyl-2-((4-(7-(((2S,5R)-5-(3-(2,2,2-trifluoroethyl)ureido)tetrahydro-2H-pyran-2-yl)methyl)-2,7-diazaspiro[3.5]nonan-2-yl)pyrimidin-5-yl)oxy)benzamide (45 mg, 12.62% yield) as a white foam: $^1$H NMR (400 MHz, DMSO-$d_6$): δ 8.30-8.24 (m, 1H), 7.72 (s, 1H), 7.68-7.61 (m, 1H), 7.33-7.22 (m, 2H), 7.10-6.99 (m, 1H), 4.71-4.57 (m, 2H), 3.85 (br s, 2H), 3.82-3.70 (m, 4H), 3.46-3.37 (m, 1H), 3.26-3.18 (m, 1H), 3.13 (q, J=6.9 Hz, 1H), 2.97 (t, J=10.7 Hz, 1H), 2.33-2.24 (m, 4H), 2.23-2.16 (m, 2H), 1.89 (br d, J=11.6 Hz, 1H), 1.66 (br s, 6H), 1.40 (dq, J=3.6, 12.4 Hz, 1H), 1.30-1.15 (m, 3H), 1.14-1.07 (m, 5H), 1.06-0.96 (m, 3H); LCMS (Method A): Rt=1.62 min, 667.1 (M+H)$^+$; HPLC (Method A): Rt=5.81 min, 97.07% (Max).

Example 38. N-Ethyl-5-fluoro-N-isopropyl-2-((4-(7-(((2S,5R)-5-(3-propylureido)tetrahydro-2H-pyran-2-yl)methyl)-2,7-diazaspiro[3.5]nonan-2-yl)pyrimidin-5-yl)oxy)benzamide (38)

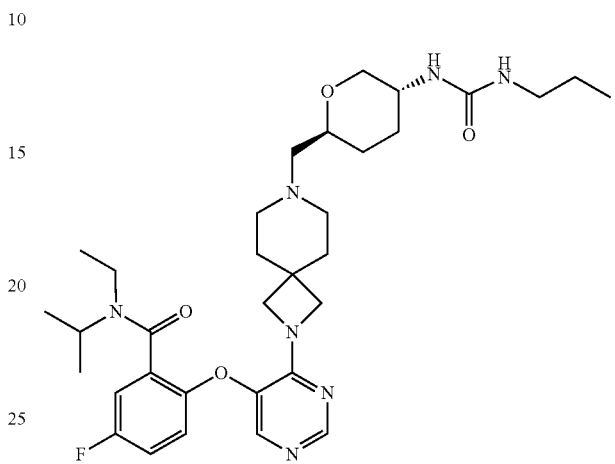

In a 25 mL two-necked dried round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (300 mg, 0.520 mmol) was dissolved in DCM (5 mL). To this solution, CDI (110 mg, 0.676 mmol) and DIPEA (0.324 mL, 1.819 mmol) were added at 25° C. under nitrogen atmosphere and the resulting reaction was stirred at 25° C. for 1 h. After that, propan-1-amine (0.064 mL, 0.780 mmol) was added to the reaction mixture and stirred at 25° C. for 16 h, monitoring the reaction progress by LCMS and TLC (10% methanol in DCM). After 16 h, the reaction mixture was diluted with DCM (25 mL) and washed with water. The organic extract was concentrated on a rotary evaporator to obtain the crude product. The crude product was purified by Prep HPLC (Method A). The fractions containing the pure product were lyophilized to obtain N-ethyl-5-fluoro-N-isopropyl-2-((4-(7-(((2S,5R)-5-(3-propylureido)tetrahydro-2H-pyran-2-yl)methyl)-2,7-diazaspiro[3.5]nonan-2-yl)pyrimidin-5-yl)oxy)benzamide (71.12 mg, 21.84% yield) as a white solid: $^1$H NMR (400 MHz, DMSO-$d_6$): δ 8.29-8.24 (m, 1H), 7.73-7.66 (m, 1H), 7.34-7.22 (m, 2H), 7.10-7.00 (m, 1H), 5.73 (t, J=5.6 Hz, 1H), 5.63 (d, J=7.9 Hz, 1H), 3.93-3.70 (m, 6H), 3.46-3.37 (m, 2H), 3.26-3.10 (m, 1H), 2.98-2.82 (m, 3H), 2.32-2.16 (m, 5H), 1.89-1.82 (m, 1H), 1.67 (br d, J=3.8 Hz, 6H), 1.35 (sxt, J=7.2 Hz, 2H), 1.29-1.15 (m, 4H), 1.15-1.07 (m, 5H), 1.06-0.97 (m, 3H), 0.82 (t, J=7.4 Hz, 3H); LCMS (Method A): Rt=1.40 min, 626.2 (M+H)$^+$; HPLC (Method A): Rt. 5.09 min, 99.90%.

Example 39. N-Ethyl-2-((4-(7-(((2S,5R)-5-(3-ethylureido)tetrahydro-2H-pyran-2-yl)methyl)-2,7-diazaspiro[3.5]nonan-2-yl)pyrimidin-5-yl)oxy)-5-fluoro-N-isopropylbenzamide (39)

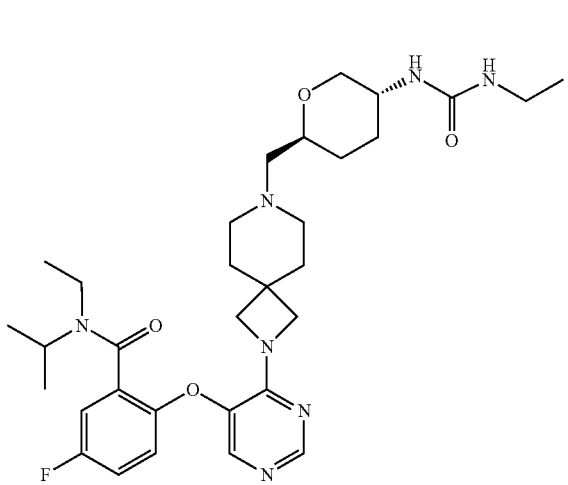 [SMILES: CCNC(=O)N[C@@H]1CC[C@@H](CN2CCC3(CC2)CN(c2ncncc2Oc2ccc(F)cc2C(=O)N(CC)C(C)C)C3)OC1]

In a dried, 25 mL two-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (300 mg, 0.520 mmol) was dissolved in DCM (5 mL). To this solution, CDI (110 mg, 0.676 mmol) and DIPEA (235 mg, 1.819 mmol) were added at 25° C. under nitrogen atmosphere and the resulting reaction was stirred at 25° C. for 1 h. To the above reaction mixture, ethanamine in THF (0.390 mL, 0.780 mmol) was added and stirred at 25° C. for 16 h, monitoring the reaction progress by LCMS and TLC (10% methanol in DCM). After 16 h, the reaction mixture was diluted with DCM (25 mL) and washed with water. The organic layer was concentrated on a rotary evaporator to obtain the crude product. The crude product was purified by Prep HPLC (Method A). The fractions containing the pure product were lyophilized to obtain N-ethyl-2-((4-(7-(((2S,5R)-5-(3-ethylureido)tetrahydro-2H-pyran-2-yl)methyl)-2,7-diazaspiro[3.5]nonan-2-yl)pyrimidin-5-yl)oxy)-5-fluoro-N-isopropylbenzamide (78.41 mg, 24.52% yield) as a white solid: $^1$H NMR (400 MHz, DMSO-$d_6$): δ 8.30-8.24 (m, 1H), 7.74-7.64 (m, 1H), 7.34-7.21 (m, 2H), 7.10-7.00 (m, 1H), 5.73-5.66 (m, 1H), 5.64 (d, J=7.9 Hz, 1H), 3.94-3.70 (m, 6H), 3.45-3.37 (m, 2H), 3.26-3.11 (m, 1H), 3.07-2.92 (m, 3H), 2.85 (t, J=10.6 Hz, 1H), 2.32-2.16 (m, 5H), 1.89-1.81 (m, 1H), 1.67 (br d, J=4.9 Hz, 5H), 1.34-1.16 (m, 4H), 1.15-1.06 (m, 5H), 1.06-0.99 (m, 3H), 0.96 (t, J=7.2 Hz, 3H); LCMS (Method A): Rt=1.54 min, 612.5 (M+H)$^+$; HPLC (Method A): Rt=4.84 min, 99.43%.

Example 40. N-((3R,6S)-6-((2-(5-(4-Fluoro-2-((S)-3-methylmorpholine-4-carbonyl)phenoxy)pyrimidin-4-yl)-2,7-diazaspiro[3.5]nonan-7-yl)methyl)tetrahydro-2H-pyran-3-yl)cyclopropanesulfonamide (40)

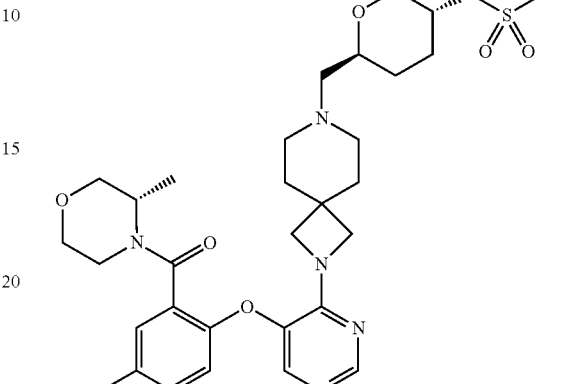

Step 1: tert-Butyl ((3R,6S)-6-((2-(5-(4-fluoro-2-((S)-3-methylmorpholine-4-carbonyl)phenoxy)pyrimidin-4-yl)-2,7-diazaspiro[3.5]nonan-7-yl)methyl)tetrahydro-2H-pyran-3-yl)carbamate

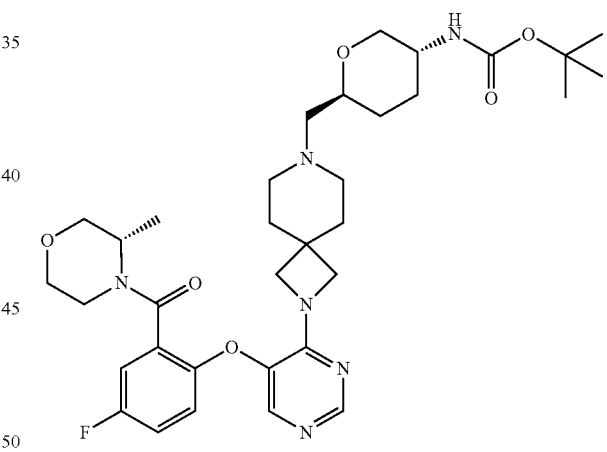

In a dried, 25 mL two-necked round bottom flask under nitrogen atmosphere, lithium 2-((4-(7-(((2S,5R)-5-((tert-butoxycarbonyl)amino)tetrahydro-2H-pyran-2-yl)methyl)-2,7-diazaspiro[3.5]nonan-2-yl)pyrimidin-5-yl)oxy)-5-fluorobenzoate (0.5 g, 0.875 mmol) was dissolved in N,N-dimethylformamide (5 mL). To this solution, (S)-3-methylmorpholine (0.097 g, 0.962 mmol), HATU (0.432 g, 1.137 mmol) and TEA (0.488 mL, 3.50 mmol) were added at 25° C. under nitrogen atmosphere and the reaction was stirred at 25° C. for 20 h. The reaction progress was monitored by TLC (10% MeOH in DCM). After 20 h, the reaction mixture was quenched with water (25 mL) and extracted with ethyl acetate (3×25 mL). The combined organic layer was dried over anhydrous sodium sulfate and filtered, and the filtrate was concentrated on a rotary evaporator (bath temperature 40° C.) to obtain the crude product.

417

The crude product was purified by column chromatography (Isolera) using 100-200 silica gel and eluting with MeOH in DCM (the desired product eluted in 3% to 4% MeOH in DCM). The fractions containing the required product were concentrated on a rotary evaporator under reduced pressure to obtain tert-butyl ((3R,6S)-6-((2-(5-(4-fluoro-2-((S)-3-methylmorpholine-4-carbonyl)phenoxy)pyrimidin-4-yl)-2,7-diazaspiro[3.5]nonan-7-yl)methyl)tetrahydro-2H-pyran-3-yl)carbamate (0.25 g, 37.1% yield) as a yellow solid: LCMS (Method A): Rt=1.557 min, 655.3 (M+H)$^+$.

Step 2: (2-((4-(7-(((2S,5R)-5-Aminotetrahydro-2H-pyran-2-yl)methyl)-2,7-diazaspiro[3.5]nonan-2-yl)pyrimidin-5-yl)oxy)-5-fluorophenyl)((S)-3-methylmorpholino)methanone, hydrochloride

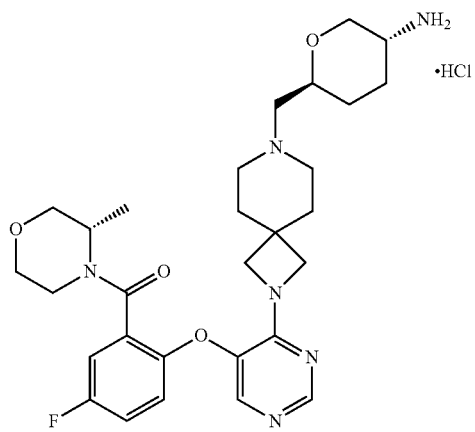 [SMILES: C[C@H]1COCCN1C(=O)c1cc(F)ccc1Oc1cncnc1N1CC2(CCN(C[C@@H]3CC[C@@H](N)CO3)CC2)C1 ; Cl]

In a dried, 25 mL two-necked round bottom flask under nitrogen atmosphere, tert-butyl ((3R,6S)-6-((2-(5-(4-fluoro-2-((S)-3-methylmorpholine-4-carbonyl)phenoxy)pyrimidin-4-yl)-2,7-diazaspiro[3.5]nonan-7-yl)methyl)tetrahydro-2H-pyran-3-yl)carbamate (0.6 g, 0.916 mmol) was dissolved in 2,2,2-triflouro ethanol (6 mL). To the resulting solution, TMS-Cl (0.150 mL, 1.174 mmol) was added dropwise at 10° C. The reaction mixture was then stirred for 1 h at 25° C., monitoring the reaction progress by TLC (10% MeOH in DCM). After 1 h, the solvent was distilled off under reduced pressure on a rotary evaporator and the residue obtained was co-distilled with ethyl acetate (2×20 mL). The residue was triturated with hexane and dried under vacuum to afford (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((S)-3-methylmorpholino)methanone, hydrochloride (0.51 g, 82.0% yield) as a light brown solid: LCMS (Method A): Rt=1.32 min, 555.3 (M+H)$^+$.

Step 3. N-((3R,6S)-6-((2-(5-(4-Fluoro-2-((S)-3-methylmorpholine-4-carbonyl)phenoxy)pyrimidin-4-yl)-2,7-diazaspiro[3.5]nonan-7-yl)methyl)tetrahydro-2H-pyran-3-yl)cyclopropanesulfonamide

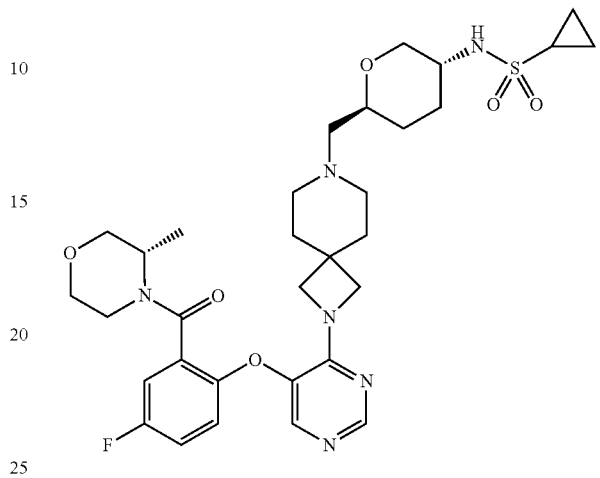

In a dried, 25 mL two-necked round bottom flask under nitrogen atmosphere, (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((S)-3-methylmorpholino)methanone, hydrochloride (0.5 g, 0.846 mmol) was dissolved in CH$_2$Cl$_2$ (5 mL) and cooled to 0° C. To this solution, DBU (1.275 mL, 8.46 mmol) was added and the reaction mixture was stirred at 0° C. for 30 min. After that, cyclopropanesulfonyl chloride (0.143 g, 1.01 mmol) was added and the reaction was then stirred at 25° C. for 12 h, monitoring the progress by TLC (10% methanol in DCM). After 12 h, the reaction mixture was quenched with water (20 mL) and extracted with DCM (2×30 mL). The combined organic layer was washed with aq. NaHCO$_3$ (2×25 mL) and brine (2×25 mL). The organic layer was dried over anhydrous sodium sulfate and filtered, and the filtrate was concentrated on a rotary evaporator (bath temperature 40° C.) to obtain the crude product. The crude product was purified by Prep HPLC (Method A). The fractions containing the pure product were lyophilized to obtain N-((3R,6S)-6-((2-(5-(4-fluoro-2-((S)-3-methylmorpholine-4-carbonyl)phenoxy)pyrimidin-4-yl)-2,7-diazaspiro[3.5]nonan-7-yl)methyl)tetrahydro-2H-pyran-3-yl)cyclopropanesulfonamide (25 mg, 4.41% yield) as an off-white solid: $^1$H NMR (400 MHz, DMSO-d$_6$): δ 8.37-8.20 (m, 1H), 7.85-7.65 (m, 1H), 7.43-7.23 (m, 2H), 7.13 (d, J=7.9 Hz, 1H), 7.09-6.98 (m, 1H), 4.52-4.11 (m, 1H), 3.95-3.82 (m, 4H), 3.81-3.61 (m, 4H), 3.59-3.49 (m, 1H), 3.25-3.08 (m, 3H), 3.05-2.98 (m, 1H), 2.32-2.14 (m, 5H), 2.05-1.95 (m, 1H), 1.76-1.63 (m, 6H), 1.48-1.33 (m, 1H), 1.31-1.17 (m, 4H), 1.14-1.06 (m, 1H), 1.00-0.84 (m, 5H); LCMS (Method A): Rt=1.37 min, 659.1 (M+H)$^+$; HPLC (Method A): Rt=2.98 min, 98.25%.

Example 41. 2-((4-(7-(((2S,5R)-5-(3-(2,2-Difluoroethyl)ureido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (41)

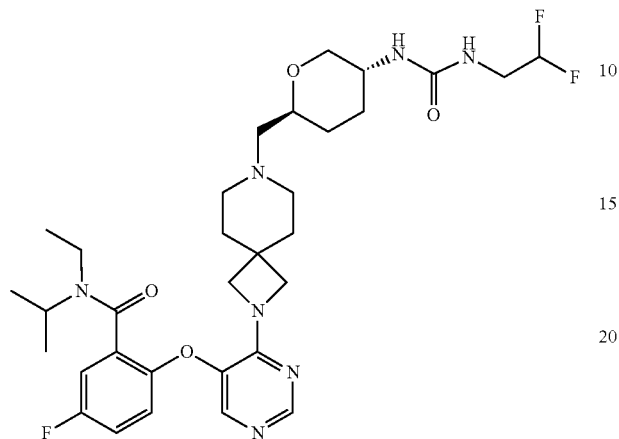

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (0.3 g, 0.520 mmol) was dissolved in $CH_2Cl_2$ (5 mL). To this solution was added CDI (0.110 g, 0.676 mmol) and DIPEA (0.363 mL, 2.079 mmol), and the reaction mixture was stirred at 25° C. After 30 mins, 2,2-difluoroethan-1-amine (0.051 g, 0.624 mmol) was added slowly and the reaction was stirred at 25° C. for 40 h, monitoring the reaction progress by TLC (10% methanol in DCM). After 40 h, the reaction was quenched with water (20 mL) and extracted with DCM (2×30 mL). The combined organic layer was washed with brine (2×30 mL), dried over anhydrous sodium sulfate, and filtered, and the filtrate was concentrated on a rotary evaporator (bath temperature 40° C.) to obtain the crude product. The crude product was purified by Prep HPLC (Method A). The fractions containing the pure product were lyophilized to obtain 2-((4-(7-(((2S,5R)-5-(3-(2,2-difluoroethyl)ureido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (85 mg, 25.06% yield) as an off-white solid: $^1$H NMR (400 MHz, DMSO-$d_6$): δ 8.28-8.23 (m, 1H), 7.74-7.66 (m, 1H), 7.34-7.21 (m, 2H), 7.09-7.00 (m, 1H), 6.15-6.07 (m, 1H), 6.01-5.92 (m, 2H), 3.90-3.71 (m, 6H), 3.46-3.36 (m, 4H), 3.26-3.12 (m, 1H), 2.88 (t, J=10.6 Hz, 1H), 2.31-2.15 (m, 5H), 1.87 (br d, J=10.9 Hz, 1H), 1.67 (br d, J=4.4 Hz, 6H), 1.35-1.23 (m, 2H), 1.21 (br s, 2H), 1.14-1.07 (m, 5H), 1.06-0.97 (m, 3H); LCMS (Method A): Rt=2.40 min, 648.4 (M+H)$^+$; HPLC (Method A): Rt=5.17 min, 99.26% (Max).

Example 42. 2-((4-(7-(((2S,5R)-5-(3-(Cyclopropylmethyl)ureido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (42)

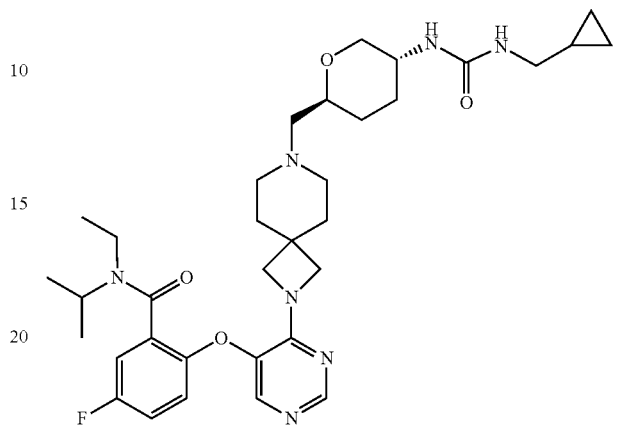

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (0.3 g, 0.520 mmol) was dissolved in DCM (5 mL). To this solution, CDI (0.110 g, 0.676 mmol) and DIPEA (0.363 mL, 2.079 mmol) were added and the reaction was stirred at 25° C. After 30 min, cyclopropylmethanamine (0.044 g, 0.624 mmol) was added slowly and the reaction was stirred at 25° C. for 17 h, monitoring the reaction progress by TLC (10% methanol in DCM). After 17 h, the reaction was quenched with water (20 mL) and extracted with DCM (2×30 mL). The combined organic layer was washed with brine (2×30 mL), dried over anhydrous sodium sulfate, and filtered, and the filtrate was concentrated on a rotary evaporator (bath temperature 40° C.) to obtain the crude product. The rude product was purified by Prep HPLC (Method A). The fractions containing the pure product were lyophilized to obtain 2-((4-(7-(((2S,5R)-5-(cyclopropylmethyl)ureido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (90 mg, 27.1%) as an off-white solid: $^1$H NMR (400 MHz, DMSO-$d_6$): δ 8.30-8.24 (m, 1H), 7.65 (s, 1H), 7.34-7.22 (m, 2H), 7.11-7.00 (m, 1H), 5.82 (s, 1H), 5.68 (d, J=7.9 Hz, 1H), 3.93-3.72 (m, 6H), 3.46-3.39 (m, 1H), 3.26-3.18 (m, 1H), 2.90-2.81 (m, 4H), 2.32-2.16 (m, 5H), 1.85 (br d, J=9.4 Hz, 1H), 1.67 (br d, J=4.8 Hz, 6H), 1.29-1.16 (m, 4H), 1.14-1.07 (m, 5H), 1.06-0.97 (m, 3H), 0.90-0.80 (m, 1H), 0.42-0.33 (m, 2H), 0.15-0.07 (m, 2H); LCMS (Method A): Rt=2.45 min, 638.4 (M+H)$^+$; HPLC (Method A): Rt=5.29 min, 99.66%.

Example 43. N-(2-Cyanoethyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (43)

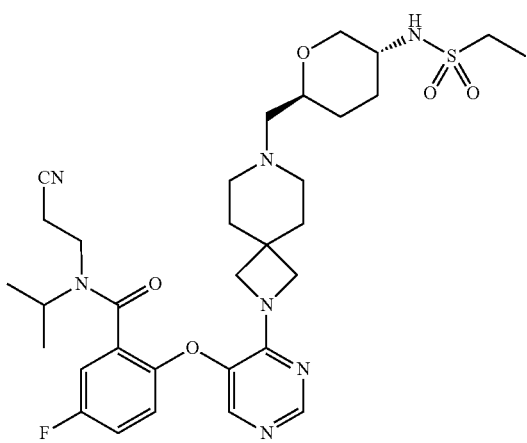 [SMILES: CCS(=O)(=O)N[C@@H]1CC[C@@H](CN2CCC3(CC2)CN(c2ncncc2Oc2ccc(F)cc2C(=O)N(CCC#N)C(C)C)C3)OC1]

In a dried, 25 mL three-necked round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (100 mg, 0.177 mmol), HATU (135 mg, 0.355 mmol) and triethylamine (0.099 mL, 0.710 mmol) were added to DMF (2 mL). To the resulting solution, 3-(isopropylamino)propanenitrile (39.8 mg, 0.355 mmol) was added at 25° C. and the reaction mixture was stirred at 25° C. for 18 h, monitoring the reaction progress by TLC (5% MeOH in dichloromethane) and LCMS. After 18 h, the reaction was quenched with water (10 mL) and extracted with EtOAc (3×15 mL). The combined organic layer was washed with water (2×10 mL) and brine (10 mL). The organic layer was dried over anhydrous sodium sulfate and filtered, and the filtrate was concentrated on a rotary evaporator under reduced pressure to obtain the crude product. The crude product was purified by prep HPLC (Method A). The fractions containing the desired product were lyophilized to obtain N-(2-cyanoethyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (41 mg, 35.1% yield) as an off-white solid: $^1$H NMR (400 MHz, DMSO-$d_6$): δ 8.34-8.23 (m, 1H), 7.81-7.69 (m, 1H), 7.35-7.22 (m, 2H), 7.10 (d, J=7.6 Hz, 1H), 6.97 (dd, J=4.4, 9.0 Hz, 1H), 3.89-3.71 (m, 6H), 3.61-3.53 (m, 2H), 3.15-3.05 (m, 1H), 3.04-2.94 (m, 3H), 2.86-2.76 (m, 2H), 2.31-2.18 (m, 5H), 2.00-1.90 (m, 1H), 1.66 (br s, 6H), 1.40 (dq, J=3.8, 12.3 Hz, 1H), 1.30-1.21 (m, 2H), 1.18 (t, J=7.3 Hz, 4H), 1.12 (br dd, J=3.3, 5.9 Hz, 5H); LCMS (Method A): Rt=2.14 min, 658.1 (M+H)$^+$; HPLC (Method A): Rt=4.84 min, 99.90%.

Example 44. N-(3,3-Difluorocyclobutyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (44)

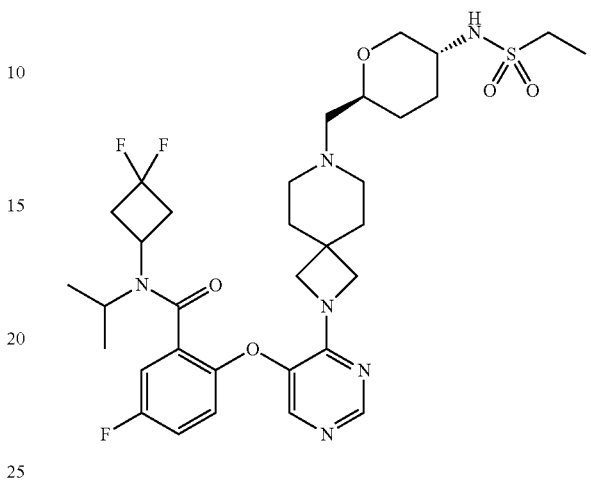

In a dried, 25 mL two-necked round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (250 mg, 0.444 mmol) was dissolved in N,N-dimethylformamide (5 mL). To this solution 3,3-difluoro-N-isopropylcyclobutan-1-amine (100 mg, 0.665 mmol), HATU (253 mg, 0.665 mmol) and TEA (0.249 mL, 1.774 mmol) were added at 25° C. under nitrogen atmosphere, and the reaction mixture stirred at 25° C. for 18 h. The reaction progress was monitored by TLC (10% MeOH in DCM). After 18 h, the reaction mixture was quenched with water (25 mL) and the aqueous layer was extracted with ethyl acetate (3×25 mL). The combined organic layer was dried over anhydrous sodium sulfate and filtered, and the filtrate was concentrated on a rotary evaporator (bath temperature 40° C.) under reduced pressure to obtain the crude product. The crude product was purified by prep HPLC (Method A). The fractions containing the desired product were lyophilized to obtain N-(3,3-difluorocyclobutyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (45 mg, 14.50% yield) as an off-white solid: $^1$H NMR (400 MHz, DMSO-$d_6$): δ 8.29 (s, 1H), 7.78 (s, 1H), 7.39-7.31 (m, 1H), 7.26 (dt, J=2.9, 8.6 Hz, 1H), 7.10 (d, J=7.5 Hz, 1H), 7.03 (dd, J=4.4, 9.1 Hz, 11H), 3.97-3.82 (m, 4H), 3.81-3.68 (m, 4H), 3.61-3.43 (m, 1H), 3.15-3.04 (m, 1H), 3.04-2.97 (m, 3H), 2.82-2.70 (m, 1H), 2.32-2.16 (m, 5H), 1.94 (br dd, J=2.8, 15.1 Hz, 1H), 1.71-1.63 (m, 5H), 1.49-1.34 (m, 2H), 1.32-1.21 (m, 2H), 1.18 (t, J=7.3 Hz, 4H), 1.13-1.06 (m, 3H), 1.02 (br d, J=6.5 Hz, 3H); LCMS (Method A): Rt=1.856 min, 695.1 (M+H)$^+$; HPLC (Method A): Rt=5.685 min, 99.33%.

Example 45. N-Ethyl-5-fluoro-N-isopropyl-2-((4-(7-(((2S,5R)-5-(phenylsulfonamido)tetrahydro-2H-pyran-2-yl)methyl)-2,7-diazaspiro[3.5]nonan-2-yl)pyrimidin-5-yl)oxy)benzamide (45)

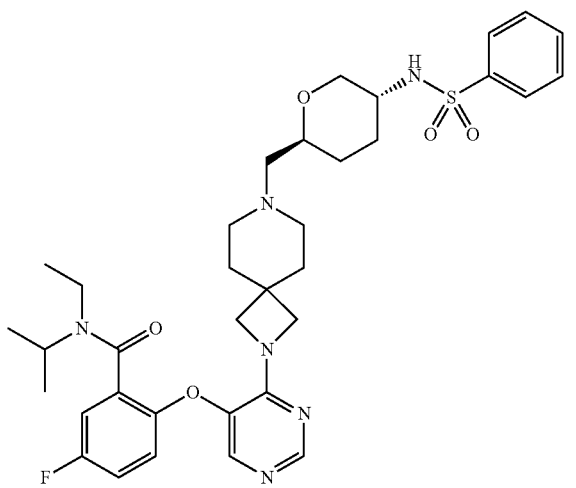 [SMILES: CCN(C(=O)c1cc(F)ccc1Oc1cncnc1N1CC2(CCN(C[C@@H]3CC[C@@H](NS(=O)(=O)c4ccccc4)CO3)CC2)C1)C(C)C]

In a dried, 25 mL three-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (300 mg, 0.520 mmol) and DBU (0.313 ml, 2.079 mmol) were dissolved in DCM (3 mL). To this solution, benzenesulfonyl chloride (138 mg, 0.780 mmol) was added at 10° C. and the reaction mixture was stirred at 25° C. for 18 h, monitoring the reaction progress by TLC. After 18 h, the reaction was quenched with water (50 mL) and 1 mL of triethylamine was added to it. The resulting suspension was extracted with 5% methanol in DCM (3×50 mL). The combined organic layer was dried over anhydrous sodium sulfate and filtered, and the filtrate was concentrated on a rotary evaporator under reduced pressure to obtain the crude product. The crude product was purified by prep HPLC (Method A). The fractions containing the desired product were lyophilized to obtain N-ethyl-5-fluoro-N-isopropyl-2-((4-(7-(((2S,5R)-5-(phenylsulfonamido)tetrahydro-2H-pyran-2-yl)methyl)-2,7-diazaspiro[3.5]nonan-2-yl)pyrimidin-5-yl)oxy)benzamide (49 mg, 13.21% yield) as an off-white solid: $^1$H NMR (400 MHz, DMSO-d$_6$): δ 8.31-8.21 (m, 1H), 7.86-7.79 (m, 2H), 7.77 (br d, J=6.1 Hz, 1H), 7.71 (s, 1H), 7.67-7.57 (m, 3H), 7.32-7.21 (m, 2H), 7.08-6.98 (m, 1H), 3.90-3.79 (m, 2H), 3.79-3.69 (m, 3H), 3.61-3.55 (m, 1H), 3.45-3.37 (m, 1H), 3.26-3.09 (m, 2H), 3.00-2.88 (m, 2H), 2.31-2.18 (m, 4H), 2.17-2.10 (m, 1H), 1.70-1.55 (m, 6H), 1.38-1.25 (m, 1H), 1.23-1.13 (m, 2H), 1.13-0.96 (m, 9H); LCMS (Method A): Rt=1.66 min, 681.3 (M+H)$^+$; HPLC (Method B): Rt=3.74 min, 95.43%.

Example 46. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide (46)

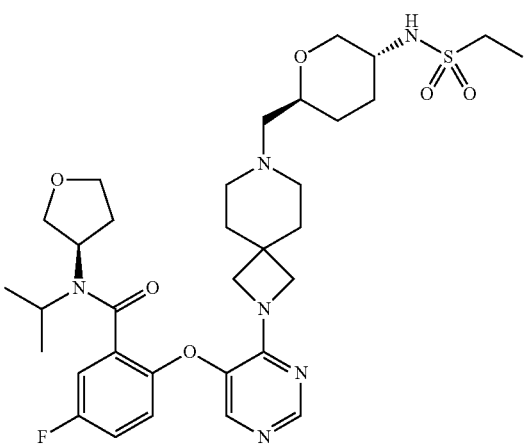 [SMILES: CCS(=O)(=O)N[C@@H]1CC[C@@H](CN2CCC3(CC2)CN(c2ncncc2Oc2ccc(F)cc2C(=O)N(C(C)C)[C@@H]2CCOC2)C3)OC1]

In a dried, 50 mL two-necked round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.3 g, 0.532 mmol) was dissolved in N,N-dimethylformamide (8 mL). To this solution, TEA (0.223 mL, 1.597 mmol), HATU (0.405 g, 1.064 mmol) and (R)—N-isopropyltetrahydrofuran-3-amine (0.193 g, 1.490 mmol) were added at 25° C. under nitrogen atmosphere and reaction was stirred at 25° C. for 16 h. The reaction progress was monitored by TLC (10% MeOH in DCM). After 16 h, the reaction mixture was quenched with water (100 mL) and the aqueous layer was extracted with ethyl acetate (3×100 mL). The combined organic layer was dried over anhydrous sodium sulfate and filtered, and the filtrate was concentrated on a rotary evaporator (bath temperature 40° C.) under reduced pressure to obtain the crude product. The crude product was purified by prep HPLC (Method A). The fractions containing the desired product were lyophilized to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide (35 mg, 9.65% yield) as an off-white solid: $^1$H NMR (400 MHz, DMSO-d$_6$): δ 8.27 (d, J=2.9 Hz, 1H), 7.73 (d, J=16.5 Hz, 1H), 7.35-7.20 (m, 2H), 7.13-6.99 (m, 2H), 4.06-3.85 (m, 4H), 3.84-3.66 (m, 7H), 3.53-3.43 (m, 1H), 3.15-3.07 (m, 1H), 3.05-2.98 (m, 3H), 2.31-2.26 (m, 3H), 2.21 (br d, J=3.1 Hz, 2H), 1.93 (br dd, J=4.1, 10.4 Hz, 2H), 1.66 (br s, 6H), 1.49-1.32 (m, 3H), 1.29-1.22 (m, 1H), 1.18 (t, J=7.3 Hz, 4H), 1.13 (br d, J=6.5 Hz, 1H), 1.06 (br dd, J=6.7, 12.2 Hz, 2H), 0.98 (br d, J=6.5 Hz, 1H); LCMS (Method A): Rt=1.653 min, 675.1 (M+H)$^+$, 99.39% (Max); HPLC (Method A): Rt=4.885 min, 99.03%.

Example 47. 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (47)

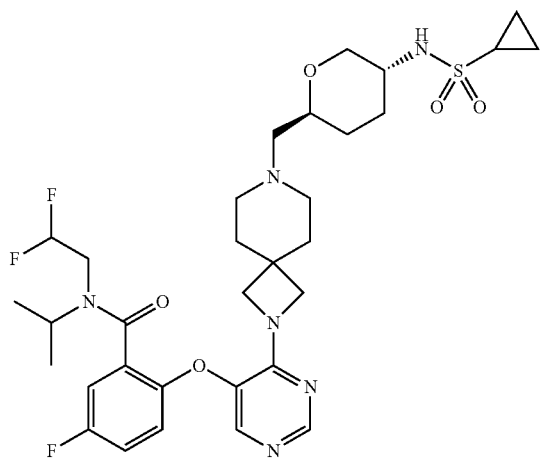 [SMILES: CC(C)N(CC(F)F)C(=O)c1cc(F)ccc1Oc1cncnc1N1CC2(CCN(C[C@@H]3CC[C@@H](NS(=O)(=O)C4CC4)CO3)CC2)C1]

In a dried, 50 mL two-necked round bottom flask under nitrogen atmosphere, lithium 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluorobenzoate (0.066 g, 0.115 mmol) was dissolved in N,N-dimethylformamide (2.5 mL). To this solution, TEA (0.048 mL, 0.344 mmol), HATU (0.087 g, 0.229 mmol) and N-(2,2-difluoroethyl)propan-2-amine, hydrochloride (0.027 g, 0.172 mmol) were added at 25° C. under nitrogen atmosphere, and the reaction mixture was stirred at 25° C. for 16 h. The reaction progress was monitored by TLC (10% MeOH in DCM). After 16 h, the reaction mixture was quenched with water (25 mL) and the aqueous layer was extracted with ethyl acetate (3×50 mL). The combined organic layer was dried over anhydrous sodium sulfate and filtered, and the filtrate was concentrated on a rotary evaporator (bath temperature 40° C.) to obtain the crude product. The crude product was purified by prep HPLC (Method A). The fractions containing the desired product were lyophilized to obtain 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (20 mg, 25.4% yield) as an off white solid: $^1$H NMR (400 MHz, DMSO-$d_6$): δ 8.39-8.14 (m, 1H), 7.85-7.68 (m, 1H), 7.44-7.20 (m, 2H), 7.12 (d, J=7.9 Hz, 1H), 7.02 (dd, J=4.4, 9.1 Hz, 1H), 6.37-6.03 (m, 1H), 3.91-3.65 (m, 8H), 3.22-3.09 (m, 1H), 3.06-2.96 (m, 1H), 2.62-2.56 (m, 1H), 2.32-2.23 (m, 4H), 2.22-2.17 (m, 1H), 2.04-1.95 (m, 1H), 1.73-1.60 (m, 5H), 1.48-1.36 (m, 1H), 1.31-1.19 (m, 2H), 1.08 (br dd, J=6.5, 15.9 Hz, 6H), 0.98-0.84 (m, 5H); LCMS (Method A): Rt=1.962 min, 681.1 (M+H)$^+$; HPLC (Method A): Rt=5.459 min, 98.92%.

Example 48. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide (48)

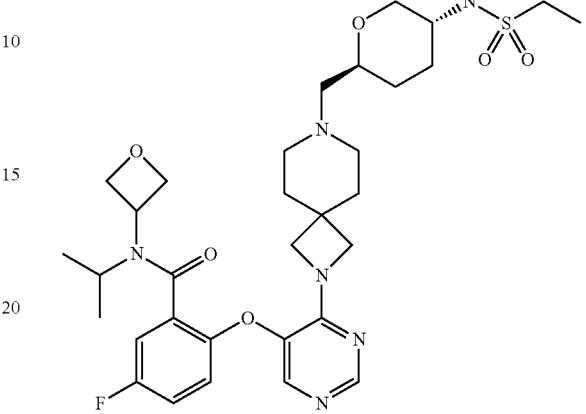

In a dried, 25 mL two-necked round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (300 mg, 0.532 mmol) was dissolved in DMF (5 mL). To this solution, N-isopropyloxetan-3-amine (61.3 mg, 0.532 mmol), HATU (304 mg, 0.798 mmol) and TEA (0.299 mL, 2.129 mmol) were added at 25° C. under nitrogen atmosphere and the reaction mixture was stirred at 25° C. for 24 h. The reaction progress was monitored by TLC (10% MeOH in DCM). After 24 h, the reaction mixture was quenched with water (25 mL) and the aqueous layer was extracted with ethyl acetate (3×25 mL). The combined organic layer was dried over anhydrous sodium sulfate and filtered, and the filtrate was concentrated on a rotary evaporator (bath temperature 40° C.) to obtain the crude product as light brown solid. The crude product was purified by Prep HPLC (Method A). The fractions containing the desired product were lyophilized to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide (116.93 mg, 32.4% yield) as an off-white solid: $^1$H NMR (400 MHz, DMSO-$d_6$): δ 8.33-8.23 (m, 1H), 7.87-7.73 (m, 1H), 7.44-7.17 (m, 2H), 7.14-6.96 (m, 2H), 5.28-5.05 (m, 1H), 4.88-4.66 (m, 1H), 4.65-4.55 (m, 2H), 4.48-4.06 (m, 1H), 3.95-3.66 (m, 6H), 3.17-3.04 (m, 1H), 3.04-2.95 (m, 3H), 2.32-2.18 (m, 5H), 1.94 (br d, J=12.4 Hz, 1H), 1.66 (br d, J=2.9 Hz, 6H), 1.51 (br d, J=5.8 Hz, 1H), 1.46-1.32 (m, 3H), 1.31-1.21 (m, 1H), 1.18 (t, J=7.3 Hz, 3H), 1.10-0.92 (m, 4H); LCMS (Method A): Rt=1.354 min, 661.3(M+H)$^+$; HPLC (Method A): Rt=4.69 min, 97.51%.

Example 49. 2-((4-(7-(((2S,5R)-5-((N,N-Dimethyl-sulfamoyl)amino)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (49)

Example 50. 2-((4-(7-(((2S,5R)-5-(Ethylsulfona-mido)tetrahydro-2H-pyran-2-yl)methyl)-2,7-diazaspiro[3.5]nonan-2-yl)pyrimidin-5-yl)oxy)-5-fluoro-N-((1s,3s)-3-hydroxycyclobutyl)-N-isopropylbenzamide (50)

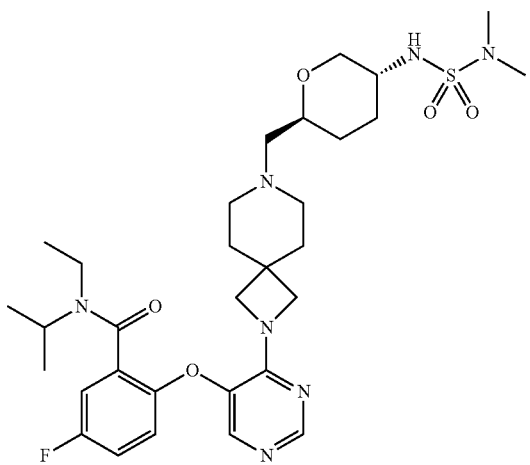 [SMILES: CCN(C(=O)c1cc(F)ccc1Oc1cncnc1N1CC2(CCN(C[C@@H]3CC[C@@H](NS(=O)(=O)N(C)C)CO3)CC2)C1)C(C)C]

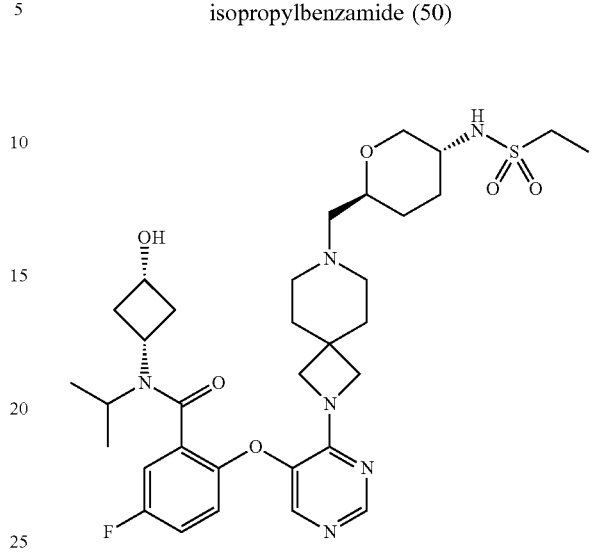

In a dried, 25 mL two-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide, hydrochloride (0.35 g, 0.606 mmol) was dissolved in DCM (5 mL). The resulting solution was cooled to 0° C. and TEA (0.423 mL, 3.03 mmol) was added to it. The reaction was stirred at 0° C. for 0.5 h and then dimethylsulfamoyl chloride (0.131 g, 0.910 mmol) was added to it and the reaction was stirred at 25° C. for 20 h. The reaction progress was monitored by TLC (10% MeOH in DCM). After 20 h, the reaction mixture was quenched with water (20 mL) and the aqueous layer was extracted with DCM (2×30 mL). The combined organic layer was dried over anhydrous sodium sulfate and filtered, and the filtrate was concentrated on a rotary evaporator under reduced pressure (bath Temperature 40° C.) to afford the crude product. The crude product was purified by Prep HPLC (Method A). The fractions containing the desired product were lyophilized to obtain 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (43 mg, 10.75% yield) as an off-white solid: $^1$H NMR (400 MHz, DMSO-$d_6$): δ 8.31-8.22 (m, 1H), 7.77-7.65 (m, 1H), 7.16 (s, 3H), 7.11-7.00 (m, 1H), 3.84 (br d, J=5.9 Hz, 3H), 3.81-3.71 (m, 3H), 3.46-3.35 (m, 1H), 3.26-3.10 (m, 1H), 3.07-2.96 (m, 2H), 2.70-2.66 (m, 1H), 2.64 (s, 6H), 2.32-2.15 (m, 5H), 1.95 (br d, J=12.8 Hz, 1H), 1.66 (br s, 5H), 1.46-1.33 (m, 1H), 1.28-1.15 (m, 3H), 1.14-1.08 (m, 5H), 1.06-0.97 (m, 3H); LCMS (Method A): Rt=2.164 min, m/z: 648.4(M+H)$^+$; HPLC (Method A): Rt=5.01 min, 98.18%.

In a dried, 25 mL two-necked round bottom flask under nitrogen atmosphere, 2-((4-(7-(((2S,5R)-5-(ethylsulfona-mido)tetrahydro-2H-pyran-2-yl)methyl)-2,7-diazaspiro[3.5]nonan-2-yl)pyrimidin-5-yl)oxy)-5-fluorobenzoic acid (0.3 g, 0.532 mmol) was dissolved in DMF (8 mL). To this solution, TEA (0.297 mL, 2.129 mmol), HATU (0.405 g, 1.064 mmol) and (1s,3s)-3-(isopropylamino)cyclobutan-1-ol (0.138 g, 1.064 mmol) were added at 25° C. under nitrogen atmosphere, and the reaction mixture was stirred at 25° C. for 16 h under nitrogen atmosphere. The reaction progress was monitored by TLC (10% MeOH in DCM). After 16 h, the reaction mixture was quenched with water (100 mL) and the aqueous layer was extracted with ethyl acetate (2×100 mL). The combined organic layer was dried over anhydrous sodium sulfate and filtered, and the filtrate was concentrated on a rotary evaporator (bath temperature 40° C.) to obtain the crude product as a brown, gummy mass. The crude product was purified by prep HPLC (Method A). The fractions containing the desired product were lyophilized to obtain 2-((4-(7-(((2S,5R)-5-(ethylsulfo-namido)tetrahydro-2H-pyran-2-yl)methyl)-2,7-diazaspiro[3.5]nonan-2-yl)pyrimidin-5-yl)oxy)-5-fluoro-N-((1s,3s)-3-hydroxycyclobutyl)-N-isopropylbenzamide (0.12 g, 33.1% yield) as an off-white solid: $^1$H NMR (400 MHz, DMSO-$d_6$): δ 8.36-8.16 (m, 1H), 7.81-7.64 (m, 1H), 7.33-7.18 (m, 1H), 7.16-6.99 (m, 3H), 5.02 (d, J=7.0 Hz, 1H), 3.94-3.75 (m, 6H), 3.69-3.50 (m, 2H), 3.17-3.05 (m, 1H), 3.04-2.96 (m, 3H), 2.95-2.77 (m, 1H), 2.33-2.12 (m, 7H), 2.00-1.83 (m, 3H), 1.67 (br s, 6H), 1.46-1.35 (m, 3H), 1.33-1.22 (m, 3H), 1.18 (t, J=7.3 Hz, 3H), 1.10-1.00 (m, 2H); LCMS (Method A): Rt=1.653 min, m/z: 675.1 (M+H)$^+$; HPLC (Method A): Rt=4.60 min, 99.9%.

Example 51. 2-((4-(7-(((2S,5R)-5-(Cyclopropane-sulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide (51)

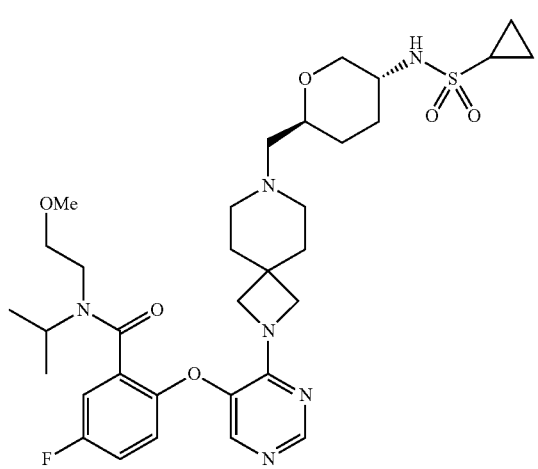 [SMILES: COCCN(C(=O)c1cc(F)ccc1Oc1cncnc1N1CC2(CCN(C[C@@H]3CC[C@@H](NS(=O)(=O)C4CC4)CO3)CC2)C1)C(C)C]

In a dried, 25 mL two-necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide, hydrochloride (0.5 g, 0.823 mmol) was dissolved in DCM (5 mL). The resulting solution was cooled to 0° C. and DBU (0.621 ml, 4.12 mmol) was added to it. The reaction was stirred at 0° C. for 0.5 h and then cyclopropanesulfonyl chloride (0.232 g, 1.647 mmol) was added to it. The reaction was then stirred at 25° C. for 18 h, monitoring the reaction progress by TLC (10% MeOH in DCM). After 18 h, the reaction mixture was quenched with water (20 mL) and the aqueous layer was extracted with DCM (2×30 mL). The combined organic layer was dried over anhydrous sodium sulfate and filtered, and the filtrate was concentrated under reduced pressure on a rotary evaporator (bath Temperature 40° C.) to afford the crude product. The crude product was purified by Prep HPLC (Method A). The fractions containing the desired product were lyophilized to obtain 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide (75 mg, 13.00% yield) as an off-white solid: $^1$H NMR (400 MHz, DMSO-$d_6$): δ 8.33-8.21 (m, 1H), 7.76-7.65 (m, 1H), 7.34-7.22 (m, 2H), 7.16-7.00 (m, 2H), 3.96-3.83 (m, 3H), 3.81-3.71 (m, 3H), 3.54-3.47 (m, 1H), 3.41-3.37 (m, 1H), 3.25 (s, 3H), 3.14 (s, 1H), 3.07-2.97 (m, 1H), 2.61-2.55 (m, 2H), 2.33-2.19 (m, 4H), 2.05-1.94 (m, 1H), 1.69 (br s, 6H), 1.49-1.36 (m, 1H), 1.31-1.17 (m, 3H), 1.09 (br d, J=6.5 Hz, 3H), 1.04 (br d, J=6.6 Hz, 3H), 0.98-0.84 (m, 5H); LCMS (Method A): Rt=1.749 min, m/z: 675.1(M+H)$^+$; HPLC (Method A): Rt=5.075 min, 96.33%.

Example 52. N-Ethyl-2-((4-(7-(((2R,5S)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (52)

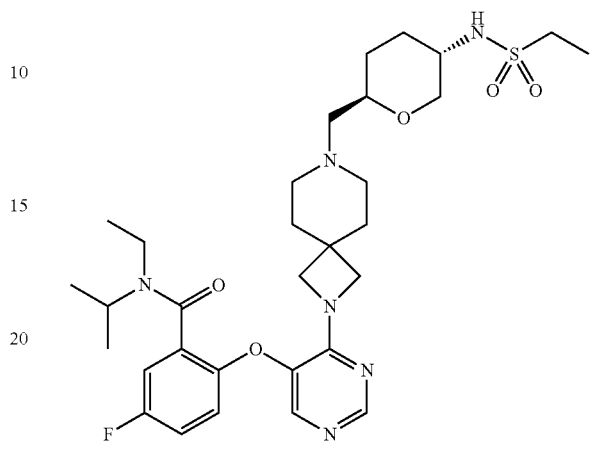

Step 1. (3S,6R)—N-Benzyl-6-(((tert-butyldiphenylsilyl)oxy)methyl)tetrahydro-2H-pyran-3-amine

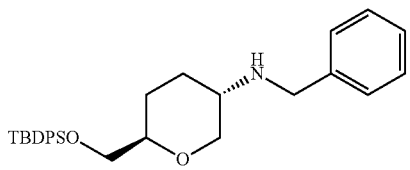

In a dried, 50 mL three-necked round bottom flask under nitrogen atmosphere, (R)-6-(((tert-butyldiphenylsilyl)oxy)methyl)dihydro-2H-pyran-3(4H)-one (2 g, 5.43 mmol; synthesized in five steps starting from racemic (3,4-dihydro-2H-pyran-2-yl)methanol as described in Bioorganic & Medicinal Chemistry 2006, 14(11), 3953-3966; Angewandte Chemie, International Edition, 54(46), 13538-13544; 2015; Tetrahedron: Asymmetry 1995, 6, (1), 97-100; Tetrahedron Letters 2009, 50(22), 2693-2696) was dissolved in methanol (20 mL). To this solution, benzylamine (1.745 g, 16.28 mmol) was added under nitrogen atmosphere and the reaction mixture was stirred at 25° C. After 1 h, LiBH$_4$ (0.130 g, 5.97 mmol) was added at −78° C. and the reaction was maintained at −78° C. for 1 h. The reaction mixture was slowly allowed to attain 25° C. and stirred for 4 h, monitoring the reaction progress by TLC (30% EtOAc in petroleum ether). There was no reaction progress observed (SM was intact). The reaction mixture was then heated at 40° C. for 16 h, monitoring the progress by TLC (30% ethyl acetate in hexane). After 16 h, the reaction mixture was partitioned between EtOAc and sat. NaHCO$_3$, and the aqueous layer was further extracted with EtOAc (2×60 mL). The combined organic layer was washed with brine, dried over Na$_2$SO$_4$, and filtered, and the filtrate was concentrated on a rotary evaporator under reduced pressure to obtain the crude product. The crude product was purified by silica gel column chromatography (Biotage Isolera) using 230-400 mesh silica gel and eluting with 20% EtOAc/hexane. The fractions containing the desired product were concentrated under reduced pressure on a rotary evaporator to obtain (3S,6R)—N-benzyl-6-(((tert-butyldiphenylsilyl)oxy)methyl)tetrahydro-2H-pyran-3-amine (2 g, 80% yield): $^1$H NMR (400 MHz, CDCl$_3$): δ 7.76-7.66 (m, 4H), 7.47-7.31 (m, 11H), 7.28-7.23 (m, 1H), 4.13-3.97 (m, 1H), 3.78-3.70 (m, 1H), 3.64-3.52 (m, 1H), 3.51-3.36 (m, 1H), 3.13-3.03 (m, 1H), 2.76-2.63 (m, 1H), 2.14-1.97 (m, 1H), 1.88-1.77 (m, 1H), 1.73-1.59 (m, 2H), 1.43-1.22 (m, 2H), 1.08 (s, 9H).

Step 2. (3S,6R)-6-(((tert-Butyldiphenylsilyl)oxy)methyl)tetrahydro-2H-pyran-3-amine

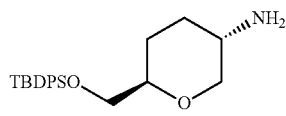

A miniclave reactor was flushed with nitrogen and charged with (3S,6R)—N-benzyl-6-(((tert-butyldiphenylsilyl)oxy)methyl)tetrahydro-2H-pyran-3-amine (2 g, 4.35 mmol) in ethanol (5 mL). 20% palladium hydroxide on carbon (0.764 g, 1.088 mmol) was added to the resulting solution under nitrogen atmosphere. The vessel was evacuated and flushed with nitrogen and then stirred under 50 psi H$_2$ for 16 h at 25° C. The reaction progress was monitored by TLC (10% methanol in dichloromethane). After 16 h, the reaction mixture was filtered through Celite® and washed with methanol, and the combined filtrate was concentrated on a rotary evaporator (bath temperature 40° C.) under reduced pressure to obtain the crude (3S,6R)-6-(((tert-butyldiphenylsilyl)oxy)methyl)tetrahydro-2H-pyran-3-amine (1.2 g, 75% crude yield) which was taken as such to the next step without purification: LCMS (Method A): Rt=2.037 min, 370.0 (M+H)$^+$, 42.68%.

Step 3. N-((3S,6R)-6-(((tert-Butyldiphenylsilyl)oxy)methyl)tetrahydro-2H-pyran-3-yl)ethanesulfonamide

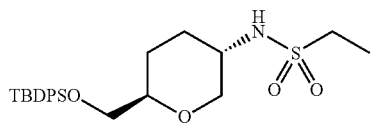

In a dried, 25 mL three-necked round bottom flask under nitrogen atmosphere, (3S,6R)-6-(((tert-butyldiphenylsilyl)oxy)methyl)tetrahydro-2H-pyran-3-amine (500 mg, 1.353 mmol) was dissolved in DCM (10 mL). To this solution, triethylamine (548 mg, 5.41 mmol) and ethanesulfonyl chloride (261 mg, 2.029 mmol) were added sequentially under nitrogen atmosphere at 0° C. The reaction mixture was continued to stir at 25° C. for 16 h, monitoring the reaction progress by TLC (30% ethyl acetate in hexane). After 16 h, the reaction mixture was quenched with water (15 mL) and the aqueous layer was extracted with DCM (4×80 mL). The combined organic layer was washed with brine, dried over anhydrous sodium sulfate, and filtered, and the filtrate was concentrated on a rotary evaporator (bath temperature 40° C.) under reduced pressure to obtain the crude product. The crude product was purified by column chromatography (Biotage Isolera) using 230-400 silica gel and eluting with a mixture of ethyl acetate and hexane (the desired product eluted in 15% ethyl acetate in hexane). The fractions containing the desired product were concentrated under reduced pressure to obtain N-((3S,6R)-6-(((tert-butyldiphenylsilyl)oxy)methyl)tetrahydro-2H-pyran-3-yl)ethanesulfonamide (200 mg, 32.0% yield): $^1$H NMR (400 MHz, DMSO-d$_6$): δ 7.70-7.56 (m, 4H), 7.51-7.39 (m, 6H), 3.88-3.83 (m, 1H), 3.67-3.58 (m, 1H), 3.57-3.50 (m, 1H), 3.16-2.98 (m, 3H), 1.98 (br d, J=8.9 Hz, 1H), 1.71 (br d, J=10.5 Hz, 1H), 1.45-1.35 (m, 1H), 1.26-1.17 (m, 3H), 1.00 (s, 9H).

Step 4. N-((3S,6R)-6-(Hydroxymethyl)tetrahydro-2H-pyran-3-yl)ethanesulfonamide

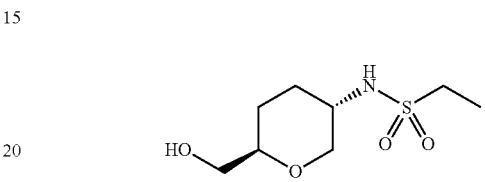

In a dried, 10 mL three-necked round bottom flask under nitrogen atmosphere, N-((3S,6R)-6-(((tert-butyldiphenylsilyl)oxy)methyl)tetrahydro-2H-pyran-3-yl)ethanesulfonamide (100 mg, 0.217 mmol) was dissolved in THF (1 mL). To this solution, TBAF (0.866 mL, 0.866 mmol) was added under nitrogen atmosphere at 0° C., and the reaction mixture was continued to stir at 25° C. for 16 h, monitoring the reaction progress by TLC (10% methanol in DCM). After 16 h, the reaction mixture was quenched with water (10 mL) and the aqueous layer was extracted with 10% methanol in DCM (4×20 mL). The organic layer was dried over anhydrous sodium sulfate and filtered, and the filtrate was concentrated on a rotary evaporator (bath temperature 40° C.) to obtain the crude product. The crude product was purified by silica gel column chromatography (Biotage Isolera) using 230-400 mesh silica gel and eluting with mixture of methanol in DCM (the desired product was eluted in 2% methanol in DCM). The fractions containing the desired product were concentrated under reduced pressure on a rotary evaporator to obtain N-((3S,6R)-6-(hydroxymethyl)tetrahydro-2H-pyran-3-yl)ethanesulfonamide (40 mg, 83% yield): $^1$H NMR (400 MHz, DMSO-d$_6$): δ 7.10 (d, J=7.6 Hz, 1H), 4.61 (t, J=5.8 Hz, 1H), 3.88-3.82 (m, 1H), 3.29-3.23 (m, 1H), 3.20-3.06 (m, 2H), 3.05-2.98 (m, 3H), 1.99-1.93 (m, 1H), 1.70-1.62 (m, 1H), 1.46-1.34 (m, 1H), 1.31-1.22 (m, 1H), 1.22-1.16 (m, 4H); LCMS (Method A): Rt=1.22 min, 224.0 (M+H)$^+$.

Step 5. ((2R,5S)-5-(Ethylsulfonamido)tetrahydro-2H-pyran-2-yl)methyl 4-methylbenzenesulfonate

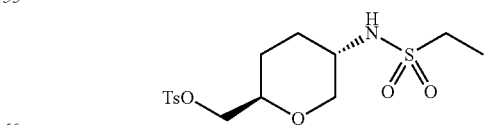

In dried, a 10 mL three-necked round bottom flask under nitrogen atmosphere, N-((3S,6R)-6-(hydroxymethyl)tetrahydro-2H-pyran-3-yl)ethanesulfonamide (80 mg, 0.358 mmol) was dissolved in DCM (5 mL). To this solution, DIPEA (0.188 mL, 1.075 mmol) was added followed by the addition of DMAP (4.38 mg, 0.036 mmol) and 4-methylbenzenesulfonyl chloride (102 mg, 0.537 mmol) at 0° C. The reaction mixture was stirred at 25° C. for 16 h, monitoring the progress by TLC (30% ethyl acetate in hexane). After 16 h, the reaction mixture was quenched with water and extracted with DCM (3×10 mL). The combined organic layer was dried over anhydrous sodium sulfate and filtered, and the filtrate was concentrated on a rotary evaporator under reduced pressure (bath temperature 45° C.) to obtain the crude product. The crude product was purified by column chromatography (Isolera) by using 100-200 mesh silica gel and eluting with 5-10% ethyl acetate in hexane as an eluent to obtain ((2R,5S)-5-(ethylsulfonamido)tetrahydro-2H-pyran-2-yl)methyl 4-methylbenzenesulfonate (70 mg, 51.8% yield).

Step 6. N-Ethyl-2-((4-(7-(((2R,5S)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide

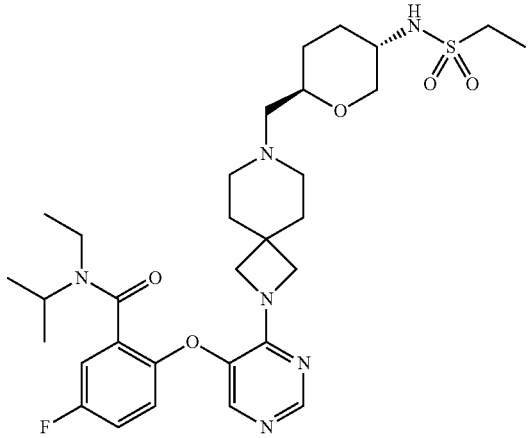

In a dried, 10 mL three-necked round bottom flask under nitrogen atmosphere, 2-((4-(2,7-diazaspiro[3.5]nonan-2-yl)pyrimidin-5-yl)oxy)-N-ethyl-5-fluoro-N-isopropylbenzamide, hydrochloride (50 mg, 0.108 mmol) was dissolved in NMP (2 mL). To this solution, $K_2CO_3$ (89 mg, 0.647 mmol) and KI (39.4 mg, 0.237 mmol) were added, followed by the addition of ((2R,5S)-5-(ethylsulfonamido)tetrahydro-2H-pyran-2-yl)methyl 4-methylbenzenesulfonate (61.0 mg, 0.162 mmol) under nitrogen atmosphere. The reaction mixture was continued to stir at 80° C. for 16 h, monitoring the progress by TLC (10% methanol in dichloromethane). After 16 h, the reaction mixture was quenched with water (2 mL) and the aqueous layer was extracted with ethyl acetate (4×10 mL). The combined organic layer was washed with brine, dried over anhydrous sodium sulfate, and filtered, and the filtrate was concentrated on a rotary evaporator (bath temperature 40° C.) under reduced pressure to obtain the crude product. The crude product was purified by Prep HPLC (Method A). The fractions containing the desired product were lyophilized to obtain N-ethyl-2-((4-(7-(((2R,5S)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (6 mg, 8.64% yield) as a white solid: $^1$H NMR (400 MHz, DMSO-$d_6$): δ 8.29-8.24 (m, 1H), 7.74-7.66 (m, 1H), 7.34-7.22 (m, 2H), 7.14-7.07 (m, 1H), 7.03 (dd, J=4.4, 9.0 Hz, 1H), 3.91-3.70 (m, 6H), 3.16-3.06 (m, 2H), 3.05-2.98 (m, 3H), 2.28 (br dd, J=6.2, 12.7 Hz, 4H), 2.23-2.16 (m, 2H), 1.94 (br d, J=12.0 Hz, 1H), 1.66 (br s, 6H), 1.47-1.36 (m, 1H), 1.24 (br s, 1H), 1.22-1.15 (m, 5H), 1.14-1.07 (m, 5H), 1.06-0.98 (m, 3H); LCMS (Method A): Rt=1.622 min, 633.3 (M+H)$^+$; HPLC (Method A): Rt=5.07 min, 98.18%.

Example 85. 2-((4-(7-(((2S,5R)-5-((1-(Difluoromethyl)-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

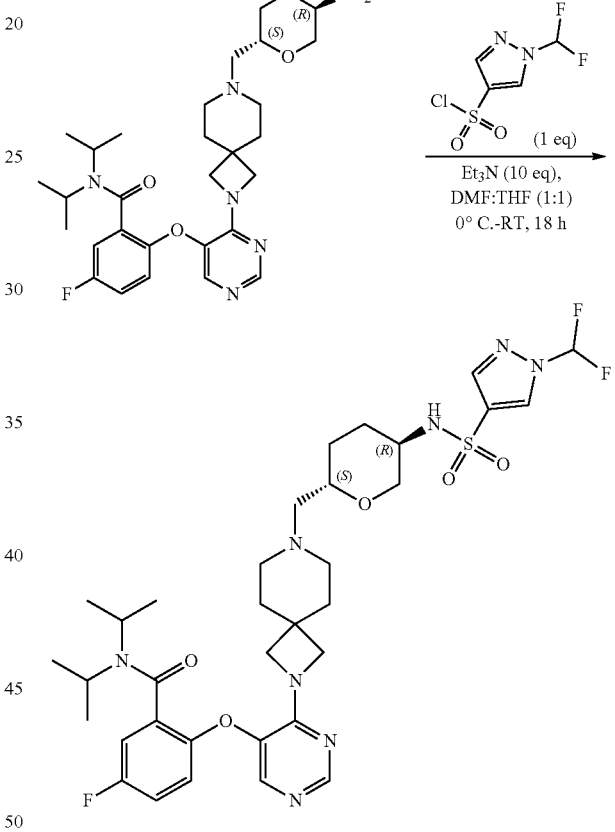

To a dried 50 mL two neck round bottom flask, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide hydrochloride (400 mg, 0.677 mmol) was added in DMF:THF (1:1) (10 mL). To this solution, Et$_3$N (0.943 mL, 6.77 mmol) and 1-(difluoromethyl)-1H-pyrazole-4-sulfonyl chloride (147 mg, 0.677 mmol) were added at 0° C., and the resulting mixture was stirred at RT for 18 h under nitrogen atmosphere. Progress of the reaction was monitored by TLC (10% MeOH in DCM). The reaction mixture was concentrated under reduced pressure to afford crude compound which was purified by purified by Prep HPLC (Method A), and the pure fractions were lyophilized to afford 2-((4-(7-(((2S,5R)-5-((1-(difluoromethyl)-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (197 mg, 38.9% yield). ¹H NMR (400 MHz, DMSO-d₆) δ 8.81 (s, 1H), 8.26 (s, 1H), 8.12 (s, 1H), 7.83 (br s, 1H), 7.73-7.68 (m, 1H), 7.26-7.19 (m, 2H), 7.08-7.00 (m, 1H), 3.98-3.76 (m, 4H), 3.75-3.64 (m, 2H), 3.58-3.39 (m, 2H), 3.31-3.26 (m, 1H), 3.14-2.94 (m, 2H), 2.33-2.11 (m, 6H), 1.81-1.70 (m, 1H), 1.69-1.54 (m, 5H), 1.44 (d, J=6.8 Hz, 3H), 1.37 (m, 1H), 1.34 (d, J=6.8 Hz, 3H), 1.26-1.13 (m, 1H), 1.09 (d, J=6.6 Hz, 3H), 0.99 (d, J=6.6 Hz, 3H); LCMS (Method C): Rt 1.82 min, m/z: 735.0 [M+H]⁺; HPLC (Method A): Rt 5.71 min, 99.08%.

Example 53. Fluoro-N-isopropyl-N-methyl-2-((4-(7-(((2S,5R)-5-((1-methyl-1H-pyrazole)-3-sulfonamido)tetrahydro-2H-pyran-2-yl)methyl)-2,7-diazaspiro[3.5]nonan-2-yl)pyrimidin-5-yl)oxy)benzamide

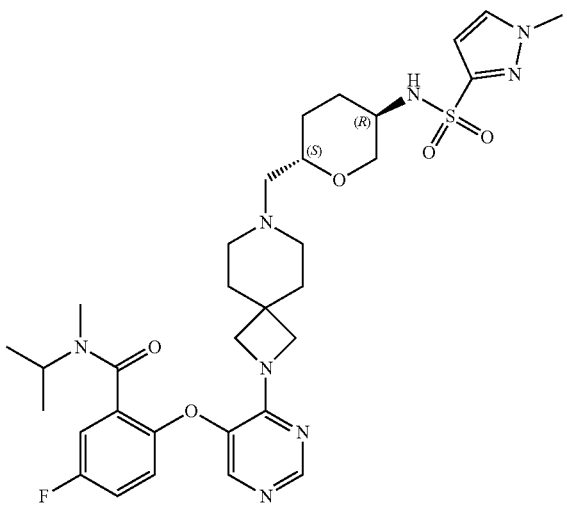

This compound was synthesized following the general procedure described for the synthesis of Example 85, except that 5 equivalents of Et₃N and 1.5 equivalents of 1-methyl-1H-pyrazole-3-sulfonyl chloride were used. The crude was purified by Prep-HPLC (Method D).

Yield: 25.6%;

¹H NMR (400 MHz, DMSO-d₆) δ 8.34-8.19 (m, 1H), 7.86 (d, J=2.3 Hz, 1H), 7.78-7.65 (m, 2H), 7.34-7.20 (m, 2H), 7.12-6.96 (m, 1H), 6.60 (d, J=2.3 Hz, 1H), 3.92 (s, 3H), 3.89-3.65 (m, 6H), 3.12-3.02 (m, 1H), 3.01-2.92 (m, 1H), 2.82-2.64 (m, 3H, N—CH₃), 2.32-2.12 (m, 6H), 1.76 (d, J=12.8 Hz, 1H), 1.70-1.57 (m, 6H), 1.41-1.28 (m, 1H), 1.11 (d, J=6.5 Hz, 3H), 1.05 (d, J=6.5 Hz, 3H);

LCMS (Method B): Rt 1.14 min, m/z: 671.6 [M+H]⁺; HPLC (Method A): Rt 4.65 min, 99.96%.

Example 54. 5-Fluoro-N-isopropyl-N-methyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)benzamide

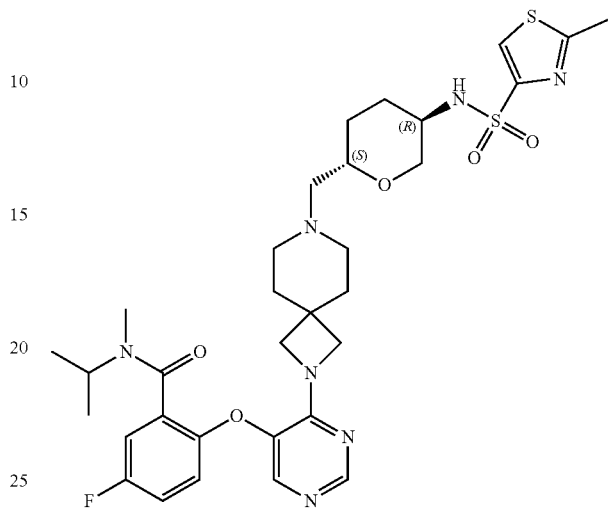

This compound was synthesized following the general procedure described for the synthesis of Example 85, except that 5 equivalents of Et₃N and 1.5 equivalents of 2-methylthiazole-4-sulfonyl chloride were used. The crude was purified by Prep-HPLC (Method D). Yield: 24.55%; ¹H NMR (400 MHz, DMSO-d₆) δ 8.33-8.21 (m, 1H), 8.17 (s, 1H), 7.92 (br s, J=1.6 Hz, 1H), 7.79-7.65 (m, 1H), 7.36-7.19 (m, 2H), 7.15-6.93 (m, 1H), 3.89-3.77 (m, 3H), 3.76-3.70 (m, 2H), 3.63-3.60 (m, 1H), 3.28-3.22 (m, 1H), 3.17-3.05 (m, 1H), 3.02-2.94 (m, 1H), 2.82-2.64 (m, 3H, N—CH₃), 2.71 (s, 3H), 2.32-2.10 (m, 6H), 1.79-1.68 (m, 1H), 1.68-1.58 (m, 5H), 1.44-1.30 (m, 1H), 1.25-1.15 (m, 1H), 1.13-1.02 (m, 6H); LCMS (Method E): Rt 1.59 min, m/z: 688.4 [M+H]⁺; HPLC (Method A): Rt 4.93 min, 99.96%.

Example 55. N-Ethyl-5-fluoro-N-isopropyl-2-((4-(7-(((2S,5R)-5-((4-methylphenyl)sulfonamido)tetrahydro-2H-pyran-2-yl)methyl)-2,7-diazaspiro[3.5]nonan-2-yl)pyrimidin-5-yl)oxy)benzamide

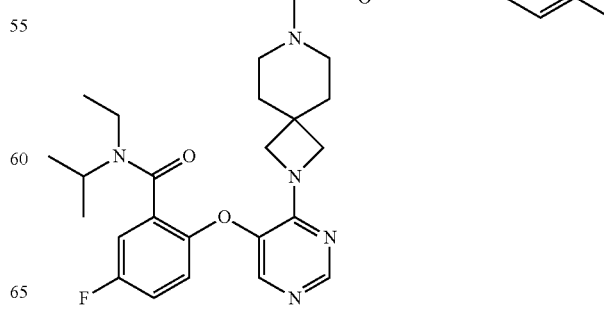

This compound was synthesized following the general procedure described for the synthesis of Example 85, except that 4 equivalents of Et₃N was used, and DCM (5 mL) was used as the solvent. The crude was purified by Prep-HPLC (Method C). Yield: 31.2%; ¹H NMR (400 MHz, DMSO-d₆) δ 8.29-8.23 (m, 1H), 7.72-7.66 (m, 4H), 7.40 (d, J=7.9 Hz, 2H), 7.32-7.21 (m, 2H), 7.04-7.01 (m, 1H), 3.83-3.73 (m, 5H), 3.62-3.53 (m, 1H), 3.28-3.18 (m, 2H), 2.98-2.85 (m, 2H), 2.39 (s, 3H), 2.21-2.08 (m, 5H), 2.17-2.08 (m, 1H), 1.69-1.54 (m, 7H), 1.38-1.24 (m, 1H), 1.19 (br s, 1H), 1.12-1.06 (m, 6H), 1.05-0.96 (m, 3H); LCMS (Method C): Rt 1.74 min, m/z: 695.3 [M+H]⁺; HPLC (Method A): Rt 5.79 min, 97.91%.

Example 56. N-Ethyl-5-fluoro-N-isopropyl-2-((4-(7-(((2S,5R)-5-((2-methylphenyl)sulfonamido)tetrahydro-2H-pyran-2-yl)methyl)-2,7-diazaspiro[3.5]nonan-2-yl)pyrimidin-5-yl)oxy)benzamide

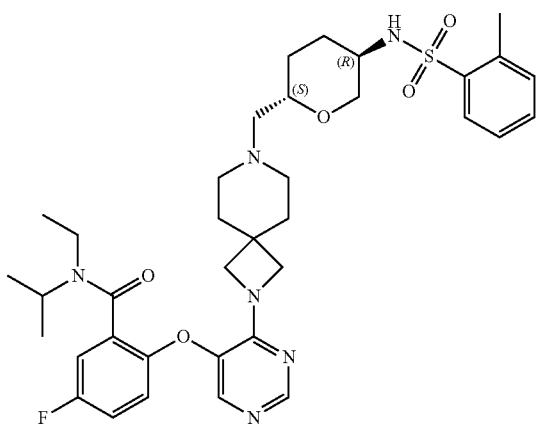

This compound was synthesized following the general procedure described for the synthesis of Example 85, except that 4 equivalents of Et₃N was used, and DCM was used as the solvent. The crude was purified by Prep-HPLC (Method B). Yield: 9.65%; ¹H NMR (400 MHz, DMSO-d₆) δ 8.28-8.23 (m, 1H), 7.88-7.84 (m, 1H), 7.79 (d, J=8.0 Hz, 1H), 7.73-7.65 (m, 1H), 7.55-7.51 (m, 1H), 7.42-7.36 (m, 2H), 7.32-7.21 (m, 2H), 7.00-7.07 (m, 1H), 3.83-3.71 (m, 5H), 3.56-3.49 (m, 1H), 3.38-3.10 (m, 2H), 3.02-2.89 (m, 2H), 2.57 (s, 3H), 2.31-2.16 (m, 5H), 2.15-2.08 (m, 1H), 1.69-1.54 (m, 7H), 1.44-1.32 (m, 1H), 1.18-1.03 (m, 10H); LCMS (Method C): Rt 1.97 min, m/z: 695.2 [M+H]⁺; HPLC (Method A): Rt 5.82 min, 99.63%.

Example 57. 2-((4-(7-(((2S,5R)-5-((3-Chlorophenyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide

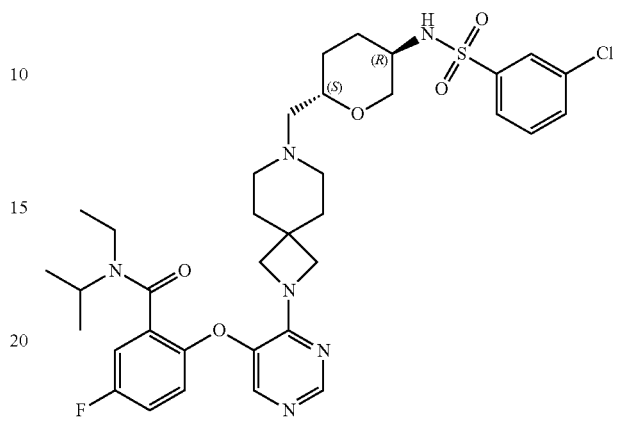

This compound was synthesized following the general procedure described for the synthesis of Example 85, except that 3 equivalents of Et₃N was used, and DCM was used as the solvent. The crude was purified by Prep-HPLC (Method B). Yield: 7.96%; ¹H NMR (400 MHz, DMSO-d₆) δ 8.29-8.23 (m, 1H), 7.93 (br d, J=6.0 Hz, 1H), 7.84-7.71 (m, 4H), 7.69-7.61 (m, 1H), 7.33-7.21 (m, 2H), 7.04-7.01 (m, 1H), 3.84-3.68 (m, 5H), 3.65-3.54 (m, 1H), 3.23 (d, J=7.5 Hz, 1H), 2.97-2.98 (m, 2H), 2.32-2.09 (m, 6H), 1.72-1.54 (m, 7H), 1.41-1.28 (m, 1H), 1.18 (br s, 3H), 1.12-1.07 (m, 5H), 1.03 (d, J=6.6 Hz, 3H); LCMS (Method C): Rt 1.97 min, m/z: 714.9 [M+H]⁺; HPLC (Method A): Rt 5.99 min, 98.65%.

Example 58. N-ethyl-5-fluoro-N-isopropyl-2-((4-(7-(((2S,5R)-5-(pyridine-2-sulfonamido)tetrahydro-2H-pyran-2-yl)methyl)-2,7-diazaspiro[3.5]nonan-2-yl)pyrimidin-5-yl)oxy)benzamide

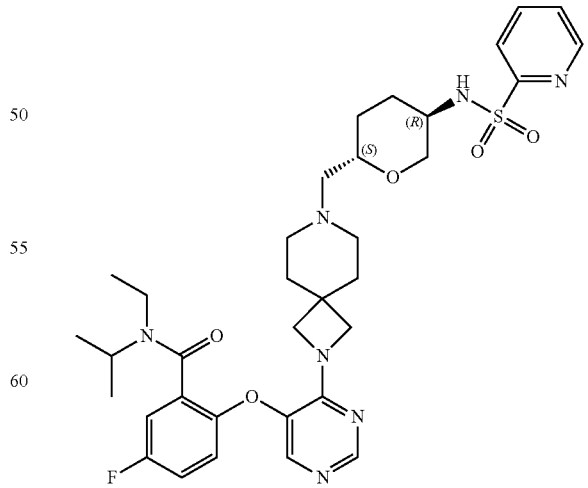

This compound was synthesized following the general procedure described for the synthesis of Example 85, except that 1 equivalent of Et₃N was used and DCM was used as the solvent. The crude was purified by Prep-HPLC (Method A). Yield: 17.84%; ¹H NMR (400 MHz, DMSO-d₆) 8.76-8.71 (m, 1H), 8.29-8.23 (m, 1H), 8.07 (dd, J=1.8, 7.8 Hz, 1H), 7.90-7.99 (m, 2H), 7.71 (s, 1H), 7.66 (ddd, J=1.1, 3.3, 4.3 Hz, 1H), 7.34-7.20 (m, 2H), 7.01-7.09 (m, 1H), 3.84 (br s, 2H), 3.80-3.69 (m, 3H), 3.67-3.61 (m, 1H), 3.36-3.43 (m, 1H), 3.27-3.22 (m, 11H), 3.20-3.10 (m, 2H), 3.02-2.93 (m, 1H), 2.31-2.10 (m, 6H), 1.60-1.68 (m, 1H), 1.68-1.56 (m, 5H), 1.32-1.41 (m, 1H), 1.13-1.21 (m, 2H), 1.13-1.06 (m, 5H), 1.04 (d, J=6.6 Hz, 3H); LCMS (Method C): Rt 1.56 min, m/z: 682.3 [M+H]⁺; HPLC (Method A): Rt 5.04 min, 99.67%.

Example 59. 2-((4-(7-(((2S,5R)-5-((2-Chlorophenyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide

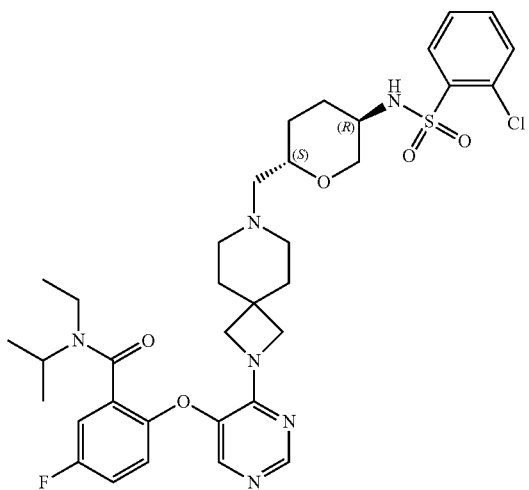

This compound was synthesized following the general procedure described for the synthesis of Example 85, except that 4 equivalents of Et₃N was used, and DCM was used as the solvent. The crude was purified by Prep-HPLC (Method D). Yield: 12.40%; ¹H NMR (400 MHz, DMSO-d₆) δ 8.30-8.22 (m, 1H), 8.01 (dd, J=1.4, 7.5 Hz, 2H), 7.74-7.61 (m, 3H), 7.59-7.50 (m, 1H), 7.33-7.21 (m, 2H), 7.03 (dd, J=4.4, 8.9 Hz, 1H), 3.92-3.81 (m, 2H), 3.79-3.69 (m, 3H), 3.63-3.54 (m, 1H), 3.34-3.41 (m, 1H), 3.27-3.11 (m, 2H), 3.08-2.95 (m, 2H), 2.34-2.18 (m, 4H), 2.17-2.09 (m, 1H), 1.73-1.56 (m, 7H), 1.38-1.48 (m, 1H), 1.19 (br s, 1H), 1.13-1.06 (m, 6H), 1.05-0.95 (m, 3H); LCMS (Method C): Rt 1.68 min, m/z: 715.2 [M+H]⁺; HPLC (Method A): Rt 5.81 min, 97.83%.

Example 60. N-ethyl-5-fluoro-N-isopropyl-2-((4-(7-(((2S,5R)-5-((3-methylphenyl)sulfonamido)tetrahydro-2H-pyran-2-yl)methyl)-2,7-diazaspiro[3.5]nonan-2-yl)pyrimidin-5-yl)oxy)benzamide

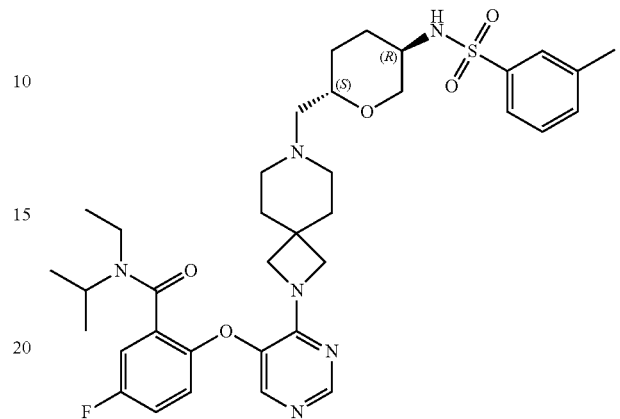

This compound was synthesized following the general procedure described for the synthesis of Example 85, except that 2 equivalents of 3-methylbenzenesulfonyl chloride and 5 equivalents of K₂CO₃ were used, and DMF was used as the solvent. The crude was purified by Prep-HPLC (Method C). Yield: 21.21%; ¹H NMR (400 MHz, DMSO-d₆) δ 8.28-8.24 (m, 1H), 7.71 (s, 2H), 7.65 (m, 2H), 7.51-7.44 (m, 2H), 7.33-7.21 (m, 2H), 7.04-7.01 (m, 1H), 3.89-3.71 (m, 5H), 3.59-3.58 (m, 1H), 3.45-3.38 (m, 1H), 3.26-3.09 (m, 2H), 2.96-2.92 (m, 2H), 2.40 (s, 3H), 2.24-2.19 (m, 4H), 2.17-2.10 (m, 1H), 1.64-1.62 (m, 7H), 1.39-1.25 (m, 1H), 1.19-1.06 (m, 7H), 1.03 (d, J=6.5 Hz, 3H); LCMS (Method C): Rt 1.34 min, m/z: 695.3 [M+H]⁺; HPLC (Method A): Rt 5.87 min, 99.31%.

Example 61. 2-((4-(7-(((2S,5R)-5-((4-Chlorophenyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide

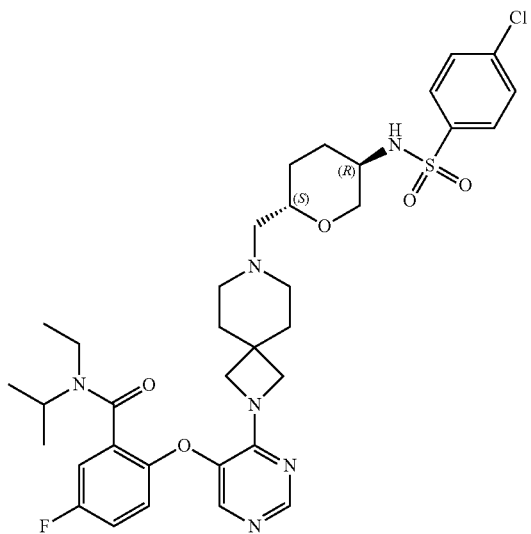

This compound was synthesized by following the general procedure described for the synthesis of Example 85. The crude was purified by Prep-HPLC (Method A). Yield: 36.5%; $^1$H NMR (400 MHz, DMSO-$d_6$) b 8.30-8.22 (m, 1H), 7.88 (br s, 1H), 7.82 (d, J=8.8 Hz, 2H), 7.73-7.64 (m, 3H), 7.34-7.20 (m, 2H), 7.02 (dd, J=4.4, 9.0 Hz, 11H), 3.84 (br s, 2H), 3.79-3.69 (m, 3H), 3.65-3.56 (m, 1H), 3.28-3.11 (m, 2H), 3.02-2.88 (m, 2H), 2.22 (dd, J=6.4, 12.9 Hz, 5H), 2.17-2.10 (m, 1H), 1.71-1.54 (m, 7H), 1.41-1.27 (m, 1H), 1.19 (br s, 2H), 1.13-1.07 (m, 5H), 1.05-0.95 (m, 3H); LCMS (Method A): Rt 2.85 min, m/z: 715.3 [M+H]$^+$; HPLC (Method A): Rt 6.03 min, 96.88%.

Example 62. N-Ethyl-5-fluoro-N-isopropyl-2-((4-(7-(((2S,5R)-5-((4-methoxyphenyl)sulfonamido)tetrahydro-2H-pyran-2-yl)methyl)-2,7-diazaspiro[3.5]nonan-2-yl)pyrimidin-5-yl)oxy)benzamide

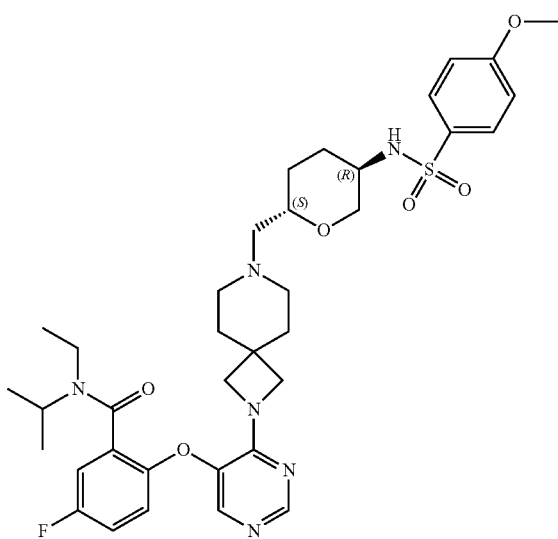

This compound was synthesized by following the general procedure described for the synthesis of Example 85. The crude was purified by Prep-HPLC (Method A). Yield: 40.6%; $^1$H NMR (400 MHz, DMSO-$d_6$) δ 8.29-8.24 (m, 1H), 7.77-7.70 (m, 3H), 7.59 (d, J=6.9 Hz, 1H), 7.34-7.20 (m, 2H), 7.15-7.08 (m, 2H), 7.02 (dd, J=4.4, 9.0 Hz, 1H), 3.84 (s, 5H), 3.79-3.70 (m, 3H), 3.61-3.54 (m, 1H), 3.44-3.37 (m, 1H), 3.26-3.10 (m, 2H), 2.98-2.83 (m, 2H), 2.35-2.18 (m, 4H), 2.17-2.09 (m, 1H), 1.70-1.55 (m, 1H), 1.69-1.54 (m, 6H), 1.39-1.24 (m, 2H), 1.14-1.07 (m, 6H), 1.05-0.97 (m, 3H); LCMS (Method A): Rt 1.89 min, m/z: 711.0 [M+H]$^+$; HPLC (Method A): Rt 5.58 min, 97.11%.

Example 63. N-Ethyl-5-fluoro-N-isopropyl-2-((4-(7-(((2S,5R)-5-(pyridine-3-sulfonamido)tetrahydro-2H-pyran-2-yl)methyl)-2,7-diazaspiro[3.5]nonan-2-yl)pyrimidin-5-yl)oxy)benzamide

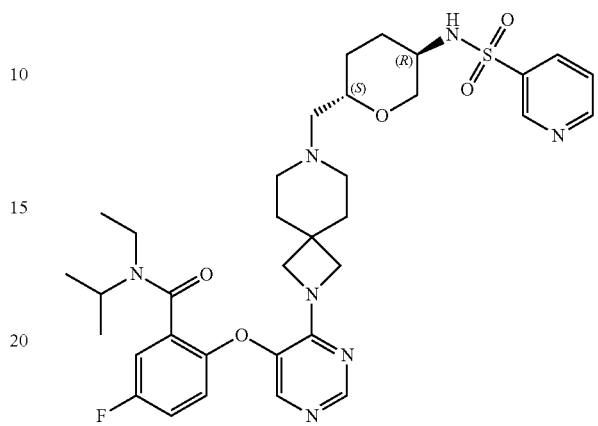

This compound was synthesized following the general procedure described for the synthesis of Example 85, except that 5 equivalents of Et$_3$N was used, and DCM was used as the solvent. The crude was purified by Prep-HPLC (Method D).

Yield: 10.81%;

$^1$H NMR (400 MHz, DMSO-$d_6$) δ 8.97 (d, J=1.9 Hz, 1H), 8.83 (dd, J=1.5, 4.8 Hz, 1H), 8.29-8.24 (m, 1H), 8.23-8.16 (m, 1H), 8.03 (br d, J=2.1 Hz, 1H), 7.74-7.61 (m, 2H), 7.34-7.19 (m, 2H), 7.10-6.98 (m, 1H), 3.92-3.69 (m, 5H), 3.64-362 (m, 1H), 3.24-3.09 (m, 2H), 3.06-2.94 (m, 2H), 2.33-2.08 (m, 6H), 1.75-1.49 (m, 7H), 1.45-1.28 (m, 1H), 1.27-0.99 (m, 7H), 1.03 (d, J=6.6 Hz, 3H); LCMS (Method A): Rt 1.79 min, m/z: 682.0 [M+H]$^+$; HPLC (Method A): Rt 4.94 min, 99.36%.

Example 64. N-Ethyl-5-fluoro-N-isopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)benzamide

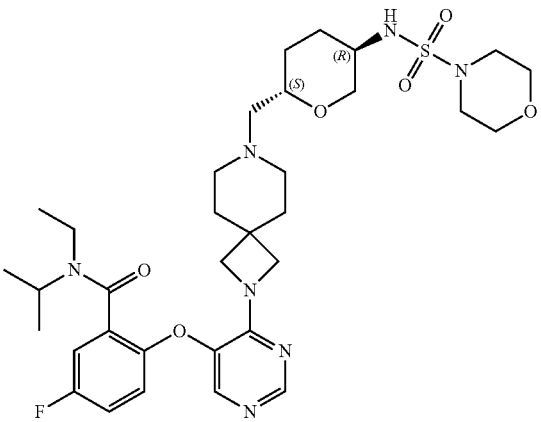

This compound was synthesized following the general procedure described for the synthesis of Example 85, except that 4 equivalents of Et₃N was used. The crude was purified by Prep-HPLC (Method K).

Yield: 15.16%;

¹H NMR (400 MHz, DMSO-d₆) δ 8.30-8.24 (m, 1H), 7.74-7.65 (m, 1H), 7.39 (d, J=7.4 Hz, 1H), 7.32-7.21 (m, 2H), 7.10-7.00 (m, 1H), 3.94-3.82 (m, 3H), 3.82-3.71 (m, 3H), 3.66-3.60 (m, 4H), 3.47-3.35 (m, 1H), 3.26-3.08 (m, 2H), 3.06-3.00 (m, 2H), 2.99-2.94 (m, 4H), 2.32-2.16 (m, 5H), 2.01-1.92 (m, 1H), 1.66 (br s, 6H), 1.48-1.33 (m, 1H), 1.30-0.99 (m, 7H), 1.04 (d, J=6.4 Hz, 3H); LCMS (Method B): Rt 2.46 min, m/z: 690.4 [M+H]⁺; HPLC (Method A): Rt 4.98 min, 98.82%.

Example 65. N-Ethyl-5-fluoro-N-isopropyl-2-((4-(7-(((2S,5R)-5-((2-methoxyphenyl)sulfonamido)tetrahydro-2H-pyran-2-yl)methyl)-2,7-diazaspiro[3.5]nonan-2-yl)pyrimidin-5-yl)oxy)benzamide

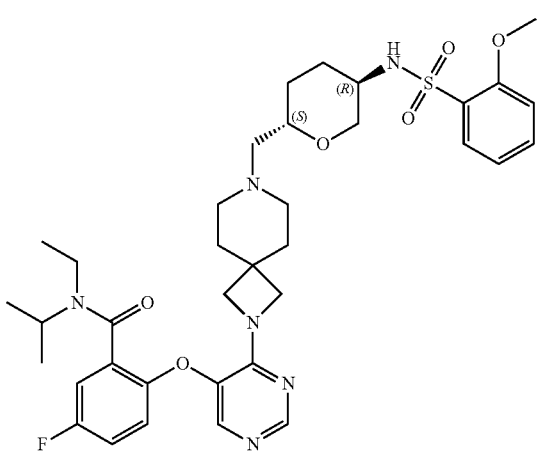

This compound was synthesized following the general procedure described for the synthesis of Example 85, except that 4 equivalents of Et₃N and 1.5 equivalents of 2-methoxybenzenesulfonyl chloride were used, and DMF:THF (1:1) was used as the solvent. The crude was purified by Prep-HPLC (Method A). Yield: 15%; ¹H NMR (400 MHz, DMSO-d₆) δ 8.28-8.23 (m, 1H), 7.75 (dd, J=1.8, 7.8 Hz, 1H), 7.72-7.65 (m, 1H), 7.64-7.58 (m, 1H), 7.35 (d, J=7.4 Hz, 1H), 7.32-7.19 (m, 3H), 7.11-7.00 (m, 2H), 3.91 (s, 3H), 3.88-3.79 (m, 2H), 3.78-3.69 (m, 3H), 3.57-3.50 (m, 11H), 3.44-3.36 (m, 1H), 3.27-3.09 (m, 2H), 3.04-2.92 (m, 2H), 2.31-2.16 (m, 5H), 2.16-2.09 (m, 1H), 1.64-1.63 (m, 6H), 1.45-1.34 (m, 1H), 1.24-1.05 (m, 7H), 1.05-0.96 (m, 3H); LCMS (Method C): Rt 1.93 min, m/z: 711.3 [M+H]⁺; HPLC (Method A): Rt 5.58 min, 97.49%.

Example 66. N-Ethyl-5-fluoro-N-isopropyl-2-((4-(7-(((2S,5R)-5-((3-methoxyphenyl)sulfonamido)tetrahydro-2H-pyran-2-yl)methyl)-2,7-diazaspiro[3.5]nonan-2-yl)pyrimidin-5-yl)oxy)benzamide

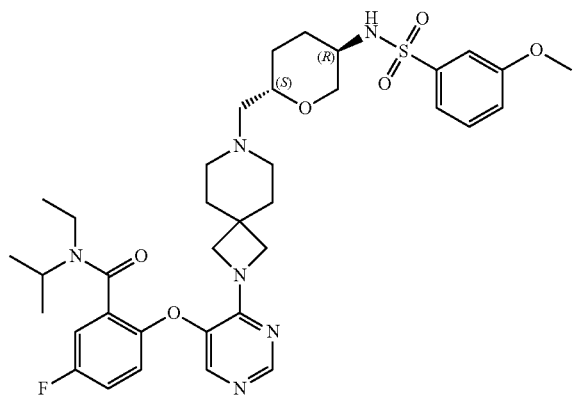

This compound was synthesized following the general procedure described for the synthesis of Example 85, except that 1.5 equivalents of 3-methoxybenzenesulfonyl chloride was used. The crude was purified by Prep-HPLC (Method B).

Yield: 21.74%;

¹H NMR (400 MHz, DMSO-d₆) δ 8.27-8.23 (m, 1H), 7.76 (d, J=6.5 Hz, 1H), 7.73-7.66 (m, 1H), 7.55-7.48 (m, 1H), 7.42-7.37 (m, 1H), 7.34-7.19 (m, 4H), 7.09-6.99 (m, 1H), 3.83 (s, 3H), 3.80-3.70 (m, 5H), 3.62-3.55 (m, 1H), 3.42-3.37 (m, 1H), 3.30-3.09 (m, 2H), 3.00-2.89 (m, 2H), 2.24-2.14 (m, 5H), 1.71-1.53 (m, 7H), 1.39-1.25 (m, 1H), 1.24-1.06 (m, 7H), 1.03 (d, J=6.4 Hz, 3H); LCMS (Method A): Rt 1.90 min, m/z: 711.4 [M+H]⁺; HPLC (Method A): Rt 5.71 min, 97.62%.

Example 67. N-Ethyl-5-fluoro-N-isopropyl-2-((4-(7-(((2S,5R)-5-((tetrahydro-2H-pyran)-4-sulfonamido)tetrahydro-2H-pyran-2-yl)methyl)-2,7-diazaspiro[3.5]nonan-2-yl)pyrimidin-5-yl)oxy)benzamide

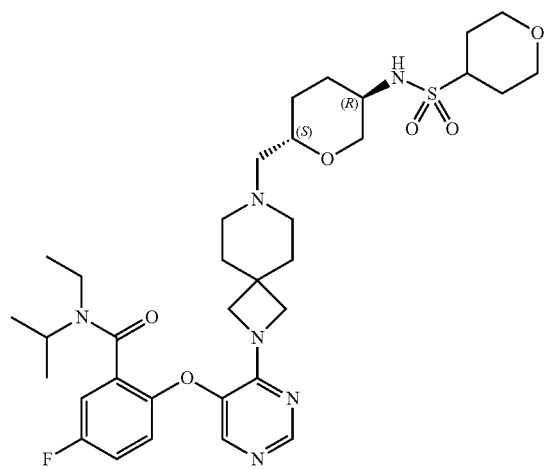

This compound was synthesized following the general procedure described for the synthesis of Example 85, except that 4 equivalents of Et₃N was used. The crude was purified by Prep-HPLC (Method B). Yield: 8.99%; ¹H NMR (400 MHz, DMSO-d₆) δ 8.27-8.25 (m, 1H), 7.74-7.65 (m, 1H), 7.34-7.21 (m, 2H), 7.17 (d, J=7.8 Hz, 11H), 7.09-6.99 (m, 1H), 3.92-3.70 (m, 8H), 3.46-3.37 (m, 1H), 3.30-3.20 (m, 2H), 3.16-2.96 (m, 3H), 2.33-2.12 (m, 6H), 2.00-1.90 (m, 1H), 1.89-1.78 (m, 2H), 1.73-1.62 (m, 6H), 1.61-1.51 (m, 2H), 1.48-1.35 (m, 1H), 1.32-1.16 (m, 3H), 1.14-0.99 (m, 5H), 1.03 (d, J=6.4 Hz, 3H); LCMS (Method A): Rt 2.05 min, m/z: 689.9 [M+H]⁺; HPLC (Method A): Rt 4.83 min, 95.39%.

Example 68. N-Ethyl-5-fluoro-N-isopropyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide

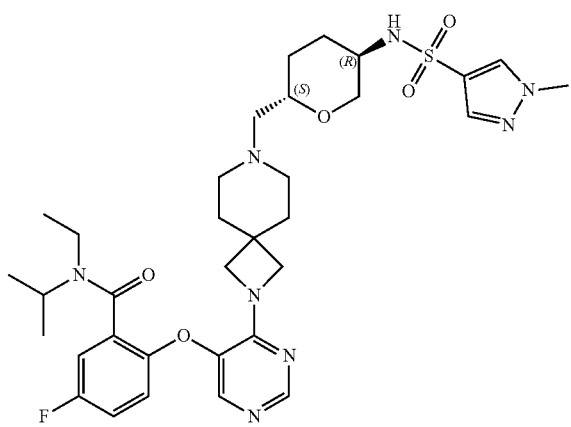

This compound was synthesized following the general procedure described for the synthesis of Example 85. The crude was purified by Prep-HPLC (Method A). Yield: 20%; ¹H NMR (400 MHz, DMSO-d₆) δ 8.29-8.19 (m, 3H), 7.75-7.65 (m, 2H), 7.33-7.22 (m, 2H), 7.09-7.00 (m, 1H), 3.89 (s. 3H), 3.87-3.65 (m, 7H), 3.24-3.11 (m, 3H), 3.02-2.92 (m, 2H), 2.32-2.13 (m, 5H), 1.74-1.57 (m, 6H), 1.40-1.28 (m, 1H), 1.26-0.99 (m, 7H), 1.03 (d, J=6.4 Hz, 3H); LCMS (Method B): Rt 1.06 min, m/z: 685.2 [M+H]⁺; HPLC (Method A): Rt 4.81 min, 98.89%.

Example 69. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide

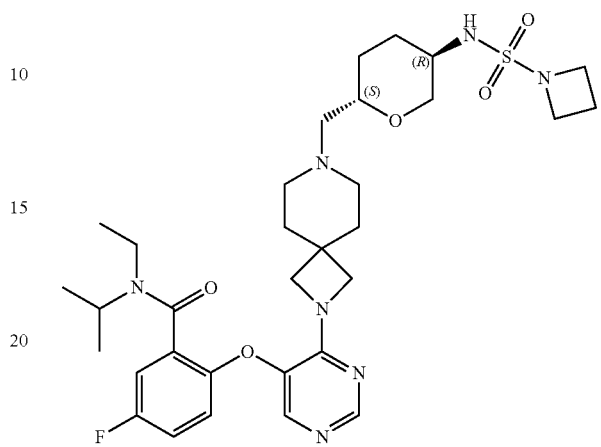

This compound was synthesized following the general procedure described for the synthesis of Example 85. The crude was purified by Prep-HPLC (Method B). Yield: 13.27%; ¹H NMR (400 MHz, DMSO-d₆) δ 8.27-8.26 (m, 1H), 7.76-7.65 (m, 1H), 7.35-7.18 (m, 3H), 7.11-6.98 (m, 1H), 3.86-3.80 (m, 3H), 3.81-3.72 (m, 3H), 3.67 (t, J=7.6 Hz, 4H), 3.64-3.63 (m, 1H), 3.41-3.37 (m, 1H), 3.25-3.23 (m, 1H), 3.16-2.95 (m, 3H), 2.31-2.16 (m, 5H), 2.10 (quin, J=7.6 Hz, 2H), 2.01-1.91 (m, 1H), 1.67 (br s, 5H), 1.45-1.31 (m, 1H), 1.29-0.99 (m, 7H), 1.04 (d, J=6.4 Hz, 3H); LCMS (Method B): Rt 1.91 min, m/z: 600.4 [M+H]⁺; HPLC (Method A): Rt 5.07 min, 98.96%.

Example 70. 2-((4-(7-(((2S,5R)-5-((3,3-Difluoroazetidine)-1-sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide

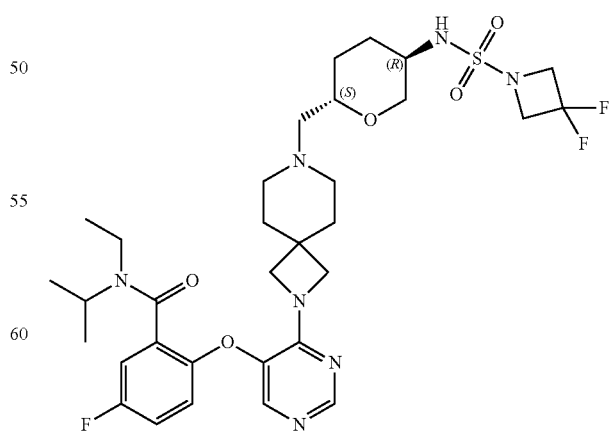

This compound was synthesized following the general procedure described for the synthesis of Example 85. The crude was purified by Prep-HPLC (Method C). Yield: 13.44%; ¹H NMR (400 MHz, DMSO-d₆) δ 8.30-8.23 (m, 1H), 7.78-7.65 (m, 2H), 7.35-7.20 (m, 2H), 7.12-7.00 (m, 1H), 4.19 (t, J=12.8 Hz, 4H), 3.91-3.81 (m, 3H), 3.81-3.70 (m, 3H), 3.44-3.38 (m, 1H), 3.32-3.06 (m, 3H), 3.04-2.97 (m, 1H), 2.32-2.15 (m, 5H), 2.03-1.91 (m, 1H), 1.73-1.61 (m, 5H), 1.46-1.33 (m, 1H), 1.32-1.14 (m, 3H), 1.14-0.99 (m, 5H), 1.04 (d, J=6.4 Hz, 3H); LCMS (Method B): Rt 1.33 min, m/z: 696.4 [M+H]⁺; HPLC (Method A): Rt 5.49 min, 97.24%.

Example 71. N-Ethyl-5-fluoro-N-isopropyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)benzamide

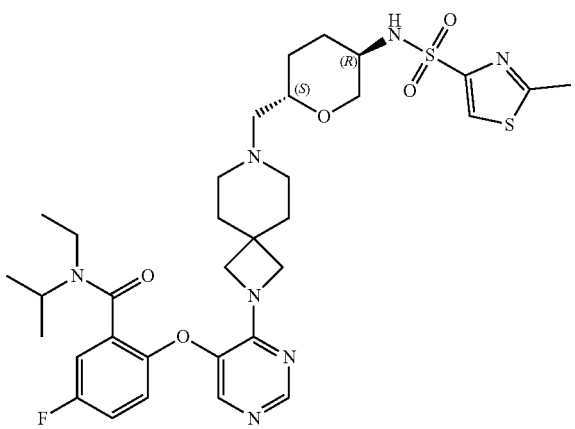

This compound was synthesized following the general procedure described for the synthesis of Example 85. The crude was purified by Prep-HPLC (Method J). Yield: 37.7%; ¹H NMR (400 MHz, DMSO-d₆) δ 8.29-8.24 (m, 1H), 8.17 (s, 1H), 7.93 (d, J=7.5 Hz, 1H), 7.73-7.66 (m, 1H), 7.33-7.21 (m, 2H), 7.09-7.00 (m, 1H), 3.91-3.81 (m, 2H), 3.80-3.69 (m, 3H), 3.66-3.59 (m, 1H), 3.39-3.38 (m, 1H), 3.27-3.05 (m, 3H), 3.02-2.93 (m, 1H), 2.71 (s, 3H), 2.27-2.15 (m, 5H), 1.75-1.73 (m, 1H), 1.69-1.58 (m, 6H), 1.44-1.30 (m, 1H), 1.24-1.14 (m, 2H), 1.13-1.06 (m, 5H), 1.04 (d, J=6.4 Hz, 3H) LCMS (Method B): Rt 1.25 min, m/z: 702.2 [M+H]⁺; HPLC (Method A): Rt 5.14 min, 96.26%.

Example 72. N-Ethyl-5-fluoro-N-isopropyl-2-((4-(7-(((2S,5R)-5-((2-methyloxazole)-5-sulfonamido)tetrahydro-2H-pyran-2-yl)methyl)-2,7-diazaspiro[3.5]nonan-2-yl)pyrimidin-5-yl)oxy)benzamide

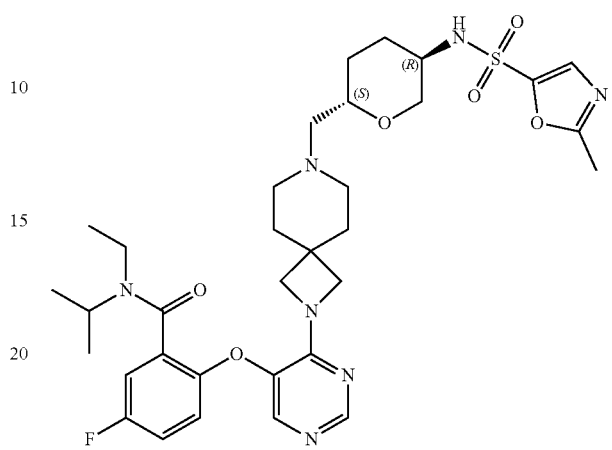

This compound was synthesized following the general procedure described for the synthesis of example 85, except that 4 equivalents of Et₃N and 1.1 equivalents of 2-methyloxazole-5-sulfonyl chloride were used. The crude was purified by Prep-HPLC (Method E). Yield: 33.6%; ¹H NMR (400 MHz, DMSO-d₆) δ 8.31-8.24 (m, 1H), 8.22 (s, 1H), 7.72-7.65 (m, 2H), 7.34-7.21 (m, 2H), 7.10-6.98 (m, 1H), 3.94-3.81 (m, 3H), 3.80-3.71 (m, 4H), 3.71-3.62 (m, 2H), 3.46-3.34 (m, 1H), 3.33-3.25 (m, 1H), 3.25-3.17 (m, 1H), 3.16-2.98 (m, 3H), 2.34-2.17 (m, 5H), 1.84-1.72 (m, 1H), 1.66 (br s, 5H), 1.47-1.33 (m, 1H), 1.26-1.15 (m, 2H), 1.13-1.06 (m, 5H), 1.03 (d, J=6.8 Hz, 3H); LCMS (Method C): Rt 1.63 min, m/z: 686.1 [M+H]⁺; HPLC (Method F): Rt 5.08 min, 99.74%.

Example 73. N-Ethyl-5-fluoro-N-isopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide

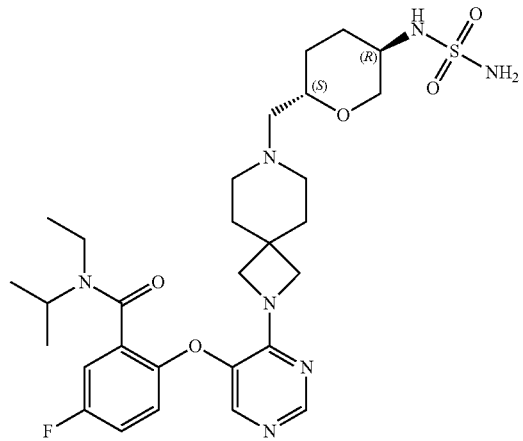

This compound was synthesized following the general procedure described for the synthesis of Example 85, except that 2 equivalents of sulfamoyl chloride and 5 equivalents of Et₃N were used. The crude was purified by Prep-HPLC (Method B). Yield: 2.15%; ¹H NMR (400 MHz, DMSO-d₆) δ 8.32-8.22 (m, 1H), 7.78-7.62 (m, 1H), 7.35-7.20 (m, 2H), 7.12-6.98 (m, 1H), 6.65-6.47 (m, 3H), 3.95-3.82 (m, 3H), 3.81-3.69 (m, 4H), 3.30-3.27 (m, 1H), 3.25-3.17 (m, 1H), 3.17-3.03 (m, 2H), 3.03-2.91 (m, 1H), 2.32-2.15 (m, 5H), 2.04-1.93 (m, 1H), 1.67-2.66 (m, 5H), 1.42-1.29 (m, 1H), 1.27-1.14 (m, 2H), 1.13-1.07 (m, 5H), 1.03 (d, J=6.8 Hz, 3H); LCMS (Method A): Rt 1.61 min, m/z: 620.2 [M+H]⁺; HPLC (Method A): Rt 4.44 min, 96.08%.

Example 74. N-Ethyl-5-fluoro-N-isopropyl-2-((4-(7-(((2S,5R)-5-((1-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy) benzamide Example 75. N-Ethyl-5-fluoro-N-isopropyl-2-((4-(7-(((2S,5R)-5-((4-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy) benzamide

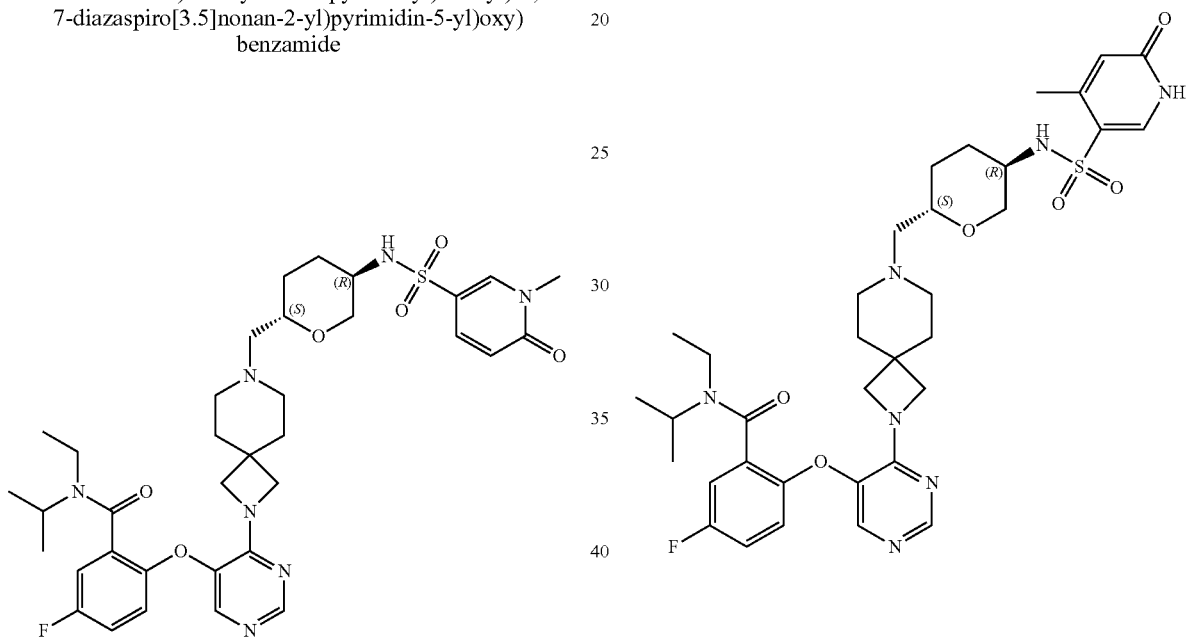

This compound was synthesized following the general procedure described for the synthesis of Example 85, except that 2 equivalents of 1-methyl-6-oxo-1,6-dihydropyridine-3-sulfonyl chloride and 6 equivalents of Et₃N were used. The crude was purified by Prep-HPLC (Method B). Yield: 4.97%; ¹H NMR (400 MHz, DMSO-d₆) δ 8.31 (d, J=2.8 Hz, 1H), 8.28-8.22 (m, 1H), 7.76-7.65 (m, 2H), 7.62 (dd, J=2.8, 9.5 Hz, 1H), 7.34-7.19 (m, 2H), 7.10-6.96 (m, 1H), 6.53 (d, J=9.6 Hz, 1H), 3.96-3.81 (m, 2H), 3.80-3.65 (m, 4H), 3.49 (s, 3H), 3.44-3.37 (m, 1H), 3.25-3.09 (m, 2H), 3.05-2.88 (m, 2H), 2.32-2.20 (m, 4H), 2.20-2.12 (m, 1H), 1.80-1.60 (m, 6H), 1.44-1.29 (m, 1H), 1.26-1.13 (m, 3H), 1.12-1.06 (m, 5H), 1.03 (d, J=6.4 Hz, 3H); LCMS (Method E): Rt 1.54 min, m/z: 712.5 [M+H]⁺; HPLC (Method A): Rt 4.61 min, 98.87%.

This compound was synthesized following the general procedure described for the synthesis of Example 85, except that 1.1 equivalents of 4-methyl-6-oxo-1,6-dihydropyridine-3-sulfonyl chloride and 5 equivalents of Et₃N were used. The crude was purified by Prep-HPLC (Method I). Yield: 14.32%; ¹H NMR (400 MHz, DMSO-d₆) δ 11.94 (br s, 1H), 8.29-8.22 (m, 1H), 7.82 (s, 1H), 7.77-7.64 (m, 2H), 7.35-7.19 (m, 2H), 7.09-6.98 (m, 1H), 6.29 (d, J=0.9 Hz, 11H), 3.93-3.69 (m, 5H), 3.68-3.61 (m, 1H), 3.23-3.07 (m, 1H), 3.06-2.83 (m, 2H), 2.35 (s, 3H), 2.31-2.11 (m, 6H), 1.80-1.54 (m, 7H), 1.47-1.32 (m, 1H), 1.27-1.13 (m, 3H), 1.13-1.06 (m, 5H), 1.03 (d, J=6.4 Hz, 3H); LCMS (Method E): Rt 1.62 min, m/z: 712.3 [M+H]⁺; HPLC (Method A): Rt 4.46 min, 99.98%.

Example 76. N-Ethyl-5-fluoro-N-isopropyl-2-((4-(7-(((2S,5R)-5-((N-methylsulfamoyl)amino)tetrahydro-2H-pyran-2-yl)methyl)-2,7-diazaspiro[3.5]nonan-2-yl)pyrimidin-5-yl)oxy)benzamide

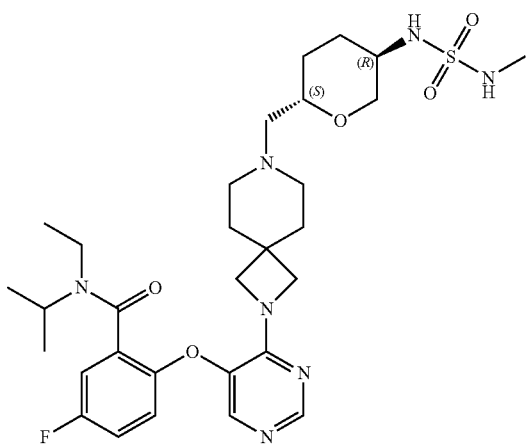

This compound was synthesized following the general procedure described for the synthesis of Example 85, except that 1.2 equivalents of methylsulfamoyl chloride was used. The crude was purified by Prep-HPLC (Method A). Yield: 31.7%; $^1$H NMR (400 MHz, DMSO-d$_6$) δ 8.30-8.23 (m, 1H), 7.74-7.65 (m, 1H), 7.34-7.20 (m, 2H), 7.10-6.99 (m, 1H), 6.90 (d, J=7.1 Hz, 1H), 6.68 (q, J=5.1 Hz, 1H), 3.92-3.82 (m, 3H), 3.81-3.69 (m, 3H), 3.46-3.39 (m, 1H), 3.30-3.09 (m, 2H), 3.05-2.92 (m, 2H), 2.43 (d, J=5.1 Hz, 3H), 2.34-2.15 (m, 5H), 2.00-1.89 (m, 1H), 1.66 (br s, 6H), 1.45-1.31 (m, 1H), 1.29-1.14 (m, 2H), 1.13-1.07 (m, 5H), 1.04 (d, J=6.8 Hz, 3H); LCMS (Method B): Rt 1.10 min, m/z: 634.2 [M+H]$^+$; HPLC (Method A): Rt 4.69 min, 98.18%.

Example 77. 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N,N-diisopropylbenzamide

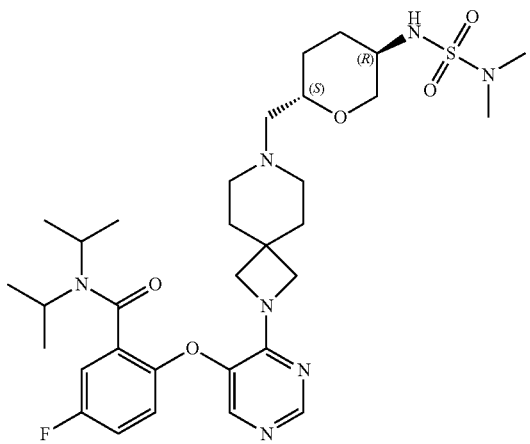

This compound was synthesized following the general procedure described for the synthesis of Example 85, except that 4 equivalents of Et$_3$N and 1.5 equivalents of dimethylsulfamoyl chloride were used. The crude was purified by Prep-HPLC (Method A). Yield: 9.89%; $^1$H NMR (400 MHz, DMSO-d$_6$) δ 8.26 (s, 1H), 7.71 (s, 1H), 7.26-7.18 (m, 3H), 7.08-7.01 (m, 1H), 3.95-3.77 (m, 5H), 3.74-3.63 (m, 1H), 3.59-3.46 (m, 1H), 3.32-2.27 (m, 1H), 3.10-2.95 (m, 2H), 2.64 (s, 6H), 2.32-2.11 (m, 6H), 2.02-1.89 (m, 1H), 1.66 (br s, 5H), 1.44 (d, J=6.8 Hz, 3H), 1.43-1.37 (m, 1H), 1.35 (d, J=6.8 Hz, 3H), 1.28-1.18 (m, 1H), 1.09 (d, J=6.6 Hz, 3H), 0.99 (d, J=6.6 Hz, 3H); LCMS (Method C): Rt 1.51 min, m/z: 662.4 [M+H]$^+$; HPLC (Method A): Rt 5.39 min, 98.39%.

Example 78. 5-Fluoro-N,N-diisopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)benzamide

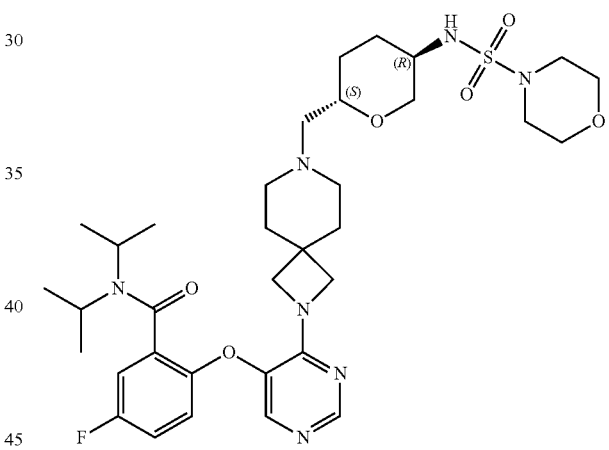

This compound was synthesized following the general procedure described for the synthesis of Example 85, except that 4 equivalents of Et$_3$N was used. The crude was purified by Prep-HPLC (Method B). Yield: 21.84%; $^1$H NMR (400 MHz, DMSO-d$_6$) δ 8.26 (s, 1H), 7.72 (s, 1H), 7.39 (d, J=7.5 Hz, 1H), 7.26-7.19 (m, 2H), 7.08-7.01 (m, 1H), 3.94-3.83 (m, 3H), 3.82-3.75 (m, 2H), 3.73-3.60 (m, 5H), 3.58-3.48 (m, 1H), 3.10-2.94 (m, 7H), 2.32-2.17 (m, 5H), 2.01-1.92 (m, 1H), 1.73-1.61 (m, 6H), 1.44 (d, J=6.6 Hz, 3H), 1.42-1.37 (m, 1H), 1.35 (d, J=6.8 Hz, 3H), 1.30-1.17 (m, 1H), 1.09 (d, J=6.6 Hz, 3H), 1.00 (d, J=6.5 Hz, 3H); LCMS (Method A): Rt 1.97 min, m/z: 704.4 [M+H]$^+$; HPLC (Method A): Rt 5.30 min, 99.69%.

Example 79. 5-Fluoro-N,N-diisopropyl-2-((4-(7-(((2S,5R)-5-((tetrahydro-2H-pyran)-4-sulfonamido)tetrahydro-2H-pyran-2-yl)methyl)-2,7-diazaspiro[3.5]nonan-2-yl)pyrimidin-5-yl)oxy)benzamide

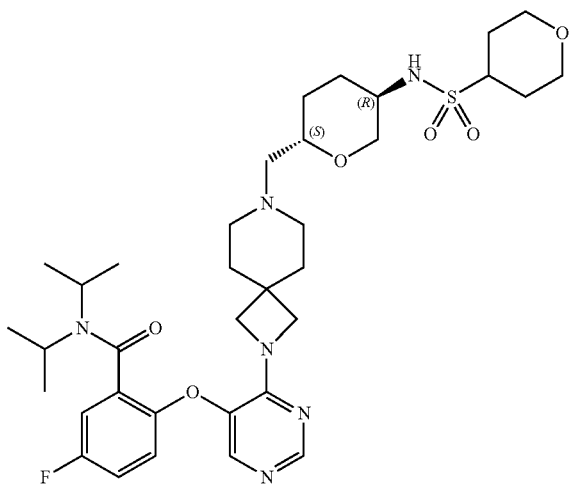

This compound was synthesized following the general procedure described for the synthesis of Example 85, except that 4 equivalents of Et₃N was used. The crude was purified by Prep-HPLC (Method B). Yield: 7.61%; ¹H NMR (400 MHz, DMSO-d₆) δ 8.26 (s, 1H), 7.72 (s, 1H), 7.28-7.20 (m, 2H), 7.17 (d, J=7.8 Hz, 1H), 7.06-7.01 (m, 1H), 4.02-3.74 (m, 7H), 3.73-3.62 (m, 1H), 3.60-3.56 (m, 1H), 3.27-3.17 (m, 1H), 3.17-3.05 (m, 2H), 3.05-2.96 (m, 1H), 2.33-2.14 (m, 6H), 2.01-1.89 (m, 1H), 1.89-1.82 (m, 2H), 1.74-1.49 (m, 8H), 1.44 (d, J=6.6 Hz, 3H), 1.42-1.37 (m, 1H), 1.35 (d, J=6.6 Hz, 3H), 1.31-1.17 (m, 2H), 1.09 (d, J=6.6 Hz, 3H), 1.00 (d, J=6.6 Hz, 3H); LCMS (Method A): Rt 1.91 min, m/z: (703.3) [M+H]⁺; HPLC (Method A): Rt 5.17 min, 97.49% (Max).

Example 80. 5-Fluoro-N,N-diisopropyl-2-((4-(7-(((2S,5R)-5-((2-methyloxazole)-5-sulfonamido)tetrahydro-2H-pyran-2-yl)methyl)-2,7-diazaspiro[3.5]nonan-2-yl)pyrimidin-5-yl)oxy)benzamide

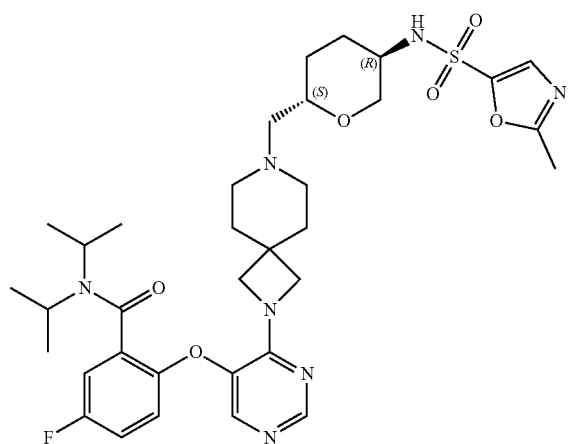

This compound was synthesized following the general procedure described for the synthesis of Example 85, except that 5 equivalents of Et₃N and 1.1 equivalents of 2-methyloxazole-5-sulfonyl chloride were used. The crude was purified by Prep-HPLC (Method B). Yield: 33.8%; ¹H NMR (400 MHz, DMSO-d₆) δ 8.39 (br s, 1H), 8.26 (s, 1H), 7.71 (s, 1H), 7.65 (s, 1H), 7.26-7.19 (m, 2H), 7.07-7.01 (m, 1H), 3.94-3.74 (m, 4H), 3.73-3.63 (m, 2H), 3.59-3.47 (m, 1H), 3.42-3.35 (m, 1H), 3.30-3.19 (m, 1H), 3.13-2.98 (m, 2H), 2.58-2.52 (m, 2H), 2.32-2.14 (m, 6H), 1.83-1.72 (m, 1H), 1.61-1.69 (m, 5H), 1.44 (d, J=6.8 Hz, 3H), 1.43-1.37 (m, 1H), 1.34 (d, J=6.8 Hz, 3H), 1.29-1.12 (m, 1H), 1.09 (d, J=6.6 Hz, 3H), 0.99 (d, J=6.6 Hz, 3H); LCMS (Method C): Rt 1.72 min, m/z: (700.1) [M+H]⁺; HPLC (Method A): Rt 5.41 min, 99.94%.

Example 81. 5-Fluoro-N,N-diisopropyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)benzamide

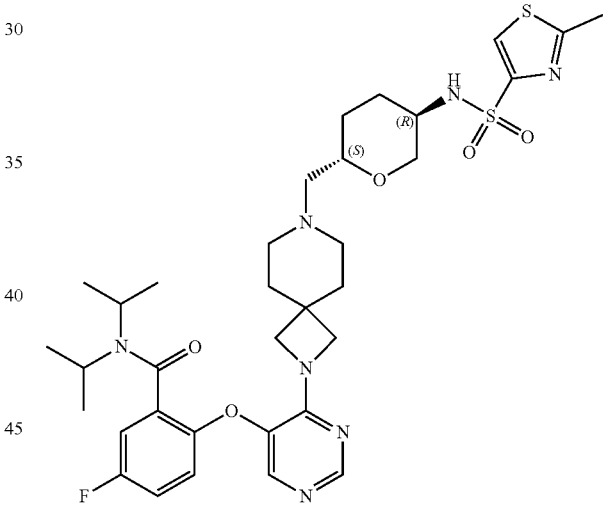

This compound was synthesized following the general procedure described for the synthesis of Example 85. The crude was purified by Prep-HPLC (Method A). Yield: 30.9%; ¹H NMR (400 MHz, DMSO-d₆) δ 8.26 (s, 1H), 8.17 (s, 1H), 7.93 (br d, J=7.3 Hz, 1H), 7.71 (s, 1H), 7.26-7.19 (m, 2H), 7.07-7.00 (m, 1H), 3.93-3.75 (m, 4H), 3.73-3.59 (m, 2H), 3.57-3.47 (m, 1H), 3.31-3.19 (m, 2H), 3.16-3.04 (m, 1H), 3.02-2.94 (m, 1H), 2.71 (s, 3H), 2.31-2.12 (m, 5H), 1.78-1.69 (m, 1H), 1.68-1.58 (m, 5H), 1.44 (d, J=6.8 Hz, 3H), 1.43-1.35 (m, 1H), 1.34 (d, J=6.8 Hz, 3H), 1.21-1.11 (m, 1H), 1.09 (d, J=6.5 Hz, 3H), 0.99 (d, J=6.6 Hz, 3H); LCMS (Method B): Rt 1.40 min, m/z: 716.3 [M+H]⁺; HPLC (Method B): Rt 5.53 min, 99.90%.

Example 82. 2-((4-(7-(((2S,5R)-5-((5-Chloro-1-methyl-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

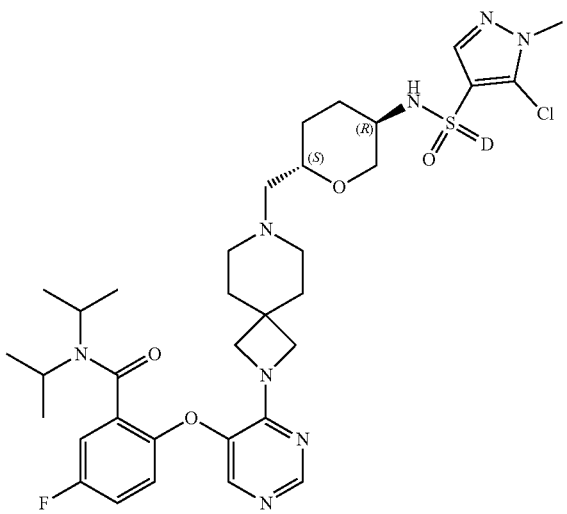

This compound was synthesized following the general procedure described for the synthesis of Example 85. The crude was purified by Prep-HPLC (Method K). Yield: 25.9%; $^1$H NMR (400 MHz, DMSO-d$_6$) δ 8.26 (s, 1H), 7.90 (d, J=6.8 Hz, 1H), 7.86 (m, 1H), 7.71 (s, 1H), 7.27-7.17 (m, 2H), 7.05-7.02 (m, 1H), 3.86 (s, 3H), 3.80-3.75 (m, 4H), 3.73-3.65 (m, 2H), 3.59-3.47 (m, 1H), 3.25-3.31 (m, 2H), 3.08-2.97 (m, 2H), 2.31-2.12 (m, 5H), 1.82-1.70 (m, 1H), 1.70-1.58 (m, 5H), 1.43 (d, J=6.8 Hz, 3H), 1.42-1.36 (m, 1H), 1.34 (d, J=6.8 Hz, 3H), 1.23-1.13 (m, 1H), 1.09 (d, J=6.6 Hz, 3H), 0.99 (d, J=6.6 Hz, 3H); LCMS (Method B): Rt 1.41 min, m/z: 733.2 [M+H]$^+$; HPLC (Method A): Rt 5.51 min, 98.26%.

Example 83. 2-((4-(7-(((2S,5R)-5-((1-Cyclopropyl-1H-pyrazole)-4-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

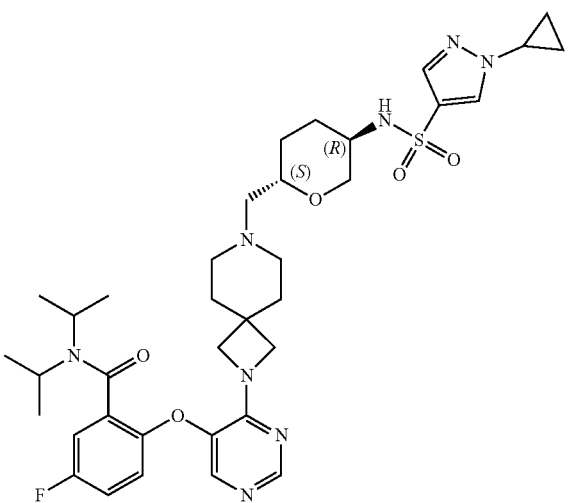

This compound was synthesized following the general procedure described for the synthesis of Example 85. The crude was purified by Prep-HPLC (Method B). Yield: 29.2%; $^1$H NMR (400 MHz, DMSO-d$_6$) δ 8.34 (s, 1H), 8.26 (s, 1H), 7.73-7.69 (m, 2H), 7.51 (d, J=6.4 Hz, 1H), 7.27-7.18 (m, 2H), 7.05-7.02 (m, 1H), 3.93-3.75 (m, 5H), 3.73-3.65 (m, 2H), 3.60-3.46 (m, 2H), 3.03-2.93 (m, 2H), 2.32-2.12 (m, 5H), 1.77-1.57 (m, 6H), 1.44 (d, J=6.6 Hz, 3H), 1.40-1.28 (m, 4H), 1.25-1.03 (m, 7H), 1.02-0.96 (m, 5H);

LCMS (Method C): Rt 1.77 min, m/z: 725.1 [M+H]$^+$;

HPLC (Method A): Rt 5.48 min, 96.42%.

Example 84. 5-Fluoro-N,N-diisopropyl-2-((4-(7-(((2S,5R)-5-((2-methylthiazole)-5-sulfonamido)tetrahydro-2H-pyran-2-yl)methyl)-2,7-diazaspiro[3.5]nonan-2-yl)pyrimidin-5-yl)oxy)benzamide

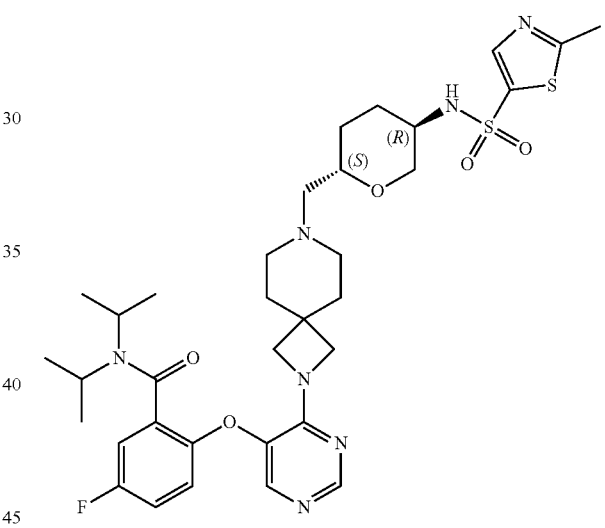

This compound was synthesized following the general procedure described for the synthesis of Example 85. The crude was purified by Prep-HPLC (Method B).

Yield: 31.7%;

$^1$H NMR (400 MHz, DMSO-d$_6$) δ 8.26 (s, 1H), 8.18 (br s, 1H), 8.06 (s, 1H), 7.71 (s, 11H), 7.26-7.19 (m, 2H), 7.06-7.01 (m, 1H), 3.95-3.74 (m, 4H), 3.68 (m, 2H), 3.58-3.45 (m, 1H), 3.29-3.24 (m, 1H), 3.11-2.97 (m, 2H), 2.73 (s, 3H), 2.30-2.14 (m, 4H), 2.20-2.13 (m, 1H), 1.80-1.57 (m, 6H), 1.44 (d, J=6.6 Hz, 3H), 1.43-1.36 (m, 1H), 1.34 (d, J=6.8 Hz, 4H), 1.26-1.13 (m, 1H), 1.09 (d, J=6.6 Hz, 3H), 0.99 (d, J=6.5 Hz, 3H);

LCMS (Method B): Rt 1.35 min, m/z: 716.3 [M+H]$^+$;

HPLC (Method G): Rt 3.73 min, 98.696%.

Example 86. 5-Fluoro-N,N-diisopropyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide

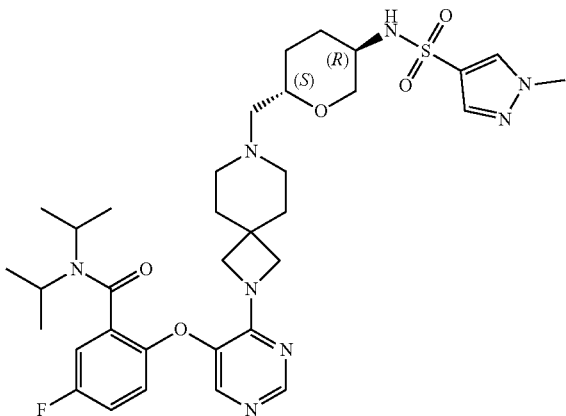

This compound was synthesized following the general procedure described for the synthesis of Example 85, except that 1.1 equivalents of 1-methyl-1H-pyrazole-4-sulfonyl chloride was used. The crude was purified by Prep-HPLC (Method G).

Yield: 31.7%;

$^1$H NMR (400 MHz, DMSO-d$_6$) δ 8.26 (s, 1H), 8.24 (s, 1H), 7.74-7.70 (m, 2H), 7.52 (br d, J=5.3 Hz, 1H), 7.26-7.19 (m, 2H), 7.06-7.01 (m, 1H), 3.89 (s, 3H), 3.88-3.83 (m, 3H), 3.82-3.76 (m, 1H), 3.73-3.64 (m, 2H), 3.57-3.47 (m, 1H), 3.31-3.22 (m, 2H), 3.03-2.90 (m, 2H), 2.32-2.20 (m, 4H), 2.19-2.12 (m, 1H), 1.78-1.70 (m, 1H), 1.69-1.57 (m, 5H), 1.44 (d, J=6.6 Hz, 3H), 1.43-1.20 (m, 1H), 1.34 (d, J=6.8 Hz, 3H), 1.22-1.12 (m, 1H), 1.09 (d, J=6.6 Hz, 3H), 0.99 (d, J=6.6 Hz, 3H);

LCMS (Method C): Rt 1.88 min, m/z: 699.6 [M+H]$^+$;
HPLC (Method G): Rt 2.93 min, 99.76%.

Example 87. 5-Fluoro-N,N-diisopropyl-2-((4-(7-(((2S,5R)-5-((1-methyl-1H-pyrazole)-3-sulfonamido)tetrahydro-2H-pyran-2-yl)methyl)-2,7-diazaspiro[3.5]nonan-2-yl)pyrimidin-5-yl)oxy)benzamide

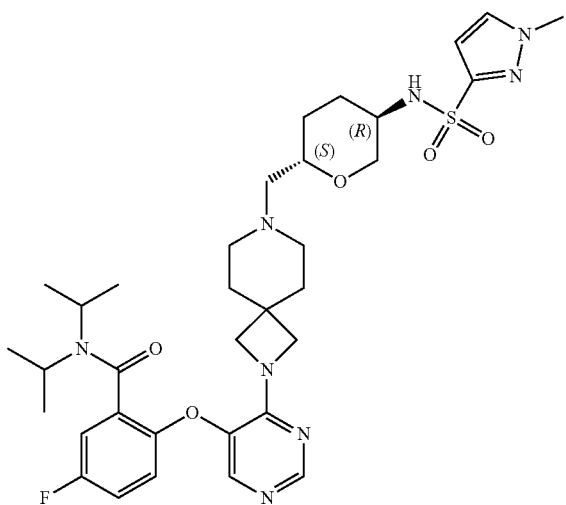

This compound was synthesized following the general procedure described for the synthesis of Example 85. The crude was purified by Prep-HPLC (Method B).

Yield: 37.6%;

$^1$H NMR (400 MHz, DMSO-d$_6$) δ 8.26 (s, 1H), 7.87 (d, J=2.3 Hz, 1H), 7.77 (d, J=7.1 Hz, 1H), 7.71 (d, J=1.0 Hz, 1H), 7.26-7.20 (m, 2H), 7.07-7.01 (m, 1H), 6.61 (d, J=2.3 Hz, 1H), 3.92 (s, 3H), 3.80-3.74 (m, 3H), 3.73-3.63 (m, 2H), 3.58-3.47 (m, 1H), 3.32-3.22 (m, 2H), 3.13-2.92 (m, 2H), 2.46-2.36 (m, 1H), 2.32-2.19 (m, 4H), 2.18-2.11 (m, 1H), 1.74-1.81 (m, 1H), 1.71-1.54 (m, 5H), 1.43 (d, J=6.8 Hz, 3H), 1.36-1.28 (m, 1H), 1.32 (d, J=6.8 Hz, 3H), 1.21-1.11 (m, 1H), 1.09 (d, J=6.6 Hz, 3H), 0.98 (d, J=6.6 Hz, 3H);

LCMS (Method B): Rt 1.28 min, m/z: 699.4 [M+H]$^+$;
HPLC (Method A): Rt 3.52 min, 99.83%.

Example 88. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

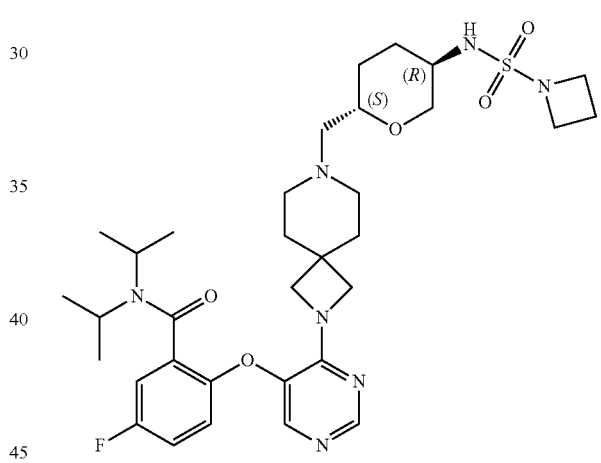

This compound was synthesized following the general procedure described for the synthesis of Example 85, except that 1.1 equivalents of azetidine-1-sulfonyl chloride was used, and DMF:THF (1:1) was used as the solvent. The crude was purified by Prep-HPLC (Method A).

Yield: 28.9%;

$^1$H NMR (400 MHz, DMSO-d$_6$) δ 8.26 (s, 1H), 7.72 (s, 1H), 7.28-7.18 (m, 3H), 7.06-7.04 (m, 1H), 3.95-3.77 (m, 5H), 3.73-3.64 (m, 5H), 3.60-3.53 (m, 1H), 3.10-2.95 (m, 2H), 2.32-2.17 (m, 6H), 2.12-2.08 (m, 3H), 2.05-1.96 m, 1H), 1.67 (br s, 5H), 1.44 (d, J=6.8 Hz, 3H), 1.42-1.36 (m, 1H) 1.34 (d, J=6.4 Hz, 3H), 1.30-1.18 (m, 1H), 1.09 (d, J=6.5 Hz, 3H), 1.00 (d, J=6.5 Hz, 3H);

LCMS (Method C): Rt 1.75 min, m/z: 674.3 [M+H]$^+$;
HPLC (Method A): Rt 5.42 min, 98.79%.

Example 89. 5-Fluoro-N,N-diisopropyl-2-((4-(7-(((2S,5R)-5-((N-isopropyl-N-methylsulfamoyl)amino)tetrahydro-2H-pyran-2-yl)methyl)-2,7-diazaspiro[3.5]nonan-2-yl)pyrimidin-5-yl)oxy)benzamide

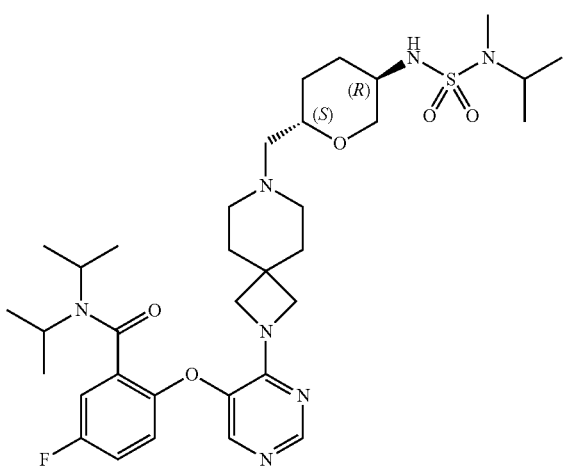

This compound was synthesized following the general procedure described for the synthesis of Example 85, except that 8 equivalents of Et₃N was used. The crude was purified by Prep-HPLC (Method B).
Yield: 9.95%;
¹H NMR (400 MHz, DMSO-d₆) δ 8.28 (s, 1H), 7.74 (s, 1H), 7.30-7.19 (m, 3H), 7.08 (br s, 1H), 4.06-3.77 (m, 7H), 3.73-3.65 (m, 1H), 3.57-3.48 (m, 1H), 3.21-3.10 (m, 2H), 3.02-2.90 (m, 2H), 2.56 (s, 3H), 2.32 (s, 1H), 2.10-1.81 (m, 4H), 1.68-1.65 (m, 1H), 1.45-1.43 (m, 4H), 1.37-1.25 (m, 4H), 1.12-1.07 (m, 10H), 0.97 (d, J=6.8 Hz, 6H);
LCMS (Method B): Rt 1.42 min, m/z: 690.6 [M+H]⁺;
HPLC (Method A): Rt 5.94 min, 99.55%.

Example 90. 5-Fluoro-N,N-diisopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide

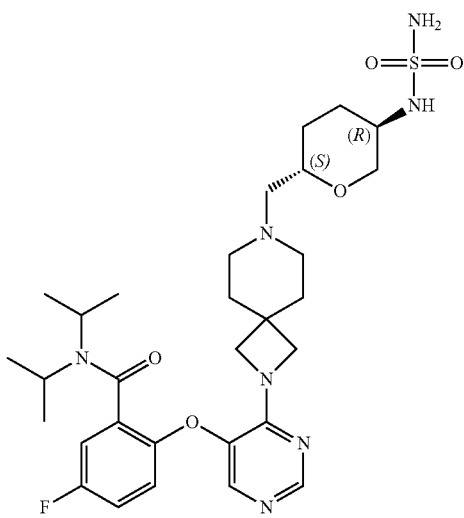

This compound was synthesized following the general procedure described for the synthesis of Example 85, except that 4 equivalents of Et₃N was used. The crude was purified by Prep-HPLC (Method B).
Yield: 6.11%;
¹H NMR (400 MHz, DMSO-d₆) δ 8.26 (s, 1H), 7.71 (s, 1H), 7.26-7.20 (m, 2H), 7.07-7.02 (m, 1H), 6.58 (d, J=7.63 Hz, 1H), 6.54 (s, 2H), 3.86-3.94 (m, 3H), 3.83-3.78 (m, 2H), 3.74-3.62 (m, 1H), 3.59-3.46 (m, 1H), 3.17-3.05 (m, 1H), 3.02-2.93 (m, 1H), 2.31-2.17 (m, 6H), 2.02-1.95 (m, 1H), 1.72-1.63 (m, 6H), 1.44 (d, J=6.75 Hz, 3H), 1.35 (d, J=6.75 Hz, 3H), 1.31-1.19 (m, 2H), 1.09 (d, J=6.63 Hz, 3H), 1.00 (d, J=6.50 Hz, 3H);
LCMS (Method D): Rt 1.59 min, m/z: 634.1 [M+H]⁺;
HPLC (Method A): Rt 4.79 min, 98.30%.

Example 91. 5-Fluoro-N,N-diisopropyl-2-((4-(7-(((2S,5R)-5-((2-methyloxazole)-4-sulfonamido)tetrahydro-2H-pyran-2-yl)methyl)-2,7-diazaspiro[3.5]nonan-2-yl)pyrimidin-5-yl)oxy)benzamide

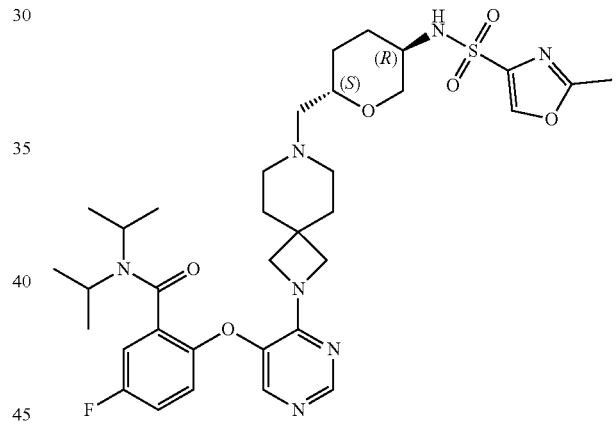

This compound was synthesized by following the general procedure described for the synthesis of Example 85. The crude was purified by prep HPLC (Method F).
Yield: 10.03%;
¹H NMR (400 MHz, DMSO-d₆) δ 8.60 (s, 1H), 8.26 (s, 1H), 8.00 (br d, J=5.1 Hz, 1H), 7.71 (s, 1H), 7.27-7.18 (m, 2H), 7.07-7.00 (m, 1H), 3.95-3.83 (m, 2H), 3.82-3.75 (m, 2H), 3.75-3.64 (m, 2H), 3.57-3.47 (m, 1H), 3.30-3.24 (m, 1H), 3.13-3.04 (m, 1H), 3.03-2.95 (m, 1H), 2.48 (s, 3H), 2.31-2.21 (m, 4H), 2.20-2.13 (m, 1H), 1.86-1.76 (m, 1H), 1.71-1.58 (m, 6H), 1.44 (d, J=6.6 Hz, 3H), 1.41-1.36 (m, 1H), 1.34 (d, J=6.6 Hz, 3H), 1.26-1.14 (m, 1H), 1.09 (d, J=6.6 Hz, 3H), 0.99 (d, J=6.6 Hz, 3H);
LCMS (Method A): Rt 1.81 min, m/z: 700.5 [M+H]⁺;
HPLC (Method A): Rt 5.38 min, 98.92%.

Example 92. 5-Fluoro-N,N-diisopropyl-2-((4-(7-(((2S,5R)-5-((1-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy) benzamide

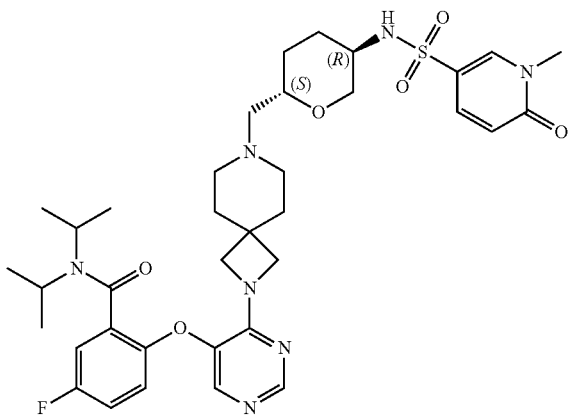

This compound was synthesized by following the general procedure described for the synthesis of Example 85. The crude was purified by prep HPLC (Method A).

Yield: 16.25%;

$^1$H NMR (400 MHz, DMSO-$d_6$) δ 8.31 (d, J=2.6 Hz, 1H), 8.26 (s, 1H), 7.71-7.70 (m, 2H), 7.62 (dd, J=2.8, 9.6 Hz, 1H), 7.27-7.18 (m, 2H), 7.03 (dd, J=4.3, 10.1 Hz, 1H), 6.53 (d, J=9.6 Hz, 1H), 3.96-3.76 (m, 4H), 3.75-3.65 (m, 2H), 3.59-3.52 (m, 1H), 3.49 (s, 3H), 3.32-3.24 (m, 2H), 3.05-2.91 (m, 2H), 2.33-2.20 (m, 4H), 2.19-2.09 (m, 1H), 1.79-1.69 (m, 1H), 1.68-1.56 (m, 5H), 1.44 (d, J=6.6 Hz, 3H), 1.34 (d, J=6.8 Hz, 3H), 1.32-1.26 (m, 1H), 1.24-1.13 (m, 1H), 1.09 (d, J=6.6 Hz, 3H), 0.99 (d, J=6.6 Hz, 3H);

LCMS (Method E): Rt 1.63 min, m/z: 735.0 [M+H]$^+$;
HPLC (Method A): Rt 4.99 min, 99.77%.

Example 93. N-Cyclopropyl-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

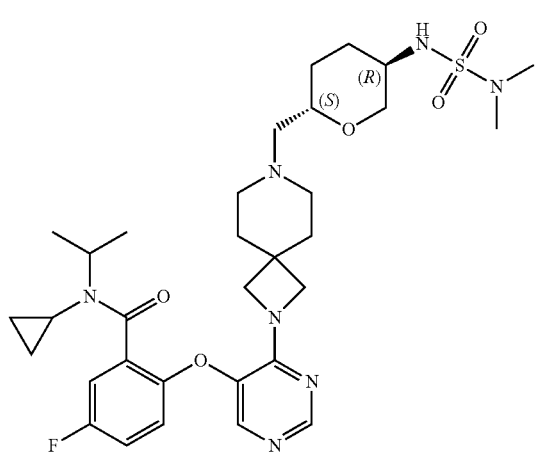

This compound was synthesized following the general procedure described for the synthesis of Example 85, except that 4 equivalents of DBU and 1.5 equivalents of dimethylsulfamoyl chloride were used. The crude was purified by prep HPLC (Method E).

Yield: 13.97%;

$^1$H NMR (400 MHz, DMSO-$d_6$) δ 8.27 (s, 1H), 7.71 (s, 1H), 7.33 (dd, J=8.38, 3.00 Hz, 1H), 7.26-7.19 (m, 2H), 7.01 (dd, J=9.07, 4.44 Hz, 11H), 4.39-4.25 (m, 1H), 3.89-3.73 (m, 6H), 3.07-2.96 (m, 2H), 2.64 (s, 6H), 2.63-2.61 (m, 1H), 2.35-2.17 (m, 6H), 2.02-1.88 (m, 1H), 1.72-1.62 (m, 5H), 1.47-1.13 (m, 8H), 0.52 (br s, 4H);

LCMS (Method C): Rt 1.72 min, m/z: 660.2 [M+H]$^+$;
HPLC (Method A): Rt 5.31 min, 99.57%.

Example 94. N-(2,2-Difluoroethyl)-5-fluoro-N-isopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy) benzamide

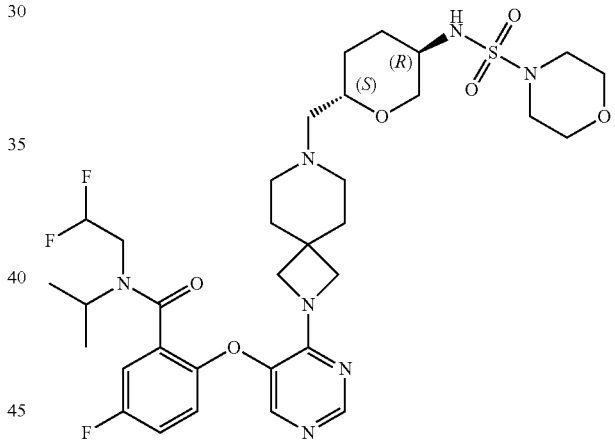

This compound was synthesized following the general procedure described for the synthesis of Example 85, except that 1.3 equivalents of morpholine-4-sulfonyl chloride was used. The crude was purified by Prep-HPLC (Method I).

Yield: 22.37%;

$^1$H NMR (400 MHz, DMSO-$d_6$) δ 8.29 (s, 1H), 7.79-7.71 (m, 1H), 7.42-7.25 (m, 3H), 7.02 (dd, J=4.2, 9.1 Hz, 1H), 6.37-6.04 (m, 1H), 3.90-3.80 (m, 4H), 3.80-3.69 (m, 4H), 3.64-3.62 (m, 5H), 3.03-2.96 (m, Hz, 6H), 2.32-2.17 (m, 5H), 2.01-1.92 (m, 1H), 1.72-1.61 (m, 5H), 1.47-1.34 (m, 1H), 1.29-1.16 (m, 2H), 1.10 (d, J=6.8 Hz, 3H), 1.06 (d, J=6.4 Hz, 3H);

LCMS (Method B): Rt 1.29 min, m/z: 726.2 [M+H]$^+$;
HPLC (Method A): Rt 5.26 min, 99.55%.

Example 95. N-(2,2-Difluoroethyl)-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

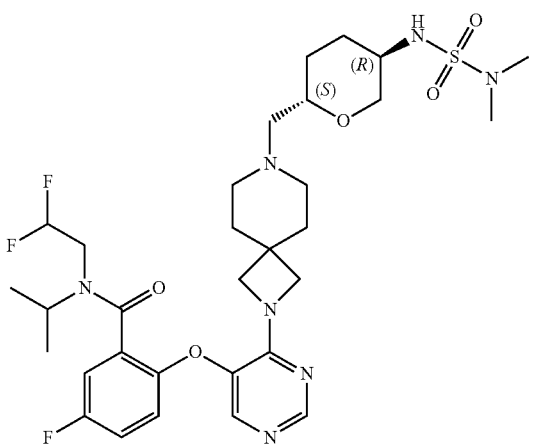

This compound was synthesized following the general procedure described for the synthesis of Example 85, except that 1.3 equivalents of dimethylsulfamoyl chloride was used. The crude was purified by Prep-HPLC (Method B).

Yield: 18.15%;

$^1$H NMR (400 MHz, DMSO-d$_6$) δ 8.29 (s, 1H), 7.77 (s, 1H), 7.38-7.25 (m, 2H), 7.20 (d, J=7.4 Hz, 1H), 7.02 (dd, J=4.4, 9.1 Hz, 1H), 6.37-6.02 (m, 1H), 3.89-3.80 (m, 4H), 3.79-3.65 (m, 4H), 3.30-3.25 (m, 1H), 3.08-2.96 (m, 2H), 2.64 (s, 6H), 2.33-2.16 (m, 5H), 2.01-1.91 (m, 1H), 1.66 (br s, 5H), 1.47-1.33 (m, 1H), 1.28-1.14 (m, 2H), 1.10 (d, J=6.4 Hz, 3H), 1.06 (d, J=6.4 Hz, 3H);

LCMS (Method A): Rt 1.97 min, m/z: 684.4 [M+H]$^+$;

HPLC (Method A): Rt 5.36 min, 97.56%.

Example 96. N-(2,2-Difluoroethyl)-5-fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide

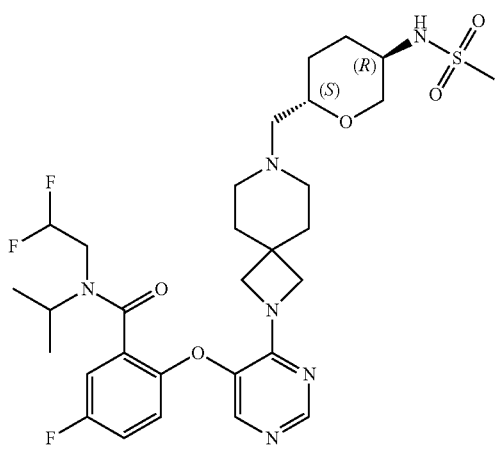

This compound was synthesized following the general procedure described for the synthesis of Example 85, except that 3.5 equivalents of DIPEA and 1.3 equivalents of methanesulfonyl chloride were used, and DCM was used as the solvent. The crude was purified by Prep-HPLC (Method B).

Yield: 42.2%;

$^1$H NMR (400 MHz, DMSO-d$_6$) δ 8.29 (s, 1H), 7.77 (s, 1H), 7.35 (dd, J=3.1, 8.3 Hz, 1H), 7.32-7.24 (m, 1H), 7.08 (d, J=7.4 Hz, 1H), 7.02 (dd, J=4.3, 9.1 Hz, 1H), 6.36-6.03 (m, 1H), 3.90-3.80 (m, 4H), 3.79-3.61 (m, 4H), 3.31-3.23 (m, 1H), 3.20-3.08 (m, 1H), 3.02-2.95 (m, 1H), 2.92 (s, 3H), 2.31-2.16 (m, 5H), 2.03-1.97 (m, 1H), 1.75-1.59 (m, 5H), 1.48-1.32 (m, 1H), 1.31-1.18 (m, 2H), 1.10 (d, J=6.4 Hz, 3H), 1.06 (d, J=6.4 Hz, 3H);

LCMS (Method A): Rt 1.88 min, m/z: 655.3 [M+H]$^+$;

HPLC (Method A): Rt 4.98 min, 99.13%.

Example 97. 2-((4-(7-(((2S,5R)-5-((N,N-Diethylsulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide

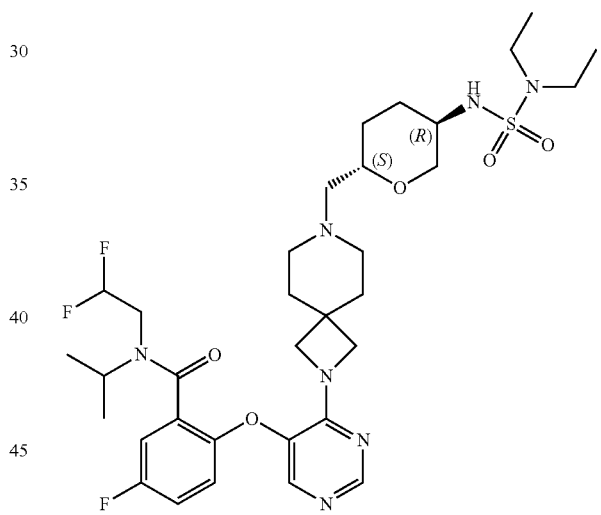

This compound was synthesized following the general procedure described for the synthesis of Example 85, except that 3.5 equivalents of DIPEA and 1.5 equivalents of diethylsulfamoyl chloride were used. The crude was purified by Prep-HPLC (Method A).

Yield: 18.59%;

$^1$H NMR (400 MHz, DMSO-d$_6$) δ 8.29 (s, 1H), 7.77 (s, 1H), 7.38-7.22 (m, 2H), 7.02 (dd, J=4.4, 9.2 Hz, 1H), 6.37-6.04 (m, 1H), 4.27-3.99 (m, 2H), 3.91-3.64 (m, 8H), 3.18-3.07 (m, 4H), 3.03-2.90 (m, 2H), 2.32-2.14 (m, 5H), 1.99-1.86 (m, 1H), 1.73-1.58 (m, 5H), 1.45-1.32 (m, 1H), 1.27-1.14 (m, 2H), 1.13-1.04 (m, 12H);

LCMS (Method C): Rt 1.87 min, m/z: 712.3 [M+H]$^+$;

HPLC (Method A): Rt 5.83 min, 99.92%.

Example 98. N-(2,2-Difluoroethyl)-5-fluoro-N-isopropyl-2-((4-(7-(((2S,5R)-5-((tetrahydro-2H-pyran)-4-sulfonamido)tetrahydro-2H-pyran-2-yl)methyl)-2,7-diazaspiro[3.5]nonan-2-yl)pyrimidin-5-yl)oxy)benzamide

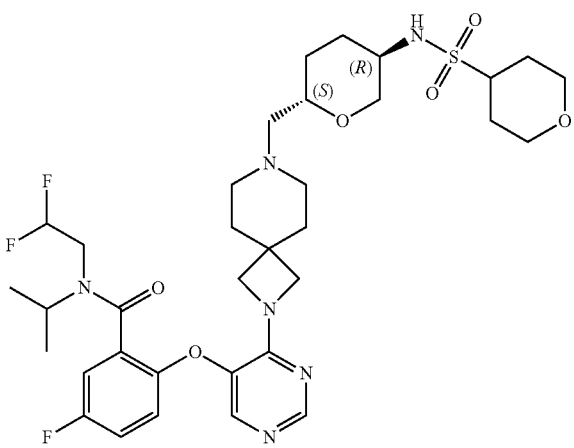

This compound was synthesized following the general procedure described for the synthesis of Example 85, except that 5 equivalents of Et₃N and 1.3 equivalents of tetrahydro-2H-pyran-4-sulfonyl chloride. After 16 h, another equivalent of tetrahydro-2H-pyran-4-sulfonyl chloride was added. The crude was purified by Prep-HPLC (Method B).

Yield: 13.70%;

$^1$H NMR (400 MHz, DMSO-d$_6$) δ 8.29 (s, 1H), 7.77 (s, 1H), 7.35 (dd, J=3.1, 8.3 Hz, H), 7.32-7.26 (m, 1H), 7.20-7.16 (m, 1H), 7.02 (dd, J=4.4, 9.1 Hz, 1H), 6.37-6.03 (m, 1H), 3.98-3.62 (m, 12H), 3.30-3.18 (m, 2H), 3.16-2.94 (m, 2H), 2.32-2.12 (m, 5H), 2.01-1.90 (m, 1H), 1.89-1.78 (m, 2H), 1.73-1.62 (m, 5H), 1.60-1.50 (m, 2H), 1.48-1.35 (m, 1H), 1.33-1.17 (m, 2H), 1.10 (d, J=6.4 Hz, 3H), 1.06 (d, J=6.4 Hz, 3H);

LCMS (Method C): Rt 1.69 min, m/z: 725.2 [M+H]⁺;
HPLC (Method A): Rt 5.10 min, 98.14%.

Example 99. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide

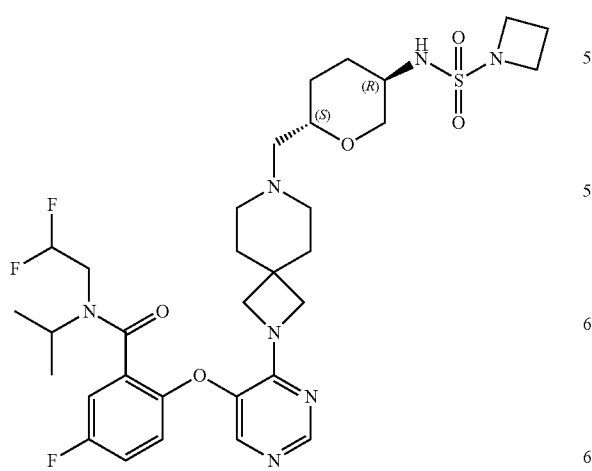

This compound was synthesized following the general procedure described for the synthesis of Example 85. The crude was purified by Prep-HPLC (Method I).

Yield: 23.76%;

$^1$H NMR (400 MHz, DMSO-d$_6$) δ 8.29 (s, 1H), 7.76 (s, 1H), 7.35 (dd, J=3.1, 8.2 Hz, 11H), 7.32-7.25 (m, 1H), 7.21 (d, J=7.8 Hz, 1H), 7.02 (dd, J=4.3, 9.1 Hz, 1H), 6.36-6.03 (m, 1H), 3.88-3.73 (m, 7H), 3.72-3.62 (m, 6H), 3.13-2.95 (m, 2H), 2.32-2.16 (m, 5H), 2.14-2.05 (m, 2H), 2.02-1.91 (m, 1H), 1.66 (br s, 5H), 1.46-1.31 (m, 1H), 1.29-1.17 (m, 2H), 1.10 (d, J=6.4 Hz, 3H), 1.06 (d, J=6.8 Hz, 3H);

LCMS (Method C): Rt 1.76 min, m/z: 696.1 [M+H]⁺;
HPLC (Method A): Rt 5.37 min, 97.72%.

Example 100. N-(2,2-Difluoroethyl)-5-fluoro-N-isopropyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide This compound was synthesized following the general procedure described for the synthesis of Example 85, except that 1.1 equivalents of 1-methyl-1H-pyrazole-4-sulfonyl chloride was used, and DMF:THF (1:1) was used as the solvent. The crude was purified by Prep-HPLC (Method B).

Yield; 30.7%;

$^1$H NMR (400 MHz, DMSO-d$_6$) δ 8.29 (s, 1H), 8.24 (s, 1H), 7.76 (s, 1H), 7.72 (s, 1H), 7.53 (br d, J=5.0 Hz, 1H), 7.41-7.20 (m, 2H), 7.01 (dd, J=4.3, 9.0 Hz, 1H), 6.40-5.93 (m, 1H), 3.89 (s, 3H), 3.86-3.56 (m, 8H), 3.32-3.24 (m, 2H), 3.07-2.88 (m, 2H), 2.36-2.06 (m, 5H), 1.82-1.54 (m, 6H), 1.43-1.28 (m, 1H), 1.26-1.18 (m, 1H), 1.10 (d, J=6.4 Hz, 3H), 1.06 (d, J=6.4 Hz, 3H);

LCMS (Method B): Rt 1.27 min, m/z: 721.0 [M+H]⁺;
HPLC (Method A): Rt 5.16 min, 99.62%.

Example 101. N-(2,2-Difluoroethyl)-5-fluoro-N-isopropyl-2-((4-(7-(((2S,5R)-5-((N-isopropyl-N-methylsulfamoyl)amino)tetrahydro-2H-pyran-2-yl)methyl)-2,7-diazaspiro[3.5]nonan-2-yl)pyrimidin-5-yl)oxy)benzamide

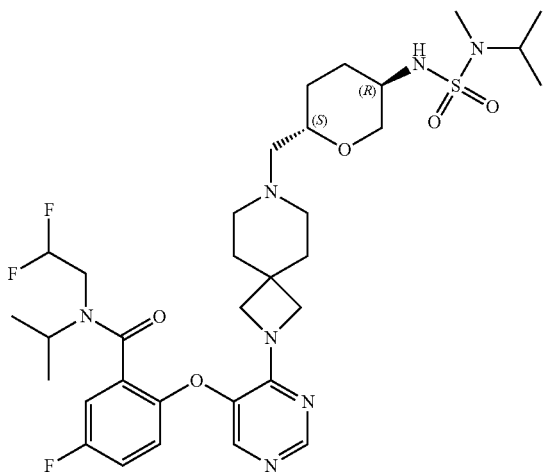

This compound was synthesized following the general procedure described for the synthesis of Example 85, except that 2 equivalents of isopropyl(methyl)sulfamoyl chloride was used. The crude was purified by Prep-HPLC (Method B).

Yield: 15.32%;

¹H NMR (400 MHz, DMSO-d₆) δ 8.29 (s, 1H), 7.77 (s, 1H), 7.40-7.23 (m, 2H), 7.12 (br d, J=7.4 Hz, 1H), 7.02 (dd, J=4.3, 9.0 Hz, 1H), 6.38-6.02 (m, 1H), 4.01-3.89 (m, 1H), 3.88-3.62 (m, 8H), 3.08-2.85 (m, 2H), 2.55 (s, 4H), 2.31-2.23 (m, 4H), 2.22-2.16 (m, 1H), 1.93-190 (m, 1H), 1.65 (br s, 5H), 1.45-1.30 (m, 1H), 1.28-1.15 (m, 2H), 1.11-1.06 (m, 12H);

LCMS (Method C): Rt 1.84 min, m/z: 712.2 [M+H]⁺;
HPLC (Method A): Rt 5.86 min, 98.98%.

Example 102. N-(2,2-Difluoroethyl)-5-fluoro-N-isopropyl-2-((4-(7-(((2S,5R)-5-((N-methylsulfamoyl)amino)tetrahydro-2H-pyran-2-yl)methyl)-2,7-diazaspiro[3.5]nonan-2-yl)pyrimidin-5-yl)oxy)benzamide

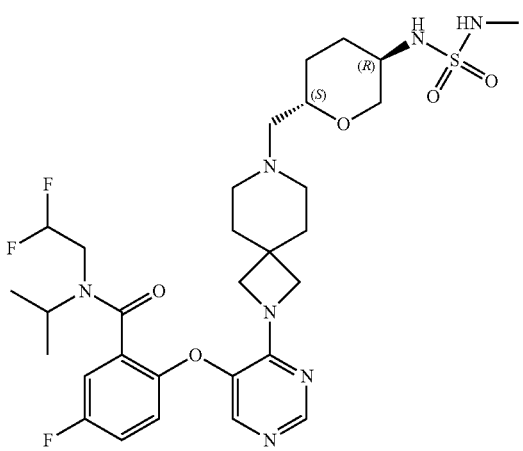

This compound was synthesized following the general procedure described for the synthesis of Example 85, except that 2 equivalents of methylsulfamoyl chloride was used. The crude was purified by prep-HPLC (Method E).

Yield: 14.44%;

¹H NMR (400 MHz, DMSO-d₆) δ 8.29 (s, 1H), 7.77 (s, 11H), 7.39-7.24 (m, 2H), 7.02 (dd, J=4.3, 9.1 Hz, 1H), 6.90 (d, J=7.1 Hz, 1H), 6.68 (q, J=5.1 Hz, 11H), 6.37-6.03 (m, 1H), 3.92-3.64 (m, 8H), 3.31-3.25 (m, 1H), 3.07-2.91 (m, 2H), 2.43 (d, J=5.1 Hz, 3H), 2.31-2.15 (m, 5H), 2.01-1.91 (m, 1H), 1.66 (br s, 5H), 1.46-1.30 (m, 1H), 1.28-1.14 (m, 2H), 1.10 (d, J=6.8 Hz, 3H), 1.06 (d, J=6.4 Hz, 3H);

LCMS (Method C): Rt 1.72 min, m/z: 670.5 [M+H]⁺;
HPLC (Method A): Rt 4.98 min, 98.07%.

Example 103. N-(2,2-Difluoroethyl)-5-fluoro-N-isopropyl-2-((4-(7-(((2S,5R)-5-((1-methyl-1H-pyrazole)-3-sulfonamido)tetrahydro-2H-pyran-2-yl)methyl)-2,7-diazaspiro[3.5]nonan-2-yl)pyrimidin-5-yl)oxy)benzamide

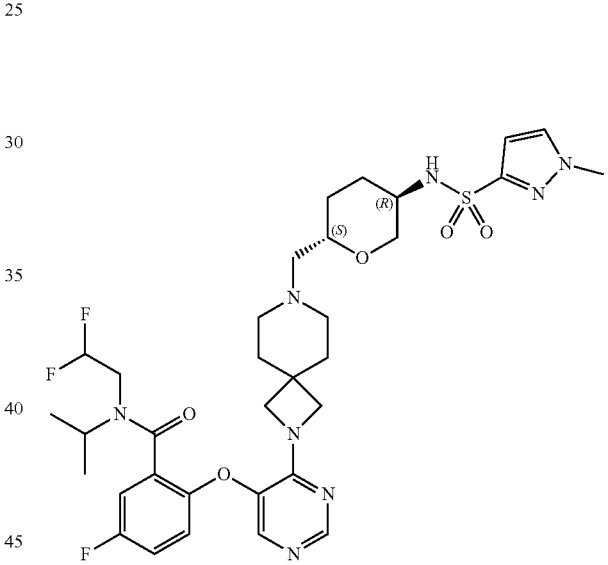

This compound was synthesized following the general procedure described for the synthesis of Example 85, except that 1.5 equivalents of 1-methyl-1H-pyrazole-3-sulfonyl chloride and 3 equivalents of Et₃N were used. The crude was purified by Prep-HPLC (Method F).

Yield: 35.6%;

¹H NMR (400 MHz, DMSO-d₆) δ 8.29 (s, 1H), 7.86 (d, J=2.3 Hz, 11H), 7.82-7.66 (m, 2H), 7.40-7.19 (m, 2H), 7.01 (dd, J=4.3, 9.1 Hz, 1H), 6.60 (d, J=2.4 Hz, 1H), 6.37-6.02 (m, 1H), 3.92 (s, 3H), 3.88-3.61 (m, 8H), 3.31-3.21 (m, 2H), 3.13-2.93 (m, 2H), 2.32-2.11 (m, 5H), 1.64-1.60 (m, 1H), 1.70-1.54 (m, 5H), 1.44-1.29 (m, 1H), 1.23-1.21 (m, 1H), 1.10 (d, J=6.4 Hz, 3H), 1.06 (d, J=6.4 Hz, 3H);

LCMS (Method B): Rt 1.67 min, m/z: 721.4 [M+H]⁺;
HPLC (Method A): Rt 5.15 min, 99.72%.

Example 104. N-(2,2-Difluoroethyl)-2-((4-(7-(((2S, 5R)-5-((1,5-dimethyl-1H-pyrazole)-4-sulfonamido) tetrahydro-2H-pyran-2-yl)methyl)-2,7-diazaspiro [3.5]nonan-2-yl)pyrimidin-5-yl)oxy)-5-fluoro-N-isopropylbenzamide

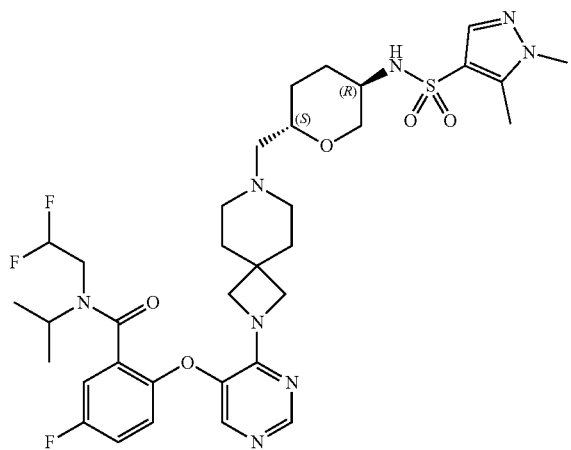

This compound was synthesized following the general procedure described for the synthesis of Example 85, except that 1.5 equivalents of 1,5-dimethyl-1H-pyrazole-4-sulfonyl chloride and 3 equivalents of Et$_3$N were used. The crude was purified by Prep-HPLC (Method A).

Yield: 31.4%;

$^1$H NMR (400 MHz, DMSO-d$_6$) δ 8.29 (s, 1H), 7.76 (s, 1H), 7.63 (s, 1H), 7.53 (br s, 1H), 7.35 (dd, J=3.1, 8.3 Hz, 1H), 7.32-7.24 (m, 1H), 7.01 (dd, J=4.3, 9.1 Hz, 1H), 6.36-6.04 (m, 1H), 3.98-3.54 (m, 9H), 3.77 (s, 3H), 3.31-3.22 (m, 1H), 3.05-2.82 (m, 2H), 2.40 (s, 3H), 2.33-2.10 (m, 5H), 1.77-1.56 (m, 6H), 1.41-1.27 (m, 1H), 1.24-1.22 (m, 1H), 1.10 (d, J=6.4 Hz, 3H), 1.06 (d, J=6.4 Hz, 3H);

LCMS (Method E): Rt 1.67 min, m/z: 735.4 [M+H]$^+$;

HPLC (Method A): Rt 5.23 min, 99.77%.

Example 105. N-(2,2-Difluoroethyl)-2-((4-(7-(((2S, 5R)-5-((1,3-dimethyl-1H-pyrazole)-4-sulfonamido) tetrahydro-2H-pyran-2-yl)methyl)-2,7-diazaspiro [3.5]nonan-2-yl)pyrimidin-5-yl)oxy)-5-fluoro-N-isopropylbenzamide

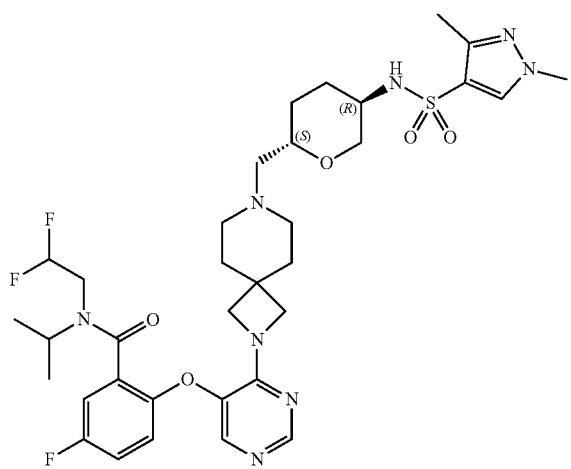

This compound was synthesized following the general procedure described for the synthesis of Example 85, except that 1.5 equivalents of 1,3-dimethyl-1H-pyrazole-4-sulfonyl chloride and 3 equivalents of Et$_3$N were used. The crude was purified by Prep-HPLC (Method A).

Yield: 15.2%;

$^1$H NMR (400 MHz, DMSO-d$_6$) δ 8.29 (s, 1H), 8.11 (s, 1H), 7.77 (s, 1H), 7.54 (br d, J=7.1 Hz, 1H), 7.35 (dd, J=3.1, 8.3 Hz, 1H), 7.31-7.25 (m, 1H), 7.02 (dd, J=4.3, 9.1 Hz, 1H), 6.36-6.02 (m, 1H), 3.91-3.58 (m, 9H), 3.80 (s, 3H), 3.30-3.22 (m, 1H), 3.07-2.83 (m, 2H), 2.32-2.03 (m, 5H), 2.25 (s, 3H), 1.78-1.54 (m, 6H), 1.45-1.29 (m, 1H), 1.24-1.22 (m, 1H), 1.10 (d, J=6.4 Hz, 3H), 1.05 (d, J=6.4 Hz, 3H);

LCMS (Method E): Rt 1.67 min, m/z: 735.4 [M+H]$^+$;

HPLC (Method A): Rt 5.20 min, 95.86%.

Example 106. N-(2,2-Difluoroethyl)-2-((4-(7-(((2S, 5R)-5-((1-ethyl-1H-pyrazole)-4-sulfonamido)tetra-hydro-2H-pyran-2-yl)methyl)-2,7-diazaspiro[3.5] nonan-2-yl)pyrimidin-5-yl)oxy)-5-fluoro-N-isopropylbenzamide

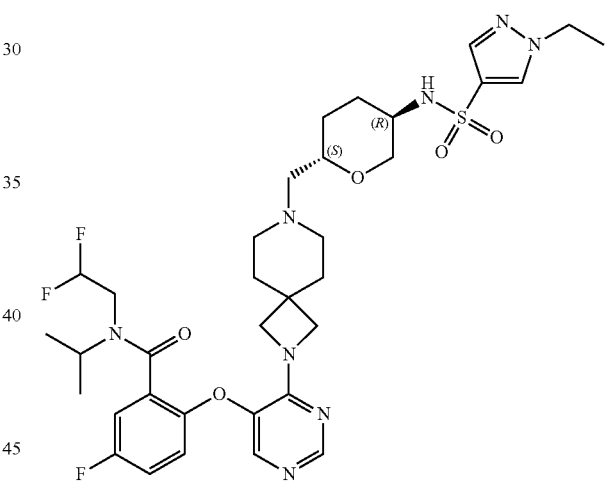

This compound was synthesized following the general procedure described for the synthesis of Example 85, except that 3 equivalents of 1-ethyl-1H-pyrazole-4-sulfonyl chloride was used. The crude was purified by Prep-HPLC (Method E).

Yield: 18.36%;

$^1$H NMR (400 MHz, DMSO-d$_6$) δ 8.32-8.25 (m, 2H), 7.76 (s, 1H), 7.73 (m, 1H), 7.51 (br d, J=6.4 Hz, 1H), 7.36-7.20 (m, 2H), 7.01 (dd, J=4.3, 9.1 Hz, 1H), 6.36-6.03 (m, 1H), 4.19 (q, J=7.3 Hz, 2H), 3.90-3.63 (m, 8H), 3.31-3.18 (m, 2H), 3.03-2.91 (m, 2H), 2.32-2.11 (m, 5H), 1.79-1.56 (m, 6H), 1.38 (t, J=7.3 Hz, 3H), 1.36-1.14 (m, 2H), 1.10 (d, J=6.4 Hz, 3H), 1.06 (d, J=6.4 Hz, 3H);

LCMS (Method E): Rt 1.72 min, m/z: (735.4) [M+H]$^+$;

HPLC (Method A): Rt 5.38 min, 98.55%.

Example 107. 2-((4-(7-(((2S,5R)-5-((N,N-Dimethyl-sulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-(2,2,2-trifluoroethyl)benzamide

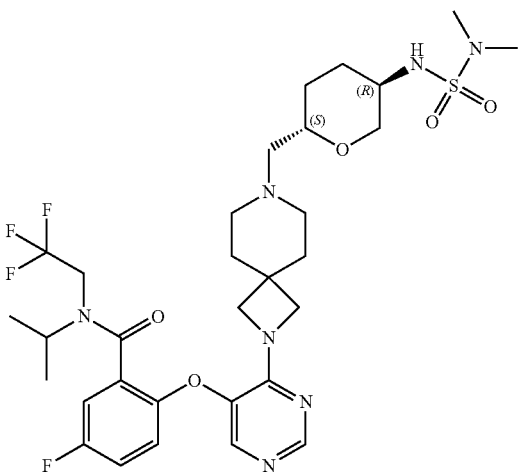

This compound was synthesized following the general procedure described for the synthesis of Example 85, except that 1.2 equivalents of dimethylsulfamoyl chloride was used. The crude was purified by Prep-HPLC (Method L).

Yield: 12.72%;

$^1$H NMR (400 MHz, DMSO-$d_6$) δ 8.29 (s, 1H), 7.77 (s, 11H), 7.38-7.27 (m, 2H), 7.20 (br d, J=7.3 Hz, 11H), 7.02 (dd, J=4.3, 9.0 Hz, 11H), 4.42-4.09 (m, 2H), 4.08-3.57 (m, 7H), 3.11-2.94 (m, 2H), 2.64 (s, 6H), 2.32-2.15 (m, 5H), 2.02-1.88 (m, 1H), 1.79-1.55 (m, 5H), 1.49-1.34 (m, 1H), 1.34-1.17 (m, 2H), 1.18-0.97 (m, 6H);

LCMS (Method B): Rt 1.30 min, m/z: 702.4 [M+H]$^+$;

HPLC (Method A): Rt 5.52 min, 98.70%.

Example 108. 5-Fluoro-N-isopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)-N-(2,2,2-trifluoroethyl)benzamide

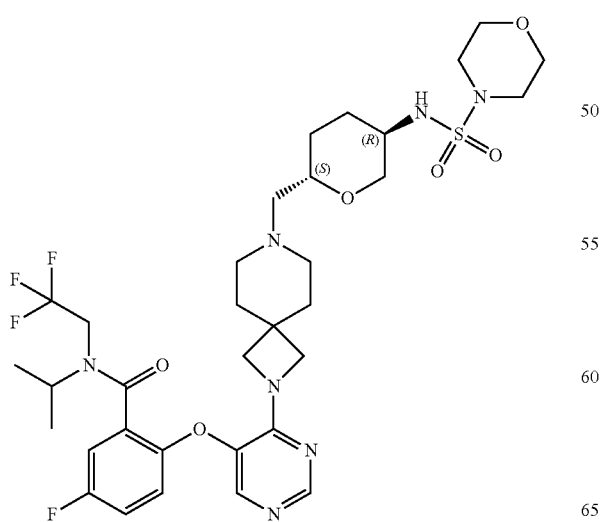

This compound was synthesized following the general procedure described for the synthesis of Example 85, except that 1.2 equivalents of morpholine-4-sulfonyl chloride was used. The crude was purified by Prep-HPLC (Method B).

Yield: 14.98%;

$^1$H NMR (400 MHz, DMSO-$d_6$) δ 8.29 (s, 1H), 7.77 (s, 1H), 7.39 (br d, J=7.5 Hz, 1H), 7.36-7.26 (m, 2H), 7.02 (dd, J=4.3, 9.0 Hz, 1H), 4.40-4.11 (m, 2H), 4.05-3.68 (m, 6H), 3.66-3.59 (m, 4H), 3.11-2.89 (m, 7H), 2.32-2.12 (m, 5H), 2.02-1.90 (m, 1H), 1.76-1.57 (m, 5H), 1.48-1.34 (m, 1H), 1.33-1.16 (m, 2H), 1.15-1.04 (m, 6H);

LCMS (Method B): Rt 1.29 min, m/z: 744.3 [M+H]$^+$;

HPLC (Method A): Rt 5.41 min, 99.96%.

Example 109. 5-Fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)-N-(2,2,2-trifluoroethyl)benzamide This compound was synthesized following the general procedure described for the synthesis of Example 85, except that 1.2 equivalents of propane-2-sulfonyl chloride was used. The crude was purified by Prep-HPLC (Method B).

Yield: 2.91%;

$^1$H NMR (400 MHz, DMSO-$d_6$) δ 8.29 (s, 1H), 7.77 (s, 1H), 7.37-7.25 (m, 2H), 7.08-6.97 (m, 2H), 4.39-4.08 (m, 2H), 3.98-3.89 (m, 1H), 3.87-3.68 (m, 5H), 3.29-3.22 (m, 1H), 3.21-2.95 (m, 3H), 2.31-2.14 (m, 5H), 2.00-1.87 (m, 1H), 1.75-1.57 (m, 5H), 1.50-1.34 (m, 1H), 1.32-1.23 (m, 2H), 1.21 (d, J=6.8 Hz, 6H), 1.16-1.03 (m, 6H);

LCMS (Method B): Rt 1.35 min, m/z: 701.2 [M+H]$^+$;

HPLC (Method A): Rt 5.54 min, 97.02%.

Example 110. N-(3,3-Difluorocyclobutyl)-5-fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)benzamide

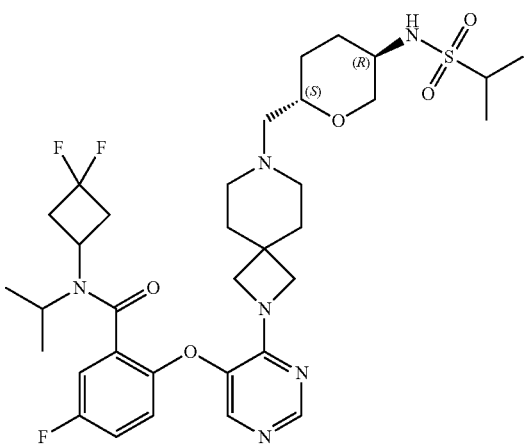

This compound was synthesized following the general procedure described for the synthesis of Example 85, except that 1.5 equivalents of propane-2-sulfonyl chloride and 5 equivalents of Et₃N were used. The crude was purified by Prep-HPLC (Method B).

Yield: 3.60%;

¹H NMR (400 MHz, DMSO-d₆) δ 8.28 (s, 1H), 7.78 (s, 1H), 7.35 (dd, J=2.9, 8.1 Hz, 1H), 7.28-7.26 (m, 1H), 7.03 (dd, J=4.3, 9.0 Hz, 1H), 6.07 (br s, 1H), 3.96-3.82 (m, 3H), 3.81-3.66 (m, 5H), 3.19-3.13 (m, 1H), 3.05-2.98 (m, 1H), 2.81-2.71 (m, 1H), 2.32-2.16 (m, 5H), 1.99-1.89 (m, 1H), 1.67 (br s, 5H), 1.50-1.29 (m, 6H), 1.24 (br s, 1H), 1.21 (d, J=6.8 Hz, 6H), 1.10 (d, J=6.4 Hz, 3H), 1.02 (d, J=6.1 Hz, 3H);

LCMS (Method A): Rt 2.05 min, m/z: 709.4 [M+H]⁺;

HPLC (Method A): Rt 5.69 min, 95.00%.

Example 111. 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-N-(3,3-difluorocyclobutyl)-5-fluoro-N-isopropylbenzamide

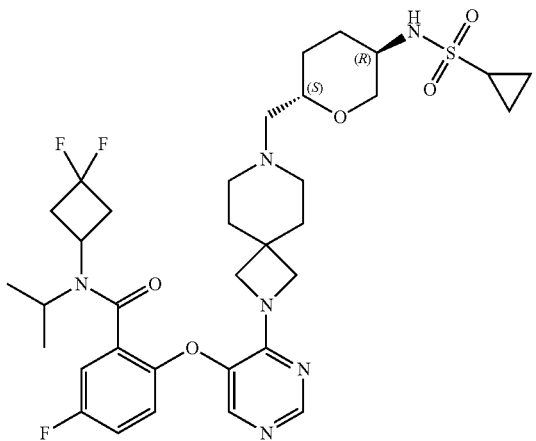

This compound was synthesized following the general procedure described for the synthesis of Example 85, except that 1.5 equivalents of cyclopropanesulfonyl chloride and 5 equivalents of Et₃N were used. The crude was purified by Prep-HPLC (Method A).

Yield: 29.5%;

¹H NMR (400 MHz, DMSO-d₆) δ 8.28 (s, 1H), 7.78 (s, 1H), 7.35 (dd, J=2.8, 8.1 Hz, 1H), 7.26 (dt, J=3.0, 8.6 Hz, 1H), 7.12 (d, J=7.8 Hz, 1H), 7.03 (dd, J=4.2, 9.1 Hz, 1H), 4.16-3.43 (m, 10H), 3.22-3.09 (m, 1H), 3.07-2.97 (m, 1H), 2.85-2.68 (m, 2H), 2.62-2.55 (m, 1H), 2.32-2.14 (m, 5H), 2.05-1.95 (m, 1H), 1.67 (br s, 5H), 1.50-1.17 (m, 3H), 1.10 (d, J=5.9 Hz, 3H), 1.02 (d, J=5.9 Hz, 3H), 0.98-0.83 (m, 4H);

LCMS (Method A): Rt 2.01 min, m/z: 707.3 [M+H]⁺;

HPLC (Method A): Rt 5.61 min, 99.51%.

Example 112. N-(3,3-Difluorocyclobutyl)-5-fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)benzamide

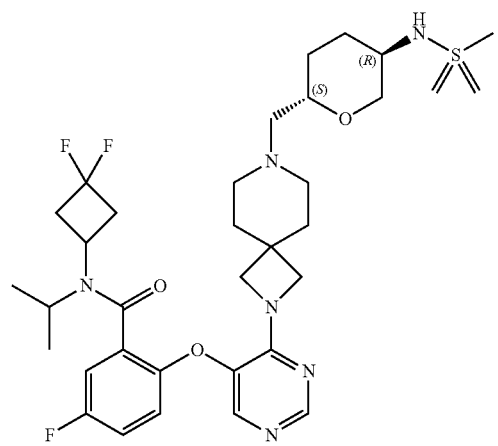

This compound was synthesized following the general procedure described for the synthesis of Example 85, except that 1.5 equivalents of methanesulfonyl chloride and 5 equivalents of Et₃N were used. The crude was purified by Prep-HPLC (Method B).

Yield: 23.34%;

¹H NMR (400 MHz, DMSO-d₆) δ 8.28 (s, 1H), 7.78 (s, 1H), 7.35 (dd, J=3.0, 8.3 Hz, 1H), 7.26 (dt, J=3.1, 8.6 Hz, 1H), 7.08 (d, J=7.3 Hz, 1H), 7.03 (dd, J=4.3, 9.1 Hz, 1H), 3.98-3.63 (m, 10H), 3.62-3.45 (m, 1H), 3.21-3.09 (m, 1H), 2.99 (t, J=10.7 Hz, 1H), 2.92 (s, 3H), 2.83-2.71 (m, 1H), 2.32-2.14 (m, 5H), 2.04-1.91 (m, 1H), 1.74-1.61 (m, 5H), 1.50-1.19 (m, 3H), 1.09 (d, J=6.0 Hz, 3H), 1.02 (d, J=6.4 Hz, 3H).

LCMS (Method A): Rt 1.94 min, m/z: 681.2 [M+H]⁺;

HPLC (Method A): Rt 5.32 min, 99.45%.

Example 113. N-(3,3-Difluorocyclobutyl)-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

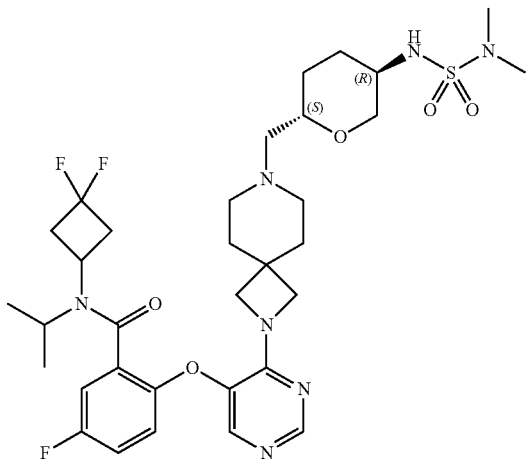

This compound was synthesized following the general procedure described for the synthesis of Example 85, except that 2 equivalents of dimethylsulfamoyl chloride and 5 equivalents of Et₃N were used. The crude was purified by Prep-HPLC (Method B).

Yield: 14.45%;

$^1$H NMR (400 MHz, DMSO-$d_6$) δ 8.28 (s, 1H), 7.78 (s, 1H), 7.35 (dd, J=3.1, 8.2 Hz, 1H), 7.26 (dt, J=3.1, 8.6 Hz, 1H), 7.20 (d, J=7.5 Hz, 1H), 7.03 (dd, J=4.4, 9.0 Hz, 1H), 4.12-3.62 (m, 8H), 3.61-3.43 (m, 1H), 3.31-3.22 (m, 1H), 3.10-2.96 (m, 2H), 2.85-2.69 (m, 2H), 2.64 (s, 6H), 2.32-2.15 (m, 5H), 2.03-1.89 (m, 1H), 1.74-1.60 (m, 5H), 1.50-1.14 (m, 3H), 1.10 (d, J=6.3 Hz, 3H), 1.02 (d, J=6.3 Hz, 3H);

LCMS (Method A): Rt 2.05 min, m/z: 710.3 [M+H]⁺;

HPLC (Method A): Rt 5.69 min, 99.08%.

Example 114. 2-((4-(7-(((2S,5R)-5-((N,N-Diethylsulfamoyl)amino)tetrahydro-2H-pyran-2-yl)methyl)-2,7-diazaspiro[3.5]nonan-2-yl)pyrimidin-5-yl)oxy)-N-(3,3-difluorocyclobutyl)-5-fluoro-N-isopropylbenzamide

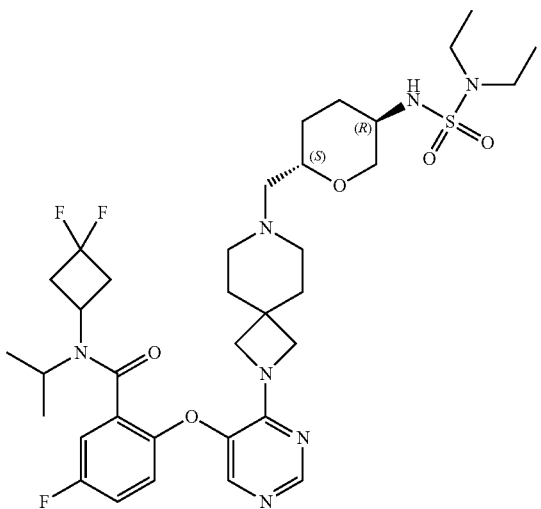

This compound was synthesized following the general procedure described for the synthesis of Example 85, except that 2 equivalents of diethylsulfamoyl chloride and 5 equivalents of Et₃N were used. The crude was purified by Prep-HPLC (Method B).

Yield: 13.52%;

$^1$H NMR (400 MHz, DMSO-$d_6$) δ 8.29 (s, 1H), 7.78 (s, 1H), 7.35 (dd, J=3.1, 8.2 Hz, 1H), 7.26 (dt, J=3.0, 8.6 Hz, 1H), 7.10 (d, J=7.3 Hz, 1H), 7.03 (dd, J=4.3, 9.2 Hz, 1H), 4.00-3.62 (m, 8H), 3.61-3.45 (m, 1H), 3.31-3.22 (m, 1H), 3.13 (q, J=7.3 Hz, 4H), 3.04-2.84 (m, 2H), 2.84-2.69 (m, 2H), 2.32-2.12 (m, 5H), 1.99-1.87 (m, 1H), 1.79-1.58 (m, 5H), 1.50-1.27 (m, 2H), 1.26-1.15 (m, 1H), 1.14-0.95 (m, 12H);

LCMS (Method A): Rt 2.05 min, m/z: 738.4 [M+H]⁺;

HPLC (Method A): Rt 6.15 min, 98.78%.

Example 115. N-(3,3-Difluorocyclobutyl)-5-fluoro-N-isopropyl-2-((4-(7-(((2S,5R)-5-(oxetane-3-sulfonamido)tetrahydro-2H-pyran-2-yl)methyl)-2,7-diazaspiro[3.5]nonan-2-yl)pyrimidin-5-yl)oxy)benzamide

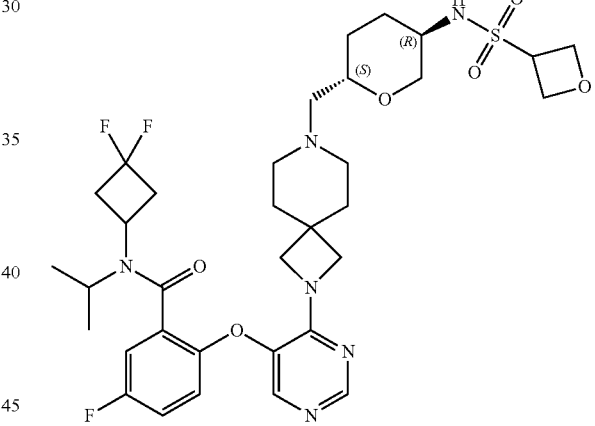

This compound was synthesized following the general procedure described for the synthesis of Example 85, except that 2 equivalents of oxetane-3-sulfonyl chloride and 5 equivalents of Et₃N were used. The crude was purified by Prep-HPLC (Method D).

Yield: 19.37%;

$^1$H NMR (400 MHz, DMSO-$d_6$) δ 8.28 (s, 1H), 7.78 (s, 1H), 7.47 (d, J=8.0 Hz, 1H), 7.35 (dd, J=2.9, 8.2 Hz, 1H), 7.26 (dt, J=3.1, 8.5 Hz, 1H), 7.03 (dd, J=4.3, 9.1 Hz, 1H), 4.84-4.70 (m, 2H), 4.69-4.56 (m, 3H), 4.12-3.62 (m, 8H), 3.61-3.45 (m, 1H), 3.30-3.23 (m, 1H), 3.19-3.07 (m, 1H), 3.02-2.95 (m, 1H), 2.84-2.69 (m, 2H), 2.32-2.14 (m, 5H), 1.85-1.94 (m, 1H), 1.75-1.59 (m, 5H), 1.50-1.16 (m, 3H), 1.10 (d, J=6.1 Hz, 3H), 1.02 (d, J=6.3 Hz, 3H);

LCMS (Method A): Rt 1.95 min, m/z: 723.3 [M+H]⁺;

HPLC (Method A): Rt 5.33 min, 98.65%.

Example 116. N-(3,3-Difluorocyclobutyl)-5-fluoro-N-isopropyl-2-((4-(7-(((2S,5R)-5-(morpholine-4-sulfonamido)tetrahydro-2H-pyran-2-yl)methyl)-2,7-diazaspiro[3.5]nonan-2-yl)pyrimidin-5-yl)oxy)benzamide

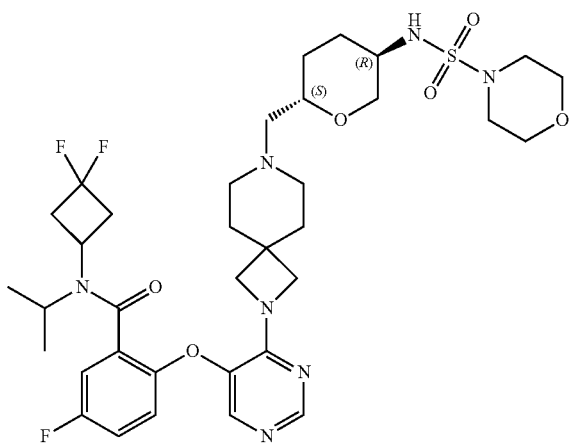

This compound was synthesized following the general procedure described for the synthesis of Example 85, except that 2 equivalents of morpholine-4-sulfonyl chloride and 5 equivalents of Et$_3$N were used. The crude was purified by Prep-HPLC (Method B).

Yield: 21.87%.

$^1$H NMR (400 MHz, DMSO-d$_6$) δ 8.28 (s, 1H), 7.78 (s, 1H), 7.39 (d, J=7.5 Hz, 1H), 7.35 (dd, J=3.0, 8.3 Hz, 1H), 7.26 (dt, J=2.9, 8.6 Hz, 1H), 7.03 (dd, J=4.4, 9.1 Hz, 1H), 3.98-3.82 (m, 4H), 3.81-3.68 (m, 4H), 3.67-3.59 (m, 5H), 3.58-3.44 (m, 1H), 3.11-2.92 (m, 6H), 2.83-2.69 (m, 2H), 2.32-2.14 (m, 5H), 1.91-1.99 (m, 1H), 1.67 (br s, 5H), 1.48-1.16 (m, 3H), 1.10 (d, J=6.3 Hz, 3H), 1.02 (d, J=6.3 Hz, 3H);

LCMS (Method C): Rt 1.78 min, m/z: 750.2 [M+H]$^+$;
HPLC (Method A): Rt 5.57 min, 99.21%.

Example 117. N-(3,3-Difluorocyclobutyl)-5-fluoro-N-isopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide

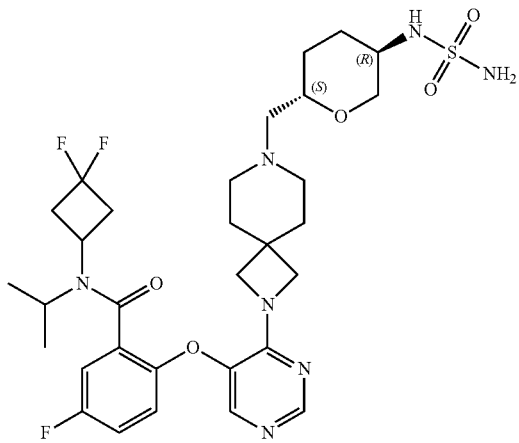

This compound was synthesized following the general procedure described for the synthesis of Example 85, except that 2 equivalents of sulfamoyl chloride and 5 equivalents of Et$_3$N were used. The crude was purified by Prep-HPLC (Method H).

Yield: 4.74%;

$^1$H NMR (400 MHz, DMSO-d$_6$) δ 8.28 (s, 1H), 7.78 (s, 1H), 7.39-7.32 (m, 1H), 7.30-7.22 (m, 1H), 7.01-7.11 (m, 1H), 6.61-6.50 (m, 3H), 3.99-3.63 (m, 8H), 3.62-3.44 (m, 1H), 3.17-3.05 (m, 1H), 3.03-2.91 (m, 1H), 2.81-2.65 (m, 2H), 2.32-2.17 (m, 6H), 2.00-1.95 (m, 1H), 1.67 (br s, 5H), 1.50-1.28 (m, 2H), 1.27-1.16 (m, 1H), 1.10 (d, J=5.5 Hz, 3H), 1.02 (d, J=5.6 Hz, 3H);

LCMS (Method C): Rt 1.65 min, m/z: 682.2 [M+H]$^+$;
HPLC (Method A): Rt 5.07 min, 98.50%.

Example 118. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-(3,3-difluorocyclobutyl)-5-fluoro-N-isopropylbenzamide

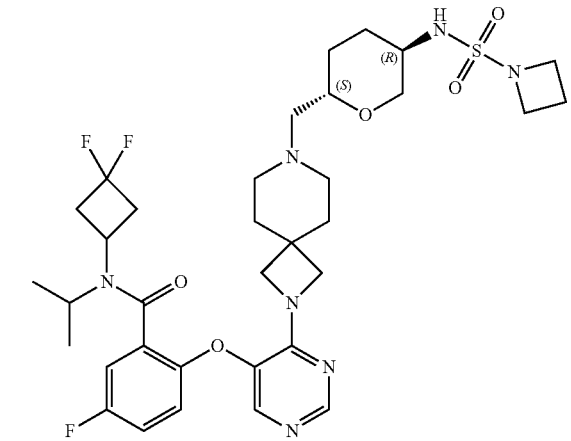

This compound was synthesized following the general procedure described for the synthesis of Example 85, except that 2 equivalents of azetidine-1-sulfonyl chloride and 5 equivalents of Et$_3$N was used. The crude was purified by Prep-HPLC (Method B).

Yield: 11.96%;

$^1$H NMR (400 MHz, DMSO-d$_6$) δ 8.29 (s, 1H), 7.78 (s, 1H), 7.41-7.30 (m, 1H), 7.29-7.16 (m, 2H), 7.03 (dd, J=4.0, 8.9 Hz, 1H), 3.98-3.72 (m, 8H), 3.67 (t, J=7.6 Hz, 4H), 3.49-3.55 (m, 1H), 3.31-3.3.25 (m, 1H), 3.12-2.95 (m, 2H), 2.86-2.70 (m, 2H), 2.32-2.16 (m, 5H), 2.10 (quin, J=7.5 Hz, 2H), 2.01-1.92 (m, 1H), 1.67 (br s, 5H), 1.49-1.19 (m, 3H), 1.10 (d, J=5.6 Hz, 3H), 1.02 (d, J=5.6 Hz, 3H);

LCMS (Method B): Rt 1.41 min, m/z: 722.2 [M+H]$^+$;
HPLC (Method A): Rt 5.69 min, 95.13%.

Example 119. N-(3,3-Difluorocyclobutyl)-5-fluoro-N-isopropyl-2-((4-(7-(((2S,5R)-5-((N-isopropyl-N-methylsulfamoyl)amino)tetrahydro-2H-pyran-2-yl)methyl)-2,7-diazaspiro[3.5]nonan-2-yl)pyrimidin-5-yl)oxy)benzamide

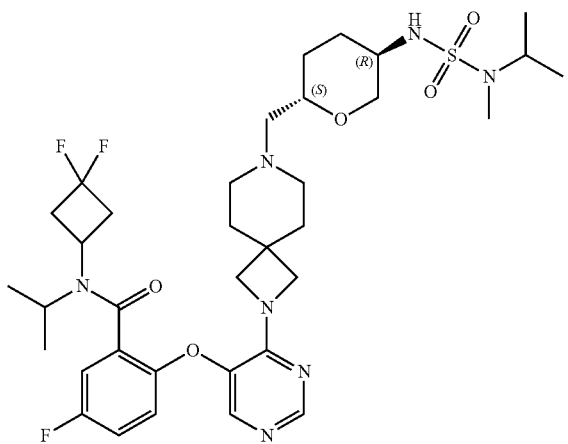

This compound was synthesized following the general procedure described for the synthesis of Example 85, except that 2 equivalents of isopropyl(methyl)sulfamoyl chloride was used. The crude was purified by Prep-HPLC (Method I).

Yield: 16.40%;

$^1$H NMR (400 MHz, DMSO-d$_6$) δ 8.28 (s, 1H), 7.78 (s, 1H), 7.40-7.30 (m, 1H), 7.30-7.21 (m, 1H), 7.11 (d, J=7.3 Hz, 1H), 7.03 (dd, J=4.1, 8.9 Hz, 1H), 4.02-3.62 (m, 9H), 3.53 (br d, J=9.0 Hz, 1H), 3.07-2.85 (m, 2H), 2.72 (br s, 2H), 2.55 (s, 3H), 2.32-2.13 (m, 6H), 1.97-1.89 (m, 1H), 1.66 (br s, 5H), 1.51-1.14 (m, 3H), 1.13-0.90 (m, 12H);

LCMS (Method C): Rt 1.92 min, m/z: 738.2 [M+H]$^+$;

HPLC (Method A): Rt 6.16 min, 99.90%.

Example 120. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)benzenesulfonamide

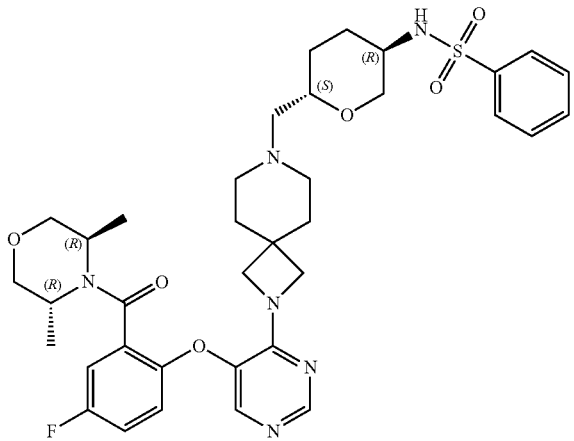

This compound was synthesized following the general procedure described for the synthesis of Example 85, except that 3 equivalents of Et$_3$N was used, and DMF (3 mL) was used as the solvent. The crude was purified by Prep-HPLC (Method I).

Yield: 36.1%;

$^1$H NMR (400 MHz, DMSO-d$_6$) δ 8.27 (s, 1H), 7.85-7.74 (m, 3H), 7.70-7.57 (m, 4H), 7.37 (dd, J=2.8, 8.1 Hz, 1H), 7.33-7.25 (m, 1H), 7.03 (dd, J=4.4, 9.0 Hz, 1H), 4.03-3.62 (m, 8H), 3.58-3.56 (m, 1H), 3.30-3.19 (m, 2H), 3.00-2.87 (m, 2H), 2.59-2.52 (m, 1H), 2.49-2.39 (m, 1H), 2.32-2.10 (m, 5H), 1.73-1.52 (m, 6H), 1.39-0.99 (m, 8H);

LCMS (Method C): Rt 1.62 min, m/z: 709.3 [M+H]$^+$;

HPLC (Method A): Rt 5.30 min, 99.49%.

Example 121. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)azetidine-1-sulfonamide

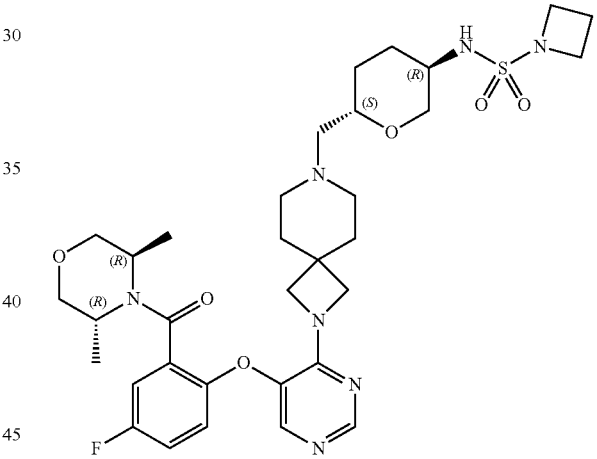

This compound was synthesized following the general procedure described for the synthesis of Example 85, except that 1.1 equivalents of azetidine-1-sulfonyl chloride was used.

The crude was purified by Prep-HPLC (Method A).

Yield: 24.91%;

$^1$H NMR (400 MHz, DMSO-d$_6$) δ 8.28 (s, 1H), 7.69 (s, 1H), 7.45-7.16 (m, 3H), 7.06-7.03 (m, 1H), 4.00-3.76 (m, 8H), 3.72-3.62 (m, 6H), 3.57-3.39 (m, 2H), 3.15-2.96 (m, 3H), 2.34-2.28 (m, 3H), 2.13-2.06 (m, 3H), 1.97 (d, J=9.9 Hz, 1H), 1.80-1.58 (m, 5H), 1.48-1.34 (m, 1H), 1.33-1.08 (m, 8H);

LCMS (Method A): Rt 1.57 min, m/z: 688.8 [M+H]$^+$;

HPLC (Method A): Rt 4.65 min, 98.11%.

Example 122. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-2-methylthiazole-4-sulfonamide

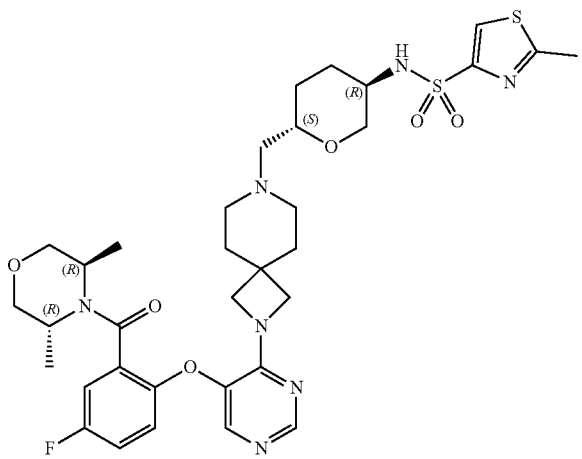

This compound was synthesized following the general procedure described for the synthesis of Example 85. The crude was purified by Prep-HPLC (Method D).

Yield: 25.3%;

$^1$H NMR (400 MHz, DMSO-$d_6$) δ 8.27 (s, 1H), 8.17 (s, 1H), 7.94 (d, J=7.5 Hz, 1H), 7.68 (s, 1H), 7.42-7.34 (m, 1H), 7.31-7.26 (m, 1H), 7.04 (dd, J=4.3, 9.1 Hz, 1H), 3.82 (br s, 7H), 3.69-3.59 (m, 2H), 3.55-3.40 (m, 1H), 3.32-3.22 (m, 2H), 3.15-3.04 (m, 1H), 3.01-2.94 (m, 1H), 2.71 (s, 3H), 2.17-2.08 (m, 5H), 1.79-1.57 (m, 7H), 1.35-1.37 (m, 1H), 1.28-1.10 (m, 7H);

LCMS (Method C): Rt 1.63 min, m/z: 730.2 [M+H]$^+$;
HPLC (Method A): Rt 4.85 min, 99.83%.

Example 123. {[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}dimethylamine

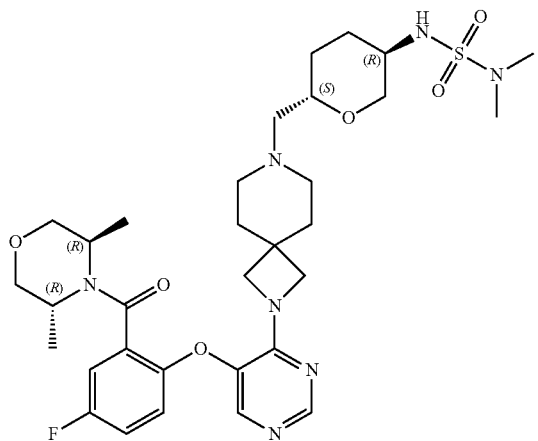

This compound was synthesized following the general procedure described for the synthesis of Example 85. The crude was purified by Prep-HPLC (Method C).

Yield: 15.90%;

$^1$H NMR (400 MHz, CDCl$_3$) δ 8.28 (s, 1H), 7.69 (s, 1H), 7.41-7.35 (m, 1H), 7.31-7.26 (m, 1H), 7.20 (d, J=7.4 Hz, 1H), 7.04 (dd, J=4.4, 9.1 Hz, 1H), 4.16-4.14 (m, 1H), 3.98-3.92 (m, 9H), 3.58-3.45 (m, 2H), 3.37-3.28 (m, 2H), 3.10-2.96 (m, 1H), 2.64 (s, 6H), 2.32-2.15 (m, 5H), 2.01-1.90 (m, 1H), 1.78-1.60 (m, 5H), 1.47-1.32 (m, 1H), 1.30-1.11 (m, 7H).

LCMS (Method B): Rt 1.20 min, m/z: 676.4 [M+H]$^+$;
HPLC (Method B): Rt 3.25 min, 93.49%.

Example 124. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)pyrrolidine-1-sulfonamide

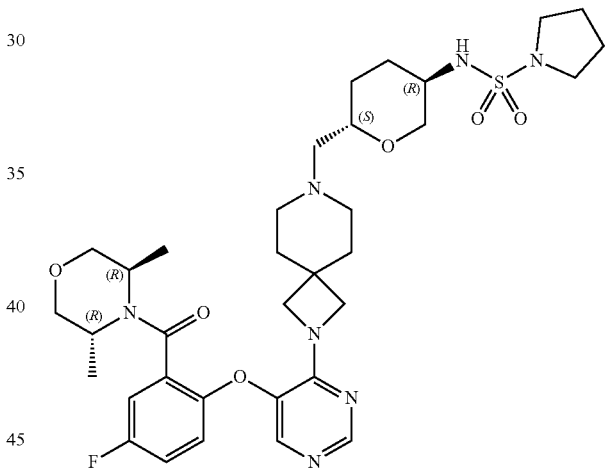

This compound was synthesized following the general procedure described for the synthesis of Example 85, except that 1.1 equivalent of pyrrolidine-1-sulfonyl chloride was used. The crude was purified by Prep-HPLC (Method D).

Yield: 35.5%;

$^1$H NMR (400 MHz, DMSO-$d_6$) δ 8.28 (s, 1H), 7.69 (s, 1H), 7.37 (dd, J=2.7, 8.2 Hz, 1H), 7.33-7.26 (m, 1H), 7.14 (d, J=7.5 Hz, 1H), 7.04 (dd, J=4.4, 9.1 Hz, 1H), 4.00-3.72 (m, 8H), 3.67-3.60 (m, 1H), 3.22-3.16 (m, 3H), 3.15-2.96 (m, 6H), 2.32-2.14 (m, 4H), 2.00-1.90 (m, 1H), 1.88-1.78 (m, 6H), 1.68 (br s, 5H), 1.46-1.32 (m, 1H), 1.31-1.09 (m, 7H);

LCMS (Method E): Rt 1.62 min, m/z: 702.4 [M−H]$^+$;
HPLC (Method A): Rt 4.97 min, 99.25%.

Example 125. {[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}(ethyl)amine

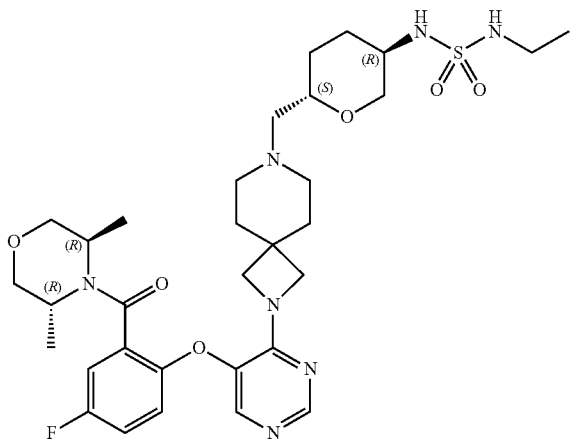

This compound was synthesized following the general procedure described for the synthesis of Example 85, except that 8 equivalents of ethylsulfamoyl chloride was used. The crude was purified by Prep-HPLC (Method A).

Yield: 15.02%;

$^1$H NMR (400 MHz, DMSO-d$_6$) δ 8.28 (s, 1H), 7.69 (s, 1H), 7.41-7.35 (m, 1H), 7.31-7.26 (m, 1H), 7.04 (dd, J=4.4, 9.0 Hz, 1H), 6.86 (d, J=6.8 Hz, 1H), 6.77 (t, J=5.8 Hz, 1H), 4.05-3.39 (m, 9H), 3.32-3.28 (m, 2H), 2.95-2.99 (m, 2H), 2.85-2.67 (m, 2H), 2.32-2.15 (m, 6H), 1.94 (d, J=12.1 Hz, 11H), 1.76-1.57 (m, 5H), 1.46-1.30 (m, 1H), 1.29-1.09 (m, 8H), 1.04 (t, J=2.8 Hz, 3H);

LCMS (Method E): Rt 1.59 min, m/z: 676.2 [M+H]$^+$;
HPLC (Method A): Rt 4.57 min, 99.24%.

Example 126. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-1-methyl-1H-pyrazole-4-sulfonamide

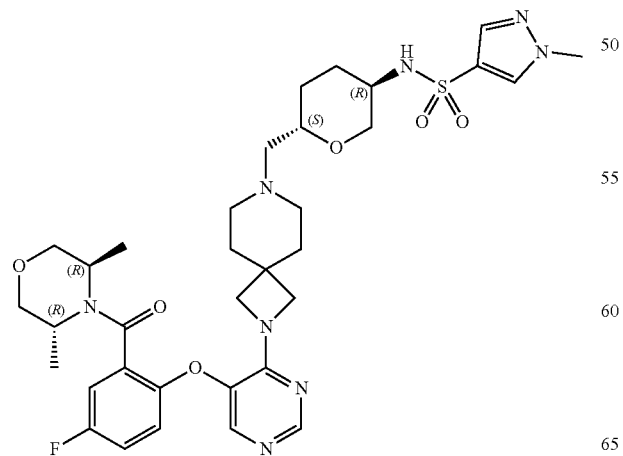

This compound was synthesized following the general procedure described for the synthesis of Example 85, except that 1.2 equivalents of 1-methyl-1H-pyrazole-4-sulfonyl chloride was used. The crude was purified by Prep-HPLC (Method B).

Yield: 17.85%;

$^1$H NMR (400 MHz, DMSO-d$_6$) δ 8.27 (s, 1H), 8.23 (s, 1H), 7.72 (s, 1H), 7.69 (s, 1H), 7.52 (br d, J=5.6 Hz, 1H), 7.37 (dd, J=2.9, 8.1 Hz, 1H), 7.33-7.25 (m, 1H), 7.03 (dd, J=4.4, 9.0 Hz, 1H), 3.88 (s, 3H), 4.04-3.74 (m, 7H), 3.72-3.58 (m, 4H), 3.57-3.43 (m, 2H), 3.04-2.89 (m, 2H), 2.32-2.12 (m, 5H), 1.80-1.52 (m, 6H), 1.43-1.01 (m, 8H);

LCMS (Method E): Rt 1.48 min, m/z: 713.4 [M+H]$^+$;
HPLC (Method A): Rt 4.53 min, 98.57%.

Example 127. N-((3R,6S)-6-((2-(5-(2-((3R,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-1-methyl-1H-pyrazole-3-sulfonamide

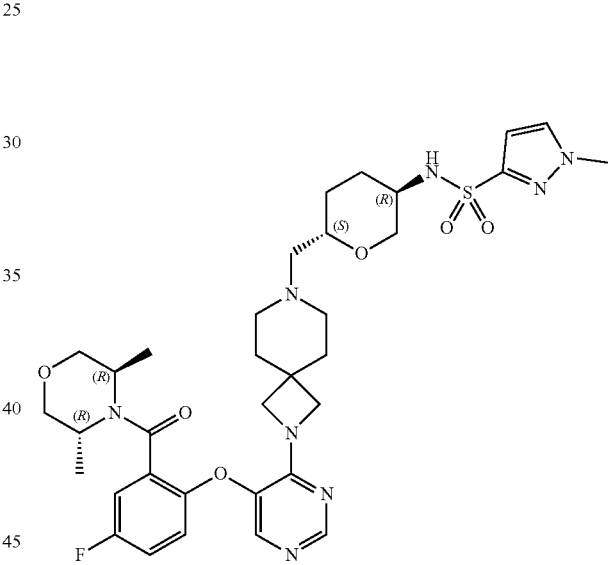

This compound was synthesized following the general procedure described for the synthesis of Example 85, except that 1.2 equivalents of 1-methyl-1H-pyrazole-3-sulfonyl chloride was used. The crude was purified by Prep-HPLC (Method D).

Yield: 24.31%;

$^1$H NMR (400 MHz, DMSO-d$_6$) δ 8.28 (s, 1H), 7.86 (d, J=2.4 Hz, 1H), 7.77-7.65 (m, 2H), 7.37 (dd, J=2.8, 8.2 Hz, 1H), 7.32-7.25 (m, 1H), 7.04 (dd, J=4.4, 9.1 Hz, 1H), 6.60 (d, J=2.3 Hz, 1H), 3.92 (s, 3H), 3.84-3.70 (m, 8H), 3.69-3.66 (m, 2H), 3.55-3.40 (m, 1H), 3.31-3.13 (m, 2H), 3.11-2.92 (m, 2H), 2.31-2.09 (m, 5H), 1.85-1.55 (m, 6H), 1.45-1.00 (m, 8H);

LCMS (Method E): Rt 1.50 min, m/z: 713.4 [M+H]$^+$;
HPLC (Method A): Rt 4.58 min, 99.91%.

Example 128. {[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}(ethyl)methylamine

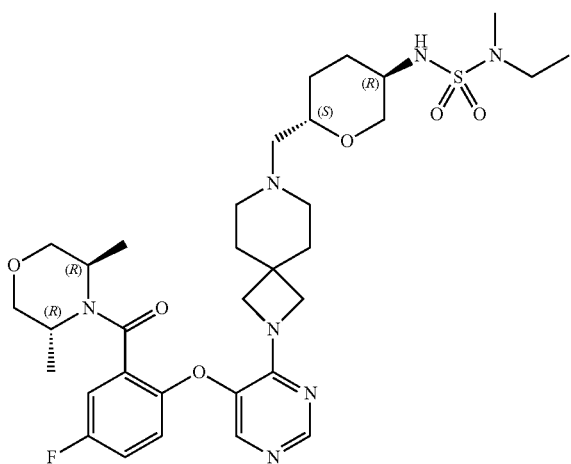

This compound was synthesized following the general procedure described for the synthesis of Example 85, except that 1.5 equivalents of ethyl(methyl)sulfamoyl chloride was used. The crude was purified by Prep-HPLC (Method A).

Yield: 18.50%;

$^1$H NMR (400 MHz, DMSO-$d_6$) δ 8.28 (s, 1H), 7.69 (s, 1H), 7.37 (dd, J=2.8, 7.9 Hz, 1H), 7.31-7.26 (m, 1H), 7.16 (br d, J=6.9 Hz, 1H), 7.04 (dd, J=4.4, 9.1 Hz, 1H), 4.04-3.57 (m, 10H), 3.30-3.19 (m, 2H), 3.14-2.92 (m, 5H), 2.64 (s, 3H), 2.32-2.11 (m, 5H), 1.99-1.90 (m, 1H), 1.78-1.59 (m, 5H), 1.46-1.33 (m, 1H), 1.31-1.12 (m, 7H), 1.08 (t, J=7.1 Hz, 3H);

LCMS (Method E): Rt 1.64 min, m/z: 690.4 [M+H]$^+$;
HPLC (Method A): Rt 5.00 min, 99.13%.

Example 129. N-{[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}-N-methylcyclopropanamine

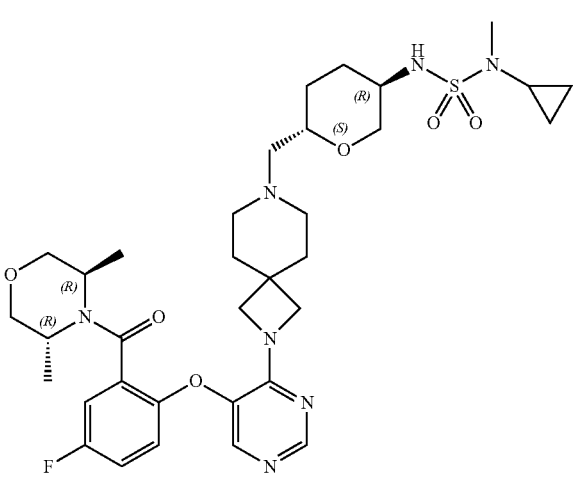

This compound was synthesized following the general procedure described for the synthesis of Example 85, except that 1.5 equivalents of cyclopropyl(methyl)sulfamoyl chloride was used. The crude was purified by Prep-HPLC (Method D).

Yield: 8.88%;

$^1$H NMR (400 MHz, DMSO-$d_6$) δ 8.28 (s, 1H), 7.69 (s, 1H), 7.37 (dd, J=2.6, 8.1 Hz, 1H), 7.33-7.23 (m, 2H), 7.04 (dd, J=4.4, 9.1 Hz, 1H), 4.03-3.56 (m, 9H), 3.31-3.19 (m, 2H), 3.11-2.96 (m, 2H), 2.67 (s, 3H), 2.32-2.15 (m, 7H), 1.99-1.92 (m, 1H), 1.79-1.56 (m, 6H), 1.46-1.35 (m, 1H), 1.28-1.13 (m, 7H), 0.72-0.56 (m, 4H);

LCMS (Method B): Rt 1.27 min, m/z: 702.4 [M+H]$^+$;
HPLC (Method A): Rt 5.06 min, 95.87%.

Example 130. N-((3R,6S)-6-((2-(5-(2-((3S,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)benzenesulfonamide

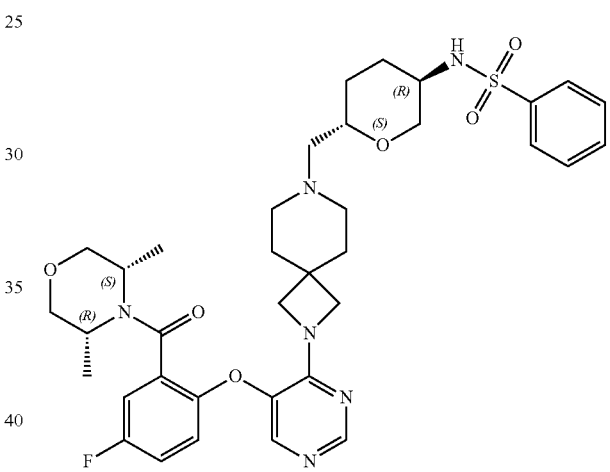

To a solution of (2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluorophenyl)((3S,5R)-3,5-dimethylmorpholino)methanone hydrochloride (250 mg, 0.413 mmol) in DMF (3 mL), Et$_3$N (125 mg, 1.239 mmol) and NaH (18.18 mg, 0.454 mmol) were added at RT under nitrogen atmosphere. To this solution, benzenesulfonyl chloride (88 mg, 0.496 mmol) was added, and the reaction mixture was stirred at RT for 18 h. The progress of the reaction was monitored by TLC (5% MeOH in DCM). The reaction was diluted with ice-cold water, and the resulting solid was filtered. The solid was dissolved in 5% methanol in DCM, and the solution was dried over sodium sulfate, and filtered, and the filtrate was concentrated on a rotary evaporator to obtain the crude product. The crude product was purified by Prep HPLC (Method I) to obtain N-((3R,6S)-6-((2-(5-(2-((3S,5R)-3,5-dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)benzenesulfonamide (65 mg, 0.092 mmol, 22.17%) as a solid. $^1$H NMR (400 MHz, DMSO-$d_6$) δ 8.32-8.23 (m, 1H), 7.85-7.80 (m, 2H), 7.77 (d, J=7.0 Hz, 2H), 7.68-7.58 (m, 3H), 7.45-7.32 (m, 1H), 7.29-7.24 (m, 1H), 7.04-7.00 (m, 1H), 4.35 (br s, 1H), 3.93-3.69 (m, 5H), 3.69-3.51 (m, 4H), 3.30-3.20 (m, 2H), 3.01-2.88 (m, 2H), 2.28-2.10 (m, 5H), 1.69-1.55 (m, 6H), 1.38-1.16 (m, 8H), 1.15-1.02 (m, 1H); LCMS (Method C): Rt 1.62 min, m/z: 709.3 [M+H]+; HPLC (Method A): Rt 5.26 min, 98.89%.

Example 131. N-((3R,6S)-6-((2-(5-(2-((3S,5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-2-methylthiazole-4-sulfonamide

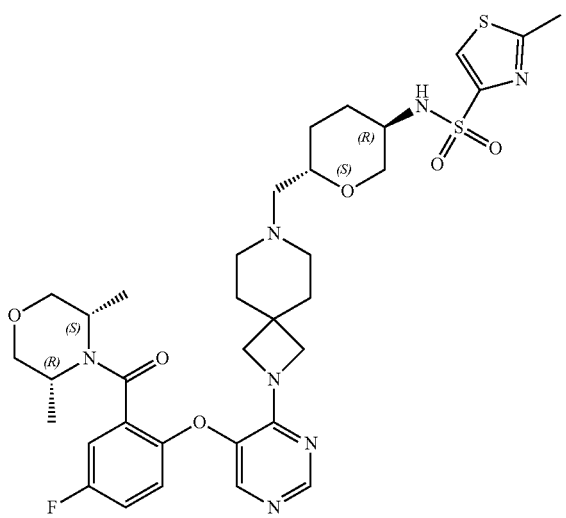

This compound was synthesized following the general procedure described for the synthesis of Example 85, except that 3 equivalents of Et₃N was used. The crude was purified by Prep-HPLC (Method B).

Yield: 17.22%;

¹H NMR (400 MHz, DMSO-d₆) δ 8.32-8.25 (m, 1H), 8.17 (s, 1H), 7.93 (br s, 1H), 7.78-7.65 (m, 1H), 7.44-7.34 (m, 1H), 7.29-7.24 (m, 1H), 7.13-7.00 (m, 1H), 4.44-4.31 (m, 1H), 3.95-3.66 (m, 6H), 3.66-3.53 (m, 3H), 3.27 (dd, J=3.0, 4.5 Hz, 1H), 3.15-3.06 (m, 1H), 3.01-2.94 (m, 1H), 2.71 (s, 3H), 2.24-2.09 (m, 6H), 1.78-1.57 (m, 6H), 1.42-1.08 (m, 9H);

LCMS (Method A): Rt 1.60 min, m/z: 728.3 [M–H]⁻;

HPLC (Method A): Rt 4.79 min, 98.93%.

Example 132. 5-Fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)-N—((R)-tetrahydrofuran-3-yl)benzamide

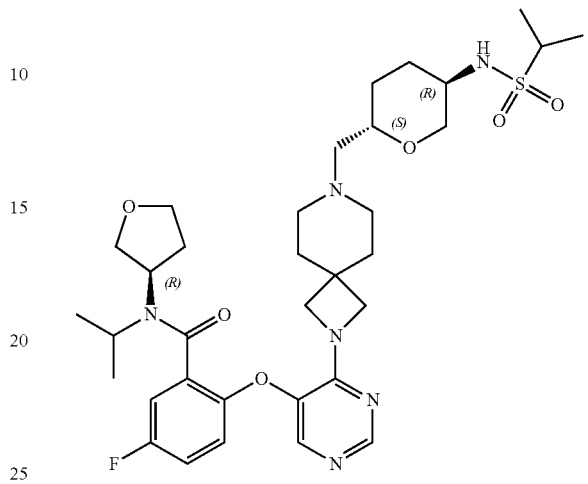

This compound was synthesized by following the general procedure described for the synthesis of Example 85, except that 4 equivalents of propane-2-sulfonyl chloride was used. The crude compound was purified by prep HPLC (Method G). Yield: 11.72%; ¹H NMR (400 MHz, DMSO-d₆) δ 8.33-8.22 (m, 1H), 7.85-7.67 (m, 1H), 7.36-7.20 (m, 2H), 7.11-7.00 (m, 2H), 4.25-3.63 (m, 10H), 3.62-3.35 (m, 1H), 3.21-3.06 (m, 3H), 3.05-2.96 (m, 1H), 2.33-2.15 (m, 5H), 2.06-1.90 (m, 2H), 1.78-1.62 (m, 5H), 1.52-1.32 (m, 3H), 1.31-1.16 (m, 8H), 1.16-0.95 (m, 5H); LCMS (Method A): Rt 1.88 min, m/z: 689.4 [M+H]⁺; HPLC (Method A): Rt 4.89 min, 97.83%.

Example 133. 5-Fluoro-N-isopropyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)-N—((R)-tetrahydrofuran-3-yl)benzamide

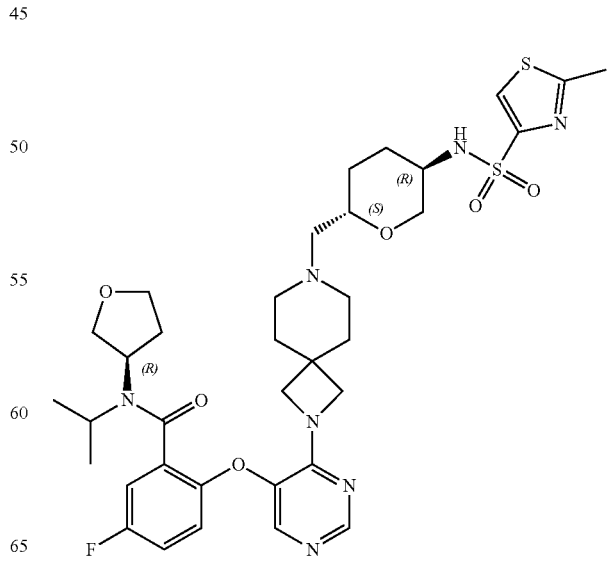

This compound was synthesized following the general procedure described for the synthesis of Example 85, except that 1.2 equivalents of 2-methylthiazole-4-sulfonyl chloride and 5 equivalents of Et$_3$N were used. The crude compound was purified by Prep-HPLC (Method F). Yield: 6.80%; $^1$H NMR (400 MHz, DMSO-d$_6$) δ 8.27 (d, J=2.8 Hz, 1H), 8.17 (s, 1H), 7.93 (d, J=7.5 Hz, 1H), 7.83-7.69 (m, 1H), 7.34-7.21 (m, 2H), 7.09-6.99 (m, 1H), 4.26-3.67 (m, 10H), 3.65-3.57 (m, 1H), 3.55-3.42 (m, 1H), 3.29-3.22 (m, 1H), 3.17-3.04 (m, 1H), 3.02-2.94 (m, 1H), 2.71 (s, 3H), 2.31-2.12 (m, 5H), 2.05-1.85 (m, 1H), 1.81-1.57 (m, 6H), 1.52-1.30 (m, 3H), 1.21-0.94 (m, 6H); LCMS (Method E): Rt 1.64 min, m/z: 744.6 [M+H]$^+$; HPLC (Method A): Rt 4.88 min, 99.45%.

Example 134. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide

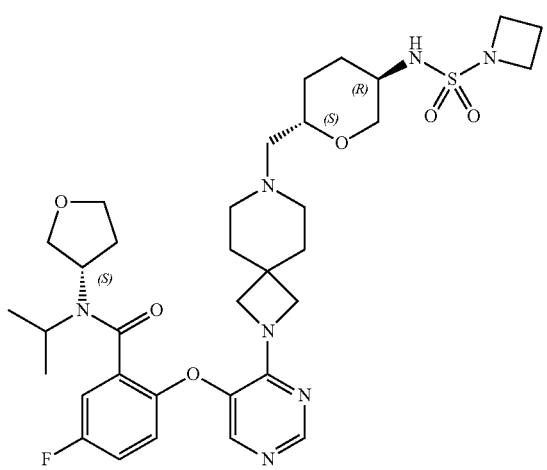

This compound was synthesized following the general procedure described for the synthesis of Example 85, except that 1.3 equivalents of azetidine-1-sulfonyl chloride and 8 equivalents of Et$_3$N were used. The crude compound was purified by Prep-HPLC (Method B). Yield: 12.51%; $^1$H NMR (400 MHz, DMSO-d$_6$) δ 8.30-8.25 (m, 1H), 7.84-7.70 (m, 1H), 7.36-7.16 (m, 3H), 7.09-7.01 (m, 1H), 4.27-3.70 (m, 10H), 3.67 (t, J=7.6 Hz, 4H), 3.61-3.39 (m, 2H), 3.14-2.95 (m, 3H), 2.32-2.16 (m, 5H), 2.15-2.04 (m, 3H), 2.03-1.88 (m, 2H), 1.76-1.60 (m, 5H), 1.50-1.32 (m, 3H), 1.30-1.17 (m, 1H), 1.16-0.96 (m, 4H); LCMS (Method A): Rt 1.22 min, m/z: 702.2 [M+H]$^+$; HPLC (Method A): Rt 4.88 min, 97.83%.

Example 135. 5-Fluoro-N-isopropyl-2-((4-(7-(((2S,5R)-5-((2-methylthiazole)-4-sulfonamido)tetrahydro-2H-pyran-2-yl)methyl)-2,7-diazaspiro[3.5]nonan-2-yl)pyrimidin-5-yl)oxy)-N—((S)-tetrahydrofuran-3-yl)benzamide

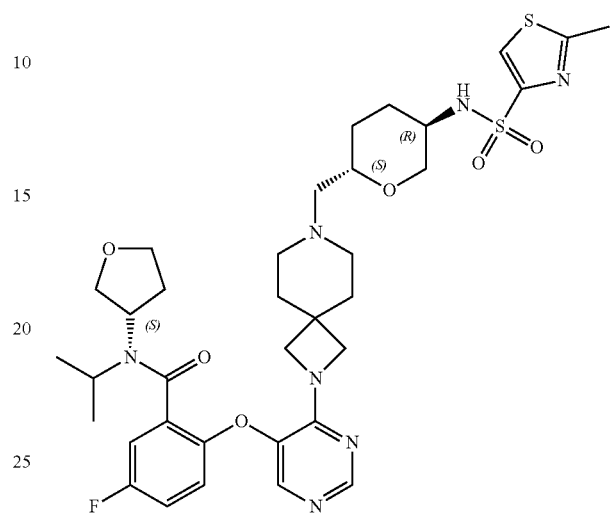

This compound was synthesized by following the general procedure described for the synthesis of Example 85, except that 5 equivalents of triethyl amine was used. The crude compound was purified by prep HPLC (Method A). Yield: 10.78%; $^1$H NMR (400 MHz, DMSO-d$_6$) δ 8.30-8.24 (m, 1H), 8.17 (s, 1H), 7.93 (br d, J=7.5 Hz, 1H), 7.85-7.68 (m, 1H), 7.35-7.21 (m, 2H), 7.10-7.00 (m, 1H), 4.27-3.66 (m, 9H), 3.65-3.41 (m, 2H), 3.29-3.22 (m, 1H), 3.16-3.03 (m, 1H), 3.01-2.93 (m, 1H), 2.71 (s, 3H), 2.31-2.13 (m, 5H), 2.04-1.85 (m, 1H), 1.83-1.54 (m, 7H), 1.52-1.30 (m, 3H), 1.26-0.92 (m, 6H); LCMS (Method A): Rt 1.64 min, m/z: 744.3 [M+H]$^+$; HPLC (Method E): Rt 4.92 min, 96.20%.

Example 136. N-(2-Cyanoethyl)-5-fluoro-N-isopropyl-2-((4-(7-(((2S,5R)-5-(phenylsulfonamido)tetrahydro-2H-pyran-2-yl)methyl)-2,7-diazaspiro[3.5]nonan-2-yl)pyrimidin-5-yl)oxy)benzamide

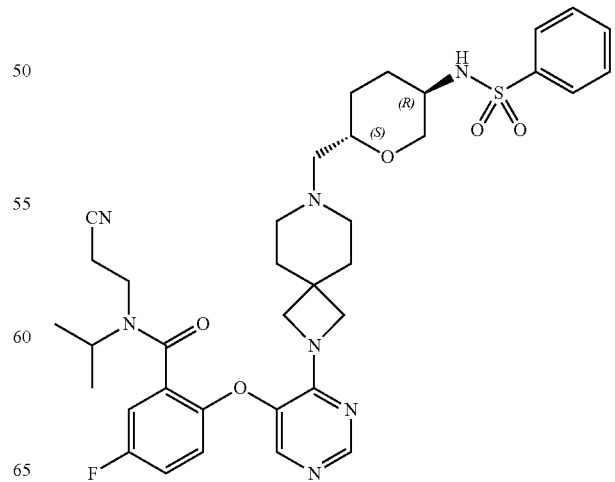

This compound was synthesized following the general procedure described for the synthesis of Example 130, except that 3 equivalents of benzenesulfonyl chloride, 2 equivalents of Et$_3$N and NaH were used. The crude was purified by Prep-HPLC (Method G). Yield: 4.96%; $^1$H NMR (400 MHz, DMSO-d$_6$) δ 8.32-8.24 (m, 1H), 7.85-7.74 (m, 4H), 7.69-7.58 (m, 3H), 7.33-7.22 (m, 2H), 6.96 (dd, J=4.4, 9.0 Hz, 11H), 3.90-3.69 (m, 5H), 3.64-3.50 (m, 3H), 3.31-3.20 (m, 1H), 3.02-2.88 (m, 2H), 2.87-2.74 (m, 2H), 2.31-2.09 (m, 5H), 1.73-1.52 (m, 6H), 1.39-1.21 (m, 2H), 1.20-0.93 (m, 7H); LCMS (Method A): Rt 1.82 min, m/z: 706.0 [M+H]$^+$; HPLC (Method A): Rt 5.36 min, 97.67%.

Example 137. 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-methylbenzamide

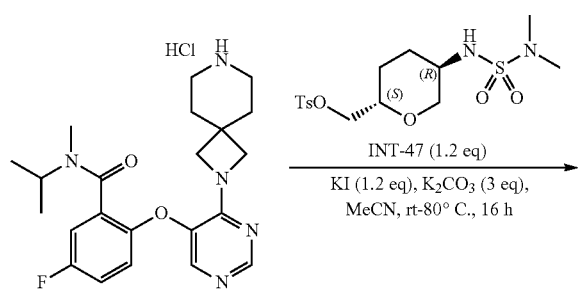

INT-47 (1.2 eq)

KI (1.2 eq), K$_2$CO$_3$ (3 eq), MeCN, rt-80° C., 16 h

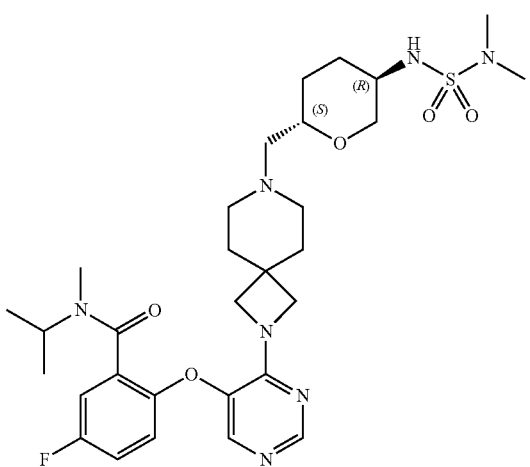

In a dried 25 mL round bottom flask under nitrogen atmosphere, 2-((4-(2,7-diazaspiro[3.5]nonan-2-yl)pyrimidin-5-yl)oxy)-5-fluoro-N-isopropyl-N-methylbenzamide hydrochloride (200 mg, 0.444 mmol) was added in ACN (5 mL). To this solution, (((2S,5R)-5-((N,N-dimethylsulfamoyl) amino)tetrahydro-2H-pyran-2-yl)methyl 4-methylbenzenesulfonate (209 mg, 0.533 mmol), K$_2$CO$_3$ (184 mg, 1.333 mmol), and KI (89 mg, 0.533 mmol) were added at RT, and the reaction was stirred at 80° C. for 18 h. The progress of the reaction was monitored by TLC (10% MeOH/DCM). The reaction mixture was diluted with ice-cold water and extracted with EtOAc (10 mL). The combined organic layer was washed with saturated aqueous sodium bicarbonate solution, and brine solution. The combined organic layer was dried over anhydrous sodium sulfate, filtered, and concentrated on a rotary evaporator to obtain crude compound. The crude compound was purified by Prep HPLC (Method F) and the pure fractions were lyophilized to obtain 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-methylbenzamide (58.17 mg, 20.56% yield). $^1$H NMR (400 MHz, DMSO-d$_6$) δ 8.27 (m, 1H), 7.71 (m, 1H), 7.32-7.17 (m, 3H), 7.12-6.98 (m, 1H), 3.91-3.79 (m, 4H), 3.78-3.72 (m, 2H), 3.08-2.96 (m, 2H), 2.82 (s, 2H), 2.66-2.62 (m, 1H), 2.64 (s, 6H), 2.32-2.17 (m, 6H), 2.21-2.16 (m, 1H), 2.01-1.91 (m, 1H), 1.66 (br s, 5H), 1.46-1.34 (m, 1H), 1.29-1.19 (m, 1H), 1.11 (d, J=6.5 Hz, 3H), 1.06 (d, J=6.6 Hz, 3H); LCMS (Method B): Rt 1.22 min, m/z: 634.3 [M+H]$^+$; HPLC (Method A): Rt 4.82 min, 97.69%.

Example 138. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N-isopropyl-N-methylbenzamide

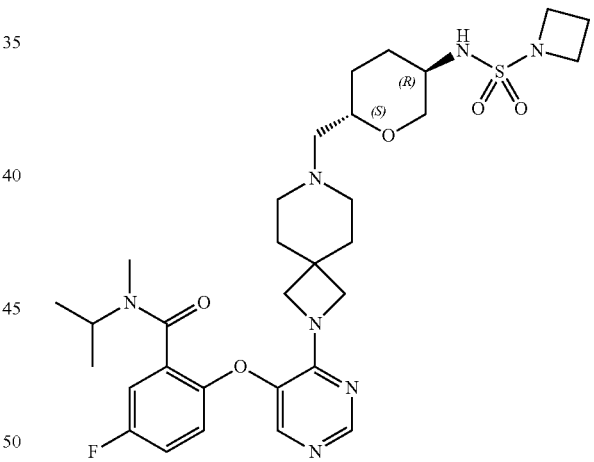

This compound was synthesized following the general procedure described for the synthesis of Example 137. The crude compound was purified by Prep HPLC (Method F).

Yield: 15.21%;

$^1$H NMR (400 MHz, DMSO-d$_6$) δ 8.28-8.24 (m, 1H), 7.73-7.68 (m, 1H), 7.31-7.22 (m, 3H), 7.09-6.98 (m, 1H), 3.90-3.71 (m, 6H), 3.67 (t, J=7.6 Hz, 4H), 3.08-2.95 (m, 2H), 2.83 (s, 2H), 2.68-2.64 (m, 2H), 2.32-2.18 (m, 5H), 2.13-2.06 (m, 2H), 1.96 (d, J=11.9 Hz, 1H), 1.67 (br s, 6H), 1.46-1.32 (m, 1H), 1.31-1.18 (m, 1H), 1.11 (d, J=6.5 Hz, 3H), 1.06 (d, J=6.6 Hz, 3H);

LCMS (Method B): Rt 1.23 min, m/z: 646.4 [M+H]$^+$;

HPLC (Method A): 4.83 min, 96.29%.

Example 139. 5-Fluoro-N-isopropyl-N-methyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide

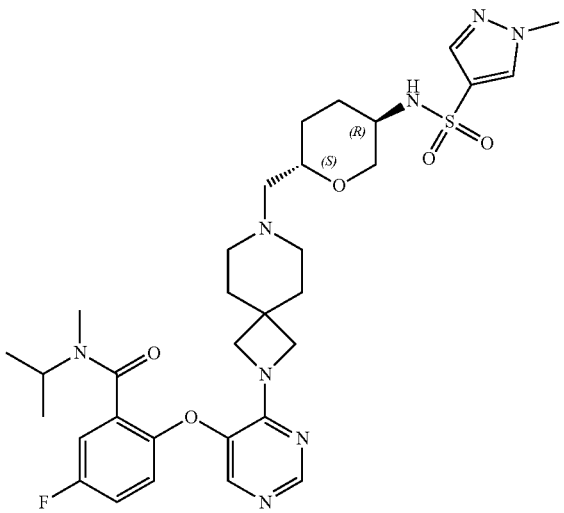

This compound was synthesized following the general procedure described for the synthesis of Example 137, except that 4.3 equivalents of K$_2$CO$_3$ and 1.1 equivalents of KI were used. The crude compound was purified by Prep-HPLC (Method D).

Yield: 27.8%;

$^1$H NMR (400 MHz, DMSO-d$_6$) δ 8.28-8.23 (m, 2H), 7.73-7.68 (m, 2H), 7.56-7.51 (m, 1H), 7.31-7.21 (m, 2H), 7.09-6.98 (m, 1H), 3.89 (s, 3H), 3.88-3.69 (m, 7H), 3.30-3.25 (m, 1H), 3.21-3.03 (m, 1H), 3.02-2.91 (m, 2H), 2.82 (s, 2H), 2.60-2.64 (m, 1H), 2.31-2.12 (m, 5H), 1.81-1.69 (m, 2H), 1.68-1.58 (m, 5H), 1.11 (d, J=6.5 Hz, 3H), 1.05 (d, J=6.5 Hz, 3H);

LCMS (Method F): Rt 1.21 min, m/z: 671.0 [M+H]$^+$;
HPLC (Method A): Rt 4.57 min, 99.93%.

Example 140. N-Ethyl-2-((4-(7-(((2S,5R)-5-((N-ethyl-N-methylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

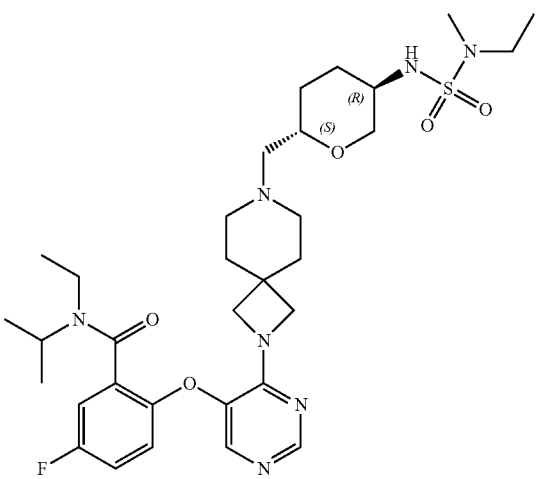

This compound was synthesized following the general procedure described for the synthesis of Example 137, except that 1.0 equivalent of KI and 1.0 equivalent of ((2S,5R)-5-((N-ethyl-N-methylsulfamoyl)amino)tetrahydro-2H-pyran-2-yl)methyl4-methylbenzenesulfonate were used. The crude compound was purified by Prep HPLC (Method B).

Yield: 25.7%;

$^1$H NMR (400 MHz, DMSO-d$_6$) δ 8.27-8.25 (m, 1H), 7.71-7.66 (m, 1H), 7.34-7.21 (m, 2H), 7.16 (br s, 1H), 7.09-7.00 (m, 1H), 3.92-3.82 (m, 3H), 3.81-3.70 (m, 3H), 3.12-3.03 (m, 3H), 3.02-2.95 (m, 2H), 2.67 (s, 3H), 2.27 (m, 5H), 2.22-2.15 (m, 1H), 1.93 (d, J=13.1 Hz, 1H), 1.66 (br s, 5H), 1.46-1.33 (m, 1H), 1.30-1.15 (m, 3H), 1.13-1.07 (m, 8H), 1.07-0.97 (m, 4H);

LCMS (Method E): Rt 1.74 min, m/z: 662.6 [M+H]$^+$;
HPLC (Method A): Rt 5.31 min, 99.94%.

Example 141. N-Ethyl-2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

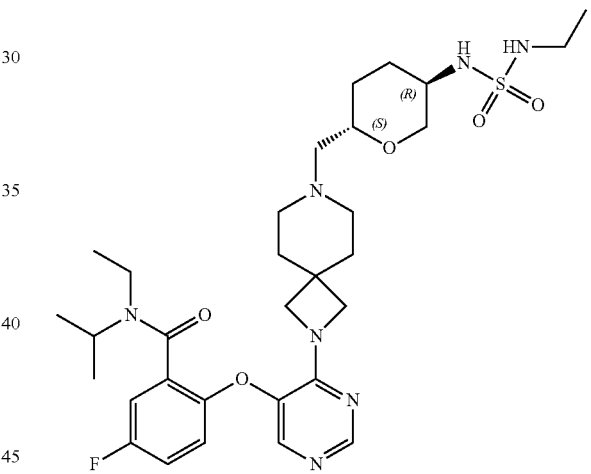

This compound was synthesized following the general procedure described for the synthesis of Example 137, except that 3.5 equivalents of K$_2$CO$_3$ and 1.5 equivalents of KI were used. The crude compound was purified by Prep-HPLC (Method E).

Yield: 39.4%;

$^1$H NMR (400 MHz, DMSO-d$_6$) δ 8.27-8.25 (m, 1H), 7.71-7.66 (m, 1H), 7.31-7.22 (m, 2H), 7.08-7.01 (m, 1H), 6.92-6.84 (m, 1H), 6.87-6.76 (m, 1H), 3.96-3.82 (m, 3H), 3.81-3.70 (m, 3H), 3.45-3.35 (m, 1H), 3.26-3.19 (m, 1H), 3.17-3.07 (m, 1H), 3.06-2.96 (m, 2H), 2.86-2.80 (m, 2H), 2.28 (dd, J=6.3, 12.9 Hz, 4H), 2.22-2.15 (m, 1H), 1.94 (d, J=12.9 Hz, 1H), 1.66 (br s, 5H), 1.44-1.32 (m, 1H), 1.28-1.15 (m, 3H), 1.13-1.02 (m, 11H);

LCMS (Method E): Rt 1.61 min, m/z: 648.5 [M+H]$^+$;
HPLC (Method A): Rt 5.00 min, 98.48%.

Example 142. 2-((4-(7-(((2S,5R)-5-((N-Cyclopropylsulfamoyl)amino)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide

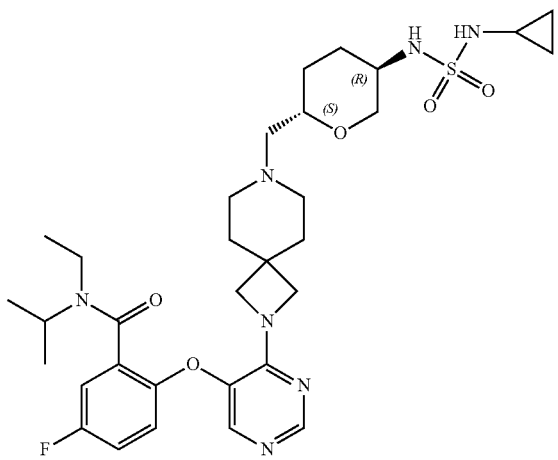

This compound was synthesized following the general procedure described for the synthesis of Example 137, except that 1 equivalent of KI was used. The crude compound was purified by Prep HPLC (Method A).

Yield: 20.37%;

$^1$H NMR (400 MHz, DMSO-d$_6$) δ 8.27-8.25 (m, 1H), 7.71-7.66 (m, 1H), 7.32-7.26 (m, 3H), 7.08-6.98 (m, 2H), 3.94-3.82 (m, 3H), 3.81-3.70 (m, 3H), 3.08-2.96 (m, 2H), 2.32-2.15 (m, 7H), 2.02-1.87 (m, 2H), 1.66 (br s, 6H), 1.47-1.33 (m, 1H), 1.29-1.15 (m, 3H), 1.14-1.07 (m, 5H), 1.06-0.95 (m, 3H), 0.56-0.45 (m, 4H);

LCMS (Method E): Rt 1.69 min, m/z: 660.5 [M+H]$^+$;
HPLC (Method A): Rt 4.96 min, 99.34%.

Example 143. 5-Fluoro-N,N-diisopropyl-2-((4-(7-(((2S,5R)-5-((N-methylsulfamoyl)amino)tetrahydro-2H-pyran-2-yl)methyl)-2,7-diazaspiro[3.5]nonan-2-yl)pyrimidin-5-yl)oxy)benzamide

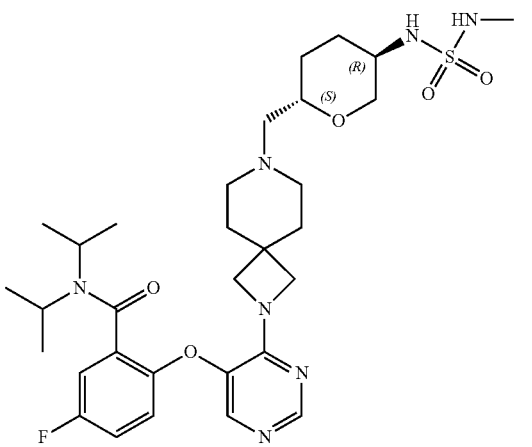

This compound was synthesized following the general procedure described for the synthesis of Example 137. The crude compound was purified by Prep HPLC (Method I).

Yield: 36.7%;

$^1$H NMR (400 MHz, DMSO-d$_6$) δ 8.26 (s, 1H), 7.71 (s, 1H), 7.24-7.20 (m, 2H), 7.05-7.03 (m, 1H), 6.91 (d, J=7.1 Hz, 1H), 6.68 (q, J=5.1 Hz, 1H), 3.95-3.75 (m, 6H), 3.70-3.66 (m, 1H), 3.58-3.48 (m, 1H), 3.31-3.25 (m, 1H), 3.07-2.93 (m, 2H), 2.43 (d, J=5.1 Hz, 3H), 2.32-2.16 (m, 6H), 2.01-1.92 (m, 1H), 1.67 (br s, 5H), 1.44 (d, J=6.6 Hz, 3H), 1.35 (d, J=6.8 Hz, 3H), 1.28-1.14 (m, 1H), 1.09 (d, J=6.6 Hz, 3H), 1.00 (d, J=6.6 Hz, 3H);

LCMS (Method C): Rt 1.650 min, m/z: 648.2 [M+H]$^+$;
HPLC (Method G): Rt 3.36 min, 98.44%.

Example 144. 2-((4-(7-(((2S,5R)-5-((N-Ethylsulfamoyl)amino)tetrahydro-2H-pyran-2-yl)methyl)-2,7-diazaspiro[3.5]nonan-2-yl)pyrimidin-5-yl)oxy)-5-fluoro-N,N-diisopropylbenzamide

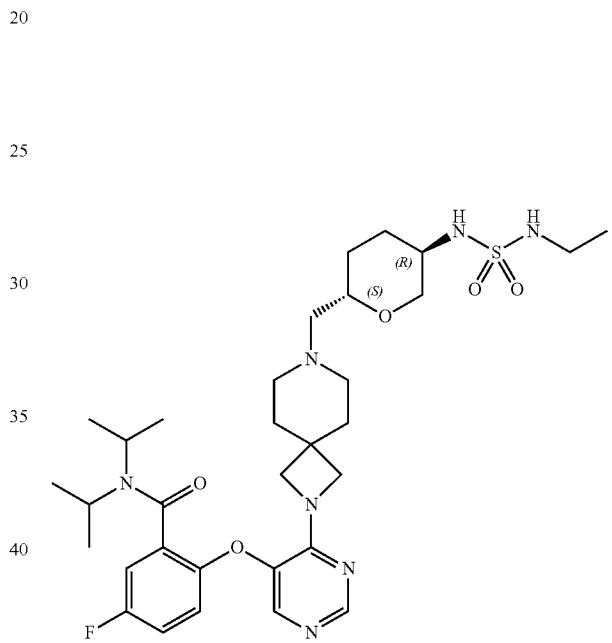

This compound was synthesized following the general procedure described for the synthesis of Example 137. The crude compound was purified by Prep-HPLC (Method D).

Yield: 10.95%;

1H NMR (400 MHz, DMSO-d$_6$) δ 8.26 (s, 1H), 7.71 (s, 1H), 7.24-7.20 (m, 2H), 7.04 (dd, J=4.3, 10.1 Hz, 1H), 6.87 (d, J=7.0 Hz, 1H), 6.78 (t, J=5.8 Hz, 1H), 3.98-3.83 (m, 3H), 3.83-3.75 (m, 2H), 3.74-3.64 (m, 1H), 3.58-3.40 (m, 2H), 3.06-2.94 (m, 2H), 2.87-2.78 (m, 2H), 2.32-2.16 (m, 6H), 1.98-1.89 (m, 2H), 1.75-1.61 (m, 5H), 1.44 (d, J=6.8 Hz, 3H), 1.38 (d, J=4.4 Hz, 1H), 1.35 (d, J=6.8 Hz, 3H), 1.26-1.15 (m, 1H), 1.05 (t, J=7.2 Hz, 3H), 1.06-1.04 (m, 2H), 1.00 (d, J=6.5 Hz, 3H);

LCMS (Method B): Rt 1.27 min, m/z: 662.4 [M+H]$^+$;
HPLC (Method A): Rt 5.27 min, 99.09%.

Example 145. N-Cyclopropyl-2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

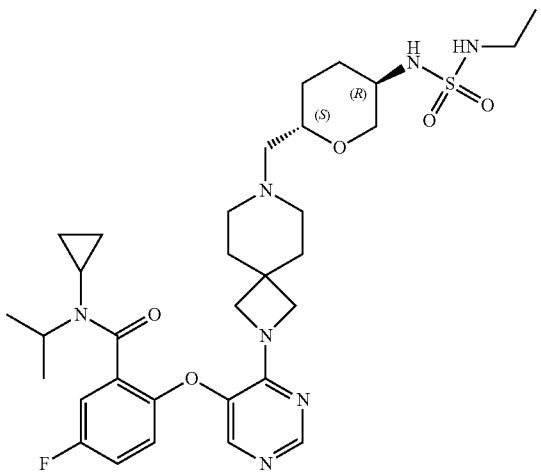

This compound was synthesized following the general procedure described for the synthesis of Example 137, except that 3.5 equivalents of K$_2$CO$_3$, 1.0 equivalent of KI, and 1.0 equivalent of ((2S,5R)-5-((N-ethylsulfamoyl)amino)tetrahydro-2H-pyran-2-yl)methyl 4-methylbenzenesulfonate were used. The crude compound was purified by Prep-HPLC (Method A).

Yield; 33.8%;

$^1$H NMR (400 MHz, DMSO-d$_6$) δ 8.27 (s, 1H), 7.71 (s, 1H), 7.32 (dd, J=2.9, 8.3 Hz, 1H), 7.23 (dt, J=3.1, 8.6 Hz, 1H), 7.01 (dd, J=4.4, 9.1 Hz, 1H), 6.87 (br s, 1H), 6.78 (br s, 1H), 4.39-4.24 (m, 1H), 3.97-3.70 (m, 5H), 3.31-3.25 (m, 1H), 3.10-2.92 (m, 2H), 2.79-2.86 (m, 2H), 2.66-2.57 (m, 1H), 2.32-2.14 (m, 5H), 1.91-1.96 (m, 1H), 1.66 (br s, 5H), 1.45-1.12 (m, 9H), 1.05 (t, J=7.2 Hz, 3H), 0.52 (br s, 4H);

LCMS (Method E): Rt 1.68 min, m/z: 660.4 [M+H]$^+$;

HPLC (Method A): Rt 5.13 min, 99.40%.

Example 146. N-Cyclopropyl-5-fluoro-N-isopropyl-2-((4-(7-(((2R,5S)-5-((N-methylsulfamoyl)amino)tetrahydro-2H-pyran-2-yl)methyl)-2,7-diazaspiro[3.5]nonan-2-yl)pyrimidin-5-yl)oxy)benzamide

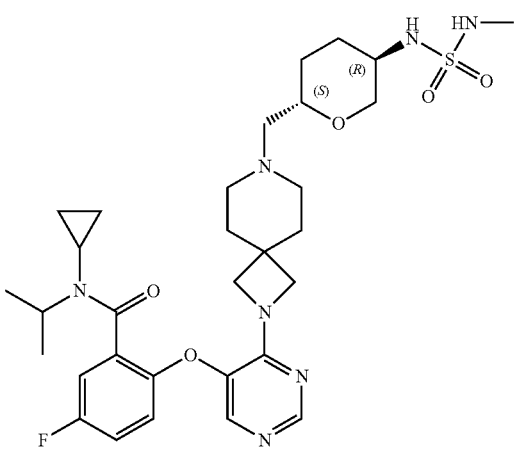

This compound was synthesized following the general procedure described for the synthesis of Example 137, except that 3.5 equivalents of K$_2$CO$_3$, 1.0 equivalent of KI, and 1.5 equivalents of ((2R,5S)-5-((N-methylsulfamoyl)amino)tetrahydro-2H-pyran-2-yl)methyl 4-methylbenzenesulfonate were used. The crude compound was purified by Prep-HPLC (Method A).

Yield: 24.81%;

$^1$H NMR (400 MHz, DMSO-d$_6$) δ 8.27 (s, 1H), 7.71 (s, 1H), 7.33 (dd, J=2.7, 8.3 Hz, 1H), 7.23 (dt, J=3.1, 8.6 Hz, 11H), 7.01 (dd, J=4.4, 9.1 Hz, 1H), 6.90 (d, J=6.9 Hz, 1H), 6.68 (q, J=5.1 Hz, 1H), 4.39-4.25 (m, 1H), 3.94-3.71 (m, 5H), 3.30-3.24 (m, 1H), 3.05-2.93 (m, 2H), 2.62-2.57 (m, 1H), 2.43 (d, J=5.1 Hz, 3H), 2.32-2.16 (m, 5H), 2.01-1.89 (m, 1H), 1.74-1.60 (m, 5H), 1.47-1.07 (m, 9H), 0.52 (br s, 4H);

LCMS (Method E): Rt 1.74 min, m/z: 646.4 [M+H]$^+$;

HPLC (Method A): Rt 4.87 min, 98.18%.

Example 147. N-(2,2-Difluoroethyl)-2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

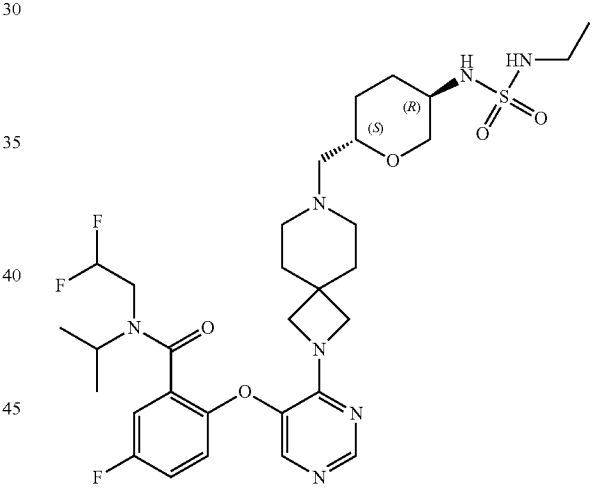

This compound was synthesized following the general procedure described for the synthesis of Example 85, except 5 equivalents of Et$_3$N and 2 equivalents of ethylsulfamoyl chloride were used. The crude compound was purified by Prep HPLC (Method A).

Yield: 12.17%;

$^1$H NMR (400 MHz, DMSO-d$_6$) δ 8.29 (s, 1H), 7.77 (s, 1H), 7.37-7.27 (m, 2H), 7.03-7.00 (m, 1H), 6.87 (br d, J=6.5 Hz, 1H), 6.78 (t, J=5.6 Hz, 1H), 6.34-6.06 (m, 1H), 3.85-3.68 (m, 8H), 2.99-2.98 (m, 2H), 2.85-2.79 (m, 2H), 2.44-2.18 (m, 6H), 1.96-1.91 (m, 1H), 1.66 (br s, 5H), 1.38-1.35 (m, 1H), 1.25-1.19 (m, 2H), 1.11-1.04 (m, 9H);

LCMS (Method C): Rt 1.71 min, m/z: 684.0 [M+H]$^+$;

HPLC (Method A): Rt 5.25 min, 99.21%.

Example 148. 2-((4-(7-(((2S,5R)-5-((N-(Cyclopropylmethyl)sulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide

Example 149. 2-((4-(7-(((2S,5R)-5-((N-Cyclopropylsulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide

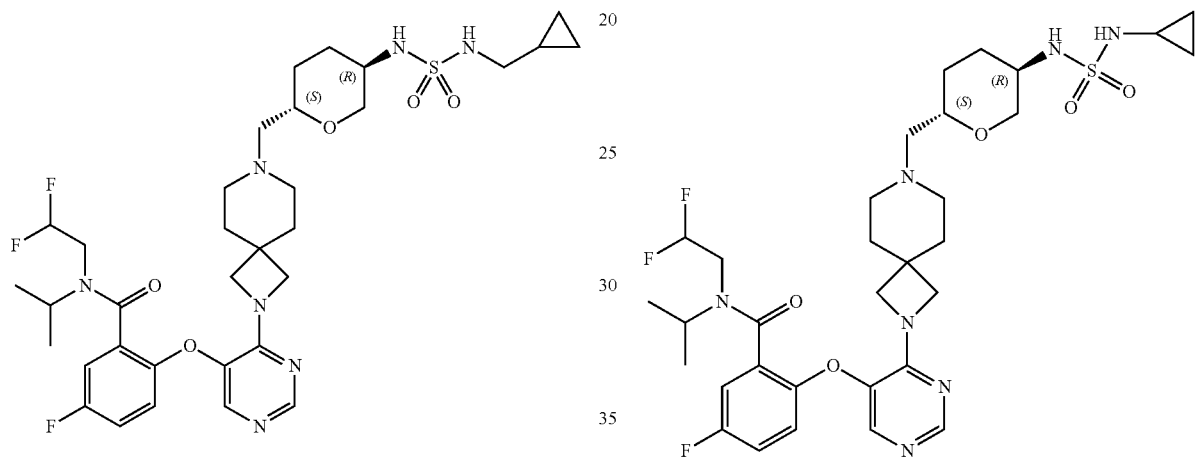

This compound was synthesized following the general procedure described for the synthesis of Example 137, except that 1 equivalent of ((2S,5R)-5-((N-(cyclopropylmethyl)sulfamoyl)amino)tetrahydro-2H-pyran-2-yl)methyl 4-methylbenzenesulfonate and 1.1 equivalents of KI were used. The crude compound was purified by Prep HPLC (Method A).

Yield: 23.80%;

$^1$H NMR (400 MHz, DMSO-d$_6$) δ 8.32-8.26 (s, 1H), 7.76 (s, 1H), 7.35 (dd, J=3.1, 8.3 Hz, 1H), 7.32-7.24 (m, 1H), 7.02 (dd, J=4.3, 9.1 Hz, 1H), 6.92 (t, J=6.1 Hz, 1H), 6.83 (d, J=7.1 Hz, 1H), 6.37-6.03 (m, 1H), 3.94-3.62 (m, 8H), 3.30-3.25 (m, 1H), 3.10-2.93 (m, 2H), 2.70-2.66 (m, 2H), 2.32-2.15 (m, 5H), 2.02-1.88 (m, 1H), 1.66 (br s, 5H), 1.43-1.27 (m, 1H), 1.27-1.14 (m, 2H), 1.08 (dd, J=6.5, 16.1 Hz, 6H), 0.98-0.86 (m, 1H), 0.47-0.37 (m, 2H), 0.21-0.11 (m, 2H);

LCMS (Method B): Rt 1.91 min, m/z: 710.3 [M+H]$^+$;

HPLC (Method A): Rt 5.53 min, 99.74%.

This compound was synthesized following the general procedure described for the synthesis of Example 137, except that 1.5 equivalent of ((2S,5R)-5-((N-cyclopropylsulfamoyl)amino)tetrahydro-2H-pyran-2-yl)methyl 4-methylbenzenesulfonate and 1 equivalent of KI were used, and ACN:NMP (3:1) was used as the solvent. The crude compound was purified by Prep HPLC (Method F).

Yield: 14.56%;

$^1$H NMR (400 MHz, DMSO-d$_6$) δ 8.36-8.23 (m, 1H), 7.84-7.69 (m, 1H), 7.38-7.24 (m, 2H), 7.23 (d, J=1.8 Hz, 1H), 7.06-6.95 (m, 2H), 6.38-6.03 (m, 1H), 3.95-3.62 (m, 8H), 3.30-3.21 (m, 1H), 3.11-2.94 (m, 2H), 2.32-2.15 (m, 6H), 1.92-2.01 (m, 1H), 1.66 (br s, 5H), 1.46-1.32 (m, 1H), 1.29-1.14 (m, 2H), 1.08 (dd, J=6.4, 15.8 Hz, 6H), 0.59-0.42 (m, 4H);

LCMS (Method E): Rt 1.78 min, m/z: 696.2 [M+H]$^+$;

HPLC (Method A): Rt 5.27 min, 98.07%.

Example 150. N-(2,2-Difluoroethyl)-5-fluoro-N-isopropyl-2-((4-(7-(((2S,5R)-5-((N-isopropylsulfamoyl)amino)tetrahydro-2H-pyran-2-yl)methyl)-2,7-diazaspiro[3.5]nonan-2-yl)pyrimidin-5-yl)oxy)benzamide

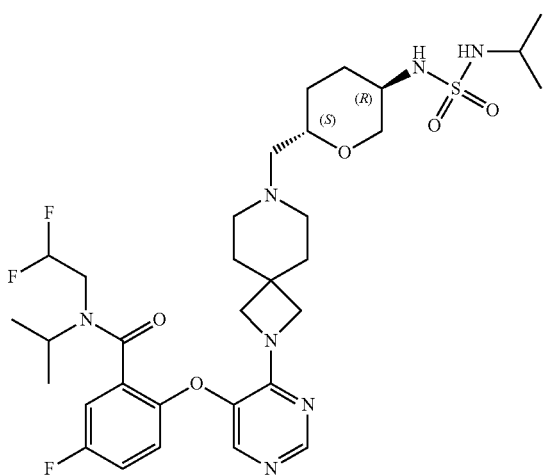

This compound was synthesized following the general procedure described for the synthesis of Example 137, except that 1.0 equivalent of KI and 1.4 equivalents of ((2S,5R)-5-((N-isopropylsulfamoyl)amino)tetrahydro-2H-pyran-2-yl)methyl 4-methylbenzenesulfonate were used. The crude compound was purified by Prep HPLC (Method D).

Yield: 10.73%;

$^1$H NMR (400 MHz, DMSO-d$_6$) δ 8.29 (s, 1H), 7.76 (s, 11H), 7.38-7.24 (m, 2H), 7.02 (dd, J=4.3, 9.1 Hz, 11H), 6.80 (d, J=6.8 Hz, 1H), 6.74 (d, J=7.3 Hz, 1H), 6.37-6.04 (m, 1H), 3.94-3.63 (m, 8H), 3.30-3.21 (m, 2H), 3.07-2.93 (m, 2H), 2.32-2.13 (m, 5H), 2.00-1.88 (m, 1H), 1.75-1.58 (m, 5H), 1.47-1.30 (m, 1H), 1.28-1.15 (m, 2H), 1.14-1.02 (m, 12H);

LCMS (Method E): Rt 1.76 min, m/z: 698.4 [M+H]$^+$;

HPLC (Method A): Rt 5.47 min, 99.83%.

Example 151. N-(2,2-Difluoroethyl)-5-fluoro-N-isopropyl-2-((4-(7-(((2S,5R)-5-((N-propylsulfamoyl)amino)tetrahydro-2H-pyran-2-yl)methyl)-2,7-diazaspiro[3.5]nonan-2-yl)pyrimidin-5-yl)oxy)benzamide

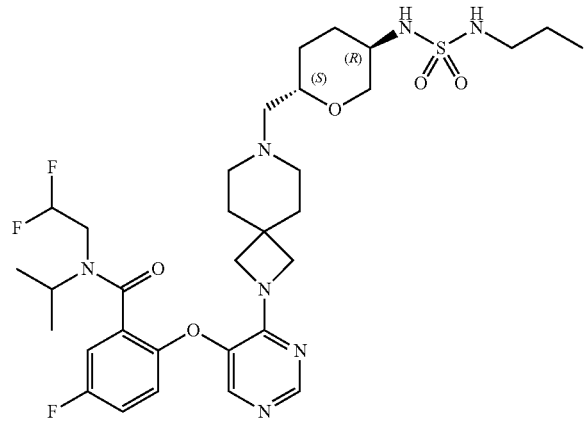

This compound was synthesized following the general procedure described for the synthesis of Example 137, except that 1 equivalent of ((2S,5R)-5-((N-propylsulfamoyl)amino)tetrahydro-2H-pyran-2-yl)methyl 4-methylbenzenesulfonate and 1.1 equivalents of KI were used. The crude compound was purified by Prep-HPLC (Method A).

Yield: 31.5%;

$^1$H NMR (400 MHz, DMSO-d$_6$) δ 8.29 (s, 1H), 7.77 (s, 11H), 7.35 (dd, J=3.1, 8.3 Hz, 1H), 7.32-7.24 (m, 1H), 7.02 (dd, J=4.3, 9.1 Hz, 1H), 6.87-6.77 (m, 2H), 6.38-6.03 (m, 1H), 3.91-3.80 (m, 4H), 3.79-3.61 (m, 4H), 3.32-3.28 (m, 1H), 3.07-2.93 (m, 2H), 2.79-2.69 (m, 2H), 2.32-2.15 (m, 5H), 2.00-1.89 (m, 1H), 1.66 (br s, 5H), 1.51-1.29 (m, 3H), 1.28-0.98 (m, 8H), 0.86 (t, J=7.4 Hz, 3H);

LCMS (Method B): Rt 1.32 min, m/z: 698.3 [M+H]$^+$;

HPLC (Method A): Rt 5.54 min, 99.01%.

Example 152. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2,2,2-trifluoroethyl)benzamide

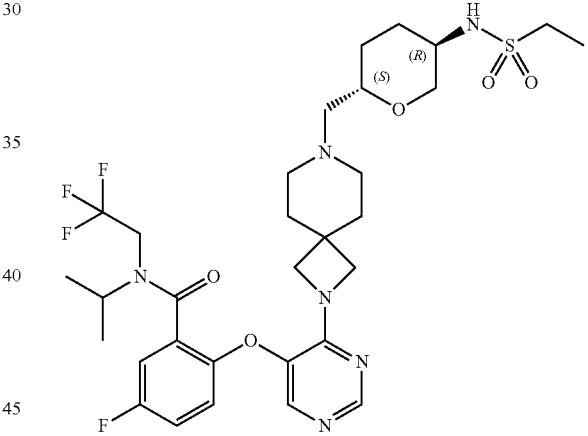

This compound was synthesized following the general procedure described for the synthesis of Example 137, except that 1.1 equivalents of ((2S,5R)-5-(ethylsulfonamido)tetrahydro-2H-pyran-2-yl)methyl 4-methylbenzenesulfonate was used, and NMP was used as the solvent. The crude compound was purified by Prep HPLC (Method B).

Yield: 16.04%;

$^1$H NMR (400 MHz, DMSO-d$_6$) δ 8.29 (s, 1H), 7.77 (s, 1H), 7.37-7.23 (m, 2H), 7.10 (d, J=7.6 Hz, 1H), 7.02 (dd, J=4.3, 9.0 Hz, 11H), 4.41-4.09 (m, 2H), 4.00-3.67 (m, 7H), 3.16-3.05 (m, 2H), 3.05-2.94 (m, 3H), 2.35-2.15 (m, 4H), 2.22-2.16 (m, 1H), 1.98-1.88 (m, 1H), 1.72-1.59 (m, 5H), 1.49-1.34 (m, 1H), 1.34-1.21 (m, 3H), 1.18 (t, J=7.3 Hz, 3H), 1.14-1.03 (m, 5H);

LCMS (Method B): Rt 1.28 min, m/z: 687.2 [M+H]$^+$;

HPLC (Method A): Rt 5.28 min, 98.91%.

Example 153. 2-((4-(7-(((2S,5R)-5-((N-Ethylsulfa-moyl)amino)tetrahydro-2H-pyran-2-yl)methyl)-2,7-diazaspiro[3.5]nonan-2-yl)pyrimidin-5-yl)oxy)-5-fluoro-N-isopropyl-N-(2,2,2-trifluoroethyl)benzamide

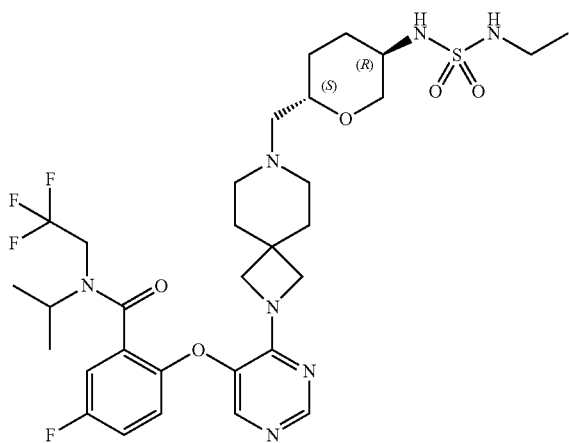

This compound was synthesized following the general procedure described for the synthesis of Example 137, except that 4 equivalents of K₂CO₃ was used. The crude compound was purified by Prep-HPLC (Method F).

Yield: 21.98%;

¹H NMR (400 MHz, DMSO-d₆) δ 8.29 (s, 1H), 7.83-7.73 (m, 1H), 7.37-7.26 (m, 2H), 7.02 (dd, J=4.3, 9.0 Hz, 1H), 6.91-6.75 (m, 2H), 4.40-4.25 (m, 1H), 4.25-4.13 (m, 1H), 3.98-3.89 (m, 1H), 3.88-3.79 (m, 3H), 3.78-3.68 (m, 2H), 3.30-3.24 (m, 1H), 3.06-2.92 (m, 2H), 2.86-2.78 (m, 2H), 2.32-2.14 (m, 5H), 2.00-1.90 (m, 1H), 1.76-1.57 (m, 5H), 1.44-1.27 (m, 2H), 1.25-1.16 (m, 1H), 1.14-1.02 (m, 9H);

LCMS (Method E): Rt 1.79 min, m/z: 702.4 [M+H]⁺;

HPLC (Method A): Rt 5.34 min, 99.26%.

Example 154. N-(3,3-Difluorocyclobutyl)-5-fluoro-N-isopropyl-2-((4-(7-(((2S,5R)-5-((N-methylsulfa-moyl)amino)tetrahydro-2H-pyran-2-yl)methyl)-2,7-diazaspiro[3.5]nonan-2-yl)pyrimidin-5-yl)oxy)benzamide

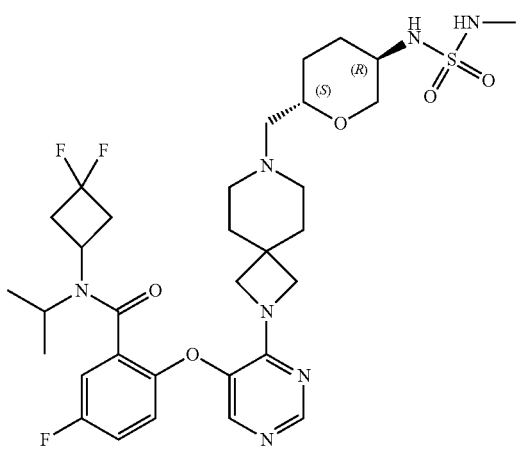

This compound was synthesized following the general procedure described for the synthesis of Example 137, except that and 1.1 equivalents of KI and 4.3 equivalents of K₂CO₃ were used, and NMP was used as the solvent. The crude compound was purified by Prep HPLC (Method B).

Yield: 27.1%;

¹H NMR (400 MHz, DMSO-d₆) δ 8.29 (s, 1H), 7.78 (s, 1H), 7.35 (dd, J=3.0, 8.0 Hz, 1H), 7.26 (dt, J=3.0, 8.6 Hz, 1H), 7.03 (dd, J=4.3, 8.9 Hz, 1H), 6.90 (d, J=7.1 Hz, 1H), 6.68 (q, J=5.1 Hz, 1H), 3.99-3.82 (m, 4H), 3.81-3.63 (m, 4H), 3.61-3.46 (m, 1H), 3.30-3.23 (m, 1H), 3.07-2.91 (m, 2H), 2.80-2.71 (m, 2H), 2.43 (d, J=5.1 Hz, 3H), 2.32-2.15 (m, 5H), 2.01-1.90 (m, 1H), 1.67 (d, J=5.0 Hz, 5H), 1.49-1.27 (m, 2H), 1.26-1.15 (m, 1H), 1.10 (d, J=6.0 Hz, 3H), 1.02 (d, J=6.5 Hz, 3H);

LCMS (Method A): Rt 1.75 min, m/z: 696.1 [M+H]⁺;

HPLC (Method A): Rt 5.32 min, 95.90%.

Example 155. N-(3,3-Difluorocyclobutyl)-2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

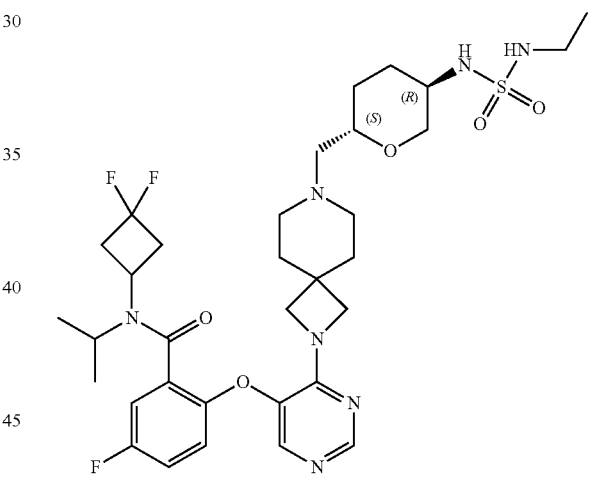

This compound was synthesized following the general procedure described for the synthesis of Example 137, except that 4.3 equivalents of K₂CO₃ and 1.1 equivalents of KI were used, and NMP was used as the solvent. The crude compound was purified by Prep HPLC (Method F).

Yield: 20.82%;

¹H NMR (400 MHz, DMSO-d₆) δ 8.28 (s, 1H), 7.78 (s, 1H), 7.35 (dd, J=2.9, 8.2 Hz, 1H), 7.26 (dt, J=3.1, 8.6 Hz, 1H), 7.03 (dd, J=4.3, 9.1 Hz, 1H), 6.86 (d, J=6.9 Hz, 1H), 6.78 (t, J=5.8 Hz, 1H), 4.01-3.82 (m, 4H), 3.80-3.64 (m, 4H), 3.63-3.43 (m, 1H), 3.29-3.21 (m, 1H), 3.07-2.92 (m, 2H), 2.89-2.78 (m, 2H), 2.77-2.69 (m, 1H), 2.46-2.38 (m, 1H), 2.32-2.15 (m, 5H), 1.99-1.90 (m, 1H), 1.67 (br s, 5H), 1.50-1.27 (m, 2H), 1.27-1.15 (m, 1H), 1.14-0.98 (m, 9H);

LCMS (Method A): Rt 1.80 min, m/z: 710.2 [M+H]⁺;

HPLC (Method A): Rt 5.55 min, 99.14%.

Example 156. N-(3,3-Difluorocyclobutyl)-5-fluoro-N-isopropyl-2-((4-(7-(((2S,5R)-5-((1-methyl-1H-pyrazole)-4-sulfonamido)tetrahydro-2H-pyran-2-yl)methyl)-2,7-diazaspiro[3.5]nonan-2-yl)pyrimidin-5-yl)oxy)benzamide

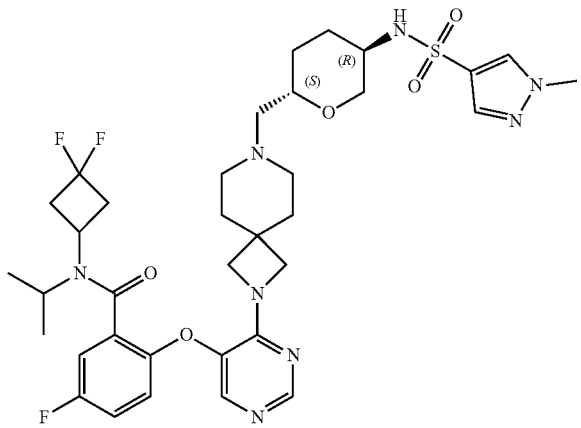

This compound was synthesized following the general procedure described for the synthesis of Example 137, except that 4.3 equivalents of $K_2CO_3$, 1 equivalent of ((2S,5R)-5-((1-methyl-1H-pyrazole)-4-sulfonamido)tetrahydro-2H-pyran-2-yl)methyl 4-methylbenzenesulfonate, and 1.1 equivalents of KI were used, and NMP was used as the solvent. The crude compound was purified by Prep HPLC (Method D).

Yield: 15.86%;

$^1$H NMR (400 MHz, DMSO-d$_6$) δ 8.28 (s, 1H), 8.24 (s, 1H), 7.78 (s, 1H), 7.72 (s, 1H), 7.52 (d, J=6.4 Hz, 1H), 7.35 (dd, J=3.1, 8.2 Hz, 1H), 7.26 (dt, J=3.0, 8.6 Hz, 1H), 7.02 (dd, J=4.3, 9.1 Hz, 1H), 3.98-3.82 (m, 6H), 3.81-3.67 (m, 5H), 3.61-3.46 (m, 1H), 3.29-3.23 (m, 1H), 3.03-2.89 (m, 2H), 2.80-2.70 (m, 1H), 2.32-2.13 (m, 5H), 1.79-1.56 (m, 7H), 1.48-1.25 (m, 2H), 1.23-1.13 (m, 1H), 1.10 (d, J=6.4 Hz, 3H), 1.02 (d, J=6.3 Hz, 3H);

LCMS (Method A): Rt 1.80 min, m/z: 747.5 [M+H]$^+$;
HPLC (Method A): Rt 6.92 min 99.38%.

Example 157. {[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}(2,2,2-trifluoroethyl)amine

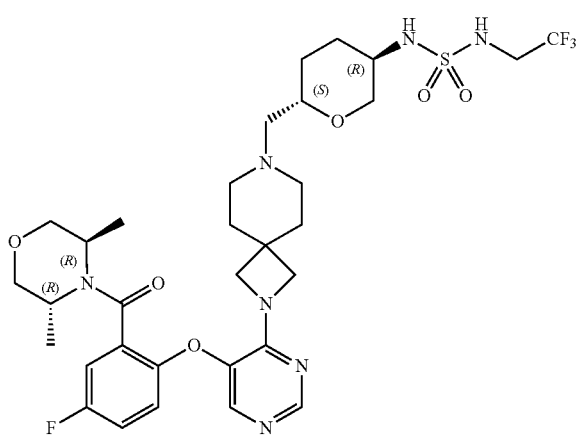

This compound was synthesized following the general procedure described for the synthesis of Example 137, except that 4.5 equivalents of $K_2CO_3$ was used, and ACN:NMP (5:1) was used as the solvent. The crude compound was purified by Prep HPLC (Method D).

Yield: 14.41%;

$^1$H NMR (400 MHz, DMSO-d$_6$) δ 8.28 (s, 1H), 7.90-7.80 (m, 1H), 7.69 (s, 1H), 7.38 (dd, J=2.4, 8.1 Hz, 11H), 7.33-7.24 (m, 1H), 7.19 (d, J=7.1 Hz, 11H), 7.04 (dd, J=4.4, 9.0 Hz, 1H), 4.05-3.70 (m, 9H), 3.69-3.46 (m, 5H), 3.11-2.94 (m, 2H), 2.32-2.16 (m, 5H), 2.02-1.90 (m, 1H), 1.66 (br s, 6H), 1.44-1.29 (m, 1H), 1.29-1.09 (m, 7H);

LCMS (Method B): Rt 1.22 min, m/z: (730.4) [M+H]$^+$;
HPLC (Method A): Rt 5.08 min, 99.45% (Max).

Example 158. (Cyclopropylmethyl)({[(3R,6S)-6-{[2-(5-{2-[(3R,5R)-3,5-dimethylmorpholine-4-carbonyl]-4-fluorophenoxy}pyrimidin-4-yl)-2,7-diazaspiro[3.5]nonan-7-yl]methyl}oxan-3-yl]sulfamoyl})amine

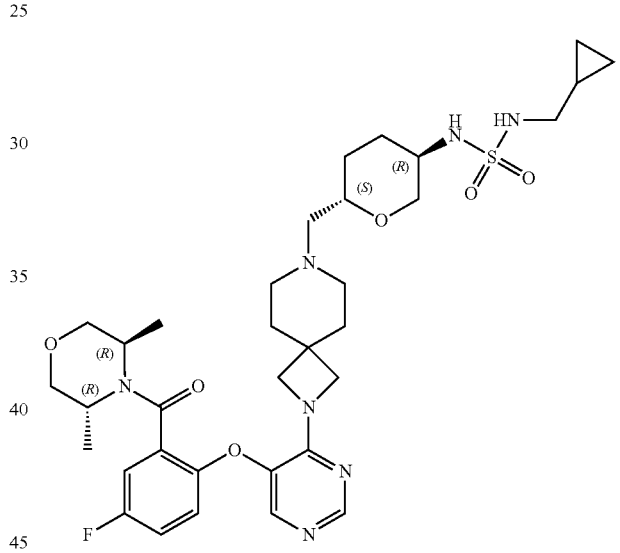

This compound was synthesized following the general procedure described for the synthesis of Example 137, except that 0.8 equivalents of ((2S,5R)-5-((N-(cyclopropylmethyl)sulfamoyl)amino)tetrahydro-2H-pyran-2-yl)methyl 4-methylbenzenesulfonate were used, and ACN:NMP (1:1) used as the solvent. The crude compound was purified by Prep HPLC (Method A).

Yield: 20.96%;

$^1$H NMR (400 MHz, DMSO-d$_6$) δ 8.28 (s, 1H), 7.69 (s, 1H), 7.39-7.37 (m, 1H), 7.34-7.24 (m, 1H), 7.04 (dd, J=4.4, 9.0 Hz, 1H), 6.92 (t, J=6.0 Hz, 1H), 6.83 (d, J=7.3 Hz, 1H), 4.03-3.44 (m, 10H), 3.30-3.25 (m, 1H), 3.11-2.91 (m, 2H), 2.68-2.65 (m, 2H), 2.32-2.16 (m, 6H), 2.01-1.89 (m, 1H), 1.77-1.61 (m, 5H), 1.42-1.05 (m, 9H), 0.98-0.88 (m, 1H), 0.45-0.39 (m, 2H), 0.19-0.13 (m, 2H);

LCMS (Method B): Rt 1.23 min, m/z: 702.6 [M+H]$^+$;
HPLC (Method A): Rt 5.02 min, 99.66%.

Example 159. N-[(3R,6S)-6-{[2-(5-{2-[(3R,5R)-3,5-Dimethylmorpholine-4-carbonyl]-4-fluorophenoxy}pyrimidin-4-yl)-2,7-diazaspiro[3.5]nonan-7-yl]methyl}oxan-3-yl](cyclopropylamino)sulfonamide

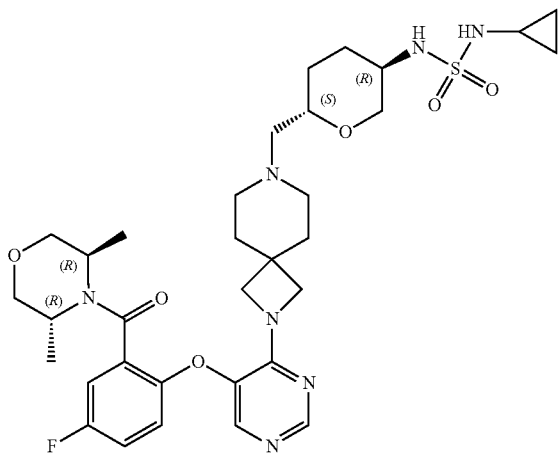

This compound was synthesized following the general procedure described for the synthesis of Example 137, except that 1 equivalent of KI was used, and ACN:NMP (5:1) was used as the solvent. The crude compound was purified by Prep HPLC (Method E).

Yield: 21.32%;
$^1$H NMR (400 MHz, DMSO-d$_6$) δ 8.28 (s, 1H), 7.69 (s, 1H), 7.39-7.37 (m, 1H), 7.31-7.26 (m, 1H), 7.23 (d, J=1.8 Hz, 1H), 7.08-6.98 (m, 2H), 4.02-3.77 (m, 9H), , 3.11-2.95 (m, 2H), 2.32-2.14 (m, 9H), 2.04-1.92 (m, 1H), 1.68 (d, J=4.8 Hz, 5H), 1.47-1.02 (m, 9H), 0.59-0.43 (m, 4H);
LCMS (Method E): Rt 1.57 min, m/z: (688.3) [M+H]$^+$;
HPLC (Method A): Rt 4.68 min, 99.37%.

Example 160. {[(3R,6S)-6-{[2-(5-{2-[(3R,5S)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}dimethylamine

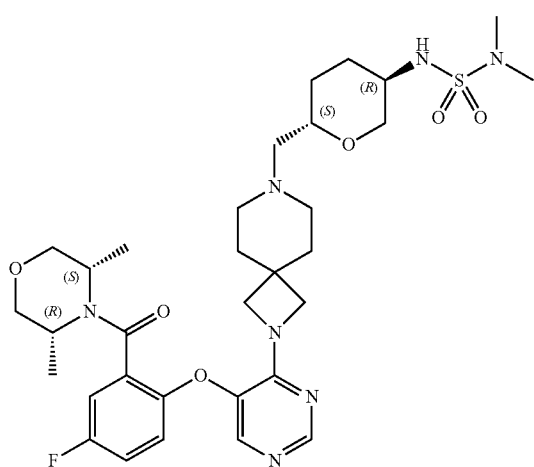

This compound was synthesized following the general procedure described for the synthesis of Example 137, except that 1.4 equivalents of (2-((4-(2,7-diazaspiro[3.5]nonan-2-yl)pyrimidin-5-yl)oxy)-5-fluorophenyl)((3S,5R)-3,5-dimethylmorpholino)methanone hydrochloride, 1 equivalent of ((2S,5R)-5-((N,N-dimethylsulfamoyl)amino)tetrahydro-2H-pyran-2-yl)methyl 4-methylbenzenesulfonate, 4 equivalents of K$_2$CO$_3$, and 1 equivalent of KI were used. The crude compound was purified by Prep-HPLC (Method E).

Yield: 12.32%;
$^1$H NMR (400 MHz, DMSO-d$_6$) δ 8.28-8.23 (m, 1H), 7.76-7.66 (m, 1H), 7.44-7.33 (m, 1H), 7.30-7.25 (m, 1H), 7.20 (d, J=7.4 Hz, 1H), 7.15-6.99 (m, 1H), 4.36 (br s, 1H), 3.99-3.53 (m, 9H), 3.10-2.95 (m, 2H), 2.68-2.65 (m, 2H), 2.64 (s, 6H), 2.32-2.16 (m, 5H), 2.00-1.92 (m, 1H), 1.66 (br s, 5H), 1.46-1.14 (m, 9H);
LCMS (Method B): Rt 1.21 min, m/z: 676.2 [M+H]$^+$;
HPLC (Method G): Rt 3.25 min, 97.51%.

Example 161. N-((3R,6S)-6-((2-(5-(2-((3R,5S)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)azetidine-1-sulfonamide

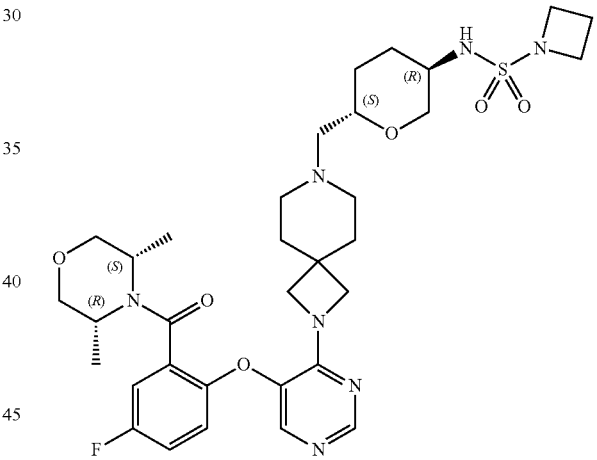

This compound was synthesized following the general procedure described for the synthesis of Example 137, except that 1.2 equivalents of (2-((4-(2,7-diazaspiro[3.5]nonan-2-yl)pyrimidin-5-yl)oxy)-5-fluorophenyl)((3S,5R)-3,5-dimethylmorpholino)methanone hydrochloride, 1 equivalent of ((2S,5R)-5-(azetidine-1-sulfonamido)tetrahydro-2H-pyran-2-yl)methyl 4-methylbenzenesulfonate, 1 equivalent of KI, and 3 equivalents of K$_2$CO$_3$ were used. The crude was purified by Prep-HPLC (Method F).

Yield: 15.46%;
$^1$H NMR (400 MHz, DMSO-d$_6$) δ 8.34-8.24 (m, 1H), 7.80-7.65 (m, 1H), 7.45-7.33 (m, 1H), 7.31-7.19 (m, 2H), 7.15-7.00 (m, 1H), 4.42-4.32 (m, 1H), 3.95-3.72 (m, 6H), 3.67 (t, J=7.6 Hz, 4H), 3.67-3.52 (m, 3H), 3.42-3.32 (m, 1H), 3.31-3.14 (m, 1H), 3.11-2.94 (m, 2H), 2.32-2.16 (m, 5H), 2.10 (quin, J=7.6 Hz, 2H), 2.01-1.91 (m, 1H), 1.67 (br s, 5H), 1.48-1.11 (m, 9H);
LCMS (Method B): Rt 1.21 min, m/z: 688.4 [M+H]$^+$;
HPLC (Method A): Rt 4.76 min, 99.23%.

Example 162: {[(3R,6S)-6-{[2-(5-{2-[(3R,5S)-3,5-Dimethylmorpholine-4-carbonyl]-4-fluorophenoxy}pyrimidin-4-yl)-2,7-diazaspiro[3.5]nonan-7-yl]methyl}oxan-3-yl]sulfamoyl}(2,2,2-trifluoroethyl)amine

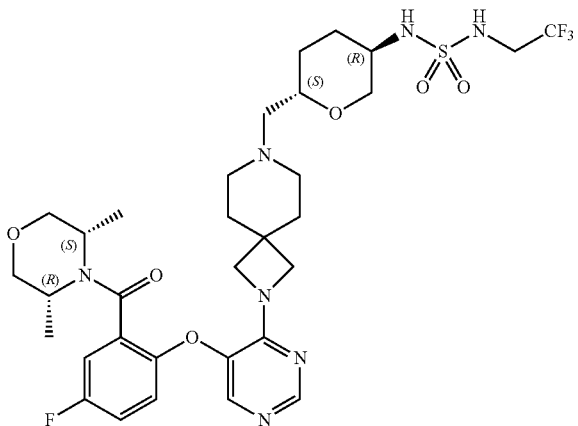

This compound was synthesized following the general procedure described for the synthesis of Example 137, except that 5 equivalents of $K_2CO_3$ and 1 equivalent of ((2S,5R)-5-((N-(2,2,2-trifluoroethyl)sulfamoyl)amino)tetrahydro-2H-pyran-2-yl)methyl 4-methylbenzenesulfonate were used, and ACN:NMP (5:1) was used as the solvent. The crude compound was purified by Prep HPLC (Method F).

Yield: 8.02%;

$^1$H NMR (400 MHz, DMSO-$d_6$) δ (8.29 (s, 1H), 7.85-7.64 (m, 2H), 7.44-7.33 (m, 1H), 7.32-7.23 (m, 1H), 7.19 (d, J=7.0 Hz, 1H), 7.14-7.00 (m, 1H), 4.44-4.28 (m, 1H), 4.01-3.49 (m, 1H), 3.32-2.90 (m, 4H), 2.32-2.15 (m, 5H), 2.03-1.91 (m, 1H), 1.67 (br s, 5H), 1.45-1.12 (m, 9H);

LCMS (Method B): Rt 1.26 min, m/z: (730.4) [M+H]$^+$;
HPLC (Method A): Rt 5.09 min, 95.12%.

Example 163. N-[(3R,6S)-6-{[2-(5-{2-[(3R,5S)-3,5-Dimethylmorpholine-4-carbonyl]-4-fluorophenoxy}pyrimidin-4-yl)-2,7-diazaspiro[3.5]nonan-7-yl]methyl}oxan-3-yl](cyclopropylamino)sulfonamide

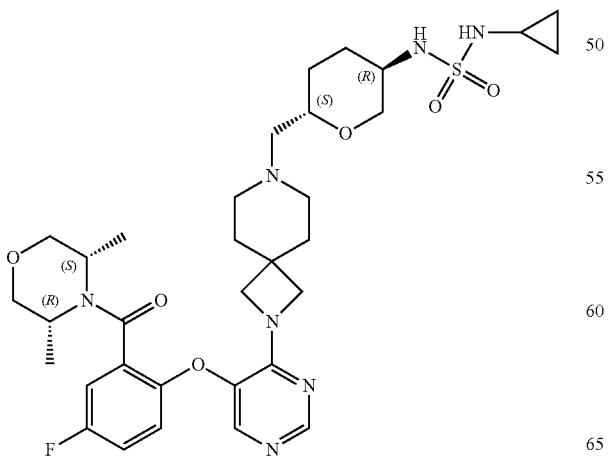

This compound was synthesized following the general procedure described for the synthesis of Example 137, except that 3.5 equivalents of $K_2CO_3$ and 1 equivalent of KI were used, and ACN:NMP (1:1) was used as the solvent. The crude compound was purified by Prep HPLC (Method A).

Yield: 8.68%;

$^1$H NMR (400 MHz, DMSO-$d_6$) δ 8.31-8.25 (m, 1H), 7.79-7.64 (m, 1H), 7.43-7.33 (m, 1H), 7.32-7.17 (m, 2H), 7.15-6.94 (m, 2H), 4.43-4.29 (m, 1H), 3.98-3.87 (m, 2H), 3.85-3.64 (m, 5H), 3.63-3.53 (m, 2H), 3.31-2.96 (m, 3H), 2.32-2.17 (m, 6H), 2.03-1.93 (m, 1H), 1.75-1.57 (m, 6H), 1.47-1.14 (m, 9H), 0.57-0.45 (m, 4H);

LCMS (Method E): Rt 1.55 min, m/z: (688.4) [M+H]$^+$;
HPLC (Method A): Rt 4.64 min, 98.15%.

Example 164. 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide

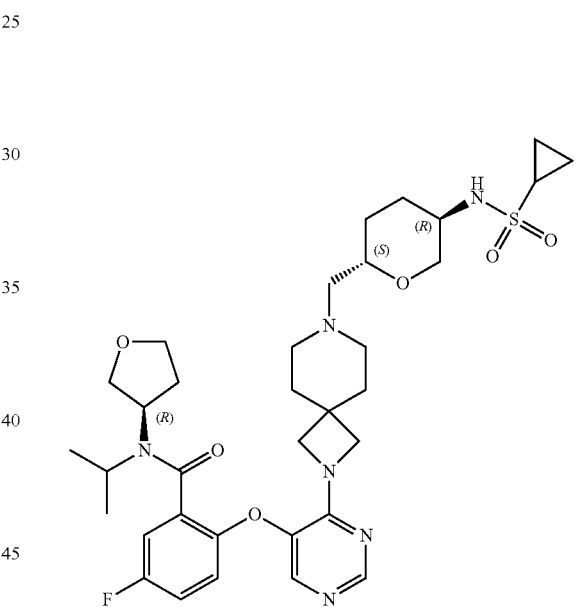

This compound was synthesized following the general procedure described for the synthesis of Example 137, except that 5 equivalents of $K_2CO_3$ and 1 equivalent of KI were used, and NMP was used as the solvent. The crude compound was purified by Prep HPLC (Method F).

Yield: 11.23%;

$^1$H NMR (400 MHz, DMSO-$d_6$) δ 8.24-8.29 (m, J=2.8 Hz, 1H), 7.86-7.68 (m, 1H), 7.36-7.20 (m, 2H), 7.12 (d, J=7.9 Hz, 11H), 7.09-7.00 (m, 1H), 4.27-3.64 (m, 10H), 3.61-3.45 (m, 1H), 3.21-3.12 (m, 1H), 3.08-2.97 (m, 1H), 2.63-2.55 (m, 3H), 2.32-2.16 (m, 5H), 2.06-1.91 (m, 2H), 1.67 (br s, 5H), 1.49-1.38 (m, 2H), 1.37-1.19 (m, 2H), 1.16-1.01 (m, 4H), 1.01-0.86 (m, 5H).

LCMS (Method E): Rt 1.59 min, m/z: 687.4 [M+H]$^+$;
HPLC (Method A): Rt 4.82 min, 99.13%.

Example 165. 2-((4-(7-(((2S,5R)-5-((N,N-Diethyl-sulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide

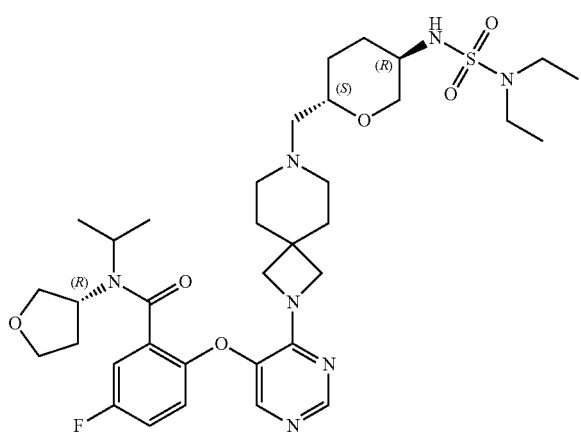

This compound was synthesized following the general procedure described for the synthesis of Example 137, except that 7 equivalents of K₂CO₃ was used, and NMP was used as the solvent. The crude compound was purified by Prep-HPLC (Method B).
Yield: 6.34%;
¹H NMR (400 MHz, DMSO-d₆) δ 8.27 (s, 1H), 7.85-7.69 (m, 1H), 7.36-7.20 (m, 2H), 7.15-7.00 (m, 2H), 4.28-3.62 (m, 11H), 3.45-3.26 (m, 2H), 3.13 (q, J=7.1 Hz, 4H), 3.04-2.89 (m, 2H), 2.31-2.15 (m, 5H), 2.05-1.86 (m, 2H), 1.66 (br s, 5H), 1.51-1.29 (m, 3H), 1.28-1.17 (m, 1H), 1.17-0.95 (m, 11H);
LCMS (Method C): Rt 1.79 min, m/z: 718.1 [M+H]⁺;
HPLC (Method A): Rt 5.41 min, 99.51%.

Example 166. 5-Fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)-N—((R)-tetrahydrofuran-3-yl)benzamide

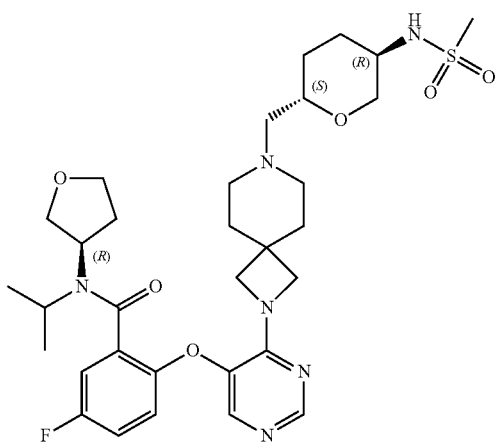

This compound was synthesized following the general procedure described for the synthesis of Example 137, except that 7 equivalents of K₂CO₃ was used, and NMP was used as the solvent. The crude compound was purified by Prep-HPLC (Method A).
Yield: 10.59%;
¹H NMR (400 MHz, DMSO-d₆) δ 8.36-8.20 (m, 1H), 7.86-7.69 (m, 1H), 7.38-7.19 (m, 2H), 7.11-7.00 (m, 2H), 4.09-3.64 (m, 11H), 3.62-3.40 (m, 2H), 3.08 (s, 1H), 3.04-2.94 (m, 1H), 2.92 (s, 3H), 2.32-2.15 (m, 5H), 2.04-1.88 (m, 2H), 1.66 (br s, 5H), 1.50-1.21 (m, 4H), 1.18-0.93 (m, 5H);
LCMS (Method A): Rt 1.63 min, m/z: 661.1 [M+H]⁺;
HPLC (Method F): Rt 4.56 min, 99.85%.

Example 167. 2-((4-(7-(((2S,5R)-5-((N,N-Dimethyl-sulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide

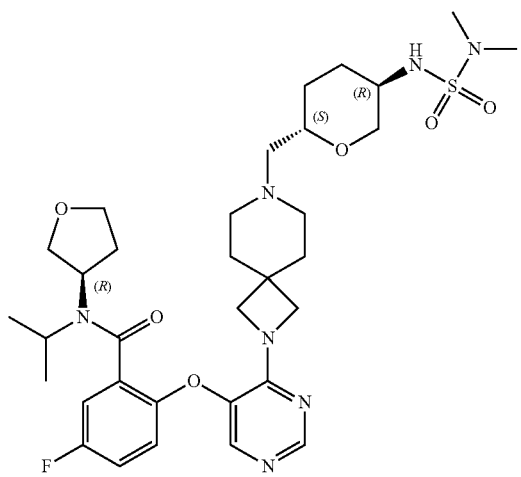

This compound was synthesized following the general procedure described for the synthesis of Example 137, except that 3.5 equivalents of K₂CO₃ and 1.1 equivalents of KI were used, and NMP was used as the solvent. The crude compound was purified by Prep HPLC (Method B).
Yield: 28.6%;
¹H NMR (400 MHz, DMSO-d₆) δ 8.32-8.21 (m, 1H), 7.85-7.69 (m, 1H), 7.37-7.16 (m, 3H), 7.10-7.00 (m, 1H), 4.28-3.62 (m, 11H), 3.61-3.36 (m, 1H), 3.31-3.22 (m, 1H), 3.09-2.94 (m, 2H), 2.64 (s, 6H), 2.32-2.15 (m, 5H), 2.05-1.86 (m, 2H), 1.66 (br s, 5H), 1.51-1.30 (m, 3H), 1.28-1.16 (m, 1H), 1.15-0.94 (m, 5H);
LCMS (Method C): Rt 1.87 min, m/z: 690.2 [M+H]⁺;
HPLC (Method A): Rt 4.88 min, 99.38%.

Example 168. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide

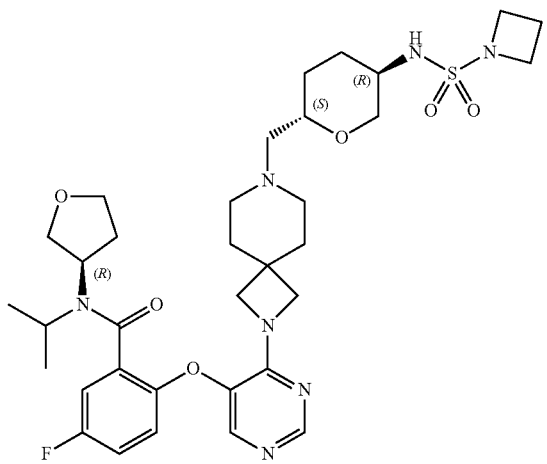

This compound was synthesized following the general procedure described for the synthesis of Example 137, except that 1 equivalent of ((2S,5R)-5-(azetidine-1-sulfonamido)tetrahydro-2H-pyran-2-yl)methyl 4-methylbenzenesulfonate, 5 equivalents of $K_2CO_3$, and 1 equivalent of KI were used. The crude compound was purified by Prep HPLC (Method E).

Yield: 11.69%;

$^1$H NMR (400 MHz, DMSO-d$_6$) δ 8.31-8.23 (m, 1H), 7.85-7.69 (m, 1H), 7.36-7.19 (m, 3H), 7.11-7.00 (m, 1H), 4.06-3.69 (m, 10H), 3.67 (t, J=7.6 Hz, 4H), 3.60-3.37 (m, 1H), 3.31-3.24 (m, 1H), 3.13-2.94 (m, 2H), 2.32-2.16 (m, 5H), 2.15-1.84 (m, 5H), 1.67 (br s, 5H), 1.51-1.31 (m, 3H), 1.30-1.18 (m, 1H), 1.16-0.95 (m, 5H);

LCMS (Method E): Rt 1.61 min, m/z: 702.5 [M+H]$^+$;
HPLC (Method A): 4.79 min, 99.80%.

Example 169. 5-Fluoro-N-isopropyl-2-((4-(7-(((2S,5R)-5-(pyrrolidine-1-sulfonamido)tetrahydro-2H-pyran-2-yl)methyl)-2,7-diazaspiro[3.5]nonan-2-yl)pyrimidin-5-yl)oxy)-N—((R)-tetrahydrofuran-3-yl)benzamide

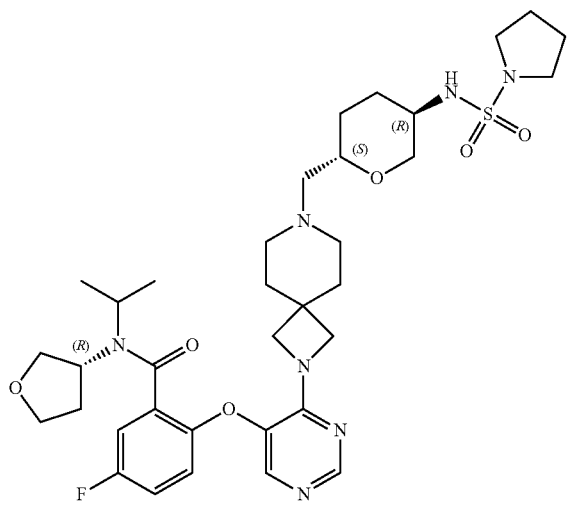

This compound was synthesized following the general procedure described for the synthesis of Example 137, except that 5 equivalents of $K_2CO_3$ and 1 equivalent of KI were used, and NMP was used as the solvent. The crude compound was purified by Prep HPLC (Method D).

Yield: 11.99%;

$^1$H NMR (400 MHz, DMSO-d$_6$) δ 8.27 (d, J=2.5 Hz, 1H), 7.84-7.69 (m, 1H), 7.34-7.21 (m, 2H), 7.14 (d, J=7.5 Hz, 1H), 7.09-6.98 (m, 1H), 4.06-3.64 (m, 10H), 3.63-3.46 (m, 1H), 3.19-2.94 (m, 7H), 2.32-2.15 (m, 5H), 2.02-1.90 (m, 2H), 1.88-1.76 (m, 5H), 1.66 (br s, 5H), 1.55-1.30 (m, 3H), 1.29-1.16 (m, 1H), 1.16-0.95 (m, 5H);

LCMS (Method B): Rt 1.30 min, m/z: 716.4 [M+H]$^+$;
HPLC (Method A): Rt 5.09 min, 96.99%.

Example 170. 2-((4-(7-(((2S,5R)-5-((N-Ethyl-N-methylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide

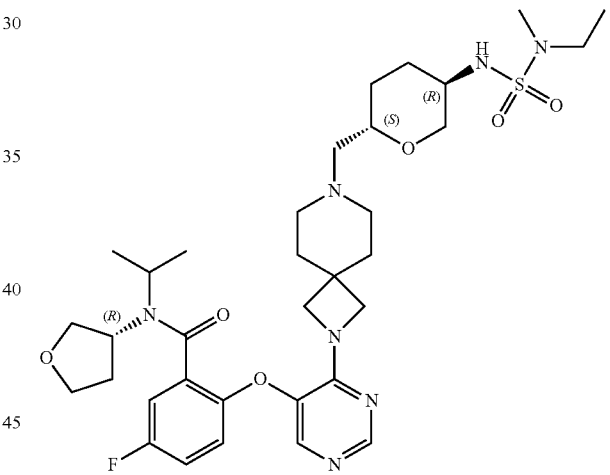

This compound was synthesized following the general procedure described for the synthesis of Example 137, except that 5 equivalents of $K_2CO_3$ and 1 equivalent of KI were used, and NMP was used as the solvent. The crude compound was purified by Prep HPLC (Method A).

Yield: 3.27%;

$^1$H NMR (400 MHz, DMSO-d$_6$) δ 8.27 (br s, 1H), 7.85-7.68 (m, 1H), 7.36-7.20 (m, 2H), 7.16 (d, J=6.6 Hz, 1H), 7.10-7.01 (m, 1H), 4.28-3.63 (m, 11H), 3.62-3.44 (m, 1H), 3.14-2.93 (m, 4H), 2.65 (s, 3H), 2.32-2.14 (m, 6H), 2.04-1.84 (m, 2H), 1.66 (br s, 5H), 1.51-1.30 (m, 3H), 1.28-1.16 (m, 1H), 1.15-0.94 (m, 8H);

LCMS (Method E): Rt 1.68 min, m/z: 704.4 [M+H]$^+$;
HPLC (Method A): Rt 5.14 min, 99.31%.

Example 171. 5-Fluoro-N-isopropyl-N—((R)-tetrahydrofuran-3-yl)-2-((4-(7-(((2S,5R)-5-((N-(2,2,2-trifluoroethyl)sulfamoyl)amino)tetrahydro-2H-pyran-2-yl)methyl)-2,7-diazaspiro[3.5]nonan-2-yl)pyrimidin-5-yl)oxy)benzamide

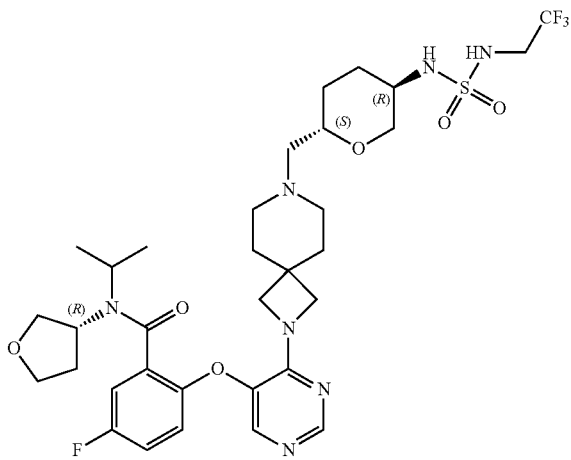

This compound was synthesized following the general procedure described for the synthesis of Example 137, except that 5 equivalents of $K_2CO_3$ and 1 equivalent of KI were used, and NMP was used as the solvent. The crude compound was purified by Prep HPLC (Method A).

Yield: 4.38%;

$^1$H NMR (400 MHz, DMSO-$d_6$) δ 8.30-8.25 (m, 1H), 7.86-7.71 (m, 2H), 7.35-7.21 (m, 2H), 7.19 (d, J=7.1 Hz, 1H), 7.08-7.01 (m, 1H), 4.27-3.66 (m, 10H), 3.65-3.53 (m, 2H), 3.53-3.37 (m, 1H), 3.10-2.94 (m, 2H), 2.33-2.15 (m, 6H), 2.11-1.84 (m, 3H), 1.67 (br s, 5H), 1.47 (d, J=6.6 Hz, 1H), 1.42-1.27 (m, 2H), 1.27-1.16 (m, 1H), 1.16-0.93 (m, 5H);

LCMS (Method E): Rt 1.68 min, m/z: 744.4 [M+H]$^+$;
HPLC (Method A): Rt 5.3 min, 99.08%.

Example 172. 2-((4-(7-(((2S,5R)-5-((N-ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N—((R)-tetrahydrofuran-3-yl)benzamide

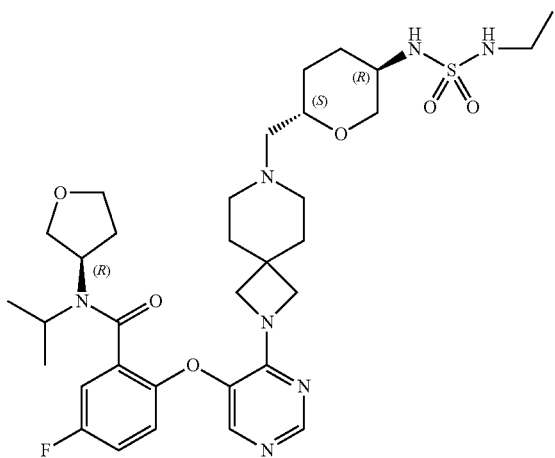

This compound was synthesized following the general procedure described for the synthesis of Example 137, except that 1.1 equivalents of ((2S,5R)-5-((N-ethylsulfamoyl)amino)tetrahydro-2H-pyran-2-yl)methyl 4-methylbenzenesulfonate, 5 equivalents of $K_2CO_3$, and 1 equivalent of KI were used, and NMP was used as the solvent. The crude compound was purified by Prep-HPLC (Method A).

Yield: 11.67%;

$^1$H NMR (400 MHz, DMSO-$d_6$) δ 8.29-8.25 (m, 1H), 7.84-7.70 (m, 1H), 7.35-7.21 (m, 2H), 7.08-7.01 (m, 1H), 6.90-6.75 (m, 2H), 4.29-3.54 (m, 11H), 3.53-3.37 (m, 1H), 3.30-3.25 (m, 1H), 3.08-2.94 (m, 2H), 2.82 (q, J=7.2 Hz, 2H), 2.32-2.13 (m, 5H), 2.06-1.85 (m, 2H), 1.76-1.59 (m, 5H), 1.51-1.29 (m, 3H), 1.27-1.17 (m, 1H), 1.16-0.93 (m, 8H)

LCMS (Method B): Rt 1.20 min, m/z: 690.6 [M+H]$^+$;
HPLC (Method A): Rt 4.70 min, 99.25%.

Example 173. 5-Fluoro-N-isopropyl-2-((4-(7-(((2S,5R)-5-(methylsulfonamido)tetrahydro-2H-pyran-2-yl)methyl)-2,7-diazaspiro[3.5]nonan-2-yl)pyrimidin-5-yl)oxy)-N—((S)-tetrahydrofuran-3-yl)benzamide

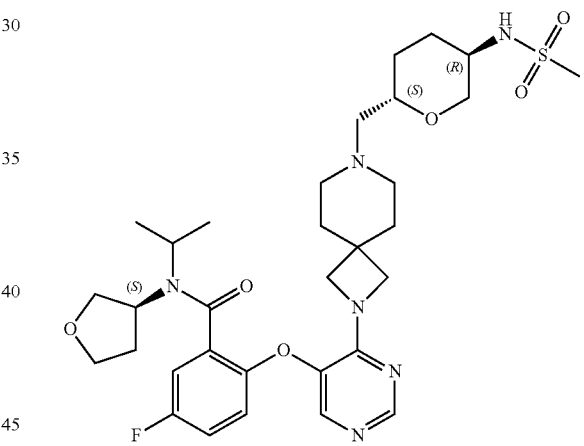

This compound was synthesized following the general procedure described for the synthesis of Example 137, except that 7 equivalents of $K_2CO_3$ and 1.6 equivalents of ((2S,5R)-5-(methylsulfonamido)tetrahydro-2H-pyran-2-yl)methyl 4-methylbenzenesulfonate were used, and ACN:NMP (3:1) was used as the solvent. The crude compound was purified by Prep-HPLC (Method I).

Yield: 15.16%;

$^1$H NMR (400 MHz, DMSO-$d_6$) δ 8.31-8.24 (m, 1H), 7.84-7.70 (m, 1H), 7.36-7.21 (m, 2H), 7.13-7.01 (m, 2H), 4.27-3.63 (m, 11H), 3.62-3.38 (m, 1H), 3.26-3.06 (m, 2H), 3.04-2.89 (m, 4H), 2.32-2.16 (m, 5H), 2.11-1.81 (m, 3H), 1.67 (br s, 5H), 1.51-1.19 (m, 4H), 1.13 (d, J=6.5 Hz, 1H), 1.06 (dd, J=6.6, 12.3 Hz, 2H), 0.98 (d, J=6.5 Hz, 1H);

LCMS (Method C): Rt 1.49 min, m/z: 661.1 [M+H]$^+$;
HPLC (Method A): Rt 4.52 min, 99.80%.

Example 174. 5-Fluoro-N-isopropyl-2-((4-(7-(((2S,5R)-5-((1-methylethyl)sulfonamido)tetrahydro-2H-pyran-2-yl)methyl)-2,7-diazaspiro[3.5]nonan-2-yl)pyrimidin-5-yl)oxy)-N—((S)-tetrahydrofuran-3-yl)benzamide

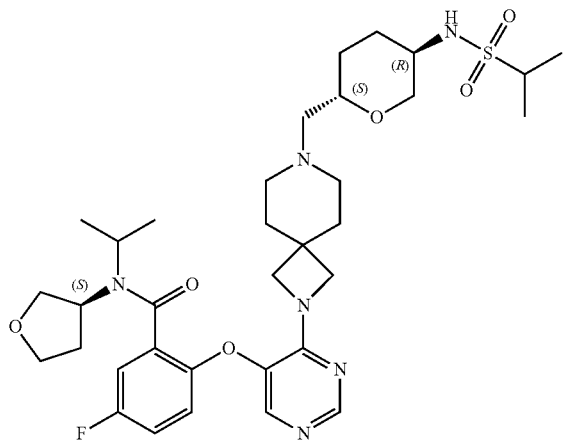

This compound was synthesized following the general procedure described for the synthesis of Example 137, except that 7 equivalents of $K_2CO_3$ and 1.6 equivalents of ((2S,5R)-5-((1-methylethyl)sulfonamido)tetrahydro-2H-pyran-2-yl)methyl 4-methylbenzenesulfonate were used, and NMP was used as the solvent. The crude compound was purified by Prep-HPLC (Method A)

Yield: 18.93%;

$^1$H NMR (400 MHz, DMSO-d$_6$) δ 8.33-8.21 (m, 1H), 7.85-7.68 (m, 1H), 7.36-7.21 (m, 2H), 7.10-7.00 (m, 2H), 4.26-3.64 (m, 10H), 3.58 (d, J=1.0 Hz, 1H), 3.30-3.25 (m, 1H), 3.21-2.97 (m, 3H), 2.32-2.15 (m, 5H), 2.07-1.86 (m, 2H), 1.66 (br s, 5H), 1.52-1.31 (m, 3H), 1.21 (d, J=6.8 Hz, 7H), 1.14-0.97 (m, 4H);

LCMS (Method A): Rt 1.59 min, m/z: 687.1 [M+H]$^+$;
HPLC (Method A): Rt 4.89 min, 98.84%.

Example 175. 2-((4-(7-(((2S,5R)-5-((N,N-Diethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide

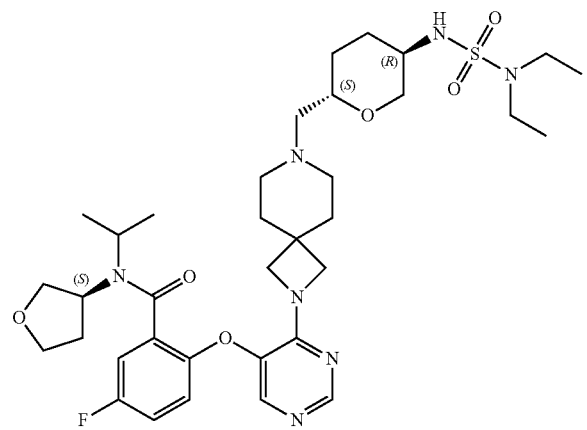

This compound was synthesized following the general procedure described for the synthesis of Example 137, except that 7 equivalents of $K_2CO_3$ was used, and NMP was used as the solvent. The crude compound was purified by Prep-HPLC (Method B).

Yield: 20.75%;

$^1$H NMR (400 MHz, DMSO-d$_6$) δ 8.30-8.24 (m, 1H), 7.84-7.69 (m, 1H), 7.35-7.21 (m, 2H), 7.16-7.00 (m, 2H), 4.27-3.63 (m, 10H), 3.61-3.40 (m, 1H), 3.29-3.23 (m, 1H), 3.13 (q, J=7.3 Hz, 4H), 3.04-2.89 (m, 2H), 2.32-2.23 (m, 4H), 2.22-2.15 (m, 2H), 2.04-1.86 (m, 2H), 1.66 (br s, 5H), 1.50-1.31 (m, 3H), 1.27-1.17 (m, 1H), 1.16-1.02 (m, 10H), 0.98 (d, J=6.6 Hz, 1H);

LCMS (Method C): Rt 1.71 min, m/z: 718.2 [M+H]$^+$;
HPLC (Method A): Rt 5.40 min, 98.11%.

Example 176. 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide

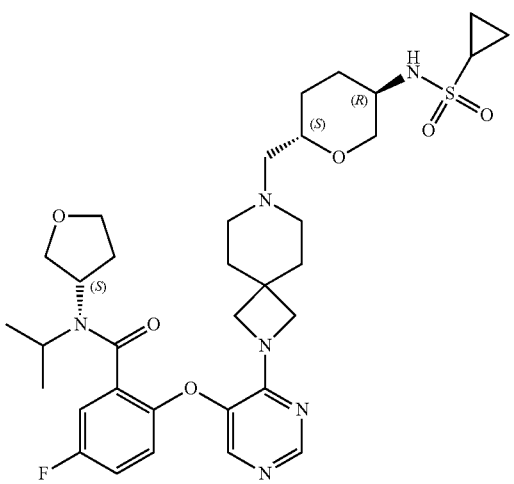

This compound was synthesized following the general procedure described for the synthesis of Example 137, except that 1.1 of KI was used, and NMP was used as the solvent. The crude compound was purified by Prep-HPLC (Method B).

Yield: 16.94%;

$^1$H NMR (400 MHz, DMSO-d$_6$) δ 8.32-8.24 (m, 1H), 7.85-7.71 (m, 1H), 7.35-7.21 (m, 2H), 7.12 (d, J=7.9 Hz, 1H), 7.04 (dd, J=4.3, 9.1 Hz, 1H), 4.28-3.54 (m, 11H), 3.52-3.36 (m, 1H), 3.25-3.10 (m, 1H), 3.08-2.98 (m, 1H), 2.64-2.53 (m, 3H), 2.32-2.16 (m, 5H), 2.10-1.86 (m, 2H), 1.67 (br s, 5H), 1.52-1.18 (m, 4H), 1.16-1.02 (m, 3H), 1.01-0.83 (m, 5H);

LCMS (Method B): Rt 1.24 min, m/z: 685.2 [M−H]$^−$;
HPLC (Method G) Rt 3.35 min, 99.53%.

Example 177. 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide

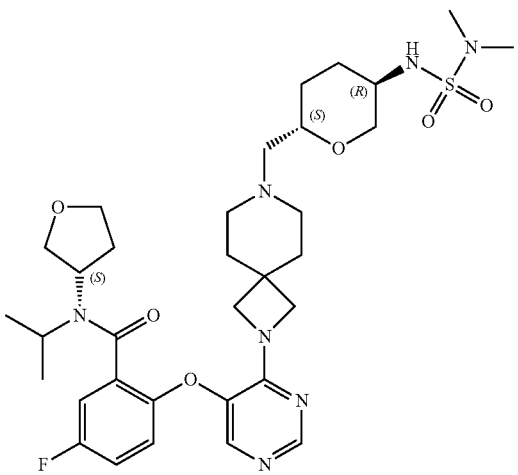

This compound was synthesized following the general procedure described for the synthesis of Example 137, except that 3.5 equivalents of K$_2$CO$_3$ and 1 equivalent of KI were used, and NMP was used as the solvent. The crude compound was purified by Prep HPLC (Method B).

Yield: 11.45%;

$^1$H NMR (400 MHz, DMSO-d$_6$) δ 8.27 (s, 1H), 7.84-7.69 (m, 1H), 7.35-7.17 (m, 3H), 7.04 (dd, J=4.0, 8.9 Hz, 1H), 4.27-3.62 (m, 11H), 3.61-3.37 (m, 2H), 3.09-2.95 (m, 2H), 2.64 (s, 6H), 2.31-2.14 (m, 6H), 2.03-1.88 (m, 2H), 1.66 (br s, 5H), 1.51-1.30 (m, 3H), 1.29-1.16 (m, 1H), 1.15-0.97 (m, 4H);

LCMS (Method C): Rt 1.94 min, m/z: 690.6 [M+H]$^+$;

HPLC (Method A): Rt 4.82 min, 99.84%.

Example 178. 5-Fluoro-N-isopropyl-2-((4-(7-(((2S,5R)-5-(pyrrolidine-1-sulfonamido)tetrahydro-2H-pyran-2-yl)methyl)-2,7-diazaspiro[3.5]nonan-2-yl)pyrimidin-5-yl)oxy)-N—((S)-tetrahydrofuran-3-yl)benzamide

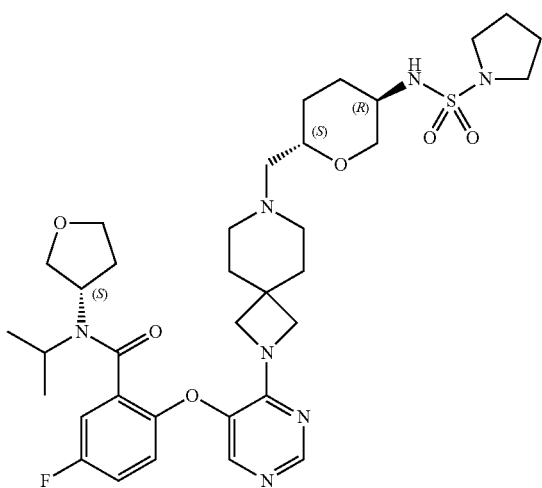

This compound was synthesized following the general procedure described for the synthesis of Example 137, except that 5 equivalents of K$_2$CO$_3$ was used, and NMP was used as the solvent. The crude compound was purified by Prep-HPLC (Method B).

Yield: 10.10%;

$^1$H NMR (400 MHz, DMSO-d$_6$) δ 8.30-8.25 (m, 1H), 7.84-7.70 (m, 1H), 7.36-7.20 (m, 2H), 7.19-7.10 (m, 1H), 7.04 (dd, J=4.2, 9.1 Hz, 1H), 4.25-3.64 (m, 10H), 3.63-3.44 (m, 1H), 3.17-2.97 (m, 7H), 2.31-2.15 (m, 5H), 2.04-1.89 (m, 2H), 1.87-1.77 (m, 5H), 1.66 (br s, 5H), 1.50-1.32 (m, 3H), 1.29-1.16 (m, 1H), 1.16-0.95 (m, 5H);

LCMS (Method A): Rt 1.75 min, m/z: 716.6 [M+H]$^+$;

HPLC (Method A): Rt 5.09 min, 95.23%.

Example 179. 2-((4-(7-(((2S,5R)-5-((N-Ethyl-N-methylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide

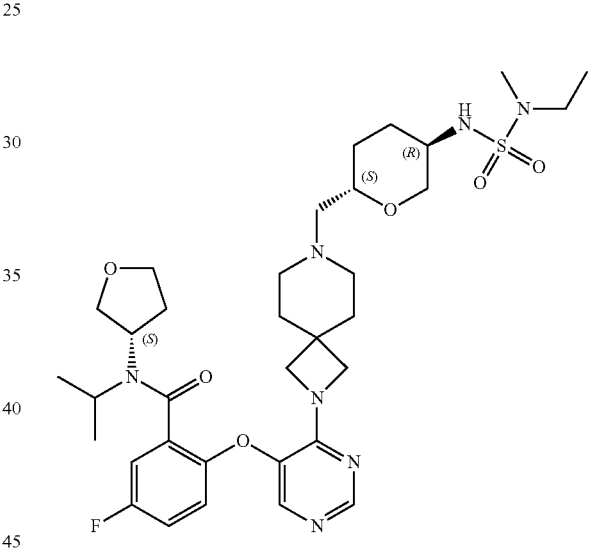

This compound was synthesized following the general procedure described for the synthesis of Example 137, except that 5 equivalents of K$_2$CO$_3$ and 1.5 equivalents of ((2S,5R)-5-((N-ethyl-N-methylsulfamoyl)amino)tetrahydro-2H-pyran-2-yl)methyl 4-methylbenzenesulfonate were used, and NMP was used as the solvent. The crude compound was purified by Prep-HPLC (Method A).

Yield: 12.33%;

$^1$H NMR (400 MHz, DMSO-d$_6$) δ 8.39-8.14 (m, 1H), 7.86-7.65 (m, 1H), 7.36-7.22 (m, 2H), 7.16 (br d, J=6.0 Hz, 1H), 7.10-7.00 (m, 1H), 4.26-3.64 (m, 11H), 3.61-3.43 (m, 1H), 3.12-3.03 (m, 2H), 2.99 (d, J=7.3 Hz, 2H), 2.65 (s, 3H), 2.31-2.16 (m, 5H), 2.05-1.88 (m, 2H), 1.66 (br s, 6H), 1.49-1.30 (m, 3H), 1.27-1.18 (m, 1H), 1.15-1.02 (m, 7H), 0.98 (d, J=6.5 Hz, 1H);

LCMS (Method E): Rt 1.69 min, m/z: 704.4 [M+H]$^+$;

HPLC (Method A): Rt 5.03 min, 98.05%.

Example 180. 2-((4-(7-(((2S,5R)-5-((N-Ethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N—((S)-tetrahydrofuran-3-yl)benzamide

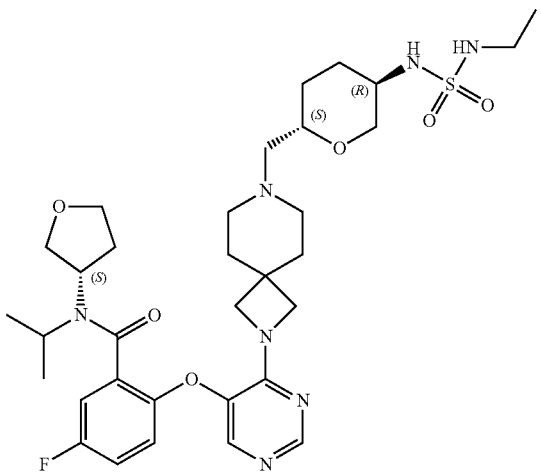

This compound was synthesized following the general procedure described for the synthesis of Example 137, except that 5 equivalents of K$_2$CO$_3$, 1.1 equivalents of ((2S,5R)-5-((N-ethylsulfamoyl)amino)tetrahydro-2H-pyran-2-yl)methyl 4-methylbenzenesulfonate were used, and ACN:NMP (3:1) was used as the solvent. The crude compound was purified by Prep-HPLC (Method A).

Yield: 3.51%;

$^1$H NMR (400 MHz, DMSO-d$_6$) δ 8.32-8.23 (m, 1H), 7.84-7.70 (m, 1H), 7.37-7.20 (m, 2H), 7.11-7.00 (m, 1H), 6.87 (br s, 1H), 6.78 (t, J=5.3 Hz, 1lH), 4.27-3.64 (m, 10H), 3.61-3.43 (m, 1H), 3.29-3.09 (m, 2H), 3.08-2.94 (m, 2H), 2.89-2.78 (m, 2H), 2.32-2.14 (m, 5H), 2.04-1.86 (m, 2H), 1.81-1.55 (m, 5H), 1.49-1.29 (m, 3H), 1.28-1.17 (m, 1H), 1.16-0.94 (m, 8H);

LCMS (Method E): Rt 1.58 min, m/z: 690.3 [M+H]$^+$;

HPLC (Method A): Rt 4.67 min 95.81%.

Example 181. N—(Cyanomethyl)-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

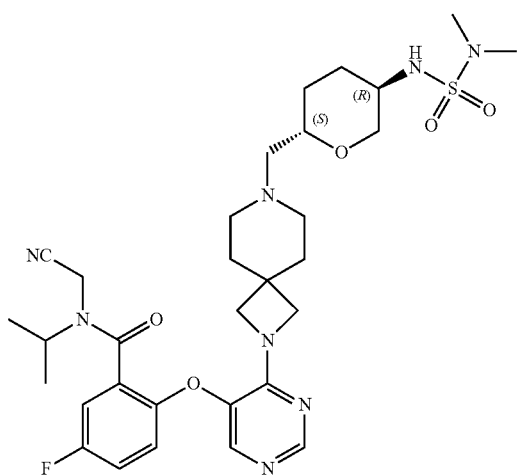

This compound was synthesized following the general procedure described for the synthesis of Example 137, except that 4 equivalents of K$_2$CO$_3$, 1.5 equivalents of ((2S,5R)-5-((N,N-dimethylsulfamoyl)amino)tetrahydro-2H-pyran-2-yl)methyl 4-methylbenzenesulfonate, and 2 equivalents of KI were used. The crude compound was purified by Prep-HPLC (Method C).

Yield: 25.2%;

$^1$H NMR (400 MHz, DMSO-d$_6$) δ 8.32-8.24 (m, 1H), 7.91-7.68 (m, 1H), 7.41-7.27 (m, 2H), 7.24-7.11 (m, 1H), 7.05 (dd, J=4.3, 9.1 Hz, 1H), 4.52-4.35 (m, 2H), 3.94-3.70 (m, 6H), 3.30-3.10 (m, 2H), 3.06-2.96 (m, 2H), 2.63 (s, 6H), 2.32-2.15 (m, 5H), 2.01-1.90 (m, 1H), 1.74-1.59 (m, 5H), 1.46-1.33 (m, 1H), 1.29-0.99 (m, 7H);

LCMS (Method E): Rt 1.59 min, m/z: 659.2 [M+H]$^+$;

HPLC (Method A): Rt 4.85 min, 99.74%.

Example 182. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-(cyanomethyl)-5-fluoro-N-isopropylbenzamide

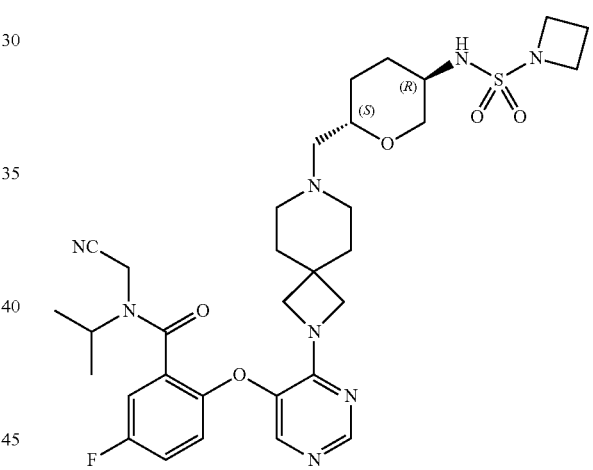

This compound was synthesized following the general procedure described for the synthesis of Example 137, except that 4 equivalents of K$_2$CO$_3$, 1.1 equivalents of ((2S,5R)-5-(azetidine-1-sulfonamido)tetrahydro-2H-pyran-2-yl)methyl 4-methylbenzenesulfonate, and 1.5 equivalents of KI were used. The crude compound was purified by Prep-HPLC (Method C).

Yield: 7.03%;

$^1$H NMR (400 MHz, DMSO-d$_6$) δ 8.28 (s, 1H), 7.78 (s, 1lH), 7.34-7.21 (m, 2H), 7.02 (dd, J=4.4, 9.8 Hz, 1H), 6.88 (br s, 1H), 4.40 (br s, 2H), 4.01-3.77 (m, 6H), 3.71 (t, J=7.6 Hz, 4H), 3.37-3.25 (m, 1H), 3.20-3.08 (m, 1H), 2.37-2.20 (m, 7H), 2.13 (quin, J=7.6 Hz, 2H), 2.00 (d, J=12.3 Hz, 1H), 1.76-1.63 (m, 5H), 1.51-1.36 (m, 1H), 1.33-1.07 (m, 7H);

LCMS (Method B): Rt 1.82 min, m/z: 671.0 [M+H]$^+$;

HPLC (Method A): Rt 4.76 min, 99.31%.

Example 183. N-(2-Cyanoethyl)-2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

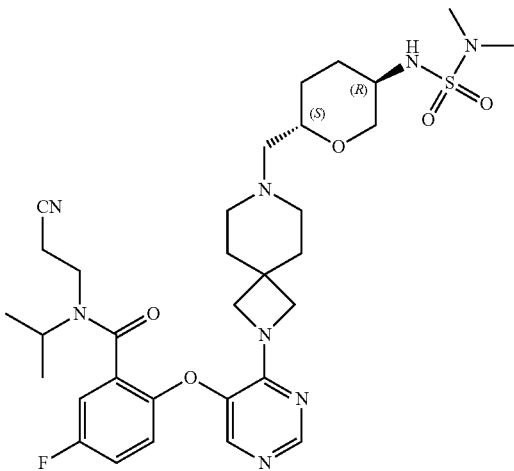

This compound was synthesized following the general procedure described for the synthesis of Example 137, except that 4 equivalents of $K_2CO_3$ and 1 equivalent of ((2S,5R)-5-((N,N-dimethylsulfamoyl)amino)tetrahydro-2H-pyran-2-yl)methyl 4-methylbenzenesulfonate were used. The crude compound was purified by Prep-HPLC (Method D).

Yield: 48.2%;

$^1$H NMR (400 MHz, DMSO-$d_6$) δ 8.33-8.26 (m, 1H), 7.81-7.73 (m, 1H), 7.34-7.23 (m, 2H), 7.20 (d, J=5.6 Hz, 1H), 6.97 (dd, J=4.4, 9.1 Hz, 1H), 3.93-3.68 (m, 6H), 3.66-3.49 (m, 2H), 3.11-2.96 (m, 2H), 2.90-2.74 (m, 2H), 2.64 (s, 6H), 2.32-2.16 (m, 6H), 2.01-1.91 (m, 1H), 1.76-1.58 (m, 6H), 1.47-1.33 (m, 1H), 1.30-1.18 (m, 2H), 1.12 (dd, J=3.4, 6.2 Hz, 5H);

LCMS (Method B): Rt 1.18 min, m/z: 673.4 [M+H]$^+$;
HPLC (Method A): Rt 5.71 min, 99.83%.

Example 184. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-N-(2-cyanoethyl)-5-fluoro-N-isopropylbenzamide

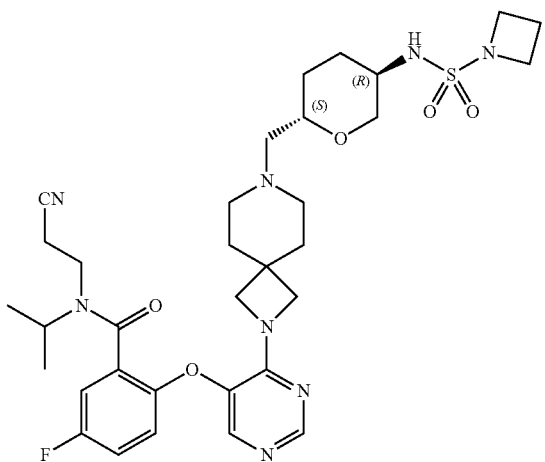

This compound was synthesized following the general procedure described for the synthesis of Example 137, except that 4 equivalents of $K_2CO_3$, 1 equivalent of ((2S,5R)-5-(azetidine-1-sulfonamido)tetrahydro-2H-pyran-2-yl)methyl 4-methylbenzenesulfonate, and 1.5 equivalent of KI were used. The crude compound was purified by Prep-HPLC (Method C).

Yield: 11.78%;

$^1$H NMR (400 MHz, DMSO-$d_6$) δ 8.30 (s, 1H), 7.78 (s, 1H), 7.36-7.19 (m, 3H), 7.07-6.90 (m, 1H), 3.92-3.72 (m, 6H), 3.67 (t, J=7.6 Hz, 4H), 3.61-3.52 (m, 2H), 3.22 (s, 3H), 3.13-2.94 (m, 2H), 2.89-2.75 (m, 2H), 2.32-2.16 (m, 5H), 2.15-2.05 (m, 2H), 2.01-1.93 (m, 1H), 1.66 (br s, 4H), 1.48-1.32 (m, 1H), 1.30-1.17 (m, 2H), 1.16-1.01 (m, 5H);

LCMS (Method E): Rt 1.745 min, m/z: 685.3 [M+H]$^+$;
HPLC (Method A): Rt 4.787 min, 98.25%.

Example 185. N-(2,2-Difluoroethyl)-2-((5-(7-(((2S,5R)-5-(ethylsulfonamido)tetrahydro-2H-pyran-2-yl)methyl)-2,7-diazaspiro[3.5]nonan-2-yl)-1,2,4-triazin-6-yl)oxy)-5-fluoro-N-isopropylbenzamide

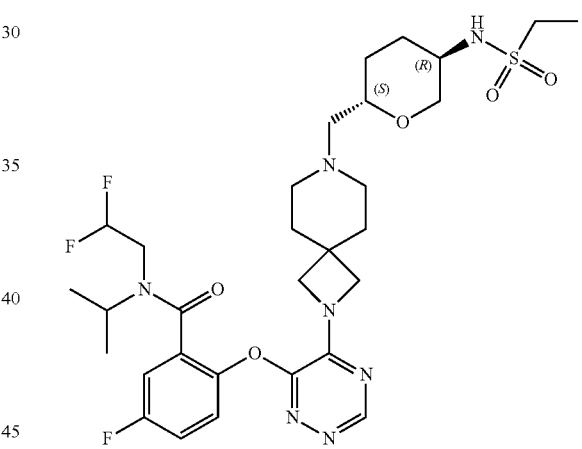

This compound was synthesized following the general procedure described for the synthesis of Example 137, except starting from Intermediate 61 and 5 equivalents of $K_2CO_3$ was used. The crude compound was purified by Prep-HPLC (Method F).

Yield: 25.4%;

$^1$H NMR (400 MHz, DMSO-$d_6$) δ 8.54-8.34 (m, 1H), 7.55-7.33 (m, 3H), 7.11 (d, J=7.6 Hz, 1H), 6.34-5.96 (m, 1H), 4.16 (br s, 2H), 3.93-3.65 (m, 5H), 3.64-3.44 (m, 1H), 3.20-2.93 (m, 4H), 2.40-2.11 (m, 6H), 2.01-1.88 (m, 1H), 1.83-1.61 (m, 5H), 1.49-1.34 (m, 1H), 1.33-0.93 (m, 8H), 0.89-0.63 (m, 3H);

LCMS (Method E): Rt 1.302 min, m/z: (670.2) [M+H]$^+$;
HPLC (Method A): Rt 5.156 min, 99.70%;
SFC (Method G): Rt 1.824 min, 98.88%.

525

Example 186. 2-((5-(7-(((2S,5R)-5-(Cyclopropane-sulfonamido)tetrahydro-2H-pyran-2-yl)methyl)-2,7-diazaspiro[3.5]nonan-2-yl)-1,2,4-triazin-6-yl)oxy)-N-(2,2-difluoroethyl)-5-fluoro-N-isopropylbenzamide

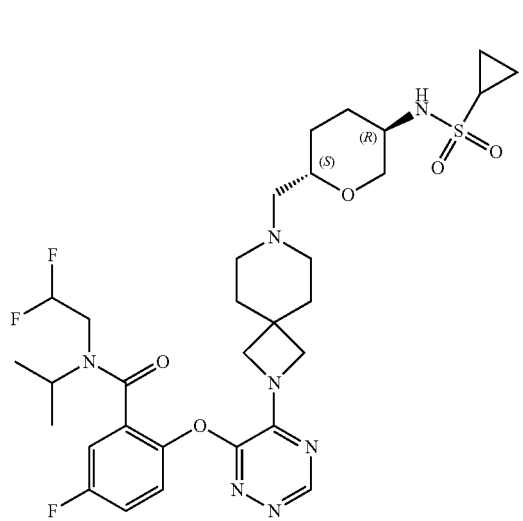

This compound was synthesized following the general procedure described for the synthesis of Example 137, except starting from Intermediate 61 and 5 equivalents of $K_2CO_3$ and 1.3 equivalents of ((2S,5R)-5-(cyclopropane-sulfonamido)tetrahydro-2H-pyran-2-yl)methyl 4-methyl-benzenesulfonate were used. The crude compound was purified by Prep-HPLC (Method H). The product fractions were concentrated, neutralized with sat $NaHCO_3$ and extracted with EtOAc (2×25 mL). The combined organic layer was dried over sodium sulfate, filtered, concentrated, and lyophilized to obtain the desired product.

Yield: 11.39%;

$^1$H NMR (400 MHz, DMSO-$d_6$) δ 8.50-8.39 (m, 1H), 7.54-7.34 (m, 3H), 7.12 (d, J=7.9 Hz, 11H), 6.34-5.94 (m, 1H), 4.27-4.07 (m, 2H), 3.96-3.48 (m, 6H), 3.24-3.10 (m, 1H), 3.10-2.98 (m, 1H), 2.65-2.54 (m, 2H), 2.36-2.15 (m, 5H), 2.07-1.93 (m, 1H), 1.83-1.63 (m, 5H), 1.51-1.34 (m, 1H), 1.33-1.00 (m, 5H), 0.98-0.68 (m, 7H);

LCMS (Method B): Rt 1.302 min, m/z: (682.2) [M+H]$^+$;
HPLC (Method A): Rt 5.156 min, 99.70%;
SFC (Method D): Rt 5.14 min, 100%.

526

Example 187. N-(2,2-Difluoroethyl)-5-fluoro-N-isopropyl-2-((5-(7-(((2S,5R)-5-((1-methyl-1H-pyrazole)-4-sulfonamido)tetrahydro-2H-pyran-2-yl)methyl)-2,7-diazaspiro[3.5]nonan-2-yl)-1,2,4-triazin-6-yl)oxy)benzamide

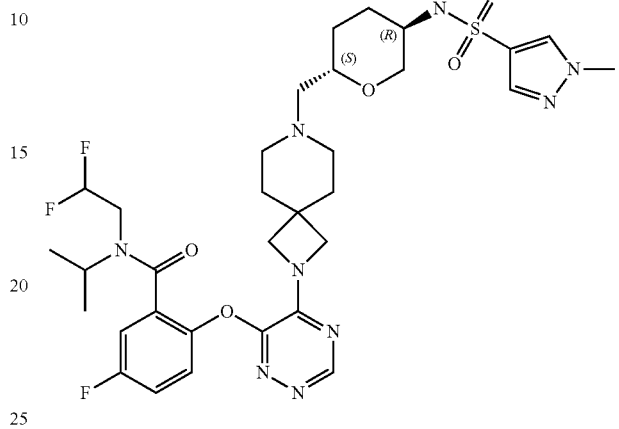

This compound was synthesized following the general procedure described for the synthesis of Example 137, except starting from Intermediate 61 and 5 equivalents of $K_2CO_3$ was used. The crude compound was purified by Prep-HPLC (Method B).

Yield; 28.6%;

$^1$H NMR (400 MHz, DMSO-$d_6$) δ 8.50-8.41 (m, 1H), 8.23 (s, 1H), 7.72 (s, 1H), 7.57-7.34 (m, 4H), 6.06 (s, 1H), 4.24-4.09 (m, 2H), 3.89 (s, 3H), 3.86-3.45 (m, 7H), 3.05-2.90 (m, 2H), 2.39-2.13 (m, 6H), 1.82-1.58 (m, 6H), 1.42-1.26 (m, 1H), 1.24-0.92 (m, 5H), 0.89-0.64 (m, 2H);

LCMS (Method E): Rt 1.611 min, m/z: (722.4) [M+H]$^+$;
HPLC (Method A): Rt 4.987 min, 99.50%;
SFC (Method H): Rt 1.47 min, 100%.

Example 188. N-(2,2-Difluoroethyl)-2-((5-(7-(((2S,5R)-5-((N-ethylsulfamoyl)amino)tetrahydro-2H-pyran-2-yl)methyl)-2,7-diazaspiro[3.5]nonan-2-yl)-1,2,4-triazin-6-yl)oxy)-5-fluoro-N-isopropylbenzamide

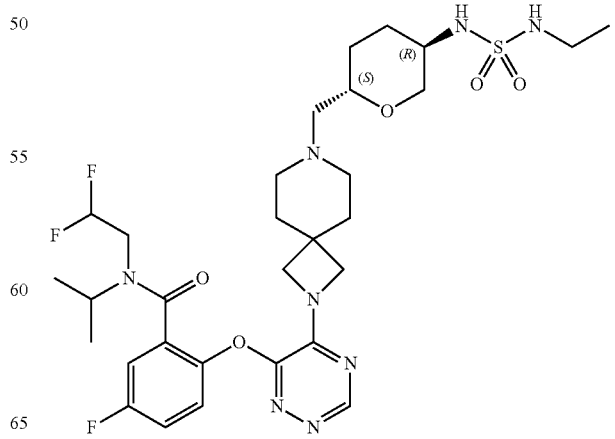

This compound was synthesized following the general procedure described for the synthesis of Example 137, except starting from Intermediate 61 and 5 equivalents of K₂CO₃ and 1.3 equivalents of ((2S,5R)-5-((N-ethylsulfamoyl)amino)tetrahydro-2H-pyran-2-yl)methyl 4-methylbenzenesulfonate were used. The crude compound was purified by Prep-HPLC (Method F).

Yield: 20.69%;

¹H NMR (400 MHz, DMSO-d₆) δ 8.52-8.37 (m, 1H), 7.53-7.34 (m, 3H), 6.90-6.73 (m, 2H), 6.33-5.93 (m, 1H), 4.16 (br s, 2H), 3.97-3.66 (m, 5H), 3.65-3.45 (m, 1H), 3.17-2.96 (m, 2H), 2.83 (q, J=7.1 Hz, 2H), 2.37-2.16 (m, 5H), 1.95 (d, J=12.1 Hz, 1H), 1.86-1.63 (m, 5H), 1.48-1.18 (m, 3H), 1.16-0.94 (m, 7H), 0.92-0.64 (m, 3H);

LCMS (Method E): Rt 1.653 min, m/z: 685.4 [M+H]⁺;

HPLC (Method F): Rt 3.115 min, 96.42%;

SFC (Method J): Rt 3.23 min, 96.88%.

Example 189. 2-((5-(7-(((2S,5R)-5-(Azetidine-1-sulfonamido)tetrahydro-2H-pyran-2-yl)methyl)-2,7-diazaspiro[3.5]nonan-2-yl)-1,2,4-triazin-6-yl)oxy)-N-(2,2-difluoroethyl)-5-fluoro-N-isopropylbenzamide

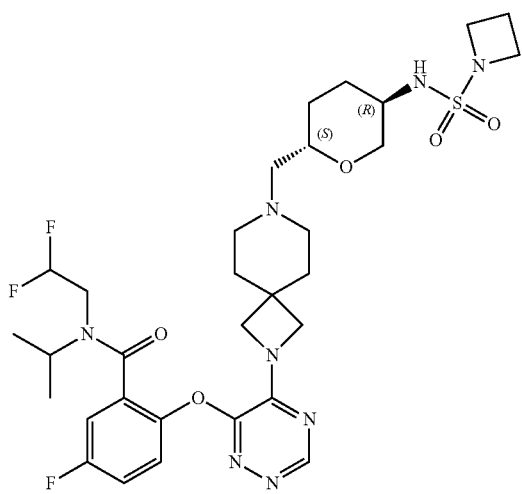

This compound was synthesized following the general procedure described for the synthesis of Example 137, except starting from Intermediate 61 and 1 equivalent of ((2S,5R)-5-(azetidine-1-sulfonamido)tetrahydro-2H-pyran-2-yl)methyl 4-methylbenzenesulfonate and 1 equivalent of KI were used, and ACN:NMP (10:1) was used as the solvent. The crude compound was purified by Prep-HPLC (Method B). Yield: 19.35%; ¹H NMR (400 MHz, DMSO-d₆) δ 8.45 (s, 1H), 7.50-7.37 (m, 3H), 7.28-7.18 (m, 1H), 6.33-5.97 (m, 1H), 4.22-4.11 (m, 2H), 3.88-3.71 (m, 5H), 3.70-3.64 (m, 5H), 3.12-2.95 (m, 3H), 2.32-2.17 (m, 4H), 2.15-1.92 (m, 4H), 1.78-1.64 (m, 5H), 1.49-1.18 (m, 3H), 1.16-1.02 (m, 3H), 0.87-0.64 (m, 3H); LCMS (Method E): Rt 1.696 min, m/z: (697.4) [M+H]⁺; HPLC (Method A): Rt 5.272 min, 96.14%; SFC (Method J): Rt 3.83 min, 97.85%.

Example 190. 2-((5-(7-(((2S,5R)-5-(Ethylsulfonamido)tetrahydro-2H-pyran-2-yl)methyl)-2,7-diazaspiro[3.5]nonan-2-yl)-1,2,4-triazin-6-yl)oxy)-5-fluoro-N-isopropyl-N-(2,2,2-trifluoroethyl) benzamide

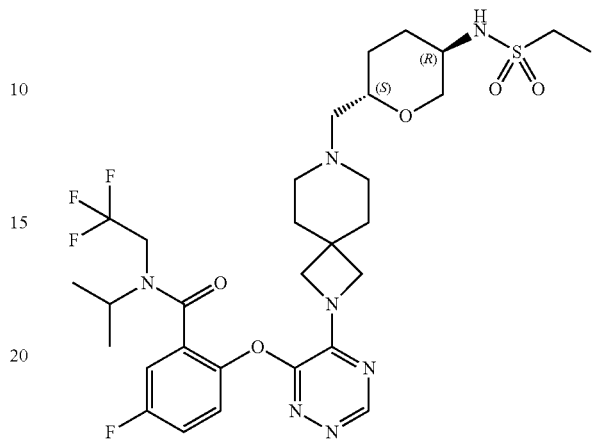

This compound was synthesized following the general procedure described for the synthesis of Example 137, except starting from Intermediate 62 and 1.5 equivalent of ((2S,5R)-5-(ethylsulfonamido)tetrahydro-2H-pyran-2-yl) methyl 4-methylbenzenesulfonate and 1.5 equivalent of KI were used, and ACN:NMP (5:1) was used as the solvent. The crude compound was purified by Prep HPLC (Method H). Yield: 21.21%; ¹H NMR (400 MHz, DMSO-d₆) δ 8.56-8.34 (m, 1H), 7.53-7.36 (m, 3H), 7.10 (d, J=7.5 Hz, 1H), 4.41-3.91 (m, 4H), 3.91-3.70 (m, 4H), 3.20-2.94 (m, 4H), 2.43-2.36 (m, 1H), 2.34-2.15 (m, 4H), 2.02-1.89 (m, 1H), 1.80-1.61 (m, 4H), 1.51-0.94 (m, 9H), 0.91-0.54 (m, 3H); LCMS (Method E): Rt 1.74 min, m/z: 688.3 [M+H]⁺; HPLC (Method A): Rt 5.18 min, 99.46%; SFC (Method B): Rt 1.78 min, 100%.

Example 191. 2-((5-(7-(((2S,5R)-5-(Cyclopropanesulfonamido)tetrahydro-2H-pyran-2-yl)methyl)-2,7-diazaspiro[3.5]nonan-2-yl)-1,2,4-triazin-6-yl)oxy)-5-fluoro-N-isopropyl-N-(2,2,2-trifluoroethyl) benzamide

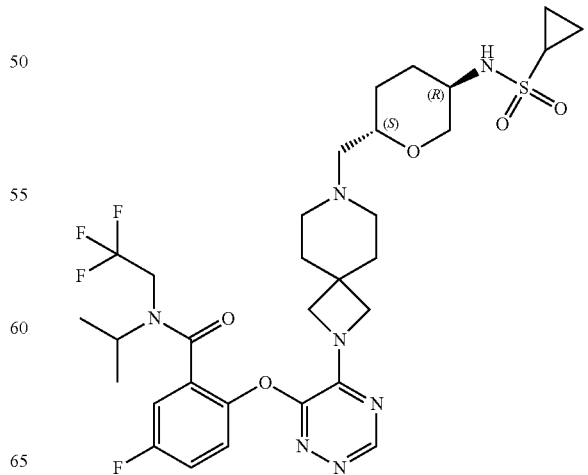

This compound was synthesized following the general procedure described for the synthesis of Example 137, except starting from Intermediate 62 and 1.5 equivalents of ((2S,5R)-5-(cyclopropanesulfonamido)tetrahydro-2H-pyran-2-yl)methyl 4-methylbenzenesulfonate and 1.5 equivalent of KI were used, and ACN:NMP (9:1) was used as the solvent. The crude compound was purified by Prep HPLC (Method G). Yield: 26.8%; $^1$H NMR (400 MHz, DMSO-$d_6$) δ 8.44 (s, 1H), 7.52-7.36 (m, 3H), 7.18-7.06 (m, 1H), 4.39-3.96 (m, 4H), 3.95-3.75 (m, 4H), 3.24-3.10 (m, 2H), 3.09-2.99 (m, 1H), 2.62-2.55 (m, 1H), 2.38-2.16 (m, 5H), 2.05-1.95 (m, 1H), 1.79-1.64 (m, 5H), 1.50-1.36 (m, 1H), 1.32-1.18 (m, 2H), 1.16-1.02 (m, 2H), 1.00-0.83 (m, 6H), 0.82-0.69 (m, 2H); LCMS (Method E): Rt 1.73 min, m/z: m/z: 700.3 [M+H]$^+$; HPLC (Method A): Rt 5.31 min, 98.82%; SFC (Method E): Rt 3.90 min, 98.78%.

Example 192. 5-Fluoro-N-isopropyl-2-((5-(7-(((2R,5S)-5-((1-methyl-1H-pyrazole)-4-sulfonamido)tetrahydro-2H-pyran-2-yl)methyl)-2,7-diazaspiro[3.5]nonan-2-yl)-1,2,4-triazin-6-yl)oxy)-N-(2,2,2-trifluoroethyl)benzamide

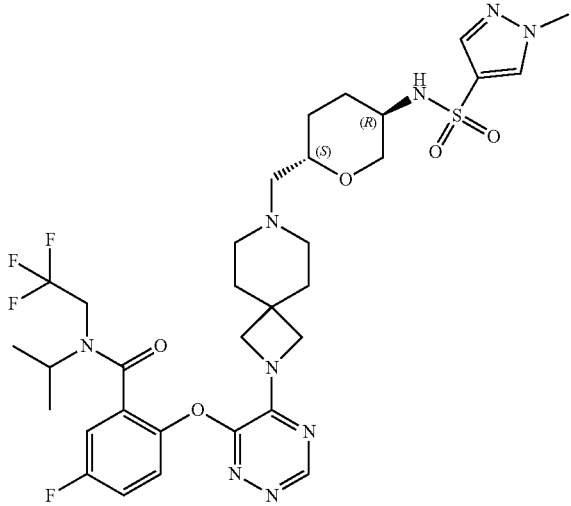

This compound was synthesized following the general procedure described for the synthesis of Example 137, except starting from Intermediate 62 and 1.5 equivalent of ((2S,5R)-5-((1-methyl-1H-pyrazole)-4-sulfonamido)tetrahydro-2H-pyran-2-yl)methyl 4-methylbenzenesulfonate and 1.5 equivalent of KI were used, and ACN:NMP (4:1) was used as the solvent. The crude compound was purified by Prep HPLC (Method B). Yield: 24.17%; $^1$H NMR (400 MHz, DMSO-$d_6$) δ 8.44 (s, 1H), 8.23 (s, 1H), 7.72 (d, J=0.8 Hz, 1H), 7.56-7.38 (m, 4H), 4.37-3.95 (m, 4H), 3.89 (s, 3H), 3.84-3.67 (m, 4H), 3.04-2.92 (m, 2H), 2.33-2.13 (m, 5H), 1.82-1.56 (m, 7H), 1.42-0.94 (m, 6H), 0.93-0.65 (m, 3H); LCMS (Method E): Rt 1.67 min, m/z: 740.3 [M+H]$^+$; HPLC (Method A): Rt 5.10 min, 99.62%; SFC (Method I): Rt 1.38 min, 98.58%.

Example 193. 2-((5-(7-(((2R,5S)-5-((N-Ethylsulfamoyl)amino)tetrahydro-2H-pyran-2-yl)methyl)-2,7-diazaspiro[3.5]nonan-2-yl)-1,2,4-triazin-6-yl)oxy)-5-fluoro-N-isopropyl-N-(2,2,2-trifluoroethyl)benzamide

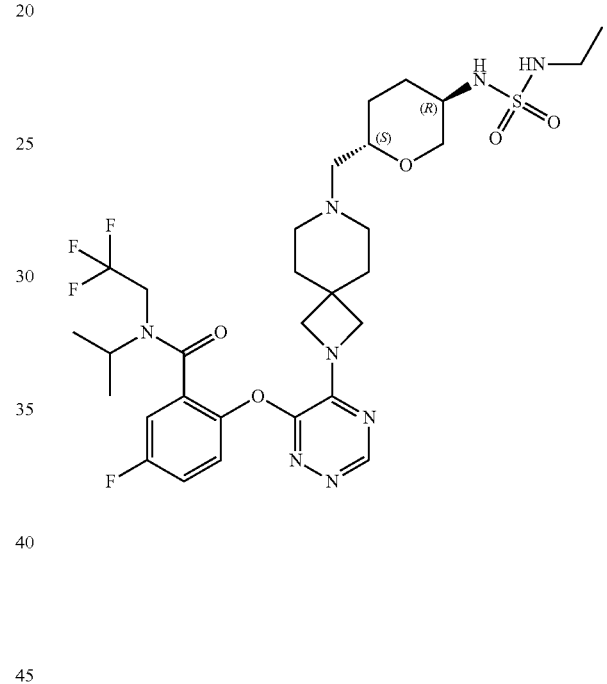

This compound was synthesized following the general procedure described for the synthesis of Example 137, except starting from Intermediate 62 and 1.5 equivalent of ((2S,5R)-5-((N-ethylsulfamoyl)amino)tetrahydro-2H-pyran-2-yl)methyl 4-methylbenzenesulfonate and 1.5 equivalent of KI were used, and ACN:NMP (5:1) was used as the solvent. The crude compound was purified by Prep HPLC (Method B).

Yield: 4.13%:

$^1$H NMR (400 MHz, DMSO-$d_6$) δ 8.44 (s, 1H), 7.53-7.37 (m, 3H), 6.87 (d, J=7.0 Hz, 1H), 6.78 (t, J=5.8 Hz, 1H), 4.40-3.93 (m, 5H), 3.93-3.73 (m, 4H), 3.08-2.93 (m, 2H), 2.88-2.76 (m, 2H), 2.38-2.16 (m, 5H), 2.01-1.89 (m, 1H), 1.81-1.61 (m, 5H), 1.46-1.29 (m, 1H), 1.28-1.14 (m, 2H), 1.06 (t, J=7.3 Hz, 6H), 0.92-0.62 (m, 3H);

LCMS (Method E): Rt 1.71 min, m/z: 703.3 [M+H]$^+$;
HPLC (Method A): Rt 5.24 min, 98.67%;
SFC (Method C): Rt 2.07 min, 98.76%.

Example 194. 2-((5-(7-(((2R,5S)-5-(Azetidine-1-sulfonamido)tetrahydro-2H-pyran-2-yl)methyl)-2,7-diazaspiro[3.5]nonan-2-yl)-1,2,4-triazin-6-yl)oxy)-5-fluoro-N-isopropyl-N-(2,2,2-trifluoroethyl)benzamide

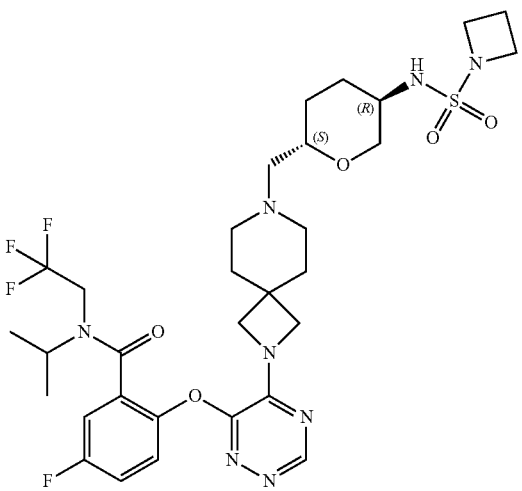

This compound was synthesized following the general procedure described for the synthesis of Example 137, except starting from Intermediate 62 and 1 equivalent of KI was used. The crude compound was purified by Prep HPLC (Method G).

Yield: 16.27%;
$^1$H NMR (400 MHz, DMSO-d$_6$) δ 8.44 (s, 1H), 7.52-7.38 (m, 3H), 7.33-7.16 (m, 1H), 4.39-3.99 (m, 4H), 3.92-3.75 (m, 4H), 3.67 (dt, J=3.0, 7.6 Hz, 5H), 3.22-2.96 (m, 4H), 2.34-2.17 (m, 4H), 2.15-2.04 (m, 3H), 2.01-1.92 (m, 1H), 1.85-1.63 (m, 5H), 1.51-1.20 (m, 3H), 1.08 (br s, 2H), 0.87-0.71 (m, 2H);
LCMS (Method E): Rt 1.75 min, m/z: 715.4 [M+H]$^+$;
HPLC (Method A): Rt 5.38 min, 96.02%;
SFC (Method J): Rt 3.40 min, 96.69%.

Example 195. 2-((5-(7-(((2S,5R)-5-(Ethylsulfonamido)tetrahydro-2H-pyran-2-yl)methyl)-2,7-diazaspiro[3.5]nonan-2-yl)-1,2,4-triazin-6-yl)oxy)-5-fluoro-N,N-diisopropylbenzamide

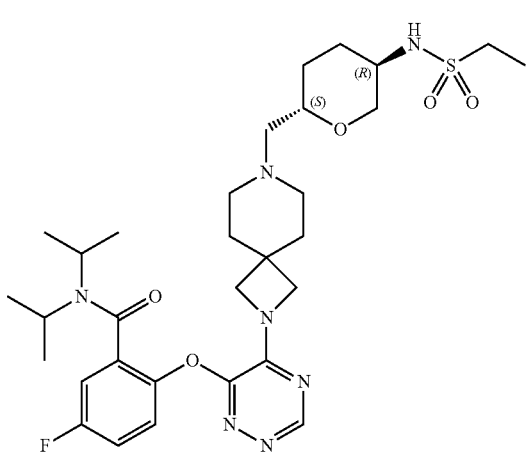

This compound was synthesized following the general procedure described for the synthesis of Example 137, except starting from Intermediate 63 and 1.3 equivalents of ((2S,5R)-5-(ethylsulfonamido)tetrahydro-2H-pyran-2-yl) methyl 4-methylbenzenesulfonate, 3.5 equivalents of K$_2$CO$_3$, and 1.3 equivalent of KI were used, and ACN:NMP (20:1) was used as the solvent. The crude compound was purified by Prep HPLC (Method B).

Yield: 34.7%;
$^1$H NMR (400 MHz, DMSO-d$_6$) δ 8.45 (s, 1H), 7.47-7.39 (m, 1H), 7.37-7.25 (m, 2H), 7.11 (br s, 1H), 4.35-4.18 (m, 2H), 3.90-3.75 (m, 3H), 3.61-3.40 (m, 2H), 3.16-2.96 (m, 5H), 2.42-2.36 (m, 1H), 2.33-2.19 (m, 4H), 2.01-1.89 (m, 1H), 1.78-1.65 (m, 5H), 1.48-1.33 (m, 4H), 1.32-1.23 (m, 4H), 1.18 (t, J=7.3 Hz, 4H), 1.07 (d, J=6.5 Hz, 3H), 0.65 (d, J=6.4 Hz, 3H);
LCMS (Method B): Rt 1.29 min, 648.2 [M+H]$^+$;
HPLC (Method A): Rt 5.06 min, 99.36%;
SFC (Method I): Rt 1.23 min, 100%.

Example 196. 2-((5-(7-(((2S,5R)-5-(Cyclopropanesulfonamido)tetrahydro-2H-pyran-2-yl)methyl)-2,7-diazaspiro[3.5]nonan-2-yl)-1,2,4-triazin-6-yl)oxy)-5-fluoro-N,N-diisopropylbenzamide

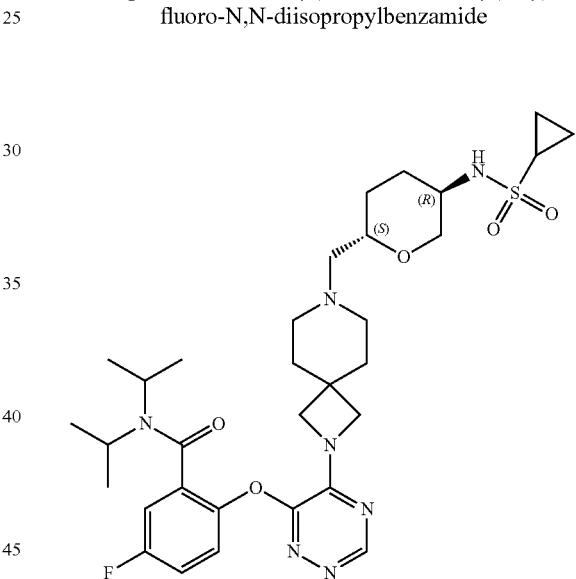

This compound was synthesized following the general procedure described for the synthesis of Example 137, except starting from Intermediate 63 and 1.3 equivalents of ((2S,5R)-5-(cyclopropanesulfonamido)tetrahydro-2H-pyran-2-yl)methyl 4-methylbenzenesulfonate, 3.5 equivalents of K$_2$CO$_3$, and 1.3 equivalents of KI were used, and ACN:NMP (10:1) was used as the solvent. The crude compound was purified by Prep HPLC (Method B).

Yield: 18.1%;
$^1$H NMR (400 MHz, DMSO-d$_6$) δ 8.45 (s, 1H), 7.43 (dd, J=4.8, 9.0 Hz, 1H), 7.38-7.24 (m, 2H), 7.19-7.01 (m, 1H), 4.36-4.14 (m, 2H), 3.95-3.72 (m, 3H), 3.65-3.38 (m, 3H), 3.22-3.09 (m, 1H), 3.08-2.95 (m, 1H), 2.64-2.54 (m, 2H), 2.36-2.16 (m, 5H), 2.07-1.93 (m, 1H), 1.81-1.62 (m, 5H), 1.50-1.36 (m, 4H), 1.34-1.20 (m, 4H), 1.07 (d, J=6.5 Hz, 3H), 1.00-0.82 (m, 4H), 0.66 (d, J=6.4 Hz, 3H);
LCMS (Method E): Rt 1.69 min, 659.5 [M+H]$^+$;
HPLC (Method A): Rt 5.00 min, 99.34%;
SFC (Method M): Rt 0.72 min, 100%.

Example 197. 5-Fluoro-N,N-diisopropyl-2-((5-(7-(((2S,5R)-5-((1-methyl-1H-pyrazole)-4-sulfonamido)tetrahydro-2H-pyran-2-yl)methyl)-2,7-diazaspiro[3.5]nonan-2-yl)-1,2,4-triazin-6-yl)oxy)benzamide

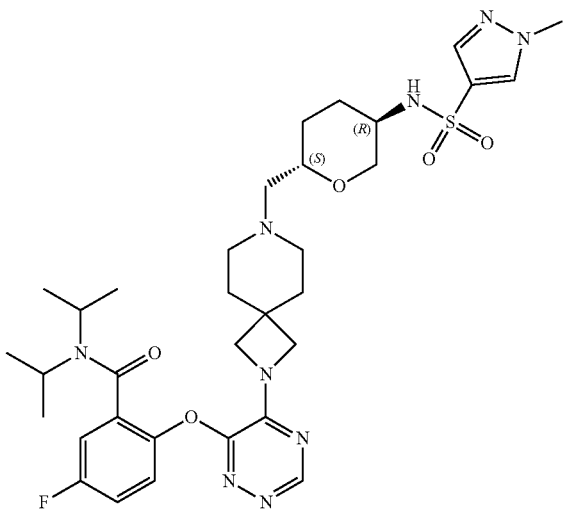

This compound was synthesized following the general procedure described for the synthesis of Example 137 starting from Intermediate 63. The crude compound was purified by Prep HPLC (Method B).

Yield: 8.11%;

$^1$H NMR (400 MHz, DMSO-d$_6$) δ 8.45 (s, 1H), 8.24 (s, 1H), 7.72 (d, J=0.6 Hz, 1H), 7.52 (d, J=5.6 Hz, 1H), 7.46-7.38 (m, 1H), 7.37-7.26 (m, 2H), 4.32-4.16 (m, 2H), 3.89 (s, 3H), 3.85-3.74 (m, 2H), 3.73-3.67 (m, 1H), 3.62-3.39 (m, 3H), 3.04-2.90 (m, 2H), 2.31-2.12 (m, 5H), 1.78-1.61 (m, 6H), 1.41 (d, J=6.6 Hz, 4H), 1.28 (d, J=6.6 Hz, 4H), 1.22-1.11 (m, 1H), 1.07 (d, J=6.5 Hz, 3H), 0.65 (d, J=6.5 Hz, 3H);

LCMS (Method E): Rt 1.64 min, 700.3 [M+H]$^+$;

HPLC (Method A): Rt 4.99 min, 99.37%;

SFC (Method B): Rt 1.65 min, 100%.

Example 198. 2-((5-(7-(((2S,5R)-5-((N-Ethylsulfamoyl)amino)tetrahydro-2H-pyran-2-yl)methyl)-2,7-diazaspiro[3.5]nonan-2-yl)-1,2,4-triazin-6-yl)oxy)-5-fluoro-N,N-diisopropylbenzamide

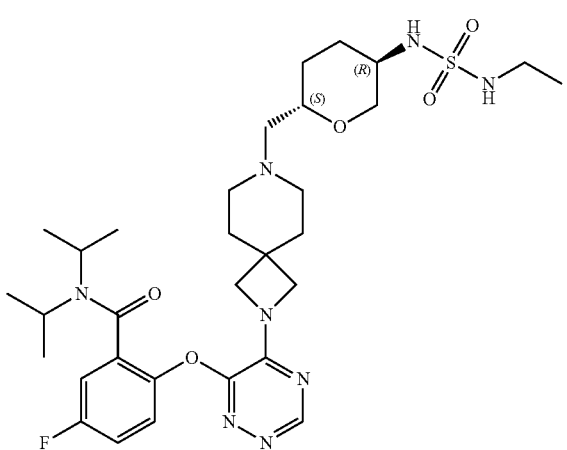

This compound was synthesized following the general procedure described for the synthesis of Example 137 starting from Intermediate 63. The crude compound was purified by Prep HPLC (Method B).

Yield: 9.88%.

$^1$H NMR (400 MHz, DMSO-d$_6$) δ 8.45 (s, 1H), 7.45-7.40 (m, 1H), 7.38-7.27 (m, 2H), 6.87 (d, J=7.1 Hz, 1H), 6.78 (t, J=5.8 Hz, 1H), 4.34-4.16 (m, 2H), 3.92-3.74 (m, 3H), 3.63-3.40 (m, 3H), 3.08-2.95 (m, 2H), 2.88-2.78 (m, 2H), 2.42-2.36 (m, 1H), 2.32-2.18 (m, 4H), 2.02-1.89 (m, 1H), 1.80-1.64 (m, 5H), 1.48-1.35 (m, 4H), 1.33-1.15 (m, 5H), 1.12-1.02 (m, 6H), 0.65 (d, J=6.5 Hz, 3H);

LCMS (Method E): Rt 1.63 min, 663.5 [M+H]$^+$;

HPLC (Method A): Rt 5.18 min, 96.87%;

SFC (Method I): Rt 1.22 min, 99.13%.

Example 199. 2-((5-(7-(((2S,5R)-5-(Azetidine-1-sulfonamido)tetrahydro-2H-pyran-2-yl)methyl)-2,7-diazaspiro[3.5]nonan-2-yl)-1,2,4-triazin-6-yl)oxy)-5-fluoro-N,N-diisopropylbenzamide

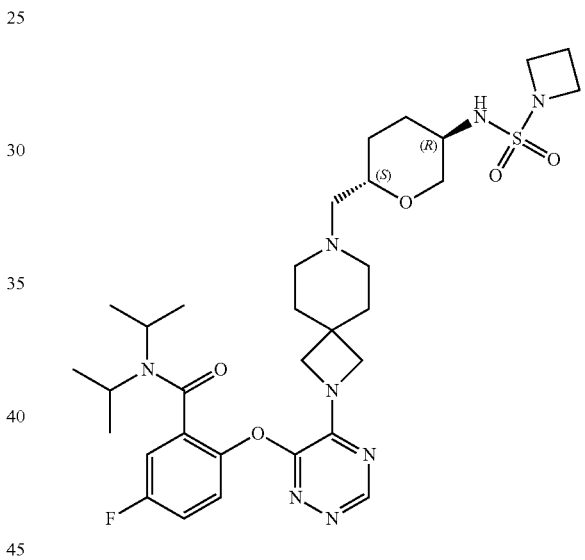

This compound was synthesized following the general procedure described for the synthesis of Example 137, except starting from Intermediate 63 and 1.3 equivalents of ((2S,5R)-5-(azetidine-1-sulfonamido)tetrahydro-2H-pyran-2-yl)methyl 4-methylbenzenesulfonate, 3.5 equivalents of K$_2$CO$_3$, and 1.3 equivalent of KI were used, and ACN:NMP (20:1) was used as the solvent. The crude compound was purified by Prep HPLC (Method E).

Yield: 9.28%;

$^1$H NMR (400 MHz, DMSO-d$_6$) δ 8.45 (s, 1H), 7.43 (dd, J=4.6, 9.0 Hz, 1H), 7.38-7.26 (m, 2H), 7.23 (br d, J=2.5 Hz, 1H), 4.33-4.17 (m, 2H), 3.95-3.74 (m, 3H), 3.71-3.64 (m, 5H), 3.62-3.53 (m, 1H), 3.50-3.41 (m, 1H), 3.12-3.00 (m, 2H), 2.32-2.17 (m, 4H), 2.10 (dquin, J=2.8, 7.6 Hz, 3H), 2.01-1.94 (m, 1H), 1.77-1.65 (m, 5H), 1.50-1.33 (m, 5H), 1.32-1.19 (m, 4H), 1.07 (d, J=6.5 Hz, 3H), 0.65 (d, J=6.4 Hz, 3H);

LCMS (Method E): Rt 1.72 min, 675.3 [M+H]$^+$;

HPLC (Method G): Rt 3.62 min, 97.74%;

SFC (Method J): Rt 3.63 min, 94.92%.

Example 200. N-Ethyl-5-fluoro-N-isopropyl-2-((4-(7-(((2S,5R)-5-(((R)-2-methylpyrrolidine)-1-sulfonamido)tetrahydro-2H-pyran-2-yl)methyl)-2,7-diazaspiro[3.5]nonan-2-yl)pyrimidin-5-yl)oxy)benzamide

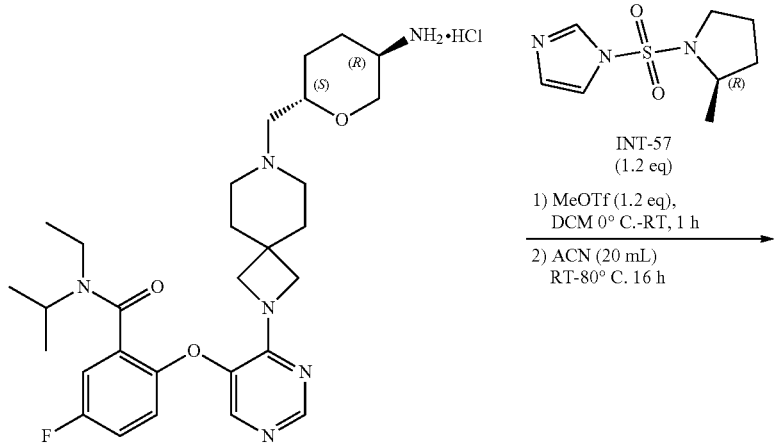

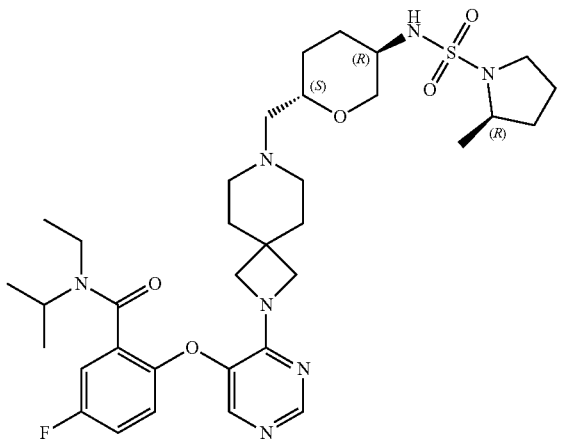

Step 1. To a dried 25 mL round bottom flask under nitrogen atmosphere, (R)-1-((2-methylpyrrolidin-1-yl)sulfonyl)-1H-imidazole (70 mg, 0.325 mmol) was added in DCM (10 mL). To this solution, MeOTf (0.037 mL, 0.325 mmol) was added at 0° C., and the reaction was stirred at RT for 1 h. The reaction mixture was concentrated under reduced pressure to obtain (R)-1-methyl-3-((2-methylpyrrolidin-1-yl)sulfonyl)-1H-imidazol-3-ium trifluoromethanesulfonate (100 mg, 0.264 mmol, 81% yield). This compound was used in the subsequent step without further purification.

Step 2. 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide hydrochloride (152 mg, 0.264 mmol) was neutralized using aqueous $Na_2CO_3$ and extracted with DCM (2×10 mL). The organic layer was dried over sodium sulfate and concentrated on a rotary evaporator under reduced pressure to obtain 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide. This compound was dissolved in ACN (20 mL) and (R)-1-methyl-3-((2-methylpyrrolidin-1-yl)sulfonyl)-1H-imidazol-3-ium trifluoromethanesulfonate (100 mg, 0.264 mmol) was added at RT. The reaction was stirred at 80° C. for 16 h, monitoring progress by LCMS. The reaction was concentrated under reduced pressure and the resulting crude compound was purified by Prep-HPLC (Method A) to obtain N-ethyl-5-fluoro-N-isopropyl-2-((4-(7-(((2S,5R)-5-(((R)-2-methylpyrrolidine)-1-sulfonamido)tetrahydro-2H-pyran-2-yl)methyl)-2,7-diazaspiro[3.5]nonan-2-yl)pyrimidin-5-yl)oxy)benzamide (58 mg, 0.082 mmol, 31.3% yield). $^1$H NMR (400 MHz, DMSO-$d_6$) δ 8.29-8.24 (m, 1H), 7.73-7.66 (m, 1H), 7.34-7.21 (m, 2H), 7.12-6.99 (m, 2H), 3.91-3.81 (m, 3H), 3.81-3.72 (m, 3H), 3.71-3.63 (m, 1H), 3.21-3.10 (m, 3H), 3.08-2.96 (m, 2H), 2.32-2.15 (m, 5H), 2.03-1.90 (m, 2H), 1.89-1.72 (m, 2H), 1.72-1.59 (m, 6H), 1.56-1.45 (m, 1H), 1.44-1.32 (m, 1H), 1.27-1.17 (m, 3H), 1.16-1.07 (m, 9H), 1.06-0.96 (m, 3H); LCMS (Method B): Rt 1.37 min, m/z: 688.4 [M+H]$^+$; HPLC (Method A): Rt 6.28 min, 97.82%; SFC (Method F): Rt 5.47 min, 100%.

Example 201. N-Ethyl-5-fluoro-N-isopropyl-2-((4-(7-(((2S,5R)-5-(((S)-2-methylpyrrolidine)-1-sulfonamido)tetrahydro-2H-pyran-2-yl)methyl)-2,7-diazaspiro[3.5]nonan-2-yl)pyrimidin-5-yl)oxy)benzamide

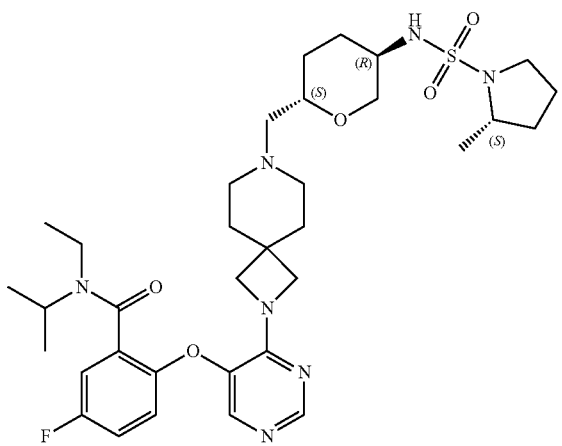

This compound was synthesized following the general procedure described for the synthesis of Example 200. The crude compound was purified by Prep HPLC (Method B).

Yield: 34.9%;

$^1$H NMR (400 MHz, DMSO-d$_6$) δ 8.32-8.22 (m, 1H), 7.84-7.70 (m, 1H), 7.35-7.21 (m, 2H), 7.12-7.01 (m, 2H), 4.28-3.62 (m, 11H), 3.59-3.44 (m, 1H), 3.61-3.38 (m, 1H), 3.23-3.11 (m, 2H), 3.11-2.96 (m, 2H), 2.32-2.17 (m, 5H), 2.04-1.91 (m, 3H), 1.90-1.73 (m, 3H), 1.72-1.61 (m, 5H), 1.56-1.44 (m, 2H), 1.43-1.31 (m, 2H), 1.28-1.18 (m, 1H), 1.17-0.95 (m, 8H); LCMS (Method B): Rt 1.41 min, m/z 688.4 [M+H]$^+$; HPLC (Method A): Rt 5.63 min, 99.97%; SFC (Method I): Rt 6.02 min, 100%.

Example 202. 5-Fluoro-N,N-diisopropyl-2-((4-(7-(((2S,5R)-5-(((S)-2-methylpyrrolidine)-1-sulfonamido)tetrahydro-2H-pyran-2-yl)methyl)-2,7-diazaspiro[3.5]nonan-2-yl)pyrimidin-5-yl)oxy)benzamide

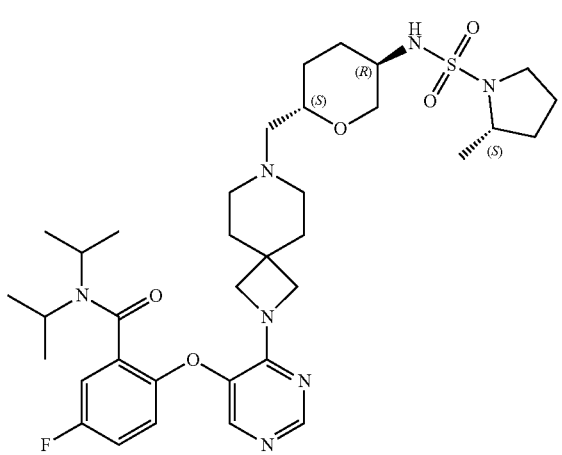

This compound was synthesized following the general procedure described for the synthesis of Example 200. The crude compound was purified by prep HPLC (Method B).

Yield: 24.47%;

$^1$H NMR (400 MHz, DMSO-d$_6$) δ 8.26 (s, 1H), 7.71 (s, 1H), 7.27-7.18 (m, 2H), 7.11-7.00 (m, 2H), 3.96-3.76 (m, 5H), 3.73-3.63 (m, 2H), 3.58-3.47 (m, 1H), 3.23-3.11 (m, 2H), 3.10-2.95 (m, 2H), 2.32-2.14 (m, 5H), 2.04-1.90 (m, 2H), 1.90-1.72 (m, 3H), 1.71-1.61 (m, 6H), 1.57-1.47 (m, 1H), 1.44 (d, J=6.8 Hz, 3H), 1.40 (d, J=3.8 Hz, 1H), 1.35 (d, J=6.8 Hz, 3H), 1.28-1.18 (m, 1H), 1.14 (d, J=6.3 Hz, 3H), 1.09 (d, J=6.6 Hz, 3H), 1.00 (d, J=6.6 Hz, 3H); LCMS (Method A): Rt 1.43 min, m/z: 702.4 [M+H]$^+$; HPLC (Method A): Rt 5.98 min, 99.73%.

Example 203. 5-Fluoro-N,N-diisopropyl-2-((4-(7-(((2S,5R)-5-(((R)-2-methylpyrrolidine)-1-sulfonamido)tetrahydro-2H-pyran-2-yl)methyl)-2,7-diazaspiro[3.5]nonan-2-yl)pyrimidin-5-yl)oxy)benzamide This compound was synthesized following the general procedure described for the synthesis of Example 200. The crude compound was purified by prep HPLC (Method B).

Yield: 37.9%;

$^1$H NMR (400 MHz, DMSO-d$_6$) δ 8.26 (s, 1H), 7.72 (s, 1H), 7.27-7.19 (m, 2H), 7.10-7.01 (m, 2H), 3.96-3.84 (m, 3H), 3.83-3.75 (m, 2H), 3.74-3.64 (m, 2H), 3.59-3.45 (m, 1H), 3.21-3.11 (m, 2H), 3.11-2.94 (m, 2H), 2.32-2.16 (m, 5H), 2.04-1.90 (m, 2H), 1.90-1.72 (m, 3H), 1.66 (br s, 6H), 1.55-1.48 (m, 1H), 1.44 (d, J=6.8 Hz, 3H), 1.41-1.37 (m, 1H), 1.35 (d, J=6.6 Hz, 3H), 1.28-1.18 (m, 1H), 1.15 (d, J=6.3 Hz, 3H), 1.09 (d, J=6.6 Hz, 3H), 1.00 (d, J=6.6 Hz, 3H); LCMS(Method C): Rt 1.88 min, m/z 702.9 [M+H]$^+$; HPLC (Method A): Rt 5.96 min, 98.98%.

Example 204. 5-Fluoro-N-isopropyl-2-((4-(7-(((2S, 5R)-5-(((R)-2-methylpyrrolidine)-1-sulfonamido)tetrahydro-2H-pyran-2-yl)methyl)-2,7-diazaspiro[3.5]nonan-2-yl)pyrimidin-5-yl)oxy)-N—((R)-tetrahydrofuran-3-yl)benzamide

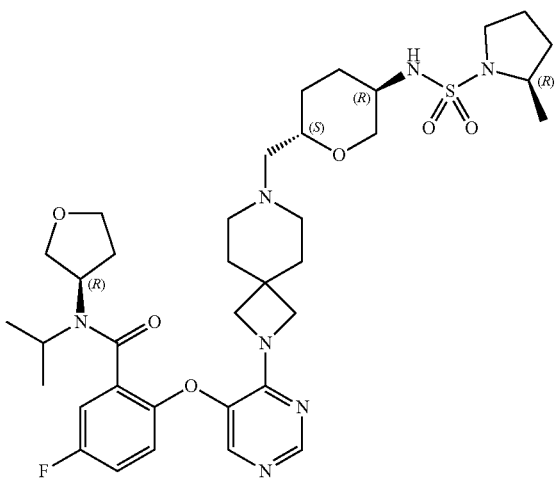

This compound was synthesized following the general procedure described for the synthesis of Example 200, except that the reaction temperature was 70° C. The crude compound was purified by prep HPLC (Method A).

Yield: 9.45%;

$^1$H NMR (400 MHz, DMSO-d$_6$) δ 8.27 (d, J=2.5 Hz, 1H), 7.84-7.70 (m, 1H), 7.36-7.20 (m, 2H), 7.12-7.01 (m, 2H), 4.09-3.63 (m, 11H), 3.62-3.41 (m, 1H), 3.20-3.11 (m, 2H), 3.10-2.95 (m, 2H), 2.32-2.14 (m, 6H), 2.04-1.89 (m, 3H), 1.88-1.73 (m, 3H), 1.66 (br s, 5H), 1.55-1.42 (m, 2H), 1.41-1.31 (m, 2H), 1.29-1.19 (m, 1H), 1.18-1.10 (m, 4H), 1.09-0.94 (m, 4H); LCMS (Method A): Rt 1.84 min, m/z: 730.6 [M+H]$^+$; HPLC (Method A): Rt 5.47 min, 97.91%.

Example 205. 5-Fluoro-N-isopropyl-2-((4-(7-(((2S, 5R)-5-(((S)-2-methylpyrrolidine)-1-sulfonamido)tetrahydro-2H-pyran-2-yl)methyl)-2,7-diazaspiro[3.5]nonan-2-yl)pyrimidin-5-yl)oxy)-N—((R)-tetrahydrofuran-3-yl)benzamide

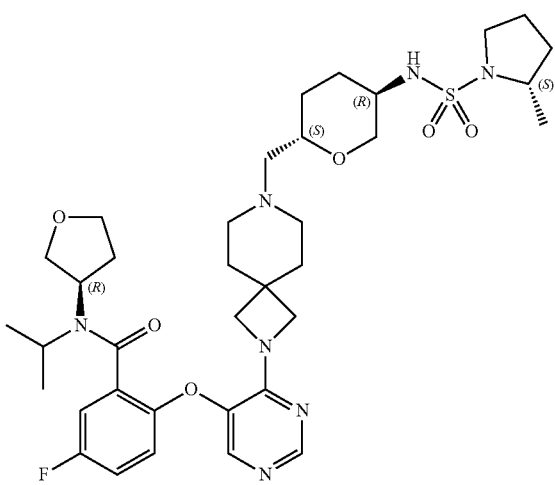

This compound was synthesized following the general procedure described for the synthesis of Example 200. The crude compound was purified by prep HPLC (Method C).

Yield: 13.34%;

$^1$H NMR (400 MHz, DMSO-d$_6$) δ 8.32-8.22 (m, 1H), 7.84-7.70 (m, 1H), 7.35-7.21 (m, 2H), 7.12-7.01 (m, 2H), 4.28-3.62 (m, 11H), 3.59-3.44 (m, 1H), 3.61-3.38 (m, 1H), 3.23-3.11 (m, 2H), 3.11-2.96 (m, 2H), 2.32-2.17 (m, 5H), 2.04-1.91 (m, 3H), 1.90-1.73 (m, 3H), 1.72-1.61 (m, 5H), 1.56-1.44 (m, 2H), 1.43-1.31 (m, 2H), 1.28-1.18 (m, 1H), 1.17-0.95 (m, 8H);

LCMS (Method E): Rt 1.78 min, m/z: 730.4 [M+H]$^+$;

HPLC (Method A): Rt 5.46 min, 97.78%.

Example 206. 5-Fluoro-N-isopropyl-2-((4-(7-(((2S, 5R)-5-(((S)-2-methylpyrrolidine)-1-sulfonamido)tetrahydro-2H-pyran-2-yl)methyl)-2,7-diazaspiro[3.5]nonan-2-yl)pyrimidin-5-yl)oxy)-N—((S)-tetrahydrofuran-3-yl)benzamide

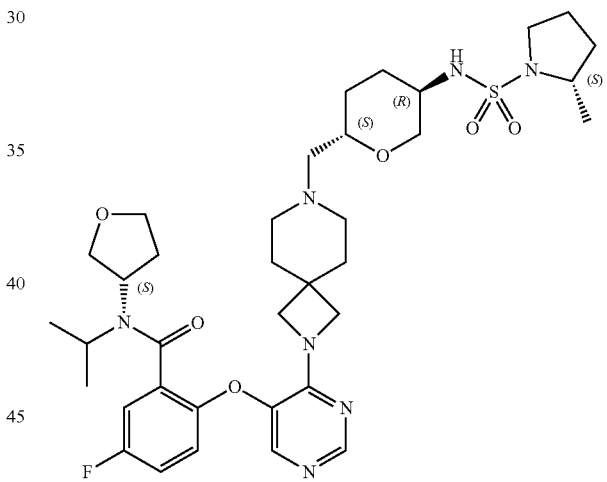

This compound was synthesized by following the general procedure-3 described for the synthesis of Example 200, except that the reaction was stirred at 90° C. The crude compound was purified by prep HPLC (Method A).

Yield: 22.12%;

$^1$H NMR (400 MHz, DMSO-d$_6$): δ 8.31-8.23 (m, 1H), 7.84-7.70 (m, 1H), 7.35-7.21 (m, 2H), 7.13-7.00 (m, 2H), 4.13 (s, 11H), 3.61-3.41 (m, 1H), 3.20-3.12 (m, 2H), 3.09-2.96 (m, 2H), 2.30-2.15 (m, 5H), 2.03-1.90 (m, 3H), 1.88-1.73 (m, 3H), 1.72-1.60 (m, 6H), 1.55-1.44 (m, 2H), 1.44-1.32 (m, 2H), 1.28-1.19 (m, 1H), 1.17-1.11 (m, 5H), 1.06 (dd, J=6.5, 12.4 Hz, 2H), 0.98 (d, J=6.6 Hz, 11H); LCMS (Method B): Rt 1.39 min, m/z: 730.4 [M+H]$^+$; HPLC (Method A): Rt 5.49 min, 97.67%.

Example 207. 5-Fluoro-N-isopropyl-2-((4-(7-(((2S, 5R)-5-(((R)-2-methylpyrrolidine)-1-sulfonamido) tetrahydro-2H-pyran-2-yl)methyl)-2,7-diazaspiro [3.5]nonan-2-yl)pyrimidin-5-yl)oxy)-N—((S)-tetrahydrofuran-3-yl)benzamide

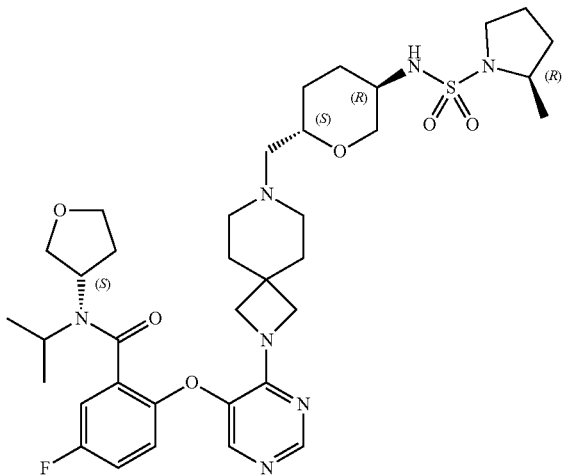

This compound was synthesized following the general procedure described for the synthesis of Example 200, except that reaction was stirred at 70° C. The crude compound was purified by Prep-HPLC (Method C).

Yield: 27.6%;

¹H NMR (400 MHz, DMSO-d₆) δ 8.34-8.18 (m, 1H), 7.86-7.69 (m, 1H), 7.37-7.21 (m, 2H), 7.10-6.99 (m, 2H), 4.29-3.63 (m, 1H), 3.63-3.36 (m, 2H), 3.30-3.24 (m, 1H), 3.23-3.10 (m, 2H), 3.10-2.94 (m, 2H), 2.41 (d, J=1.8 Hz, 1H), 2.32-2.14 (m, 5H), 2.06-1.88 (m, 3H), 1.87-1.73 (m, 2H), 1.72-1.60 (m, 5H), 1.55 (s, 1H), 1.41-1.31 (m, 2H), 1.30-1.19 (m, 1H), 1.18-0.93 (m, 8H); LCMS (Method A): Rt 1.84 min, 730.6 [M+H]⁺; HPLC (Method A): Rt 5.39 min, 97.97%.

Example 208. (R)—N-((3R,6S)-6-((2-(5-(2-((3R, 5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-2-methylpyrrolidine-1-sulfonamide

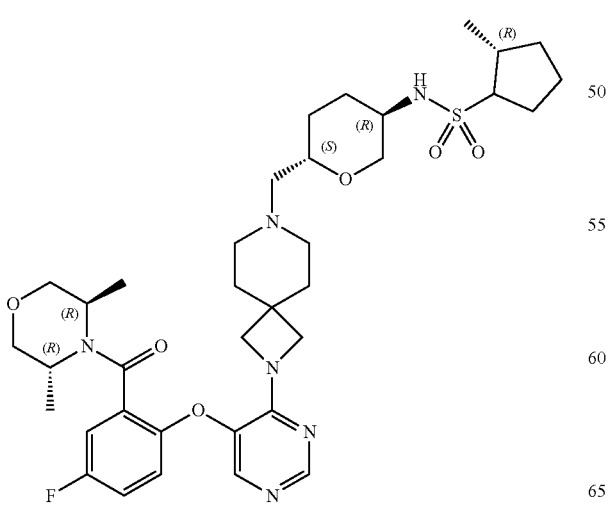

This compound was synthesized following the general procedure described for the synthesis of Example 200. The crude compound was purified by prep HPLC (Method A).

Yield: 35.7%;

¹H NMR (400 MHz, DMSO-d₆) δ 8.28 (s, 1H), 7.69 (s, 1H), 7.37 (dd, J=2.6, 7.9 Hz, 1H), 7.29 (dt, J=3.1, 8.6 Hz, 1H), 7.04 (dd, J=4.4, 9.1 Hz, 2H), 3.98-3.61 (m, 10H), 3.57-3.36 (m, 2H), 3.31-3.22 (m, 2H), 3.19-3.10 (m, 2H), 3.09-2.95 (m, 2H), 2.32-2.15 (m, 5H), 2.02-1.90 (m, 2H), 1.89-1.73 (m, 2H), 1.71-1.62 (m, 5H), 1.56-1.46 (m, 1H), 1.45-1.32 (m, 1H), 1.30-1.10 (m, 10H); LCMS (Method C): Rt 1.72 min, m/z: 716.6 [M+H]⁺; HPLC (Method A): Rt 4.65 min, 99.86%.

Example 209. (S)—N-((3R,6S)-6-((2-(5-(2-((3R, 5R)-3,5-Dimethylmorpholine-4-carbonyl)-4-fluorophenoxy)pyrimidin-4-yl)-2,7-diazaspiro[3.5]nonan-7-yl)methyl)tetrahydro-2H-pyran-3-yl)-2-methylpyrrolidine-1-sulfonamide

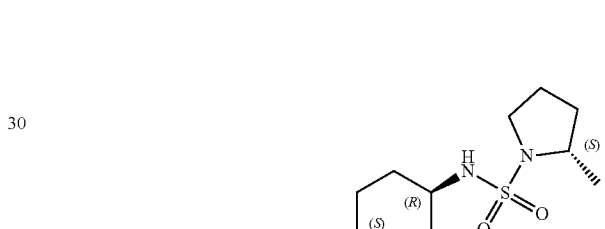

This compound was synthesized following the general procedure described for the synthesis of Example 200. The crude compound was purified by prep HPLC (Method B).

Yield: 36.3%;

¹H NMR (400 MHz, DMSO-d₆) δ 8.28 (s, 1H), 7.69 (s, 1H), 7.38 (dd, J=2.8, 8.1 Hz, 1H), 7.29 (dt, J=3.1, 8.6 Hz, 1H), 7.14-6.99 (m, 2H), 3.96-3.74 (m, 7H), 3.73-3.62 (m, 2H), 3.54-3.42 (m, 1H), 3.22-3.12 (m, 2H), 3.09-2.96 (m, 2H), 2.28 (dd, J=6.3, 12.9 Hz, 4H), 2.22-2.15 (m, 2H), 2.03-1.89 (m, 3H), 1.88-1.73 (m, 3H), 1.72-1.61 (m, 5H), 1.56-1.48 (m, 1H), 1.44-1.31 (m, 2H), 1.29-1.11 (m, 10H); LCMS (Method A): Rt 1.76 min, m/z: 716.6 [M+H]⁺; HPLC (Method C): Rt 5.31 min, 98.79%.

Example 210. 5-Fluoro-N,N-diisopropyl-2-((4-(7-(((2S,5R)-5-(((S)-3-methoxypyrrolidine)-1-sulfonamido)tetrahydro-2H-pyran-2-yl)methyl)-2,7-diazaspiro[3.5]nonan-2-yl)pyrimidin-5-yl)oxy)benzamide
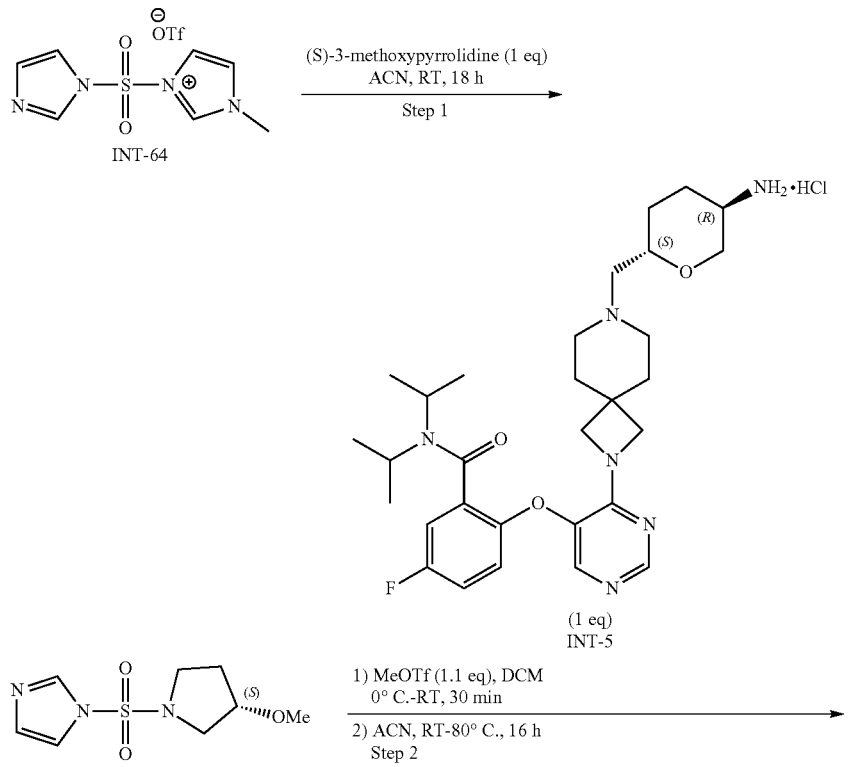
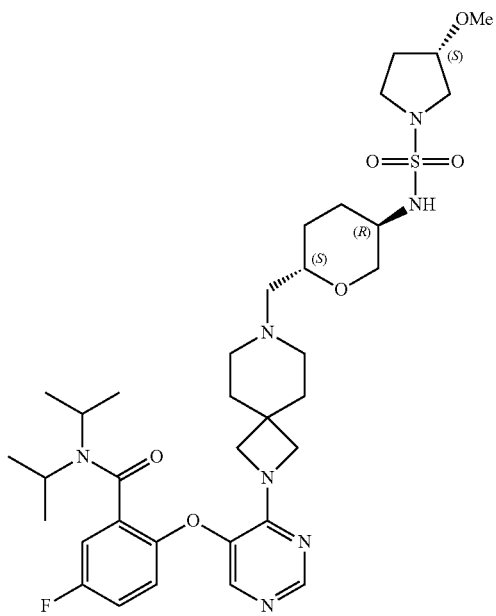
Example 210

Step 1. (S)-1-((3-Methoxypyrrolidin-1-yl)sulfonyl)-1H-imidazole

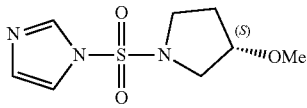

To a stirred solution of 3-((1H-imidazol-1-yl)sulfonyl)-1-methyl-1H-imidazol-3-ium trifluoromethanesulfonate (800 mg, 2.208 mmol) in ACN (20 mL), (S)-3-methoxypyrrolidine (223 mg, 2.208 mmol) was added at 0° C. under nitrogen atmosphere. The reaction mixture was stirred at RT for 18 h, and the reaction progress was monitored by LCMS. After completion, the reaction was concentrated under reduced pressure to obtain the crude product. The crude was purified by Prep-HPLC (Method D) to obtain (S)-1-((3-methoxypyrrolidin-1-yl)sulfonyl)-1H-imidazole (250 mg, 47.7% yield) as a liquid. $^1$H NMR (400 MHz, DMSO-d$_6$) δ 8.22-8.16 (m, 1H), 7.69-7.65 (m, 1H), 7.15-7.11 (m, 1H), 3.92-3.87 (m, 1H), 3.48-3.42 (m, 2H), 3.03 (s, 3H), 3.31-3.22 (m, 2H), 1.97-1.83 (m, 2H); LCMS (Method B): Rt 1.14 min, 232.2 [M+H]$^+$, 97.38%.

Step 2. 5-Fluoro-N,N-diisopropyl-2-((4-(7-(((2S,5R)-5-(((S)-3-methoxypyrrolidine)-1-sulfonamido)tetrahydro-2H-pyran-2-yl)methyl)-2,7-diazaspiro[3.5]nonan-2-yl)pyrimidin-5-yl)oxy)benzamide (Example 210)

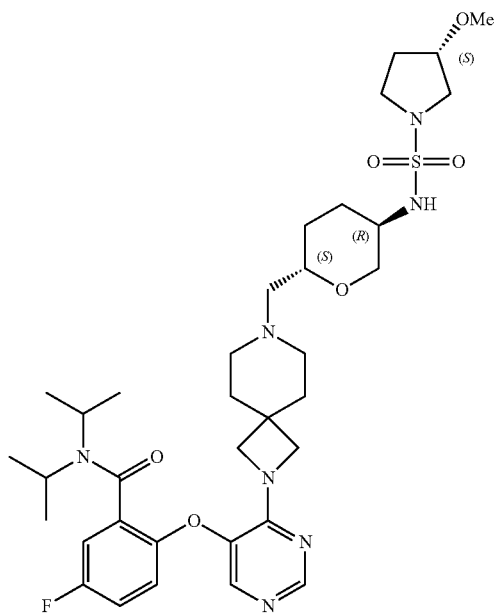

To a dried 50 mL round bottom flask under nitrogen atmosphere, (S)-1-((3-methoxypyrrolidin-1-yl)sulfonyl)-1H-imidazole (100 mg, 0.432 mmol) was added in DCM (10 mL). To this reaction mixture, MeOTf (0.052 mL, 0.476 mmol) was added at 0° C. and the resulting reaction was stirred at RT for 30 min. After completion, the reaction mixture was concentrated under reduced pressure to afford the crude material. The crude material was dissolved in CH$_3$CN (25 mL) and ((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide hydrochloride (256 mg, 0.432 mmol) was added at RT under nitrogen atmosphere. The resulting reaction mixture was heated at 80° C. for 16 h. The reaction progress was monitored by LCMS. After completion, the reaction mixture was concentrated on a rotary evaporator under reduced pressure to obtain the crude compound. The crude product was purified by Prep-HPLC (Method B) to obtain 5-fluoro-N,N-diisopropyl-2-((4-(7-(((2S,5R)-5-(((S)-3-methoxypyrrolidine)-1-sulfonamido)tetrahydro-2H-pyran-2-yl)methyl)-2,7-diazaspiro[3.5]nonan-2-yl)pyrimidin-5-yl)oxy)benzamide (62 mg, 19.94% yield). $^1$H NMR (400 MHz, DMSO-d$_6$) δ 8.26 (s, 1H), 7.71 (s, 1H), 7.26-7.17 (m, 3H), 7.07-7.00 (m, 1H), 4.01-3.93 (m, 1H), 3.92-3.83 (m, 3H), 3.83-3.76 (m, 2H), 3.74-3.65 (m, 1H), 3.58-3.48 (m, 1H), 3.29-3.24 (m, 2H), 3.22 (s, 3H), 3.19-3.13 (m, 3H), 3.08-2.95 (m, 2H), 2.32-2.23 (m, 4H), 2.22-2.16 (m, 1H), 2.00-1.89 (m, 3H), 1.76-1.59 (m, 6H), 1.44 (d, J=6.8 Hz, 3H), 1.35 (d, J=6.6 Hz, 4H), 1.28-1.15 (m, 1H), 1.09 (d, J=6.6 Hz, 3H), 1.00 (d, J=6.5 Hz, 3H); LCMS (Method B): Rt 1.33 min, 718.3 [M+H]$^+$, HPLC (Method A): Rt 5.42 min, 99.84%.

Example 211. 5-Fluoro-N,N-diisopropyl-2-((4-(7-(((2S,5R)-5-(((R)-3-methoxypyrrolidine)-1-sulfonamido)tetrahydro-2H-pyran-2-yl)methyl)-2,7-diazaspiro[3.5]nonan-2-yl)pyrimidin-5-yl)oxy)benzamide

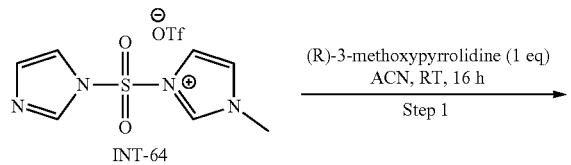

INT-64

(R)-3-methoxypyrrolidine (1 eq)
ACN, RT, 16 h

Step 1

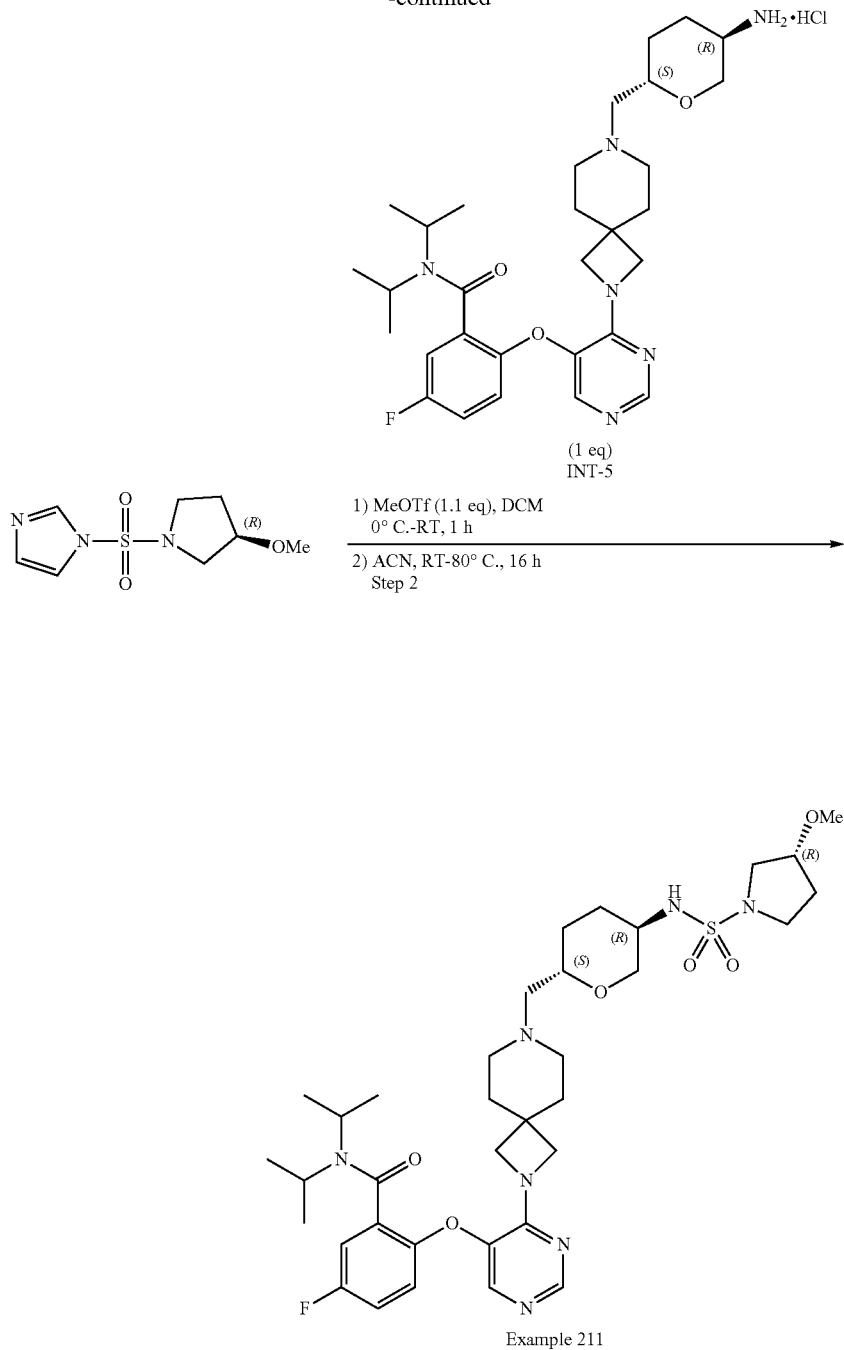

Example 211

Step 1. (R)-1-((3-Methoxypyrrolidin-1-yl)sulfonyl)-1H-imidazole

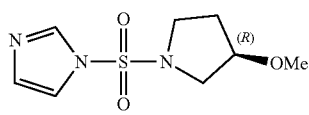

To a stirred solution of 3-((1H-imidazol-1-yl)sulfonyl)-1-methyl-1H-imidazol-3-ium trifluoromethanesulfonate (800 mg, 2.208 mmol) in ACN (20 mL), (R)-3-methoxypyrrolidine (223 mg, 2.208 mmol) was added at 0° C. under nitrogen. The reaction was stirred at RT for 16 h. The reaction progress was monitored by LCMS. After completion, the reaction mixture was concentrated under reduced pressure to obtain the crude. The crude product was purified by Prep-HPLC (Method B) to obtain (R)-1-((3-methoxypyrrolidin-1-yl)sulfonyl)-1H-imidazole (250 mg, 47.5% yield) as a liquid. $^1$H NMR (400 MHz, DMSO-$d_6$) δ 8.22-8.16 (m, 1H), 7.69-7.65 (m, 1H), 7.16-7.01 (m, 1H), 3.91-3.85 (m, 1H), 3.43 (s, 2H), 3.32-3.21 (m, 2H), 3.06 (s, 3H), 1.87-1.83 (m, 2H); LCMS (Method B): Rt 1.15 min, m/z: 232.2 [M+H]$^+$, 96.96%.

Step 2. 5-Fluoro-N,N-diisopropyl-2-((4-(7-(((2S,5R)-5-(((R)-3-methoxypyrrolidine)-1-sulfonamido)tetrahydro-2H-pyran-2-yl)methyl)-2,7-diazaspiro[3.5]nonan-2-yl)pyrimidin-5-yl)oxy)benzamide (Example 211)

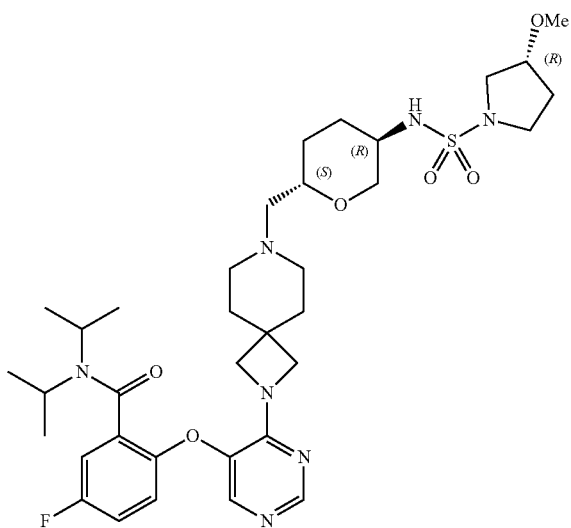

To a dried 100 mL round bottom flask under nitrogen atmosphere, (R)-1-((3-methoxypyrrolidin-1-yl)sulfonyl)-1H-imidazole (100 mg, 0.432 mmol) was added in DCM (10 mL). To this reaction mixture, MeOTf (0.052 mL, 0.476 mmol) was added at 0° C. and the resulting reaction was stirred at RT for 1 h. After completion, the reaction mixture was concentrated under reduced pressure to obtain the crude. The crude material was dissolved in ACN (25 mL) and 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide hydrochloride (256 mg, 0.432 mmol) was added at RT under nitrogen atmosphere. The resulting reaction mixture was heated at 80° C. for 16 h. The reaction progress was monitored by LCMS. After completion, the reaction mixture was concentrated on a rotary evaporator under reduced pressure to obtain the crude compound. The crude was purified by Prep-HPLC (Method F) to obtain 5-fluoro-N,N-diisopropyl-2-((4-(7-(((2S,5R)-5-(((R)-3-methoxypyrrolidine)-1-sulfonamido)tetrahydro-2H-pyran-2-yl)methyl)-2,7-diazaspiro[3.5]nonan-2-yl)pyrimidin-5-yl)oxy)benzamide (48 mg, 15.40% yield) as a solid. $^1$H NMR (400 MHz, DMSO-$d_6$) δ 8.26 (s, 1H), 7.71 (s, 1H), 7.26-7.16 (m, 3H), 7.04 (dd, J=4.3, 10.1 Hz, 1H), 4.02-3.74 (m, 6H), 3.74-3.63 (m, 1H), 3.59-3.46 (m, 1H), 3.31-3.10 (m, 9H), 3.10-2.94 (m, 2H), 2.32-2.15 (m, 5H), 2.04-1.87 (m, 3H), 1.76-1.57 (m, 5H), 1.44 (d, J=6.8 Hz, 3H), 1.41-1.31 (m, 4H), 1.28-1.15 (m, 1H), 1.09 (d, J=6.5 Hz, 3H), 1.00 (d, J=6.5 Hz, 3H). LCMS (Method B): Rt 1.38 min, 718.3 [M+H]$^+$; HPLC (Method A): Rt 5.43 min, 99.61%.

Example 212. 5-Fluoro-N,N-diisopropyl-2-((4-(7-(((2S,5R)-5-(((R)-2-(methoxymethyl)pyrrolidine)-1-sulfonamido)tetrahydro-2H-pyran-2-yl)methyl)-2,7-diazaspiro[3.5]nonan-2-yl)pyrimidin-5-yl)oxy)benzamide

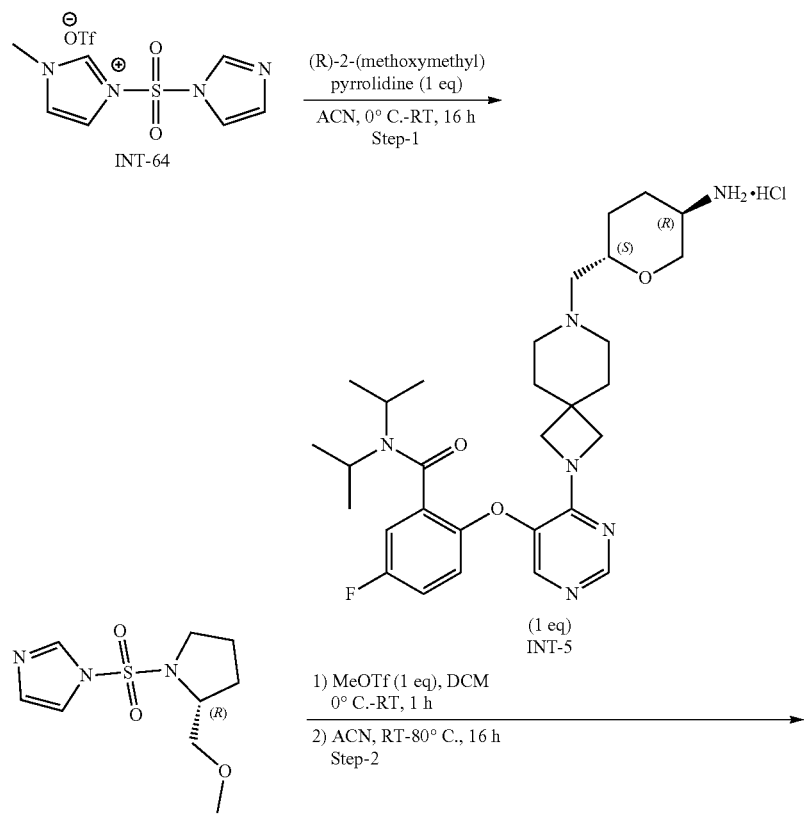

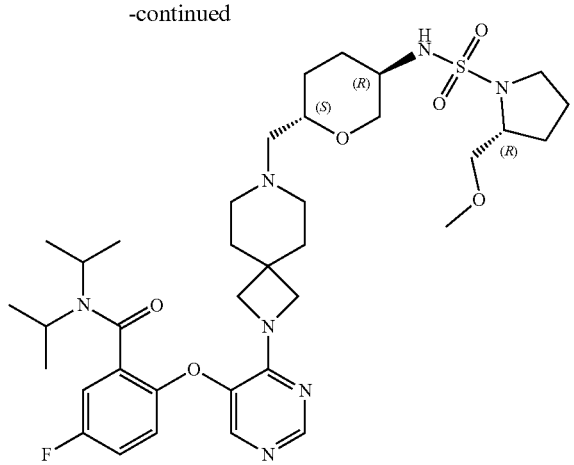

Example 212

Step 1. (R)-1-((2-(methoxymethyl)pyrrolidin-1-yl)sulfonyl)-1H-imidazole

Step 2. 5-Fluoro-N,N-diisopropyl-2-((4-(7-(((2S,5R)-5-(((R)-2-(methoxymethyl)pyrrolidine)-1-sulfonamido)tetrahydro-2H-pyran-2-yl)methyl)-2,7-diazaspiro[3.5]nonan-2-yl)pyrimidin-5-yl)oxy)benzamide (Example 212)

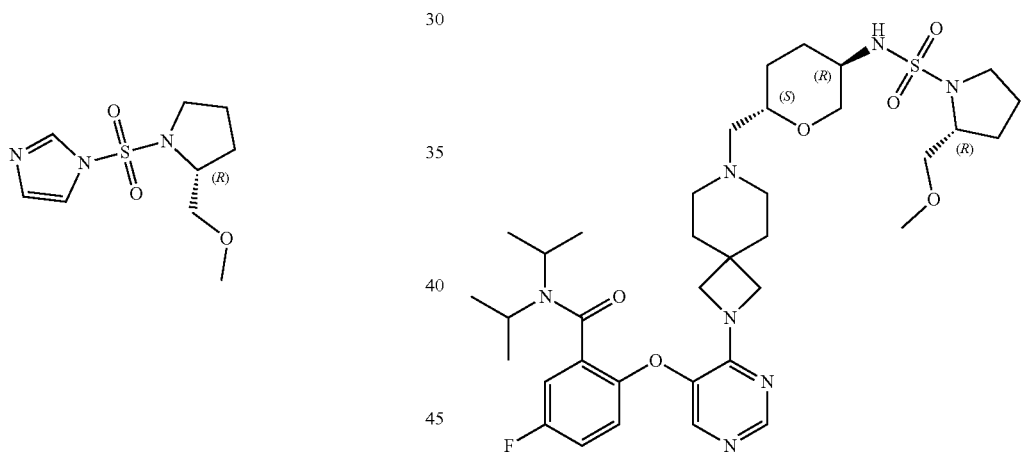

To a dried 100 mL round bottom flask under nitrogen atmosphere, 3-((1H-imidazol-1-yl)sulfonyl)-1-methyl-1H-imidazol-3-ium trifluoromethanesulfonate (0.7 g, 1.932 mmol) was added in ACN (20 mL). To this solution, (R)-2-(methoxymethyl)pyrrolidine (0.293 g, 1.932 mmol) was added at 0° C. and the reaction was stirred at RT for 16 h. The reaction progress was monitored by LCMS. The reaction mixture was concentrated under reduced pressure to obtain the crude compound. The crude compound was purified by Prep-HPLC (Method A) to afford (R)-1-((2-(methoxymethyl)pyrrolidin-1-yl)sulfonyl)-1H-imidazole (90 mg, 17.50% yield). LCMS (Method A): Rt 1.40 min, m/z: 246.1 [M+H]$^+$, 92.15%.

To a dried round bottom flask under nitrogen atmosphere, (R)-1-((2-(methoxymethyl)pyrrolidin-1-yl)sulfonyl)-1H-imidazole (100 mg, 0.408 mmol) was added in DCM (10 mL). To this solution, MeOTf (0.045 mL, 0.408 mmol) was added at 0° C., and the reaction was stirred at RT for 1 h. The reaction mixture was concentrated under reduced pressure to obtain the crude material. The crude material was dissolved in ACN (10 mL) and 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide hydrochloride (241 mg, 0.408 mmol; this compound was neutralized using aqueous NaHCO$_3$ and used in the reaction) in ACN (10 mL) was added at RT under nitrogen atmosphere. The reaction was stirred at 80° C. for 16 h. The reaction progress was monitored by LCMS. The reaction mixture was concentrated under reduced pressure to obtain crude material. The crude material was purified by Prep-HPLC (Method D) to afford 5-fluoro-N,N-diisopropyl-2-((4-(7-(((2S,5R)-5-(((R)-2-(methoxymethyl)pyrrolidine)-1- sulfonamido)tetrahydro-2H-pyran-2-yl)methyl)-2,7-diazaspiro[3.5]nonan-2-yl)pyrimidin-5-yl)oxy)benzamide (45 mg, 14.96% yield) as a solid. ¹H NMR (400 MHz, DMSO-d₆) δ 8.26 (s, 1H), 7.71 (s, 1H), 7.28-7.13 (m, 3H), 7.07-7.01 (m, 1H), 3.94-3.77 (m, 5H), 3.74-3.63 (m, 2H), 3.58-3.48 (m, 1H), 3.40 (dd, J=3.6, 9.3 Hz, 1H), 3.28-3.25 (m, 3H), 3.24-2.95 (m, 6H), 2.32-2.15 (m, 5H), 2.02-1.91 (m, 1H), 1.90-1.74 (m, 5H), 1.73-1.60 (m, 5H), 1.44 (d, J=6.8 Hz, 3H), 1.41-1.31 (m, 4H), 1.29-1.16 (m, 1H), 1.09 (d, J=6.6 Hz, 3H), 0.99 (d, J=6.6 Hz, 3H); LCMS (Method E): Rt 1.86 min, m/z: 732.5 [M+H]⁺; HPLC (Method A): Rt 5.75 min, 99.22%.

Example 213. 5-Fluoro-N,N-diisopropyl-2-((4-(7-(((2S,5R)-5-(((S)-2-(methoxymethyl)pyrrolidine)-1-sulfonamido)tetrahydro-2H-pyran-2-yl)methyl)-2,7-diazaspiro[3.5]nonan-2-yl)pyrimidin-5-yl)oxy)benzamide

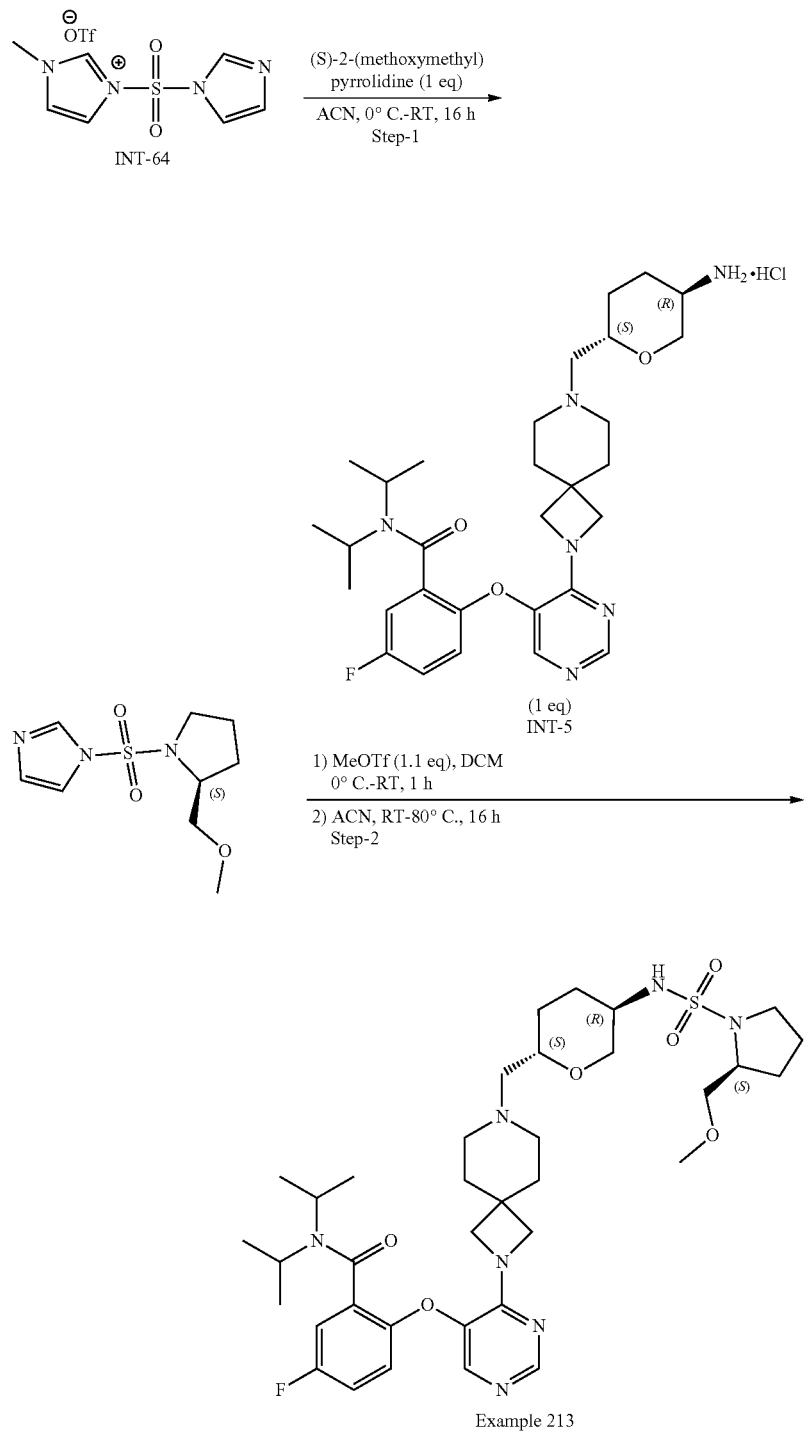

Example 213

Step 1. (S)-1-((2-(methoxymethyl)pyrrolidin-1-yl)sulfonyl)-1H-imidazole

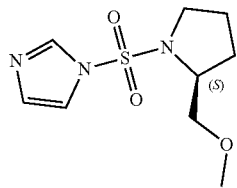

To a 100 mL dried round bottom flask under nitrogen atmosphere, 3-((1H-imidazol-1-yl)sulfonyl)-1-methyl-1H-imidazol-3-ium trifluoromethanesulfonate (1 g, 2.76 mmol) was added to ACN (20 mL). To this reaction mixture, (S)-2-(methoxymethyl)pyrrolidine hydrochloride (0.419 g, 2.76 mmol; this compound was neutralized by passing through SCX cartridge) was added at 0° C. under nitrogen atmosphere. The reaction mixture was stirred at RT. The progress of the reaction was monitored by LCMS. After completion, the reaction mixture was quenched with water, and the aqueous layer was washed with EtOAc (3×20 mL). The aqueous layer was concentrated to obtain the crude compound. The crude compound was purified Prep-HPLC to obtain (S)-1-((2-(methoxymethyl)pyrrolidin-1-yl)sulfonyl)-1H-imidazole (100 mg, 14.07% yield) as a clear liquid. LCMS (Method B): Rt 1.31 min, 246.3 [M+H]$^+$, 95.25%.

Step 2. 5-Fluoro-N,N-diisopropyl-2-((4-(7-(((2S,5R)-5-(((S)-2-(methoxymethyl)pyrrolidine)-1-sulfonamido)tetrahydro-2H-pyran-2-yl)methyl)-2,7-diazaspiro[3.5]nonan-2-yl)pyrimidin-5-yl)oxy)benzamide (Example 213)

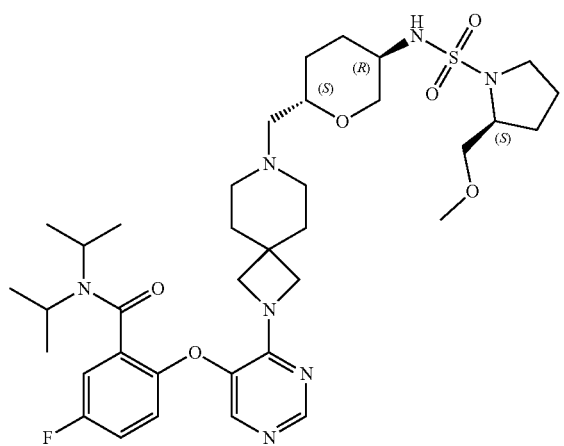

To a dried round bottom flask under nitrogen atmosphere, (S)-1-((2-(methoxymethyl)pyrrolidin-1-yl)sulfonyl)-1H-imidazole (100 mg, 0.408 mmol) was dissolved in DCM (10 mL). To this reaction mixture, MeOTf (0.049 ml, 0.448 mmol) was added at 0° C. The reaction was stirred at RT for 1 h and concentrated under reduced pressure to obtain (S)-1-((2-(methoxymethyl)pyrrolidin-1-yl)sulfonyl)-1H-imidazole trifluoromethanesulfonate. To this reaction mixture, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide hydrochloride (241 mg, 0.408 mmol; this compound was neutralized using aqueous NaHCO$_3$ and used in the reaction) in ACN (20 mL) was added at RT. The reaction was stirred at 80° C. Progress of the reaction was monitored by LCMS. After completion, the reaction was concentrated on a rotary evaporator under reduced pressure to obtain the crude product. The crude compound was purified by prep-HPLC to give 5-fluoro-N,N-diisopropyl-2-((4-(7-(((2S,5R)-5-(((S)-2-(methoxymethyl)pyrrolidine)-1-sulfonamido)tetrahydro-2H-pyran-2-yl)methyl)-2,7-diazaspiro[3.5]nonan-2-yl)pyrimidin-5-yl)oxy)benzamide (45 mg, 0.061 mmol, 14.91% yield) as a solid. $^1$H NMR (400 MHz, DMSO-d$_6$) δ 8.26 (s, 1H), 7.71 (s, 1H), 7.26-7.19 (m, 2H), 7.17 (br d, J=7.3 Hz, 1H), 7.04 (dd, J=4.3, 10.0 Hz, 1H), 3.95-3.83 (m, 3H), 3.83-3.76 (m, 2H), 3.74-3.64 (m, 2H), 3.59-3.48 (m, 1H), 3.42-3.37 (m, 1H), 3.26 (s, 3H), 3.24-3.19 (m, 1H), 3.18-3.04 (m, 4H), 3.03-2.96 (m, 1H), 2.32-2.16 (m, 5H), 1.95 (br d, J=11.5 Hz, 1H), 1.90-1.75 (m, 5H), 1.73-1.60 (m, 5H), 1.44 (d, J=6.6 Hz, 3H), 1.42-1.30 (m, 4H), 1.29-1.17 (m, 1H), 1.09 (d, J=6.6 Hz, 3H), 1.00 (d, J=6.6 Hz, 3H); LCMS (Method B): Rt 1.42 min, 732.4 [M+H]$^+$; HPLC (Method A): Rt 5.76 min, 98.83%.

Example 214. N-(2,2-difluoroethyl)-5-fluoro-2-((4-(7-(((2S,5R)-5-((N-(3-hydroxypropyl)-N-methylsulfamoyl)amino)tetrahydro-2H-pyran-2-yl)methyl)-2,7-diazaspiro[3.5]nonan-2-yl)pyrimidin-5-yl)oxy)-N-isopropylbenzamide

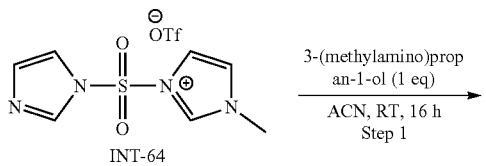

-continued

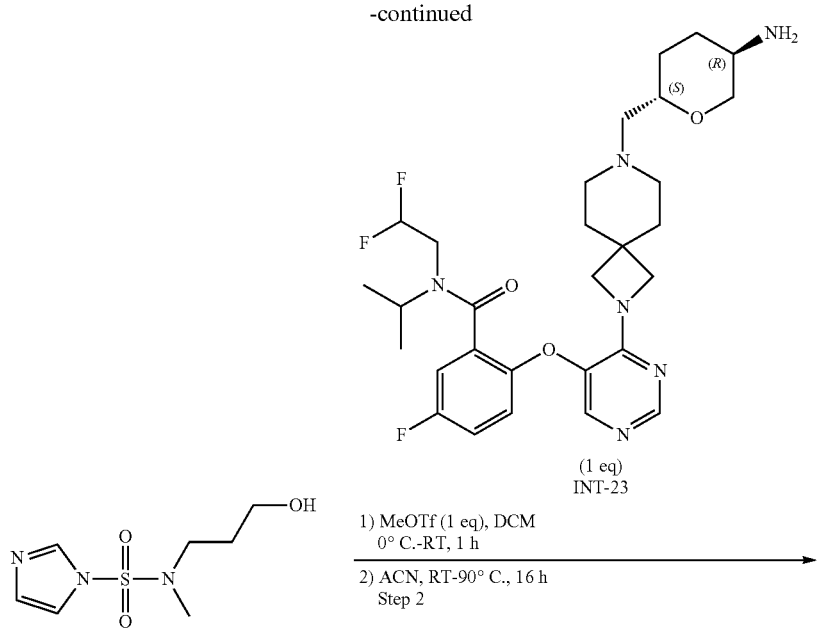

(1 eq)
INT-23

1) MeOTf (1 eq), DCM
0° C.-RT, 1 h
2) ACN, RT-90° C., 16 h
Step 2

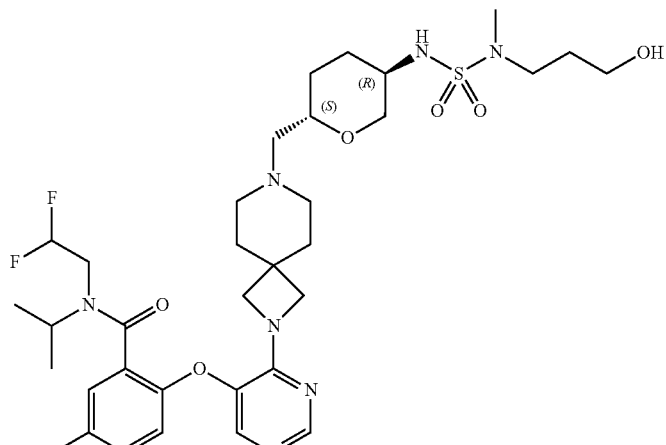

Example 214

Step 1. N-(3-Hydroxypropyl)-N-methyl-1H-imidazole-1-sulfonamide

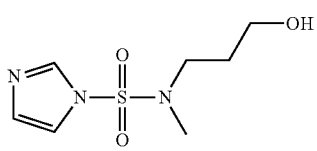

To a stirred solution of 3-((1H-imidazol-1-yl)sulfonyl)-1-methyl-1H-imidazol-3-ium trifluoromethanesulfonate (1.1 g, 3.04 mmol) in ACN (15 mL), 3-(methylamino)propan-1-ol (0.541 g, 6.07 mmol) was added at 0° C. under nitrogen atmosphere. The reaction was stirred at RT for 16 h. The progress of the reaction was monitored by LCMS. After completion, the reaction mixture was concentrated under reduced pressure to obtain the crude product. The crude product was purified by Prep-HPLC (Method-H) to obtain N-(3-hydroxypropyl)-N-methyl-1H-imidazole-1-sulfonamide (0.094 g, 13.70% yield) as a solid. $^1$H NMR (400 MHz, DMSO-$d_6$) δ 8.21-8.12 (m, 1H), 7.68-7.60 (m, 1H), 7.20-7.09 (m, 1H), 4.50-4.41 (m, 1H), 3.47-3.38 (m, 2H), 3.24-3.09 (m, 2H), 2.88-2.79 (m, 3H), 1.75-1.54 (m, 2H); LCMS (Method A): Rt 1.17 min, 220.1 [M+H]$^+$.

Step 2. N-(2,2-Difluoroethyl)-5-fluoro-2-((4-(7-(((2S,5R)-5-((N-(3-hydroxypropyl)-N-methylsulfa-moyl)amino)tetrahydro-2H-pyran-2-yl)methyl)-2,7-diazaspiro[3.5]nonan-2-yl)pyrimidin-5-yl)oxy)-N-isopropylbenzamide (Example 214)

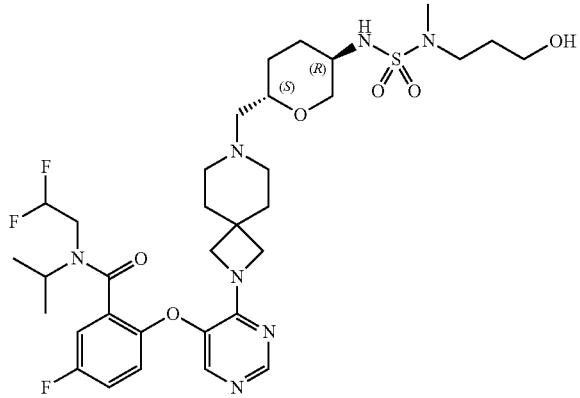

To a dried 25 mL round bottom flask under nitrogen atmosphere, N-(3-hydroxypropyl)-N-methyl-1H-imidazole-1-sulfonamide (0.09 g, 0.410 mmol) was added in DCM (5 mL). To this reaction mixture, MeOTf (0.045 mL, 0.410 mmol) was added at 0° C. The reaction was stirred at RT for 1 h. The reaction mixture was concentrated under reduced pressure to afford the crude material. The crude material was dissolved in ACN (15 mL) and 2-((4-(7-(((2S,5R)-5-amino-tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (0.25 g, 0.434 mmol) was added. The resulting mixture was heated at 90° C. for 16 h. The reaction progress was monitored by TLC and LCMS. The reaction mixture was concentrated under reduced pressure to afford crude product. The crude material was purified by Prep-HPLC (Method A) to obtain N-(2,2-difluoroethyl)-5-fluoro-2-((4-(7-(((2S,5R)-5-((N-(3-hydroxypropyl)-N-methylsulfamoyl)amino)tetrahydro-2H-pyran-2-yl)methyl)-2,7-diazaspiro[3.5]nonan-2-yl)pyrimidin-5-yl)oxy)-N-isopropylbenzamide (0.045 g, 14.12% yield) as a solid. $^1$H NMR (400 MHz, DMSO-d$_6$) δ 8.32-8.25 (m, 1H), 7.76 (s, 1H), 7.35 (dd, J=3.1, 8.3 Hz, 1H), 7.32-7.24 (m, 1H), 7.20-7.08 (m, 1H), 7.02 (dd, J=4.4, 9.1 Hz, 1H), 6.37-6.02 (m, 1H), 4.47 (br s, 1H), 3.90-3.80 (m, 4H), 3.79-3.62 (m, 4H), 3.47-3.37 (m, 3H), 3.11-3.02 (m, 2H), 3.01-2.94 (m, 2H), 2.65 (s, 3H), 2.27 (dd, J=6.2, 12.9 Hz, 4H), 2.21-2.14 (m, 1H), 2.00-1.90 (m, 1H), 1.76-1.54 (m, 7H), 1.46-1.31 (m, 1H), 1.29-1.15 (m, 2H), 1.10 (d, J=6.5 Hz, 3H), 1.06 (d, J=6.5 Hz, 3H); LCMS (Method E): Rt 1.63 min, 728.4 [M+H]$^+$; HPLC (Method F): Rt 2.82 min, 99.05%.

Example 215. N-Ethyl-5-fluoro-N-isopropyl-2-((4-(7-(((2S,5R)-5-(3-phenylureido)tetrahydro-2H-pyran-2-yl)methyl)-2,7-diazaspiro[3.5]nonan-2-yl)pyrimidin-5-yl)oxy)benzamide To a dried 100 mL round bottom flask under nitrogen atmosphere, aniline (100 mg, 1.074 mmol) was added in DCM (20 mL). To this reaction mixture, triphosgene (382 mg, 1.289 mmol) and Et$_3$N (0.898 mL, 6.44 mmol) were added at 0° C. The reaction was stirred at RT for 1 h. The reaction mixture was concentrated under reduced pressure to obtain the crude compound. The crude compound was dissolved in DCM (20 mL). To this solution, 2-((4-(7-(((2S, 5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide hydrochloride (496 mg, 0.859 mmol) was added and the reaction was stirred at RT for 12 h. The progress of the reaction was monitored by TLC (10% MeOH in DCM). The reaction was quenched with water (10 mL) and extracted with EtOAc (3×50 mL). The combined organic layer was dried over sodium sulfate and concentrated under reduced pressure to obtain the crude material. The crude was purified by Prep-HPLC (Method B) to afford N-ethyl-5-fluoro-N-isopropyl-2-((4-(7-(((2S,5R)-5-(3-phenylureido)tetrahydro-2H-pyran-2-yl)methyl)-2,7-diazaspiro[3.5]nonan-2-yl)pyrimidin-5-yl)oxy)benzamide (35 mg, 28.1% yield) as a solid. $^1$H NMR (400 MHz, DMSO-d$_6$) δ 8.57 (m, 1H), 8.31-8.23 (m, 1H), 7.74-7.64 (m, 1H), 7.37 (dd, J=1.0, 8.6 Hz, 2H), 7.33-7.15 (m, 4H), 7.11-6.99 (m, 1H), 6.92-6.82 (m, 1H), 6.30 (br d, J=7.6 Hz, 1H), 3.95-3.82 (m, 3H), 3.82-3.70 (m, 3H), 3.56-3.38 (m, 3H), 3.27-3.10 (m, 2H), 2.95 (t, J=10.5 Hz, 1H), 2.32-2.17 (m, 4H), 1.95-1.83 (m, 1H), 1.76-1.62 (m, 5H), 1.43-1.16 (m, 4H), 1.15-1.07 (m, 5H), 1.07-0.96 (m, 3H); LCMS (Method C): Rt 1.04 min, m/z: 600.6 [M+H]$^+$; HPLC (Method B): Rt 3.72 min, 96.46%.

Example 216: N-Ethyl-2-((4-(7-(((2S,5R)-5-(ethyl-sulfonamido)tetrahydro-2H-pyran-2-yl)methyl)-2,7-diazaspiro[3.5]nonan-2-yl)-2-methylpyrimidin-5-yl)oxy)-5-fluoro-N-isopropylbenzamide
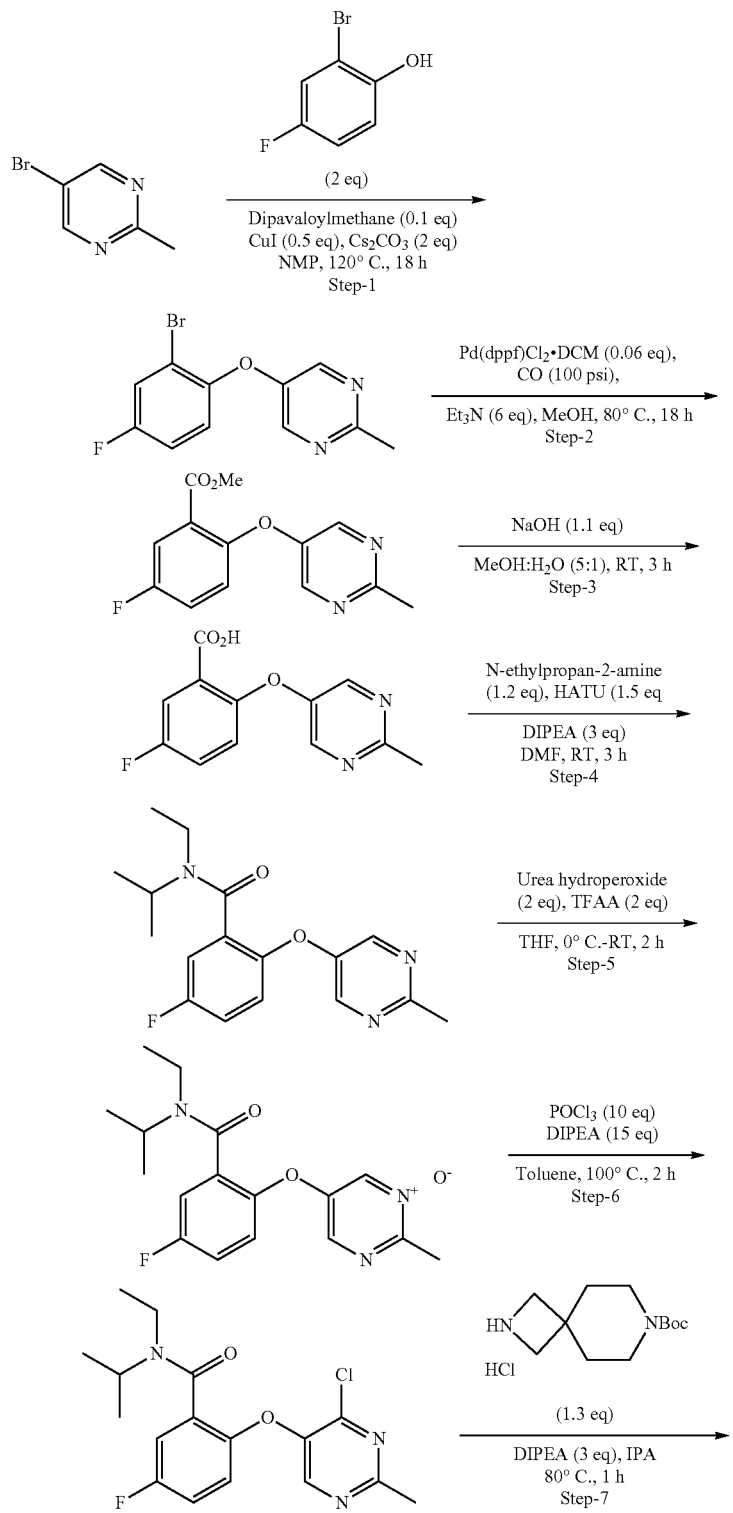

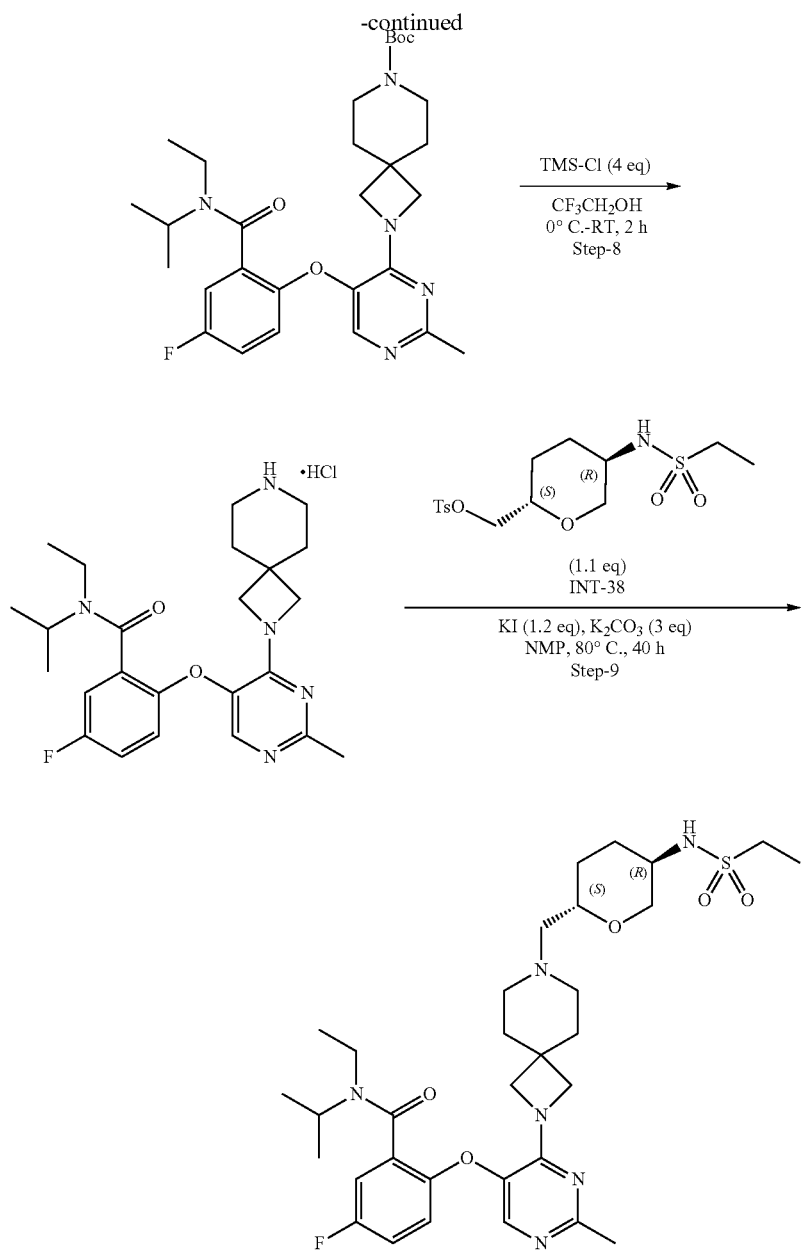

Example 216

Step 1.
5-(2-Bromo-4-fluorophenoxy)-2-methylpyrimidine

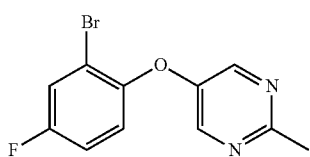 [SMILES: Cc1ncc(Oc2ccc(F)cc2Br)cn1]

In a dried sealed tube under nitrogen atmosphere, 2-bromo-4-fluorophenol (39.7 g, 208 mmol) and 5-bromo-2-methylpyrimidine (18 g, 104 mmol) were dissolved in NMP (160 mL). To this solution, $Cs_2CO_3$ (67.8 g, 208 mmol), 2,2,6,6-tetramethylheptane-3,5-dione (1.917 g, 10.40 mmol), and CuI (10.12 g, 52.0 mmol) were added at RT and the reaction was stirred at 120° C. for 18 h. The progress of the reaction was monitored by TLC (10% EtOAc in hexane). The reaction mixture was diluted with water (300 mL) and extracted with EtOAc (3×200 mL). The combined organic layer was washed with brine (150 mL), dried over anhydrous sodium sulfate, and filtered, and the filtrate was concentrated under reduced pressure to afford crude compound. The crude was purified by silica gel column chromatography using 15% EtOAc in hexane as an eluent to obtain 5-(2-bromo-4-fluorophenoxy)-2-methylpyrimidine (4.8 g, 13.50% yield). LCMS (Method B): Rt 1.87 min, m/z: 285.1 [M+H]$^+$, 82.81%.

Step 2.
5-Fluoro-2-((2-methylpyrimidin-5-yl)oxy)benzoic acid

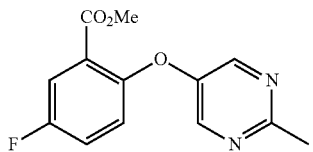 [SMILES: COC(=O)c1cc(F)ccc1Oc1cnc(C)nc1]

To a 300 mL Tini Clave vessel, 5-(2-bromo-4-fluorophenoxy)-2-methylpyrimidine (4.8 g, 16.96 mmol) was added in MeOH (50 mL). To this solution, Et₃N (14.18 mL, 102 mmol) and 1,1'-bis(diphenylphosphino)ferrocenedichloro palladium(II) dichloromethane complex (0.744 g, 1.017 mmol) were added. The reaction mixture was stirred at 80° C. for 18 h under a carbon monoxide atmosphere (100 psi). The progress of the reaction was monitored by TLC (5% MeOH in DCM). The reaction mixture was diluted with 10% MeOH in DCM and filtered through Celite®. The filtrate was concentrated under reduced pressure to afford the crude compound. The crude product was purified by silica gel column chromatography using 21% EtOAc in hexane as an eluent to obtain methyl 5-fluoro-2-((2-methylpyrimidin-5-yl)oxy)benzoate (3 g, 65.8% yield). LCMS (Method B): 1.63 min, m/z: 263.3 [M+H]⁺, 97.55%.

Step 3.
5-Fluoro-2-((2-methylpyrimidin-5-yl)oxy)benzoic acid

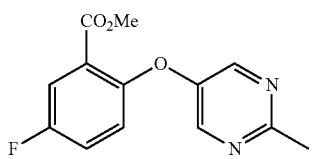 [SMILES: COC(=O)c1cc(F)ccc1Oc1cnc(C)nc1]

To a 100 mL round bottom flask, methyl 5-fluoro-2-((2-methylpyrimidin-5-yl)oxy)benzoate (2.5 g, 9.53 mmol) was added in MeOH (20 mL) and water (4.00 mL). To this solution, NaOH (0.419 g, 10.49 mmol) was added at 0° C. and the reaction was stirred at RT for 3 h. The reaction progress was monitored by TLC (100% EtOAc). The reaction mixture was concentrated and co-distilled with toluene to obtain crude 5-fluoro-2-((2-methylpyrimidin-5-yl)oxy)benzoic acid (3 g). This compound was used in the subsequent step without further purification. LCMS (Method B): Rt 1.37 min, m/z: 249.2 [M−H]⁻, 83.41%.

Step 4. N-Ethyl-5-fluoro-N-isopropyl-2-((2-methylpyrimidin-5-yl)oxy)benzamide

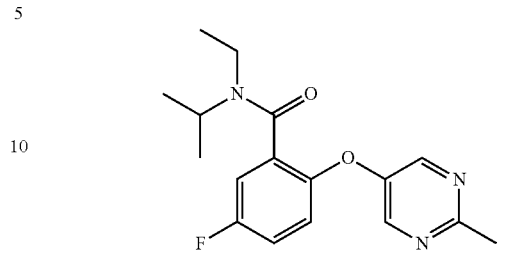

To a 50 mL round bottom flask, 5-fluoro-2-((2-methylpyrimidin-5-yl)oxy)benzoic acid (3 g, 12.09 mmol) was added in DMF (10 mL). To this solution, DIPEA (6.33 mL, 36.3 mmol), HATU (6.89 g, 18.13 mmol), and N-ethylpropan-2-amine (1.264 g, 14.50 mmol) were added at 0° C. under nitrogen atmosphere, and the reaction was stirred at RT for 3 h. The reaction mixture was diluted with water (25 mL) and extracted with EtOAc (2×30 mL). The combined organic layer was washed with brine solution (5 mL), dried over anhydrous sodium sulfate, and filtered. The filtrate was concentrated under reduced pressure to obtain the crude compound. The crude was purified by silica gel column chromatography using 35% EtOAc in hexane as an eluent to obtain N-ethyl-5-fluoro-N-isopropyl-2-((2-methylpyrimidin-5-yl)oxy)benzamide (2.2 g, 28.6% yield). LCMS (Method B): Rt 1.70 min, m/z: 318.2 [M+H]⁺, 49.94%.

Step 5. 5-(2-(Ethyl(isopropyl)carbamoyl)-4-fluorophenoxy)-2-methylpyrimidine 1-oxide

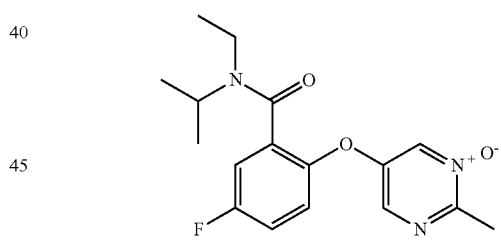

To a dried 50 mL round bottom flask, N-ethyl-5-fluoro-N-isopropyl-2-((2-methylpyrimidin-5-yl)oxy)benzamide (1 g, 3.15 mmol) was added in THF (20 mL). To this solution, urea hydrogen peroxide (0.593 g, 6.30 mmol) and TFAA (0.908 mL, 6.43 mmol) were added at 0° C. under nitrogen atmosphere. The reaction was stirred at RT for 2 h. The progress of the reaction was monitored by TLC (40% EtOAc in hexane). The reaction mixture was diluted with EtOAc (20 mL) and washed with saturated aq. NaHCO₃ (10 mL) and then with saturated sodium thiosulfate solution (10 mL). The combined organic layer was washed with brine (10 mL), dried over anhydrous Na₂SO₄, and filtered. The filtrate was concentrated under reduced pressure to obtain the crude compound. The crude compound was triturated with hexane to obtain 5-(2-(ethyl(isopropyl)carbamoyl)-4-fluorophenoxy)-2-methylpyrimidine 1-oxide (1 g, 76% yield). LCMS (Method B): Rt 1.52 min, m/z: 332.4 [M−H]⁻, 76.41%.

Step 6. 2-((4-Chloro-2-methylpyrimidin-5-yl)oxy)-N-ethyl-5-fluoro-N-isopropylbenzamide

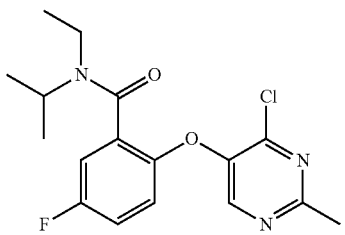 [SMILES: CCN(C(=O)c1cc(F)ccc1Oc1cnc(C)nc1Cl)C(C)C]

To solution of 5-(2-(ethyl(isopropyl)carbamoyl)-4-fluorophenoxy)-2-methylpyrimidine 1-oxide (1 g, 3.00 mmol) in toluene (10 mL), DIPEA (7.86 mL, 45.0 mmol) and POCl₃ (2.80 mL, 30.0 mmol) were added at RT. The reaction was stirred at 100° C. for 2 h. The progress of the reaction was monitored by TLC (50% EtOAc in hexane). The reaction mixture was concentrated under reduced pressure to obtain the crude compound. The crude compound was purified by silica gel flash column chromatography using 48% EtOAc in hexane as an eluent to obtain 2-((4-chloro-2-methylpyrimidin-5-yl)oxy)-N-ethyl-5-fluoro-N-isopropylbenzamide (455 mg, 40.8% yield) as a liquid. LCMS (Method B): Rt 1.98 min, m/z: 352.2 [M+H]⁺, 94.68%.

Step 7. tert-Butyl 2-(5-(2-(ethyl(isopropyl)carbamoyl)-4-fluorophenoxy)-2-methylpyrimidin-4-yl)-2,7-diazaspiro[3.5]nonane-7-carboxylate

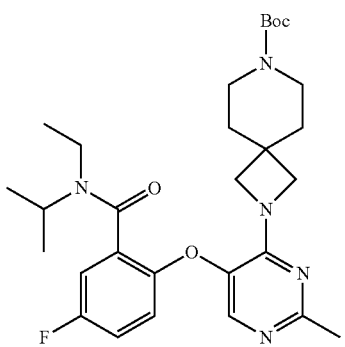 [SMILES: CCN(C(=O)c1cc(F)ccc1Oc1cnc(C)nc1N1CC2(CCN(C(=O)OC(C)(C)C)CC2)C1)C(C)C]

In a 25 mL round bottom flask, 2-((4-chloro-2-methylpyrimidin-5-yl)oxy)-N-ethyl-5-fluoro-N-isopropylbenzamide (350 mg, 0.995 mmol) was added in isopropanol (4 mL). To this solution, DIPEA (0.521 mL, 2.98 mmol) and tert-butyl 2,7-diazaspiro[3.5]nonane-7-carboxylate hydrochloride (340 mg, 1.293 mmol) were added and the reaction was stirred at 80° C. for 1 h. The reaction mixture was concentrated under reduced pressure to obtain crude material. The crude was purified by silica gel flash column chromatography using 40-50% EtOAc in hexane as an eluent to obtain tert-butyl 2-(5-(2-(ethyl(isopropyl)carbamoyl)-4-fluorophenoxy)-2-methylpyrimidin-4-yl)-2,7-diazaspiro[3.5]nonane-7-carboxylate (520 mg, 93% yield) as a solid. LCMS (Method B): Rt 1.67 min, m/z: 542.2 [M+H]⁺, 96.66%.

Step 8. N-Ethyl-5-fluoro-N-isopropyl-2-((2-methyl-4-(2,7-diazaspiro[3.5]nonan-2-yl)pyrimidin-5-yl)oxy)benzamide hydrochloride

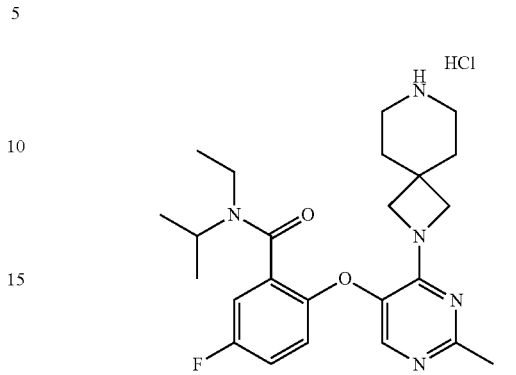

To a dried 50 mL round bottom flask, tert-butyl 2-(5-(2-(ethyl(isopropyl)carbamoyl)-4-fluorophenoxy)-2-methylpyrimidin-4-yl)-2,7-diazaspiro[3.5]nonane-7-carboxylate (520 mg, 0.960 mmol) was added in 2,2,2-trifluoroethanol (5 mL). To this solution, TMSCI (0.491 mL, 3.84 mmol) was added at 0° C. under nitrogen atmosphere. The reaction was stirred at RT for 2 h. The reaction progress was monitored by TLC (10% MeOH in DCM). The reaction mixture was concentrated under reduced pressure to obtain N-ethyl-5-fluoro-N-isopropyl-2-((2-methyl-4-(2,7-diazaspiro[3.5]nonan-2-yl)pyrimidin-5-yl)oxy)benzamide hydrochloride (500 mg, 0.96 mmol). LCMS (Method C): Rt 1.45 min, m/z: 442.1 [M+H]⁺, 97.25%.

Step 9. N-Ethyl-2-((4-(7-(((2S,5R)-5-(ethylsulfonamido)tetrahydro-2H-pyran-2-yl)methyl)-2,7-diazaspiro[3.5]nonan-2-yl)-2-methylpyrimidin-5-yl)oxy)-5-fluoro-N-isopropylbenzamide (Example 216)

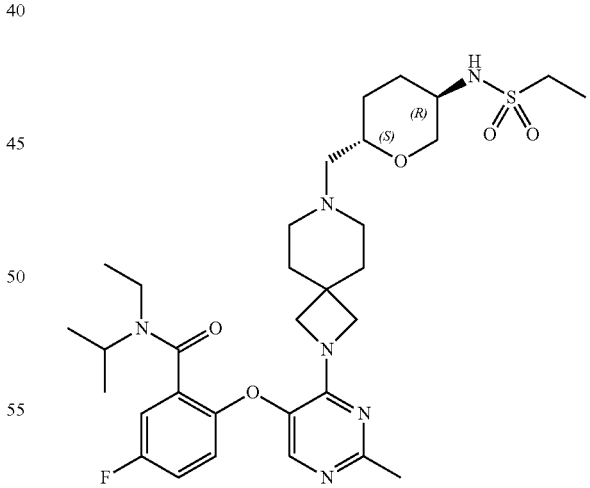

To a dried 25 mL round bottom flask, N-ethyl-5-fluoro-N-isopropyl-2-((2-methyl-4-(2,7-diazaspiro[3.5]nonan-2-yl)pyrimidin-5-yl)oxy)benzamide hydrochloride (520 mg, 1.088 mmol) was added in NMP (8 mL) under nitrogen atmosphere, then ((2S,5R)-5-(ethylsulfonamido)tetrahydro-2H-pyran-2-yl)methyl 4-methylbenzenesulfonate (452 mg, 1.197 mmol) was added. To this solution, K₂CO₃ (451 mg, 3.26 mmol) and KI (217 mg, 1.305 mmol) were added at RT and the reaction was stirred at 80° C. for 40 h. The reaction progress was monitored by TLC (10% MeOH in DCM). The reaction was diluted with EtOAc (30 mL) and filtered. The filtrate was washed with ice-cold water (3×10 mL), dried over sodium sulfate, and concentrated under reduced pressure to obtain the crude compound. The crude was purified by Prep-HPLC (Method B) to obtain N-ethyl-2-((4-(7-(((2S,5R)-5-(ethylsulfonamido)tetrahydro-2H-pyran-2-yl)methyl)-2,7-diazaspiro[3.5]nonan-2-yl)-2-methylpyrimidin-5-yl)oxy)-5-fluoro-N-isopropylbenzamide (190 mg, 26.9% yield). $^1$H NMR (400 MHz, DMSO-$d_6$) δ 7.69-7.58 (m, 1H), 7.31-7.17 (m, 2H), 7.10 (d, J=7.6 Hz, 1H), 6.99-6.90 (m, 1H), 3.92-3.65 (m, 6H), 3.46-3.36 (m, 1H), 3.31-3.19 (m, 2H), 3.18-3.05 (m, 2H), 3.04-2.95 (m, 3H), 2.35 (s, 3H), 2.31-2.15 (m, 5H), 2.00-1.88 (m, 1H), 1.73-1.57 (m, 5H), 1.47-1.34 (m, 1H), 1.31-0.96 (m, 13H); LCMS (Method B): Rt 1.15 min, m/z: 647.3 [M+H]$^+$; HPLC (Method A): Rt 5.03 min, 99.60%.

Example 217. N-Ethyl-5-fluoro-N-isopropyl-2-((4-(7-(((2S,5R)-5-((2-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy)benzamide

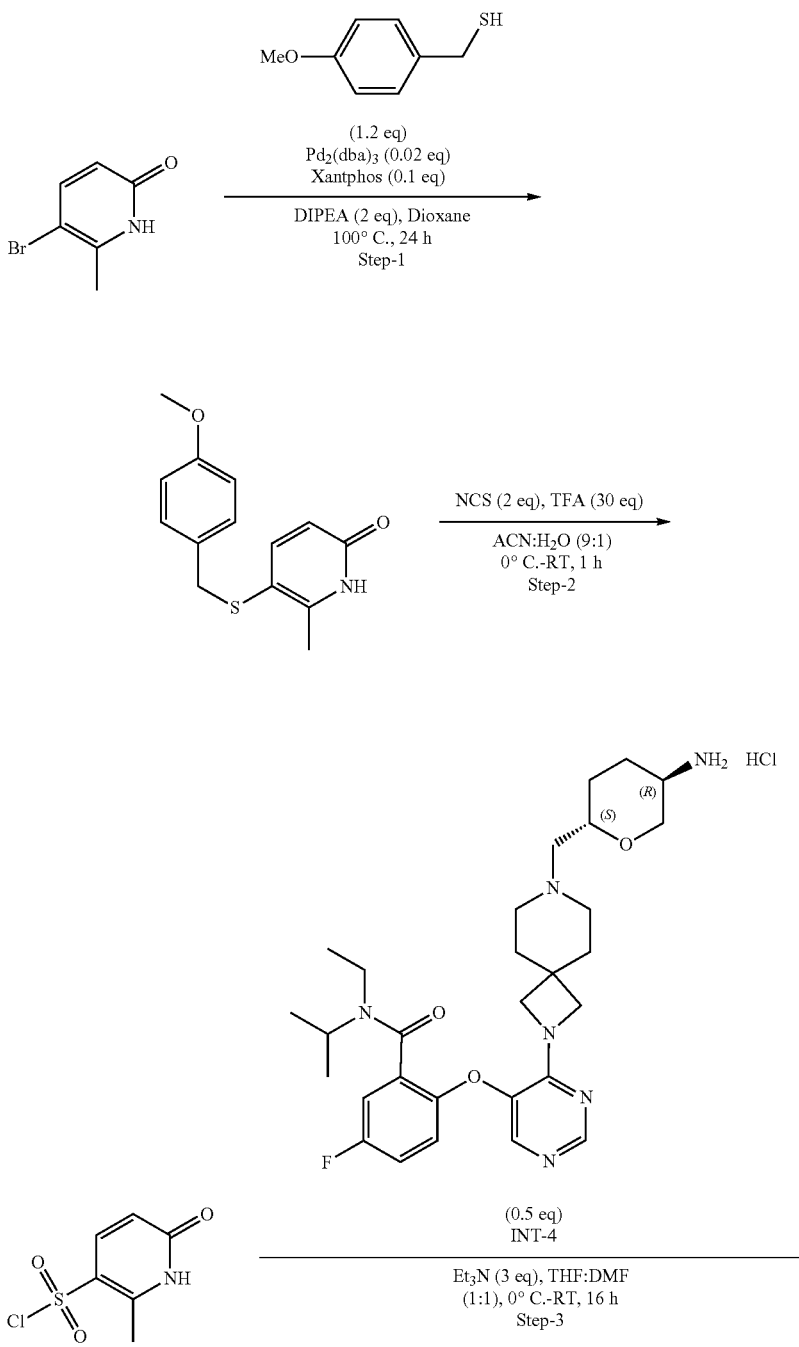

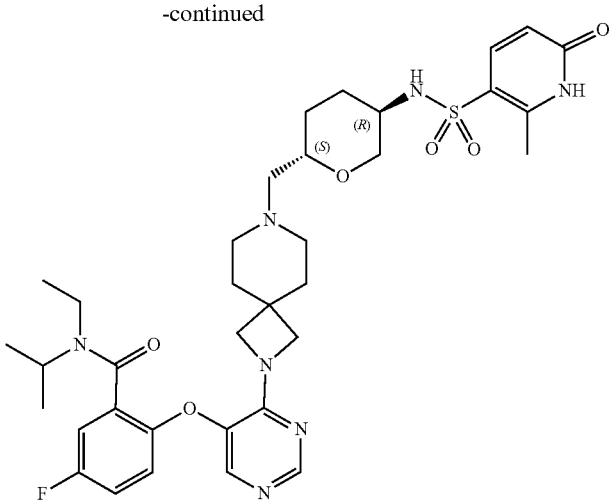

Example 217

Step 1. 5-((4-Methoxybenzyl)thio)-6-methylpyridin-2(1H)-one

To a 100 mL round bottom flask, 5-bromo-6-methylpyridin-2(1H)-one (500 mg, 2.66 mmol) was added in 1,4-dioxane (15 mL). To this solution, (4-methoxyphenyl)methanethiol (492 mg, 3.19 mmol), Xantphos (154 mg, 0.266 mmol), DIPEA (0.929 mL, 5.32 mmol) and Pd$_2$(dba)$_3$ (48.7 mg, 0.053 mmol) were added, and the reaction mixture was purged with argon for 10 min. The resulting reaction was stirred at 100° C. for 24 h. The progress of the reaction was monitored by TLC (50% EtOAc in hexane). The reaction mixture was diluted with water and extracted with EtOAc (3×50 mL). The combined organic layer was dried over sodium sulfate and concentrated under reduced pressure to obtain the crude compound. The crude was purified by silica gel flash column chromatography using 30% EtOAc in hexane as an eluent to obtain 5-((4-methoxybenzyl)thio)-6-methylpyridin-2(1H)-one (600 mg, mmol, 43.0% yield) as a solid.

LCMS (Method B): Rt 1.64 min, 262.2 [M+H]$^+$.

Step 2. 2-Methyl-6-oxo-1,6-dihydropyridine-3-sulfonyl chloride

To a 50 mL round bottom flask, 5-((4-methoxybenzyl)thio)-6-methylpyridin-2(1H)-one (400 mg, 1.531 mmol) was added in ACN:H$_2$O (9:1) (20 mL). To this solution, TFA (3.54 mL, 45.9 mmol) and NCS (409 mg, 3.06 mmol) were added at 0° C., and the reaction was stirred at RT for 1 h. The reaction progress was monitored by TLC (70% EtOAc in hexane). The reaction mixture was concentrated under reduced pressure to obtain 2-methyl-6-oxo-1,6-dihydropyridine-3-sulfonyl chloride (800 mg, 93% yield) as a liquid.

LCMS (Method B): Rt 1.14 min, 208.0 [M+H]$^+$.

Step 3. N-Ethyl-5-fluoro-N-isopropyl-2-((4-(7-(((2S, 5R)-5-((2-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy) benzamide (Example 217)

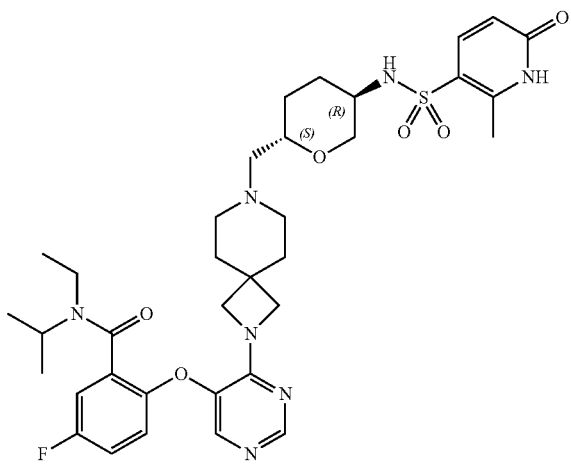

To a dried 25 mL round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide hydrochloride (400 mg, 0.740 mmol) was added in THF: DMF (1:1) (8 mL). To this solution, Et$_3$N (0.607 mL, 4.44 mmol) and 2-methyl-6-oxo-1,6-dihydropyridine-3-sulfonyl chloride (307 mg, 1.480 mmol) were added, and the reaction was stirred at RT for 16 h. The reaction progress was monitored by TLC (10% MeOH in DCM). The reaction was quenched with water and extracted with EtOAc (3×20 mL). The combined organic layer was dried over sodium sulfate and concentrated under reduced pressure to obtain crude material. The crude was purified by Prep-HPLC (Method A) to obtain N-ethyl-5-fluoro-N-isopropyl-2-((4-(7-(((2S,5R)-5-((2-methyl-6-oxo-1,6-dihydropyridine)-3-sulfonamido) tetrahydro-2H-pyran-2-yl)methyl)-2,7-diazaspiro[3.5] nonan-2-yl)pyrimidin-5-yl)oxy)benzamide (25 mg, 4.68% yield) as a solid. $^1$H NMR (400 MHz, DMSO-d$_6$) δ 8.30-8.23 (m, 1H), 7.80-7.62 (m, 3H), 7.34-7.20 (m, 2H), 7.09-6.98 (m, 1H), 6.25 (d, J=9.8 Hz, 1H), 3.84 (br s, 2H), 3.80-3.69 (m, 3H), 3.68-3.63 (m, 1H), 3.47-3.39 (m, 1H), 3.18-3.08 (m, 1H), 3.06-2.95 (m, 1H), 2.94-2.84 (m, 1H), 2.48 (s, 3H), 2.32-2.20 (m, 4H), 2.19-2.12 (m, 1H), 1.81-1.70 (m, 1H), 1.69-1.55 (m, 6H), 1.37 (dq, J=4.0, 12.4 Hz, 1H), 1.18 (d, J=9.4 Hz, 2H), 1.24 (s, 1H), 1.14-1.06 (m, 6H), 1.06-0.96 (m, 3H); LCMS (Method B): Rt 1.18 min, m/z: 712.6 [M+H]$^+$; HPLC (Method A): Rt 4.48 min, 98.61%.

Example 218. N-Ethyl-5-fluoro-N-isopropyl-2-((4-(7-(((2S,5R)-5-((5-methyl-6-oxo-1,6-dihydropyridine)-3-sulfonamido)tetrahydro-2H-pyran-2-yl) methyl)-2,7-diazaspiro[3.5]nonan-2-yl)pyrimidin-5-yl)oxy)benzamide

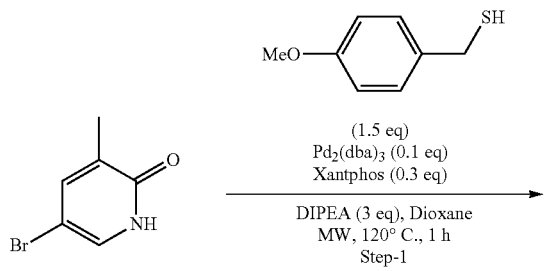

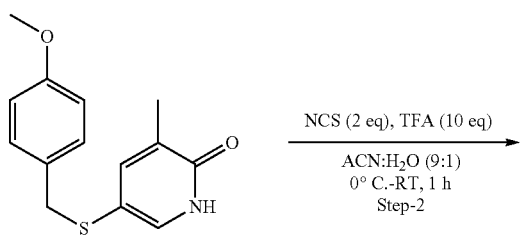

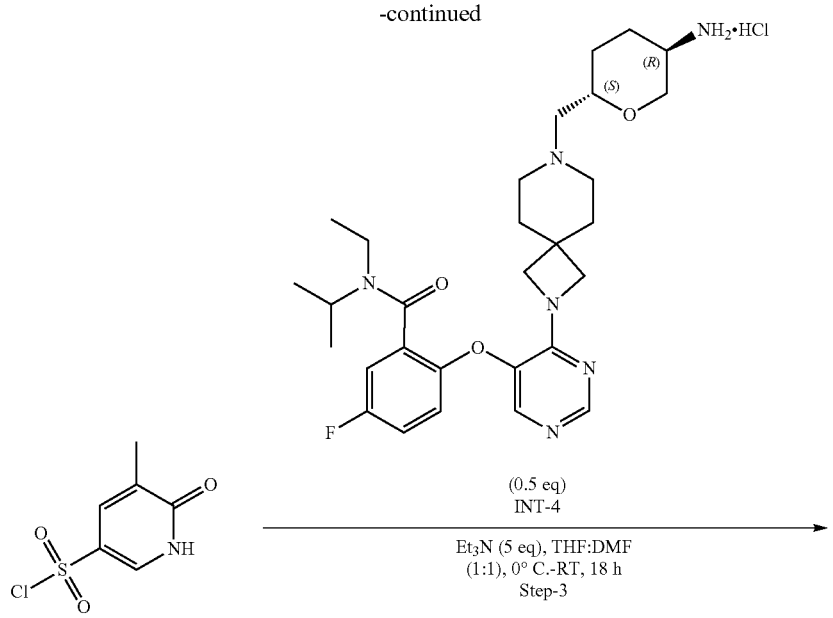

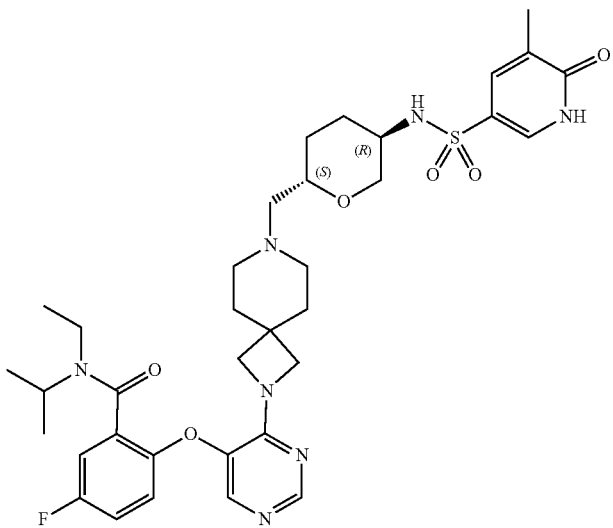

Example 218

Step 1. 5-((4-Methoxybenzyl)thio)-3-methylpyridin-2(1H)-one

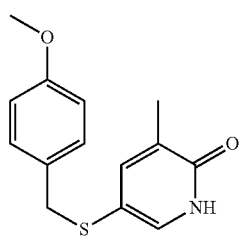 [SMILES: COc1ccc(CSc2c[nH]c(=O)c(C)c2)cc1]

To a 25 mL microwave vial, 5-bromo-3-methylpyridin-2(1H)-one (500 mg, 2.66 mmol) was added in 1,4-dioxane (15 mL). To this solution, (4-methoxyphenyl)methanethiol (615 mg, 3.99 mmol), Xantphos (462 mg, 0.798 mmol), DIPEA (1.390 mL, 7.98 mmol) and Pd$_2$(dba)$_3$ (244 mg, 0.266 mmol) were added, and the reaction mixture was purged with argon for 5 min. The reaction mixture was irradiated in the microwave at 120° C. for 1 h. The reaction progress was monitored by TLC (0.5% MeOH in DCM). The reaction mixture was diluted with EtOAc (50 mL) and filtered through Celite®. The filtrate was concentrated under reduced pressure to obtain crude material. The crude was purified by 200-400 mesh silica gel flash column chromatography using 0-4% MeOH in DCM as an eluent to obtain 5-((4-methoxybenzyl)thio)-3-methylpyridin-2(1H)-one (409 mg, 53.1% yield). LCMS (Method B): Rt 1.68 min, m/z: 262.2 [M+H]$^+$, 90.25%.

Step 2.
5-Methyl-6-oxo-1,6-dihydropyridine-3-sulfonyl chloride

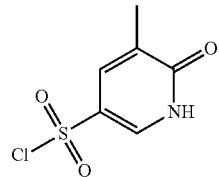

In a 100 mL round bottom flask, 5-((4-methoxybenzyl)thio)-3-methylpyridin-2(1H)-one (0.4 g, 1.531 mmol) and NCS (0.409 g, 3.06 mmol) were dissolved in ACN:H$_2$O (9:1) (15 mL). To this solution, TFA (1.179 mL, 15.31 mmol) was added dropwise at 0° C., and the reaction was stirred at RT for 1 h. The reaction progress was monitored by LCMS. The reaction was concentrated to obtain the crude compound. The crude was washed with toluene to obtain 5-methyl-6-oxo-1,6-dihydropyridine-3-sulfonyl chloride (0.85 g, 70.3% yield) a solid. LCMS (Method B): Rt 1.39 min, m/z: 206.2, [M−H]$^-$, 26.23%.

Step 3. N-Ethyl-5-fluoro-N-isopropyl-2-((4-(7-(((2S,5R)-5-((5-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy)benzamide (Example 218)

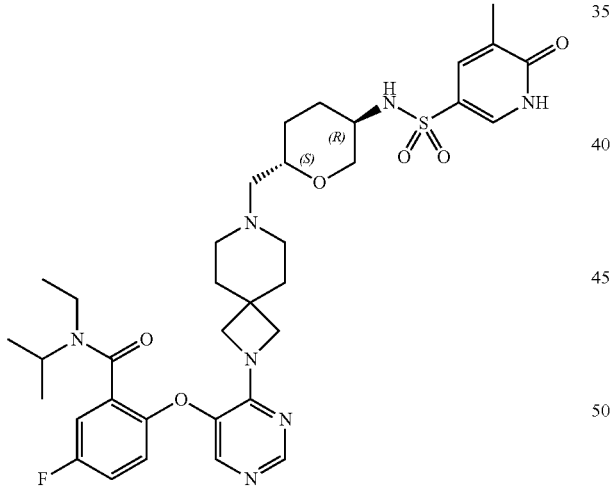

To a 25 mL round bottom flask, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-ethyl-5-fluoro-N-isopropylbenzamide hydrochloride (400 mg, 0.693 mmol) was added in DMF:THF (1:1) (8 mL). To this solution, 5-methyl-6-oxo-1,6-dihydropyridine-3-sulfonyl chloride (288 mg, 1.386 mmol) and Et$_3$N (0.483 mL, 3.47 mmol) were added, and the reaction was stirred at RT for 18 h. The reaction progress was monitored by LCMS. The reaction was quenched with water (30 mL) and extracted with 5% MeOH in DCM (3×35 mL). The combined organic layer was dried over anhydrous sodium sulfate and filtered, and the filtrate was concentrated under reduced pressure to obtain crude compound. The crude was purified by Prep-HPLC (Method C), and product fractions were lyophilized to obtain N-ethyl-5-fluoro-N-isopropyl-2-((4-(7-(((2S,5R)-5-((5-methyl-6-oxo-1,6-dihydropyridine)-3-sulfonamido)tetrahydro-2H-pyran-2-yl)methyl)-2,7-diazaspiro[3.5]nonan-2-yl)pyrimidin-5-yl)oxy)benzamide (39 mg, 7.49% yield) as a solid. $^1$H NMR (400 MHz, DMSO-d$_6$) δ 11.94 (br s, 1H), 8.36-8.16 (m, 1H), 7.76-7.64 (m, 2H), 7.60 (d, J=6.4 Hz, 1H), 7.52 (s, 1H), 7.34-7.21 (m, 2H), 7.10-6.99 (m, 1H), 3.94-3.64 (m, 7H), 3.23-3.09 (m, 1H), 3.05-2.88 (m, 2H), 2.32-2.11 (m, 6H), 2.02 (s, 3H), 1.73 (d, J=11.9 Hz, 1H), 1.69-1.55 (m, 5H), 1.43-1.27 (m, 1H), 1.26-1.14 (m, 3H), 1.13-1.06 (m, 5H), 1.06-0.95 (m, 3H); LCMS (Method E): Rt 1.65 min, m/z: 712.3 [M+H]$^+$; HPLC (Method B): Rt 4.59 min, 94.80%.

Example 219. N-Ethyl-5-fluoro-N-isopropyl-2-((4-(7-(((2S,5R)-5-(vinylsulfonamido)tetrahydro-2H-pyran-2-yl)methyl)-2,7-diazaspiro[3.5]nonan-2-yl)pyrimidin-5-yl)oxy)benzamide

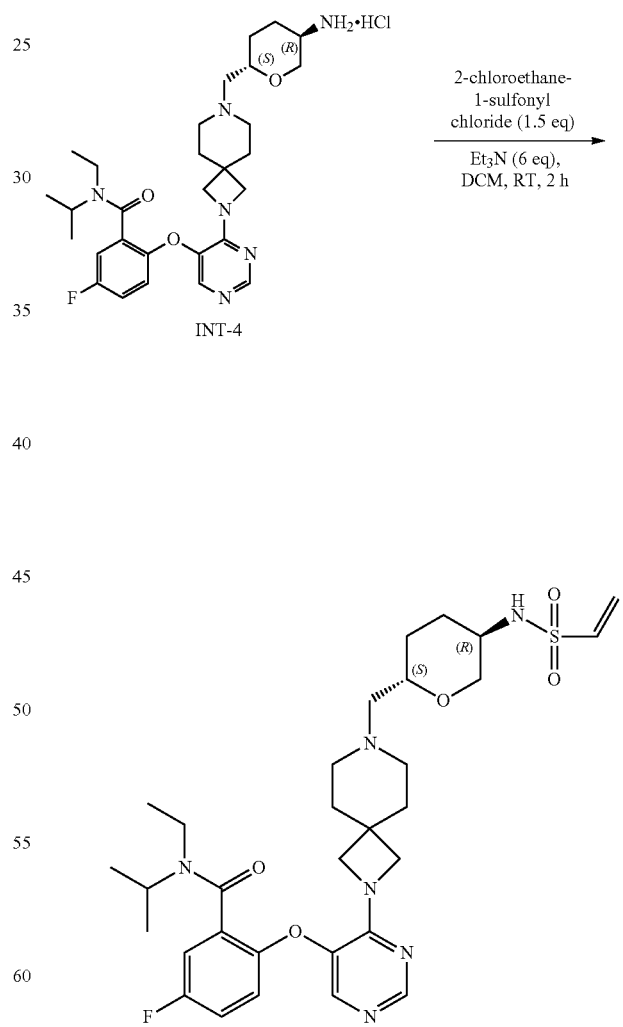

Example 219

To a stirred solution of 2-((4-(7-(((2S,5R)-5-aminotetrahydro-2H-pyran-2-yl)methyl)-2,7-diazaspiro[3.5]nonan-2- yl)pyrimidin-5-yl)oxy)-N-ethyl-5-fluoro-N-isopropylbenzamide (500 mg, 0.925 mmol) in DCM (25 mL), Et₃N (468 mg, 4.62 mmol) was added at 0° C., and the reaction was stirred for 10 min. To this reaction mixture, 2-chloroethane-1-sulfonyl chloride (226 mg, 1.387 mmol) was added at 0° C. The resulting reaction was allowed to stir at RT for 2 h under nitrogen atmosphere. The reaction was monitored by LCMS. The reaction mixture was concentrated under reduced pressure to afford crude material. The crude material was purified by prep-HPLC (Method A), and product fractions were lyophilized to afford N-ethyl-5-fluoro-N-isopropyl-2-((4-(7-(((2S,5R)-5-(vinylsulfonamido)tetrahydro-2H-pyran-2-yl)methyl)-2,7-diazaspiro[3.5]nonan-2-yl)pyrimidin-5-yl)oxy)benzamide (14.07 mg, 2.296% yield) as a solid. ¹H NMR (400 MHz, DMSO-d₆) δ 8.30-8.23 (m, 1H), 7.74-7.65 (m, 1H), 7.38 (br s, 1H), 7.33-7.22 (m, 2H), 7.09-7.01 (m, 1H), 6.76 (dd, J=9.9, 16.4 Hz, 1H), 6.04 (d, J=16.5 Hz, 1H), 5.94 (d, J=9.9 Hz, 1H), 3.92-3.69 (m, 6H), 3.23-3.11 (m, 1H), 3.06-2.92 (m, 2H), 2.31-2.22 (m, 4H), 2.21-2.15 (m, 1H), 1.96-1.82 (m, 1H), 1.74-1.57 (m, 6H), 1.47-1.32 (m, 1H), 1.28-1.14 (m, 4H), 1.14-1.06 (m, 5H), 1.05-0.96 (m, 3H); LCMS (Method E): Rt 1.46 min, m/z: 631.4 [M+H]⁺; HPLC (Method A): Rt 4.97 min, 95.180%.

Example 220. 2-((4-(7-(((2S,5R)-5-((2-(Dimethylamino)ethyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide

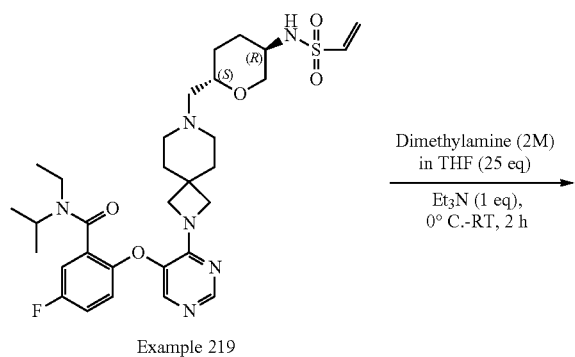

Example 219

Dimethylamine (2M) in THF (25 eq)
Et₃N (1 eq), 0° C.-RT, 2 h
→

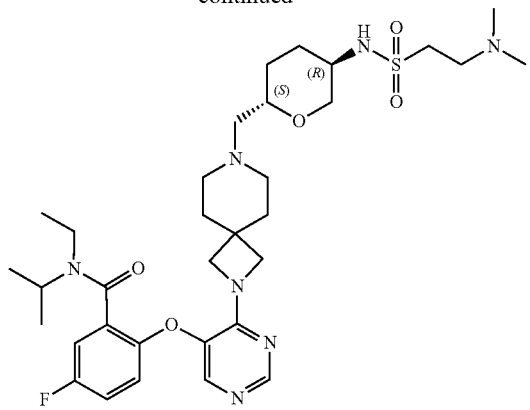

Example 220

To a stirred solution of N-ethyl-5-fluoro-N-isopropyl-2-((4-(7-(((2S,5R)-5-(vinylsulfonamido)tetrahydro-2H-pyran-2-yl)methyl)-2,7-diazaspiro[3.5]nonan-2-yl)pyrimidin-5-yl)oxy)benzamide (520 mg, 0.824 mmol) in dimethylamine (10 mL, 20.00 mmol, 2M in THF) at 0° C., Et₃N (83 mg, 0.824 mmol) was added at 0° C., and the reaction was stirred at RT for 2 h. The reaction progress was monitored by TLC (10% MeOH in DCM). The reaction mixture was concentrated under reduced pressure to obtain crude material. The crude was purified by prep-HPLC (Method C) and the product fractions were lyophilized to obtain 2-((4-(7-(((2S,5R)-5-((2-(dimethylamino)ethyl)sulfonamido)tetrahydro-2H-pyran-2-yl)methyl)-2,7-diazaspiro[3.5]nonan-2-yl)pyrimidin-5-yl)oxy)-N-ethyl-5-fluoro-N-isopropylbenzamide (48 mg, 8.50% yield) as a solid. ¹H NMR (400 MHz, DMSO-d₆) δ 8.30-8.21 (m, 1H), 7.75-7.63 (m, 1H), 7.34-7.21 (m, 2H), 7.13 (d, J=7.4 Hz, 1H), 7.09-7.00 (m, 1H), 3.93-3.69 (m, 6H), 3.19-3.09 (m, 4H), 3.04-2.96 (m, 1H), 2.62-2.55 (m, 2H), 2.32-2.24 (m, 4H), 2.21 (d, J=4.5 Hz, 1H), 2.15 (s, 7H), 2.00-1.89 (m, 1H), 1.67 (d, J=4.9 Hz, 5H), 1.39-1.35 (m, 1H), 1.32-1.16 (m, 3H), 1.15-0.95 (m, 9H); LCMS (Method E): Rt 1.64 min, m/z: 676.1 [M+H]⁺; HPLC (Method A): Rt 4.66 min, 98.664%.

Example 221. 2-((4-(7-(((2S,5R)-5-(1-Oxa-6-azaspiro[3.3]heptane-6-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

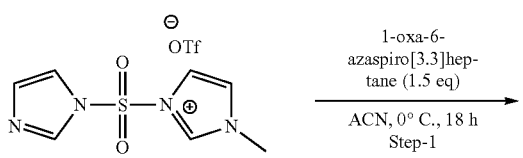

INT-64

1-oxa-6-azaspiro[3.3]heptane (1.5 eq)
ACN, 0° C., 18 h
Step-1
→

-continued

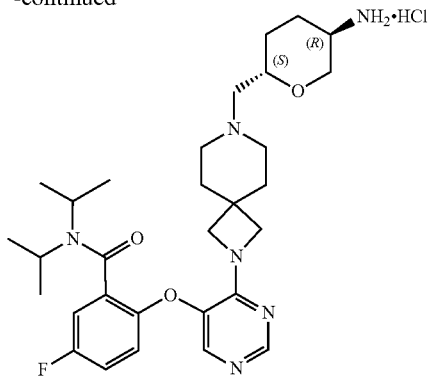

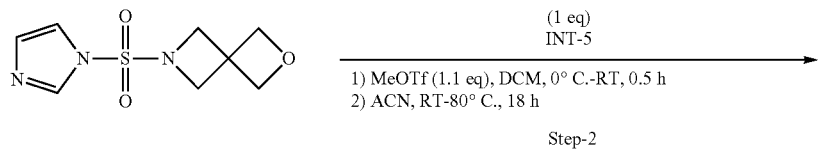

Step-2

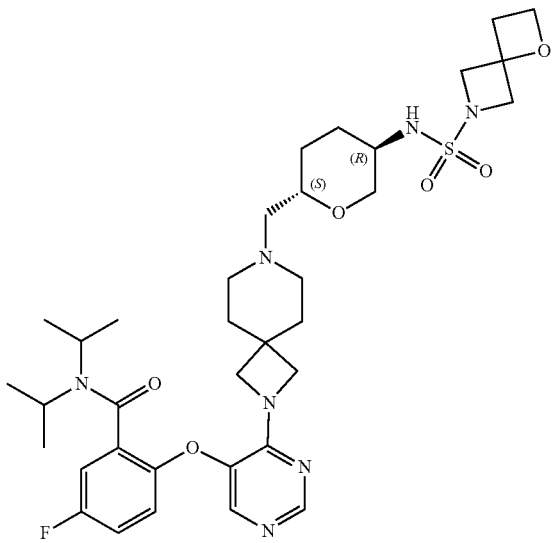

Example 221

Step 1. 6-((1H-Imidazol-1-yl)sulfonyl)-1-oxa-6-azaspiro[3.3]heptane

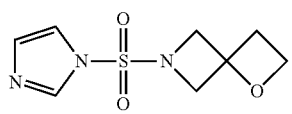 [SMILES: O=S(=O)(N1CC2(CCO2)C1)n1ccnc1]

To a dried 25 mL round bottom flask, 3-((1H-imidazol-1-yl)sulfonyl)-1-methyl-1H-imidazol-3-ium trifluoromethanesulfonate (250 mg, 0.690 mmol)) was added in ACN (5 mL), and then (1-oxa-6-azaspiro[3.3]heptane (103 mg, 1.035 mmol) was added at 0° C. under nitrogen atmosphere. The reaction was stirred at RT for 18 h. The reaction progress was monitored by LCMS. The reaction mixture was concentrated under reduced pressure, and the crude material was purified by Prep-HPLC to afford 6-((1H-imidazol-1-yl)sulfonyl)-1-oxa-6-azaspiro[3.3]heptane (80 mg, 49.8% yield) as a solid. LCMS (Method A): Rt 1.34 min, m/z: 230.0 [M+H]$^+$, 98.52%.

Step 2. 2-((4-(7-(((2S,5R)-5-(1-Oxa-6-azaspiro[3.3]
heptane-6-sulfonamido)tetrahydro-2H-pyran-2-yl)
methyl)-2,7-diazaspiro[3.5]nonan-2-yl)pyrimidin-5-
yl)oxy)-5-fluoro-N,N-diisopropylbenzamide
(Example 221)

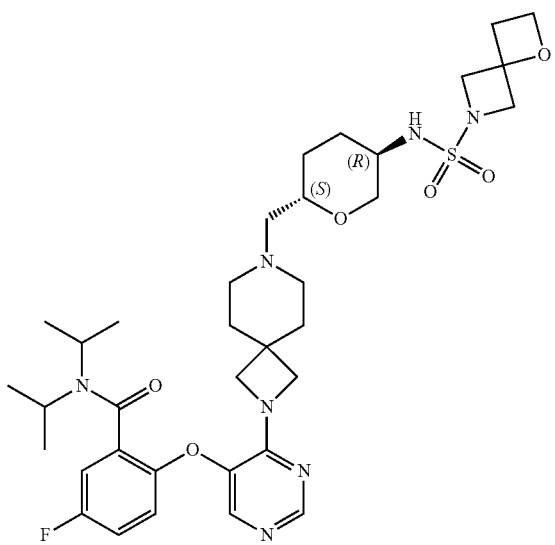

To a dried 100 mL round bottom flask under nitrogen atmosphere, 6-((1H-imidazol-1-yl)sulfonyl)-1-oxa-6-azaspiro[3.3]heptane (80 mg, 0.349 mmol) was added in DCM (10 mL), and then MeOTf (0.042 mL, 0.384 mmol) was added at 0° C. The reaction was stirred at RT for 30 min, then the reaction was concentrated under reduced pressure to obtain crude material. The crude was dissolved in ACN (20 mL), then 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide (206 mg, 0.349 mmol)) was added at RT. The reaction was heated at 80° C. for 18 h. The progress of the reaction was monitored by LCMS. The reaction mixture was concentrated under reduced pressure to obtain the crude compound. The crude was purified by Prep-HPLC (Method B) to obtain 2-((4-(7-(((2S,5R)-5-(1-oxa-6-azaspiro[3.3]heptane-6-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (65.59 mg, 26.1% yield) as a solid. $^1$H NMR (400 MHz, DMSO-$d_6$) δ 8.26 (s, 1H), 7.71 (s, 1H), 7.35 (br s, 1H), 7.26-7.19 (m, 2H), 7.04 (dd, J=4.2, 9.8 Hz, 1H), 4.39 (t, J=7.4 Hz, 2H), 3.89 (d, J=9.8 Hz, 4H), 3.85-3.74 (m, 6H), 3.68 (td, J=6.4, 12.9 Hz, 1H), 3.56-3.50 (m, 1H), 3.02-2.94 (m, 1H), 2.83 (t, J=7.4 Hz, 2H), 2.31-2.15 (m, 5H), 1.94 (m, 1H), 1.66 (br s, 6H), 1.44 (d, J=6.8 Hz, 3H), 1.40 (br s, 1H), 1.34 (d, J=6.6 Hz, 3H), 1.30-1.15 (m, 2H), 1.09 (d, J=6.5 Hz, 3H), 0.99 (d, J=6.5 Hz, 3H); LCMS (Method C): Rt 1.72 min, m/z: 716.6 [M+H]$^+$; HPLC (Method B): Rt 5.30 min, 99.47%.

Example 222. 2-((4-(7-(((2S,5R)-5-(2-Oxa-6-azaspiro[3.3]heptane-6-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

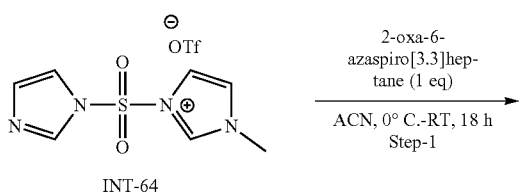

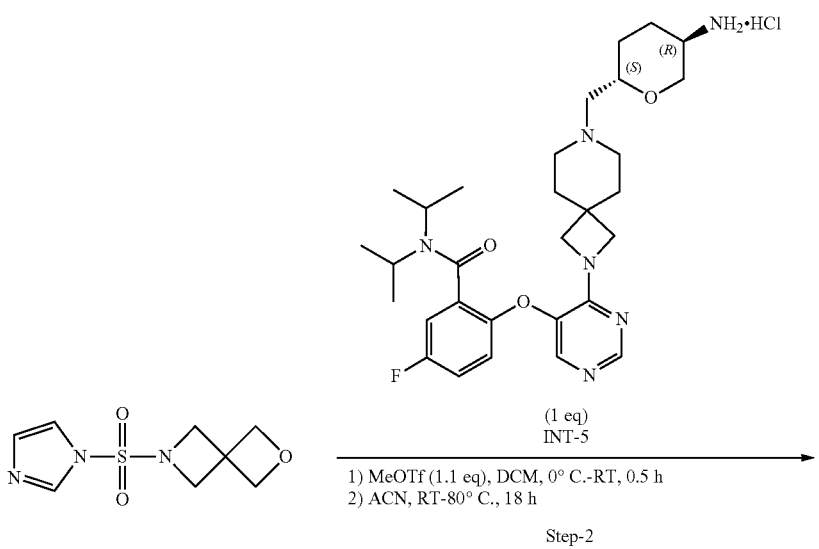

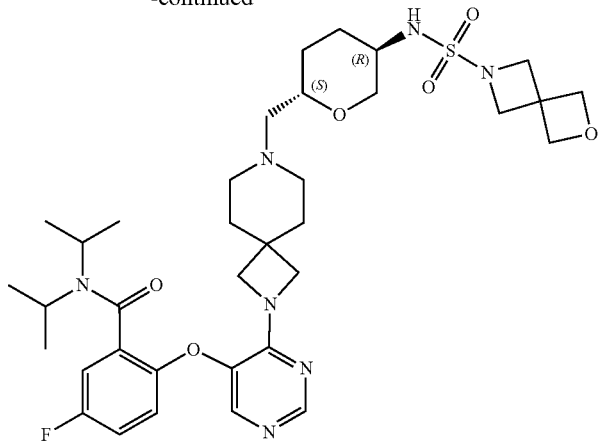

Example 222

Step 1. 6-((1H-Imidazol-1-yl)sulfonyl)-2-oxa-6-azaspiro[3.3]heptane

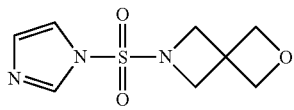 [SMILES: O=S(=O)(N1CC2(COC2)C1)n1ccnc1]

To a dried 25 mL round bottom flask, 3-((1H-imidazol-1-yl)sulfonyl)-1-methyl-1H-imidazol-3-ium trifluoromethanesulfonate (500 mg, 1.380 mmol) was added in ACN (5 mL), then 2-oxa-6-azaspiro[3.3]heptane (137 mg, 1.380 mmol) was added at 0° C. under nitrogen atmosphere. The reaction was stirred at RT for 18 h. The progress of the reaction was monitored by LCMS. The reaction mixture was concentrated under reduced pressure, and the crude was purified by Prep-HPLC to obtain 6-((1H-imidazol-1-yl)sulfonyl)-2-oxa-6-azaspiro[3.3]heptane (200 mg, 57.4% yield) as a solid. LCMS (Method A): Rt 1.21 min, m/z: 230.1 [M+H]+, 90.78%.

Step 2. 2-((4-(7-(((2S,5R)-5-(2-Oxa-6-azaspiro[3.3]heptane-6-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (Example 222)

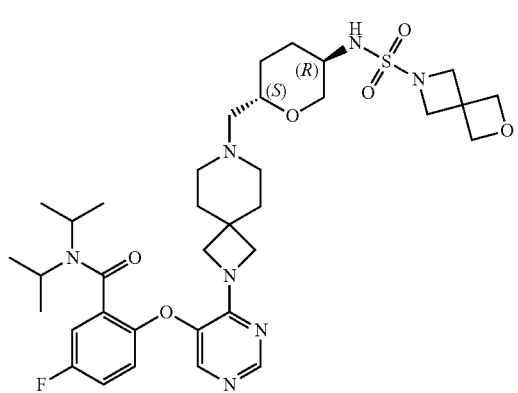

To a 50 mL dried round bottom flask under nitrogen atmosphere, 6-((1H-imidazol-1-yl)sulfonyl)-2-oxa-6-azaspiro[3.3]heptane (100 mg, 0.436 mmol) was added in DCM (5 mL). To this reaction mixture, MeOTf (0.053 mL, 0.480 mmol) was added at 0° C. The reaction mixture was stirred at RT for 30 min and then concentrated under reduced pressure in inert atmosphere to obtain a crude compound. The crude residue was dissolved in ACN (20 mL), then 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide (258 mg, 0.436 mmol) was added at RT. The reaction was stirred at 80° C. for 18 h. The progress of the reaction was monitored by LCMS. The reaction mixture was concentrated under reduced pressure and the crude was purified by Prep-HPLC (Method B) to obtain 2-((4-(7-(((2S,5R)-5-(2-oxa-6-azaspiro[3.3]heptane-6-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (66.47 mg, 20.51% yield) as a solid. $^1$H NMR (400 MHz, DMSO-$d_6$) δ 8.26 (s, 1H), 7.72 (s, 1H), 7.31 (d, J=3.6 Hz, 1H), 7.26-7.19 (m, 2H), 7.07-7.01 (m, 1H), 4.65 (s, 4H), 3.97-3.73 (m, 9H), 3.73-3.63 (m, 1H), 3.58-3.46 (m, 1H), 3.08-2.93 (m, 2H), 2.32-2.22 (m, 4H), 2.21-2.15 (m, 1H), 1.98-1.87 (m, 1H), 1.78-1.54 (m, 6H), 1.44 (d, J=6.8 Hz, 3H), 1.39 (d, J=4.4 Hz, 1H), 1.35 (d, J=6.6 Hz, 3H), 1.30-1.14 (m, 2H), 1.09 (d, J=6.6 Hz, 3H), 0.99 (d, J=6.6 Hz, 3H); LCMS (Method A): Rt 1.74 min, m/z: 716.1 [M+H]+; HPLC (Method A): Rt 5.12 min, 96.34%.

Example 223. 2-((4-(7-(((2S,5R)-5-(6-Oxa-2-azaspiro[3.4]octane-2-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide
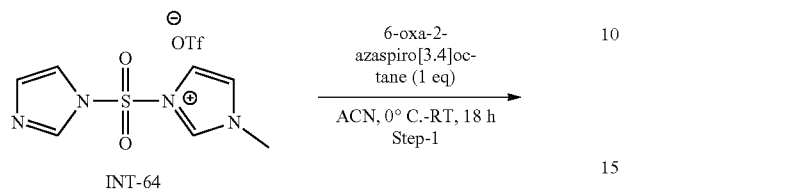
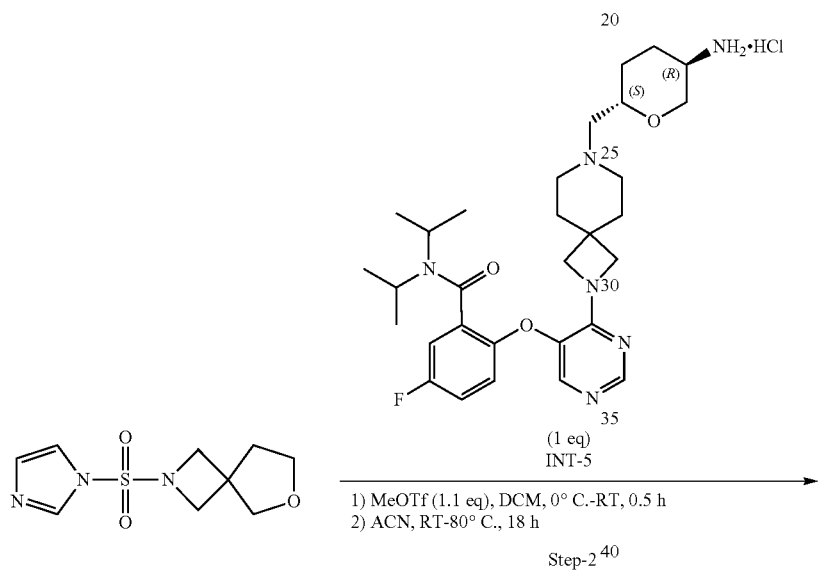
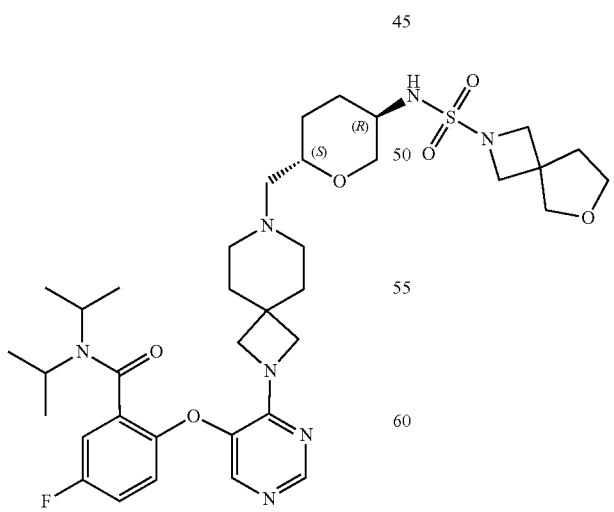
Example 223

Step 1. 2-((JH-Imidazol-1-yl)sulfonyl)-6-oxa-2-azaspiro[3.4]octane

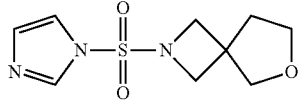 [SMILES: O=S(=O)(N1CC2(CCOC2)C1)n1ccnc1]

To a 25 mL round bottom flask under nitrogen atmosphere, 3-((1H-imidazol-1-yl)sulfonyl)-1-methyl-1H-imidazol-3-ium trifluoromethanesulfonate (500 mg, 1.38 mmol) was added in ACN (5 mL), then 6-oxa-2-azaspiro[3.4]octane (156 mg, 1.38 mmol) was added at 0° C. The reaction was stirred at RT for 18 h. The progress of the reaction was monitored by LCMS. The reaction mixture was concentrated under reduced pressure, and the crude was purified by Prep-HPLC to obtain 2-((1H-imidazol-1-yl)sulfonyl)-6-oxa-2-azaspiro[3.4]octane (88 mg, 0.362 mmol, 26.2% yield) as a solid. LCMS (Method D): Rt 1.34 min, m/z: 244.1 [M+H]$^+$, 21.25%.

Step 2. 2-((4-(7-(((2S,5R)-5-(6-Oxa-2-azaspiro[3.4]octane-2-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (Example 223)

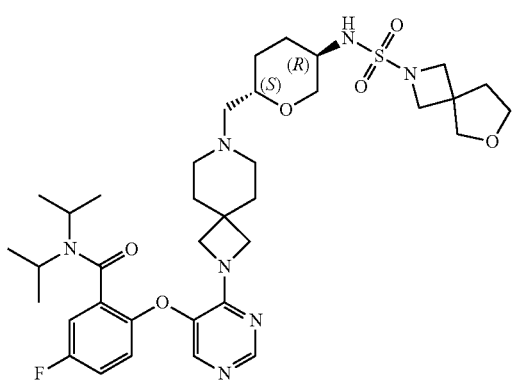

To a dried 50 mL round bottom flask under nitrogen atmosphere, 2-((1H-imidazol-1-yl)sulfonyl)-6-oxa-2-azaspiro[3.4]octane (100 mg, 0.411 mmol) was added in DCM (10 mL). To this solution, MeOTf (74.2 mg, 0.452 mmol) was added at 0° C., and the reaction was stirred at RT for 30 min. The reaction mixture was concentrated under reduced pressure and the crude was dissolved in ACN (20 mL) under nitrogen atmosphere. To this solution, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide (243 mg, 0.411 mmol) was added at RT, and the reaction was stirred at 80° C. for 18 h. The reaction progress was monitored by LCMS. The reaction mixture was concentrated under reduced pressure and purified by Prep-HPLC (Method B) to obtain 2-((4-(7-(((2S,5R)-5-(6-oxa-2-azaspiro[3.4]octane-2-sulfonamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (130.32 mg, 43.3% yield) as a solid. $^1$H NMR (400 MHz, DMSO-d$_6$) δ 8.26 (s, 1H), 7.71 (s, 1H), 7.30 (d, J=7.9 Hz, 1H), 7.26-7.19 (m, 2H), 7.04 (dd, J=4.3, 10.1 Hz, 1H), 3.94-3.83 (m, 3H), 3.82-3.77 (m, 2H), 3.73 (s, 2H), 3.71-3.62 (m, 8H), 3.53 (td, J=6.6, 13.5 Hz, 1H), 3.13-3.03 (m, 1H), 3.03-2.95 (m, 1H), 2.28 (dd, J=6.3, 12.9 Hz, 4H), 2.22-2.16 (m, 1H), 2.07 (t, J=6.9 Hz, 2H), 1.96 (d, J=12.0 Hz, 1H), 1.74-1.59 (m, 6H), 1.44 (d, J=6.6 Hz, 3H), 1.39 (m, 1H), 1.35 (d, J=6.6 Hz, 3H), 1.30-1.18 (m, 1H), 1.09 (d, J=6.6 Hz, 3H), 1.00 (d, J=6.5 Hz, 3H); LCMS (Method A): Rt 1.78 min, m/z: 730.2 [M+H]$^+$; HPLC (Method B): Rt 5.30 min, 99.79%.

Example 224. 5-Fluoro-2-((4-(7-(((2S,5R)-5-((hexahydro-1H-furo[3,4-c]pyrrole)-5-sulfonamido)tetrahydro-2H-pyran-2-yl)methyl)-2,7-diazaspiro[3.5]nonan-2-yl)pyrimidin-5-yl)oxy)-N,N-diisopropylbenzamide

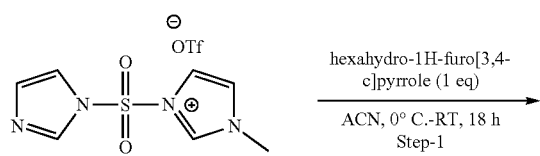

INT-64

591

-continued

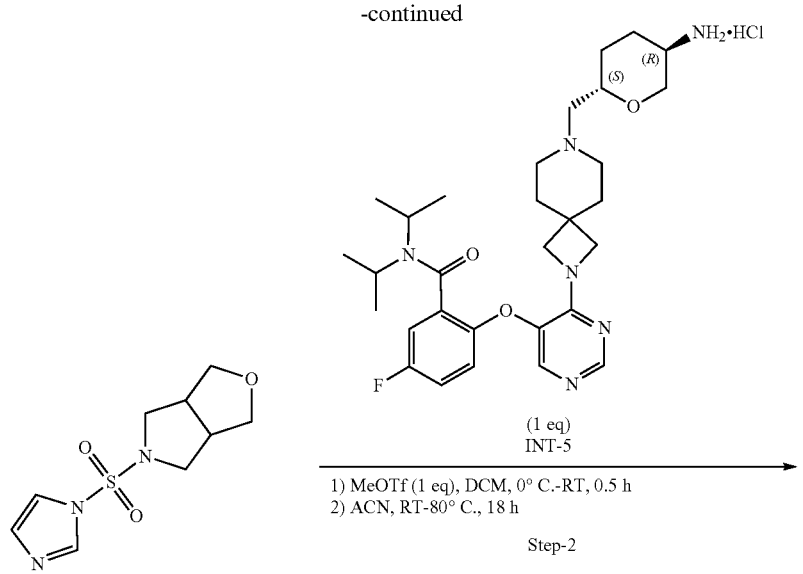

(1 eq)
INT-5

1) MeOTf (1 eq), DCM, 0° C.-RT, 0.5 h
2) ACN, RT-80° C., 18 h

Step-2

592

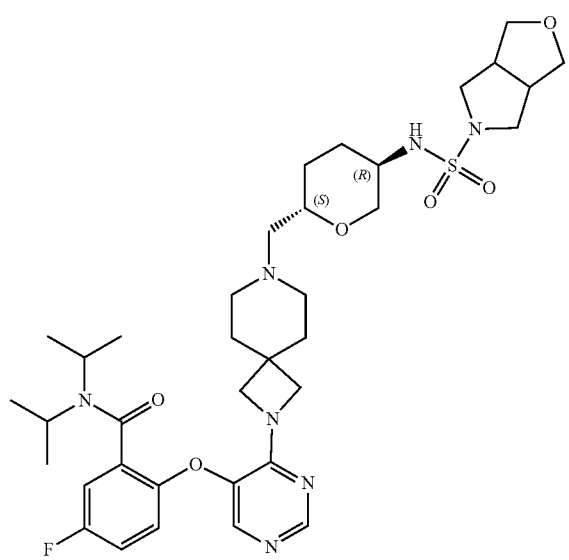

Example 224

Step 1. 5-((1H-imidazol-1-yl)sulfonyl)hexahydro-1H-furo[3,4-c]pyrrole

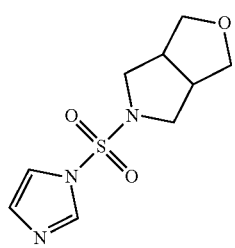 [SMILES: O=S(=O)(N1CC2COCC2C1)n1ccnc1]

To a 25 mL round bottom flask under nitrogen atmosphere, 3-((1H-imidazol-1-yl)sulfonyl)-1-methyl-1H-imidazol-3-ium trifluoromethanesulfonate (1.3 g, 3.59 mmol) was added in ACN (15 mL). To this solution, hexahydro-1H-furo[3,4-c]pyrrole (0.406 g, 3.59 mmol) was added at 0° C. The reaction was stirred at RT for 18 h. The progress of the reaction was monitored by LCMS. The reaction mixture was concentrated under reduced pressure, and the crude was purified by Prep-HPLC (Method B) to obtain 5-((1H-imidazol-1-yl)sulfonyl)hexahydro-1H-furo[3,4-c]pyrrole (300 mg, 34.4% yield) as a solid. LCMS (Method B): Rt 1.35 min, m/z: 244.1 [M+H]$^+$, 31.3%.

Step 2. 5-Fluoro-2-((4-(7-(((2S,5R)-5-((hexahydro-1H-furo[3,4-c]pyrrole)-5-sulfonamido)tetrahydro-2H-pyran-2-yl)methyl)-2,7-diazaspiro[3.5]nonan-2-yl)pyrimidin-5-yl)oxy)-N,N-diisopropylbenzamide (Example 224)

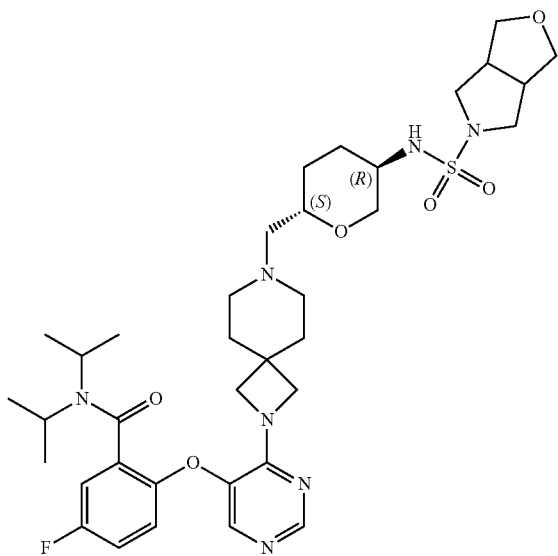

To a dried 50 mL round bottom flask under nitrogen atmosphere, 5-((1H-imidazol-1-yl)sulfonyl)hexahydro-1H-furo[3,4-c]pyrrole (160 mg, 0.658 mmol) was added in DCM (5 mL). To this solution, MeOTf (108 mg, 0.658 mmol) was added at 0° C. The reaction was stirred at RT for 0.5 h. The reaction mixture was concentrated under reduced pressure and the residue was dissolved in ACN (15 mL). To this solution, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide (389 mg, 0.658 mmol) was added at RT, and the reaction was stirred at 80° C. for 18 h. The reaction progress was monitored by LCMS. The reaction mixture was concentrated under reduced pressure, and the crude was purified by Prep-HPLC (Method B) to obtain 5-fluoro-2-((4-(7-(((2S,5R)-5-((hexahydro-1H-furo[3,4-c]pyrrole)-5-sulfonamido)tetrahydro-2H-pyran-2-yl)methyl)-2,7-diazaspiro[3.5]nonan-2-yl)pyrimidin-5-yl)oxy)-N,N-diisopropylbenzamide (72.37 mg, 15.05% yield) as a solid. $^1$H NMR (400 MHz, DMSO-$d_6$) δ 8.26 (s, 1H), 7.71 (s, 1H), 7.28 (br s, 1H), 7.26-7.19 (m, 2H), 7.04 (dd, J=4.3, 10.1 Hz, 1H), 3.96-3.83 (m, 3H), 3.82-3.77 (m, 2H), 3.76-3.64 (m, 4H), 3.60-3.43 (m, 4H), 3.25-3.16 (m, 2H), 3.12-2.96 (m, 2H), 2.94-2.83 (m, 4H), 2.32-2.14 (m, 5H), 2.02-1.91 (m, 1H), 1.77-1.59 (m, 5H), 1.44 (d, J=6.8 Hz, 3H), 1.42-1.37 (m, 1H), 1.35 (d, J=6.8 Hz, 3H), 1.28-1.16 (m, 1H), 1.09 (d, J=6.6 Hz, 3H), 1.00 (d, J=6.6 Hz, 3H); LCMS (Method F): Rt 1.83 min, m/z: 730.9 [M+H]$^+$; HPLC (Method A): Rt 5.29 min, 99.86%.

Example 225. 2-((4-(7-(((2S,5R)-5-(Ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

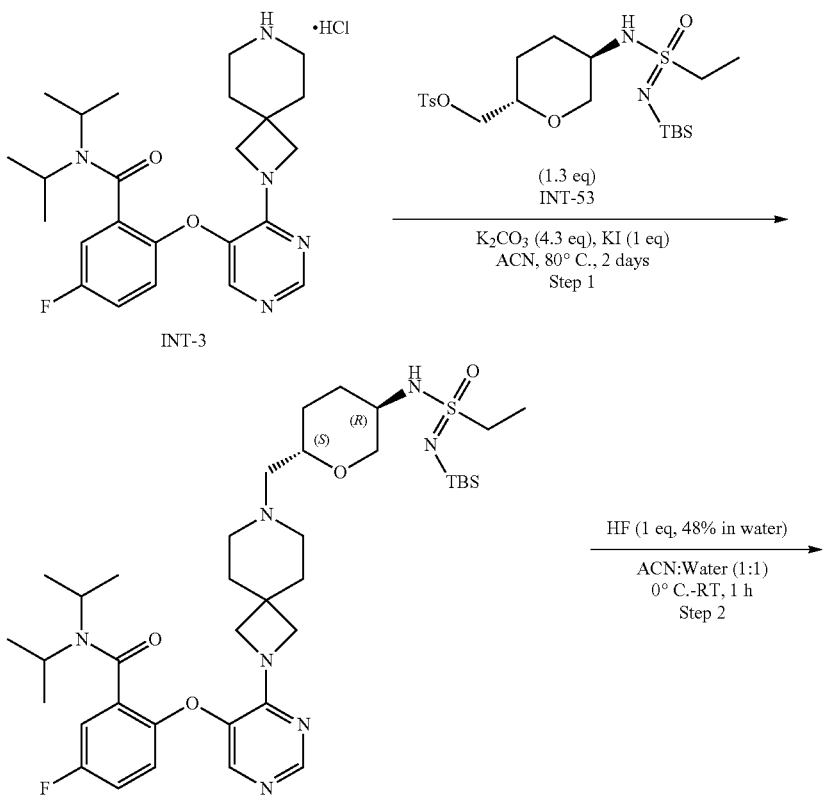

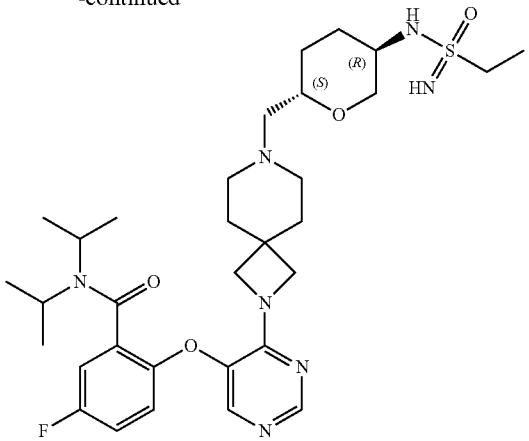

Example 225

Step 1. 2-((4-(7-(((2S,5R)-5-(N'-(tert-Butyldimethyl-silyl)ethylsulfonoamidimidamido)tetrahydro-2H-pyran-2-yl)methyl)-2,7-diazaspiro[3.5]nonan-2-yl) pyrimidin-5-yl)oxy)-5-fluoro-N,N-diisopropylbenzamide

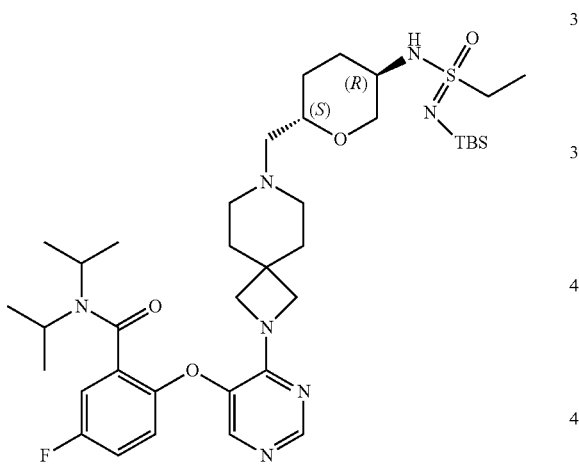

To a 25 mL dried round bottom flask under nitrogen atmosphere, 2-((4-(2,7-diazaspiro[3.5]nonan-2-yl)pyrimidin-5-yl)oxy)-5-fluoro-N,N-diisopropylbenzamide hydrochloride (253 mg, 0.530 mmol) was added in ACN (5 mL). To this reaction mixture, K$_2$CO$_3$ (242 mg, 1.752 mmol), KI (67.7 mg, 0.408 mmol), and ((2S,5R)-5-(N'-(tert-butyldimethylsilyl)ethylsulfonoamidimidamido)tetrahydro-2H-pyran-2-yl)methyl 4-methyl benzenesulfonate (200 mg, 0.408 mmol) were added at RT under nitrogen atmosphere. The resulting reaction was heated at 80° C. for 2 days. The reaction progress was monitored by TLC (10% MeOH in DCM). After completion, the reaction mixture was quenched with water (15 mL) and extracted with ethyl acetate (3×20 mL). The combined organic layer was dried over anhydrous sodium sulfate and filtered, and the filtrate was concentrated under reduced pressure to obtain the crude product. The crude compound was purified by Biotage-isolera one column chromatography using 0-10% MeOH in DCM. The desired product eluted in 6-8% MeOH in DCM) to obtain 2-((4-(7-(((2S,5R)-5-(N'-(tert-butyldimethylsilyl)ethyl-sulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropyl benzamide (180 mg, 37.2% yield) as a solid. LCMS (Method A): Rt 2.44 min, m/z: (761.2) [M+H]$^+$, 64.05%.

Step 2. 2-((4-(7-(((2S,5R)-5-(Ethylsulfonoamidimi-damido)tetrahydro-2H-pyran-2-yl)methyl)-2,7-diazaspiro[3.5]nonan-2-yl)pyrimidin-5-yl)oxy)-5-fluoro-N,N-diisopropylbenzamide (Example 225)

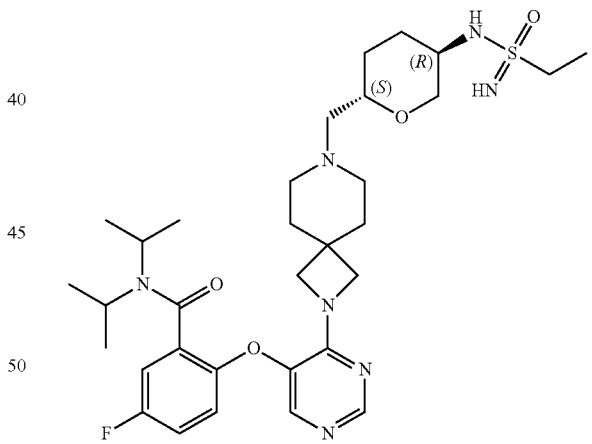

To a 50 mL plastic vial under argon atmosphere, 2-((4-(7-(((2S,5R)-5-(N'-(tert-butyldimethylsilyl)ethylsulfono-amidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (170 mg, 0.224 mmol) was added in ACN (1 mL) and water (1 mL). The reaction mixture was cooled to 0° C. and HF (1 mL, 0.224 mmol, 48% in water) was added. The reaction mixture was allowed to warm to RT and stirred for 1 h. The reaction progress was monitored by TLC (10% MeOH in DCM). After completion, the reaction mixture was concentrated, and the pH was adjusted to 9 using NaHCO$_3$ solution. The mixture was extracted with 10% MeOH in DCM (2×50 mL), and the organic layer was dried over anhydrous sodium sulfate, filtered, and concentrated under reduced pressure to obtain a crude product. The crude product was purified by Prep-HPLC (Method B), and pure fractions were lyophilized to obtain 2-((4-(7-(((2S,5R)-5-(ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (62 mg, 42.8% yield) as a solid. $^1$H NMR (400 MHz, DMSO-d$_6$) δ 8.26 (s, 1H), 7.71 (s, 1H), 7.27-7.18 (m, 2H), 7.09-7.00 (m, 1H), 6.44-6.33 (m, 1H), 4.02-3.74 (m, 5H), 3.73-3.62 (m, 1H), 3.53-3.51 (m, 1H), 3.29 (dd, J=4.6, 5.8 Hz, 2H), 3.20-3.02 (m, 1H), 3.01-2.84 (m, 3H), 2.32-2.13 (m, 5H), 1.99-1.84 (m, 1H), 1.75-1.56 (m, 5H), 1.44 (d, J=6.8 Hz, 3H), 1.41-1.30 (m, 4H), 1.28-1.14 (m, 5H), 1.09 (d, J=6.6 Hz, 3H), 1.00 (d, J=6.5 Hz, 3H); LCMS (Method A): Rt 1.65 min, m/z: (646.8) [M+H]$^+$; HPLC (Method A): Rt 4.65 min, 99.64; SFC (Method A): Peak 1: Rt 2.27 min, 55.73% and Peak 2: Rt 3.62 min 44.27%.

Example 226. 2-((4-(7-(((2S,5R)-5-((S)-Ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide and Example 227. 2-((4-(7-(((2S,5R)-5-((R)-Ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

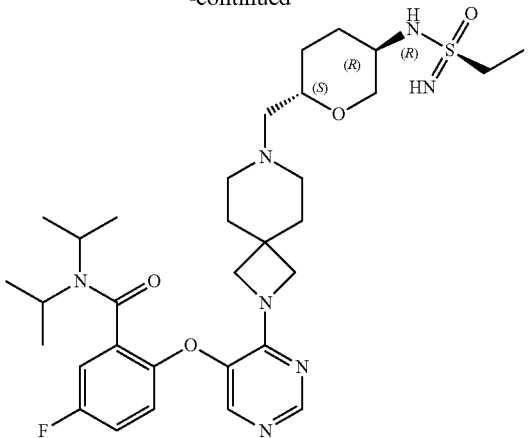

Example 227

Step 1. 2-((4-(7-(((2S,5R)-5-(ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

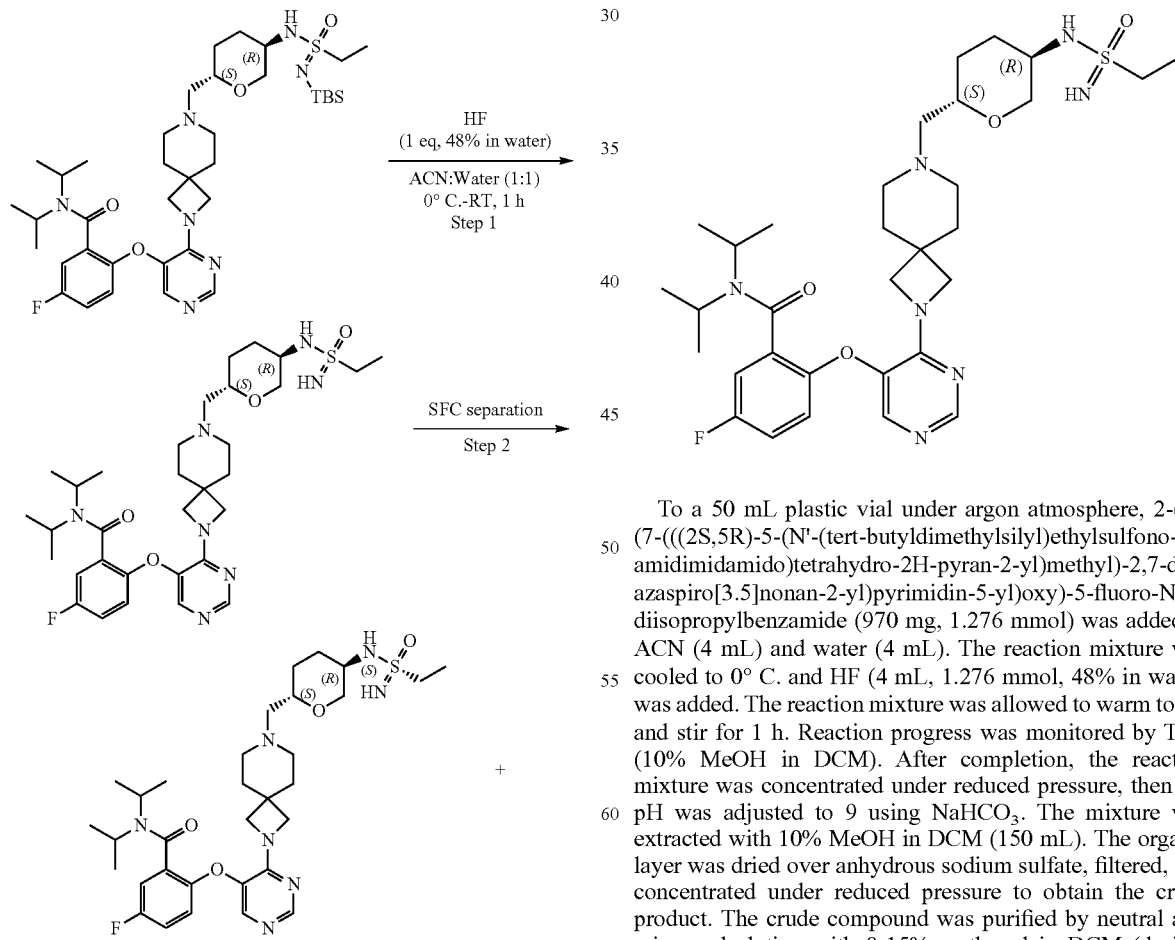

Example 226

To a 50 mL plastic vial under argon atmosphere, 2-((4-(7-(((2S,5R)-5-(N'-(tert-butyldimethylsilyl)ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (970 mg, 1.276 mmol) was added in ACN (4 mL) and water (4 mL). The reaction mixture was cooled to 0° C. and HF (4 mL, 1.276 mmol, 48% in water) was added. The reaction mixture was allowed to warm to RT and stir for 1 h. Reaction progress was monitored by TLC (10% MeOH in DCM). After completion, the reaction mixture was concentrated under reduced pressure, then the pH was adjusted to 9 using NaHCO$_3$. The mixture was extracted with 10% MeOH in DCM (150 mL). The organic layer was dried over anhydrous sodium sulfate, filtered, and concentrated under reduced pressure to obtain the crude product. The crude compound was purified by neutral alumina and eluting with 0-15% methanol in DCM (desired product was eluted in 5% methanol in DCM) to obtain 2-((4-(7-(((2S,5R)-5-(ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (550 mg) as a solid.

Step 2. The above racemic compound was purified by Chiral SFC (Method A). The pure fractions were concentrated under reduced pressure and lyophilized to afford the separated enantiomers.

Example 226

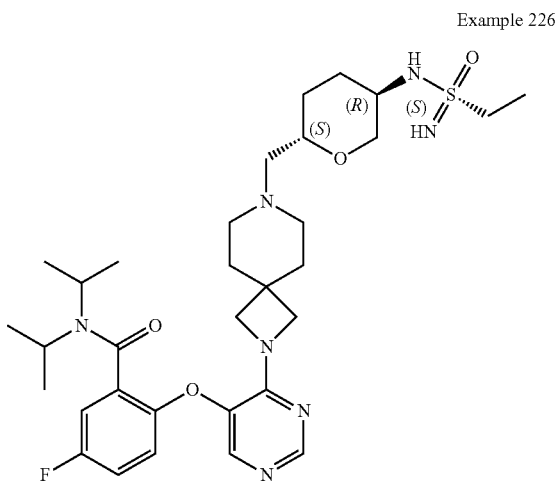

Example 227

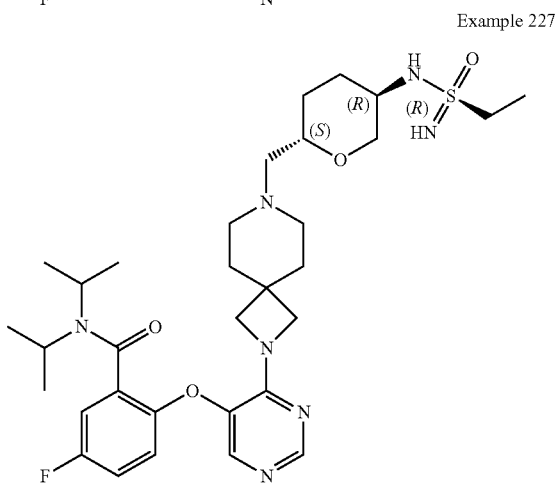

Example 226 (Isomer 1): 2-((4-(7-(((2S,5R)-5-((E1)-Ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide Yield: 28.3%;

$^1$H NMR (400 MHz, DMSO-d$_6$) δ 8.26 (s, 1H), 7.71 (s, 1H), 7.27-7.19 (m, 2H), 7.08-7.01 (m, 1H), 6.51-6.27 (m, 1H), 3.95-3.73 (m, 5H), 3.73-3.62 (m, 1H), 3.58-3.46 (m, 1H), 3.23 (s, 2H), 3.18-3.05 (m, 1H), 2.99-2.86 (m, 3H), 2.32-2.22 (m, 4H), 2.21-2.16 (m, 1H), 1.99-1.84 (m, 1H), 1.73-1.59 (m, 5H), 1.44 (d, J=6.8 Hz, 3H), 1.35 (d, J=6.6 Hz, 4H), 1.29-1.14 (m, 5H), 1.09 (d, J=6.5 Hz, 3H), 1.00 (d, J=6.6 Hz, 3H);

LCMS (Method B): Rt 1.16 min, m/z: (646.4) [M+H]$^+$;

HPLC (Method A): Rt 4.63 min, 99.20%;

SFC (Method K): Rt 9.58 min, 100%.

Example 227 (Isomer 2): 2-((4-(7-(((2S,5R)-5-((E2)-Ethylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide Yield: 23.44%;

$^1$H NMR (400 MHz, DMSO-d$_6$) δ 8.26 (s, 11H), 7.71 (d, J=0.6 Hz, 11H), 7.28-7.18 (m, 2H), 7.09-7.00 (m, 1H), 6.57-6.31 (m, 1H), 3.96-3.75 (m, 5H), 3.73-3.64 (m, 1H), 3.59-3.47 (m, 1H), 3.29-3.25 (m, 1H), 3.23-3.00 (m, 2H), 2.99-2.87 (m, 3H), 2.33-2.16 (m, 5H), 1.97-1.85 (m, 1H), 1.74-1.59 (m, 5H), 1.44 (d, J=6.8 Hz, 3H), 1.35 (d, J=6.8 Hz, 4H), 1.28-1.14 (m, 5H), 1.09 (d, J=6.6 Hz, 3H), 1.00 (d, J=6.6 Hz, 3H);

LCMS (Method B): Rt 1.16 min, m/z: (646.6) [M+H]$^+$;

HPLC (Method F): Rt 4.62 min, 96.12%;

SFC (Method K): Rt 12.16 min, 100%.

Note: The absolute stereochemistry of the isomers was assigned arbitrarily.

Example 228. 5-Fluoro-N,N-diisopropyl-2-((4-(7-(((2S,5R)-5-(phenylsulfonoamidimidamido)tetrahydro-2H-pyran-2-yl)methyl)-2,7-diazaspiro[3.5]nonan-2-yl)pyrimidin-5-yl)oxy)benzamide

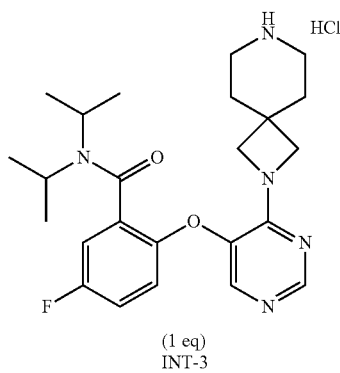

(1 eq)
INT-3

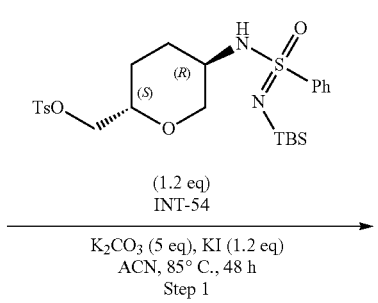

(1.2 eq)
INT-54

$\xrightarrow{\text{K}_2\text{CO}_3 \text{ (5 eq), KI (1.2 eq)}}_{\text{ACN, 85° C., 48 h}}$
Step 1

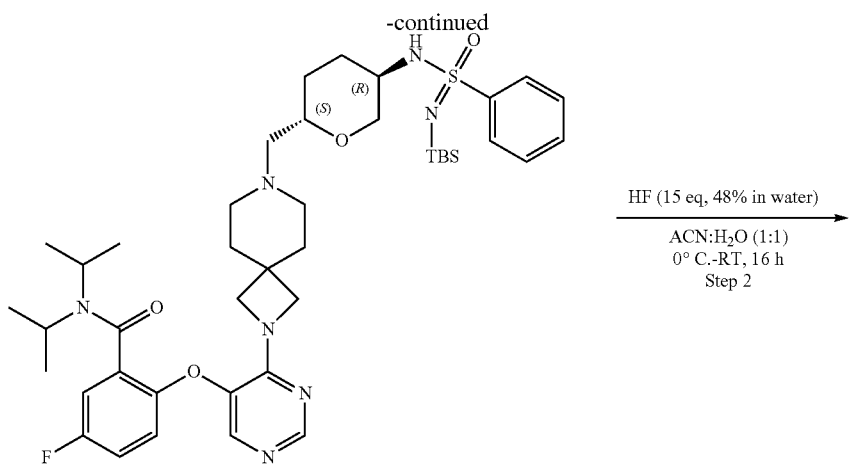

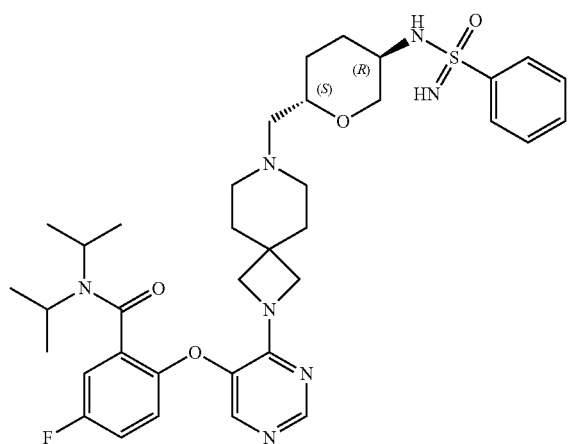

Example 228

Step 1. 2-((4-(7-(((2S,5R)-5-(N'-(tert-Butyldimethylsilyl)phenylsulfonoamidimidamido)tetrahydro-2H-pyran-2-yl)methyl)-2,7-diazaspiro[3.5]nonan-2-yl) pyrimidin-5-yl)oxy)-5-fluoro-N,N-diisopropylbenzamide

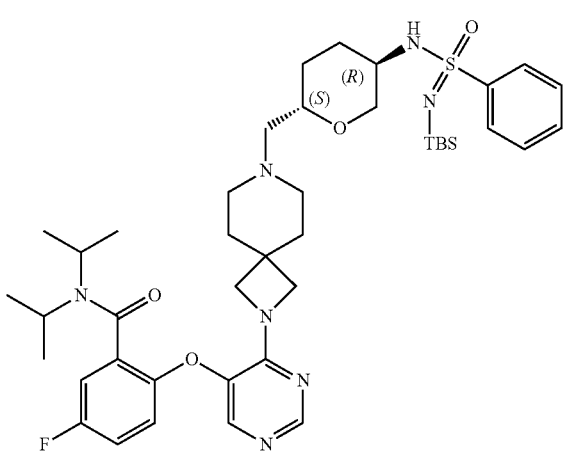

In a 50 mL round bottom flask under nitrogen atmosphere, 2-((4-(2,7-diazaspiro[3.5]nonan-2-yl)pyrimidin-5-yl)oxy)-5-fluoro-N,N-diisopropylbenzamide hydrochloride (300 mg, 0.628 mmol) was added in ACN (10 mL). To this reaction mixture, $K_2CO_3$ (434 mg, 3.14 mmol), KI (125 mg, 0.753 mmol), and ((2S,5R)-5-(N'-(tert-butyldimethylsilyl) phenylsulfonoamidimidamido)tetrahydro-2H-pyran-2-yl) methyl 4-methylbenzenesulfonate (406 mg, 0.753 mmol) were added at RT, and the reaction was heated to 85° C. The reaction progress was monitored by TLC (10% methanol in DCM). After 48 h, the reaction mixture was poured into $H_2O$ (20 mL) and extracted with EtOAc (2×25 mL). The combined organic layer was washed with $H_2O$ (2×20 mL), dried over $Na_2SO_4$, and filtered. The filtrate was concentrated under reduced pressure to obtain a crude compound (0.4 g). The crude compound was purified by silica gel column chromatography using 0-7% methanol in DCM. The product fractions were concentrated under reduced pressure to obtain 2-((4-(7-(((2S,5R)-5-(N'-(tert-butyl dimethylsilyl)phenylsulfonoamidimidamido)tetrahydro-2H-pyran-2-yl) methyl)-2,7-diazaspiro [3.5]nonan-2-yl)pyrimidin-5-yl) oxy)-5-fluoro-N,N-diisopropylbenzamide (250 mg, 49.3% yield) as a semi solid. LCMS (Method E): Rt 2.67 min, m/z: 809.4 [M+H]+, 90.48%.

Step 2. 5-Fluoro-N,N-diisopropyl-2-((4-(7-(((2S,5R)-5-(phenylsulfonoamidimidamido)tetrahydro-2H-pyran-2-yl)methyl)-2,7-diazaspiro[3.5]nonan-2-yl)pyrimidin-5-yl)oxy)benzamide (Example 228)

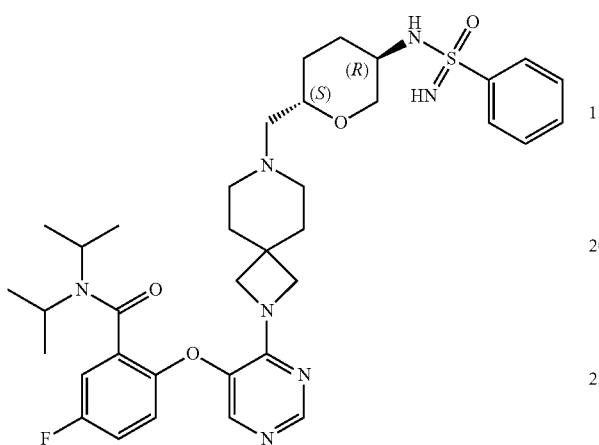

To a 50 mL plastic container under nitrogen atmosphere, 2-((4-(7-(((2S,5R)-5-(N'-(tert-butyldimethylsilyl)phenylsulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (250 mg, 0.309 mmol) was added in ACN (5 mL) and water (5 mL) at 0° C. To this reaction mixture, HF (0.080 mL, 4.64 mmol, 48% in water) was added at 0° C., and the reaction was stirred at RT for 16 h. The reaction was monitored by TLC (10% MeOH in DCM). The reaction mixture was poured into ice-cold water (10 mL), then the pH was adjusted to 7 using solid NaHCO$_3$. The mixture was extracted with 10% MeOH in DCM (2×25 mL). The combined organic layer was dried over Na$_2$SO$_4$, filtered, and concentrated under reduced pressure to obtain the crude compound. The crude was purified by Prep-HPLC (Method E) and pure fractions were lyophilized to obtain 5-fluoro-N,N-diisopropyl-2-((4-(7-(((2S,5R)-5-(phenylsulfonoamidimidamido)tetrahydro-2H-pyran-2-yl)methyl)-2,7-diazaspiro[3.5]nonan-2-yl)pyrimidin-5-yl)oxy)benzamide (97 mg, 44.9% yield) as a solid. $^1$H NMR (400 MHz, DMSO-d$_6$) δ 8.25 (s, 1H), 7.92-7.83 (m, 2H), 7.71 (s, 1H), 7.59-7.48 (m, 3H), 7.29-7.17 (m, 2H), 7.03 (dd, J=4.3, 10.1 Hz, 1H), 6.97 (br s, 1H), 4.27-4.15 (m, 1H), 3.94-3.73 (m, 4H), 3.73-3.64 (m, 1H), 3.62-3.46 (m, 2H), 3.27-3.15 (m, 1H), 3.31-3.14 (m, 1H), 3.04-2.81 (m, 2H), 2.32-2.08 (m, 5H), 1.73-1.48 (m, 6H), 1.43 (d, J=6.6 Hz, 3H), 1.38-1.21 (m, 4H), 1.09 (d, J=6.6 Hz, 4H), 0.99 (d, J=6.6 Hz, 3H); LCMS (Method E): Rt 1.71 min, m/z: 694.5 [M+H]$^+$; HPLC (Method A): Rt 5.25 min, 99.48%.

Example 229 (Isomer 1). 5-Fluoro-N,N-diisopropyl-2-((4-(7-(((2S,5R)-5-((R)-phenylsulfonoamidimidamido)tetrahydro-2H-pyran-2-yl)methyl)-2,7-diazaspiro[3.5]nonan-2-yl)pyrimidin-5-yl)oxy)benzamide and Example 230 (Isomer 2). 5-Fluoro-N,N-diisopropyl-2-((4-(7-(((2S,5R)-5-((S)-phenylsulfonoamidimidamido)tetrahydro-2H-pyran-2-yl)methyl)-2,7-diazaspiro[3.5]nonan-2-yl)pyrimidin-5-yl)oxy)benzamide

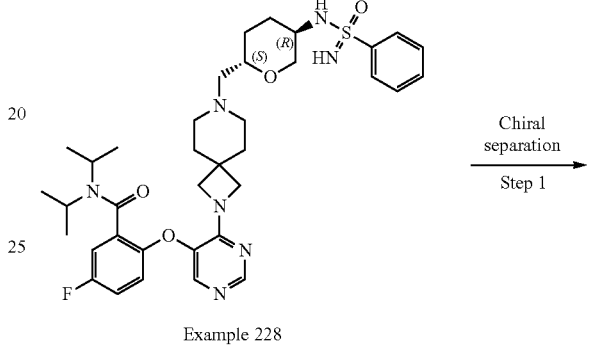

Example 228

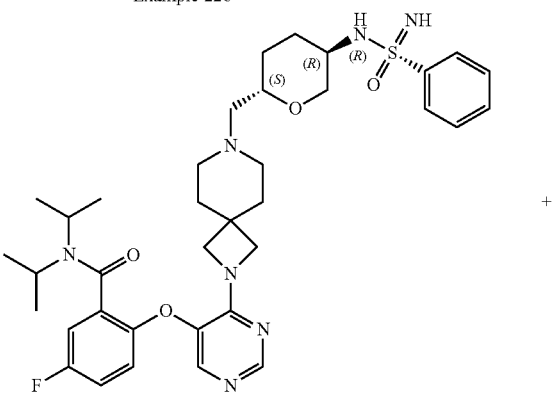

Example 229

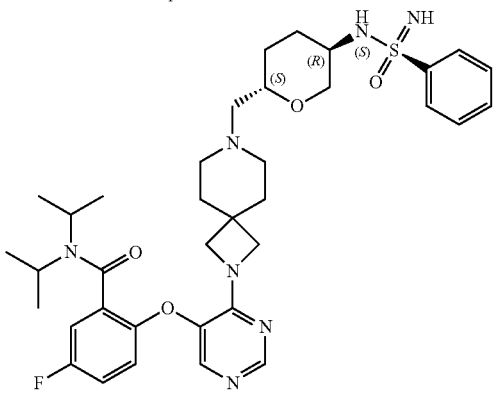

Example 230

Step 1. The above racemic compound (90 mg) (Example 228) was purified by chiral SFC (Method B). The pure fractions were concentrated under reduced pressure and lyophilized to afford the separated enantiomers.

Example 229 (Isomer 1). 5-Fluoro-N,N-diisopropyl-2-((4-(7-(((2S,5R)-5-((E1)-phenylsulfonoamidimidamido)tetrahydro-2H-pyran-2-yl)methyl)-2,7-diazaspiro[3.5]nonan-2-yl)pyrimidin-5-yl)oxy)benzamide Yield: 23.72%;
$^{1}$H NMR (400 MHz, DMSO-d$_{6}$) δ 8.26 (s, 1H), 7.88 (dd, J=1.5, 7.9 Hz, 2H), 7.71 (s, 1H), 7.60-7.49 (m, 3H), 7.26-7.18 (m, 2H), 7.08-6.91 (m, 2H), 4.31-4.09 (m, 1H), 3.96-3.73 (m, 4H), 3.73-3.63 (m, 1H), 3.60-3.46 (m, 2H), 3.28-3.14 (m, 2H), 3.03-2.85 (m, 2H), 2.31-2.07 (m, 6H), 1.72-1.51 (m, 5H), 1.43 (d, J=6.8 Hz, 3H), 1.34 (d, J=6.8 Hz, 3H), 1.30-1.23 (m, 1H), 1.09 (d, J=6.6 Hz, 4H), 0.99 (d, J=6.5 Hz, 3H);
LCMS (Method C): Rt 1.33 min, m/z: (694.3) [M+H]$^{+}$;
HPLC (Method B): Rt 2.67 min, 99.58%;
SFC (Method L): Rt 1.92 min, 100%.

Example 230 (Isomer 2). 5-Fluoro-N,N-diisopropyl-2-((4-(7-(((2S,5R)-5-((E2)-phenylsulfonoamidimidamido)tetrahydro-2H-pyran-2-yl)methyl)-2,7-diazaspiro[3.5]nonan-2-yl)pyrimidin-5-yl)oxy)benzamide Yield: 15.58%;
$^{1}$H NMR (400 MHz, DMSO-d$_{6}$) δ 8.25 (s, 1H), 7.89 (dd, J=1.4, 7.8 Hz, 2H), 7.71 (d, J=0.8 Hz, 1H), 7.60-7.48 (m, 3H), 7.27-7.16 (m, 2H), 7.09 (s, 2H), 4.31-4.05 (m, 1H), 3.99-3.73 (m, 4H), 3.73-3.62 (m, 1H), 3.62-3.47 (m, 2H), 3.27-3.12 (m, 2H), 3.05-2.81 (m, 2H), 2.32-2.03 (m, 5H), 1.76-1.48 (m, 6H), 1.43 (d, J=6.6 Hz, 3H), 1.37-1.24 (m, 4H), 1.16-1.03 (m, 4H), 0.99 (d, J=6.6 Hz, 3H);
LCMS (Method A): Rt 1.33 min, m/z: (694.4) [M+H]$^{+}$;
HPLC (Method F): Rt 2.59 min, 98.26%;
SFC (Method L): Rt 2.46 min, 99.11%.
Note: The absolute stereochemistry of the isomers was assigned arbitrarily.

Example 231. 5-Fluoro-N,N-diisopropyl-2-((4-(7-(((2S,5R)-5-(N'-methylethylsulfonoamidimidamido)tetrahydro-2H-pyran-2-yl)methyl)-2,7-diazaspiro[3.5]nonan-2-yl)pyrimidin-5-yl)oxy)benzamide

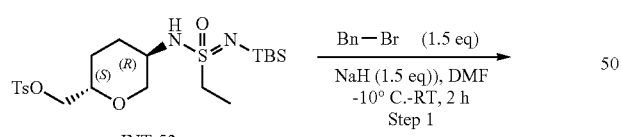

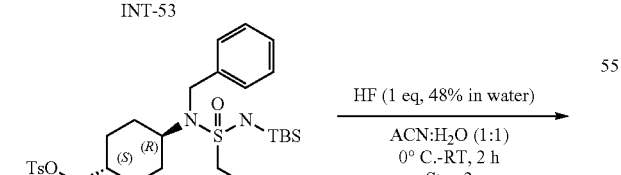

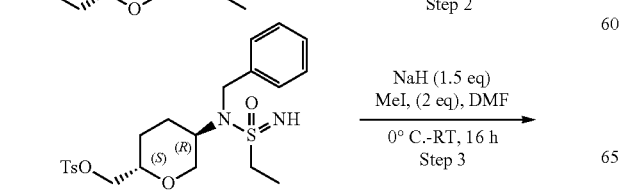

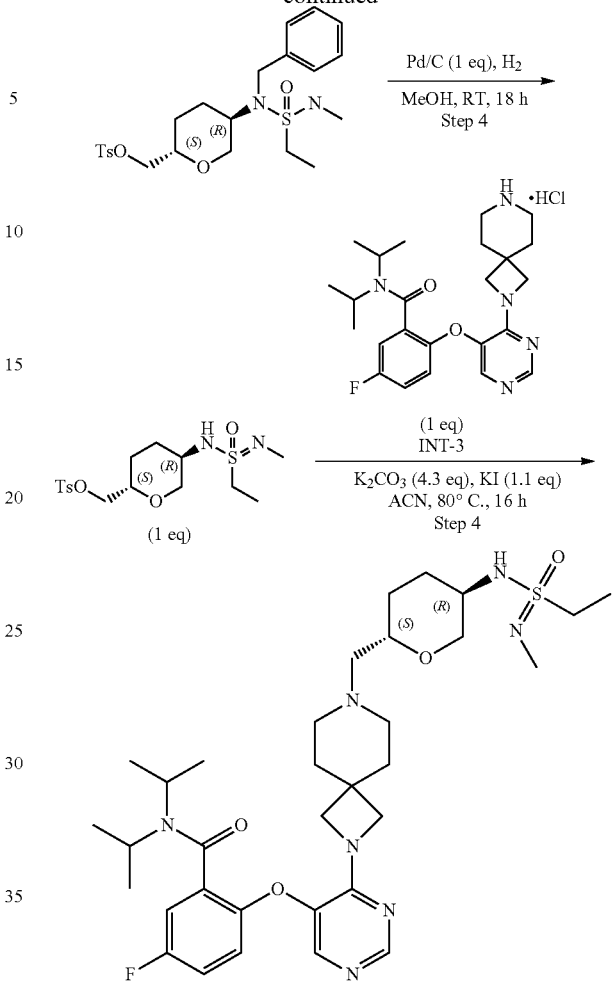

Example 231

Step 1. ((2S,5R)-5-(N-Benzyl-N'-(tert-butyldimethylsilyl)ethylsulfonoamidimidamido)tetrahydro-2H-pyran-2-yl)methyl 4-methylbenzenesulfonate

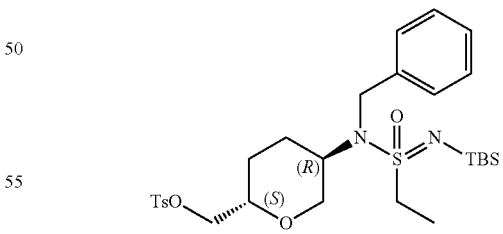

To a dried 100 mL round bottom flask under nitrogen atmosphere, ((2S,5R)-5-(N'-(tert-butyldimethylsilyl)ethylsulfonoamidimidamido)tetrahydro-2H-pyran-2-yl)methyl 4-methylbenzenesulfonate (1 g, 2.038 mmol) was added in DMF (20 mL). To this reaction mixture, NaH (0.122 g, 3.06 mmol) was added at −10° C., and the reaction was stirred for 10 min. To this mixture, benzyl bromide (0.363 mL, 3.06 mmol) was added dropwise at RT. The reaction was stirred at RT for 2 h. The reaction progress was monitored by TLC (30% EtOAc in hexane). The reaction mixture was quenched with water (200 mL) and extracted with EtOAc (150 mL). The combined organic layer was dried over anhydrous sodium sulfate, filtered, and concentrated under reduced pressure to obtain the crude product. The crude compound was purified by silica gel column chromatography using 30% EtOAc in hexane as an eluent to obtain ((2S,5R)-5-(N-benzyl-N'-(tert-butyldimethylsilyl)ethylsulfonoamidimidamido)tetrahydro-2H-pyran-2-yl)methyl 4-methylbenzenesulfonate (700 mg, 59.0% yield) as a liquid. $^1$H NMR (400 MHz, DMSO-d$_6$) b 7.77-7.70 (m, 2H), 7.51-7.42 (m, 2H), 7.39-7.29 (m, 4H), 7.28-7.22 (m, 1H), 4.57-4.42 (m, 1H), 4.39-4.14 (m, 1H), 3.97-3.90 (m, 1H), 3.90-3.81 (m, 1H), 3.81-3.68 (m, 1H), 3.66-3.44 (m, 1H), 3.31-3.22 (m, 1H), 3.10-2.83 (m, 3H), 2.42 (s, 3H), 1.90-1.51 (m, 3H), 1.36-1.22 (m, 1H), 1.20-1.15 (m, 3H), 0.86 (d, J=8.50 Hz, 9H), 0.07 (d, J=5.50 Hz, 3H), 0.02 (d, J=6.88 Hz, 3H); LCMS (Method E): Rt 2.80 min, m/z: 581.8 [M+H]$^+$; 98.52%.

Step 2. ((2S,5R)-5-(N-Benzylethylsulfonoamidimidamido)tetrahydro-2H-pyran-2-yl)methyl 4-methylbenzenesulfonate

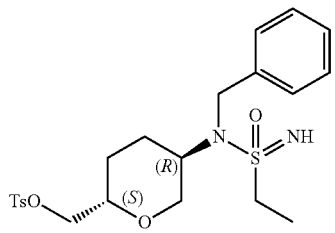

To a dried 50 mL round bottom flask under argon atmosphere, ((2S,5R)-5-(N-benzyl-N'-(tert-butyldimethylsilyl)ethylsulfonoamidimidamido)tetrahydro-2H-pyran-2-yl)methyl 4-methylbenzenesulfonate (700 mg, 1.20 mmol) was added in ACN (4 mL) and water (4 mL). The reaction mixture was cooled to 0° C., and HF (249 mg, 1.205 mmol, 48% in water) was added. The reaction was allowed to warm to RT and stir for 2 h. The reaction progress was monitored by TLC (30% EtOAc in hexane). After completion, the reaction mixture was concentrated under reduced pressure, and the pH was adjusted to 9 using aq. NaHCO$_3$. The aqueous layer was extracted with 10% MeOH in DCM (2×100 mL). The combined organic layer was dried over anhydrous sodium sulfate, filtered, and concentrated under reduced pressure to obtain ((2S,5R)-5-(N-benzylethylsulfonoamidimidamido)tetrahydro-2H-pyran-2-yl)methyl 4-methylbenzenesulfonate (500 mg, 85% yield) as a liquid. $^1$H NMR (400 MHz, DMSO-d$_6$) δ 7.77-7.71 (m, 2H), 7.50-7.43 (m, 2H), 7.41-7.36 (m, 2H), 7.35-7.21 (m, 3H), 4.53-4.47 (m, 1H), 4.32-4.19 (m, 1H), 3.96-3.90 (m, 1H), 3.87-3.81 (m, 2H), 3.79-3.66 (m, 1H), 3.65-3.54 (m, 11H), 3.29-3.23 (m, 1H), 3.02-2.88 (m, 3H), 2.42 (s, 3H), 1.89-1.79 (m, 1H), 1.68-1.51 (m, 2H), 1.40-1.23 (m, 1H), 1.19 (t, J=7.32 Hz, 3H); LCMS (Method B): Rt 2.09 min, m/z: 467.2 [M+H]$^+$, 95.13%.

Step 3. ((2S,5R)-5-(N-Benzyl-N'-methylethylsulfonoamidimidamido)tetrahydro-2H-pyran-2-yl)methyl 4-methylbenzenesulfonate

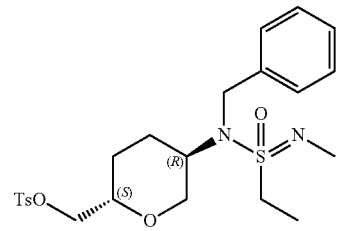

To a dried 50 mL round bottom flask under nitrogen atmosphere, ((2S,5R)-5-(N-benzylethylsulfonoamidimidamido)tetrahydro-2H-pyran-2-yl)methyl 4-methylbenzenesulfonate (500 mg, 1.072 mmol) was added in DMF (10 mL). The reaction mixture was cooled to 0° C., and NaH (64.3 mg, 1.607 mmol) was added, then the reaction was stirred for 10 min. To this reaction mixture, MeI (0.134 mL, 2.143 mmol) was added, and the reaction mixture was warmed to RT and stirred for 16 h. The reaction progress was monitored by TLC (60% EtOAc in hexane). After completion, the reaction was quenched with aq. NH$_4$Cl and extracted with EtOAc (3×50 mL). The combined organic layer was dried over anhydrous sodium sulfate, filtered, and concentrated under reduced pressure to obtain ((2S,5R)-5-(N-benzyl-N'-methylethylsulfonoamidimidamido)tetrahydro-2H-pyran-2-yl)methyl 4-methylbenzenesulfonate (500 mg, 91% yield) as a liquid. LCMS (Method B): Rt 2.14 min, m/z: 481.2 [M+H]$^+$; 93.59%.

Step 4. ((2S,5R)-5-(N'-Methylethylsulfonoamidimidamido)tetrahydro-2H-pyran-2-yl)methyl 4-methylbenzenesulfonate

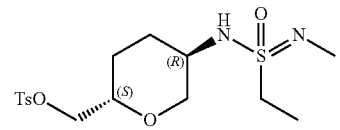

To a dried 100 mL round bottom flask under nitrogen atmosphere, ((2S,5R)-5-(N-benzyl-N'-methylethylsulfonoamidimidamido)tetrahydro-2H-pyran-2-yl)methyl 4-methylbenzenesulfonate (470 mg, 0.978 mmol) was added in methanol (10 mL). The reaction mixture was purged with nitrogen for 10 min, then Pd—C(520 mg, 0.489 mmol) was added at RT, and the reaction was stirred for 16 h under a hydrogen atmosphere (balloon pressure). The reaction progress was monitored by TLC (60% EtOAc in hexane). The starting material was not consumed, so an additional portion of Pd—C(520 mg, 0.489 mmol) was added and the reaction was stirred at RT for another 2 h. After completion, the reaction mixture was filtered through Celite®, and the filter pad was washed with methanol (50 mL). The filtrate was concentrated under reduced pressure to obtain crude ((2S,5R)-5-(N'-methylethylsulfonoamidimidamido)tetrahydro-2H-pyran-2-yl)methyl 4-methylbenzenesulfonate (255 mg, 65.2% yield). LCMS (Method B): Rt 1.51 min, m/z: 391.4 [M+H]$^+$; 97.64%.

Step 5. 5-Fluoro-N,N-diisopropyl-2-((4-(7-(((2S, 5R)-5-(N'-methylethylsulfonoamidimidamido)tetrahydro-2H-pyran-2-yl)methyl)-2,7-diazaspiro[3.5]nonan-2-yl)pyrimidin-5-yl)oxy)benzamide (Example 231)

Example 232. 5-Fluoro-N,N-diisopropyl-2-((4-(7-(((2S,5R)-5-(N'-methylphenylsulfonoamidimidamido)tetrahydro-2H-pyran-2-yl)methyl)-2,7-diazaspiro[3.5]nonan-2-yl)pyrimidin-5-yl)oxy)benzamide

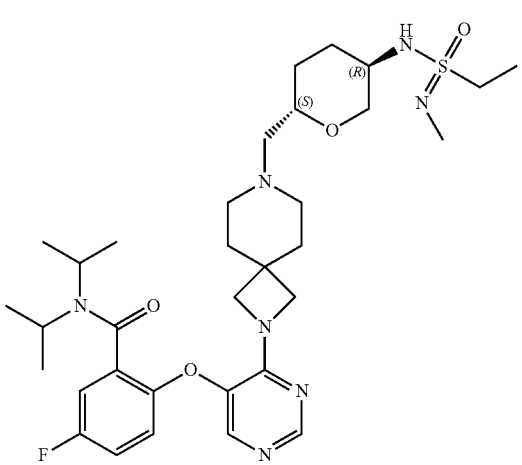

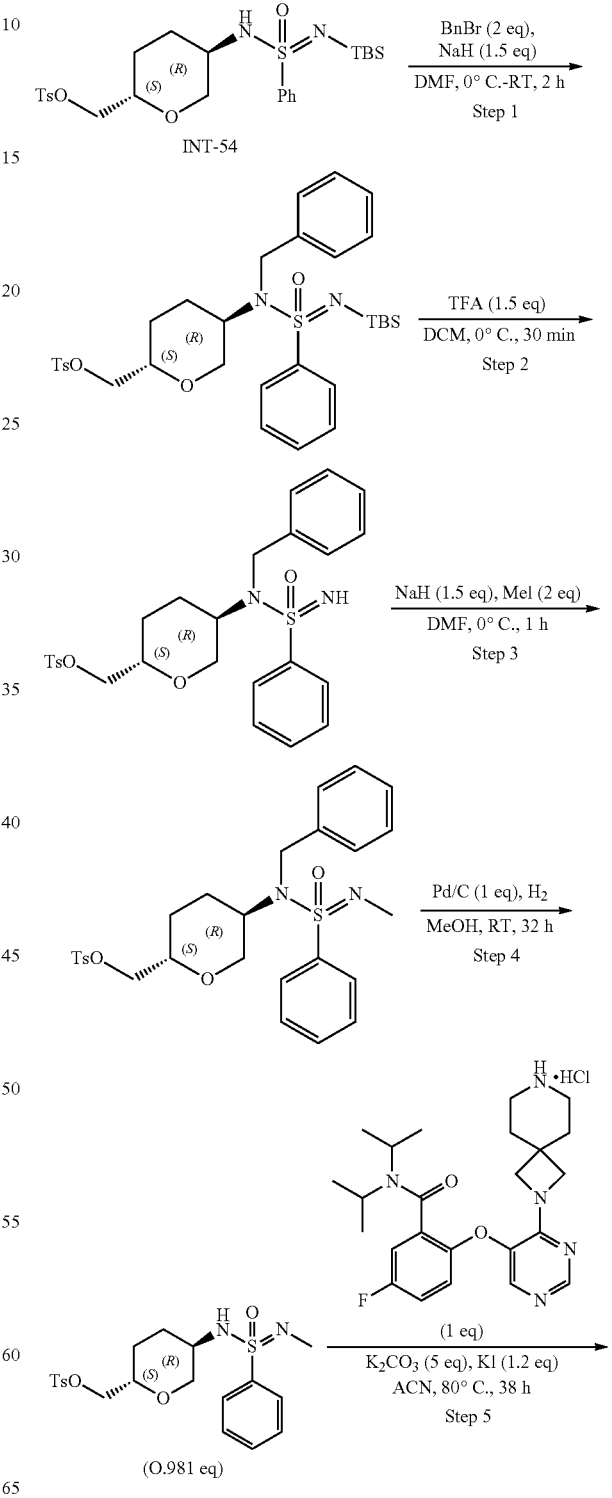

To a dried 50 mL round bottom flask under nitrogen atmosphere, 2-((4-(2,7-diazaspiro[3.5]nonan-2-yl)pyrimidin-5-yl)oxy)-5-fluoro-N,N-diisopropylbenzamide hydrochloride (300 mg, 0.628 mmol) was added in ACN (10 mL). To this reaction mixture, $K_2CO_3$ (373 mg, 2.70 mmol), KI (115 mg, 0.690 mmol), and ((2S,5R)-5-(N'-methylethylsulfonoamidimidamido)tetrahydro-2H-pyran-2-yl)methyl 4-methylbenzenesulfonate (245 mg, 0.628 mmol) were added at RT. The reaction was heated at 80° C. for 16 h. The reaction progress was monitored by TLC (10% MeOH in DCM). After completion, the reaction mixture was quenched with water (50 mL), and the aqueous layer was extracted with EtOAc (2×100 mL). The combined organic layer was dried over anhydrous sodium sulfate, filtered, and concentrated on a rotary evaporator under reduced pressure to obtain the crude compound. The crude compound was purified by Prep-HPLC (Method C) and pure fractions were lyophilized to obtain 5-fluoro-N,N-diisopropyl-2-((4-(7-(((2S,5R)-5-(N'-methylethylsulfonoamidimidamido)tetrahydro-2H-pyran-2-yl)methyl)-2,7-diazaspiro[3.5]nonan-2-yl)pyrimidin-5-yl)oxy)benzamide (100 mg, 24.06% yield) as a solid. $^1$H NMR (400 MHz, DMSO-$d_6$) δ 8.26 (s, 1H), 7.71 (s, 1H), 7.29-7.17 (m, 2H), 7.13-7.00 (m, 1H), 6.10 (br s, 1H), 3.97-3.75 (m, 4H), 3.75-3.60 (m, 2H), 3.59-3.47 (m, 1H), 3.19-3.05 (m, 1H), 3.02-2.83 (m, 4H), 2.32-2.14 (m, 5H), 1.93-1.78 (m, 1H), 1.76-1.55 (m, 6H), 1.44 (d, J=6.8 Hz, 3H), 1.35 (d, J=6.6 Hz, 4H), 1.25-1.06 (m, 7H), 1.00 (d, J=6.5 Hz, 3H) (3 protons merged with solvent peaks); LCMS (Method E): Rt 1.58 min, m/z: 660.9 [M+H]$^+$; HPLC (Method A): Rt 4.81 min, 99.62%.

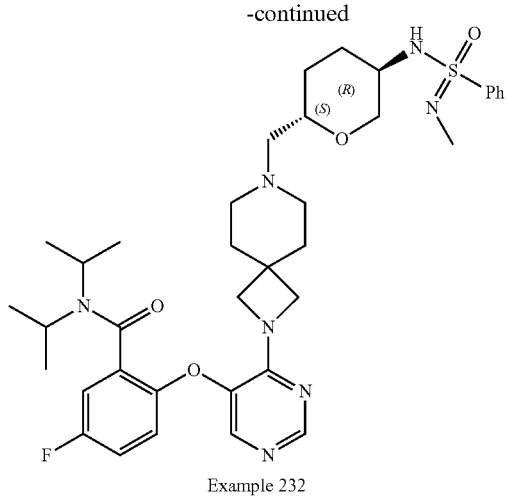

Example 232

Step 1. ((2S,5R)-5-(N-Benzyl-N'-(tert-butyldimethylsilyl)phenylsulfonoamidimidamido)tetrahydro-2H-pyran-2-yl)methyl 4-methylbenzenesulfonate

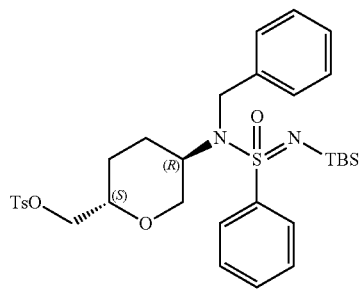

To a 50 mL round bottom flask under nitrogen atmosphere, NaH (0.167 g, 4.18 mmol) was added in DMF (15 mL) at 0° C. To this solution, ((2S,5R)-5-(N'-(tert-butyldimethylsilyl)phenylsulfonoamidimidamido)tetrahydro-2H-pyran-2-yl)methyl 4-methyl benzenesulfonate (1.5 g, 2.78 mmol) in DMF (7 mL) was added and the reaction was stirred for 10 min. To this reaction mixture, benzyl bromide (0.661 mL, 5.57 mmol) was added, and the reaction was stirred at RT. The reaction progress was monitored by TLC (30% EtOAc in hexane). After 2 h, the reaction mixture was cooled to 0° C., quenched with saturated NH₄Cl solution (20 mL), and extracted with EtOAc (2×25 mL). The combined organic layer was washed with ice-cold water (2×20 mL), dried over Na₂SO₄, and filtered, and the filtrate was concentrated under reduced pressure to obtain crude product (2.1 g). The crude product was purified by silica gel column chromatography using 17% EtOAc in hexane as an eluent. The product fractions were concentrated under reduced pressure to obtain ((2S,5R)-5-(N-benzyl-N'-(tert-butyldimethylsilyl)phenylsulfonoamidimidamido)tetrahydro-2H-pyran-2-yl)methyl 4-methylbenzenesulfonate (1.4 g, 78% yield) as a solid. ¹H NMR (400 MHz, DMSO-$d_6$) δ 7.86-7.77 (m, 2H), 7.74-7.69 (m, 2H), 7.63-7.54 (m, 3H), 7.47-7.40 (m, 2H), 7.39-7.29 (m, 4H), 7.27-7.20 (m, 1H), 4.71-4.44 (m, 1H), 4.36-4.25 (m, 1H), 3.90-3.84 (m, 1H), 3.83-3.75 (m, 1H), 3.70-3.60 (m, 1H), 3.32-3.24 (m, 1H), 3.15-3.18 (m, 1H), 2.92-2.76 (m, 1H), 2.41 (s, 3H), 1.54-1.32 (m, 2H), 1.54-1.26 (m, 1H), 1.14-1.01 (m, 1H), 0.82 (d, J=5.13 Hz, 9H), −0.02 (d, J=6.00 Hz, 3H), −0.04 (d, J=1.88 Hz, 3H); LCMS (Method E): Rt 2.84 min, m/z: 629.3 [M+H]⁺, 97.87%.

Step 2. ((2S,5R)-5-(N-Benzylphenylsulfonoamidimidamido)tetrahydro-2H-pyran-2-yl)methyl 4-methylbenzenesulfonate

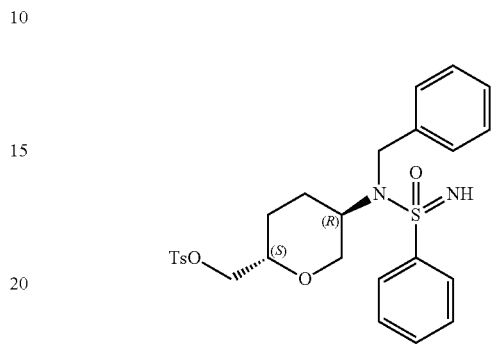

To a 50 mL round bottom flask, ((2S,5R)-5-(N-benzyl-N'-(tert-butyldimethylsilyl)phenylsulfonoamidimidamido)tetrahydro-2H-pyran-2-yl)methyl 4-methyl benzenesulfonate (1.3 g, 2.067 mmol) was added in DCM (20 mL). The reaction mixture was cooled to 0° C. and trifluoroacetic acid (0.239 mL, 3.10 mmol) in DCM (2.00 mL) was added slowly. The reaction was stirred at 0° C. for 30 min. The reaction progress was monitored by TLC (30% EtOAc in hexane). The reaction mixture was quenched with saturated NaHCO₃ solution (10 mL) and extracted with DCM (2×20 mL). The combined organic layer was dried over Na₂SO₄, filtered, and concentrated under reduced pressure to obtain ((2S,5R)-5-(N-benzylphenylsulfonoamidimidamido)tetrahydro-2H-pyran-2-yl)methyl 4-methylbenzenesulfonate (1 g, 87% yield) as a solid. ¹H NMR (400 MHz, DMSO-$d_6$) δ 7.93-7.87 (m, 2H), 7.72 (d, J=8.25 Hz, 2H), 7.66-7.53 (m, 3H), 7.45 (d, J=8.00 Hz, 2H), 7.42-7.22 (m, 5H), 4.61-4.49 (m, 1H), 4.28-4.09 (m, 1H), 3.94-3.76 (m, 3H), 3.22-3.13 (m, 2H), 2.88-2.70 (m, 1H), 2.41 (s, 3H), 1.52-1.37 (m, 3H), 1.24-1.08 (m, 2H); LCMS (Method E): Rt 2.14 min, m/z: 515.2 [M+H]⁺, 93.02%.

Step 3. ((2S,5R)-5-(N-Benzyl-N'-methylphenylsulfonoamidimidamido)tetrahydro-2H-pyran-2-yl)methyl 4-methylbenzenesulfonate

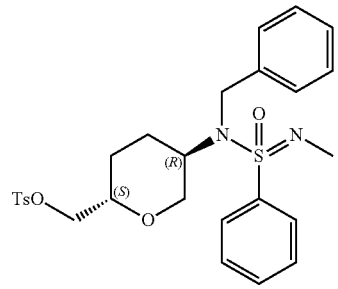

To a 50 mL round bottom flask under nitrogen atmosphere, NaH (0.117 g, 2.91 mmol) was added in DMF (15 mL) at 0° C. To this solution, ((2S,5R)-5-(N-benzylphenylsulfonoamidimidamido)tetrahydro-2H-pyran-2-yl) methyl 4-methylbenzenesulfonate (1 g, 1.943 mmol) was added in DMF (5 mL) at 0° C., and the reaction was stirred for 15 min. To this reaction mixture, MeI (0.242 mL, 3.89 mmol) was added at 0° C. and the reaction was stirred for 1 h. The reaction progress was monitored by TLC (30% EtOAc in hexane). After reaction completion, the reaction mixture was quenched with saturated $NH_4Cl$ solution (25 mL) and extracted with EtOAc (2×50 mL). The combined organic layer was washed with $H_2O$ (2×20 mL), dried over $Na_2SO_4$, and filtered, and the filtrate was concentrated under reduced pressure to obtain the crude product (1.1 g). The crude product was purified by silica gel column chromatography using 10% EtOAc in hexane as an eluent. The product fractions were concentrated under reduced pressure to obtain ((2S,5R)-5-(N-benzyl-N'-methylphenylsulfonoamidimidamido)tetrahydro-2H-pyran-2-yl)methyl 4-methylbenzenesulfonate (0.7 g, 66.4% yield) as a semisolid. $^1$H NMR (400 MHz, DMSO-$d_6$) δ 7.95-7.90 (m, 2H), 7.73 (d, J=8.25 Hz, 2H), 7.68-7.55 (m, 3H), 7.45 (d, J=8.38 Hz, 2H), 7.39-7.21 (m, 5H), 4.66-4.03 (m, 2H), 3.97-3.76 (m, 2H), 3.69-3.56 (m, 1H), 3.27-3.20 (m, 1H), 3.14-2.79 (m, 2H), 2.74 (d, J=6.13 Hz, 3H), 2.42 (s, 3H), 1.64-1.36 (m, 3H), 1.28-1.07 (m, 1H); LCMS (Method E): Rt 2.28 min, m/z: 529.4 [M+H]$^+$, 97.38%.

Step 4. ((2S,5R)-5-(N'-Methylphenylsulfonoamidimidamido)tetrahydro-2H-pyran-2-yl)methyl 4-methylbenzenesulfonate

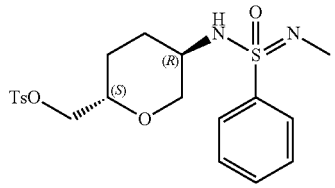

To a 50 mL round bottom flask under nitrogen atmosphere, ((2S,5R)-5-(N-benzyl-N'-methylphenylsulfonoamidimidamido)tetrahydro-2H-pyran-2-yl)methyl 4-methyl benzenesulfonate (700 mg, 1.324 mmol) was added in MeOH (30 mL). The reaction mixture was purged with nitrogen for 10 min and then Pd/C (1409 mg, 1.324 mmol) was added. The reaction mixture was stirred at RT under hydrogen bladder pressure for 16 h. LCMS showed 18% product formation and 80% starting material. The reaction mixture was filtered through Celite®, and the filter pad was washed with methanol (50 mL). The filtrate was concentrated under reduced pressure to obtain crude material (650 mg). The crude was dissolved in methanol (30 mL) and fresh Pd/C (1409 mg, 1.324 mmol) was added under nitrogen atmosphere. The reaction mixture was stirred at RT under hydrogen bladder pressure for another 16 h. LCMS showed 38% product formation and 50% starting material. The reaction mixture was filtered through Celite®, and the filter pad was washed with methanol (50 mL). The filtrate was concentrated under reduced pressure to obtain crude compound (550 mg). The crude compound was purified by silica gel column chromatography using 50% EtOAc in hexane as an eluent. The product fractions were concentrated under reduced pressure to obtain ((2S,5R)-5-(N'-methylphenylsulfonoamidimidamido)tetrahydro-2H-pyran-2-yl) methyl 4-methylbenzenesulfonate (180 mg, 30.4% yield) as a semisolid. $^1$H NMR (400 MHz, DMSO-$d_6$) δ 7.76-7.83 (m, 4H), 7.52-7.62 (m, 3H), 7.49 (d, J=8.50 Hz, 2H), 6.72 (br s, 1H), 3.96-4.01 (m, 1H), 3.84-3.92 (m, 1H), 3.63-3.82 (m, 1H), 3.38-3.47 (m, 1H), 3.27-3.10 (m, 1H), 2.97-3.10 (m, 1H), 2.43 (s, 3H), 2.35 (br s, 3H), 1.34-1.57 (m, 3H), 1.20-1.28 (m, 1H); LCMS (Method A): Rt 1.96 min, m/z: (439.4) [M+H]J, 98.16%.

Step 5. 5-Fluoro-N,N-diisopropyl-2-((4-(7-(((2S,5R)-5-(N'-methylphenylsulfonoamidimidamido)tetrahydro-2H-pyran-2-yl)methyl)-2,7-diazaspiro[3.5]nonan-2-yl)pyrimidin-5-yl)oxy)benzamide
(Example 232)

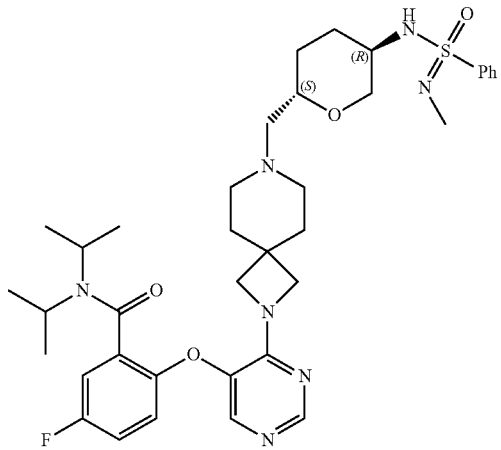

To a 50 mL round bottom flask under nitrogen atmosphere, 2-((4-(2,7-diazaspiro[3.5]nonan-2-yl)pyrimidin-5-yl)oxy)-5-fluoro-N,N-diisopropylbenzamide hydrochloride (200 mg, 0.418 mmol) was added in ACN (10 mL) at RT. To this reaction mixture, $K_2CO_3$ (289 mg, 2.092 mmol), KI (83 mg, 0.502 mmol) and ((2S,5R)-5-(N'-methylphenylsulfonoamidimidamido)tetrahydro-2H-pyran-2-yl)methyl 4-methylbenzenesulfonate (180 mg, 0.410 mmol) were added at RT. The reaction was stirred at 80° C. for 38 h. The reaction was monitored by TLC (10% MeOH in DCM). The reaction mixture was quenched with water (20 mL) and extracted with EtOAc (2×30 mL). The combined organic layer was dried over $Na_2SO_4$, and filtered, and the filtrate was concentrated under reduced pressure to obtain crude compound. The crude compound was purified by Prep-HPLC (Method C) and the pure fractions were lyophilized to obtain 5-fluoro-N,N-diisopropyl-2-((4-(7-(((2S,5R)-5-(N'-methylphenylsulfonoamidimidamido)tetrahydro-2H-pyran-2-yl)methyl)-2,7-diazaspiro[3.5]nonan-2-yl)pyrimidin-5-yl)oxy)benzamide (70 mg, 22.91% yield) as a solid. $^1$H NMR (400 MHz, DMSO-$d_6$) δ 8.26 (s, 1H), 7.82 (br d, J=6.0 Hz, 2H), 7.71 (s, 1H), 7.62-7.52 (m, 3H), 7.28-7.19 (m, 2H), 7.08-7.01 (m, 1H), 6.70 (br s, 1H), 3.95-3.76 (m, 4H), 3.75-3.61 (m, 2H), 3.59-3.47 (m, 1H), 3.24-2.97 (m, 3H), 2.38-2.14 (m, 10H), 2.02-1.85 (m, 1H), 1.81-1.57 (m, 5H), 1.44 (d, J=6.5 Hz, 3H), 1.35 (d, J=6.6 Hz, 3H), 1.27-1.16 (m, 1H), 1.09 (d, J=6.5 Hz, 3H), 1.00 (d, J=6.4 Hz, 3H); LCMS (Method A): Rt 2.75 min, m/z: 708.4 [M+H]$^+$; HPLC (Method G): Rt 3.207 min, 96.96%.

Example 233. 2-((4-(7-(((2S,5R)-5-(Cyclopropane-sulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

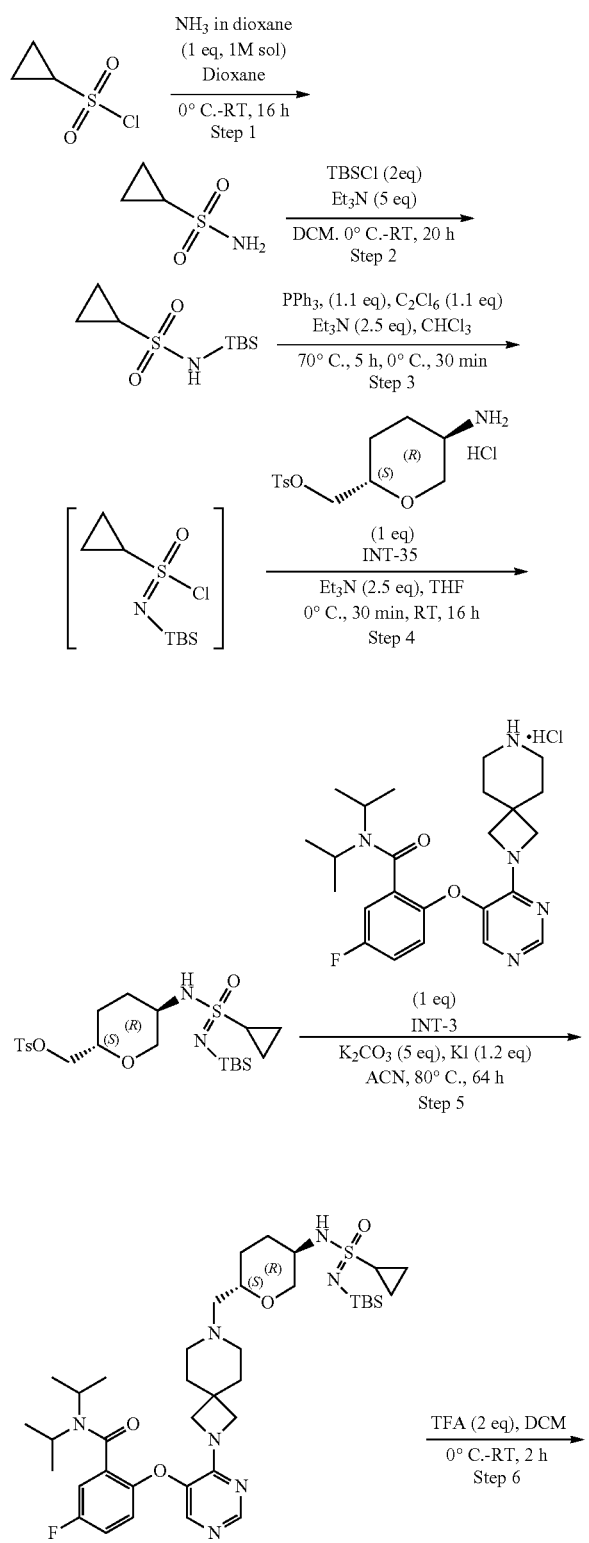

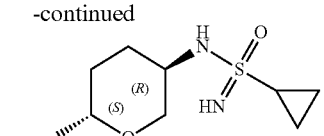

Example 233

Step 1: Cyclopropanesulfonamide

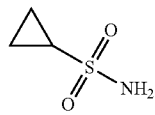

To a dried 500 mL round bottom flask under nitrogen atmosphere, ammonia in dioxane (71.1 mL, 71.1 mmol, 1.0 M) was added, followed by dropwise addition of a solution of cyclopropane sulfonyl chloride (10 g, 71.1 mmol) in dioxane (100 mL) at 0° C. The reaction was stirred at 0° C. for 20 min, then was allowed to warm to RT and stir for 16 h. The reaction progress was monitored by TLC (30% EtOAc in hexane). After reaction completion, the reaction was quenched with water (200 mL) and extracted with EtOAc (2×200 mL). The combined organic layer was dried over sodium sulfate, and filtered, and the filtrate was concentrated under reduced pressure to obtain crude cyclopropanesulfonamide (7.5 g, 85% yield) as a solid. This crude product was directly used for next step without purification. LCMS ELSD (Method E): Rt 0.386 min, m/z: 120.1 (M−H)⁻, 97.53%.

Step 2. N-(tert-Butyldimethylsilyl)cyclopropanesulfonamide

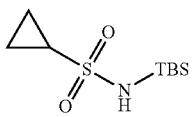

To a stirred solution of cyclopropanesulfonamide (7.5 g, 61.9 mmol) in DCM (200 mL) was added Et₃N (43.1 mL, 310 mmol) at 0° C. To this reaction mixture, TBDMS-Cl (21.45 mL, 124 mmol) in DCM (200 mL) was added dropwise at 0° C., and the reaction was allowed to warm to RT and stir for 20 h. The progress of the reaction was monitored by TLC (30% EtOAc in hexane). After reaction completion, the reaction was quenched with water (100 mL)

and extracted with EtOAc (3×200 mL). The combined organic layer was dried over sodium sulfate, and filtered, and the filtrate was concentrated under reduced pressure to obtain the crude product. The crude product was purified by Biotage-isolera one column chromatography using EtOAc in hexane as an eluent. The desired product eluted in 21% EtOAc in hexane. The product fractions were concentrated under reduced pressure to obtain N-(tert-butyldimethylsilyl) cyclopropanesulfonamide (5.2 g, 22.38% yield) as a solid. LCMS ELSD (Method E): Rt 1.96 min, m/z: (236.1) [M+H]$^+$; 62.72%.

Step 3 and 4. ((2S,5R)-5-(N'-(tert-Butyldimethylsilyl)cyclopropanesulfonoamidimidamido)tetrahydro-2H-pyran-2-yl)methyl 4-methylbenzenesulfonate

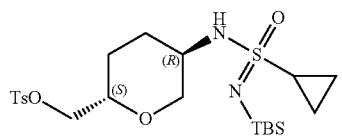

To a dried 250 mL round bottom flask under argon atmosphere, triphenylphosphine (1.226 g, 4.67 mmol) and hexachloroethane (1.106 g, 4.67 mmol) were added in chloroform (25 mL). The reaction was heated at 70° C. for 5 h. The formation of white suspension was observed. The reaction mixture was cooled to RT, then Et$_3$N (2.96 mL, 21.24 mmol) was added and the reaction was stirred for 10 min. The formation of yellow suspension was observed. The reaction mixture was cooled to 0° C. and N-(tert-butyldimethylsilyl)cyclopropanesulfonamide (1.0 g, 4.25 mmol) in chloroform (10 mL) was added dropwise. The reaction was stirred for 30 min. To this reaction mixture, ((2S,5R)-5-aminotetrahydro-2H-pyran-2-yl)methyl 4-methylbenzenesulfonate hydrochloride (1.367 g, 4.25 mmol) and Et$_3$N (2.96 mL, 21.24 mmol) in THF (10 mL) were added dropwise at 0° C. The reaction was stirred for additional 30 min, then was warmed to RT and stirred for 16 h. The progress of the reaction was monitored by TLC (40% EtOAc in hexane). After reaction completion, the reaction was quenched with water (100 mL) and extracted with EtOAc (3×100 mL). The combined organic layer was dried over sodium sulfate, and filtered, and the filtrate was concentrated on a rotary evaporator under reduced pressure to obtain the crude product. The crude product was purified by Biotage-isolera one column chromatography eluting EtOAc in hexane. The desired product eluted in 32% EtOAc in hexane. The product fractions were concentrated under reduced pressure to obtain ((2S,5R)-5-(N'-(tert-butyldimethylsilyl)cyclopropanesulfonoamidimidamido)tetrahydro-2H-pyran-2-yl)methyl 4-methylbenzenesulfonate (650 mg, 9.41% yield)) as a gummy solid. LCMS ELSD (Method E): Rt 2.53 min, m/z: (503.3) [M+H]$^+$; 30.93%.

Step 5. 2-((4-(7-(((2S,5R)-5-(N'-(tert-Butyldimethylsilyl)cyclopropanesulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide

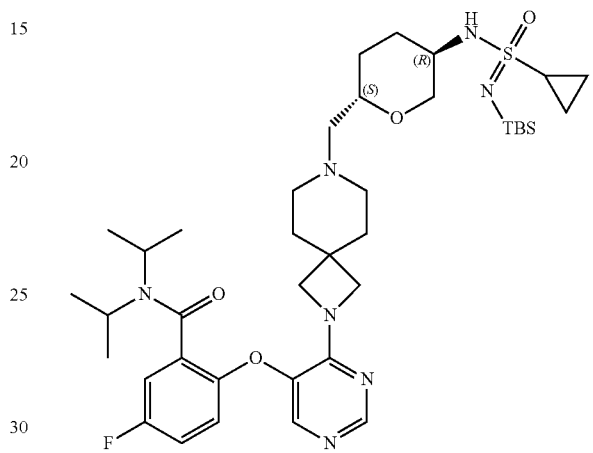

To a 100 mL round bottom flask under nitrogen atmosphere, 2-((4-(2,7-diazaspiro[3.5]nonan-2-yl)pyrimidin-5-yl)oxy)-5-fluoro-N,N-diisopropylbenzamide hydrochloride (600 mg, 1.255 mmol) was added in ACN (25 mL). To this reaction mixture, K$_2$CO$_3$ (867 mg, 6.28 mmol), KI (250 mg, 1.506 mmol), and ((2S,5R)-5-(N'-(tert-butyldimethylsilyl)cyclopropanesulfonoamidimidamido)tetrahydro-2H-pyran-2-yl)methyl 4-methylbenzene sulfonate (631 mg, 1.255 mmol) were added at RT. The reaction was stirred at 80° C. for 24 h. The progress of the reaction was monitored by TLC (10% methanol in DCM). The starting materials were not consumed completely. The reaction was heated to 80° C. for another 40 h. After reaction completion, the reaction was quenched with water (100 mL) and extracted with EtOAc (3×20 mL). The combined organic layer was dried over sodium sulfate, and filtered, and the filtrate was concentrated under reduced pressure to obtain the crude product. The crude product was purified by silica gel column chromatography using 6% MeOH in DCM as an eluent to obtain 2-((4-(7-(((2S,5R)-5-(N'-(tert-butyldimethylsilyl)cyclopropane sulfonoamidimidamido)tetrahydro-2H-pyran-2-yl) methyl)-2,7-diazaspiro[3.5]nonan-2-yl)pyrimidin-5-yl) oxy)-5-fluoro-N,N-diisopropylbenzamide (320 mg, 27.4% yield) as a solid. LCMS (Method E): Rt 2.51 min, m/z: 773.0 [M+H]$^+$; 82.88%.

Step 6. 2-((4-(7-(((2S,5R)-5-(Cyclopropanesulfono-amidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (Example 233)

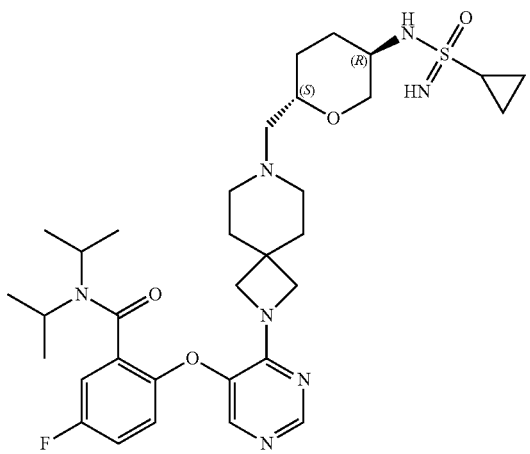

To a dried 50 mL round bottom flask under nitrogen atmosphere, 2-((4-(7-(((2S,5R)-5-(N'-(tert-butyldimethylsi-lyl)cyclopropanesulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (200 mg, 0.259 mmol) was added in DCM (10 mL) at 0° C. To this solution, TFA (0.040 mL, 0.518 mmol) in DCM (5.00 mL) was added at 0° C., and the reaction was warmed to RT and stirred at RT for 2 h. The reaction progress was monitored by TLC (50% EtOAc in hexane). After reaction completion, reaction was quenched with water and extracted with 10% MeOH in DCM (2×100 mL). The combined organic layer was dried over sodium sulfate and concentrated on a rotary evaporator under reduced pressure to obtain crude product. The crude was purified by Prep-HPLC (Method A) and pure fractions were lyophilized to obtain 2-((4-(7-(((2S,5R)-5-(cyclopropanesulfonoamidimidamido)tetrahydro-2H-pyran-2-yl)methyl)-2,7-diazaspiro[3.5]nonan-2-yl)pyrimidin-5-yl)oxy)-5-fluoro-N,N-diisopropylbenzamide (95 mg, 53.7% yield) as a solid. $^1$H NMR (400 MHz, DMSO-$d_6$) δ 8.26 (s, 1H), 7.71 (s, 1H), 7.28-7.18 (m, 2H), 7.09-6.98 (m, 1H), 6.40 (br s, 1H), 4.02-3.76 (m, 5H), 3.74-3.63 (m, 1H), 3.59-3.38 (m, 2H), 3.31-3.04 (m, 3H), 3.04-2.91 (m, 1H), 2.48-2.41 (m, 1H), 2.33-2.15 (m, 5H), 2.05-1.88 (m, 1H), 1.67-1.65 (m, 5H), 1.44 (d, J=6.8 Hz, 3H), 1.35 (d, J=6.6 Hz, 4H), 1.28-1.16 (m, 1H), 1.09 (d, J=6.6 Hz, 3H), 1.00 (d, J=6.6 Hz, 3H), 0.95-0.78 (m, 4H); LCMS (Method B): Rt 1.13 min, m/z: 658.6 [M+H]$^+$; HPLC (Method K): Rt 3.09 min, 95.45%.

Example 234. 5-Fluoro-N,N-diisopropyl-2-((4-(7-(((2S,5R)-5-((2-methyl-1H-imidazole)-5-sulfona-mido)tetrahydro-2H-pyran-2-yl)methyl)-2,7-diaz-aspiro[3.5]nonan-2-yl)pyrimidin-5-yl)oxy)benzamide

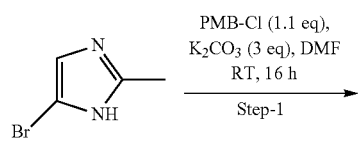

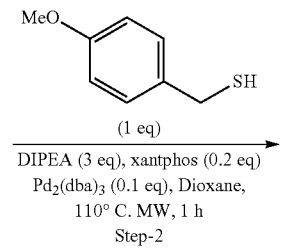

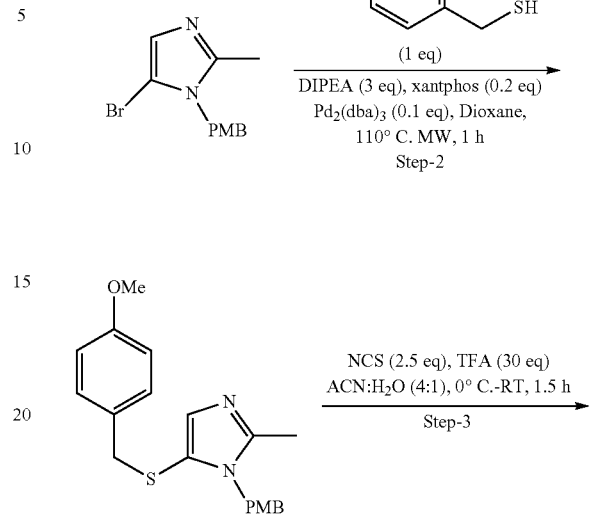

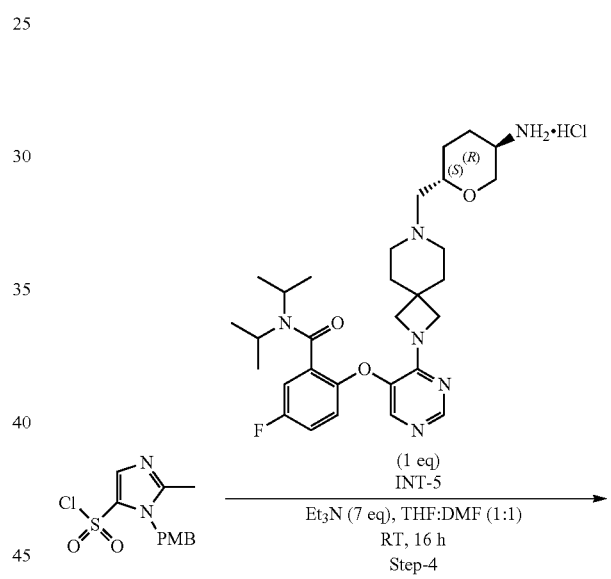

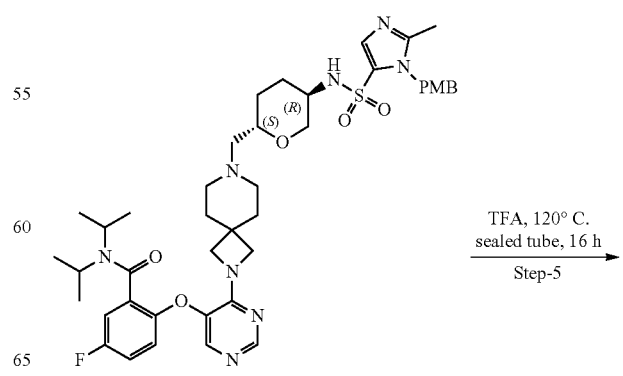

621

-continued

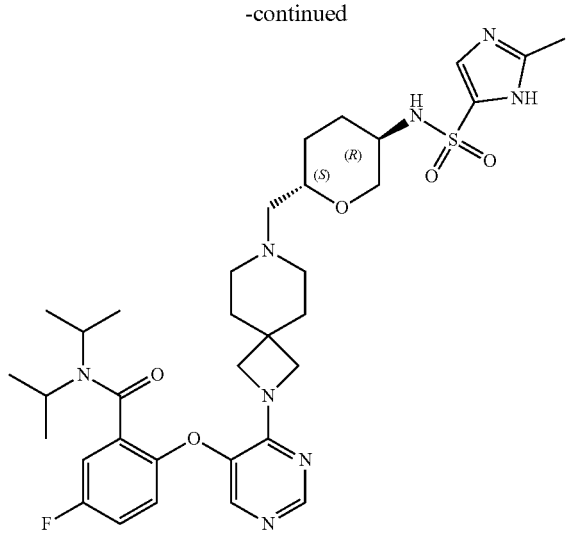

Example 234

Step 1.
5-Bromo-1-(4-methoxybenzyl)-2-methyl-1H-imidazole

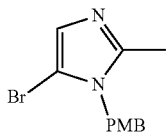

To a stirred solution of 5-bromo-2-methyl-1H-imidazole (0.7 g, 4.35 mmol) in DMF (10 mL), K$_2$CO$_3$ (1.803 g, 13.04 mmol) was added at 0° C., and the reaction was stirred for 5 min. To this reaction mixture, 1-(chloromethyl)-4-methoxybenzene (0.749 g, 4.78 mmol) was added at 0° C., then the reaction was stirred for 16 h at RT. The reaction progress was monitored by TLC (50% EtOAc in hexane). After reaction completion, the reaction was diluted with water (100 mL) and extracted with DCM (2×80 mL). The combined organic layer was washed with brine (60 mL), dried over anhydrous sodium sulfate, and filtered, and the filtrate was concentrated under reduced pressure to afford crude (2 g). The crude compound was purified by silica-gel column chromatography using 22% EtOAc in hexane as an eluent to obtain 5-bromo-1-(4-methoxybenzyl)-2-methyl-1H-imidazole (1 g, 77% yield). $^1$H NMR (400 MHz, CDCl$_3$) δ 7.06 (d, J=8.76 Hz, 2H), 6.90 (d, J=8.63 Hz, 2H), 6.77 (s, 1H), 4.95 (s, 2H), 3.83 (s, 3H), 2.36 (s, 3H); LCMS (Method B): Rt 1.38 min, 282.2 [M+H]$^+$.

622

Step 2. 1-(4-Methoxybenzyl)-5-((4-methoxybenzyl)thio)-2-methyl-1H-imidazole

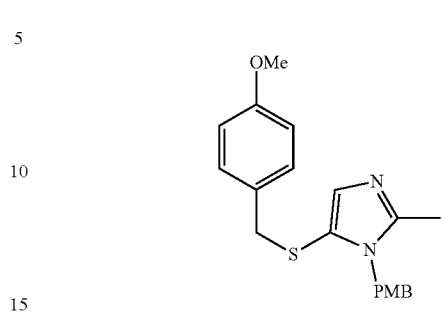

To a microwave vial, 5-bromo-1-(4-methoxybenzyl)-2-methyl-1H-imidazole (0.547 g, 1.945 mmol) was added in 1,4-dioxane (10 mL), and the solution was purged with nitrogen gas for 15 min. To this solution, (4-methoxyphenyl)methanethiol (0.3 g, 1.945 mmol), DIPEA (1.048 mL, 5.84 mmol), Xantphos (0.225 g, 0.389 mmol), and Pd$_2$(dba)$_3$ (0.178 g, 0.195 mmol) were added, and the mixture was purged with nitrogen gas for 5 min. The reaction mixture was heated at 110° C. for 1 h in a microwave. The reaction was monitored by TLC and LCMS. After 1 h, the reaction was cooled to RT, and filtered through Celite®. The filter bed was washed with EtOAc (25 mL). The filtrate was concentrated under reduced pressure to afford the crude compound. The crude compound was purified by prep-HPLC (Method A) to obtain 1-(4-methoxybenzyl)-5-((4-methoxybenzyl)thio)-2-methyl-1H-imidazole (0.24 g, 29.6% yield). $^1$H NMR (400 MHz, CDCl$_3$) δ 7.20-7.07 (m, 2H), 6.98-6.72 (m, 6H), 6.68-6.51 (m, 1H), 4.93-4.83 (m, 2H), 3.96-4.07 (m, 2H), 3.88-3.71 (m, 6H), 2.43-2.33 (m, 3H); LCMS (Method A): Rt 1.96 min, m/z: 355.4 [M+H]$^+$.

Step 3. 1-(4-Methoxybenzyl)-2-methyl-1H-imidazole-5-sulfonyl chloride

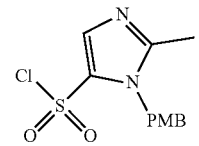

To a stirred solution of 1-(4-methoxybenzyl)-5-((4-methoxybenzyl)thio)-2-methyl-1H-imidazole (1.5 g, 4.23 mmol) in ACN (30 mL):water (6.67 mL), TFA (9.71 mL, 127 mmol) and N-chlorosuccinimide (1.413 g, 10.58 mmol) were added at 0° C. under nitrogen atmosphere. The reaction was allowed to stir at RT for 1.5 h. The reaction was quenched with water (50 mL) and extracted with EtOAc (2×150 mL). The combined organic layer was washed with brine (50 mL), dried over anhydrous sodium sulfate, and filtered, and the filtrate was concentrated under reduced pressure to afford crude product. The crude product was purified by silica-gel column chromatography using 40-50% EtOAc and hexane as an eluent to obtain 1-(4-methoxybenzyl)-2-methyl-1H-imidazole-5-sulfonyl chloride (0.74 g, 51.2% yield). $^1$H NMR (400 MHz, CDCl$_3$) δ 7.53-7.50 (m, 1H), 7.15-7.11 (m, 2H), 6.98-6.94 (m, 2H), 5.06-5.01 (m, 2H), 3.87-3.84 (m, 3H), 2.54-2.46 (m, 3H); LCMS (Method B): Rt 1.76 min, m/z: 301.1 [M+H]$^+$.

623

Step 4. 5-Fluoro-N,N-diisopropyl-2-((4-(7-(((2S,5R)-5-((1-(4-methoxybenzyl)-2-methyl-1H-imidazole)-5-sulfonamido)tetrahydro-2H-pyran-2-yl)methyl)-2,7-diazaspiro[3.5]nonan-2-yl)pyrimidin-5-yl)oxy)benzamide

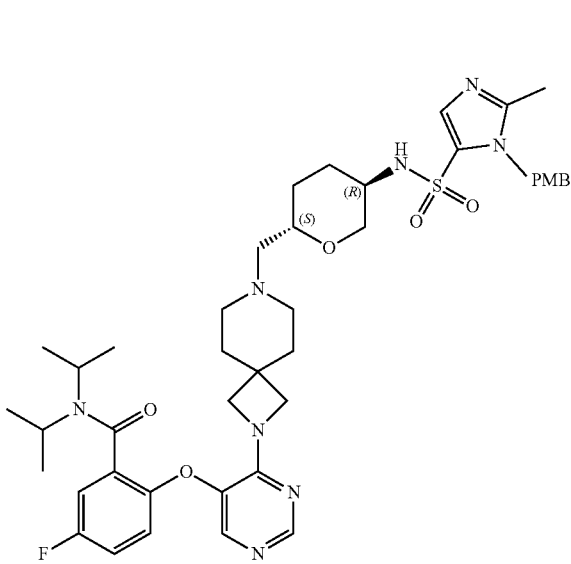

To a stirred solution of 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N,N-diisopropylbenzamide hydrochloride (1 g, 1.692 mmol) in dry THF:DMF (1:1) (15 mL), Et$_3$N (1.179 mL, 8.46 mmol) was added at RT under nitrogen atmosphere. The reaction was stirred at RT for 5 min. To this mixture, 1-(4-methoxybenzyl)-2-methyl-1H-imidazole-5-sulfonyl chloride (0.458 g, 1.522 mmol) was added dropwise and the reaction was stirred at RT. The progress of the reaction was monitored by TLC and LCMS. After 16 h, the reaction was quenched with saturated sodium chloride (50 mL) and extracted with EtOAc (2×150 mL). The combined organic extract was washed with NH$_4$Cl (50 mL), dried over anhydrous sodium sulfate, and filtered, and the filtrate was concentrated under reduced pressure to afford crude compound. The crude compound was purified by silica gel column chromatography using 5% MeOH in DCM as an eluent to obtain 5-fluoro-N,N-diisopropyl-2-((4-(7-(((2S,5R)-5-((1-(4-methoxybenzyl)-2-methyl-1H-imidazole)-5-sulfonamido)tetrahydro-2H-pyran-2-yl)methyl)-2,7-diazaspiro[3.5]nonan-2-yl)pyrimidin-5-yl)oxy)benzamide (0.85 g, 47.9% yield) as a solid. LCMS (Method B): Rt 1.95 min, m/z: 817.2 [M−H]$^-$.

624

Step 5. 5-Fluoro-N,N-diisopropyl-2-((4-(7-(((2S,5R)-5-((2-methyl-1H-imidazole)-5-sulfonamido)tetrahydro-2H-pyran-2-yl)methyl)-2,7-diazaspiro[3.5]nonan-2-yl)pyrimidin-5-yl)oxy)benzamide (Example 234)

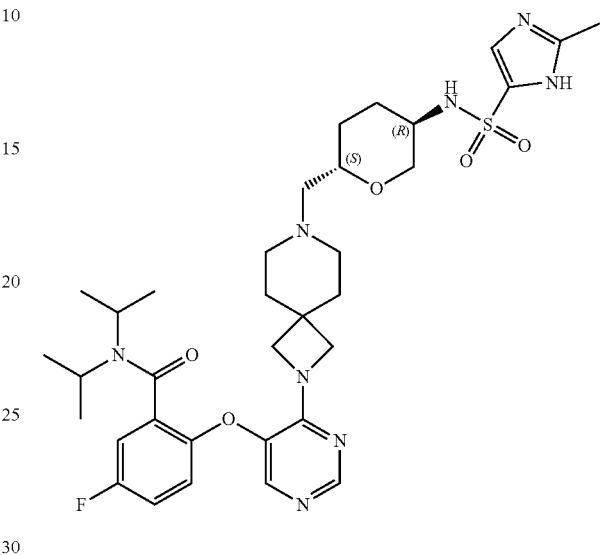

To a 100 mL sealed tube, 5-fluoro-N,N-diisopropyl-2-((4-(7-(((2S,5R)-5-((1-(4-methoxybenzyl)-2-methyl-1H-imidazole)-5-sulfonamido)tetrahydro-2H-pyran-2-yl)methyl)-2,7-diazaspiro[3.5]nonan-2-yl)pyrimidin-5-yl)oxy)benzamide (0.2 g, 0.244 mmol) was added in TFA (20 mL). The resulting reaction mixture was stirred at 120° C. for 16 h. The reaction was monitored by TLC. The reaction was quenched with brine solution (100 mL) and extracted with EtOAc (2×250 mL). The combined organic layer was dried over anhydrous sodium sulfate, and filtered, and the filtrate was concentrated under reduced pressure to afford crude compound. The crude compound was purified by Prep-HPLC (Method A) and lyophilized to afford 5-fluoro-N,N-diisopropyl-2-((4-(7-(((2S,5R)-5-((2-methyl-1H-imidazole)-5-sulfonamido)tetrahydro-2H-pyran-2-yl)methyl)-2,7-diazaspiro[3.5]nonan-2-yl)pyrimidin-5-yl)oxy)benzamide (0.085 g, 48.3% yield). $^1$H NMR (400 MHz, DMSO-d$_6$): δ 12.35 (br s, 1H), 8.25 (s, 1H), 7.71 (s, 1H), 7.54 (s, 1H), 7.53-7.39 (m, 1H), 7.29-7.18 (m, 2H), 7.10-6.99 (m, 1H), 3.92-3.76 (m, 3H), 3.73-3.62 (m, 2H), 3.52-3.32 (m, 1H), 3.27-3.23 (m, 1H), 3.18-3.08 (m, 1H), 3.04-2.91 (m, 2H), 2.30 (s, 3H), 2.27-2.12 (m, 2H), 1.79-1.70 (m, 1H), 1.68-1.58 (m, 6H), 1.44 (d, J=6.8 Hz, 3H), 1.34 (d, J=6.6 Hz, 3H), 1.10-1.08 (m, 6H), 0.99 (d, J=6.5 Hz, 3H), 0.88 (d, J=2.0 Hz, 2H); LCMS (Method E): Rt 1.58 min, m/z: 697.7 [M−H]$^-$; HPLC (Method A): Rt 4.73 min, 97.49%.

Example 235. N-(2,2-Difluoroethyl)-2-((4-(7-(((2S, 5R)-5-((N-(2,2-difluoroethyl)sulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

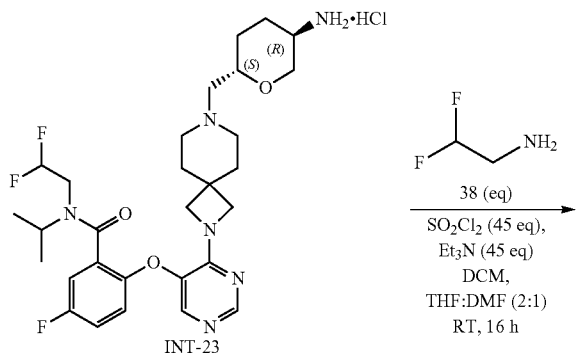

To a dried 100 mL round bottom flask under nitrogen atmosphere, sulfuryl chloride (0.602 mL, 7.40 mmol) was added in DCM (10 mL). To this solution, 2,2-difluoroethan-1-amine (500 mg, 6.17 mmol) and Et$_3$N (1.032 mL, 7.40 mmol) were added at −10° C. To this reaction mixture, 2-((4-(7-(((2S,5R)-5-aminotetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide hydrochloride (100 mg, 0.163 mmol) in DMF:THF (1:2) (15 mL) was added. To this reaction mixture, Et$_3$N (8.60 mL, 61.7 mmol) was added and the reaction was stirred at RT for 16 h. The progress of the reaction was monitored by LCMS. The reaction mixture was quenched with water and extracted with EtOAc (3×20 mL). The combined organic layer was dried over sodium sulfate, and filtered, and the filtrate was concentrated under reduced pressure to obtain crude compound. The crude was purified by Prep-HPLC (Method B) to afford N-(2,2-difluoroethyl)-2-((4-(7-(((2S,5R)-5-((N-(2,2-difluoroethyl)sulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide (85 mg, 1.91% yield) as a solid. $^1$H NMR (400 MHz, DMSO-d$_6$) δ 8.29 (s, 1H), 7.74 (s, 1H), 7.28-7.24 (m, 1H), 7.35-7.26 (m, 2H), 7.20-7.12 (m, J=7.1 Hz, 1H), 7.03-7.00 (m, 1H), 6.37-5.84 (m, 2H), 3.97-3.59 (m, 8H), 3.31-3.26 (m, 3H), 3.09-2.94 (m, 2H), 2.32-2.13 (m, 5H), 1.99-1.90 (m, 1H), 1.66 (br s, 5H), 1.44-1.29 (m, 1H), 1.26-1.14 (m, 2H), 1.11-1.05 (m, 6H); LCMS (Method E): Rt 1.88 min, m/z: 720.2 [M+H]$^+$; HPLC (Method A): Rt 5.38 min, 99.69%.

Example 236. 2-((4-(7-(((2S,5R)-5-((3-(Benzyloxy)azetidine)-1-sulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide

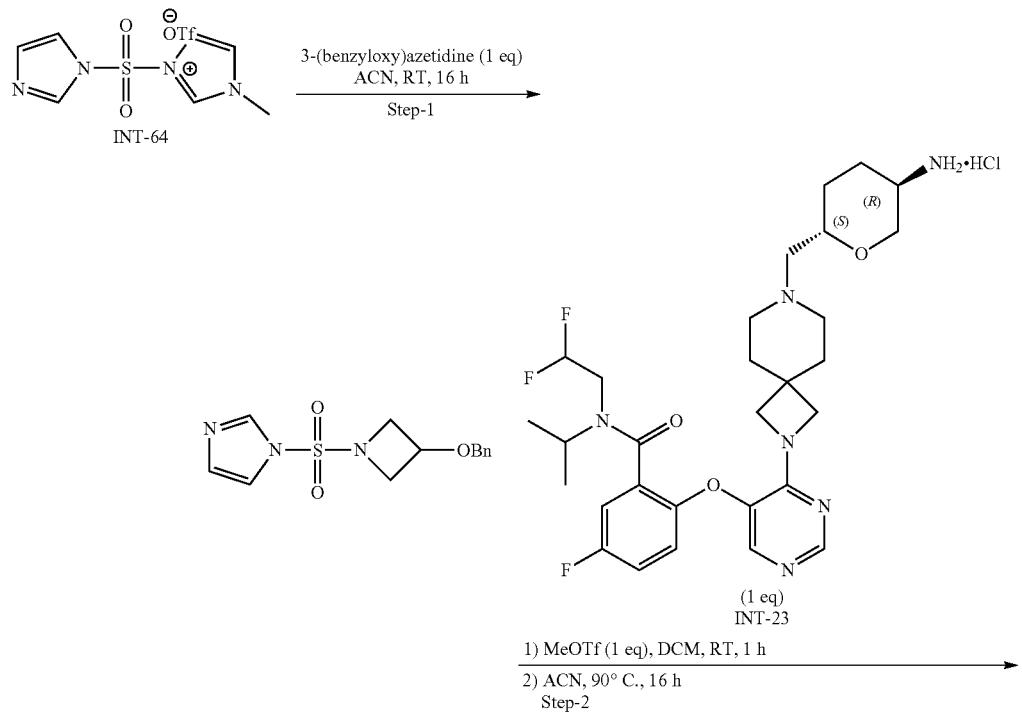

-continued

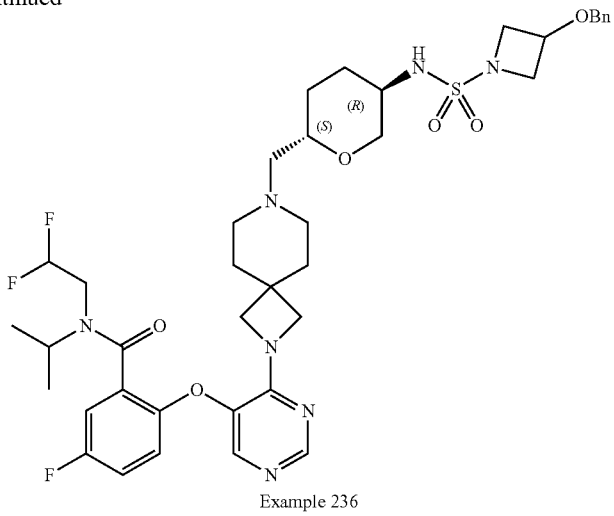

Example 236

Step 1. 1-((3-(Benzyloxy)azetidin-1-yl)sulfonyl)-1H-imidazole

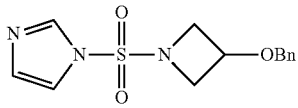 [SMILES: O=S(=O)(N1CC(OCc2ccccc2)C1)n1ccnc1]

To a stirred solution of 3-((1H-imidazol-1-yl)sulfonyl)-1-methyl-1H-imidazol-3-ium trifluoromethanesulfonate (3.0 g, 9.19 mmol) in ACN (35 mL) at 0° C. under nitrogen atmosphere was added 3-(benzyloxy)azetidine (1.5 g, 9.19 mmol). The reaction was stirred at RT for 16 h. The progress of the reaction was monitored by LCMS. The reaction mixture was concentrated under reduced pressure, and the crude was purified by prep HPLC to obtain 1-((3-(benzyloxy)azetidin-1-yl)sulfonyl)-1H-imidazole (800 mg, 14.82% yield). LCMS (Method A): Rt 1.71 min, m/z: 294.2 [M+H]$^+$.

Step 2. 2-((4-(7-(((2S,5R)-5-((3-(Benzyloxy)azetidine)-1-sulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (Example 236)

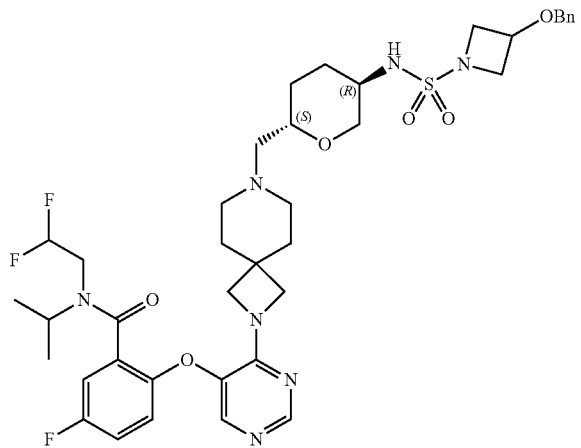

To a stirred solution of 1-((3-(benzyloxy)azetidin-1-yl)sulfonyl)-1H-imidazole (100 mg, 0.341 mmol) in DCM (5 mL) was added methyl trifluoromethanesulfonate (0.037 mL, 0.341 mmol) at 0° C. under nitrogen atmosphere. The resulting reaction was allowed to stir at RT for 1 h. After completion, the reaction was concentrated under reduced pressure to afford crude 3-((3-(benzyloxy)azetidin-1-yl)sulfonyl)-1-methyl-1H-imidazol-3-ium trifluoromethanesulfonate (160 mg, 99.2% yield) as a pale brown solid. This crude compound (159 mg, 0.347 mmol) was added to a stirred solution of 2-((4-(7-(((2S,5R)-5-aminotetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (200 mg, 0.347 mmol) in ACN (10 mL) at RT under nitrogen atmosphere. The reaction was stirred at 90° C. for 16 h. The progress of the reaction was monitored by LCMS. The reaction mixture was concentrated under reduced pressure and the crude was purified by silica gel column chromatography using 10% MeOH in DCM as an eluent to obtain partially purified material (220 mg, 63.7%). 40 mg of this material was further purified by Prep-HPLC (Method A) to obtain 2-((4-(7-(((2S,5R)-5-((3-(benzyloxy)azetidine)-1-sulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (8.85 mg, 6.31% yield) as solid. $^1$H NMR (400 MHz, DMSO-d$_6$) δ 8.29 (s, 1H), 7.77 (s, 1H), 7.42-7.24 (m, 8H), 7.02 (dd, J=4.4, 9.1 Hz, 1H), 6.38-6.03 (m, 1H), 4.44 (s, 2H), 4.36-4.26 (m, 1H), 3.93-3.63 (m, 10H), 3.56 (dd, J=5.4, 8.2 Hz, 2H), 3.32-3.21 (m, 2H), 3.12-2.93 (m, 2H), 2.32-2.14 (m, 4H), 2.01-1.91 (m, 1H), 1.69-1.61 (m, 5H), 1.44-1.30 (m, 1H), 1.29-1.15 (m, 2H), 1.10 (dd, J=6.8, 3H), 1.06 (d, J=6.8, 3H); LCMS (Method B): Rt 1.62 min, m/z: 802.2 [M+H]$^+$; HPLC (Method A): Rt 6.22 min, 99.84%.

Example 237. N-(2,2-Difluoroethyl)-5-fluoro-2-((4-(7-((((2S,5R)-5-((3-hydroxyazetidine)-1-sulfonamido)tetrahydro-2H-pyran-2-yl)methyl)-2,7-diazaspiro[3.5]nonan-2-yl)pyrimidin-5-yl)oxy)-N-isopropylbenzamide

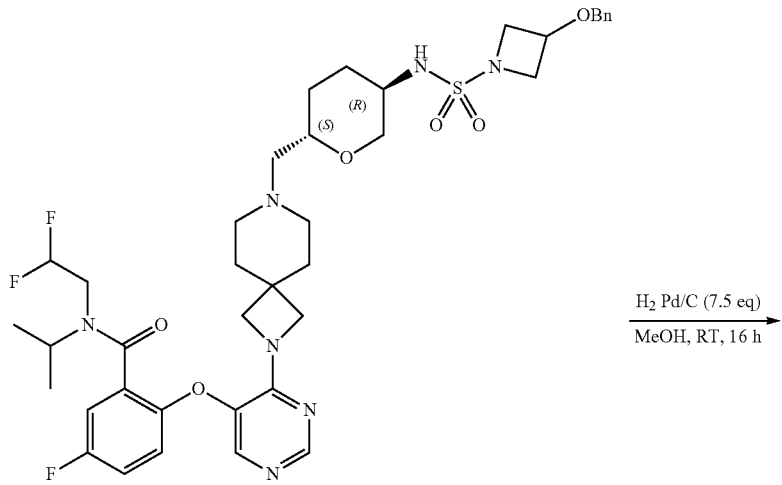

To a solution of 2-((4-(7-((((2S,5R)-5-((3-(benzyloxy)azetidine)-1-sulfonamido)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (150 mg, 0.187 mmol) in MeOH (10 mL), Pd—C(150 mg, 1.410 mmol) was added under nitrogen atmosphere. The reaction mixture was stirred under hydrogen atmosphere at RT for 16 h. The reaction mixture was degassed with nitrogen then was filtered through Celite®. The filtrate was concentrated under reduced pressure to afford crude compound. The crude compound was purified by prep HPLC (Method A) and lyophilized to obtain N-(2,2-difluoroethyl)-5-fluoro-2-((4-(7-((((2S,5R)-5-((3-hydroxyazetidine)-1-sulfonamido)tetrahydro-2H-pyran-2-yl)methyl)-2,7-diazaspiro[3.5]nonan-2-yl)pyrimidin-5-yl)oxy)-N-isopropylbenzamide (19.52 mg, 14.62% yield)) as a solid. $^1$H NMR (400 MHz, DMSO-$d_6$) δ 8.29 (s, 1H), 7.77 (s, 1H), 7.40-7.22 (m, 3H), 7.02 (dd, J=4.4, 9.1 Hz, 1H), 6.38-6.03 (m, 1H), 5.74 (d, J=6.0 Hz, 1H), 4.41-4.29 (m, 1H), 3.90-3.81 (m, 4H), 3.80-3.68 (m, 6H), 3.52-3.47 (m, 2H), 3.30-3.25 (m, 3H), 3.13-2.94 (m, 2H), 2.31-2.16 (m, 5H), 2.02-1.91 (m, 1H), 1.66 (br s, 5H), 1.46-1.31 (m, 1H), 1.29-1.16 (m, 2H), 1.08 1.11-1.05 (m, 6H); LCMS (Method E): Rt 1.61 min, m/z: 712.3 [M+H]$^+$; HPLC (Method A): Rt 4.84 min, 99.73%; SFC (Method J): Rt 1.52 min, 97.55%.

Example 238. 2-((4-(7-(((2S,5R)-5-((N-(2-Benzyloxy)ethyl)-N-methylsulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide
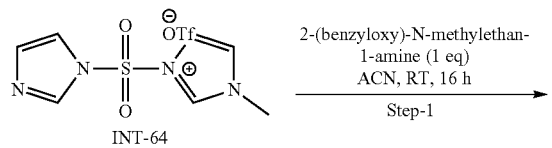
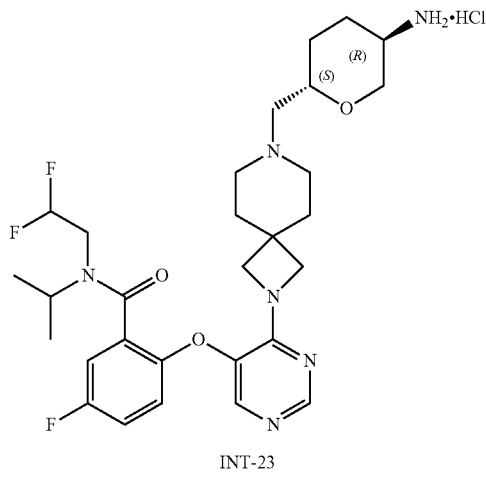
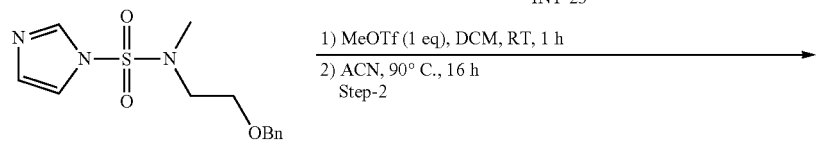
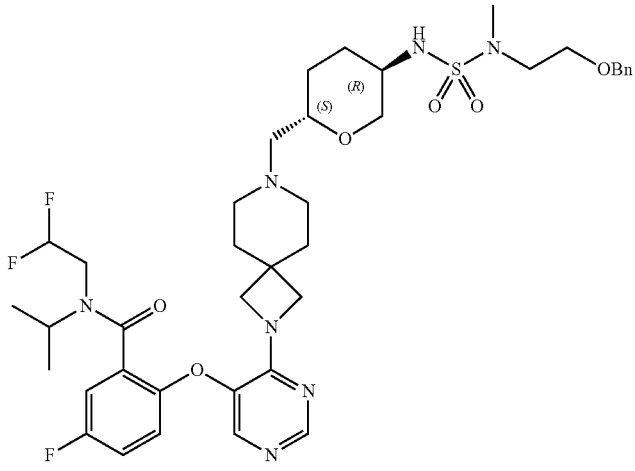
Example 238

Step 1. N-(2-(Benzyloxy)ethyl)-N-methyl-1H-imidazole-1-sulfonamide

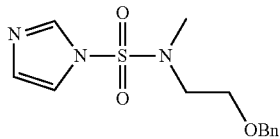 [SMILES: CN(CCOCc1ccccc1)S(=O)(=O)n1ccnc1]

To a stirred solution of 2-(benzyloxy)-N-methylethan-1-amine (1 g, 6.05 mmol) in ACN (20 mL), 3-((1H-imidazol-1-yl)sulfonyl)-1-methyl-1H-imidazol-3-ium trifluoromethanesulfonate (4.39 g, 12.10 mmol) was added at 0° C. under nitrogen atmosphere. The reaction was stirred at RT for 16 h. The progress of the reaction was monitored by LCMS. The reaction mixture was concentrated under reduced pressure to obtain the crude product. The crude product was purified by prep-HPLC to obtain N-(2-(benzyloxy)ethyl)-N-methyl-1H-imidazole-1-sulfonamide (400 mg, 21.93% yield) as a solid. $^1$H NMR (400 MHz, DMSO-d$_6$) δ 8.18 (s, 1H), 7.65 (t, J=1.38 Hz, 1H), 7.39-7.28 (m, 5H), 7.16-7.10 (m, 1H), 4.46 (s, 2H), 3.58-3.53 (m, 2H), 3.46-3.41 (m, 2H), 2.89 (s, 3H); LCMS (Method A): Rt 1.77 min, 296.1 [M+H]$^+$.

Step 2. 2-((4-(7-(((2S,5R)-5-((N-(2-(Benzyloxy)ethyl)-N-methylsulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (Example 238)

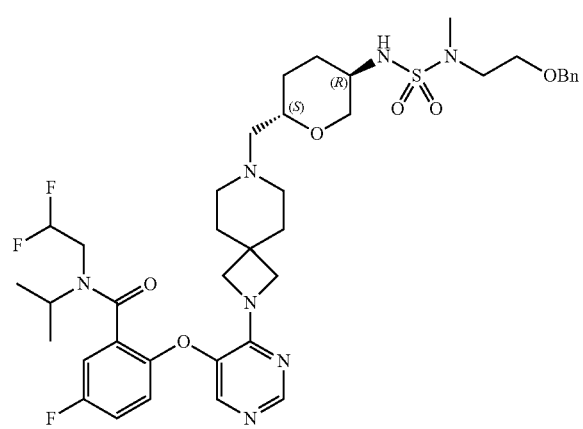

To a stirred solution of N-(2-(benzyloxy)ethyl)-N-methyl-1H-imidazole-1-sulfonamide (250 mg, 0.846 mmol) in DCM (10 mL) was added methyl trifluoromethanesulfonate (0.093 ml, 0.846 mmol) at 0° C. under nitrogen atmosphere. The resulting reaction was allowed to stir at RT for 1 h. After completion, the reaction mixture was concentrated under reduced pressure to afford the crude 3-(N-(2-(benzyloxy)ethyl)-N-methylsulfamoyl)-1-methyl-1H-imidazol-3-ium trifluoromethanesulfonate (380 mg, 98% yield) as a white solid. This crude compound (239 mg, 0.520 mmol) was added to a stirred solution of 2-((4-(7-(((2S,5R)-5-amino-tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (300 mg, 0.520 mmol) in ACN (20 mL) at 0° C. under nitrogen atmosphere. The reaction was stirred at 90° C. for 16 h. The reaction progress was monitored by TLC (10% MeOH in DCM). The reaction was quenched with water (50 mL) and extracted with EtOAc (3×100 mL). The combined organic layer was washed with 10% NH$_4$Cl solution, dried over anhydrous sodium sulfate, filtered, and concentrated under reduced pressure to obtain crude compound (400 mg, 82% yield). 100 mg of this crude compound was purified by Prep-HPLC (Method B) to obtain 2-((4-(7-(((2S,5R)-5-((N-(2-(benzyloxy)ethyl)-N-methylsulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (15 mg, 0.609% yield) as a solid. $^1$H NMR (400 MHz, DMSO-d$_6$) δ 8.29 (s, 1H), 7.77 (s, 1H), 7.40-7.24 (m, 8H), 7.02 (dd, J=4.4, 9.1 Hz, 1H), 6.37-6.03 (m, 1H), 4.50 (s, 2H), 3.89-3.81 (m, 3H), 3.79-3.64 (m, 4H), 3.61-3.57 (m, 2H), 3.22-3.28 (m, 2H), 3.19-3.14 (m, 1H), 3.02-2.97 (m, 1H), 2.75-2.72 (m, 3H), 2.30-2.14 (m, 5H), 1.97-1.90 (m, 1H), 1.70-1.59 (m, 5H), 1.37-1.32 (m, 1H), 1.27-1.15 (m, 3H), 1.12-1.02 (m, 7H); LCMS (Method E): Rt 98.82 min, m/z: 818.3 [M+H]$^+$; HPLC (Method F): Rt 4.43 min, 97.80%.

Example 239. N-(2,2-difluoroethyl)-5-fluoro-2-((4-(7-(((2S,5R)-5-((N-(2-hydroxyethyl)-N-methylsulfamoyl)amino)tetrahydro-2H-pyran-2-yl)methyl)-2,7-diazaspiro[3.5]nonan-2-yl)pyrimidin-5-yl)oxy)-N-isopropylbenzamide

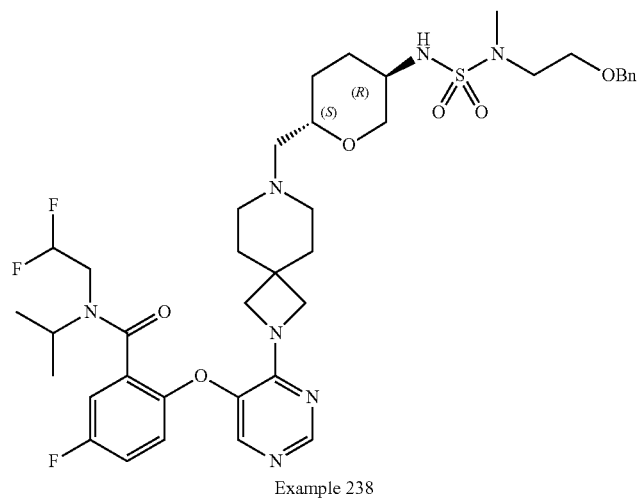

Example 238

H$_2$ Pd/C (0.5 eq)
MeOH, RT, 16 h

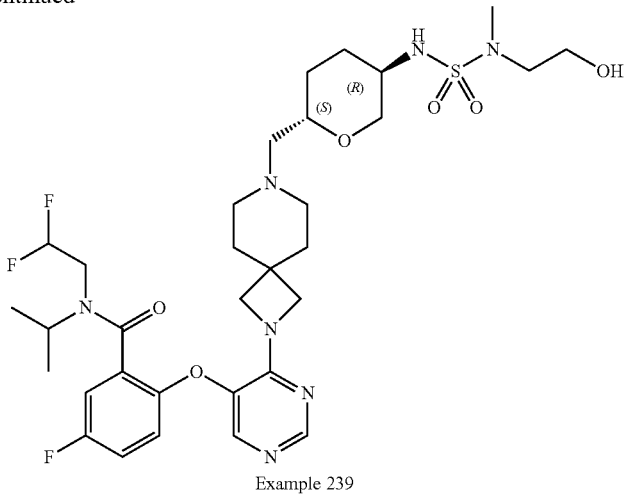

Example 239

To a solution of 2-((4-(7-(((2S,5R)-5-((N-(2-(benzyloxy)ethyl)-N-methylsulfamoyl)amino)tetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (100 mg, 0.124 mmol) in MeOH (20 mL), 10% Pd/C (66.2 mg, 0.062 mmol) was added under nitrogen atmosphere. The reaction mixture was stirred under hydrogen atmosphere at RT for 16 h. The reaction mixture was degassed with nitrogen gas and filtered through Celite®. The filter bed was washed with methanol (50 mL). The filtrate was concentrated under reduced pressure to afford crude product (liquid). The crude compound (170 mg) was purified by Prep-HPLC (Method B) and lyophilized to obtain N-(2,2-difluoroethyl)-5-fluoro-2-((4-(7-(((2S,5R)-5-((N-(2-hydroxyethyl)-N-methylsulfamoyl)amino)tetrahydro-2H-pyran-2-yl)methyl)-2,7-diazaspiro[3.5]nonan-2-yl)pyrimidin-5-yl)oxy)-N-isopropylbenzamide (48 mg, 53.2% yield) a solid. $^1$H NMR (400 MHz, DMSO-$d_6$) δ 8.29 (s, 1H), 7.76 (s, 1H), 7.35 (dd, J=3.0, 8.1 Hz, 1H), 7.32-7.22 (m, 1H), 7.18-7.10 (m, 1H), 7.02 (dd, J=4.3, 9.0 Hz, 1H), 6.38-6.02 (m, 1H), 4.73 (t, J=5.3 Hz, 1H), 3.85-3.73 (m, 4H), 3.79-3.62 (m, 5H), 3.55-3.50 (m, 2H), 3.07 (t, J=6.1 Hz, 2H), 3.04-2.95 (m, 2H), 2.72 (s, 3H), 2.31-2.21 (m, 4H), 2.20-2.14 (m, 1H), 2.01-1.91 (m, 1H), 1.65 (br s, 5H), 1.45-1.30 (m, 1H), 1.29-1.17 (m, 2H), 1.16-1.01 (m, 6H); LCMS (Method E): Rt 1.71 min, m/z: 712.6 [M−H]$^-$; HPLC (Method A): Rt 4.86 min, 98.587%; SFC (Method J): Rt 3.11 min, 98.497%.

Example 240. N-(2,2-Difluoroethyl)-5-fluoro-N-isopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide

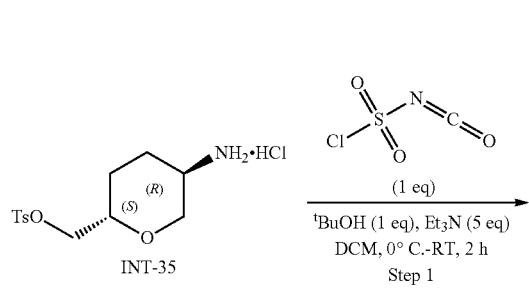

INT-35

$^t$BuOH (1 eq), Et$_3$N (5 eq)
DCM, 0° C.-RT, 2 h
Step 1

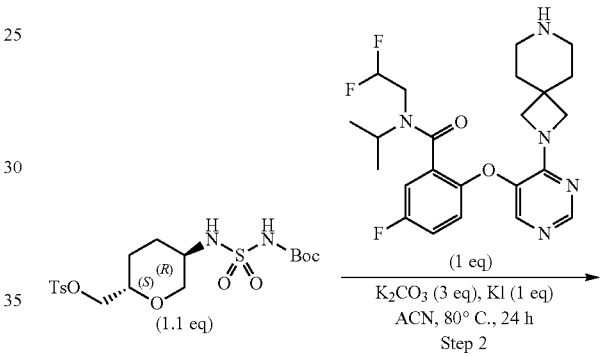

(1 eq)
K$_2$CO$_3$ (3 eq), KI (1 eq)
ACN, 80° C., 24 h
Step 2

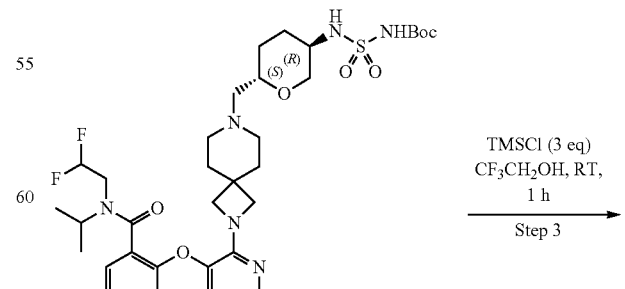

TMSCl (3 eq)
CF$_3$CH$_2$OH, RT,
1 h
Step 3

637

-continued

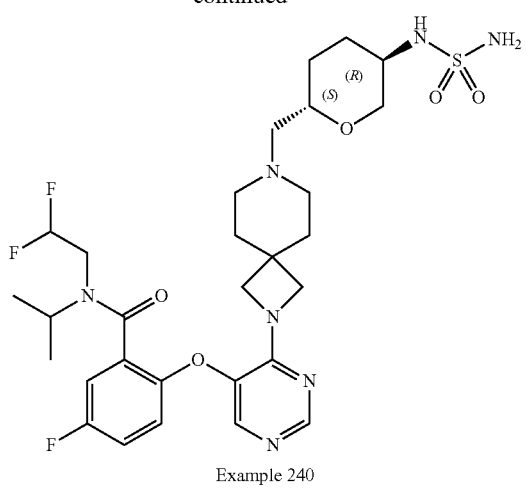

Example 240

Step 1. ((2S,5R)-5-((N-(tert-Butoxycarbonyl)sulfamoyl)amino)tetrahydro-2H-pyran-2-yl)methyl 4-methylbenzenesulfonate

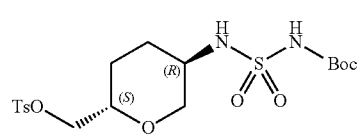

To a stirred solution of chlorosulfonyl isocyanate (0.189 mL, 2.175 mmol) in DCM (2 mL), 2-methylpropan-2-ol (0.206 mL, 2.175 mmol) in DCM (2 mL) was added dropwise at 0° C. under nitrogen atmosphere. Then the resulting solution was added to a solution of ((2S,5R)-5-aminotetrahydro-2H-pyran-2-yl)methyl 4-methylbenzenesulfonate hydrochloride (700 mg, 2.175 mmol) and Et$_3$N (1.516 mL, 10.88 mmol) in DCM (10 mL) at 0° C. The reaction was stirred at 0° C. for 5 min and then at RT for 2 h. The progress of the reaction was monitored by TLC (10% MeOH in DCM). After completion, the reaction mixture was quenched with water and extracted with DCM (3×50 mL). The combined organic layer was dried over sodium sulfate, and filtered, and the filtrate was concentrated under reduced pressure to obtain the crude product. The crude product was purified by silica gel column chromatography using 60-70% EtOAc in hexane as an eluent to obtain ((2S,5R)-5-((N-(tert-butoxycarbonyl)sulfamoyl)amino)tetrahydro-2H-pyran-2-yl)methyl 4-methylbenzenesulfonate (700 mg, 67.5% yield). $^1$H NMR (400 MHz, DMSO-d$_6$) δ 10.88 (s, 1H), 7.73-7.80 (m, 3H), 7.47-7.51 (m, 2H), 3.97-4.01 (m, 1H), 3.87-3.93 (m, 1H), 3.70-3.77 (m, 1H), 3.37-3.44 (m, 1H), 2.98-3.13 (m, 2H), 2.43 (s, 3H), 1.82-1.90 (m, 1H), 1.54-1.60 (m, 1H), 1.43 (s, 9H), 1.35-1.41 (m, 1H), 1.21-1.28 (m, 1H); LCMS (Method E): Rt 1.546 min, m/z: (462.9) [M−H]$^−$; 97.40%.

638

Step 2. tert-Butyl (N-((3R,6S)-6-((2-(5-(2-((2,2-difluoroethyl)(isopropyl)carbamoyl)-4-fluorophenoxy)pyrimidin-4-yl)-2,7-diazaspiro[3.5]nonan-7-yl)methyl)tetrahydro-2H-pyran-3-yl)sulfamoyl)carbamate To a dried 100 mL round bottom flask under nitrogen atmosphere, 2-((4-(2,7-diazaspiro[3.5]nonan-2-yl)pyrimidin-5-yl)oxy)-N-(2,2-difluoroethyl)-5-fluoro-N-isopropylbenzamide (600 mg, 1.294 mmol) was added in ACN (30 mL). To this reaction mixture, ((2S,5R)-5-((N-(tert-butoxycarbonyl)sulfamoyl)amino)tetrahydro-2H-pyran-2-yl) methyl 4-methylbenzenesulfonate (661 mg, 1.424 mmol), K$_2$CO$_3$ (537 mg, 3.88 mmol), and KI (215 mg, 1.294 mmol) were added at RT under nitrogen atmosphere. The reaction was stirred at 80° C. for 24 h. The progress of the reaction was monitored by TLC (10% MeOH in DCM). After completion, the reaction mixture was quenched with water and extracted with 10% MeOH in DCM (3×70 mL). The combined organic layer was dried over sodium sulfate, and filtered, and the filtrate was concentrated on a rotary evaporator under reduced pressure to obtain the crude product. The crude product was purified by silica gel column chromatography using 7% MeOH in DCM as an eluent to obtain tert-butyl (N-((3R,6S)-6-((2-(5-(2-((2,2-difluoroethyl)(isopropyl)carbamoyl)-4-fluorophenoxy)pyrimidin-4-yl)-2,7-diazaspiro[3.5]nonan-7-yl)methyl)tetrahydro-2H-pyran-3-yl)sulfamoyl)carbamate (650 mg, 58.8% yield) as colorless liquid. LCMS (Method E): Rt 1.54 min, m/z: 756.2 [M+H]$^+$, 88.48%.

Step 3. N-(2,2-Difluoroethyl)-5-fluoro-N-isopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide (Example 240)

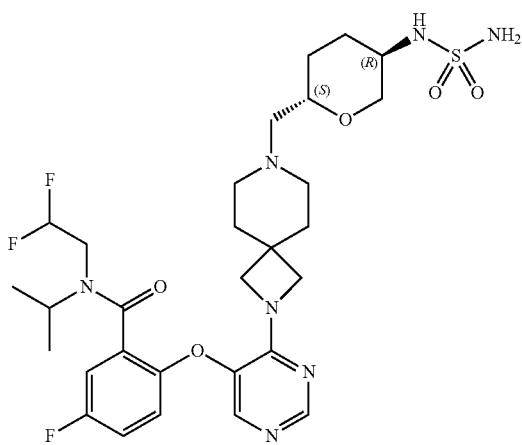

To a dried 50 mL round bottom flask under nitrogen atmosphere, tert-butyl (N-((3R,6S)-6-((2-(5-(2-((2,2-difluoroethyl)(isopropyl)carbamoyl)-4-fluorophenoxy)pyrimidin-4-yl)-2,7-diazaspiro[3.5]nonan-7-yl)methyl)tetrahydro-2H-pyran-3-yl)sulfamoyl)carbamate (650 mg, 0.860 mmol) was added in 2,2,2-trifluoroethanol (10 mL). To this reaction mixture, TMSCl (0.330 mL, 2.58 mmol) was added at 0° C., and the reaction was stirred at RT for 1 h. The progress of the reaction was monitored by TLC (10% MeOH in DCM). After reaction completion, the reaction mixture was directly concentrated under reduced pressure and the crude was purified by prep-HPLC (Method B). The pure fractions were lyophilized to obtain N-(2,2-difluoroethyl)-5-fluoro-N-isopropyl-2-((4-(7-(((2S,5R)-5-(sulfamoylamino)tetrahydro-2H-pyran-2-yl)methyl)-2,7-diazaspiro[3.5]nonan-2-yl)pyrimidin-5-yl)oxy)benzamide (255 mg, 45.2% yield) as a solid. $^1$H NMR (400 MHz, DMSO-$d_6$) δ 8.22 (s, 1H), 7.81-7.70 (m, 1H), 7.39-7.22 (m, 2H), 7.02 (dd, J=4.4, 9.1 Hz, 1H), 6.62-6.50 (m, 3H), 6.38-6.03 (m, 1H), 4.00-3.62 (m, 8H), 3.30-3.24 (m, 1H), 3.18-3.05 (m, 1H), 3.02-2.92 (m, 1H), 2.33-2.15 (m, 5H), 2.04-1.94 (m, 1H), 1.66 (br s, 5H), 1.43-1.28 (m, 1H), 1.28-1.15 (m, 2H), 1.07 (d, J=6.4 Hz, 3H), 1.03 (d, J=6.4 Hz, 3H); LCMS (Method E): Rt 1.60 min, m/z: 656.2 [M+H]$^+$; HPLC (Method F): Rt 4.77 min, 99.96%.

Example 241. N-(2,2-Difluoroethyl)-5-fluoro-2-((4-(7-(((2S,5R)-5-((4-fluoro-1-methyl-1H-pyrazole)-3-sulfonamido)tetrahydro-2H-pyran-2-yl)methyl)-2,7-diazaspiro[3.5]nonan-2-yl)pyrimidin-5-yl)oxy)-N-isopropylbenzamide

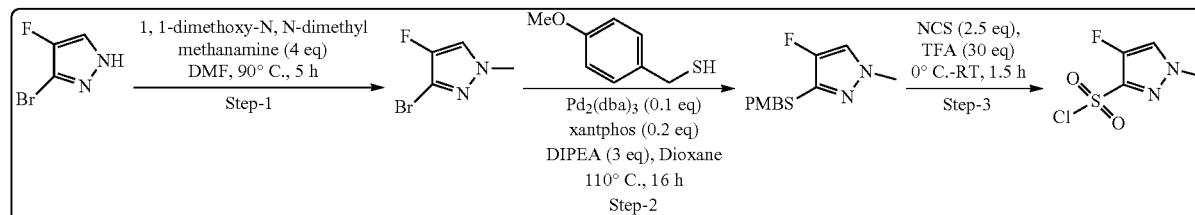

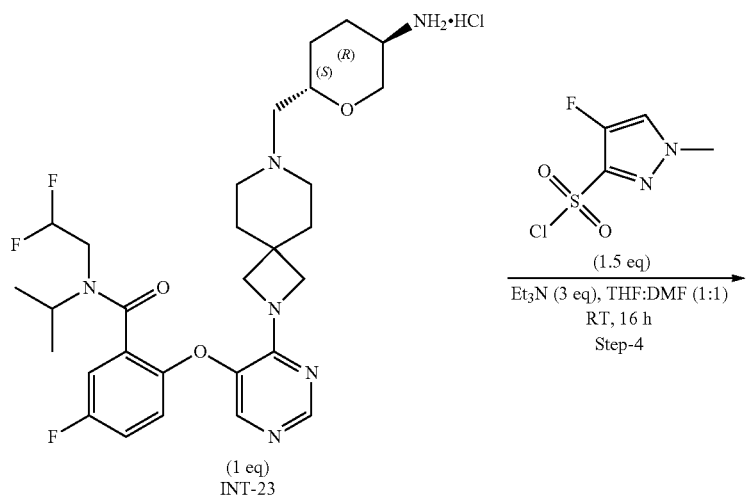

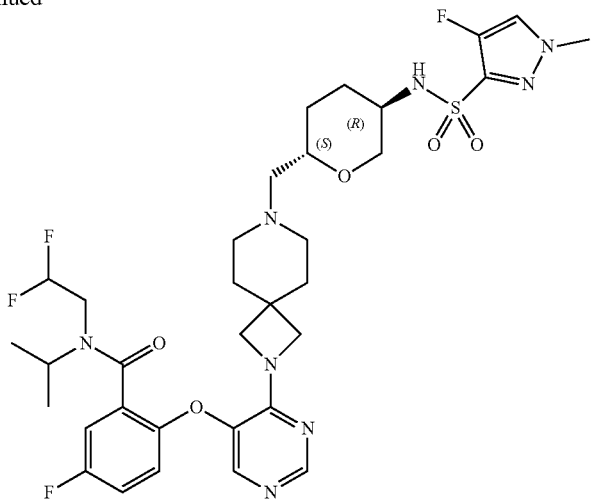

Example 241

Step 1. 3-Bromo-4-fluoro-1-methyl-1H-pyrazole

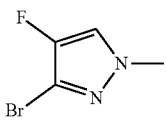

To a stirred solution of 3-bromo-4-fluoro-1H-pyrazole (0.75 g, 4.55 mmol) in dry DMF (2.5 mL), 1,1-dimethoxy-N,N-dimethylmethanamine (2.435 mL, 18.19 mmol) was added. The resulting reaction was stirred at 90° C. for 5 h under nitrogen atmosphere. The reaction progress was monitored by TLC and LCMS. After 5 h, the reaction mixture was quenched with brine solution (50 mL) and extracted with EtOAc (2×150 mL). The combined organic layer was dried over anhydrous sodium sulfate, and filtered, and the filtrate was concentrated under reduced pressure to afford crude 3-bromo-4-fluoro-1-methyl-1H-pyrazole (0.75 g, 91% yield) as a liquid. $^1$HNMR (400 MHz, CDCl$_3$): δ 7.28-7.23 (m, 1H), 3.85 (s, 3H); LCMS (Method B): Rt 1.41 min, m/z: 179.0 [M+H]$^+$ and 181.0 [M+H+2]$^+$.

Step 2. 4-Fluoro-3-((4-methoxybenzyl)thio)-1-methyl-1H-pyrazole

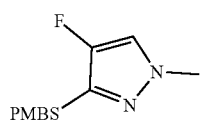

In a sealed tube, to a solution of (4-methoxyphenyl)methanethiol (600 mg, 3.89 mmol) in 1,4-dioxane (20 mL), DIPEA (2.155 mL, 11.67 mmol) and 3-bromo-4-fluoro-1-methyl-1H-pyrazole (696 mg, 3.89 mmol) were added, and the reaction mixture was degassed using nitrogen. To this reaction mixture, Xantphos (450 mg, 0.778 mmol) and Pd$_2$(dba)$_3$ (356 mg, 0.389 mmol) were added, and the mixture was degassed further using nitrogen for 5 min. The resulting reaction was stirred at 110° C. for 16 h. The reaction was monitored by TLC (30% EtOAc in hexane). After reaction completion, the reaction mixture was filtered through a pad of Celite®, and the filter pad was washed with EtOAc. The filtrate was concentrated under reduced pressure to obtain the crude product. The crude product was purified by silica gel column chromatography using 20-30% EtOAc in hexane as an eluent to obtain 4-fluoro-3-((4-methoxybenzyl)thio)-1-methyl-1H-pyrazole (480 mg, 43.5% yield) as a solid. The product formation was confirmed by NOE study. $^1$H NMR (400 MHz, DMSO-d$_6$) δ 7.85 (d, J=5.00 Hz, 1H), 7.17 (d, J=8.63 Hz, 2H), 6.84 (d, J=8.63 Hz, 2H), 4.01 (s, 2H), 3.76 (s, 3H), 3.72 (s, 3H); LCMS (Method B): Rt 1.937 min, m/z: 253.2 [M+H]$^+$.

Step 3. 4-Fluoro-1-methyl-1H-pyrazole-3-sulfonyl chloride

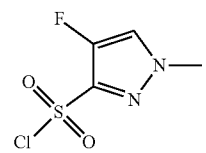

To a stirred solution of 4-fluoro-3-((4-methoxybenzyl)thio)-1-methyl-1H-pyrazole (400 mg, 1.585 mmol) in ACN (10 mL) and water (2.22 mL), N-chlorosuccinimide (529 mg, 3.96 mmol) and TFA (3.66 mL, 47.6 mmol) were added under nitrogen atmosphere at 0° C. The reaction was allowed to stir at RT for 1.5 h. The reaction was monitored by TLC (30% EtOAc in hexane). The reaction mixture was quenched with water (20 mL) and extracted with EtOAc (2×80 mL). The combined organic layer was washed with brine (80 mL), dried over anhydrous sodium sulfate, and filtered, and the filtrate was concentrated under reduced pressure to afford 4-fluoro-1-methyl-1H-pyrazole-3-sulfonyl chloride (700 mg, 61.8% yield). LCMS (Method A): Rt 1.592 min, m/z: 198.9 [M+H]$^+$. This product was used without further purification.

Step 4. N-(2,2-Difluoroethyl)-5-fluoro-2-((4-(7-(((2S,5R)-5-((4-fluoro-1-methyl-1H-pyrazole)-3-sulfonamido)tetrahydro-2H-pyran-2-yl)methyl)-2,7-diazaspiro[3.5]nonan-2-yl)pyrimidin-5-yl)oxy)-N-isopropylbenzamide (Example 241)

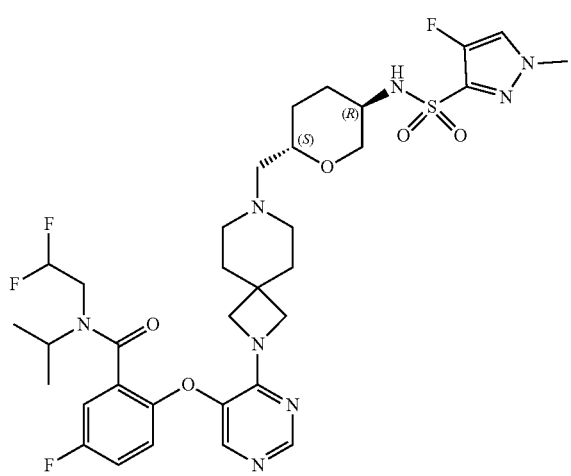

To a stirred solution of 2-((4-(7-(((2S,5R)-5-aminotetrahydro-2H-pyran-2-yl)methyl)-2,7-diazaspiro[3.5]nonan-2-yl)pyrimidin-5-yl)oxy)-N-(2,2-difluoroethyl)-5-fluoro-N-isopropylbenzamide (400 mg, 0.694 mmol) in DMF (8 mL), Et$_3$N (0.290 mL, 2.081 mmol) was added. To this solution, 4-fluoro-1-methyl-1H-pyrazole-3-sulfonyl chloride (207 mg, 1.040 mmol) in THF (8.00 mL) was added at 0° C. under nitrogen atmosphere. The reaction was stirred at RT for 16 h. The reaction progress was monitored by TLC (10% MeOH in DCM). After reaction completion, the reaction mixture was quenched with water (50 mL) and extracted with EtOAc (3×80 mL). The combined organic layer was dried over anhydrous sodium sulfate, and filtered, and the filtrate was concentrated on a rotary evaporator to obtain the crude product. The crude product was purified by Prep-HPLC (Method B) and lyophilized to obtain N-(2,2-difluoroethyl)-5-fluoro-2-((4-(7-(((2S,5R)-5-((4-fluoro-1-methyl-1H-pyrazole)-3-sulfonamido)tetrahydro-2H-pyran-2-yl)methyl)-2,7-diazaspiro[3.5]nonan-2-yl)pyrimidin-5-yl)oxy)-N-isopropylbenzamide (205 mg, 38.9% yield) as a solid. $^1$H NMR (400 MHz, DMSO-d$_6$) δ 8.29 (s, 1H), 8.18-7.99 (m, 2H), 7.81-7.71 (m, 1H), 7.40-7.23 (m, 2H), 7.07-6.97 (m, 1H), 6.38-6.03 (m, 1H), 3.85 (s, 3H), 3.93-3.79 (m, 3H), 3.79-3.64 (m, 5H), 3.24-3.30 (m, 1H), 3.17-3.04 (m, 1H), 3.03-2.94 (m, 1H), 2.32-2.12 (m, 5H), 1.85-1.75 (m, 1H), 1.64 (br s, 5H), 1.42-1.32 (m, 1H), 1.15-1.12 (m, 2H), 1.10 (d, J=6.40 Hz, 3H), 1.06 (d, J=6.80 Hz, 3H); LCMS (Method B): Rt 1.471 min, m/z: 739.3 [M+H]$^+$; HPLC (Method A): Rt 5.377 min, 97.314%.

Example 242. N-(3,3-Difluoropropyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide

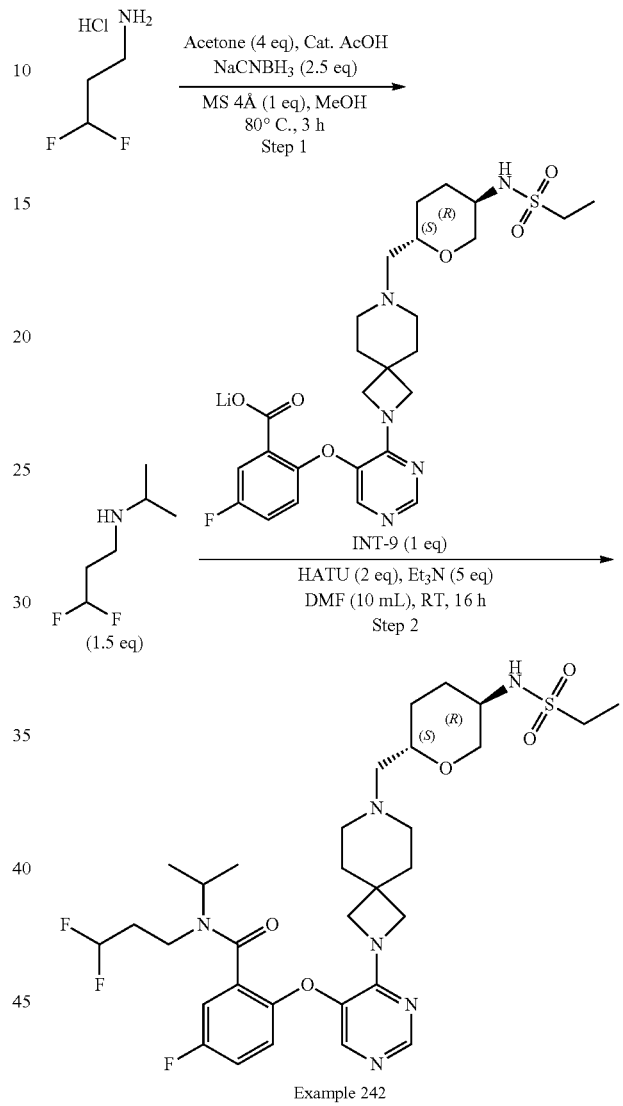

Step 1. 3,3-Difluoro-N-isopropylpropan-1-amine

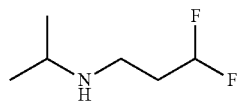

To a stirred solution of 3,3-difluoropropan-1-amine hydrochloride (0.7 g, 5.32 mmol) in methanol (10 mL), acetone (1.653 mL, 21.28 mmol) and AcOH (0.304 mL, 5.32 mmol) were added at RT under nitrogen atmosphere. To this reaction mixture, NaCNBH$_3$ (0.836 g, 13.30 mmol) and molecular sieves 4 Å (1 g, 5.32 mmol) were added, and the reaction was stirred at 80° C. for 3 h, then at RT for 16 h.

After reaction completion, the reaction mixture was concentrated, and EtOAc (50 mL) was added to the residue. The mixture was stirred for 5 min, then was filtered through a pad of Celite®. The filtrate was washed with sodium bicarbonate solution (25 mL), and the organic layer was dried over sodium sulfate, and filtered, and the filtrate was concentrated under reduced pressure to obtain crude 3,3-difluoro-N-isopropylpropan-1-amine (0.23 g, 31.5% yield) as an oil.

Step 2. N-(3,3-difluoropropyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (Example 242)

To a stirred solution of 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.5 g, 0.887 mmol) in DMF (10 mL), Et₃N (0.618 mL, 4.44 mmol) was added. To this reaction mixture, HATU (0.675 g, 1.774 mmol) and 3,3-difluoro-N-isopropylpropan-1-amine (0.183 g, 1.331 mmol) were added, and the reaction was stirred at RT for 16 h. The progress of the reaction was monitored by TLC (10% MeOH in DCM). After completion, the reaction mixture was diluted with water and extracted with EtOAc (20 mL). The combined organic layer was dried over sodium sulfate, and filtered, and the filtrate was concentrated under reduced pressure to obtain a crude product. The crude product was purified by prep-HPLC (Method A) to afford N-(3,3-difluoropropyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (0.09 g, 14.79% yield) as a solid. ¹H NMR (400 MHz, DMSO-d₆) δ 8.28-8.14 (m, 1H), 7.74-7.66 (m, 1H), 7.38-7.33 (m, 1H), 7.29-7.24 (m, 1H), 7.12-7.10 (m, 1H), 7.07-7.02 (m, 1H), 6.32-6.01 (m, 1H), 4.00-3.72 (m, 6H), 3.56-3.36 (m, 2H), 3.30-3.19 (m, 1H), 3.17-2.95 (m, 4H), 2.32-1.88 (m, 8H), 1.84-1.58 (m, 5H), 1.49-1.33 (m, 1H), 1.23-1.12 (m, 5H), 1.08 (d, J=6.40 Hz, 3H), 1.03 (d, J=6.40 Hz, 3H); LCMS (Method A): Rt 1.940 min, m/z: 683.4 [M−H]⁻; HPLC (Method A): Rt 5.198 min, 98.562%.

Example 243. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((1r,3r)-3-fluorocyclobutyl)-N-isopropylbenzamide

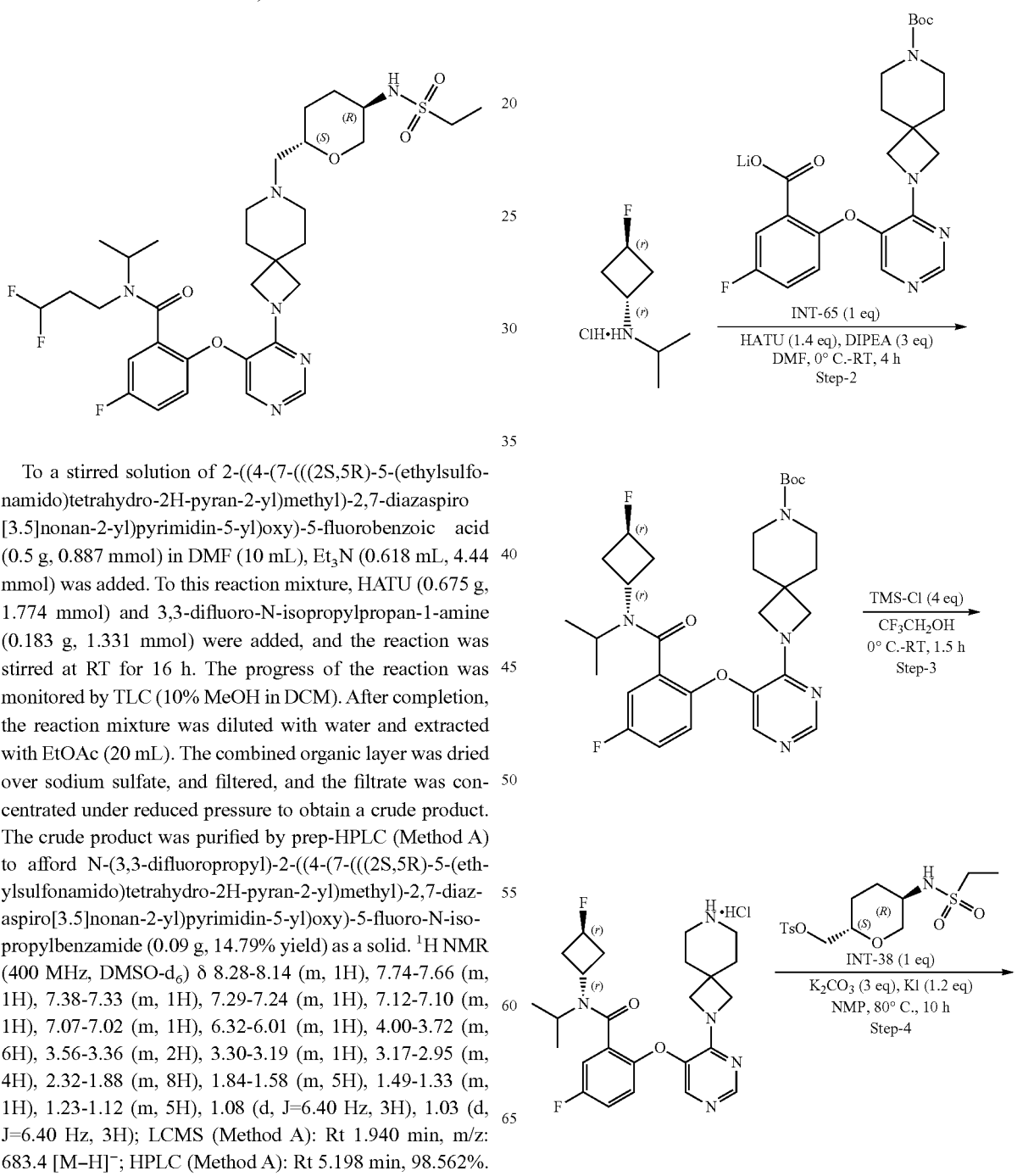

-continued

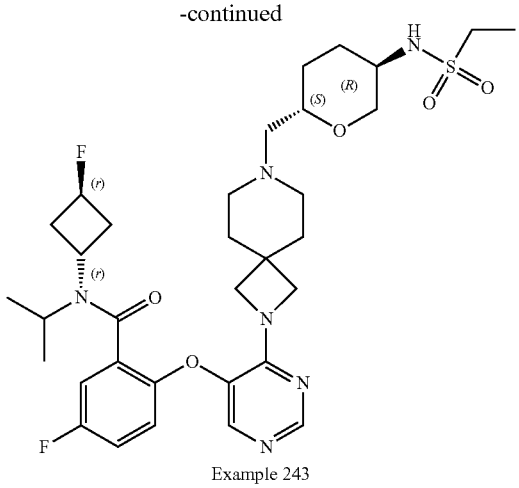

Example 243

Step 1. (1r,3r)-3-fluoro-N-isopropylcyclobutan-1-amine hydrochloride

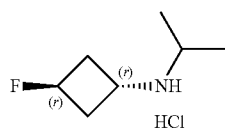

To a 50 mL sealed tube, (1r,3r)-3-fluorocyclobutan-1-amine hydrochloride (400 mg, 3.19 mmol) was added in ACN (10 mL). To this solution, 2-iodopropane (0.954 mL, 9.56 mmol) and K₂CO₃ (1321 mg, 9.56 mmol) were added. The reaction was stirred at 80° C. for 20 h in a sealed tube. Reaction progress was monitored by TLC (10% MeOH in DCM). The reaction mixture was filtered through a pad of Celite® and washed with EtOAc (15 mL). To this filtrate, 4M HCl in dioxane (3.19 mL, 12.74 mmol) was added at 0° C., and the solution was stirred at RT. After 30 min, the reaction was concentrated under reduced pressure to obtain crude (1r,3r)-3-fluoro-N-isopropylcyclobutan-1-amine hydrochloride (440 mg, 82% yield) as a solid. $^1$H NMR (400 MHz, DMSO-$d_6$) δ 9.35 (br s, 2H), 5.48-5.21 (m, 1H), 4.06-3.60 (m, 1H), 3.28-3.18 (m, 1H), 3.13-2.95 (m, 1H), 2.77-2.62 (m, 2H), 2.50-2.44 (m, 2H), 1.22 (d, J=6.8 Hz, 6H).

Step 2. tert-Butyl 2-(5-(4-fluoro-2-(((1r,3r)-3-fluorocyclobutyl)(isopropyl)carbamoyl)phenoxy)pyrimidin-4-yl)-2,7-diazaspiro[3.5]nonane-7-carboxylate

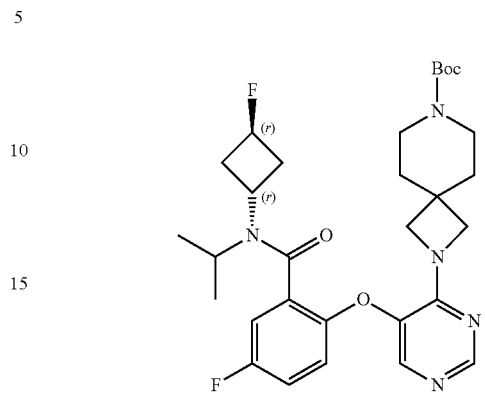

To a 50 mL round bottom flask, lithium 2-((4-(7-(tert-butoxycarbonyl)-2,7-diazaspiro[3.5]nonan-2-yl)pyrimidin-5-yl)oxy)-5-fluorobenzoate (1080 mg, 2.326 mmol) was added in DMF (8 mL). To this solution, DIPEA (1.219 mL, 6.98 mmol) and HATU (1238 mg, 3.26 mmol) were added at 0° C., and the reaction was stirred for 5 min. Then, (1r,3r)-3-fluoro-N-isopropylcyclobutan-1-amine hydrochloride (390 mg, 2.326 mmol) was added at 0° C., and the reaction was allowed to stir at RT for 4 h. The reaction was diluted with EtOAc (30 mL) and washed with ice-cold water. The organic layer was dried over sodium sulfate, and filtered, and the filtrate was concentrated. The crude material was purified by silica gel column chromatography using 2-7% MeOH in DCM as an eluent to obtain tert-butyl 2-(5-(4-fluoro-2-(((1r,3r)-3-fluorocyclobutyl)(isopropyl) carbamoyl) phenoxy)pyrimidin-4-yl)-2,7-diazaspiro[3.5] nonane-7-carboxylate (990 mg, 71.6% ) as a liquid. LCMS (Method B): Rt 1.92 min, m/z: 572.3 [M+H]⁺, 96.17%.

Step 3. 2-((4-(2,7-Diazaspiro[3.5]nonan-2-yl)pyrimidin-5-yl)oxy)-5-fluoro-N-((1r,3r)-3-fluorocyclobutyl)-N-isopropylbenzamide hydrochloride

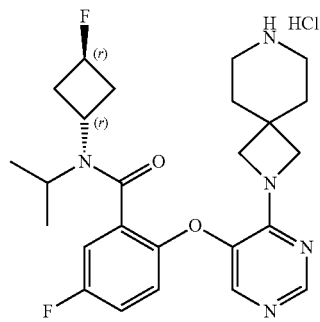

To a 50 mL round bottom flask, tert-butyl 2-(5-(4-fluoro-2-(((1r,3r)-3-fluorocyclobutyl)(isopropyl) carbamoyl)phenoxy)pyrimidin-4-yl)-2,7-diazaspiro[3.5]nonane-7-carboxylate (990 mg, 1.732 mmol) was added in 2,2,2-trifluoroethanol (5 mL). The solution was cooled to 0° C., then TMSCl (0.885 mL, 6.93 mmol) was added. The reaction was stirred at RT for 1.5 h. The progress of the reaction was monitored by TLC (10% MeOH in DCM). The reaction mixture was concentrated under reduced pressure to obtain 2-((4-(2,7-diazaspiro[3.5]nonan-2-yl)pyrimidin-5-yl)oxy)-5-fluoro-N-((1r,3r)-3-fluorocyclobutyl)-N-isopropylbenzamide hydrochloride (870 mg, 94% yield) as a viscous liquid. LCMS (Method B): Rt 1.14 min, m/z: 472.2 [M+H]⁺, 94.58%.

Step 4. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((1r,3r)-3-fluorocyclobutyl)-N-isopropylbenzamide (Example 243)

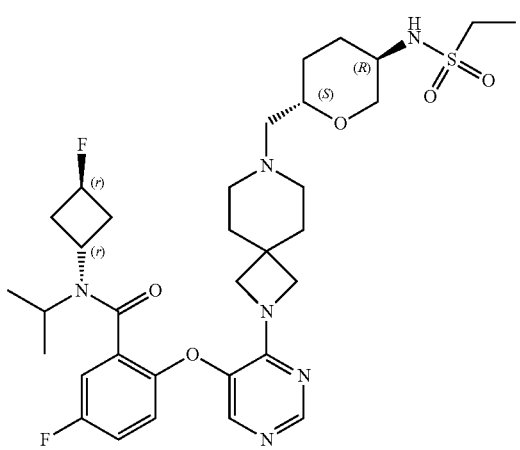

To a dried 25 mL round bottom flask under nitrogen atmosphere, 2-((4-(2,7-diazaspiro[3.5]nonan-2-yl)pyrimidin-5-yl)oxy)-5-fluoro-N-((1r,3r)-3-fluorocyclobutyl)-N-isopropylbenzamide hydrochloride (500 mg, 0.984 mmol) was added in NMP (5 mL). To this solution, ((2S,5R)-5-(ethylsulfonamido)tetrahydro-2H-pyran-2-yl)methyl 4-methylbenzenesulfonate (372 mg, 0.984 mmol), K₂CO₃ (408 mg, 2.95 mmol), and KI (196 mg, 1.181 mmol) were added, and the reaction was stirred at 80° C. for 10 h. The progress of the reaction was monitored by TLC (10% MeOH in DCM). The reaction mixture was diluted with EtOAc (30 mL) and washed with ice-cold water (3×30 mL). The combined organic layer was dried over sodium sulfate, and filtered, and the filtrate was concentrated to obtain the crude compound. The crude was purified by Prep-HPLC (Method A) to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((1r,3r)-3-fluorocyclobutyl)-N-isopropylbenzamide (208 mg, 31.1% yield). ¹H NMR (400 MHz, DMSO-d₆) δ 8.27-8.25 (m, 1H), 8.19 (s, 1H), 7.78-7.74 (m, 1H), 7.31-7.16 (m, 2H), 7.11-7.03 (m, 2H), 4.92-4.63 (m, 1H), 3.83-3.78 (m, 7H), 3.46-3.34 (m, 5H), 3.32-3.30 (m, 2H), 3.04-2.95 (m, 3H), 3.02-2.97 (m, 2H), 2.34-2.31 (m, 4H), 1.99-1.89 (m, 1H), 1.67 (br s, 4H), 1.49-1.35 (m, 2H), 1.33-1.22 (m, 2H), 1.18 (t, J=7.3 Hz, 3H), 1.11-0.95 (m, 3H); LCMS (Method C): Rt 1.69 min, m/z: 677.1 [M+H]⁺; HPLC (Method G): Rt 3.46 min, 99.51%.

Example 244. 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((1s,3s)-3-fluorocyclobutyl)-N-isopropylbenzamide

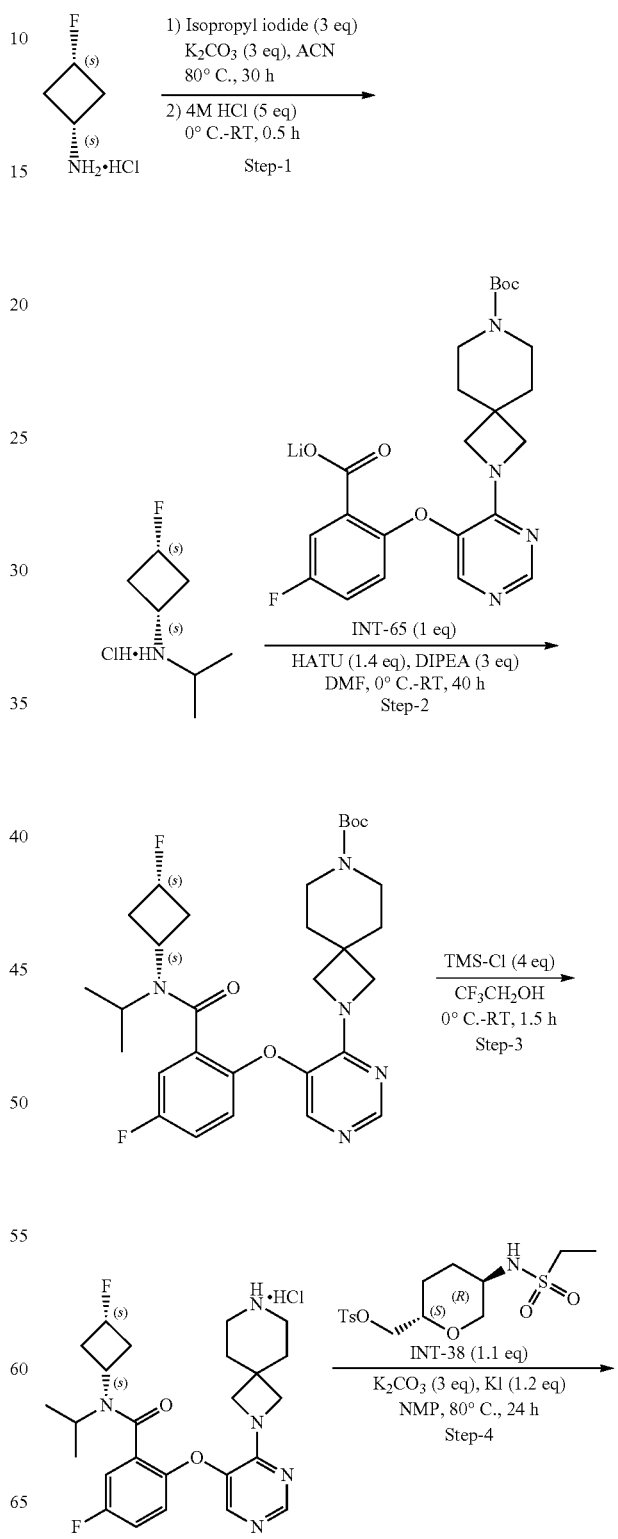

-continued

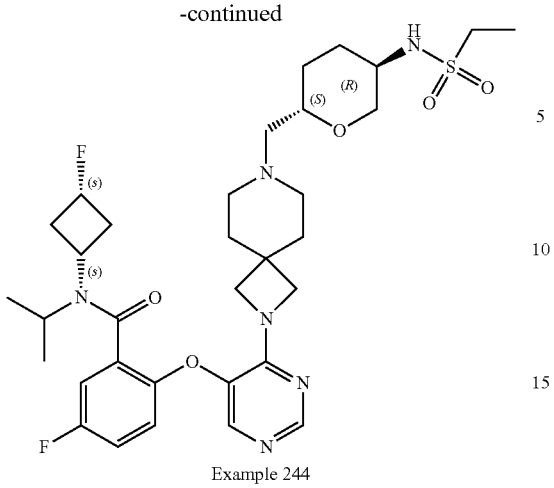

Example 244

Step 1.
(1s,3s)-3-Fluoro-N-isopropylcyclobutan-1-amine hydrochloride

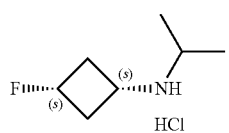

To a 50 mL sealed tube, (1s,3s)-3-fluorocyclobutan-1-amine hydrochloride (500 mg, 3.98 mmol) was added in ACN (10 mL). To this solution, 2-iodopropane (1.192 mL, 11.95 mmol) and K$_2$CO$_3$ (1651 mg, 11.95 mmol) were added. The reaction was stirred at 80° C. for 30 h. The reaction was monitored by TLC (10% MeOH in DCM). The reaction mixture was filtered through a pad of Celite® and the filter pad was washed with EtOAc (10 mL). To this filtrate, 4 M HCl in dioxane (4.98 mL, 19.91 mmol) was added at 0° C., and the reaction was stirred at RT for 30 min. The reaction was then concentrated under reduced pressure to obtain crude (1s,3s)-3-fluoro-N-isopropylcyclobutan-1-amine hydrochloride (550 mg, 82% yield) as a solid. $^1$H NMR (400 MHz, DMSO-d$_6$) δ 9.30 (br s, 2H), 5.01-4.72 (m, 1H), 3.66-3.55 (m, 1H), 3.36-3.28 (m, 1H), 3.27-3.16 (m, 1H), 2.74-2.66 (m, 2H), 2.53-2.40 (m, 2H), 1.35-1.16 (m, 6H).

Step 2. tert-Butyl 2-(5-(4-fluoro-2-(((1s,3s)-3-fluorocyclobutyl)(isopropyl)carbamoyl) phenoxy)pyrimidin-4-yl)-2,7-diazaspiro[3.5]nonane-7-carboxylate

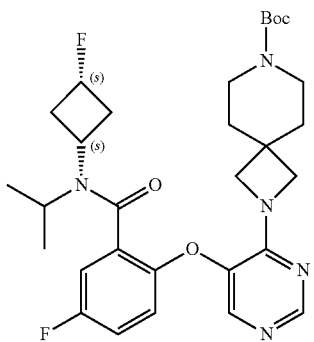

To a 25 mL round bottom flask, 2-((4-(7-(tert-butoxycarbonyl)-2,7-diazaspiro[3.5]nonan-2-yl)pyrimidin-5-yl)oxy)-5-fluorobenzoic acid (700 mg, 1.527 mmol) was added in DMF (2 mL), and the solution was cooled to 0° C. To this cooled solution, DIPEA (0.800 mL, 4.58 mmol) and HATU (813 mg, 2.137 mmol) were added, and the reaction was stirred for 5 min. Then, (1s,3s)-3-fluoro-N-isopropylcyclobutan-1-amine hydrochloride (333 mg, 1.986 mmol) was added, and the reaction was allowed to stir at RT for 40 h. The progress of the reaction was monitored by TLC (10% MeOH in DCM). The reaction mixture was diluted with EtOAc (15 mL) and washed with ice-cold water (3×10 mL). The organic layer was dried over sodium sulfate, and filtered, and the filtrate was concentrated under reduced pressure. The crude compound was purified by silica-gel column chromatography using 1-10% MeOH in DCM as an eluent to obtain tert-butyl 2-(5-(4-fluoro-2-(((1s,3s)-3-fluorocyclobutyl)(isopropyl) carbamoyl)phenoxy)pyrimidin-4-yl)-2,7-diazaspiro[3.5]nonane-7-carboxylate (500 mg, 57.3% yield) as a solid. LCMS (Method B): Rt 1.883 min, m/z: 572.2 [M+H]$^+$, 92.92%.

Step 3. 2-((4-(2,7-Diazaspiro[3.5]nonan-2-yl)pyrimidin-5-yl)oxy)-5-fluoro-N-((1s,3s)-3-fluorocyclobutyl)-N-isopropylbenzamide hydrochloride

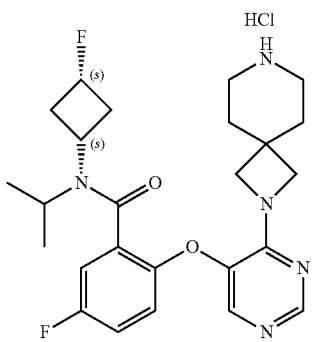

To a 25 mL dried round bottom flask, tert-butyl 2-(5-(4-fluoro-2-(((1s,3s)-3-fluorocyclobutyl)(isopropyl)carbamoyl)phenoxy)pyrimidin-4-yl)-2,7-diazaspiro[3.5]nonane-7-carboxylate (350 mg, 0.612 mmol) was added in 2,2,2- trifluoroethanol (4 mL). To this solution, TMS-Cl (0.313 mL, 2.449 mmol) was added at 0° C., and the reaction was stirred at RT for 1.5 h. The progress of the reaction was monitored by TLC (10% MeOH in DCM). The reaction was concentrated under reduced pressure to obtain 2-((4-(2,7-diazaspiro[3.5]nonan-2-yl)pyrimidin-5-yl)oxy)-5-fluoro-N-((1s,3s)-3-fluorocyclobutyl)-N-isopropylbenzamide hydrochloride (310 mg, 100% yield) as brown liquid. This compound was used in the subsequent step without further purification.

Step 4. 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((1s,3s)-3-fluorocyclobutyl)-N-isopropylbenzamide
(Example 244)

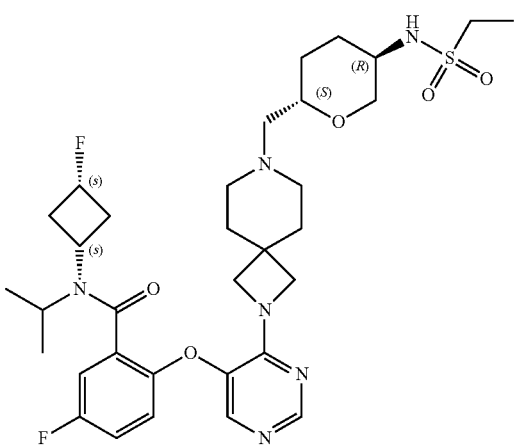

To a 25 mL round bottom flask, 2-((4-(2,7-diazaspiro[3.5]nonan-2-yl)pyrimidin-5-yl)oxy)-5-fluoro-N-((1s,3s)-3-fluorocyclobutyl)-N-isopropylbenzamide hydrochloride (310 mg, 0.610 mmol) was added in NMP (12 mL). To this solution, ((2S,5R)-5-(ethylsulfonamido)tetrahydro-2H-pyran-2-yl)methyl 4-methylbenzenesulfonate (253 mg, 0.671 mmol), $K_2CO_3$ (253 mg, 1.831 mmol), and KI (122 mg, 0.732 mmol) were added at RT, and the reaction was stirred at 80° C. for 24 h. The progress of the reaction was monitored by TLC (10% MeOH in DCM). The reaction mixture was diluted with EtOAc (30 mL) and filtered. The filtrate was washed with water (3×15 mL). The organic layer was dried over sodium sulfate, and filtered, and the filtrate was concentrated under reduced pressure to obtain the crude compound. The crude was purified by prep-HPLC (Method B) to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((1s,3s)-3-fluorocyclobutyl)-N-isopropylbenzamide (58 mg, 13.94% yield) as a solid. $^1$H NMR (400 MHz, DMSO-$d_6$) δ 8.31-8.21 (m, 1H), 7.82-7.72 (m, 1H), 7.34-7.14 (m, 2H), 7.12-7.01 (m, 2H), 4.94-4.59 (m, 1H), 3.99-3.63 (m, 7H), 3.56-3.41 (m, 1H), 3.28-3.17 (m, 1H), 3.16-2.95 (m, 5H), 2.33-2.24 (m, 4H), 2.23-2.14 (m, 2H), 2.00-1.89 (m, 1H), 1.67 (br s, 5H), 1.49-1.33 (m, 3H), 1.33-1.13 (m, 3H), 1.19 (t, J=2.4 Hz, 3H), 1.07-0.99 (m, 4H); LCMS (Method C): Rt 1.68 min, m/z: 677.1 [M+H]$^+$; HPLC (Method A): Rt 5.25 min, 99.23%.

Example 245. N-((1s,3s)-3-(difluoromethyl)cyclobutyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide

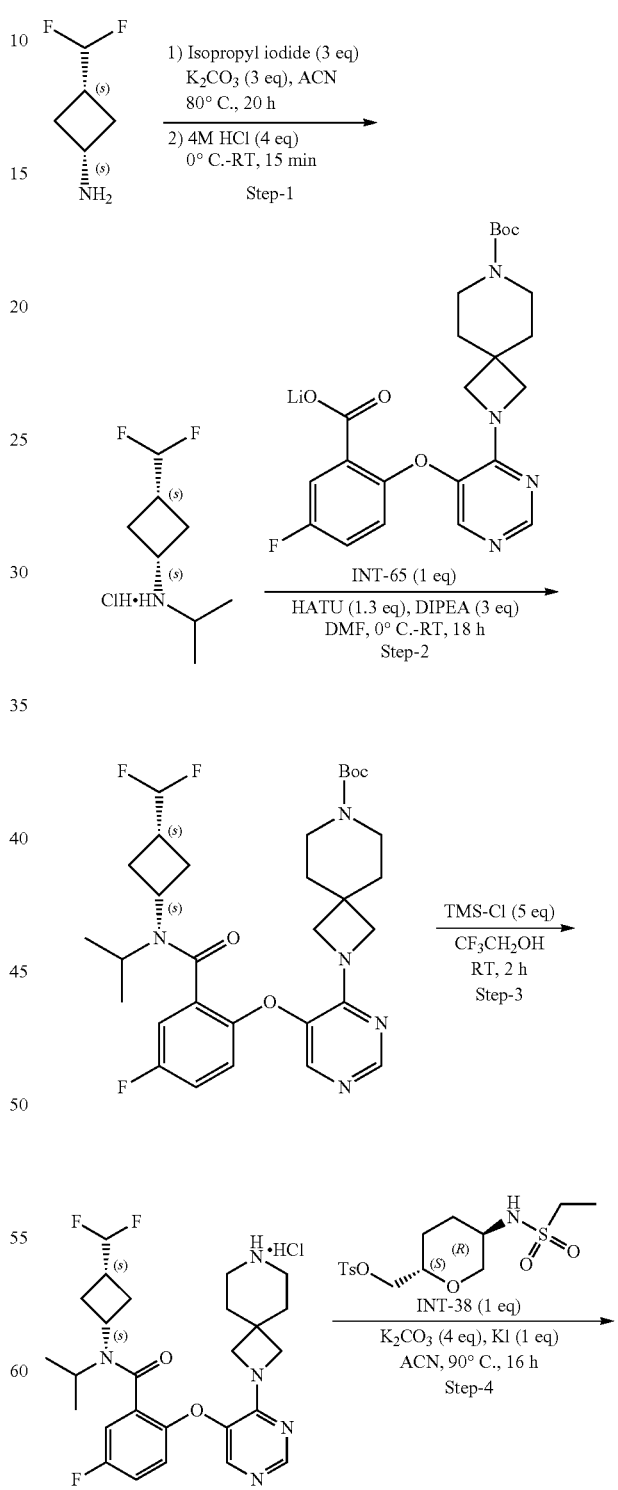

655

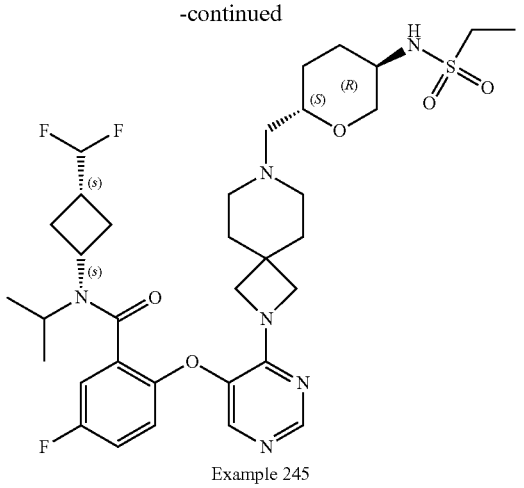

Example 245

Step 1. (1s,3s)-3-(Difluoromethyl)-N-isopropylcyclobutan-1-amine hydrochloride

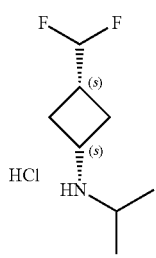

To a 25 mL round bottom flask under nitrogen atmosphere, (((1s,3s)-3-(difluoromethyl)cyclopedia)-14-azaneyl) chloronium (300 mg, 1.904 mmol) was added in ACN (5 mL). To this reaction mixture, 2-iodopropane (0.570 mL, 5.71 mmol) and K$_2$CO$_3$ (789 mg, 5.71 mmol) were added at RT, and the reaction mixture was stirred at 80° C. for 20 h. The progress of the reaction was monitored by TLC (5% MeOH/DCM). The reaction mixture was diluted with EtOAc and filtered through Celite®. To this filtrate, 4M in HCl (1.904 mL, 7.61 mmol) was added at 0° C., and the reaction mixture was stirred for 15 min at RT. The reaction was concentrated under reduced pressure to obtain (1r,3r)-3-(difluoromethyl)-N-isopropylcyclobutan-1-amine hydrochloride (580 mg, 2.90 mmol, 153% yield) as a solid. The crude compound was used in the subsequent step without further purification.

656

Step 2. tert-Butyl 2-(5-(2-(((1s,3s)-3-(difluoromethyl)cyclobutyl)(isopropyl)carbamoyl)-4-fluorophenoxy)pyrimidin-4-yl)-2,7-diazaspiro[3.5]nonane-7-carboxylate

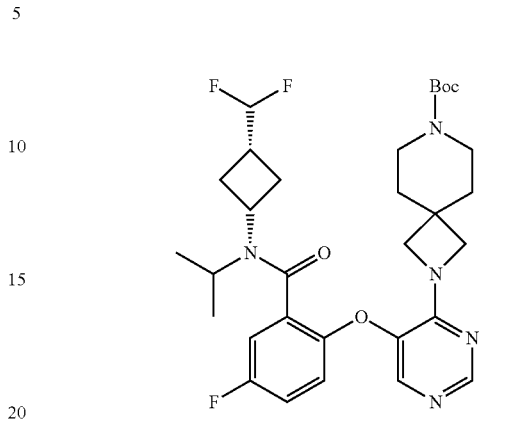

To a 25 mL round bottom flask, lithium 2-((4-(7-(tert-butoxycarbonyl)-2,7-diazaspiro[3.5]nonan-2-yl)pyrimidin-5-yl)oxy)-5-fluorobenzoate (698 mg, 1.502 mmol) was added in DMF (5 mL). The solution was cooled to 0° C., and DIPEA (0.787 mL, 4.51 mmol) and HATU (743 mg, 1.953 mmol) were added, and the reaction was stirred for 5 min. (1s,3s)-3-(difluoromethyl)-N-isopropylcyclobutan-1-amine hydrochloride (300 mg, 1.502 mmol) was added to the reaction mixture at 0° C. The reaction was stirred at RT for 18 h. Progress of the reaction was monitored by TLC (10% MeOH in DCM). After completion, the reaction mixture was diluted with water (15 mL) and extracted with EtOAc (15 mL×3). The combined organic layer was washed with brine (10 mL), dried over anhydrous sodium sulfate, filtered, and concentrated under reduced pressure to obtain crude compound. The crude was purified by silica gel column chromatography using 72% EtOAc in hexane as an eluent to obtain tert-butyl 2-(5-(2-(((1s,3s)-3-(difluoromethyl)cyclobutyl)(isopropyl)carbamoyl)-4-fluorophenoxy)pyrimidin-4-yl)-2,7-diazaspiro[3.5]nonane-7-carboxylate (200 mg, 0.193 mmol, 12.86% yield) as a liquid. LCMS (Method C): Rt 2.09 min, m/z: 604.7 [M+H]$^+$, 58.13%.

Step 3. 2-((4-(2,7-Diazaspiro[3.5]nonan-2-yl)pyrimidin-5-yl)oxy)-N-((1s,3s)-3-(difluoromethyl)cyclobutyl)-5-fluoro-N-isopropylbenzamide hydrochloride

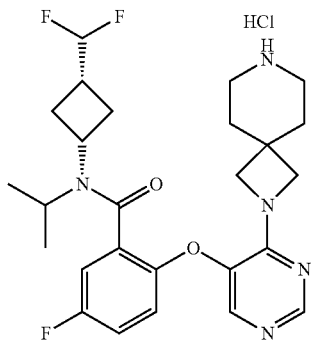

To a dried 25 mL round bottom flask, tert-butyl 2-(5-(2-(((1s,3s)-3-(difluoromethyl)cyclobutyl)(isopropyl)carbamoyl)-4-fluorophenoxy)pyrimidin-4-yl)-2,7-diazaspiro[3.5]
nonane-7-carboxylate (200 mg, 0.331 mmol) was added in
2,2,2-trifluoroethanol (2 mL). To this reaction mixture,
TMSCI (0.212 mL, 1.656 mmol) was added at 0° C., and the
reaction was stirred at RT for 2 h. Progress of the reaction
was monitored by TLC (10% MeOH in DCM). After
completion, the reaction mixture was concentrated under
reduced pressure to afford 2-((4-(2,7-diazaspiro[3.5]nonan-
2-yl)pyrimidin-5-yl)oxy)-N-((1s,3s)-3-(difluoromethyl)cy-
clobutyl)-5-fluoro-N-isopropylbenzamide (200 mg, 77%
yield). LCMS (Method C): Rt 1.59 min, m/z: 504.3 [M+H]$^+$,
64.51%.

Step 4. N-((1s,3s)-3-(Difluoromethyl)cyclobutyl)-2-
((4-(7-(((2S,5R)-5-(ethylsulfonamido)tetrahydro-2H-
pyran-2-yl)methyl)-2,7-diazaspiro[3.5]nonan-2-yl)
pyrimidin-5-yl)oxy)-5-fluoro-N-isopropylbenzamide
(Example 245)

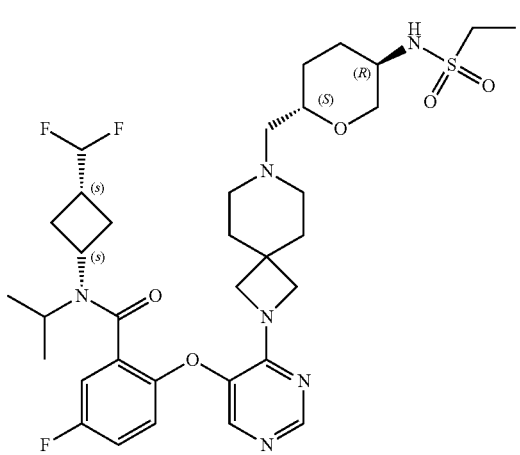

To a dried 50 mL round bottom flask under nitrogen
atmosphere, 2-((4-(2,7-diazaspiro[3.5]nonan-2-yl)pyrimi-
din-5-yl)oxy)-N-((1s,3s)-3-(difluoromethyl)cyclobutyl)-5-
fluoro-N-isopropylbenzamide (191 mg, 0.379 mmol) was
added in ACN (5 mL). To this reaction mixture, K$_2$CO$_3$ (161
mg, 1.166 mmol), ((2S,5R)-5-(ethylsulfonamido)tetra-
hydro-2H-pyran-2-yl)methyl 4-methylbenzenesulfonate
(110 mg, 0.291 mmol), and KI (48.4 mg, 0.291 mmol) were
added at RT. The reaction was stirred at 90° C. for 16 h.
Progress of the reaction was monitored by TLC (10% MeOH
in DCM). After completion, the reaction mixture was diluted
with ice cold water (10 mL) and extracted with EtOAc (2×5
mL). The combined organic extract was washed with satu-
rated aqueous sodium bicarbonate solution (5 mL) and brine
solution (5 mL), dried over anhydrous sodium sulfate,
filtered, and concentrated under reduced pressure. The
resulting crude compound was purified by prep-HPLC
(Method K) to obtain N-((1s,3s)-3-(difluoromethyl)cy-
clobutyl)-2-((4-(7-(((2S,5R)-5-(ethylsulfonamido)tetra-
hydro-2H-pyran-2-yl)methyl)-2,7-diazaspiro[3.5]nonan-2-
yl)pyrimidin-5-yl)oxy)-5-fluoro-N-isopropylbenzamide
(42.45 mg, 20.47% yield) as a solid. $^1$H NMR (400 MHz,
DMSO-d$_6$) δ 8.26 (d, J=13.9 Hz, 1H), 7.78 (s, 1H), 7.36-
7.15 (m, 2H), 7.13-7.00 (m, 2H), 6.29-5.91 (m, 1H), 4.13-
3.62 (m, 7H), 3.56-3.36 (m, 1H), 3.17-2.86 (m, 5H), 2.32-
2.14 (m, 6H), 2.13-1.99 (m, 2H), 1.98-1.86 (m, 2H), 1.67 (br
s, 5H), 1.49-1.34 (m, 3H), 1.33-1.22 (m, 3H), 1.18 (t, J=7.2
Hz, 3H), 1.12-0.94 (m, 3H); LCMS (Method B): Rt 1.40
min, m/z: 709.5 [M+H]$^+$; HPLC (Method A): Rt 5.59 min,
99.90%.

Example 246. N-((1r,3r)-3-(Difluoromethyl)cy-
clobutyl)-2-((4-(7-(((2S,5R)-5-(ethylsulfonamido)
tetrahydro-2H-pyran-2-yl)methyl)-2,7-diazaspiro
[3.5]nonan-2-yl)pyrimidin-5-yl)oxy)-5-fluoro-N-
isopropylbenzamide

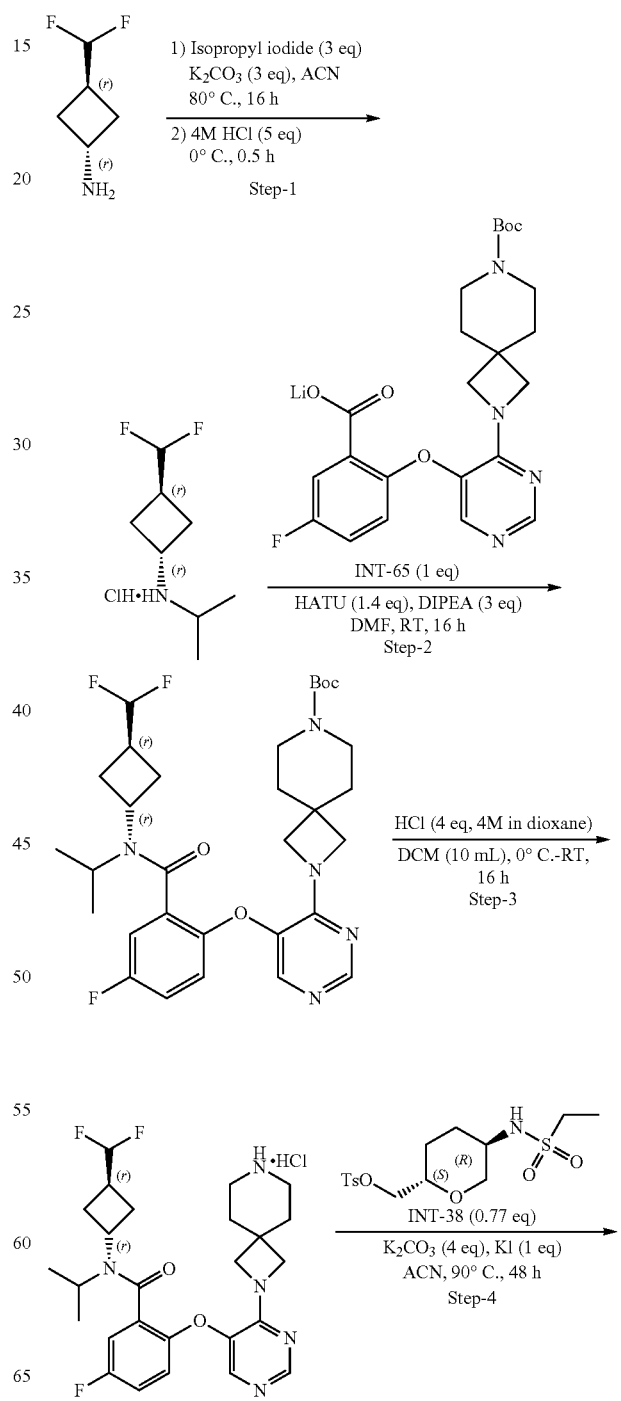

659
-continued

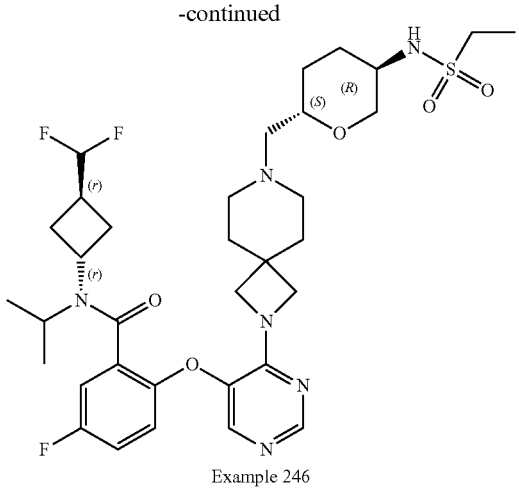

Example 246

Step 1. (1r,3r)-3-(Difluoromethyl)-N-isopropylcyclobutan-1-amine hydrochloride

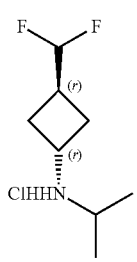

To a 100 mL round bottom flask under nitrogen atmosphere, (1r,3r)-3-(difluoromethyl)cyclobutan-1-amine (400 mg, 3.30 mmol) was added in ACN (20 mL). To this solution K$_2$CO$_3$ (1369 mg, 9.91 mmol) and 2-iodopropane (0.991 mL, 9.91 mmol) were added at RT. The reaction mixture was stirred at 80° C. for 16 h. Progress of the reaction was monitored by TLC (10% MeOH in DCM). The reaction mixture was filtered through Celite®, and the filtrate was treated with 4M HCl in 1,4-dioxane (4.13 mL, 16.51 mmol) at 0° C. and stirred for 30 min. The reaction mixture was concentrated to obtain (1r,3r)-3-(difluoromethyl)-N-isopropylcyclobutan-1-amine hydrochloride (600 mg, 3.00 mmol, 91% yield) as a brown liquid. The resulting compound was used in the subsequent step without further purification.

660

Step 2. tert-Butyl 2-(5-(2-(((1r,3r)-3-(difluoromethyl)cyclobutyl)(isopropyl)carbamoyl)-4-fluorophenoxy)pyrimidin-4-yl)-2,7-diazaspiro[3.5]nonane-7-carboxylate

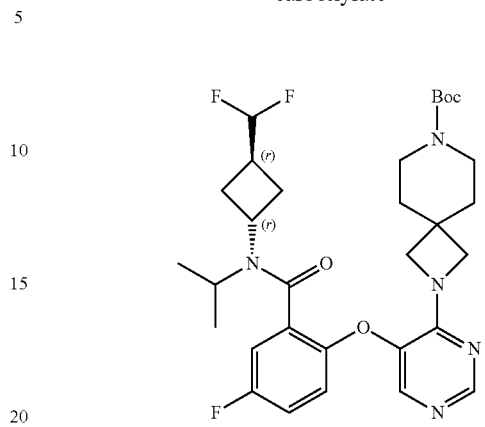

To a 50 mL round bottom flask, 2-((4-(7-(tert-butoxycarbonyl)-2,7-diazaspiro[3.5]nonan-2-yl)pyrimidin-5-yl)oxy)-5-fluorobenzoic acid (1 g, 2.181 mmol) and (1r,3r)-3-(difluoromethyl)-N-isopropylcyclobutan-1-amine hydrochloride (0.435 g, 2.181 mmol) were added in DMF (5 mL). To this solution, DIPEA (1.143 mL, 6.54 mmol) and HATU (1.161 g, 3.05 mmol) were added at RT under nitrogen atmosphere, and the reaction was stirred for 16 h. Progress of the reaction was monitored by TLC (10% methanol and DCM). The reaction mixture was quenched with water and extracted with EtOAc (3×20 mL). The combined organic layers were dried over sodium sulfate and concentrated obtain crude product which was further purified by silica gel column chromatography using 60% EtOAc in hexane as an eluent to obtain tert-butyl 2-(5-(2-(((1r,3r)-3-(difluoromethyl)cyclobutyl)(isopropyl)carbamoyl)-4-fluorophenoxy)pyrimidin-4-yl)-2,7-diazaspiro[3.5]nonane-7-carboxylate (770 mg, 0.641 mmol, 29.4% yield). LCMS (Method B): Rt 1.96 min, m/z: 604.4 [M+H]$^+$.

Step 3. 2-((4-(2,7-Diazaspiro[3.5]nonan-2-yl)pyrimidin-5-yl)oxy)-N-((1r,3r)-3-(difluoromethyl)cyclobutyl)-5-fluoro-N-isopropylbenzamide hydrochloride

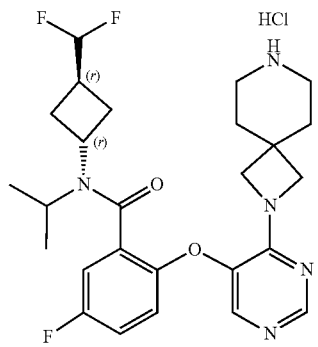

To a 50 mL round bottom flask, tert-butyl 2-(5-(2-(((1r,3r)-3-(difluoromethyl)cyclobutyl)(isopropyl)carbamoyl)-4-fluorophenoxy)pyrimidin-4-yl)-2,7-diazaspiro[3.5]nonane-7-carboxylate (500 mg, 0.828 mmol) was added in DCM (10 mL). To this reaction mixture, 4M HCl in 1,4-dioxane (0.621 mL, 2.485 mmol) was added at 0° C. under nitrogen atmosphere, and the reaction was stirred at RT for 16 h. Progress of the reaction was monitored by TLC (10% methanol and DCM). The reaction mixture was concentrated under reduced pressure to obtain crude2-((4-(2,7-diazaspiro[3.5]nonan-2-yl)pyrimidin-5-yl)oxy)-N-((1r,3r)-3-(difluoromethyl)cyclobutyl)-5-fluoro-N-isopropylbenzamide hydrochloride (600 mg, 0.720 mmol, 87% yield) as a solid. LCMS (Method B): Rt 1.26 min, m/z: 504.2 [M+H]+, 65.8%.

Step 4. N-((1r,3r)-3-(Difluoromethyl)cyclobutyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (Example 246)

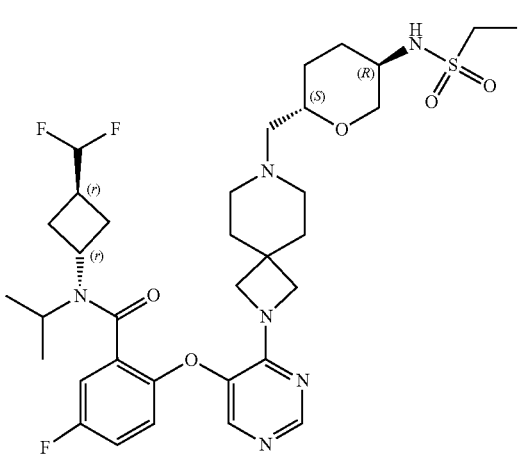

To a 50 mL round bottom flask under nitrogen atmosphere, 2-((4-(2,7-diazaspiro[3.5]nonan-2-yl)pyrimidin-5-yl)oxy)-N-((1r,3r)-3-(difluoromethyl)cyclobutyl)-5-fluoro-N-isopropylbenzamide hydrochloride (558 mg, 1.033 mmol) was added in ACN (10 mL). To this solution $K_2CO_3$ (439 mg, 3.18 mmol), KI (132 mg, 0.795 mmol), and ((2S,5R)-5-(ethylsulfonamido)tetrahydro-2H-pyran-2-yl)methyl 4-methylbenzenesulfonate (300 mg, 0.795 mmol) were added at RT, and the reaction was stirred at 90° C. for 48 h. Progress of the reaction was monitored by TLC (10% Methanol in DCM). The reaction mixture was quenched with water and extracted with EtOAc (3×20 mL). The combined organic layer was dried over sodium sulfate and concentrated under reduced pressure to obtain crude compound. The crude compound was purified by Prep-HPLC (Method A) to obtain N-((1r,3r)-3-(difluoromethyl)cyclobutyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (38 mg, 6.62% yield). $^1$H NMR (400 MHz, DMSO-$d_6$) δ 8.32-8.21 (m, 1H), 7.79-7.60 (m, 1H), 7.37-7.01 (m, 4H), 6.44-5.95 (m, 1H), 4.10-3.63 (m, 7H), 3.45-3.33 (m, 2H), 3.19-3.04 (m, 2H), 3.04-2.89 (m, 4H), 2.86-2.70 (m, 1H), 2.32-2.10 (m, 7H), 2.06-1.89 (m, 1H), 1.78-1.60 (m, 5H), 1.52-1.21 (m, 5H), 1.18 (t, J=7.3 Hz, 3H), 1.10-0.93 (m, 3H); LCMS (Method C): Rt 1.88 min, m/z: 709.6 [M+H]+; HPLC (Method A): Rt 5.58 min, 98.11%.

Example 247. 2-((4-(7-(((2S,5R)-5-(Cyclopropanesulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide

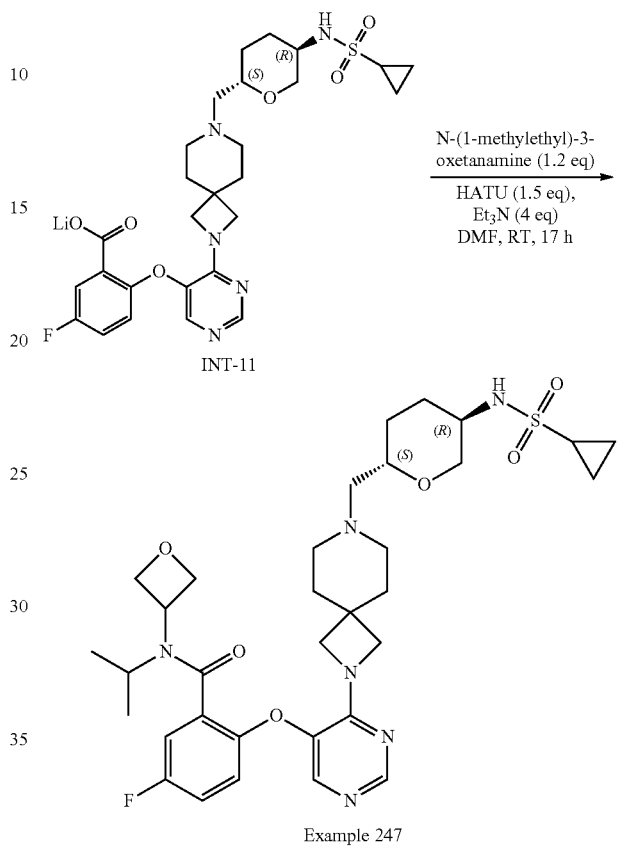

To a dried 25 mL round bottom flask under nitrogen atmosphere, lithium 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluorobenzoate (0.3 g, 0.516 mmol) was added in DMF (5 mL). To this reaction mixture, N-isopropyloxetan-3-amine (0.071 g, 0.619 mmol), HATU (0.294 g, 0.774 mmol) and Et$_3$N (0.288 mL, 2.063 mmol) were added at RT, and the reaction was stirred for 17 h. The reaction progress was monitored by TLC (10% MeOH in DCM). The reaction was quenched with water (20 mL) and extracted with EtOAc (2×40 mL).

The combined organic layer was dried over anhydrous sodium sulfate, filtered, and concentrated under reduced pressure to obtain crude compound. The crude compound was purified by Prep-HPLC (Method B) to obtain 2-((4-(7-(((2S,5R)-5-(cyclopropanesulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide (65 mg, 18.53% yield) as a solid. $^1$H NMR (400 MHz, DMSO-$d_6$) δ 8.28-8.26 (m, 1H), 7.86-7.73 (m, 1H), 7.41-7.18 (m, 2H), 7.12 (d, J=7.8 Hz, 1H), 7.08-6.99 (m, 1H), 5.25-5.08 (m, 1H), 4.87-4.39 (m, 3H), 3.94-3.66 (m, 6H), 3.21-3.09 (m, 1H), 3.07-2.98 (m, 1H), 2.62-2.58 (m, 1H), 2.32-2.16 (m, 6H), 1.99 (d, J=12.1 Hz, 1H), 1.74-1.58 (m, 6H), 1.51-1.19 (m, 5H), 1.10-1.02 (m, 2H), 1.01-0.96

(m, 2H), 0.95-0.83 (m, 4H); LCMS (Method A): Rt 2.00 min, m/z: (673.8) [M+H]+; HPLC (Method A): Rt 4.63 min, 98.96%.

Example 248. 2-((4-(7-(((2S,5R)-5-(Azetidine-1-sulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide

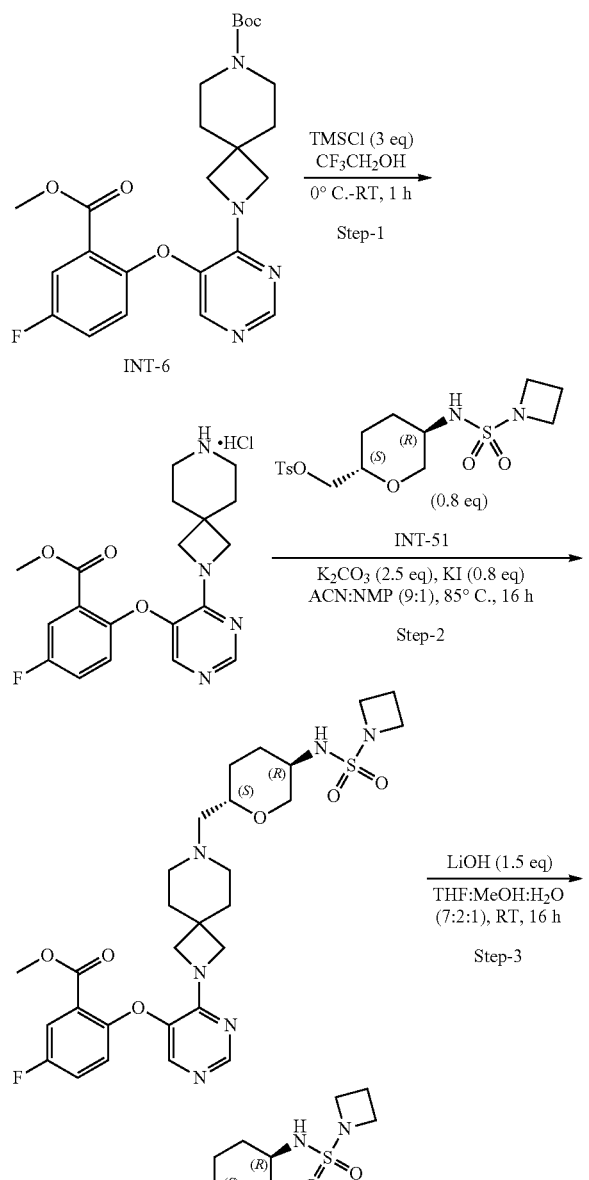

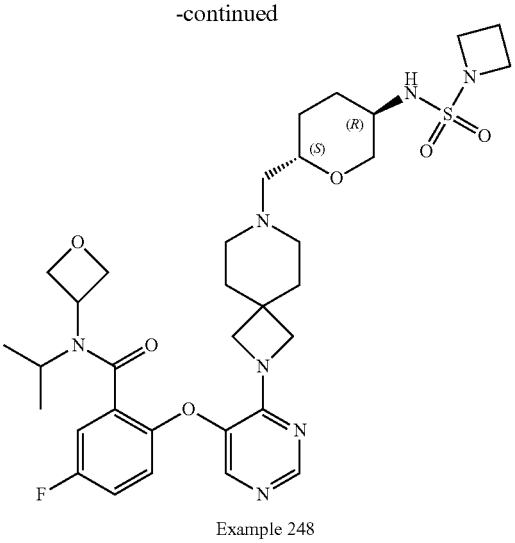

Example 248

Step 1. Methyl 2-((4-(2,7-diazaspiro[3.5]nonan-2-yl)pyrimidin-5-yl)oxy)-5-fluorobenzoate hydrochloride

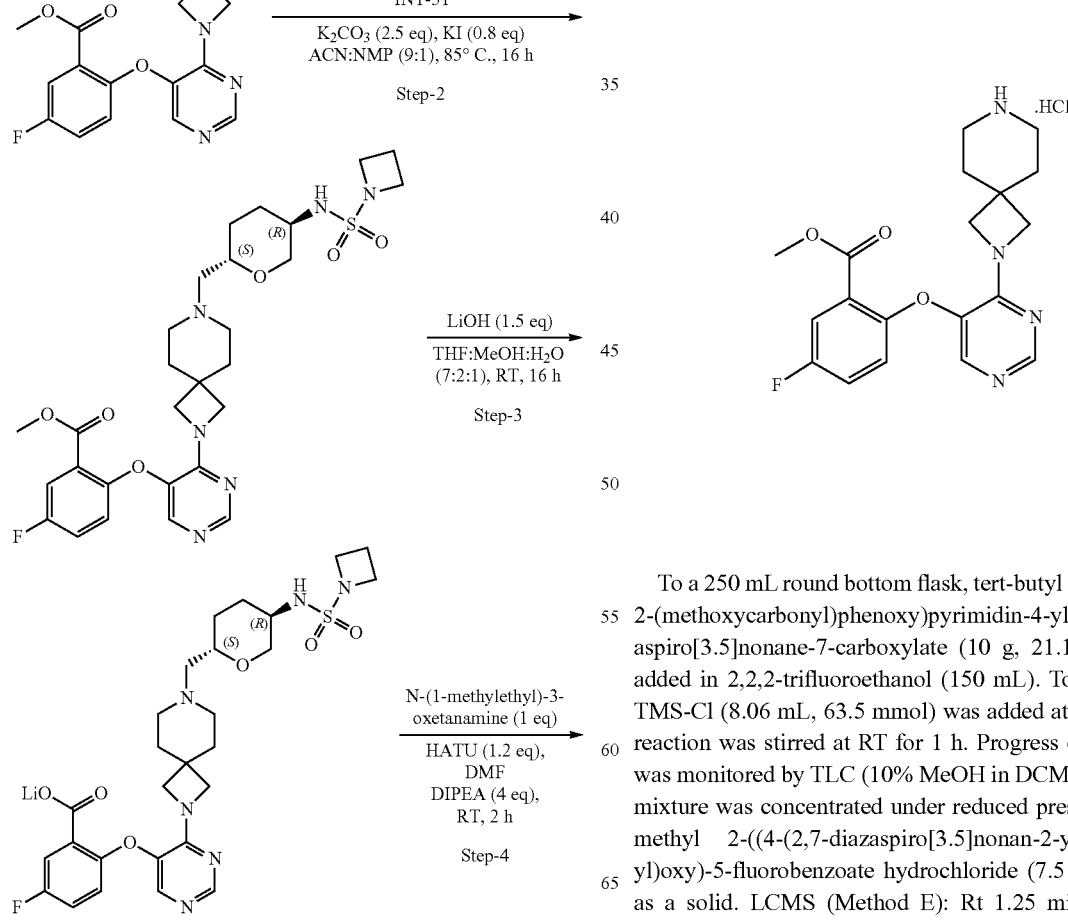

To a 250 mL round bottom flask, tert-butyl 2-(5-(4-fluoro-2-(methoxycarbonyl)phenoxy)pyrimidin-4-yl)-2,7-diazaspiro[3.5]nonane-7-carboxylate (10 g, 21.16 mmol) was added in 2,2,2-trifluoroethanol (150 mL). To this solution, TMS-Cl (8.06 mL, 63.5 mmol) was added at 0° C., and the reaction was stirred at RT for 1 h. Progress of the reaction was monitored by TLC (10% MeOH in DCM). The reaction mixture was concentrated under reduced pressure to obtain methyl 2-((4-(2,7-diazaspiro[3.5]nonan-2-yl)pyrimidin-5-yl)oxy)-5-fluorobenzoate hydrochloride (7.5 g, 86% yield) as a solid. LCMS (Method E): Rt 1.25 min, m/z: 373.2 [M+H]+ 98.75%.

Step 2. Methyl 2-((4-(7-(((2S,5R)-5-(azetidine-1-sulfonamido)tetrahydro-2H-pyran-2-yl)methyl)-2,7-diazaspiro[3.5]nonan-2-yl)pyrimidin-5-yl)oxy)-5-fluorobenzoate

Step 3. Lithium 2-((4-(7-(((2S,5R)-5-(azetidine-1-sulfonamido)tetrahydro-2H-pyran-2-yl)methyl)-2,7-diazaspiro[3.5]nonan-2-yl)pyrimidin-5-yl)oxy)-5-fluorobenzoate

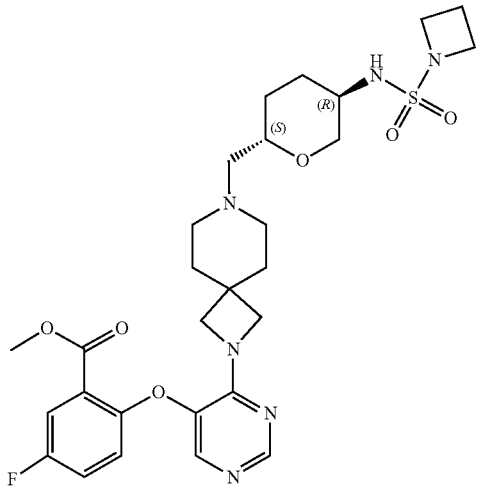

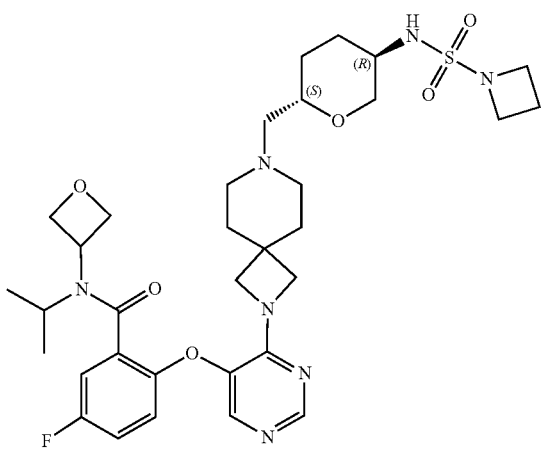

To a 50 mL round bottom flask, methyl 2-((4-(2,7-diazaspiro[3.5]nonan-2-yl)pyrimidin-5-yl)oxy)-5-fluorobenzoate hydrochloride (0.303 g, 0.742 mmol) was added in ACN:THF (9:1) (22 mL). To this solution, K$_2$CO$_3$ (0.256 g, 1.854 mmol), KI (0.103 g, 0.618 mmol) and ((2S,5R)-5-(azetidine-1-sulfonamido)tetrahydro-2H-pyran-2-yl)methyl 4-methylbenzenesulfonate (0.25 g, 0.618 mmol) were added at RT, and the reaction was stirred at 85° C. for 16 h. Progress of the reaction was monitored by TLC (10% MeOH in DCM). The reaction mixture was diluted with water (50 mL) and extracted with 10% MeOH in DCM (2×50 mL). The combined organic layer was dried over sodium sulfate, filtered, and concentrated under reduced pressure to afford crude compound. The crude compound was purified by silica gel column chromatography using 10% MeOH in DCM as an eluent to obtain methyl 2-((4-(7-(((2S,5R)-5-(azetidine-1-sulfonamido)tetrahydro-2H-pyran-2-yl)methyl)-2,7-diazaspiro[3.5]nonan-2-yl)pyrimidin-5-yl)oxy)-5-fluorobenzoate (0.15 g, 33.7% yield) a solid. LCMS (Method A): Rt 1.77 min, m/z: 605.5 [M+H]$^+$, 83.98%.

To a 25 mL round bottom flask, methyl 2-((4-(7-(((2S,5R)-5-(azetidine-1-sulfonamido)tetrahydro-2H-pyran-2-yl)methyl)-2,7-diazaspiro[3.5]nonan-2-yl)pyrimidin-5-yl)oxy)-5-fluorobenzoate (0.15 g, 0.248 mmol) was added in THF:MeOH (7:2) (9 mL). To this reaction mixture, LiOH (8.91 mg, 0.372 mmol, in 1 mL H$_2$O) was added at RT, and the reaction was stirred for 16 h. Progress of the reaction was monitored by TLC (10% MeOH in DCM). The reaction mixture was concentrated under reduced pressure, and co-distilled with toluene to obtain lithium 2-((4-(7-(((2S,5R)-5-(azetidine-1-sulfonamido)tetrahydro-2H-pyran-2-yl)methyl)-2,7-diazaspiro[3.5]nonan-2-yl)pyrimidin-5-yl)oxy)-5-fluorobenzoate (0.149 g, 100% yield) as a solid. LCMS (Method E): Rt: 1.15 min, m/z: 591.3 [M+H]$^+$78%.

Step 4. 2-((4-(7-(((2S,5R)-5-(Azetidine-J-sulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide (Example 248)

To a 100 mL round bottom flask under nitrogen atmosphere, lithium 2-((4-(7-(((2S,5R)-5-(azetidine-1-sulfonamido)tetrahydro-2H-pyran-2-yl)methyl)-2,7-diazaspiro[3.5]nonan-2-yl)pyrimidin-5-yl)oxy)-5-fluorobenzoate (150 mg, 0.251 mmol) was added in DMF (10 mL). To this reaction mixture, DIPEA (0.176 mL, 1.006 mmol), HATU (115 mg, 0.302 mmol) and N-isopropyloxetan-3-amine (29.0 mg, 0.251 mmol) were added at 0° C. The reaction mixture was stirred at RT for 2 h. Progress of the reaction was monitored by LCMS. The reaction was quenched with water and extracted with EtOAc (3×30 mL). The combined organic layer was dried over sodium sulfate and concentrated under reduced pressure to obtain crude compound. The crude compound was purified by prep-HPLC (Method A) to obtain 2-((4-(7-(((2S,5R)-5-(azetidine-1-sulfonamido)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide (32.29 mg, 18.00% yield) as a solid. $^1$H NMR (400 MHz, DMSO-d$_6$) δ 8.27 (s, 1H), 7.74 (s, 1H), 7.42-7.17 (m, 3H), 7.08-6.98 (m, 1H), 5.25-5.07 (m, 2H), 4.87-4.66 (m, 1H), 4.65-4.55 (m, 2H), 3.96-3.71 (m, 6H), 3.67 (t, J=7.6 Hz, 4H), 3.33-3.28 (m, 1H), 3.17-3.10 (m, 2H), 2.32-2.16 (m, 7H), 2.14-2.06 (m, 2H), 2.02-1.92 (m, 1H), 1.73-1.59 (m, 5H), 1.53-1.48 (m, 1H), 1.45-0.94 (m, 6H); LCMS (Method B): 1.21 min, 688.4 [M+H]$^+$; HPLC (Method A): Rt 4.64 min, 96.40%.

Example 249. 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide

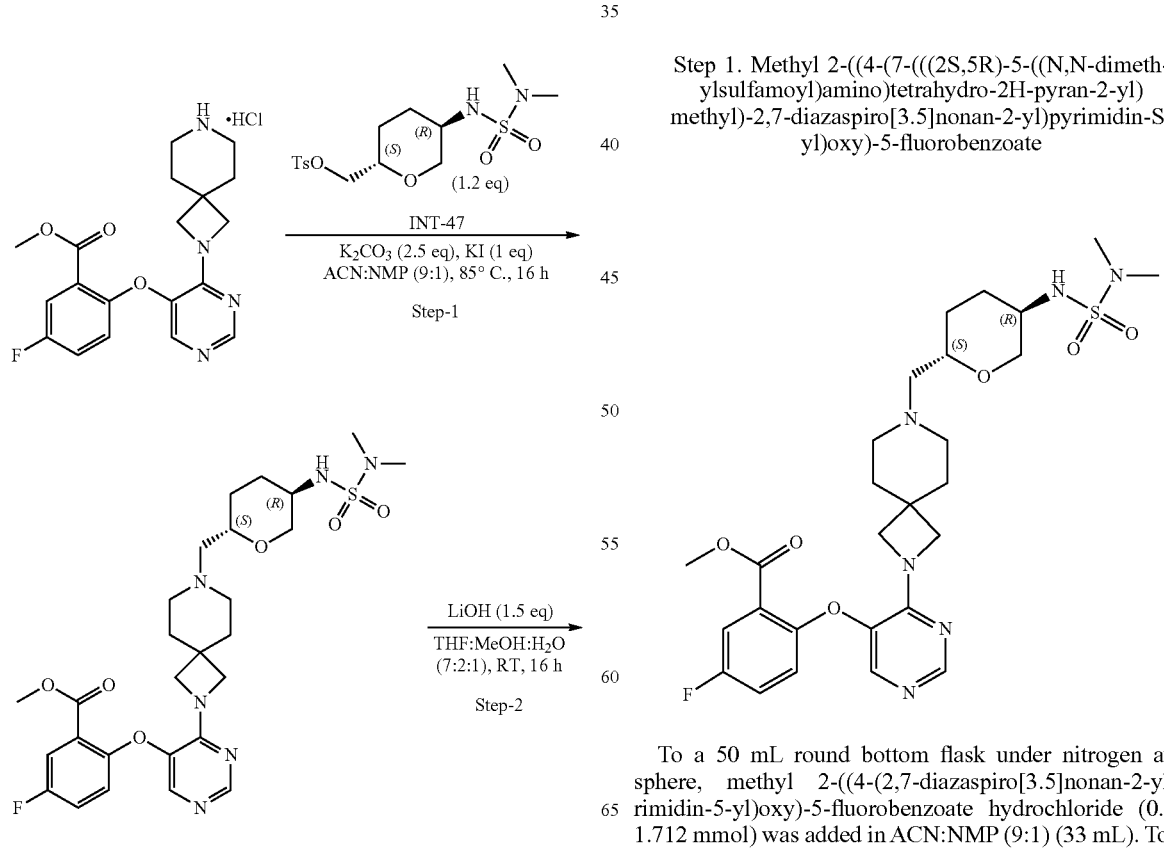

Example 249

Step 1. Methyl 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluorobenzoate

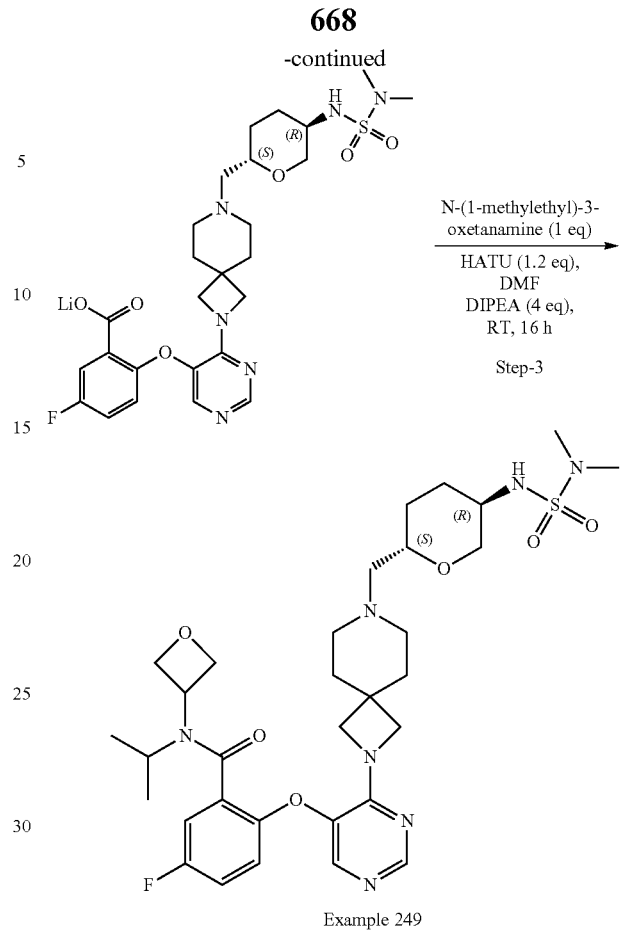

To a 50 mL round bottom flask under nitrogen atmosphere, methyl 2-((4-(2,7-diazaspiro[3.5]nonan-2-yl)pyrimidin-5-yl)oxy)-5-fluorobenzoate hydrochloride (0.7 g, 1.712 mmol) was added in ACN:NMP (9:1) (33 mL). To this solution, K$_2$CO$_3$ (0.710 g, 5.14 mmol), KI (0.284 g, 1.712 mmol), and ((2S,5R)-5-((N,N-dimethylsulfamoyl)amino)tetrahydro-2H-pyran-2-yl)methyl 4-methylbenzenesulfonate (0.806 g, 2.055 mmol) were added at RT, and the reaction was stirred at 85° C. for 16 h. Progress of the reaction was monitored by TLC (10% MeOH in DCM). The reaction mixture was diluted with water (50 mL) and extracted with 10% MeOH in DCM (2×50 mL). The combined organic layer was dried over sodium sulfate, filtered, and concentrated under reduced pressure to obtain crude compound. The crude compound was purified by silica gel column chromatography using 10% MeOH in DCM as an eluent to afford methyl 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluorobenzoate (0.36 g, 33.9% yield) as a semi solid. LCMS (Method A): 1.97 min, m/z: 593.3 [M+H]⁺ 95.55%.

Step 2. Lithium 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluorobenzoate

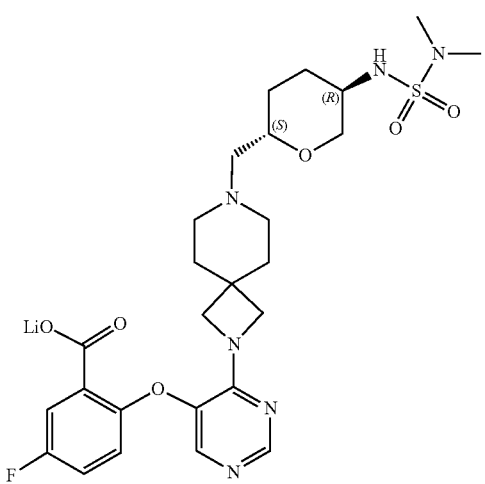

To a 25 mL round bottom flask, methyl 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluorobenzoate (0.36 g, 0.607 mmol) was added in THF:MeOH (7:2) (9 mL). To this solution LiOH (0.022 g, 0.911 mmol, in 1 mL H₂O) was added, and the reaction was stirred for 16 h at RT. Progress of the reaction was monitored by TLC (10% MeOH in DCM). The reaction mixture was concentrated under reduced pressure and the residue was co-distilled with toluene (2×10 mL) to afford lithium 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluorobenzoate (0.34 g, 96% yield) as a solid. LCMS (Method A): 1.48 min, m/z: 579.3 [M+H]⁺ 84.97%.

Step 3. 2-((4-(7-(((2S,5R)-5-((N,N-Dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide (Example 249)

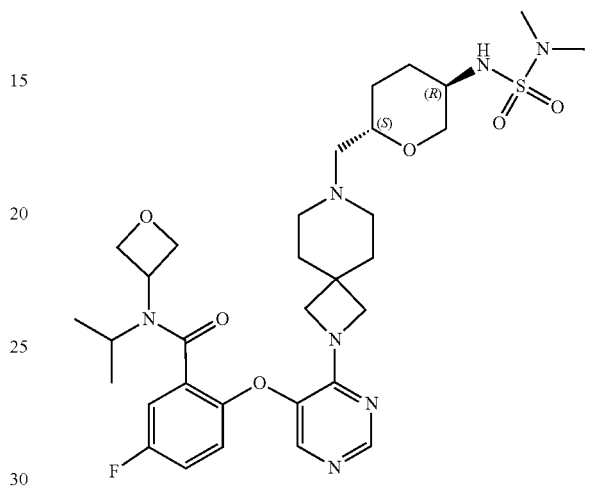

To a dried 100 mL round bottom flask under nitrogen atmosphere, lithium 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluorobenzoate (340 mg, 0.582 mmol) was added in DMF (10 mL). To this reaction mixture, DIPEA (0.396 mL, 2.326 mmol), HATU (265 mg, 0.698 mmol), and N-isopropyloxetan-3-amine (67.0 mg, 0.582 mmol) were added at 0° C., and the reaction was stirred at RT for 16 h. Progress of the reaction was monitored by LCMS. The reaction mixture was diluted with water and extracted with EtOAc (3×30 mL). The combined organic layer was dried over sodium sulfate and concentrated under reduced pressure to obtain crude compound. The crude was purified by Prep-HPLC (Method B) to obtain 2-((4-(7-(((2S,5R)-5-((N,N-dimethylsulfamoyl)amino)tetrahydro-2H-pyran-2-yl)methyl)-2,7-diazaspiro[3.5]nonan-2-yl)pyrimidin-5-yl)oxy)-5-fluoro-N-isopropyl-N-(oxetan-3-yl)benzamide (59.93 mg, 14.93% yield) as a solid. ¹H NMR (400 MHz, DMSO-d₆) δ 8.27 (s, 1H), 7.75 (s, 1H), 7.30-7.19 (m, 2H), 7.01 (dd, J=4.3, 9.3 Hz, 1H), 6.85 (d, J=6.1 Hz, 1H), 5.12-4.83 (m, 1H), 4.82-4.70 (m, 1H), 4.60 (t, J=6.6 Hz, 2H), 3.97-3.77 (m, 6H), 3.37-3.26 (m, 1H), 3.09-3.06 (m, 3H), 2.68 (s, 6H), 2.37-2.30 (m, 6H), 2.27-2.21 (m, 1H), 2.06-1.95 (m, 1H), 1.74-1.67 (m, 5H), 1.49-1.38 (m, 1H), 1.33-1.12 (m, 6H); LCMS (Method B): Rt 1.20 min, m/z: 676.4 [M+H]⁺; HPLC (Method A): Rt 4.63 min, 97.89%.

Example 250. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(tetrahydro-2H-pyran-4-yl)benzamide

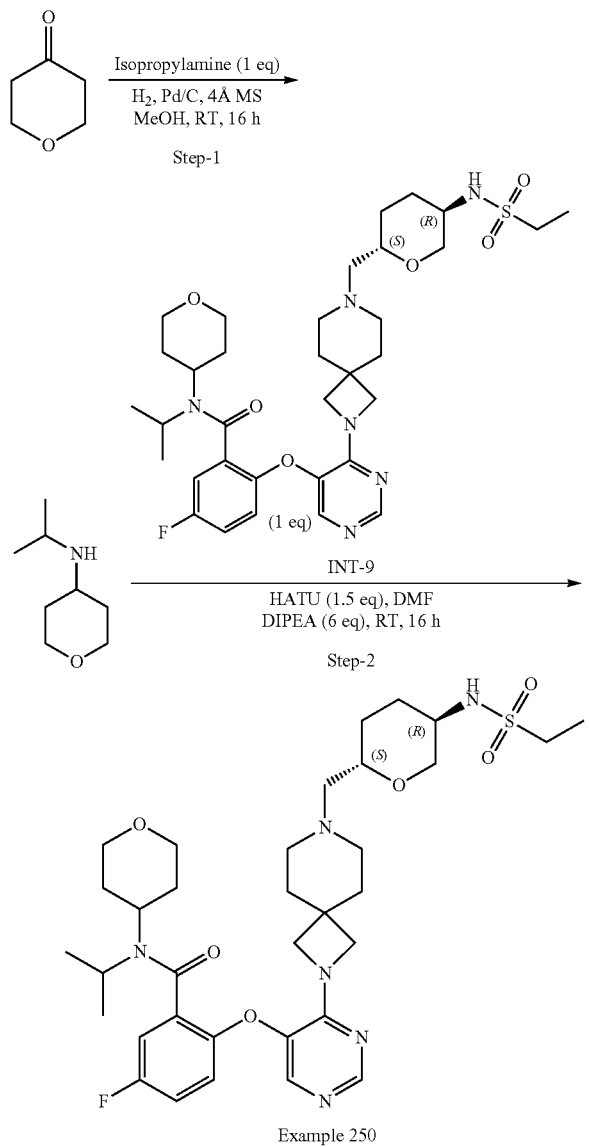

Step 1: N-Isopropyltetrahydro-2H-pyran-4-amine

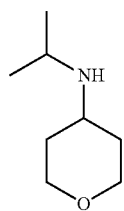

To a dried 250 mL round bottom flask, tetrahydro-4H-pyran-4-one (1 g, 9.99 mmol) was added in MeOH (20 mL). To this reaction mixture, palladium on carbon (200 mg, 0.188 mmol), isopropylamine (0.856 mL, 9.99 mmol), and molecular sieves 4 Å (500 mg, 9.99 mmol) were added at RT. The reaction was stirred at RT for 16 h. The reaction mixture was filtered through Celite®, and the filtrate was concentrated under reduced pressure to obtain N-isopropyltetrahydro-2H-pyran-4-amine (1 g, 69.9% yield) as a liquid. $^1$H NMR (400 MHz, DMSO-$d_6$) δ 4.05-3.95 (m, 2H), 3.42 (dt, J=12.0, 2.0 Hz, 2H), 3.15-2.97 (m, 1H), 2.83-2.72 (m, 1H), 1.88-1.79 (m, 2H), 1.43-1.31 (m, 2H), 1.07 (d, J=6.4 Hz, 6H).

Step 2. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(tetrahydro-2H-pyran-4-yl)benzamide (Example 250)

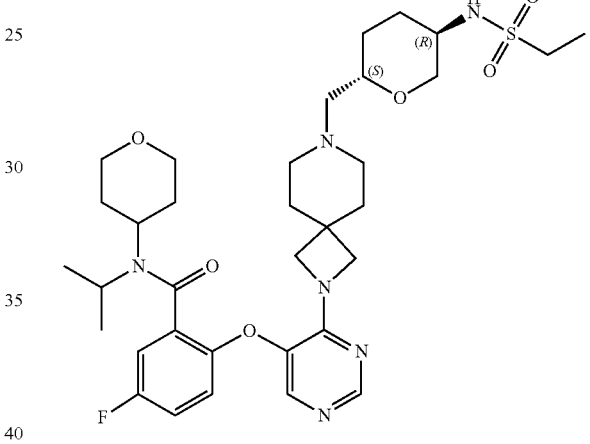

To a dried 100 mL round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (350 mg, 0.621 mmol) was added in DMF (20 mL). To this reaction mixture, N-isopropyltetrahydro-2H-pyran-4-amine (89 mg, 0.621 mmol), DIPEA (0.651 mL, 3.73 mmol), and HATU (354 mg, 0.931 mmol) were added at RT. The reaction mixture was stirred for 16 h. Progress of the reaction was monitored by TLC (10% MeOH in DCM). The reaction mixture was quenched with water and extracted with EtOAc (3×50 mL). The combined organic layer was dried over sodium sulfate and concentrated under reduced pressure to obtain the crude product. The crude compound was purified by Prep-HPLC (Method A) to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(tetrahydro-2H-pyran-4-yl)benzamide (16 mg, 36.5% yield) as a solid. $^1$H NMR (400 MHz, DMSO-$d_6$) δ 8.30-8.22 (m, 1H), 7.77-7.65 (m, 1H), 7.31-7.20 (m, 2H), 7.15-7.00 (m, 2H), 3.95-3.68 (m, 8H), 3.59-3.51 (m, 1H), 3.48-3.37 (m, 2H), 3.15-2.96 (m, 5H), 2.32-2.16 (m, 5H), 2.02-1.88 (m, 1H), 1.80-1.56 (m, 7H), 1.50-1.25 (m, 7H), 1.17 (t, J=7.2 Hz, 3H), 1.25-1.01 (m, 4H); LCMS (Method B): Rt 1.08 min, m/z: 689.2 [M+H]$^+$; HPLC (Method A): Rt 4.76 min, 94.83%.

Example 251. N-((1R,2R,4S)-7-Oxabicyclo[2.2.1]heptan-2-yl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide
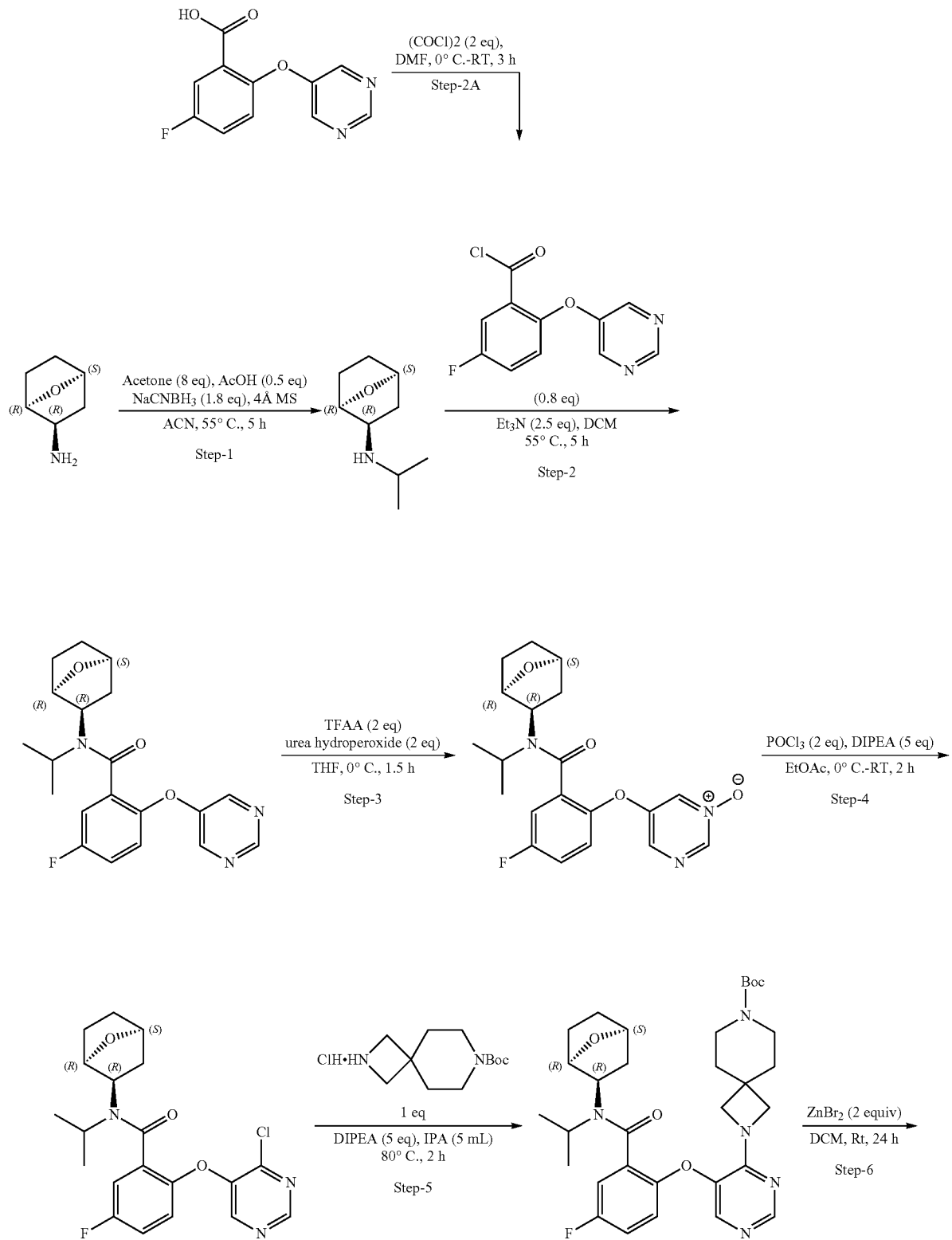

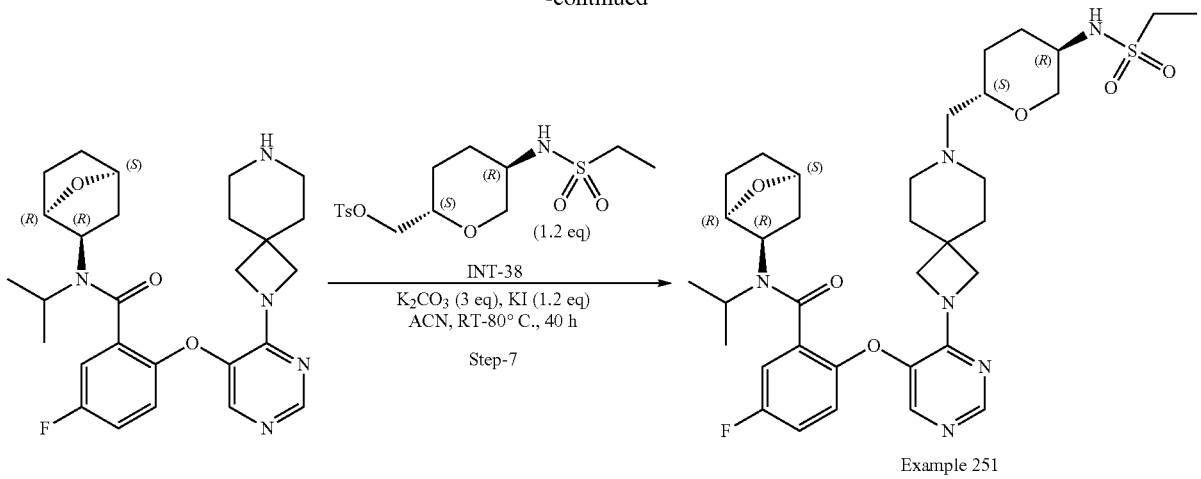

Example 251

Step 1. (1R,2R,4S)—N-Isopropyl-7-oxabicyclo[2.2.1]heptan-2-amine

Step 2. N-((1R,2R,4S)-7-Oxabicyclo[2.2.1]heptan-2-yl)-5-fluoro-N-isopropyl-2-(pyrimidin-5-yloxy)benzamide

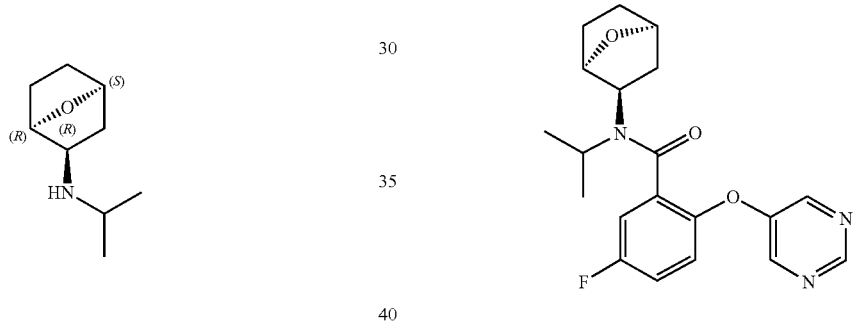

To a dried 50 mL round bottom flask under nitrogen atmosphere, 7-oxabicyclo[2.2.1]heptan-2-amine (Essen Scientific LLC; CAS No. 58564-87-7; 470 mg, 4.15 mmol) was added in MeOH (20 mL). To this reaction mixture, acetone (2.462 mL, 33.2 mmol), AcOH (0.119 mL, 2.077 mmol), and 4A molecular sieves (400 mg, 4.15 mmol) were added at RT, and the reaction was stirred for 2 h. To this reaction mixture, sodium cyanoborohydride (470 mg, 7.48 mmol) was added at 0° C., and the resulting reaction was stirred at 55° C. for 5 h. Progress of the reaction was monitored by TLC (10% MeOH in DCM). The reaction mixture was filtered and concentrated under reduced pressure, followed by trituration with 30% EtOAc in hexane (3×10 mL) to afford (1R,2R,4S)—N-isopropyl-7-oxabicyclo[2.2.1]heptan-2-amine (600 mg, 93% yield). $^1$H NMR (400 MHz, DMSO-$d_6$) δ 4.35 (t, J=5.6 Hz, 1H), 4.30 (t, J=5.2 Hz, 1H), 3.12-3.04 (m, 1H), 2.58-2.65 (m, 1H), 2.12-2.02 (m, 1H), 1.98-1.87 (m, 1H), 1.67 (br s, 1H), 1.60-1.32 (m, 3H), 0.91-1.01 (m, 6H), 0.90-0.82 (m, 1H).

Step 2A: To a dried 50 mL round bottom flask under nitrogen atmosphere, 5-fluoro-2-(pyrimidin-5-yloxy)benzoic acid (900 mg, 3.84 mmol) was added in DCM (15 mL). To this reaction mixture, oxalyl chloride (0.659 mL, 7.69 mmol) and DMF (0.030 mL, 0.384 mmol) were added at 0° C. The reaction mixture was stirred at RT for 3 h. Progress of the reaction was monitored by TLC (50% EtOAc in hexane). The reaction mixture was concentrated under reduced pressure to afford 5-fluoro-2-(pyrimidin-5-yloxy)benzoyl chloride (900 mg, 2.88 mmol, 75% yield) as a solid.

Step 2: To a dried 50 mL round bottom flask under nitrogen atmosphere, 5-fluoro-2-(pyrimidin-5-yloxy)benzoyl chloride (600 mg, 2.375 mmol) was added in DCM (4 mL). To this reaction mixture, (1R,2R,4S)—N-isopropyl-7-oxabicyclo[2.2.1]heptan-2-amine (442 mg, 2.85 mmol) and DIPEA (1.279 mL, 7.13 mmol) were added at 0° C. The reaction mixture was stirred at 55° C. for 5 h. Progress of the reaction was monitored by TLC (100% EtOAc). The reaction was quenched with water (40 mL) and extracted with DCM (3×30 mL). The combined organic layer was dried over sodium sulfate and concentrated under reduced pressure to obtain the crude compound. The crude compound was purified by silica gel column chromatography using 6% MeOH in DCM as an eluent to obtain N-((1R,2R,4S)-7-oxabicyclo[2.2.1]heptan-2-yl)-5-fluoro-N-isopropyl-2-(pyrimidin-5-yloxy)benzamide (450 mg, 45.6% yield) as sticky solid. LCMS (Method A): Rt 1.67 min, m/z: 372.1 [M+H]⁺, 89.49%.

Step 3. 5-(2-(((1R,2R,4S)-7-Oxabicyclo[2.2.1]heptan-2-yl)(isopropyl)carbamoyl)-4-fluorophenoxy)pyrimidine 1-oxide

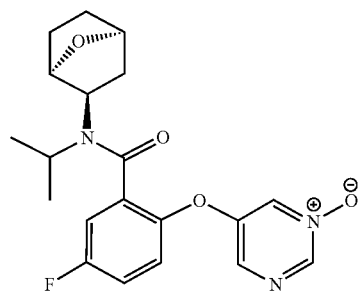 [SMILES: CC(C)N(C(=O)c1cc(F)ccc1Oc1cnc[n+]([O-])c1)[C@@H]1C[C@@H]2CC[C@H]1O2]

To a dried 50 mL round bottom flask under nitrogen atmosphere, N-((1R,2R,4S)-7-oxabicyclo[2.2.1]heptan-2-yl)-5-fluoro-N-isopropyl-2-(pyrimidin-5-yloxy)benzamide (450 mg, 1.212 mmol) was added in THF (5 mL). The reaction mixture cooled to −10° C., and urea hydrogen peroxide (228 mg, 2.423 mmol) was added. To this reaction mixture, TFAA (0.337 mL, 2.423 mmol) was added dropwise over a period of 10 min. The reaction mixture was stirred at RT for 1.5 h. Progress of the reaction was monitored by TLC (80% EtOAc in hexane). The reaction mixture was quenched with aqueous sodium bicarbonate (50 mL) and extracted with EtOAc (4×30 mL). The combined organic layer was washed with aqueous sodium thiosulfate (3×25 mL), dried over sodium sulfate, and concentrated under reduced pressure to obtain the crude compound. The crude compound was triturated with heptane (15 mL) to obtain 5-(2-(((1R,2R,4S)-7-oxabicyclo[2.2.1]heptan-2-yl)(isopropyl)carbamoyl)-4-fluorophenoxy)pyrimidine 1-oxide (430 mg, 81% yield) as sticky solid. LCMS (Method A): Rt 1.48 min, m/z: 386 [M+H]⁺, 87.92%.

Step 4. N—((1R,2R,4S)-7-Oxabicyclo[2.2.1]heptan-2-yl)-2-((4-chloropyrimidin-5-yl)oxy)-5-fluoro-N-isopropylbenzamide

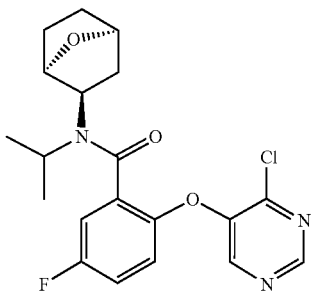 [SMILES: CC(C)N(C(=O)c1cc(F)ccc1Oc1cncnc1Cl)[C@@H]1C[C@@H]2CC[C@H]1O2]

To a dried 25 mL two neck round bottom flask under nitrogen atmosphere, 5-(2-(((1S,2S,4R)-7-oxabicyclo[2.2.1]heptan-2-yl)(isopropyl)carbamoyl)-4-fluorophenoxy)pyrimidine 1-oxide (430 mg, 1.110 mmol) was added in EtOAc (5 mL). To this reaction mixture, POCl₃ (0.203 mL, 2.220 mmol) and DIPEA (0.969 mL, 5.55 mmol) were added at −10° C. The reaction mixture was stirred at 0° C. for 10 min and at RT for 2 h. Progress of the reaction was monitored by TLC (50% EtOAc in hexane). The reaction mixture was concentrated under reduced pressure and purified by silica gel column chromatography using 35% EtOAc in hexane as an eluent to obtain N-((1R,2R,4S)-7-oxabicyclo[2.2.1]heptan-2-yl)-2-((4-chloropyrimidin-5-yl)oxy)-5-fluoro-N-isopropylbenzamide (190 mg, 35.7% yield). LCMS (Method A): Rt 2.00 min, m/z: 406.1 [M+H]⁺, 84.7%.

Step 5. tert-Butyl 2-(5-(2-(((1R,2R,4S)-7-oxabicyclo[2.2.1]heptan-2-yl)(isopropyl)carbamoyl)-4-fluorophenoxy)pyrimidin-4-yl)-2,7-diazaspiro[3.5]nonane-7-carboxylate

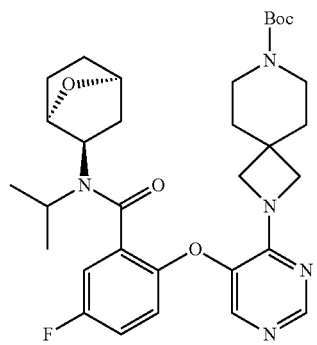 [SMILES: CC(C)N(C(=O)c1cc(F)ccc1Oc1cncnc1N1CC2(CCN(C(=O)OC(C)(C)C)CC2)C1)[C@@H]1C[C@@H]2CC[C@H]1O2]

To a dried 25 mL two neck round bottom flask under nitrogen atmosphere, N-((1R,2R,4S)-7-oxabicyclo[2.2.1]heptan-2-yl)-2-((4-chloropyrimidin-5-yl)oxy)-5-fluoro-N-isopropylbenzamide (190 mg, 0.468 mmol) was added in 2-propanol (5 mL). To this reaction mixture, tert-butyl 2,7-diazaspiro[3.5]nonane-7-carboxylate hydrochloride (123 mg, 0.468 mmol) and DIPEA (0.420 mL, 2.341 mmol) were added at RT, and the reaction was stirred at 80° C. for 2 h. The reaction was monitored by TLC (80% EtOAc in hexane). After completion, the reaction mixture was concentrated and purified by silica gel column chromatography using 4% MeOH in DCM as an eluent to obtain tert-butyl 2-(5-(2-(((1R,2R,4S)-7-oxabicyclo[2.2.1]heptan-2-yl)(isopropyl)carbamoyl)-4-fluorophenoxy)pyrimidin-4-yl)-2,7-diazaspiro[3.5]nonane-7-carboxylate (220 mg, 73.1% yield) as a solid. LCMS (Method A): Rt 1.83 min, m/z: 596.4 [M+H]⁺, 92.61%.

Step 6. 2-((4-(2,7-Diazaspiro[3.5]nonan-2-yl)pyrimidin-5-yl)oxy)-N-((1R,2R,4S)-7-oxabicyclo[2.2.1]heptan-2-yl)-5-fluoro-N-isopropylbenzamide

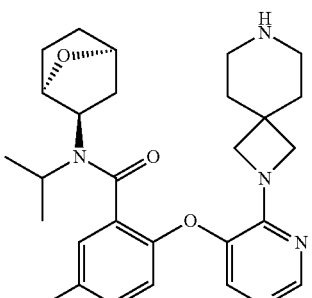

To a dried 10 mL round bottom flask under nitrogen atmosphere, tert-butyl 2-(5-(2-(((1R,2R,4S)-7-oxabicyclo[2.2.1]heptan-2-yl)(isopropyl)carbamoyl)-4-fluorophenoxy)pyrimidin-4-yl)-2,7-diazaspiro[3.5]nonane-7-carboxylate (0.030 g, 0.050 mmol) was added in DCM (2 mL). To this reaction mixture, ZnBr₂ (0.023 g, 0.101 mmol) was added, and the reaction was stirred at RT for 24 h. Progress of the reaction was monitored by TLC (10% MeOH in DCM). The reaction mixture was diluted with aqueous sodium bicarbonate and filtered. The resulting solid was collected and co-distilled with ACN to obtain 2-((4-(2,7-diazaspiro[3.5]nonan-2-yl)pyrimidin-5-yl)oxy)-N-((1R,2R,4S)-7-oxabicyclo[2.2.1]heptan-2-yl)-5-fluoro-N-isopropylbenzamide (40 mg, 94% yield). LCMS (Method A): Rt 1.42 min, 496.1 [M+H]⁺, 58.57%.

Step 7. N-((1R,2R,4S)-7-Oxabicyclo[2.2.1]heptan-2-yl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (Example 251)

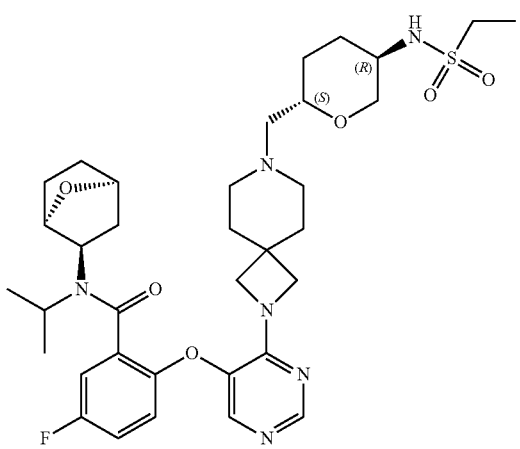

To a 25 mL round bottom flask under nitrogen atmosphere, 2-((4-(2,7-diazaspiro[3.5]nonan-2-yl)pyrimidin-5-yl)oxy)-N-((1S,2S,4R)-7-oxabicyclo[2.2.1]heptan-2-yl)-5-fluoro-N-isopropylbenzamide (70 mg, 0.141 mmol) was added in ACN (3 mL). To this reaction mixture, K₂CO₃ (20.91 mg, 0.151 mmol), KI (10.05 mg, 0.061 mmol), and ((2S,5R)-5-(ethylsulfonamido)tetrahydro-2H-pyran-2-yl)methyl 4-methylbenzenesulfonate (22.85 mg, 0.061 mmol) were added at RT. The reaction was stirred at 80° C. for 40 h. Progress of the reaction was monitored by TLC (10% MeOH and DCM). The reaction mixture was filtered through Celite®, and the filtrate was concentrated under reduced pressure to obtain crude compound. The crude was purified by Prep-HPLC (Method A) to obtain N-((1R,2R,4S)-7-oxabicyclo[2.2.1]heptan-2-yl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (8.7 mg, 8.63% yield) as a solid. ¹H NMR (400 MHz, DMSO-d₆) δ 8.34-8.18 (m, 1H), 7.71 (br s, 1H), 7.27-7.16 (m, 2H), 7.08-6.92 (m, 1H), 6.83-6.78 (m, 1H), 4.60-4.38 (m, 2H), 3.86 (br s, 7H), 3.15-2.99 (m, 6H), 2.33-2.18 (m, 5H), 2.06-1.94 (m, 2H), 1.69 (br s, 5H), 1.64-1.52 (m, 3H), 1.49-1.41 (m, 2H), 1.36-1.16 (m, 11H); LCMS (Method B): Rt 1.50 min, m/z: 701.3 [M+H]⁺; HPLC (Method A): Rt 4.88 min, m/z: 98.18%.

Example 252. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-oxaspiro[3.3]heptan-6-yl)benzamide

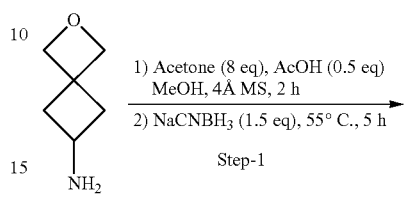

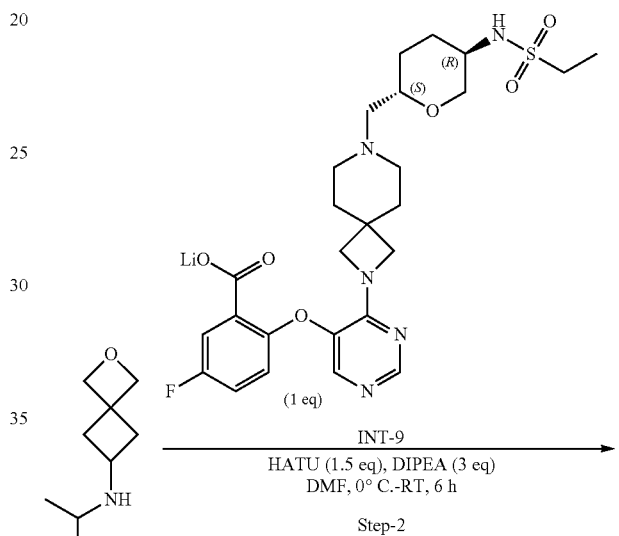

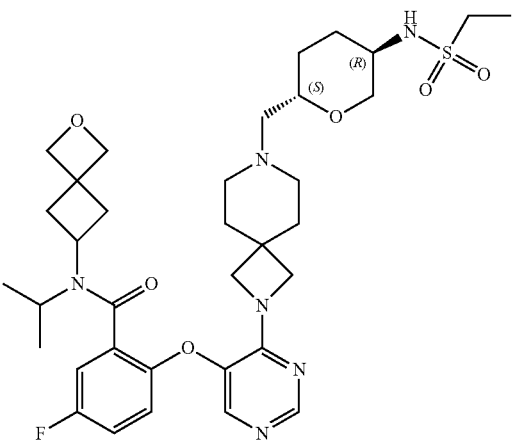

Example 252

Step 1. N-Isopropyl-2-oxaspiro[3.3]heptan-6-amine

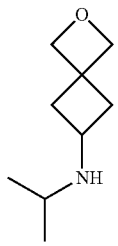

To a dried 25 mL round bottom flask under nitrogen atmosphere, 2-oxaspiro[3.3]heptan-6-amine (300 mg, 2.65 mmol) was added in methanol (5 mL). To this reaction mixture, acetone (1.579 mL, 21.21 mmol), AcOH (0.076 mL, 1.326 mmol), and molecular sieves 4A (584 mg, 1.326 mmol) were added at 0° C., and the reaction was stirred at RT for 2 h. The reaction mixture was cooled to 0° C., sodium cyanoborohydride (250 mg, 3.98 mmol) was added, and the reaction was continued 55° C. for 5 h. Progress of the reaction was monitored by TLC (10% MeOH and DCM). The reaction mixture was filtered through Celite® and concentrated under reduced pressure to obtain N-isopropyl-2-oxaspiro[3.3]heptan-6-amine (500 mg, 94% yield) as a solid. LCMS (Method A): Rt 0.42 min, 156.2 [M+H]$^+$, 77.35%.

Step 2. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-oxaspiro[3.3]heptan-6-yl)benzamide (Example 252)

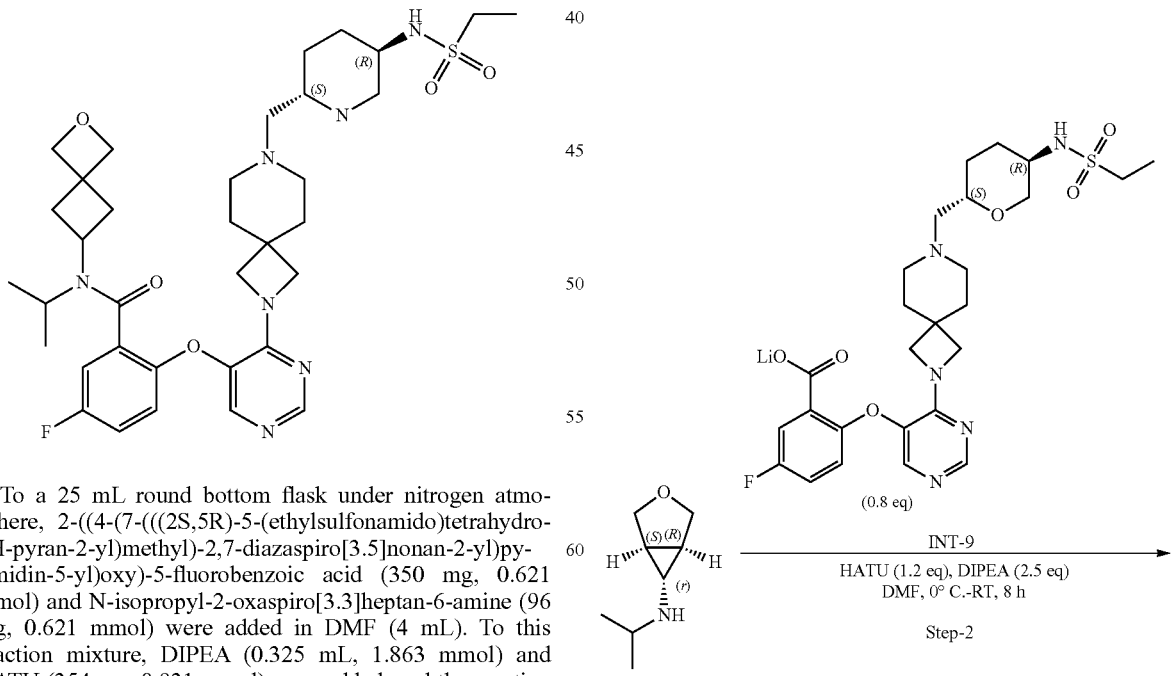

To a 25 mL round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (350 mg, 0.621 mmol) and N-isopropyl-2-oxaspiro[3.3]heptan-6-amine (96 mg, 0.621 mmol) were added in DMF (4 mL). To this reaction mixture, DIPEA (0.325 mL, 1.863 mmol) and HATU (354 mg, 0.931 mmol) were added, and the reaction was stirred at RT for 6 h. Progress of the reaction was monitored by TLC (10% methanol in DCM). The reaction mixture was concentrated under reduced pressure to obtain crude compound. The crude was purified by Prep-HPLC (Method A) to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-(2-oxaspiro[3.3]heptan-6-yl)benzamide (27 mg, 6.20% yield) as a solid. $^1$H NMR (400 MHz, DMSO-d$_6$) δ 8.31-8.23 (m, 1H), 7.76 (s, 1H), 7.30-6.98 (m, 4H), 4.63-4.38 (m, 4H), 3.96-3.73 (m, 6H), 3.71-3.61 (m, 1H), 3.43 (s, 1H), 3.18-2.90 (m, 6H), 2.47-2.36 (m, 2H), 2.32-2.12 (m, 6H), 1.98-1.89 (m, 1H), 1.68 (br s, 5H), 1.47-1.34 (m, 2H), 1.32-1.22 (m, 2H), 1.18 (t, J=7.3 Hz, 3H), 1.08-0.90 (m, 4H); LCMS (Method B): Rt 1.24 min, m/z: 701.0 [M+H]$^+$; HPLC (Method A): Rt 2.74 min, 99.96%.

Example 253. N-((1R,5S,6r)-3-Oxabicyclo[3.1.0]hexan-6-yl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide

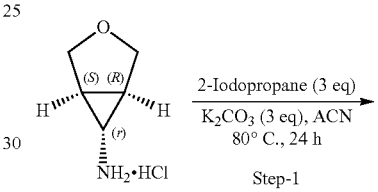

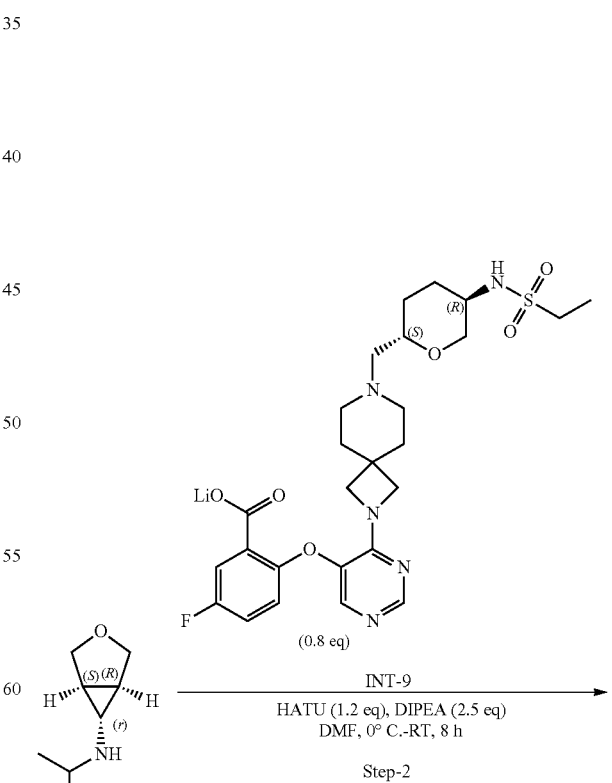

Step 1. (1R,5S,6r)-N-Isopropyl-3-oxabicyclo[3.1.0]hexan-6-amine

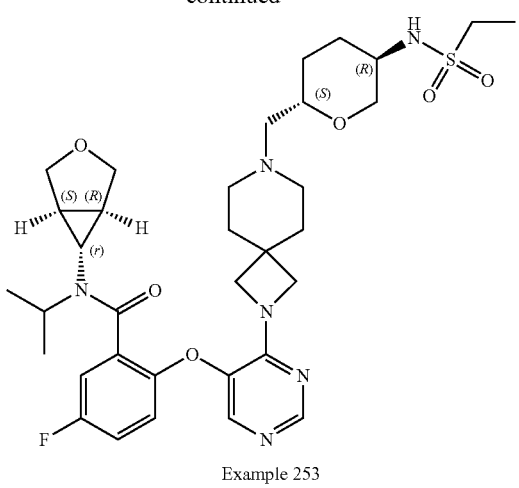

Example 253

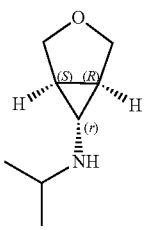

To a dried 25 mL round bottom flask under nitrogen atmosphere, trans-6-amino-3-oxabicyclo[3.1.0]hexane hydrochloride (Habo Hong Kong Co. Limited; CAS No. 1048962-49-7 (100 mg, 0.738 mmol) was added in ACN (10 mL). To this reaction mixture, 2-iodopropane (0.221 mL, 2.213 mmol) and K$_2$CO$_3$ (306 mg, 2.213 mmol) were added at RT, and the reaction was stirred at 80° C. for 24 h. Progress of the reaction was monitored by TLC (10% MeOH in DCM). The reaction mixture was concentrated and diluted with EtOAc (40 mL). The resulting solution was filtered through Celite®, and the filtrate was concentrated under reduced pressure to afford (1R,5S,6r)-N-isopropyl-3-oxabicyclo[3.1.0]hexan-6-amine (130 mg, 82% yield). $^1$H NMR (400 MHz, DMSO-d$_6$) δ 9.18 (br s, 2H), 3.95-3.80 (m, 2H), 3.67-3.44 (m, 2H), 2.30 (br s, 1H), 2.20 (br s, 1H), 1.40-1.32 (m, 2H), 1.26 (d, J=6.4 Hz, 6H).

Step 2. N-((1R,5S,6r)-3-Oxabicyclo[3.1.0]hexan-6-yl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (Example 253)

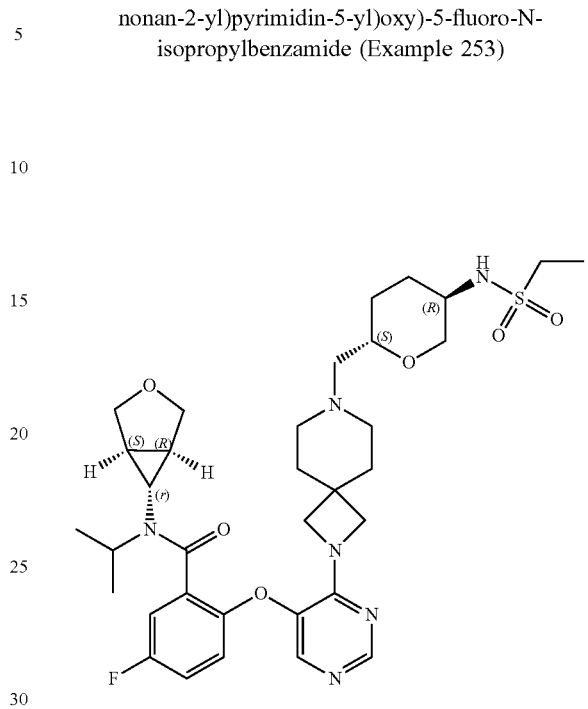

To a dried 25 mL round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (350 mg, 0.621 mmol) was added in DMF (5 mL). To this reaction mixture, DIPEA (0.325 mL, 1.863 mmol), HATU (354 mg, 0.931 mmol), and (1R,5S,6r)-N-isopropyl-3-oxabicyclo[3.1.0]hexan-6-amine (105 mg, 0.745 mmol) were added at RT. The reaction mixture was stirred at RT for 8 h. Progress of the reaction was monitored by TLC (10% MeOH in DCM). The reaction mixture was diluted with water (40 mL) and extracted with EtOAc (3×40 mL). The combined organic layer was dried over sodium sulfate and concentrated under reduced pressure to obtain crude compound. The crude was purified by Prep-HPLC (Method A) to obtain N-((1R,5S,6r)-3-oxabicyclo[3.1.0]hexan-6-yl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (166.61 mg, 39.0% yield) as a solid. $^1$H NMR (400 MHz, DMSO-d$_6$) δ 8.27 (s, 1H), 7.57 (s, 1H), 7.38 (dd, J=3.0, 8.4 Hz, 1H), 7.26 (dt, J=3.1, 8.6 Hz, 1H), 7.15-7.05 (m, 2H), 4.35-4.25 (m, 1H), 3.95-3.74 (m, 6H), 3.53-3.38 (m, 3H), 3.16-2.94 (m, 5H), 2.41 (br s, 1H), 2.32-2.15 (m, 5H), 1.99-1.76 (m, 3H), 1.75-1.61 (m, 5H), 1.50-1.33 (m, 1H), 1.32-1.13 (m, 11H); LCMS (Method 13): Rt 1.63 min, m/z: 687.3 [M+H]$^+$; HPLC (Method A): Rt 4.71 min, 99.86%.

Example 254. 5-Fluoro-N-isopropyl-N-(2-methoxyethyl)-2-((4-(7-(((2S,5R)-5-(phenylsulfonamido)tetrahydro-2H-pyran-2-yl)methyl)-2,7-diazaspiro[3.5]nonan-2-yl)pyrimidin-5-yl)oxy)benzamide

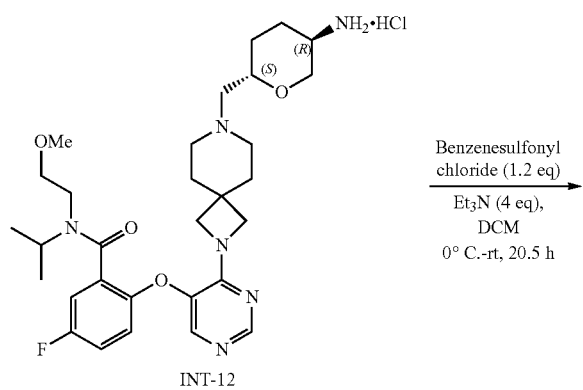

To a dried 25 mL two necked round bottom flask under nitrogen atmosphere, 2-((4-(7-(((2S,5R)-5-aminotetrahydro-2H-pyran-2-yl)methyl)-2,7-diazaspiro[3.5]nonan-2-yl)pyrimidin-5-yl)oxy)-5-fluoro-N-isopropyl-N-(2-methoxyethyl)benzamide hydrochloride (0.3 g, 0.494 mmol) was added in DCM (5 mL). The reaction mixture was cooled to 0° C., and Et$_3$N (0.275 mL, 1.976 mmol) was added, and the reaction was stirred at 0° C. for 0.5 h. To this reaction mixture, benzenesulfonyl chloride (0.105 g, 0.593 mmol) was added, and the reaction was stirred at RT for 20 h. Progress of the reaction was monitored by TLC (10% MeOH in DCM). The reaction was quenched with water (20 mL) and extracted with DCM (2×30 mL). The organic layer was dried over anhydrous sodium sulfate, filtered, and concentrated under reduced pressure to afford the crude compound. The crude was purified by Prep-HPLC (Method C) to obtain 5-fluoro-N-isopropyl-N-(2-methoxyethyl)-2-((4-(7-(((2S,5R)-5-(phenylsulfonamido)tetrahydro-2H-pyran-2-yl)methyl)-2,7-diazaspiro[3.5]nonan-2-yl)pyrimidin-5-yl)oxy)benzamide (65 mg, 18.16% yield) as solid. $^1$H NMR (400 MHz, DMSO-d$_6$) δ 8.27-8.25 (m, 1H), 7.85-7.80 (m, 2H), 7.79-7.72 (m, 1H), 7.69-7.57 (m, 4H), 7.32-7.22 (m, 2H), 7.08-6.99 (m, 1H), 3.94-3.62 (m, 5H), 3.61-3.56 (m, 1H), 3.54-3.41 (m, 2H), 3.41-3.36 (m, 1H), 3.29-3.21 (m, 4H), 3.13 (s, 1H), 3.06-2.87 (m, 2H), 2.32-2.08 (m, 4H), 1.76-1.51 (m, 6H), 1.41-1.13 (m, 4H), 1.13-0.99 (m, 6H); LCMS (Method B): Rt 1.23 min, m/z: (711.2) [M+H]$^+$; HPLC (Method K): Rt 3.72 min, 98.15%.

Example 255. N—((R)-2,3-Dihydroxypropyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide

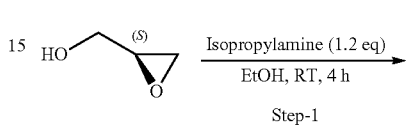

Step-1

Step-2

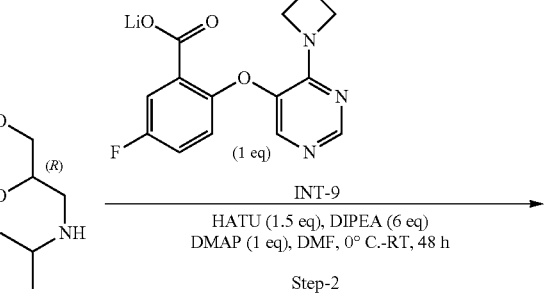

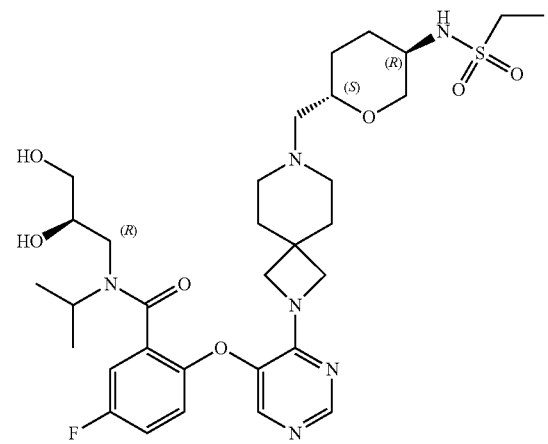

Step 1. (R)-3-(Isopropylamino)propane-1,2-diol

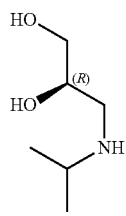

To a dried 100 mL round bottom flask under nitrogen atmosphere, isopropylamine (0.694 mL, 8.10 mmol) was added in EtOH (10 mL). To this reaction mixture, (S)-oxiran-2-ylmethanol (500 mg, 6.75 mmol) was added at RT, and the reaction was stirred at RT for 4 h. The reaction mixture was concentrated under reduced pressure to obtain (R)-3-(isopropylamino)propane-1,2-diol (550 mg, 61.2% yield) as a colorless liquid. The crude compound was used in the next step without further purification.

Step 2: N—((R)-2,3-Dihydroxypropyl)-2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropylbenzamide (Example 255)

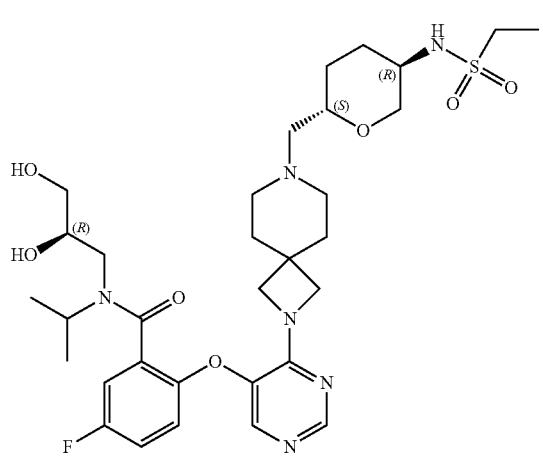

To a dried 100 mL two necked round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (400 mg, 0.710 mmol) was added in DMF (10 mL). To this solution, HATU (405 mg, 1.064 mmol), DIPEA (0.744 mL, 4.26 mmol), and DMAP (87 mg, 0.710 mmol) were added at RT. The reaction was stirred at RT for 30 min. To this reaction mixture, (R)-3-(isopropylamino)propane-1,2-diol (189 mg, 1.419 mmol) was added, and the reaction was continued at RT for 48 h. Progress of the reaction was monitored by TLC (10% MeOH in DCM). The reaction was diluted with water and extracted with EtOAc (3×50 mL). The combined organic layer was dried over sodium sulfate and concentrated under reduced pressure to obtain the crude product. The crude was purified by Prep-HPLC (Method G), and pure fractions were lyophilized to obtain N—((R)-2,3-dihydroxypropyl)-2-((4-(7-(((2S,5R)-5-(ethylsulfonamido) tetrahydro-2H-pyran-2-yl)methyl)-2,7-diazaspiro[3.5] nonan-2-yl)pyrimidin-5-yl)oxy)-5-fluoro-N-isopropylbenzamide (40 mg, 8.19% yield) as a solid. $^1$H NMR (400 MHz, DMSO-d$_6$) δ 8.31-8.24 (m, 1H), 7.80-7.65 (m, 1H), 7.38-7.17 (m, 2H), 7.10 (d, J=7.5 Hz, 1H), 7.05-6.93 (m, 1H), 4.90-4.67 (m, 1H), 4.58-4.44 (m, 1H), 3.96-3.68 (m, 7H), 3.60-3.43 (m, 1H), 3.41-3.34 (m, 2H), 3.18-2.93 (m, 6H), 2.32-2.15 (m, 6H), 1.89-2.00 (m, 1H), 1.67 (br s, 5H), 1.47-1.33 (m, 1H), 1.30-1.21 (m, 3H), 1.18 (t, J=7.3 Hz, 3H), 1.14-1.01 (m, 4H); LCMS (Method B): Rt 2.11 min, m/z: 679.4 [M+H]$^+$; HPLC (Method A): Rt 4.05 min, 98.58%.

Example 256. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((E1)-2-hydroxycyclobutyl)-N-isopropylbenzamide (Isomer-1) and

Example 257. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((E2)-2-hydroxycyclobutyl)-N-isopropylbenzamide (Isomer-2)

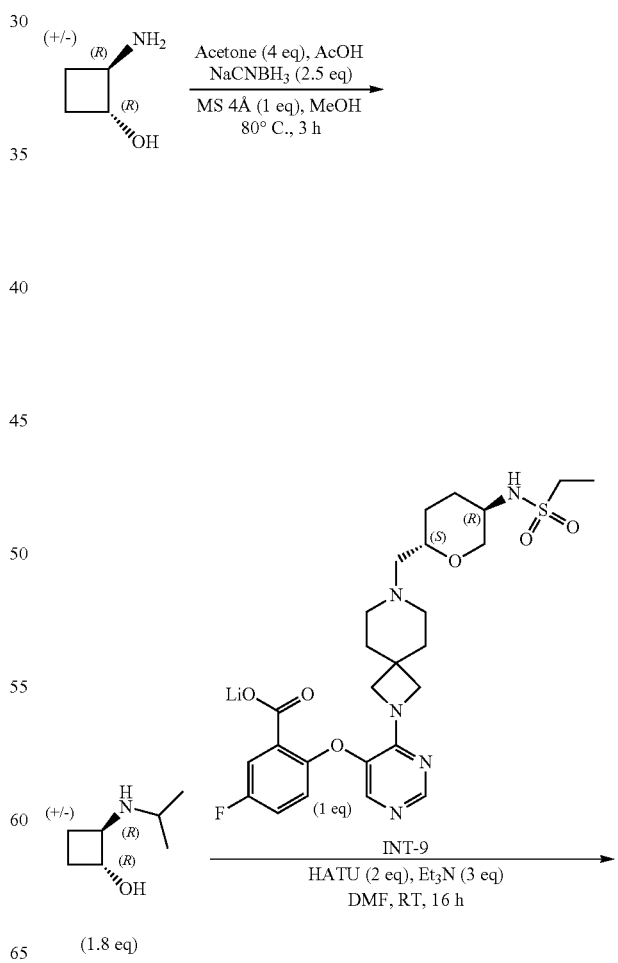

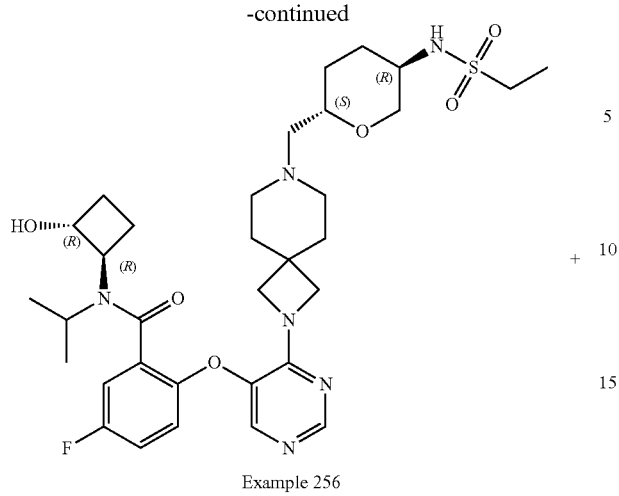

Example 256

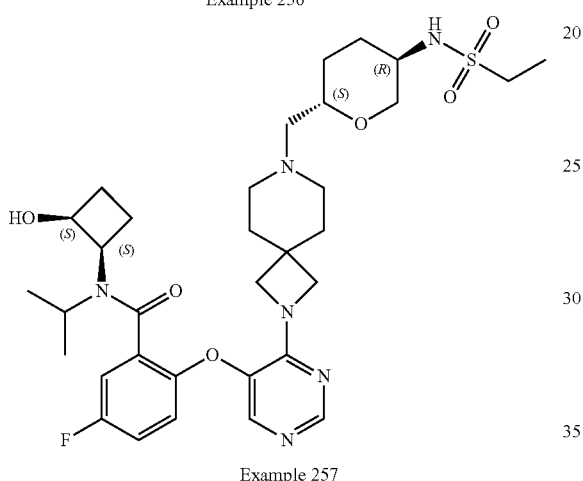

Example 257

Step 1. (1R,2R)-2-(Isopropylamino)cyclobutan-1-ol

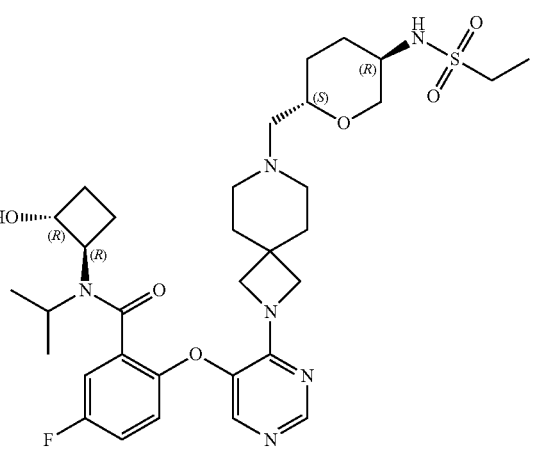

To a 100 mL round bottom flask under nitrogen atmosphere, (±)-trans-2-aminocyclobutan-1-ol (0.225 g, 2.58 mmol) was added in MeOH (15 mL). To this solution, acetone (0.765 mL, 10.33 mmol) and AcOH (0.155 g, 2.58 mmol) were added, and the reaction was stirred for 10 min at RT. To this reaction mixture, NaCNBH₃ (0.406 g, 6.46 mmol) and molecular sieves 4 Å (300 mg) were added at RT, and the reaction was stirred at 80° C. for 3 h. After completion, the reaction mixture was concentrated and diluted with EtOAc (25 mL). The resulting solution was filtered through Celite®, and the filtrate was dried over sodium sulfate, filtered, and concentrated under reduced pressure to afford (1R,2R)-2-(isopropylamino)cyclobutan-1-ol (0.124 g, 37.2% yield) as a semisolid. ¹H NMR (400 MHz, DMSO-d₆) δ 4.05-5.94 (m, 1H), 3.64-3.52 (m, 1H), 2.93-2.84 (m, 1H), 2.83-2.74 (m, 1H), 1.92-1.74 (m, 3H), 1.35-1.21 (m, 1H), 1.03-0.89 (m, 6H).

Step 2. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((E)-2-hydroxycyclobutyl)-N-isopropylbenzamide (Isomer-1) (Example 256)

2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-s-fluoro-N-((E2)-2-hydroxycyclobutyl)-N-isopropylbenzamide (Isomer-2) (Example 257)

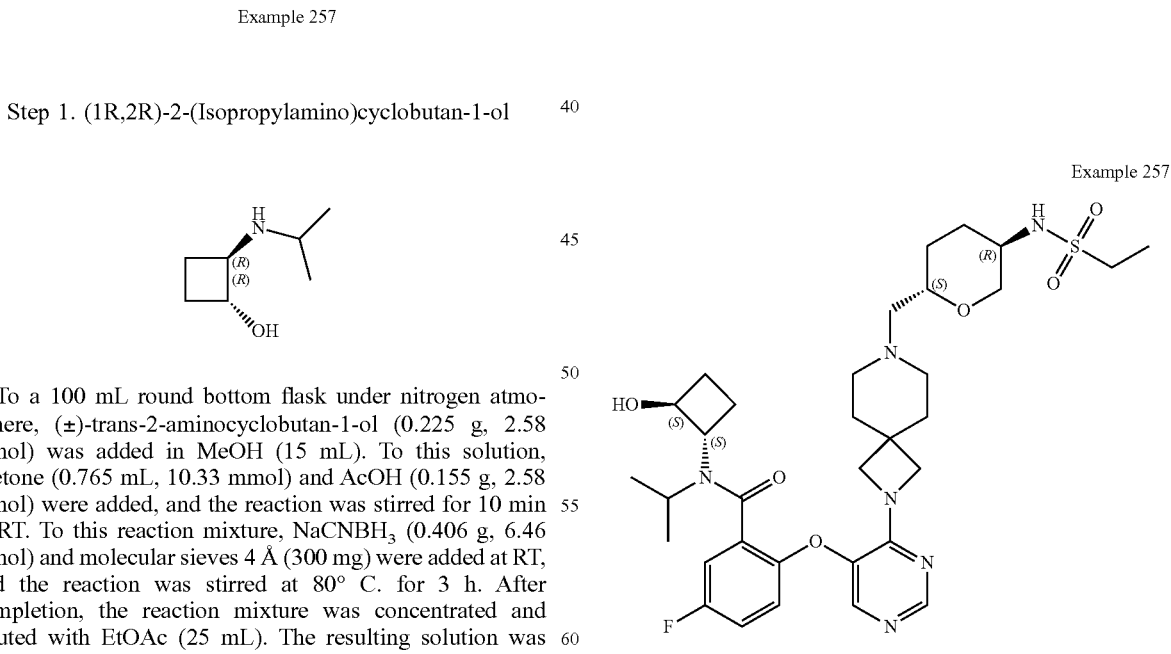

Example 256

Example 257

To a 100 mL round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.3 g, 0.532 mmol) was added in DMF (8 mL). To this reaction mixture, Et₃N (0.223 mL, 1.597 mmol), HATU (0.405 g, 1.064 mmol), and (1R,2R)-2-(isopropylamino)cyclobutan-1-ol (0.124 g, 0.958 mmol) were added at RT. The reaction mixture was stirred at RT for 16 h. Progress of the reaction was monitored by TLC. The reaction mixture was quenched with water (100 mL) and extracted with EtOAc (2×100 mL). The combined organic layer was dried over anhydrous sodium sulfate and concentrated on rotary evaporator to obtain crude. The crude product was purified by Prep-HPLC (Method C) followed by chiral SFC (Method C). The pure fractions were concentrated and lyophilized to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((E1)-2-hydroxycyclobutyl)-N-isopropylbenzamide (Example-256) (0.045 g, 12.40% yield) and 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((E2)-2-hydroxycyclobutyl)-N-isopropylbenzamide (Example-257) (0.04 g, 11.03% yield) as a solids. Note: the absolute stereochemistry of the isomers was assigned arbitrarily.

Example 256 (Isomer-1). 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((E1)-2-hydroxycyclobutyl)-N-isopropylbenzamide

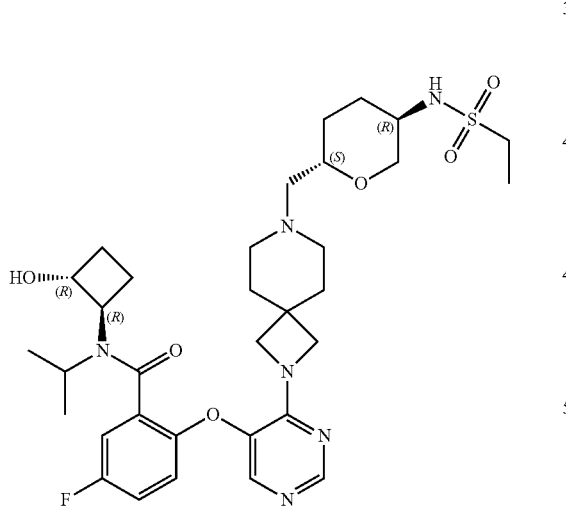

Yield: 12.40%; $^1$H NMR (400 MHz, DMSO-d$_6$) δ 8.33-8.19 (m, 1H), 7.82-7.62 (m, 1H), 7.32-6.92 (m, 4H), 5.57-4.77 (m, 1H), 4.17-3.72 (m, 6H), 3.72-3.39 (m, 2H), 3.17-2.93 (m, 4H), 2.32-2.15 (m, 5H), 2.11-1.75 (m, 3H), 1.75-1.56 (m, 6H), 1.53-1.30 (m, 5H), 1.30-1.22 (m, 3H), 1.18 (t, J=7.3 Hz, 3H), 1.12-0.98 (m, 3H); LCMS (Method A): Rt 2.33 min, m/z: 675.4 [M+H]$^+$; HPLC (Method A): Rt 4.5 min, 99.70%; SFC (Method K): Rt 6.57 min, 98.56%.

Example 257 (Isomer-2). 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((E2)-2-hydroxycyclobutyl)-N-isopropylbenzamide

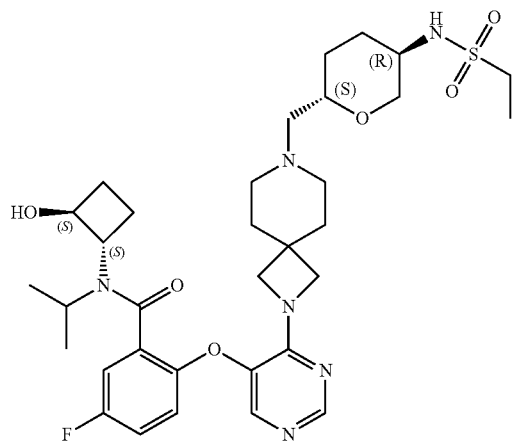

Yield: 11.03%; $^1$H NMR (400 MHz, DMSO-d$_6$) δ 8.35-8.15 (m, 1H), 7.84-7.59 (m, 1H), 7.35-6.91 (m, 4H), 5.54-4.74 (m, 1H), 4.15-3.99 (m, 2H), 3.95-3.75 (m, 5H), 3.71-3.62 (m, 1H), 3.16-2.94 (m, 4H), 2.32-2.16 (m, 5H), 2.12-1.80 (m, 2H), 1.75-1.54 (m, 6H), 1.53-1.34 (m, 5H), 1.31-1.14 (m, 7H), 1.13-0.96 (m, 3H); LCMS (Method A): Rt 2.33 min, 675.4 [M+H]$^+$; HPLC (Method A): Rt 4.50 min, 99.61%; SFC (Method K): Rt 9.64 min, 100%.

Example 258. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-((1R,2S)-2-hydroxycyclobutyl)-N-isopropylbenzamide

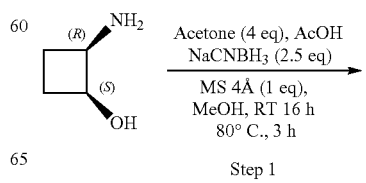

Step 1

-continued

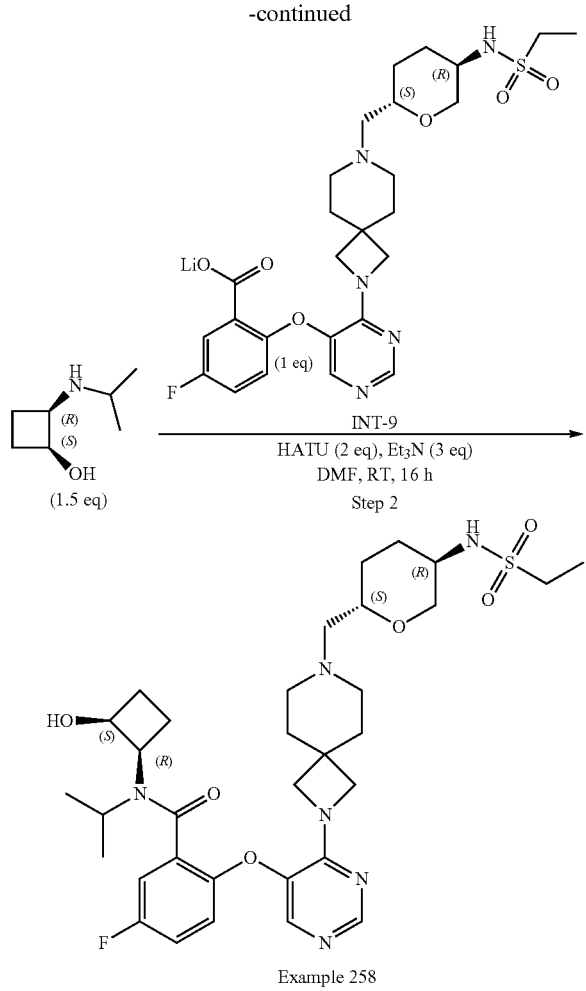

Step 1. (1S,2R)-2-(Isopropylamino)cyclobutan-1-ol

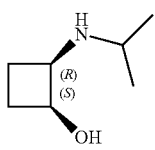

To a 100 mL round bottom flask under nitrogen atmosphere, (1S,2R)-2-aminocyclobutan-1-ol (0.25 g, 2.87 mmol) was added in MeOH (15 mL). To this reaction mixture, acetone (0.850 mL, 11.48 mmol) and AcOH (0.172 g, 2.87 mmol) were added, and the reaction was stirred at RT for 10 min. To this reaction mixture, NaCNBH$_3$ (0.451 g, 7.17 mmol) and molecular sieves 4 Å (300 mg) were added. The reaction was stirred at RT for 16 h and 80° C. for 3 h. After completion, the reaction mixture was concentrated and diluted with EtOAc (25 mL). The solution was filtered through Celite® and concentrated under reduced pressure to obtain (1S,2R)-2-(isopropylamino)cyclobutan-1-ol (0.067 g, 18.07% yield) as a liquid. $^1$H NMR (400 MHz, DMSO-d$_6$) (4.09-4.16 (m, 1H), 3.39-3.30 (m, 2H), 3.26-3.20 (m, 1H), 2.78-2.67 (m, 1H), 1.97-1.87 (m, 2H), 1.72-1.56 (m, 2H), 0.98-0.90 (m, 6H).

Step 2. 2-((4-(7-(((2S,5R)-5-(Ethylsulfonamido)
tetrahydro-2H-pyran-2-yl)methyl)-2,7-diazaspiro
[3.5]nonan-2-yl)pyrimidin-5-yl)oxy)-5-fluoro-N-
((1R,2S)-2-hydroxycyclobutyl)-N-
isopropylbenzamide (Example 258)

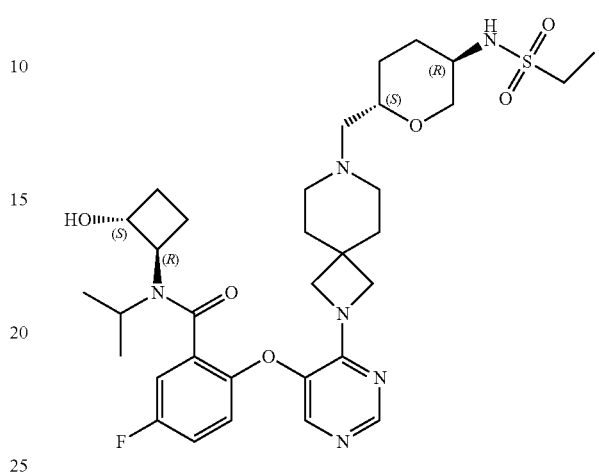

To a 50 mL round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.2 g, 0.355 mmol) was added in DMF (6 mL). To this solution, Et$_3$N (0.148 mL, 1.064 mmol), HATU (0.270 g, 0.710 mmol), and (1S,2R)-2-(isopropylamino)cyclobutan-1-ol (0.069 g, 0.532 mmol) were added at RT. The reaction was stirred at RT for 16 h. Progress of the reaction was monitored by TLC. The reaction mixture was quenched with water (100 mL) and extracted with EtOAc (2×100 mL). The combined organic layer was dried over anhydrous sodium sulfate and concentrated under reduced pressure to obtain crude compound. The crude compound was purified by Prep-HPLC (Method C) and pure fractions were lyophilized to afford 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((1R,2S)-2-hydroxycyclobutyl)-N-isopropylbenzamide (0.05 g, 20.62% yield) as a solid. $^1$H NMR (400 MHz, DMSO-d$_6$) δ 8.32-8.16 (m, 1H), 7.88-7.60 (m, 1H), 7.40-6.99 (m, 4H), 5.36-5.03 (m, 1H), 4.68-4.31 (m, 1H), 4.26-3.64 (m, 7H), 3.17-2.90 (m, 5H), 2.32-2.08 (m, 7H), 2.02-1.78 (m, 3H), 1.67 (m, 5H), 1.59-1.32 (m, 4H), 1.31-0.97 (m, 8H); LCMS (Method A): Rt 2.60 min, m/z: 675.3 [M+H]$^+$; HPLC (Method A): Rt 4.77 min, 98.742%.

Example 259. 2-((4-(7-(((2S,5R)-5-(Ethylsulfona-
mido)tetrahydro-2H-pyran-2-yl)methyl)-2,7-diaz-
aspiro[3.5]nonan-2-yl)pyrimidin-5-yl)oxy)-5-fluoro-
N-((1r,3r)-3-hydroxycyclobutyl)-N-
isopropylbenzamide

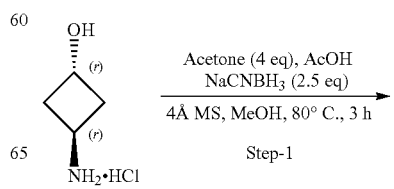

Step-1

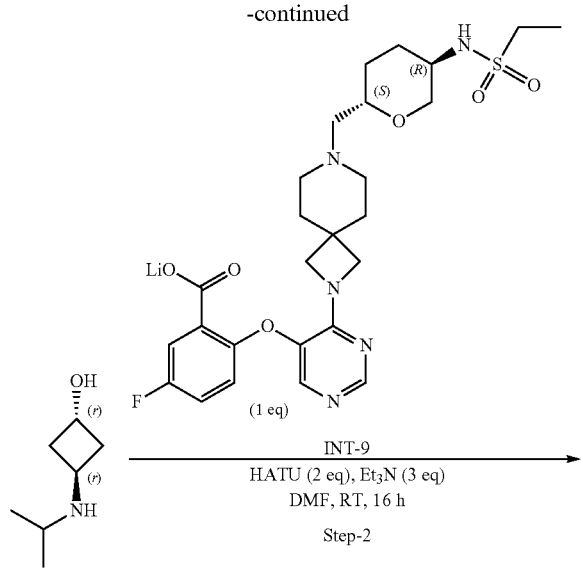

INT-9

HATU (2 eq), Et₃N (3 eq)
DMF, RT, 16 h

Step-2

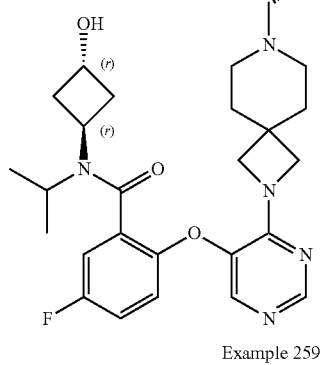

Example 259

Step 1. (1r,3r)-3-(Isopropylamino)cyclobutan-1-ol

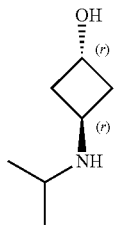

To a 50 mL round bottom flask under nitrogen atmosphere, (1r,3r)-3-aminocyclobutan-1-ol hydrochloride (0.5 g, 4.05 mmol) was added in methanol (15 mL). To this solution, acetone (1.199 mL, 16.18 mmol) and AcOH (0.243 g, 4.05 mmol) were added at RT, and the reaction was stirred for 10 min at RT. To this reaction mixture, NaCNBH₃ (0.636 g, 10.11 mmol) and molecular sieves 4 Å (0.25 g) were added, and the reaction was continued at 80° C. for 3 h. After completion, the reaction mixture was concentrated and diluted with EtOAc (30 mL). The EtOAc layer was filtered through Celite® the filtrate was concentrated under reduced pressure to obtain (1r,3r)-3-(isopropyl amino)cyclobutan-1-ol (0.238 g, 45.5% yield) as a semisolid. The crude compound was used without further purification.

Step 2. 2-((4-(7-(((2S,5R)-5-(Ethylsulfonamido) tetrahydro-2H-pyran-2-yl)methyl)-2,7-diazaspiro [3.5]nonan-2-yl)pyrimidin-5-yl)oxy)-5-fluoro-N-((1r,3r)-3-hydroxycyclobutyl)-N-isopropylbenzamide (Example 259)

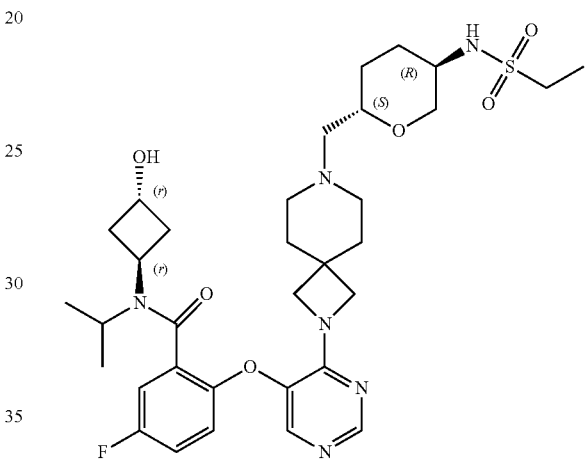

To a 50 mL round bottom flask under nitrogen atmosphere, 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluorobenzoic acid (0.3 g, 0.532 mmol) was added in DMF (8 mL). To this reaction mixture, Et₃N (0.223 mL, 1.597 mmol), HATU (0.405 g, 1.064 mmol), and (1r,3r)-3-(isopropylamino)cyclobutan-1-ol (0.138 g, 1.064 mmol) were added at RT. The reaction mixture was stirred at RT for 16 h. Progress of the reaction was monitored by TLC. The reaction mixture was quenched with water (100 mL) and extracted with EtOAc (2×100 mL). The combined organic layer was dried over anhydrous sodium sulfate and concentrated on a rotary evaporator to obtain the crude compound. The crude was purified by Prep-HPLC (Method A) to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-((1r,3r)-3-hydroxycyclobutyl)-N-isopropylbenzamide (0.105 g, 28.9% yield) as a solid. ¹H NMR (400 MHz, DMSO-d₆) δ 8.26 (d, J=7.3 Hz, 1H), 7.73-7.68 (m, 1H), 7.31-7.01 (m, 4H), 4.91 (t, J=4.1 Hz, 1H), 4.44-4.32 (m, 1H), 4.22-4.02 (m, 1H), 3.98-3.73 (m, 5H), 3.72-3.62 (m, 1H), 3.23-2.90 (m, 5H), 2.32-2.14 (m, 6H), 2.10-1.76 (m, 4H), 1.67 (br s, 5H), 1.48-1.33 (m, 3H), 1.32-1.21 (m, 3H), 1.18 (t, J=7.3 Hz, 3H), 1.08-0.93 (m, 3H); LCMS (Method C): Rt 1.27 min, m/z: 675.3 [M+H]⁺; HPLC (Method A): Rt 4.37 min, 99.58%.

Example 260. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-phenylbenzamide

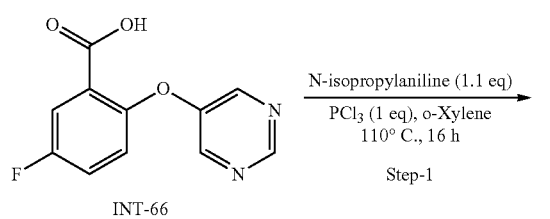

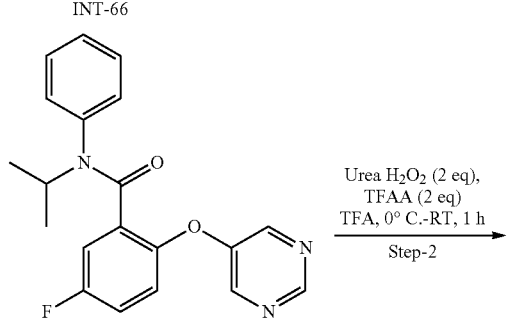

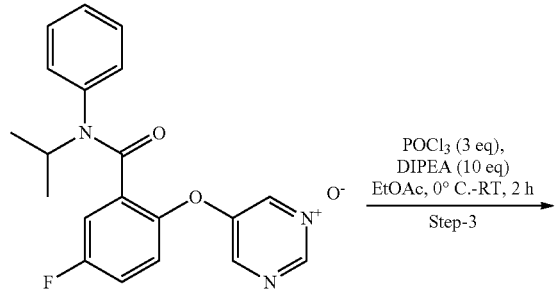

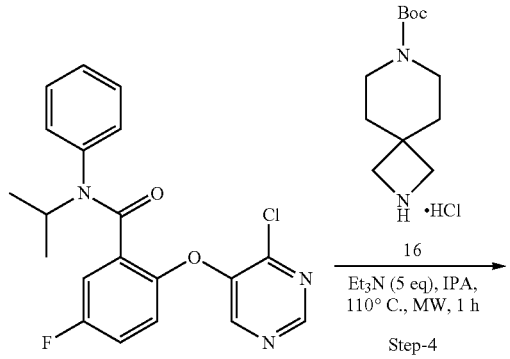

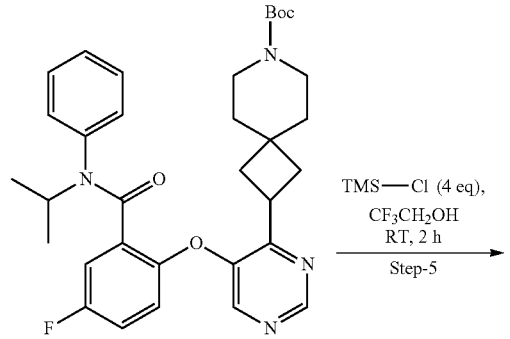

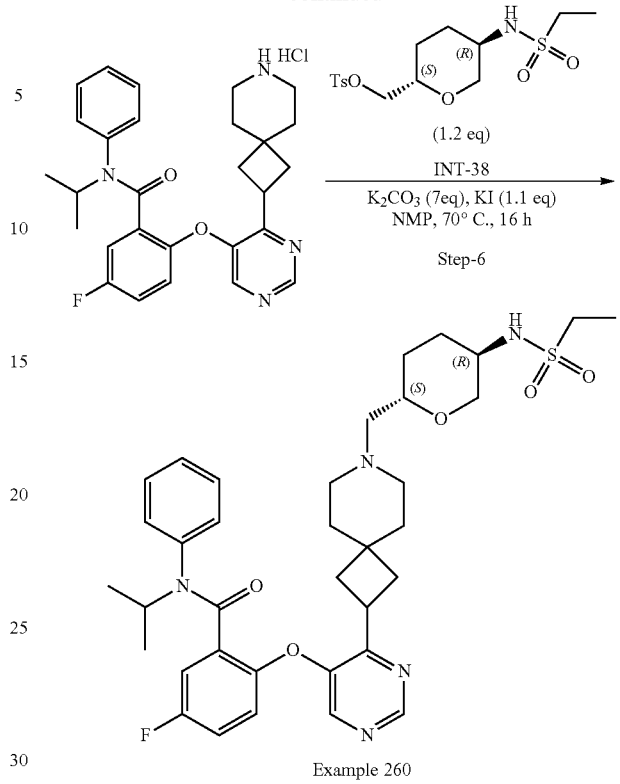

Step 1. 5-Fluoro-N-isopropyl-N-phenyl-2-(pyrimidin-5-yloxy)benzamide

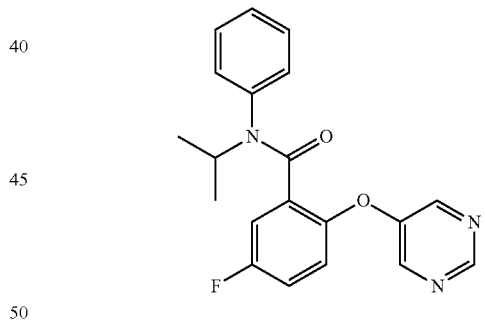

To a 100 mL two neck round bottom flask under nitrogen atmosphere, 5-fluoro-2-(pyrimidin-5-yloxy)benzoic acid (1.6 g, 6.83 mmol) was added in o-xylene (25 mL). To this reaction mixture, N-isopropylaniline (1.109 g, 8.20 mmol) and PCl₃ (0.598 mL, 6.83 mmol) were added at RT. The reaction mixture was stirred at 110° C. for 16 h. Progress of the reaction was monitored by TLC. The reaction mixture was concentrated, diluted with aqueous NaHCO₃ solution (15 mL), and extracted with EtOAc (100 mL). The combined organic layer was dried over anhydrous sodium sulfate, filtered, and concentrated under reduced pressure to obtain the crude product. The crude product was purified by silica gel column chromatography using 40% EtOAc in hexane as an eluent to obtain 5-fluoro-N-isopropyl-N-phenyl-2-(pyrimidin-5-yloxy)benzamide (1.14 g, 43.2% yield) as a semisolid. ¹H NMR (400 MHz, CDCl₃) δ 8.05-9.90 (m, 1H), 8.48-8.32 (m, 2H), 7.32-7.22 (m, 3H), 7.14-7.02 (m, 2H), 6.99-6.66 (m, 3H), 5.95-4.18 (m, 1H), 1.22-1.08 (m, 6H); LCMS (Method A): Rt 1.66 min, m/z: 352.1 [M+H]$^+$, 91.42%.

Step 2. 5-(4-Fluoro-2-(isopropyl(phenyl)carbamoyl) phenoxy)pyrimidine 1-oxide

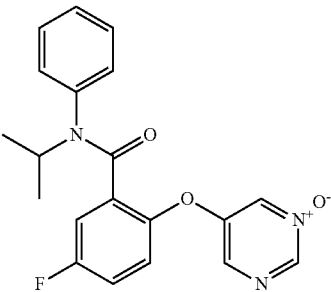

To a 100 mL two neck round bottom flask under nitrogen atmosphere, 5-fluoro-N-isopropyl-N-phenyl-2-(pyrimidin-5-yloxy)benzamide (1.14 g, 3.24 mmol) was added in THF (15 mL). To this solution, urea hydrogen peroxide (0.610 g, 6.49 mmol) was added, and TFAA (0.915 mL, 6.49 mmol) was added dropwise over a period of 1 h at 0° C. After completion, the reaction mixture was quenched with aqueous sodium bicarbonate solution (15 mL) and extracted with EtOAc (3×25 mL). The combined organic layer was dried over sodium sulfate, filtered, and concentrated under reduced pressure to obtain crude 5-(4-fluoro-2-(isopropyl (phenyl)carbamoyl)phenoxy)pyrimidine 1-oxide (1.2 g, 87% yield) as a sticky liquid. This compound was used without further purification. LCMS (Method A): Rt 1.61 min, m/z: 368.1 [M+H]$^+$, 86.16%.

Step 3. 2-((4-Chloropyrimidin-5-yl)oxy)-5-fluoro-N-isopropyl-N-phenylbenzamide

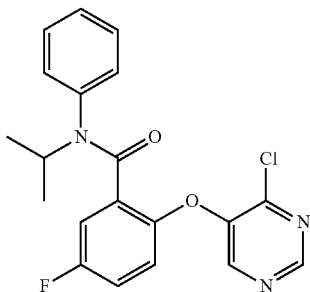 [SMILES: CC(C)N(C(=O)c1cc(F)ccc1Oc1cncnc1Cl)c1ccccc1]

To a 100 mL round bottom flask under nitrogen atmosphere, 5-(4-fluoro-2-(isopropyl(phenyl)carbamoyl)phenoxy)pyrimidine 1-oxide (1.2 g, 3.27 mmol) was added in EtOAc (25 mL). To this reaction mixture, DIPEA (5.69 mL, 32.7 mmol) was added at −5° C., and POCl$_3$ (0.916 mL, 9.80 mmol) was added at 0° C. over a period of 10 min. The reaction mixture was stirred at RT for 2 h. Progress of the reaction was monitored by TLC (20% EtOAc in hexane). After completion, the reaction mixture was quenched with ice and basified with Na$_2$CO$_3$ solution to pH 8. The resulting mixture was extracted with EtOAc (3×35 mL). The combined organic layer was dried over anhydrous Na$_2$SO$_4$, filtered, and concentrated under reduced pressure to afford the crude compound. The crude compound was purified by silica gel column chromatography using 50% EtOAc in hexane as an eluent to obtain 2-((4-chloropyrimidin-5-yl) oxy)-5-fluoro-N-isopropyl-N-phenylbenzamide (0.575 g, 42.4% yield) as a semisolid. $^1$H NMR (400 MHz, CDCl$_3$) δ 8.77-8.74 (m, 1H), 8.16-8.12 (m, 1H), 7.28-7.21 (m, 5H), 6.94-6.88 (m, 2H), 6.76 (dd, J=8.76, 4.38 Hz, 1H), 5.08-5.00 (m, 1H), 1.18 (d, J=6.88 Hz, 6H); LCMS (Method A): Rt 1.77 min, m/z: 386.0 [M+H]$^+$, 81.41%.

Step 4. tert-Butyl 2-(5-(4-Fluoro-2-(isopropyl(phenyl)carbamoyl) phenoxy)pyrimidin-4-yl)-2,7-diazaspiro[3.5]nonane-7-carboxylate

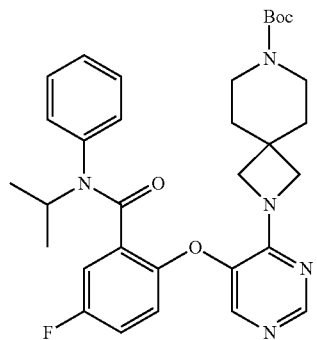 [SMILES: CC(C)N(C(=O)c1cc(F)ccc1Oc1cncnc1N1CC2(CCN(C(=O)OC(C)(C)C)CC2)C1)c1ccccc1]

To a 30 mL microwave vial under nitrogen atmosphere, tert-butyl 2,7-diazaspiro[3.5]nonane-7-carboxylate hydrochloride (0.34 g, 1.294 mmol) was added in IPA (10 mL). To this solution, Et$_3$N (0.902 mL, 6.47 mmol) and 2-((4-chloropyrimidin-5-yl)oxy)-5-fluoro-N-isopropyl-N-phenylbenzamide (0.499 g, 1.294 mmol) were added at RT. The reaction mixture was stirred under microwave condition at 110° C. for 1 h. Progress of the reaction progress was monitored by TLC. After completion, the reaction mixture was concentrated under reduced pressure to obtain the crude product. The crude product was purified by silica gel column chromatography using 100% EtOAc as an eluent to obtain tert-butyl 2-(5-(4-fluoro-2-(isopropyl(phenyl)carbamoyl) phenoxy)pyrimidin-4-yl)-2,7-diazaspiro[3.5]nonane-7-carboxylate (0.5 g, 63.8% yield) as a solid. $^1$H NMR (400 MHz, CDCl$_3$) δ 8.46-8.38 (m, 1H), 7.58-7.48 (m, 1H), 7.28-7.26 (m, 3H), 7.09-7.03 (m, 2H), 6.95-6.90 (m, 1H), 6.85-6.74 (m, 1H), 6.55-6.47 (m, 1H), 5.14-5.03 (m, 1H), 4.07-3.98 (m, 4H), 3.44-3.36 (m, 4H), 1.81-1.75 (m, 4H), 1.50-1.46 (m, 9H), 1.23-1.17 (m, 6H); LCMS (Method A): Rt 1.94 min, m/z: 576.3 [M+H]$^+$, 95.27%.

Step 5. 2-((4-(2,7-Diazaspiro[3.5]nonan-2-yl)pyrimidin-5-yl)oxy)-5-fluoro-N-isopropyl-N-phenylbenzamide hydrochloride

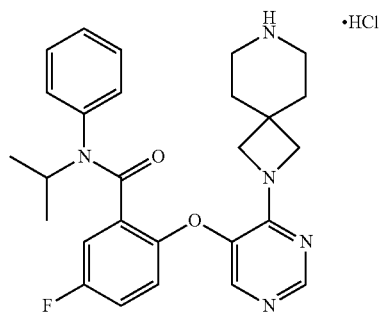 [SMILES: Cl ; CC(C)N(C(=O)c1cc(F)ccc1Oc1cncnc1N1CC2(CCNCC2)C1)c1ccccc1]

To a 50 mL round bottom flask under nitrogen atmosphere, tert-butyl 2-(5-(4-fluoro-2-(isopropyl(phenyl) carbamoyl)phenoxy)pyrimidin-4-yl)-2,7-diazaspiro[3.5]nonane-7-carboxylate (0.58 g, 1.007 mmol) was added in trifluoroethanol (8 mL). To this solution, TMS-Cl (0.511 mL, 4.03 mmol) was added at 0° C. and the reaction was stirred at RT for 1 h. After completion, the reaction mixture was concentrated under reduced pressure to obtain 2-((4-(2, 7-diazaspiro[3.5]nonan-2-yl)pyrimidin-5-yl)oxy)-5-fluoro-N-isopropyl-N-phenylbenzamide hydrochloride (0.52 g, 97% yield) as a solid. LCMS (Method A): Rt 1.50 min, m/z: 476.4 [M+H]$^+$, 98.39%.

Step 6. 2-((4-(7-(((2S,5R)-5-(Ethylsulfonamido) tetrahydro-2H-pyran-2-yl)methyl)-2,7-diazaspiro [3.5]nonan-2-yl)pyrimidin-5-yl)oxy)-5-fluoro-N-isopropyl-N-phenylbenzamide (Example 260)

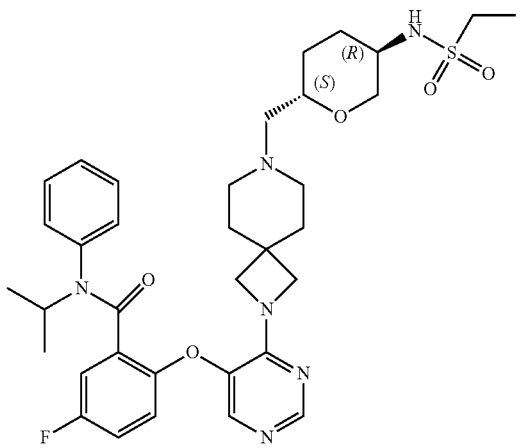

To a 50 mL round bottom flask under nitrogen atmosphere, 2-((4-(2,7-diazaspiro[3.5]nonan-2-yl)pyrimidin-5-yl)oxy)-5-fluoro-N-isopropyl-N-phenylbenzamide hydrochloride (0.52 g, 1.016 mmol) was added in NMP (15 mL). To this solution, K$_2$CO$_3$ (0.982 g, 7.11 mmol), KI (0.185 g, 1.117 mmol), and ((2S,5R)-5-(ethylsulfonamido)tetrahydro-2H-pyran-2-yl)methyl 4-methylbenzenesulfonate (0.460 g, 1.219 mmol)) were added at RT. The reaction mixture was stirred at 70° C. for 16 h. After completion, the reaction was quenched with water (25 mL) and extracted with EtOAc (3×50 mL). The combined organic layer was dried over sodium sulfate and concentrated under reduced pressure to obtain the crude product. The crude compound was purified by Prep-HPLC (Method G) to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N-isopropyl-N-phenylbenzamide (0.3 g, 43.0% yield) as a solid. $^1$H NMR (400 MHz, DMSO-d$_6$) δ 8.30 (s, 1H), 7.46 (s, 1H), 7.34-7.14 (m, 6H), 7.10 (d, J=7.6 Hz, 1H), 6.96 (dd, J=3.2, 8.6 Hz, 1H), 6.68 (dd, J=4.4, 9.1 Hz, 1H), 4.92-4.89 (m, 1H), 3.94-3.76 (m, 5H), 3.50-3.39 (m, 1H) 3.18-2.93 (m, 4H), 2.32-2.14 (m, 6H), 1.99-1.90 (m, 1H), 1.73-1.61 (m, 5H), 1.47-1.33 (m, 1H), 1.32-1.23 (m, 1H), 1.16 (t, J=7.2 Hz, 3H), 1.07 (d, J=6.8 Hz, 6H); LCMS (Method A): Rt 1.87 min, m/z: 681.0 [M+H]$^+$; HPLC (Method A): Rt 5.46 min, 99.14%.

Example 261. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N,N-diphenylbenzamide

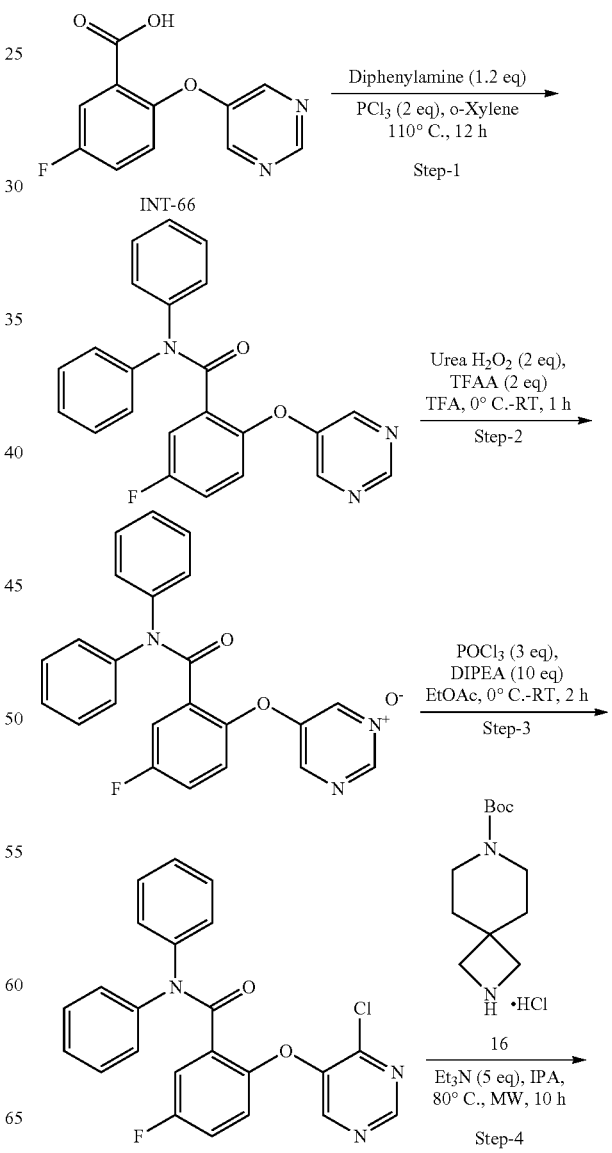

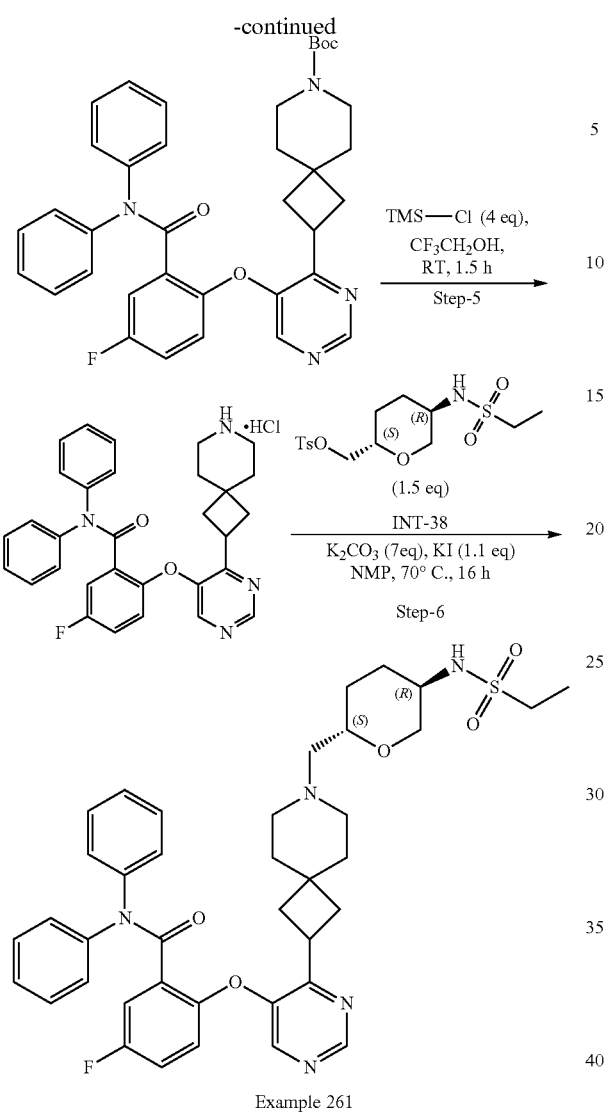

Example 261

Step 1. 5-Fluoro-N,N-diphenyl-2-(pyrimidin-5-yloxy)benzamide

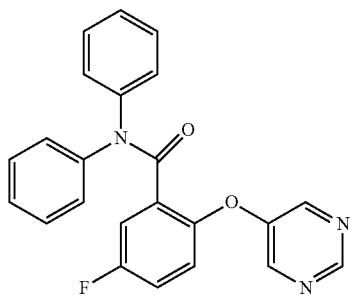 [SMILES: O=C(c1cc(F)ccc1Oc1cncnc1)N(c1ccccc1)c1ccccc1]

To a 100 mL two neck round bottom flask under nitrogen atmosphere, 5-fluoro-2-(pyrimidin-5-yloxy)benzoic acid (3 g, 12.81 mmol) was added in o-xylene (50 mL). To this solution, diphenylamine (2.60 g, 15.37 mmol) and PCl$_3$ (2.241 mL, 25.6 mmol) were added at RT, and the reaction was stirred at 110° C. for 12 h. Progress of the reaction was monitored by TLC. The reaction mixture was concentrated, quenched with NaHCO$_3$ solution (15 mL), and extracted with EtOAc (3×40 mL). The organic layer was dried over anhydrous sodium sulfate, filtered, and concentrated under reduced pressure to obtain the crude product. The crude product was purified by silica gel column chromatography using 50% EtOAc in hexane as an eluent to obtain 5-fluoro-N,N-diphenyl-2-(pyrimidin-5-yloxy)benzamide (0.66 g, 8.09% yield) as a solid. LCMS (Method A): Rt 1.87 min, m/z: 386.3 [M+H]$^+$, 60.56%.

Step 2. 5-(2-(Diphenylcarbamoyl)-4-fluorophenoxy) pyrimidine 1-oxide

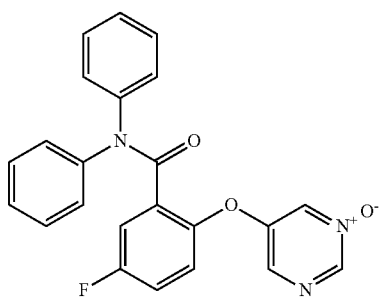

To a 100 mL round bottom flask under nitrogen atmosphere, 5-fluoro-N,N-diphenyl-2-(pyrimidin-5-yloxy)benzamide (0.66 g, 1.713 mmol) was added in THF (15 mL). To this solution, urea hydrogen peroxide (0.322 g, 3.43 mmol) was added, and TFAA (0.476 mL, 3.43 mmol) was added dropwise, maintaining the reaction temperature below 10° C. The reaction mixture was stirred at 10° C. for 1 h. After completion, the reaction mixture was quenched with sodium bicarbonate solution (12 mL) and extracted with EtOAc (3×35 mL). The combined organic layers were dried over sodium sulfate, filtered, and concentrated under reduced pressure to obtain crude 5-(2-(diphenylcarbamoyl)-4-fluorophenoxy)pyrimidine 1-oxide (0.7 g, 58.8% yield) as a light yellow gum. LCMS (Method A): Rt 1.74 min, m/z: 402.1 [M+H]$^+$, 57.75%. This product was used without further purification.

Step 3. 2-((4-Chloropyrimidin-5-yl)oxy)-5-fluoro-N,N-diphenylbenzamide

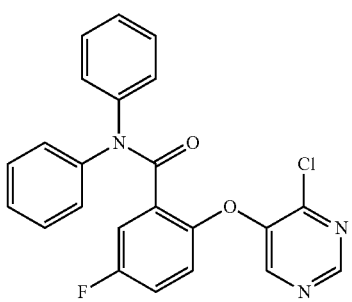 [SMILES: O=C(c1cc(F)ccc1Oc1cncnc1Cl)N(c1ccccc1)c1ccccc1]

To a 100 mL round bottom flask under nitrogen atmosphere, 5-(2-(diphenylcarbamoyl)-4-fluorophenoxy)pyrimidine 1-oxide (0.7 g, 1.744 mmol) was added in EtOAc (15 mL). To this reaction mixture, DIPEA (3.04 mL, 17.44 mmol) was added at −5° C. POCl₃ (0.489 mL, 5.23 mmol) was added to the reaction mixture over a period of 10 min at 0° C. The reaction was stirred at RT for 2 h. Progress of the reaction was monitored by TLC (20% EtOAc in hexane). After completion, the reaction mixture was concentrated under reduced pressure to afford the crude compound. The crude compound was purified by silica gel column chromatography using 50% EtOAc in hexane as an eluent to obtain 2-((4-chloropyrimidin-5-yl)oxy)-5-fluoro-N,N-diphenylbenzamide (0.35 g, 36.4% yield) as a semi solid. ¹H NMR (400 MHz, DMSO-d₆) δ 8.84-8.80 (m, 1H), 8.04-8.00 (m, 1H), 7.62-7.57 (m, 1H), 7.33-7.26 (m, 7H), 7.24-7.15 (m, 5H); LCMS (Method A): Rt 2.11 min, m/z: 420.2 [M+H]⁺, 76.23%.

Step 4. tert-Butyl 2-(5-(2-(Diphenylcarbamoyl)-4-fluorophenoxy)pyrimidin-4-yl)-2,7-diazaspiro[3.5]nonane-7-carboxylate

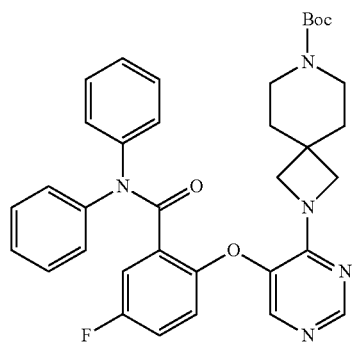 [SMILES: CC(C)(C)OC(=O)N1CCC2(CC1)CN(c1ncncc1Oc1ccc(F)cc1C(=O)N(c1ccccc1)c1ccccc1)C2]

To a 100 mL round bottom flask under nitrogen atmosphere, tert-butyl 2,7-diazaspiro[3.5]nonane-7-carboxylate hydrochloride (0.22 g, 0.837 mmol) was added in IPA (10 mL). To this solution, Et₃N (0.583 mL, 4.19 mmol) and 2-((4-chloropyrimidin-5-yl)oxy)-5-fluoro-N,N-diphenylbenzamide (0.351 g, 0.837 mmol) were added at RT. The reaction mixture was stirred at 80° C. for 10 h. Progress of the reaction was monitored by TLC. The reaction mixture was concentrated under reduced pressure to obtain the crude compound. The crude compound was purified by silica gel column chromatography using 4% MeOH in DCM as an eluent to obtain tert-butyl 2-(5-(2-(diphenylcarbamoyl)-4-fluorophenoxy)pyrimidin-4-yl)-2,7-diazaspiro [3.5] nonane-7-carboxylate (0.38 g, 68.5% yield) as a solid. ¹H NMR (400 MHz, DMSO-d₆) δ 8.34-8.30 (m, 1H), 7.52-7.47 (m, 1H), 7.36-7.21 (m, 1H), 7.14-7.07 (m, 1H), 6.77-6.71 (m, 1H), 3.93-3.86 (m, 4H), 3.30-3.25 (m, 4H), 1.71-1.64 (m, 4H), 1.41-1.39 (m, 9H); LCMS (Method A): Rt 2.21 min, m/z: 610.3 [M+H]⁺, 91.47%.

Step 5. 2-((4-(2,7-Diazaspiro[3.5]nonan-2-yl)pyrimidin-5-yl)oxy)-5-fluoro-N,N-diphenyl benzamide hydrochloride

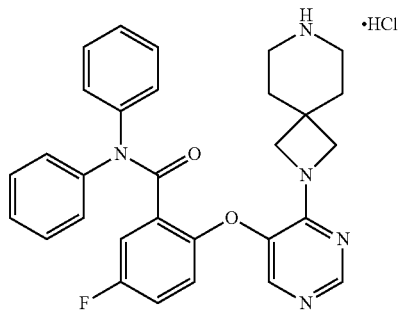 [SMILES: Cl ; O=C(c1cc(F)ccc1Oc1cncnc1N1CC2(CCNCC2)C1)N(c1ccccc1)c1ccccc1]

To a 50 mL two neck round bottom flask under nitrogen atmosphere, tert-butyl 2-(5-(2-(diphenylcarbamoyl)-4-fluorophenoxy)pyrimidin-4-yl)-2,7-diazaspiro[3.5]nonane-7-carboxylate (0.38 g, 0.623 mmol) was added in trifluoroethanol (8 mL). To this solution, TMS-Cl (0.237 mL, 1.870 mmol) was added at 0° C., and the reaction was stirred at RT for 1.5 h. After completion, the reaction mixture was concentrated under reduced pressure to obtain 2-((4-(2,7-diazaspiro[3.5]nonan-2-yl)pyrimidin-5-yl)oxy)-5-fluoro-N,N-diphenylbenzamide hydrochloride (0.35 g, 99% yield) as a solid. LCMS (Method A): Rt 1.87 min, m/z: 510.2 [M+H]⁺, 96.63%. The product crude product was used without further purification.

Step 6. 2-((4-(7-(((2S,5R)-5-(Ethylsulfonamido)tetrahydro-2H-pyran-2-yl)methyl)-2,7-diazaspiro[3.5]nonan-2-yl)pyrimidin-5-yl)oxy)-5-fluoro-N,N-diphenylbenzamide (Example 261)

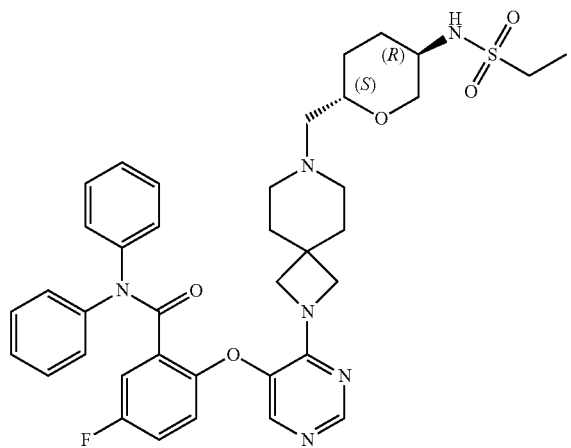

To a 50 mL round bottom flask under nitrogen atmosphere, 2-((4-(2,7-diazaspiro[3.5]nonan-2-yl)pyrimidin-5-yl)oxy)-5-fluoro-N,N-diphenylbenzamide hydrochloride (0.35 g, 0.641 mmol) was added in NMP (12 mL). To this solution, K₂CO₃ (0.620 g, 4.49 mmol), KI (0.117 g, 0.705 mmol), and ((2S,5R)-5-(ethylsulfonamido)tetrahydro-2H-pyran-2-yl)methyl 4-methylbenzenesulfonate (0.363 g, 0.961 mmol) were added at RT. The reaction mixture was stirred at 70° C. for 16 h. After completion, the reaction was quenched with water (25 mL) and extracted with EtOAc (3×50 mL). The combined organic layer was dried over sodium sulfate and concentrated under reduced pressure to obtain the crude compound. The crude compound was purified by Prep-HPLC (Method B) and pure fractions were lyophilized to obtain 2-((4-(7-(((2S,5R)-5-(ethylsulfonamido)tetrahydro-2H-pyran-2-yl)methyl)-2,7-diazaspiro[3.5]nonan-2-yl)pyrimidin-5-yl)oxy)-5-fluoro-N,N-diphenylbenzamide (0.11 g, 22.88% yield) as a solid. $^1$H NMR (400 MHz, DMSO-$d_6$) δ 8.31 (s, 1H), 7.57-7.16 (m, 12H), 7.14-7.06 (m, 2H), 6.73 (dd, J=4.3, 9.1 Hz, 1H), 3.94-3.75 (m, 5H), 3.38-3.28 (m, 1H), 3.18-2.91 (m, 5H), 2.32-2.15 (m, 5H), 2.00-1.90 (m, 1H), 1.77-1.61 (m, 5H), 1.60-1.31 (m, 1H), 1.29-1.22 (m, 1H), 1.18 (t, J=7.3 Hz, 3H); LCMS (Method C): Rt 2.16 min, m/z: 713.3 [M−H]$^−$; HPLC (Method A): Rt 5.66 min, 95.34%.

Example 262: N-(2,2-Difluoroethyl)-2-((4-(7-(((2S,5R)-5-((N-(ethyl-$d_5$)sulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide

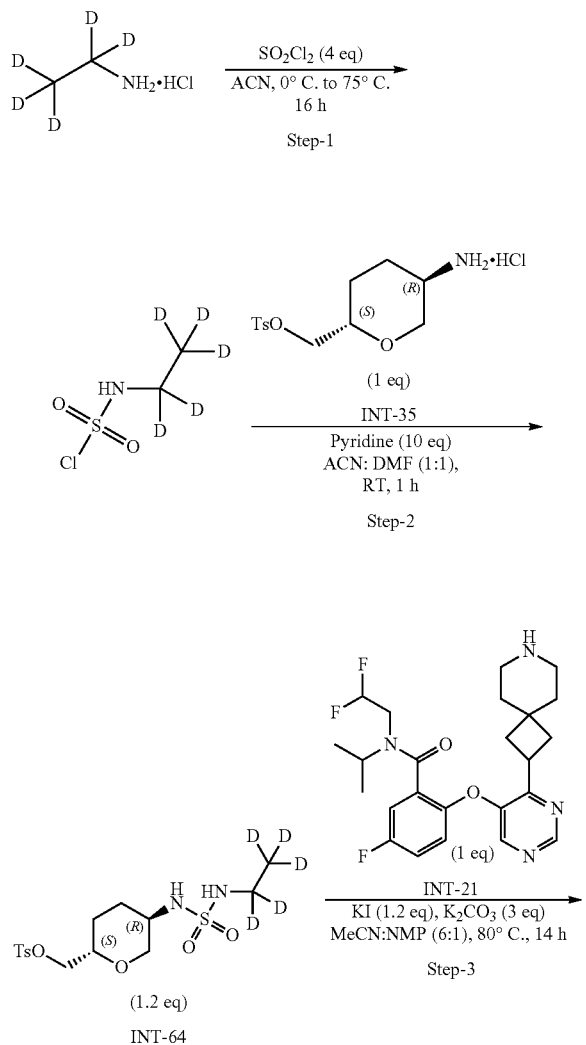

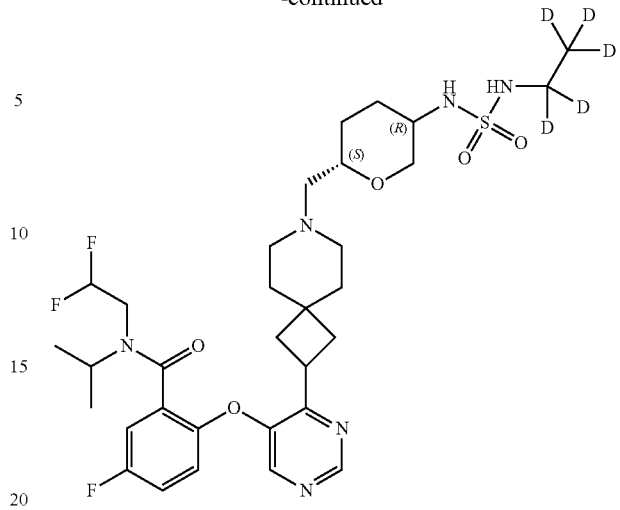

Step 1. (Ethyl-$d_5$)sulfamoyl chloride

To a 25 mL round bottom flask under nitrogen atmosphere, ethan-$d_5$-1-amine hydrochloride (250 mg, 2.89 mmol) was added in ACN (2.5 mL). To this solution, sulfuryl chloride (1559 mg, 11.55 mmol) was added at 0° C., and the reaction mixture was stirred at 75° C. for 16 h. The reaction mixture was concentrated under reduced pressure, and the resulting crude compound was triturated with methyl tert-butyl ether. The solid material was removed by filtration, and the filtrate was concentrated under reduced pressure to obtain crude (ethyl-$d_5$)sulfamoyl chloride (350 mg). This crude material was used in the next step without further purification.

Step 2. ((2S,5R)-5-((N-(Ethyl-$d_5$)sulfamoyl)amino)tetrahydro-2H-pyran-2-yl)methyl 4-methylbenzenesulfonate To a 25 mL round bottom flask under nitrogen atmosphere, ((2S,5R)-5-aminotetrahydro-2H-pyran-2-yl)methyl 4-methylbenzenesulfonate hydrochloride (300 mg, 0.93 mmol) was added in ACN:DMF (1:1) (3 mL). To this solution, pyridine (0.75 mL, 9.32 mmol) was added, and the mixture was stirred at RT for 2 min. To this reaction, (ethyl-$d_5$)sulfamoyl chloride (346 mg, 2.33 mmol) was added at 0° C., and the reaction was stirred for 1 h. The progress of the reaction was monitored by TLC (10% MeOH in DCM). The reaction mixture was diluted with water (25 mL) and extracted with EtOAc (2×50 mL). The combined organic layer was washed with water (2×50 mL) and brine solution (50 mL). The organic layer was dried over anhydrous Na$_2$SO$_4$ and filtered, and the filtrate was concentrated under reduced pressure to obtain the crude compound.

The crude compound was purified by silica gel column chromatography using 50% EtOAc in hexane as an eluent to obtain ((2S,5R)-5-((N-(ethyl-$d_5$)sulfamoyl)amino)tetrahydro-2H-pyran-2-yl)methyl 4-methylbenzenesulfonate (80 mg, 21.6%). $^1$H NMR (400 MHz, DMSO-$d_6$) δ 7.78 (d, J=8.4 Hz, 2H), 7.49 (d, J=8.0 Hz, 2H), 6.87 (d, J=7.2 Hz, 1H), 6.76 (s, 1H), 4.07-3.96 (m, 1H), 3.94-3.83 (m, 2H), 3.44-3.35 (m, 1H), 3.03-2.92 (m, 2H), 2.43 (s, 3H), 1.97-1.89 (m, 1H), 1.61-1.51 (m, 1H), 1.21-1.41 (m, 2H); LCMS (Method B): Rt 1.86 min, m/z: 398.1 [M+H]$^+$, 98.26%.

Step 3. N-(2,2-Difluoroethyl)-2-((4-(7-(((2S,5R)-5-((N-(ethyl-d₅)sulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide To a 25 mL round bottom flask under nitrogen atmosphere, 2-((4-(2,7-diazaspiro[3.5]nonan-2-yl)pyrimidin-5-yl)oxy)-N-(2,2-difluoroethyl)-5-fluoro-N-isopropylbenzamide (80 mg, 0.173 mmol) was added in ACN:NMP (6:1) (7 mL). To this solution, $K_2CO_3$ (71.6 mg, 0.518 mmol), KI (34.4 mg, 0.207 mmol), and ((2S,5R)-5-((N-(ethyl-d₅)sulfamoyl)amino)tetrahydro-2H-pyran-2-yl)methyl 4-methylbenzenesulfonate (82 mg, 0.207 mmol) were added at RT, and the reaction was stirred at 80° C. for 14 h. The progress of the reaction was monitored by TLC (10% MeOH in DCM). The reaction mixture was diluted with EtOAc (15 mL) and washed with water (3×10 mL), and 5% aq. $NH_4Cl$ solution (3×10 mL). The combined organic layer was dried over anhydrous $Na_2SO_4$ and filtered, and the filtrate was concentrated under reduced pressure to obtain the crude compound. The crude compound was purified by silica gel column chromatography using 10% MeOH in DCM as an eluent to obtain N-(2,2-difluoroethyl)-2-((4-(7-(((2S,5R)-5-((N-(ethyl-d₅)sulfamoyl)amino)tetrahydro-2H-pyran-2-yl)methyl)-2,7-diazaspiro[3.5]nonan-2-yl)pyrimidin-5-yl)oxy)-5-fluoro-N-isopropylbenzamide (45 mg, 38%) as a solid. $^1$H NMR (400 MHz, DMSO-d₆) δ 8.30 (s, 1H), 7.78 (s, 11H), 7.40-7.25 (m, 2H), 7.14-6.71 (m, 3H), 6.68-6.12 (m, 1H), 4.05-3.62 (m, 9H), 3.48-3.37 (m, 1H), 3.23-2.82 (m, 4H), 2.35-2.14 (m, 3H), 2.05-1.90 (m, 1H), 1.75-1.59 (m, 5H), 1.48-1.33 (m, 1H), 1.24-1.16 (m, 1H), 1.15-0.99 (m, 6H); LCMS (Method E): Rt 1.71 min, m/z: 689.1 [M+H]⁺; HPLC (Method A): Rt 5.27 min, 98.86%; SFC (Method L): Rt 1.30 min, 100%.

Example 263. Menin-MLL Competition and MV4; 11 Cell Proliferation Assays

Menin-MLL is a competition assay between human Menin and N-terminal portion of human MLL representing amino acids 4-43 of the protein. The interaction between Menin and MLL peptide was monitored by HTRF employing Terbium labeled anti-His6 antibody directed to the N-terminal His6-tag on recombinant Menin and FITC group covalently attached to the MLL peptide. The N-terminal fragment of MLL, retained in all MLL fusion proteins, is involved in the interactions with Menin, and this protein-protein interaction is critical for the MLL fusion proteins mediated leukemogenic transformations.

For $IC_{50}$ determination test compounds were prepared as 10 mM DMSO stock solutions. Considering DMSO as the vehicle in the assay system. Lower sub-stocks of 50 μM were prepared from the 10 mM stock solution. To test the compounds in assay, 3.16-fold serial dilutions are made in 100% DMSO. Mid-stock of 50× compounds (50 μM) were serially diluted (3.16 fold) in 100% DMSO in Polypropylene plate. In assay plate 1 micro-litre of the previously prepared compound dilution was stamped. H-FL-Menin diluted to 4 nM in assay buffer (50 mM Tris-HCl, pH 7.4, 50 mM NaCl, freshly prepared 1 mM DTT, 0.01% BSA, 0.005% Triton X-100) was pre-incubated with 8 nM anti-His6-Tb for 30 min at room temperature. FITC-MLL-4-43 was diluted to 2 nM in assay buffer and 25 μL was dispensed into each well of the assay plate followed by addition of 25 μl of pre-incubated H-FL-Menin and anti-His6-Tb mixture. Final concentration H-FL-Menin diluted to 1 nM in assay plate with 2 nM anti-His6-Tb and 1 nM FITC-MLL-4-43. After 1 hr incubation at room temperature, the HTRF signal was measured on the Spark multi-label plate reader. Resulting data were captured as a ratio of RFU520/RFU485×1000. The max values were obtained from 0% inhibition in presence of 2% DMSO and the min. values were 100% inhibition in presence of 1 μM reference compound.

Cell Proliferation Assay—MV4;11

Compounds were evaluated for its capacity to inhibit the proliferation of the MLLr leukemia cell line MV4-11 that harbors an MLL1-AF4 fusion protein. MV4-11 cells were cultured for 72 hours with limiting dilutions of compounds and viability was measured using CellTiter-Glo.

Compounds were dissolved to obtain as 10 mM solution in DMSO. The stock was diluted 1:5 to the top concentration of 2 mM in 100% DMSO. For $IC_{50}$ determination, serial 1:3.16 dilutions were prepared in 100% DMSO by diluting 20 μL into 43.5 μL of DMSO for 8 concentrations. Each prepared DMSO solution were further diluted 1:500 in the cell culture media to obtain the 2× dosing solutions. The final concentrations of tested compounds in the cell culture media ranged from 0.632 nM to 2000 nM.

MV4-11 cells were cultured in IMDM with 10% FBS and 1× Penicillin-Streptomycin at 5% $CO_2$ and 37° C. A cell suspension was prepared containing 15,000 cells/ml in the culture medium and 100 μL of this suspension was added per well to a 96-well cell culture plate. Then, 100 μL of 2× dosing media containing test compounds were added bringing the total volume to 200 μL. These cells were cultured for 72 hours at 37° C. and 5% $CO_2$ in a humidified incubator.

After 72 hours, the cultured cells were mixed and 100p L was transferred to a 96-well black plate. Cell Titer Glo (100 μl) was then added to this plate. The plate was mixed with shaking for 15 mins at RT, the luminescence was then measured using Tecan Spark 20M spectrophotometer. Cell Viability (%) was determined by RLU of test/RLU average vehicle control*100 and % max inhibition was determined by 100−(% cell viability remaining at the top concentration of compound).

TABLE 2

Shows the Menin $IC_{50}$ (nM) and the $IC_{50}$ (nM) against MV4; 11 leukemia cell line. Data are provided below ("n/a" refers to data not available; "+++" means <100 nM; "++" means ≥100 nM and <1000 nM; and "+" means ≥1000 nM).

| Compound ID No. | Menin $IC_{50}$ (nM) | MV4; 11 $IC_{50}$ (nM) |
|---|---|---|
| 1 | +++ | +++ |
| 2 | +++ | +++ |
| 3 | +++ | +++ |
| 4 | +++ | +++ |
| 5 | +++ | +++ |
| 6 | +++ | +++ |
| 7 | +++ | +++ |
| 8 | +++ | +++ |
| 9 | +++ | +++ |
| 10 | +++ | +++ |
| 11 | +++ | +++ |
| 12 | +++ | +++ |
| 13 | +++ | +++ |
| 14 | +++ | +++ |
| 15 | +++ | +++ |
| 16 | +++ | +++ |
| 17 | +++ | +++ |
| 18 | +++ | +++ |
| 19 | +++ | +++ |
| 20 | +++ | +++ |
| 21 | +++ | +++ |
| 22 | +++ | ++ |
| 23 | +++ | ++ |
| 24 | +++ | +++ |

TABLE 2-continued

Shows the Menin IC$_{50}$ (nM) and the IC$_{50}$ (nM) against MV4; 11 leukemia cell line. Data are provided below ("n/a" refers to data not available; "+++" means <100 nM; "++" means ≥100 nM and <1000 nM; and "+" means ≥1000 nM).

| Compound ID No. | Menin IC$_{50}$ (nM) | MV4; 11 IC$_{50}$ (nM) |
|---|---|---|
| 25 | +++ | +++ |
| 26 | +++ | +++ |
| 27 | +++ | ++ |
| 28 | +++ | ++ |
| 29 | +++ | +++ |
| 30 | +++ | +++ |
| 31 | +++ | +++ |
| 32 | +++ | ++ |
| 33 | +++ | +++ |
| 34 | +++ | +++ |
| 35 | +++ | +++ |
| 36 | +++ | +++ |
| 37 | +++ | +++ |
| 38 | +++ | ++ |
| 39 | +++ | +++ |
| 40 | +++ | ++ |
| 41 | +++ | ++ |
| 42 | +++ | ++ |
| 43 | +++ | ++ |
| 44 | +++ | +++ |
| 45 | +++ | +++ |
| 46 | +++ | +++ |
| 47 | +++ | +++ |
| 48 | +++ | +++ |
| 49 | +++ | +++ |
| 50 | +++ | +++ |
| 51 | +++ | +++ |
| 52 | +++ | ++ |
| 53 | n/a | +++ |
| 54 | n/a | +++ |
| 55 | n/a | +++ |
| 56 | n/a | +++ |
| 57 | n/a | +++ |
| 58 | n/a | +++ |
| 59 | n/a | +++ |
| 60 | n/a | +++ |
| 61 | n/a | +++ |
| 62 | n/a | +++ |
| 63 | n/a | +++ |
| 64 | n/a | +++ |
| 65 | n/a | +++ |
| 66 | n/a | +++ |
| 67 | n/a | +++ |
| 68 | n/a | +++ |
| 69 | n/a | +++ |
| 70 | n/a | +++ |
| 71 | n/a | +++ |
| 72 | n/a | +++ |
| 73 | n/a | ++ |
| 74 | n/a | +++ |
| 75 | n/a | +++ |
| 76 | n/a | +++ |
| 77 | n/a | +++ |
| 78 | n/a | +++ |
| 79 | n/a | +++ |
| 80 | n/a | +++ |
| 81 | n/a | +++ |
| 82 | n/a | +++ |
| 83 | n/a | +++ |
| 84 | n/a | +++ |
| 85 | n/a | +++ |
| 86 | n/a | +++ |
| 87 | n/a | +++ |
| 88 | n/a | +++ |
| 89 | n/a | +++ |
| 90 | n/a | +++ |
| 91 | n/a | +++ |
| 92 | n/a | +++ |
| 93 | n/a | +++ |
| 94 | n/a | +++ |
| 95 | n/a | +++ |
| 96 | n/a | +++ |
| 97 | n/a | +++ |
| 98 | n/a | +++ |
| 99 | n/a | +++ |
| 100 | n/a | +++ |
| 101 | n/a | +++ |
| 102 | n/a | +++ |
| 103 | n/a | +++ |
| 104 | n/a | +++ |
| 105 | n/a | +++ |
| 106 | n/a | +++ |
| 107 | n/a | +++ |
| 108 | n/a | +++ |
| 109 | n/a | +++ |
| 110 | n/a | +++ |
| 111 | n/a | +++ |
| 112 | n/a | +++ |
| 113 | n/a | +++ |
| 114 | n/a | +++ |
| 115 | n/a | +++ |
| 116 | n/a | +++ |
| 117 | n/a | +++ |
| 118 | n/a | +++ |
| 119 | n/a | +++ |
| 120 | n/a | +++ |
| 121 | n/a | +++ |
| 122 | n/a | +++ |
| 123 | n/a | +++ |
| 124 | n/a | +++ |
| 125 | n/a | +++ |
| 126 | n/a | +++ |
| 127 | n/a | +++ |
| 128 | n/a | +++ |
| 129 | n/a | +++ |
| 130 | n/a | +++ |
| 131 | n/a | +++ |
| 132 | n/a | +++ |
| 133 | n/a | +++ |
| 134 | n/a | +++ |
| 135 | n/a | +++ |
| 136 | n/a | +++ |
| 137 | n/a | +++ |
| 138 | n/a | +++ |
| 139 | n/a | ++ |
| 140 | n/a | +++ |
| 141 | n/a | +++ |
| 142 | n/a | +++ |
| 143 | n/a | +++ |
| 144 | n/a | +++ |
| 145 | n/a | +++ |
| 146 | n/a | +++ |
| 147 | n/a | +++ |
| 148 | n/a | +++ |
| 149 | n/a | +++ |
| 150 | n/a | +++ |
| 151 | n/a | +++ |
| 152 | n/a | +++ |
| 153 | n/a | +++ |
| 154 | n/a | +++ |
| 155 | n/a | +++ |
| 156 | n/a | +++ |
| 157 | n/a | +++ |
| 158 | n/a | +++ |
| 159 | n/a | +++ |
| 160 | n/a | +++ |
| 161 | n/a | +++ |
| 162 | n/a | +++ |
| 163 | n/a | +++ |
| 164 | n/a | +++ |
| 165 | n/a | +++ |
| 166 | n/a | +++ |
| 167 | n/a | +++ |
| 168 | n/a | +++ |
| 169 | n/a | +++ |
| 170 | n/a | +++ |

TABLE 2-continued

Shows the Menin IC$_{50}$ (nM) and the IC$_{50}$ (nM) against MV4; 11 leukemia cell line. Data are provided below ("n/a" refers to data not available; "+++" means <100 nM; "++" means ≥100 nM and <1000 nM; and "+" means ≥1000 nM).

| Compound ID No. | Menin IC$_{50}$ (nM) | MV4; 11 IC$_{50}$ (nM) |
|---|---|---|
| 171 | n/a | +++ |
| 172 | n/a | +++ |
| 173 | n/a | +++ |
| 174 | n/a | +++ |
| 175 | n/a | +++ |
| 176 | n/a | +++ |
| 177 | n/a | +++ |
| 178 | n/a | +++ |
| 179 | n/a | +++ |
| 180 | n/a | +++ |
| 181 | n/a | +++ |
| 182 | n/a | +++ |
| 183 | n/a | +++ |
| 184 | n/a | +++ |
| 185 | n/a | +++ |
| 186 | n/a | +++ |
| 187 | n/a | +++ |
| 188 | n/a | +++ |
| 189 | n/a | +++ |
| 190 | n/a | +++ |
| 191 | n/a | +++ |
| 192 | n/a | +++ |
| 193 | n/a | +++ |
| 194 | n/a | +++ |
| 195 | n/a | +++ |
| 196 | n/a | +++ |
| 197 | n/a | +++ |
| 198 | n/a | +++ |
| 199 | n/a | +++ |
| 200 | n/a | +++ |
| 201 | n/a | +++ |
| 202 | n/a | +++ |
| 203 | n/a | +++ |
| 204 | n/a | +++ |
| 205 | n/a | +++ |
| 206 | n/a | +++ |
| 207 | n/a | +++ |
| 208 | n/a | +++ |
| 209 | n/a | +++ |
| 210 | n/a | +++ |
| 211 | n/a | +++ |
| 212 | n/a | +++ |
| 213 | n/a | +++ |
| 214 | n/a | +++ |
| 215 | n/a | ++ |
| 216 | n/a | ++ |
| 217 | n/a | +++ |
| 218 | n/a | +++ |
| 219 | n/a | +++ |
| 220 | n/a | ++ |
| 221 | n/a | +++ |
| 222 | n/a | +++ |
| 223 | n/a | +++ |
| 224 | n/a | +++ |
| 225 | n/a | ++ |
| 226 | n/a | ++ |
| 227 | n/a | +++ |
| 228 | n/a | +++ |
| 229 | n/a | +++ |
| 230 | n/a | +++ |
| 231 | n/a | +++ |
| 232 | n/a | ++ |
| 233 | n/a | +++ |
| 234 | n/a | +++ |
| 235 | n/a | +++ |
| 236 | n/a | +++ |
| 237 | n/a | +++ |
| 238 | n/a | +++ |
| 239 | n/a | +++ |
| 240 | n/a | +++ |
| 241 | n/a | +++ |
| 242 | n/a | +++ |
| 243 | n/a | +++ |
| 244 | n/a | +++ |
| 245 | n/a | +++ |
| 246 | n/a | +++ |
| 247 | n/a | +++ |
| 248 | n/a | +++ |
| 249 | n/a | +++ |
| 250 | n/a | +++ |
| 251 | n/a | +++ |
| 252 | n/a | +++ |
| 253 | n/a | ++ |
| 254 | n/a | +++ |
| 255 | n/a | ++ |
| 256 | n/a | +++ |
| 257 | n/a | ++ |
| 258 | n/a | +++ |
| 259 | n/a | +++ |

Example 264. Patch Clamp Assay

The 35 mm culture dishes upon which cells were seeded at a density allowing single cells to be recorded were placed on the dish holder of the microscope and continuously perfused (at approximately 1 mL/min) with the bath solution described in section 4.6. All solutions applied to cells including the pipette solution were maintained at room temperature (19° C. to 30° C.). After formation of a Gigaohm seal between the patch electrodes and individual hERG stably transfected HEK 293 cells (pipette resistance range: 2.0 MΩ to 7.0 MΩ; seal resistance range: >1GΩ) the cell membrane across the pipette tip was ruptured to assure electrical access to the cell interior (whole-cell patch-configuration). In case the quality of the seal was poor, the process of seal formation was repeated with a different cell and a new pipette. As soon as a stable seal could be established, hERG outward tail currents were measured upon depolarization of the cell membrane to +20 mV for 2s (activation of channels) from a holding potential of −80 mV and upon subsequent repolarization to −40 mV for 3 s. This voltage protocol (as shown below) was run at least 10 times at intervals of 10 s. If current density was judged to be too low for measurement, another cell was recorded.

Once control recordings have been accomplished, cells were continuously perfused with a bath solution containing the test item as detailed in section 4.8.2, 0.3% DMSO or 100 nM E-4031. During wash-in of the test item the voltage protocol indicated above was run continuously again at 10 s intervals until the steady-state level of block was reached.

As hERG tail currents were inhibited by each test items by more than 30%, a concentration-response curve was generated and the IC50 was calculated using SigmaPlot 11.0.

The IC50 was determined by fitting the dose response curve with a 2-parameter logistic function (amax=100%).

TABLE 3

Shows the results from the patch clamp assay, including the percentage of hERG remaining after treatment with individual compound (μM) and the IC$_{50}$ (μM) hERG. The percentage of hERG remaining after treatment with individual compound (μM) is provided below ("n/a" refers to data not available; "+" means <33%; "++" means ≥33% and <66%; and "+++" means ≥66%).
IC50 (μM) hERG data are provided below ("n/a" refers to data not available; "+" Means <25 μM; "++" means ≥25 μM and <50 μM; and "+++" means ≥50 μM).

| Compound | hERG % Remaining | | | | | hERG IC$_{50}$ (μM) |
|---|---|---|---|---|---|---|
| | 1 μM | 3 μM | 10 μM | 30 μM | 100 μM | |
| SNDX-5613 | +++ | +++ | ++ | ++ | + | + |
| 1 | n/a | n/a | +++ | ++ | n/a | n/a |
| 2 | n/a | n/a | +++ | +++ | n/a | n/a |
| 4 | n/a | n/a | +++ | +++ | n/a | +++ |
| 6 | n/a | n/a | +++ | ++ | n/a | n/a |
| 11 | n/a | n/a | + | + | n/a | n/a |
| 12 | +++ | +++ | +++ | +++ | ++ | +++ |
| 13 | +++ | +++ | +++ | ++ | ++ | +++ |
| 14 | n/a | +++ | +++ | ++ | + | ++ |
| 15 | n/a | +++ | +++ | ++ | + | ++ |
| 16 | n/a | n/a | +++ | +++ | n/a | n/a |
| 19 | n/a | n/a | +++ | ++ | n/a | n/a |
| 21 | n/a | n/a | ++ | + | n/a | n/a |
| 33 | n/a | n/a | +++ | +++ | n/a | n/a |
| 34 | +++ | +++ | +++ | ++ | + | ++ |
| 37 | n/a | n/a | + | + | n/a | n/a |
| 43 | n/a | n/a | +++ | ++ | n/a | n/a |
| 44 | n/a | n/a | +++ | ++ | n/a | n/a |
| 45 | n/a | n/a | ++ | + | n/a | n/a |
| 47 | n/a | n/a | +++ | ++ | n/a | n/a |
| 49 | n/a | n/a | +++ | +++ | n/a | +++ |
| 58 | n/a | n/a | +++ | ++ | n/a | n/a |
| 59 | n/a | n/a | + | + | n/a | n/a |
| 62 | n/a | n/a | + | + | n/a | n/a |
| 63 | n/a | n/a | +++ | ++ | n/a | n/a |
| 64 | n/a | n/a | +++ | ++ | n/a | n/a |
| 65 | n/a | n/a | ++ | + | n/a | n/a |
| 66 | n/a | n/a | + | + | n/a | n/a |
| 68 | n/a | n/a | +++ | +++ | n/a | +++ |
| 69 | n/a | n/a | +++ | ++ | n/a | ++ |
| 71 | n/a | n/a | +++ | ++ | n/a | n/a |
| 72 | n/a | n/a | ++ | + | n/a | n/a |
| 75 | n/a | n/a | n/a | +++ | n/a | n/a |
| 76 | n/a | n/a | +++ | +++ | n/a | n/a |
| 78 | n/a | n/a | +++ | +++ | n/a | n/a |
| 80 | n/a | n/a | ++ | + | n/a | n/a |
| 81 | n/a | n/a | ++ | ++ | n/a | n/a |
| 82 | n/a | n/a | ++ | + | n/a | n/a |
| 83 | n/a | n/a | +++ | ++ | n/a | n/a |
| 84 | n/a | n/a | ++ | + | n/a | n/a |
| 85 | n/a | n/a | ++ | + | n/a | n/a |
| 86 | n/a | n/a | +++ | +++ | n/a | +++ |
| 87 | n/a | n/a | n/a | +++ | n/a | n/a |
| 88 | n/a | n/a | n/a | +++ | n/a | n/a |
| 89 | n/a | n/a | n/a | ++ | n/a | n/a |
| 90 | n/a | n/a | +++ | +++ | n/a | n/a |
| 91 | n/a | n/a | n/a | ++ | n/a | n/a |
| 93 | +++ | +++ | +++ | ++ | + | +++ |
| 94 | n/a | n/a | +++ | ++ | n/a | n/a |
| 95 | n/a | n/a | +++ | ++ | n/a | + |
| 97 | n/a | n/a | ++ | + | n/a | n/a |
| 99 | n/a | n/a | +++ | ++ | n/a | n/a |
| 100 | n/a | n/a | +++ | +++ | n/a | +++ |
| 101 | n/a | n/a | n/a | + | n/a | n/a |
| 102 | n/a | n/a | n/a | +++ | n/a | +++ |
| 103 | n/a | n/a | n/a | +++ | n/a | n/a |
| 104 | n/a | n/a | n/a | +++ | n/a | n/a |
| 105 | n/a | n/a | n/a | +++ | n/a | n/a |
| 107 | n/a | n/a | +++ | ++ | n/a | n/a |
| 111 | n/a | n/a | ++ | + | n/a | n/a |
| 113 | n/a | n/a | +++ | ++ | n/a | n/a |
| 114 | n/a | n/a | + | + | n/a | n/a |
| 118 | n/a | n/a | ++ | + | n/a | n/a |
| 119 | n/a | n/a | n/a | + | n/a | n/a |
| 120 | n/a | n/a | +++ | ++ | n/a | n/a |
| 121 | n/a | n/a | n/a | +++ | n/a | n/a |
| 122 | n/a | n/a | n/a | +++ | n/a | +++ |
| 123 | n/a | n/a | n/a | +++ | n/a | n/a |
| 125 | n/a | n/a | n/a | +++ | n/a | n/a |
| 130 | n/a | n/a | +++ | ++ | n/a | n/a |
| 134 | n/a | n/a | n/a | +++ | n/a | n/a |
| 136 | n/a | n/a | +++ | + | n/a | n/a |
| 138 | n/a | n/a | n/a | +++ | n/a | n/a |
| 141 | n/a | n/a | n/a | +++ | n/a | n/a |
| 142 | n/a | n/a | n/a | ++ | n/a | n/a |
| 143 | n/a | n/a | n/a | +++ | +++ | +++ |
| 144 | n/a | n/a | n/a | +++ | n/a | n/a |
| 145 | n/a | n/a | n/a | +++ | n/a | n/a |
| 147 | n/a | n/a | +++ | +++ | n/a | +++ |
| 148 | n/a | n/a | n/a | +++ | n/a | n/a |
| 149 | n/a | n/a | n/a | +++ | n/a | n/a |
| 153 | n/a | n/a | n/a | +++ | | +++ |
| 154 | n/a | n/a | +++ | ++ | n/a | n/a |
| 155 | n/a | n/a | +++ | ++ | n/a | n/a |
| 156 | n/a | n/a | n/a | +++ | n/a | n/a |
| 158 | n/a | n/a | n/a | +++ | n/a | n/a |
| 161 | n/a | n/a | n/a | +++ | n/a | n/a |
| 164 | n/a | n/a | +++ | +++ | n/a | n/a |
| 165 | n/a | n/a | +++ | ++ | n/a | n/a |
| 167 | n/a | n/a | n/a | +++ | +++ | +++ |
| 175 | n/a | n/a | ++ | + | n/a | n/a |
| 176 | n/a | n/a | +++ | +++ | +++ | +++ |
| 177 | n/a | n/a | +++ | +++ | n/a | n/a |
| 181 | n/a | n/a | n/a | +++ | n/a | n/a |
| 182 | n/a | n/a | n/a | +++ | n/a | n/a |
| 183 | n/a | n/a | n/a | +++ | n/a | n/a |
| 189 | n/a | n/a | n/a | +++ | n/a | n/a |
| 193 | n/a | n/a | n/a | +++ | n/a | +++ |
| 196 | n/a | n/a | n/a | +++ | n/a | n/a |
| 198 | n/a | n/a | n/a | +++ | n/a | n/a |
| 199 | n/a | n/a | n/a | +++ | n/a | n/a |
| 200 | n/a | n/a | ++ | + | n/a | n/a |
| 201 | n/a | n/a | n/a | + | n/a | n/a |
| 202 | n/a | n/a | n/a | + | n/a | n/a |
| 203 | n/a | n/a | n/a | + | n/a | n/a |
| 208 | n/a | n/a | n/a | +++ | n/a | n/a |
| 209 | n/a | n/a | n/a | +++ | n/a | n/a |
| 210 | n/a | n/a | n/a | +++ | n/a | n/a |
| 211 | n/a | n/a | n/a | +++ | n/a | n/a |
| 214 | n/a | n/a | n/a | +++ | n/a | n/a |
| 217 | n/a | n/a | n/a | +++ | n/a | n/a |
| 218 | n/a | n/a | n/a | + | n/a | n/a |
| 223 | n/a | n/a | n/a | +++ | n/a | n/a |
| 224 | n/a | n/a | n/a | +++ | n/a | n/a |
| 231 | n/a | n/a | n/a | +++ | n/a | n/a |
| 235 | n/a | n/a | n/a | +++ | n/a | n/a |
| 239 | n/a | n/a | n/a | +++ | n/a | n/a |
| 240 | n/a | n/a | n/a | +++ | n/a | +++ |
| 241 | n/a | n/a | n/a | ++ | n/a | n/a |
| 244 | n/a | n/a | +++ | ++ | n/a | n/a |
| 248 | n/a | n/a | n/a | +++ | n/a | n/a |
| 249 | n/a | n/a | n/a | +++ | n/a | n/a |
| 258 | n/a | n/a | +++ | ++ | n/a | n/a |

Example 265. Determination of Binding Constants to Menin-MLL

For Ki determination, individual compounds were prepared as 10 mM DMSO stock solutions. Considering DMSO as the vehicle in the assay system. Lower sub-stocks of 16

µM were prepared from the 10 mM stock solution. To test the compounds in assay, 3.16-fold serial dilutions are made in 100% DMSO. Mid-stock of 50× compounds (16 µM) were serially diluted (3.16 fold) in 100% DMSO in Polypropylene plate. In assay plate 1 micro-litre of the previously prepared compound dilution was stamped. H-FL-Menin diluted to 1 nM in assay buffer (50 mM Tris-HCl, pH 7.4, 50 mM NaCL, freshly prepared 1 mM DTT, 0.01% BSA, 0.005% Triton X-100) and pre-incubated with 2 nM anti-His6-Tb for 30 min at room temperature and then 25 µl was dispensed into each well. FITC-MLL-4-43 was diluted to 6.4 nM in assay buffer and 25 µL was dispensed into each well of the assay plate followed by addition of 25 µl of pre-incubated H-FL-Menin and anti-His6-Tb mixture. Final concentration H-FL-Menin diluted to 0.25 nM in assay plate with 0.5 nM anti-His6-Tb and 3.2 nM FITC-MLL-4-43. After 24 hr incubation at room temperature, the HTRF signal was measured on the Spark multi-label plate reader. Resulting data were captured as a ratio of RFU520/RFU485×1000. The max values were obtained from 0% inhibition in presence of 2% DMSO and the min. values were 100% inhibition in presence of 320 nM reference compound.

TABLE 4

Shows the Menin-MLL binding data according to Homogeneous Time Resolved Fluorescence (HTRF) assay with individual compound in $EC_{50}$ (nM) and Ki (nM). $EC_{50}$ data (nM) are provided below ("n/a" refers to data not available; "+++" means <50 nM; "++" means ≥50 nM and <100 nM; and "+" means ≥100 nM). Ki data (nM) are provided below ("n/a" refers to data not available; "+++" means <1.0 nM; "++" means ≥1.0 nM and <1.5 nM; and "+" means ≥2.0 nM).

| Compound Number | Menin-MLL Ki HTRF Assay: EC50 (nM) | Menin-MLL Ki HTRF Assay: Ki (nM) |
|---|---|---|
| 1 | +++ | +++ |
| 2 | +++ | +++ |
| 3 | +++ | +++ |
| 4 | +++ | +++ |
| 5 | +++ | +++ |
| 6 | +++ | +++ |
| 7 | +++ | +++ |
| 8 | +++ | +++ |
| 9 | +++ | +++ |
| 10 | +++ | +++ |
| 11 | +++ | +++ |
| 12 | +++ | +++ |
| 13 | +++ | +++ |
| 14 | +++ | +++ |
| 15 | +++ | +++ |
| 16 | +++ | +++ |
| 17 | +++ | +++ |
| 18 | +++ | +++ |
| 19 | +++ | +++ |
| 20 | +++ | +++ |
| 21 | +++ | +++ |
| 22 | +++ | +++ |
| 23 | +++ | +++ |
| 24 | +++ | +++ |
| 25 | +++ | +++ |
| 26 | +++ | +++ |
| 28 | +++ | +++ |
| 29 | +++ | +++ |
| 30 | +++ | +++ |
| 31 | +++ | +++ |
| 32 | +++ | +++ |
| 33 | +++ | +++ |
| 34 | +++ | +++ |
| 35 | +++ | +++ |
| 36 | +++ | +++ |
| 37 | +++ | +++ |
| 38 | ++ | ++ |
| 39 | +++ | +++ |
| 41 | ++ | +++ |
| 42 | + | ++ |
| 43 | +++ | +++ |
| 44 | +++ | +++ |
| 45 | +++ | +++ |
| 46 | +++ | +++ |
| 47 | +++ | +++ |
| 48 | +++ | +++ |
| 49 | +++ | +++ |
| 50 | +++ | +++ |
| 51 | +++ | n/a |
| 52 | +++ | n/a |
| 53 | n/a | +++ |
| 54 | n/a | +++ |
| 55 | +++ | +++ |
| 56 | +++ | +++ |
| 57 | +++ | +++ |
| 58 | +++ | +++ |
| 59 | +++ | +++ |
| 60 | +++ | +++ |
| 61 | +++ | +++ |
| 62 | +++ | +++ |
| 63 | +++ | +++ |
| 64 | +++ | +++ |
| 65 | +++ | +++ |
| 66 | +++ | +++ |
| 67 | +++ | +++ |
| 68 | +++ | +++ |
| 69 | +++ | +++ |
| 70 | +++ | +++ |
| 71 | +++ | +++ |
| 72 | n/a | +++ |
| 73 | n/a | +++ |
| 74 | n/a | +++ |
| 75 | n/a | +++ |
| 76 | +++ | +++ |
| 77 | +++ | +++ |
| 78 | +++ | +++ |
| 79 | +++ | +++ |
| 80 | n/a | +++ |
| 81 | n/a | +++ |
| 82 | n/a | +++ |
| 83 | n/a | +++ |
| 84 | n/a | +++ |
| 85 | n/a | +++ |
| 86 | n/a | +++ |
| 87 | n/a | +++ |
| 88 | n/a | +++ |
| 89 | n/a | +++ |
| 90 | n/a | +++ |
| 91 | n/a | +++ |
| 92 | n/a | +++ |
| 93 | +++ | +++ |
| 94 | +++ | +++ |
| 95 | +++ | +++ |
| 96 | +++ | +++ |
| 97 | +++ | +++ |
| 98 | +++ | +++ |
| 99 | n/a | +++ |
| 100 | n/a | +++ |
| 101 | n/a | +++ |
| 102 | n/a | +++ |
| 103 | n/a | +++ |
| 104 | n/a | +++ |
| 105 | n/a | +++ |
| 106 | n/a | +++ |
| 107 | +++ | +++ |
| 108 | +++ | +++ |
| 109 | +++ | +++ |

TABLE 4-continued

Shows the Menin-MLL binding data according to Homogeneous Time Resolved Fluorescence (HTRF) assay with individual compound in EC$_{50}$ (nM) and Ki (nM). EC$_{50}$ data (nM) are provided below ("n/a" refers to data not available; "+++" means <50 nM; "++" means ≥50 nM and <100 nM; and "+" means ≥100 nM). Ki data (nM) are provided below ("n/a" refers to data not available; "+++" means <1.0 nM; "++" means ≥1.0 nM and <1.5 nM; and "+" means ≥2.0 nM).

| Compound Number | Menin-MLL Ki HTRF Assay: EC50 (nM) | Menin-MLL Ki HTRF Assay: Ki (nM) |
|---|---|---|
| 110 | +++ | +++ |
| 111 | +++ | +++ |
| 112 | +++ | +++ |
| 113 | +++ | +++ |
| 114 | +++ | +++ |
| 115 | +++ | +++ |
| 116 | +++ | +++ |
| 117 | +++ | +++ |
| 118 | n/a | +++ |
| 119 | n/a | +++ |
| 120 | +++ | +++ |
| 121 | n/a | +++ |
| 122 | n/a | +++ |
| 123 | n/a | +++ |
| 124 | n/a | +++ |
| 125 | n/a | +++ |
| 126 | n/a | +++ |
| 127 | n/a | +++ |
| 128 | n/a | +++ |
| 129 | n/a | +++ |
| 130 | +++ | +++ |
| 131 | n/a | +++ |
| 132 | +++ | +++ |
| 133 | n/a | +++ |
| 134 | n/a | +++ |
| 135 | n/a | +++ |
| 136 | +++ | +++ |
| 137 | n/a | +++ |
| 138 | n/a | +++ |
| 139 | n/a | +++ |
| 140 | n/a | +++ |
| 141 | n/a | +++ |
| 142 | n/a | +++ |
| 143 | n/a | +++ |
| 144 | n/a | +++ |
| 145 | n/a | +++ |
| 146 | n/a | +++ |
| 147 | n/a | +++ |
| 148 | n/a | +++ |
| 149 | n/a | +++ |
| 150 | n/a | +++ |
| 151 | n/a | +++ |
| 152 | +++ | +++ |
| 153 | n/a | +++ |
| 154 | n/a | +++ |
| 155 | n/a | +++ |
| 156 | n/a | +++ |
| 157 | n/a | +++ |
| 158 | n/a | +++ |
| 159 | n/a | +++ |
| 160 | n/a | +++ |
| 161 | n/a | +++ |
| 162 | n/a | +++ |
| 163 | n/a | +++ |
| 164 | +++ | +++ |
| 165 | n/a | +++ |
| 166 | n/a | +++ |
| 167 | n/a | +++ |
| 168 | n/a | +++ |
| 169 | n/a | +++ |
| 170 | n/a | +++ |
| 171 | n/a | +++ |
| 172 | n/a | +++ |
| 173 | n/a | +++ |
| 174 | n/a | +++ |
| 175 | n/a | +++ |
| 176 | n/a | +++ |
| 177 | n/a | +++ |
| 178 | n/a | +++ |
| 179 | n/a | +++ |
| 180 | n/a | +++ |
| 181 | n/a | +++ |
| 182 | n/a | +++ |
| 183 | n/a | +++ |
| 184 | n/a | +++ |
| 185 | n/a | +++ |
| 186 | n/a | +++ |
| 187 | n/a | +++ |
| 188 | n/a | +++ |
| 189 | n/a | +++ |
| 190 | n/a | +++ |
| 191 | n/a | +++ |
| 192 | n/a | +++ |
| 193 | n/a | +++ |
| 194 | n/a | +++ |
| 195 | n/a | +++ |
| 196 | n/a | +++ |
| 197 | n/a | +++ |
| 198 | n/a | +++ |
| 199 | n/a | +++ |
| 200 | n/a | +++ |
| 201 | n/a | +++ |
| 202 | n/a | +++ |
| 203 | n/a | +++ |
| 204 | n/a | +++ |
| 205 | n/a | +++ |
| 206 | n/a | +++ |
| 207 | n/a | +++ |
| 208 | n/a | +++ |
| 209 | n/a | +++ |
| 210 | n/a | +++ |
| 211 | n/a | +++ |
| 212 | n/a | +++ |
| 213 | n/a | +++ |
| 214 | n/a | +++ |
| 215 | ++ | n/a |
| 216 | n/a | ++ |
| 217 | n/a | +++ |
| 218 | n/a | +++ |
| 219 | n/a | +++ |
| 220 | n/a | ++ |
| 221 | n/a | +++ |
| 222 | n/a | +++ |
| 223 | n/a | +++ |
| 224 | n/a | +++ |
| 225 | n/a | +++ |
| 226 | n/a | +++ |
| 227 | n/a | +++ |
| 228 | n/a | +++ |
| 229 | n/a | +++ |
| 230 | n/a | +++ |
| 231 | n/a | +++ |
| 232 | n/a | +++ |
| 233 | n/a | +++ |
| 234 | n/a | +++ |
| 235 | n/a | +++ |
| 236 | n/a | +++ |
| 237 | n/a | +++ |
| 238 | n/a | +++ |
| 239 | n/a | +++ |
| 240 | n/a | +++ |
| 241 | n/a | +++ |
| 242 | +++ | +++ |
| 243 | n/a | +++ |
| 244 | n/a | +++ |
| 245 | n/a | +++ |

TABLE 4-continued

Shows the Menin-MLL binding data according to Homogeneous Time Resolved Fluorescence (HTRF) assay with individual compound in EC$_{50}$ (nM) and Ki (nM). EC$_{50}$ data (nM) are provided below ("n/a" refers to data not available; "+++" means <50 nM; "++" means ≥50 nM and <100 nM; and "+" means ≥100 nM). Ki data (nM) are provided below ("n/a" refers to data not available; "+++" means <1.0 nM; "++" means ≥1.0 nM and <1.5 nM; and "+" means ≥2.0 nM).

| Compound Number | Menin-MLL Ki HTRF Assay: EC50 (nM) | Menin-MLL Ki HTRF Assay: Ki (nM) |
| --- | --- | --- |
| 246 | n/a | +++ |
| 247 | +++ | +++ |
| 248 | n/a | +++ |
| 249 | n/a | +++ |
| 250 | +++ | n/a |
| 251 | n/a | +++ |
| 252 | n/a | +++ |
| 253 | n/a | +++ |
| 254 | +++ | +++ |
| 255 | +++ | +++ |
| 256 | +++ | +++ |
| 257 | +++ | +++ |
| 258 | +++ | +++ |
| 259 | +++ | +++ |
| 260 | +++ | n/a |
| 261 | +++ | n/a |

EQUIVALENTS

While we have described a number of embodiments of this disclosure, it is apparent that our basic examples may be altered to provide other embodiments that utilize the compounds and methods of this disclosure. The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art. The foregoing description has been presented only for the purposes of illustration and is not intended to limit the disclosure to the precise form disclosed, but by the claims appended hereto.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

What is claimed is:

1. A compound of Formula 0,

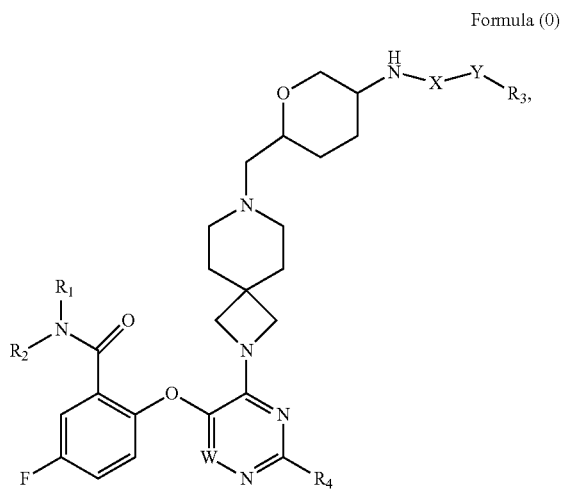

Formula (0)

a stereoisomer thereof, or a pharmaceutically acceptable salt thereof, wherein

W is N or CH;

X is C=O, S(=O)(=NR$_5$), or S(=O)$_2$;

Y is NH, O, or a bond;

R$_1$ is C$_1$-C$_6$ alkyl, C$_2$-C$_6$ alkenyl, C$_2$-C$_6$ alkynyl, C$_1$-C$_6$ alkoxy, C$_3$-C$_{12}$ cycloalkyl, C$_6$-C$_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted by one or more halo, OH, OBn, oxo, CN, N(R$_N$)$_2$, C$_1$-C$_6$ alkyl, C$_1$-C$_6$ haloalkyl, C$_3$-C$_6$ cycloalkyl, or C$_1$-C$_6$ alkoxy;

R$_2$ is C$_1$-C$_6$ alkyl, C$_2$-C$_6$ alkenyl, C$_2$-C$_6$ alkynyl, C$_1$-C$_6$ alkoxy, C$_3$-C$_{12}$ cycloalkyl, C$_6$-C$_{10}$ aryl, 5- to 10-membered heteroaryl, or 3- to 12-membered heterocyclyl; wherein the alkyl, alkenyl, alkynyl, alkoxy, cycloalkyl, aryl, heteroaryl, or heterocyclyl is optionally substituted with one or more halo, OH, OBn, oxo, CN, N(R$_N$)$_2$, C$_1$-C$_6$ alkyl, C$_1$-C$_6$ haloalkyl, C$_3$-C$_6$ cycloalkyl, or C$_1$-C$_6$ alkoxy;

R$_1$ and R$_2$ optionally form a 3- to 12-membered heterocyclyl, wherein the heterocyclyl is optionally substituted with one or more C$_1$-C$_6$ alkyl, halo, OH, CN, or C$_1$-C$_6$ alkoxy;

R$_3$ is H, C$_1$-C$_6$ alkyl, C$_2$-C$_6$ alkenyl, C$_2$-C$_6$ alkynyl, C$_1$-C$_6$ alkoxy, C$_3$-C$_{12}$ cycloalkyl, NH$_2$, NH—C$_1$-C$_6$ alkyl, N—(C$_1$-C$_6$ alkyl)$_2$, C$_6$-C$_{10}$ aryl, 5- to 10-membered heteroaryl, 3- to 12-membered heterocyclyl, wherein the alkyl, alkenyl, alkynyl, alkoxy, cycloalkyl, aryl, heteroaryl, or heterocyclyl is optionally substituted with one or more halo, OH, OBn, oxo, CN, N(R$_N$)$_2$, C$_1$-C$_6$ alkyl, C$_1$-C$_6$ haloalkyl, C$_3$-C$_6$ cycloalkyl, C$_1$-C$_6$ alkoxy or aryl;

R$_4$ is H, halo, C$_1$-C$_6$ alkyl, C$_1$-C$_6$ alkoxy, C$_1$-C$_6$ haloalkyl, or N(R$_N$)$_2$;

each R$_N$ is independently H, C$_1$-C$_6$ alkyl, or C$_1$-C$_6$ haloalkyl; and each $R_5$ is independently H, $C_1$-$C_6$ alkyl, or $C_1$-$C_6$ haloalkyl.

2. The compound of claim 1, wherein W is N or CH.

3. The compound of claim 2, wherein X is C=O, or S(=O)$_2$.

4. The compound of claim 3, wherein Y is NH, O, or a bond.

5. The compound of claim 4, wherein $R_1$ is $C_1$-$C_6$ alkyl, $C_2$-$C_6$ alkenyl, $C_2$-$C_6$ alkynyl, $C_1$-$C_6$ alkoxy, wherein the alkyl, alkenyl, alkynyl, alkoxy is optionally substituted by one or more halo, OH, OBn, oxo, CN, or $C_3$-$C_6$ cycloalkyl.

6. The compound of claim 5, wherein $R_1$ is ethyl substituted by one or more halo.

7. The compound of claim 6, wherein $R_1$ is —CH$_2$—CHF$_2$, or —CH$_2$—CF$_3$.

8. The compound of claim 5, wherein $R_1$ is isopropyl.

9. The compound of claim 4, wherein $R_1$ is $C_3$-$C_{12}$ cycloalkyl, $C_6$-$C_{10}$ aryl, 5- to 10-membered heteroaryl, or 3- to 12-membered heterocyclyl, wherein the cycloalkyl, aryl, heteroaryl, or heterocyclyl is optionally substituted by one or more halo, OH, oxo, CN, $C_1$-$C_6$ alkyl, $C_1$-$C_6$ haloalkyl, $C_3$-$C_6$ cycloalkyl, or $C_1$-$C_6$ alkoxy.

10. The compound of claim 9, wherein $R_2$ is $C_1$-$C_6$ alkyl, $C_1$-$C_6$ alkoxy, wherein the alkyl, alkoxy is optionally substituted by one or more halo, OH, oxo, CN, $C_1$-$C_6$ alkyl, $C_1$-$C_6$ haloalkyl, $C_3$-$C_6$ cycloalkyl, or $C_1$-$C_6$ alkoxy.

11. The compound of claim 10, wherein $R_2$ is ethyl.

12. The compound of claim 10, wherein $R_2$ is propyl.

13. The compound of claim 10, wherein $R_2$ is isopropyl.

14. The compound of claim 10, wherein $R_3$ is H, $C_1$-$C_6$ alkyl, $C_2$-$C_6$ alkenyl, $C_2$-$C_6$ alkynyl, $C_1$-$C_6$ alkoxy, NH$_2$, NH—$C_1$-$C_6$ alkyl, N—($C_1$-$C_6$ alkyl)$_2$, wherein the alkyl, alkenyl, alkynyl, alkoxy, is optionally substituted with one or more halo, OH, oxo, CN, $C_1$-$C_6$ alkyl, $C_1$-$C_6$ haloalkyl, $C_3$-$C_6$ cycloalkyl, or $C_1$-$C_6$ alkoxy.

15. The compound of claim 10, wherein $R_3$ is $C_1$-$C_6$ alkyl, NH—$C_1$-$C_6$ alkyl, N—($C_1$-$C_6$ alkyl)$_2$, or 5- to 10-membered heteroaryl, wherein the alkyl or heteroaryl is optionally substituted with one or more halo, $C_1$-$C_6$ alkyl, $C_1$-$C_6$ haloalkyl, $C_3$-$C_6$ cycloalkyl, or $C_1$-$C_6$ alkoxy.

16. The compound of claim 10, wherein $R_3$ is $C_3$-$C_{12}$ cycloalkyl, $C_6$-$C_{10}$ aryl, 5- to 10-membered heteroaryl, 3- to 12-membered heterocyclyl, wherein the cycloalkyl, aryl, heteroaryl, or heterocyclyl is optionally substituted with one or more halo, OH, oxo, CN, $C_1$-$C_6$ alkyl, $C_1$-$C_6$ haloalkyl, $C_3$-$C_6$ cycloalkyl, or $C_1$-$C_6$ alkoxy.

17. The compound of claim 10, wherein $R_3$ is $C_1$-$C_3$ alkyl, NH—$C_1$-$C_3$ alkyl, N—($C_1$-$C_3$ alkyl)$_2$, or 5- to 6-membered heteroaryl, wherein the alkyl or heteroaryl is optionally substituted with one or more halo, $C_1$-$C_6$ alkyl, $C_1$-$C_6$ haloalkyl, $C_3$-$C_6$ cycloalkyl, or $C_1$-$C_6$ alkoxy.

18. The compound of claim 14, $R_4$ is H or halo.

19. The compound of claim 1, wherein each $R_5$ is independently H, or $C_1$-$C_6$ alkyl.

20. The compound of claim 1, wherein each $R_5$ is H.

21. A compound selected from:

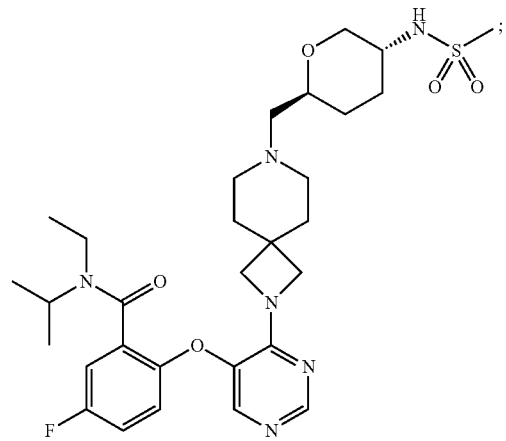

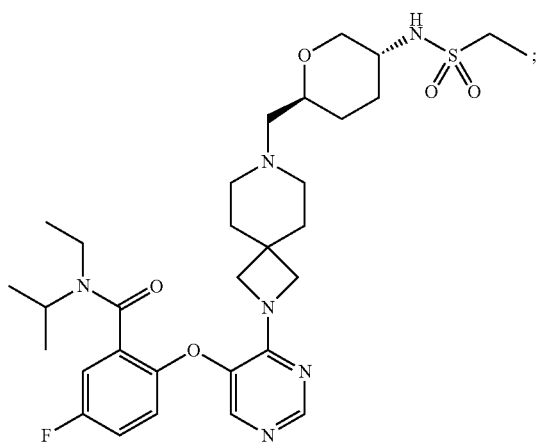

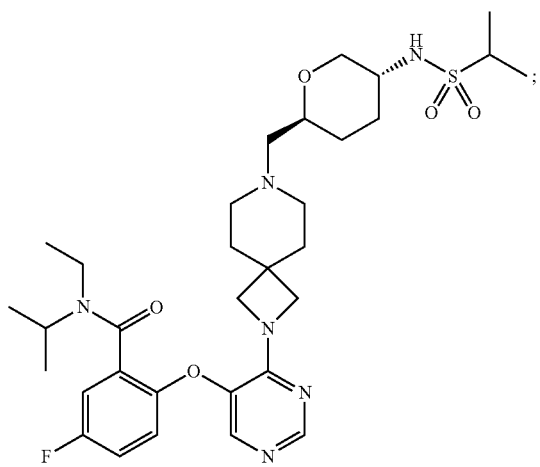

725
-continued
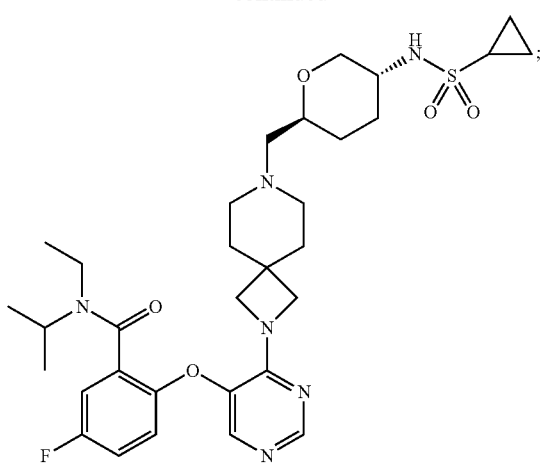
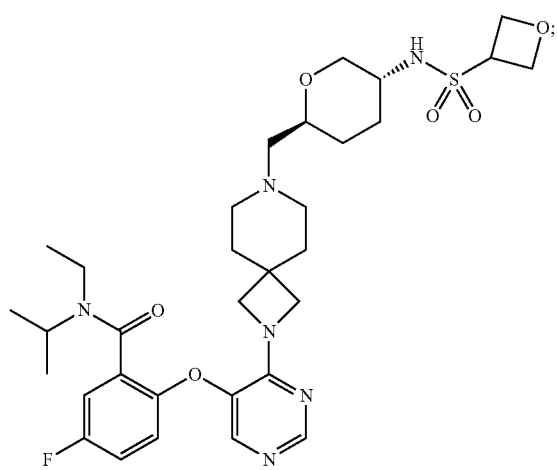
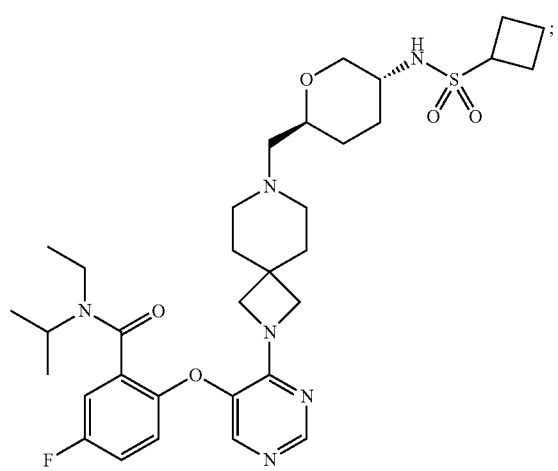
726
-continued
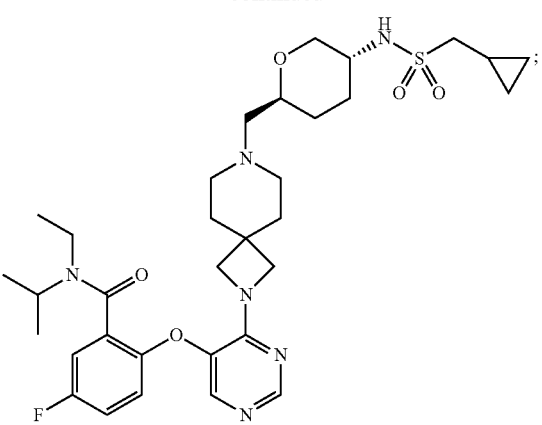
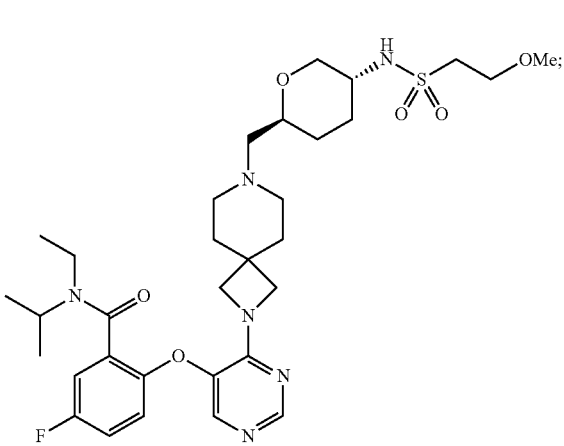
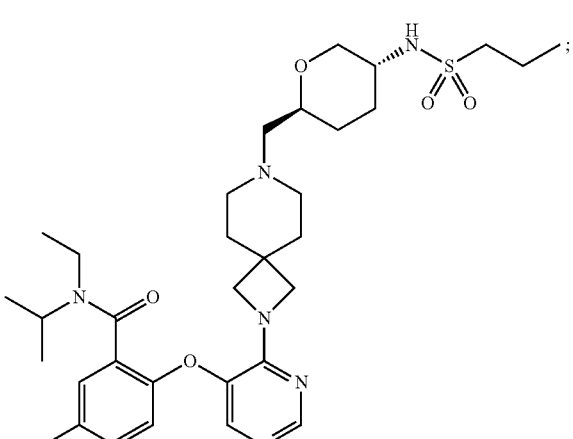

727
-continued
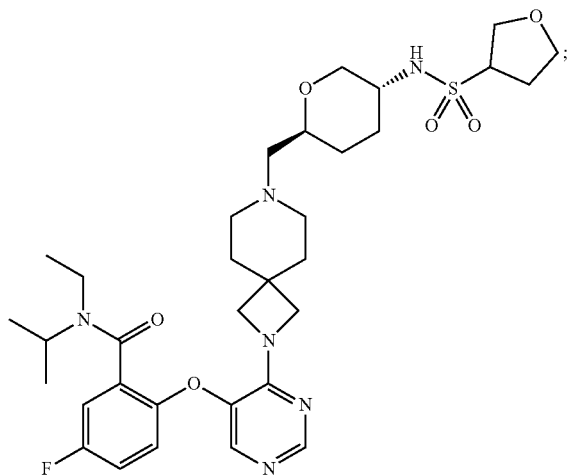
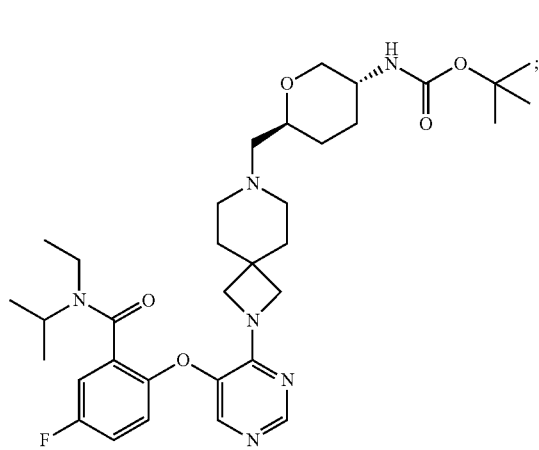
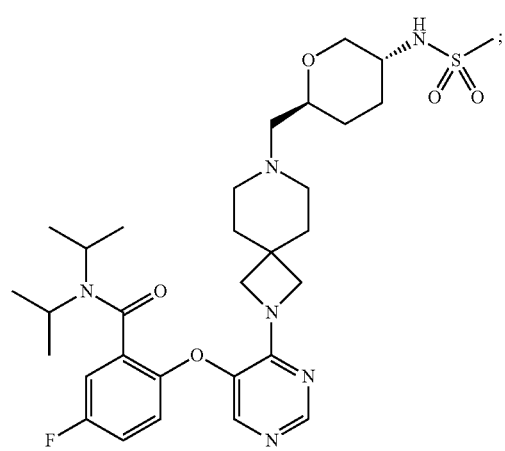
728
-continued
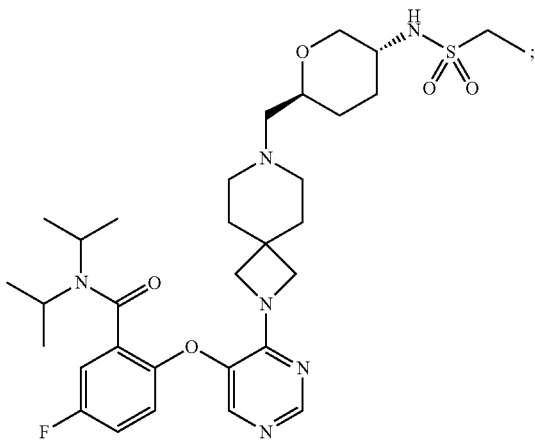
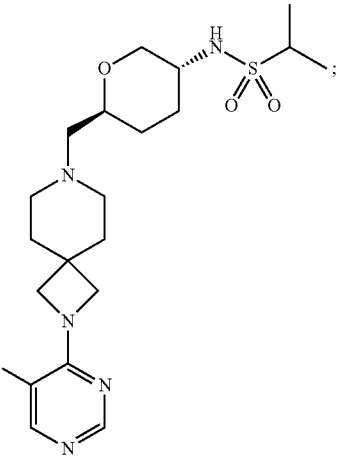
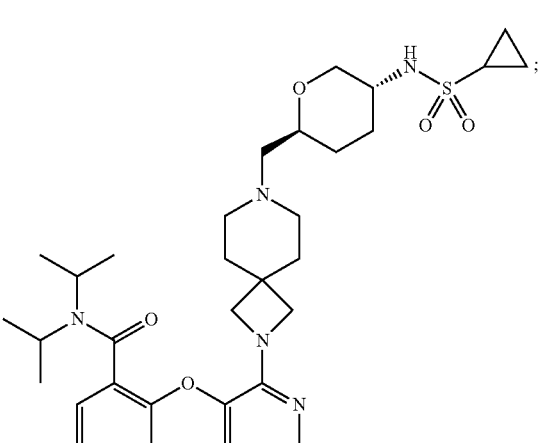

729
-continued
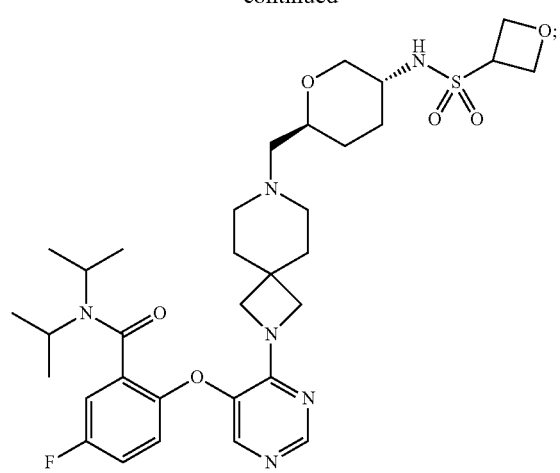
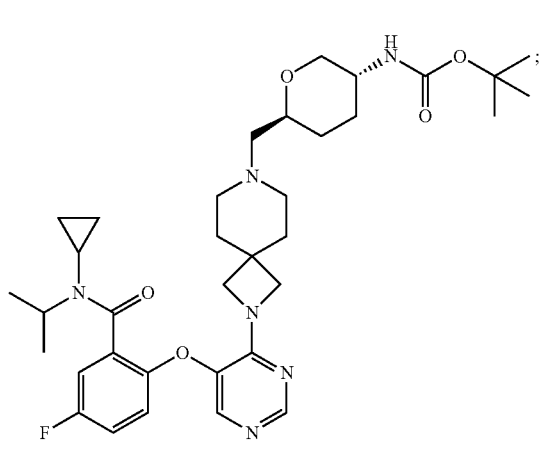
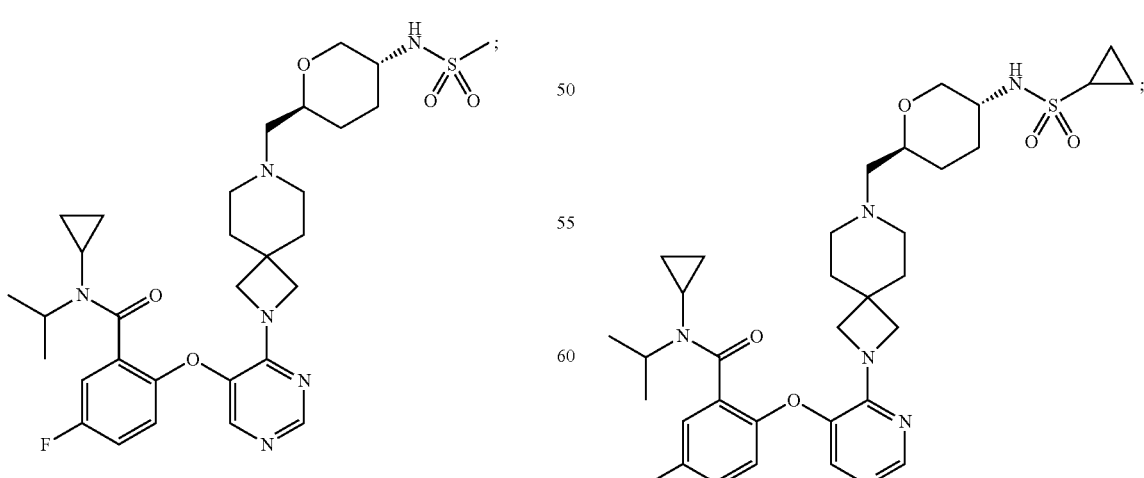
730
-continued
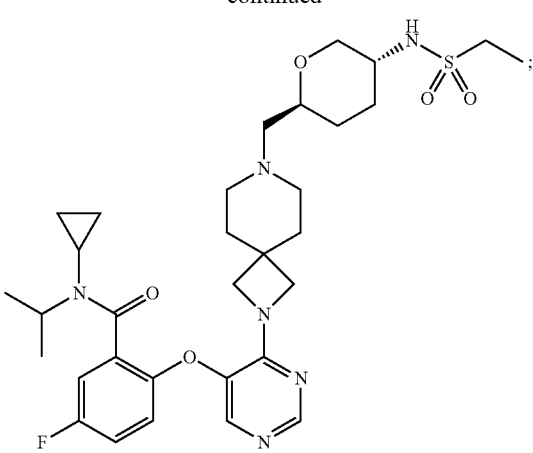
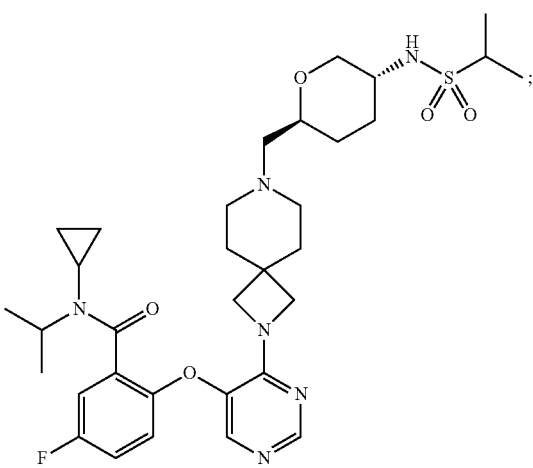
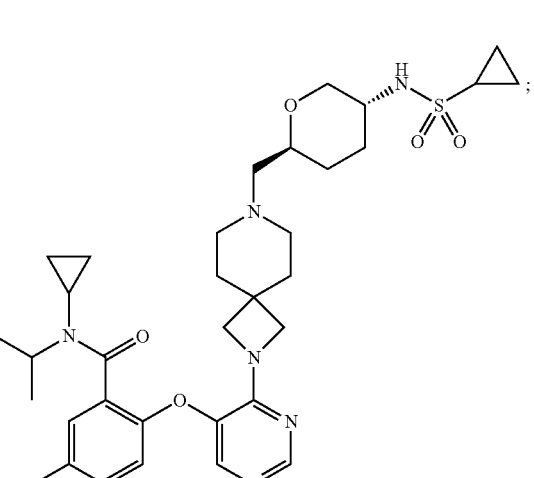

731
-continued
732
-continued
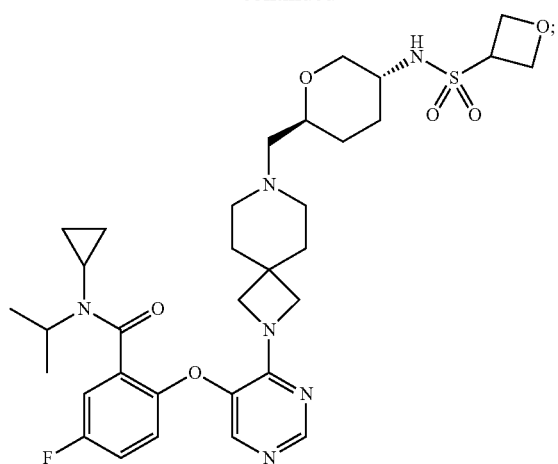
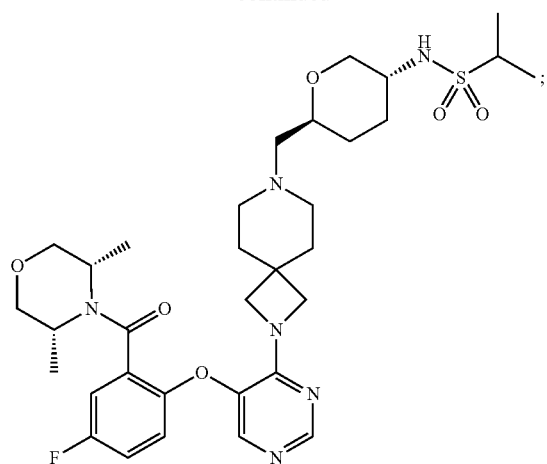
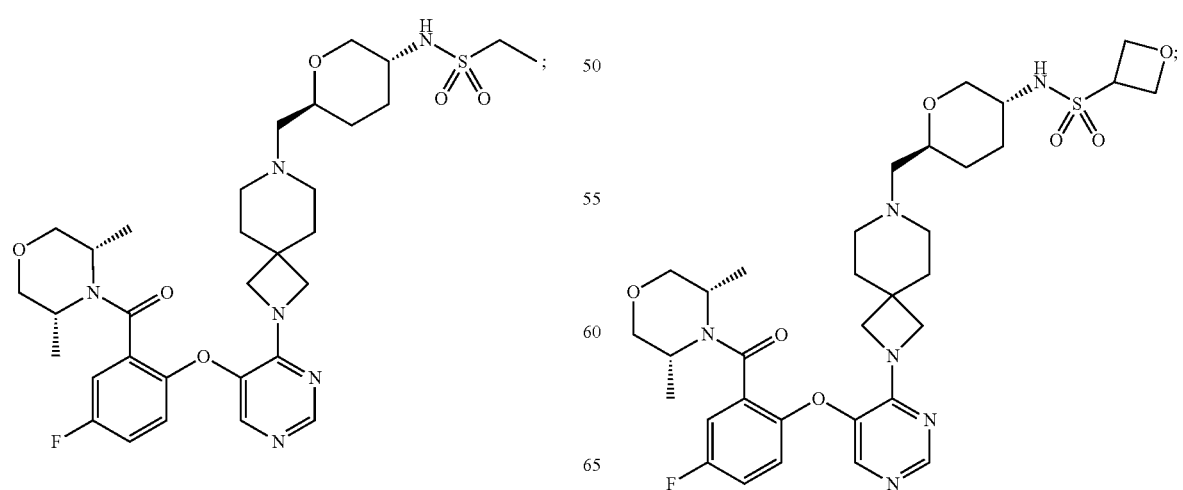
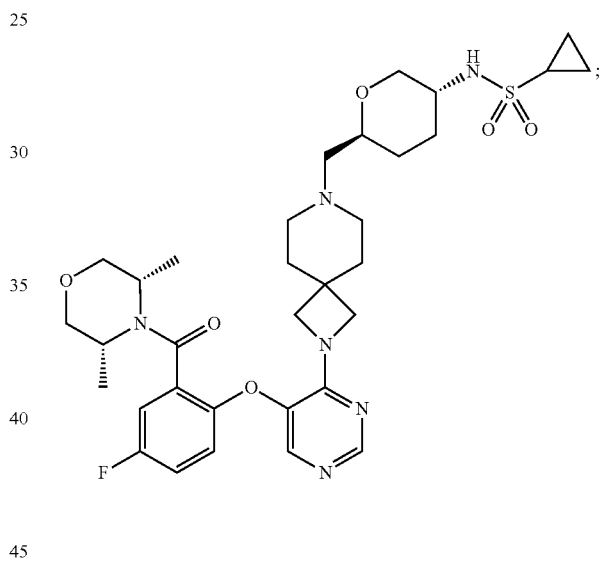

733
-continued
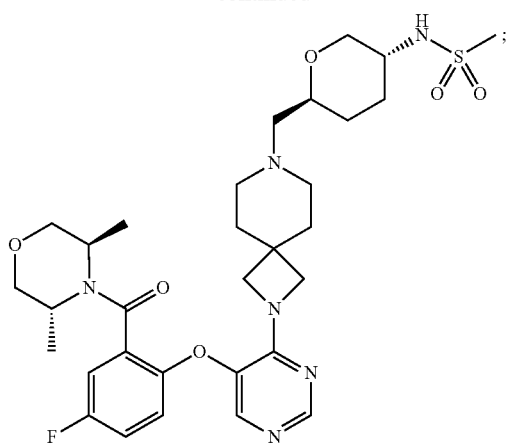
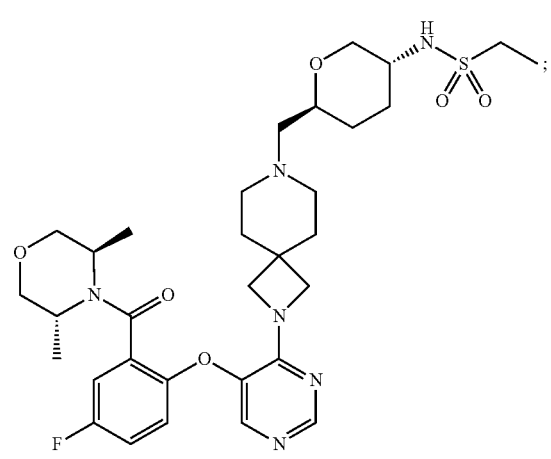
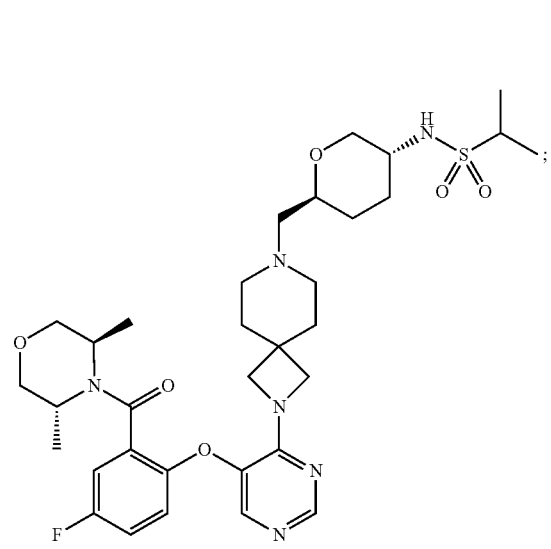
734
-continued
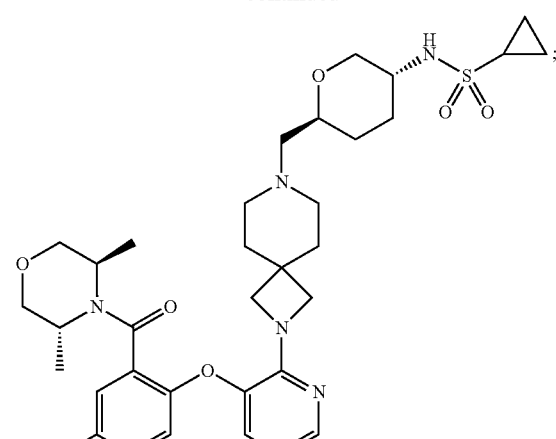
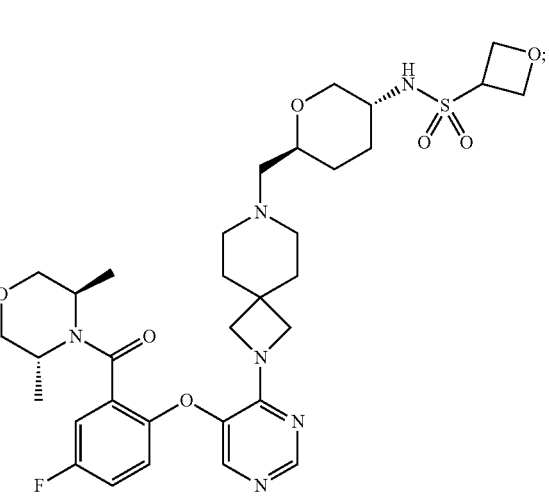
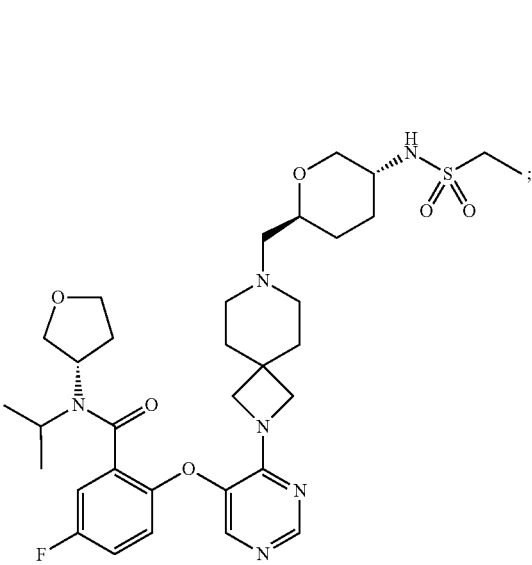

735
-continued
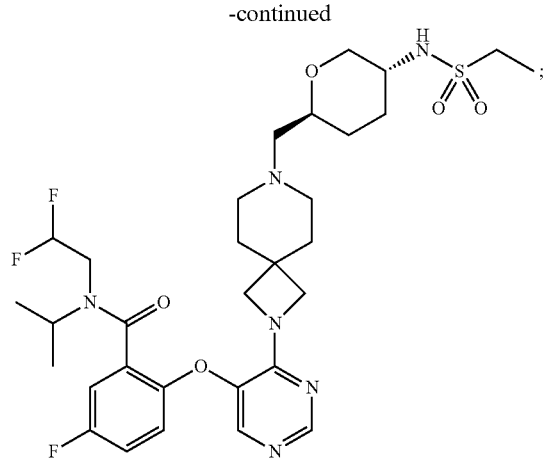
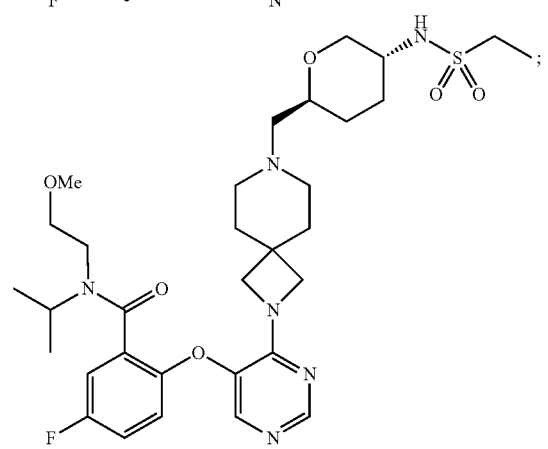
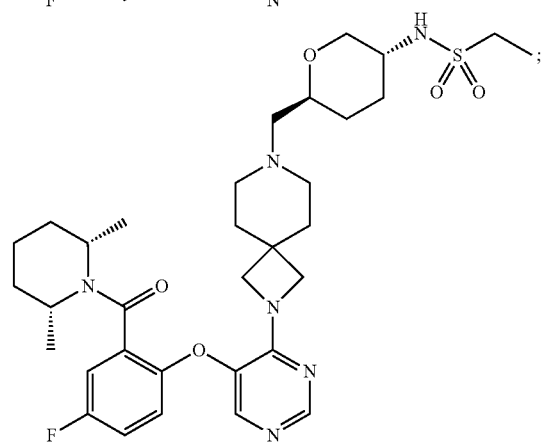
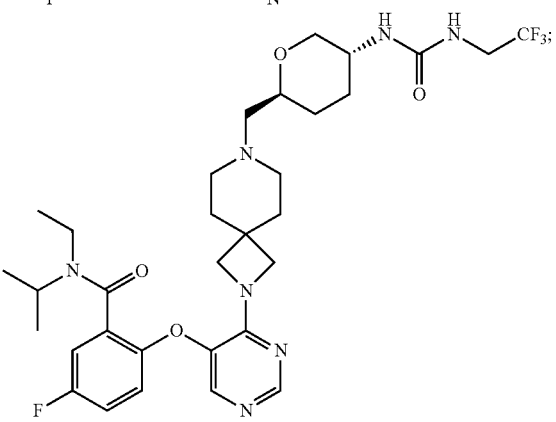
736
-continued
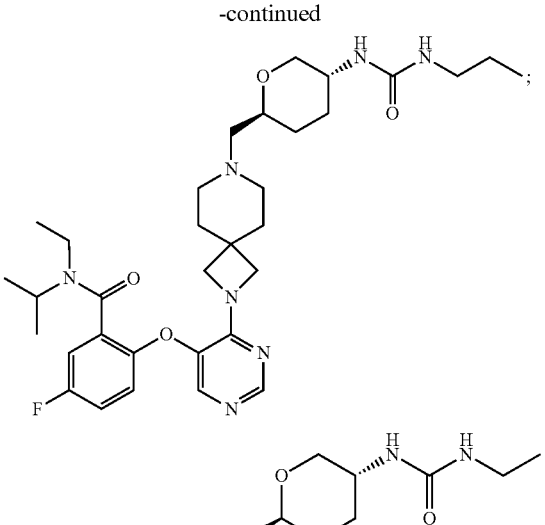
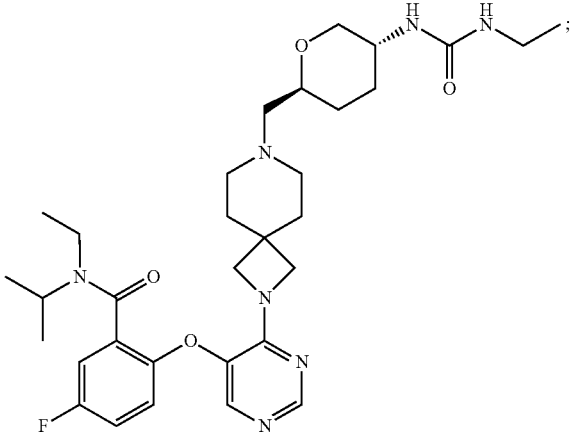
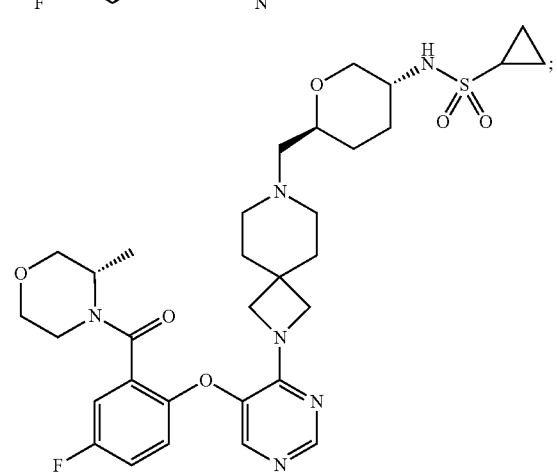
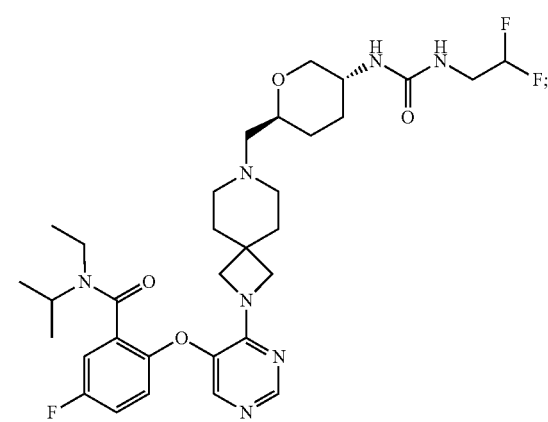

737
-continued
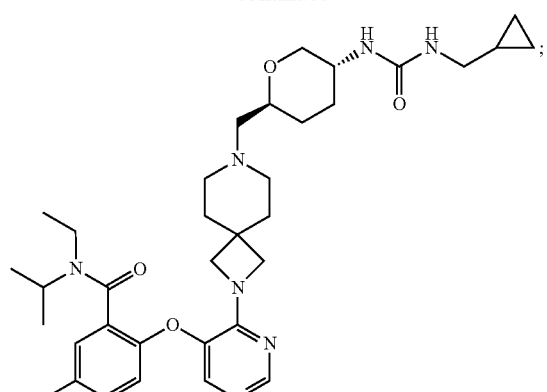
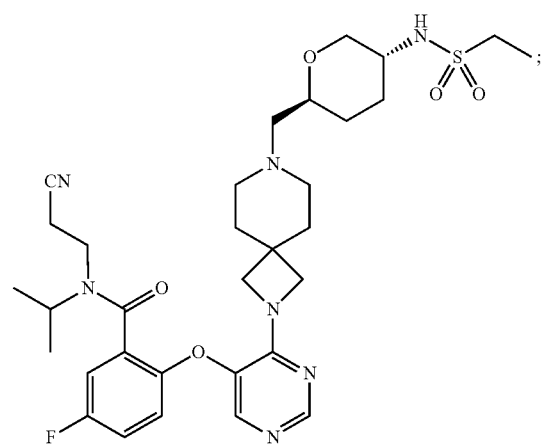
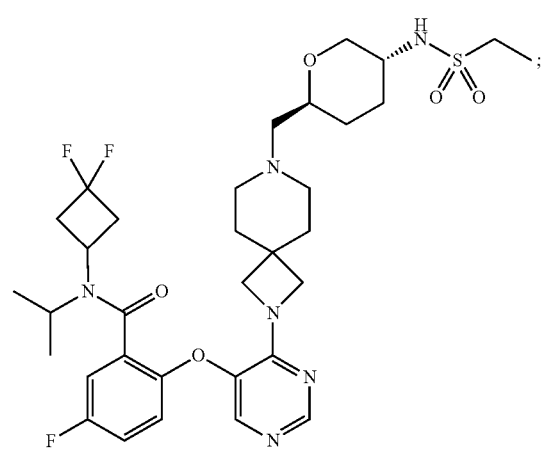
738
-continued
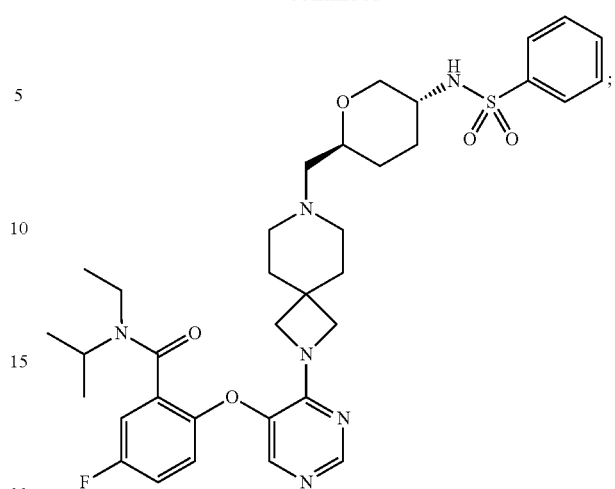
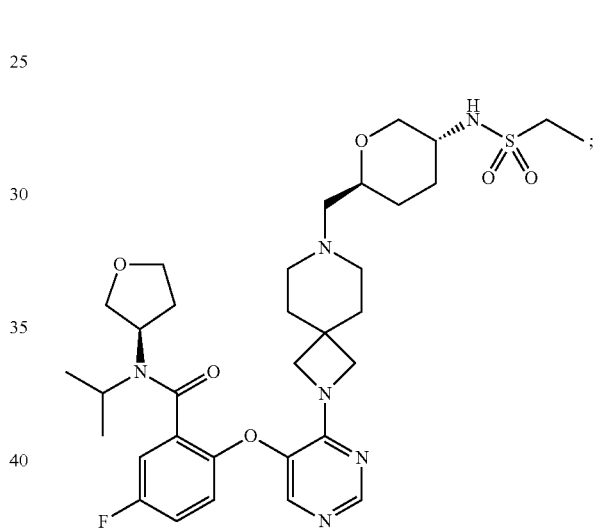
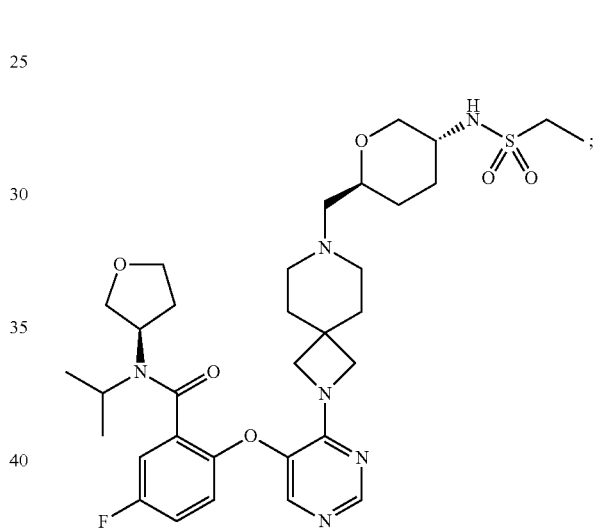

739
-continued
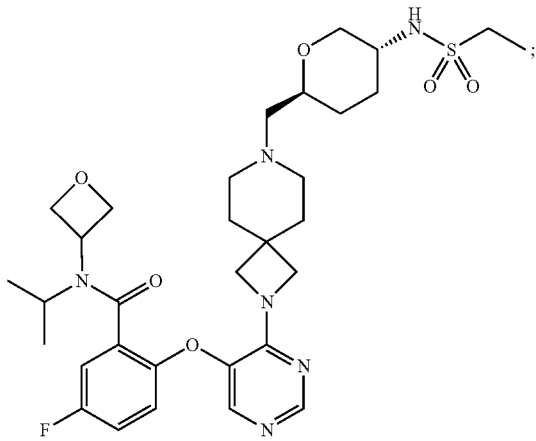
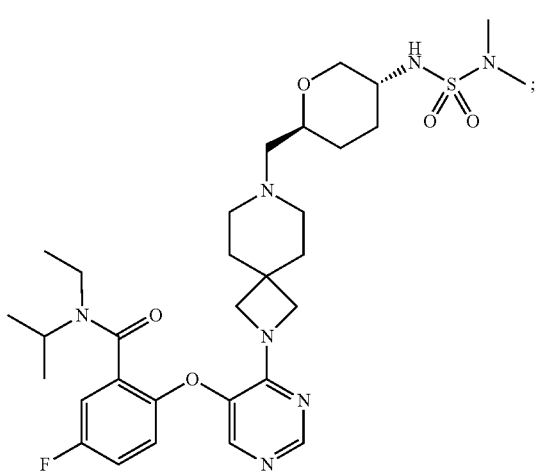
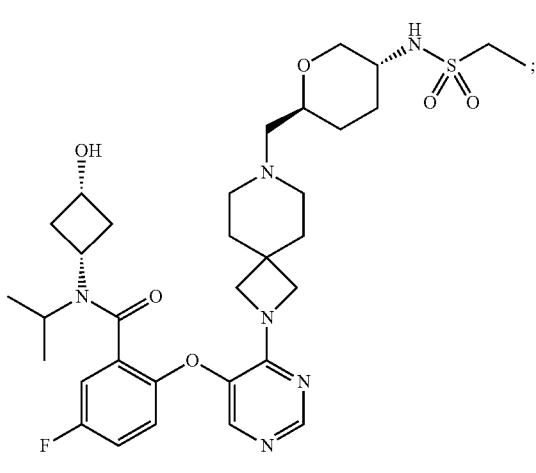
740
-continued
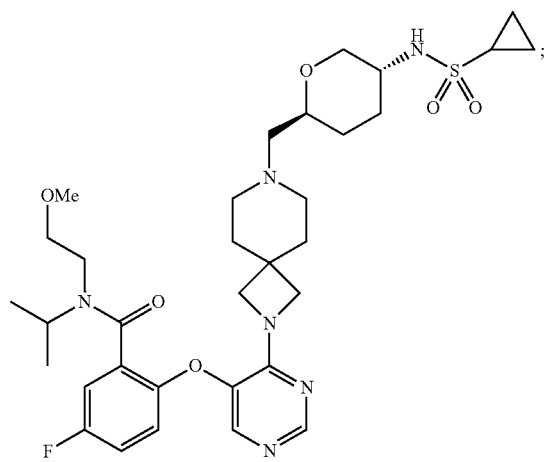
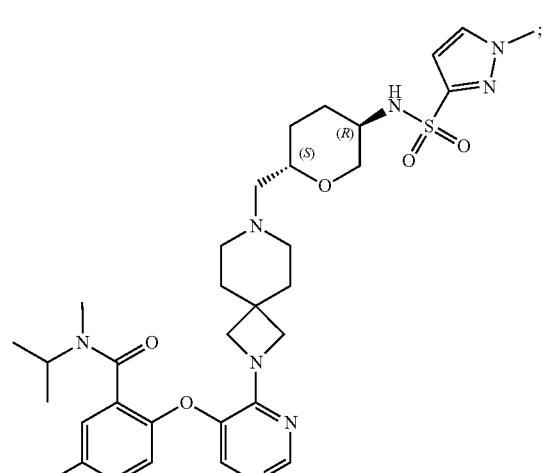

741
-continued
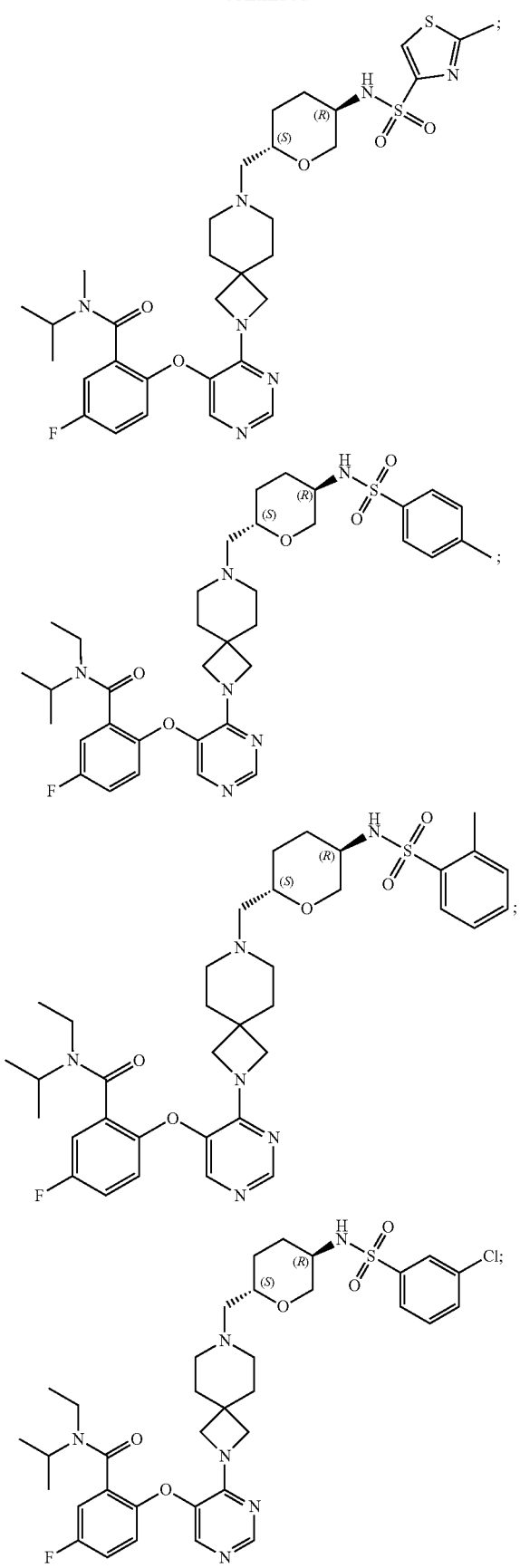
742
-continued
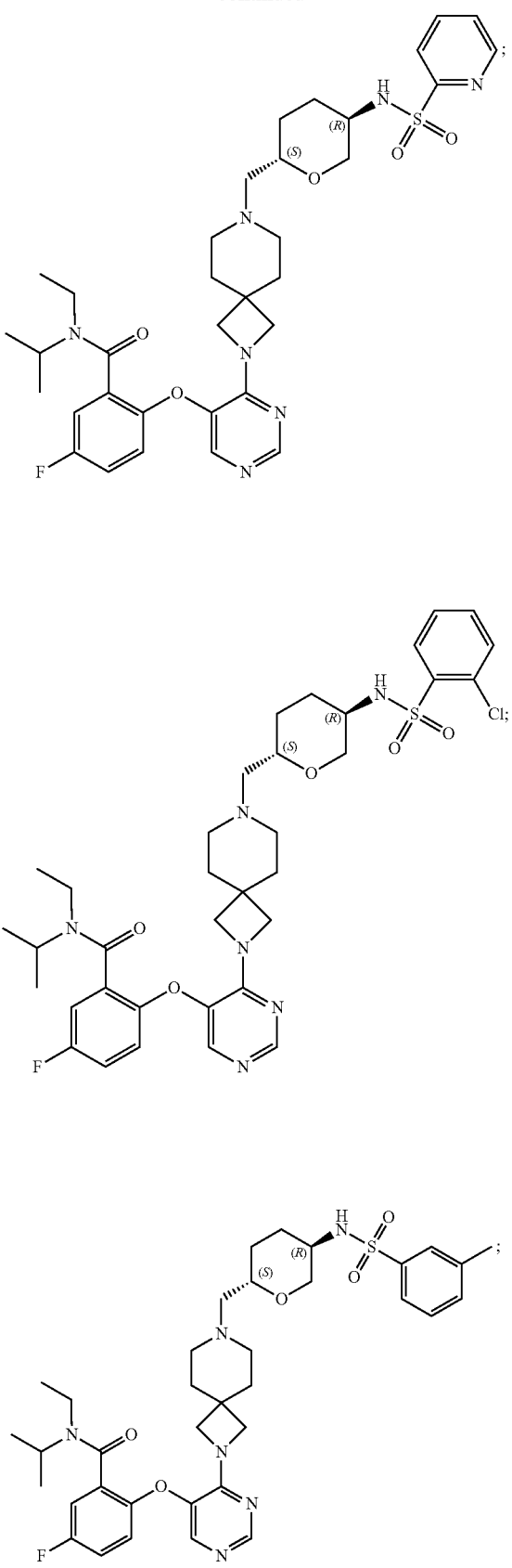

743
-continued
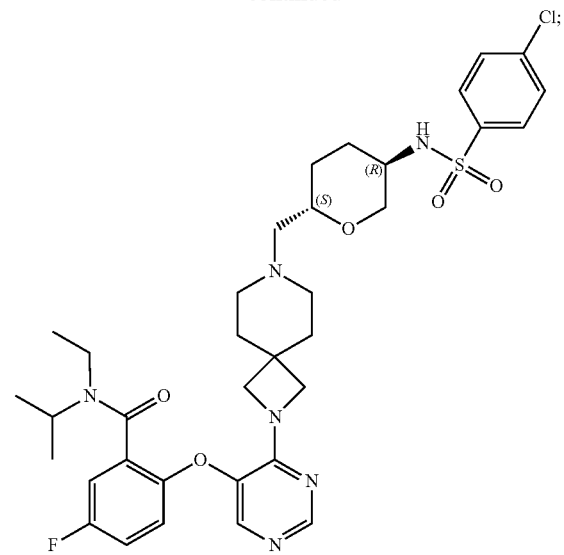
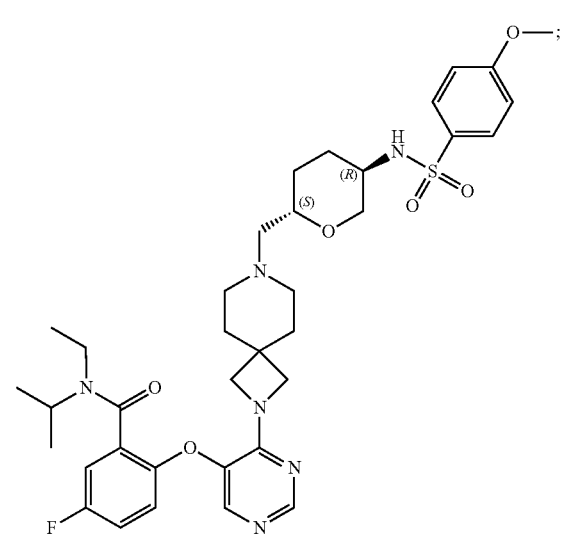
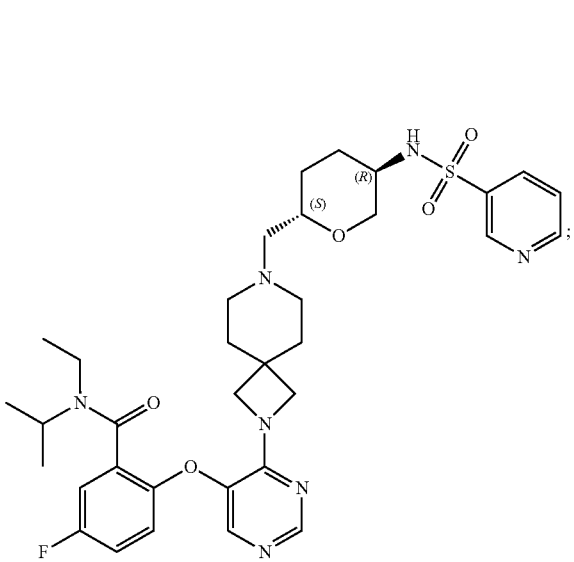
744
-continued
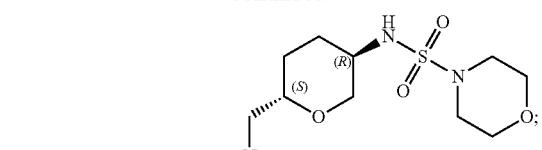
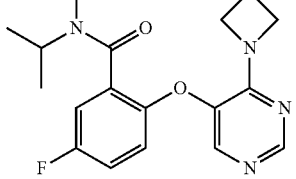
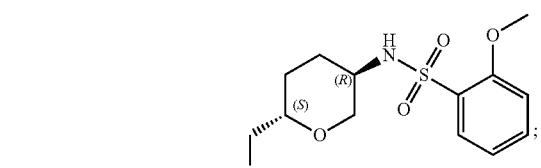
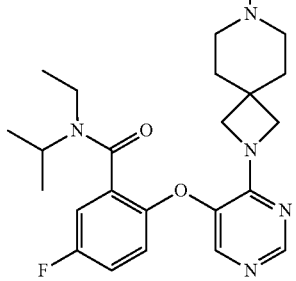
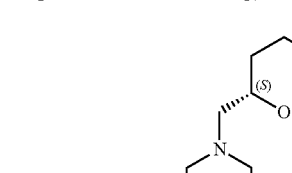
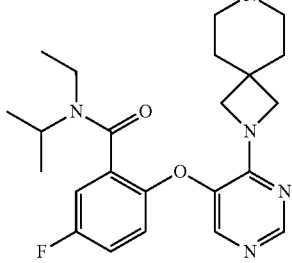

745
-continued
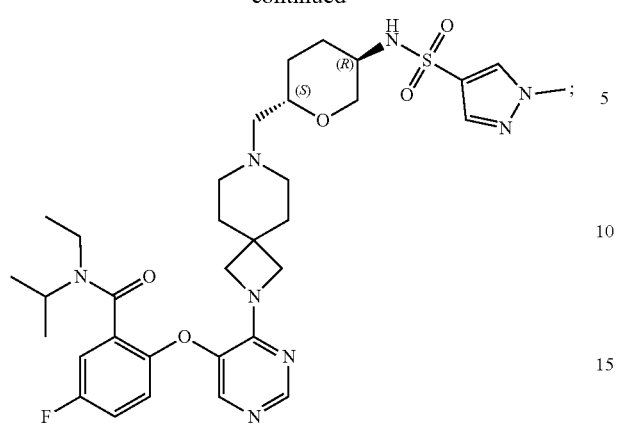
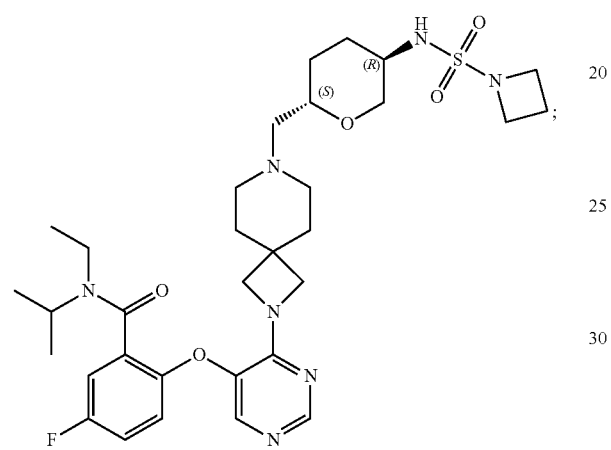
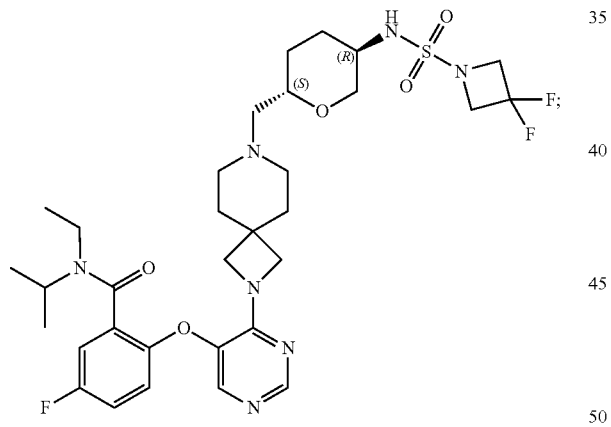
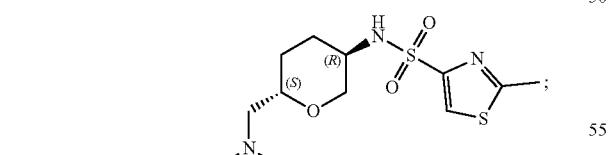
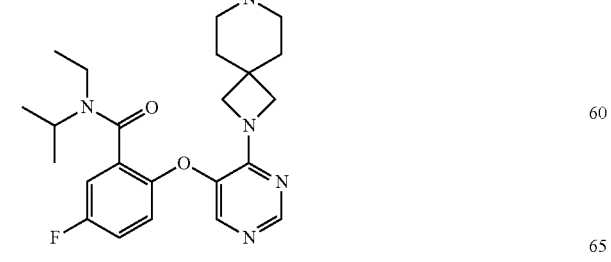
746
-continued
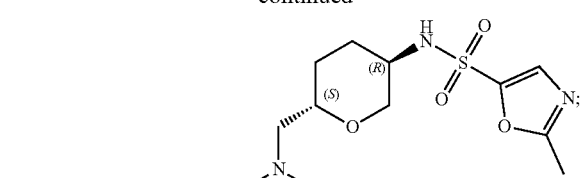
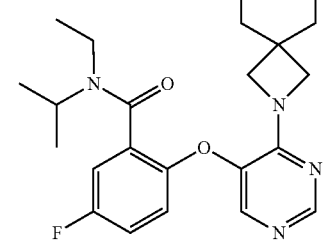
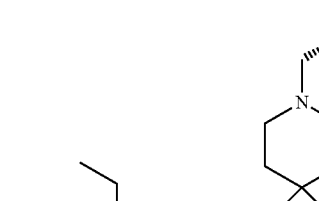
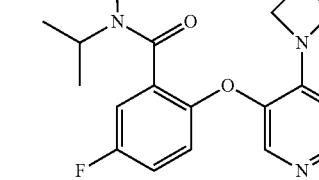
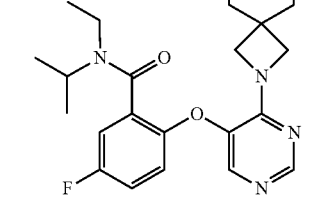

747
-continued
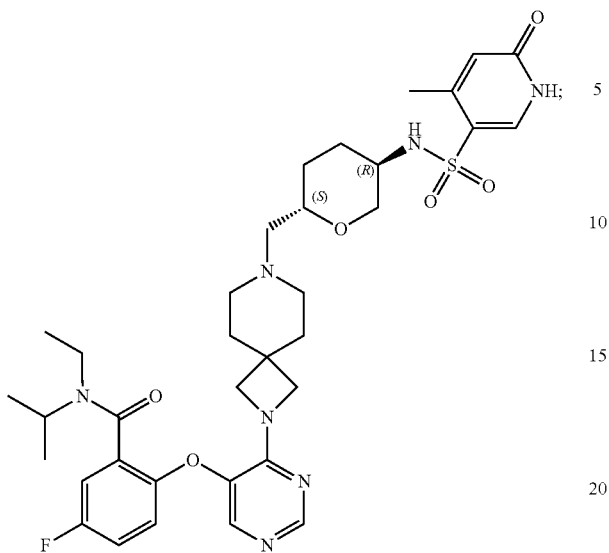
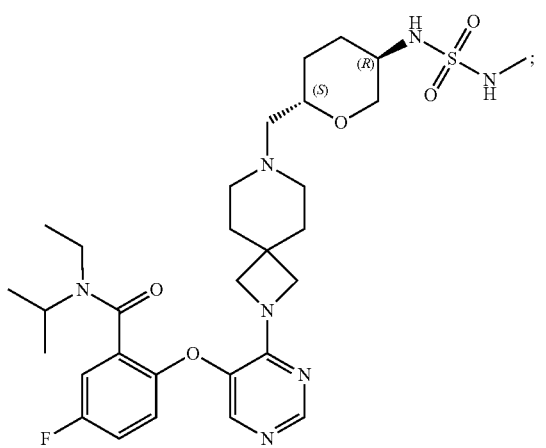
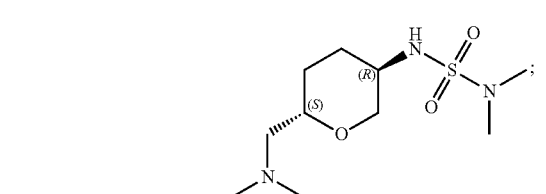
748
-continued
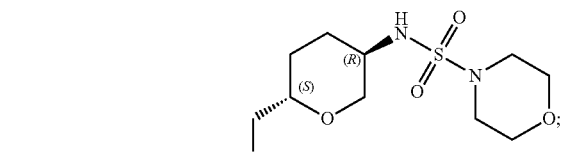
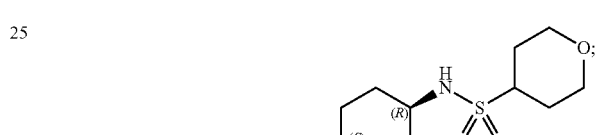
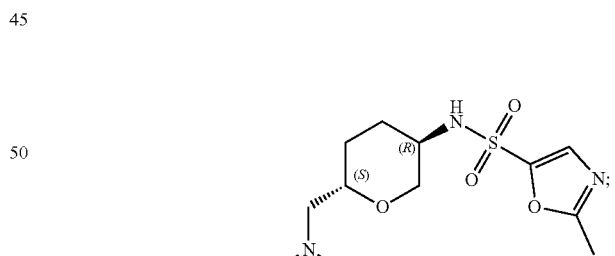
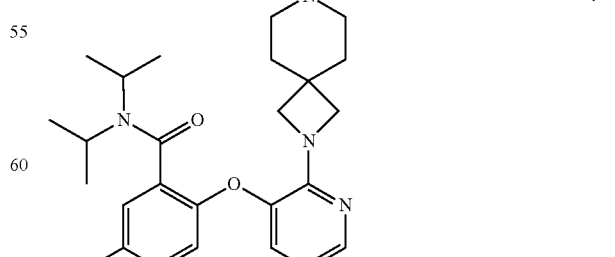

749
-continued
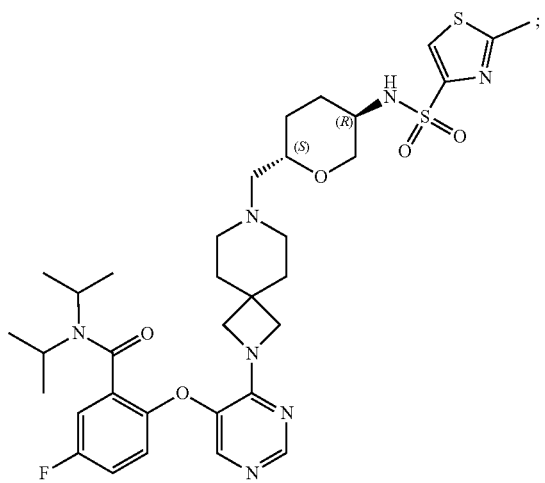
750
-continued
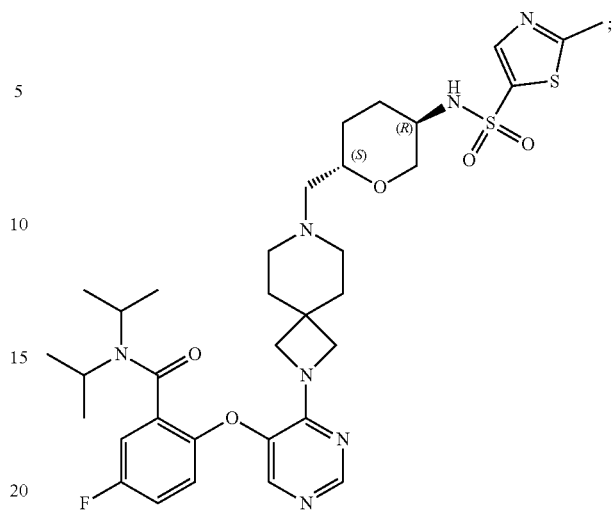
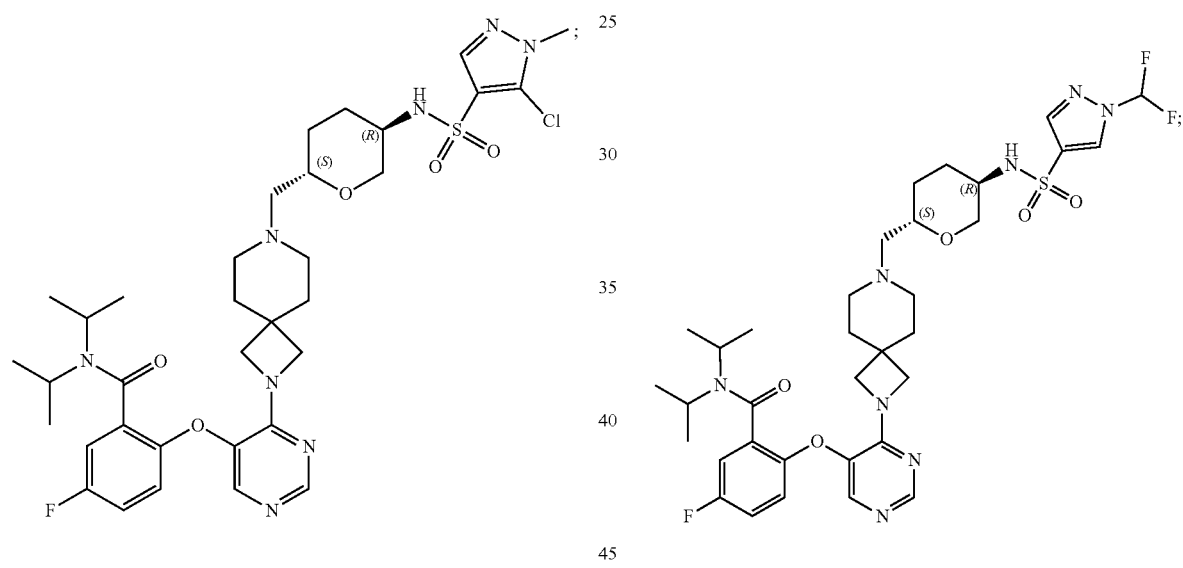
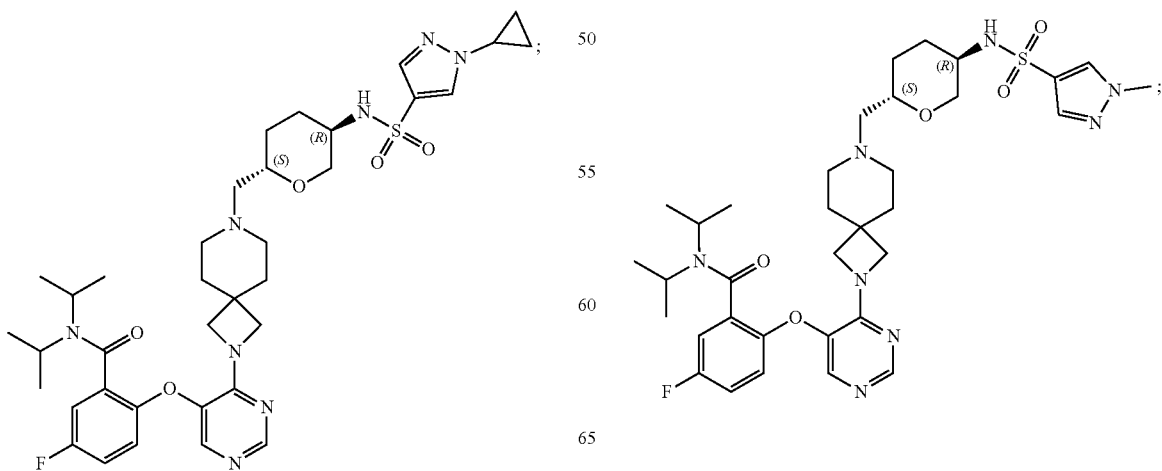

751
-continued
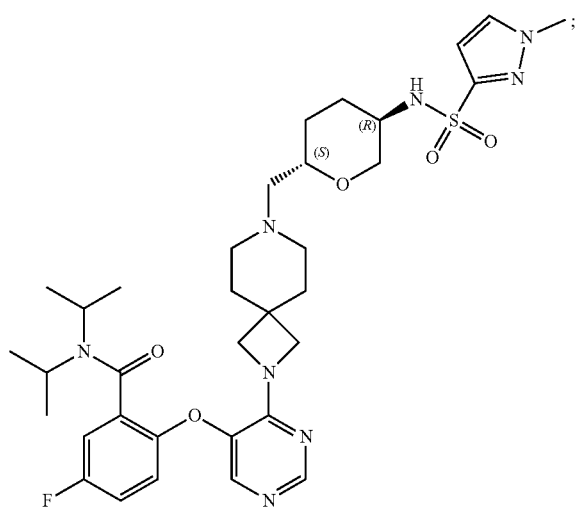
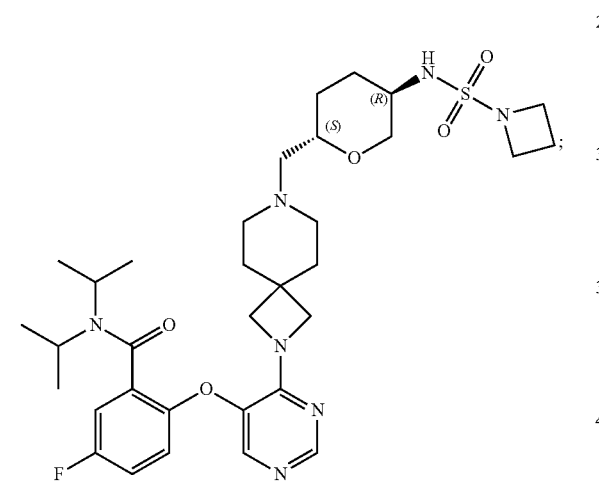
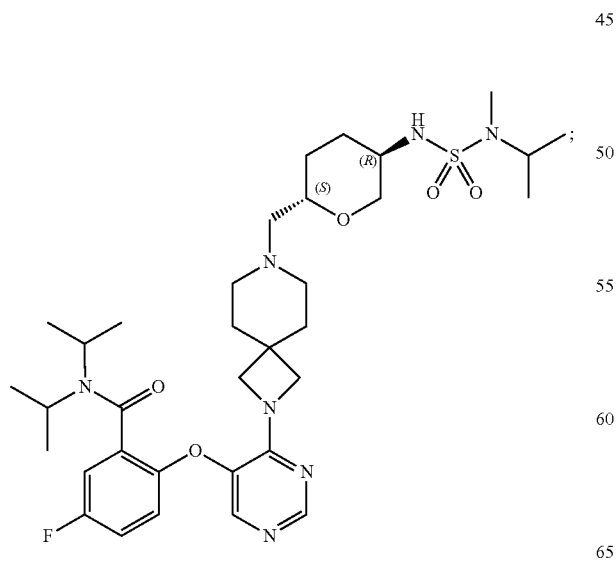
752
-continued
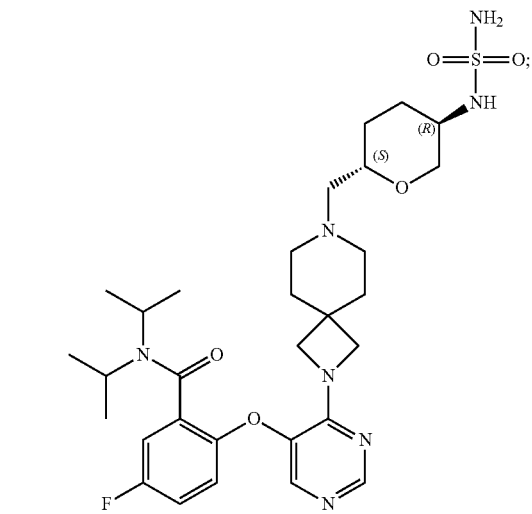
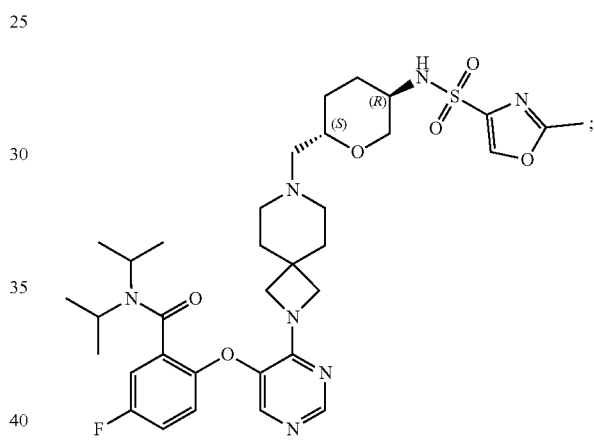

753
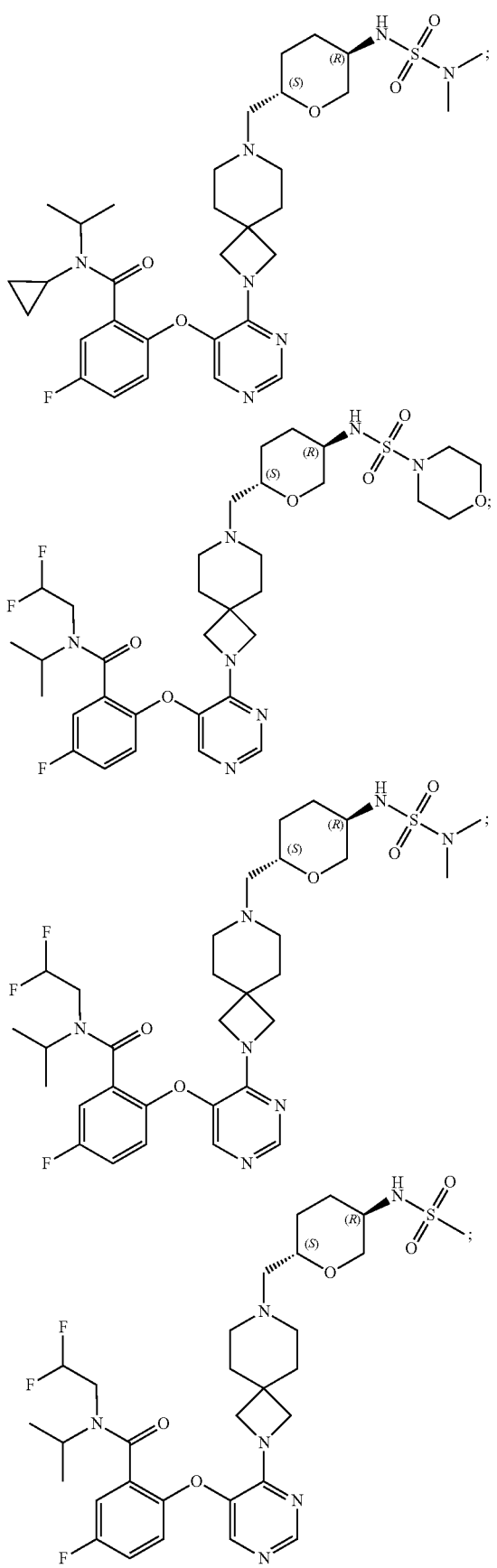
754
-continued
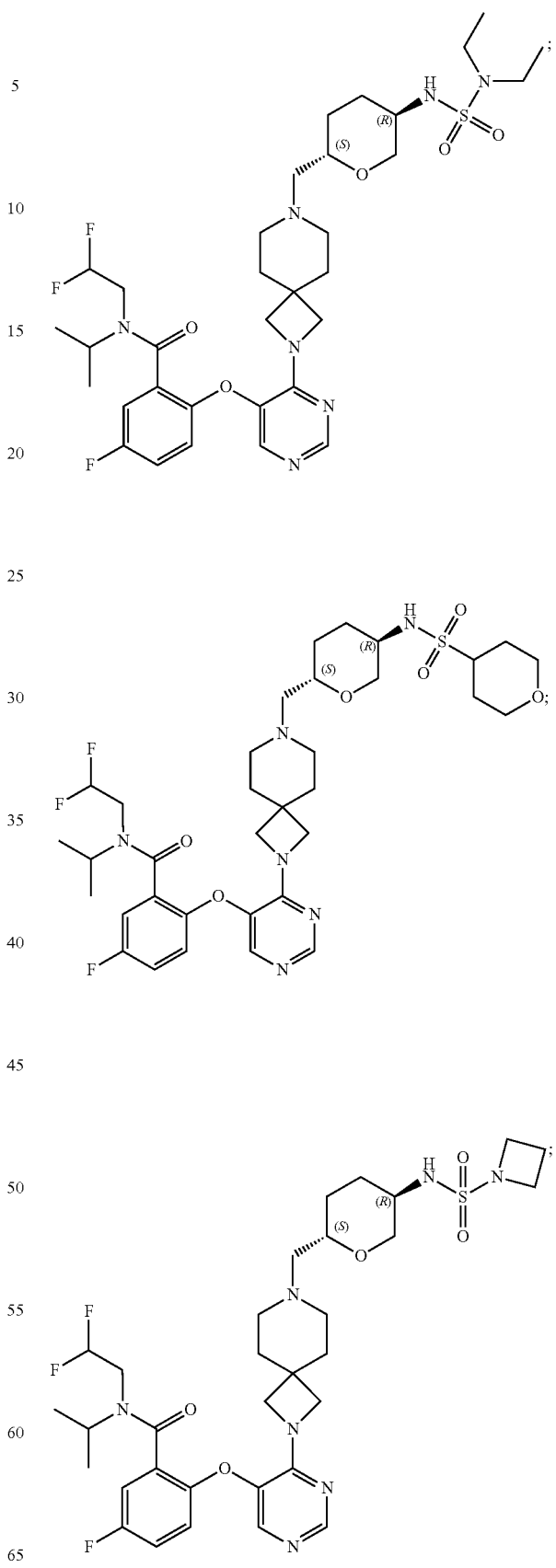

755
-continued
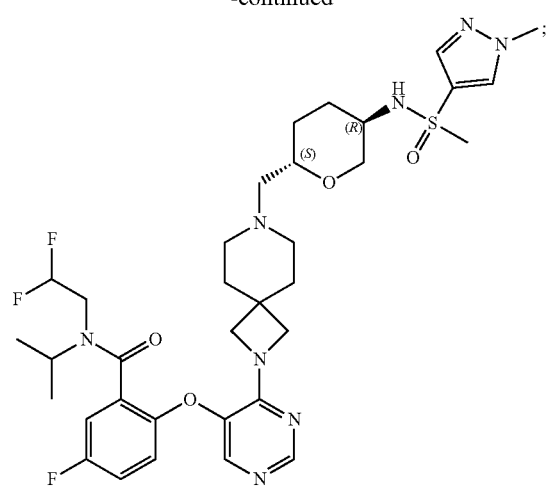
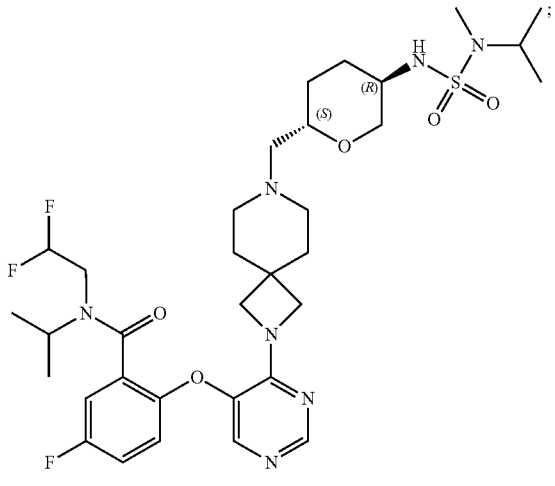
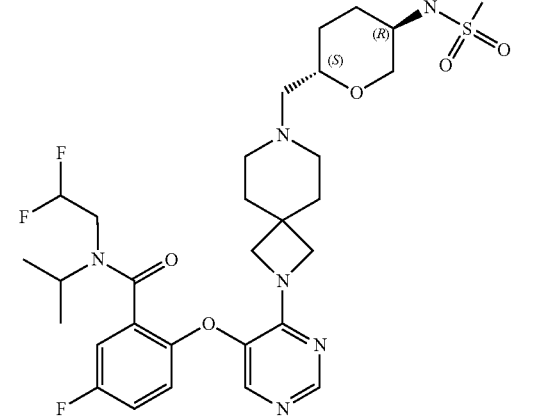
756
-continued
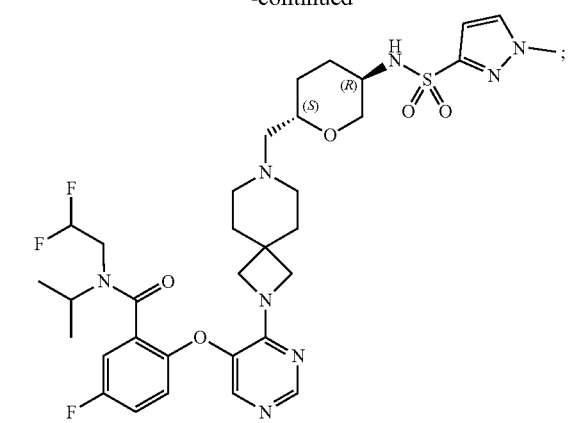
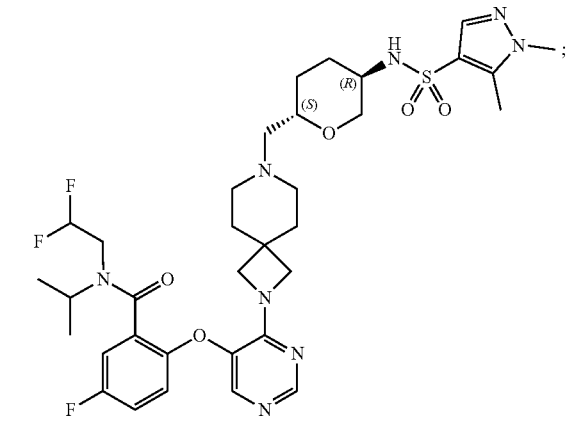
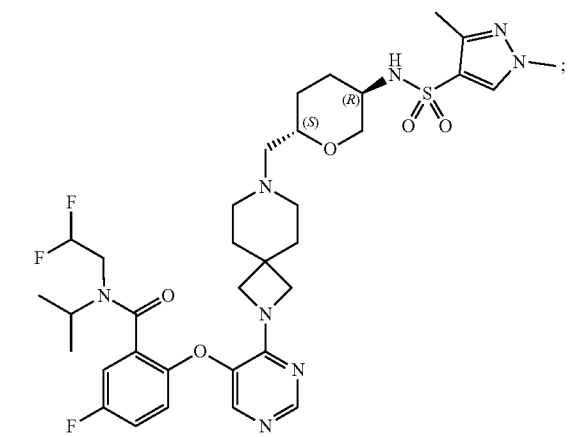
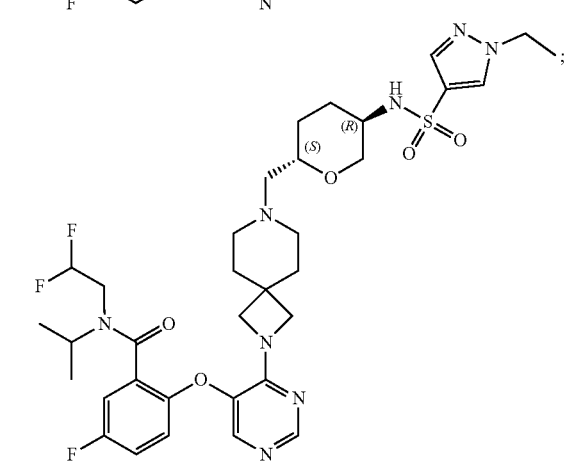

757
-continued
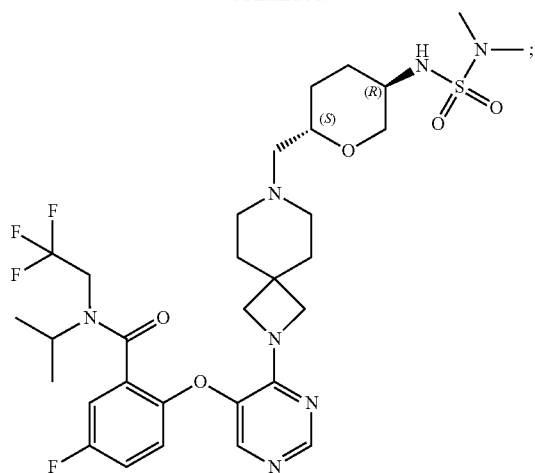
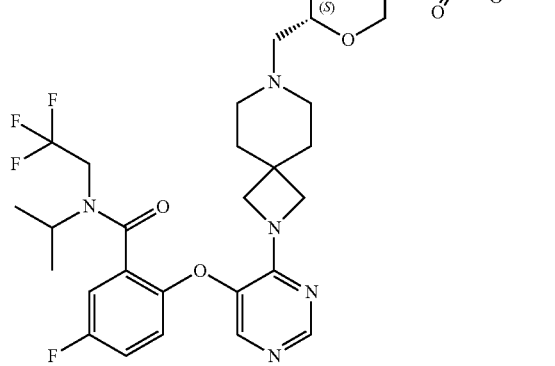
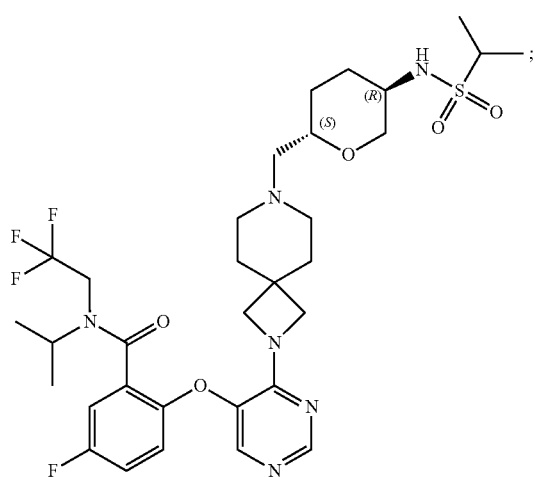
758
-continued
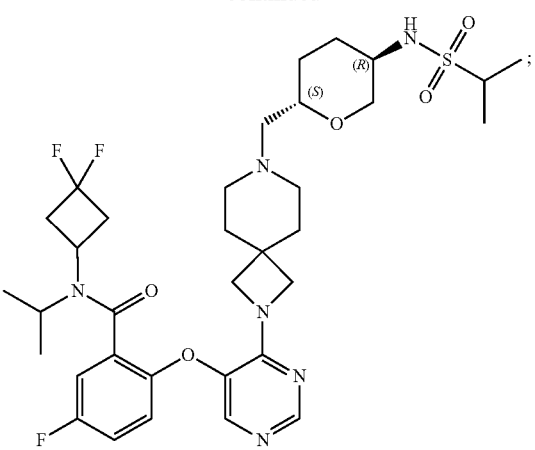
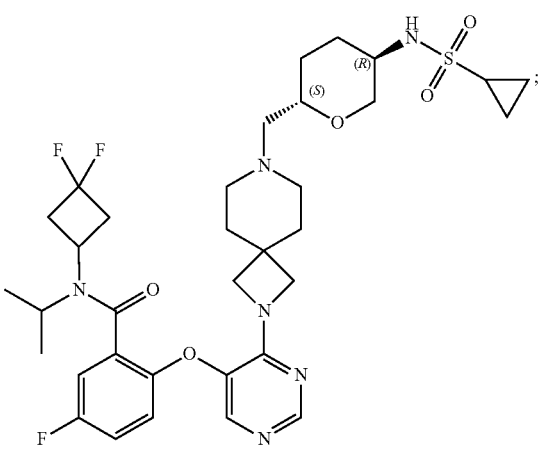
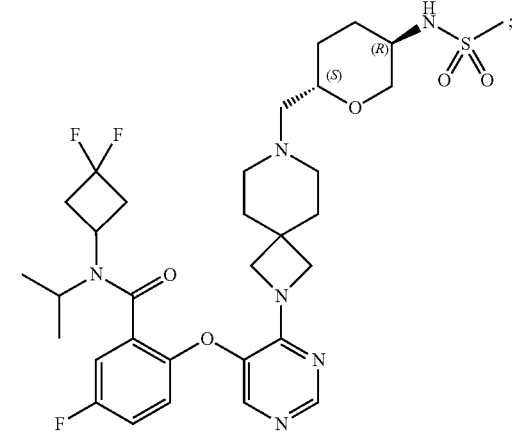

759
-continued
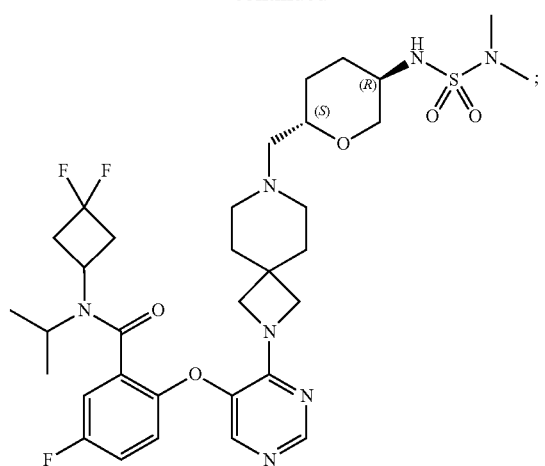
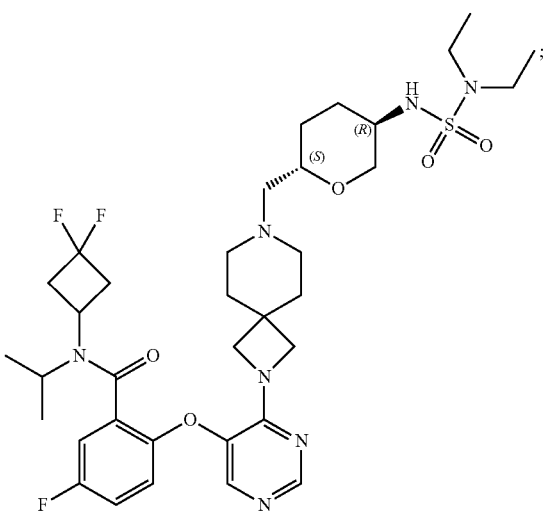
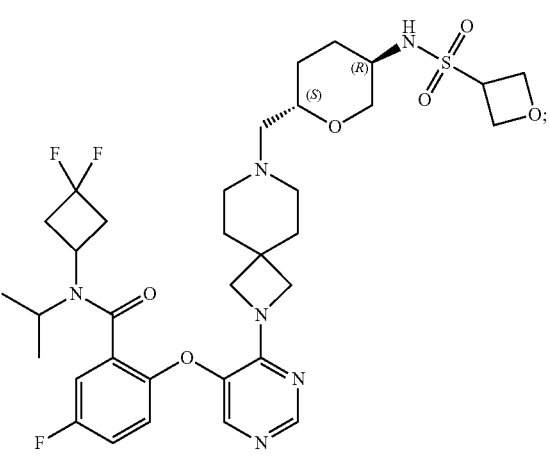
760
-continued
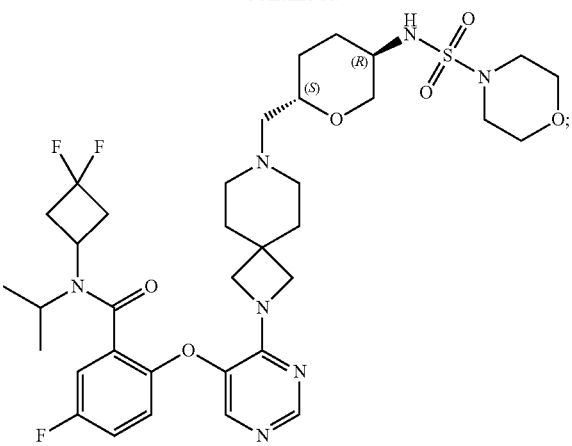
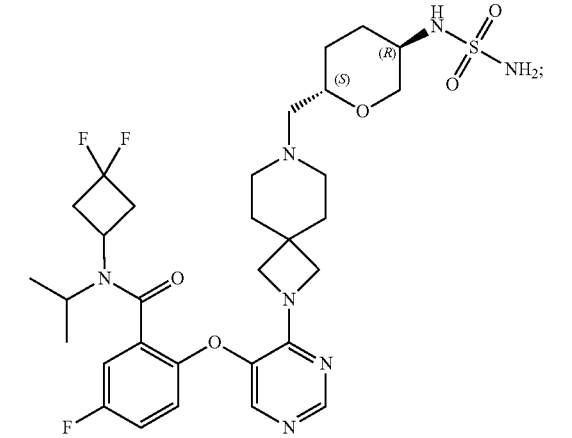
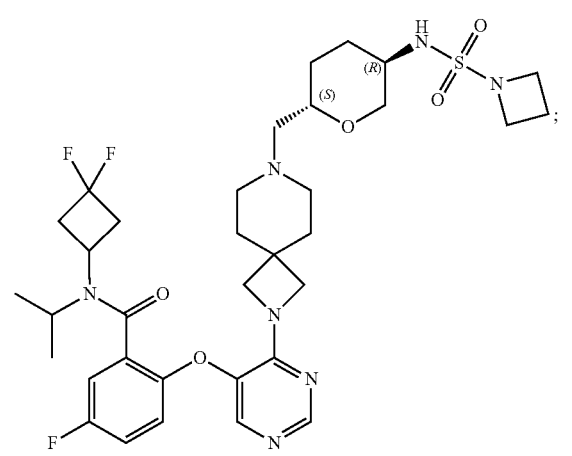

761
-continued
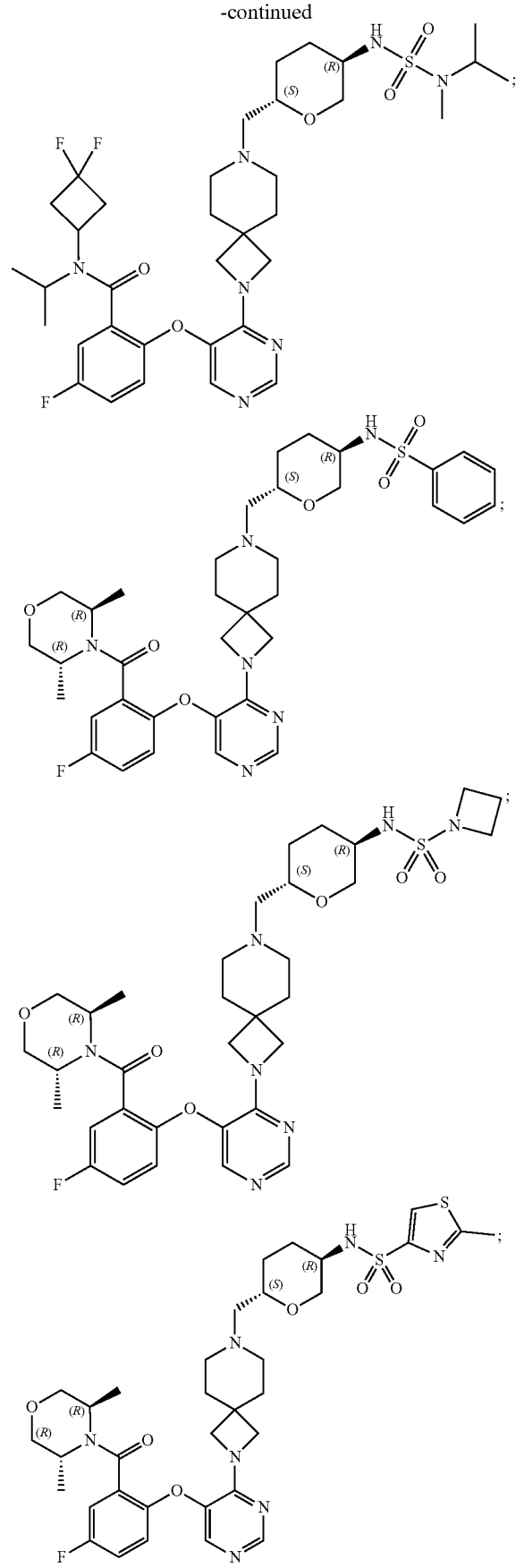
762
-continued
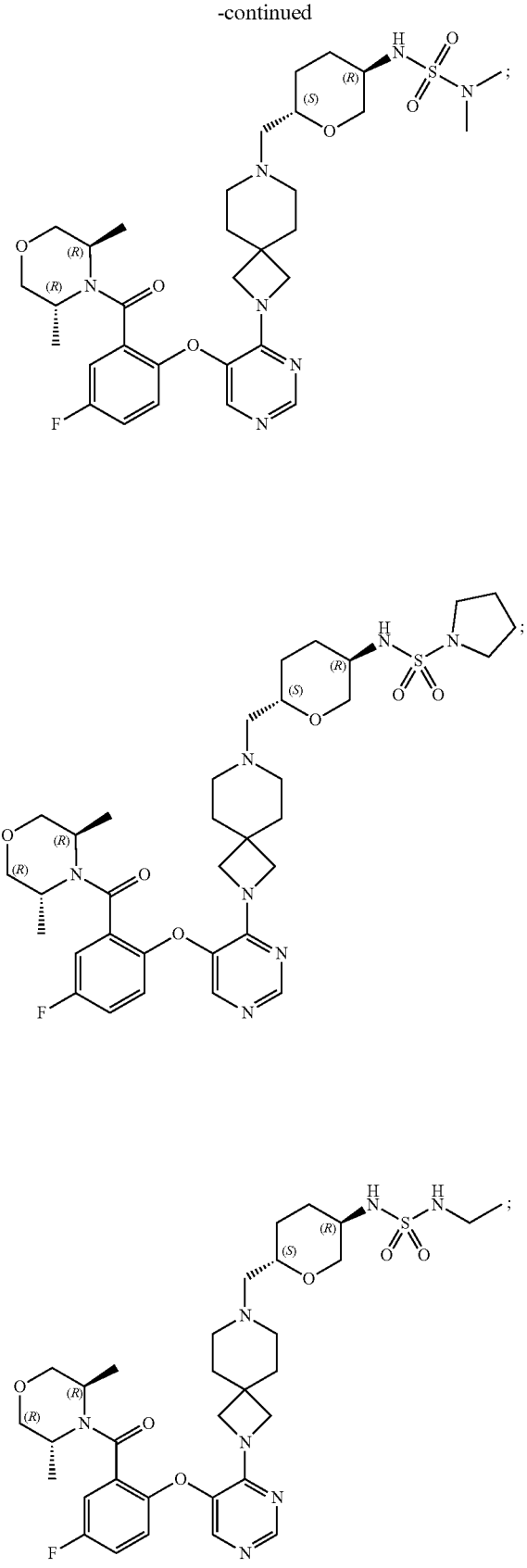

763
764

765
-continued
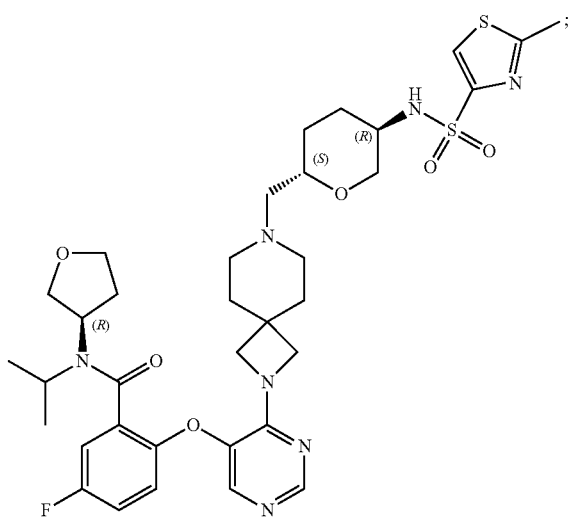
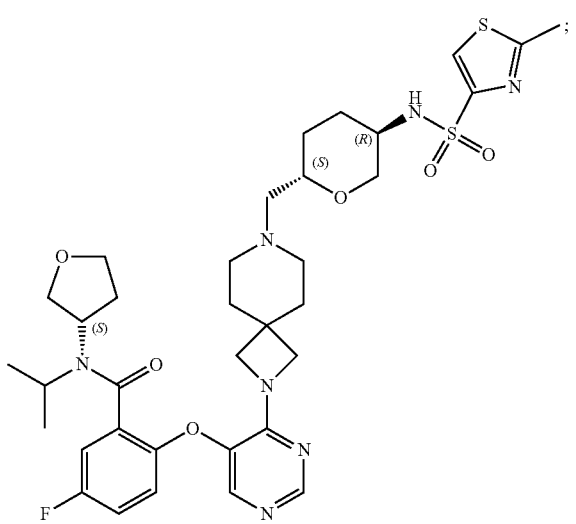
766
-continued
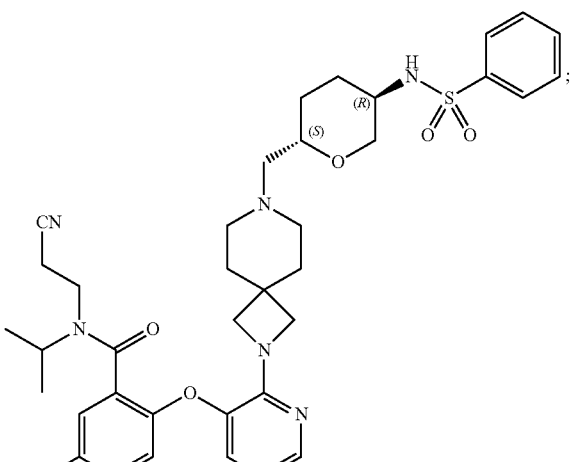
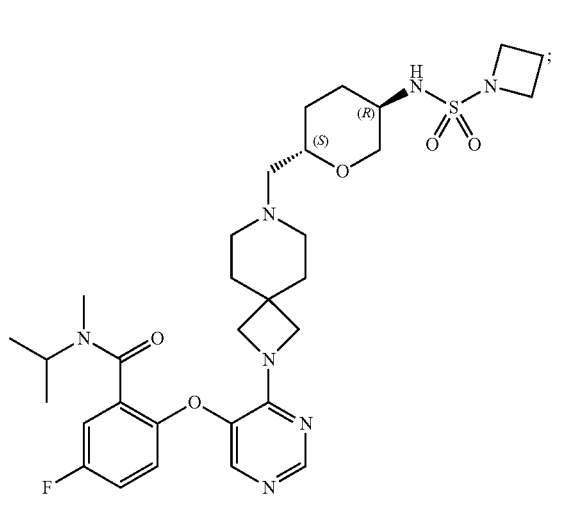

767
-continued
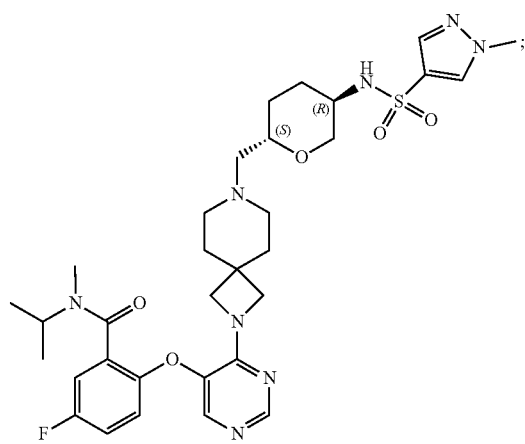
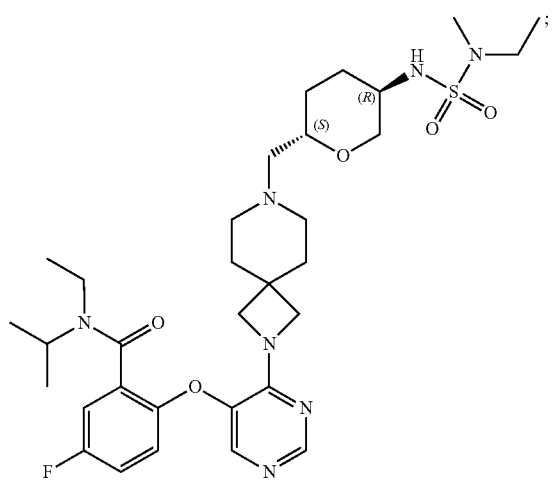
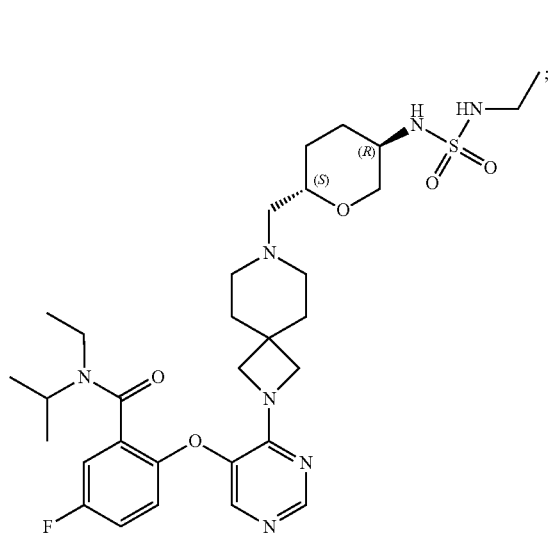
768
-continued
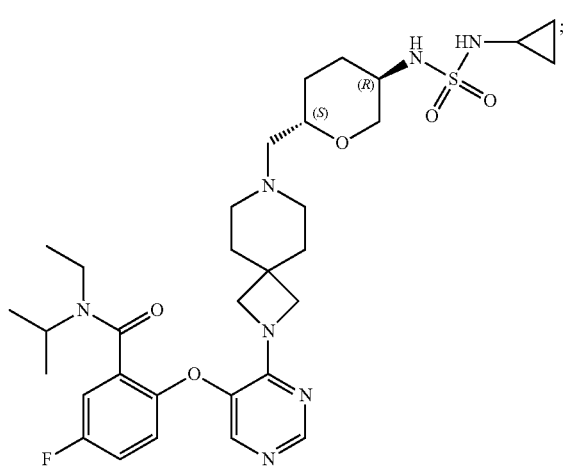
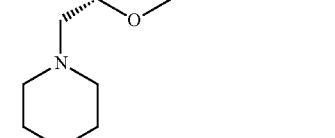

769
-continued
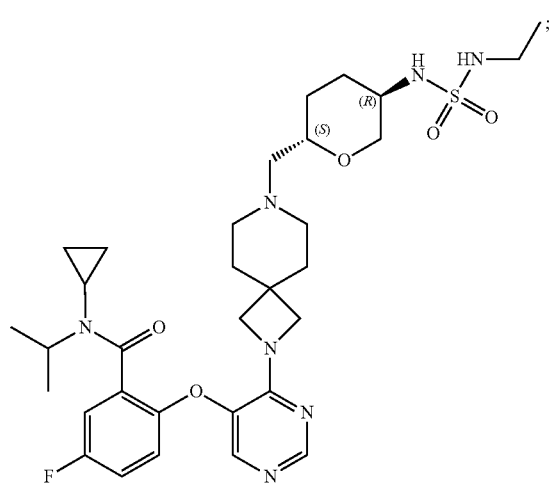
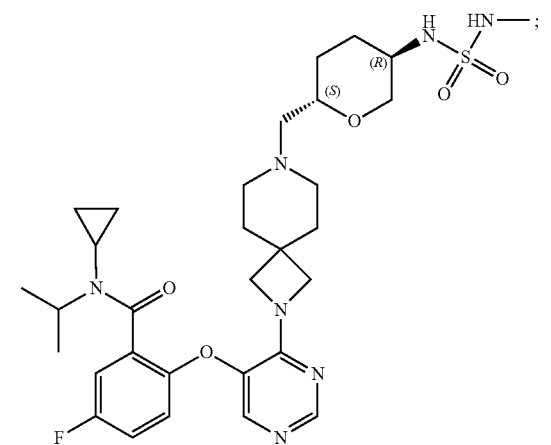
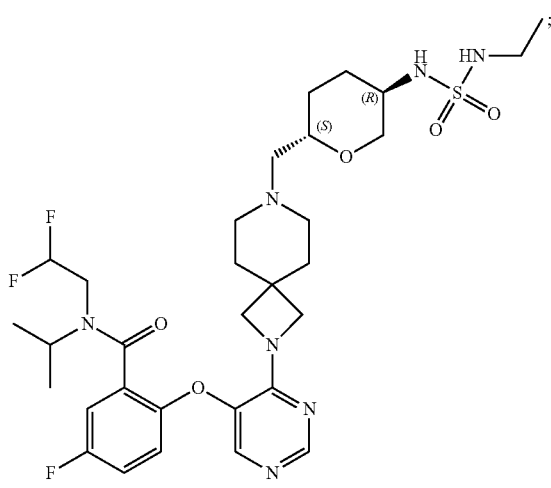
770
-continued
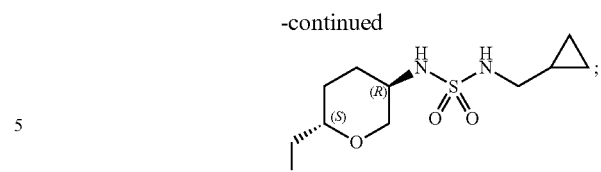
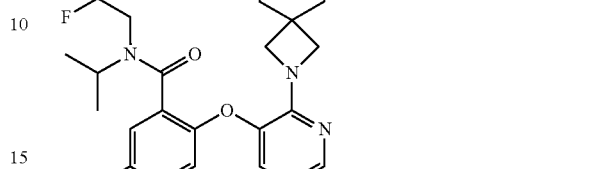
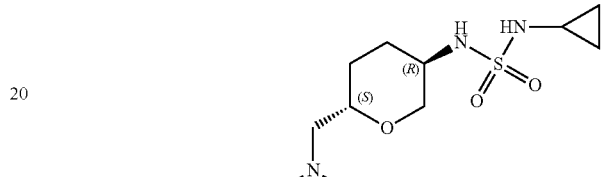
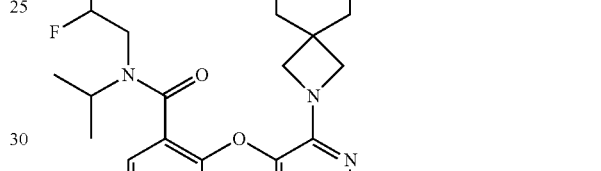
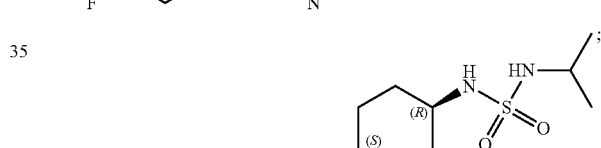
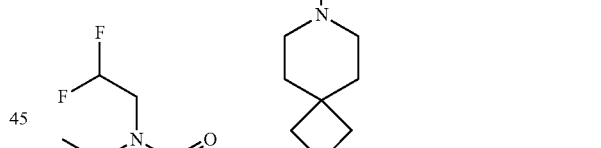

771
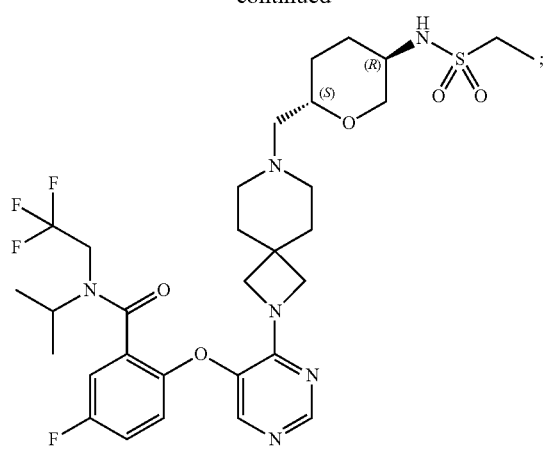
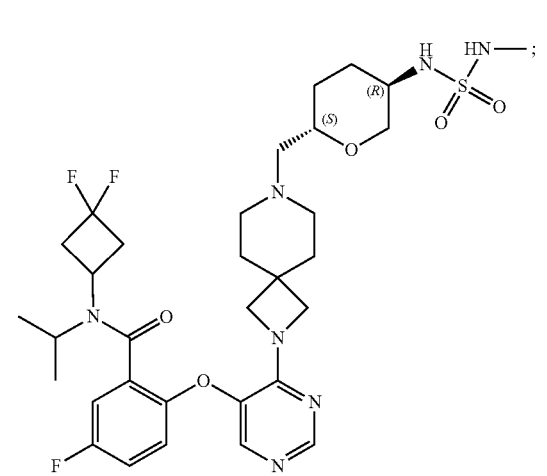
772
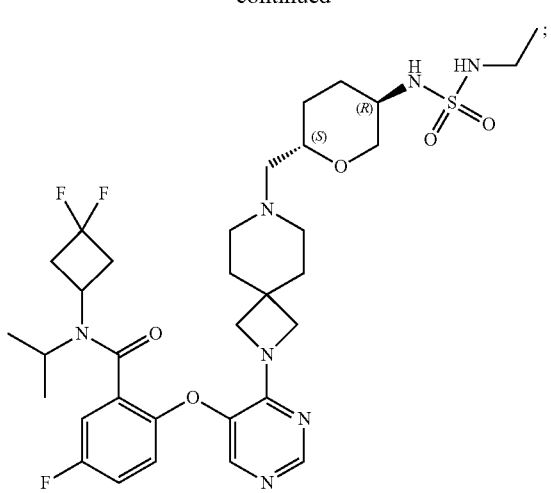

773
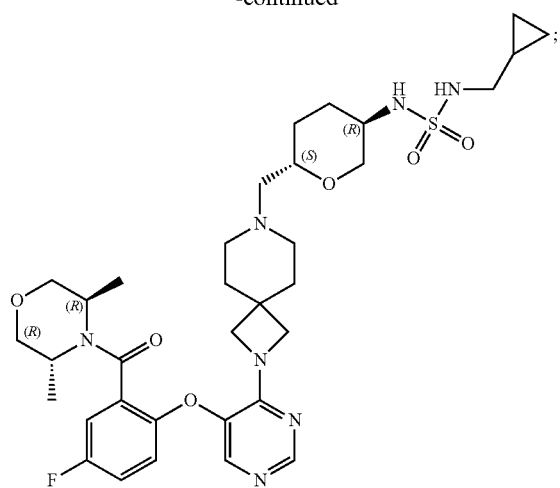
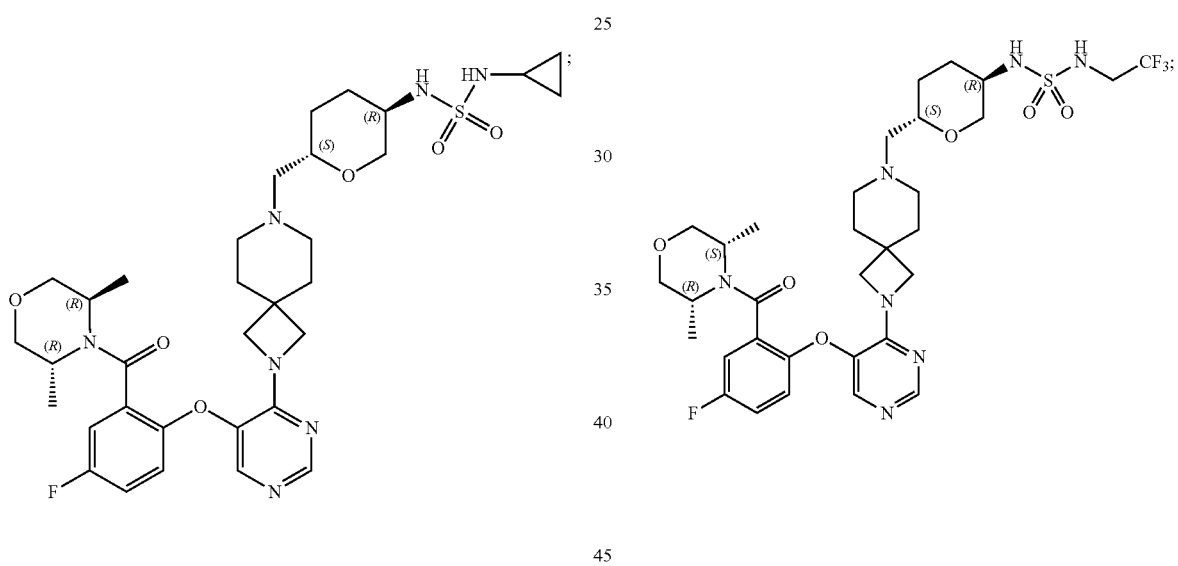
774
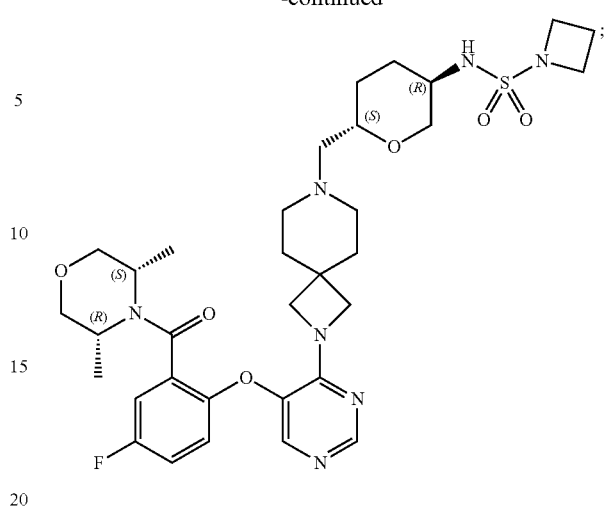
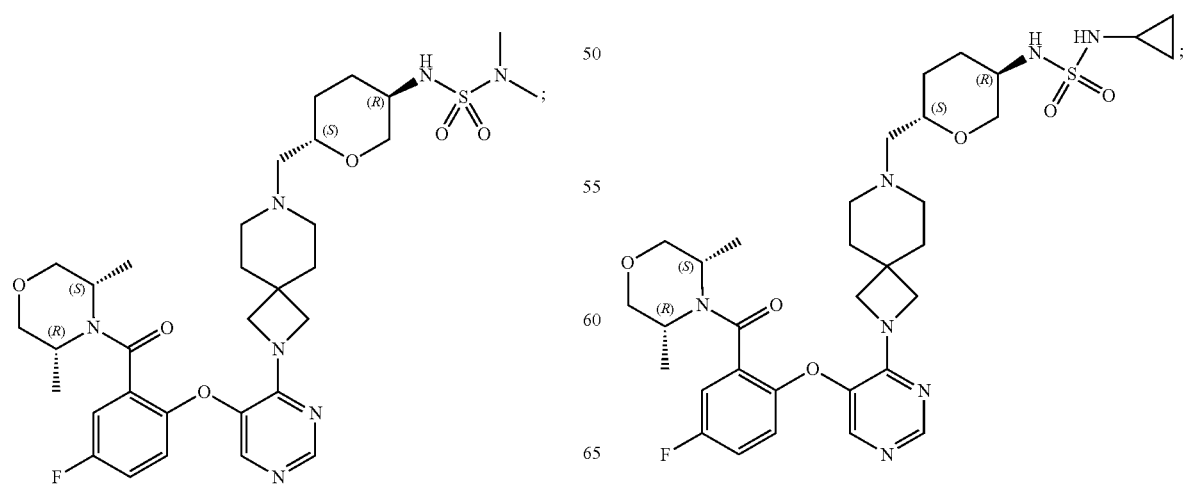

775
-continued
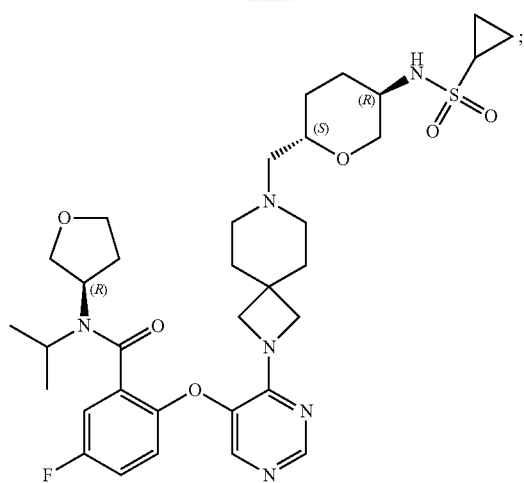
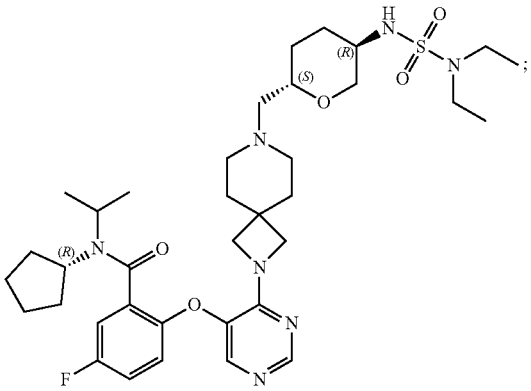
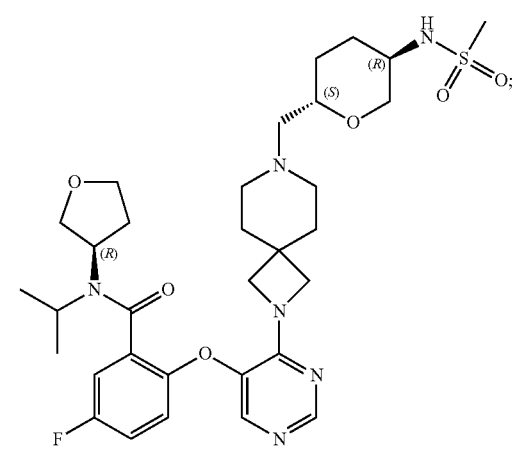
776
-continued
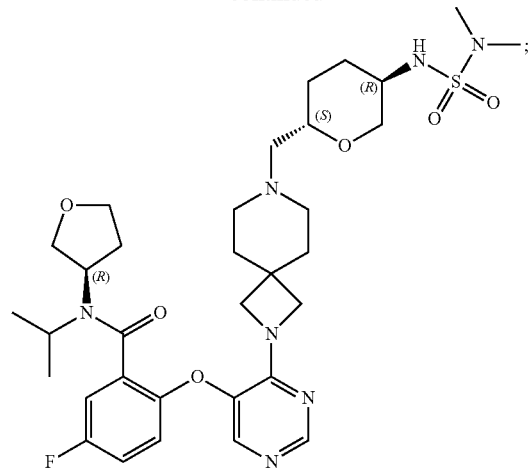
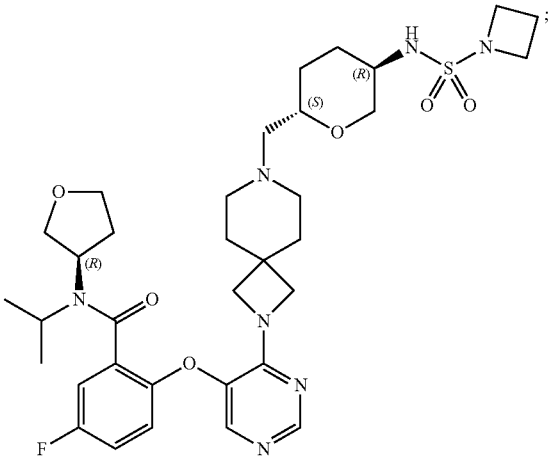
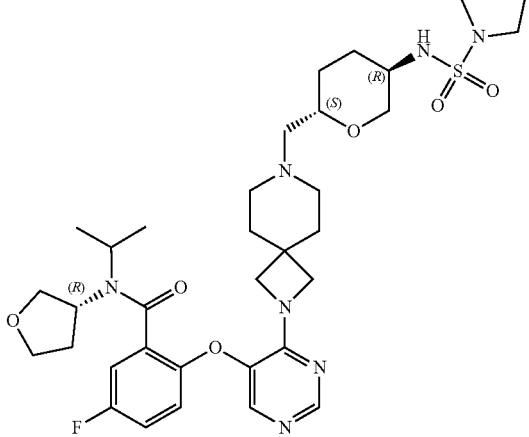

777
-continued
778
-continued
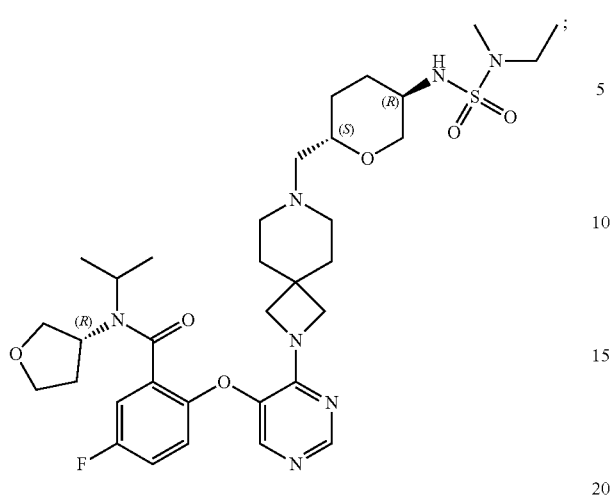
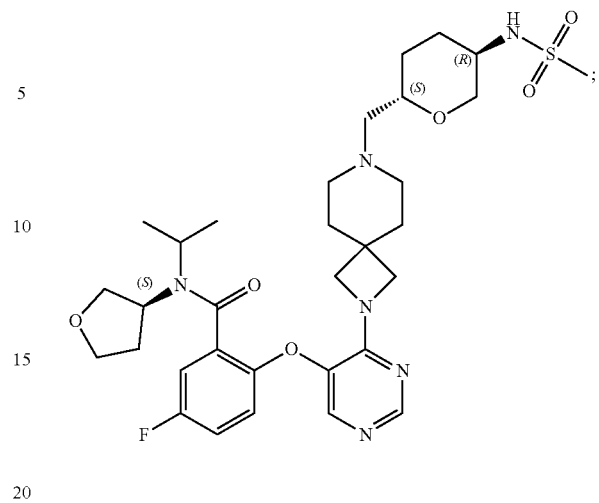
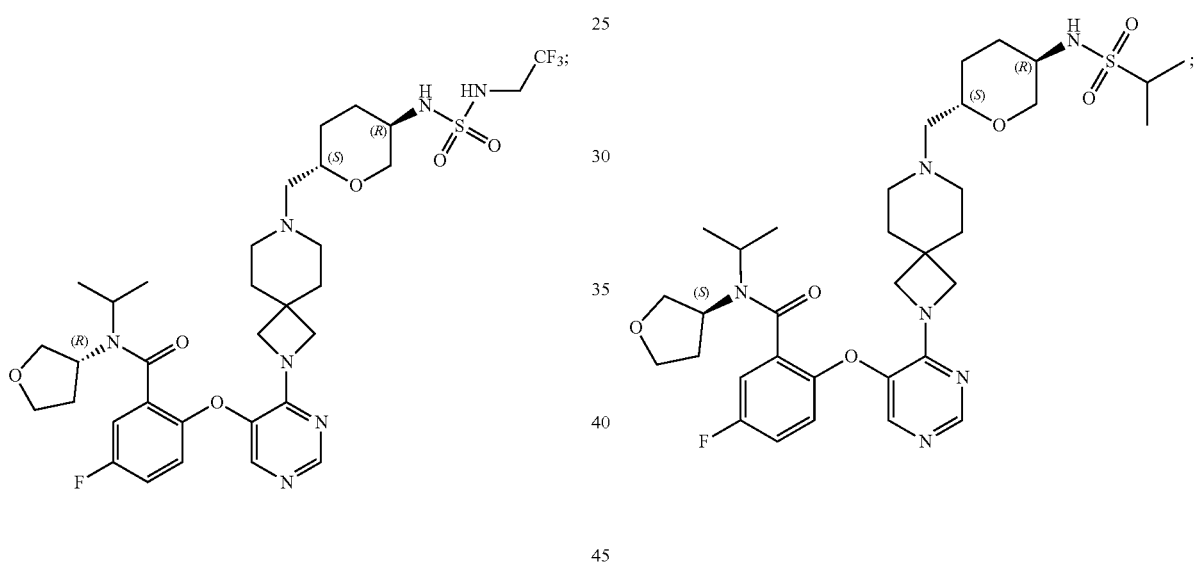
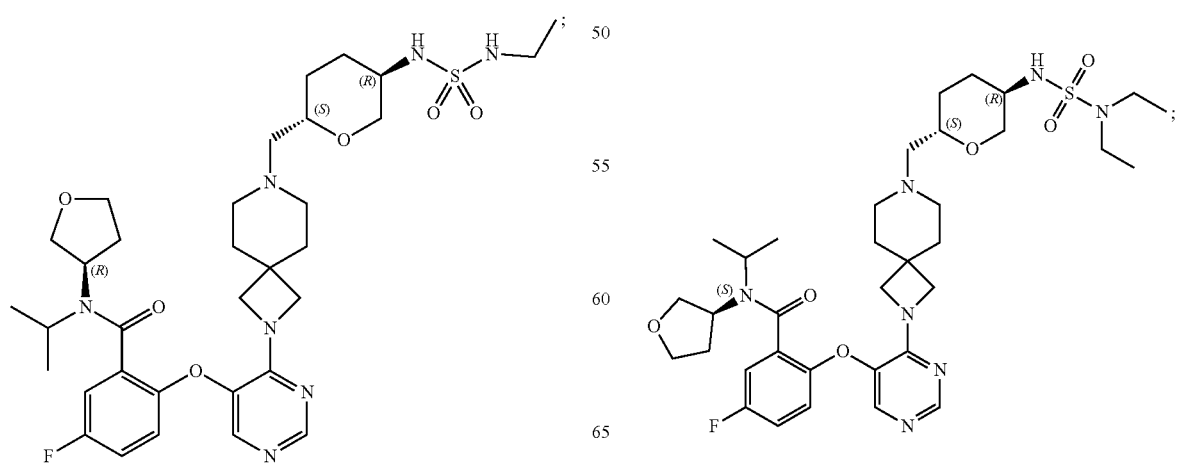

779
-continued
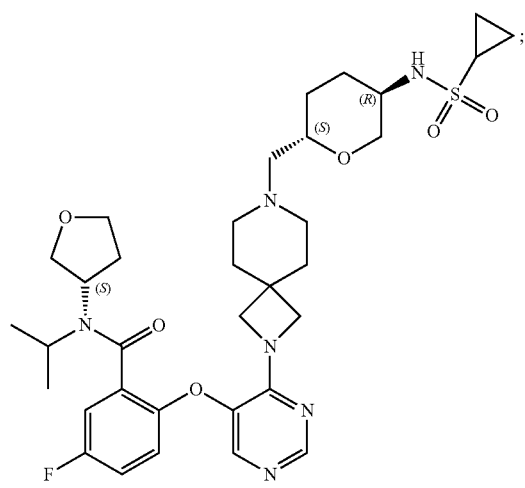
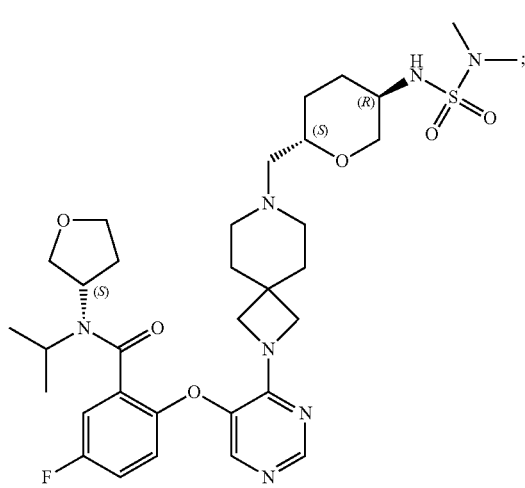
780
-continued
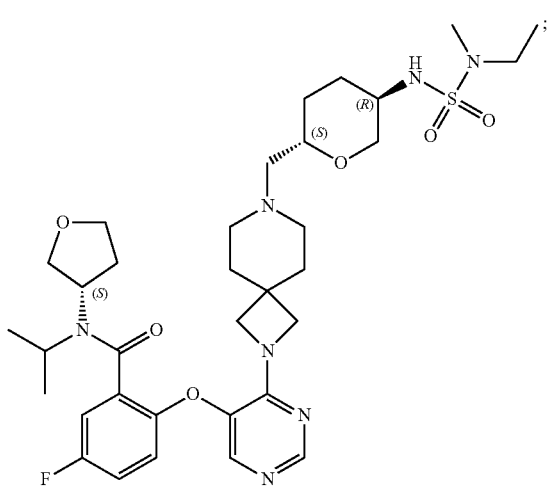
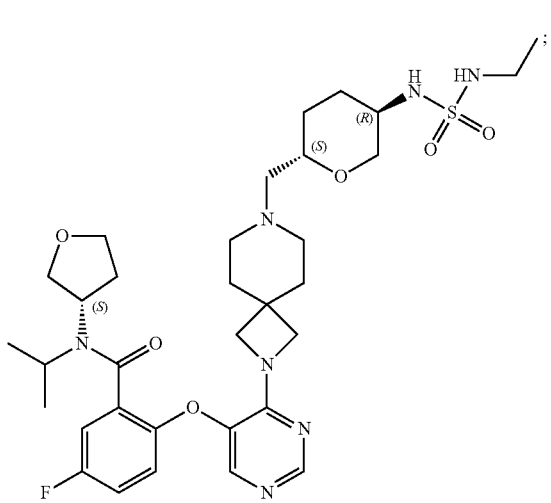
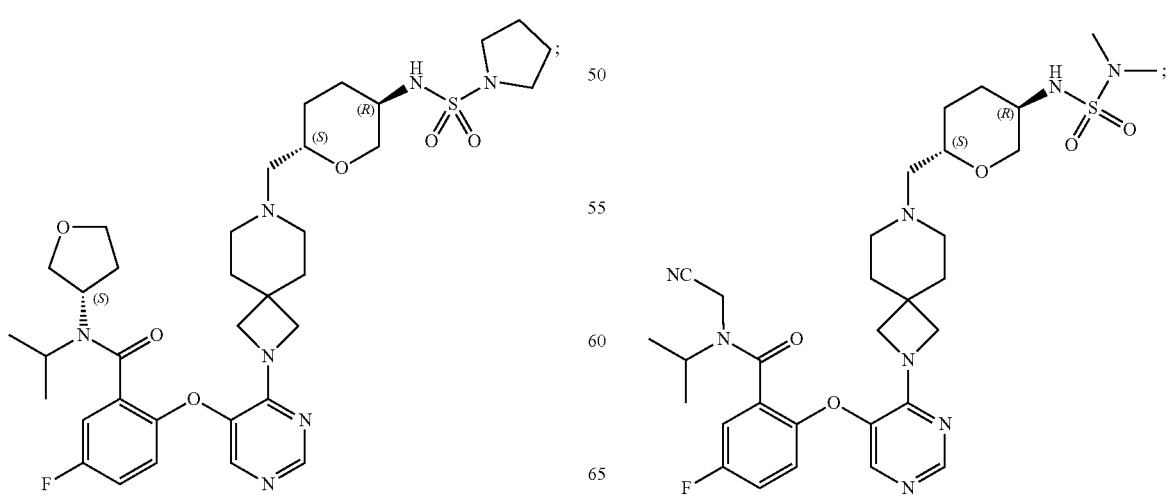

781
-continued
782
-continued
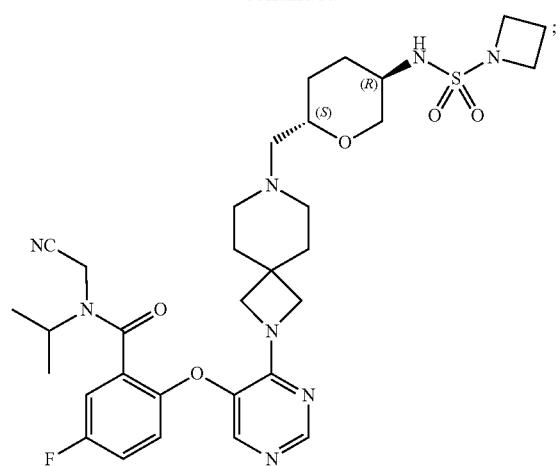
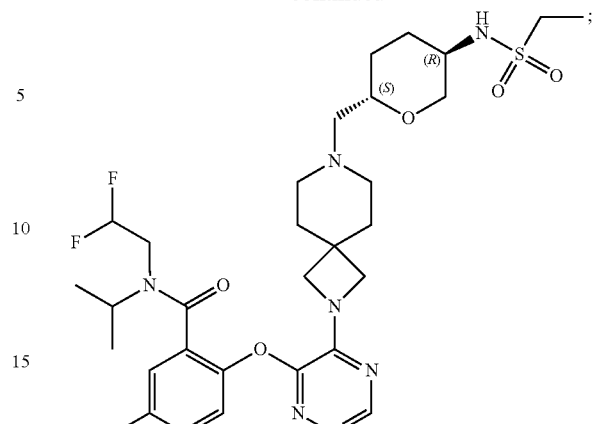

783
-continued
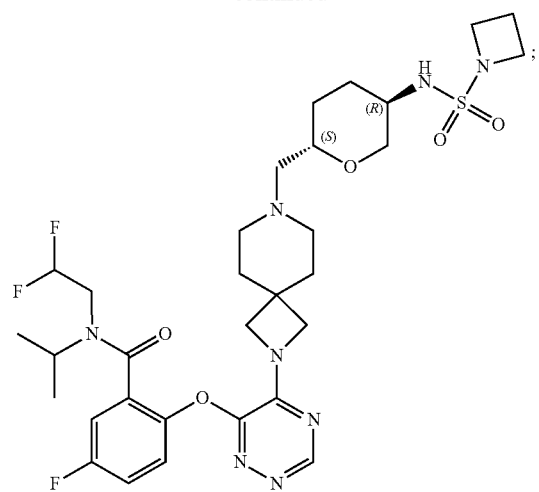
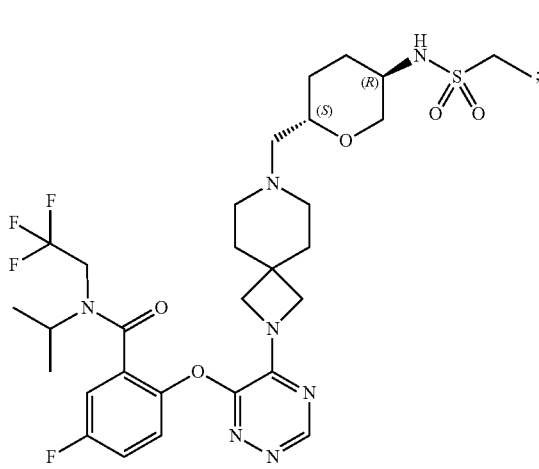
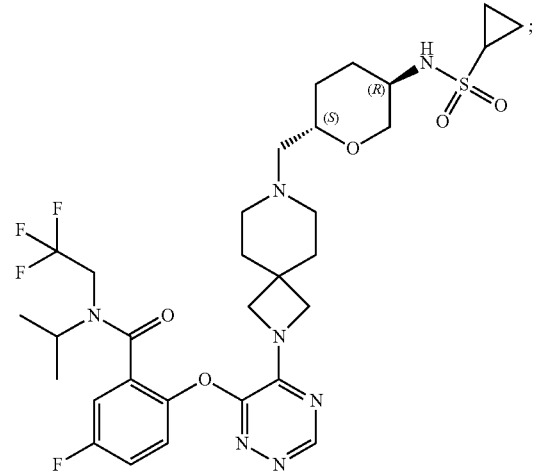
784
-continued
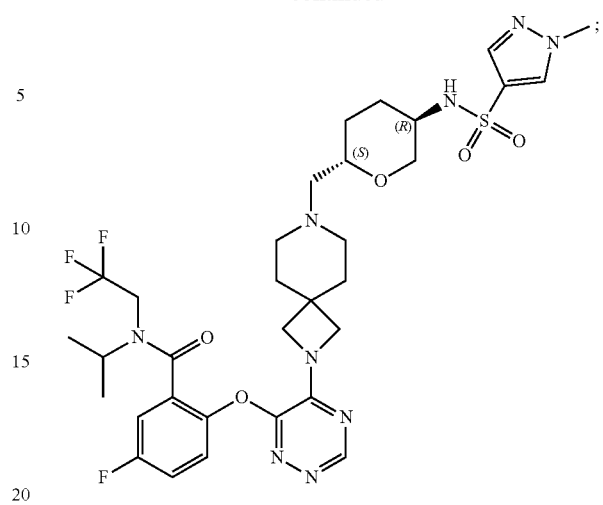
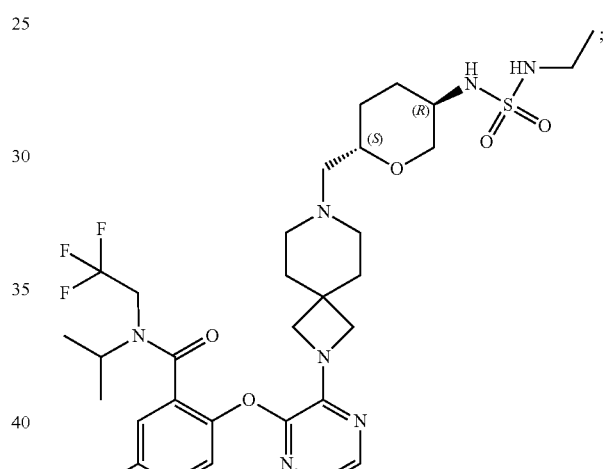
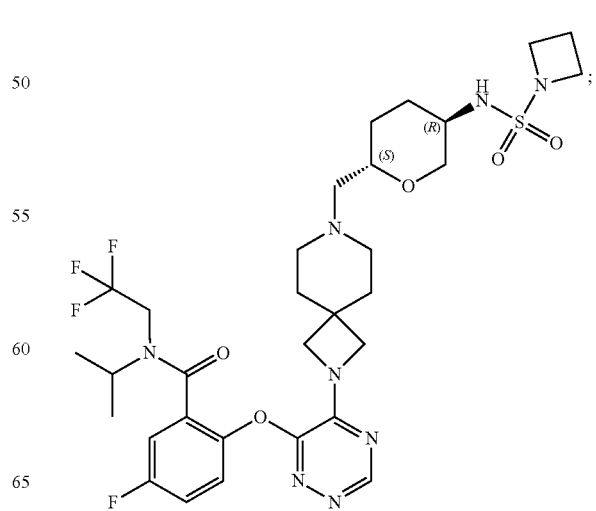

785
-continued
786
-continued
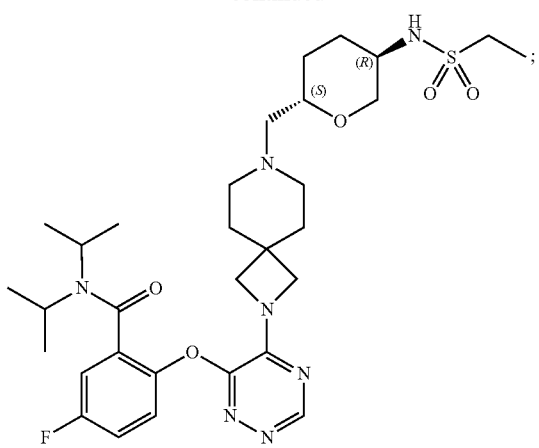
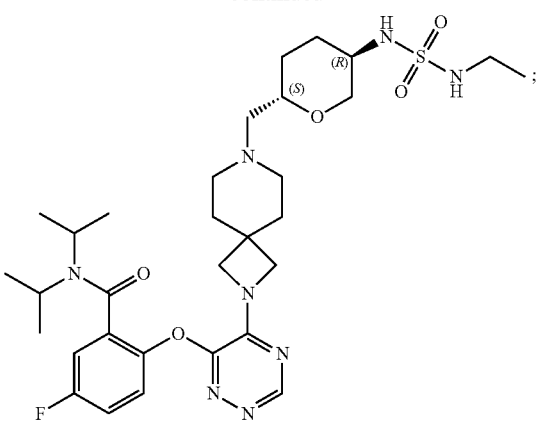

787
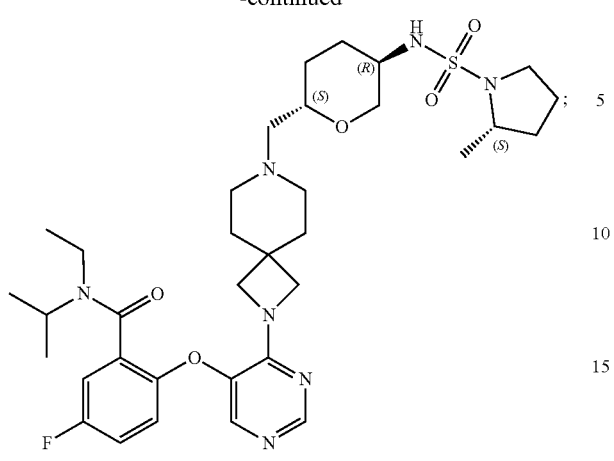
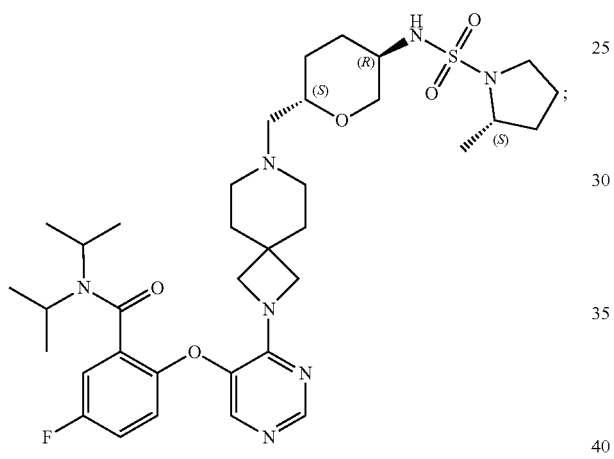
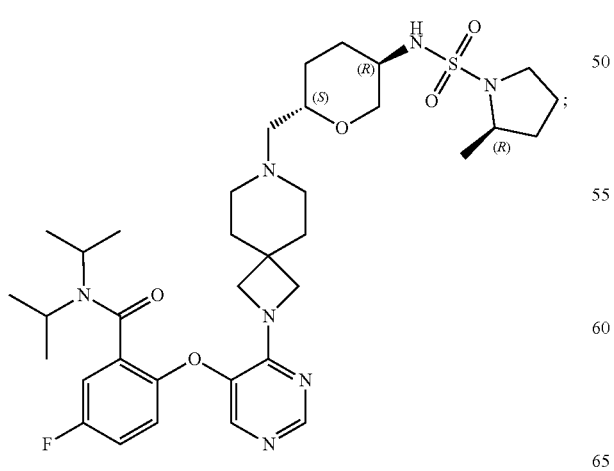
788
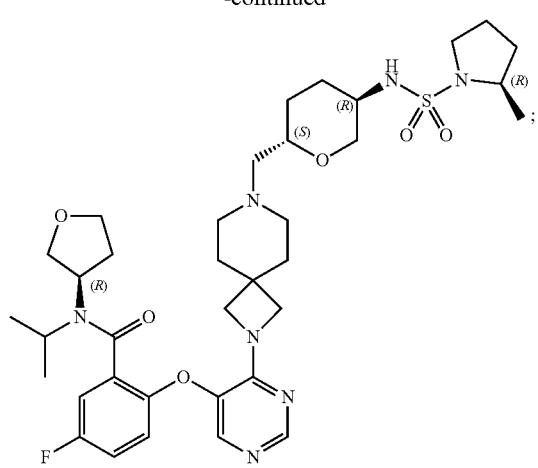
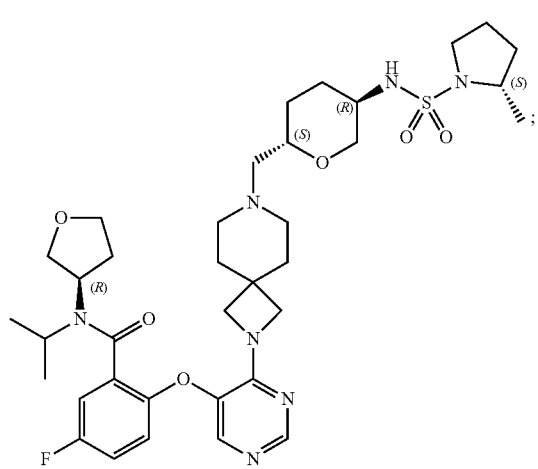
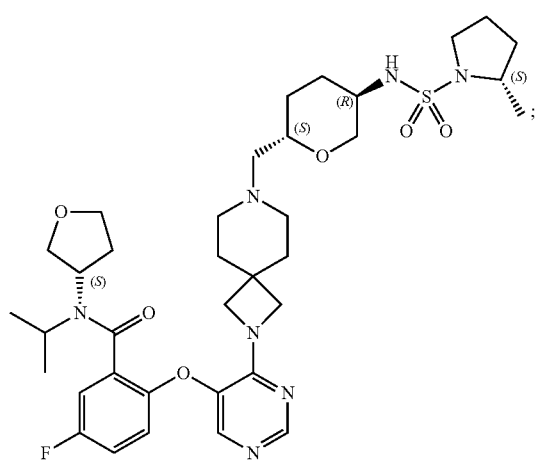

789
-continued
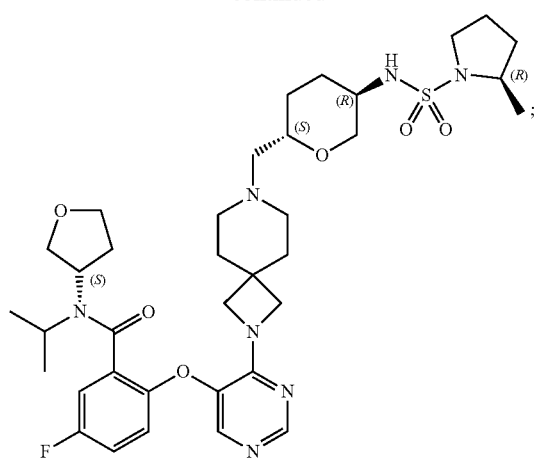
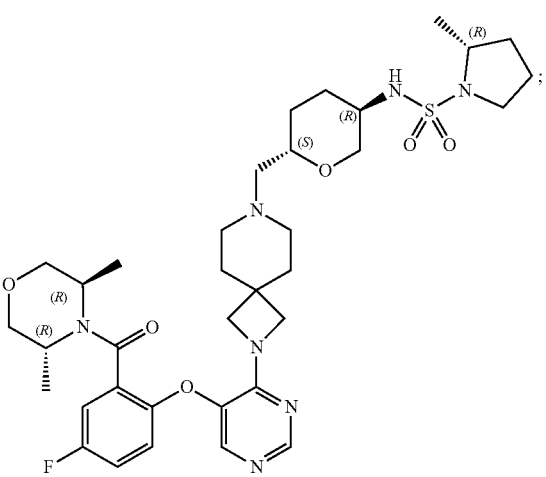
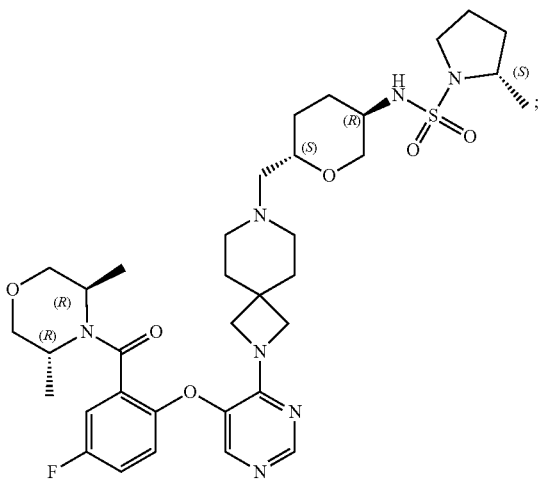
790
-continued
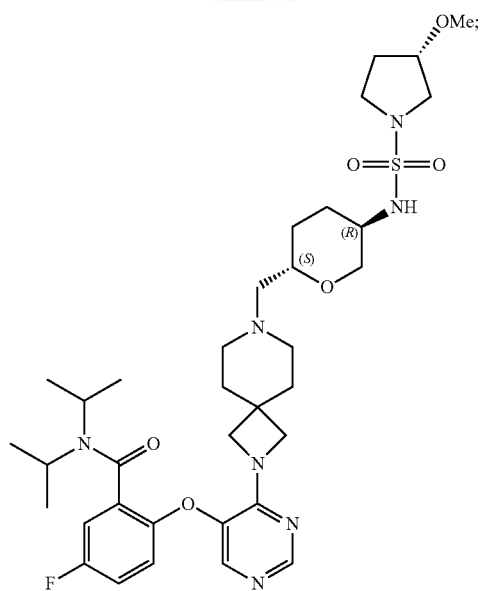
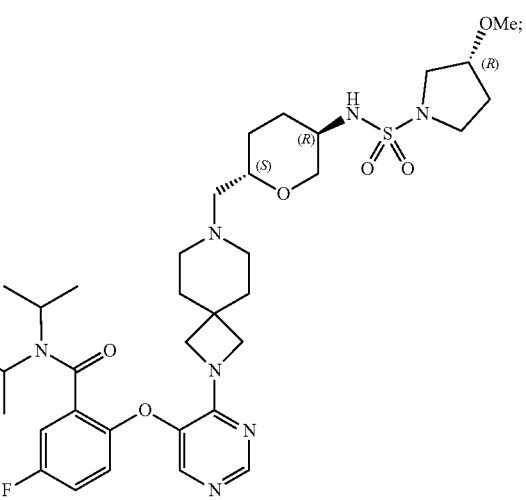
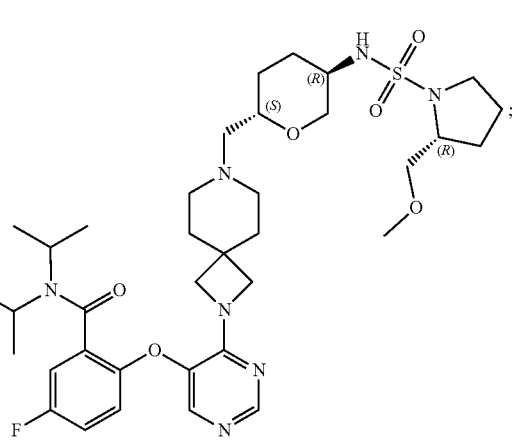

791
-continued
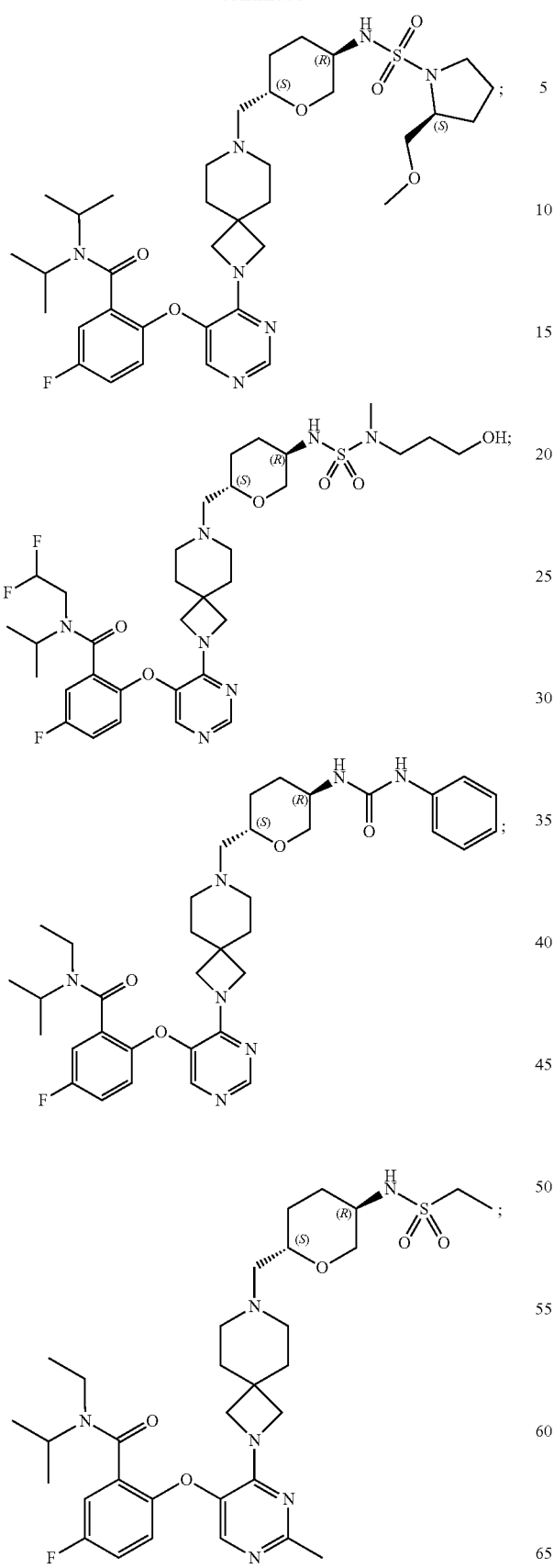
792
-continued
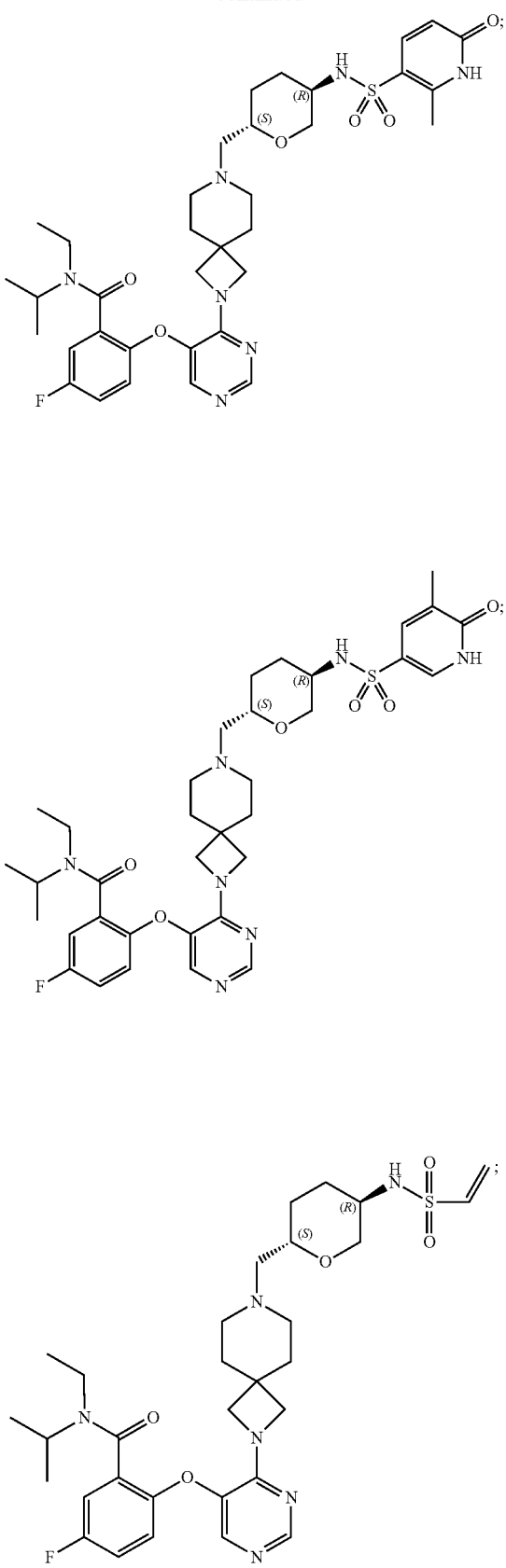

793
-continued
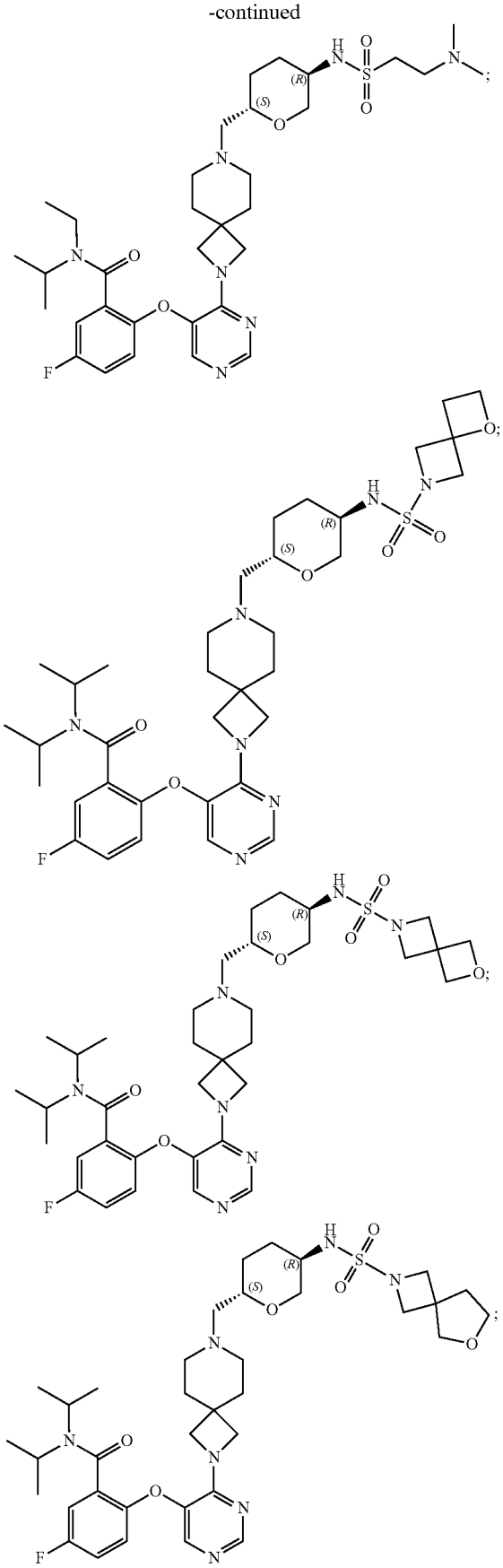
794
-continued
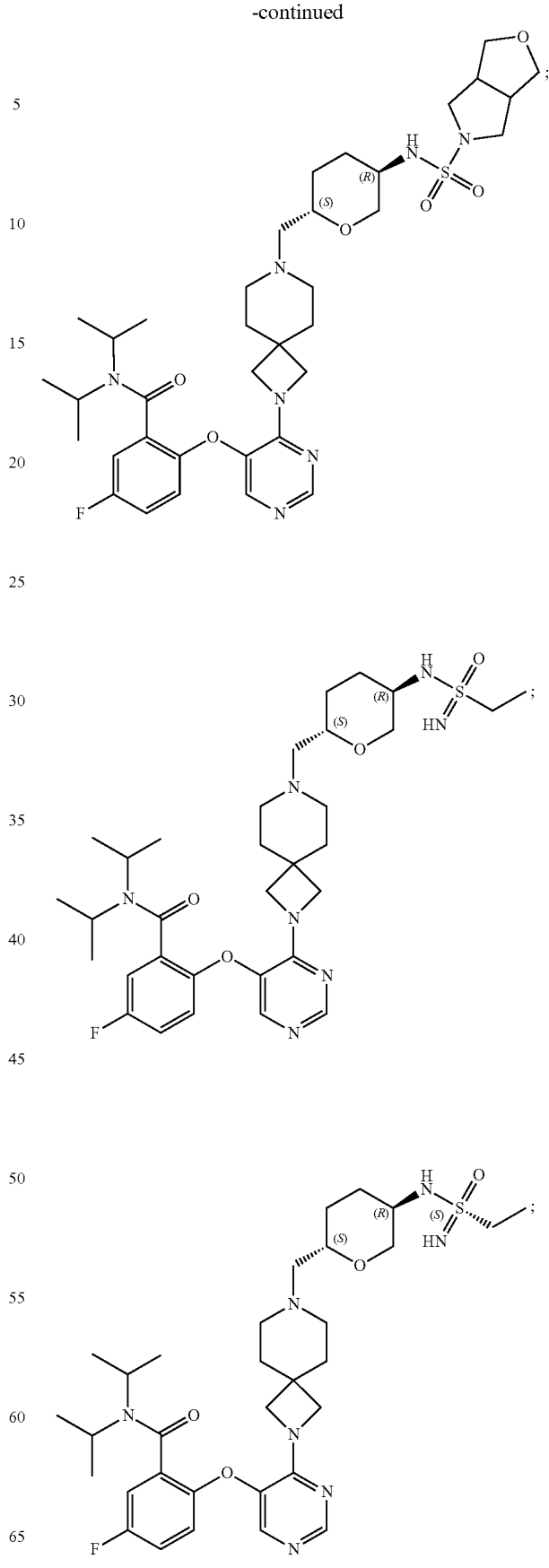

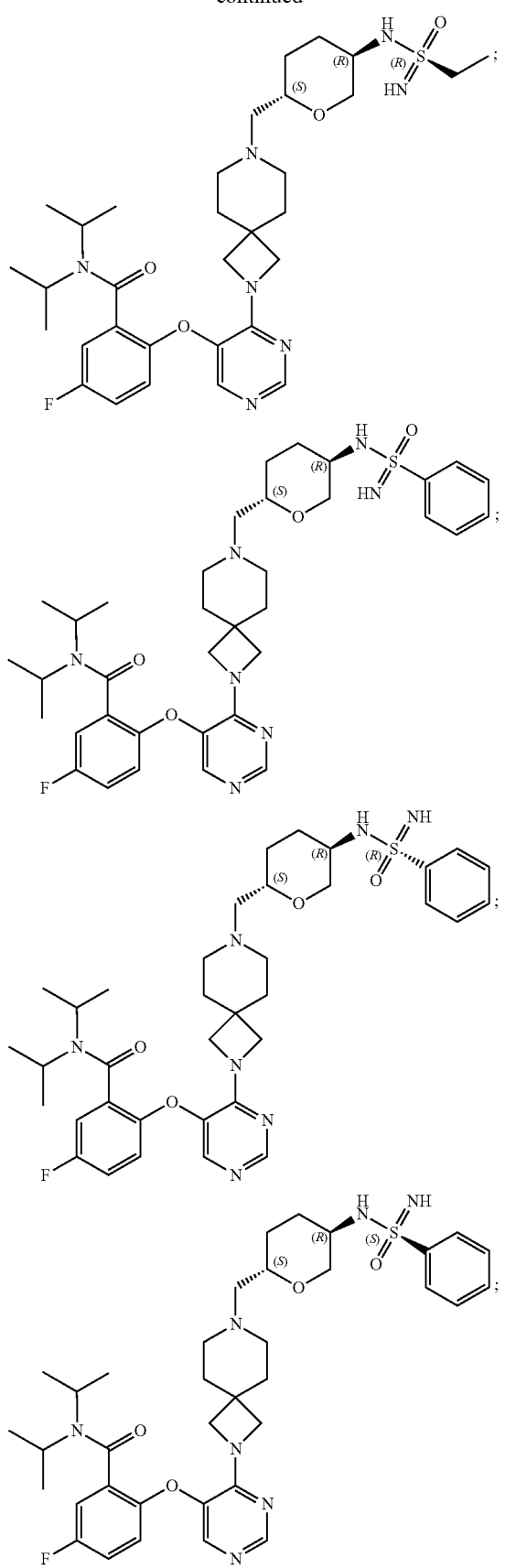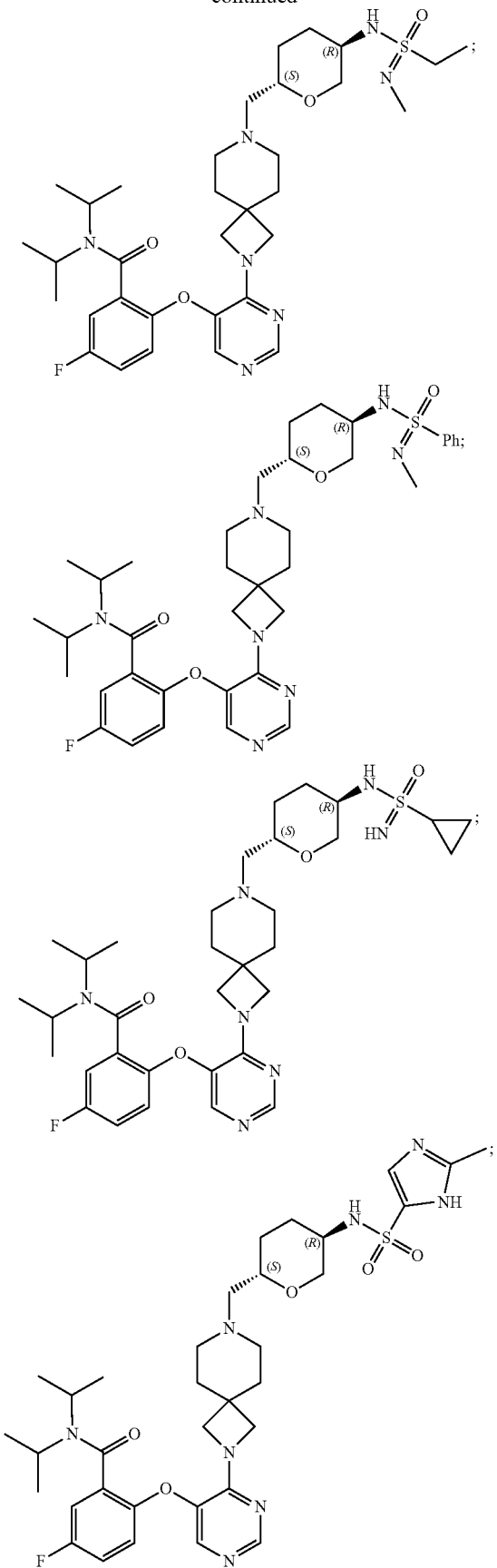

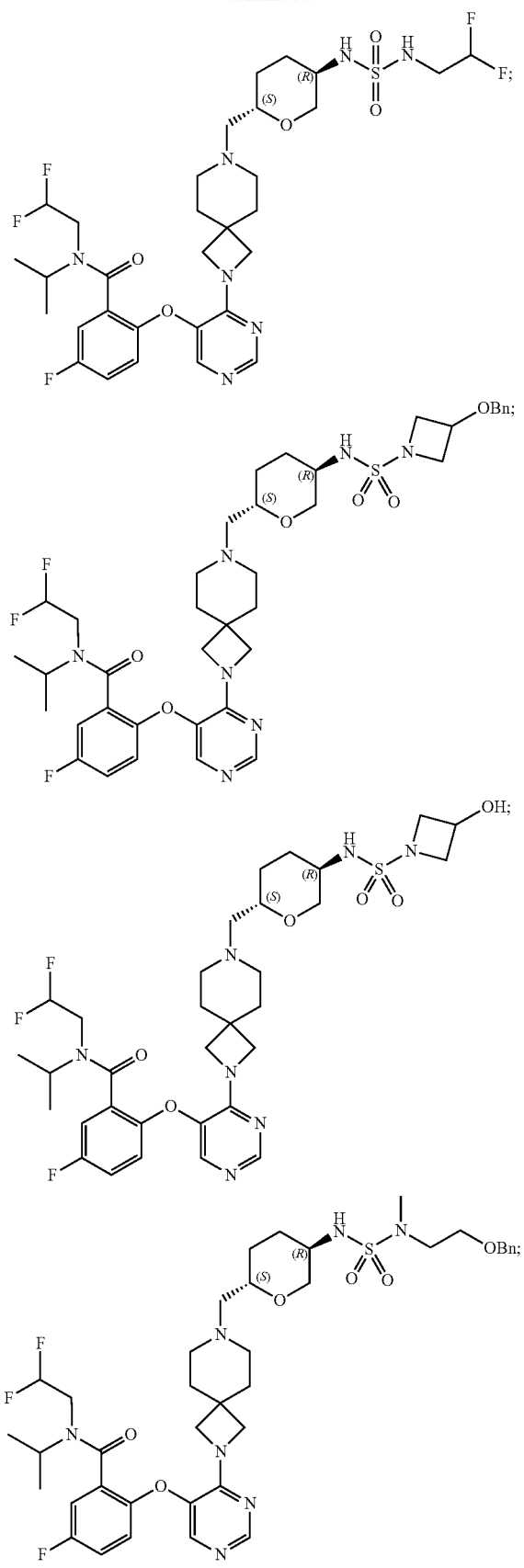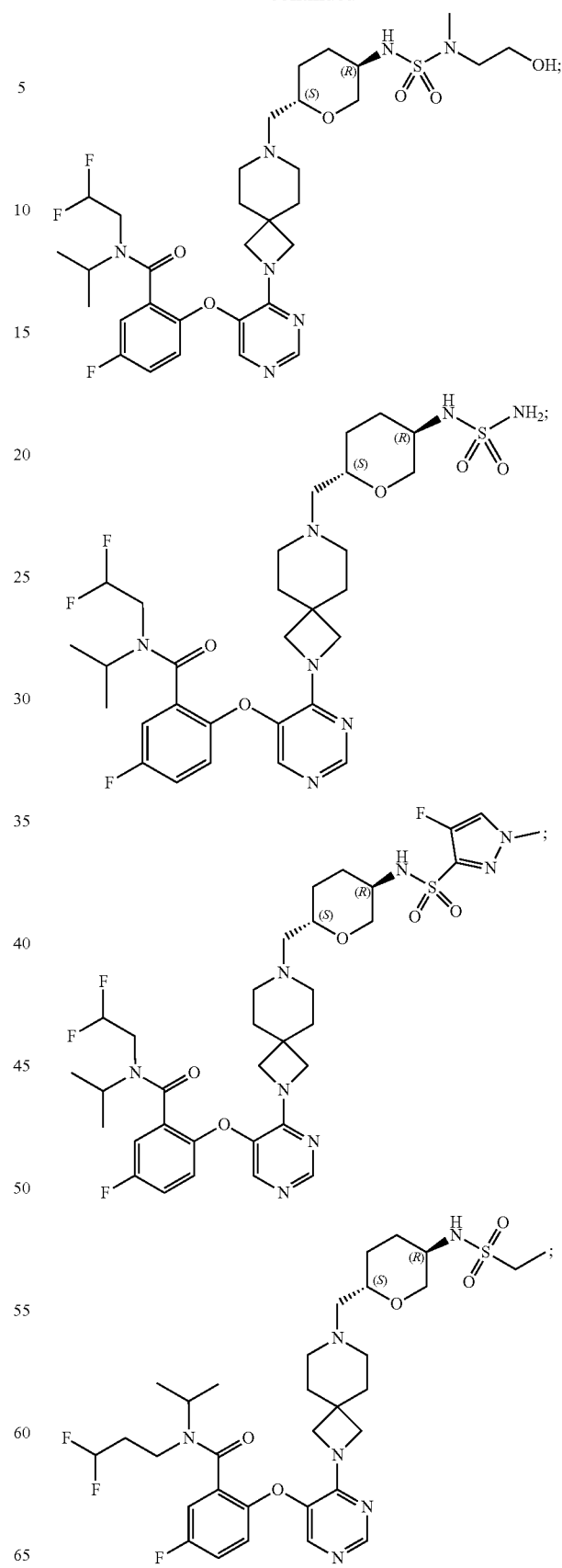

799
-continued
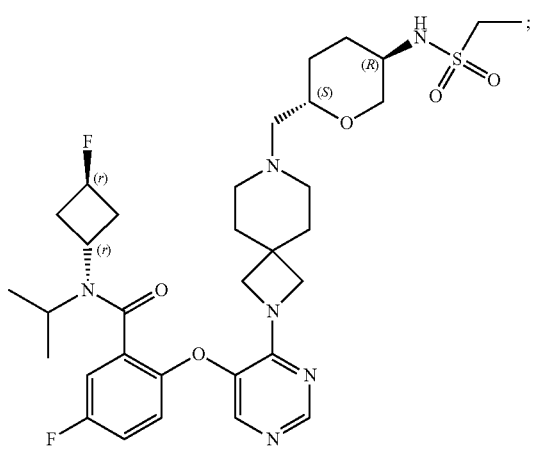
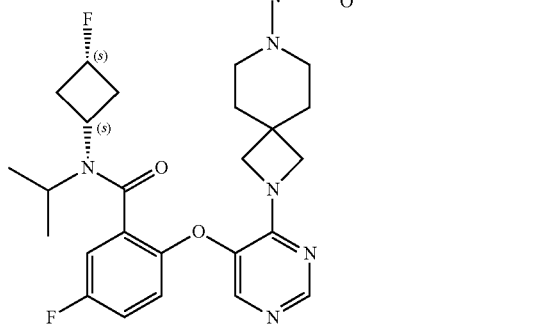
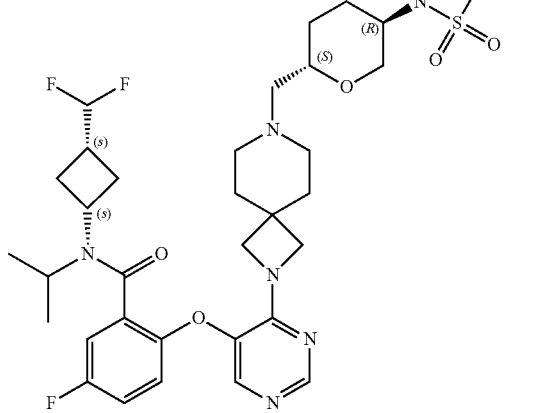
800
-continued
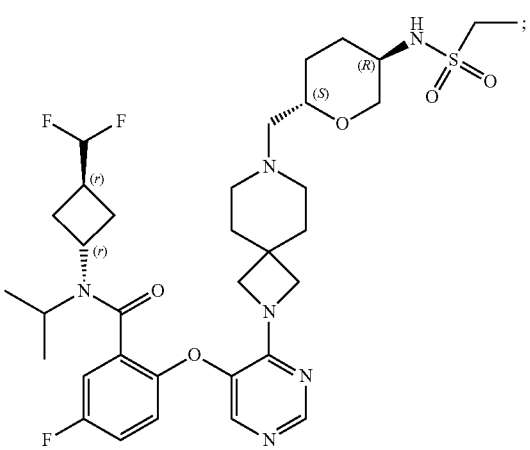
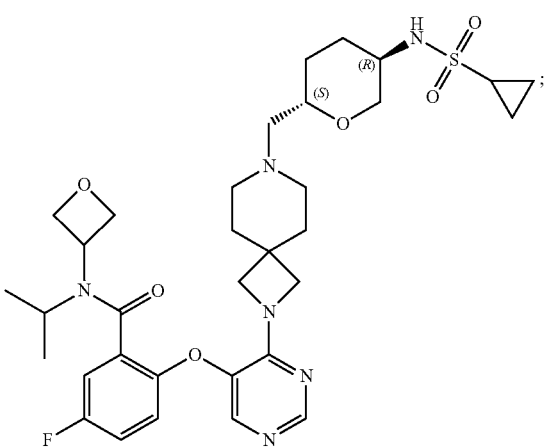
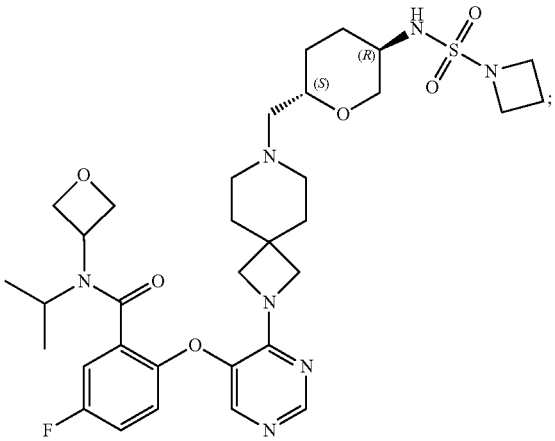

801
-continued
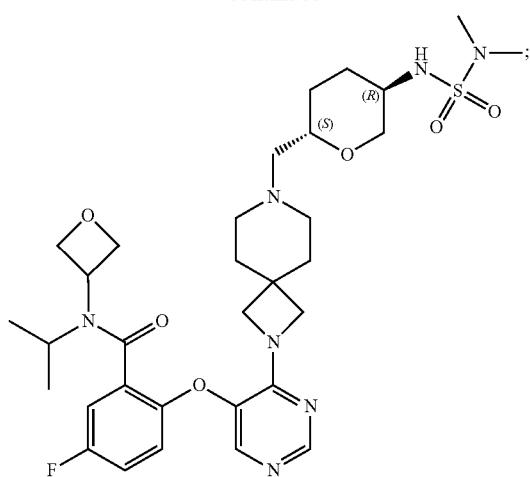
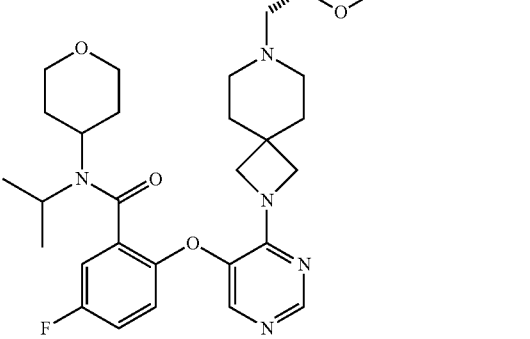
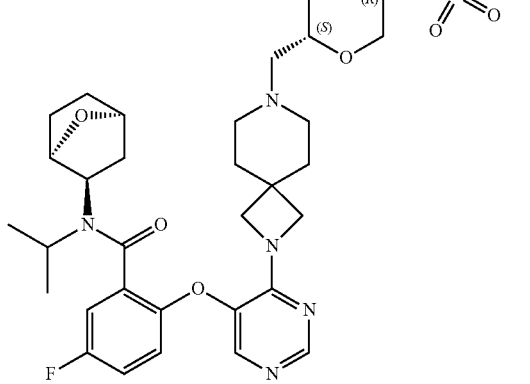
802
-continued
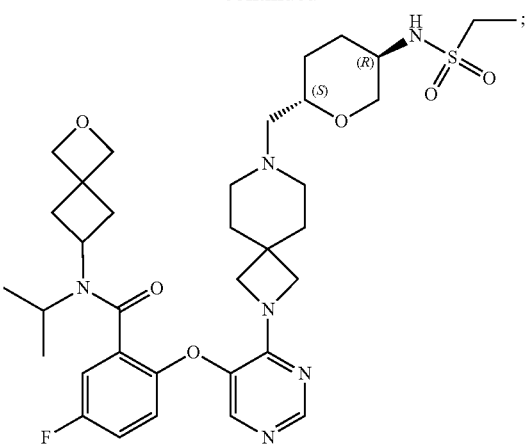
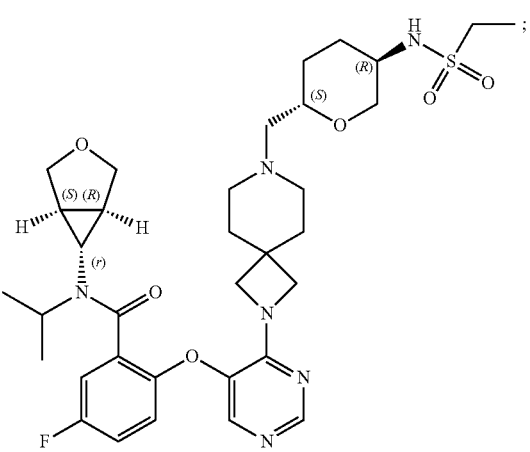
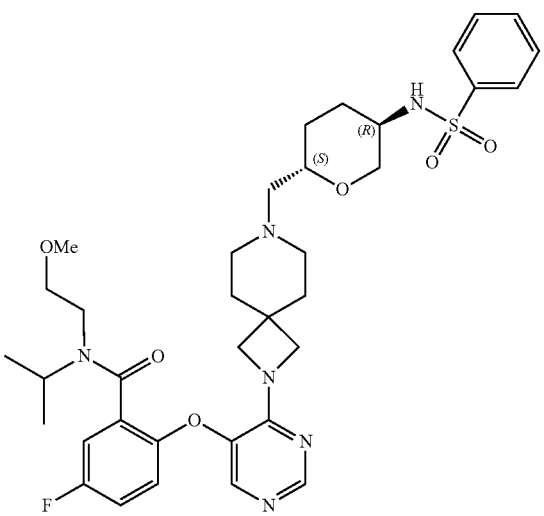

803
-continued
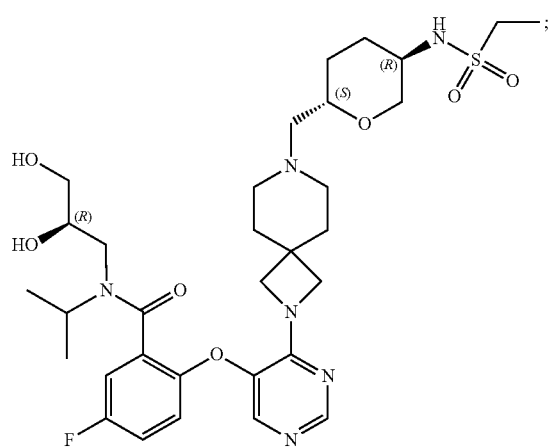
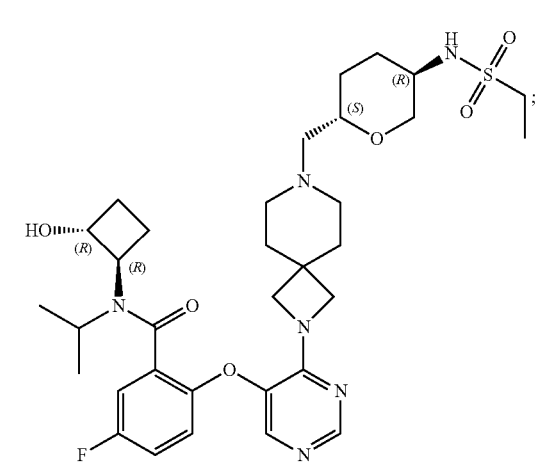
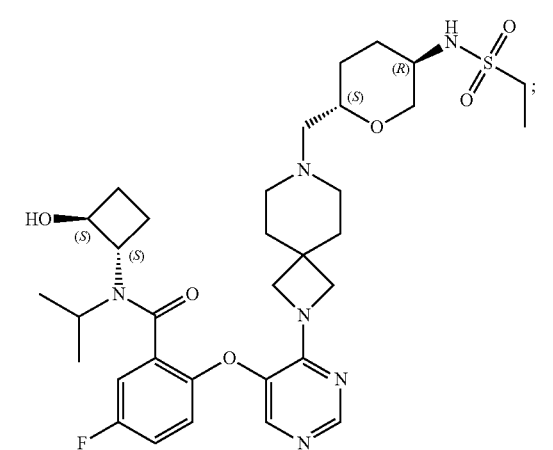
804
-continued
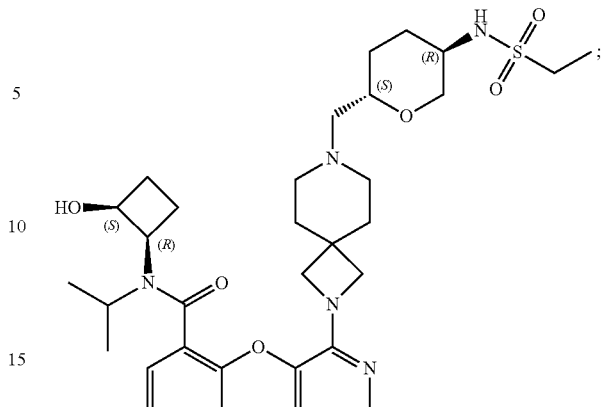
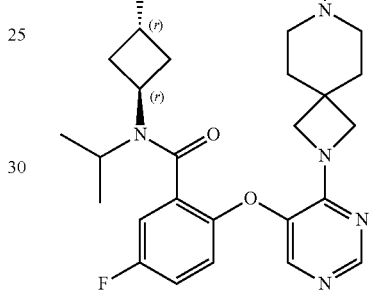
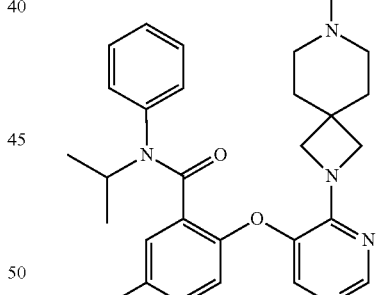
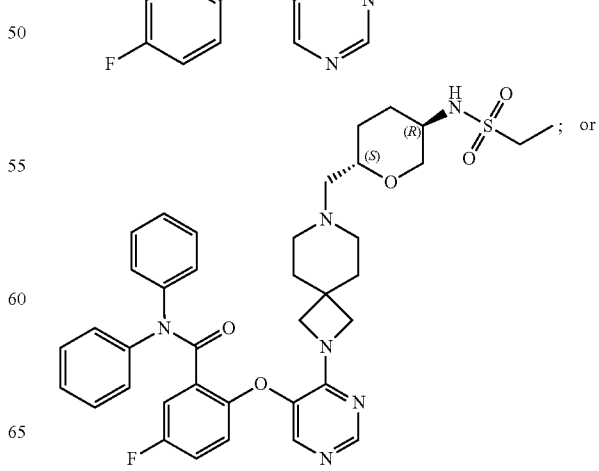

-continued

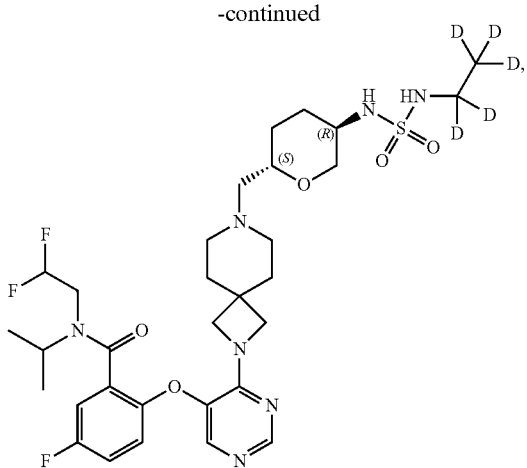

or a stereoisomer thereof, or a pharmaceutically acceptable salt thereof.

22. The compound according to claim 1, wherein the compound is useful for the treatment of leukemia in a subject in need thereof, wherein the compound minimizes hERG binding, and wherein the treatment comprises administering to the subject a therapeutically effective amount of the compound of claim 1.

23. A pharmaceutical composition comprising a compound of claim 1, or a pharmaceutically acceptable salt thereof, and at least one pharmaceutically acceptable carrier.

24. A method of inhibiting the interaction between menin and MLL comprising contacting the menin and MLL with a compound of claim 1.

25. A method of treating leukemia in a patient comprising administering to the patient a compound of claim 1.

26. The method of claim 25, wherein the leukemia is mixed lineage leukemia (MLL), MLL-related leukemia, MLL-associated leukemia, MLL-positive leukemia, MLL-induced leukemia, rearranged mixed lineage leukemia (MLL-r), leukemia associated with a MLL rearrangement or a rearrangement of the MLL gene, acute leukemia, chronic leukemia, indolent leukemia, lymphoblastic leukemia, lymphocytic leukemia, myeloid leukemia, myelogenous leukemia, childhood leukemia, acute lymphocytic leukemia (ALL), acute myeloid leukemia (AML), acute granulocytic leukemia, acute nonlymphocytic leukemia, chronic lymphocytic leukemia (CLL), chronic myelogenous leukemia (CML), therapy related leukemia, hairy cell leukemia, T-cell prolymphocytic leukemia (T-PLL), large granular lymphocytic leukemia, meningeal leukemia, leukemic leptomeningitis, or leukemic meningitis.

27. The method of claim 25, wherein the leukemia is an abstract nucleophosmin (NPM1)-mutated acute myeloid leukemia.

28. The compound of claim 1, for use in treating or preventing a disease caused by, or associated with, menin expression, activity, and/or function, wherein the disease is leukemia and wherein the treatment comprises administering to a subject in need thereof a therapeutically effective amount of the compound of claim 1.

* * * * *